(12) United States Patent
Vargeese et al.

(10) Patent No.: US 10,724,035 B2
(45) Date of Patent: Jul. 28, 2020

(54) OLIGONUCLEOTIDE COMPOSITIONS AND METHODS THEREOF

(71) Applicant: WAVE LIFE SCIENCES LTD., Singapore (SG)

(72) Inventors: Chandra Vargeese, Schwenksville, PA (US); Meena, Belmont, MA (US); Nenad Svrzikapa, Cambridge, MA (US); Susovan Mohapatra, Belmont, MA (US); Christopher J. Francis, Arlington, MA (US); Gregory L. Verdine, Boston, MA (US); Anna Sokolovska, Somerville, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 4 days.

(21) Appl. No.: 16/098,836

(22) PCT Filed: May 3, 2017

(86) PCT No.: PCT/US2017/030753
§ 371 (c)(1),
(2) Date: Nov. 2, 2018

(87) PCT Pub. No.: WO2017/192664
PCT Pub. Date: Nov. 9, 2017

(65) Prior Publication Data
US 2020/0056173 A1      Feb. 20, 2020

Related U.S. Application Data

(60) Provisional application No. 62/447,832, filed on Jan. 18, 2017, provisional application No. 62/331,960, filed on May 4, 2016.

(30) Foreign Application Priority Data

Jul. 22, 2016  (WO) ................ PCT/US2016/043542

(51) Int. Cl.
| | | |
|---|---|---|
| *A61K 31/712* | (2006.01) | |
| *A61K 31/7125* | (2006.01) | |
| *C12N 15/11* | (2006.01) | |
| *C12N 15/113* | (2010.01) | |

(52) U.S. Cl.
CPC .......... *C12N 15/111* (2013.01); *C12N 15/113* (2013.01); *C12N 2310/11* (2013.01); *C12N 2310/14* (2013.01); *C12N 2310/315* (2013.01); *C12N 2310/321* (2013.01); *C12N 2310/346* (2013.01); *C12N 2310/50* (2013.01)

(58) Field of Classification Search
None
See application file for complete search history.

(56) References Cited

U.S. PATENT DOCUMENTS

| | | |
|---|---|---|
| 5,792,615 A | 8/1998 | Arnold, Jr. et al. |
| 6,172,209 B1 | 1/2001 | Manoharan et al. |
| 6,639,022 B2 | 10/2003 | Michels et al. |
| 6,639,062 B2 | 10/2003 | Manoharan et al. |
| 6,867,294 B1 | 3/2005 | Sanghvi et al. |
| 7,015,315 B1 | 3/2006 | Cook et al. |
| RE39,464 E | 1/2007 | Cook et al. |
| 7,947,658 B2 | 5/2011 | Aronin et al. |
| 7,951,934 B2 | 5/2011 | Freier |
| 8,415,465 B2 | 4/2013 | Freier |
| 8,470,987 B2 | 6/2013 | Wada et al. |
| 8,481,710 B2 | 7/2013 | Davidson et al. |
| 8,679,750 B2 | 3/2014 | Hayden et al. |
| 8,680,063 B2 | 3/2014 | Aronin et al. |
| 8,822,671 B2 | 9/2014 | Shimizu et al. |
| 8,859,755 B2 | 10/2014 | Wada et al. |
| 8,906,873 B2 | 12/2014 | Hung et al. |
| 8,952,145 B2 | 2/2015 | Freier |
| 8,957,040 B2 | 2/2015 | Bennett et al. |
| 8,987,222 B2 | 3/2015 | Aronin et al. |
| 9,006,198 B2 | 4/2015 | Bennett et al. |
| 9,057,066 B2 | 6/2015 | Hung et al. |

(Continued)

FOREIGN PATENT DOCUMENTS

| | | |
|---|---|---|
| EP | 2062980 A2 | 5/2009 |
| EP | 2161038 A1 | 3/2010 |

(Continued)

OTHER PUBLICATIONS

U.S. Appl. No. 16/087,577, filed Sep. 21, 2018, Butler et al.

(Continued)

*Primary Examiner* — Jennifer Pitrak McDonald
(74) *Attorney, Agent, or Firm* — Choate, Hall & Stewart LLP; Brenda Herschbach Jarrell; Xiaodong Li

(57) ABSTRACT

Among other things, the present disclosure relates to chirally controlled oligonucleotides of select designs, chirally controlled oligonucleotide compositions, and methods of making and using the same. In some embodiments, a provided chirally controlled oligonucleotide composition provides different cleavage patterns of a nucleic acid polymer than a reference oligonucleotide composition. In some embodiments, a provided chirally controlled oligonucleotide composition provides single site cleavage within a complementary sequence of a nucleic acid polymer. In some embodiments, a chirally controlled oligonucleotide composition has any sequence of bases, and/or pattern or base modifications, sugar modifications, backbone modifications and/or stereochemistry, or combination of these elements, described herein.

12 Claims, 104 Drawing Sheets

Specification includes a Sequence Listing.

(56) References Cited

U.S. PATENT DOCUMENTS

| | | | |
|---|---|---|---|
| 9,260,716 | B2 | 2/2016 | Davidson et al. |
| 9,273,315 | B2 | 3/2016 | Hung et al. |
| 9,353,372 | B2 | 5/2016 | Freier |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,683,236 | B2 | 6/2017 | Hung et al. |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,479,995 | B2 | 11/2019 | Vargeese et al. |
| 2002/0082227 | A1 | 6/2002 | Henry |
| 2004/0213780 | A1 | 10/2004 | Krainc |
| 2005/0042646 | A1 | 2/2005 | Davidson et al. |
| 2005/0096284 | A1 | 5/2005 | McSwiggen |
| 2005/0277133 | A1 | 12/2005 | McSwiggen |
| 2006/0257912 | A1 | 11/2006 | Kaemmerer et al. |
| 2007/0099860 | A1 | 5/2007 | Sah et al. |
| 2007/0161590 | A1 | 7/2007 | Van Bilsen et al. |
| 2007/0299027 | A1 | 12/2007 | Hung et al. |
| 2008/0015158 | A1 | 1/2008 | Ichiro et al. |
| 2008/0274989 | A1 | 11/2008 | Davidson et al. |
| 2009/0186410 | A1 | 7/2009 | Aronin et al. |
| 2010/0120900 | A1 | 5/2010 | van Bilsen et al. |
| 2010/0325746 | A9 | 12/2010 | Kaemmerer et al. |
| 2011/0105587 | A1 | 5/2011 | Fishcher et al. |
| 2012/0136039 | A1 | 5/2012 | Aronin et al. |
| 2013/0046008 | A1 | 2/2013 | Bennett et al. |
| 2013/0178612 | A1 | 7/2013 | Wada et al. |
| 2014/0142160 | A1 | 5/2014 | Lee et al. |
| 2014/0221395 | A1 | 8/2014 | Dhanoa |
| 2014/0256578 | A1 | 9/2014 | Hayden et al. |
| 2014/0303235 | A1 | 10/2014 | Oestergaard et al. |
| 2014/0303238 | A1 | 10/2014 | Linsley et al. |
| 2014/0309279 | A1 | 10/2014 | Oestergaard et al. |
| 2014/0323707 | A1 | 10/2014 | Seth et al. |
| 2015/0051389 | A1 | 2/2015 | Seth et al. |
| 2015/0275208 | A1 | 10/2015 | Oestergaard et al. |
| 2015/0292015 | A1 | 10/2015 | Bennett et al. |
| 2015/0335708 | A1 | 11/2015 | Froelich et al. |
| 2015/0376625 | A1 | 12/2015 | Oestergaard et al. |
| 2016/0017327 | A1 | 1/2016 | Rudnicki et al. |
| 2016/0251653 | A1 | 9/2016 | Davidson et al. |
| 2017/0029457 | A1 | 2/2017 | Verdine et al. |
| 2017/0044526 | A1 | 2/2017 | Wan et al. |
| 2017/0275621 | A1 | 9/2017 | Butler et al. |
| 2018/0216107 | A1 | 8/2018 | Frank-Kamenetsky et al. |
| 2019/0008986 | A1 | 1/2019 | Butler et al. |
| 2019/0077817 | A1 | 3/2019 | Butler et al. |
| 2019/0106696 | A1 | 4/2019 | Meena et al. |
| 2019/0127733 | A1 | 5/2019 | Butler et al. |

FOREIGN PATENT DOCUMENTS

| | | |
|---|---|---|
| EP | 2316967 A1 | 5/2011 |
| EP | 2422819 A2 | 2/2012 |
| EP | 2428227 A1 | 3/2012 |
| EP | 2 873 674 A1 | 5/2015 |
| JP | 2003/238586 A | 8/2003 |
| JP | 2011-184318 A | 9/2011 |
| WO | WO-2005/014609 A2 | 2/2005 |
| WO | WO-2005/023828 A1 | 3/2005 |
| WO | WO-2005/027980 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/121960 A2 | 11/2006 |
| WO | WO-2007/002904 A2 | 1/2007 |
| WO | WO-2007/051045 A2 | 5/2007 |
| WO | WO-2007/089584 A2 | 8/2007 |
| WO | WO-2007/089611 A2 | 8/2007 |
| WO | WO-2008/005562 A2 | 1/2008 |
| WO | WO-2008/021136 A2 | 2/2008 |
| WO | WO-2008/049085 A1 | 4/2008 |
| WO | WO-2008/151833 A2 | 12/2008 |
| WO | WO-2009/007855 A2 | 1/2009 |
| WO | WO-2009/135322 A1 | 11/2009 |
| WO | WO-2009/143391 A2 | 11/2009 |
| WO | WO-2009/148605 A2 | 12/2009 |
| WO | WO-2010/064146 A2 | 6/2010 |
| WO | WO-2011/005761 A1 | 1/2011 |
| WO | WO-2011/015572 A1 | 2/2011 |
| WO | WO-2011/015573 A1 | 2/2011 |
| WO | WO-2011/032045 A1 | 3/2011 |
| WO | WO-2011/034072 A1 | 3/2011 |
| WO | WO-2011/082281 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2012/039448 A1 | 3/2012 |
| WO | WO-2012/073857 A1 | 6/2012 |
| WO | WO-2012109395 A1 | 8/2012 |
| WO | WO-2013/012758 A1 | 1/2013 |
| WO | WO-2013/022966 A1 | 2/2013 |
| WO | WO-2013/022984 A1 | 2/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/179626 A2 | 11/2014 |
| WO | WO-2015/051214 A1 | 4/2015 |
| WO | WO-2015/070212 A1 | 5/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/079183 A1 | 5/2016 |
| WO | WO-2016/102664 A1 | 6/2016 |
| WO | WO-2016/127002 A1 | 8/2016 |
| WO | WO-2016/130589 A2 | 8/2016 |
| WO | WO-2016/161374 A1 | 10/2016 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/03260 A1 | 2/2019 |
| WO | WO-2019/032612 A1 | 2/2019 |
| WO | WO-2019/055951 A1 | 3/2019 |
| WO | WO-2019/075357 A1 | 4/2019 |

OTHER PUBLICATIONS

U.S. Appl. No. 16/098,658, filed Nov. 2, 2018, Vargeese et al.
U.S. Appl. No. 16/098,836, filed Nov. 2, 2018, Vargeese et al.
U.S. Appl. No. 16/182,302, filed Nov. 6, 2018, Shimizu et al.
U.S. Appl. No. 16/298,971, filed Mar. 11, 2019, Verdine et al.
U.S. Appl. No. 16/305,937, filed Nov. 30, 2018, Zhang et al.
U.S. Appl. No. 16/320,379, filed Jan. 24, 2019, Yang et al.
U.S. Appl. No. 16/463,328, filed May 22, 2019, Butler et al.

(56) References Cited

OTHER PUBLICATIONS

Agrawal, S. et al., Mixed-backbone oligonucleotides as second generation antisense oligonucleotides: In vitro and in vivo studies, Proc. Natl. Acad. Sci. USA, 94: 2620-2625 (1997).

Amarzguioui et al., Tolerance for mutations and chemical modifications in a siRNA, Nucleic Acids Research 31(2): 589-595 (2003).

Bachelin et al., Structure of a Stereoregular Phosphorothioate DNA/RNA duplex, Nat. Struct. Biol., 5(4): 271-276 (1998).

Boudreau, R.L. et al., Nonallele-specific silencing of mutant and wild-type huntingtin demonstrates therapeutic efficacy in Huntington's disease mice, 17(6): 1053-1063 (2009).

Burgers et al., Absolute configuration of the diastereomers of adenosine 5' -O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).

Cankurtaran, E.S. et al., Clinical Experience with Risperidone and Memantine in the Treatment of Huntington's Disease, Journal of the National Medical Association, 98(8): 1353-1355 (2006).

Chan, J.H.P. et al., Antisense Oligonucleotides: From Design to Therapeutic Application, Clinical and Experimental Pharmacology and Physiology, 33: 544-540 (2006).

Clark, J.H, Flouride Ion as a Base in Organic Synthesis, Chemical Reviews, 1980 American Chemical Society 80(5): 429-452 (1980).

Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).

Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).

Crooke, S.T., Molecular mechanisms of action of antisense drugs, Biochemica et Biophysica Acta, 1489: 31-44 (1999).

Crooke, S.T., Progress in Antisense Technology, Annu. Rev. Med., 55: 61-95 (2004).

Ferreira, F. et al., Lewis acid deprotection of silyl-protected oligonucleotides and base-sensitive oligonucleotide analogues, Tetrahedron Letters, 45(33):6287-6290 (2004).

Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).

Harper, S.Q. et al., RNA interference improves motor and neuropathological abnormalities in a Huntington's disease mouse model, Proc. Natl. Acad. Sci. USA, 102(16): 5820-5825 (2005).

Hohjoh, H., Disease-Causing Allele-Specific Silencing by RNA Interference, Pharmaceuticals, 6: 522-535 (2013).

Hu, J. et al., Allele-Selective Inhibition of Huntingtin Expression by Switching to an miRNA-like RNAi Mechanism, Chemistry & Biology 17: 1183-1188 (2010).

Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).

Hung, S. Stereopure oligonucleotides as a therapeutic approach to rare neurological diseases. Paper presented at: Huntington's Society of Canada 2017 National Conference (Nov. 2017).

International Search Report for PCT/US2016/043542, 6 pages (dated Dec. 28, 2016).

International Search Report for PCT/US2016/043598, 4 pages (dated Nov. 28, 2016).

International Search Report for PCT/US2017/030753, 6 pages (dated Sep. 26, 2017).

Ionis Pharmaceuticals, Inc., Ionis Pharmaceuticals Licenses IONIS-HTT Rx to Partner Following Successful Phase 1/2a Study in Patients with Huntington's Disease, Press Release, 2 pages (Dec. 11, 2017).

Iwamoto, N. et al., Control of phosphorothioate stereochemistry substantially increases the efficacy of antisense oligonucleotides, Nature Biotechnol, 35(9): 845-851 (2017), with Supplemental Data, 14 pages.

Iwamoto, N. et al., Control of phosphorothioate stereochemistry substantially increases the efficacy of antisense oligonucleotides, Nature Biotechnology, 1-7 pages (2017). All Supplemental Data, 8-53 pages (2017).

Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).

Iwamoto, N. From Stereopurity to precision medicine: Optimizing the properties of antisense nucleic acid therapeutics. Paper presented at: BioJapan, Yokohama, Japan (Oct. 11, 2018).

Jiang, J. et al., Allele-Specific Silencing of Mutant Myh6 Transcripts in Mice Suppresses Hypertrophic Cardiomyopathy, Science, 342: 111-114 (2013).

Kandasamy, P. et al., From stereopurity to precision medicine: Optimizing the properties of antisense nucleic acid therapeutics. Paper presented at: the 45th International Symposium on Nucleic Acid Chemistry, Kyoto, Japan (Nov. 7-9, 2018).

Kay, C. et al., Personalized gene silencing therapeutics for Huntington disease, Clinical Genetics, 1-8 (2014).

Kim, M., Beta conformation of polyglutamine track revealed by a crystal structure of Huntingtin N-terminal region with insertion of three histidine residues, Prion, 7(3): 221-228 (2013).

Kordasiewicz, H.B. et al., Sustained therapeutic reversal of Huntington's disease by transient repression of huntingtin synthesis, Neuron, 74(6): 1031-1044 (2012).

Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).

Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).

Krakowiak, A. et al., Influence of P-Chirality of Phosphorothioate Oligonucleotides on the Activity of Amv-Reverse Transcriptase, Nucleosides & Nucleotides, 17(9-11): 1823-1834 (1998).

Kremer, B. et al., A Worldwide Study of the Huntington's Disease Mutation, The New England Journal of Medicine, 330(20): 1401-1406 (1994).

Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).

Leviten, M., Wave's Purity Progress, Biocentury, 1-6 (Sep. 28, 2017).

Liu, W. et al., Increased Steady-State Mutant Huntingtin mRNA in Huntington's Disease Brain, Journal of Huntington's Disease 2: 491-500 (2013).

Martin, P., A New Access to 2'-O-alkylated Ribonucleosides and Properties of 2'-O-Alkylated Oligoribonucleotides, Helv. Chim. Acta., Abstract Only, 78: 486-504 (1995).

McBride, J.L. et al., Prelinical Safety of RNAi-Mediated HTT Suppression in the Rhesus Macaque as a Potential Therapy for Huntington's Disease, Molecular Therapy, 19: 1-11 (2011).

Meena, Control of Human RNase H Mediated Cleavage by Stereopure Phosphorothioate Oligonucleotides, WAVE Life Sciences, TIDES Meeting, 23 pages (May 3-6, 2015).

Meena, Development of Allele Specific Antisense Oligonucleotides, WAVE Life Sciences, ACS Central Regional Meeting (CERM), Covington, KY (May 19, 2016).

Meena, Development of Allele Specific Antisense Oligonucleotides, WAVE Life Sciences, TIDES Meeting (May 11, 2016).

Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page (2016).

Meena, et al., Therapeutic Implications of Controlling P-Chirality in Phosphorothioate Oligonucleotides, TIDES Poster (May 12-15, 2014).

(56) References Cited

OTHER PUBLICATIONS

Meena, et al., Therapeutic Implications of Controlling P-Chirality in Phosphorothioate Oligonucleotides, TIDES, San Diego, WAVE Life Sciences, Poster, 1 page (May 3-6, 2014).
Meena, Optimization of Antisense Drugs by P-Stereochemistry Control, WAVE Life Sciences, OTS Annual Meeting 2014, Oligonucleotide Therapeutics Society, 13 pages (Oct. 12-14, 2014).
Mohapatra, S. LCMS/hybridization ELISA approaches for bioanalysis of stereopure oligonucleotides. Paper presented at: American Association of Pharmaceutical Scientists Annual Meeting, Washington, DC USA (Nov. 4-7, 2018).
Monteys, A.M. et al., Artificial miRNAs Targeting Mutant Huntingtin Show Preferential Silencing In Vitro and In Vivo, Molecular THerapy—Nucleic Acids, 4: e234 1-11 (2015).
Mujeeb, A. et al., High-Resolution NMR of an Antisense DNA. RNA Hybrid Containing Alternating Chirally Pure R p Methylphosphonates in the DNA Backbone+, 36(9): 2371-2379 (1997).
Nowotny, M. et al., Structure of human RNase H1 complexed with an RNA/DNA hybrid: insight into HIV reverse transcription, Mol Cell, 28(2):264-76 (2007).
Oka, N. and Wada, T., Stereocontrolled synthesis of oligonucleotide analogs containing chiral internucleotidic phosphorus atoms, Chemical Society Reviews, 40(12):5829-5843 (2011).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Ostergaard, M.E. et al., Efficient Synthesis and Biological Evaluation of 5'-GalNAc Conjugated Antisense Oligonucleotides, Bioconjugate. Chem., 26: 1452-1455 (2015).
Panzara, M. et al., Stereopure nucleic acid therapies in development for the treatment of genetic neurological diseases, Poster presented at: 19th Annual Meeting of the American Society of Experimental Neurotherapeutics, Rockville, MD, Poster 39 (Mar. 15, 2017).
Panzara, M. Stereopure nucleic acid therapies in development for the treatment of genetic neurological diseases, Neurotherapeutics, Abstract, 14: 821-822 (2017).
Panzara, M. Stereopure nucleic acid therapies in development for the treatment of genetic neurological diseases, Paper presented at: 19th Annual Meeting of the American Society of Experimental Neurotherapeutics, Rockville, MD USA (Mar. 15, 2017).
Panzara, M. Stereopure nucleic acid therapies in development for the treatment of genetic neurological diseases. Paper presented at: International Society for CNS Drug Development (ISCDD) Annual Meeting, Las Vegas, NV USA (Mar. 24, 2017).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Pfister, E.L. et al., Five siRNAs targeting three SNPs may provide therapy for three-quarters of Huntington's disease patients, 19(9): 774-778 (2009).
Rossetti, G., Structural aspects of the Huntingtin protein investigated by biocomputing methods, Thesis, RWTH Aachen University, Forschungszentrum Juelich, 173 pages (2011).
Scrimgeour, E.M. Huntington Disease (Chorea) in the Middle East, Squ. Med. J., 9(1): 16-23 (2009).
Seth, P., and Olson, R., Nucleic Acid Therapeutics—Making Sense of Antisesnse, 2016 Drug Design and Delivery Symposium, ACS Webinar, 1-36 (Jul. 26, 2016).
Singhrao, S.K. et al., Increased Complement Biosynthesis by Microglia and Complement Activation on Neurons in Huntington's Disease, Experimental Neurology, 159: 362-376 (1999).
Skotte, N.H. et al., Allele-specific suppression of mutant huntingtin using antisense oligonucleotides: providing a therapeutic option for all Huntington disease patients, PLoS One, 9(9): e107434 1-18 (2014).
Stec, W.J. et al., Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Vargeese, C. From Stereopurity to precision medicine: Optimising the properties of antisense nucleic acid therapeutics, Paper presented at: TIDES Europe: Oligonucleotide and Peptide Therapeutics, Amsterdam, The Netherlands (Nov. 7, 2018).
Vargeese, C. From Stereopurity to precision medicine: Optimizing the properties of antisense nucleic acid therapeutics, Paper presented at: Nature Conference on RNA at the Bench and Bedside, La Jolla, CA USA (Oct. 8, 2018).
Vargeese, C. Pharmacologic properties of stereopure oligonucleotides. Paper presented at: 44th International Symposium on Nucleic Acids Chemistry, Tokyo, Japan (Nov. 14-16, 2017).
Vargeese, C. Stereochemical control of antisense oligonucleotides enhances target efficacy. Paper presented at: the 14th Annual Meeting of the Oligonucleotide Therapeutic Society, Seattle, WA USA (Oct. 3, 2018).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, poster setup prior to presentation (first known to Applicant late Oct. 12, 2014, PST), poster presentation Oct. 13, 2014.
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleotides containing chiral phosphorothioate linkages, Nucleic Acid Research, 42: 13456-13468 (2014). Supplementary Information, 14 pages.
Warby, S.C. et al., CAG expansion in the Huntington disease gene is associated with a specific and targetable predisposing haplogroup, Am. J. Hum. Genet., 84(3): 351-366 (2009).
WAVE Life Sciences Press Release, WAVE Life Sciences Announces Plan to Deliver Six Clinical Programs by 2018, 6 pages (Jan. 29, 2016).
WAVE Life Sciences Press Release, WAVE Life Sciences Receives Orphan Drug Designation from FDA for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).
WAVE Life Sciences Press Release, WAVE Life Sciences Reports Second Quarter 2016 Financial Results and Provides Business Update, 10 pages (Aug. 15, 2016).
Wild, E. et al., Quantification of mutant huntingtin protein in cerebrospinal fluid from Huntington's disease patients, The Journal of Clinical Investigation, 125(5): 1979-1986 (2015).
Woolf, T.M. et al., Specificity of antisense oligonucleotides in vivo, Prov. Natl. Aca. Sci. USA, 89: 7305-7309 (1992).
Wozniak, L.A. et al., Chirality at phosphorus: hybrid duplexes of chimeric oligonucleotides containing methylphosphonothioate linkages with complementary DNA and RNA, Journal of Organometallic Chemistry, 690(10): 2658-2663 (2005).
Written Opinion for PCT/US2016/043542, 14 pages (dated Dec. 28, 2016).
Written Opinion for PCT/US2016/043598, 10 pages (dated Nov. 28, 2016).
Written Opinion for PCT/US2017/030753, 13 pages (dated Sep. 26, 2017).
Yu, D. et al., Single-Stranded RNAs Use RNAi to Potently and Allele-Selectively Inhibit Mutant Huntingtin Expression, Cell, 150: 895-908 (2012).
Yu, D. et al., Stereo-Enriched Phosphorothioate Oligodeoxynucleotides: Synthesis, Biophysical and Biological Properties, Bioorganic & Medicinal Chemitry, 8: 275-284 (2000).
Zhang, Y. et al., Structural Isosteres of Phosphate Groups in the Protein Data Bank, J. Chem. Inf. Model, 1-18 (2017).
Zhang, Y., Investigating phosphate structural replacements through computational and experimental approaches, Academic Dissertain, University of Helsinki, 119 pages (2014).
Zhong, Z. et al., WAVE Life Sciences: Developing Stereopure Nucleic Acid Therapies for the Treatment of Genetic Neurological

(56) References Cited

OTHER PUBLICATIONS

Diseases, World CNS Summit 2017, Boston, MA, WAVE Life Sciences, Poster, 1 page (Feb. 20-22, 2017).

Zhong, Z. Stereochemical control of antisense oligonucleotides enhances target efficacy. Paper presented at: TIDES: Oligonucleotide and Peptide Therapeutics, Boston, MA USA (May 9, 2018).

Zhong, Z. WAVE Life Sciences: Developing stereopure nucleic acid therapies for the treatment of serious genetically defined diseases, Paper presented at: ALS Drug Discovery Roundtable Meeting, Boston, MA (Apr. 25, 2017).

Ostergaard, M.E. et al., Differential Effects on Allele Selective Silencing of Mutant Huntingtin by Two Stereoisomers of a,β-Constrained Nucleic Acid, ACS Chem. Biol., 9: 1975-1979 (2014).

Guerciolini, R., Allele-selective Silencing of Mutant Huntingtin by Stereopure Oligonucleotides, WAVE Life Sciences, Huntington's Disease Society of America, HDSA Presentation 2016 (Jun. 3, 2016).

Kay, C. et al., Huntingtin Haplotypes Provide Prioritized Target Panels for Allele-specific Silencing in Huntington Disease Patients of European Ancestry, The American Society of Gene & Cell Therapy, 1-13 (2015).

Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).

U.S. Appl. No. 16/551,503, filed Aug. 26, 2019, Vargeese et al.

U.S. Appl. No. 16/782,021, filed Feb. 4, 2020, Frank-Kamenetsky et al.

Gagnon, K. T. et al., Allele-Selective Inhibitions of Mutant Huntingtin Expression with Antisense Oligonucleotide Targeting the Expanded CAG Repeat, Biochemistry 49(47): 10166-10178 (2010).

Miniarikova, J. et al., Design Characterization, and Lead Selection of Therapeutic miRNAs Targeting Huntingtin for Development of Gene Therapy for Huntington's Disease, Molecular Therapy—Nucleic Acids, 5(3): e297 (2016).

(PANEL A)

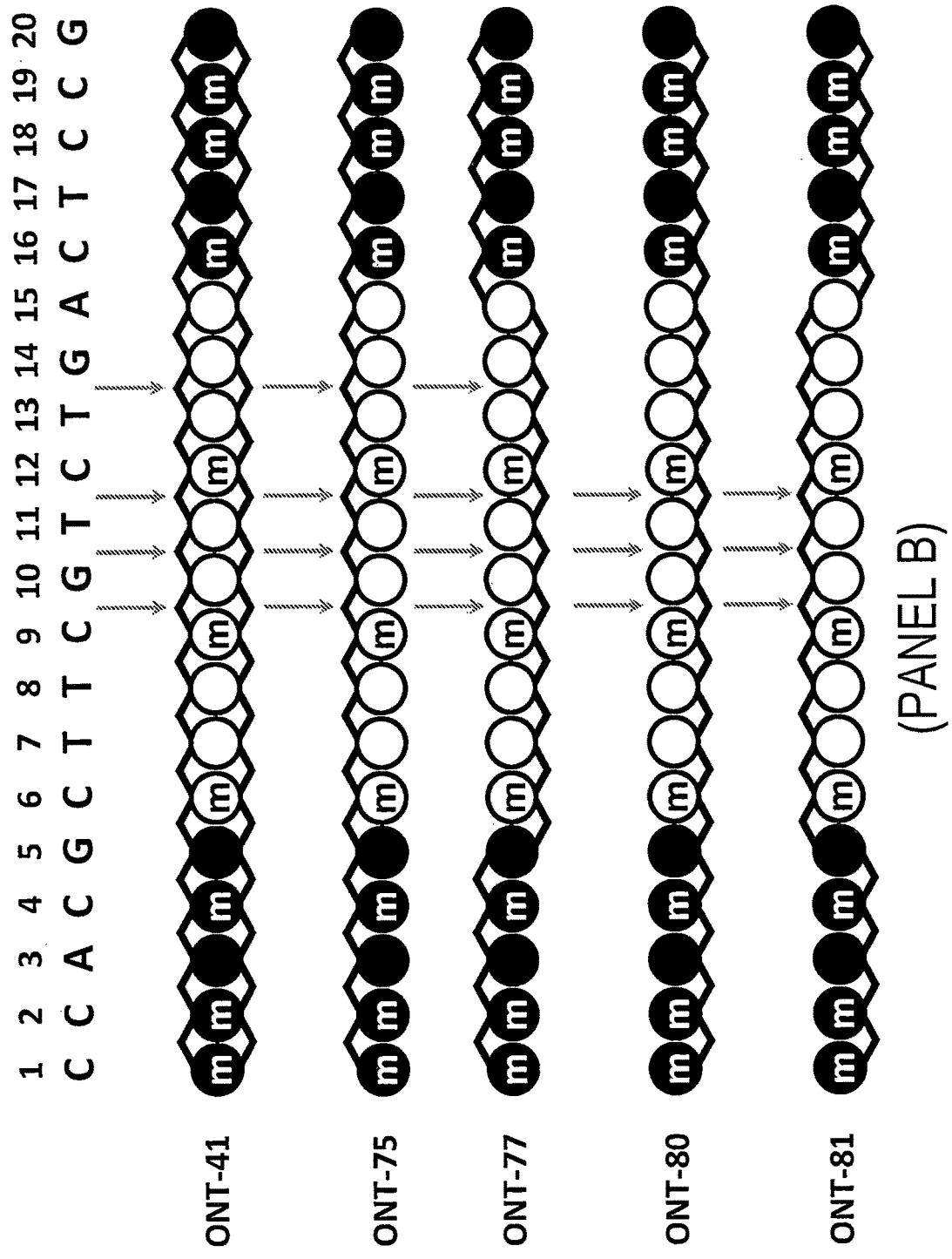
FIG. 9 (CONTINUED) (PANEL B)

(PANEL C)

(PANEL A)

(PANEL B)

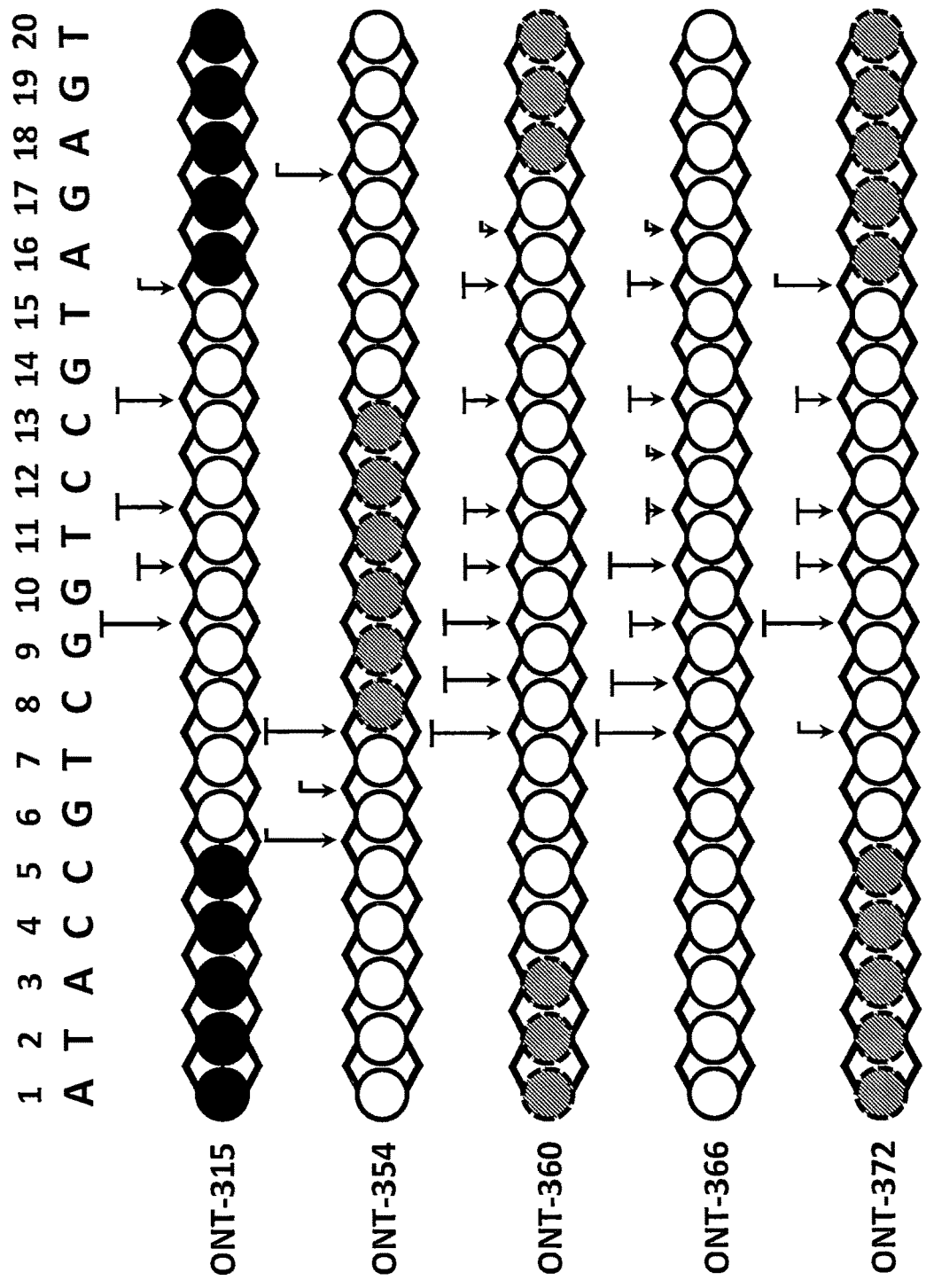
FIG. 10 (CONTINUED) (PANEL C)

(PANEL A)

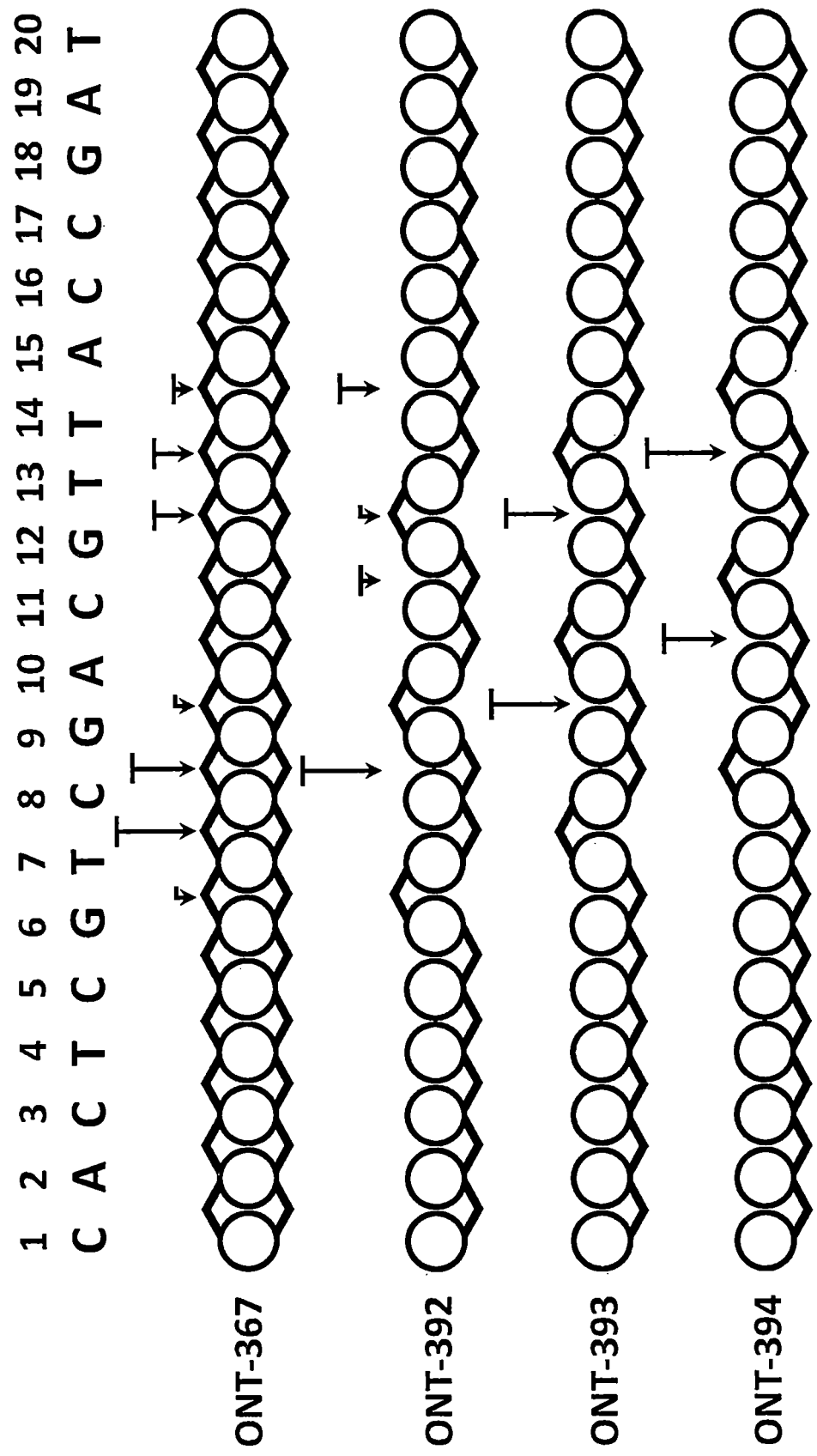
FIG. 11 (CONTINUED) (PANEL B)

(PANEL A)

(PANEL B)

(PANEL A)

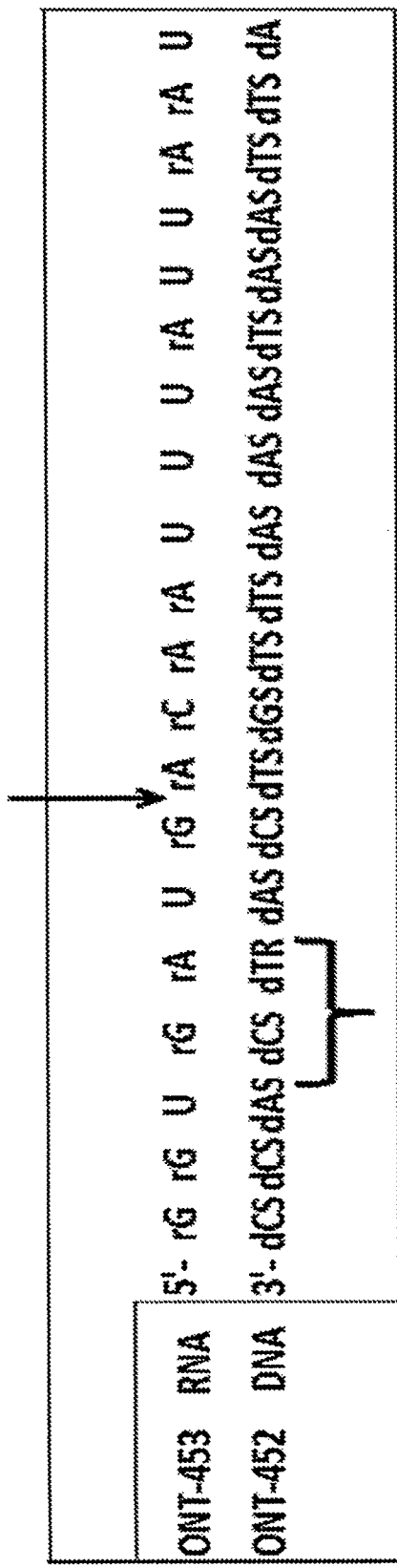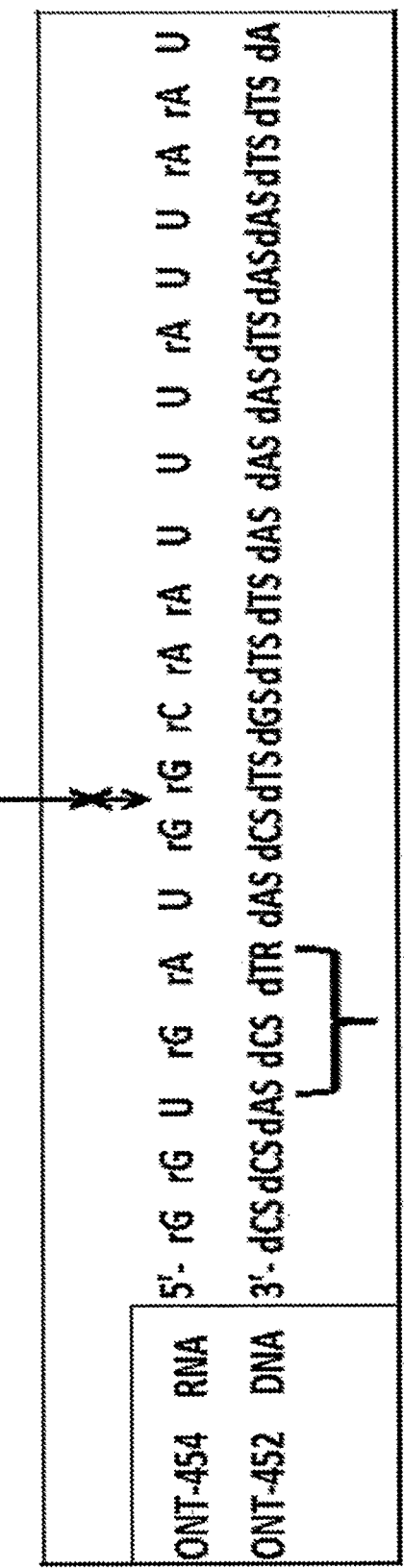
FIG. 22 (PANEL B) (CONTINUED)

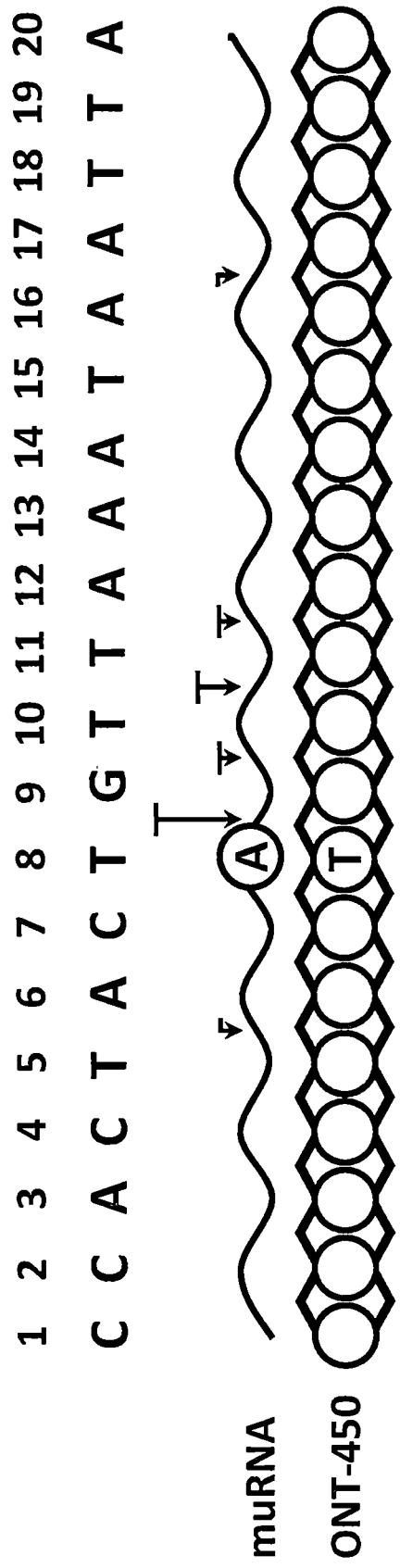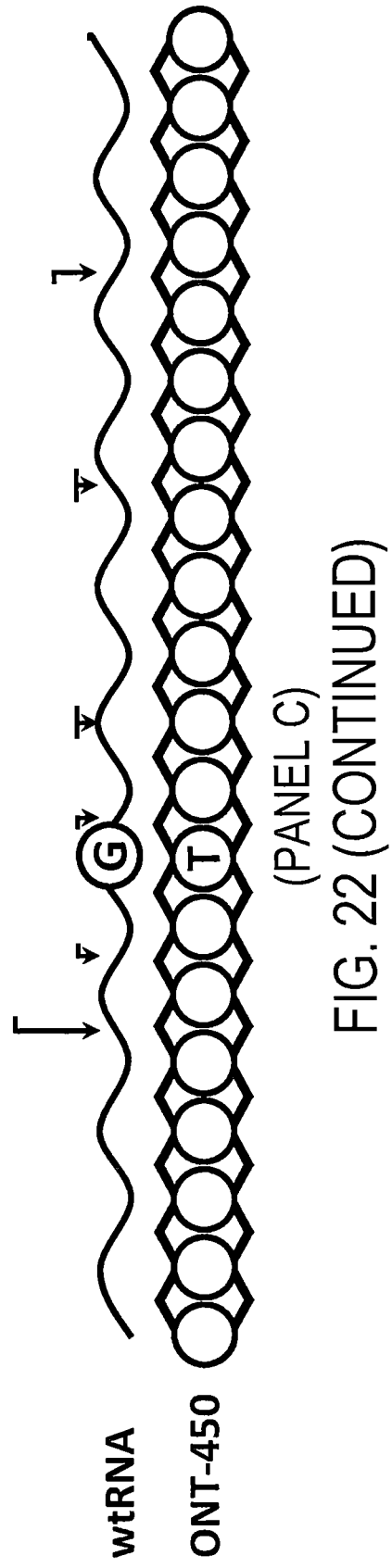
FIG. 22 (CONTINUED) (PANEL C)

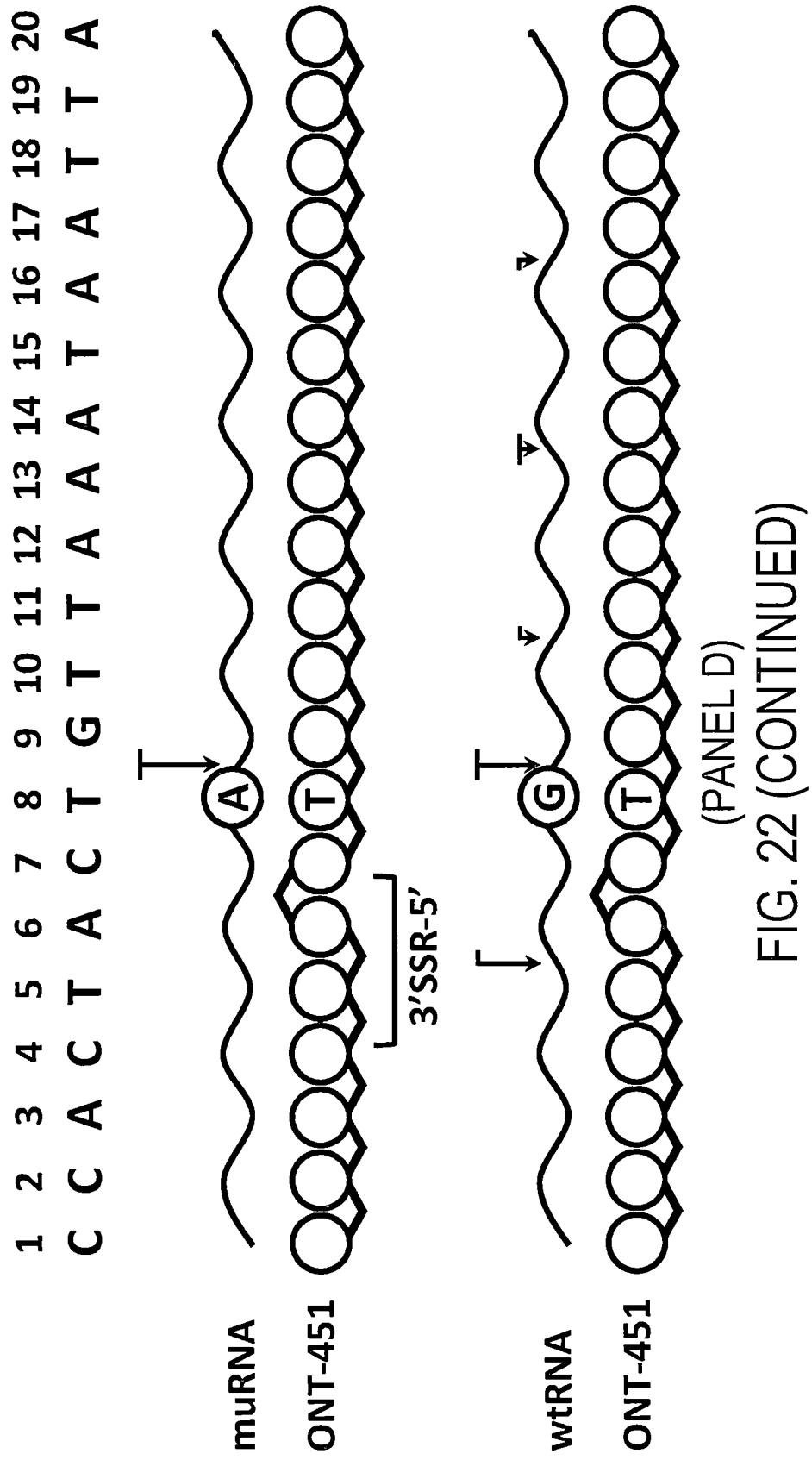
FIG. 22 (CONTINUED) (PANEL D)

(PANEL E)

(PANEL F)

(PANEL G)

(PANEL H)

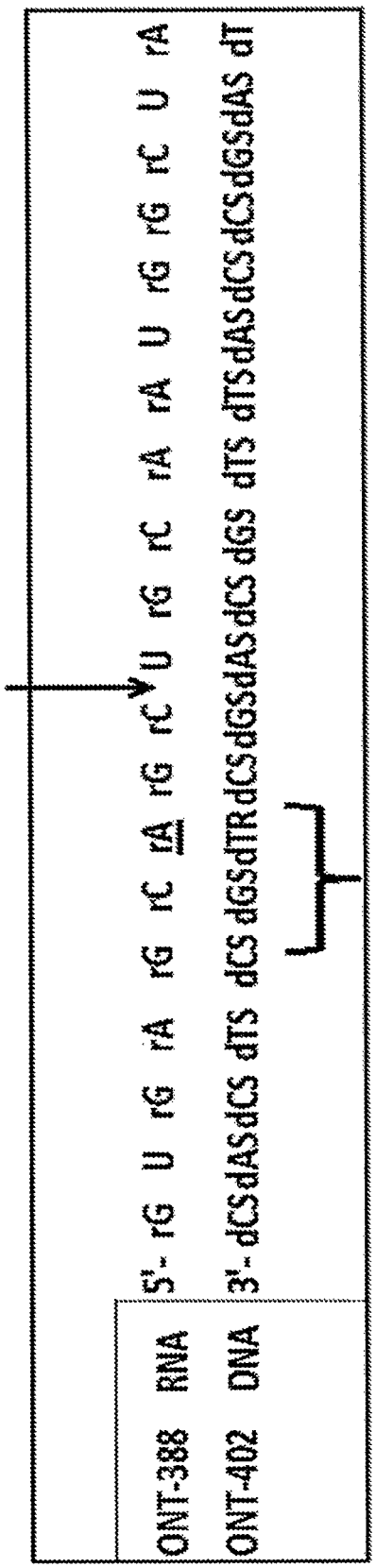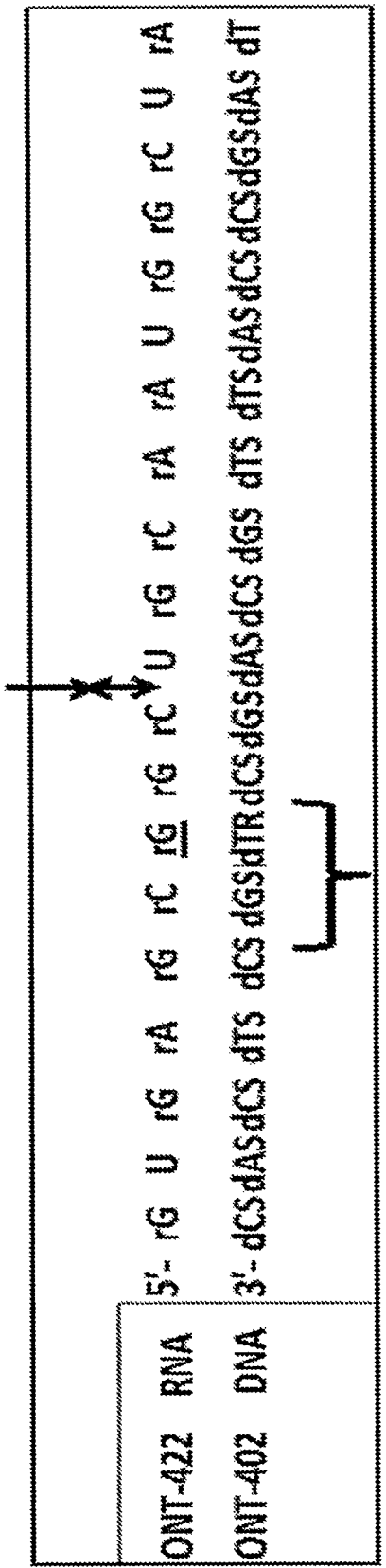
FIG. 23 (PANEL A)

Representative mutant allele

| | | |
|---|---|---|
| ONT-388 | RNA | 5'- rG U rG rA rG rC rA rA U rG rG rC U rA |
| ONT-400 | DNA | 3'- dCS dAS dCS dTS dCR dGS dTS dCS dGS dAS dCS dTS dAS dCS dGS dAS dT |

3'-SSR-5'

Representative wild type allele

| | | |
|---|---|---|
| ONT-422 | RNA | 5'- rG U rG rA rG rC rA rA U rG rG rC U rA |
| ONT-400 | DNA | 3'- dCS dAS dCS dTS dCR dGS dTS dCS dGS dAS dCS dTS dAS dCS dGS dAS dT |

3'-SSR-5'

(PANEL B)
FIG. 23 (CONTINUED)

(PANEL C)

(PANEL A)

(PANEL B)

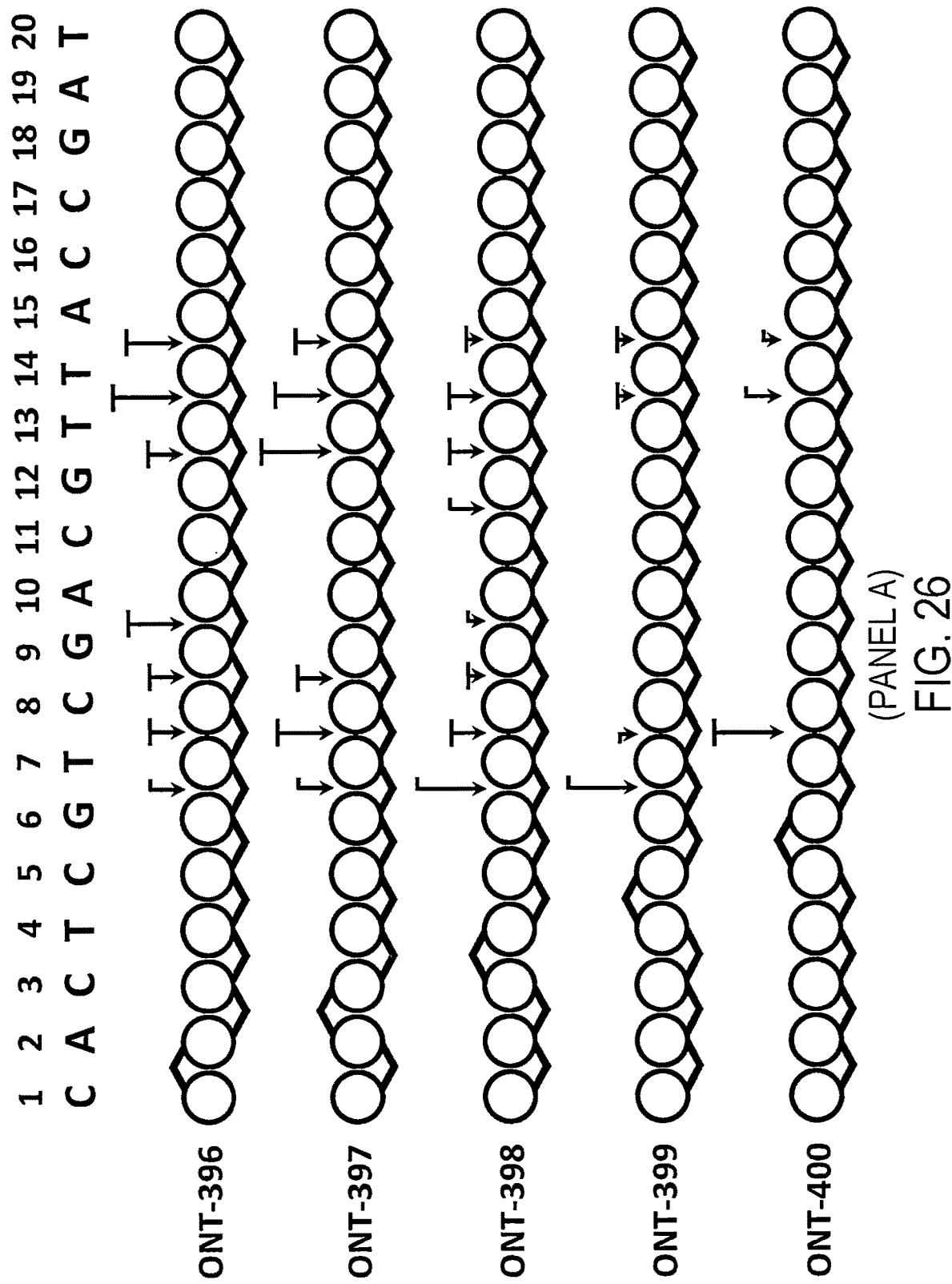
FIG. 26 (PANEL A)

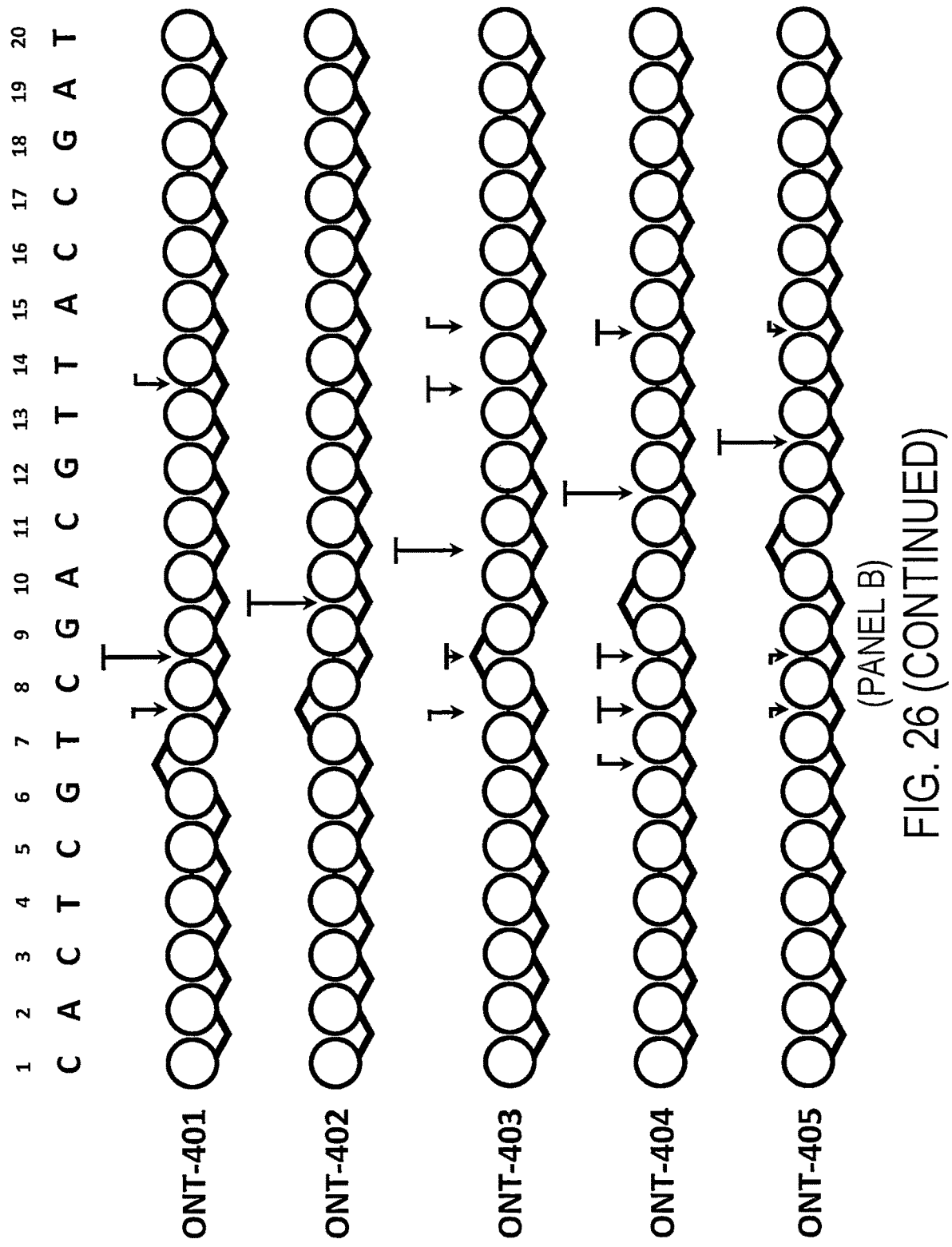
FIG. 26 (CONTINUED) (PANEL B)

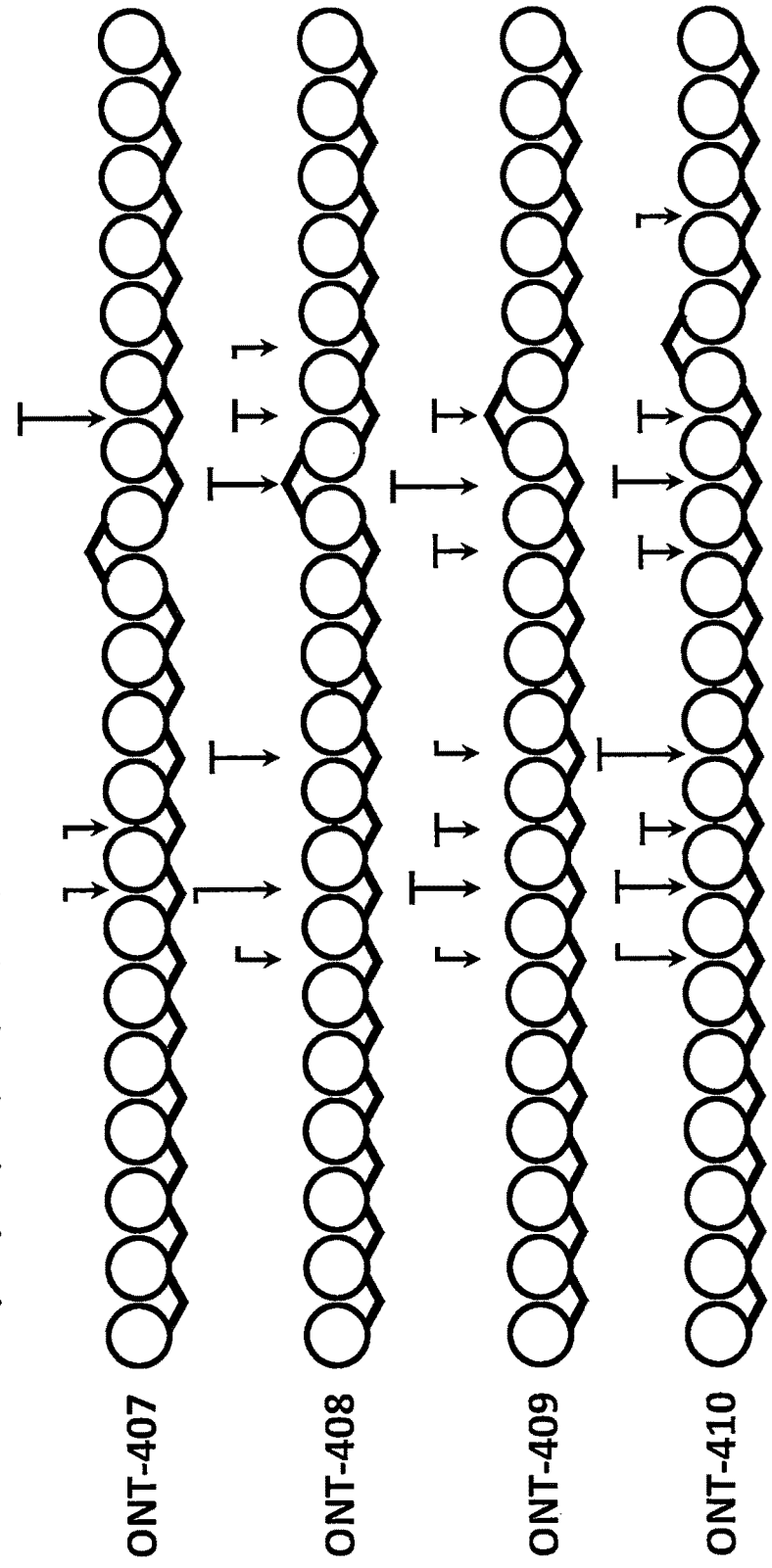
FIG. 26 (CONTINUED) (PANEL C)

(PANEL D)

(PANEL A)

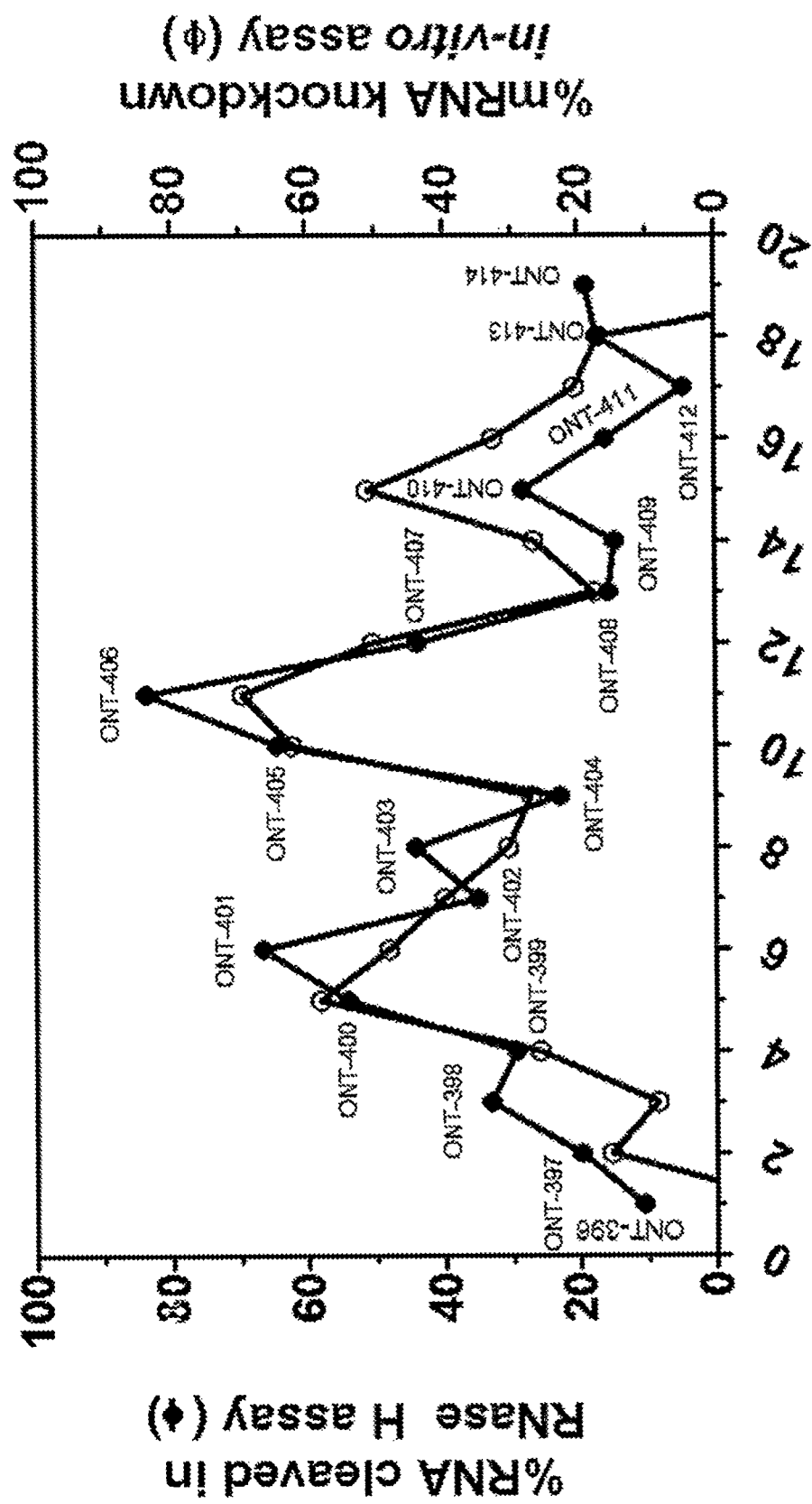
FIG. 27 (CONTINUED) (PANEL B)

(PANEL A)

(PANEL B)

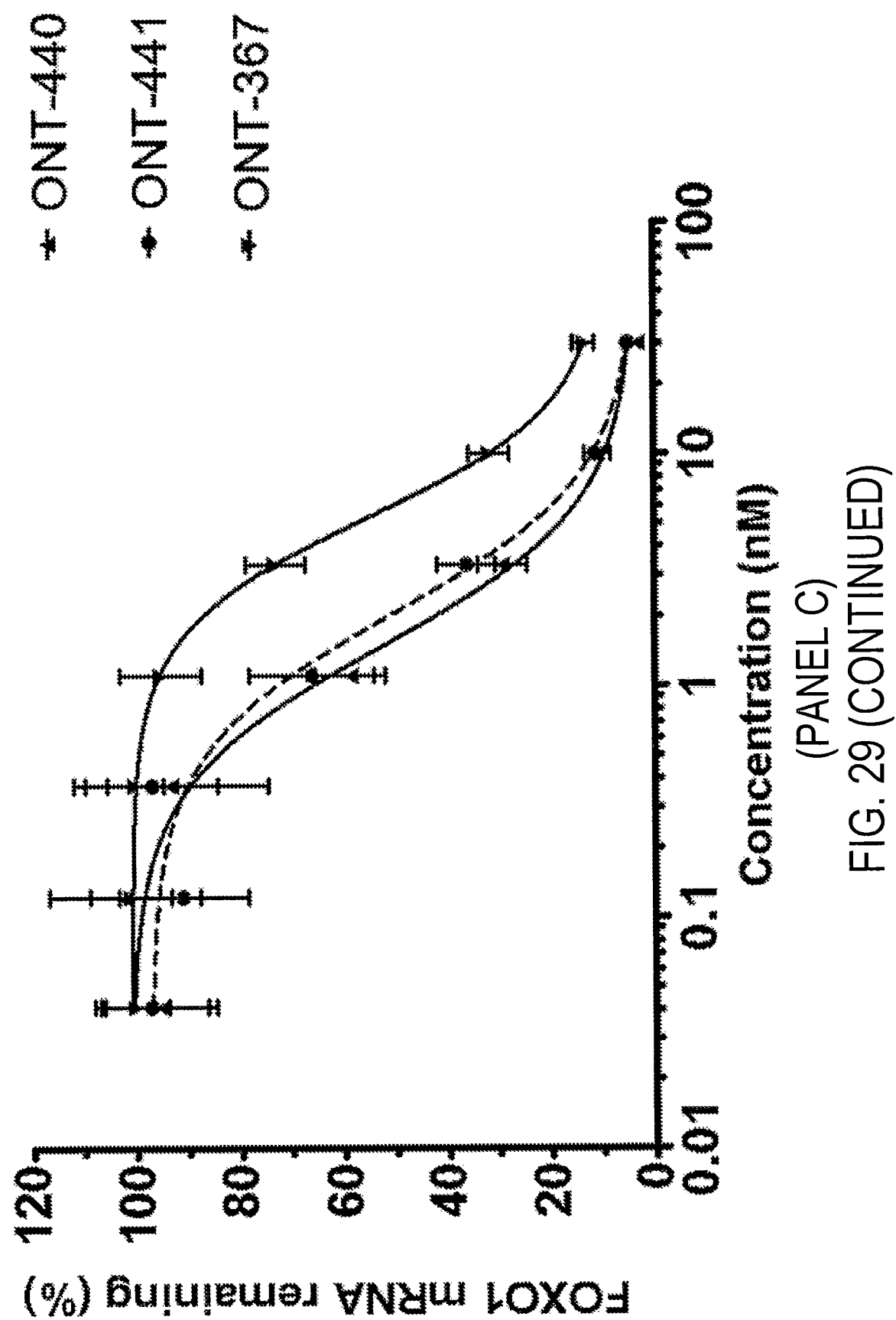
FIG. 29 (CONTINUED) (PANEL C)

(PANEL A)

(PANEL B)

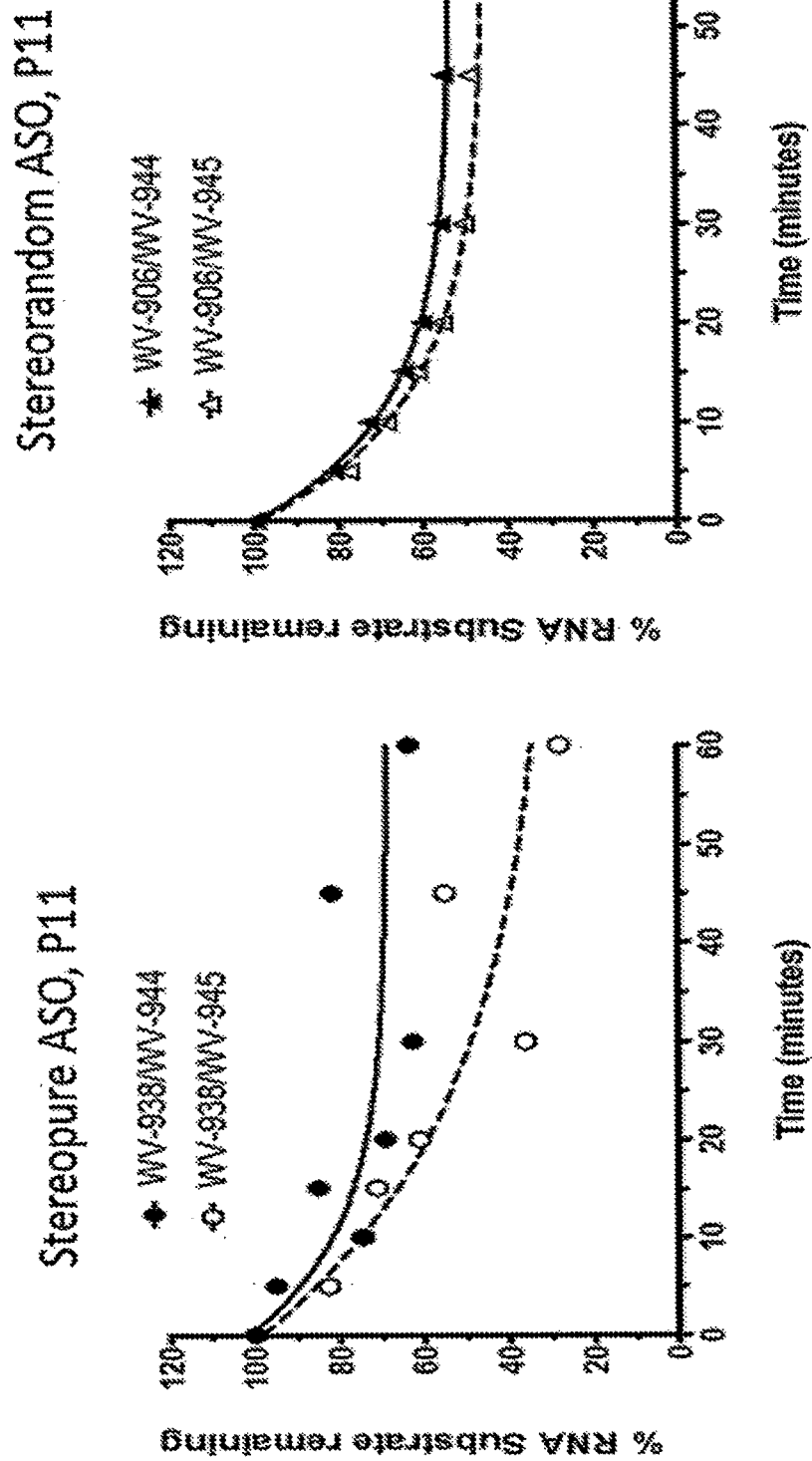
FIG. 31 (CONTINUED) (PANEL C)

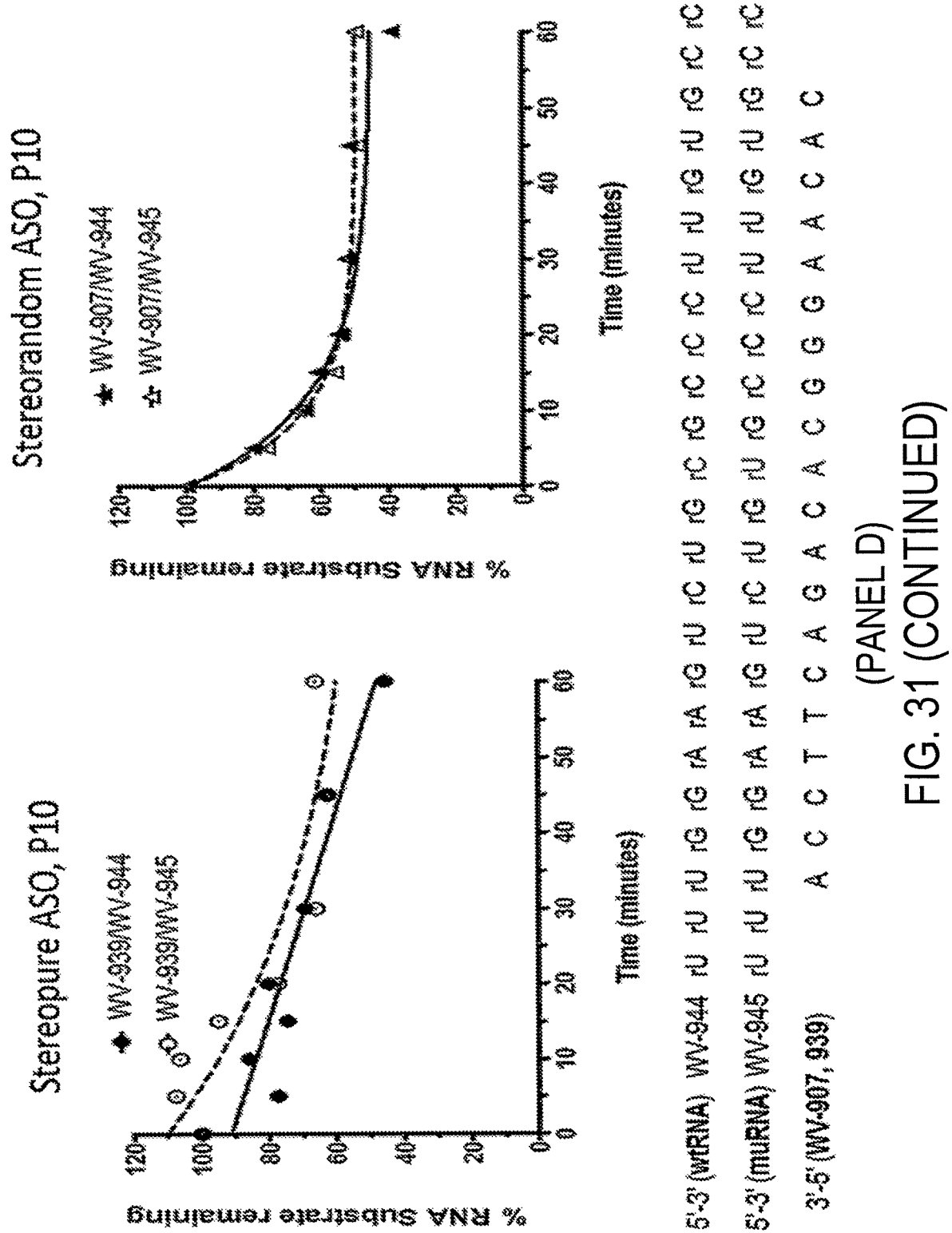
FIG. 31 (CONTINUED) (PANEL D)

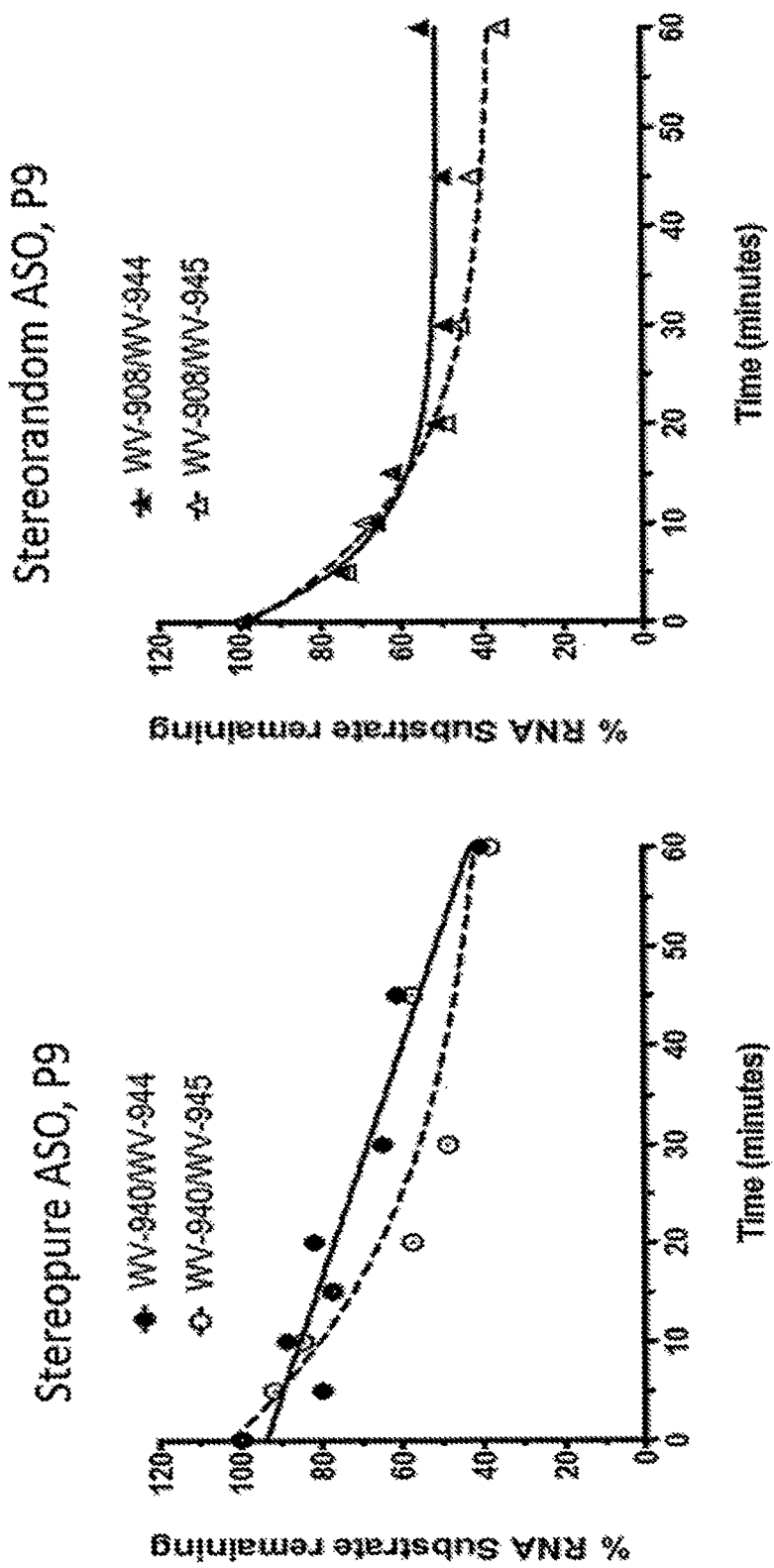
FIG. 31 (CONTINUED) (PANEL E)

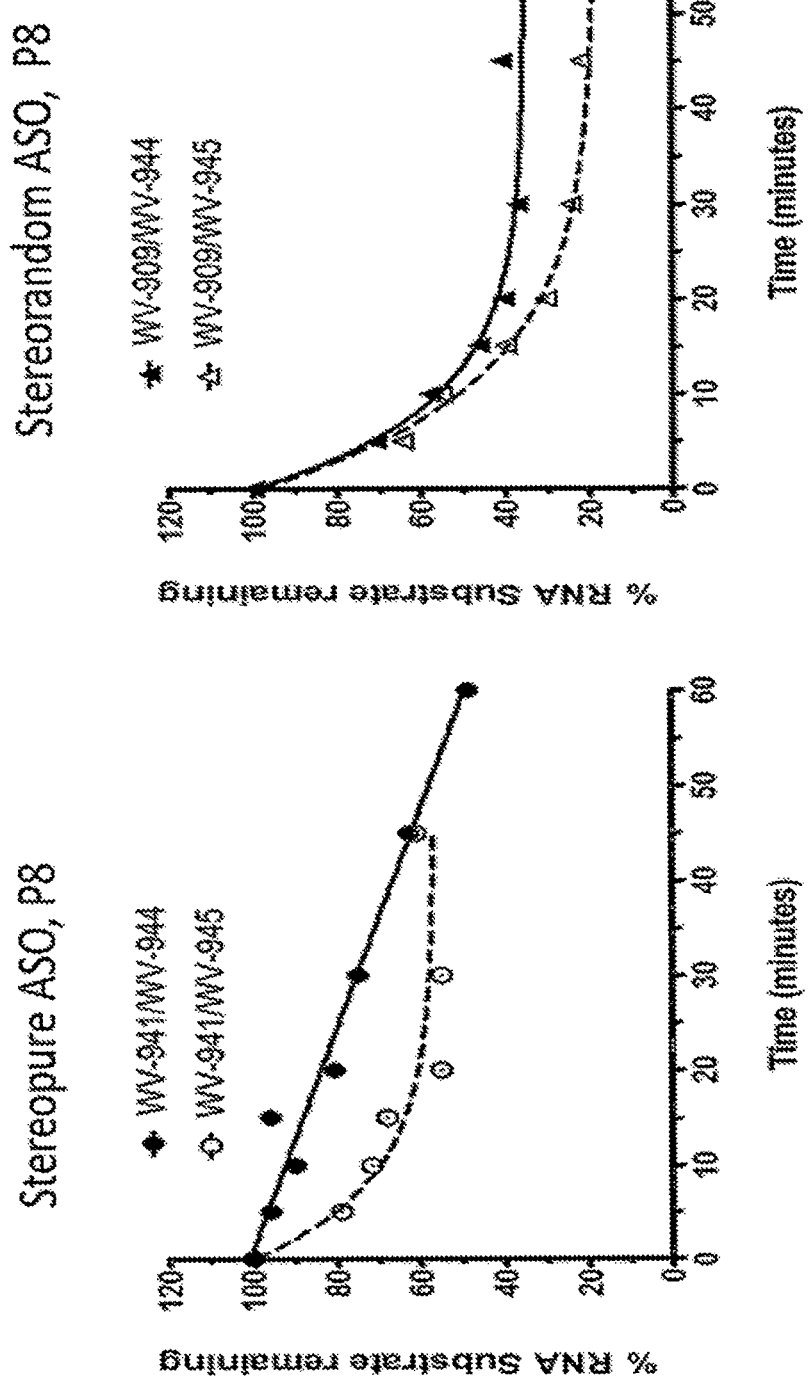
FIG. 31 (CONTINUED) (PANEL F)

(PANEL A)

(PANEL B)

(PANEL C)

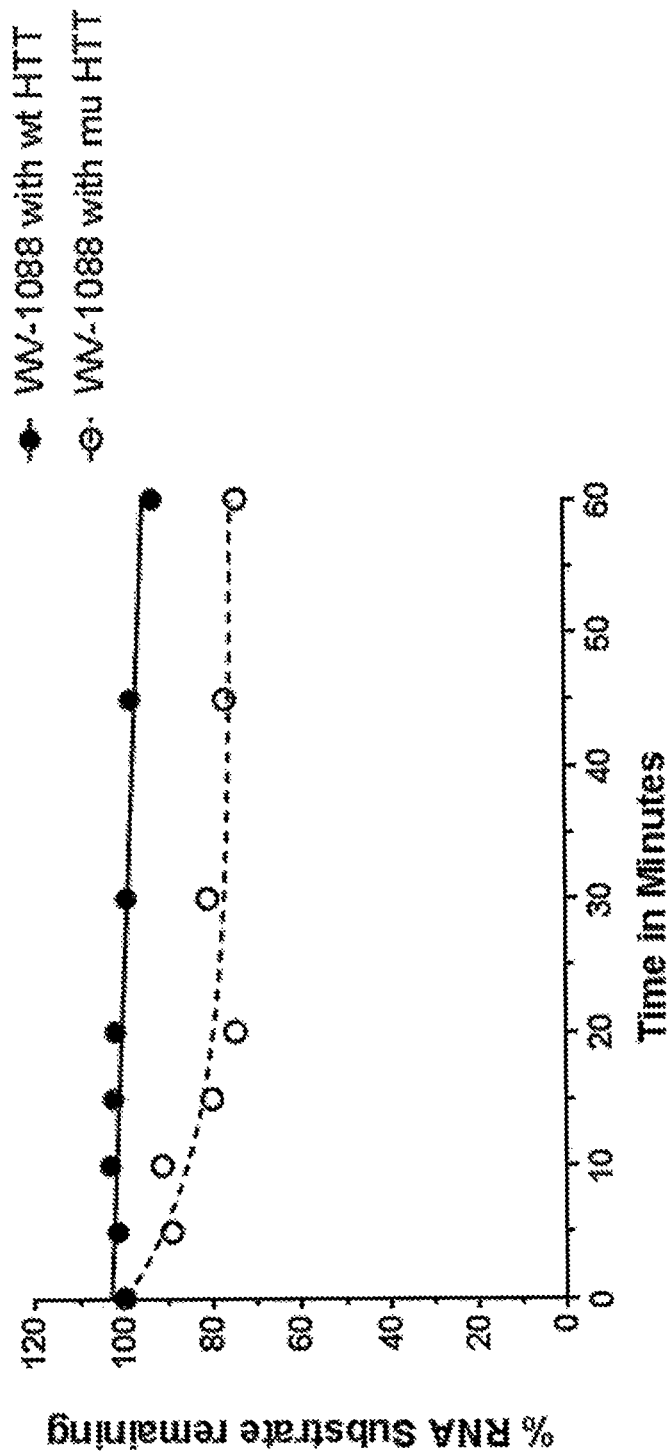
FIG. 32 (PANEL D) (CONTINUED)

(PANEL E)

(PANEL F)

(PANEL G)

(PANEL H)

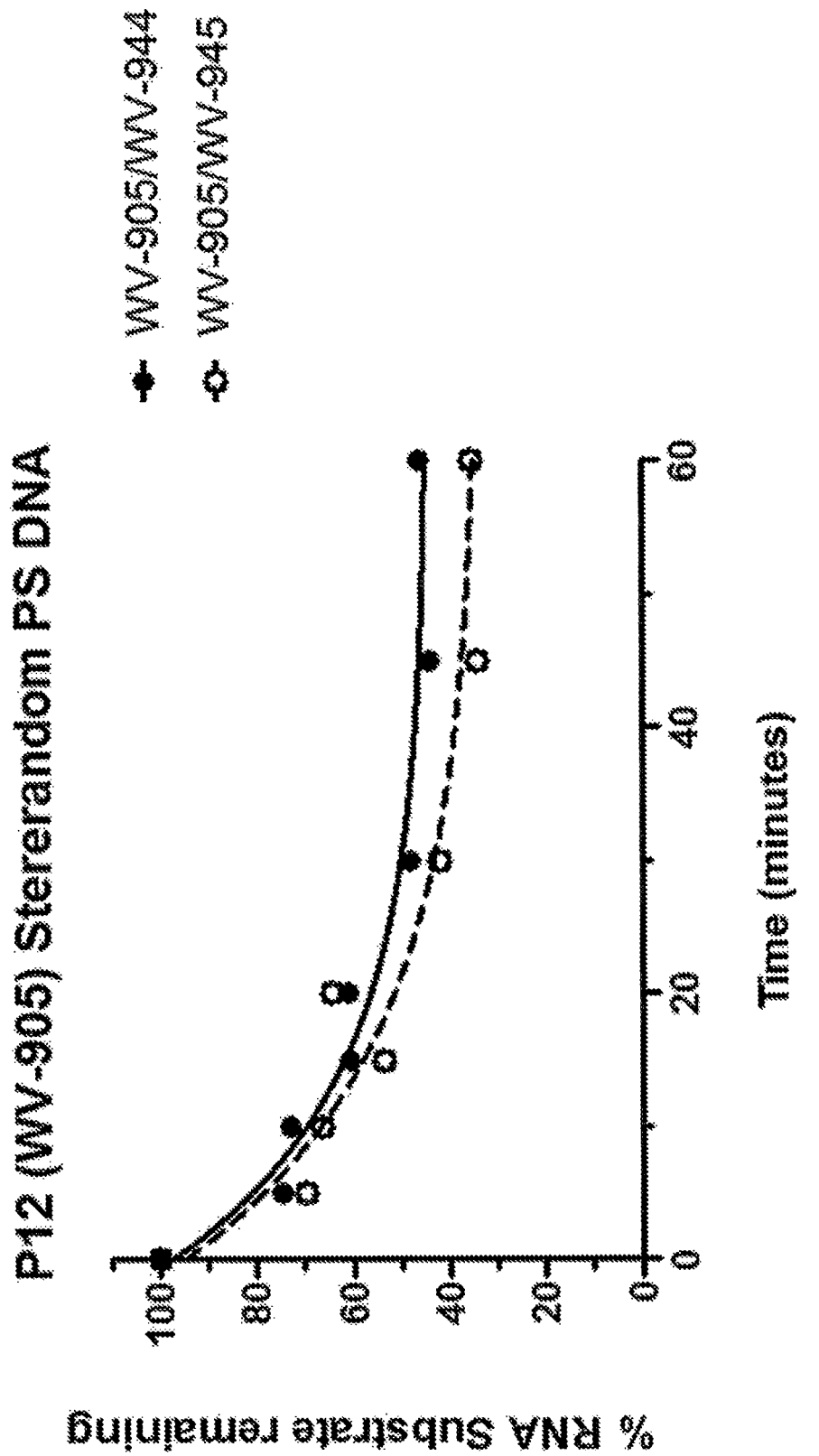
FIG. 32 (PANEL I) (CONTINUED)

(PANEL J)

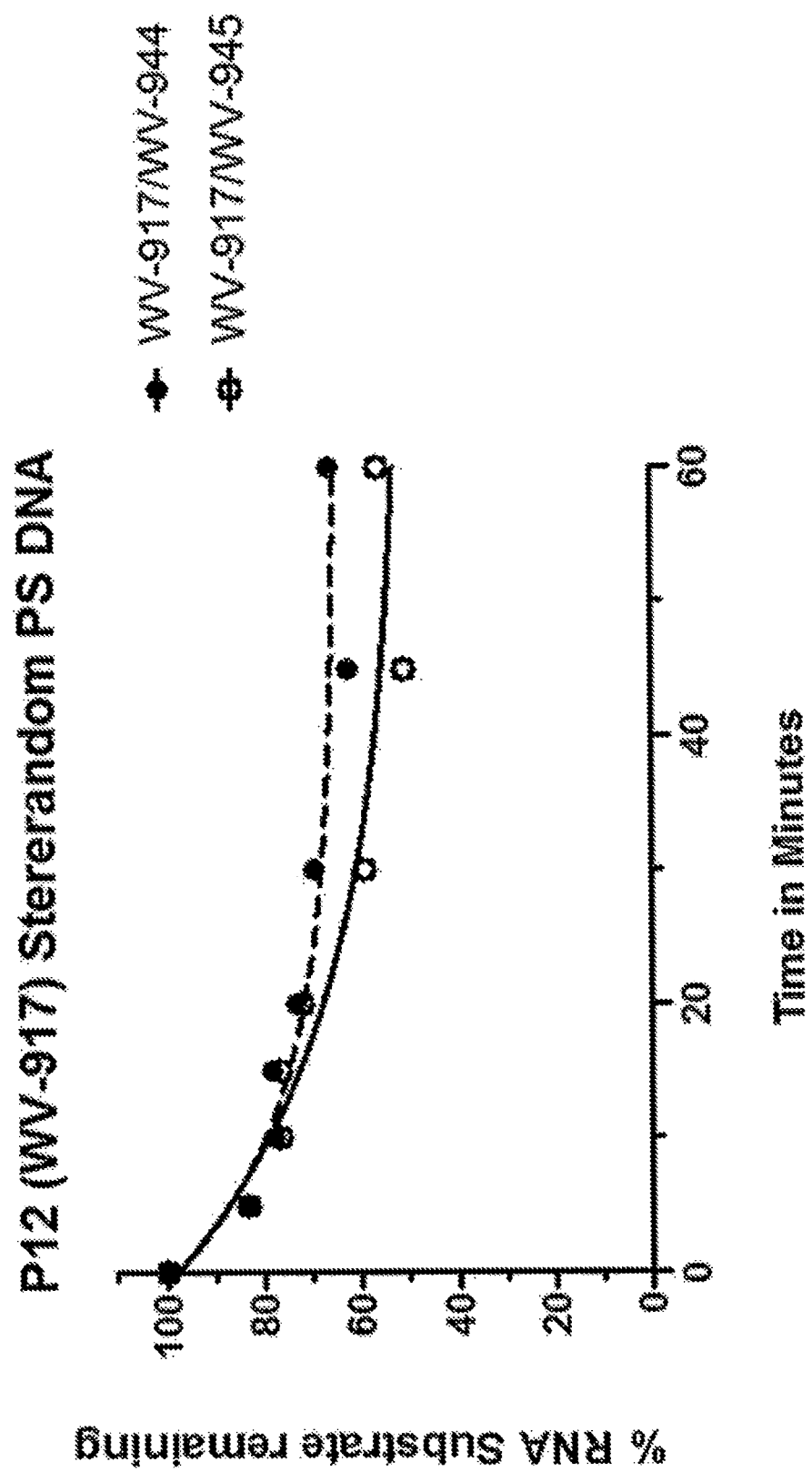
FIG. 32 (CONTINUED) (PANEL K)

(PANEL L)

(PANEL M)

(PANEL N)

(PANEL A)

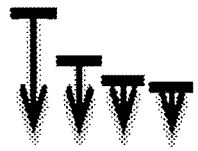 Ranked cleavage site when both 5' P and 3' OH fragments were identified

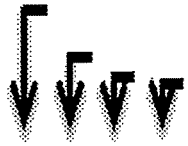 Ranked cleavage site when only 3' OH fragments were identified

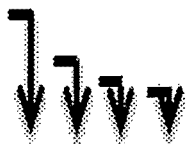 Ranked cleavage site when only 5' P fragments were identified

 The highest amount of metabolite represents the relative major cleavage site

 This size arrow represents 50-99% of the metabolite relative to the major metabolite

 This size arrow represents 10-49% of the metabolite relative to the major arrow

 This size arrow represents <10% of the metabolite relative to the major arrow (PANEL B)
FIG. 33 (CONTINUED)

(PANEL A)

```
                        1  2  3  4  5  6  7  8  9 10 11 12 13 14 15 16 17 18 19 20 21 22 23 24 25

5'-3' (WT RNA), WV-944  U  U  U  G  G  A  A  G  U  C  U  G  C  G  C  C  C  U  U  G  U  G  C  C  C
3'-5' ASO, WV-1086                  C  T  T  C  A  G  A  C  A  C  G  G  G  A  A  C  A  C  G  G
                                          3'-SR

5'-3' (muRNA), WV-945   U  U  U  G  G  A  A  G  U  C  U  G  U  G  C  C  C  U  U  G  U  G  C  C  C
3'-5' ASO, WV-1086                  C  T  T  C  A  G  A  C  A  C  G  G  G  A  A  C  A  C  G  G

5'-3' (WT RNA), WV-944  U  U  U  G  G  A  A  G  U  C  U  G  C  G  C  C  C  U  U  G  U  G  C  C  C
3'-5' ASO, WV-1086                  C  T  T  C  A  G  A  C  A  C  G  G  G  A  A  C  A  C  G  G

5'-3' (muRNA), WV-945   U  U  U  G  G  A  A  G  U  C  U  G  U  G  C  C  C  U  U  G  U  G  C  C  C
3'-5' ASO, WV-1086                  C  T  T  C  A  G  A  C  A  C  G  G  G  A  A  C  A  C  G  G

5'-3' (WT RNA), WV-944  U  U  U  G  G  A  A  G  U  C  U  G  C  G  C  C  C  U  U  G  U  G  C  C  C
3'-5' ASO, WV-1087                  C  T  T  C  A  G  A  C  A  C  G  G  G  A  A  C  A  C  G  G

5'-3' (muRNA), WV-945   U  U  U  G  G  A  A  G  U  C  U  G  U  G  C  C  C  U  U  G  U  G  C  C  C
3'-5' ASO, WV-1087                  C  T  T  C  A  G  A  C  A  C  G  G  G  A  A  C  A  C  G  G

5'-3' (WT RNA), WV-944  U  U  U  G  G  A  A  G  U  C  U  G  C  G  C  C  C  U  U  G  U  G  C  C  C
3'-5' ASO, WV-1088                  C  T  T  C  A  G  A  C  A  C  G  G  G  A  A  C  A  C  G  G

5'-3' (muRNA), WV-945   U  U  U  G  G  A  A  G  U  C  U  G  U  G  C  C  C  U  U  G  U  G  C  C  C
3'-5' ASO, WV-1088                  C  T  T  C  A  G  A  C  A  C  G  G  G  A  A  C  A  C  G  G
```

(PANEL B)

FIG. 34 (CONTINUED)

5'-3' (WT RNA), WV-944    U U U G G A A G U C U G C G C C U U G U G C C C
3'-5' ASO, WV-1089                  C T T C A G A C A C G G G A A C A C G G

5'-3' (mu RNA), WV-945    U U U G G A A G U C U G U G C C U U G U G C C C
3'-5' ASO, WV-1089                  C T T C A G A C A C G G G A A C A C G G

5'-3' (WT RNA), WV-944    U U U G G A A G U C U G C G C C U U G U G C C C
3'-5' ASO, WV-1090                  C T T C A G A C A C G G G A A C A C G G

5'-3' (mu RNA), WV-945    U U U G G A A G U C U G U G C C U U G U G C C C
3'-5' ASO, WV-1090                  C T T C A G A C A C G G G A A C A C G G

5'-3' (WT RNA), WV-944    U U U G G A A G U C U G C G C C U U G U G C C C
3'-5' ASO, WV-1091                  C T T C A G A C A C G G G A A C A C G G

5'-3' (mu RNA), WV-945    U U U G G A A G U C U G U G C C U U G U G C C C
3'-5' ASO, WV-1091                  C T T C A G A C A C G G G A A C A C G G

5'-3' (WT RNA), WV-944    U U U G G A A G U C U G C G C C U U G U G C C C
3'-5' ASO, WV-1092                  C T T C A G A C A C G G G A A C A C G G

5'-3' (mu RNA), WV-945    U U U G G A A G U C U G U G C C U U G U G C C C
3'-5' ASO, WV-1092                  C T T C A G A C A C G G G A A C A C G G (PANEL C)

UPLC-MS ANALYSIS [MW]: CALCD 6623.04, FOUND 6622.8

WV2603.01

UPLC(RP) ANALYSIS

UPLC(RP) ANALYSIS

UPLC-MS ANALYSIS [MW]: CALCD 6557.02, FOUND 6576.2

| NG_009378 | | | | | | | | | | | | | | | | | | | | | | | | | |
|---|---|---|---|---|---|---|---|---|---|---|---|---|---|---|---|---|---|---|---|---|---|---|---|---|---|
| position | -3221300 | | | | | | | | | | -3221200 | | | | | -3221100 | | | | -3221050 | | | | -3221000 | |
| SNP | rs362307 | | | | | | | | | | | | | | | | | | rs362306 | | | | | rs362268 | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
| 5'-3' (WV-944) wt RNA | rU | rU | rU | rG | rG | rA | rA | rG | rU | rC | rU | rG | rC | rG | rC | rC | rC | rU | rG | rU | rU | rG | rC | rC | rC |
| 5'-3' (WV-945) mu RNA | rU | rU | rU | rG | rG | rA | rA | rG | rU | rC | rU | rG | rU | rG | rC | rC | rC | rU | rG | rU | rU | rG | rC | rC | rC |
| 3'-5' (WV-936) | | | | | | | T | T | C | A | G | A | C | G | G | G | A | A | C | A | C | G | G | | |
| 3'-5' (WV-937) | | | C | C | C | T | T | C | A | G | A | C | A | C | G | G | A | A | C | A | C | G | | | |
| 3'-5' (WV-938) | | | | C | C | T | T | C | A | G | A | C | A | C | G | G | A | A | C | A | C | G | | | |
| 3'-5' (WV-939) | A | A | A | C | C | T | T | C | A | G | A | C | A | C | G | G | A | A | C | A | C | | | | |
| 3'-5' (WV-940) | | A | A | C | C | T | T | C | A | G | A | C | A | C | G | G | A | A | C | A | | | | | |
| 3'-5' (WV-941) | A | A | A | C | C | T | T | C | A | G | A | C | A | C | G | G | A | A | C | | | | | | |

FIG. 42

OLIGONUCLEOTIDE COMPOSITIONS AND METHODS THEREOF

CROSS-REFERENCE TO RELATED APPLICATIONS

This application is a U.S. National Stage Application of International PCT Application Number PCT/US2017/030753, filed May 3, 2017, which claims priority to United States Provisional Application Nos. 62/331,960, filed May 4, 2016, and 62/447,832, filed Jan. 18, 2017, and PCT Application No. PCT/US2016/043542, filed Jul. 22, 2016, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Nov. 2, 2018, is named Sequence Listing.txt and is 420,880 bytes in size.

BACKGROUND

Oligonucleotides are useful in various applications such as therapeutic, diagnostic, research and nanomaterials applications. The use of naturally occurring nucleic acids (e.g., unmodified DNA or RNA) for therapeutics can be limited, for example, because of their instability against extra- and intracellular nucleases and/or their poor cell penetration and distribution. There is a need for new and improved oligonucleotides and oligonucleotide compositions, such as, e.g., new antisense and siRNA oligonucleotides and oligonucleotide compositions.

SUMMARY

Among other things, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have significant impact on properties, e.g., activities, of oligonucleotides. In some embodiments, the present disclosure demonstrates that oligonucleotide compositions comprising oligonucleotides with controlled structural elements, e.g., controlled chemical modification and/or controlled backbone stereochemistry patterns, provide unexpected properties, including but not limited to those described herein. In some embodiments, the present disclosure demonstrates that combinations of chemical modifications and stereochemistry can provide unexpected, greatly improved properties (e.g., bioactivity, selectivity, etc.). In some embodiments, the present disclosure provides an oligonucleotide composition of oligonucleotides having a particular sequence of bases, and/or pattern of sugar modifications (e.g., 2'-OMe, 2'-F, 2'-MOE, etc.), and/or pattern or base modifications (e.g., 5-methylcytosine), and/or pattern of backbone modifications (phosphorothioate or modified phosphorothioate), and/or pattern of stereochemistry of backbone chiral centers (e.g., each phosphorothioate is Sp or Rp).

In some embodiments, modifications of internucleotidic linkages can convert phosphorus atoms in modified linkages into chiral centers. For example, in a phosphorothioate (PS) modification, one of the non-bridging oxygen (O) atoms bonded to a phosphorus (P) atom is replaced with a sulfur (S) atom. A consequence of using PS modification in oligonucleotide synthesis is that it creates a chiral center at phosphorus, which can have either an "Sp" or "Rp" configuration. For instance, a conventional stereorandom PS-modified oligonucleotide composition having 19 PS linkages [e.g., having 20 nucleotides in length, 19 PS modifications, each with two possible stereochemistries (Sp or Rp) at each PS modification] is a random mixture of over 500,000 ($2^{19}$) stereoisomers, each having the same nucleotide sequence (e.g., sequence of bases) but differing in the stereochemistry along their backbones; such a composition is a "stereorandom" oligonucleotide composition. In some embodiments, in contrast to stereorandom compositions, a chirally controlled oligonucleotide composition is a substantially pure preparation of a single oligonucleotide in that a predetermined level of the oligonucleotides in the composition have a common base sequence and length, a common pattern of backbone linkages, and a common pattern of backbone chiral centers. In some embodiments, some oligonucleotide compositions are stereopure (i.e., a chirally controlled oligonucleotide composition), wherein the stereochemistry at each PS is defined (Sp or Rp). In some embodiments, in a stereorandom compositions of oligonucleotides, the various oligonucleotides can have the same base sequence, same pattern of sugar modifications (e.g., 2'-OMe, 2'-F, 2'-OME, etc.), same pattern of base modifications (e.g., 5-methylcytosine), and same pattern of backbone modifications (phosphate or PS), but different patterns of backbone chiral centers, and their levels are random from non-stereocontrolled synthesis (not pre-determined as through stereocontrolled synthesis as certain methods exemplified herein using chiral auxiliaries). A chirally controlled oligonucleotide composition can be selected to have greater desired biological activity (e.g., greater activities, efficiency in RNA interference or RNAse H-mediated pathways, etc.) and decreased undesired activity (e.g., undesired immunogenicity, toxicity, etc.) than a stereorandom preparation of oligonucleotides of the same base sequence. In some embodiments, a chirally controlled oligonucleotide composition is better able to differentiate between a mutant (mu) and a wild-type (wt) HTT sequence (with a single nt difference).

Among other things, the present disclosure encompasses the recognition that stereorandom oligonucleotide preparations contain a plurality of distinct chemical entities that differ from one another, e.g., in the stereochemical structure of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence and/or chemical modifications, they are different chemical entities at least due to their different backbone stereochemistry, and they can have, as demonstrated herein, different properties, e.g., bioactivities. Among other things, the present disclosure provides new compositions that are or contain particular stereoisomers of oligonucleotides of interest. In some embodiments, a particular stereoisomer may be defined, for example, by its base sequence, its length, its pattern of backbone linkages, and its pattern of backbone chiral centers. As is understood in the art, in some embodiments, base sequence may refer to the identity and/or modification status of base residues in an oligonucleotide and/or to the hybridization character (i.e., the ability to hybridize with particular complementary residues) of such residues.

The present disclosure demonstrates, among other things, that individual stereoisomers of a particular oligonucleotide can show different stability and/or activity (e.g., functional and/or toxicity properties) from each other. Moreover, the present disclosure demonstrates that stability and/or activity improvements achieved through inclusion and/or location of particular chiral structures within an oligonucleotide can be comparable to, or even better than those achieved through use of particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]).

Among other things, the present disclosure recognizes that, in some embodiments, properties (e.g., stability and/or activities) of an oligonucleotide can be adjusted by optimizing its pattern of backbone chiral centers, optionally in combination with adjustment/optimization of one or more other features (e.g., linkage pattern, nucleoside modification pattern, etc.) of the oligonucleotide.

In some embodiments, the present disclosure provides compositions of oligonucleotides, wherein the oligonucleotides have a common pattern of backbone chiral centers which, unexpectedly, greatly enhances the stability and/or biological activity of the oligonucleotides. In some embodiments, a pattern of backbone chiral centers provides increased stability. In some embodiments, a pattern of backbone chiral centers provides surprisingly increased activity. In some embodiments, a pattern of backbone chiral centers provides increased stability and activity. In some embodiments, when an oligonucleotide is utilized to cleave a nucleic acid polymer, a pattern of backbone chiral centers, surprisingly by itself, changes the cleavage pattern of a target nucleic acid polymer. In some embodiments, a pattern of backbone chiral centers effectively prevents cleavage at secondary sites. In some embodiments, a pattern of backbone chiral centers creates new cleavage sites. In some embodiments, a pattern of backbone chiral centers minimizes the number of cleavage sites. In some embodiments, a pattern of backbone chiral centers minimizes the number of cleavage sites so that a target nucleic acid polymer is cleaved at only one site within the sequence of the target nucleic acid polymer that is complementary to the oligonucleotide. In some embodiments, a pattern of backbone chiral centers enhances cleavage efficiency at a cleavage site. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity between two target sequences differing only by a single nucleotide polymorphism (SNP). In some embodiments, a pattern of backbone chiral centers, such as those in provided oligonucleotides having the structure of formula O—I, comprises one or more repeats of, or is $(Sp)_m(Rp)_n$, $(Rp)_n(Sp)_m$, $(Np)_t(Rp)_n(Sp)_m$, or $(Sp)_t(Rp)_n(Sp)_m$. In some embodiments described herein, m is 1-50; and n is 1-10; and t is 1-50. In some embodiments, a pattern of backbone chiral centers comprises or is $(Sp)_m(Rp)_n$, $(Rp)_n(Sp)_m$, $(Np)_t(Rp)_n(Sp)_m$, or $(Sp)_t(Rp)_n(Sp)_m$. In some embodiments, a pattern of backbone chiral centers comprises or is $(Rp)_n(Sp)_m$, $(Np)_t(Rp)_n(Sp)_m$, or $(Sp)_t(Rp)_n(Sp)_m$, wherein m>2. In some embodiments, a pattern of backbone chiral centers is a sequence comprising at least 5, 6, 7, 8, 9, or 10 or more consecutive (Sp) positions. In some embodiments, a pattern of backbone chiral centers is a sequence comprising at least 5 consecutive (Sp) positions. In some embodiments, a pattern of backbone chiral centers is a sequence comprising at least 8 consecutive (Sp) positions. In some embodiments, a pattern of backbone chiral centers is a sequence comprising at least 10 consecutive (Sp) positions. In some embodiments, a pattern of backbone chiral centers is a sequence consisting of all (Sp) with a single (Rp). In some embodiments, a pattern of backbone chiral centers is a sequence consisting of all (Sp) with a single (Rp) at or adjacent to the position of a SNP. In some embodiments, a pattern of backbone chiral centers is a sequence consisting of all (Sp) with a single (Rp), wherein the molecule has a wing-core-wing format. In some embodiments, a pattern of backbone chiral centers is a sequence consisting of all (Sp) with a single (Rp), wherein the molecule has a wing-core-wing format, wherein the wing on the 5' end is 1-9 nt long, the core is 1-15 nt long, and the wing on the 3' end is 1-9 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 1-15 nt long, and the wing on the 3' end is 5 nt long. In some embodiments, a pattern of backbone chiral centers is a sequence consisting of all (Sp) with a single (Rp), wherein the molecule has a wing-core-wing format, wherein the wing on the 5' end is 1-9 nt long, the core is 10 nt long, and the wing on the 3' end is 1-9 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long, and at least one wing comprises a nucleotide with a 2'-OMe modification. In some embodiments, a pattern of backbone chiral centers is a sequence consisting of all (Sp) with a single (Rp), wherein the molecule has a wing-core-wing format, wherein each wing comprises at least one nucleotide with a 2'-OMe modification. In some embodiments, a pattern of backbone chiral centers is a sequence consisting of all (Sp) with a single (Rp), wherein the molecule has a wing-core-wing format, wherein each nucleotide in both wings has a 2'-OMe modification. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long, and each nucleotide in each wing has a 2'-OMe modification. In some embodiments, the oligonucleotide is single-stranded and has a wing-core-wing format, wherein the wing on the 5' end of the molecule comprises 4 to 8 nt, each of which has a 2'-OMe modification and wherein the nt at the 5' end of the molecule has a phosphorothioate in the Sp conformation; the core comprises 8 to 12 nt, each of which is DNA (2'-H), wherein each has a phosphorothioate in the Sp position except one nt which has the phosphorothioate in the Rp position; and wherein the wing on the 3' end of the molecule comprises 4 to 8 nt, each of which has a 2'-OMe modification, and wherein the nt at the 3' end of the molecule comprises a phosphorothioate in the Sp conformation. In some embodiments, the oligonucleotide is single-stranded and has a wing-core-wing format, wherein the wing on the 5' end of the molecule comprises 6 nt, each of which has a 2'-OMe modification and wherein the nt at the 5' end of the molecule has a phosphorothioate in the Sp conformation; the core comprises 10 nt, each of which is DNA (2'-H), wherein each has a phosphorothioate in the Sp position except one nt which has the phosphorothioate in the Rp position; and wherein the wing on the 3' end of the molecule comprises 6 nt, each of which has a 2'-OMe modification, and wherein the nt at the 3' end of the molecule comprises a phosphorothioate in the Sp conformation.

In some embodiments, the present disclosure recognizes that chemical modifications, such as modifications of nucleosides and internucleotidic linkages, can provide enhanced properties. In some embodiments, the present disclosure demonstrates that combinations of chemical modifications and stereochemistry can provide unexpected, greatly improved properties (e.g., bioactivity, selectivity, etc.). In some embodiments, chemical combinations, such as modifications of sugars, bases, and/or internucleotidic linkages, are combined with stereochemistry patterns, e.g., $(Rp)_n (Sp)_m$, $(Np)_t(Rp)_n(Sp)_m$, or $(Sp)_t(Rp)_n(Sp)_m$, to provide oligonucleotides and compositions thereof with surprisingly enhanced properties. In some embodiments, a provided oligonucleotide composition is chirally controlled, and comprises a combination of 2'-modification of one or more sugar moieties, one or more natural phosphate linkages, one or more phosphorothioate linkages, and a stereochemistry pattern of $(Rp)_n(Sp)_m$, $(Np)_t(Rp)_n(Sp)_m$, or $(Sp)_t(Rp)_n(Sp)_m$, wherein m>2.

In some embodiments, the present disclosure provides an oligonucleotide having the structure of formula O—I:

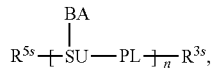

O-I or a salt thereof, wherein:
$R^{5s}$ is R' or —Y—R';
each R' is independently —R, —C(O)R, —CO$_2$R, or —SO$_2$R, or:
  two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms;
each R is independently hydrogen, or an optionally substituted group selected from $C_{1-30}$ aliphatic, $C_{1-30}$ heteroaliphatic having 1-10 heteroatoms, $C_{6-30}$ aryl, a 5-30 membered heteroaryl ring having 1-10 heteroatoms, and a 3-30 membered heterocyclic ring having 1-10 heteroatoms; or:
  two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms;
Y is —O—, —S—, —N(L-R$^1$)—, or L;
L is a covalent bond, or a bivalent or multivalent, optionally substituted, linear or branched group selected from $C_{1-30}$ aliphatic and $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, —Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^1$ is halogen, R, or an optionally substituted $C_1$-$C_{50}$ aliphatic wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, -Cy-, —O—, -S-, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
-Cy- is an optionally substituted bivalent ring selected from 3-30 membered carbocyclylene, 6-30 membered arylene, 5-30 membered heteroarylene having 1-10 heteroatoms, and 3-30 membered heterocyclylene having 1-10 heteroatoms;
BA is an optionally substituted group selected from $C_{1-30}$ cycloaliphatic, $C_{6-30}$ aryl, $C_{3-30}$ heterocyclyl having 1-10 heteroatoms, $C_{5-30}$ heteroaryl having 1-10 heteroatoms, a natural nucleobase moiety, and a modified nucleobase moiety, or

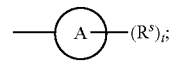

Ring A is an optionally substituted multivalent, monocyclic, bicyclic or polycyclic, saturated, partially unsaturated, or aryl 3-30 membered ring having, in addition to the intervening atoms, 0-10 heteroatoms;
each $R^s$ is independently $R^1$, -L-$R^1$, R', or -L-R';
t is 0-5;
SU is L, or

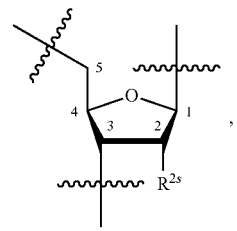

wherein SU is connected to PL through C3;
PL is

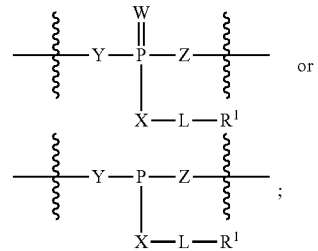

W is O, S or Se;

each of X and Z is independently —O—, —S—, —N(LR¹)—, or L;

R²$^s$ is —F, —CN, —N₃, —NO, —NO₂, —R'—OR', —SR', —N(R')₂, —O-L-OR', —O-L-SR', or —O-L-N(R')₂, or R²$^s$ is L connecting C2 with C1, C2, C3, C4 or C5;

n is an integer greater than 3; and

R³$^s$ is R', —Y—R', —SU(BA)-Y—R', or —SU(BA)-Y-solid support.

In some embodiments, at least one PL is a chiral linkage. In some embodiments, at least 2, 3, 4, 5, 6, 7, 8, 9, 10, 11, 12, 13, 14, 15, 16, 17, 18, 19 or 20 PL are independently chiral linkages in that the phosphorus atom is asymmetric. In some embodiments, at least 5, 6, 7, 8, 9, 10, 11, 12, 13, 14, 15, 16, 17, 18, 19 or 20 PL are chiral in that the phosphorus atom is asymmetric. In some embodiments, provided oligonucleotides comprise at least 5 chiral PL. In some embodiments, provided oligonucleotides comprise at least 6 chiral PL. In some embodiments, provided oligonucleotides comprise at least 7 chiral PL. In some embodiments, provided oligonucleotides comprise at least 8 chiral PL. In some embodiments, provided oligonucleotides comprise at least 9 chiral PL. In some embodiments, provided oligonucleotides comprise at least 10 chiral PL. In some embodiments, provided oligonucleotides comprise at least 11 chiral PL. In some embodiments, provided oligonucleotides comprise at least 12 chiral PL. In some embodiments, provided oligonucleotides comprise at least 13 chiral PL. In some embodiments, at least 5, 6, 7, 8, 9, 10, 11, 12, 13, 14, 15, 16, 17, 18, 19 or 20 PL are chiral and consecutive (no non-chiral PLs in between).

In some embodiments, a chiral PL has a diastereopurity of 50%, 55%, 60%, 65%, 70%, 75%, 80%, 85%, 90%, 91%, 92%, 93%, 94%, 95%, 96%, 97%, 98%, 99% or more. In some embodiments, each PL independently has a diastereopurity of 50%, 55%, 60%, 65%, 70%, 75%, 80%, 85%, 90%, 91%, 92%, 93%, 94%, 95%, 96%, 97%, 98%, 99% or more. In some embodiments, a provided oligonucleotide has a diastereopurity of 50%, 55%, 60%, 65%, 70%, 75%, 80%, 85%, 90%, 91%, 92%, 93%, 94%, 95%, 96%, 97%, 98%, 99% or more. In some embodiments, a diastereopurity is 50% or more. In some embodiments, a diastereopurity is 60% or more. In some embodiments, a diastereopurity is 70% or more. In some embodiments, a diastereopurity is 80% or more. In some embodiments, a diastereopurity is 85% or more. In some embodiments, a diastereopurity is 90% or more. In some embodiments, a diastereopurity is 91% or more. In some embodiments, a diastereopurity is 92% or more. In some embodiments, a diastereopurity is 93% or more. In some embodiments, a diastereopurity is 94% or more. In some embodiments, a diastereopurity is 95% or more. In some embodiments, a diastereopurity is 96% or more. In some embodiments, a diastereopurity is 97% or more. In some embodiments, a diastereopurity is 98% or more. In some embodiments, a diastereopurity is 99% or more.

In some embodiments, at least one PL is a natural phosphate linkage. In some embodiments, at least 2, 3, 4, 5, 6, 7, 8, 9, 10, 11, 12, 13, 14, 15, 16, 17, 18, 19 or 20 PL are natural phosphate linkages. In some embodiments, at least 5, 6, 7, 8, 9, 10, 11, 12, 13, 14, 15, 16, 17, 18, 19 or 20 PL are natural phosphate linkages. In some embodiments, provided oligonucleotides comprise at least 5 natural phosphate linkages. In some embodiments, provided oligonucleotides comprise at least 6 natural phosphate linkages. In some embodiments, provided oligonucleotides comprise at least 7 natural phosphate linkages. In some embodiments, provided oligonucleotides comprise at least 8 natural phosphate linkages. In some embodiments, provided oligonucleotides comprise at least 9 natural phosphate linkages. In some embodiments, provided oligonucleotides comprise at least 10 natural phosphate linkages. In some embodiments, provided oligonucleotides comprise at least 11 natural phosphate linkages. In some embodiments, provided oligonucleotides comprise at least 12 natural phosphate linkages. In some embodiments, provided oligonucleotides comprise at least 13 natural phosphate linkages. In some embodiments, at least 2, 3, 4, 5, 6, 7, 8, 9, 10, 11, 12, 13, 14, 15, 16, 17, 18, 19 or 20 natural phosphate linkages are consecutive. In some embodiments, at least 2 natural phosphate linkages are consecutive. In some embodiments, at least 3 natural phosphate linkages are consecutive. In some embodiments, at least 4 natural phosphate linkages are consecutive. In some embodiments, at least 5 natural phosphate linkages are consecutive. In some embodiments, at least 6 natural phosphate linkages are consecutive. In some embodiments, provided oligonucleotides comprise one or more stretches of consecutive natural phosphate linkages, each stretch independently comprises 2, 3, 4, 5, 6, 7, 8, 9, 10 or more natural phosphate linkages. In some embodiments, each stretch independently comprises 2 or more natural phosphate linkages. In some embodiments, each stretch independently comprises 3 or more natural phosphate linkages. In some embodiments, each stretch independently comprises 4 or more natural phosphate linkages. In some embodiments, each stretch independently comprises 5 or more natural phosphate linkages. In some embodiments, each stretch independently comprises 6 or more natural phosphate linkages.

In some embodiments, a provided oligonucleotide comprises a base sequence that shares 60%, 65%, 70%, 75%, 80%, 85%, 90%, 91%, 92%, 93%, 94%, 95%, 96%, 97%, 98%, 99% or more identity with a 10, 11, 12, 13, 14, 15, 16, 17, 18, 19, 20, 21, 22, 23, 24, 25, 26, 27, 28, 29, 30-bp sequence spanning a SNP. In some embodiments, a SNP is related to mHTT, for example, those described herein associated with expanded CAG repeats. In some embodiments, a provided oligonucleotide comprises a sequence that matches a SNP on the same allele as a characteristic sequence associated with a disease (e.g., expanded CAP repeats for Huntington's disease), so that levels of transcripts associated with a disease (e.g., transcripts with expanded CAG repeats, mutations, etc.) are selectively decreased. Example SNPs, for example, those described in the present disclosure, are widely known in the art and can be targeted in accordance with the present disclosure.

In some embodiments, a provided oligonucleotide comprises a base sequence that shares 60%, 65%, 70%, 75%, 80%, 85%, 90%, 95% or 100% identity with GGCACAAGGGCACAGACUUC (SEQ ID NO: 821). In some embodiments, the sequence of a provided oligonucleotide comprises GGCACAAGGGCACAGACUUC (SEQ ID NO: 821). In some embodiments, the sequence of a provided oligonucleotide is GGCACAAGGGCACAGACUUC (SEQ ID NO: 821). In some embodiments, the sequence of a provided oligonucleotide comprises at least 15 contiguous nt of GGCACAAGGGCACAGACUUC (SEQ ID NO: 821). In some embodiments, the sequence of a provided oligonucleotide comprises the sequence of GGCACAAGGGCACAGACUUC (SEQ ID NO: 821) with 0, 1, 2, 3, 4 or 5 mismatches. In some embodiments, a provided oligonucleotide comprises a base sequence that shares 60%, 65%, 70%, 75%, 80%, 85%, 90%, 95% or 100% identity with GCACAAGGGCACAGACUUCC (SEQ ID NO: 822). In some embodiments, the sequence of a provided oligonucleotide comprises GCACAAGGGCACAGACUUCC (SEQ ID NO: 822). In some embodiments, the sequence of a provided oligonucleotide is GCACAAGGGCACAGACUUCC (SEQ ID NO: 822). In some embodiments, the sequence of a provided oligonucleotide comprises at least 15 contiguous nt of GCACAAGGGCACAGACUUCC (SEQ ID NO: 822). In some embodiments, the sequence of a provided oligonucleotide comprises the sequence of GCACAAGGGCACAGACUUCC (SEQ ID NO: 822) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with GCACACAGTAGATGAGGGAG (SEQ ID NO: 1113). In some embodiments, the sequence of a provided oligonucleotide comprises GCACACAGTAGATGAGGGAG (SEQ ID NO: 1113). In some embodiments, the sequence of a provided oligonucleotide is GCACACAGTAGATGAGGGAG (SEQ ID NO: 1113). In some embodiments, the sequence of a provided oligonucleotide comprises at least 15 contiguous nt of GCACACAGTAGATGAGGGAG (SEQ ID NO: 1113). In some embodiments, the sequence of a provided oligonucleotide comprises the sequence of GCACACAGTAGATGAGGGAG (SEQ ID NO: 1113) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with GGGUCCTCCCCACAGAGGGA (SEQ ID NO: 1107). In some embodiments, the sequence of a provided oligonucleotide comprises GGGUCCTCCCCACAGAGGGA (SEQ ID NO: 1107). In some embodiments, the sequence of a provided oligonucleotide is GGGUCCTCCCCACAGAGGGA (SEQ ID NO: 1107). In some embodiments, the sequence of a provided oligonucleotide comprises at least 15 contiguous nt of GGGUCCTCCCCACAGAGGGA (SEQ ID NO: 1107). In some embodiments, the sequence of a provided oligonucleotide comprises the sequence of GGGUCCTCCCCACAGAGGGA (SEQ ID NO: 1107) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with GUGCACACAGTAGATGAGGG (SEQ ID NO: 1115). In some embodiments, the sequence of a provided oligonucleotide comprises GUGCACACAGTAGATGAGGG (SEQ ID NO: 1115). In some embodiments, the sequence of a provided oligonucleotide is GUGCACACAGTAGATGAGGG (SEQ ID NO: 1115). In some embodiments, the sequence of a provided oligonucleotide comprises at least 15 contiguous nt of GUGCACACAGTAGATGAGGG (SEQ ID NO: 1115). In some embodiments, the sequence of a provided oligonucleotide comprises the sequence of GUGCACACAGTAGATGAGGG (SEQ ID NO: 1115) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with CACAAGGGCACAGACUUCCA (SEQ ID NO: 823). In some embodiments, the sequence of a provided oligonucleotide comprises CACAAGGGCACAGACUUCCA (SEQ ID NO: 823). In some embodiments, the sequence of a provided oligonucleotide is CACAAGGGCACAGACUUCCA (SEQ ID NO: 823). In some embodiments, the sequence of a provided oligonucleotide comprises at least 15 contiguous nt of CACAAGGGCACAGACUUCCA (SEQ ID NO: 823). In some embodiments, the sequence of a provided oligonucleotide comprises the sequence of CACAAGGGCACAGACUUCCA (SEQ ID NO: 823) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with UGCACACAGTAGATGAGGGA (SEQ ID NO: 1114). In some embodiments, the sequence of a provided oligonucleotide comprises UGCACACAGTAGATGAGGGA (SEQ ID NO: 1114). In some embodiments, the sequence of a provided oligonucleotide is UGCACACAGTAGATGAGGGA (SEQ ID NO: 1114). In some embodiments, the sequence of a provided oligonucleotide comprises at least 15 contiguous nt of UGCACACAGTAGATGAGGGA (SEQ ID NO: 1114). In some embodiments, the sequence of a provided oligonucleotide comprises the sequence of UGCACACAGTAGATGAGGGA (SEQ ID NO: 1114) with 0, 1, 2, 3, 4 or 5 mismatches.

In some embodiments, a provided oligonucleotide comprises a base sequence that shares 60%, 65%, 70%, 75%, 80%, 85%, 90%, 95% or 100% identity with GGCACAAGGGCACAGACUUC (SEQ ID NO: 821). In some embodiments, the sequence of a provided oligonucleotide comprises GGCACAAGGGCACAGACUUC (SEQ ID NO: 821). In some embodiments, the sequence of a provided oligonucleotide is GGCACAAGGGCACAGACUUC (SEQ ID NO: 821). In some embodiments, the sequence of a provided oligonucleotide comprises at least 15 contiguous nt of GGCACAAGGGCACAGACUUC (SEQ ID NO: 821). In some embodiments, the sequence of a provided oligonucleotide comprises the sequence of GGCACAAGGGCACAGACUUC (SEQ ID NO: 821) with 0, 1, 2, 3, 4 or 5 mismatches.

In some embodiments, n is 4-200. In some embodiments, n is 5-200. In some embodiments, n is 6-200. In some embodiments, n is 7-200. In some embodiments, n is 8-200. In some embodiments, n is 9-200. In some embodiments, n is 10-200. In some embodiments, n is 11-200. In some embodiments, n is 12-200. In some embodiments, n is 13-200. In some embodiments, n is 14-200. In some embodiments, n is 15-200. In some embodiments, n is 16-200. In some embodiments, n is 17-200. In some embodiments, n is 18-200. In some embodiments, n is 19-200. In some embodiments, n is 20-200. In some embodiments, n is from 5, 6, 7, 8, 9, 10, 11, 12, 13, 14, 15, 16, 17, 18, 19, 20, 21, 22, 23, 24, or 25 to 25, 30, 35, 40, 45, 50, 60, 70, 80, 90, 100, 110, 120, 130, 140, 150 or 200.

In some embodiments, a provided oligonucleotide has the structure of formula O—I, wherein:

n is 9-100;

the oligonucleotide comprises at least 5, 6, 7, 8, 9 or more chiral PL;

the oligonucleotide comprises one or more stretches of consecutive natural phosphate linkages, wherein each stretch of natural phosphate linkages independently comprises at least 2, 3, 4 or more consecutive natural phosphate linkages; and wherein at least 5, 6, 7, 8, 9 or more chiral PL independently have a diastereopurity of 90%, 91%, 92%, 93%, 94%, 95% or more.

In some embodiments, the present disclosure provides a chirally controlled oligonucleotide composition comprising oligonucleotides having the structure of formula O—I, which composition is a substantially pure preparation of a single oligonucleotide in that a predetermined level of the oligonucleotides in the composition have the same structure of formula O—I.

In some embodiments, the present disclosure provides a chirally controlled oligonucleotide composition comprising oligonucleotides having the structure of formula O—I, wherein the oligonucleotides having the structure of formula O—I have a diastereopurity of 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more in the composition. In some embodiments, a diastereopurity is $(DPS)^n$, e.g., $(80\%)^n$, $(85\%)^n$, $(90\%)^n$, $(91\%)^n$, $(92\%)^n$, $(93\%)^n$, $(94\%)^n$, $(95\%)^n$, $(96\%)^n$, $(97\%)^n$, $(98\%)^n$, $(99\%)^n$, or more, wherein n is the number of chiral PL, and each DPS is independently a diastereopurity of a chiral PL. As appreciated by a person having ordinary skill in the art, DPS from dimers (e.g., BA(x)-PL-BA(x+1)) may be used for calculation of diastereopurity of longer oligonucleotides (e.g., BA(1) . . . BA(x)-PL-BA(x+1) . . . BA(n)). In some embodiments, a provided oligonucleotide comprises at least 5, 6, 7, 8, 9, 10, 11, 12, 13, 14, or 15 chiral PL. In some embodiments, a provided oligonucleotide comprises at least 10, 11, 12, 13, 14, or 15 chiral PL.

In some embodiments, the P in PL is P*, an asymmetric phosphorus atom and is either Rp or Sp. In some embodiments, PL has the structure of formula

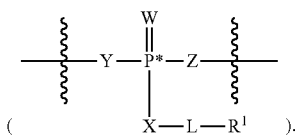

In some embodiments, PL has the structure of

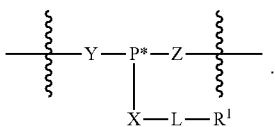

In some embodiments, PL has the structure of formula I:

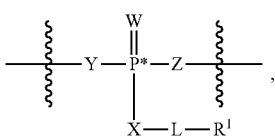

(I)

wherein:
P* is an asymmetric phosphorus atom and is either Rp or Sp;
W is O, S or Se;
each of X, Y and Z is independently —O—, —S—, —N(-L-R¹)—, or L;
L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')₂—, -Cy-, —O—, —S—, —S—S—, —N(R')—, —C(O)—, —C(S)—, —C(NR')—, —C(O)N(R')—, —N(R')C(O)—, —N(R')C(O)O—, —OC(O)N(R)—, —S(O)—, —S(O)₂—, —S(O)₂N(R)—, —N(R')S(O)₂—, —SC(O)—, —C(O)S—, —OC(O)—, and —C(O)O—;

$R^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')₂—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R)—, —S(O)—, —S(O)₂—, —S(O)₂N(R')—, —N(R')S(O)₂—, —SC(O)—, —C(O)S—, —OC(O)—, and —C(O)O— each R' is independently —R, —C(O)R, —CO₂R, or –SO₂R, or:
two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

independently represents a connection to a nucleoside.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')₂—, —Cy—, —O—, —S—, —S—S—, —N(R')—, —C(O)—, —C(S)—, —C(NR')—, —C(O)N(R')—, —N(R')C(O)N (R')—, —N(R')C(O)—, —N(R')C(O)O—, —OC(O)N (R')—, —S(O)—, S(O)₂—, —S(O)₂N(R')—, —N(R') S(O)₂—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C(R')₂—, -Cy-, —O—, —S—, —S—S—, —N(R')—, —C(O)—, —C(S)—, —C(NR')—, —C(O)N(R')—, —N(R')C(O)N (R')—, —N(R')C(O)—, —N(R')C(O)O—, —OC(O)N (R')—, —S(O)—, —S(O)₂—, —S(O)₂N(R')—, —N(R) S(O)₂—, —SC(O)—, —C(O)S—, —OC(O)—, or —C(O)O—; each R' is independently —R, —C(O)R, —CO₂R, or –SO₂R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl; and
each

independently represents a connection to a nucleoside.

In some embodiments, the present disclosure provides a chirally controlled oligonucleotide composition comprising oligonucleotides defined by having:
1) a common base sequence and length;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, the present disclosure provides a chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

In some embodiments, the present disclosure provides a chirally controlled oligonucleotide composition comprising oligonucleotides of a particular oligonucleotide type characterized by:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

Among other things, the present disclosure recognizes that combinations of oligonucleotide structural elements (e.g., patterns of chemical modifications, backbone linkages, backbone chiral centers, and/or backbone phosphorus modifications) can provide surprisingly improved properties such as bioactivities. In some embodiments, the present disclosure provides an oligonucleotide composition comprising a predetermined level of oligonucleotides which comprise one or more wing regions and a common core region, wherein:
each wing region independently has a length of two or more bases, and independently and optionally comprises one or more chiral internucleotidic linkages;
the core region independently has a length of two or more bases, and independently comprises one or more chiral internucleotidic linkages, and the common core region has:
1) a common base sequence and length;
2) a common pattern of backbone linkages; and
3) a common pattern of backbone chiral centers.

In some embodiments, provided oligonucleotides, for example, oligonucleotides of an oligonucleotide type in provided compositions, have the structure of formula O—I.

In some embodiments, in an oligonucleotide comprising a wing-core-wing format, a "wing" is a portion of the oligonucleotide on the 5' or 3' end of the core, with the "core" (alternatively designated a "gap") between the two wings. In some embodiments, an oligonucleotide can have a single wing and a single core; in such cases, the wing is on the 5' or the 3' end of the oligonucleotide. A wing and core can be defined by any of several structural elements (e.g., modifications or patterns of modifications of sugar, base, backbone or backbone stereochemistry, etc.). In some embodiments, a wing and core is defined by nucleoside modifications, wherein a wing comprises a nucleoside modification that the core region does not have. In some embodiments, oligonucleotides in provided compositions have a wing-core structure of nucleoside modification. In some embodiments, oligonucleotides in provided compositions have a core-wing structure of nucleoside modification. In some embodiments, oligonucleotides in provided compositions have a wing-core-wing structure of nucleoside modification. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, each sugar moiety in the wing region has the same 2'-modification, and the core region has no 2'-modifications. In some embodiments, when two or more wings are present, each sugar moiety in a wing region has the same 2'-modification, yet the common 2'-modification in a first wing region can either be the same as or different from the common 2'-modification in a second wing region.

In some embodiments, each wing comprises at least one chiral internucleotidic linkage and at least one natural phosphate linkage. In some embodiments, each wing comprises at least one modified sugar moiety. In some embodiments, each wing sugar moiety is modified. In some embodiments, a wing sugar moiety is modified by a modification that is absent from the core region. In some embodiments, a wing region only has modified internucleotidic linkages at one or both of its ends. In some embodiments, a wing region only has a modified internucleotidic linkage at its 5'-end. In some embodiments, a wing region only has a modified internucleotidic linkage at its 3'-end. In some embodiments, a wing region only has modified internucleotidic linkages at its 5'- and 3'-ends. In some embodiments, a wing is to the 5'-end of a core, and the wing only has a modified internucleotidic linkage at its 5'-end. In some embodiments, a wing is to the 5'-end of a core, and the wing only has a modified internucleotidic linkage at its 3'-end. In some embodiments, a wing is to the 5'-end of a core, and the wing only has modified internucleotidic linkages at both its 5'- and 3'-ends. In some embodiments, a wing is to the 3'-end of a core, and the wing only has a modified internucleotidic linkage at its 5'-end. In some embodiments, a wing is to the 3'-end of a core, and the wing only has a modified internucleotidic linkage at its 3'-end. In some embodiments, a wing is to the 3'-end of a core, and the wing only has modified internucleotidic linkages at both its 5'- and 3'-ends. In some embodiments, the modification(s) to the sugar moiety or internucleotidic linkage or other modifications in one wing can differ from those in another wing.

In some embodiments, each internucleotidic linkage within a core region is modified. In some embodiments, each internucleotidic linkage within a core region is chiral. In some embodiments, a core region has a pattern of backbone chiral centers of $(Sp)_m(Rp)_n$, $(Rp)_n(Sp)_m$, $(Np)_t(Rp)_n(Sp)_m$, or $(Sp)_t(Rp)_n(Sp)_m$. In some embodiments, a core region has a pattern of backbone chiral centers of $(Rp)_n(Sp)_m$, $(Np)_t(Rp)_n(Sp)_m$, or $(Sp)_t(Rp)_n(Sp)_m$, wherein m>2. Among other things, the present disclosure demonstrates that, in some embodiments, such patterns can provide or enhance controlled cleavage of a target sequence, e.g., an RNA sequence.

In some embodiments, oligonucleotides in provided compositions have a common pattern of backbone phosphorus modifications. In some embodiments, a provided composition is an oligonucleotide composition that is chirally controlled in that the composition contains a predetermined level of oligonucleotides of an individual oligonucleotide type, wherein an oligonucleotide type is defined by:
1) base sequence;
2) pattern of backbone linkages;
3) pattern of backbone chiral centers; and
4) pattern of backbone phosphorus modifications.

In some embodiments, a particular oligonucleotide type may be defined by
1A) base identity;
1B) pattern of base modification;
1C) pattern of sugar modification;
2) pattern of backbone linkages;
3) pattern of backbone chiral centers; and
4) pattern of backbone phosphorus modifications.

Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, oligonucleotides of a particular type are chemically identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S$^-$, and –L–R$^1$ of formula I).

In some embodiments, the sequence of the oligonucleotide comprises or consists of the sequence of any oligonucleotide disclosed herein. In some embodiments, the sequence of the oligonucleotide comprises or consists of the sequence of any oligonucleotide selected from Tables N1, N2, N3, N4 and 8. In some embodiments, the sequence of the oligonucleotide comprises or consists of the sequence of any oligonucleotide selected from Tables N1A, N2A, N3A, N4A and 8. In some embodiments, the sequence of the oligonucleotide in a stereopure (chirally controlled) oligonucleotide composition comprises or consists of the sequence of WV-937, WV-190, WV-1901, WV-1087, WV-2378, WV-2380, WV-1510, WV-2619, WV-2611, WV-1497, WV-2602, WV-2618, or WV-2601. In some embodiments, the sequence of the oligonucleotide in a stereopure (chirally controlled) oligonucleotide composition comprises or consists of the sequence of WV-937. In some embodiments, the sequence of the oligonucleotide in a stereopure (chirally controlled) oligonucleotide composition comprises or consists of the sequence of WV-1090. In some embodiments, the sequence of the oligonucleotide in a stereopure (chirally controlled) oligonucleotide composition comprises or consists of the sequence of WV-1091. In some embodiments, the sequence of the oligonucleotide in a stereopure (chirally controlled) oligonucleotide composition comprises or consists of the sequence of WV-1087. In some embodiments, the sequence of the oligonucleotide in a stereopure (chirally controlled) oligonucleotide composition comprises or consists of the sequence of WV-2601. In some embodiments, the sequence of the oligonucleotide in a stereopure (chirally controlled) oligonucleotide composition comprises or consists of the sequence of WV-2611. In some embodiments, the sequence of the oligonucleotide in a stereopure (chirally controlled) oligonucleotide composition comprises or consists of the sequence of WV-2378. In some embodiments, the sequence of the oligonucleotide in a stereopure (chirally controlled) oligonucleotide composition comprises or consists of the sequence of WV-2380. In some embodiments, the sequence of the oligonucleotide in a stereopure (chirally controlled) oligonucleotide composition comprises or consists of the sequence of WV-1510. In some embodiments, the sequence of the oligonucleotide in a stereopure (chirally controlled) oligonucleotide composition comprises or consists of the sequence of WV-2619. In some embodiments, the sequence of the oligonucleotide in a stereopure (chirally controlled) oligonucleotide composition comprises or consists of the sequence of WV-2611. In some embodiments, the sequence of the oligonucleotide in a stereopure (chirally controlled) oligonucleotide composition comprises or consists of the sequence of WV-1497. In some embodiments, the sequence of the oligonucleotide in a stereopure (chirally controlled) oligonucleotide composition comprises or consists of the sequence of WV-2602. In some embodiments, the sequence of the oligonucleotide in a stereopure (chirally controlled) oligonucleotide composition comprises or consists of the sequence of WV-2618. In some embodiments, the sequence of the oligonucleotide in a stereopure (chirally controlled) oligonucleotide composition comprises or consists of the sequence of WV-2601.

Among other things, the present disclosure recognizes the challenge of stereoselective (rather than stereorandom or racemic) preparation of oligonucleotides. Among other things, the present disclosure provides methods and reagents for stereoselective preparation of oligonucleotides comprising multiple (e.g., more than 5, 6, 7, 8, 9, or 10) internucleotidic linkages, and particularly for oligonucleotides comprising multiple (e.g., more than 5, 6, 7, 8, 9, or 10) chiral internucleotidic linkages. In some embodiments, in a stereorandom or racemic preparation of oligonucleotides, at least one chiral internucleotidic linkage is formed with less than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 95:5 diastereoselectivity. In some embodiments, for a stereoselective or chirally controlled preparation of oligonucleotides, each chiral internucleotidic linkage is formed with greater than 96:4 diastereoselectivity. In some embodiments, for a stereoselective or chirally controlled preparation of oligonucleotides, each chiral internucleotidic linkage is formed with greater than 97:3 diastereoselectivity. In some embodiments, for a stereoselective or chirally controlled preparation of oligonucleotides, each chiral internucleotidic linkage is formed with greater than 98:2 diastereoselectivity. In some embodiments, for a stereoselective or chirally controlled preparation of oligonucleotides, each chiral internucleotidic linkage is formed with greater than 99:1 diastereoselectivity. In some embodiments, diastereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

Among other things, it is surprisingly found that certain provided oligonucleotide compositions achieve unprecedented control of cleavage of target sequences, e.g., cleavage of target RNA by RNase H. In some embodiments, the present disclosure demonstrates that precise control of chemical and stereochemical attributes of oligonucleotides achieves improved activity of oligonucleotide preparations as compared with otherwise comparable preparations for which stereochemical attributes are not controlled. Among other things, the present disclosure specifically demonstrates improved rate, degree, and or specificity of cleavage of nucleic acid targets to which provided oligonucleotides hybridize.

In some embodiments, the present disclosure provides various uses of oligonucleotide compositions. Among other things, the present disclosure demonstrates that by controlling structural elements of oligonucleotides, such as base sequence, chemical modifications, stereochemistry, etc., properties of oligonucleotides can be greatly improved. For example, in some embodiments, the present disclosure provides methods for highly selective suppression of transcripts of a target nucleic acid sequence. In some embodiments, the present disclosure provides methods for treating a subject by suppressing transcripts from a disease-causing copy (e.g., a disease-causing allele). In some embodiments, the present disclosure provides methods for designing and preparing oligonucleotide compositions with surprisingly enhanced activity and/or selectivity when suppressing a transcript of a target sequence. In some embodiments, the present disclosure provides methods for designing and/or preparing oligonucleotide compositions which provide allele-specific suppression of a transcript from a target nucleic acid sequence.

In some embodiments, the present disclosure provides a method for controlled cleavage of a nucleic acid polymer, the method comprising steps of:
  contacting a nucleic acid polymer whose nucleotide sequence comprises a target sequence with a chirally controlled oligonucleotide composition comprising oligonucleotides of a particular oligonucleotide type characterized by:
    1) a common base sequence and length, wherein the common base sequence is or comprises a sequence that is complementary to a target sequence found in the nucleic acid polymer;
    2) a common pattern of backbone linkages; and
    3) a common pattern of backbone chiral centers;
  which composition is chirally controlled in that it is enriched, relative to a substantially racemic preparation of oligonucleotides having the particular base sequence and length, for oligonucleotides of the particular oligonucleotide type.

In some embodiments, the present disclosure provides a method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
  contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
    1) the particular base sequence and length;
    2) a particular pattern of backbone linkages; and
    3) a particular pattern of backbone chiral centers.

In some embodiments, the present disclosure provides a method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
    1) a common base sequence and length; and
    2) a common pattern of backbone linkages;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

In some embodiments, the present disclosure provides a method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
    1) a common base sequence and length; and
    2) a common pattern of backbone linkages;
    3) a common pattern of backbone chiral centers;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

In some embodiments, transcripts of the target nucleic acid sequence are suppressed at a greater level than a level of suppression observed for any one of the similar nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
- contacting a sample comprising transcripts of the target nucleic acid sequence with an oligonucleotide composition comprising oligonucleotides having:
  1) a common base sequence and length; and
  2) a common pattern of backbone linkages;
- wherein the common base sequence is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
- contacting a sample comprising transcripts of the target nucleic acid sequence with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
- which composition is chirally controlled in that it is enriched, relative to a substantially racemic preparation of oligonucleotides having the same base sequence and length, for oligonucleotides of the particular oligonucleotide type;
- wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
- contacting a sample comprising transcripts of the target gene with an oligonucleotide composition comprising oligonucleotides having:
  1) a common base sequence and length;
  2) a common pattern of backbone linkages;
- wherein the common base sequence is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
- contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
- which composition is chirally controlled in that it is enriched, relative to a substantially racemic preparation of oligonucleotides having the same base sequence and length, for oligonucleotides of the particular oligonucleotide type;
- wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
- contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;
- which composition is chirally controlled in that it is enriched, relative to a substantially racemic preparation of oligonucleotides having the same base sequence and length, for oligonucleotides of the particular oligonucleotide type;
- wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of both the target allele and another allele of the same gene, transcripts of the particular allele are suppressed at a level at least 2 fold greater than a level of suppression observed for another allele of the same gene.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:

contacting a sample comprising transcripts of the target nucleic acid sequence with an oligonucleotide composition comprising oligonucleotides having:
1) a common base sequence and length;
2) a common pattern of backbone linkages;
wherein the common base sequence is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
a) greater than when the composition is absent;
b) greater than a level of suppression observed for another allele of the same nucleic acid sequence; or
c) both greater than when the composition is absent, and greater than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:

contacting a sample comprising transcripts of the target nucleic acid sequence with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
a) greater than when the composition is absent;
b) greater than a level of suppression observed for another allele of the same nucleic acid sequence; or
c) both greater than when the composition is absent, and greater than a level of suppression observed for another allele of the same nucleic acid sequence.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with an oligonucleotide composition comprising oligonucleotides having:
1) a common base sequence and length; and
2) a common pattern of backbone linkages;
wherein the common base sequence is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with an oligonucleotide composition comprising oligonucleotides of a particular oligonucleotide type characterized by:

1) a common base sequence and length;
2) a common pattern of backbone linkages;

wherein the common base sequence is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
  a) at least 2 fold in that transcripts from the particular allele are detected in amounts that are 2 fold lower when the composition is present relative to when it is absent;
  b) at least 2 fold greater than a level of suppression observed for another allele of the same gene; or
  c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
  1) a common base sequence and length;
  2) a common pattern of backbone linkages;
  3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
  a) at least 2 fold in that transcripts from the particular allele are detected in amounts that are 2 fold lower when the composition is present relative to when it is absent;
  b) at least 2 fold greater than a level of suppression observed for another allele of the same gene; or
  c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, a nucleotide characteristic sequence comprises a mutation that defines the target sequence relative to other similar sequences. In some embodiments, a nucleotide characteristic sequence comprises a point mutation that defines the target sequence relative to other similar sequences. In some embodiments, a nucleotide characteristic sequence comprises a SNP that defines the target sequence relative to other similar sequences.

In some embodiments, the present disclosure provides a method for preparing an oligonucleotide composition comprising oligonucleotides of a particular sequence, which composition provides selective suppression of a transcript of a target sequence, comprising providing a chirally controlled oligonucleotide composition comprising oligonucleotides of a particular oligonucleotide type characterized by:
  1) a common base sequence which is the same as the particular sequence;
  2) a common pattern of backbone linkages; and
  3) a common pattern of backbone chiral centers, which pattern comprises $(Sp)_m(Rp)_n$, $(Rp)_n(Sp)_m$, $(Np)_t(Rp)_n(Sp)_m$, or $(Sp)_t(Rp)_n(Sp)_m$, wherein:
  m is 1-50;
  n is 1-10;
  t is 1-50; and
  each Np is independent Rp or Sp.

In general, activities of oligonucleotide compositions as described herein can be assessed using any appropriate assay. Relative activities for different compositions (e.g., stereocontrolled vs non-stereocontrolled, and/or different stereocontrolled compositions) are typically desirably determined in the same assay, in some embodiments substantially simultaneously and in some embodiments with reference to historical results.

Those of skill in the art will be aware of and/or will readily be able to develop appropriate assays for particular oligonucleotide compositions. The present disclosure provides descriptions of certain particular assays, for example that may be useful in assessing one or more features of oligonucleotide composition behavior with respect to RNAse H cleavage of a target sequence.

For example, certain assays that may be useful in the assessment of one or more features (e.g., rate, extent, and/or selectivity of cleavage) of RNase H cleavage may include an assay as described in any assay described and/or exemplified herein (e.g., in one or more of Examples 4, 9-10, 12, 14, 17-20, etc.).

In some embodiments, the present disclosure recognizes that a base sequence can impact properties of oligonucleotides. The present disclosure demonstrates that chemical and stereochemical modifications, combined with designed base sequences, can provide oligonucleotide compositions with unexpectedly improved properties (e.g., surprisingly higher activity, and/or selectivity, etc.). In some embodiments, oligonucleotides having a common base sequence complementary to a characteristic sequence element of a target nucleic acid sequence provide better activity compared to another common base sequence complementary to the characteristic sequence element of a target nucleic acid sequence. In some embodiments, oligonucleotides having a common base sequence complementary to a characteristic sequence element of a target nucleic acid sequence provide better selectivity compared to another common base sequence complementary to the characteristic sequence element of a target nucleic acid sequence.

In some embodiments, a composition of oligonucleotides having a common base sequence complementary to a characteristic sequence element of a target nucleic acid sequence, when compared to another composition of oligonucleotides having another common base sequence complementary to the characteristic sequence element of the target nucleic acid sequence, provides higher cleavage rate of a transcript from the target nucleic acid sequence, and/or a cleavage pattern which has only one major cleavage site, and the major cleavage site is within or close to the nucleotide characteristic sequence. In some embodiments, a composition of oligonucleotides having a complementary common base sequence, when compared to another composition of oligonucleotides having another complementary common base sequence, provide higher cleavage rate of a transcript from the target nucleic acid sequence, and a cleavage pattern which has only one major cleavage site, and the major cleavage site is within or close to a nucleotide characteristic sequence. In some embodiments, greater than 50%, 60%, 70%, 80% or 90% of cleavage occurs at the one major cleavage site, for example, when measured by a suitable method, e.g., an RNase H assay. In some embodiments, a composition of oligonucleotides having a complementary common base sequence, when compared to another composition of oligonucleotides having another complementary common base sequence, provides higher cleavage rate of a transcript from the target nucleic acid sequence, and a cleavage pattern which has only one major cleavage site, and the major cleavage site is within or close to a mutation or a SNP that defines the target sequence relative to other similar sequences. In some embodiments, a mutation is a point mutation. In some embodiments, a major cleavage site is next to a mutation or a SNP that defines the target sequence relative to other similar sequences. In some embodiments, each common base sequence is 100% complementary to the characteristic sequence element of the target nucleic acid sequence. In some embodiments, a major cleavage site is within less than 5, 4, 3, or 1 internucleotidic linkage from a mutation or a SNP that defines the target sequence relative to other similar sequences. In some embodiments, a major cleavage site is within less than 5, 4, 3, or 1 internucleotidic linkage from a mutation or a SNP that defines the target sequence relative to other similar sequences, and is within less than 5, 4, 3, or 1 internucleotidic linkage from a cleavage site when a stereorandom composition of oligonucleotides having the same common sequence, and/or a composition of DNA oligonucleotides having the same common sequence, is used. In some embodiments, a major cleavage site is a cleavage site when a stereorandom composition of oligonucleotides having the same common sequence is used. In some embodiments, a major cleavage site is a major cleavage site when a stereorandom composition of oligonucleotides having the same common sequence is used. In some embodiments, a major cleavage site is a cleavage site when a composition of DNA oligonucleotides having the same common sequence is used. In some embodiments, a major cleavage site is a major cleavage site when a composition of DNA oligonucleotides having the same common sequence is used.

In some embodiments, when comparing effects of a first and a second common base sequences, a stereorandom composition of oligonucleotides having a first common base sequence may be compared to a stereorandom composition of oligonucleotides having a second common base sequence. In some embodiments, a stereorandom composition is a composition of oligonucleotides having a common base sequence, a common pattern of nucleoside modifications, and a common pattern of backbone linkages. In some embodiments, a stereorandom composition is a composition of oligonucleotides having a common base sequence, a common pattern of nucleoside modifications, wherein each internucleotidic linkage is phosphorothioate. In some embodiments, when comparing effects of a first and a second common base sequences, a chirally controlled oligonucleotide composition of oligonucleotides having a first common base sequence may be compared to a chirally controlled oligonucleotide composition of oligonucleotides having a second common base sequence. In some embodiments, oligonucleotides in a chirally controlled oligonucleotide composition have a common base sequence, a common pattern of nucleoside modifications, a common pattern of backbone linkages, a common pattern of backbone chiral centers, and a common pattern of backbone phosphorus modifications. In some embodiments, each internucleotidic linkage is phosphorothioate.

In some embodiments, oligonucleotide compositions and technologies described herein are particularly useful in the treatment of Huntington's disease. For example, in some embodiments, the present disclosure defines stereochemically controlled oligonucleotide compositions that direct cleavage (e.g., RNase H-mediated cleavage) of nucleic acids associated with Huntington's disease. In some embodiments, such compositions direct preferential cleavage of a Huntington's disease-associated allele of a particular target sequence, relative to one or more (e.g., all non-Huntington's disease-associated) other alleles of the sequence.

Huntington's disease is an inherited disease that can cause progressive degeneration of nerve cells in the brain and affect a subject's motor and cognitive abilities. In some embodiments, Huntington's disease is an autosomal dominant disorder. In some embodiments, it is caused by mutations in the Huntingtin gene. Normal HTT gene contains 10 to 35 CAG tri-nucleotide repeats (SEQ ID NO: 1). People with 40 or more repeats often develop the disorder. In some embodiments, the expanded CAG segment on the first exon of HTT gene leads to the production of an abnormally long version of the Huntingtin protein (expanded polyglutamine tract) which is cut into smaller, toxic fragments that bind together and accumulate in neurons, disrupting the normal functions of these cells. Warby et al. (Am J Hum Genet. 2009, 84(3), 351-366) reported many SNPs that are associated with disease chromosomes and have stronger linkage associations with CAG expansion than those reported before. Many SNPs highly associated with CAG expansion do not segregate independently and are in Linkage Disequilibrium with each other. Among other things, the present disclosure recognizes that strong association between specific SNPs and CAG expanded chromosomes provides an attractive therapeutic opportunity for the treatment of Huntington Disease, e.g., through antisense therapy. Furthermore, the association of specific SNPs combined with high rates of heterozygosity in HD patients provides suitable targets for allele-specific knockdown of the mutant gene product. For example references, see Liu et al. Journal of Huntington's Disease 2, 2013, 491-500; Aronin, Neil and Pfister, Edith WO 2010/118263 A1; Pfister et al. Current Biology 2009, 19, 774-778.

In some embodiments, a targeted SNP of the present disclosure has high frequency of heterozygosity in HD and has a particular variant associated with the mutant HTT allele. In some embodiments, a SNP is rs362307. In some embodiments, a SNP is rs7685686. In some embodiments, a SNP may not be linked but may have a high heterozygous frequency. In some embodiments, a SNP is rs362268 (3'-UTR region). In some embodiments, a SNP is rs362306 (3'-UTR region). In some embodiments, a SNP is rs2530595. In some embodiments, a SNP is rs362331.

In some embodiments, a provided method for treating or preventing Huntington's disease in a subject, comprising administering to the subject a provided oligonucleotide compositions. In some embodiments, a provided method for treating or preventing Huntington's disease in a subject, comprising administering to the subject a chirally controlled oligonucleotide composition comprising oligonucleotides of a particular oligonucleotide type characterized by:

1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

In some embodiments, a provided method ameliorates a symptom of Huntington's disease. In some embodiments, a provided method slows onset of Huntington's disease. In some embodiments, a provided method slows progression of Huntington's disease.

In some embodiments, the present disclosure provides methods for identifying patients for a given oligonucleotide composition. In some embodiments, the present disclosure provides methods for patient stratification. In some embodiments, a provided method comprises identifying a mutation and/or SNP associated with a disease-causing allele. For example, in some embodiments, a provided method comprises identifying in a subject a SNP associated with expanded CAG repeats that are associated with or causing Huntington's disease.

In some embodiments, a subject has a SNP in the subject's Huntingtin gene. In some embodiments, a subject has a SNP, wherein one allele is mutant Huntingtin associated with expanded CAG repeats. In some embodiments, a subject has a SNP selected from rs362307, rs7685686, rs362268, rs2530595, rs362331, or rs362306. In some embodiments, oligonucleotides of a provided composition have a sequence complementary to a sequence comprising a SNP from the disease-causing allele (mutant), and the composition selectively suppresses expression from the diseasing-causing allele.

In some embodiments, the sequence of oligonucleotides in provided technologies (compounds, compositions, methods, etc.) comprises, consists of, or is the sequence of any oligonucleotide described herein. In some embodiments, a sequence is selected from Tables N1A, N2A, N3A, N4A or 8. In some embodiments, the sequence of the oligonucleotide in a stereopure (chirally controlled) oligonucleotide composition comprises or consists of the sequence of WV-2378, WV-2380, WV-1510, WV-2619, WV-2611, WV-1497, WV-2602, WV-2618, or WV-2601. In some embodiments, the sequence of the oligonucleotide in a stereopure (chirally controlled) oligonucleotide composition comprises or consists of the sequence of WV-2378. In some embodiments, the sequence of the oligonucleotide in a stereopure (chirally controlled) oligonucleotide composition comprises or consists of the sequence of WV-2380. In some embodiments, the sequence of the oligonucleotide in a stereopure (chirally controlled) oligonucleotide composition comprises or consists of the sequence of WV-1510. In some embodiments, the sequence of the oligonucleotide in a stereopure (chirally controlled) oligonucleotide composition comprises or consists of the sequence of WV-2619. In some embodiments, the sequence of the oligonucleotide in a stereopure (chirally controlled) oligonucleotide composition comprises or consists of the sequence of WV-2611. In some embodiments, the sequence of the oligonucleotide in a stereopure (chirally controlled) oligonucleotide composition comprises or consists of the sequence of WV-1497. In some embodiments, the sequence of the oligonucleotide in a stereopure (chirally controlled) oligonucleotide composition comprises or consists of the sequence of WV-2602. In some embodiments, the sequence of the oligonucleotide in a stereopure (chirally controlled) oligonucleotide composition comprises or consists of the sequence of WV-2618. In some embodiments, the sequence of the oligonucleotide in a stereopure (chirally controlled) oligonucleotide composition comprises or consists of the sequence of WV-2601.

In some embodiments, provided oligonucleotide compositions comprises a lipid and an oligonucleotide. In some embodiments, a lipid is conjugated to an oligonucleotide.

In some embodiments, a composition comprises an oligonucleotide and a lipid selected from the list of: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl. In some embodiments, a composition comprises an oligonucleotide and a lipid selected from the list of: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl.

In some embodiments, a composition comprises an oligonucleotide and a lipid selected from:

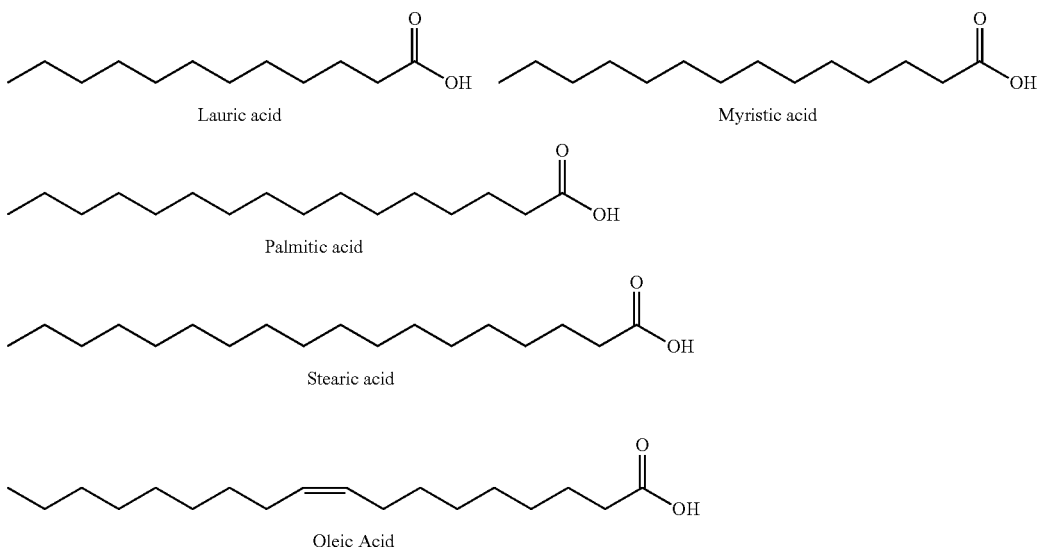

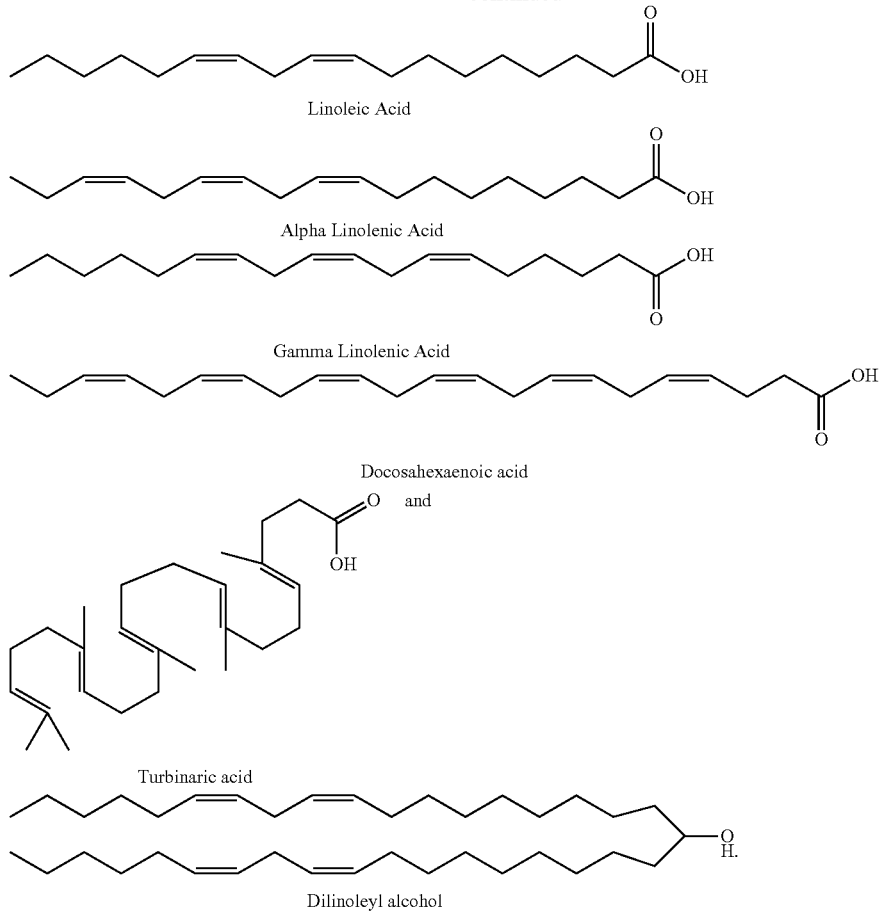

Linoleic Acid

Alpha Linolenic Acid

Gamma Linolenic Acid

Docosahexaenoic acid and

Turbinaric acid

Dilinoleyl alcohol

In some embodiments, a composition comprises an oligonucleotide and a lipid, wherein the lipid comprises a $C_{10}$-$C_{40}$ linear, saturated or partially unsaturated, aliphatic chain, optionally substituted with one or more $C_{1-4}$ aliphatic group.

In some embodiments, an oligonucleotide composition comprises a plurality of oligonucleotides, which share:
1) a common base sequence;
2) a common pattern of backbone linkages; and
3) a common pattern of backbone phosphorus modifications;
wherein one or more oligonucleotides of the plurality are individually conjugated to a lipid.

In some embodiments, a chirally controlled oligonucleotide composition comprises a plurality of oligonucleotides, which share:
1) a common base sequence;
2) a common pattern of backbone linkages; and
3) a common pattern of backbone phosphorus modifications;
wherein:
the composition is chirally controlled in that the plurality of oligonucleotides share the same stereochemistry at one or more chiral internucleotidic linkages;
one or more oligonucleotides of the plurality are individually conjugated to a lipid; and one or more oligonucleotides of the plurality are optionally and individually conjugated to a targeting compound or moiety.

In some embodiments, a method of delivering an oligonucleotide to a cell or tissue in a human subject, comprises:
(a) Providing a composition of any one of the embodiments described herein; and
(b) Administering the composition to the human subject such that the oligonucleotide is delivered to a cell or tissue in the subject.

In some embodiments, a method for delivering an oligonucleotide to a cell or tissue comprises preparing a composition according to any one of the embodiments described herein and contacting the cell or tissue with the composition.

In some embodiments, a method of modulating the level of a transcript or gene product of a gene in a cell, the method comprises the step of contacting the cell with a composition according to any one of the embodiments described herein, wherein the oligonucleotide is capable of modulating the level of the transcript or gene product.

In some embodiments, a method for inhibiting expression of a gene in a cell or tissue comprises preparing a composition according to any one of the embodiments described herein and treating the cell or tissue with the composition.

In some embodiments, a method for inhibiting expression of a gene in a cell or tissue in a mammal comprises preparing a composition according to any one of the embodiments described herein and administering the composition to the mammal.

In some embodiments, a method of treating a disease that is caused by the over-expression of one or several proteins in a cell or tissue in a subject, said method comprises the administration of a composition according to any one of the embodiments described herein to the subject.

In some embodiments, a method of treating a disease that is caused by a reduced, suppressed or missing expression of one or several proteins in a subject, said method comprises the administration of a composition according to any one of the embodiments described herein to the subject.

In some embodiments, a method for generating an immune response in a subject, said method comprises the administration of a composition according to any one of the embodiments described herein to the subject, wherein the biologically active compound is an immunomodulating nucleic acid.

In some embodiments, a method for treating a sign and/or symptom of Huntington's Disease by providing a composition of any one of the embodiments described herein and administering the composition to the subject.

In some embodiments, a method of modulating the amount of RNaseH-mediated cleavage in a cell, the method comprises the step of contacting the cell with a composition according to any one of the embodiments described herein, wherein the oligonucleotide is capable of modulating the amount of RNaseH-mediated cleavage.

In some embodiments, a method of administering an oligonucleotide to a subject in need thereof, comprises steps of providing a composition comprises the agent a lipid, and administering the composition to the subject, wherein the agent is any agent disclosed herein, and wherein the lipid is any lipid disclosed herein.

In some embodiments, a method of treating a disease in a subject, the method comprises steps of providing a composition comprises the agent a lipid, and administering a therapeutically effective amount of the composition to the subject, wherein the agent is any agent disclosed herein, and wherein the lipid is any lipid disclosed herein, and wherein the disease is any disease disclosed herein.

In some embodiments, a lipid comprises an optionally substituted $C_{10}$-$C_{40}$ saturated or partially unsaturated aliphatic chain.

In some embodiments, a lipid comprises an optionally substituted $C_{10}$-$C_{40}$ linear, saturated or partially unsaturated, aliphatic chain.

In some embodiments, a lipid comprises a $C_{10}$-$C_{40}$ linear, saturated or partially unsaturated, aliphatic chain, optionally substituted with one or more $C_{1-4}$ aliphatic group.

In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{40}$ linear, saturated or partially unsaturated, aliphatic chain.

In some embodiments, a lipid comprises two or more optionally substituted $C_{10}$-$C_{40}$ linear, saturated or partially unsaturated, aliphatic chain.

In some embodiments, a lipid comprises no tricyclic or polycyclic moiety.

In some embodiments, a lipid has the structure of $R^1$—COOH, wherein $R^1$ is an optionally substituted $C_{10}$-$C_{40}$ saturated or partially unsaturated aliphatic chain.

The composition or method of any one of claim 16, wherein the lipid is conjugated through its carboxyl group.

The composition or method according to any one of the embodiments described herein, wherein the lipid is selected from:

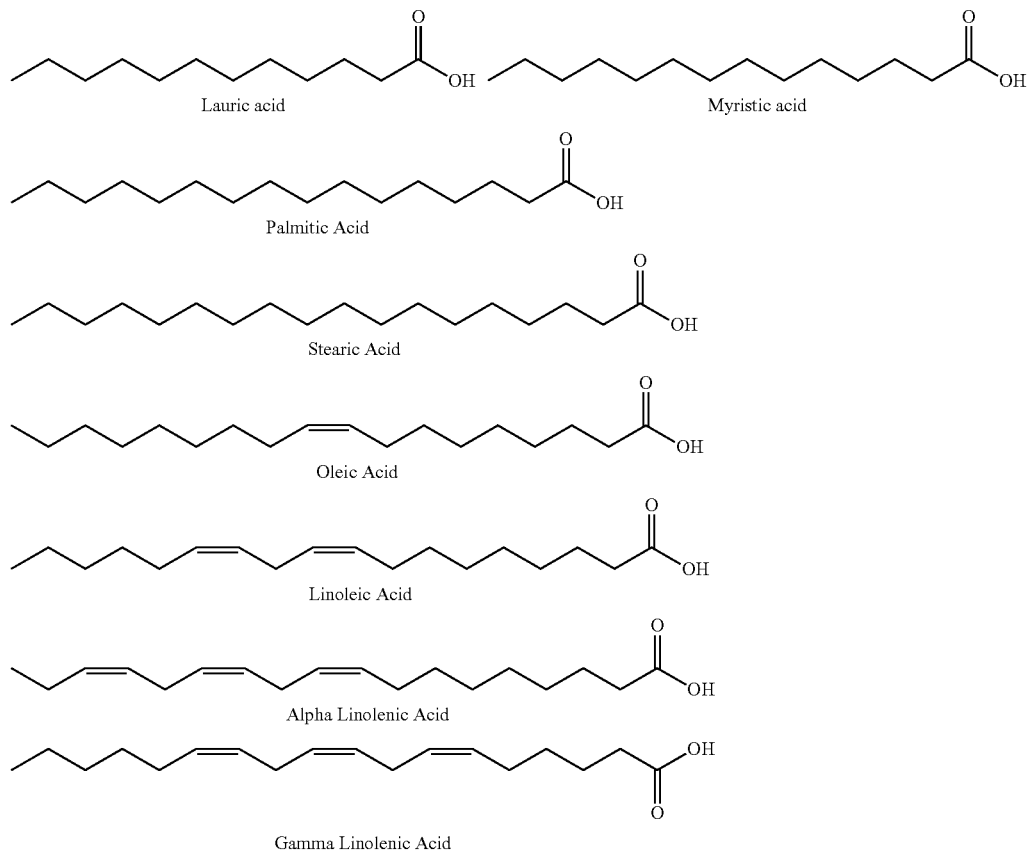

Lauric acid

Myristic acid

Palmitic Acid

Stearic Acid

Oleic Acid

Linoleic Acid

Alpha Linolenic Acid

Gamma Linolenic Acid

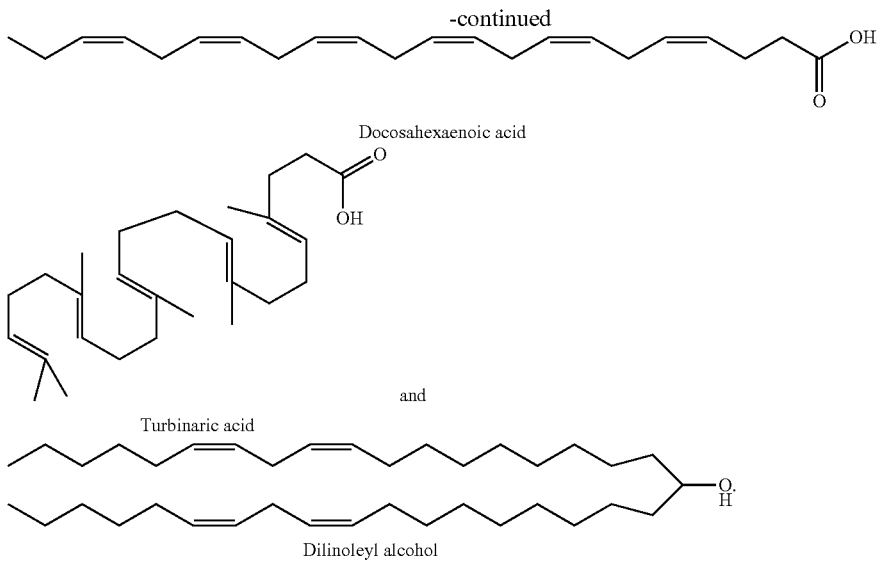

In some embodiments, a lipid is conjugated to the oligonucleotide.

In some embodiments, a lipid is directly conjugated to the oligonucleotide.

In some embodiments, a lipid is conjugated to the oligonucleotide via a linker.

In some embodiments, a linker is selected from: an uncharged linker; a charged linker; a linker comprises an alkyl; a linker comprises a phosphate; a branched linker; an unbranched linker; a linker comprises at least one cleavage group; a linker comprises at least one redox cleavage group; a linker comprises at least one phosphate-based cleavage group; a linker comprises at least one acid-cleavage group; a linker comprises at least one ester-based cleavage group; and a linker comprises at least one peptide-based cleavage group.

In some embodiments, each oligonucleotide of the plurality is individually conjugated to the same lipid at the same location.

In some embodiments, a lipid is conjugated to an oligonucleotide through a linker.

In some embodiments, one or more oligonucleotides of the plurality are independently conjugated to a targeting compound or moiety.

In some embodiments, one or more oligonucleotides of the plurality are independently conjugated to a lipid and a targeting compound or moiety.

In some embodiments, one or more oligonucleotides of the plurality are independently conjugated to a lipid at one end and a targeting compound or moiety at the other.

In some embodiments, oligonucleotides of the plurality share the same chemical modification patterns.

In some embodiments, oligonucleotides of the plurality share the same chemical modification patterns comprises one or more base modifications.

In some embodiments, oligonucleotides of the plurality share the same chemical modification patterns comprises one or more sugar modifications.

In some embodiments, a common base sequence is capable of hybridizing with a transcript in a cell, which transcript contains a mutation that is linked to Huntington's Disease, or whose level, activity and/or distribution is linked to Huntington's Disease.

In some embodiments, an oligonucleotide is a nucleic acid.

In some embodiments, an oligonucleotide is an oligonucleotide.

In some embodiments, an oligonucleotide is an oligonucleotide which participates in RNaseH-mediated cleavage of a mutant Huntingtin gene mRNA.

In some embodiments, a disease or disorder is Huntington's Disease.

In some embodiments, a lipid comprises an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{80}$ saturated or partially unsaturated, aliphatic chain.

In some embodiments, a lipid comprises an optionally substituted $C_{10}$-$C_{80}$ linear, saturated or partially unsaturated, aliphatic chain.

In some embodiments, a lipid comprises an optionally substituted $C_{10}$-$C_{60}$ saturated or partially unsaturated, aliphatic chain.

In some embodiments, a lipid comprises an optionally substituted $C_{10}$-$C_{60}$ linear, saturated or partially unsaturated, aliphatic chain.

In some embodiments, a lipid comprises an optionally substituted $C_{10}$-$C_{40}$ saturated or partially unsaturated, aliphatic chain.

In some embodiments, a lipid comprises an optionally substituted $C_{10}$-$C_{40}$ linear, saturated or partially unsaturated, aliphatic chain.

In some embodiments, a lipid comprises an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{60}$ saturated or partially unsaturated, aliphatic chain.

In some embodiments, a lipid comprises an optionally substituted $C_{10}$-$C_{60}$ linear, saturated or partially unsaturated, aliphatic chain.

In some embodiments, a lipid comprises an optionally substituted $C_{10}$-$C_{40}$ linear, saturated or partially unsaturated, aliphatic chain.

In some embodiments, a lipid comprises an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{40}$ saturated or partially unsaturated, aliphatic chain.

In some embodiments, a lipid comprises an optionally substituted $C_{10}$-$C_{40}$ linear, saturated or partially unsaturated, aliphatic chain.

In some embodiments, a composition further comprises one or more additional components selected from: a polynucleotide, carbonic anhydrase inhibitor, a dye, an intercalating agent, an acridine, a cross-linker, psoralene, mitomycin C, a porphyrin, TPPC4, texaphyrin, Sapphyrin, a polycyclic aromatic hydrocarbon phenazine, dihydrophenazine, an artificial endonuclease, a chelating agent, EDTA, an alkylating agent, a phosphate, an amino, a mercapto, a PEG, PEG-40K, MPEG, [MPEG]$_2$, a polyamino, an alkyl, a substituted alkyl, a radiolabeled marker, an enzyme, a hapten biotin, a transport/absorption facilitator, aspirin, vitamin E, folic acid, a synthetic ribonuclease, a protein, a glycoprotein, a peptide, a molecule having a specific affinity for a co-ligand, an antibody, a hormone, a hormone receptor, a non-peptidic species, a lipid, a lectin, a carbohydrate, a vitamin, a cofactor, selectivity agent, or a drug. In some embodiments, a composition further comprises one or more additional components selected from: a polynucleotide, carbonic anhydrase inhibitor, a dye, an intercalating agent, an acridine, a cross-linker, psoralene, mitomycin C, a porphyrin, TPPC4, texaphyrin, Sapphyrin, a polycyclic aromatic hydrocarbon phenazine, dihydrophenazine, an artificial endonuclease, a chelating agent, EDTA, an alkylating agent, a phosphate, an amino, a mercapto, a PEG, PEG-40K, MPEG, [MPEG]$_2$, a polyamino, an alkyl, a substituted alkyl, a radiolabeled marker, an enzyme, a hapten biotin, a transport/absorption facilitator, aspirin, vitamin E, folic acid, a synthetic ribonuclease, a protein, a glycoprotein, a peptide, a molecule having a specific affinity for a co-ligand, an antibody, a hormone, a hormone receptor, a non-peptidic species, a lipid, a lectin, a carbohydrate, a vitamin, a cofactor, or a drug.

In some embodiments, the present disclosure provides an oligonucleotide conjugated to a selectivity agent. In some embodiments, the present disclosure provides a composition comprising an oligonucleotide or oligonucleotide type comprising a selectivity agent. In some embodiments, a selectivity agent binds specifically to one or more neurotransmitter transporters selected from the group consisting of a dopamine transporter (DAT), a serotonin transporter (SERT), and a norepinephrine transporter (NET). In some embodiments, a selectivity agent is selected from the group consisting of a dopamine reuptake inhibitor (DRI), a selective serotonin reuptake inhibitor (SSRI), a noradrenaline reuptake inhibitor (NRI), a norepinephrine-dopamine reuptake inhibitor (NDRI), and a serotonin-norepinephrine-dopamine reuptake inhibitor (SNDRI). In some embodiments, a selectivity agent is selected from the group consisting of a triple reuptake inhibitor, a noradrenaline dopamine double reuptake inhibitor, a serotonin single reuptake inhibitor, a noradrenaline single reuptake inhibitor, and a dopamine single reuptake inhibitor. In some embodiments, a selectivity agent is selected from the group consisting of a dopamine reuptake inhibitor (DRI), a Norepinephrine-Dopamine Reuptake Inhibitor (NDRI) and a serotonin-Norepinephrine-Dopamine Reuptake Inhibitor (SNDRI). In some embodiments, a selectivity agent is selected from the selectivity agents which are described in U.S. Pat. Nos. 9,084,825; and 9,193,969; and WO2011131693, WO2014064258.

In some embodiments, a lipid comprises a $C_{10}$-$C_{80}$ linear, saturated or partially unsaturated, aliphatic chain.

In some embodiments, a composition further comprises a linker linking the oligonucleotide and the lipid, wherein the linker is selected from: an uncharged linker; a charged linker; a linker comprises an alkyl; a linker comprises a phosphate; a branched linker; an unbranched linker; a linker comprises at least one cleavage group; a linker comprises at least one redox cleavage group; a linker comprises at least one phosphate-based cleavage group; a linker comprises at least one acid-cleavage group; a linker comprises at least one ester-based cleavage group; a linker comprises at least one peptide-based cleavage group.

In some embodiments, an oligonucleotide comprises or consists of or is an oligonucleotide or oligonucleotide composition or chirally controlled oligonucleotide composition.

In some embodiments, an oligonucleotide comprises or consists of or is an oligonucleotide composition or chirally controlled oligonucleotide composition, wherein the sequence of the oligonucleotide comprises or consists of the sequence of any oligonucleotide described herein.

In some embodiments, an oligonucleotide comprises or consists of or is an oligonucleotide composition or chirally controlled oligonucleotide composition, wherein the sequence of the oligonucleotide comprises or consists of the sequence of any oligonucleotide listed in Table 4.

In some embodiments, an oligonucleotide comprises or consists of or is an oligonucleotide composition or chirally controlled oligonucleotide composition, wherein the sequence of the oligonucleotide comprises or consists of the sequence of a splice-switching oligonucleotide.

The composition or method of any of the embodiments described herein, wherein the oligonucleotide is a chirally controlled oligonucleotide composition.

The composition or method of any of the embodiments described herein, wherein the disease or disorder is Huntington's Disease.

The composition or method of any of the embodiments described herein, wherein the oligonucleotide is capable of participating in RNaseH-mediated cleavage of a mutant Huntingtin gene mRNA.

The composition or method of any of the embodiments described herein, wherein the oligonucleotide comprises, consists of or is the sequence of any oligonucleotide disclosed herein.

The composition or method of any of the embodiments described herein, wherein the oligonucleotide is capable of differentiating between a wild-type and a mutant Huntingtin allele.

The composition or method of any of the embodiments described herein, wherein the oligonucleotide is capable of participating in RNaseH-mediated cleavage of a mutant Huntingtin gene mRNA.

The composition or method of any of the embodiments described herein, wherein the oligonucleotide comprises, consists of or is the sequence of any oligonucleotide disclosed in Table 4.

In some embodiments, an oligonucleotide comprises or consists of or is an oligonucleotide or oligonucleotide composition or chirally controlled oligonucleotide composition, wherein the sequence of the oligonucleotide comprises or consists of the sequence of any of: WV-2378, WV-2380, WV-1510, WV-2619, WV-2611, WV-1497, WV-2602, WV-2618, or WV-2601. In some embodiments, the sequence of the oligonucleotide in a stereopure (chirally controlled) oligonucleotide composition comprises or consists of the sequence of WV-2378, WV-2380, WV-1510, WV-2619, WV-2611, WV-1497, WV-2602, WV-2618, or WV-2601. In some embodiments, the sequence of the oligonucleotide in a stereopure (chirally controlled) oligonucleotide composition comprises or consists of the sequence of WV-2378. In some embodiments, the sequence of the oligonucleotide in a stereopure (chirally controlled) oligonucleotide composition comprises or consists of the sequence of WV-2380. In some embodiments, the sequence of the oligonucleotide in a stereopure (chirally controlled) oligonucleotide composition comprises or consists of the sequence of WV-1510. In some embodiments, the sequence of the oligonucleotide in a stereopure (chirally controlled) oligonucleotide composition comprises or consists of the sequence of WV-2619. In some embodiments, the sequence of the oligonucleotide in a stereopure (chirally controlled) oligonucleotide composition comprises or consists of the sequence of WV-2611. In some embodiments, the sequence of the oligonucleotide in a stereopure (chirally controlled) oligonucleotide composition comprises or consists of the sequence of WV-1497. In some embodiments, the sequence of the oligonucleotide in a stereopure (chirally controlled) oligonucleotide composition comprises or consists of the sequence of WV-2602. In some embodiments, the sequence of the oligonucleotide in a stereopure (chirally controlled) oligonucleotide composition comprises or consists of the sequence of WV-2618. In some embodiments, the sequence of the oligonucleotide in a stereopure (chirally controlled) oligonucleotide composition comprises or consists of the sequence of WV-2601.

In some embodiments, a sequence of an oligonucleotide includes any one or more of: base sequence (including length); pattern of chemical modifications to sugar and base moieties; pattern of backbone linkages; pattern of natural phosphate linkages, phosphorothioate linkages, phosphorothioate triester linkages, and combinations thereof; pattern of backbone chiral centers; pattern of stereochemistry (Rp/Sp) of chiral internucleotidic linkages; pattern of backbone phosphorus modifications; pattern of modifications on the internucleotidic phosphorus atom, such as —S$^-$, and -L-R' of formula I.

In some embodiments, the present disclosure provides a chirally controlled oligonucleotide composition comprising oligonucleotides of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type, wherein the oligonucleotides target a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation.

In some embodiments, the present disclosure provides a method for cleavage of a nucleic acid having a base sequence comprising a target sequence, the method comprising steps of:

(a) contacting a nucleic acid having a base sequence comprising a target sequence with a chirally controlled oligonucleotide composition comprising oligonucleotides of a particular oligonucleotide type characterized by:
1) a common base sequence and length, wherein the common base sequence is or comprises a sequence that is complementary to the target sequence in the nucleic acid;
2) a common pattern of backbone linkages; and
3) a common pattern of backbone chiral centers;

which composition is chirally controlled in that it is enriched, relative to a substantially racemic preparation of oligonucleotides having the particular base sequence and length, for oligonucleotides of the particular oligonucleotide type, wherein the oligonucleotide targets a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation.

In some embodiments, the present disclosure provides a method for cleavage of a nucleic acid having a base sequence comprising a target sequence, the method comprising steps of:

(a) contacting a nucleic acid having a base sequence comprising a target sequence with a chirally controlled oligonucleotide composition comprising oligonucleotides of a particular oligonucleotide type characterized by:
1) a common base sequence and length, wherein the common base sequence is or comprises a sequence that is complementary to the target sequence in the nucleic acid;
2) a common pattern of backbone linkages; and
3) a common pattern of backbone chiral centers;

which composition is chirally controlled in that it is enriched, relative to a substantially racemic preparation of oligonucleotides having the particular base sequence and length, for oligonucleotides of the particular oligonucleotide type, wherein the oligonucleotide targets a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation; and (b) cleavage of the nucleic acid mediated by a RNAseH or RNA interference mechanism.

In some embodiments, a provided composition further comprises a selectivity agent selected from: the group of compounds which binds specifically to one or more neurotransmitter transporters selected from the group consisting of a dopamine transporter (DAT), a serotonin transporter (SERT), and a norepinephrine transporter (NET); the group consisting of a dopamine reuptake inhibitor (DRI), a selective serotonin reuptake inhibitor (SSRI), a noradrenaline reuptake inhibitor (NRI), a norepinephrine-dopamine reuptake inhibitor (NDRI), and a serotonin-norepinephrine-dopamine reuptake inhibitor (SNDRI); the group consisting of a triple reuptake inhibitor, a noradrenaline dopamine double reuptake inhibitor, a serotonin single reuptake inhibitor, a noradrenaline single reuptake inhibitor, and a dopamine single reuptake inhibitor; and the group consisting of a dopamine reuptake inhibitor (DRI), a Norepinephrine-Dopamine Reuptake Inhibitor (NDRI) and a serotonin-Norepinephrine-Dopamine Reuptake Inhibitor (SNDRI).

In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of any of any oligonucleotide selected from Tables N1A, N2A, N3A, N4A and 8; and WV-2378, WV-2380, WV-1510, WV-2619, WV-2611, WV-1497, WV-2602, WV-2618, or WV-2601. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2378. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2380. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-1510. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2619. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2611. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-1497. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2602. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2618. In some embodiments, a provided composition comprises oligonucleotides wherein the base sequence, pattern of backbone linkages and/or pattern of backbone chiral centers of the oligonucleotides comprises or consists of the base sequence, pattern of backbone linkages and/or pattern of backbone chiral centers of WV-2601.

In some embodiments, a provided composition comprises oligonucleotides wherein the base sequence, pattern of backbone linkages and/or pattern of backbone chiral centers of the oligonucleotides comprises or consists of the base sequence, and pattern of backbone linkages, and/or pattern of backbone chiral centers of any of any oligonucleotide selected from Tables N1A, N2A, N3A, N4A and 8; and WV-2378, WV-2380, WV-1510, WV-2619, WV-2611, WV-1497, WV-2602, WV-2618, or WV-2601. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2378. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2380. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-1510. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2619. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2611. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-1497. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2602. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2618. In some embodiments, a provided composition comprises oligonucleotides wherein the base sequence, and pattern of backbone linkages, and/or pattern of backbone chiral centers of the oligonucleotides comprises or consists of the base sequence, and pattern of backbone linkages, and/or pattern of backbone chiral centers of WV-2601.

In some embodiments, a provided composition comprises oligonucleotides wherein the base sequence, pattern of backbone linkages and/or pattern of backbone chiral centers of the oligonucleotides comprises or consists of the base sequence, and pattern of backbone linkages, and pattern of backbone chiral centers of any of any oligonucleotide selected from Tables N1A, N2A, N3A, N4A and 8; and WV-2378, WV-2380, WV-1510, WV-2619, WV-2611, WV-1497, WV-2602, WV-2618, or WV-2601. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2378. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2380. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-1510. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2619. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2611. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-1497. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2602. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of WV-2618. In some embodiments, a provided composition comprises oligonucleotides wherein the base sequence, and pattern of backbone linkages, and pattern of backbone chiral centers of the oligonucleotides comprises or consists of the base sequence, and pattern of backbone linkages, and pattern of backbone chiral centers of or WV-2601.

Definitions

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In some embodiments, aliphatic groups contain 1-50 aliphatic carbon atoms. Unless otherwise specified, aliphatic groups contain 1-10 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic or bicyclic $C_3$-$C_{10}$ hydrocarbon that is completely saturated or that contains one or more units of unsaturation, but which is not aromatic, that has a single point of attachment to the rest of the molecule. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkylene: The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Alkenylene: The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl" used alone or as part of a larger moiety as in "aralkyl," "aralkoxy," or "aryloxyalkyl," refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Characteristic structural element: The term "characteristic structural element" refers to a distinctive structural element (e.g., core structure, collection of pendant moieties, sequence element, etc) that is found in all members of a family of polypeptides, small molecules, or nucleic acids, and therefore can be used by those of ordinary skill in the art to define members of the family.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Equivalent agents: Those of ordinary skill in the art, reading the present disclosure, will appreciate that the scope of useful agents in the context of the present disclosure is not limited to those specifically mentioned or exemplified herein. In particular, those skilled in the art will recognize that active agents typically have a structure that consists of a core and attached pendant moieties, and furthermore will appreciate that simple variations of such core and/or pendant moieties may not significantly alter activity of the agent. For example, in some embodiments, substitution of one or more pendant moieties with groups of comparable three-dimensional structure and/or chemical reactivity characteristics may generate a substituted compound or portion equivalent to a parent reference compound or portion. In some embodiments, addition or removal of one or more pendant moieties may generate a substituted compound equivalent to a parent reference compound. In some embodiments, alteration of core structure, for example by addition or removal of a small number of bonds (typically not more than 5, 4, 3, 2, or 1 bonds, and often only a single bond) may generate a substituted compound equivalent to a parent reference compound. In many embodiments, equivalent compounds may be prepared by methods illustrated in general reaction schemes as, for example, described below, or by modifications thereof, using readily available starting materials, reagents and conventional or provided synthesis procedures. In these reactions, it is also possible to make use of variants, which are in themselves known, but are not mentioned here.

Equivalent Dosage: The term "equivalent dosage" is used herein to compare dosages of different pharmaceutically active agents that effect the same biological result. Dosages of two different agents are considered to be "equivalent" to one another in accordance with the present disclosure if they achieve a comparable level or extent of the biological result. In some embodiments, equivalent dosages of different pharmaceutical agents for use in accordance with the present disclosure are determined using in vitro and/or in vivo assays as described herein. In some embodiments, one or more lysosomal activating agents for use in accordance with the present disclosure is utilized at a dose equivalent to a dose of a reference lysosomal activating agent; in some such embodiments, the reference lysosomal activating agent for such purpose is selected from the group consisting of small molecule allosteric activators (e.g., pyrazolpyrimidines), imminosugars (e.g., isofagomine), antioxidants (e.g., n-acetyl-cysteine), and regulators of cellular trafficking (e.g., Rabla polypeptide).

Heteroaliphatic: The term "heteroaliphatic" refers to an aliphatic group wherein one or more units selected from C, CH, $CH_2$, or $CH_3$ are independently replaced by a heteroatom. In some embodiments, a heteroaliphatic group is heteroalkyl. In some embodiments, a heteroaliphatic group is heteroalkenyl.

Heteroaryl: The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" means one or more of oxygen, sulfur, nitrogen, phosphorus, boron, selenium, or silicon (including, any oxidized form of nitrogen, boron, selenium, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)). In some embodiments, a heteroatom is oxygen, sulfur, nitrogen, phosphorus, boron or silicon. In some embodiments, a heteroatom is oxygen, sulfur, nitrogen, phosphorus, or silicon. In some embodiments, a heteroatom is oxygen, sulfur, nitrogen, or silicon. In some embodiments, a heteroatom is oxygen, sulfur, nitrogen, or phosphorus. In some embodiments, a heteroatom is oxygen, sulfur, or nitrogen.

Heterocycle: As used herein, the terms "heterocycle," "heterocyclyl," "heterocyclic radical," and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Intraperitoneal: The phrases "intraperitoneal administration" and "administered intraperitoneally" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Lower alkyl: The term "lower alkyl" refers to a $C_{1-4}$ straight or branched alkyl group. Example lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally substituted: As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR, —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R)S(O)$_2$R$^\dagger$; wherein each R$^\dagger$ is independently hydrogen, C$_{1-6}$ aliphatic which may be substituted as defined below, unsubstituted —OPh, or an unsubstituted 5-6 membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12 membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prodrug: A general, a "prodrug," as that term is used herein and as is understood in the art, is an entity that, when administered to an organism, is metabolized in the body to deliver an active (e.g., therapeutic or diagnostic) agent of interest. Typically, such metabolism involves removal of at least one "prodrug moiety" so that the active agent is formed. Various forms of "prodrugs" are known in the art. For examples of such prodrug moieties, see:

a) *Design of Prodrugs*, edited by H. Bundgaard, (Elsevier, 1985) and Methods in Enzymology, 42:309-396, edited by K. Widder, et al. (Academic Press, 1985);

b) *Prodrugs and Targeted Delivery*, edited by by J. Rautio (Wiley, 2011);

c) *Prodrugs and Targeted Delivery*, edited by by J. Rautio (Wiley, 2011);

d) A Textbook of Drug Design and Development, edited by Krogsgaard-Larsen;

e) Bundgaard, Chapter 5 "Design and Application of Prodrugs", by H. Bundgaard, p. 113-191 (1991);

f) Bundgaard, *Advanced Drug Delivery Reviews*, 8:1-38 (1992);

g) Bundgaard, et al., *Journal of Pharmaceutical Sciences*, 77:285 (1988); and h) Kakeya, et al., *Chem. Pharm. Bull.*, 32:692 (1984).

As with other compounds described herein, prodrugs may be provided in any of a variety of forms, e.g., crystal forms, salt forms etc. In some embodiments, prodrugs are provided as pharmaceutically acceptable salts thereof.

Protecting group: The term "protecting group," as used herein, is well known in the art and includes those described in detail in *Protecting Groups in Organic Synthesis*, T. W. Greene and P. G. M. Wuts, $3^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. June 2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methyl sulfonyl ethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzylthiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, 0-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)

ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, t-butoxymethyl, methoxymethyl, tetrahydropyranyl, 1-ethoxyethyl, 1-(2-chloroethoxy)ethyl, 2-trimethyl silylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenyl sulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group.

In some embodiments, a phosphorus protecting group is a group attached to the internucleotide phosphorus linkage throughout oligonucleotide synthesis. In some embodiments, the phosphorus protecting group is attached to the sulfur atom of the internucleotide phosphorothioate linkage. In some embodiments, the phosphorus protecting group is attached to the oxygen atom of the internucleotide phosphorothioate linkage. In some embodiments, the phosphorus protecting group is attached to the oxygen atom of the internucleotide phosphate linkage. In some embodiments the phosphorus protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 4-[N-methyl-N-(2,2,2-trifluoroacetyl)amino]butyl.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises any one or more of: bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Stereochemically isomeric forms: The phrase "stereochemically isomeric forms," as used herein, refers to different compounds made up of the same atoms bonded by the same sequence of bonds but having different three-dimensional structures which are not interchangeable. In some embodiments of the disclosure, provided chemical compositions may be or include pure preparations of individual stereochemically isomeric forms of a compound; in some embodiments, provided chemical compositions may be or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. In some embodiments, if a particular enantiomer of a compound of the present disclosure is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments of the disclosure, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid" includes any nucleotides, modified variants thereof, analogs thereof, and polymers thereof. The term "polynucleotide" as used herein refer to a polymeric form of nucleotides of any length, either ribonucleotides (RNA) or deoxyribonucleotides (DNA) or modified variants or analogs thereof. These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotide linkages"). The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly-refers to a nucleic acid containing 2 to about 10,000 nucleotide monomer units and wherein the prefix oligo-refers to a nucleic acid containing 2 to about 200 nucleotide monomer units.

Nucleotide: The term "nucleotide" as used herein refers to a monomeric unit of a polynucleotide that consists of a heterocyclic base, a sugar, and one or more phosphate groups or phosphorus-containing internucleotidic linkages. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. Other analogs (e.g., artificial nucleic acids or components which can be incorporated into a nucleic acid or artificial nucleic acid) include: boranophosphate RNA, FANA, locked nucleic acids (LNA), Morpholinos, peptidic nucleic acids (PNA), threose nucleic acid (TNA), and glycol nucleic acid (GNA). These skilled in the art are aware of a variety of modified nucleotides or nucleotide analogs, including, for example, those described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

Nucleoside: The term "nucleoside" refers to a moiety wherein a nucleobase or a modified nucleobase is covalently bound to a sugar or modified sugar.

Sugar: The term "sugar" refers to a monosaccharide in closed and/or open form. Sugars include, but are not limited to, ribose, deoxyribose, pentofuranose, pentopyranose, and hexopyranose moieties. As used herein, the term also encompasses structural analogs used in lieu of conventional sugar molecules, such as glycol, polymer of which forms the backbone of the nucleic acid analog, glycol nucleic acid ("GNA").

Modified sugar: The term "modified sugar" refers to a moiety that can replace a sugar. The modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex.

Chiral ligand: The term "chiral ligand" or "chiral auxiliary" refers to a moiety that is chiral and can be incorporated into a reaction so that the reaction can be carried out with certain stereoselectivity.

Condensing reagent: In a condensation reaction, the term "condensing reagent" refers to a reagent that activates a less reactive site and renders it more susceptible to attack by another reagent. In some embodiments, such another reagent is a nucleophile.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Linking moiety: The term "linking moiety" refers to any moiety optionally positioned between the terminal nucleoside and the solid support or between the terminal nucleoside and another nucleoside, nucleotide, or nucleic acid.

DNA molecule: A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

Coding sequence: A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, be located 3' to the coding sequence. The term "non-coding sequence" or "non-coding region" refers to regions of a polynucleotide sequence that are not translated into amino acids (e.g. 5' and 3' un-translated regions).

Reading frame: The term "reading frame" refers to one of the six possible reading frames, three in each direction, of the double stranded DNA molecule. The reading frame that is used determines which codons are used to encode amino acids within the coding sequence of a DNA molecule.

Antisense: As used herein, an "antisense" nucleic acid molecule comprises a nucleotide sequence which is complementary to a "sense" nucleic acid, which, in some embodiments, encodes a protein, e.g., complementary to the coding strand of a double-stranded cDNA molecule, complementary to an mRNA sequence or complementary to the coding strand of a gene. Accordingly, an antisense nucleic acid molecule can associate via hydrogen bonds to a sense nucleic acid molecule. In some embodiments, an antisense oligonucleotide is an oligonucleotide which participates in RNase H-mediated cleavage; for example, an antisense oligonucleotide hybridizes in a sequence-specific manner to a portion of a target mRNA, thus targeting the mRNA for cleavage by RNase H. In some embodiments, an antisense oligonucleotide is able to differentiate between a wild-type and a mutant allele of a target. In some embodiments, an antisense oligonucleotide significantly participates in RNase H-mediated cleavage of a mutant allele but participates in RNase H-mediated cleavage of a wild-type allele to a much less degree (e.g., does not significantly participate in RNase H-mediated cleavage of the wild-type allele of the target).

Wobble position: As used herein, a "wobble position" refers to the third position of a codon. Mutations in a DNA molecule within the wobble position of a codon, in some embodiments, result in silent or conservative mutations at the amino acid level. For example, there are four codons that encode Glycine, i.e., GGU, GGC, GGA and GGG, thus mutation of any wobble position nucleotide, to any other nucleotide selected from A, U, C and G, does not result in a change at the amino acid level of the encoded protein and, therefore, is a silent substitution.

Silent substitution: a "silent substitution" or "silent mutation" is one in which a nucleotide within a codon is modified, but does not result in a change in the amino acid residue encoded by the codon. Examples include mutations in the third position of a codon, as well in the first position of certain codons such as in the codon "CGG" which, when mutated to AGG, still encodes Arg.

Gene: The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

Complementary DNA: As used herein, a "complementary DNA" or "cDNA" includes recombinant polynucleotides synthesized by reverse transcription of mRNA and from which intervening sequences (introns) have been removed.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and)(BLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g.,)(BLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Heterologous: A "heterologous" region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

Transition mutation: The term "transition mutations" refers to base changes in a DNA sequence in which a pyrimidine (cytidine (C) or thymidine (T)) is replaced by another pyrimidine, or a purine (adenosine (A) or guanosine (G)) is replaced by another purine.

Transversion mutation: The term "transversion mutations" refers to base changes in a DNA sequence in which a pyrimidine (cytidine (C) or thymidine (T)) is replaced by a purine (adenosine (A) or guanosine (G)), or a purine is replaced by a pyrimidine.

Oligonucleotide: the term "oligonucleotide" refers to a polymer or oligomer of nucleotide monomers, containing any combination of nucleobases, modified nucleobases, sugars, modified sugars, phosphate bridges, or modified phosphorus atom bridges (also referred to herein as "internucleotidic linkage", defined further herein).

Oligonucleotides can be single-stranded or double-stranded. As used herein, the term "oligonucleotide strand" encompasses a single-stranded oligonucleotide. A single-stranded oligonucleotide can have double-stranded regions and a double-stranded oligonucleotide can have single-stranded regions. Example oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, G-quadruplex oligonucleotides, RNA activators, immuno-stimulatory oligonucleotides, and decoy oligonucleotides.

Double-stranded and single-stranded oligonucleotides that are effective in inducing RNA interference are also referred to as siRNA, RNAi agent, or iRNA agent, herein. In some embodiments, these RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g., by Dicer, to produce smaller oligonucleotides that can enter the RISC machinery and participate in RISC mediated cleavage of a target sequence, e.g. a target mRNA.

Oligonucleotides of the present disclosure can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Internucleotidic linkage: As used herein, the phrase "internucleotidic linkage" refers generally to the phosphorus-containing linkage between nucleotide units of an oligonucleotide, and is interchangeable with "inter-sugar linkage" and "phosphorus atom bridge," as used above and herein. In some embodiments, an internucleotidic linkage is a phosphodiester linkage, as found in naturally occurring DNA and RNA molecules. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described below. In some embodiments, an internucleotidic linkage is a phosphotriester linkage, phosphorothioate diester linkage

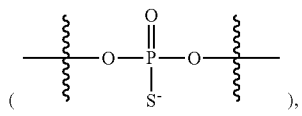

or modified phosphorothioate triester linkage. It is understood by a person of ordinary skill in the art that the internucleotidic linkage may exist as an anion or cation at a given pH due to the existence of acid or base moieties in the linkage.

Unless otherwise specified, when used with an oligonucleotide sequence, each of s, s1, s2, s3, s4, s5, s6 and s7 independently represents the following modified internucleotidic linkage as illustrated in Table 1, below.

TABLE 1

| Symbol | Example Modified Internucleotidic Linkage. Modified Internucleotidic Linkage |
|---|---|
| s | phosphorothioate |
| s1 | |
| s2 | |
| s3 | |
| s4 | |
| s5 | |
| s6 | |
| s7 | |

TABLE 1-continued
Example Modified Internucleotidic Linkage.
| Symbol | Modified Internucleotidic Linkage |
|---|---|
| s8 | 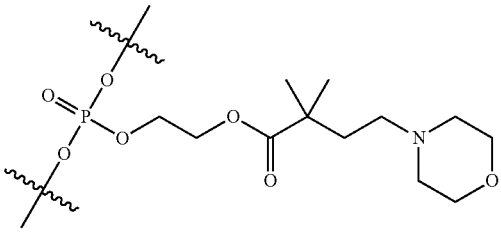 |
| s9 | 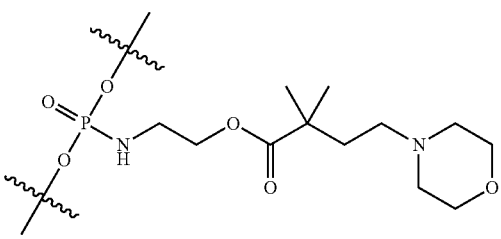 |
| s10 | 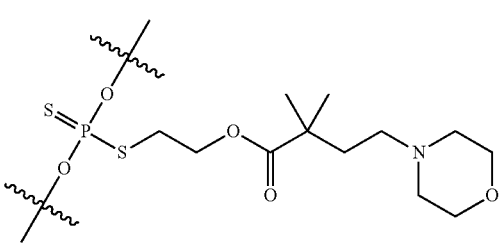 |
| s11 | 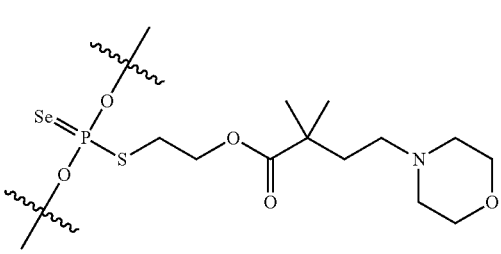 |
| s12 | 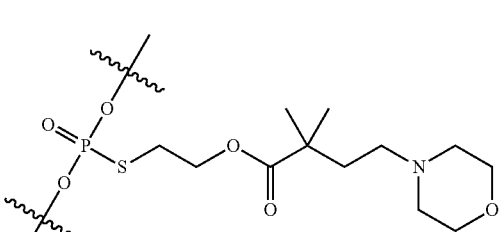 |
| s13 | 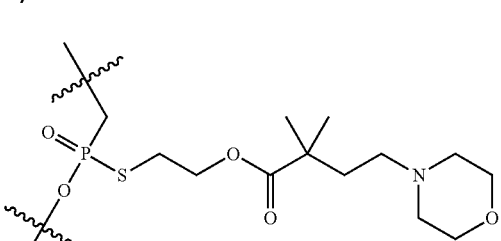 |
| s14 | 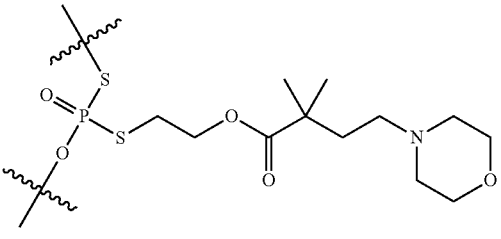 [SMILES: *OP(=O)(S*)SCCOC(=O)C(C)(C)CCN1CCOCC1] |
| s15 | 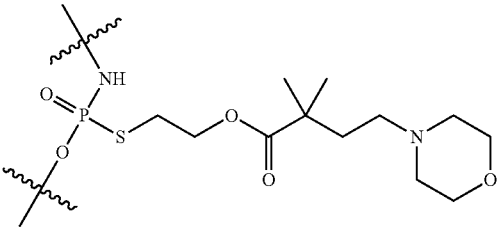 [SMILES: *NP(=O)(O*)SCCOC(=O)C(C)(C)CCN1CCOCC1] |
| s16 | 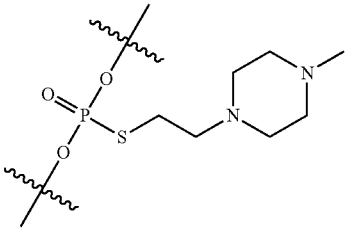 [SMILES: *OP(=O)(O*)SCCN1CCN(C)CC1] |
| s17 | 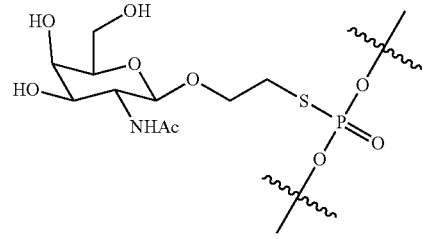 [SMILES: *OP(=O)(O*)SCCOC1OC(CO)C(O)C(O)C1NC(C)=O] |
| s18 | 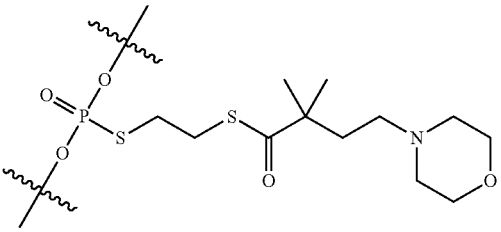 [SMILES: *OP(=O)(O*)SCCSC(=O)C(C)(C)CCN1CCOCC1] |
For instance, (Rp, Sp)-ATsCs1GA has 1) a phosphorothioate internucleotidic linkage
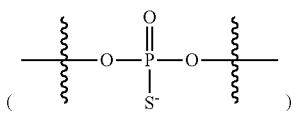
between T and C; and 2) a phosphorothioate triester internucleotidic linkage having the structure of

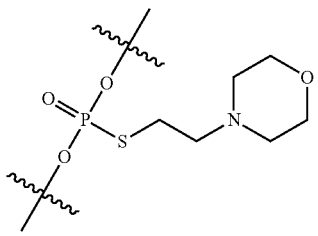 [SMILES: *OP(=O)(O*)SCCN1CCOCC1]

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively. For instance, All-(Rp)-GsCsCsTsCsAsGsTsCsTsGsCsTsTsC-sGsCsAsCsC (SEQ ID NO: 2) indicates that all the chiral linkage phosphorus atoms in the oligonucleotide have Rp configuration; All-(Sp)-GsCsCsTsCsAsGsTsCsTsGsCsTsT-sCsGsCsAsCsC (SEQ ID NO: 3) indicates that all the chiral linkage phosphorus atoms in the oligonucleotide have Sp configuration.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR¹" groups in formula I). Oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. The present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in predetermined relative amounts.

Chiral control: As used herein, "chiral control" refers to an ability to control the stereochemical designation of every chiral linkage phosphorus within an oligonucleotide strand. The phrase "chirally controlled oligonucleotide" refers to an oligonucleotide which exists in a single diastereomeric form with respect to the chiral linkage phosphorus. Chirally controlled oligonucleotides are prepared from chirally controlled oligonucleotide synthesis.

Chirally controlled oligonucleotide composition: As used herein, the phrase "chirally controlled oligonucleotide composition" refers to an oligonucleotide composition that contains predetermined levels of individual oligonucleotide types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a mixture of multiple oligonucleotide types. Example chirally controlled oligonucleotide compositions are described further herein.

Chirally pure: as used herein, the phrase "chirally pure" is used to describe a chirally controlled oligonucleotide composition in which all of the oligonucleotides exist in a single diastereomeric form with respect to the linkage phosphorus.

Chirally uniform: as used herein, the phrase "chirally uniform" is used to describe an oligonucleotide molecule or type in which all nucleotide units have the same stereochemistry at the linkage phosphorus. For instance, an oligonucleotide whose nucleotide units all have Rp stereochemistry at the linkage phosphorus is chirally uniform. Likewise, an oligonucleotide whose nucleotide units all have Sp stereochemistry at the linkage phosphorus is chirally uniform.

Predetermined: By predetermined is meant deliberately selected, for example as opposed to randomly occurring or achieved. Those of ordinary skill in the art, reading the present specification, will appreciate that the present disclosure provides new and surprising technologies that permit selection of particular oligonucleotide types for preparation and/or inclusion in provided compositions, and further permits controlled preparation of precisely the selected particular types, optionally in selected particular relative amounts, so that provided compositions are prepared. Such provided compositions are "predetermined" as described herein. Compositions that may contain certain individual oligonucleotide types because they happen to have been generated through a process that cannot be controlled to intentionally generate the particular oligonucleotide types is not a "predetermined" composition. In some embodiments, a predetermined composition is one that can be intentionally reproduced (e.g., through repetition of a controlled process).

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is P* of formula I. In some embodiments, a linkage phosphorus atom is chiral. In some embodiments, a chiral linkage phosphorus atom is P* of formula I.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X—L-R' wherein each of X, L and R¹ is independently as defined and described herein and below.

Blockmer: the term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphorus linkage are referred to as a "block".

In some embodiments, a blockmer is a "stereoblockmer," e.g., at least two consecutive nucleotide units have the same stereochemistry at the linkage phosphorus. Such at least two consecutive nucleotide units form a "stereoblock." For instance, (Sp, Sp)-ATsCs1GA is a stereoblockmer because at least two consecutive nucleotide units, the Ts and the Cs1, have the same stereochemistry at the linkage phosphorus (both Sp). In the same oligonucleotide (Sp, Sp)-ATsCs1GA, TsCs1 forms a block, and it is a stereoblock.

In some embodiments, a blockmer is a "P-modification blockmer," e.g., at least two consecutive nucleotide units have the same modification at the linkage phosphorus. Such at least two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block. For instance, (Rp, Rp, Rp, Rp, Rp, Sp, Sp, Sp)-AAsTsCsGsAs1Ts1Cs1Gs1ATCG (SEQ ID NO: 4) is a stereoblockmer with respect to the stereoblock AsTsCsGsAs1 (all Rp at linkage phosphorus) or Ts1Cs1Gs1 (all Sp at linkage phosphorus), a P-modification blockmer with respect to the P-modification block AsTsCsGs (all s linkage) or As1Ts1Cs1Gs1 (all s1 linkage), or a linkage blockmer with respect to the linkage block AsTsCsGs (all Rp at linkage phosphorus and all s linkage) or Ts1Cs1Gs1 (all Sp at linkage phosphorus and all s1 linkage).

Altmer: the term "altmer," as used herein, refers to an oligonucleotide strand whose pattern of structural features characterizing each individual nucleotide unit is characterized in that no two consecutive nucleotide units of the oligonucleotide strand share a particular structural feature at the internucleotidic phosphorus linkage. In some embodiments, an altmer is designed such that it comprises a repeating pattern. In some embodiments, an altmer is designed such that it does not comprise a repeating pattern.

In some embodiments, an altmer is a "stereoaltmer," e.g., no two consecutive nucleotide units have the same stereochemistry at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTsGsCsTsTsCsGsCsAsCsC (SEQ ID NO: 5).

In some embodiments, an altmer is a "P-modification altmer" e.g., no two consecutive nucleotide units have the same modification at the linkage phosphorus. For instance, All-(Sp)-CAs1GsT, in which each linkage phosphorus has a different P-modification than the others.

In some embodiments, an altmer is a "linkage altmer," e.g., no two consecutive nucleotide units have identical stereochemistry or identical modifications at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCs1CsTs1CsAs1GsTs1CsTs1GsCs1TsTs2CsGs3Cs As4CsC (SEQ ID NO: 6).

Unimer: the term "unimer," as used herein, refers to an oligonucleotide strand whose pattern of structural features characterizing each individual nucleotide unit is such that all nucleotide units within the strand share at least one common structural feature at the internucleotidic phosphorus linkage. By common structural feature is meant common stereochemistry at the linkage phosphorus or a common modification at the linkage phosphorus.

In some embodiments, a unimer is a "stereounimer," e.g., all nucleotide units have the same stereochemistry at the linkage phosphorus. For instance, All-(Sp)-CsAs1GsT, in which all the linkages have Sp phosphorus.

In some embodiments, a unimer is a "P-modification unimer", e.g., all nucleotide units have the same modification at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTsGsCsTsTsCsGsCsAsCsC (SEQ ID NO: 7), in which all the internucleotidic linkages are phosphorothioate diester.

In some embodiments, a unimer is a "linkage unimer," e.g., all nucleotide units have the same stereochemistry and the same modifications at the linkage phosphorus. For instance, All-(Sp)-GsCsCsTsCsAsGsTsCsTsGsCsTsTsCsGsCsAsCsC (SEQ ID NO: 8), in which all the internucleotidic linkages are phosphorothioate diester having Sp linkage phosphorus.

Gapmer: as used herein, the term "gapmer" refers to an oligonucleotide strand characterized in that at least one internucleotidic phosphorus linkage of the oligonucleotide strand is a phosphate diester linkage, for example such as those found in naturally occurring DNA or RNA. In some embodiments, more than one internucleotidic phosphorus linkage of the oligonucleotide strand is a phosphate diester linkage such as those found in naturally occurring DNA or RNA. For instance, All-(Sp)-CAs1GsT, in which the internucleotidic linkage between C and A is a phosphate diester linkage.

Skipmer: as used herein, the term "skipmer" refers to a type of gapmer in which every other internucleotidic phosphorus linkage of the oligonucleotide strand is a phosphate diester linkage, for example such as those found in naturally occurring DNA or RNA, and every other internucleotidic phosphorus linkage of the oligonucleotide strand is a modified internucleotidic linkage. For instance, All-(Sp)-AsTCs1GAs2TCs3G.

For purposes of this disclosure, the chemical elements are identified in accordance with the Periodic Table of the Elements, CAS version, Handbook of Chemistry and Physics, 67th Ed., 1986-87, inside cover.

The methods and structures described herein relating to compounds and compositions of the disclosure also apply to the pharmaceutically acceptable acid or base addition salts and all stereoisomeric forms of these compounds and compositions.

Figure 31:
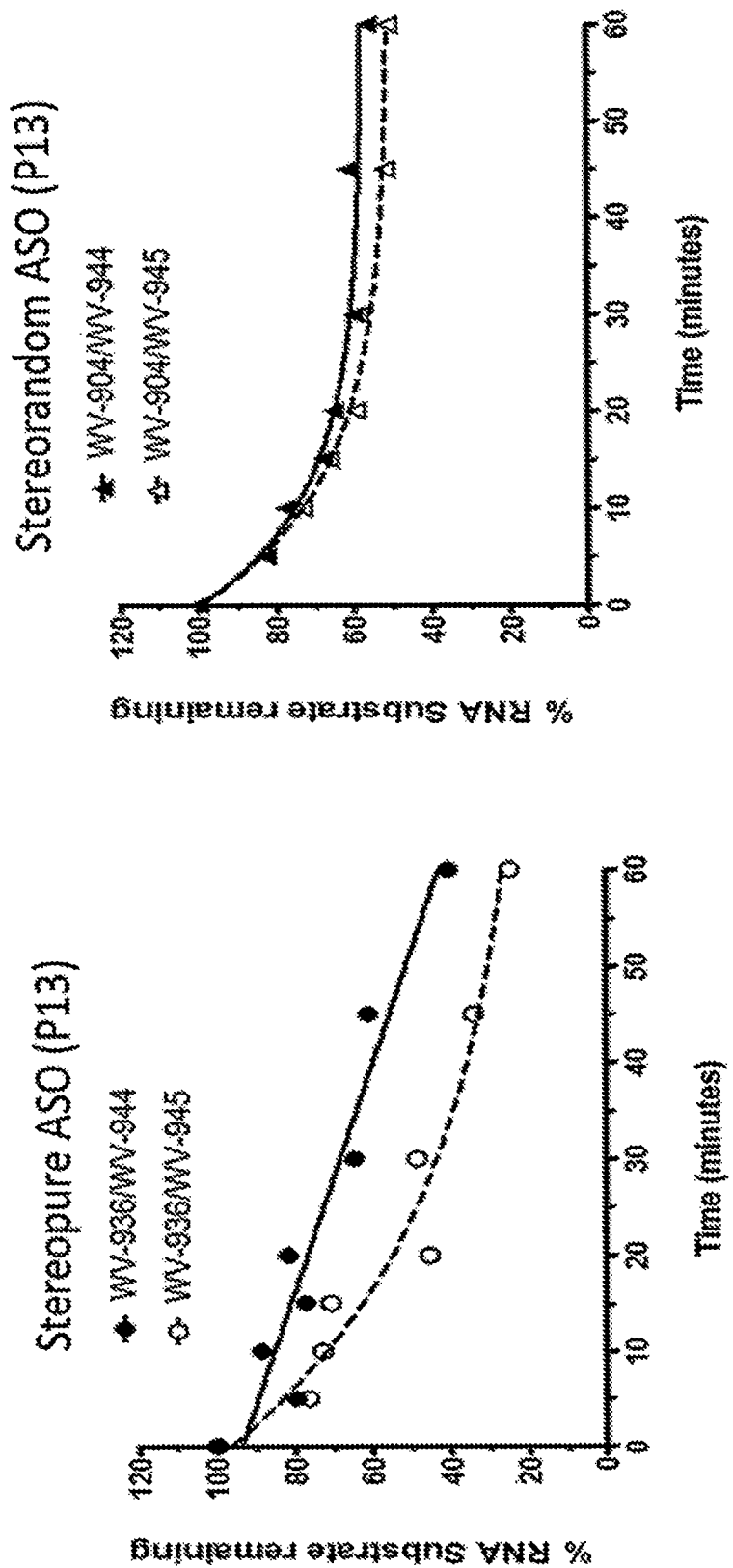
Figure 31:
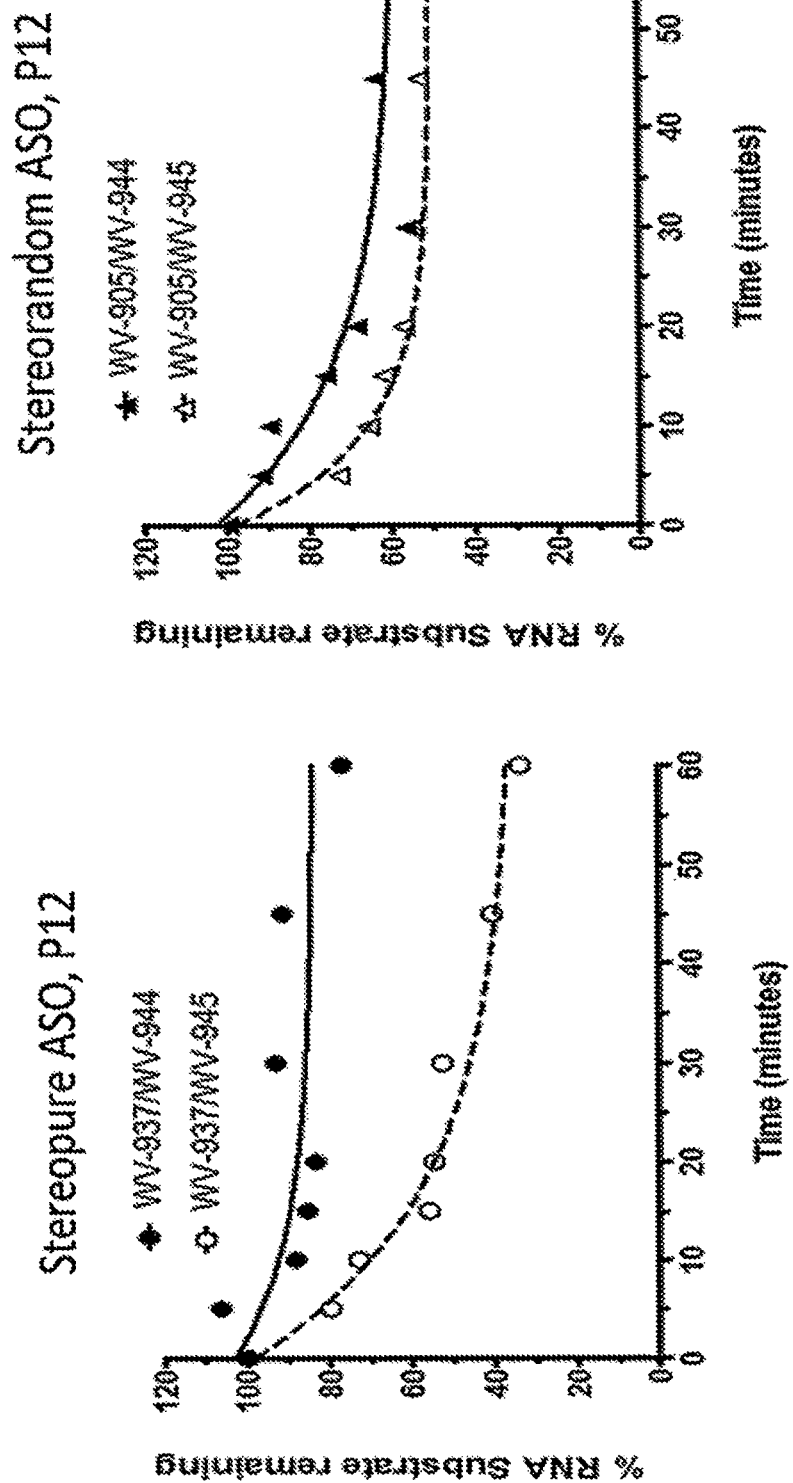

FIG. 31. Example RNA cleavage rates. Duplexes were incubated with RNase H1C in the presence of 1×RNase H buffer at 37° C. Reactions were quenched at fixed time points by addition of 30 mM Na$_2$EDTA. Cleavage rates were determined by measuring amount of full length RNA remaining in the reaction mixtures. Compositions used include: WV-944 (SEQ ID NO: 791), WV-945 (SEQ ID NO: 792), WV-936 (SEQ ID NO: 162), WV-904 (SEQ ID NO: 130), WV-937 (SEQ ID NO: 163), WV-905 (SEQ ID NO: 131), WV-938 (SEQ ID NO: 164), WV-906 (SEQ ID NO: 132), WV-939 (SEQ ID NO: 165), WV-907 (SEQ ID NO: 133), WV-940 (SEQ ID NO: 166), WV-908 (SEQ ID NO: 34), WV-941 (SEQ ID NO: 167), and WV-909 (SEQ ID NO: 135).

Figure 32:
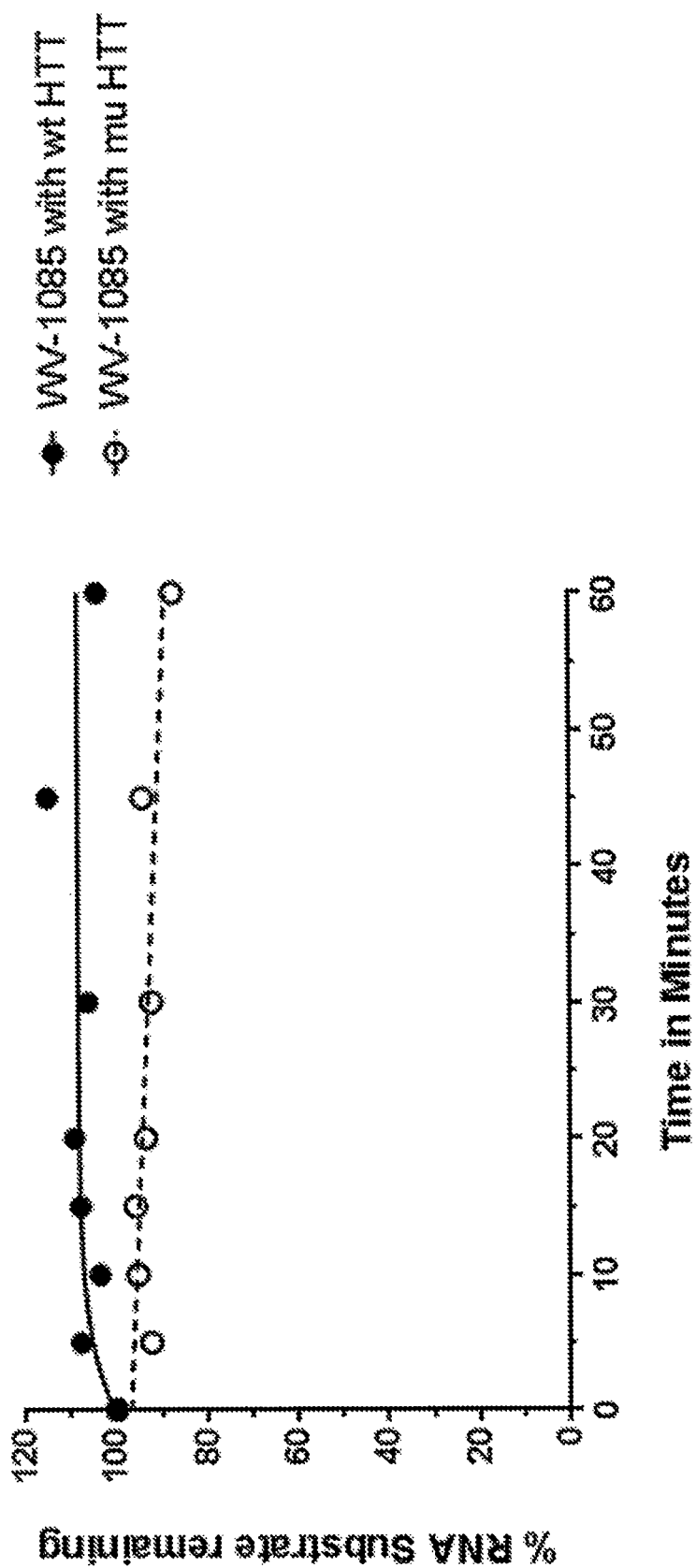
Figure 32:
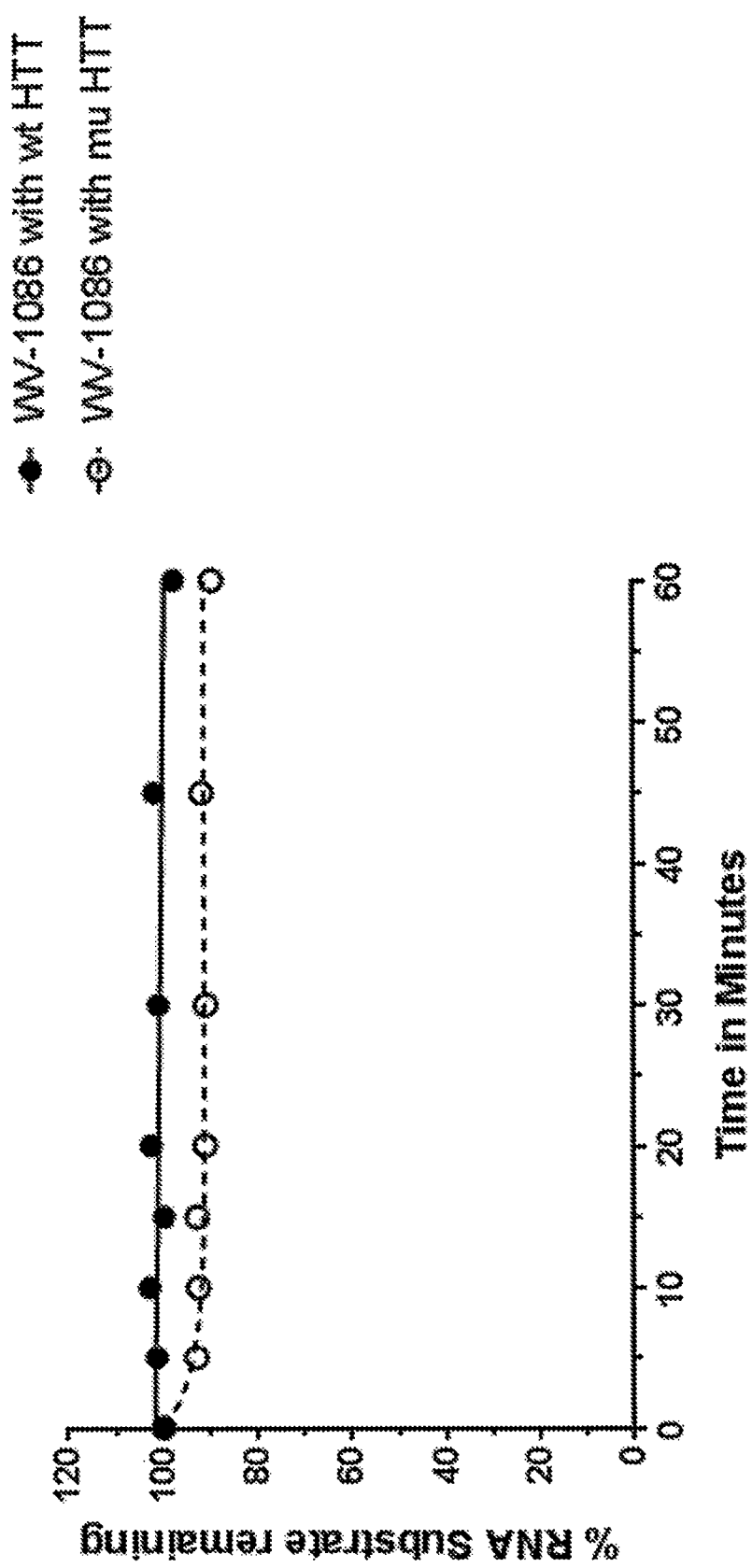
Figure 32:
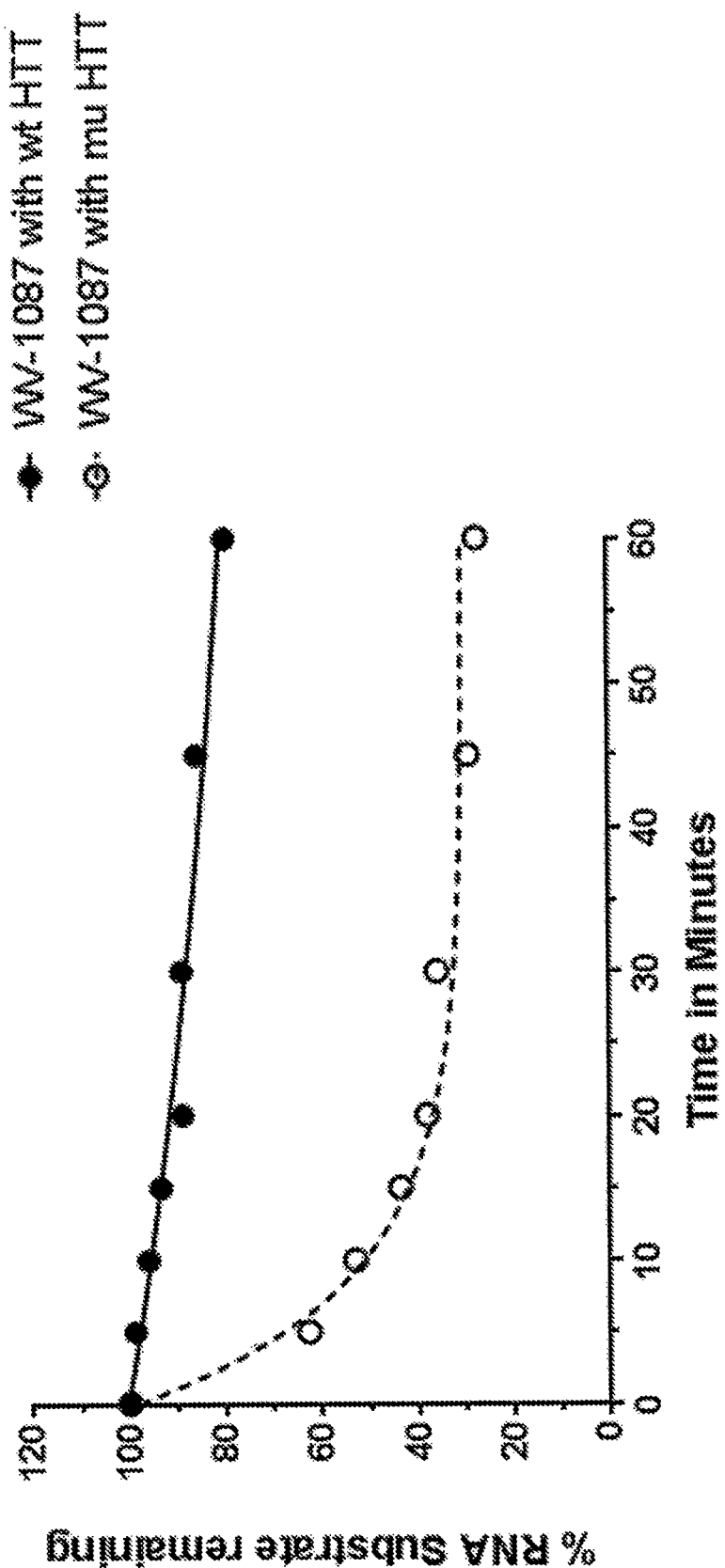
Figure 32:
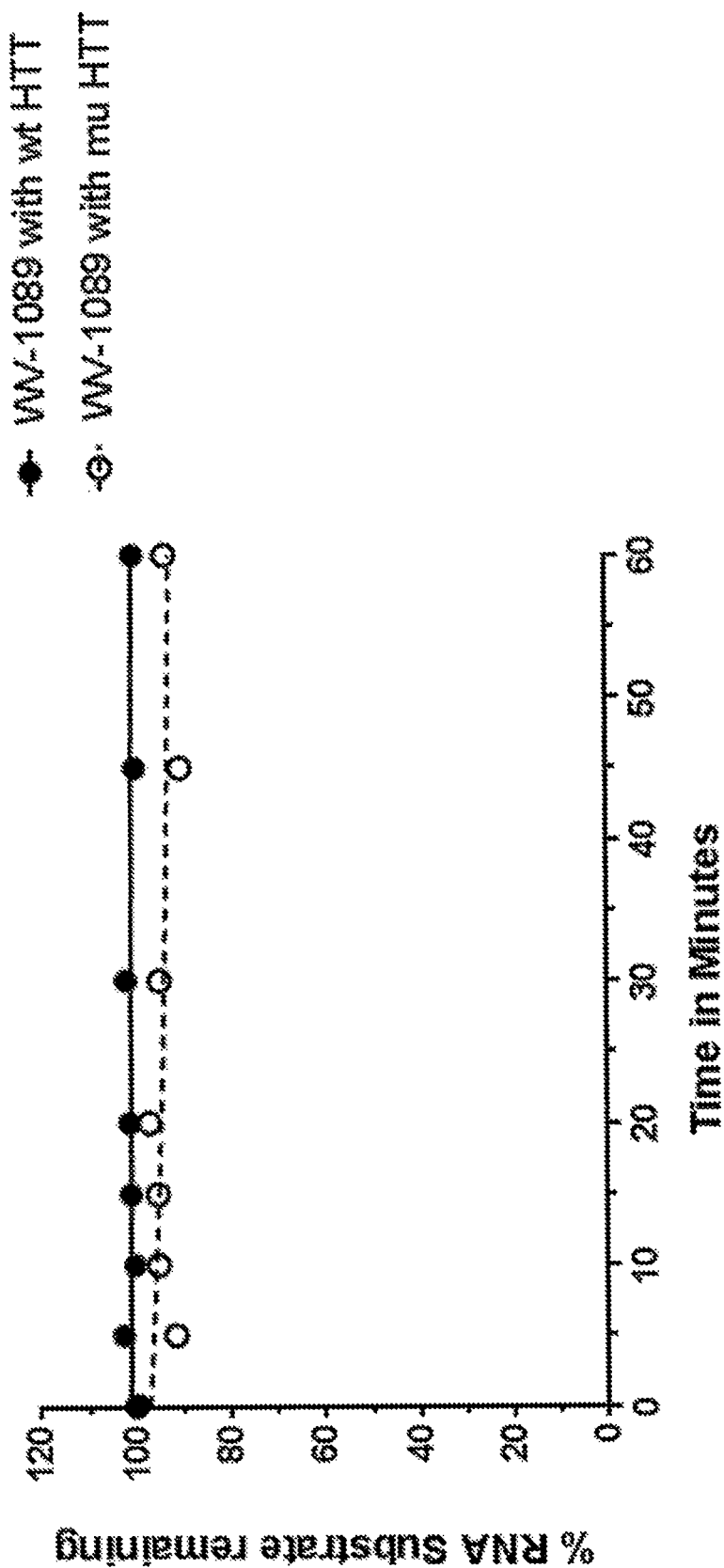
Figure 32:
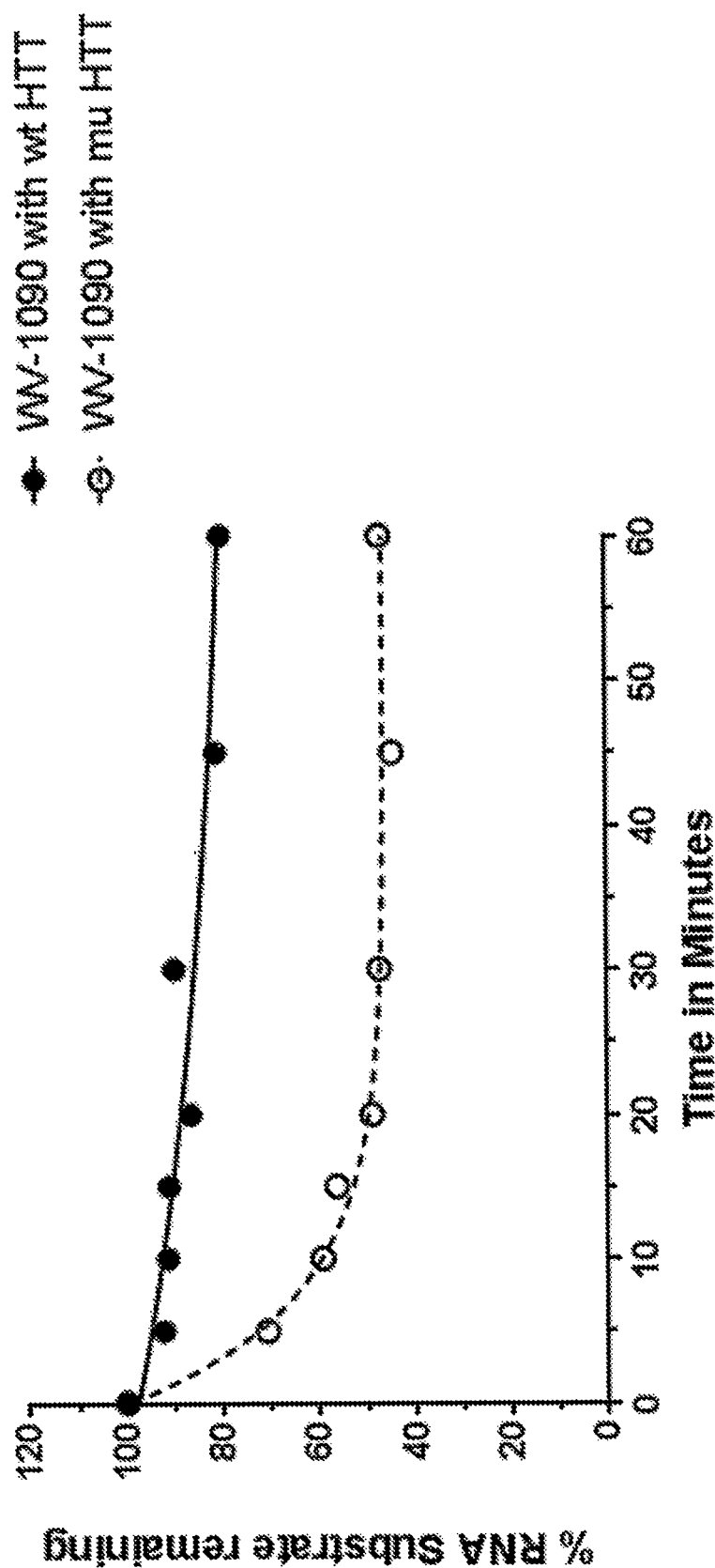
Figure 32:
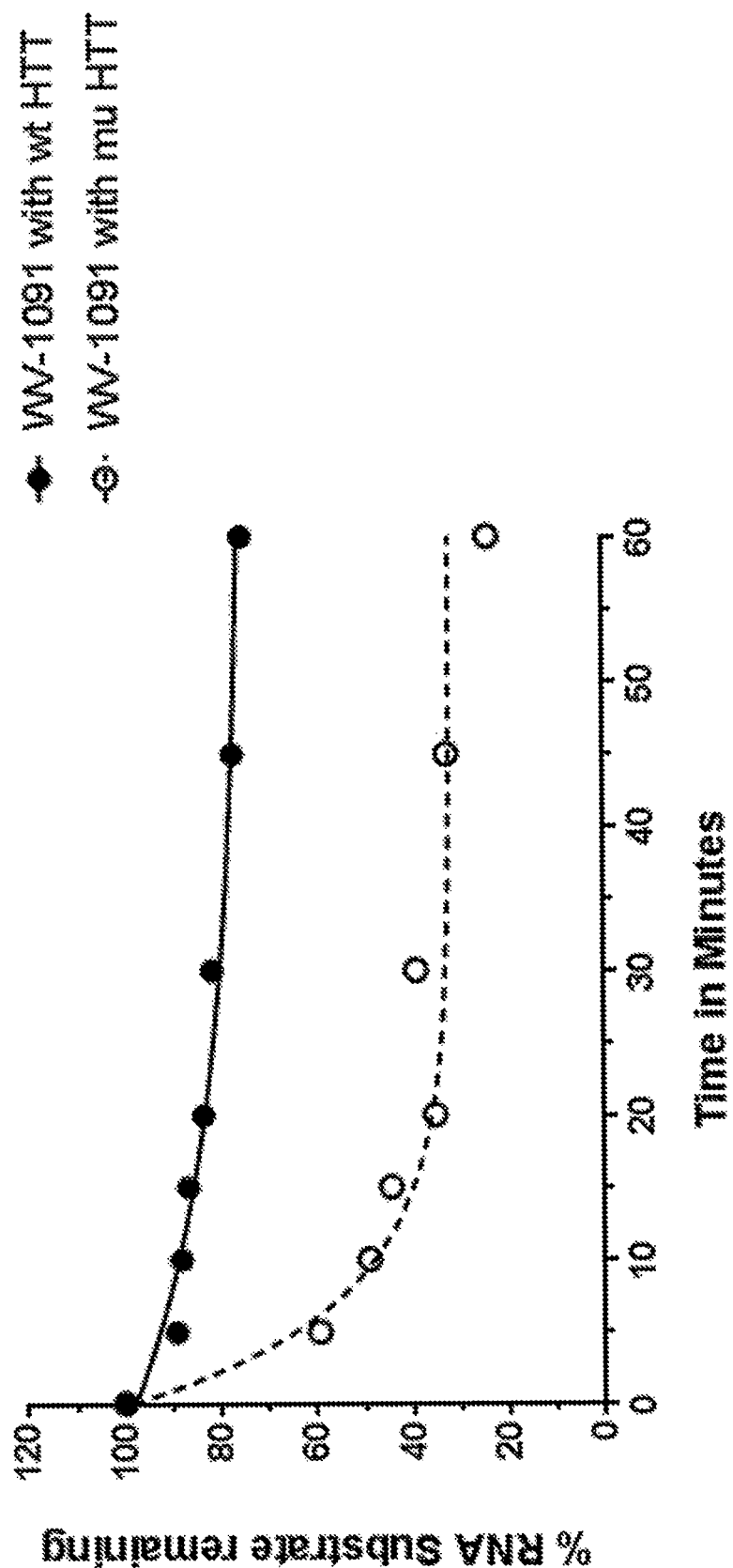
Figure 32:
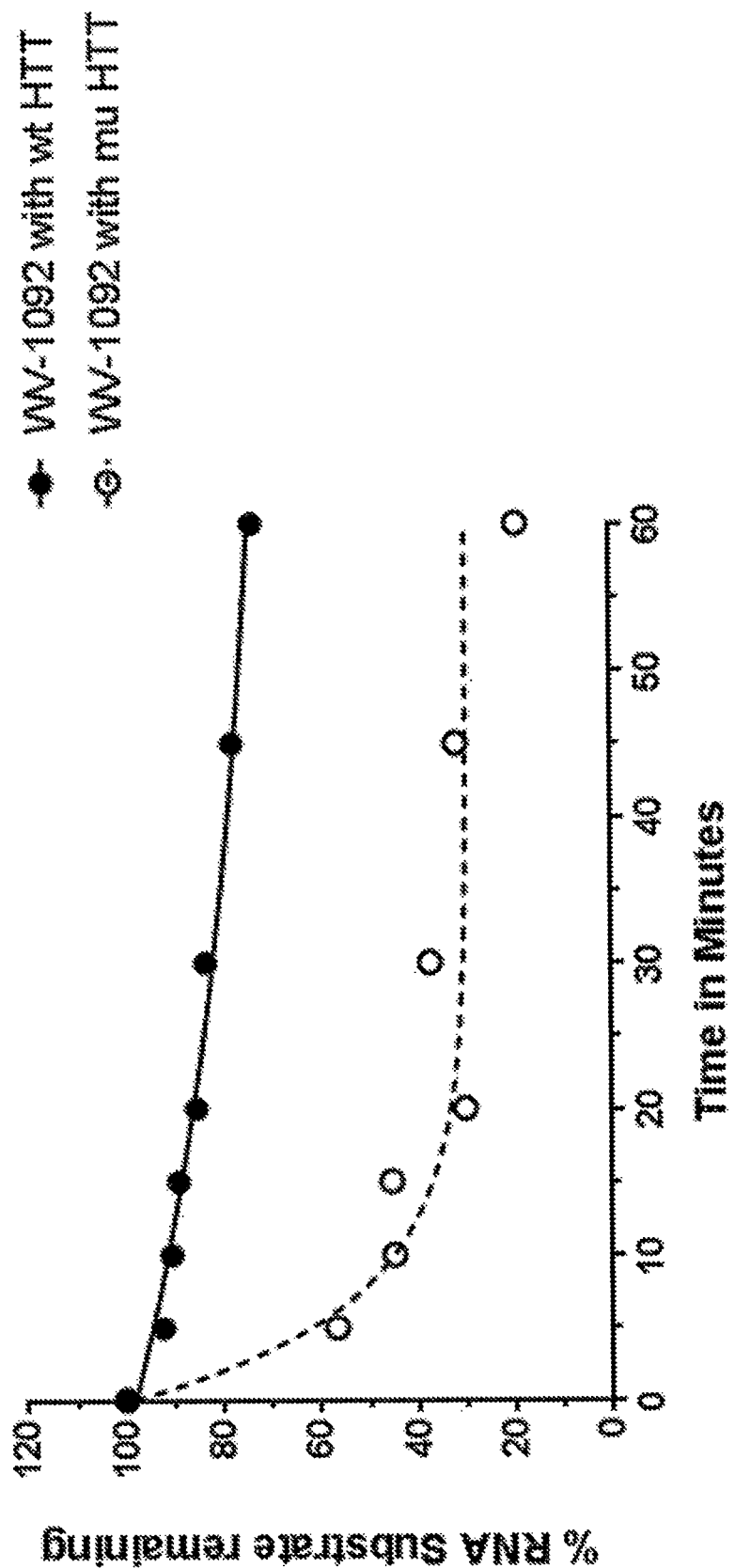
Figure 32:
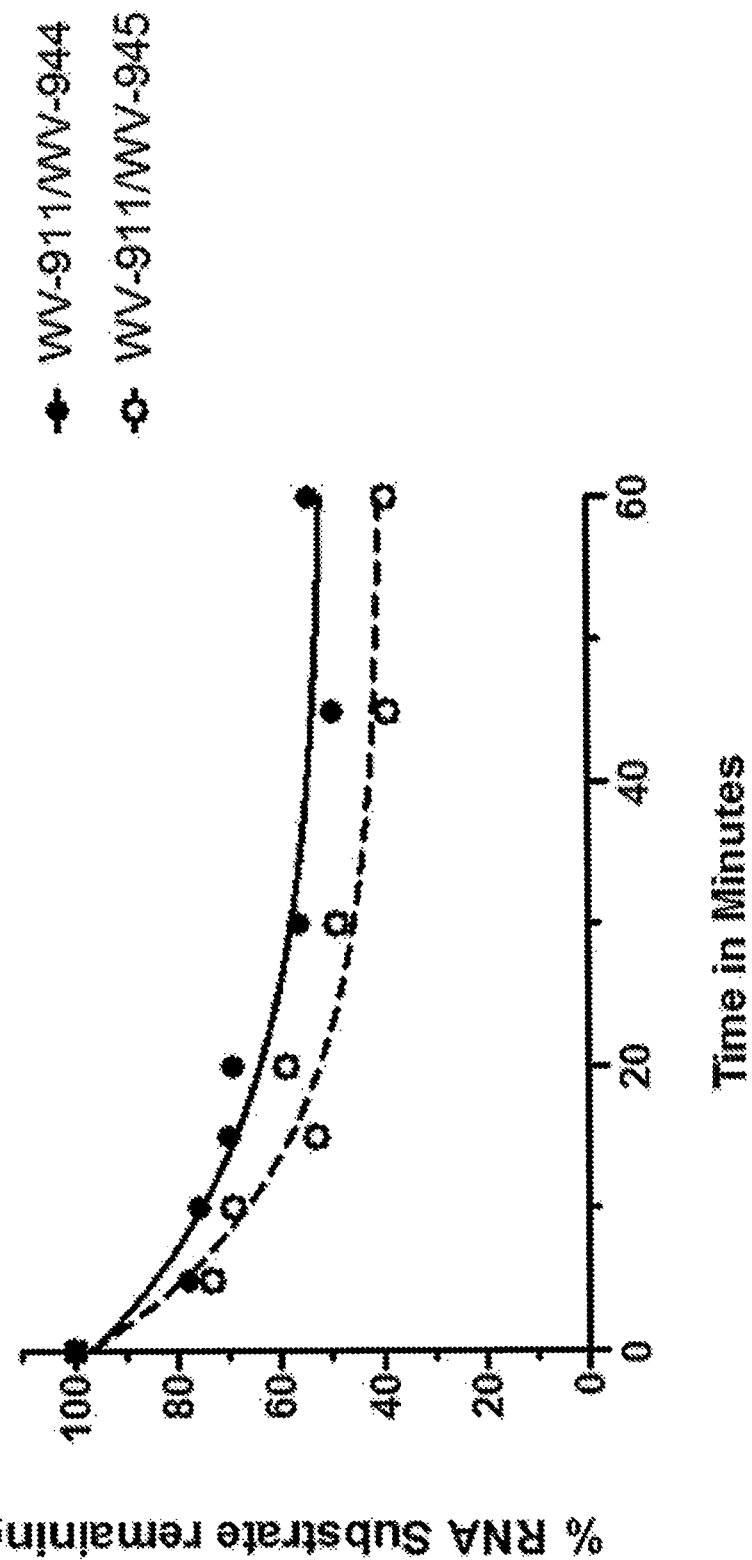
Figure 32:
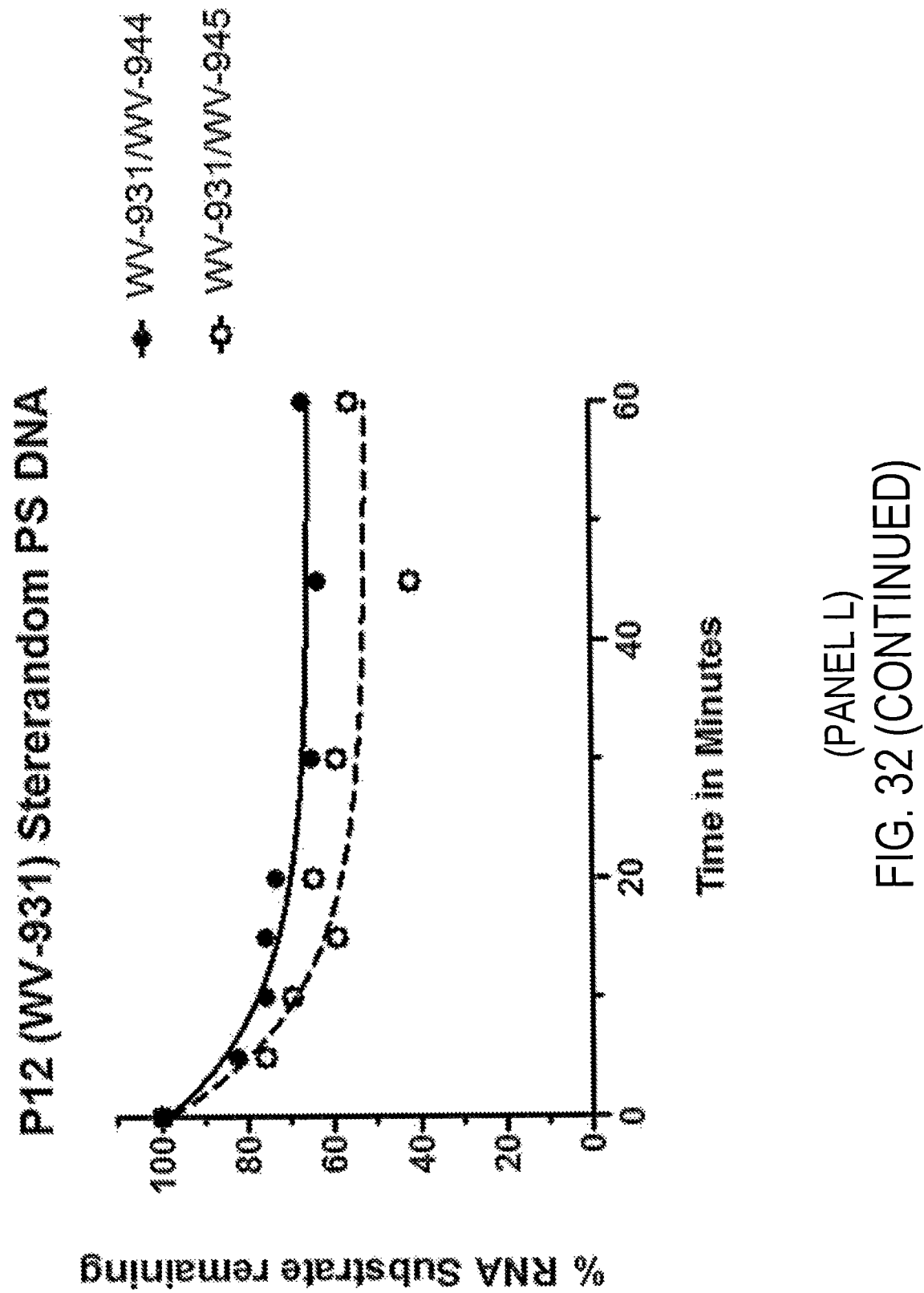
Figure 32:
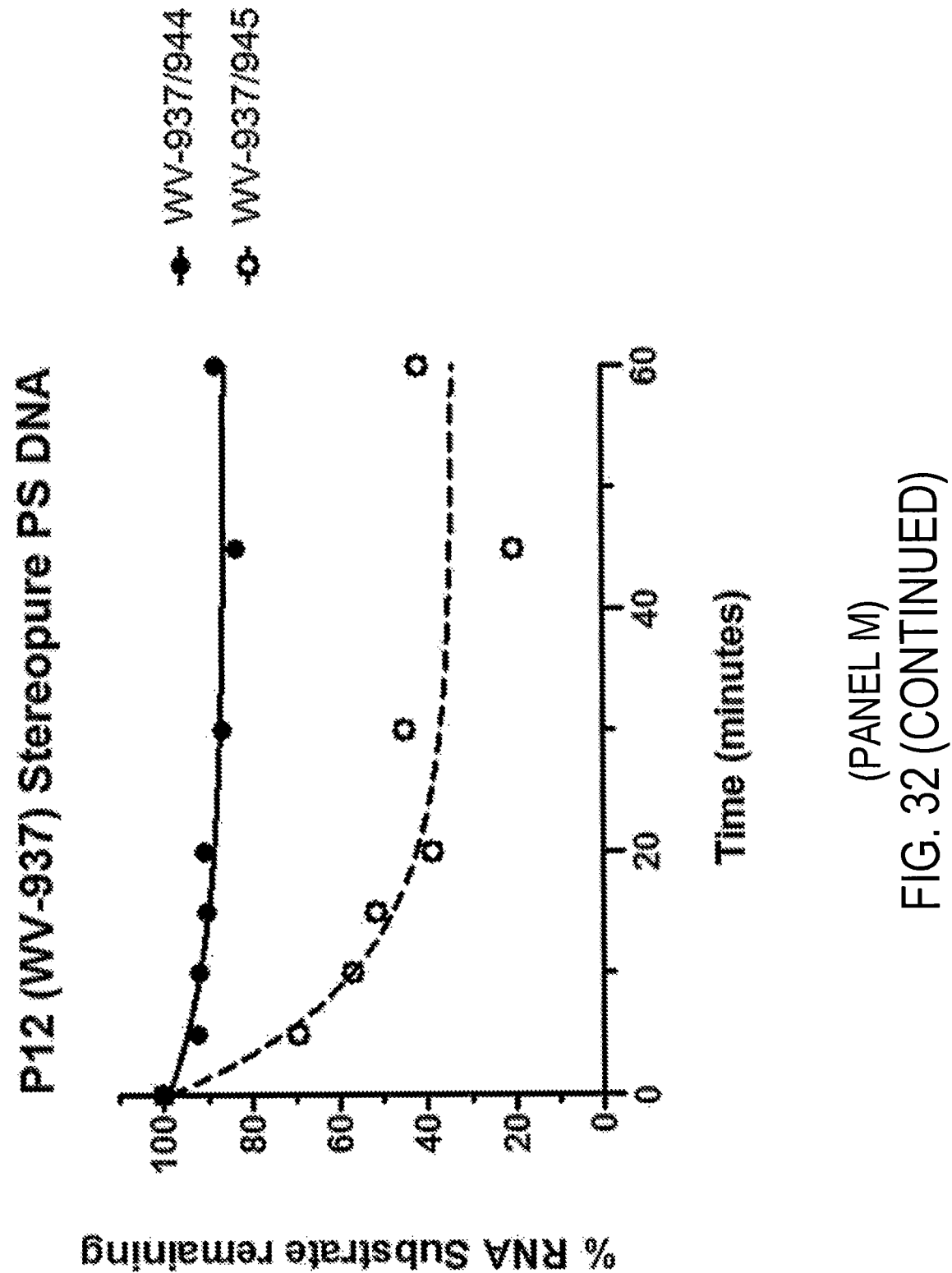
Figure 32:
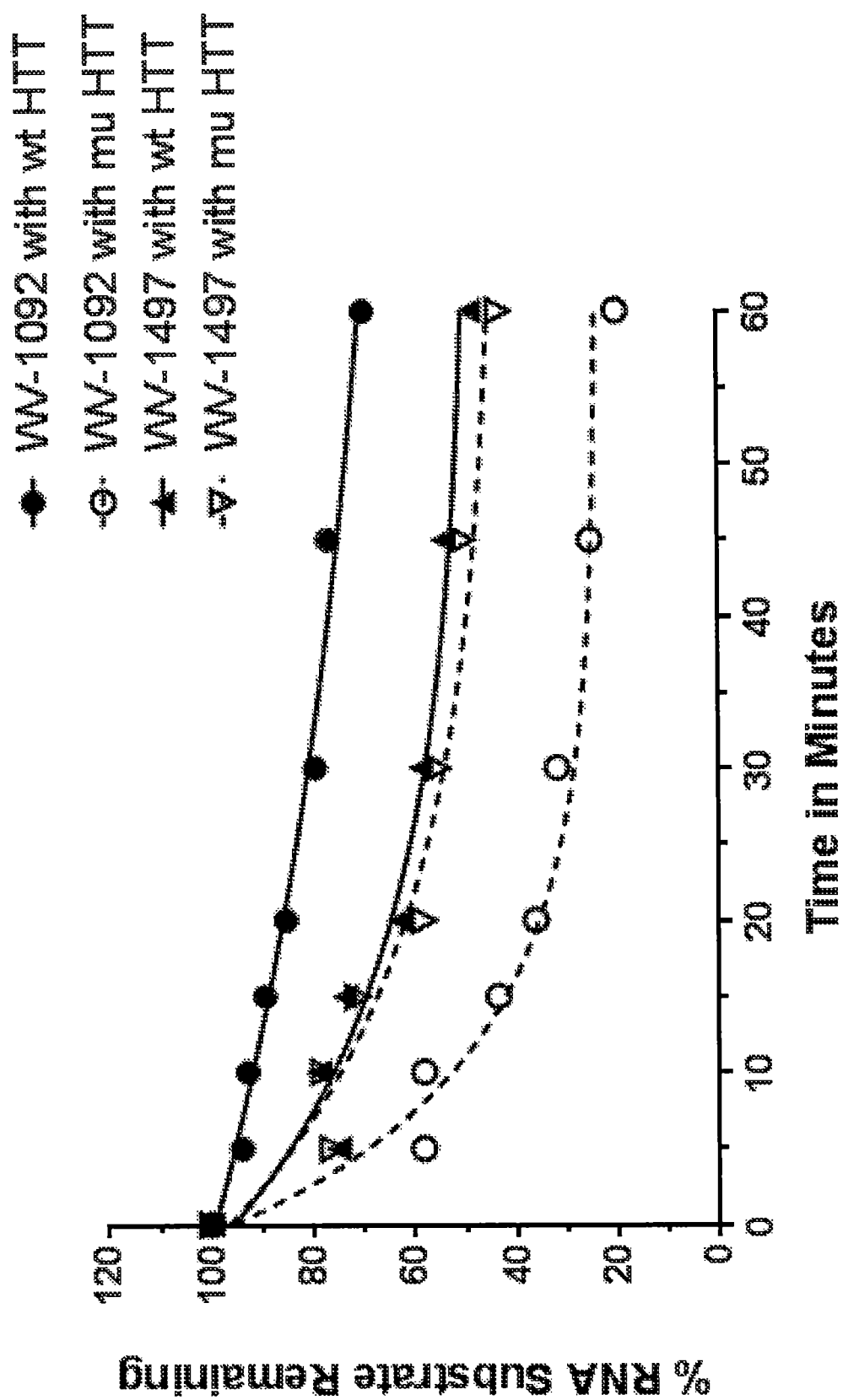

FIG. 32. A-N: RNA cleavage rates in RNase H assay for certain compositions targeting rs362307. Some of these compositions are stereorandom and some chirally controlled. Compositions used include: WV-1085, WV-1086, WV-1087, WV-1088, WV-1089, WV-1090, WV-1091, WV-1092, WV-905, WV-944, WV-945, WV-911, WV-917, WV-931, WV-937, and WV-1497.

Figure 33:
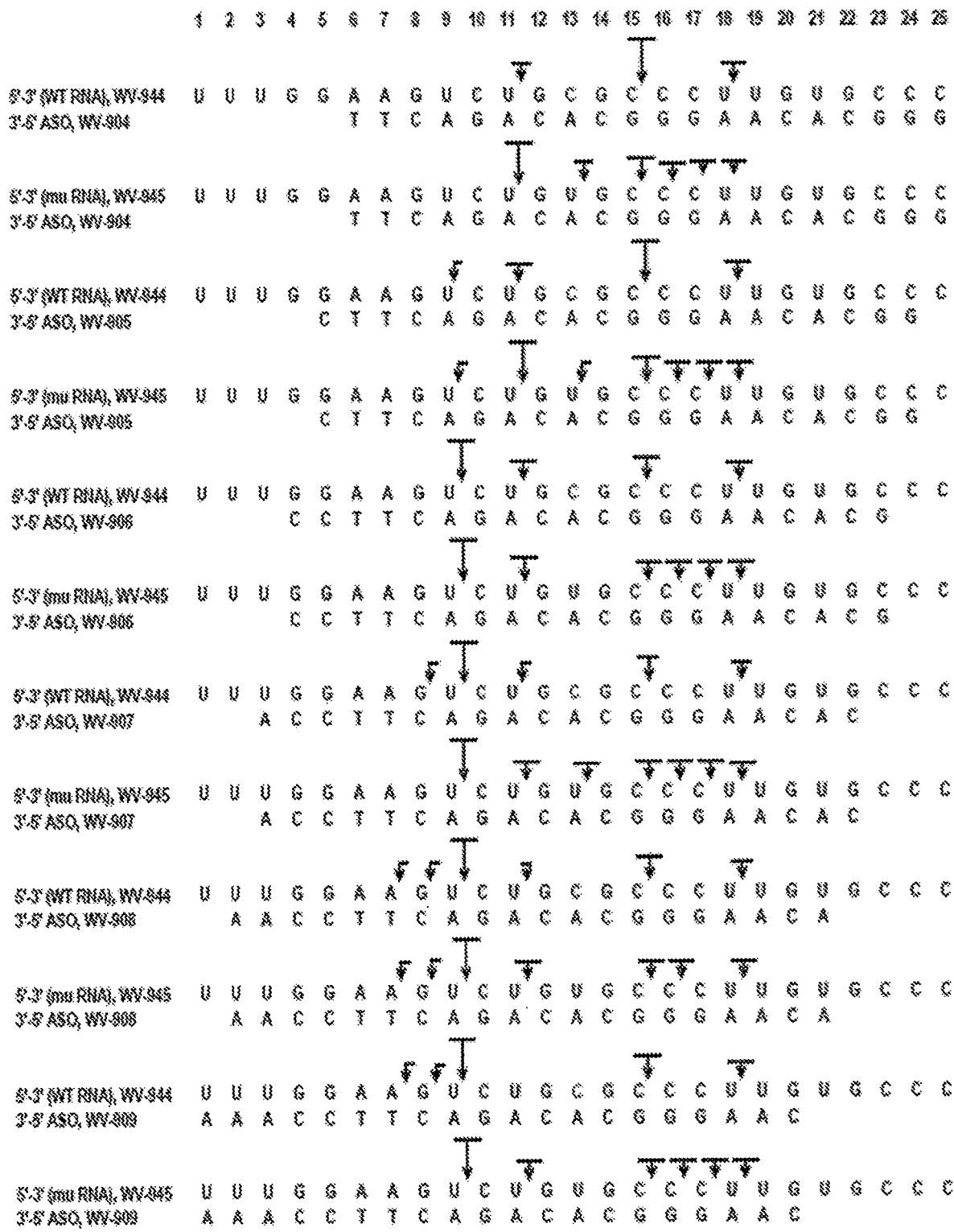

FIG. 33. A: Example cleavage maps. Cleavage maps were derived from reaction mixtures obtained after 5 minutes of incubation of respective duplexes with RNase H1C in the presence of 1×RNaseH buffer at 37° C. B: Legend. Arrows indicate sites of cleavage. (┬) indicates that both fragments, 5'-phosphate species as well as 3'-OH species were identified. (┌) indicates that only 5'-OH 3'-OH species was detected and (┐) indicates that 5'-Phosphate component was detected. Length of an arrow signifies the amount of fragment present in the reaction mixture which was determined from the ratio of UV peak area to theoretical extinction coefficient of that fragment. Only in the cases where 5'-OH 3'-OH fragments were not detected in the reaction mixture, the 5'-phosphate species peak was used for quantification. Compositions used include: WV-944 (SEQ ID NO: 791), WV-945 (SEQ ID NO: 792), WV-904 (SEQ ID NO: 130), WV-905 (SEQ ID NO: 131), WV-906 (SEQ ID NO: 132), WV-907 (SEQ ID NO: 133), WV-908 (SEQ ID NO: 134), and WV-909 (SEQ ID NO: 135).

Figure 34:
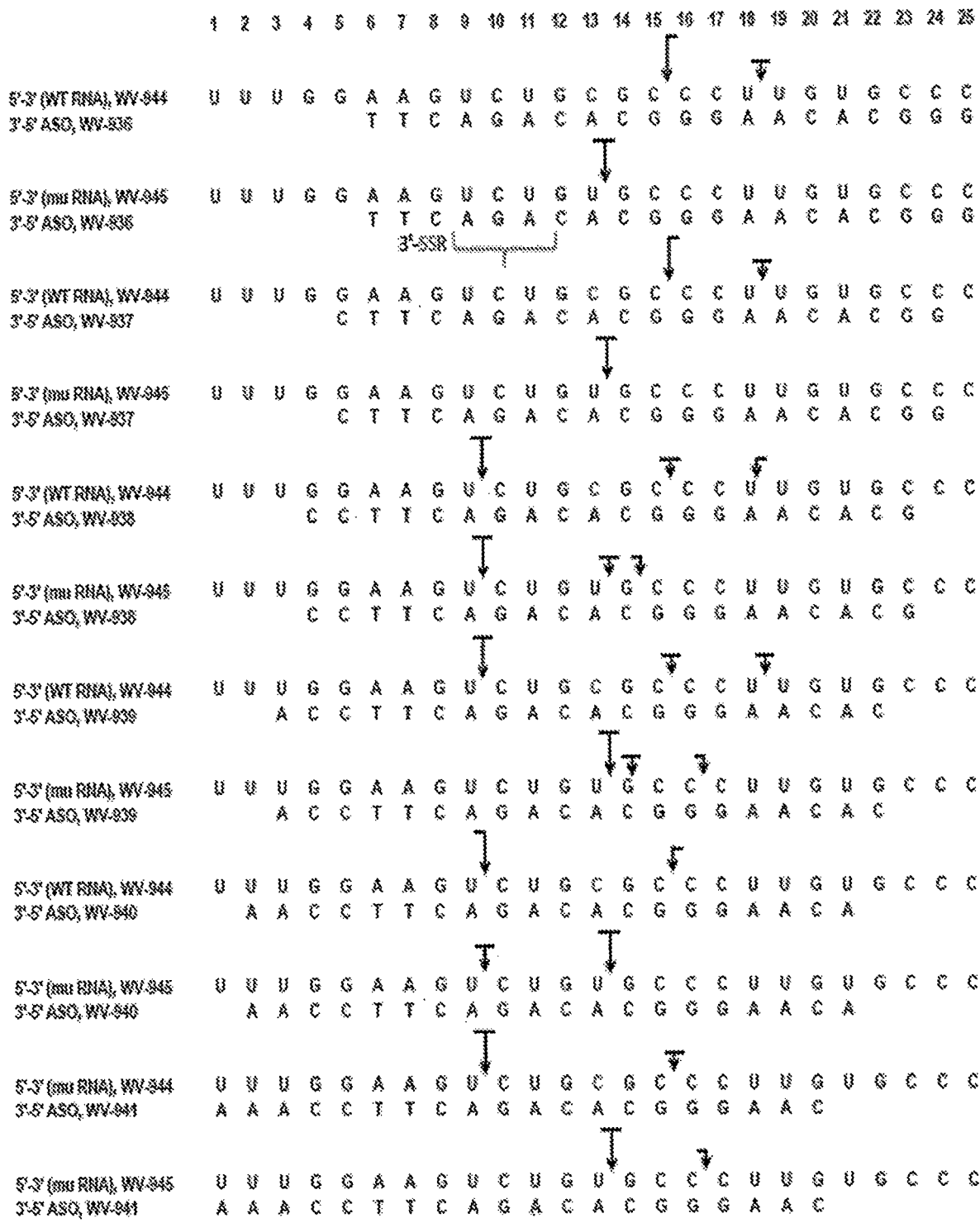

FIG. 34. Example cleavage maps. Example cleavage maps. Cleavage maps were derived from reaction mixtures obtained after 30 minutes of incubation of respective duplexes with RNase H1C in the presence of 1×RNase H buffer at 37° C. For legend, see FIG. 33. Compositions used include: WV-944 (SEQ ID NO: 791), WV-945 (SEQ ID NO: 792), WV-936 (SEQ ID NO: 162), WV-937 (SEQ ID NO: 163), WV-938 (SEQ ID NO: 164), WV-939 (SEQ ID NO: 165), WV-940 (SEQ ID NO: 166), WV-941 (SEQ ID NO: 167), WV-1085 (SEQ ID NO: 168), WV-1086 (SEQ ID NO: 169), WV-1087 (SEQ ID NO: 170), WV-1088 (SEQ ID NO: 171), WV-1089 (SEQ ID NO: 172), WV-1090 (SEQ ID NO: 173), WV-1091 (SEQ ID NO: 174), and WV-1092 (SEQ ID NO: 175).

Figure 35:
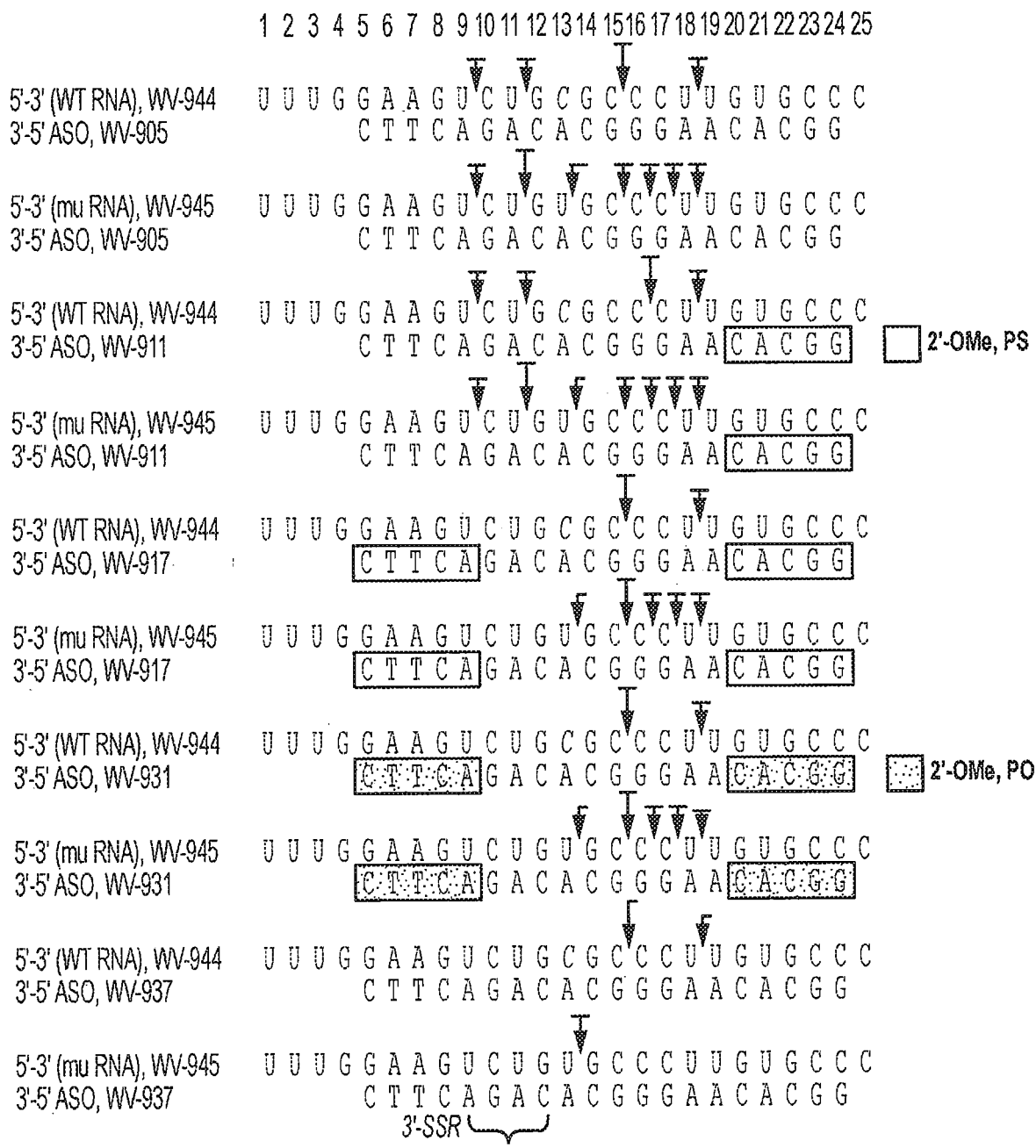

FIG. 35. Example cleavage maps. For legend, see FIG. 33. Compositions used include: WV-944 (SEQ ID NO: 791), WV-945 (SEQ ID NO: 792), WV-905 (SEQ ID NO: 131), WV-911 (SEQ ID NO: 137), WV-917 (SEQ ID NO: 143), WV-931 (SEQ ID NO: 157), and WV-937 (SEQ ID NO: 163).

Figure 36:
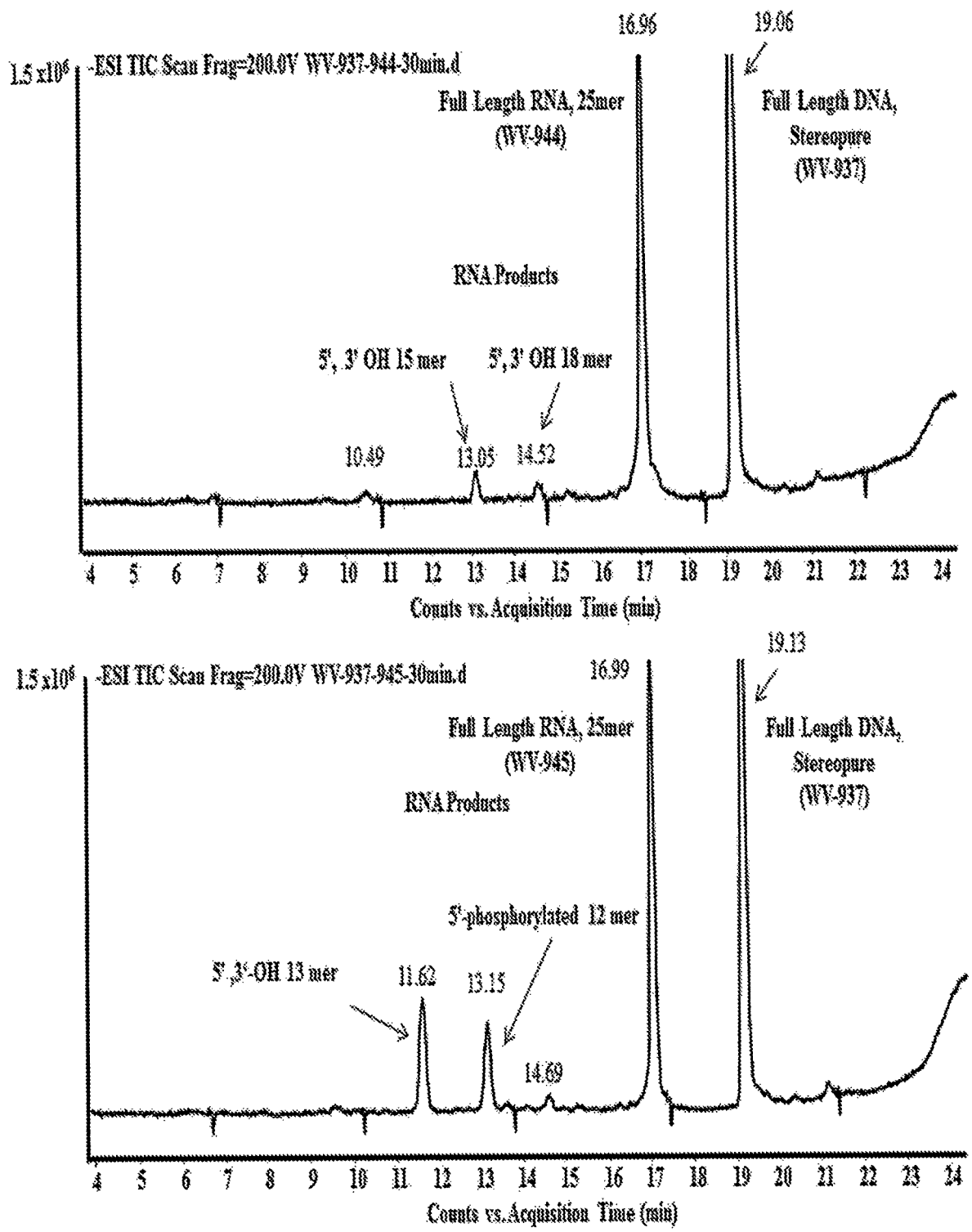

FIG. 36. Total ion chromatogram of RNase H cleavage reaction for WV-937 when duplexed with WT HTT RNA (WV-944, upper panel) or mu HTT RNA (WV-945, lower panel). Following quenching of the enzymatic reaction with disodium EDTA after 30 minutes, the RNase H cleavage products were chromatographically resolved and analyzed using an Agilent 1290 UPLC coupled with an Agilent 6230 MS-TOF mass spectrometer. The high mass accuracy high resolution MS spectra for each identified peak was extracted and deconvoluted. Identification of the metabolites which led to determination of position of cleavage was done by comparing the deconvoluted average masses to masses of predicted RNA metabolites.

Figure 37:
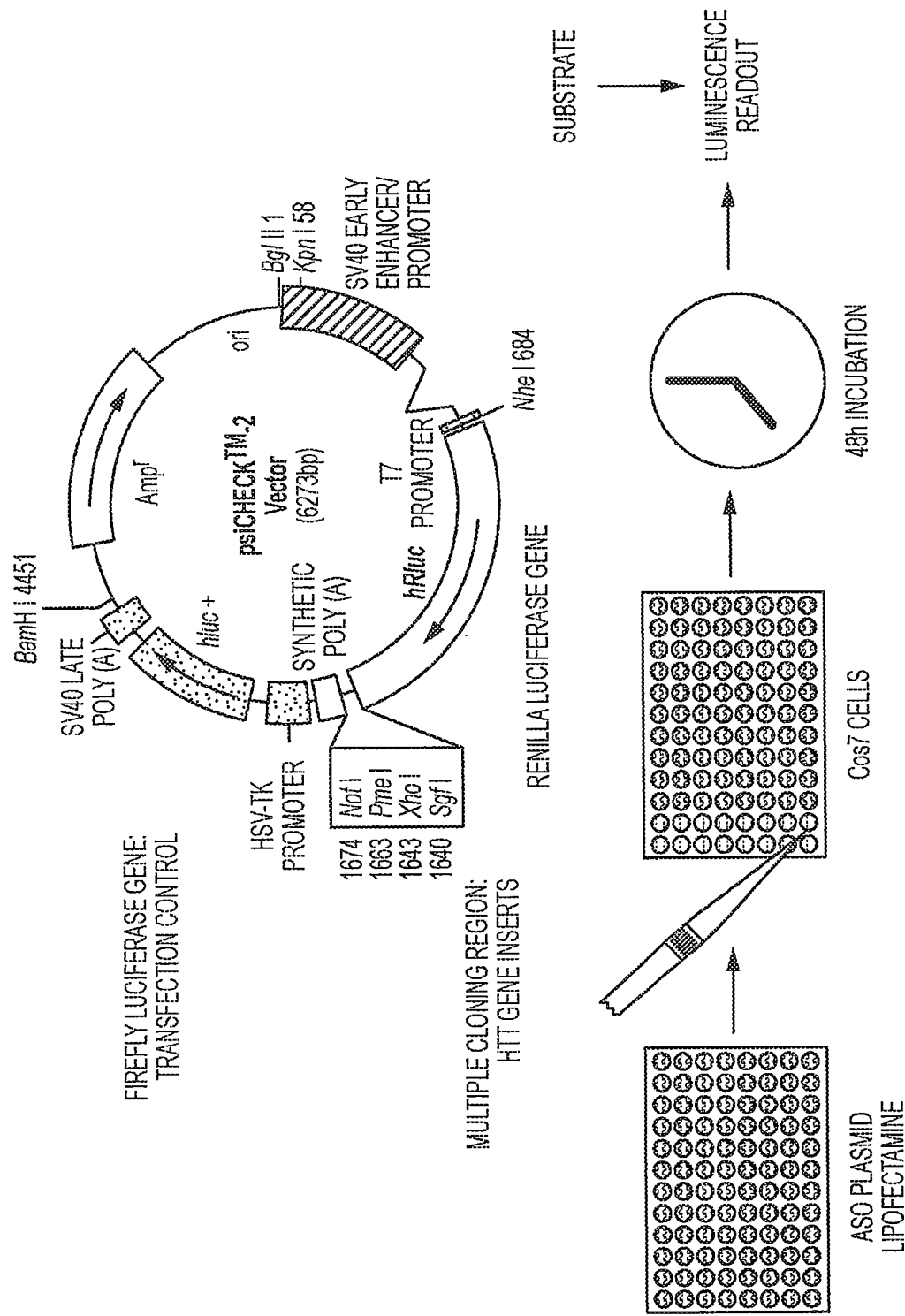

FIG. 37. Illustration of the Luciferase Reporter-based screening.

Figure 38A:
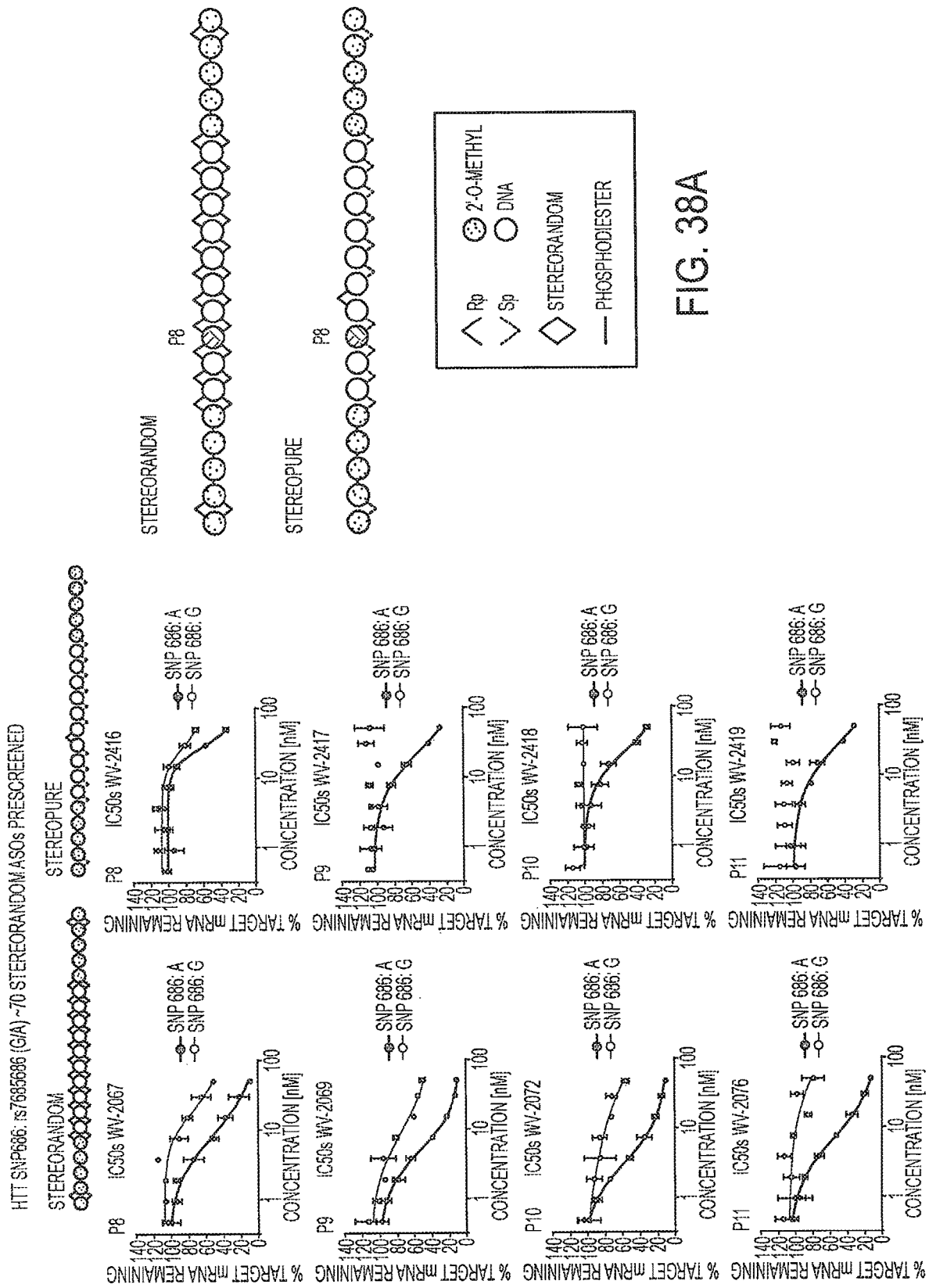
Figure 38B:
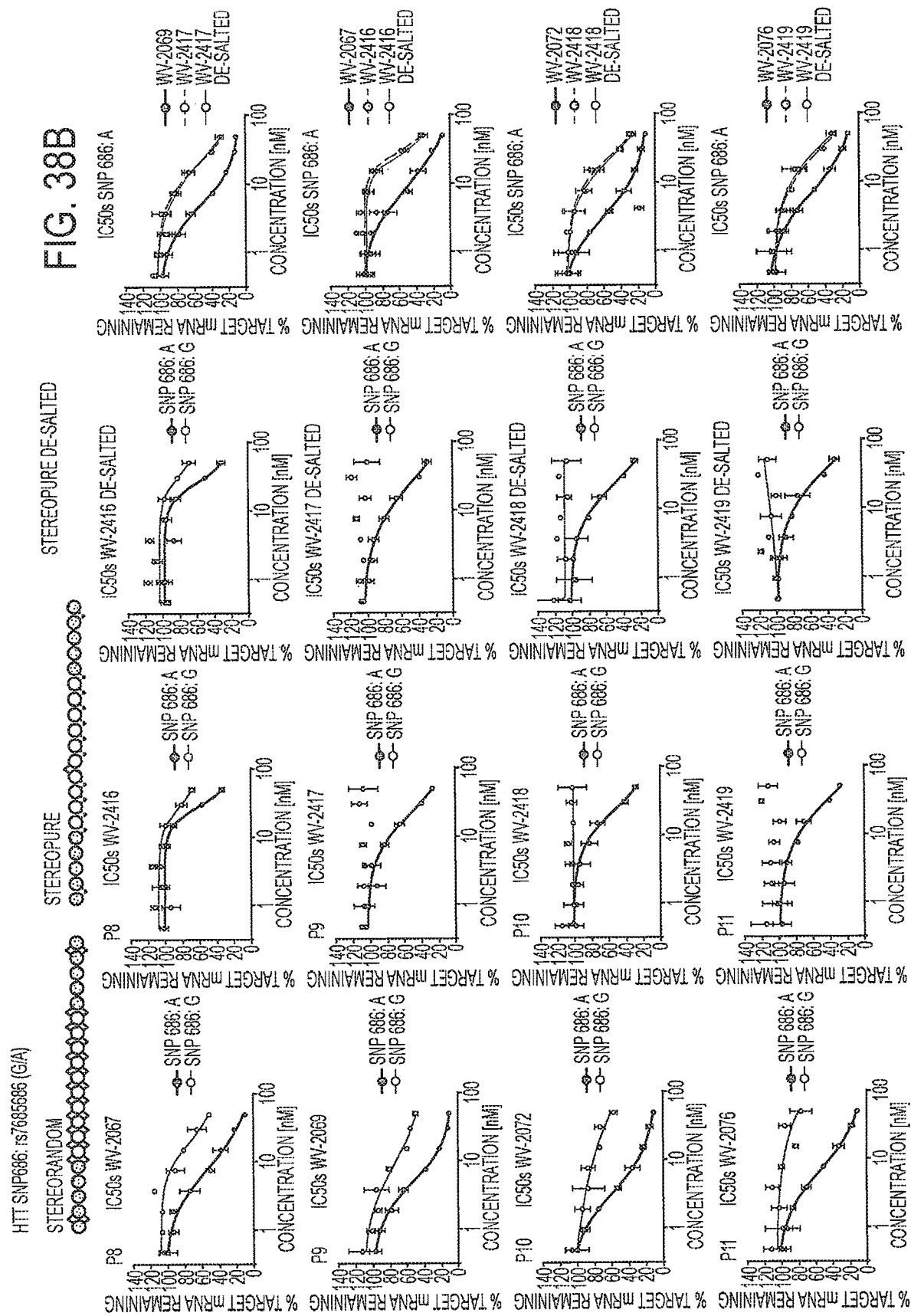
Figure 38C:
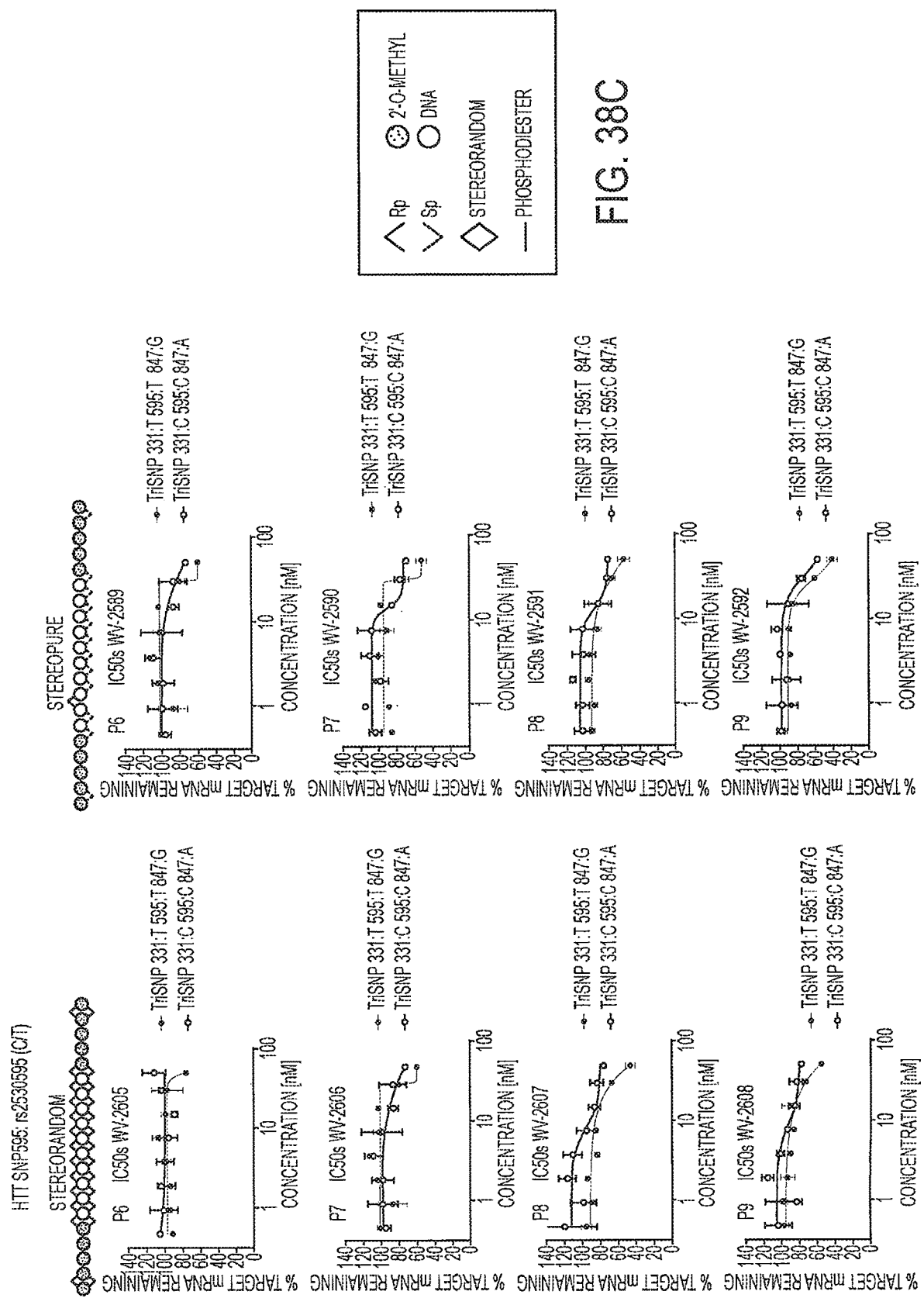
Figure 38D:
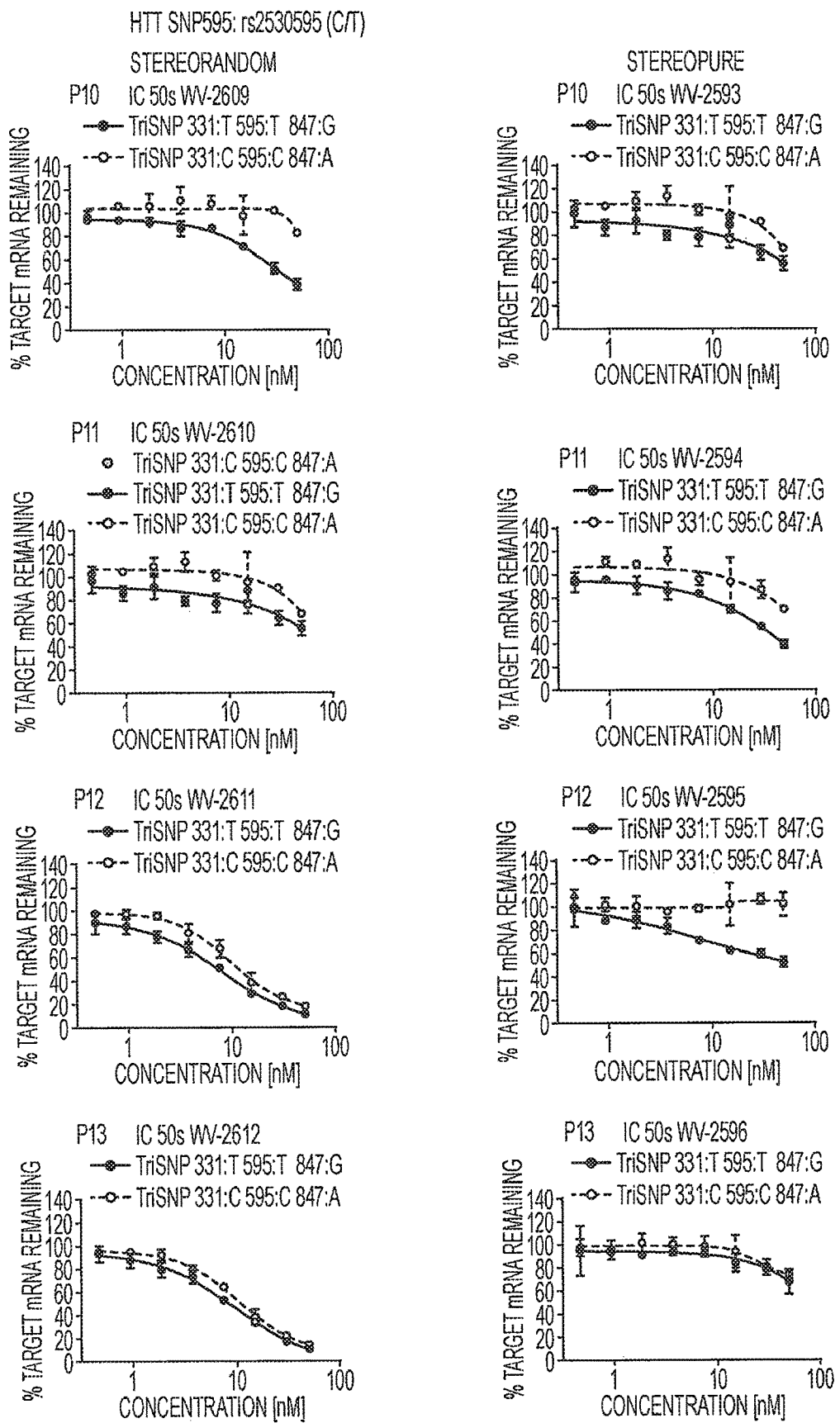
Figure 38E:
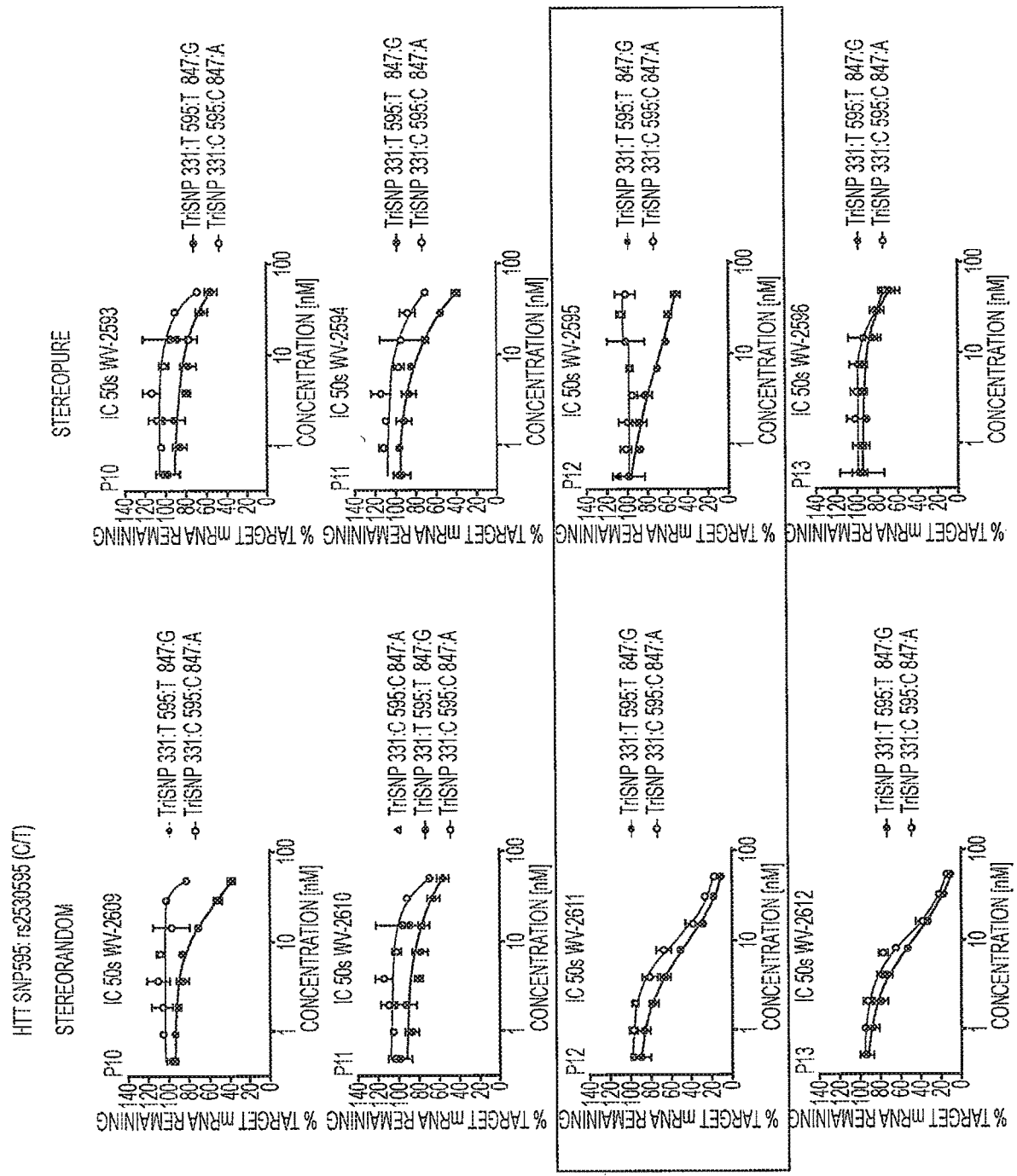
Figure 38F:
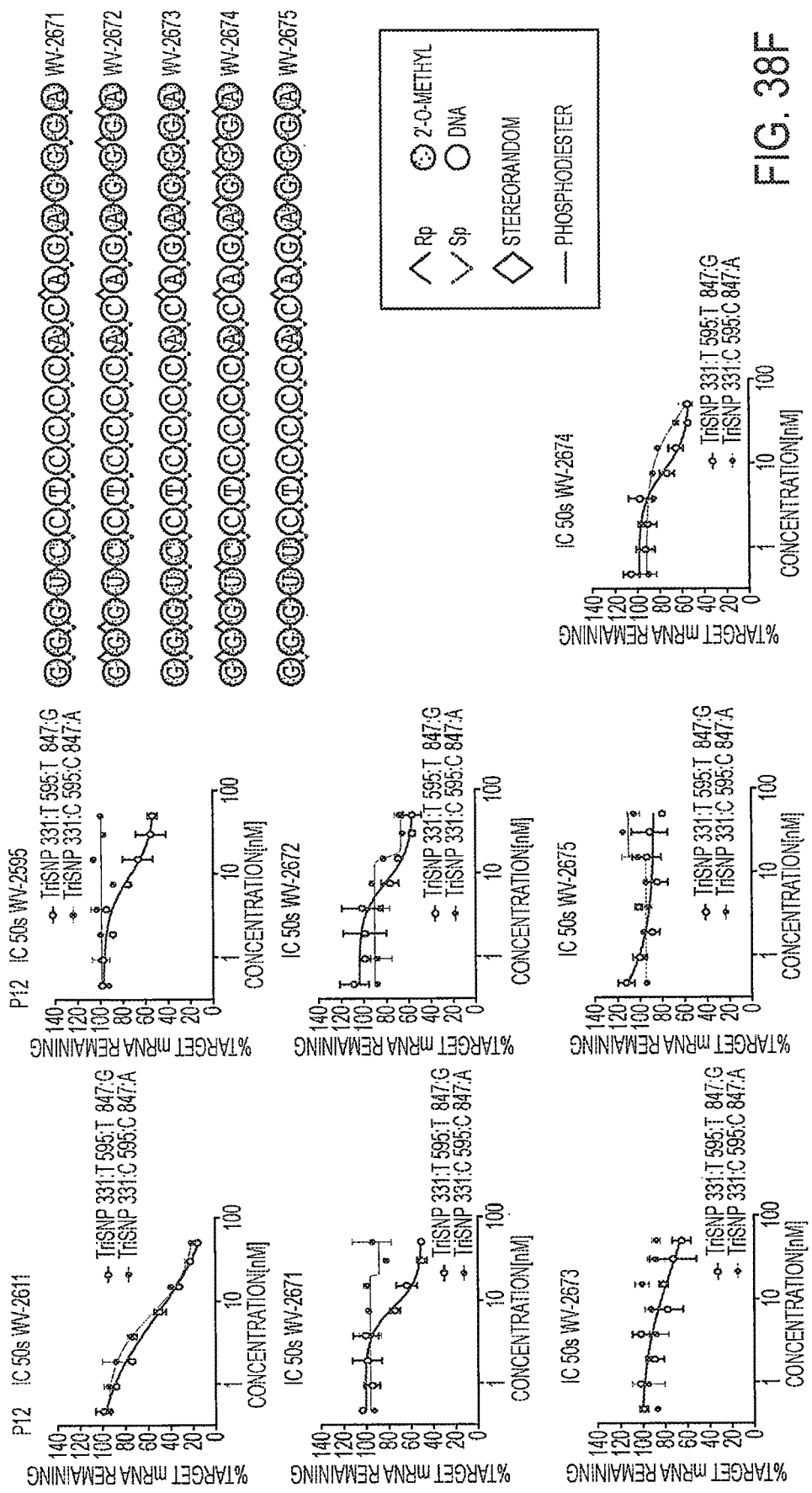
Figure 38G:
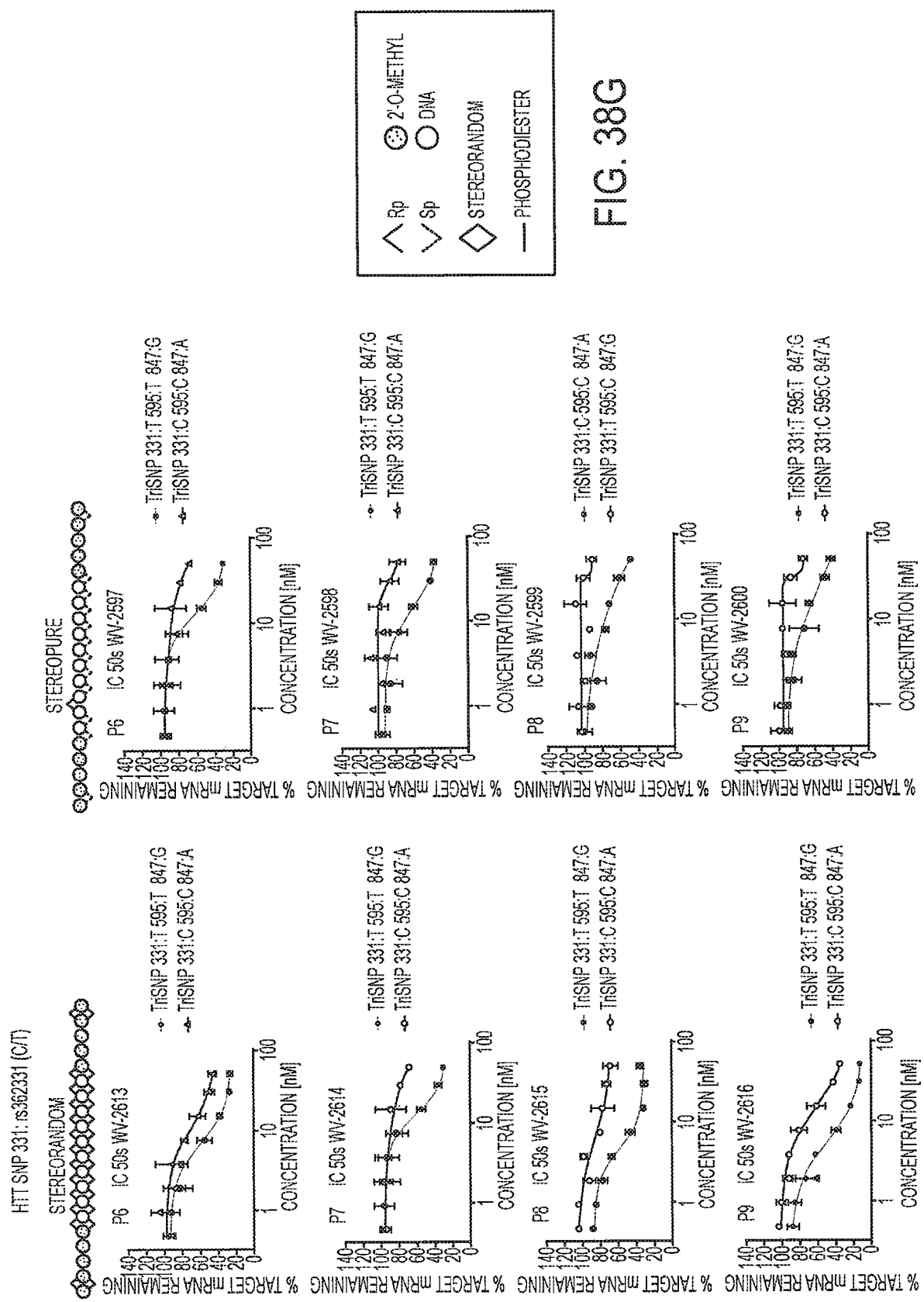
Figure 38H:
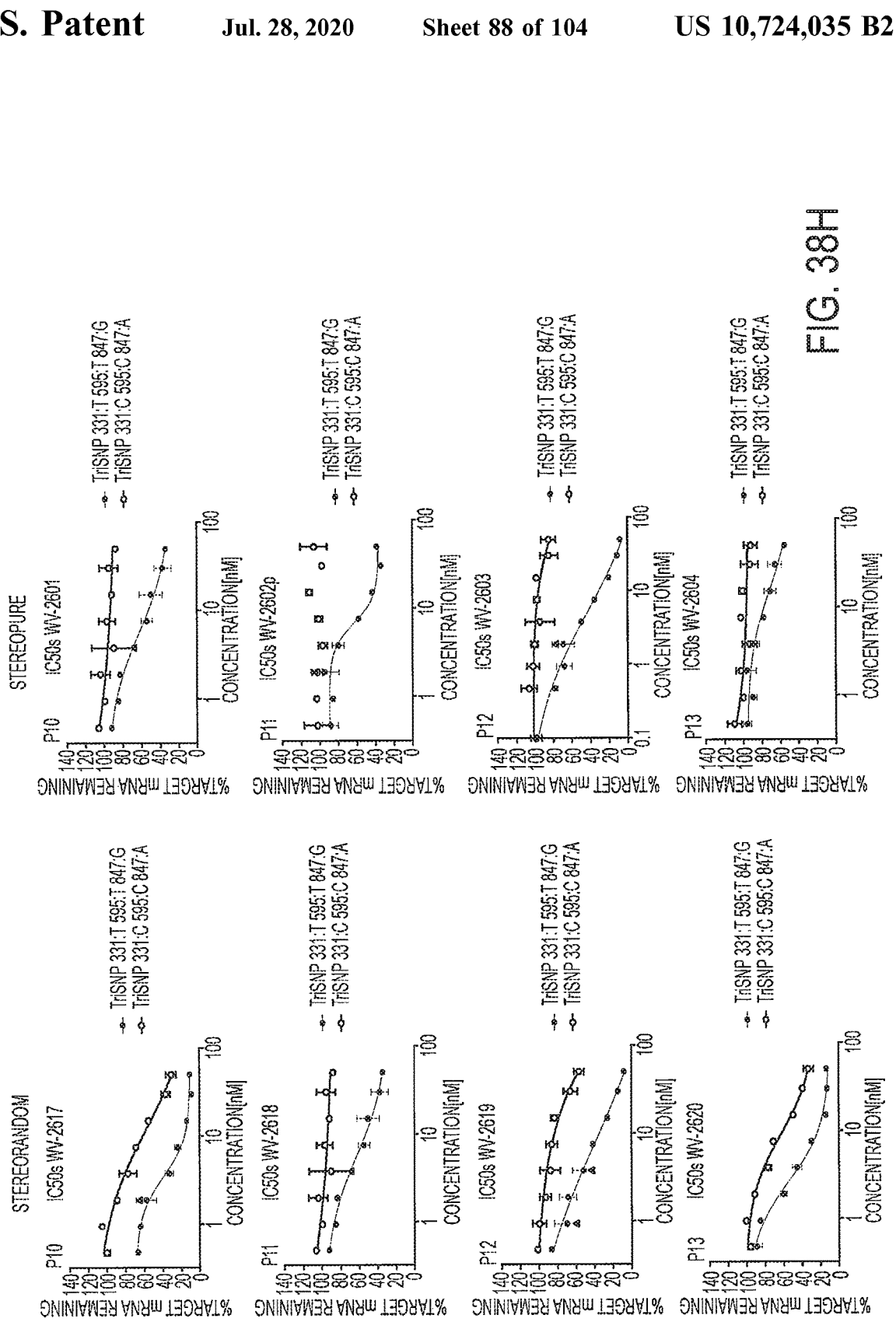
Figure 38I:
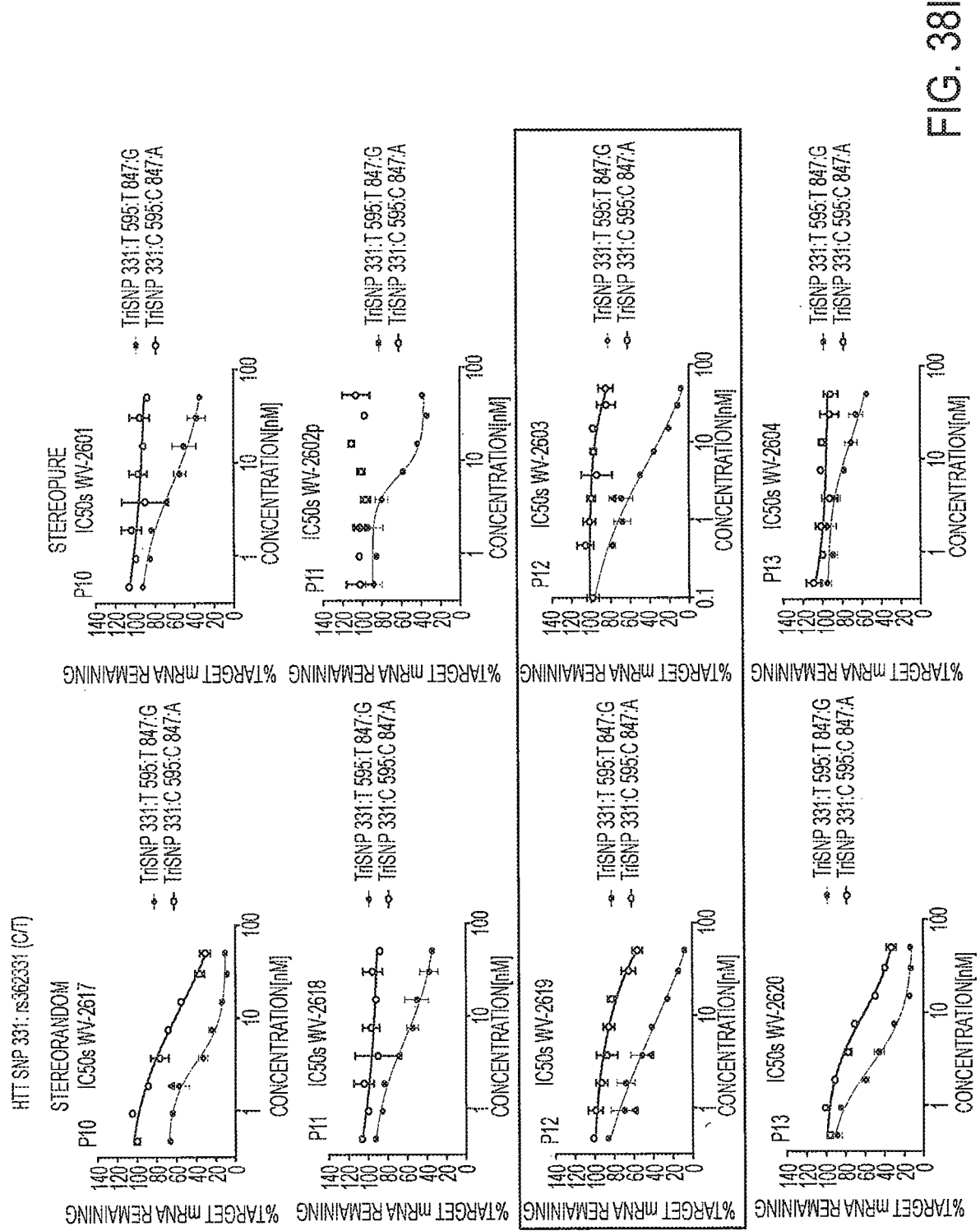

FIGS. 38A-38I. FIGS. 38A-38I and 39A-39G show the activity of various HTT oligonucleotides. Dose-response curves for HTT silencing in reporter-based assay in COS7 cells after transfection of ASOs targeting rs362331_T or rs2530595 T SNPs. ASO specificity is increased with no significant loss of potency by addition of stereopure design (calculated IC50s specified). Data are representative of 2 independent experiments. Lines indicate fit curves, error bars indicate standard deviations. In the figures, the location of the SNP is indicated. Compositions tested in FIG. 38 include: WV-2067, WV-2416, WV-2069, WV-2417, WV-2072, WV-2418, WV-2076, WV-2419, WV-2605, WV-2589, WV-2606, WV-2590, WV-2607, WV-2591, WV-2608, WV-2592, WV-2609, WV-2593, WV-2610, WV-2594, WV-2611, WV-2595, WV-2612, WV-2596, WV-2611, WV-2595, WV-2671, WV-2672, WV-2673, WV-2675, WV-2674, WV-2613, WV-2597, WV-2614, WV-2598, WV-2615, WV-2599, WV-2616, WV-2600, WV-2617, WV-2601, WV-2618, WV-2602, WV-2619, WV-2603, WV-2620, and WV-2604. FIG. 38F discloses SEQ ID NOS 1475, 1459 and 1487-1491, respectively, in order of appearance.

Figure 39A:
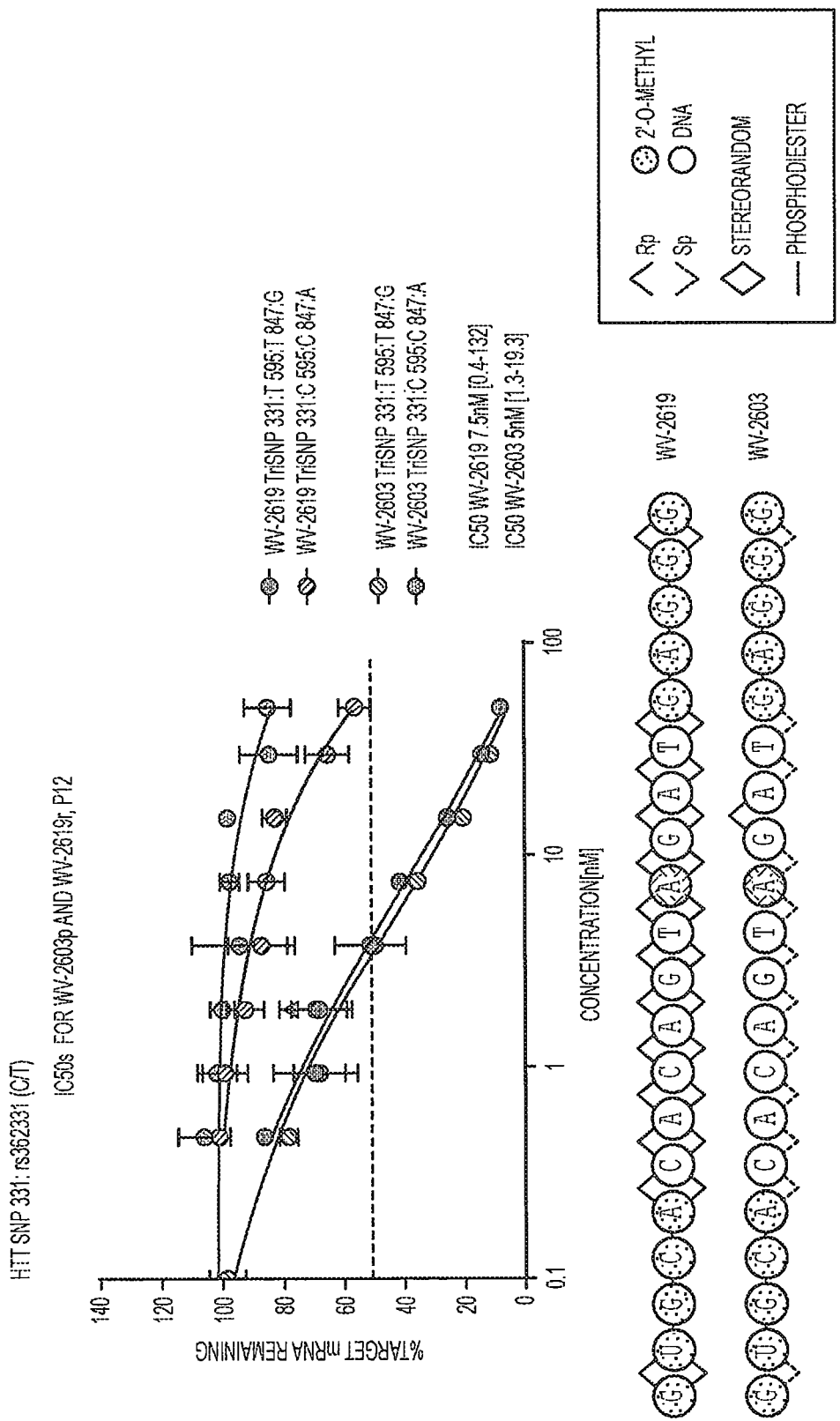
Figure 39B:
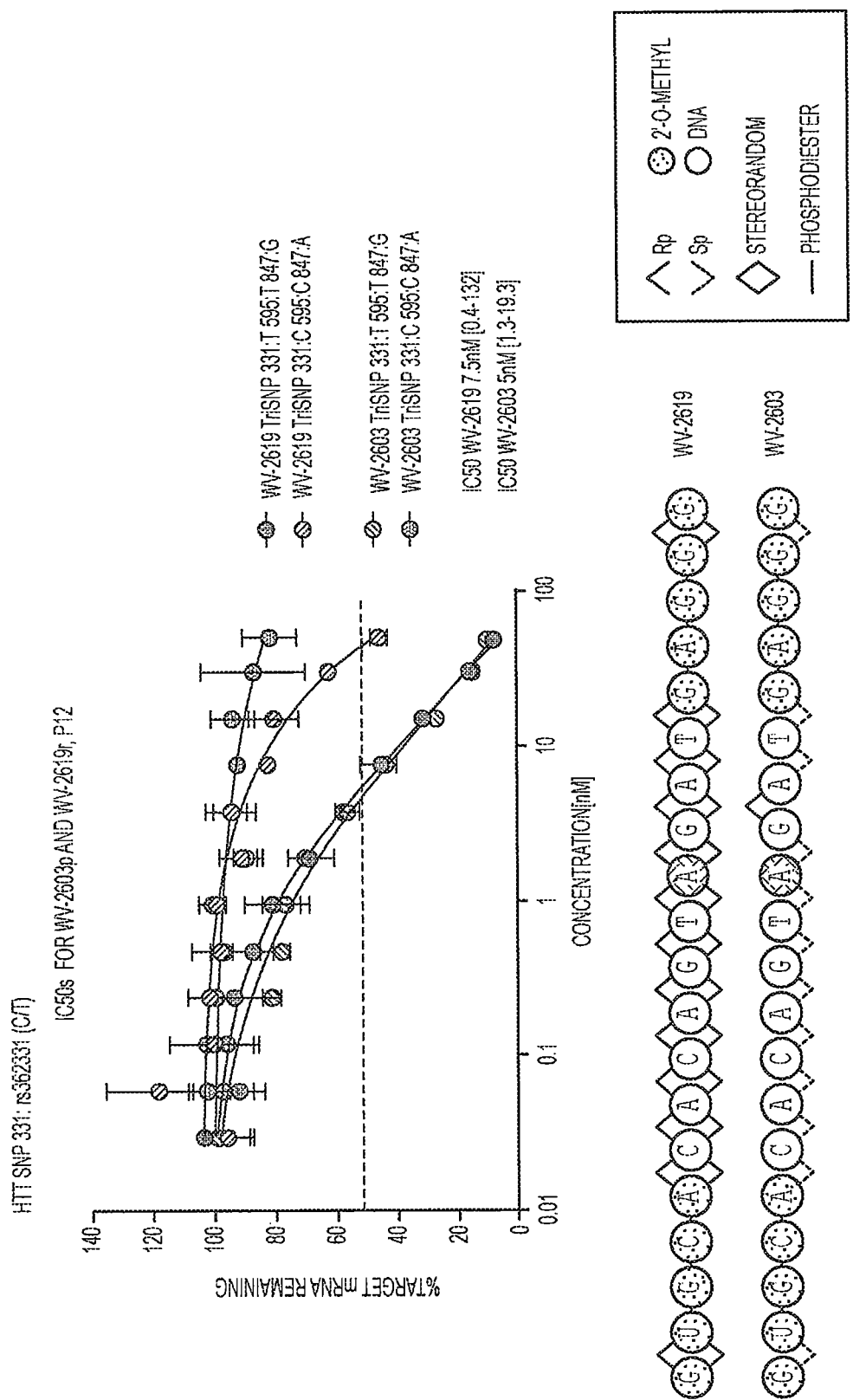
Figure 39C:
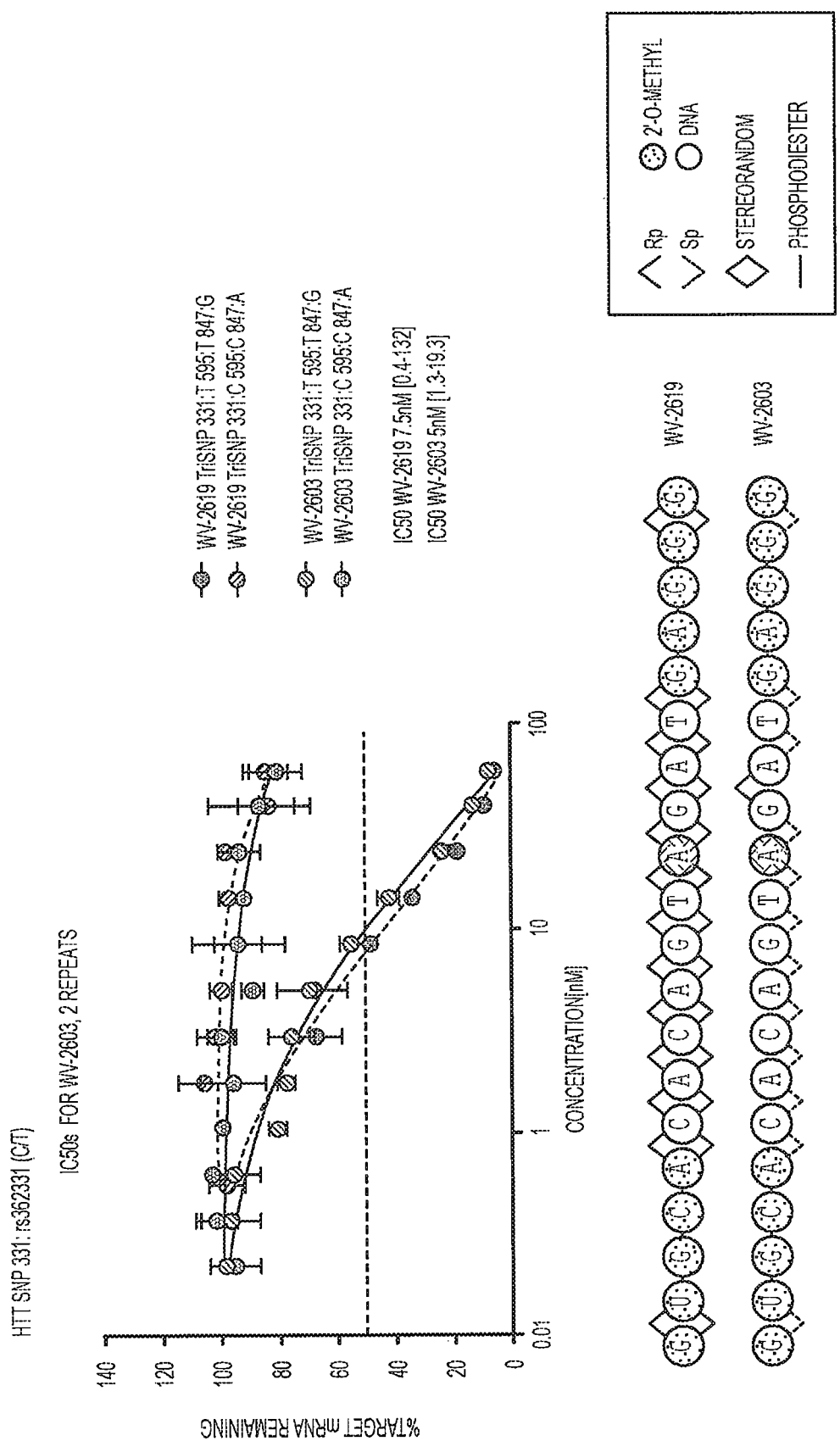
Figure 39D:
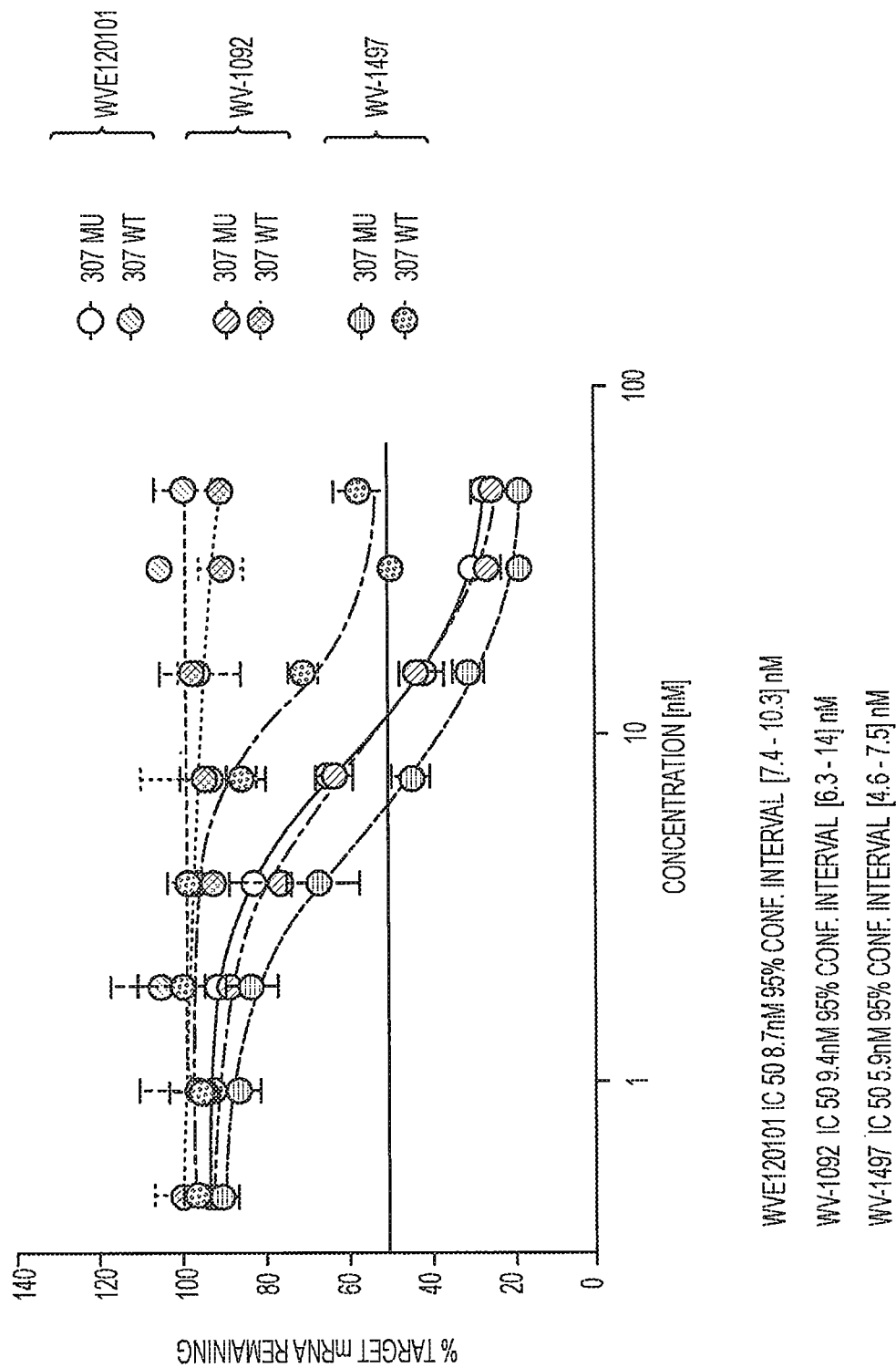
Figure 39E:
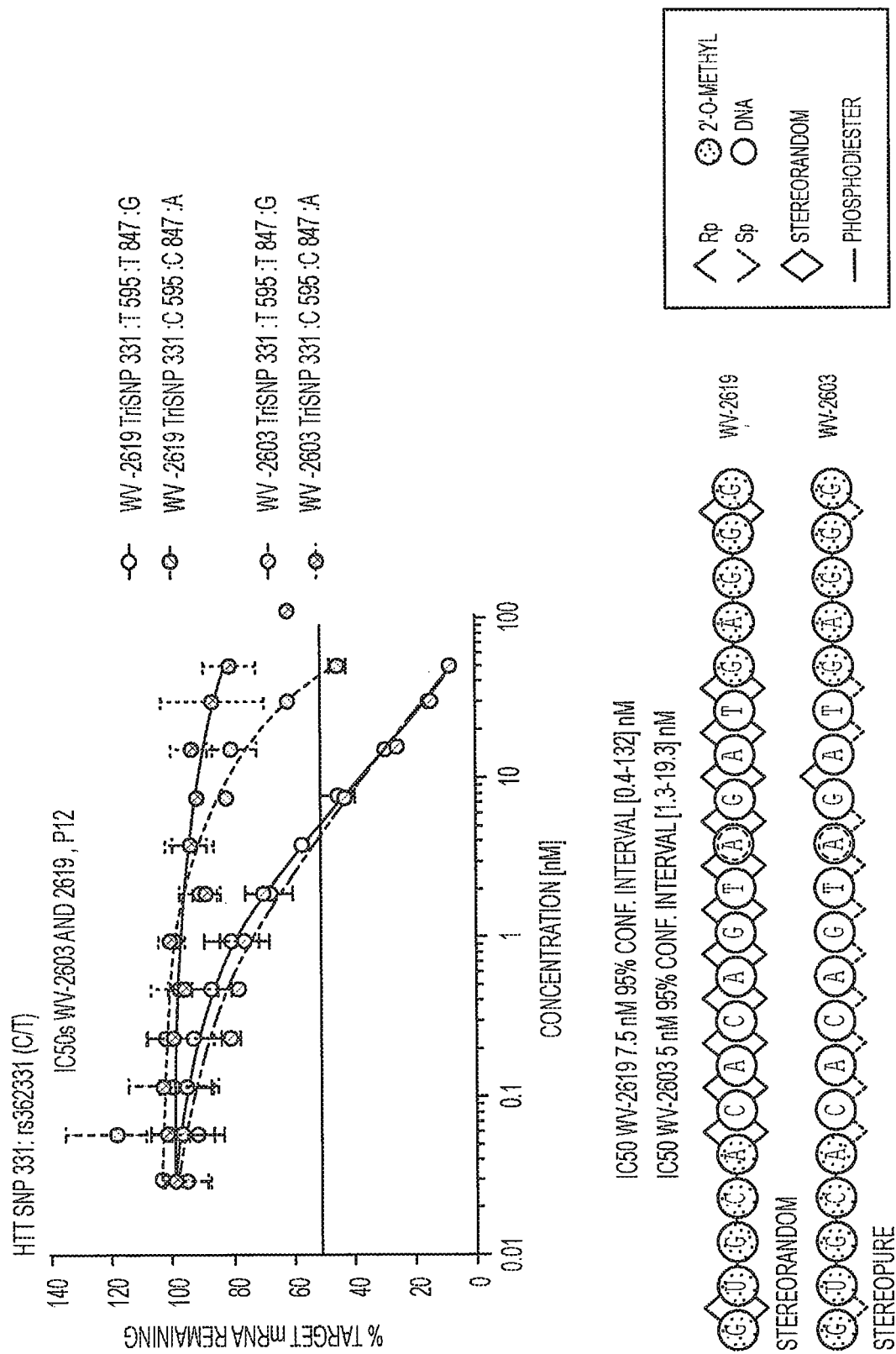
Figure 39F:
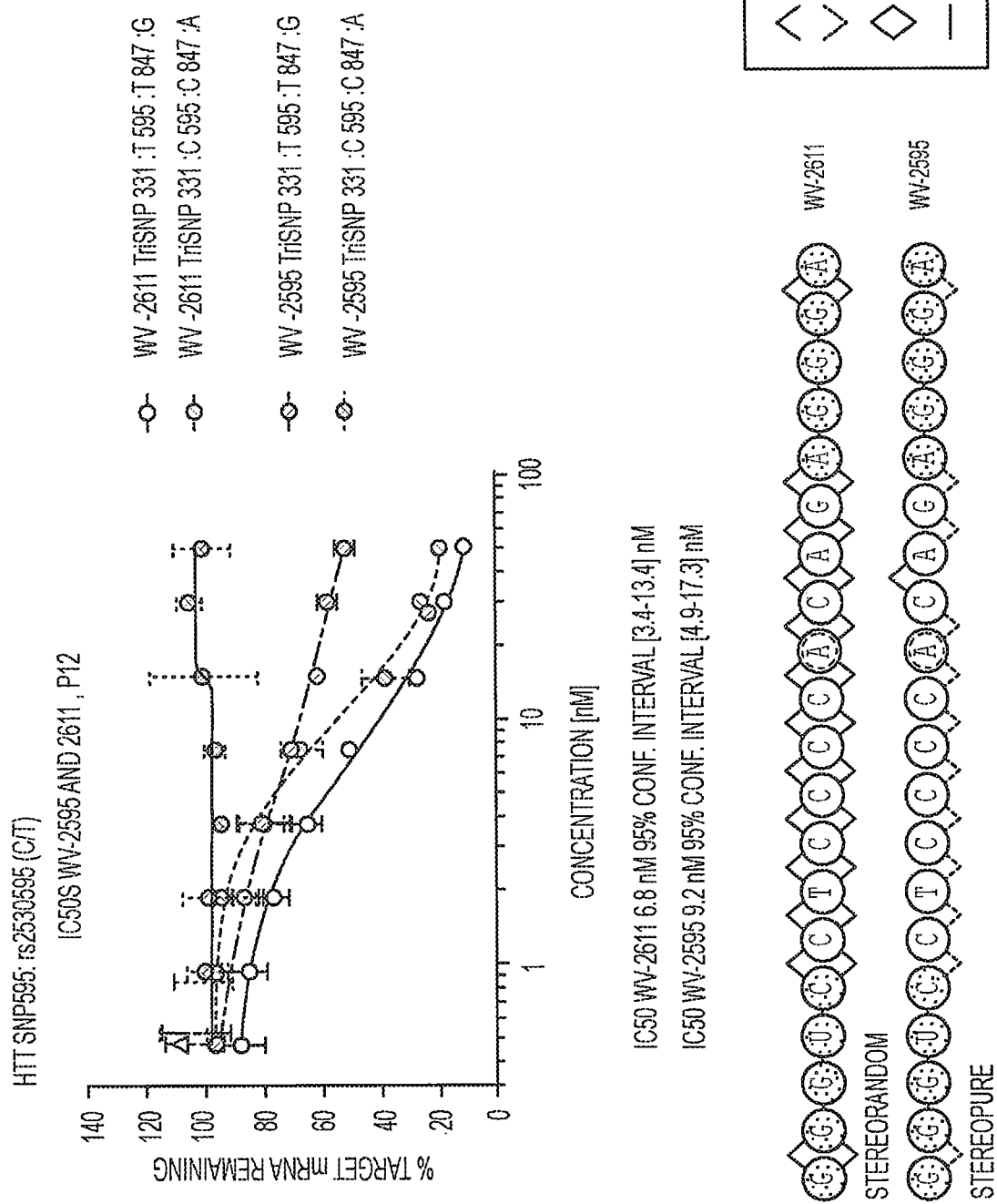
Figure 39G:
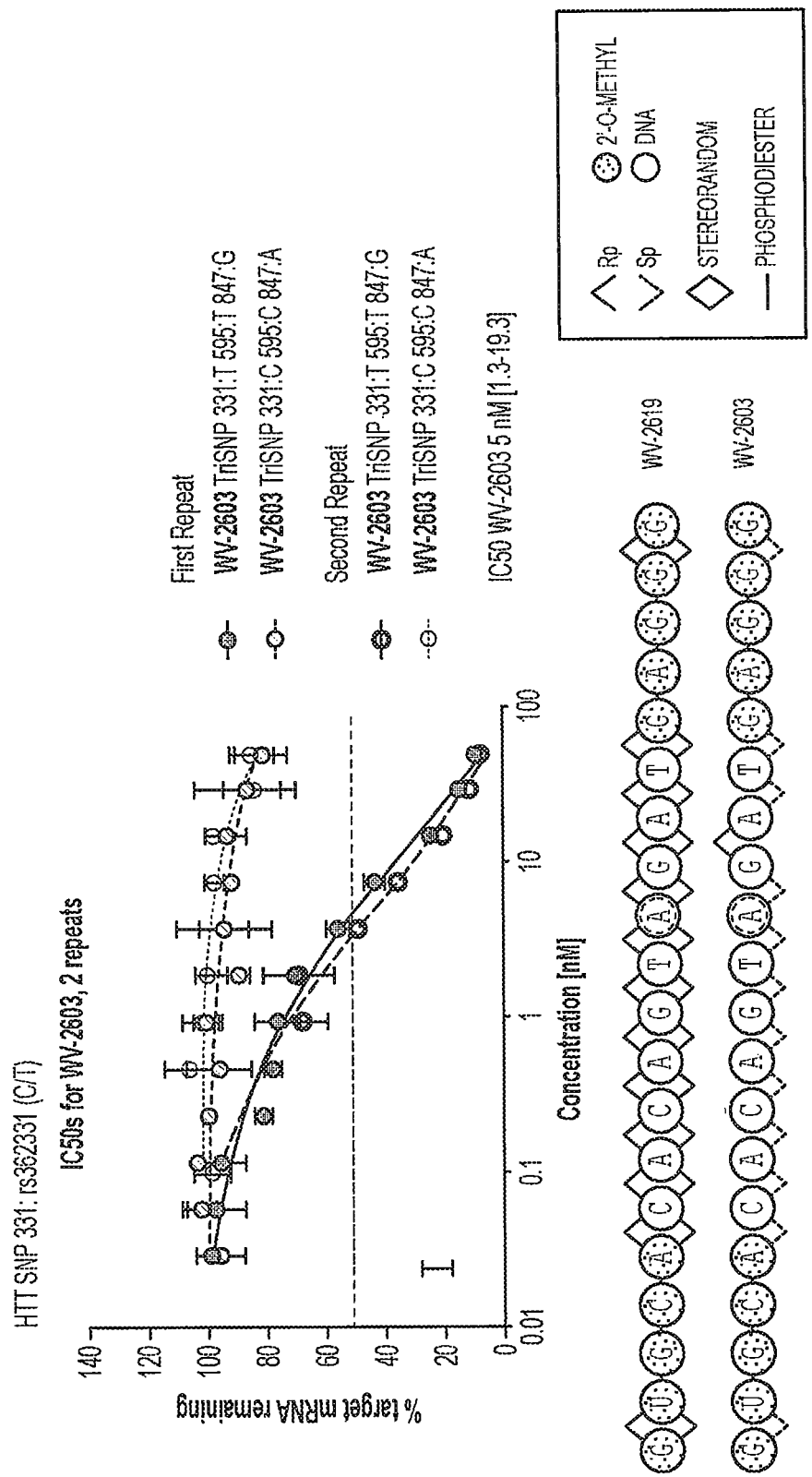
Figure 40A:
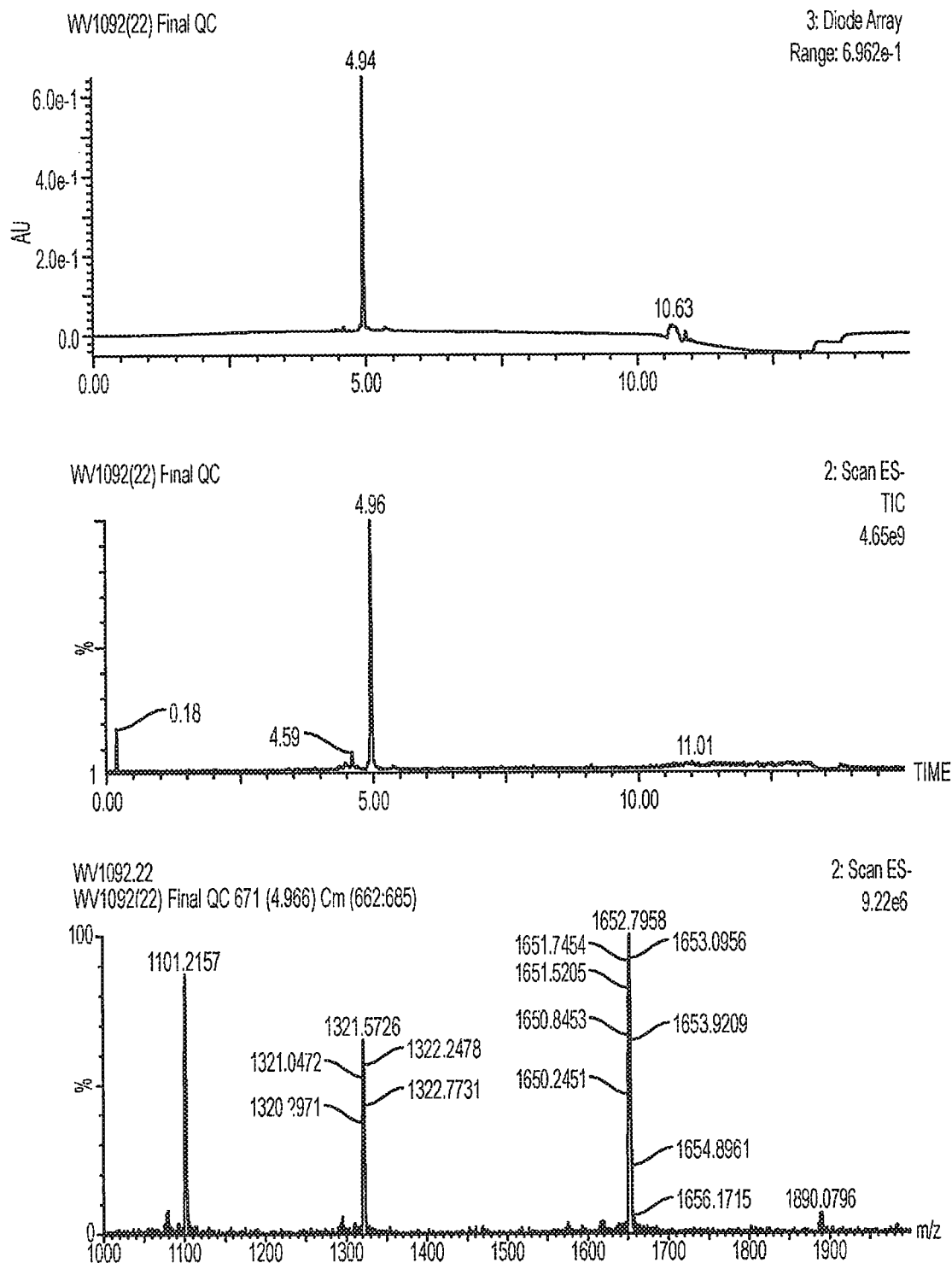
Figure 40B:
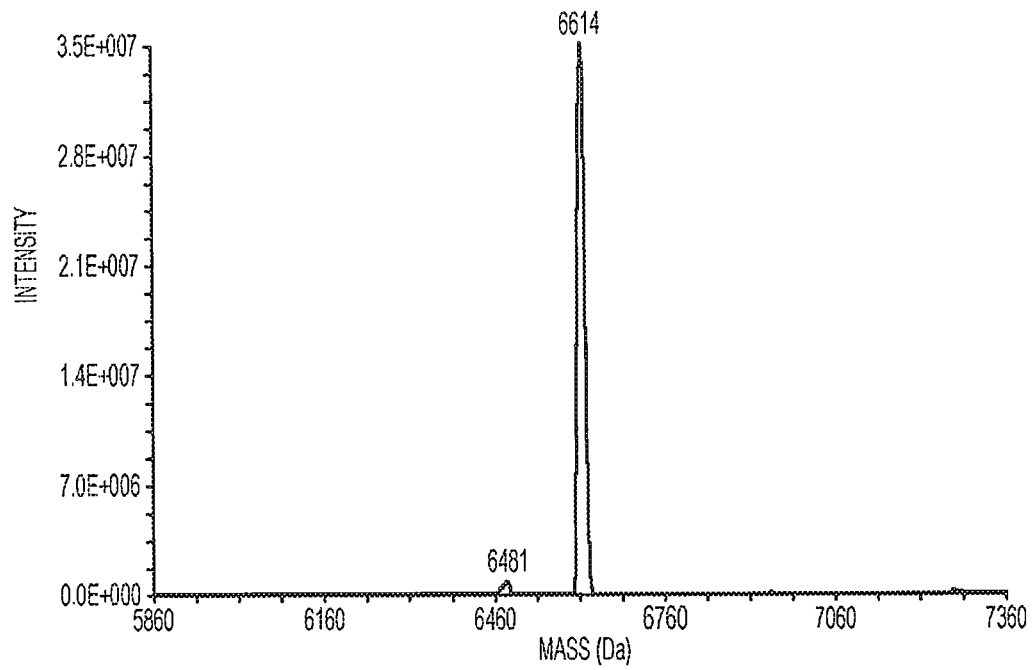
Figure 40B:
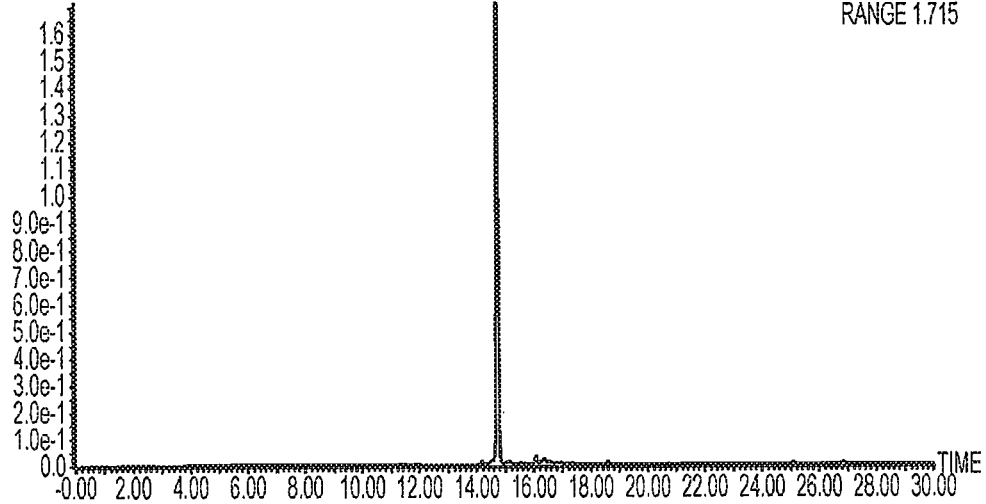
Figure 40C:
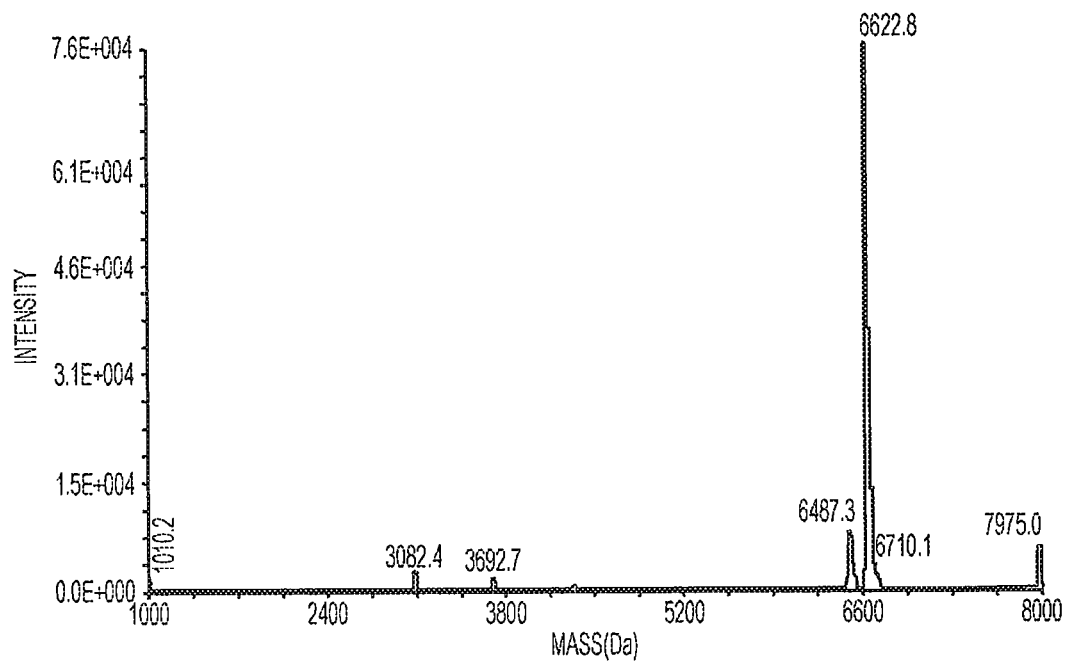
Figure 40C:
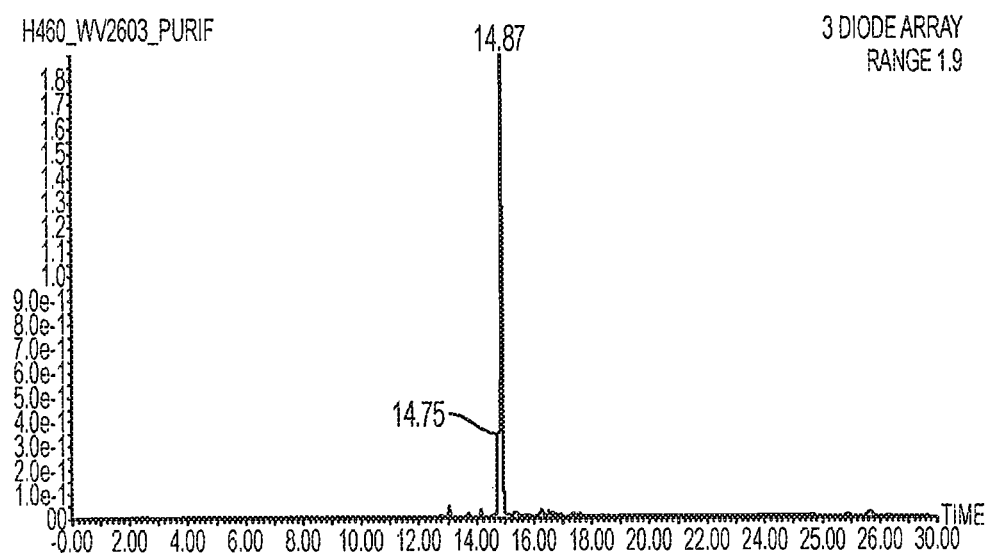
Figure 40D:
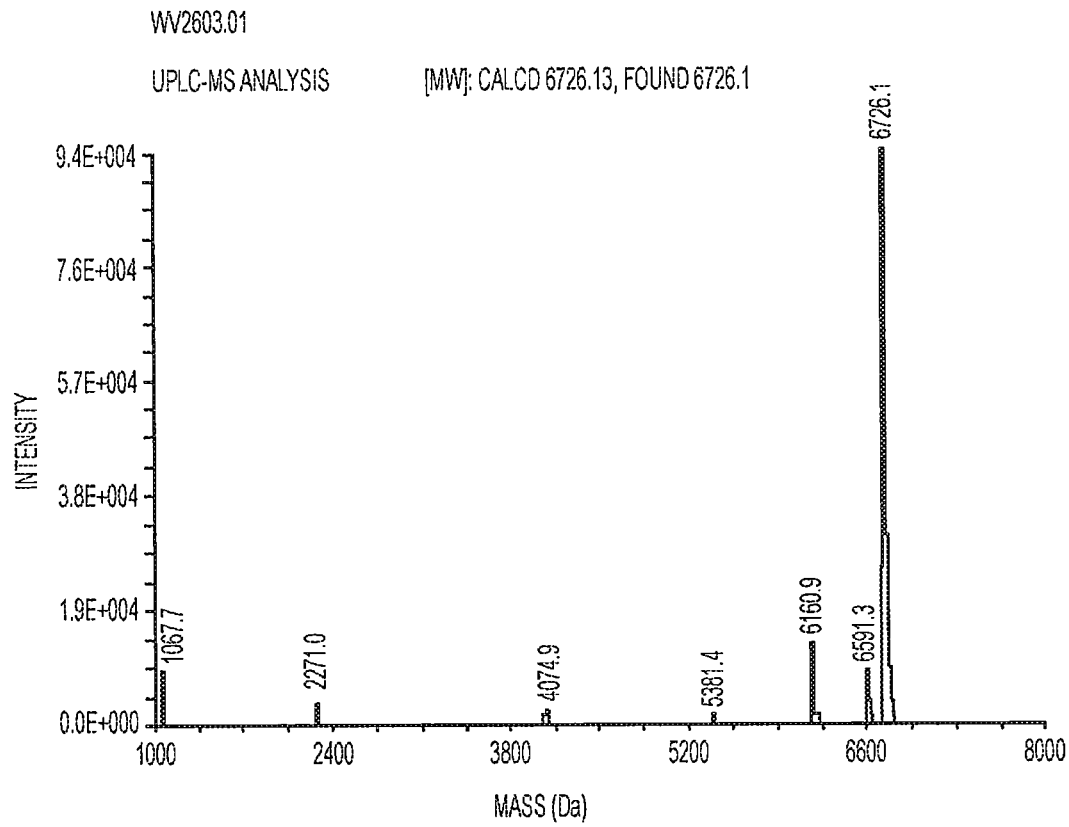

FIGS. 39A-39G. Dose-response curves for HTT silencing in reporter-based assay in COS7 cells after transfection of ASOs. Compositions tested include: WVE120101, WV-1092, WV-1497, WV-2619, WV-2603, WV-2611, and WV-2595. IC$_{50}$ data is also shown. FIG. 39A discloses SEQ ID NOS 1483 and 1467, respectively, in order of appearance. FIG. 39B discloses SEQ ID NOS 1483 and 1467, respectively, in order of appearance. FIG. 39C discloses SEQ ID NOS 1483 and 1467, respectively, in order of appearance. FIG. 39E discloses SEQ ID NOS 1483 and 1467, respectively, in order of appearance. FIG. 39F discloses SEQ ID NOS 1475 and 1459, respectively, in order of appearance. FIG. 39G discloses SEQ ID NOS 1483 and 1467, respectively, in order of appearance.

FIGS. 40A-40D. FIGS. 40A-40D shows liquid chromatograph and mass spectra data for oligonucleotides: WV1092.22 (WV-1092), WV2595.01 (WV-2595) and WV2603.01 (WV-2603). The suffixes (01), (02), 0.01, 0.02, 0.22, etc., as used herein, indicate batch numbers.

Figure 41:
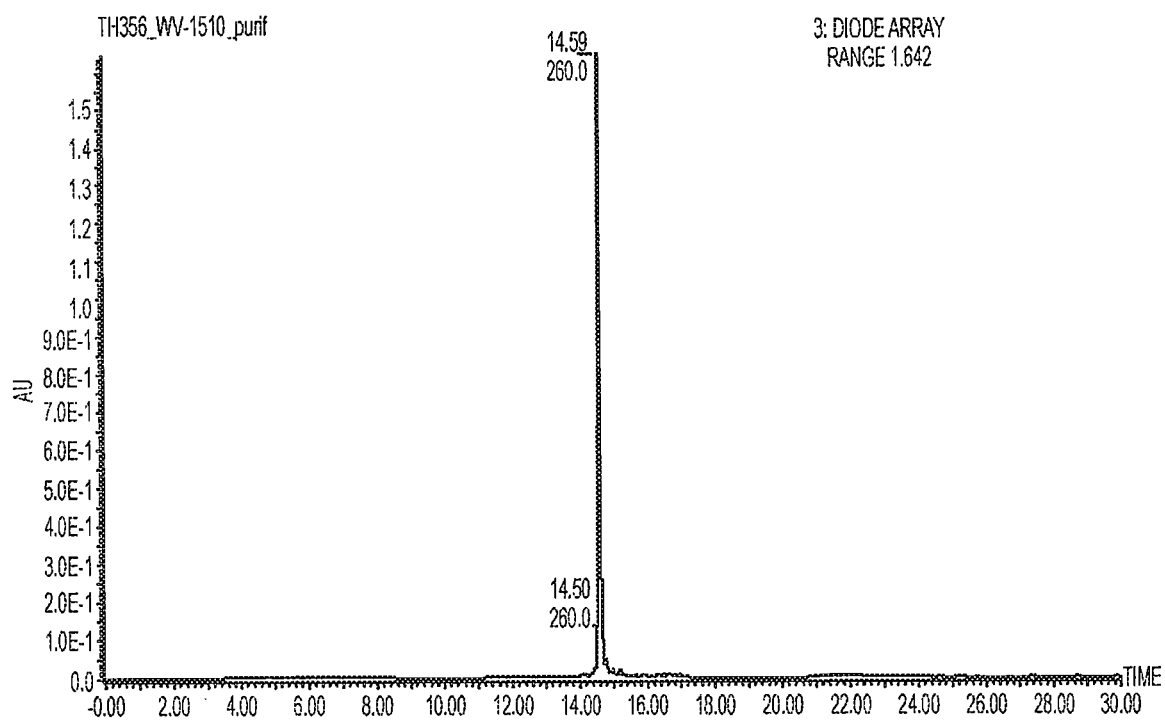
Figure 41:
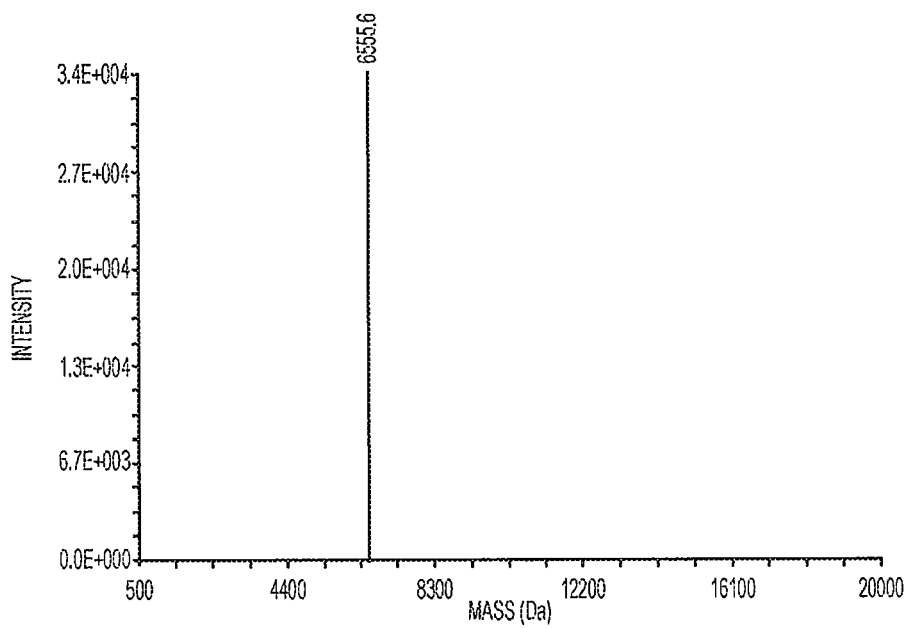
Figure 41:
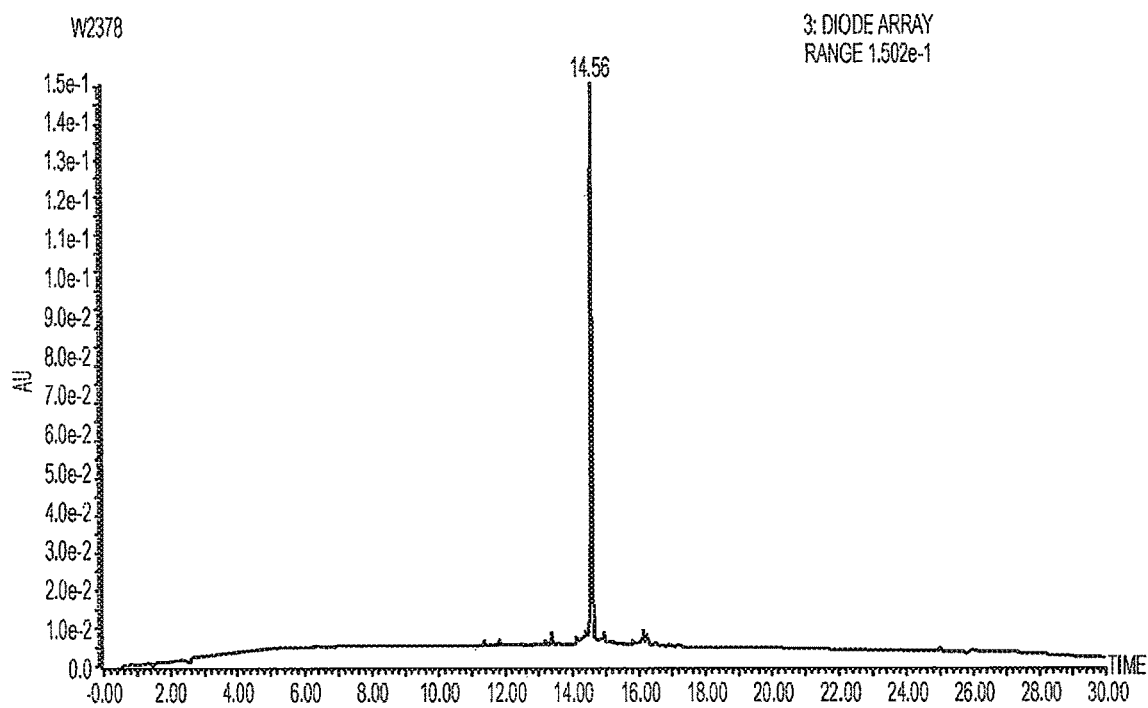
Figure 41:
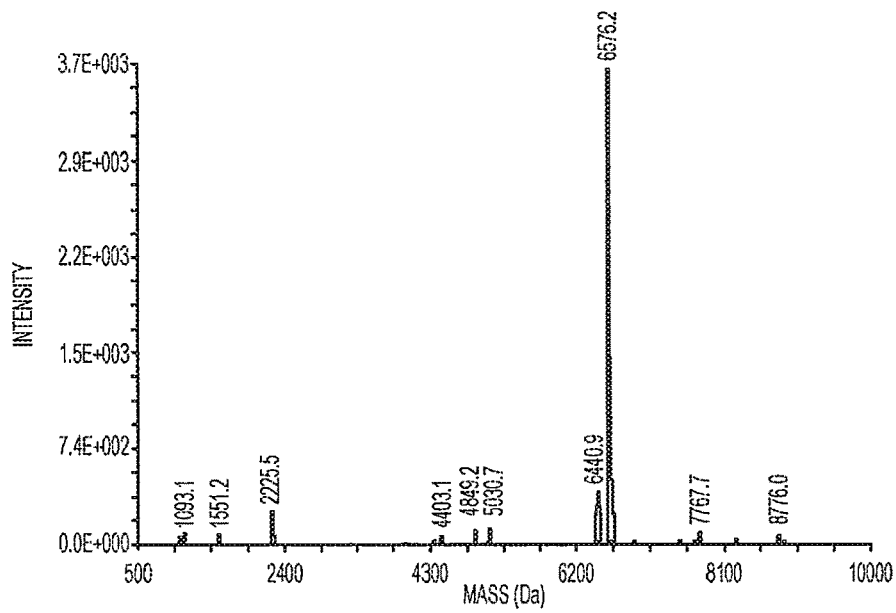
Figure 41:
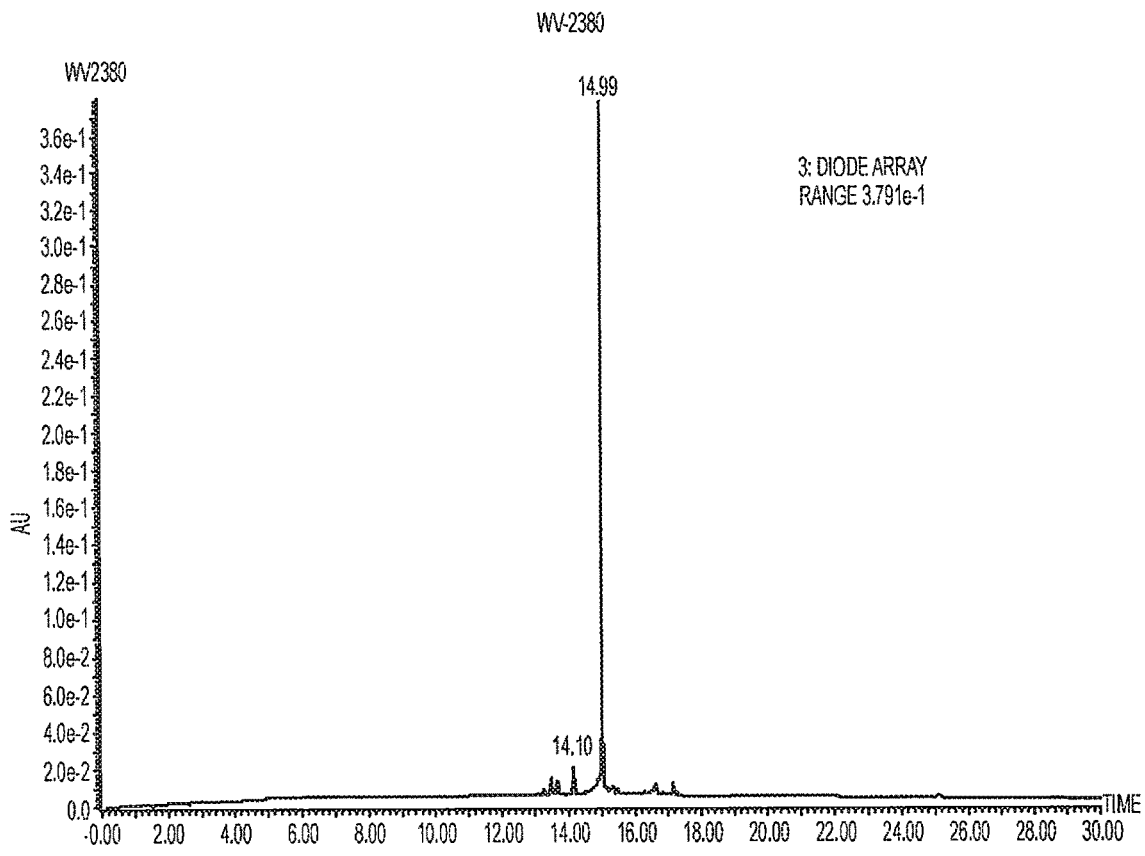
Figure 41:
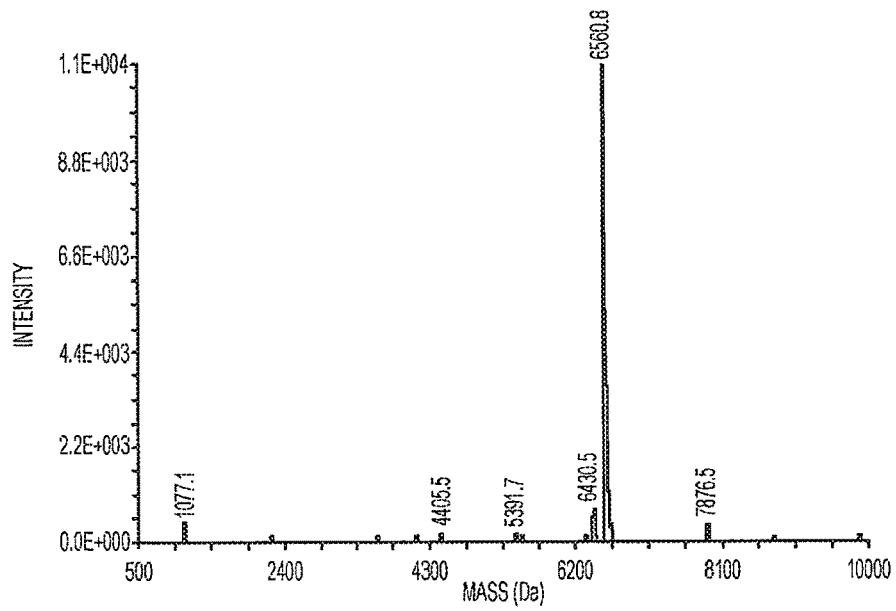

FIG. 41. FIG. 41 shows liquid chromatograph and mass spectra data for oligonucleotides: WV-1510, WV-2378 and WV-2380.

FIG. 42. Example tested sequences (SEQ ID NOS 775-782, respectively, in order of appearance).

DETAILED DESCRIPTION OF CERTAIN EMBODIMENTS

Synthetic oligonucleotides provide useful molecular tools in a wide variety of applications. For example, oligonucleotides are useful in therapeutic, diagnostic, research, and new nanomaterials applications. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain backbone modifications, which render these molecules less susceptible to degradation. From a structural point of view, such modifications to internucleotide phosphate linkages introduce chirality. It has become clear that certain properties of oligonucleotides may be affected by the configurations of the phosphorus atoms that form the backbone of the oligonucleotides. For example, in vitro studies have shown that the properties of antisense nucleotides such as binding affinity, sequence specific binding to the complementary RNA, stability to nucleases are affected by, inter alia, chirality of the backbone (e.g., the configurations of the phosphorus atoms).

Among other things, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have significant impact on properties, e.g., activities, of oligonucleotides. In some embodiments, the present disclosure demonstrates that oligonucleotide compositions comprising oligonucleotides with controlled structural elements, e.g., controlled chemical modification and/or controlled backbone stereochemistry patterns, provide unexpected properties, including but not limited to those described herein. In some embodiments, the present disclosure provide an oligonucleotide composition comprises a predetermined level of oligonucleotides of an individual oligonucleotide type which are chemically identical, e.g., they have the same base sequence, the same pattern of nucleoside modifications (modifications to sugar and base moieties, if any), the same pattern of backbone chiral centers, and the same pattern of backbone phosphorus modifications.

Among other things, the present disclosure encompasses the recognition that stereorandom oligonucleotide preparations contain a plurality of distinct chemical entities that differ from one another, e.g., in the stereochemical structure of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence, they are different chemical entities at least due to their different backbone stereochemistry, and they can have, as demonstrated herein, different properties, e.g., bioactivities. A stereopure (or "chirally controlled") oligonucleotide composition or preparation can have improved bioactivity compared to a stereorandom oligonucleotide preparation which is otherwise identical (e.g., both the stereopure and stereorandom versions have the same base sequence, pattern of base and sugar modifications, etc.). For example, stereorandom oligonucleotide WV-1497 composition and a stereopure oligonucleotide WV-1092 composition both have the same sequence of bases and identical patterns of sugar modifications and backbone linkages, differing only in stereochemistry. However, at higher concentrations, there was a marked difference in the ability of the stereopure WV-1092 composition and the stereorandom WV-1497 composition to differentiate between wt and mutant HTT (which differ in only one nt). At the high concentration, both knocked down the mutant HTT to a great degree, which is desirable; but stereopure WV-1092 showed only a small knock down of wildtype HTT, while WV-1497 showed significantly more knock down of wt HTT, which is less desirable in some instances.

Chirally controlled oligonucleotide compositions of both WVE120101 and WV-1092 were able to differentiate between wt and mutant versions of SNP rs362307, which differ by one nt; both WVE120101 and WV-1092 significantly knocked down the mutant allele but not the wt, while the stereorandom version, WV-1497, was not able to significantly differentiate between the wt and mutant alleles (see FIG. 39D). The modified sequences of WVE120101 and WV-1092 are identical. In some embodiments, the disclosure pertains to a chirally controlled oligonucleotide composition of WV-2378. In some embodiments, the disclosure pertains to a chirally controlled oligonucleotide composition of WV-2380. In some embodiments, the disclosure pertains to a chirally controlled oligonucleotide composition of WV-1510. In some embodiments, the disclosure pertains to a chirally controlled oligonucleotide composition of WV-2619. In some embodiments, the disclosure pertains to a chirally controlled oligonucleotide composition of WV-2611. In some embodiments, the disclosure pertains to a chirally controlled oligonucleotide composition of WV-1497. In some embodiments, the disclosure pertains to a chirally controlled oligonucleotide composition of WV-2602. In some embodiments, the disclosure pertains to a chirally controlled oligonucleotide composition of WV-2618. In some embodiments, the disclosure pertains to a chirally controlled oligonucleotide composition of or WV-2601.

A chirally controlled oligonucleotide composition of WV-2595 was able to differentiate between the C and T alleles at SNP rs2530595, which also differ at only the one nt. Stereopure WV-2595 significantly knocked down the T allele but not the C allele, unlike the stereorandom oligonucleotide composition of WV-2611, which was not able to significantly differentiate the alleles (see FIG. 39F). The sequence of WV-2595 is 5'-mG*mGmGmUmC*C*T*C*C*C*C*A*C*A*G*mAmGmGmG*mA-3' (SEQ ID NO: 10) or 5'-mG*SmGmGmUmC*SC*ST*SC*SC*SC*SC*SA*SC*RA*SG*SmAmGmGmG*SmA-3' (SEQ ID NO: 11) with certain stereochemistry information.

A stereopure oligonucleotide composition of WV-2603 was able to differentiate between the C and T alleles of SNP rs362331, which also differ at only the one nt. Stereopure WV-2603 significantly knocked down the T allele but not the C allele, unlike the stereorandom oligonucleotide composition of WV-2619, which was not able to significantly differentiate between the alleles (see FIGS. 39A, 39B, 39C and 39E). The sequence of WV-2603 is 5'-mG*mUmGmCmA*C*A*C*A*G*T*A*G*A*T*mGmAmGmG*mG-3' (SEQ ID NO: 12) or 5'-mG*SmUmGmCmA*SC*SA*SC*SA*SG*ST*SA*SG*RA*ST*SmGmAmGmG*SmG-3' (SEQ ID NO: 13) with certain stereochemistry information.

In some embodiments, the sequence of the oligonucleotide in a stereopure (chirally controlled) oligonucleotide composition comprises or consists of the sequence of any oligonucleotide disclosed herein. In some embodiments, the sequence of the oligonucleotide in a stereopure (chirally controlled) oligonucleotide composition comprises or consists of the sequence of any oligonucleotide selected from Tables N1, N2, N3, N4 and 8. In some embodiments, the sequence of the oligonucleotide in a stereopure (chirally controlled) oligonucleotide composition comprises or consists of the sequence of any oligonucleotide selected from Tables N1A, N2A, N3A, N4A and 8. In some embodiments, the disclosure pertains to a chirally controlled oligonucleotide composition of WV-1087. In some embodiments, the disclosure pertains to a chirally controlled oligonucleotide composition of WV-1090. In some embodiments, the disclosure pertains to a chirally controlled oligonucleotide composition of WV-1091. In some embodiments, the disclosure pertains to a chirally controlled oligonucleotide composition of WV-937. In some embodiments, the disclosure pertains to a chirally controlled oligonucleotide composition of WV-1092. In some embodiments, the disclosure pertains to a chirally controlled oligonucleotide composition of WV-2378. In some embodiments, the disclosure pertains to a chirally controlled oligonucleotide composition of WV-2380. In some embodiments, the disclosure pertains to a chirally controlled oligonucleotide composition of WV-1510. In some embodiments, the disclosure pertains to a chirally controlled oligonucleotide composition of WV-2619. In some embodiments, the disclosure pertains to a chirally controlled oligonucleotide composition of WV-2611. In some embodiments, the disclosure pertains to a chirally controlled oligonucleotide composition of WV-1497. In some embodiments, the disclosure pertains to a chirally controlled oligonucleotide composition of WV-2602. In some embodiments, the disclosure pertains to a chirally controlled oligonucleotide composition of WV-2618. In some embodiments, the disclosure pertains to a chirally controlled oligonucleotide composition of or WV-2601.

Each oligonucleotide described herein comprising a HTT sequence represents an HTT oligonucleotide which was designed, constructed and tested in various assays, in some embodiments, one or more in vitro assays. Each HTT oligonucleotide listed in any of Tables N1A, N2A, N3A, N4A and 8, or described elsewhere herein, was designed, constructed and tested in various assays, in some embodiments, one or more in vitro assays. For example, HTT oligonucleotides described herein were tested in a dual luciferase reporter assay. In some embodiments, HTT oligonucleotides were tested in one or more other assays described in this disclosure and/or in the art in accordance with the present disclosure. In some embodiments, HTT oligonucleotides which were found to be particularly efficacious in the dual luciferase assay were tested in further in vitro and in vivo assays in accordance with the present disclosure.

In some embodiments, a sequence of an oligonucleotide in a stereopure (chirally controlled) oligonucleotide composition includes any one or more of: base sequence (including length); pattern of chemical modifications to sugar and base moieties; pattern of backbone linkages; pattern of natural phosphate linkages, phosphorothioate linkages, phosphorothioate triester linkages, and combinations thereof; pattern of backbone chiral centers; pattern of stereochemistry (Rp/Sp) of chiral internucleotidic linkages; pattern of backbone phosphorus modifications; pattern of modifications on the internucleotidic phosphorus atom, such as and -L-R$^1$ of formula I.

Among other things, the present disclosure provides new compositions that are or contain particular stereoisomers of oligonucleotides of interest. In some embodiments, a particular stereoisomer may be defined, for example, by its base sequence, its length, its pattern of backbone linkages, and its pattern of backbone chiral centers. As is understood in the art, in some embodiments, base sequence may refer to the identity and/or modification status of nucleoside residues (e.g., of sugar and/or base components, relative to standard naturally occurring nucleotides such as adenine, cytosine, guanosine, thymine, and uracil) in an oligonucleotide and/or to the hybridization character (i.e., the ability to hybridize with particular complementary residues) of such residues. In some embodiments, oligonucleotides in provided compositions comprise sugar modifications, e.g., 2'-modifications, at e.g., a wing region. In some embodiments, oligonucleotides in provided compositions comprise a region in the middle, e.g., a core region, that has no sugar modifications.

The present disclosure demonstrates, among other things, that individual stereoisomers of a particular oligonucleotide can show different stability and/or activity (e.g., functional and/or toxicity properties) from each other. Moreover, the present disclosure demonstrates that stability and/or activity improvements achieved through inclusion and/or location of particular chiral structures within an oligonucleotide can be comparable to, or even better than those achieved through use of particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]).

Among other things, the present disclosure recognizes that, in some embodiments, properties (e.g., stability and/or activities) of an oligonucleotide can be adjusted by optimizing its pattern of backbone chiral centers, optionally in combination with adjustment/optimization of one or more other features (e.g., linkage pattern, nucleoside modification pattern, etc.) of the oligonucleotide. In some embodiments, the present disclosure provides oligonucleotide compositions wherein the oligonucleotides comprise nucleoside modifications, chiral internucleotidic linkages and natural phosphate linkages. For example, WV-1092 comprises 2'-OMe modifications, phosphate linkages in its 5'- and 3'-wing regions, and phosphorothioate linkages in its core regions.

In some embodiments, the present disclosure demonstrates that stability improvements achieved through inclusion and/or location of particular chiral structures within an oligonucleotide can be comparable to, or even better than those achieved through use of modified backbone linkages, bases, and/or sugars (e.g., through use of certain types of modified phosphates, 2'-modifications, base modifications, etc.). The present disclosure, in some embodiments, also demonstrates that activity improvements achieved through inclusion and/or location of particular chiral structures within an oligonucleotide can be comparable to, or even better than those achieved through use of modified backbone linkages, bases, and/or sugars (e.g., through use of certain types of modified phosphates, 2'-modifications, base modifications, etc.).

In some embodiments, inclusion and/or location of particular chiral linkages within an oligonucleotide can surprisingly change the cleavage pattern of a nucleic acid polymer when such an oligonucleotide is utilized for cleaving said nucleic acid polymer. For example, in some embodiments, a pattern of backbone chiral centers provides unexpectedly high cleavage efficiency of a target nucleic acid polymer. In some embodiments, a pattern of backbone chiral centers provides new cleavage sites. In some embodiments, a pattern of backbone chiral centers provides fewer cleavage sites, for example, by blocking certain existing cleavage sites. Even more unexpectedly, in some embodiments, a pattern of backbone chiral centers provides cleavage at only one site of a target nucleic acid polymer within the sequence that is complementary to an oligonucleotide utilized for cleavage. In some embodiments, higher cleavage efficiency is achieved by selecting a pattern of backbone chiral centers to minimize the number of cleavage sites.

In some embodiments, the present disclosure provides compositions of oligonucleotides, wherein the oligonucleotides have a common pattern of backbone chiral centers which, unexpectedly, greatly enhances the stability and/or biological activity of the oligonucleotides. In some embodiments, a pattern of backbone chiral centers provides increased stability. In some embodiments, a pattern of backbone chiral centers provides surprisingly increased activity. In some embodiments, a pattern of backbone chiral centers provides increased stability and activity. In some embodiments, when an oligonucleotide is utilized to cleave a nucleic acid polymer, a pattern of backbone chiral centers, surprisingly by itself, changes the cleavage pattern of a target nucleic acid polymer. In some embodiments, a pattern of backbone chiral centers effectively prevents cleavage at secondary sites. In some embodiments, a pattern of backbone chiral centers creates new cleavage sites. In some embodiments, a pattern of backbone chiral centers minimizes the number of cleavage sites. In some embodiments, a pattern of backbone chiral centers minimizes the number of cleavage sites so that a target nucleic acid polymer is cleaved at only one site within the sequence of the target nucleic acid polymer that is complementary to the oligonucleotide (e.g., cleavage at other sites cannot be readily detected by a certain method; in some embodiments, greater than 85%, 90%, 91%, 92%, 93%, 94%, 95%, 96%, 97%, 98% or 99% cleavage occurs at such a site). In some embodiments, a pattern of backbone chiral centers enhances cleavage efficiency at a cleavage site. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity between two target sequences differing only by a single nucleotide polymorphism (SNP). In some embodiments, a pattern of backbone chiral centers increase cleavage at a cleavage site of a stereorandom or DNA oligonucleotide composition. In some embodiments, a pattern of backbone chiral centers increase cleavage at a major cleavage site of a stereorandom or DNA oligonucleotide composition. In some embodiments, such a site is a major cleavage site of oligonucleotides having the pattern of backbone chiral centers. In some embodiments, a site is considered a major site if it is a site having the most, or the second, third, fourth or fifth most cleavage, or a site where greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of cleavage occurs. In some embodiments, a pattern of backbone chiral centers comprises or is $(Sp)_m(Rp)_n$, $(Rp)_n(Sp)_m$, $(Np)_t(Rp)_n(Sp)_m$, or $(Sp)_t(Rp)_n(Sp)_m$. In some embodiments, a pattern of backbone chiral centers comprises or is $(Rp)_n(Sp)_m$, $(Np)_t(Rp)_n(Sp)_m$, or $(Sp)_t(Rp)_n(Sp)_m$, wherein m>2. In some embodiments, a pattern of backbone chiral centers comprises or is $(Rp)_n(Sp)_m$, $(Np)_t(Rp)_n(Sp)_m$, or $(Sp)_t(Rp)_n(Sp)_m$, wherein n is 1, t>1, and m>2. In some embodiments, m>3. In some embodiments, m>4.

In some embodiments, the present disclosure recognizes that chemical modifications, such as modifications of nucleosides and internucleotidic linkages, can provide enhanced properties. In some embodiments, the present disclosure demonstrates that combinations of chemical modifications and stereochemistry can provide unexpected, greatly improved properties (e.g., bioactivity, selectivity, etc.). In some embodiments, chemical combinations, such as modifications of sugars, bases, and/or internucleotidic linkages, are combined with stereochemistry patterns, e.g., $(Rp)_n$ $(Sp)_m$, $(Np)_t(Rp)_n(Sp)_m$, or $(Sp)_t(Rp)_n(Sp)_m$, to provide oligonucleotides and compositions thereof with surprisingly enhanced properties. In some embodiments, a provided oligonucleotide composition is chirally controlled, and comprises a combination of 2'-modification of one or more sugar moieties, one or more natural phosphate linkages, one or more phosphorothioate linkages, and a stereochemistry pattern of $(Rp)_n(Sp)_m$, $(Np)_t(Rp)_n(Sp)_m$, or $(Sp)_t$ $(Rp)_n(Sp)_m$, wherein m>2. In some embodiments, n is 1, t>1, and m>2. In some embodiments, m>3. In some embodiments, m>4.

In some embodiments, the present disclosure provides a chirally controlled oligonucleotide composition comprising oligonucleotides defined by having:

1) a common base sequence and length;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, a common base sequence and length may be referred to as a common base sequence. In some embodiments, oligonucleotides having a common base sequence may have the same pattern of nucleoside modifications, e.g., sugar modifications, base modifications, etc. In some embodiments, a pattern of nucleoside modifications may be represented by a combination of locations and modifications. For example, for WV-1092, the pattern of nucleoside modifications is 5×2'-OMe (2'-OMe modification on sugar moieties)-DNA (no 2'-modifications on the sugar moiety)-5×2'-OMe from the 5'-end to the 3'-end. In some embodiments, a pattern of backbone linkages comprises locations and types (e.g., phosphate, phosphorothioate, substituted phosphorothioate, etc.) of each internucleotidic linkages. In some embodiments, an oligonucleotide can have a specified pattern of backbone linkages. In some embodiments, an oligonucleotide has a pattern of backbone linkages of $_n$PS-$_n$PO-$_n$PS-$_n$PO-$_n$PS, wherein PO is phosphate (phosphorodiester), PS is phosphorothioate, and n is 1-15, and each occurrence of n can be the same or different. In some embodiments, at least one n is greater than 2, 3, 4, 5, 6, 7, 8, 9, 10, 11, 12, 13, 14, 15, 16, 17, 18, 19, or 20. In some embodiments, at least one n for PS is greater than 2, 3, 4, 5, 6, 7, 8, 9, 10, 11, 12, 13, 14, 15, 16, 17, 18, 19, or 20. In some embodiments, the n for the PS between the two PO is greater than 2, 3, 4, 5, 6, 7, 8, 9, 10, 11, 12, 13, 14, 15, 16, 17, 18, 19, or 20. In some embodiments, n is greater than 5. In some embodiments, n is greater than 6. In some embodiments, n is greater than 7. In some embodiments, n is greater than 8. In some embodiments, n is greater than 9. In some embodiments, n is greater than 10. In some embodiments, n is greater than 11. In some embodiments, n is greater than 12. In some embodiments, n is greater than 13. In some embodiments, n is greater than 14. In some embodiments, n is greater than 15. In some embodiments, an oligonucleotide has a pattern of backbone linkages of 1-5PS-1-7PO-5-15PS-1-7 PO— 1-5PS (meaning 1 to 5 phosphorothioates, 1 to 7 phosphates, 5 to 15 phosphorothioates, 1 to 7 phosphates, and 1 to 5 phosphorothioates). In some embodiments, the oligonucleotide has a pattern of backbone linkages, from 5' to 3', of 1PS-3PO-11PS-3PO-1PS (meaning 1 phosphorothioate, 3 phosphates, 11 phosphorothioates, 3 phosphates, and 1 phosphorothioate, and which can alternatively be represented as $PS_1$ $PO_3$ $PS_{11}$ $PO_3$ $PS_1$). For example, for WV-1092, the pattern of backbone linkages is 1PS-3PO-11PS-3PO-1PS from the 5'-end to the 3'-end. In some embodiments, an oligonucleotide has a pattern of backbone linkages of 1-5PS-1-7PO-5-15PS-1-7PO-1-5PS, wherein each PS is Sp except for one Rp. In some embodiments, the oligonucleotide has a pattern of backbone linkages of 1-5PS-1-7PO-5-15PS-1-7PO-1-5PS, wherein each PS is Sp except one PS at any position from the $5^{th}$ to $15^{th}$ PS is Rp. In some embodiments, the oligonucleotide has a pattern of backbone linkages of 1-5PS-1-7PO-5-15PS-1-7PO-1-5PS, wherein each PS is Sp except that the $10^{th}$ PS counting from the 5' end is Rp. In some embodiments, the oligonucleotide has a pattern of backbone linkages of 1-5PS-1-7PO-5-15PS-1-7PO-1-5PS, wherein each PS is Sp except that the $9^{th}$ counting from the 5' end PS is Rp. In some embodiments, the oligonucleotide has a pattern of backbone linkages of 1-5PS-1-7PO-5-15PS-1-7PO-1-5PS, wherein each PS is Sp except that the 11th PS counting from the 5' end is Rp. A pattern of backbone chiral centers of an oligonucleotide can be designated by a combination of linkage phosphorus stereochemistry (Rp/Sp) from 5' to 3'. For example, WV-1092 has a pattern of 1S-3PO (phosphate)-8S-1R-2S-3PO-1S, and WV-937 has a pattern of 12S-1R-6S. In some embodiments, all non-chiral linkages (e.g., PO) may be omitted when describing a pattern of backbone chiral centers. As exemplified above, locations of non-chiral linkages may be obtained, for example, from pattern of backbone linkages. Any sequence disclosed herein can be combined with any patterns of backbone linkages and/or any patterns of backbone chiral centers disclosed herein. Base sequences, patterns of backbone linkages, patterns of stereochemistry (e.g., Rp or Sp), patterns of base modifications, patterns of backbone chiral centers, etc. are presented in 5' to 3' direction unless otherwise indicated.

In some embodiments, the present disclosure provides a chirally controlled oligonucleotide composition comprising oligonucleotides of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type.

An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1,2-bensodithiol-3-one 1,1-dioxide (BDTD), a well-known process in the art. In some embodiments, substantially racemic preparation of oligonucleotides provides substantially racemic oligonucleotide compositions (or chirally uncontrolled oligonucleotide compositions).

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1,2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, at least two couplings of a nucleotide monomer have a diastereoselectivity lower than about 60:40, 70:30, 80:20, 85:15, 90:10, 91:9, 92:8, 97:3, 98:2, or 99:1. In some embodiments, at least three couplings of a nucleotide monomer have a diastereoselectivity lower than about 60:40, 70:30, 80:20, 85:15, 90:10, 91:9, 92:8, 97:3, 98:2, or 99:1. In some embodiments, at least four couplings of a nucleotide monomer have a diastereoselectivity lower than about 60:40, 70:30, 80:20, 85:15, 90:10, 91:9, 92:8, 97:3, 98:2, or 99:1. In some embodiments, at least five couplings of a nucleotide monomer have a diastereoselectivity lower than about 60:40, 70:30, 80:20, 85:15, 90:10, 91:9, 92:8, 97:3, 98:2, or 99:1. In some embodiments, in a stereorandom or racemic preparations, at least one internucleotidic linkage has a diastereoselectivity lower than about 60:40, 70:30, 80:20, 85:15, 90:10, 91:9, 92:8, 97:3, 98:2, or 99:1. In some embodiments, at least two internucleotidic linkages have a diastereoselectivity lower than about 60:40, 70:30, 80:20, 85:15, 90:10, 91:9, 92:8, 97:3, 98:2, or 99:1. In some embodiments, at least three internucleotidic linkages have a diastereoselectivity lower than about 60:40, 70:30, 80:20, 85:15, 90:10, 91:9, 92:8, 97:3, 98:2, or 99:1. In some embodiments, at least four internucleotidic linkages have a diastereoselectivity lower than about 60:40, 70:30, 80:20, 85:15, 90:10, 91:9, 92:8, 97:3, 98:2, or 99:1. In some embodiments, at least five internucleotidic linkages have a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, a diastereoselectivity is lower than about 92:8. In some embodiments, a diastereoselectivity is lower than about 93:7. In some embodiments, a diastereoselectivity is lower than about 94:6. In some embodiments, a diastereoselectivity is lower than about 95:5. In some embodiments, a diastereoselectivity is lower than about 96:4. In some embodiments, a diastereoselectivity is lower than about 97:3. In some embodiments, a diastereoselectivity is lower than about 98:2. In some embodiments, a diastereoselectivity is lower than about 99:1. In some embodiments, at least one coupling has a diastereoselectivity lower than about 90:10. In some embodiments, at least two couplings have a diastereoselectivity lower than about 90:10. In some embodiments, at least three couplings have a diastereoselectivity lower than about 90:10. In some embodiments, at least four couplings have a diastereoselectivity lower than about 90:10. In some embodiments, at least five couplings have a diastereoselectivity lower than about 90:10. In some embodiments, at least one internucleotidic linkage has a diastereoselectivity lower than about 90:10. In some embodiments, at least two internucleotidic linkages have a diastereoselectivity lower than about 90:10. In some embodiments, at least three internucleotidic linkages have a diastereoselectivity lower than about 90:10. In some embodiments, at least four internucleotidic linkages have a diastereoselectivity lower than about 90:10. In some embodiments, at least five internucleotidic linkages have a diastereoselectivity lower than about 90:10.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage. For example, diastereoselectivity of the underlined coupling or linkage in WV-1092 mG*SmGmCmAmC*SA*SA*SG*SG*S G*SC*SA* SC*RA*SG*SmAmCmUmU*SmC (SEQ ID NO: 14) can be assessed from coupling two G moieties under the same or comparable conditions, e.g., monomers, chiral auxiliaries, solvents, activators, temperatures, etc.

In some embodiments, the present disclosure provides chirally controlled (and/or stereochemically pure) oligonucleotide compositions comprising oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

In some embodiments, the present disclosure provides chirally controlled oligonucleotide composition of oligonucleotides in that the composition is enriched, relative to a substantially racemic preparation of the same oligonucleotides, for oligonucleotides of a single oligonucleotide type. In some embodiments, the present disclosure provides chirally controlled oligonucleotide composition of oligonucleotides in that the composition is enriched, relative to a substantially racemic preparation of the same oligonucleotides, for oligonucleotides of a single oligonucleotide type that share:
1) a common base sequence and length;
2) a common pattern of backbone linkages; and
3) a common pattern of backbone chiral centers.

In some embodiments, the present disclosure provides a chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have identical structures.

In some embodiments, oligonucleotides of an oligonucleotide type have a common pattern of backbone phosphorus modifications and a common pattern of sugar modifications. In some embodiments, oligonucleotides of an oligonucleotide type have a common pattern of backbone phosphorus modifications and a common pattern of base modifications. In some embodiments, oligonucleotides of an oligonucleotide type have a common pattern of backbone phosphorus modifications and a common pattern of nucleoside modifications. In some embodiments, oligonucleotides of an oligonucleotide type are identical.

In some embodiments, a chirally controlled oligonucleotide composition is a substantially pure preparation of an oligonucleotide type in that oligonucleotides in the composition that are not of the oligonucleotide type are impurities form the preparation process of said oligonucleotide type, in some case, after certain purification procedures.

In some embodiments, at least about 20% of the oligonucleotides in the composition have a common base sequence and length, a common pattern of backbone linkages, and a common pattern of backbone chiral centers. In some embodiments, at least about 25% of the oligonucleotides in the composition have a common base sequence and length, a common pattern of backbone linkages, and a common pattern of backbone chiral centers. In some embodiments, at least about 30% of the oligonucleotides in the composition have a common base sequence and length, a common pattern of backbone linkages, and a common pattern of backbone chiral centers. In some embodiments, at least about 35% of the oligonucleotides in the composition have a common base sequence and length, a common pattern of backbone linkages, and a common pattern of backbone chiral centers. In some embodiments, at least about 40% of the oligonucleotides in the composition have a common base sequence and length, a common pattern of backbone linkages, and a common pattern of backbone chiral centers. In some embodiments, at least about 45% of the oligonucleotides in the composition have a common base sequence and length, a common pattern of backbone linkages, and a common pattern of backbone chiral centers. In some embodiments, at least about 50% of the oligonucleotides in the composition have a common base sequence and length, a common pattern of backbone linkages, and a common pattern of backbone chiral centers. In some embodiments, at least about 55% of the oligonucleotides in the composition have a common base sequence and length, a common pattern of backbone linkages, and a common pattern of backbone chiral centers. In some embodiments, at least about 60% of the oligonucleotides in the composition have a common base sequence and length, a common pattern of backbone linkages, and a common pattern of backbone chiral centers. In some embodiments, at least about 65% of the oligonucleotides in the composition have a common base sequence and length, a common pattern of backbone linkages, and a common pattern of backbone chiral centers. In some embodiments, at least about 70% of the oligonucleotides in the composition have a common base sequence and length, a common pattern of backbone linkages, and a common pattern of backbone chiral centers. In some embodiments, at least about 75% of the oligonucleotides in the composition have a common base sequence and length, a common pattern of backbone linkages, and a common pattern of backbone chiral centers. In some embodiments, at least about 80% of the oligonucleotides in the composition have a common base sequence and length, a common pattern of backbone linkages, and a common pattern of backbone chiral centers. In some embodiments, at least about 85% of the oligonucleotides in the composition have a common base sequence and length, a common pattern of backbone linkages, and a common pattern of backbone chiral centers. In some embodiments, at least about 90% of the oligonucleotides in the composition have a common base sequence and length, a common pattern of backbone linkages, and a common pattern of backbone chiral centers. In some embodiments, at least about 92% of the oligonucleotides in the composition have a common base sequence and length, a common pattern of backbone linkages, and a common pattern of backbone chiral centers. In some embodiments, at least about 94% of the oligonucleotides in the composition have a common base sequence and length, a common pattern of backbone linkages, and a common pattern of backbone chiral centers. In some embodiments, at least about 95% of the oligonucleotides in the composition have a common base sequence and length, a common pattern of backbone linkages, and a common pattern of backbone chiral centers. In some embodiments, at least about 91%, 92%, 93%, 94%, 95%, 96%, 97%, 98%, or 99% of the oligonucleotides in the composition have a common base sequence and length, a common pattern of backbone linkages, and a common pattern of backbone chiral centers. In some embodiments, greater than about 99% of the oligonucleotides in the composition have a common base sequence and length, a common pattern of backbone linkages, and a common pattern of backbone chiral centers. In some embodiments, purity of a chirally controlled oligonucleotide composition of an oligonucleotide can be expressed as the percentage of oligonucleotides in the composition that have a common base sequence and length, a common pattern of backbone linkages, and a common pattern of backbone chiral centers.

In some embodiments, oligonucleotides having a common base sequence and length, a common pattern of backbone linkages, and a common pattern of backbone chiral centers have a common pattern of backbone phosphorus modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have a common pattern of backbone phosphorus modifications and a common pattern of sugar modifications. In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers are identical.

In some embodiments, oligonucleotides in provided compositions have a common pattern of backbone phosphorus modifications. In some embodiments, a common base sequence is a base sequence of an oligonucleotide type. In some embodiments, a provided composition is an oligonucleotide composition that is chirally controlled in that the composition contains a predetermined level of oligonucleotides of an individual oligonucleotide type, wherein an oligonucleotide type is defined by:
1) base sequence;
2) pattern of backbone linkages;
3) pattern of backbone chiral centers; and
4) pattern of backbone phosphorus modifications.

As noted above and understood in the art, in some embodiments, base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, a particular oligonucleotide type may be defined by
1A) base identity;
1B) pattern of base modification;
1C) pattern of sugar modification;
2) pattern of backbone linkages;
3) pattern of backbone chiral centers; and
4) pattern of backbone phosphorus modifications.

Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, oligonucleotides of a particular type are identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S⁻, and -L-R$^1$ of formula I).

In some embodiments, purity of a chirally controlled oligonucleotide composition of an oligonucleotide type is expressed as the percentage of oligonucleotides in the composition that are of the oligonucleotide type. In some embodiments, at least about 10% of the oligonucleotides in a chirally controlled oligonucleotide composition are of the same oligonucleotide type. In some embodiments, at least about 20% of the oligonucleotides in a chirally controlled oligonucleotide composition are of the same oligonucleotide type. In some embodiments, at least about 30% of the oligonucleotides in a chirally controlled oligonucleotide composition are of the same oligonucleotide type. In some embodiments, at least about 40% of the oligonucleotides in a chirally controlled oligonucleotide composition are of the same oligonucleotide type. In some embodiments, at least about 50% of the oligonucleotides in a chirally controlled oligonucleotide composition are of the same oligonucleotide type. In some embodiments, at least about 60% of the oligonucleotides in a chirally controlled oligonucleotide composition are of the same oligonucleotide type. In some embodiments, at least about 70% of the oligonucleotides in a chirally controlled oligonucleotide composition are of the same oligonucleotide type. In some embodiments, at least about 80% of the oligonucleotides in a chirally controlled oligonucleotide composition are of the same oligonucleotide type. In some embodiments, at least about 90% of the oligonucleotides in a chirally controlled oligonucleotide composition are of the same oligonucleotide type. In some embodiments, at least about 92% of the oligonucleotides in a chirally controlled oligonucleotide composition are of the same oligonucleotide type. In some embodiments, at least about 94% of the oligonucleotides in a chirally controlled oligonucleotide composition are of the same oligonucleotide type. In some embodiments, at least about 95% of the oligonucleotides in a chirally controlled oligonucleotide composition are of the same oligonucleotide type. In some embodiments, at least about 96% of the oligonucleotides in a chirally controlled oligonucleotide composition are of the same oligonucleotide type. In some embodiments, at least about 97% of the oligonucleotides in a chirally controlled oligonucleotide composition are of the same oligonucleotide type. In some embodiments, at least about 98% of the oligonucleotides in a chirally controlled oligonucleotide composition are of the same oligonucleotide type. In some embodiments, at least about 99% of the oligonucleotides in a chirally controlled oligonucleotide composition are of the same oligonucleotide type.

In some embodiments, purity of a chirally controlled oligonucleotide composition can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed may be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%. In some embodiments, a coupling step has a stereoselectivity of virtually 100% in that all detectable product from the coupling step by an analytical method (e.g., NMR, HPLC, etc) has the intended stereoselectivity.

Among other things, the present disclosure recognizes that combinations of oligonucleotide structural elements (e.g., patterns of chemical modifications, backbone linkages, backbone chiral centers, and/or backbone phosphorus modifications) can provide surprisingly improved properties such as bioactivities.

In some embodiments, the present disclosure provides an oligonucleotide composition comprising a predetermined level of oligonucleotides which comprise one or more wing regions and a common core region, wherein:

each wing region independently has a length of two or more bases, and independently and optionally comprises one or more chiral internucleotidic linkages;

the core region independently has a length of two or more bases, and independently comprises one or more chiral internucleotidic linkages, and the common core region has:

1) a common base sequence and length;
2) a common pattern of backbone linkages; and
3) a common pattern of backbone chiral centers.

In some embodiments, a wing region comprises a structural feature that is not in a core region. In some embodiments, a wing and core can be defined by any structural elements, e.g., base modifications (e.g., methylated/non-methylated, methylation at position 1/methylation at position 2, etc.), sugar modifications (e.g., modified/non-modified, 2'-modification/another type of modification, one type of 2'-modification/another type of 2'-modification, etc.), backbone linkage types (e.g., phosphate/phosphorothioate, phosphorothioate/substituted phosphorothioate, etc.), backbone chiral center stereochemistry(e.g., all Sp/all Rp, (SpRp) repeats/all Rp, etc.), backbone phosphorus modification types (e.g., s1/s2, s1/s3, etc.), etc.

In some embodiments, a wing and core is defined by nucleoside modifications, wherein a wing comprises a nucleoside modification that the core region does not have. In some embodiments, a wing and core is defined by sugar modifications, wherein a wing comprises a sugar modification that the core region does not have. In some embodiments, a sugar modification is a 2'-modification. In some embodiments, a sugar modification is 2'-OR'. In some embodiments, a sugar modification is 2'-MOE. In some embodiments, a sugar modification is 2'-OMe. Additionally example sugar modifications are described in the present disclosure.

In some embodiments, oligonucleotides in provided compositions have a wing-core structure (hemimer). In some embodiments, oligonucleotides in provided compositions have a wing-core structure of nucleoside modifications. In some embodiments, oligonucleotides in provided compositions have a core-wing structure (another type of hemimer). In some embodiments, oligonucleotides in provided compositions have a core-wing structure of nucleoside modifications. In some embodiments, oligonucleotides in provided compositions have a wing-core-wing structure (gapmer). In some embodiments, oligonucleotides in provided compositions have a wing-core-wing structure of nucleoside modifications. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, a core region has no sugar modification. In some embodiments, each sugar moiety in the wing region has the same 2'-modification, and the core region has no 2'-modifications. In some embodiments, when two or more wings are present, each wing is defined by its own modifications. In some embodiments, each wing has its own characteristic sugar modification. In some embodiments, each wing has the same characteristic sugar modification differentiating it from a core. In some embodiments, each wing sugar moiety has the same modification. In some embodiments, each wing sugar moiety has the same 2'-modification. In some embodiments, each sugar moiety in a wing region has the same 2'-modification, yet the common 2'-modification in a first wing region can either be the same as or different from the common 2'-modification in a second wing region. In some embodiments, each sugar moiety in a wing region has the same 2'-modification, and the common 2'-modification in a first wing region is the same as the common 2'-modification in a second wing region. In some embodiments, each sugar moiety in a wing region has the same 2'-modification, and the common 2'-modification in a first wing region is different from the common 2'-modification in a second wing region.

In some embodiments, provided chirally controlled (and/or stereochemically pure) preparations are antisense oligonucleotides (e.g., chiromersen). In some embodiments, provided chirally controlled (and/or stereochemically pure) preparations are siRNA oligonucleotides. In some embodiments, a provided chirally controlled oligonucleotide composition is of oligonucleotides that can be antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant. In some embodiments, a chirally controlled oligonucleotide composition is of antisense oligonucleotides. In some embodiments, a chirally controlled oligonucleotide composition is of antagomir oligonucleotides. In some embodiments, a chirally controlled oligonucleotide composition is of microRNA oligonucleotides. In some embodiments, a chirally controlled oligonucleotide composition is of pre-microRNA oligonucleotides. In some embodiments, a chirally controlled oligonucleotide composition is of antimir oligonucleotides. In some embodiments, a chirally controlled oligonucleotide composition is of supermir oligonucleotides. In some embodiments, a chirally controlled oligonucleotide composition is of ribozyme oligonucleotides. In some embodiments, a chirally controlled oligonucleotide composition is of U1 adaptor oligonucleotides. In some embodiments, a chirally controlled oligonucleotide composition is of RNA activator oligonucleotides. In some embodiments, a chirally controlled oligonucleotide composition is of RNAi agent oligonucleotides. In some embodiments, a chirally controlled oligonucleotide composition is of decoy oligonucleotides. In some embodiments, a chirally controlled oligonucleotide composition is of triplex forming oligonucleotides. In some embodiments, a chirally controlled oligonucleotide composition is of aptamer oligonucleotides. In some embodiments, a chirally controlled oligonucleotide composition is of adjuvant oligonucleotides.

In some embodiments, provided chirally controlled (and/or stereochemically pure) preparations are of oligonucleotides that include one or more modified backbone linkages, bases, and/or sugars.

In some embodiments, a provided oligonucleotide comprises one or more chiral, modified phosphate linkages. In some embodiments, a provided oligonucleotide comprises two or more chiral, modified phosphate linkages. In some embodiments, a provided oligonucleotide comprises three or more chiral, modified phosphate linkages. In some embodiments, a provided oligonucleotide comprises four or more chiral, modified phosphate linkages. In some embodiments, a provided oligonucleotide comprises five or more chiral, modified phosphate linkages. In some embodiments, a provided oligonucleotide comprises 1, 2, 3, 4, 5, 6, 7, 8, 9, 10, 11, 12, 13, 14, 15, 16, 17, 18, 19, 20, 21, 22, 23, 24, or 25 chiral, modified phosphate linkages. In some embodiments, a provided oligonucleotide type comprises 5 or more chiral, modified phosphate linkages. In some embodiments, a provided oligonucleotide type comprises 6 or more chiral, modified phosphate linkages. In some embodiments, a provided oligonucleotide type comprises 7 or more chiral, modified phosphate linkages. In some embodiments, a provided oligonucleotide type comprises 8 or more chiral, modified phosphate linkages. In some embodiments, a provided oligonucleotide type comprises 9 or more chiral, modified phosphate linkages. In some embodiments, a provided oligonucleotide type comprises 10 or more chiral, modified phosphate linkages. In some embodiments, a provided oligonucleotide type comprises 11 or more chiral, modified phosphate linkages. In some embodiments, a provided oligonucleotide type comprises 12 or more chiral, modified phosphate linkages. In some embodiments, a provided oligonucleotide type comprises 13 or more chiral, modified phosphate linkages. In some embodiments, a provided oligonucleotide type comprises 14 or more chiral, modified phosphate linkages. In some embodiments, a provided oligonucleotide type comprises 15 or more chiral, modified phosphate linkages. In some embodiments, a provided oligonucleotide type comprises 16 or more chiral, modified phosphate linkages. In some embodiments, a provided oligonucleotide type comprises 17 or more chiral, modified phosphate linkages. In some embodiments, a provided oligonucleotide type comprises 18 or more chiral, modified phosphate linkages. In some embodiments, a provided oligonucleotide type comprises 19 or more chiral, modified phosphate linkages. In some embodiments, a provided oligonucleotide type comprises 20 or more chiral, modified phosphate linkages. In some embodiments, a provided oligonucleotide type comprises 21 or more chiral, modified phosphate linkages. In some embodiments, a provided oligonucleotide type comprises 22 or more chiral, modified phosphate linkages. In some embodiments, a provided oligonucleotide type comprises 23 or more chiral, modified phosphate linkages. In some embodiments, a provided oligonucleotide type comprises 24 or more chiral, modified phosphate linkages. In some embodiments, a provided oligonucleotide type comprises 25 or more chiral, modified phosphate linkages.

In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages. Example such chiral, modified phosphate linkages are described above and herein. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages in the Sp configuration.

In some embodiments, provided chirally controlled (and/or stereochemically pure) preparations are of a stereochemical purity of greater than about 80%. In some embodiments, provided chirally controlled (and/or stereochemically pure) preparations are of a stereochemical purity of greater than about 85%. In some embodiments, provided chirally controlled (and/or stereochemically pure) preparations are of a stereochemical purity of greater than about 90%. In some embodiments, provided chirally controlled (and/or stereochemically pure) preparations are of a stereochemical purity of greater than about 91%. In some embodiments, provided chirally controlled (and/or stereochemically pure) preparations are of a stereochemical purity of greater than about 92%. In some embodiments, provided chirally controlled (and/or stereochemically pure) preparations are of a stereochemical purity of greater than about 93%. In some embodiments, provided chirally controlled (and/or stereochemically pure) preparations are of a stereochemical purity of greater than about 94%. In some embodiments, provided chirally controlled (and/or stereochemically pure) preparations are of a stereochemical purity of greater than about 95%. In some embodiments, provided chirally controlled (and/or stereochemically pure) preparations are of a stereochemical purity of greater than about 96%. In some embodiments, provided chirally controlled (and/or stereochemically pure) preparations are of a stereochemical purity of greater than about 97%. In some embodiments, provided chirally controlled (and/or stereochemically pure) preparations are of a stereochemical purity of greater than about 98%. In some embodiments, provided chirally controlled (and/or stereochemically pure) preparations are of a stereochemical purity of greater than about 99%.

In some embodiments, a chiral, modified phosphate linkage is a chiral phosphorothioate linkage, i.e., phosphorothioate internucleotidic linkage. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10, 20, 30, 40, 50, 60, 70, 80, or 90% chiral phosphorothioate internucleotidic linkages of a provided oligonucleotide are of the Sp conformation. In some embodiments, at least about 10% chiral phosphorothioate internucleotidic linkages of a provided oligonucleotide are of the Sp conformation. In some embodiments, at least about 20% chiral phosphorothioate internucleotidic linkages of a provided oligonucleotide are of the Sp conformation. In some embodiments, at least about 30% chiral phosphorothioate internucleotidic linkages of a provided oligonucleotide are of the Sp conformation. In some embodiments, at least about 40% chiral phosphorothioate internucleotidic linkages of a provided oligonucleotide are of the Sp conformation. In some embodiments, at least about 50% chiral phosphorothioate internucleotidic linkages of a provided oligonucleotide are of the Sp conformation. In some embodiments, at least about 60% chiral phosphorothioate internucleotidic linkages of a provided oligonucleotide are of the Sp conformation. In some embodiments, at least about 70% chiral phosphorothioate internucleotidic linkages of a provided oligonucleotide are of the Sp conformation. In some embodiments, at least about 80% chiral phosphorothioate internucleotidic linkages of a provided oligonucleotide are of the Sp conformation. In some embodiments, at least about 90% chiral phosphorothioate internucleotidic linkages of a provided oligonucleotide are of the Sp conformation. In some embodiments, at least about 95% chiral phosphorothioate internucleotidic linkages of a provided oligonucleotide are of the Sp conformation. In some embodiments, at least about 10, 20, 30, 40, 50, 60, 70, 80, or 90% chiral phosphorothioate internucleotidic linkages of a provided oligonucleotide are of the Rp conformation. In some embodiments, at least about 10% chiral phosphorothioate internucleotidic linkages of a provided oligonucleotide are of the Rp conformation. In some embodiments, at least about 20% chiral phosphorothioate internucleotidic linkages of a provided oligonucleotide are of the Rp conformation. In some embodiments, at least about 30% chiral phosphorothioate internucleotidic linkages of a provided oligonucleotide are of the Rp conformation. In some embodiments, at least about 40% chiral phosphorothioate internucleotidic linkages of a provided oligonucleotide are of the Rp conformation. In some embodiments, at least about 50% chiral phosphorothioate internucleotidic linkages of a provided oligonucleotide are of the Rp conformation. In some embodiments, at least about 60% chiral phosphorothioate internucleotidic linkages of a provided oligonucleotide are of the Rp conformation. In some embodiments, at least about 70% chiral phosphorothioate internucleotidic linkages of a provided oligonucleotide are of the Rp conformation. In some embodiments, at least about 80% chiral phosphorothioate internucleotidic linkages of a provided oligonucleotide are of the Rp conformation. In some embodiments, at least about 90% chiral phosphorothioate internucleotidic linkages of a provided oligonucleotide are of the Rp conformation. In some embodiments, at least about 95% chiral phosphorothioate internucleotidic linkages of a provided oligonucleotide are of the Rp conformation. In some embodiments, less than about 10, 20, 30, 40, 50, 60, 70, 80, or 90% chiral phosphorothioate internucleotidic linkages of a provided oligonucleotide are of the Rp conformation. In some embodiments, less than about 10% chiral phosphorothioate internucleotidic linkages of a provided oligonucleotide are of the Rp conformation. In some embodiments, less than about 20% chiral phosphorothioate internucleotidic linkages of a provided oligonucleotide are of the Rp conformation. In some embodiments, less than about 30% chiral phosphorothioate internucleotidic linkages of a provided oligonucleotide are of the Rp conformation. In some embodiments, less than about 40% chiral phosphorothioate internucleotidic linkages of a provided oligonucleotide are of the Rp conformation. In some embodiments, less than about 50% chiral phosphorothioate internucleotidic linkages of a provided oligonucleotide are of the Rp conformation. In some embodiments, less than about 60% chiral phosphorothioate internucleotidic linkages of a provided oligonucleotide are of the Rp conformation. In some embodiments, less than about 70% chiral phosphorothioate internucleotidic linkages of a provided oligonucleotide are of the Rp conformation. In some embodiments, less than about 80% chiral phosphorothioate internucleotidic linkages of a provided oligonucleotide are of the Rp conformation. In some embodiments, less than about 90% chiral phosphorothioate internucleotidic linkages of a provided oligonucleotide are of the Rp conformation. In some embodiments, less than about 95% chiral phosphorothioate internucleotidic linkages of a provided oligonucleotide are of the Rp conformation. In some embodiments, a provided oligonucleotide has only one Rp chiral phosphorothioate internucleotidic linkages. In some embodiments, a provided oligonucleotide has only one Rp chiral phosphorothioate internucleotidic linkages, wherein all internucleotide linkages are chiral phosphorothioate internucleotidic linkages. In some embodiments, a chiral phosphorothioate internucleotidic linkage is a chiral phosphorothioate diester linkage. In some embodiments, each chiral phosphorothioate internucleotidic linkage is independently a chiral phosphorothioate diester linkage. In some embodiments, each internucleotidic linkage is independently a chiral phosphorothioate diester linkage. In some embodiments, each internucleotidic linkage is independently a chiral phosphorothioate diester linkage, and only one is Rp.

In some embodiments, provided chirally controlled (and/or stereochemically pure) preparations are of oligonucleotides that contain one or more modified bases. In some embodiments, provided chirally controlled (and/or stereochemically pure) preparations are of oligonucleotides that contain no modified bases. Example such modified bases are described above and herein.

In some embodiments, oligonucleotides of provided compositions comprise at least 2, 3, 4, 5, 6, 7, 8, 9 or 10 natural phosphate linkages. In some embodiments, oligonucleotides of provided compositions comprise at least one natural phosphate linkage. In some embodiments, oligonucleotides of provided compositions comprise at least two natural phosphate linkages. In some embodiments, oligonucleotides of provided compositions comprise at least three natural phosphate linkages. In some embodiments, oligonucleotides of provided compositions comprise at least four natural phosphate linkages. In some embodiments, oligonucleotides of provided compositions comprise at least five natural phosphate linkages. In some embodiments, oligonucleotides of provided compositions comprise at least six natural phosphate linkages. In some embodiments, oligonucleotides of provided compositions comprise at least seven natural phosphate linkages. In some embodiments, oligonucleotides of provided compositions comprise at least eight natural phosphate linkages. In some embodiments, oligonucleotides of provided compositions comprise at least nine natural phosphate linkages. In some embodiments, oligonucleotides of provided compositions comprise at least ten natural phosphate linkages.

In some embodiments, oligonucleotides of provided compositions comprise 2, 3, 4, 5, 6, 7, 8, 9 or 10 natural phosphate linkages. In some embodiments, oligonucleotides of provided compositions comprise one natural phosphate linkage. In some embodiments, oligonucleotides of provided compositions comprise two natural phosphate linkages. In some embodiments, oligonucleotides of provided compositions comprise three natural phosphate linkages. In some embodiments, oligonucleotides of provided compositions comprise four natural phosphate linkages. In some embodiments, oligonucleotides of provided compositions comprise five natural phosphate linkages. In some embodiments, oligonucleotides of provided compositions comprise six natural phosphate linkages. In some embodiments, oligonucleotides of provided compositions comprise seven natural phosphate linkages. In some embodiments, oligonucleotides of provided compositions comprise eight natural phosphate linkages. In some embodiments, oligonucleotides of provided compositions comprise nine natural phosphate linkages. In some embodiments, oligonucleotides of provided compositions comprise ten natural phosphate linkages.

In some embodiments, oligonucleotides of provided compositions comprise at least 2, 3, 4, 5, 6, 7, 8, 9 or 10 consecutive natural phosphate linkages. In some embodiments, oligonucleotides of provided compositions comprise at least two consecutive natural phosphate linkages. In some embodiments, oligonucleotides of provided compositions comprise at least three consecutive natural phosphate linkages. In some embodiments, oligonucleotides of provided compositions comprise at least four consecutive natural phosphate linkages. In some embodiments, oligonucleotides of provided compositions comprise at least five consecutive natural phosphate linkages. In some embodiments, oligonucleotides of provided compositions comprise at least six consecutive natural phosphate linkages. In some embodiments, oligonucleotides of provided compositions comprise at least seven consecutive natural phosphate linkages. In some embodiments, oligonucleotides of provided compositions comprise at least eight consecutive natural phosphate linkages. In some embodiments, oligonucleotides of provided compositions comprise at least nine consecutive natural phosphate linkages. In some embodiments, oligonucleotides of provided compositions comprise at least ten consecutive natural phosphate linkages.

In some embodiments, oligonucleotides of provided compositions comprise 2, 3, 4, 5, 6, 7, 8, 9 or 10 consecutive natural phosphate linkages. In some embodiments, oligonucleotides of provided compositions comprise two consecutive natural phosphate linkages. In some embodiments, oligonucleotides of provided compositions comprise three consecutive natural phosphate linkages. In some embodiments, oligonucleotides of provided compositions comprise four consecutive natural phosphate linkages. In some embodiments, oligonucleotides of provided compositions comprise five consecutive natural phosphate linkages. In some embodiments, oligonucleotides of provided compositions comprise six consecutive natural phosphate linkages. In some embodiments, oligonucleotides of provided compositions comprise seven consecutive natural phosphate linkages. In some embodiments, oligonucleotides of provided compositions comprise eight consecutive natural phosphate linkages. In some embodiments, oligonucleotides of provided compositions comprise nine consecutive natural phosphate linkages. In some embodiments, oligonucleotides of provided compositions comprise ten consecutive natural phosphate linkages.

In some embodiments, provided chirally controlled (and/or stereochemically pure) preparations are of oligonucleotides having a common base sequence of at least 8 bases. In some embodiments, provided chirally controlled (and/or stereochemically pure) preparations are of oligonucleotides having a common base sequence of at least 9 bases. In some embodiments, provided chirally controlled (and/or stereochemically pure) preparations are of oligonucleotides having a common base sequence of at least 10 bases. In some embodiments, provided chirally controlled (and/or stereochemically pure) preparations are of oligonucleotides having a common base sequence of at least 11 bases. In some embodiments, provided chirally controlled (and/or stereochemically pure) preparations are of oligonucleotides having a common base sequence of at least 12 bases. In some embodiments, provided chirally controlled (and/or stereochemically pure) preparations are of oligonucleotides having a common base sequence of at least 13 bases. In some embodiments, provided chirally controlled (and/or stereochemically pure) preparations are of oligonucleotides having a common base sequence of at least 14 bases. In some embodiments, provided chirally controlled (and/or stereochemically pure) preparations are of oligonucleotides having a common base sequence of at least 15 bases. In some embodiments, provided chirally controlled (and/or stereochemically pure) preparations are of oligonucleotides having a common base sequence of at least 16 bases. In some embodiments, provided chirally controlled (and/or stereochemically pure) preparations are of oligonucleotides having a common base sequence of at least 17 bases. In some embodiments, provided chirally controlled (and/or stereochemically pure) preparations are of oligonucleotides having a common base sequence of at least 18 bases. In some embodiments, provided chirally controlled (and/or stereochemically pure) preparations are of oligonucleotides having a common base sequence of at least 19 bases. In some embodiments, provided chirally controlled (and/or stereochemically pure) preparations are of oligonucleotides having a common base sequence of at least 20 bases. In some embodiments, provided chirally controlled (and/or stereochemically pure) preparations are of oligonucleotides having a common base sequence of at least 21 bases. In some embodiments, provided chirally controlled (and/or stereochemically pure) preparations are of oligonucleotides having a common base sequence of at least 22 bases. In some embodiments, provided chirally controlled (and/or stereochemically pure) preparations are of oligonucleotides having a common base sequence of at least 23 bases. In some embodiments, provided chirally controlled (and/or stereochemically pure) preparations are of oligonucleotides having a common base sequence of at least 24 bases. In some embodiments, provided chirally controlled (and/or stereochemically pure) preparations are of oligonucleotides having a common base sequence of at least 25 bases. In some embodiments, provided chirally controlled (and/or stereochemically pure) preparations are of oligonucleotides having a common base sequence of at least 30, 35, 40, 45, 50, 55, 60, 65, 70, or 75 bases.

In some embodiments, provided chirally controlled (and/or stereochemically pure) preparations comprise oligonucleotides containing one or more residues which are modified at the sugar moiety. In some embodiments, provided chirally controlled (and/or stereochemically pure) preparations comprise oligonucleotides containing one or more residues which are modified at the 2' position of the sugar moiety (referred to herein as a "2'-modification"). Examples of such modifications are described above and herein and include, but are not limited to, 2'-OMe, 2'-MOE, 2'-LNA, 2'-F, FRNA, FANA, S-cEt, etc. In some embodiments, provided chirally controlled (and/or stereochemically pure) preparations comprise oligonucleotides containing one or more residues which are 2'-modified. For example, in some embodiments, provided oligonucleotides contain one or more residues which are 2'-O-methoxyethyl (2'-MOE)-modified residues. In some embodiments, provided chirally controlled (and/or stereochemically pure) preparations comprise oligonucleotides which do not contain any 2'-modifications. In some embodiments, provided chirally controlled (and/or stereochemically pure) preparations are oligonucleotides which do not contain any 2'-MOE residues. That is, in some embodiments, provided oligonucleotides are not MOE-modified. Additional example sugar modifications are described in the present disclosure.

In some embodiments, provided oligonucleotides are of a general motif of wing-core or core-wing (hemimer, also represented herein generally as X—Y or Y—X, respectively). In some embodiments, provided oligonucleotides are of a general motif of wing-core-wing (gapmer, also represented herein generically as X—Y—X). In some embodiments, each wing independently contains one or more residues having a particular modification, which modification is absent from the core "Y" portion. In some embodiments, each wing independently contains one or more residues having a particular nucleoside modification, which modification is absent from the core "Y" portion. In some embodiments, each wing independently contains one or more residues having a particular base modification, which modification is absent from the core "Y" portion. In some embodiments, each wing independently contains one or more residues having a particular sugar modification, which modification is absent from the core "Y" portion. Example sugar modifications are widely known in the art. In some embodiments, a sugar modification is a modification selected from those modifications described in U.S. Pat. No. 9,006,198, which sugar modifications are incorporated herein by references. Additional example sugar modifications are described in the present disclosure. In some embodiment, each wing contains one or more residues having a 2' modification that is not present in the core portion. In some embodiments, a 2'-modification is 2'-OR', wherein R' is as defined and described in the present disclosure.

In some embodiments, provided oligonucleotides have a wing-core motif represented as X—Y, or a core-wing motif represented as Y—X, wherein the residues at the "X" portion are sugar modified residues of a particular type and the residues in the core "Y" portion are not sugar modified residues of the same particular type. In some embodiments, provided oligonucleotides have a wing-core-wing motif represented as X—Y—X, wherein the residues at each "X" portion are sugar modified residues of a particular type and the residues in the core "Y" portion are not sugar modified residues of the same particular type. In some embodiments, provided oligonucleotides have a wing-core motif represented as X—Y, or a core-wing motif represented as Y—X, wherein the residues at the "X" portion are 2'-modified residues of a particular type and the residues in the core "Y" portion are not 2'-modified residues of the same particular type. In some embodiments, provided oligonucleotides have a wing-core motif represented as X—Y, wherein the residues at the "X" portion are 2'-modified residues of a particular type and the residues in the core "Y" portion are not 2'-modified residues of the same particular type. In some embodiments, provided oligonucleotides have a core-wing motif represented as Y—X, wherein the residues at the "X" portion are 2'-modified residues of a particular type and the residues in the core "Y" portion are not 2'-modified residues of the same particular type. In some embodiments, provided oligonucleotides have a wing-core-wing motif represented as X—Y—X, wherein the residues at each "X" portion are 2'-modified residues of a particular type and the residues in the core "Y" portion are not 2'-modified residues of the same particular type. In some embodiments, provided oligonucleotides have a wing-core motif represented as X—Y, wherein the residues at the "X" portion are 2'-modified residues of a particular type and the residues in the core "Y" portion are 2'-deoxyribonucleoside. In some embodiments, provided oligonucleotides have a core-wing motif represented as Y—X, wherein the residues at the "X" portion are 2'-modified residues of a particular type and the residues in the core "Y" portion are 2'-deoxyribonucleoside. In some embodiments, provided oligonucleotides have a wing-core-wing motif represented as X—Y—X, wherein the residues at each "X" portion are 2'-modified residues of a particular type and the residues in the core "Y" portion are 2'-deoxyribonucleoside. In some embodiments, provided oligonucleotides have a wing-core-wing motif represented as X—Y—X, wherein the residues at each "X" portion are 2'-modified residues of a particular type and the residues in the core "Y" portion are 2'-deoxyribonucleoside. For instance, in some embodiments, provided oligonucleotides have a wing-core-wing motif represented as X—Y—X, wherein the residues at each "X" portion are 2'-MOE-modified residues and the residues in the core "Y" portion are not 2'-MOE-modified residues. In some embodiments, provided oligonucleotides have a wing-core-wing motif represented as X—Y—X, wherein the residues at each "X" portion are 2'-MOE-modified residues and the residues in the core "Y" portion are 2'-deoxyribonucleoside. One of skill in the relevant arts will recognize that all such 2'-modifications described above and herein are contemplated in the context of such X—Y, Y—X and/or X—Y—X motifs.

In some embodiments, a wing has a length of one or more bases. In some embodiments, a wing has a length of two or more bases. In some embodiments, a wing has a length of three or more bases. In some embodiments, a wing has a length of four or more bases. In some embodiments, a wing has a length of five or more bases. In some embodiments, a wing has a length of six or more bases. In some embodiments, a wing has a length of seven or more bases. In some embodiments, a wing has a length of eight or more bases. In some embodiments, a wing has a length of nine or more bases. In some embodiments, a wing has a length of ten or more bases. In some embodiments, a wing has a length of 11 or more bases. In some embodiments, a wing has a length of 12 or more bases. In some embodiments, a wing has a length of 13 or more bases. In some embodiments, a wing has a length of 14 or more bases. In some embodiments, a wing has a length of 15 or more bases. In some embodiments, a wing has a length of 16 or more bases. In some embodiments, a wing has a length of 17 or more bases. In some embodiments, a wing has a length of 18 or more bases. In some embodiments, a wing has a length of 19 or more bases. In some embodiments, a wing has a length of ten or more bases.

In some embodiments, a wing has a length of one base. In some embodiments, a wing has a length of two bases. In some embodiments, a wing has a length of three bases. In some embodiments, a wing has a length of four bases. In some embodiments, a wing has a length of five bases. In some embodiments, a wing has a length of six bases. In some embodiments, a wing has a length of seven bases. In some embodiments, a wing has a length of eight bases. In some embodiments, a wing has a length of nine bases. In some embodiments, a wing has a length of ten bases. In some embodiments, a wing has a length of 11 bases. In some embodiments, a wing has a length of 12 bases. In some embodiments, a wing has a length of 13 bases. In some embodiments, a wing has a length of 14 bases. In some embodiments, a wing has a length of 15 bases. In some embodiments, a wing has a length of 16 bases. In some embodiments, a wing has a length of 17 bases. In some embodiments, a wing has a length of 18 bases. In some embodiments, a wing has a length of 19 bases. In some embodiments, a wing has a length of ten bases.

In some embodiments, a wing comprises one or more chiral internucleotidic linkages. In some embodiments, a wing comprises one or more natural phosphate linkages. In some embodiments, a wing comprises one or more chiral internucleotidic linkages and one or more natural phosphate linkages. In some embodiments, a wing comprises one or more chiral internucleotidic linkages and two or more natural phosphate linkages. In some embodiments, a wing comprises one or more chiral internucleotidic linkages and two or more natural phosphate linkages, wherein two or more natural phosphate linkages are consecutive. In some embodiments, a wing comprises no chiral internucleotidic linkages. In some embodiments, each wing linkage is a natural phosphate linkage. In some embodiments, a wing comprises no phosphate linkages. In some embodiments, each wing is independently a chiral internucleotidic linkage.

In some embodiments, each wing independently comprises one or more chiral internucleotidic linkages. In some embodiments, each wing independently comprises one or more natural phosphate linkages. In some embodiments, each wing independently comprises one or more chiral internucleotidic linkages and one or more natural phosphate linkages. In some embodiments, each wing independently comprises one or more chiral internucleotidic linkages and two or more natural phosphate linkages. In some embodiments, each wing independently comprises one or more chiral internucleotidic linkages and two or more natural phosphate linkages, wherein two or more natural phosphate linkages are consecutive.

In some embodiments, each wing independently comprises at least one chiral internucleotidic linkage. In some embodiments, each wing independently comprises at least two chiral internucleotidic linkages. In some embodiments, each wing independently comprises at least three chiral internucleotidic linkages. In some embodiments, each wing independently comprises at least four chiral internucleotidic linkages. In some embodiments, each wing independently comprises at least five chiral internucleotidic linkages. In some embodiments, each wing independently comprises at least six chiral internucleotidic linkages. In some embodiments, each wing independently comprises at least seven chiral internucleotidic linkages. In some embodiments, each wing independently comprises at least eight chiral internucleotidic linkages. In some embodiments, each wing independently comprises at least nine chiral internucleotidic linkages. In some embodiments, each wing independently comprises at least ten chiral internucleotidic linkages. In some embodiments, each wing independently comprises at least 11 chiral internucleotidic linkages. In some embodiments, each wing independently comprises at least 12 chiral internucleotidic linkages. In some embodiments, each wing independently comprises at least 13 chiral internucleotidic linkages. In some embodiments, each wing independently comprises at least 14 chiral internucleotidic linkages. In some embodiments, each wing independently comprises at least 15 chiral internucleotidic linkages. In some embodiments, each wing independently comprises at least 16 chiral internucleotidic linkages. In some embodiments, each wing independently comprises at least 17 chiral internucleotidic linkages. In some embodiments, each wing independently comprises at least 18 chiral internucleotidic linkages. In some embodiments, each wing independently comprises at least 19 chiral internucleotidic linkages. In some embodiments, each wing independently comprises at least 20 chiral internucleotidic linkages.

In some embodiments, each wing independently comprises one chiral internucleotidic linkage. In some embodiments, each wing independently comprises two chiral internucleotidic linkages. In some embodiments, each wing independently comprises three chiral internucleotidic linkages. In some embodiments, each wing independently comprises four chiral internucleotidic linkages. In some embodiments, each wing independently comprises five chiral internucleotidic linkages. In some embodiments, each wing independently comprises six chiral internucleotidic linkages. In some embodiments, each wing independently comprises seven chiral internucleotidic linkages. In some embodiments, each wing independently comprises eight chiral internucleotidic linkages. In some embodiments, each wing independently comprises nine chiral internucleotidic linkages. In some embodiments, each wing independently comprises ten chiral internucleotidic linkages. In some embodiments, each wing independently comprises 11 chiral internucleotidic linkages. In some embodiments, each wing independently comprises 12 chiral internucleotidic linkages. In some embodiments, each wing independently comprises 13 chiral internucleotidic linkages. In some embodiments, each wing independently comprises 14 chiral internucleotidic linkages. In some embodiments, each wing independently comprises 15 chiral internucleotidic linkages. In some embodiments, each wing independently comprises 16 chiral internucleotidic linkages. In some embodiments, each wing independently comprises 17 chiral internucleotidic linkages. In some embodiments, each wing independently comprises 18 chiral internucleotidic linkages. In some embodiments, each wing independently comprises 19 chiral internucleotidic linkages. In some embodiments, each wing independently comprises 20 chiral internucleotidic linkages.

In some embodiments, each wing independently comprises at least one consecutive natural phosphate linkage. In some embodiments, each wing independently comprises at least two consecutive chiral internucleotidic linkages. In some embodiments, each wing independently comprises at least three consecutive chiral internucleotidic linkages. In some embodiments, each wing independently comprises at least four consecutive chiral internucleotidic linkages. In some embodiments, each wing independently comprises at least five consecutive chiral internucleotidic linkages. In some embodiments, each wing independently comprises at least six consecutive chiral internucleotidic linkages. In some embodiments, each wing independently comprises at least seven consecutive chiral internucleotidic linkages. In some embodiments, each wing independently comprises at least eight consecutive chiral internucleotidic linkages. In some embodiments, each wing independently comprises at least nine consecutive chiral internucleotidic linkages. In some embodiments, each wing independently comprises at least ten consecutive chiral internucleotidic linkages. In some embodiments, each wing independently comprises at least 11 consecutive chiral internucleotidic linkages. In some embodiments, each wing independently comprises at least 12 consecutive chiral internucleotidic linkages. In some embodiments, each wing independently comprises at least 13 consecutive chiral internucleotidic linkages. In some embodiments, each wing independently comprises at least 14 consecutive chiral internucleotidic linkages. In some embodiments, each wing independently comprises at least 15 consecutive chiral internucleotidic linkages. In some embodiments, each wing independently comprises at least 16 consecutive chiral internucleotidic linkages. In some embodiments, each wing independently comprises at least 17 consecutive chiral internucleotidic linkages. In some embodiments, each wing independently comprises at least 18 consecutive chiral internucleotidic linkages. In some embodiments, each wing independently comprises at least 19 consecutive chiral internucleotidic linkages. In some embodiments, each wing independently comprises at least 20 consecutive chiral internucleotidic linkages.

In some embodiments, each wing independently comprises one consecutive natural phosphate linkage. In some embodiments, each wing independently comprises two consecutive chiral internucleotidic linkages. In some embodiments, each wing independently comprises three consecutive chiral internucleotidic linkages. In some embodiments, each wing independently comprises four consecutive chiral internucleotidic linkages. In some embodiments, each wing independently comprises five consecutive chiral internucleotidic linkages. In some embodiments, each wing independently comprises six consecutive chiral internucleotidic linkages. In some embodiments, each wing independently comprises seven consecutive chiral internucleotidic linkages. In some embodiments, each wing independently comprises eight consecutive chiral internucleotidic linkages. In some embodiments, each wing independently comprises nine consecutive chiral internucleotidic linkages. In some embodiments, each wing independently comprises ten consecutive chiral internucleotidic linkages. In some embodiments, each wing independently comprises 11 consecutive chiral internucleotidic linkages. In some embodiments, each wing independently comprises 12 consecutive chiral internucleotidic linkages. In some embodiments, each wing independently comprises 13 consecutive chiral internucleotidic linkages. In some embodiments, each wing independently comprises 14 consecutive chiral internucleotidic linkages. In some embodiments, each wing independently comprises 15 consecutive chiral internucleotidic linkages. In some embodiments, each wing independently comprises 16 consecutive chiral internucleotidic linkages. In some embodiments, each wing independently comprises 17 consecutive chiral internucleotidic linkages. In some embodiments, each wing independently comprises 18 consecutive chiral internucleotidic linkages. In some embodiments, each wing independently comprises 19 consecutive chiral internucleotidic linkages. In some embodiments, each wing independently comprises 20 consecutive chiral internucleotidic linkages.

In some embodiments, each wing independently comprises at least one natural phosphate linkage. In some embodiments, each wing independently comprises at least two natural phosphate linkages. In some embodiments, each wing independently comprises at least three natural phosphate linkages. In some embodiments, each wing independently comprises at least four natural phosphate linkages. In some embodiments, each wing independently comprises at least five natural phosphate linkages. In some embodiments, each wing independently comprises at least six natural phosphate linkages. In some embodiments, each wing independently comprises at least seven natural phosphate linkages. In some embodiments, each wing independently comprises at least eight natural phosphate linkages. In some embodiments, each wing independently comprises at least nine natural phosphate linkages. In some embodiments, each wing independently comprises at least ten natural phosphate linkages. In some embodiments, each wing independently comprises at least 11 natural phosphate linkages. In some embodiments, each wing independently comprises at least 12 natural phosphate linkages. In some embodiments, each wing independently comprises at least 13 natural phosphate linkages. In some embodiments, each wing independently comprises at least 14 natural phosphate linkages. In some embodiments, each wing independently comprises at least 15 natural phosphate linkages. In some embodiments, each wing independently comprises at least 16 natural phosphate linkages. In some embodiments, each wing independently comprises at least 17 natural phosphate linkages. In some embodiments, each wing independently comprises at least 18 natural phosphate linkages. In some embodiments, each wing independently comprises at least 19 natural phosphate linkages. In some embodiments, each wing independently comprises at least 20 natural phosphate linkages.

In some embodiments, each wing independently comprises one natural phosphate linkage. In some embodiments, each wing independently comprises two natural phosphate linkages. In some embodiments, each wing independently comprises three natural phosphate linkages. In some embodiments, each wing independently comprises four natural phosphate linkages. In some embodiments, each wing independently comprises five natural phosphate linkages. In some embodiments, each wing independently comprises six natural phosphate linkages. In some embodiments, each wing independently comprises seven natural phosphate linkages. In some embodiments, each wing independently comprises eight natural phosphate linkages. In some embodiments, each wing independently comprises nine natural phosphate linkages. In some embodiments, each wing independently comprises ten natural phosphate linkages. In some embodiments, each wing independently comprises 11 natural phosphate linkages. In some embodiments, each wing independently comprises 12 natural phosphate linkages. In some embodiments, each wing independently comprises 13 natural phosphate linkages. In some embodiments, each wing independently comprises 14 natural phosphate linkages. In some embodiments, each wing independently comprises 15 natural phosphate linkages. In some embodiments, each wing independently comprises 16 natural phosphate linkages. In some embodiments, each wing independently comprises 17 natural phosphate linkages. In some embodiments, each wing independently comprises 18 natural phosphate linkages. In some embodiments, each wing independently comprises 19 natural phosphate linkages. In some embodiments, each wing independently comprises 20 natural phosphate linkages.

In some embodiments, each wing independently comprises at least one consecutive natural phosphate linkage. In some embodiments, each wing independently comprises at least two consecutive natural phosphate linkages. In some embodiments, each wing independently comprises at least three consecutive natural phosphate linkages. In some embodiments, each wing independently comprises at least four consecutive natural phosphate linkages. In some embodiments, each wing independently comprises at least five consecutive natural phosphate linkages. In some embodiments, each wing independently comprises at least six consecutive natural phosphate linkages. In some embodiments, each wing independently comprises at least seven consecutive natural phosphate linkages. In some embodiments, each wing independently comprises at least eight consecutive natural phosphate linkages. In some embodiments, each wing independently comprises at least nine consecutive natural phosphate linkages. In some embodiments, each wing independently comprises at least ten consecutive natural phosphate linkages. In some embodiments, each wing independently comprises at least 11 consecutive natural phosphate linkages. In some embodiments, each wing independently comprises at least 12 consecutive natural phosphate linkages. In some embodiments, each wing independently comprises at least 13 consecutive natural phosphate linkages. In some embodiments, each wing independently comprises at least 14 consecutive natural phosphate linkages. In some embodiments, each wing independently comprises at least 15 consecutive natural phosphate linkages. In some embodiments, each wing independently comprises at least 16 consecutive natural phosphate linkages. In some embodiments, each wing independently comprises at least 17 consecutive natural phosphate linkages. In some embodiments, each wing independently comprises at least 18 consecutive natural phosphate linkages. In some embodiments, each wing independently comprises at least 19 consecutive natural phosphate linkages. In some embodiments, each wing independently comprises at least 20 consecutive natural phosphate linkages.

In some embodiments, each wing independently comprises one consecutive natural phosphate linkage. In some embodiments, each wing independently comprises two consecutive natural phosphate linkages. In some embodiments, each wing independently comprises three consecutive natural phosphate linkages. In some embodiments, each wing independently comprises four consecutive natural phosphate linkages. In some embodiments, each wing independently comprises five consecutive natural phosphate linkages. In some embodiments, each wing independently comprises six consecutive natural phosphate linkages. In some embodiments, each wing independently comprises seven consecutive natural phosphate linkages. In some embodiments, each wing independently comprises eight consecutive natural phosphate linkages. In some embodiments, each wing independently comprises nine consecutive natural phosphate linkages. In some embodiments, each wing independently comprises ten consecutive natural phosphate linkages. In some embodiments, each wing independently comprises 11 consecutive natural phosphate linkages. In some embodiments, each wing independently comprises 12 consecutive natural phosphate linkages. In some embodiments, each wing independently comprises 13 consecutive natural phosphate linkages. In some embodiments, each wing independently comprises 14 consecutive natural phosphate linkages. In some embodiments, each wing independently comprises 15 consecutive natural phosphate linkages. In some embodiments, each wing independently comprises 16 consecutive natural phosphate linkages. In some embodiments, each wing independently comprises 17 consecutive natural phosphate linkages. In some embodiments, each wing independently comprises 18 consecutive natural phosphate linkages. In some embodiments, each wing independently comprises 19 consecutive natural phosphate linkages. In some embodiments, each wing independently comprises 20 consecutive natural phosphate linkages.

In some embodiments, a wing comprises only one chiral internucleotidic linkage. In some embodiments, a 5'-end wing comprises only one chiral internucleotidic linkage. In some embodiments, a 5'-end wing comprises only one chiral internucleotidic linkage at the 5'-end of the wing. In some embodiments, a 5'-end wing comprises only one chiral internucleotidic linkage at the 5'-end of the wing, and the chiral internucleotidic linkage is Rp. In some embodiments, a 5'-end wing comprises only one chiral internucleotidic linkage at the 5'-end of the wing, and the chiral internucleotidic linkage is Sp. In some embodiments, a 3'-end wing comprises only one chiral internucleotidic linkage at the 3'-end of the wing. In some embodiments, a 3'-end wing comprises only one chiral internucleotidic linkage at the 3'-end of the wing, and the chiral internucleotidic linkage is Rp. In some embodiments, a 3'-end wing comprises only one chiral internucleotidic linkage at the 3'-end of the wing, and the chiral internucleotidic linkage is Sp.

In some embodiments, a wing comprises two or more natural phosphate linkages. In some embodiments, all phosphate linkages within a wing are consecutive, and there are no non-phosphate linkages between any two phosphate linkages within a wing.

In some embodiments, a linkage connecting a wing and a core is considered part of the core when describing linkages, e.g., linkage chemistry, linkage stereochemistry, etc. For example, in WV-1092, mG*SmGmCmAmC*SA*SA*SG*SG*SG*SC*S A*SC*RA*SG*SmAmCm UmU*SmC (SEQ ID NO: 15), the underlined linkages may be considered as part of the core (bold), its 5'-wing (having 2'-OMe on sugar moieties) has one single Sp phosphorothioate linkages at its 5'-end, its 3'-wing (having 2'-OMe on sugar moieties) has one Sp phosphorothioate linkage at its 3'-end, and its core has no 2'-modifications on sugar).

In some embodiments, a 5'-internucleotidic linkage connected to a sugar moiety without a 2'-modification is a modified linkage. In some embodiments, a 5'-internucleotidic linkage connected to a sugar moiety without a 2'-modification is a linkage having the structure of formula I. In some embodiments, a 5'-internucleotidic linkage connected to a sugar moiety without a 2'-modification is phosphorothioate linkage. In some embodiments, a 5'-internucleotidic linkage connected to a sugar moiety without a 2'-modification is a substituted phosphorothioate linkage. In some embodiments, a 5'-internucleotidic linkage connected to a sugar moiety without a 2'-modification is a phosphorothioate triester linkage. In some embodiments, each 5'-internucleotidic linkage connected to a sugar moiety without a 2'-modification is a modified linkage. In some embodiments, each 5'-internucleotidic linkage connected to a sugar moiety without a 2'-modification is a linkage having the structure of formula I. In some embodiments, each 5'-internucleotidic linkage connected to a sugar moiety without a 2'-modification is phosphorothioate linkage. In some embodiments, each 5'-internucleotidic linkage connected to a sugar moiety without a 2'-modification is a substituted phosphorothioate linkage. In some embodiments, each 5'-internucleotidic linkage connected to a sugar moiety without a 2'-modification is a phosphorothioate triester linkage.

In some embodiments, a 3'-internucleotidic linkage connected to a sugar moiety without a 2'-modification is a modified linkage. In some embodiments, a 3'-internucleotidic linkage connected to a sugar moiety without a 2'-modification is a linkage having the structure of formula I. In some embodiments, a 3'-internucleotidic linkage connected to a sugar moiety without a 2'-modification is phosphorothioate linkage. In some embodiments, a 3'-internucleotidic linkage connected to a sugar moiety without a 2'-modification is a substituted phosphorothioate linkage. In some embodiments, a 3'-internucleotidic linkage connected to a sugar moiety without a 2'-modification is a phosphorothioate triester linkage. In some embodiments, each 3'-internucleotidic linkage connected to a sugar moiety without a 2'-modification is a modified linkage. In some embodiments, each 3'-internucleotidic linkage connected to a sugar moiety without a 2'-modification is a linkage having the structure of formula I. In some embodiments, each 3'-internucleotidic linkage connected to a sugar moiety without a 2'-modification is phosphorothioate linkage. In some embodiments, each 3'-internucleotidic linkage connected to a sugar moiety without a 2'-modification is a substituted phosphorothioate linkage. In some embodiments, each 3'-internucleotidic linkage connected to a sugar moiety without a 2'-modification is a phosphorothioate triester linkage.

In some embodiments, both internucleotidic linkages connected to a sugar moiety without a 2'-modification are modified linkages. In some embodiments, both internucleotidic linkages connected to a sugar moiety without a 2'-modification are linkage having the structure of formula I. In some embodiments, both internucleotidic linkages connected to a sugar moiety without a 2'-modification are phosphorothioate linkages. In some embodiments, both internucleotidic linkages connected to a sugar moiety without a 2'-modification are substituted phosphorothioate linkages. In some embodiments, both internucleotidic linkages connected to a sugar moiety without a 2'-modification are phosphorothioate triester linkages. In some embodiments, each internucleotidic linkage connected to a sugar moiety without a 2'-modification is a modified linkage. In some embodiments, each internucleotidic linkage connected to a sugar moiety without a 2'-modification is a linkage having the structure of formula I. In some embodiments, each internucleotidic linkage connected to a sugar moiety without a 2'-modification is phosphorothioate linkage. In some embodiments, each internucleotidic linkage connected to a sugar moiety without a 2'-modification is a substituted phosphorothioate linkage. In some embodiments, each internucleotidic linkage connected to a sugar moiety without a 2'-modification is a phosphorothioate triester linkage.

In some embodiments, a sugar moiety without a 2'-modification is a sugar moiety found in a natural DNA nucleoside.

In some embodiments, for a wing-core-wing structure, the 5'-end wing comprises only one chiral internucleotidic linkage. In some embodiments, for a wing-core-wing structure, the 5'-end wing comprises only one chiral internucleotidic linkage at the 5'-end of the wing. In some embodiments, for a wing-core-wing structure, the 3'-end wing comprises only one chiral internucleotidic linkage. In some embodiments, for a wing-core-wing structure, the 3'-end wing comprises only one chiral internucleotidic linkage at the 3'-end of the wing. In some embodiments, for a wing-core-wing structure, each wing comprises only one chiral internucleotidic linkage. In some embodiments, for a wing-core-wing structure, each wing comprises only one chiral internucleotidic linkage, wherein the 5'-end wing comprises only one chiral internucleotidic linkage at its 5'-end; and the 3'-end wing comprises only one chiral internucleotidic linkage at its 3'-end. In some embodiments, the only chiral internucleotidic linkage in the 5'-wing is Rp. In some embodiments, the only chiral internucleotidic linkage in the 5'-wing is Sp. In some embodiments, the only chiral internucleotidic linkage in the 3'-wing is Rp. In some embodiments, the only chiral internucleotidic linkage in the 3'-wing is Sp. In some embodiments, the only chiral internucleotidic linkage in both the 5'- and the 3'-wings are Sp. In some embodiments, the only chiral internucleotidic linkage in both the 5'- and the 3'-wings are Rp. In some embodiments, the only chiral internucleotidic linkage in the 5'-wing is Sp, and the only chiral internucleotidic linkage in the 3'-wing is Rp. In some embodiments, the only chiral internucleotidic linkage in the 5'-wing is Rp, and the only chiral internucleotidic linkage in the 3'-wing is Sp.

In some embodiments, a wing comprises two chiral internucleotidic linkages. In some embodiments, a wing comprises only two chiral internucleotidic linkages, and one or more natural phosphate linkages. In some embodiments, a wing comprises only two chiral internucleotidic linkages, and two or more natural phosphate linkages. In some embodiments, a wing comprises only two chiral internucleotidic linkages, and two or more consecutive natural phosphate linkages. In some embodiments, a wing comprises only two chiral internucleotidic linkages, and two consecutive natural phosphate linkages. In some embodiments, a wing comprises only two chiral internucleotidic linkages, and three consecutive natural phosphate linkages. In some embodiments, a 5'-wing (to a core) comprises only two chiral internucleotidic linkages, one at its 5'-end and the other at its 3'-end, with one or more natural phosphate linkages in between. In some embodiments, a 5'-wing (to a core) comprises only two chiral internucleotidic linkages, one at its 5'-end and the other at its 3'-end, with two or more natural phosphate linkages in between. In some embodiments, a 3'-wing (to a core) comprises only two chiral internucleotidic linkages, one at its 3'-end and the other at its 3'-end, with one or more natural phosphate linkages in between. In some embodiments, a 3'-wing (to a core) comprises only two chiral internucleotidic linkages, one at its 3'-end and the other at its 3'-end, with two or more natural phosphate linkages in between.

In some embodiments, a 5'-wing comprises only two chiral internucleotidic linkages, one at its 5'-end and the other at its 3'-end, with one or more natural phosphate linkages in between, and the 3'-wing comprise only one internucleotidic linkage at its 3'-end. In some embodiments, a 5'-wing (to a core) comprises only two chiral internucleotidic linkages, one at its 5'-end and the other at its 3'-end, with two or more natural phosphate linkages in between, and the 3'-wing comprise only one internucleotidic linkage at its 3'-end. In some embodiments, each chiral internucleotidic linkage independently has its own stereochemistry. In some embodiments, both chiral internucleotidic linkages in the 5'-wing have the same stereochemistry. In some embodiments, both chiral internucleotidic linkages in the 5'-wing have different stereochemistry. In some embodiments, both chiral internucleotidic linkages in the 5'-wing are Rp. In some embodiments, both chiral internucleotidic linkages in the 5'-wing are Sp. In some embodiments, chiral internucleotidic linkages in the 5'- and 3'-wings have the same stereochemistry. In some embodiments, chiral internucleotidic linkages in the 5'- and 3'-wings are Rp. In some embodiments, chiral internucleotidic linkages in the 5'- and 3'-wings are Sp. In some embodiments, chiral internucleotidic linkages in the 5'- and 3'-wings have different stereochemistry.

In some embodiments, a core region has a length of one or more bases. In some embodiments, a core region has a length of two or more bases. In some embodiments, a core region has a length of three or more bases. In some embodiments, a core region has a length of four or more bases. In some embodiments, a core region has a length of five or more bases. In some embodiments, a core region has a length of six or more bases. In some embodiments, a core region has a length of seven or more bases. In some embodiments, a core region has a length of eight or more bases. In some embodiments, a core region has a length of nine or more bases. In some embodiments, a core region has a length of ten or more bases. In some embodiments, a core region has a length of 11, 12, 13, 14, 15, 16, 17, 18, 19, 20, 25, or more bases. In certain embodiments, a core region has a length of 11 or more bases. In certain embodiments, a core region has a length of 12 or more bases. In certain embodiments, a core region has a length of 13 or more bases. In certain embodiments, a core region has a length of 14 or more bases. In certain embodiments, a core region has a length of 15 or more bases. In certain embodiments, a core region has a length of 16 or more bases. In certain embodiments, a core region has a length of 17 or more bases. In certain embodiments, a core region has a length of 18 or more bases. In certain embodiments, a core region has a length of 19 or more bases. In certain embodiments, a core region has a length of 20 or more bases. In certain embodiments, a core region has a length of more than 20 bases. In certain embodiments, a core region has a length of 2 bases. In certain embodiments, a core region has a length of 3 bases. In certain embodiments, a core region has a length of 4 bases. In certain embodiments, a core region has a length of 5 bases. In certain embodiments, a core region has a length of 6 bases. In certain embodiments, a core region has a length of 7 bases. In certain embodiments, a core region has a length of 8 bases. In certain embodiments, a core region has a length of 9 bases. In certain embodiments, a core region has a length of 10 bases. In certain embodiments, a core region has a length of 11 bases. In certain embodiments, a core region has a length of 12 bases. In certain embodiments, a core region has a length of 13 bases. In certain embodiments, a core region has a length of 14 bases. In certain embodiments, a core region has a length of 15 bases. In certain embodiments, a core region has a length of 16 bases. In certain embodiments, a core region has a length of 17 bases. In certain embodiments, a core region has a length of 18 bases. In certain embodiments, a core region has a length of 19 bases. In certain embodiments, a core region has a length of 20 bases.

In some embodiments, a core comprises one or more chiral internucleotidic linkages. In some embodiments, a core comprises one or more natural phosphate linkages. In some embodiments, a core independently comprises one or more chiral internucleotidic linkages and one or more natural phosphate linkages. In some embodiments, a core comprises no phosphate linkages. In some embodiments, each core linkage is a chiral internucleotidic linkage.

In some embodiments, a core comprises at least one natural phosphate linkage. In some embodiments, a core comprises at least two chiral internucleotidic linkages. In some embodiments, a core comprises at least three chiral internucleotidic linkages. In some embodiments, a core comprises at least four chiral internucleotidic linkages. In some embodiments, a core comprises at least five chiral internucleotidic linkages. In some embodiments, a core comprises at least six chiral internucleotidic linkages. In some embodiments, a core comprises at least seven chiral internucleotidic linkages. In some embodiments, a core comprises at least eight chiral internucleotidic linkages. In some embodiments, a core comprises at least nine chiral internucleotidic linkages. In some embodiments, a core comprises at least ten chiral internucleotidic linkages. In some embodiments, a core comprises at least 11 chiral internucleotidic linkages. In some embodiments, a core comprises at least 12 chiral internucleotidic linkages. In some embodiments, a core comprises at least 13 chiral internucleotidic linkages. In some embodiments, a core comprises at least 14 chiral internucleotidic linkages. In some embodiments, a core comprises at least 15 chiral internucleotidic linkages. In some embodiments, a core comprises at least 16 chiral internucleotidic linkages. In some embodiments, a core comprises at least 17 chiral internucleotidic linkages. In some embodiments, a core comprises at least 18 chiral internucleotidic linkages. In some embodiments, a core comprises at least 19 chiral internucleotidic linkages. In some embodiments, a core comprises at least 20 chiral internucleotidic linkages.

In some embodiments, a core comprises one natural phosphate linkage. In some embodiments, a core comprises two chiral internucleotidic linkages. In some embodiments, a core comprises three chiral internucleotidic linkages. In some embodiments, a core comprises four chiral internucleotidic linkages. In some embodiments, a core comprises five chiral internucleotidic linkages. In some embodiments, a core comprises six chiral internucleotidic linkages. In some embodiments, a core comprises seven chiral internucleotidic linkages. In some embodiments, a core comprises eight chiral internucleotidic linkages. In some embodiments, a core comprises nine chiral internucleotidic linkages. In some embodiments, a core comprises ten chiral internucleotidic linkages. In some embodiments, a core comprises 11 chiral internucleotidic linkages. In some embodiments, a core comprises 12 chiral internucleotidic linkages. In some embodiments, a core comprises 13 chiral internucleotidic linkages. In some embodiments, a core comprises 14 chiral internucleotidic linkages. In some embodiments, a core comprises 15 chiral internucleotidic linkages. In some embodiments, a core comprises 16 chiral internucleotidic linkages. In some embodiments, a core comprises 17 chiral internucleotidic linkages. In some embodiments, a core comprises 18 chiral internucleotidic linkages. In some embodiments, a core comprises 19 chiral internucleotidic linkages. In some embodiments, a core comprises 20 chiral internucleotidic linkages.

In some embodiments, a core region has a pattern of backbone chiral centers comprising $(Sp)_m(Rp)_n$, $(Rp)_n(Sp)_m$, $(Np)_t(Rp)_n(Sp)_m$, or $(Sp)_t(Rp)_n(Sp)_m$, wherein each of m, n, t and Np is independently as defined and described in the present disclosure. In some embodiments, a core region has a pattern of backbone chiral centers comprising $(Sp)_m(Rp)_n$, $(Rp)_n(Sp)_m$, $(Np)_t(Rp)_n(Sp)_m$, or $(Sp)_t(Rp)_n(Sp)_m$. In some embodiments, a core region has a pattern of backbone chiral centers comprising $(Sp)_m(Rp)_n$. In some embodiments, a core region has a pattern of backbone chiral centers comprising $(Sp)_m(Rp)_n$, wherein m>2 and n is 1. In some embodiments, a core region has a pattern of backbone chiral centers comprising $(Rp)_n(Sp)_m$. In some embodiments, a core region has a pattern of backbone chiral centers comprising $(Rp)_n(Sp)_m$, wherein m>2 and n is 1. In some embodiments, a core region has a pattern of backbone chiral centers comprising $(Np)_t(Rp)_n(Sp)_m$. In some embodiments, a core region has a pattern of backbone chiral centers comprising $(Np)_t(Rp)_n(Sp)_m$, wherein m>2 and n is 1. In some embodiments, a core region has a pattern of backbone chiral centers comprising $(Np)_t(Rp)_n(Sp)_m$, wherein t>2, m>2 and n is 1. In some embodiments, a core region has a pattern of backbone chiral centers comprising $(Sp)_t(Rp)_n(Sp)_m$. In some embodiments, a core region has a pattern of backbone chiral centers comprising $(Sp)_t(Rp)_n(Sp)_m$, wherein m>2 and n is 1. In some embodiments, a core region has a pattern of backbone chiral centers comprising $(Sp)_t(Rp)_n(Sp)_m$, wherein t>2, m>2 and n is 1. Among other things, the present disclosure demonstrates that, in some embodiments, such patterns can provide and/or enhance controlled cleavage, improved cleavage rate, selectivity, etc., of a target sequence, e.g., an RNA sequence. Example patterns of backbone chiral centers are described in the present disclosure.

In some embodiments, at least 60% of the chiral internucleotidic linkages in the core region are Sp. In some embodiments, at least 65% of the chiral internucleotidic linkages in the core region are Sp. In some embodiments, at least 66% of the chiral internucleotidic linkages in the core region are Sp. In some embodiments, at least 67% of the chiral internucleotidic linkages in the core region are Sp. In some embodiments, at least 70% of the chiral internucleotidic linkages in the core region are Sp. In some embodiments, at least 75% of the chiral internucleotidic linkages in the core region are Sp. In some embodiments, at least 80% of the chiral internucleotidic linkages in the core region are Sp. In some embodiments, at least 85% of the chiral internucleotidic linkages in the core region are Sp. In some embodiments, at least 90% of the chiral internucleotidic linkages in the core region are Sp. In some embodiments, at least 95% of the chiral internucleotidic linkages in the core region are Sp.

In some embodiments, a wing-core-wing (i.e., X—Y—X) motif is represented numerically as, e.g., 5-10-4, meaning the wing to the 5'-end of the core is 5 bases in length, the core region is 10 bases in length, and the wing region to the 3'-end of the core is 4-bases in length. In some embodiments, a wing-core-wing motif is any of, e.g. 2-16-2, 3-14-3, 4-12-4, 5-10-5, 2-9-6, 3-9-3, 3-9-4, 3-9-5, 4-7-4, 4-9-3, 4-9-4, 4-9-5, 4-10-5, 4-11-4, 4-11-5, 5- 7-5, 5-8-6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5.

In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, the internucleosidic linkages of provided oligonucleotides of such wing-core-wing (i.e., X—Y—X) motifs are all chiral, modified phosphate linkages. In some embodiments, the internucleosidic linkages of provided oligonucleotides of such wing-core-wing (i.e., X—Y—X) motifs are all chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral, modified phosphate internucleotidic linkages. In some embodiments, chiral internucleotidic linkages of provided oligonucleotides of such wing-core-wing motifs are at least about 10, 20, 30, 40, 50, 60, 70, 80, or 90% chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral phosphorothioate internucleotidic linkages of the Sp conformation.

In some embodiments, each wing region of a wing-core-wing motif optionally contains chiral, modified phosphate internucleotidic linkages. In some embodiments, each wing region of a wing-core-wing motif optionally contains chiral phosphorothioate internucleotidic linkages. In some embodiments, each wing region of a wing-core-wing motif contains chiral phosphorothioate internucleotidic linkages. In some embodiments, the two wing regions of a wing-core-wing motif have the same internucleotidic linkage stereochemistry. In some embodiments, the two wing regions have different internucleotidic linkage stereochemistry. In some embodiments, each internucleotidic linkage in the wings is independently a chiral internucleotidic linkage.

In some embodiments, the core region of a wing-core-wing motif optionally contains chiral, modified phosphate internucleotidic linkages. In some embodiments, the core region of a wing-core-wing motif optionally contains chiral phosphorothioate internucleotidic linkages. In some embodiments, the core region of a wing-core-wing motif comprises a repeating pattern of internucleotidic linkage stereochemistry. In some embodiments, the core region of a wing-core-wing motif has a repeating pattern of internucleotidic linkage stereochemistry. In some embodiments, the core region of a wing-core-wing motif comprises repeating pattern of internucleotidic linkage stereochemistry, wherein the repeating pattern is $(Sp)_m Rp$ or $Rp(Sp)_m$, wherein m is 1-50. In some embodiments, the core region of a wing-core-wing motif comprises repeating pattern of internucleotidic linkage stereochemistry, wherein the repeating pattern is $(Sp)_m Rp$ or $Rp(Sp)_m$, wherein m is 1-50. In some embodiments, the core region of a wing-core-wing motif comprises repeating pattern of internucleotidic linkage stereochemistry, wherein the repeating pattern is $(Sp)_m Rp$, wherein m is 1-50. In some embodiments, the core region of a wing-core-wing motif comprises repeating pattern of internucleotidic linkage stereochemistry, wherein the repeating pattern is $Rp(Sp)_m$, wherein m is 1-50. In some embodiments, the core region of a wing-core-wing motif has repeating pattern of internucleotidic linkage stereochemistry, wherein the repeating pattern is $(Sp)_m Rp$ or $Rp(Sp)_m$, wherein m is 1-50. In some embodiments, the core region of a wing-core-wing motif has repeating pattern of internucleotidic linkage stereochemistry, wherein the repeating pattern is $(Sp)_mRp$, wherein m is 1-50. In some embodiments, the core region of a wing-core-wing motif has repeating pattern of internucleotidic linkage stereochemistry, wherein the repeating pattern is $Rp(Sp)_m$, wherein m is 1-50. In some embodiments, the core region of a wing-core-wing motif has repeating pattern of internucleotidic linkage stereochemistry, wherein the repeating pattern is a motif comprising at least 33% of internucleotidic linkage in the S conformation. In some embodiments, the core region of a wing-core-wing motif has repeating pattern of internucleotidic linkage stereochemistry, wherein the repeating pattern is a motif comprising at least 50% of internucleotidic linkage in the S conformation. In some embodiments, the core region of a wing-core-wing motif has repeating pattern of internucleotidic linkage stereochemistry, wherein the repeating pattern is a motif comprising at least 66% of internucleotidic linkage in the S conformation. In some embodiments, the core region of a wing-core-wing motif has repeating pattern of internucleotidic linkage stereochemistry, wherein the repeating pattern is a repeating triplet motif selected from RpRpSp and SpSpRp. In some embodiments, the core region of a wing-core-wing motif has repeating pattern of internucleotidic linkage stereochemistry, wherein the repeating pattern is a repeating RpRpSp. In some embodiments, the core region of a wing-core-wing motif has repeating pattern of internucleotidic linkage stereochemistry, wherein the repeating pattern is a repeating SpSpRp.

In some embodiments, the present disclosure provides a chirally controlled oligonucleotide composition of an oligonucleotide type whose pattern of backbone chiral centers in the core region comprises $(Sp)_mRp$ or $Rp(Sp)_m$. In some embodiments, the present disclosure provides a chirally controlled oligonucleotide composition of an oligonucleotide type whose pattern of backbone chiral centers in the core region comprises $Rp(Sp)_m$. In some embodiments, the present disclosure provides a chirally controlled oligonucleotide composition of an oligonucleotide type whose pattern of backbone chiral centers in the core region comprises $(Sp)_mRp$. In some embodiments, m is 2. In some embodiments, the present disclosure provides a chirally controlled oligonucleotide composition of an oligonucleotide type whose pattern of backbone chiral centers in the core region comprises $Rp(Sp)_2$. In some embodiments, the present disclosure provides a chirally controlled oligonucleotide composition of an oligonucleotide type whose pattern of backbone chiral centers in the core region comprises $(Sp)_2Rp(Sp)_2$. In some embodiments, the present disclosure provides a chirally controlled oligonucleotide composition of an oligonucleotide type whose pattern of backbone chiral centers in the core region comprises $(Rp)_2Rp(Sp)_2$. In some embodiments, the present disclosure provides a chirally controlled oligonucleotide composition of an oligonucleotide type whose pattern of backbone chiral centers in the core region comprises $RpSpRp(Sp)_2$. In some embodiments, the present disclosure provides a chirally controlled oligonucleotide composition of an oligonucleotide type whose pattern of backbone chiral centers in the core region comprises $SpRpRp(Sp)_2$. In some embodiments, the present disclosure provides a chirally controlled oligonucleotide composition of an oligonucleotide type whose pattern of backbone chiral centers in the core region comprises $(Sp)_2Rp$.

In some embodiments, the present disclosure provides a chirally controlled oligonucleotide composition of an oligonucleotide type whose pattern of backbone chiral centers comprises $(Sp)_mRp$ or $Rp(Sp)_m$. In some embodiments, the present disclosure provides a chirally controlled oligonucleotide composition of an oligonucleotide type whose pattern of backbone chiral centers comprises $Rp(Sp)_m$. In some embodiments, the present disclosure provides a chirally controlled oligonucleotide composition of an oligonucleotide type whose pattern of backbone chiral centers comprises $(Sp)_mRp$. In some embodiments, m is 2. In some embodiments, the present disclosure provides a chirally controlled oligonucleotide composition of an oligonucleotide type whose pattern of backbone chiral centers comprises $Rp(Sp)_2$. In some embodiments, the present disclosure provides a chirally controlled oligonucleotide composition of an oligonucleotide type whose pattern of backbone chiral centers comprises $(Sp)_2Rp(Sp)_2$. In some embodiments, the present disclosure provides a chirally controlled oligonucleotide composition of an oligonucleotide type whose pattern of backbone chiral centers comprises $(Rp)_2Rp(Sp)_2$. In some embodiments, the present disclosure provides a chirally controlled oligonucleotide composition of an oligonucleotide type whose pattern of backbone chiral centers comprises $RpSpRp(Sp)_2$. In some embodiments, the present disclosure provides a chirally controlled oligonucleotide composition of an oligonucleotide type whose pattern of backbone chiral centers comprises $SpRpRp(Sp)_2$. In some embodiments, the present disclosure provides a chirally controlled oligonucleotide composition of an oligonucleotide type whose pattern of backbone chiral centers comprises $(Sp)_2Rp$.

As defined herein, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is greater than 25.

In some embodiments, a repeating pattern is $(Sp)_m(Rp)_n$, wherein n is 1-10, and m is independently as defined above and described herein. In some embodiments, the present disclosure provides a chirally controlled oligonucleotide composition of an oligonucleotide type whose pattern of backbone chiral centers comprises $(Sp)_m(Rp)_n$. In some embodiments, the present disclosure provides a chirally controlled oligonucleotide composition of an oligonucleotide type whose pattern of backbone chiral centers in the core region comprises $(Sp)_m(Rp)_n$. In some embodiments, a repeating pattern is $(Rp)_n(Sp)_m$, wherein n is 1-10, and m is independently as defined above and described herein. In some embodiments, the present disclosure provides a chirally controlled oligonucleotide composition of an oligonucleotide type whose pattern of backbone chiral centers comprises $(Rp)_n(Sp)_m$. In some embodiments, the present disclosure provides a chirally controlled oligonucleotide composition of an oligonucleotide type whose pattern of backbone chiral centers in the core region comprises $(Rp)_n$ $(Sp)_m$. In some embodiments, $(Rp)_n(Sp)_m$ is $(Rp)(Sp)_2$. In some embodiments, $(Sp)_n(Rp)_m$ is $(Sp)_2(Rp)$.

In some embodiments, the present disclosure provides a chirally controlled oligonucleotide composition of an oligonucleotide type whose pattern of backbone chiral centers comprises $(Sp)_m(Rp)_n(Sp)_t$. In some embodiments, a repeating pattern is $(Sp)_m(Rp)_n(Sp)_t$, wherein n is 1-10, t is 1-50, and m is as defined above and described herein. In some embodiments, the present disclosure provides a chirally controlled oligonucleotide composition of an oligonucleotide type whose pattern of backbone chiral centers in the core region comprises $(Sp)_m(Rp)_n(Sp)_t$. In some embodiments, a repeating pattern is $(Sp)_t(Rp)_n(Sp)_m$, wherein n is 1-10, t is 1-50, and m is as defined above and described herein. In some embodiments, the present disclosure provides a chirally controlled oligonucleotide composition of an oligonucleotide type whose pattern of backbone chiral centers comprises $(Sp)_t(Rp)_n(Sp)_m$. In some embodiments, the present disclosure provides a chirally controlled oligonucleotide composition of an oligonucleotide type whose pattern of backbone chiral centers in the core region comprises $(Sp)_t(Rp)_n(Sp)_m$.

In some embodiments, a repeating pattern is $(Np)_t(Rp)_n(Sp)_m$, wherein n is 1-10, t is 1-50, Np is independently Rp or Sp, and m is as defined above and described herein. In some embodiments, the present disclosure provides a chirally controlled oligonucleotide composition of an oligonucleotide type whose pattern of backbone chiral centers comprises $(Np)_t(Rp)_n(Sp)_m$. In some embodiments, the present disclosure provides a chirally controlled oligonucleotide composition of an oligonucleotide type whose pattern of backbone chiral centers in the core region comprises $(Np)_t(Rp)_n(Sp)_m$. In some embodiments, a repeating pattern is $(Np)_m(Rp)_n(Sp)_t$, wherein n is 1-10, t is 1-50, Np is independently Rp or Sp, and m is as defined above and described herein. In some embodiments, the present disclosure provides a chirally controlled oligonucleotide composition of an oligonucleotide type whose pattern of backbone chiral centers comprises $(Np)_m(Rp)_n(Sp)_t$. In some embodiments, the present disclosure provides a chirally controlled oligonucleotide composition of an oligonucleotide type whose pattern of backbone chiral centers in the core region comprises $(Np)_m(Rp)_n(Sp)_t$. In some embodiments, Np is Rp. In some embodiments, Np is Sp. In some embodiments, all Np are the same. In some embodiments, all Np are Sp. In some embodiments, at least one Np is different from the other Np. In some embodiments, t is 2.

As defined herein, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

As defined herein, t is 1-50. In some embodiments, t is 1. In some embodiments, t is 2-50. In some embodiments, t is 2, 3, 4, 5, 6, 7 or 8. In some embodiments, t is 3, 4, 5, 6, 7 or 8. In some embodiments, t is 4, 5, 6, 7 or 8. In some embodiments, t is 5, 6, 7 or 8. In some embodiments, t is 6, 7 or 8. In some embodiments, t is 7 or 8. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20. In some embodiments, t is 21. In some embodiments, t is 22. In some embodiments, t is 23. In some embodiments, t is 24. In some embodiments, t is 25. In some embodiments, t is greater than 25.

In some embodiments, at least one of m and t is greater than 2. In some embodiments, at least one of m and t is greater than 3. In some embodiments, at least one of m and t is greater than 4. In some embodiments, at least one of m and t is greater than 5. In some embodiments, at least one of m and t is greater than 6. In some embodiments, at least one of m and t is greater than 7. In some embodiments, at least one of m and t is greater than 8. In some embodiments, at least one of m and t is greater than 9. In some embodiments, at least one of m and t is greater than 10. In some embodiments, at least one of m and t is greater than 11. In some embodiments, at least one of m and t is greater than 12. In some embodiments, at least one of m and t is greater than 13. In some embodiments, at least one of m and t is greater than 14. In some embodiments, at least one of m and t is greater than 15. In some embodiments, at least one of m and t is greater than 16. In some embodiments, at least one of m and t is greater than 17. In some embodiments, at least one of m and t is greater than 18. In some embodiments, at least one of m and t is greater than 19. In some embodiments, at least one of m and t is greater than 20. In some embodiments, at least one of m and t is greater than 21. In some embodiments, at least one of m and t is greater than 22. In some embodiments, at least one of m and t is greater than 23. In some embodiments, at least one of m and t is greater than 24. In some embodiments, at least one of m and t is greater than 25.

In some embodiments, each one of m and t is greater than 2. In some embodiments, each one of m and t is greater than 3. In some embodiments, each one of m and t is greater than 4. In some embodiments, each one of m and t is greater than 5. In some embodiments, each one of m and t is greater than 6. In some embodiments, each one of m and t is greater than 7. In some embodiments, each one of m and t is greater than 8. In some embodiments, each one of m and t is greater than 9. In some embodiments, each one of m and t is greater than 10. In some embodiments, each one of m and t is greater than 11. In some embodiments, each one of m and t is greater than 12. In some embodiments, each one of m and t is greater than 13. In some embodiments, each one of m and t is greater than 14. In some embodiments, each one of m and t is greater than 15. In some embodiments, each one of m and t is greater than 16. In some embodiments, each one of m and t is greater than 17. In some embodiments, each one of m and t is greater than 18. In some embodiments, each one of m and t is greater than 19. In some embodiments, each one of m and t is greater than 20.

In some embodiments, the sum of m and t is greater than 3. In some embodiments, the sum of m and t is greater than 4. In some embodiments, the sum of m and t is greater than 5. In some embodiments, the sum of m and t is greater than 6. In some embodiments, the sum of m and t is greater than 7. In some embodiments, the sum of m and t is greater than 8. In some embodiments, the sum of m and t is greater than 9. In some embodiments, the sum of m and t is greater than 10. In some embodiments, the sum of m and t is greater than 11. In some embodiments, the sum of m and t is greater than 12. In some embodiments, the sum of m and t is greater than 13. In some embodiments, the sum of m and t is greater than 14. In some embodiments, the sum of m and t is greater than 15. In some embodiments, the sum of m and t is greater than 16. In some embodiments, the sum of m and t is greater than 17. In some embodiments, the sum of m and t is greater than 18. In some embodiments, the sum of m and t is greater than 19. In some embodiments, the sum of m and t is greater than 20. In some embodiments, the sum of m and t is greater than 21. In some embodiments, the sum of m and t is greater than 22. In some embodiments, the sum of m and t is greater than 23. In some embodiments, the sum of m and t is greater than 24. In some embodiments, the sum of m and t is greater than 25.

In some embodiments, n is 1, and at least one of m and t is greater than 1. In some embodiments, n is 1 and each of m and t is independently greater than 1. In some embodiments, m>n and t>n. In some embodiments, $(Sp)_m(Rp)_n(Sp)_t$ is $(Sp)_2Rp(Sp)_2$. In some embodiments, $(Sp)_t(Rp)_n(Sp)_m$ is $(Sp)_2Rp(Sp)_2$. In some embodiments, $(Sp)_t(Rp)_n(Sp)_m$ is $SpRp(Sp)_2$. In some embodiments, $(Np)_t(Rp)_n(Sp)_m$ is $(Np)_t Rp(Sp)_m$. In some embodiments, $(Np)_t(Rp)_n(Sp)_m$ is $(Np)_2 Rp(Sp)_m$. In some embodiments, $(Np)_t(Rp)_n(Sp)_m$ is $(Rp)_2 Rp(Sp)_m$. In some embodiments, $(Np)_t(Rp)_n(Sp)_m$ is $(Sp)_2 Rp(Sp)_m$. In some embodiments, $(Np)_t(Rp)_n(Sp)_m$ is $RpSpRp(Sp)_m$. In some embodiments, $(Np)_t(Rp)_n(Sp)_m$ is $SpRpRp(Sp)_m$.

In some embodiments, $(Sp)_t(Rp)_n(Sp)_m$ is SpRpSpSp. In some embodiments, $(Sp)_t(Rp)_n(Sp)_m$ is $(Sp)_2Rp(Sp)_2$. In some embodiments, $(Sp)_t(Rp)_n(Sp)_m$ is $(Sp)_3Rp(Sp)_3$. In some embodiments, $(Sp)_t(Rp)_n(Sp)_m$ is $(Sp)_4Rp(Sp)_4$. In some embodiments, $(Sp)_t(Rp)_n(Sp)_m$ is $(Sp)_5Rp(Sp)_5$. In some embodiments, $(Sp)_t(Rp)_n(Sp)_m$ is $SpRp(Sp)_5$. In some embodiments, $(Sp)_t(Rp)_n(Sp)_m$ is $(Sp)_2Rp(Sp)_5$. In some embodiments, $(Sp)_t(Rp)_n(Sp)_m$ is $(Sp)_3Rp(Sp)_5$. In some embodiments, $(Sp)_t(Rp)_n(Sp)_m$ is $(Sp)_4Rp(Sp)_5$. In some embodiments, $(Sp)_t(Rp)_n(Sp)_m$ is $(Sp)_5Rp(Sp)_5$.

In some embodiments, $(Sp)_m(Rp)_n(Sp)_t$ is $(Sp)_2Rp(Sp)_2$. In some embodiments, $(Sp)_m(Rp)_n(Sp)_t$ is $(Sp)_3Rp(Sp)_3$. In some embodiments, $(Sp)_m(Rp)_n(Sp)_t$ is $(Sp)_4Rp(Sp)_4$. In some embodiments, $(Sp)_m(Rp)_n(Sp)_t$ is $(Sp)_mRp(Sp)_5$. In some embodiments, $(Sp)_m(Rp)_n(Sp)_t$ is $(Sp)_2Rp(Sp)_5$. In some embodiments, $(Sp)_m(Rp)_n(Sp)_t$ is $(Sp)_3Rp(Sp)_5$. In some embodiments, $(Sp)_m(Rp)_n(Sp)_t$ is $(Sp)_4Rp(Sp)_5$. In some embodiments, $(Sp)_m(Rp)_n(Sp)_t$ is $(Sp)_5Rp(Sp)_5$.

In some embodiments, the core region comprises at least one Rp internucleotidic linkage. In some embodiments, the core region of a wing-core-wing motif comprises at least one Rp internucleotidic linkage. In some embodiments, a core region comprises at least one Rp phosphorothioate internucleotidic linkage. In some embodiments, the core region of a wing-core-wing motif comprises at least one Rp phosphorothioate internucleotidic linkage. In some embodiments, the core region of a wing-core-wing motif comprises only one Rp phosphorothioate internucleotidic linkage. In some embodiments, a core region motif comprises at least two Rp internucleotidic linkages. In some embodiments, the core region of a wing-core-wing motif comprises at least two Rp internucleotidic linkages. In some embodiments, the core region of a wing-core-wing motif comprises at least two Rp phosphorothioate internucleotidic linkages. In some embodiments, a core region comprises at least three Rp internucleotidic linkages. In some embodiments, the core region of a wing-core-wing motif comprises at least three Rp internucleotidic linkages. In some embodiments, the core region comprises at least three Rp phosphorothioate internucleotidic linkages. In some embodiments, the core region of a wing-core-wing motif comprises at least three Rp phosphorothioate internucleotidic linkages. In some embodiments, a core region comprises at least 4, 5, 6, 7, 8, 9, or 10 Rp internucleotidic linkages. In some embodiments, the core region of a wing-core-wing motif comprises at least 4, 5, 6, 7, 8, 9, or 10 Rp internucleotidic linkages. In some embodiments, a core region comprises at least 4, 5, 6, 7, 8, 9, or 10 Rp phosphorothioate internucleotidic linkages. In some embodiments, the core region of a wing-core-wing motif comprises at least 4, 5, 6, 7, 8, 9, or 10 Rp phosphorothioate internucleotidic linkages.

In certain embodiments, a wing-core-wing motif is a 5-10-5 motif wherein the residues at each wing region are 2'-modified residues. In certain embodiments, a wing-core-wing motif is a 5-10-5 motif wherein the residues at each wing region are 2'-OR'-modified residues. In certain embodiments, a wing-core-wing motif is a 5-10-5 motif wherein the residues at each wing region are 2'-MOE-modified residues. In certain embodiments, a wing-core-wing motif is a 5-10-5 motif wherein the residues at each wing region are 2'-OMe-modified residues. In certain embodiments, a wing-core-wing motif is a 5-10-5 motif wherein the residues in the core region are 2'-deoxyribonucleoside residues. In certain embodiments, a wing-core-wing motif is a 5-10-5 motif, wherein all internucleotidic linkages are phosphorothioate linkages. In certain embodiments, a wing-core-wing motif is a 5-10-5 motif, wherein all internucleotidic linkages are chiral phosphorothioate linkages. In certain embodiments, a wing-core-wing motif is a 5-10-5 motif wherein the residues at each wing region are 2'-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-OR'-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-MOE-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-OMe-modified residues, the residues in the core region are 2'-deoxyribonucleoside residues, and all internucleotidic linkages in the core region are chiral phosphorothioate linkages.

In some embodiments, residues at the "X" wing region are not 2'-MOE-modified residues. In certain embodiments, a wing-core motif is a motif wherein the residues at the "X" wing region are not 2'-MOE-modified residues. In certain embodiments, a core-wing motif is a motif wherein the residues at the "X" wing region are not 2'-MOE-modified residues. In certain embodiments, a wing-core-wing motif is a motif wherein the residues at each "X" wing region are not 2'-MOE-modified residues. In certain embodiments, a wing-core-wing motif is a 5-10-5 motif wherein the residues at each "X" wing region are not 2'-MOE-modified residues. In certain embodiments, a wing-core-wing motif is a 5-10-5 motif wherein the residues in the core "Y" region are 2'-deoxyribonucleoside residues. In certain embodiments, a wing-core-wing motif is a 5-10-5 motif, wherein all internucleotidic linkages are phosphorothioate internucleotidic linkages. In certain embodiments, a wing-core-wing motif is a 5-10-5 motif, wherein all internucleotidic linkages are chiral phosphorothioate internucleotidic linkages. In certain embodiments, a wing-core-wing motif is a 5-10-5 motif wherein the residues at each "X" wing region are not 2'-MOE-modified residues, the residues in the core "Y" region are 2'-deoxyribonucleoside, and all internucleotidic linkages are chiral phosphorothioate internucleotidic linkages.

As understood by a person having ordinary skill in the art, provided oligonucleotides and compositions, among other things, can target a great number of nucleic acid polymers. For instance, in some embodiments, provided oligonucleotides and compositions may target a transcript of a nucleic acid sequence, wherein a common base sequence of oligonucleotides (e.g., a base sequence of an oligonucleotide type) comprises or is a sequence complementary to a sequence of the transcript. In some embodiments, a common base sequence comprises a sequence complimentary to a sequence of a target. In some embodiments, a common base sequence is a sequence complimentary to a sequence of a target. In some embodiments, a common base sequence comprises or is a sequence 100% complimentary to a sequence of a target. In some embodiments, a common base sequence comprises a sequence 100% complimentary to a sequence of a target. In some embodiments, a common base sequence is a sequence 100% complimentary to a sequence of a target. In some embodiments, a common base sequence in a core comprises or is a sequence complimentary to a sequence of a target. In some embodiments, a common base sequence in a core comprises a sequence complimentary to a sequence of a target. In some embodiments, a common base sequence in a core is a sequence % complimentary to a sequence of a target. In some embodiments, a common base sequence in a core comprises or is a sequence 100% complimentary to a sequence of a target. In some embodiments, a common base sequence in a core comprises a sequence 100% complimentary to a sequence of a target. In some embodiments, a common base sequence in a core is a sequence 100% complimentary to a sequence of a target.

In some embodiments, as described in this disclosure, provided oligonucleotides and compositions may provide new cleavage patterns, higher cleavage rate, higher cleavage degree, higher cleavage selectivity, etc. In some embodiments, provided compositions can selectively suppress (e.g., cleave) a transcript from a target nucleic acid sequence which has one or more similar sequences exist within a subject or a population, each of the target and its similar sequences contains a specific nucleotidic characteristic sequence element that defines the target sequence relative to the similar sequences. In some embodiments, for example, a target sequence is a wild-type allele or copy of a gene, and a similar sequence is a sequence has very similar base sequence, e.g., a sequence having SNP, mutations, etc.; In some embodiments, a characteristic sequence element defines that target sequence relative to the similar sequence: for example, when a target sequence is a Huntington's disease-associated allele with T at rs362307 (U in the corresponding RNA; C for the non-disease-associated allele), a characteristic sequence comprises this SNP.

In some embodiments, a similar sequence has greater than 60%, 65%, 70%, 75%, 80%, 85%, 90%, 91%, 92%, 93%, 94%, 95%, 96%, 97%, 98% or 99% sequence homology with a target sequence. In some embodiments, a target sequence is a disease-causing copy of a nucleic acid sequence comprising one or more mutations and/or SNPs, and a similar sequence is a copy not causing the disease (wild type). In some embodiments, a target sequence comprises a mutation, wherein a similar sequence is the corresponding wild-type sequence. In some embodiments, a target sequence is a mutant allele, while a similar sequence is a wild-type allele. In some embodiments, a target sequence comprises a SNP that is associated with a disease-causing allele, while a similar sequence comprises the same SNP that is not associated with the disease-causing allele. In some embodiments, the region of a target sequence that is complementary to a common base sequence of a provided oligonucleotide composition has greater than 60%, 65%, 70%, 75%, 80%, 85%, 90%, 91%, 92%, 93%, 94%, 95%, 96%, 97%, 98% or 99% sequence homology with the corresponding region of a similar sequence. In some embodiments, the region of a target sequence that is complementary to a common base sequence of a provided oligonucleotide composition differs from the corresponding region of a similar sequence at less than 5, less than 4, less than 3, less than 2, or only 1 base pairs. In some embodiments, the region of a target sequence that is complementary to a common base sequence of a provided oligonucleotide composition differs from the corresponding region of a similar sequence only at a mutation site or SNP site. In some embodiments, the region of a target sequence that is complementary to a common base sequence of a provided oligonucleotide composition differs from the corresponding region of a similar sequence only at a mutation site. In some embodiments, the region of a target sequence that is complementary to a common base sequence of a provided oligonucleotide composition differs from the corresponding region of a similar sequence only at a SNP site.

In some embodiments, a common base sequence comprises or is a sequence complementary to a characteristic sequence element. In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments, a common base sequence in a core comprises or is a sequence complementary to a characteristic sequence element. In some embodiments, a common base sequence in a core comprises a sequence complementary to a characteristic sequence element. In some embodiments, a common base sequence in a core is a sequence complementary to a characteristic sequence element. In some embodiments, a common base sequence in a core comprises or is a sequence 100% complementary to a characteristic sequence element. In some embodiments, a common base sequence in a core comprises a sequence 100% complementary to a characteristic sequence element. In some embodiments, a common base sequence in a core is a sequence 100% complementary to a characteristic sequence element.

In some embodiments, a characteristic sequence element comprises or is a mutation. In some embodiments, a characteristic sequence element comprises a mutation. In some embodiments, a characteristic sequence element is a mutation. In some embodiments, a characteristic sequence element comprises or is a point mutation. In some embodiments, a characteristic sequence element comprises a point mutation. In some embodiments, a characteristic sequence element is a point mutation. In some embodiments, a characteristic sequence element comprises or is a SNP. In some embodiments, a characteristic sequence element comprises a SNP. In some embodiments, a characteristic sequence element is a SNP.

In some embodiments, a common base sequence 100% matches a target sequence, which it does not 100% match a similar sequence of the target sequence. For example, in some embodiments, a common base sequence matches a mutation in the disease-causing copy or allele of a target nucleic acid sequence, but does not match a non-disease-causing copy or allele at the mutation site; in some other embodiments, a common base sequence matches a SNP in the disease-causing allele of a target nucleic acid sequence, but does not match a non-disease-causing allele at the corresponding site. In some embodiments, a common base sequence in a core 100% matches a target sequence, which it does not 100% match a similar sequence of the target sequence. For example, in WV-1092, its common base sequence (and its common base sequence in its core) matches the disease-associated U, but not the non-disease-associated (wild-type) C at rs362307.

Among other things, the present disclosure recognizes that a base sequence may have impact on oligonucleotide properties. In some embodiments, a base sequence may have impact on cleavage pattern of a target when oligonucleotides having the base sequence are utilized for suppressing a target, e.g., through a pathway involving RNase H: for example, FIG. 33 demonstrates that structurally similar (all phosphorothioate linkages, all stereorandom) oligonucleotides have different sequences may have different cleavage patterns. In some embodiments, a common base sequence of a non-stereorandom oligonucleotide compositions (e.g., certain oligonucleotide compositions provided in the present disclosure) is a base sequence that when applied to a DNA oligonucleotide composition (e.g., ONT-415) or a stereorandom all-phosphorothioate oligonucleotide composition (e.g., WV-905), cleavage pattern of the DNA (DNA cleavage pattern) and/or the stereorandom all-phosphorothioate (stereorandom cleavage pattern) composition has a cleavage site within or in the vicinity of a characteristic sequence element. In some embodiments, a cleavage site within or in the vicinity is within a sequence complementary to a core region of a common sequence. In some embodiments, a cleavage site within or in the vicinity is within a sequence 100% complementary to a core region of a common sequence.

In some embodiments, a common base sequence is a base sequence that has a cleavage site within or in the vicinity of a characteristic sequence element in its DNA cleavage pattern. In some embodiments, a common base sequence is a base sequence that has a cleavage site within a characteristic sequence element in its DNA cleavage pattern. In some embodiments, a common base sequence is a base sequence that has a cleavage site in the vicinity of a characteristic sequence element in its DNA cleavage pattern. In some embodiments, a common base sequence is a base sequence that has a cleavage site in the vicinity of a mutation or SNP of a characteristic sequence element in its DNA cleavage pattern. In some embodiments, a common base sequence is a base sequence that has a cleavage site in the vicinity of a mutation in its DNA cleavage pattern. In some embodiments, a common base sequence is a base sequence that has a cleavage site in the vicinity of a SNP in its DNA cleavage pattern.

In some embodiments, a common base sequence is a base sequence that has a cleavage site within or in the vicinity of a characteristic sequence element in its stereorandom cleavage pattern. In some embodiments, a common base sequence is a base sequence that has a cleavage site within a characteristic sequence element in its stereorandom cleavage pattern. In some embodiments, a common base sequence is a base sequence that has a cleavage site in the vicinity of a characteristic sequence element in its stereorandom cleavage pattern. In some embodiments, a common base sequence is a base sequence that has a cleavage site in the vicinity of a mutation or SNP of a characteristic sequence element in its stereorandom cleavage pattern. In some embodiments, a common base sequence is a base sequence that has a cleavage site in the vicinity of a mutation in its stereorandom cleavage pattern. In some embodiments, a common base sequence is a base sequence that has a cleavage site in the vicinity of a SNP in its stereorandom cleavage pattern.

In some embodiments, a common base sequence is a base sequence that has a cleavage site in the vicinity of a mutation of a characteristic sequence element in its DNA and/or stereorandom cleavage pattern. In some embodiments, a common base sequence is a base sequence that has a cleavage site in the vicinity of a mutation in its DNA and/or stereorandom cleavage pattern. In some embodiments, a common base sequence is a base sequence that has a cleavage site in the vicinity of a mutation in its DNA cleavage pattern. In some embodiments, a cleavage site in the vicinity of a mutation is at a mutation, i.e., a cleavage site is at the internucleotidic linkage of a mutated nucleotide (e.g., if a mutation is at A in the target sequence of GGGACGTCTT, the cleavage is between A and C). In some embodiments, a cleavage site in the vicinity is a cleavage site 0, 1, 2, 3, 4, 5, 6, 7, 8, 9, or 10 internucleotidic linkages away from a mutation, where 0 means cleavage at the mutation site (e.g., if a mutation is at A in the target sequence of GGGACGTCTT, the cleavage is between A and C for 0 internucleotidic linkage away; a cleavage site 1 internucleotidic linkage away from the mutation is between G and A to the 5' from the mutation or between C and G to the 3' from the mutation). In some embodiments, a cleavage site in the vicinity is a cleavage site 0, 1, 2, 3, 4, or 5 internucleotidic linkages away from a mutation. In some embodiments, a cleavage site in the vicinity is a cleavage site 0, 1, 2, 3, 4, or 5 internucleotidic linkages away to the 5' from a mutation. In some embodiments, a cleavage site in the vicinity is a cleavage site 0, 1, 2, 3, 4, or 5 internucleotidic linkages away to the 3' from a mutation. In some embodiments, a cleavage site in the vicinity is a cleavage site 0, 1, 2, 3, 4, or 5 internucleotidic linkages away from a mutation. In some embodiments, a cleavage site in the vicinity is a cleavage site 0, 1, 2, 3, 4, or 5 internucleotidic linkages away to the 5' from a mutation. In some embodiments, a cleavage site in the vicinity is a cleavage site 0, 1, 2, 3, 4, or 5 internucleotidic linkages away to the 3' from a mutation. In some embodiments, a cleavage site in the vicinity is a cleavage site 0, 1, 2, 3, or 4 internucleotidic linkages away from a mutation. In some embodiments, a cleavage site in the vicinity is a cleavage site 0, 1, 2, 3, or 4 internucleotidic linkages away to the 5' from a mutation. In some embodiments, a cleavage site in the vicinity is a cleavage site 0, 1, 2, 3, or 4 internucleotidic linkages away to the 3' from a mutation. In some embodiments, a cleavage site in the vicinity is a cleavage site 0, 1, 2, or 3 internucleotidic linkages away from a mutation. In some embodiments, a cleavage site in the vicinity is a cleavage site 0, 1, 2, or 3 internucleotidic linkages away to the 5' from a mutation. In some embodiments, a cleavage site in the vicinity is a cleavage site 0, 1, 2, or 3 internucleotidic linkages away to the 3' from a mutation. In some embodiments, a cleavage site in the vicinity is a cleavage site 0, 1, or 2 internucleotidic linkages away from a mutation. In some embodiments, a cleavage site in the vicinity is a cleavage site 0, 1, or 2 internucleotidic linkages away to the 5' from a mutation. In some embodiments, a cleavage site in the vicinity is a cleavage site 0, 1, or 2 internucleotidic linkages away to the 3' from a mutation. In some embodiments, a cleavage site in the vicinity is a cleavage site 0 or 1 internucleotidic linkage away from a mutation. In some embodiments, a cleavage site in the vicinity is a cleavage site 0 or 1 internucleotidic linkage away to the 5' from a mutation. In some embodiments, a cleavage site in the vicinity is a cleavage site 0 or 1 internucleotidic linkage away to the 3' from a mutation. In some embodiments, a cleavage site in the vicinity is a cleavage site 0 internucleotidic linkage away from a mutation. In some embodiments, a cleavage site in the vicinity is a cleavage site one internucleotidic linkage away from a mutation. In some embodiments, a cleavage site in the vicinity is a cleavage site one internucleotidic linkage away to the 5' from a mutation. In some embodiments, a cleavage site in the vicinity is a cleavage site one internucleotidic linkage away to the 3' from a mutation. In some embodiments, a cleavage site in the vicinity is a cleavage site two internucleotidic linkages away from a mutation. In some embodiments, a cleavage site in the vicinity is a cleavage site two internucleotidic linkages away to the 5' from a mutation. In some embodiments, a cleavage site in the vicinity is a cleavage site two internucleotidic linkages away to the 3' from a mutation. In some embodiments, a cleavage site in the vicinity is a cleavage site three internucleotidic linkages away from a mutation. In some embodiments, a cleavage site in the vicinity is a cleavage site three internucleotidic linkages away to the 5' from a mutation. In some embodiments, a cleavage site in the vicinity is a cleavage site three internucleotidic linkages away to the 3' from a mutation. In some embodiments, a cleavage site in the vicinity is a cleavage site four internucleotidic linkages away from a mutation. In some embodiments, a cleavage site in the vicinity is a cleavage site four internucleotidic linkages away to the 5' from a mutation. In some embodiments, a cleavage site in the vicinity is a cleavage site four internucleotidic linkages away to the 3' from a mutation. In some embodiments, a cleavage site in the vicinity is a cleavage site five internucleotidic linkages away from a mutation. In some embodiments, a cleavage site in the vicinity is a cleavage site five internucleotidic linkages away to the 5' from a mutation. In some embodiments, a cleavage site in the vicinity is a cleavage site five internucleotidic linkages away to the 3' from a mutation.

In some embodiments, a common base sequence is a base sequence that has a cleavage site in the vicinity of a SNP of a characteristic sequence element in its DNA and/or stereorandom cleavage pattern. In some embodiments, a common base sequence is a base sequence that has a cleavage site in the vicinity of a SNP in its DNA and/or stereorandom cleavage pattern. In some embodiments, a common base sequence is a base sequence that has a cleavage site in the vicinity of a SNP in its DNA cleavage pattern. In some embodiments, a cleavage site in the vicinity of a SNP is at a SNP, i.e., a cleavage site is at the internucleotidic linkage of a nucleotide at a SNP (e.g., for the target of WV-905, G*G*C*A*C*A*A*G*G*G*C*A*C*A*G*A*C*T*T*C (SEQ ID NO: 17), which comprises rUrUrUrGrGrArArGrUrCrUrGrUr<u>Gr</u>CrCrCrUrUrGrUrGrCrCrC (SEQ ID NO: 18) (r5362307 bolded), the cleavage is between the bolded rU and the underlined rG immediately after it). In some embodiments, a cleavage site in the vicinity is a cleavage site 0, 1, 2, 3, 4, 5, 6, 7, 8, 9, or 10 internucleotidic linkages away from a SNP, where 0 means cleavage at a SNP (e.g., for the target of WV-905, G*G*C*A*C*A*A*G*G*G*C*A*C*A*G*A*C*T*T*C (SEQ ID NO: 17), which comprises rUrUrUrGrGrArArGrUrCrUrGrUr<u>Gr</u>CrCrCrUrUrGrUrGrCrCrC (SEQ ID NO: 18) (r5362307 bolded), the cleavage is between the bolded rU and the underlined rG immediately after it for 0 internucleotidic linkage away; a cleavage site 1 internucleotidic linkage away from a SNP is between the rG and rU to the 5' from the SNP (underlined: rUrUrUrGrGrArArGrUrCrUrGr<u>UrGr</u>CrCrCrUrUrGrUrGrCrCrC (SEQ ID NO: 18)), or between rG and rC to the 3'-end of the SNP (underlined: rUrUrUrGrGrArArGrUrCrUrGrUr<u>GrCr</u>CrCrUrUrGrUrGrCrCrC (SEQ ID NO: 18))). In some embodiments, a cleavage site in the vicinity is a cleavage site 0, 1, 2, 3, 4, or 5 internucleotidic linkages away from a SNP. In some embodiments, a cleavage site in the vicinity is a cleavage site 0, 1, 2, 3, 4, or 5 internucleotidic linkages away to the 5' from a SNP. In some embodiments, a cleavage site in the vicinity is a cleavage site 0, 1, 2, 3, 4, or 5 internucleotidic linkages away to the 3' from a SNP. In some embodiments, a cleavage site in the vicinity is a cleavage site 0, 1, 2, 3, 4, or 5 internucleotidic linkages away from a SNP. In some embodiments, a cleavage site in the vicinity is a cleavage site 0, 1, 2, 3, 4, or 5 internucleotidic linkages away to the 5' from a SNP. In some embodiments, a cleavage site in the vicinity is a cleavage site 0, 1, 2, 3, 4, or 5 internucleotidic linkages away to the 3' from a SNP. In some embodiments, a cleavage site in the vicinity is a cleavage site 0, 1, 2, 3, or 4 internucleotidic linkages away from a SNP. In some embodiments, a cleavage site in the vicinity is a cleavage site 0, 1, 2, 3, or 4 internucleotidic linkages away to the 5' from a SNP. In some embodiments, a cleavage site in the vicinity is a cleavage site 0, 1, 2, 3, or 4 internucleotidic linkages away to the 3' from a SNP. In some embodiments, a cleavage site in the vicinity is a cleavage site 0, 1, 2, or 3 internucleotidic linkages away from a SNP. In some embodiments, a cleavage site in the vicinity is a cleavage site 0, 1, 2, or 3 internucleotidic linkages away to the 5' from a SNP. In some embodiments, a cleavage site in the vicinity is a cleavage site 0, 1, 2, or 3 internucleotidic linkages away to the 3' from a SNP. In some embodiments, a cleavage site in the vicinity is a cleavage site 0, 1, or 2 internucleotidic linkages away from a SNP. In some embodiments, a cleavage site in the vicinity is a cleavage site 0, 1, or 2 internucleotidic linkages away to the 5' from a SNP. In some embodiments, a cleavage site in the vicinity is a cleavage site 0, 1, or 2 internucleotidic linkages away to the 3' from a SNP. In some embodiments, a cleavage site in the vicinity is a cleavage site 0 or 1 internucleotidic linkage away from a SNP. In some embodiments, a cleavage site in the vicinity is a cleavage site 0 or 1 internucleotidic linkage away to the 5' from a SNP. In some embodiments, a cleavage site in the vicinity is a cleavage site 0 or 1 internucleotidic linkage away to the 3' from a SNP. In some embodiments, a cleavage site in the vicinity is a cleavage site 0 internucleotidic linkage away from a SNP. In some embodiments, a cleavage site in the vicinity is a cleavage site one internucleotidic linkage away from a SNP. In some embodiments, a cleavage site in the vicinity is a cleavage site one internucleotidic linkage away to the 5' from a SNP. In some embodiments, a cleavage site in the vicinity is a cleavage site one internucleotidic linkage away to the 3' from a SNP. In some embodiments, a cleavage site in the vicinity is a cleavage site two internucleotidic linkages away from a SNP. In some embodiments, a cleavage site in the vicinity is a cleavage site two internucleotidic linkages away to the 5' from a SNP. In some embodiments, a cleavage site in the vicinity is a cleavage site two internucleotidic linkages away to the 3' from a SNP. In some embodiments, a cleavage site in the vicinity is a cleavage site three internucleotidic linkages away from a SNP. In some embodiments, a cleavage site in the vicinity is a cleavage site three internucleotidic linkages away to the 5' from a SNP. In some embodiments, a cleavage site in the vicinity is a cleavage site three internucleotidic linkages away to the 3' from a SNP. In some embodiments, a cleavage site in the vicinity is a cleavage site four internucleotidic linkages away from a SNP. In some embodiments, a cleavage site in the vicinity is a cleavage site four internucleotidic linkages away to the 5' from a SNP. In some embodiments, a cleavage site in the vicinity is a cleavage site four internucleotidic linkages away to the 3' from a SNP. In some embodiments, a cleavage site in the vicinity is a cleavage site five internucleotidic linkages away from a SNP. In some embodiments, a cleavage site in the vicinity is a cleavage site five internucleotidic linkages away to the 5' from a SNP. In some embodiments, a cleavage site in the vicinity is a cleavage site five internucleotidic linkages away to the 3' from a SNP. For example, FIG. 33 demonstrates that stereorandom cleavage pattern of the WV-905 sequence has cleavage sites at the SNP (between CUGU and GCCC), two internucleotidic linkages away (between GUCU and GUGC, and between GUGC and CCUU), three internucleotidic linkages away (between UGCC and CUUG); four internucleotidic linkages away (between GCCC and UUGU, and AAGU and CUGU), and five internucleotidic linkages away (between CCCU and UGUG).

In some embodiments, a cleavage site within or in the vicinity of a characteristic sequence element, e.g., in the vicinity of a mutation, a SNP, etc., is a major cleavage site of a DNA and/or stereorandom cleavage pattern. In some embodiments, a cleavage site within or in the vicinity of a characteristic sequence element is a major cleavage site of a DNA cleavage pattern. In some embodiments, a cleavage site within or in the vicinity of a characteristic sequence element is a major cleavage site of a stereorandom cleavage pattern. In some embodiments, a cleavage site in the vicinity of a mutation is a major cleavage site of a DNA cleavage pattern. In some embodiments, a cleavage site in the vicinity of a mutation is a major cleavage site of a stereorandom cleavage pattern. In some embodiments, a cleavage site in the vicinity of a SNP is a major cleavage site of a DNA cleavage pattern. In some embodiments, a cleavage site in the vicinity of a SNP is a major cleavage site of a stereorandom cleavage pattern. In some embodiments, a major cleavage site is within a sequence complementary to a core region of a common sequence. In some embodiments, a major cleavage site is within a sequence 100% complementary to a core region of a common sequence.

In some embodiments, a major cleavage site is a site having the most, or the second, third, fourth or fifth most cleavage. In some embodiments, a major cleavage site is a site having the most, or the second, third, or fourth most cleavage. In some embodiments, a major cleavage site is a site having the most, or the second, or third most cleavage. In some embodiments, a major cleavage site is a site having the most or the second most cleavage. In some embodiments, a major cleavage site is a site having the most cleavage. In some embodiments, a major cleavage site is a site having the second most cleavage. In some embodiments, a major cleavage site is a site having the third most cleavage. In some embodiments, a major cleavage site is a site having the fourth most cleavage. In some embodiments, a major cleavage site is a site having the fifth most cleavage.

In some embodiments, a major cleavage site is a site wherein greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of cleavage occurs. In some embodiments, a major cleavage site is a site wherein greater than 5% of cleavage occurs. In some embodiments, a major cleavage site is a site wherein greater than 10% of cleavage occurs. In some embodiments, a major cleavage site is a site wherein greater than 15% of cleavage occurs. In some embodiments, a major cleavage site is a site wherein greater than 20% of cleavage occurs. In some embodiments, a major cleavage site is a site wherein greater than 25% of cleavage occurs. In some embodiments, a major cleavage site is a site wherein greater than 30% of cleavage occurs. In some embodiments, a major cleavage site is a site wherein greater than 35% of cleavage occurs. In some embodiments, a major cleavage site is a site wherein greater than 40% of cleavage occurs. In some embodiments, a major cleavage site is a site wherein greater than 45% of cleavage occurs. In some embodiments, a major cleavage site is a site wherein greater than 50% of cleavage occurs. In some embodiments, a major cleavage site is a site wherein greater than 55% of cleavage occurs. In some embodiments, a major cleavage site is a site wherein greater than 60% of cleavage occurs. In some embodiments, a major cleavage site is a site wherein greater than 65% of cleavage occurs. In some embodiments, a major cleavage site is a site wherein greater than 70% of cleavage occurs. In some embodiments, a major cleavage site is a site wherein greater than 75% of cleavage occurs. In some embodiments, a major cleavage site is a site wherein greater than 80% of cleavage occurs. In some embodiments, a major cleavage site is a site wherein greater than 85% of cleavage occurs. In some embodiments, a major cleavage site is a site wherein greater than 90% of cleavage occurs. In some embodiments, a major cleavage site is a site wherein greater than 91% of cleavage occurs. In some embodiments, a major cleavage site is a site wherein greater than 92% of cleavage occurs. In some embodiments, a major cleavage site is a site wherein greater than 93% of cleavage occurs. In some embodiments, a major cleavage site is a site wherein greater than 94% of cleavage occurs. In some embodiments, a major cleavage site is a site wherein greater than 95% of cleavage occurs. In some embodiments, a major cleavage site is a site wherein greater than 96% of cleavage occurs. In some embodiments, a major cleavage site is a site wherein greater than 97% of cleavage occurs. In some embodiments, a major cleavage site is a site wherein greater than 98% of cleavage occurs. In some embodiments, a major cleavage site is a site wherein greater than 99% of cleavage occurs. In some embodiments, a major cleavage site is a site wherein 100% of cleavage occurs.

In some embodiments, a major cleavage site is a site wherein greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of a target is cleaved. In some embodiments, a major cleavage site is a site wherein greater than 5% of a target is cleaved. In some embodiments, a major cleavage site is a site wherein greater than 10% of a target is cleaved. In some embodiments, a major cleavage site is a site wherein greater than 15% of a target is cleaved. In some embodiments, a major cleavage site is a site wherein greater than 20% of a target is cleaved. In some embodiments, a major cleavage site is a site wherein greater than 25% of a target is cleaved. In some embodiments, a major cleavage site is a site wherein greater than 30% of a target is cleaved. In some embodiments, a major cleavage site is a site wherein greater than 35% of a target is cleaved. In some embodiments, a major cleavage site is a site wherein greater than 40% of a target is cleaved. In some embodiments, a major cleavage site is a site wherein greater than 45% of a target is cleaved. In some embodiments, a major cleavage site is a site wherein greater than 50% of a target is cleaved. In some embodiments, a major cleavage site is a site wherein greater than 55% of a target is cleaved. In some embodiments, a major cleavage site is a site wherein greater than 60% of a target is cleaved. In some embodiments, a major cleavage site is a site wherein greater than 65% of a target is cleaved. In some embodiments, a major cleavage site is a site wherein greater than 70% of a target is cleaved. In some embodiments, a major cleavage site is a site wherein greater than 75% of a target is cleaved. In some embodiments, a major cleavage site is a site wherein greater than 80% of a target is cleaved. In some embodiments, a major cleavage site is a site wherein greater than 85% of a target is cleaved. In some embodiments, a major cleavage site is a site wherein greater than 90% of a target is cleaved. In some embodiments, a major cleavage site is a site wherein greater than 91% of a target is cleaved. In some embodiments, a major cleavage site is a site wherein greater than 92% of a target is cleaved. In some embodiments, a major cleavage site is a site wherein greater than 93% of a target is cleaved. In some embodiments, a major cleavage site is a site wherein greater than 94% of a target is cleaved. In some embodiments, a major cleavage site is a site wherein greater than 95% of a target is cleaved. In some embodiments, a major cleavage site is a site wherein greater than 96% of a target is cleaved. In some embodiments, a major cleavage site is a site wherein greater than 97% of a target is cleaved. In some embodiments, a major cleavage site is a site wherein greater than 98% of a target is cleaved. In some embodiments, a major cleavage site is a site wherein greater than 99% of a target is cleaved. In some embodiments, a major cleavage site is a site wherein 100% of a target is cleaved. In some embodiments, a cleavage pattern may not have a major cleavage site as no site reaches an absolute cleavage threshold level.

As a person having ordinary skill in the art understands, various methods may be useful for generating cleavage patterns and/or identify cleavage sites, including major cleavage site. In some embodiments, an example of such an assay is an RNase cleavage assay as described herein; for example results, see FIG. 33, FIG. 34, etc.

In some embodiments, the present disclosure recognizes location effects of a sequence motif complementary to a characteristic sequence element. In some embodiments, the present disclosure recognizes location effects of a sequence motif complementary to a mutation. In some embodiments, the present disclosure recognizes location effects of a sequence motif complementary to a SNP.

In some embodiments, position 11, 12 or 13 of a sequence as counted from its 5'-terminus aligns with a characteristic sequence element. In some embodiments, position 11 of a sequence as counted from its 5'-terminus aligns with a characteristic sequence element. In some embodiments, position 12 of a sequence as counted from its 5'-terminus aligns with a characteristic sequence element. In some embodiments, position 13 of a sequence as counted from its 5'-terminus aligns with a characteristic sequence element. In some embodiments, position 8, 9 or 10 of a sequence as counted from its 3'-terminus aligns with a characteristic sequence element. In some embodiments, position 8 of a sequence as counted from its 3'-terminus aligns with a characteristic sequence element. In some embodiments, position 9 of a sequence as counted from its 3'-terminus aligns with a characteristic sequence element. In some embodiments, position 10 of a sequence as counted from its 3'-terminus aligns with a characteristic sequence element. In some embodiments, position 6, 7, or 8 of a core region as counted from the 5'-terminus of the core region aligns with a characteristic sequence element. In some embodiments, position 6 of a core region as counted from the 5'-terminus of the core region aligns with a characteristic sequence element. In some embodiments, position 7 of a core region as counted from the 5'-terminus of the core region aligns with a characteristic sequence element. In some embodiments, position 8 of a core region as counted from the 5'-terminus of the core region aligns with a characteristic sequence element. In some embodiments, position 3, 4, or 5 of a core region as counted from the 3'-terminus of the core region aligns with a characteristic sequence element. In some embodiments, position 3 of a core region as counted from the 3'-terminus of the core region aligns with a characteristic sequence element. In some embodiments, position 4 of a core region as counted from the 3'-terminus of the core region aligns with a characteristic sequence element. In some embodiments, position 5 of a core region as counted from the 3'-terminus of the core region aligns with a characteristic sequence element.

In some embodiments, position 11, 12 or 13 of a sequence as counted from its 5'-terminus aligns with a mutation. In some embodiments, position 11 of a sequence as counted from its 5'-terminus aligns with a mutation. In some embodiments, position 12 of a sequence as counted from its 5'-terminus aligns with a mutation. In some embodiments, position 13 of a sequence as counted from its 5'-terminus aligns with a mutation. In some embodiments, position 8, 9 or 10 of a sequence as counted from its 3'-terminus aligns with a mutation. In some embodiments, position 8 of a sequence as counted from its 3'-terminus aligns with a mutation. In some embodiments, position 9 of a sequence as counted from its 3'-terminus aligns with a mutation. In some embodiments, position 10 of a sequence as counted from its 3'-terminus aligns with a mutation. In some embodiments, position 6, 7, or 8 of a core region as counted from the 5'-terminus of the core region aligns with a mutation. In some embodiments, position 6 of a core region as counted from the 5'-terminus of the core region aligns with a mutation. In some embodiments, position 7 of a core region as counted from the 5'-terminus of the core region aligns with a mutation. In some embodiments, position 8 of a core region as counted from the 5'-terminus of the core region aligns with a mutation. In some embodiments, position 3, 4, or 5 of a core region as counted from the 3'-terminus of the core region aligns with a mutation. In some embodiments, position 3 of a core region as counted from the 3'-terminus of the core region aligns with a mutation. In some embodiments, position 4 of a core region as counted from the 3'-terminus of the core region aligns with a mutation. In some embodiments, position 5 of a core region as counted from the 3'-terminus of the core region aligns with a mutation.

In some embodiments, position 11, 12 or 13 of a sequence as counted from its 5'-terminus aligns with a SNP. In some embodiments, position 11 of a sequence as counted from its 5'-terminus aligns with a SNP. In some embodiments, position 12 of a sequence as counted from its 5'-terminus aligns with a SNP. In some embodiments, position 13 of a sequence as counted from its 5'-terminus aligns with a SNP. In some embodiments, position 8, 9 or 10 of a sequence as counted from its 3'-terminus aligns with a SNP. In some embodiments, position 8 of a sequence as counted from its 3'-terminus aligns with a SNP. In some embodiments, position 9 of a sequence as counted from its 3'-terminus aligns with a SNP. In some embodiments, position 10 of a sequence as counted from its 3'-terminus aligns with a SNP. In some embodiments, position 6, 7, or 8 of a core region as counted from the 5'-terminus of the core region aligns with a SNP. In some embodiments, position 6 of a core region as counted from the 5'-terminus of the core region aligns with a SNP. In some embodiments, position 7 of a core region as counted from the 5'-terminus of the core region aligns with a SNP. In some embodiments, position 8 of a core region as counted from the 5'-terminus of the core region aligns with a SNP. In some embodiments, position 3, 4, or 5 of a core region as counted from the 3'-terminus of the core region aligns with a SNP. In some embodiments, position 3 of a core region as counted from the 3'-terminus of the core region aligns with a SNP. In some embodiments, position 4 of a core region as counted from the 3'-terminus of the core region aligns with a SNP. In some embodiments, position 5 of a core region as counted from the 3'-terminus of the core region aligns with a SNP.

In some embodiments, a common base sequence comprises or is a sequence complementary to a nucleic acid sequence. In some embodiments, a common base sequence comprises or is a sequence 100% complementary to a nucleic acid sequence. In some embodiments, a common base sequence comprises or is a sequence complementary to a disease-causing nucleic acid sequence. In some embodiments, a common base sequence comprises or is a sequence 100% complementary to a disease-causing nucleic acid sequence. In some embodiments, a common base sequence comprises or is a sequence complementary to a characteristic sequence element of disease-causing nucleic acid sequence, which characteristic sequences differentiate a disease-causing nucleic acid sequence from a non-diseasing-causing nucleic acid sequence. In some embodiments, a common base sequence comprises or is a sequence 100% complementary to a characteristic sequence element of disease-causing nucleic acid sequence, which characteristic sequences differentiate a disease-causing nucleic acid sequence from a non-diseasing-causing nucleic acid sequence. In some embodiments, a common base sequence comprises or is a sequence complementary to a disease-associated nucleic acid sequence. In some embodiments, a common base sequence comprises or is a sequence 100% complementary to a disease-associated nucleic acid sequence. In some embodiments, a common base sequence comprises or is a sequence complementary to a characteristic sequence element of disease-associated nucleic acid sequence, which characteristic sequences differentiate a disease-associated nucleic acid sequence from a non-diseasing-associated nucleic acid sequence. In some embodiments, a common base sequence comprises or is a sequence 100% complementary to a characteristic sequence element of disease-associated nucleic acid sequence, which characteristic sequences differentiate a disease-associated nucleic acid sequence from a non-diseasing-associated nucleic acid sequence.

In some embodiments, a common base sequence comprises or is a sequence complementary to a gene. In some embodiments, a common base sequence comprises or is a sequence 100% complementary to a gene. In some embodiments, a common base sequence comprises or is a sequence complementary to a characteristic sequence element of a gene, which characteristic sequences differentiate the gene from a similar sequence sharing homology with the gene. In some embodiments, a common base sequence comprises or is a sequence 100% complementary to a characteristic sequence element of a gene, which characteristic sequences differentiate the gene from a similar sequence sharing homology with the gene. In some embodiments, a common base sequence comprises or is a sequence complementary to characteristic sequence element of a target gene, which characteristic sequences comprises a mutation that is not found in other copies of the gene, e.g., the wild-type copy of the gene, another mutant copy the gene, etc. In some embodiments, a common base sequence comprises or is a sequence 100% complementary to characteristic sequence element of a target gene, which characteristic sequences comprises a mutation that is not found in other copies of the gene, e.g., the wild-type copy of the gene, another mutant copy the gene, etc.

In some embodiments, a common base sequence comprises or is a sequence complementary to a sequence comprising a SNP. In some embodiments, a common base sequence comprises or is a sequence complementary to a sequence comprising a SNP, and the common base sequence is 100% complementary to the SNP that is associated with a disease. For example, in some embodiments, a common base sequence is 100% complementary to a SNP associated with a Huntington's disease-associated (or -causing) allele. In some embodiments, a common base sequence is that of WV-1087. In some embodiments, a common base sequence is that of WV-1090. In some embodiments, a common base sequence is that of WV-1091. In some embodiments, a common base sequence is that of WV-937. In some embodiments, a common base sequence is that of WV-2378. In some embodiments, a common base sequence is that of WV-2380. In some embodiments, a common base sequence is that of WV-1090. In some embodiments, a common base sequence is that of WV-1091. In some embodiments, a common base sequence is that of WV-1510. In some embodiments, a common base sequence is that of WV-937. In some embodiments, a common base sequence is that of WV-2611. In some embodiments, a common base sequence is that of WV-1497. In some embodiments, a common base sequence is that of WV-2602. In some embodiments, a common base sequence is that of WV-2618. In some embodiments, a common base sequence is that of WV-2601. In some embodiments, a common base sequence is that of WV-1092, which is 100% complementary to the disease-associated allele in many Huntington's disease patients at rs362307. In some embodiments, a SNP is rs362307. In some embodiments, a SNP is rs7685686. In some embodiments, a SNP is rs362268. In some embodiments, a SNP is rs362306. In some embodiments, a SNP is rs362331. In some embodiments, a SNP is rs2530595. In some embodiments, other example SNP site may be any of the Huntingtin site disclosed in the present disclosure.

In some embodiments, a common base sequence comprises a sequence found in GCCTCAGTCTGCTTCGCACC (SEQ ID NO: 19). In some embodiments, a common base sequence comprises a sequence found in GCCTCAGTCTGCTTCGCACC (SEQ ID NO: 19), wherein the sequence found in GCCTCAGTCTGCTTCGCACC (SEQ ID NO: 19) comprises at least 15 nucleotides. In some embodiments, a common base sequence is GCCTCAGTCTGCTTCGCACC (SEQ ID NO: 19).

In some embodiments, a common base sequence comprises a sequence found in GAGCAGCTGCAACCTGGCAA (SEQ ID NO: 20). In some embodiments, a common base sequence comprises a sequence found in GAGCAGCTGCAACCTGGCAA (SEQ ID NO: 20), wherein the sequence found in GAGCAGCTGCAACCTGGCAA (SEQ ID NO: 20) comprises at least 15 nucleotides. In some embodiments, a common base sequence is GAGCAGCTG-CAACCTGGCAA (SEQ ID NO: 20). In some embodiments, a common base sequence is GGGCA-CAAGGGCACAGACTT (SEQ ID NO: 21). In some embodiments, a common base sequence is GAGCAGCTG-CAACCTGGCAA (SEQ ID NO: 20). In some embodiments, a common base sequence is GCACAAGGGCACA-GACTTCC (SEQ ID NO: 22). In some embodiments, a common base sequence is CACAAGGGCACAGACT-TCCA (SEQ ID NO: 23). In some embodiments, a common base sequence is ACAAGGGCACAGACTTCCAA (SEQ ID NO: 24). In some embodiments, a common base sequence is CAAGGGCACAGACTTCCAAA (SEQ ID NO: 25). In some embodiments, a common base sequence comprises a sequence found in GAGCAGCTGCAACCTG-GCAA (SEQ ID NO: 20). In some embodiments, a common base sequence comprises a sequence found in GAGCAGCT-GCAACCTGGCAA (SEQ ID NO: 20), wherein the sequence found in GAGCAGCTGCAACCTGGCAA (SEQ ID NO: 20) comprises at least 15 nucleotides. In some embodiments, a common base sequence is GAGCAGCTG-CAACCTGGCAA (SEQ ID NO: 20). In some embodiments, a common base sequence is GAGCAGCTGCAAC-CTGGCAA (SEQ ID NO: 20). In some embodiments, a common base sequence is AGCAGCTGCAACCTG-GCAAC (SEQ ID NO: 26). In some embodiments, a common base sequence is GCAGCTGCAACCTGGCAACA (SEQ ID NO: 27). In some embodiments, a common base sequence is CAGCTGCAACCTGGCAACAA (SEQ ID NO: 28). In some embodiments, a common base sequence is AGCTGCAACCTGGCAACAAC (SEQ ID NO: 29). In some embodiments, a common base sequence is GCTG-CAACCTGGCAACAACC (SEQ ID NO: 30). In some embodiments, a common base sequence comprises a sequence found in GGGCCAACAGCCAGCCTGCA (SEQ ID NO: 31). In some embodiments, a common base sequence comprises a sequence found in GGGCCAACA-GCCAGCCTGCA (SEQ ID NO: 31), wherein the sequence found in GGGCCAACAGCCAGCCTGCA (SEQ ID NO: 31) comprises at least 15 nucleotides. In some embodiments, a common base sequence is GGGCCAACAGCCAGCCT-GCA (SEQ ID NO: 31). In some embodiments, a common base sequence is GGGCCAACAGCCAGCCTGCA (SEQ ID NO: 31). In some embodiments, a common base sequence is GGCCAACAGCCAGCCTGCAG (SEQ ID NO: 32). In some embodiments, a common base sequence is GCCAACAGCCAGCCTGCAGG (SEQ ID NO: 33). In some embodiments, a common base sequence is CCAACA-GCCAGCCTGCAGGA (SEQ ID NO: 34). In some embodiments, a common base sequence is CAACAGCCAGCCT-GCAGGAG (SEQ ID NO: 35). In some embodiments, a common base sequence is AACAGCCAGCCTGCAG-GAGG (SEQ ID NO: 36). In some embodiments, a common base sequence comprises a sequence found in ATTAATAAATTGTCATCACC (SEQ ID NO: 37). In some embodiments, a common base sequence comprises a sequence found in ATTAATAAATTGTCATCACC (SEQ ID NO: 37), wherein the sequence found in ATTAATAAATT-GTCATCACC (SEQ ID NO: 37) comprises at least 15 nucleotides. In some embodiments, a common base sequence is ATTAATAAATTGTCATCACC (SEQ ID NO: 37). In some embodiments, a common base sequence is ATTAATAAATTGTCATCACC (SEQ ID NO: 37).

In some embodiments, the present disclosure provides stereochemical design parameters for oligonucleotides. That is, among other things, the present disclosure demonstrates impact of stereochemical structure at different positions along an oligonucleotide chain, for example on stability and/or activity of the oligonucleotide, including on interaction of the oligonucleotide with a cognate ligand and/or with a processing enzyme. The present disclosure specifically provides oligonucleotides whose structure incorporates or reflects the design parameters. Such oligonucleotides are new chemical entities relative to stereorandom preparations having the same base sequence and length.

In some embodiments, the present disclosure provides stereochemical design parameters for antisense oligonucleotides. In some embodiments, the present disclosure specifically provides design parameter for oligonucleotides that may be bound and/or cleaved by RNaseH. In some embodiments, the present disclosure provides stereochemical design parameters for siRNA oligonucleotides. In some embodiments, the present disclosure specifically provides design parameters for oligonucleotides that may be bound and/or cleaved by, e.g., DICER, Argonaute proteins (e.g., Argonaute-1 and Argonaute-2), etc.

In some embodiments, a single oligonucleotide of a provided composition comprises a region in which at least one of the first, second, third, fifth, seventh, eighth, ninth, eighteenth, nineteenth and twentieth internucleotidic linkages is chiral. In some embodiments, at least two of the first, second, third, fifth, seventh, eighth, ninth, eighteenth, nineteenth and twentieth internucleotidic linkages are chiral. In some embodiments, at least three of the first, second, third, fifth, seventh, eighth, ninth, eighteenth, nineteenth and twentieth internucleotidic linkages are chiral. In some embodiments, at least four of the first, second, third, fifth, seventh, eighth, ninth, eighteenth, nineteenth and twentieth internucleotidic linkages are chiral. In some embodiments, at least five of the first, second, third, fifth, seventh, eighth, ninth, eighteenth, nineteenth and twentieth internucleotidic linkages are chiral. In some embodiments, at least six of the first, second, third, fifth, seventh, eighth, ninth, eighteenth, nineteenth and twentieth internucleotidic linkages are chiral. In some embodiments, at least seven of the first, second, third, fifth, seventh, eighth, ninth, eighteenth, nineteenth and twentieth internucleotidic linkages are chiral. In some embodiments, at least eight of the first, second, third, fifth, seventh, eighth, ninth, eighteenth, nineteenth and twentieth internucleotidic linkages are chiral. In some embodiments, at least nine of the first, second, third, fifth, seventh, eighth, ninth, eighteenth, nineteenth and twentieth internucleotidic linkages are chiral. In some embodiments, one of the first, second, third, fifth, seventh, eighth, ninth, eighteenth, nineteenth and twentieth internucleotidic linkages is chiral. In some embodiments, two of the first, second, third, fifth, seventh, eighth, ninth, eighteenth, nineteenth and twentieth internucleotidic linkages are chiral. In some embodiments, three of the first, second, third, fifth, seventh, eighth, ninth, eighteenth, nineteenth and twentieth internucleotidic linkages are chiral. In some embodiments, four of the first, second, third, fifth, seventh, eighth, ninth, eighteenth, nineteenth and twentieth internucleotidic linkages are chiral. In some embodiments, five of the first, second, third, fifth, seventh, eighth, ninth, eighteenth, nineteenth and twentieth internucleotidic linkages are chiral. In some embodiments, six of the first, second, third, fifth, seventh, eighth, ninth, eighteenth, nineteenth and twentieth internucleotidic linkages are chiral. In some embodiments, seven of the first, second, third, fifth, seventh, eighth, ninth, eighteenth, nineteenth and twentieth internucleotidic linkages are chiral. In some embodiments, eight of the first, second, third, fifth, seventh, eighth, ninth, eighteenth, nineteenth and twentieth internucleotidic linkages are chiral. In some embodiments, nine of the first, second, third, fifth, seventh, eighth, ninth, eighteenth, nineteenth and twentieth internucleotidic linkages are chiral. In some embodiments, ten of the first, second, third, fifth, seventh, eighth, ninth, eighteenth, nineteenth and twentieth internucleotidic linkages are chiral.

In some embodiments, a single oligonucleotide of a provided composition comprises a region in which at least one of the first, second, third, fifth, seventh, eighteenth, nineteenth and twentieth internucleotidic linkages is chiral. In some embodiments, at least two of the first, second, third, fifth, seventh, eighteenth, nineteenth and twentieth internucleotidic linkages are chiral. In some embodiments, at least three of the first, second, third, fifth, seventh, eighteenth, nineteenth and twentieth internucleotidic linkages are chiral. In some embodiments, at least four of the first, second, third, fifth, seventh, eighteenth, nineteenth and twentieth internucleotidic linkages are chiral. In some embodiments, at least five of the first, second, third, fifth, seventh, eighteenth, nineteenth and twentieth internucleotidic linkages are chiral. In some embodiments, at least six of the first, second, third, fifth, seventh, eighteenth, nineteenth and twentieth internucleotidic linkages are chiral. In some embodiments, at least seven of the first, second, third, fifth, seventh, eighteenth, nineteenth and twentieth internucleotidic linkages are chiral. In some embodiments, one of the first, second, third, fifth, seventh, eighteenth, nineteenth and twentieth internucleotidic linkages is chiral. In some embodiments, two of the first, second, third, fifth, seventh, eighteenth, nineteenth and twentieth internucleotidic linkages are chiral. In some embodiments, three of the first, second, third, fifth, seventh, eighteenth, nineteenth and twentieth internucleotidic linkages are chiral. In some embodiments, four of the first, second, third, fifth, seventh, eighteenth, nineteenth and twentieth internucleotidic linkages are chiral. In some embodiments, five of the first, second, third, fifth, seventh, eighteenth, nineteenth and twentieth internucleotidic linkages are chiral. In some embodiments, six of the first, second, third, fifth, seventh, eighteenth, nineteenth and twentieth internucleotidic linkages are chiral. In some embodiments, seven of the first, second, third, fifth, seventh, eighteenth, nineteenth and twentieth internucleotidic linkages are chiral. In some embodiments, eight of the first, second, third, fifth, seventh, eighteenth, nineteenth and twentieth internucleotidic linkages are chiral.

In some embodiments, a single oligonucleotide of a provided composition comprises a region in which at least one of the first, second, third, fifth, seventh, eighth, ninth, eighteenth, nineteenth and twentieth internucleotidic linkages is chiral, and at least one internucleotidic linkage is achiral. In some embodiments, a single oligonucleotide of a provided composition comprises a region in which at least one of the first, second, third, fifth, seventh, eighteenth, nineteenth and twentieth internucleotidic linkages is chiral, and at least one internucleotidic linkage is achiral. In some embodiments, at least two internucleotidic linkages are achiral. In some embodiments, at least three internucleotidic linkages are achiral. In some embodiments, at least four internucleotidic linkages are achiral. In some embodiments, at least five internucleotidic linkages are achiral. In some embodiments, at least six internucleotidic linkages are achiral. In some embodiments, at least seven internucleotidic linkages are achiral. In some embodiments, at least eight internucleotidic linkages are achiral. In some embodiments, at least nine internucleotidic linkages are achiral. In some embodiments, at least 10 internucleotidic linkages are achiral. In some embodiments, at least 11 internucleotidic linkages are achiral. In some embodiments, at least 12 internucleotidic linkages are achiral. In some embodiments, at least 13 internucleotidic linkages are achiral. In some embodiments, at least 14 internucleotidic linkages are achiral. In some embodiments, at least 15 internucleotidic linkages are achiral. In some embodiments, at least 16 internucleotidic linkages are achiral. In some embodiments, at least 17 internucleotidic linkages are achiral. In some embodiments, at least 18 internucleotidic linkages are achiral. In some embodiments, at least 19 internucleotidic linkages are achiral. In some embodiments, at least 20 internucleotidic linkages are achiral. In some embodiments, one internucleotidic linkage is achiral. In some embodiments, two internucleotidic linkages are achiral. In some embodiments, three internucleotidic linkages are achiral. In some embodiments, four internucleotidic linkages are achiral. In some embodiments, five internucleotidic linkages are achiral. In some embodiments, six internucleotidic linkages are achiral. In some embodiments, seven internucleotidic linkages are achiral. In some embodiments, eight internucleotidic linkages are achiral. In some embodiments, nine internucleotidic linkages are achiral. In some embodiments, 10 internucleotidic linkages are achiral. In some embodiments, 11 internucleotidic linkages are achiral. In some embodiments, 12 internucleotidic linkages are achiral. In some embodiments, 13 internucleotidic linkages are achiral. In some embodiments, 14 internucleotidic linkages are achiral. In some embodiments, 15 internucleotidic linkages are achiral. In some embodiments, 16 internucleotidic linkages are achiral. In some embodiments, 17 internucleotidic linkages are achiral. In some embodiments, 18 internucleotidic linkages are achiral. In some embodiments, 19 internucleotidic linkages are achiral. In some embodiments, 20 internucleotidic linkages are achiral. In some embodiments, a single oligonucleotide of a provided composition comprises a region in which all internucleotidic linkages, except the at least one of the first, second, third, fifth, seventh, eighth, ninth, eighteenth, nineteenth and twentieth internucleotidic linkages which is chiral, are achiral.

In some embodiments, a single oligonucleotide of a provided composition comprises a region in which at least one of the first, second, third, fifth, seventh, eighth, ninth, eighteenth, nineteenth and twentieth internucleotidic linkages is chiral, and at least one internucleotidic linkage is phosphate. In some embodiments, a single oligonucleotide of a provided composition comprises a region in which at least one of the first, second, third, fifth, seventh, eighteenth, nineteenth and twentieth internucleotidic linkages is chiral, and at least one internucleotidic linkage is phosphate. In some embodiments, at least two internucleotidic linkages are phosphate. In some embodiments, at least three internucleotidic linkages are phosphate. In some embodiments, at least four internucleotidic linkages are phosphate. In some embodiments, at least five internucleotidic linkages are phosphate. In some embodiments, at least six internucleotidic linkages are phosphate. In some embodiments, at least seven internucleotidic linkages are phosphate. In some embodiments, at least eight internucleotidic linkages are phosphate. In some embodiments, at least nine internucleotidic linkages are phosphate. In some embodiments, at least 10 internucleotidic linkages are phosphate. In some embodiments, at least 11 internucleotidic linkages are phosphate. In some embodiments, at least 12 internucleotidic linkages are phosphate. In some embodiments, at least 13 internucleotidic linkages are phosphate. In some embodiments, at least 14 internucleotidic linkages are phosphate. In some embodiments, at least 15 internucleotidic linkages are phosphate. In some embodiments, at least 16 internucleotidic linkages are phosphate. In some embodiments, at least 17 internucleotidic linkages are phosphate. In some embodiments, at least 18 internucleotidic linkages are phosphate. In some embodiments, at least 19 internucleotidic linkages are phosphate. In some embodiments, at least 20 internucleotidic linkages are phosphate. In some embodiments, one internucleotidic linkage is phosphate. In some embodiments, two internucleotidic linkages are phosphate. In some embodiments, three internucleotidic linkages are phosphate. In some embodiments, four internucleotidic linkages are phosphate. In some embodiments, five internucleotidic linkages are phosphate. In some embodiments, six internucleotidic linkages are phosphate. In some embodiments, seven internucleotidic linkages are phosphate. In some embodiments, eight internucleotidic linkages are phosphate. In some embodiments, nine internucleotidic linkages are phosphate. In some embodiments, 10 internucleotidic linkages are phosphate. In some embodiments, 11 internucleotidic linkages are phosphate. In some embodiments, 12 internucleotidic linkages are phosphate. In some embodiments, 13 internucleotidic linkages are phosphate. In some embodiments, 14 internucleotidic linkages are phosphate. In some embodiments, 15 internucleotidic linkages are phosphate. In some embodiments, 16 internucleotidic linkages are phosphate. In some embodiments, 17 internucleotidic linkages are phosphate. In some embodiments, 18 internucleotidic linkages are phosphate. In some embodiments, 19 internucleotidic linkages are phosphate. In some embodiments, 20 internucleotidic linkages are phosphate. In some embodiments, a single oligonucleotide of a provided composition comprises a region in which all internucleotidic linkages, except the at least one of the first, second, third, fifth, seventh, eighth, ninth, eighteenth, nineteenth and twentieth internucleotidic linkages which is chiral, are phosphate.

In some embodiments, a single oligonucleotide of a provided composition comprises a region in which at least one of the first, second, third, fifth, seventh, eighth, ninth, eighteenth, nineteenth and twentieth internucleotidic linkages are chiral, and at least 10% of all the internucleotidic linkages in the region is achiral. In some embodiments, a single oligonucleotide of a provided composition comprises a region in which at least one of the first, second, third, fifth, seventh, eighteenth, nineteenth and twentieth internucleotidic linkages is chiral, and at least 10% of all the internucleotidic linkages in the region are achiral. In some embodiments, at least 20% of all the internucleotidic linkages in the region are achiral. In some embodiments, at least 30% of all the internucleotidic linkages in the region are achiral. In some embodiments, at least 40% of all the internucleotidic linkages in the region are achiral. In some embodiments, at least 50% of all the internucleotidic linkages in the region are achiral. In some embodiments, at least 60% of all the internucleotidic linkages in the region are achiral. In some embodiments, at least 70% of all the internucleotidic linkages in the region are achiral. In some embodiments, at least 80% of all the internucleotidic linkages in the region are achiral. In some embodiments, at least 90% of all the internucleotidic linkages in the region are achiral. In some embodiments, at least 50% of all the internucleotidic linkages in the region are achiral. In some embodiments, an achiral internucleotidic linkage is a phosphate linkage. In some embodiments, each achiral internucleotidic linkage in a phosphate linkage.

In some embodiments, the first internucleotidic linkage of the region is an Sp modified internucleotidic linkage. In some embodiments, the first internucleotidic linkage of the region is an Rp modified internucleotidic linkage. In some embodiments, the second internucleotidic linkage of the region is an Sp modified internucleotidic linkage. In some embodiments, the second internucleotidic linkage of the region is an Rp modified internucleotidic linkage. In some embodiments, the third internucleotidic linkage of the region is an Sp modified internucleotidic linkage. In some embodiments, the third internucleotidic linkage of the region is an Rp modified internucleotidic linkage. In some embodiments, the fifth internucleotidic linkage of the region is an Sp modified internucleotidic linkage. In some embodiments, the fifth internucleotidic linkage of the region is an Rp modified internucleotidic linkage. In some embodiments, the seventh internucleotidic linkage of the region is an Sp modified internucleotidic linkage. In some embodiments, the seventh internucleotidic linkage of the region is an Rp modified internucleotidic linkage. In some embodiments, the eighth internucleotidic linkage of the region is an Sp modified internucleotidic linkage. In some embodiments, the eighth internucleotidic linkage of the region is an Rp modified internucleotidic linkage. In some embodiments, the ninth internucleotidic linkage of the region is an Sp modified internucleotidic linkage. In some embodiments, the ninth internucleotidic linkage of the region is an Rp modified internucleotidic linkage. In some embodiments, the eighteenth internucleotidic linkage of the region is an Sp modified internucleotidic linkage. In some embodiments, the eighteenth internucleotidic linkage of the region is an Rp modified internucleotidic linkage. In some embodiments, the nineteenth internucleotidic linkage of the region is an Sp modified internucleotidic linkage. In some embodiments, the nineteenth internucleotidic linkage of the region is an Rp modified internucleotidic linkage. In some embodiments, the twentieth internucleotidic linkage of the region is an Sp modified internucleotidic linkage. In some embodiments, the twentieth internucleotidic linkage of the region is an Rp modified internucleotidic linkage.

In some embodiments, the region has a length of at least 21 bases. In some embodiments, the region has a length of 21 bases. In some embodiments, a single oligonucleotide in a provided composition has a length of at least 21 bases. In some embodiments, a single oligonucleotide in a provided composition has a length of 21 bases.

In some embodiments, a chiral internucleotidic linkage has the structure of formula I. In some embodiments, a chiral internucleotidic linkage is phosphorothioate. In some embodiments, each chiral internucleotidic linkage in a single oligonucleotide of a provided composition independently has the structure of formula I. In some embodiments, each chiral internucleotidic linkage in a single oligonucleotide of a provided composition is a phosphorothioate.

In some embodiments, oligonucleotides of the present disclosure comprise one or more modified sugar moieties. In some embodiments, oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198 and WO2014/012081, the sugar and base modifications of each of which are incorporated herein by reference.

In some embodiments, a sugar modification is a 2'-modification. Commonly used 2'-modifications include but are not limited to 2'-OR', wherein $R^1$ is not hydrogen. In some embodiments, a modification is 2'-OR, wherein R is optionally substituted aliphatic. In some embodiments, a modification is 2'-OMe. In some embodiments, a modification is 2'-MOE. In some embodiments, the present disclosure demonstrates that inclusion and/or location of particular chirally pure internucleotidic linkages can provide stability improvements comparable to or better than those achieved through use of modified backbone linkages, bases, and/or sugars. In some embodiments, a provided single oligonucleotide of a provided composition has no modifications on the sugars. In some embodiments, a provided single oligonucleotide of a provided composition has no modifications on 2'-positions of the sugars (i.e., the two groups at the 2'-position are either —H/—H or —H/—OH). In some embodiments, a provided single oligonucleotide of a provided composition does not have any 2'-MOE modifications.

In some embodiments, a 2'-modification is —O-L- or -L-which connects the 2'-carbon of a sugar moiety to another carbon of a sugar moiety. In some embodiments, a 2'-modification is -O-L- or -L-which connects the 2'-carbon of a sugar moiety to the 4'-carbon of a sugar moiety. In some embodiments, a 2'-modification is S-cEt. In some embodiments, a modified sugar moiety is an LNA moiety.

In some embodiments, a 2'-modification is —F. In some embodiments, a 2'-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a single oligonucleotide in a provided composition is a better substrate for Argonaute proteins (e.g., hAgo-1 and hAgo-2) compared to stereorandom oligonucleotide compositions. Selection and/or location of chirally pure linkages as described in the present closure are useful design parameters for oligonucleotides that interacting with such proteins, such as siRNA.

In some embodiments, a single oligonucleotide in a provided composition has at least about 25% of its internucleotidic linkages in Sp configuration. In some embodiments, a single oligonucleotide in a provided composition has at least about 30% of its internucleotidic linkages in Sp configuration. In some embodiments, a single oligonucleotide in a provided composition has at least about 35% of its internucleotidic linkages in Sp configuration. In some embodiments, a single oligonucleotide in a provided composition has at least about 40% of its internucleotidic linkages in Sp configuration. In some embodiments, a single oligonucleotide in a provided composition has at least about 45% of its internucleotidic linkages in Sp configuration. In some embodiments, a single oligonucleotide in a provided composition has at least about 50% of its internucleotidic linkages in Sp configuration. In some embodiments, a single oligonucleotide in a provided composition has at least about 55% of its internucleotidic linkages in Sp configuration. In some embodiments, a single oligonucleotide in a provided composition has at least about 60% of its internucleotidic linkages in Sp configuration. In some embodiments, a single oligonucleotide in a provided composition has at least about 65% of its internucleotidic linkages in Sp configuration. In some embodiments, a single oligonucleotide in a provided composition has at least about 70% of its internucleotidic linkages in Sp configuration. In some embodiments, a single oligonucleotide in a provided composition has at least about 75% of its internucleotidic linkages in Sp configuration. In some embodiments, a single oligonucleotide in a provided composition has at least about 80% of its internucleotidic linkages in Sp configuration. In some embodiments, a single oligonucleotide in a provided composition has at least about 85% of its internucleotidic linkages in Sp configuration. In some embodiments, a single oligonucleotide in a provided composition has at least about 90% of its internucleotidic linkages in Sp configuration.

In some embodiments, oligonucleotides in a provided composition is not an oligonucleotide selected from: $T_kT_k{}^mC_kAGT{}^mCATGA{}^mCT_kT{}^mC_k{}^mC_k$ (SEQ ID NO: 38), wherein each nucleoside followed by a subscript 'k' indicates a (S)-cEt modification, R is Rp phosphorothioate linkage, S is Sp phosphorothioate linkage, each $^mC$ is a 5-methylcytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSRRRRSR, RRRRRRRRRR and SSSSSSSSSS.

In some embodiments, a single oligonucleotide in a provided composition is not an oligonucleotide selected from: $T_kT_k{}^mC_kAGT{}^mCATGA{}^mCTT_k{}^mC_k{}^mC_k$ (SEQ ID NO: 39), wherein each nucleoside followed by a subscript 'k' indicates a (S)-cEt modification, R is Rp phosphorothioate linkage, S is Sp phosphorothioate linkage, each $^mC$ is a 5-methylcytosine modified nucleoside and all core internucleoside linkages are phosphorothioates (PS) with stereochemistry patterns selected from: RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSRRRRSR, RRRRRRRRRR and SSSSSSSSSS.

Chirally Controlled Oligonucleotides and Chirally Controlled Oligonucleotide Compositions The present disclosure provides chirally controlled oligonucleotides, and chirally controlled oligonucleotide compositions which are of high crude purity and of high diastereomeric purity. In some embodiments, the present disclosure provides chirally controlled oligonucleotides, and chirally controlled oligonucleotide compositions which are of high crude purity. In some embodiments, the present disclosure provides chirally controlled oligonucleotides, and chirally controlled oligonucleotide compositions which are of high diastereomeric purity.

In some embodiments, a chirally controlled oligonucleotide composition is a substantially pure preparation of an oligonucleotide type in that oligonucleotides in the composition that are not of the oligonucleotide type are impurities form the preparation process of said oligonucleotide type, in some case, after certain purification procedures.

In some embodiments, the present disclosure provides oligonucleotides comprising one or more diastereomerically pure internucleotidic linkages with respect to the chiral linkage phosphorus. In some embodiments, the present disclosure provides oligonucleotides comprising one or more diastereomerically pure internucleotidic linkages having the structure of formula I. In some embodiments, the present disclosure provides oligonucleotides comprising one or more diastereomerically pure internucleotidic linkages with respect to the chiral linkage phosphorus, and one or more phosphate diester linkages. In some embodiments, the present disclosure provides oligonucleotides comprising one or more diastereomerically pure internucleotidic linkages having the structure of formula I, and one or more phosphate diester linkages. In some embodiments, the present disclosure provides oligonucleotides comprising one or more diastereomerically pure internucleotidic linkages having the structure of formula I-c, and one or more phosphate diester linkages. In some embodiments, such oligonucleotides are prepared by using stereoselective oligonucleotide synthesis, as described in this application, to form pre-designed diastereomerically pure internucleotidic linkages with respect to the chiral linkage phosphorus. For instance, in one example oligonucleotide of (Rp/Sp, Rp/Sp, Rp/Sp, Rp, Rp, Sp, Sp, Sp, Sp, Sp Sp, Sp, Sp, Sp, Rp, Rp, Rp, Rp, Rp)-d [GsCsCsTsCsAsGsTsCsTsGsCsTsTsCsGs1Cs1As1CsC] (SEQ ID NO: 40), the first three internucleotidic linkages are constructed using traditional oligonucleotide synthesis method, and the diastereomerically pure internucleotidic linkages are constructed with stereochemical control as described in this application. Example internucleotidic linkages, including those having structures of formula I, are further described below.

In some embodiments, the present disclosure provides a chirally controlled oligonucleotide, wherein at least two of the individual internucleotidic linkages within the oligonucleotide have different stereochemistry and/or different P-modifications relative to one another. In certain embodiments, the present disclosure provides a chirally controlled oligonucleotide, wherein at least two individual internucleotidic linkages within the oligonucleotide have different P-modifications relative to one another. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphorothioate triester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate triester internucleotidic linkage.

In certain embodiments, a modified internucleotidic linkages has the structure of formula I:

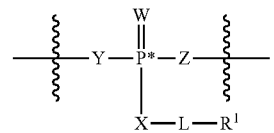

wherein each variable is as defined and described below. In some embodiments, a linkage of formula I is chiral. In some embodiments, the present disclosure provides a chirally controlled oligonucleotide comprising one or more modified internucleotidic linkages of formula I. In some embodiments, the present disclosure provides a chirally controlled oligonucleotide comprising one or more modified internucleotidic linkages of formula I, and wherein individual internucleotidic linkages of formula I within the oligonucleotide have different P-modifications relative to one another. In some embodiments, the present disclosure provides a chirally controlled oligonucleotide comprising one or more modified internucleotidic linkages of formula I, and wherein individual internucleotidic linkages of formula I within the oligonucleotide have different —X-L-$R^1$ relative to one another. In some embodiments, the present disclosure provides a chirally controlled oligonucleotide comprising one or more modified internucleotidic linkages of formula I, and wherein individual internucleotidic linkages of formula I within the oligonucleotide have different X relative to one another. In some embodiments, the present disclosure provides a chirally controlled oligonucleotide comprising one or more modified internucleotidic linkages of formula I, and wherein individual internucleotidic linkages of formula I within the oligonucleotide have different -L-$R^1$ relative to one another. In some embodiments, a chirally controlled oligonucleotide is an oligonucleotide in a provided composition that is of the particular oligonucleotide type. In some embodiments, a chirally controlled oligonucleotide is an oligonucleotide in a provided composition that has the common base sequence and length, the common pattern of backbone linkages, and the common pattern of backbone chiral centers.

In some embodiments, the present disclosure provides a chirally controlled oligonucleotide, wherein at least two of the individual internucleotidic linkages within the oligonucleotide have different stereochemistry and/or different P-modifications relative to one another. In some embodiments, the present disclosure provides a chirally controlled oligonucleotide, wherein at least two of the individual internucleotidic linkages within the oligonucleotide have different stereochemistry relative to one another, and wherein at least a portion of the structure of the chirally controlled oligonucleotide is characterized by a repeating pattern of alternating stereochemisty.

In some embodiments, the present disclosure provides a chirally controlled oligonucleotide, wherein at least two of the individual internucleotidic linkages within the oligonucleotide have different P-modifications relative to one another, in that they have different X atoms in their —$XLR^1$ moieties, and/or in that they have different L groups in their —$XLR^1$ moieties, and/or that they have different $R^1$ atoms in their —$XLR^1$ moieties.

In some embodiments, the present disclosure provides a chirally controlled oligonucleotide, wherein at least two of the individual internucleotidic linkages within the oligonucleotide have different stereochemistry and/or different P-modifications relative to one another and the oligonucleotide has a structure represented by the following formula:

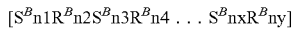

wherein:
each $R^B$ independently represents a block of nucleotide units having the R configuration at the linkage phosphorus;
each $S^B$ independently represents a block of nucleotide units having the S configuration at the linkage phosphorus;
each of n1-ny is zero or an integer, with the requirement that at least one odd n and at least one even n must be non-zero so that the oligonucleotide includes at least two individual internucleotidic linkages with different stereochemistry relative to one another; and
wherein the sum of n1-ny is between 2 and 200, and in some embodiments is between a lower limit selected from the group consisting of 2, 3, 4, 5, 6, 7, 8, 9, 10, 11, 12, 13, 14, 15, 16, 17, 18, 19, 20, 21, 22, 23, 24, 25 or more and an upper limit selected from the group consisting of 5, 10, 15, 20, 25, 30, 35, 40, 45, 50, 55, 60, 65, 70, 75, 80, 85, 90, 95, 100, 110, 120, 130, 140, 150, 160, 170, 180, 190, and 200, the upper limit being larger than the lower limit.

In some such embodiments, each n has the same value; in some embodiments, each even n has the same value as each other even n; in some embodiments, each odd n has the same value each other odd n; in some embodiments, at least two even ns have different values from one another; in some embodiments, at least two odd ns have different values from one another.

In some embodiments, at least two adjacent ns are equal to one another, so that a provided oligonucleotide includes adjacent blocks of S stereochemistry linkages and R stereochemistry linkages of equal lengths. In some embodiments, provided oligonucleotides include repeating blocks of S and R stereochemistry linkages of equal lengths. In some embodiments, provided oligonucleotides include repeating blocks of S and R stereochemistry linkages, where at least two such blocks are of different lengths from one another; in some such embodiments each S stereochemistry block is of the same length, and is of a different length from each R stereochemistry length, which may optionally be of the same length as one another.

In some embodiments, at least two skip-adjacent ns are equal to one another, so that a provided oligonucleotide includes at least two blocks of linkages of a first stereochemistry that are equal in length to one another and are separated by a block of linkages of the other stereochemistry, which separating block may be of the same length or a different length from the blocks of first stereochemistry.

In some embodiments, ns associated with linkage blocks at the ends of a provided oligonucleotide are of the same length. In some embodiments, provided oligonucleotides have terminal blocks of the same linkage stereochemistry. In some such embodiments, the terminal blocks are separated from one another by a middle block of the other linkage stereochemistry.

In some embodiments, a provided oligonucleotide of formula $[S^B n1 R^B n2 S^B n3 R^B n4 \ldots S^B nx R^B ny]$ is a stereoblockmer. In some embodiments, a provided oligonucleotide of formula $[S^B n1 R^B n2 S^B n3 R^B n4 \ldots S^B nx R^B ny]$ is a stereoskipmer. In some embodiments, a provided oligonucleotide of formula $[S^B n1 R^B n2 S^B n3 R^B n4 \ldots S^B nx R^B ny]$ is a stereoaltmer. In some embodiments, a provided oligonucleotide of formula $[S^B n1 R^B n2 S^B n3 R^B n4 \ldots S^B nx R^B ny]$ is a gapmer.

In some embodiments, a provided oligonucleotide of formula $[S^B n1 R^B n2 S^B n3 R^B n4 \ldots S^B nx R^B ny]$ is of any of the above described patterns and further comprises patterns of P-modifications. For instance, in some embodiments, a provided oligonucleotide of formula $[S^B n1 R^B n2 S^B n3 R^B n4 \ldots S^B nx R^B ny]$ and is a stereoskipmer and P-modification skipmer. In some embodiments, a provided oligonucleotide of formula $[S^B n1 R^B n2 S^B n3 R^B n4 \ldots S^B nx R^B ny]$ and is a stereoblockmer and P-modification altmer. In some embodiments, a provided oligonucleotide of formula $[S^B n1 R^B n2 S^B n3 R^B n4 \ldots S^B nx R^B ny]$ and is a stereoaltmer and P-modification blockmer.

In some embodiments, a provided oligonucleotide of formula $[S^B n1 R^B n2 S^B n3 R^B n4 \ldots S^B nx R^B ny]$ is a chirally controlled oligonucleotide comprising one or more modified internucleotidic linkages independently having the structure of formula I:

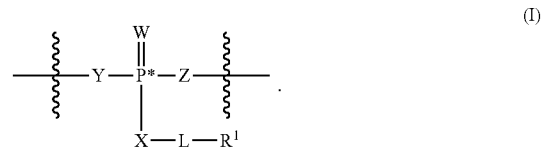

In some embodiments, a modified internucleotidic linkage in a provided oligonucleotide, for example, PL in a provided oligonucleotide of formula O—I, has the structure of formula I, wherein:

P* is an asymmetric phosphorus atom and is either Rp or Sp;

W is O, S or Se;

each of X, Y and Z is independently —O—, —S—, —N(-L-R$^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—;

$R^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O— each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

independently represents a connection to a nucleoside.

In some embodiments, the present disclosure provides oligonucleotides comprising one or more modified internucleotidic linkages independently having the structure of formula I:

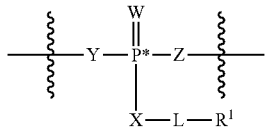

(I)

wherein:

P* is an asymmetric phosphorus atom and is either Rp or Sp;

W is O, S or Se;

each of X, Y and Z is independently —O—, —S—, —N(-L-$R^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—;

$R^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O— each R' is independently —R, —C(O)R, —CO$_2$R, or —SO$_2$R, or:

two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

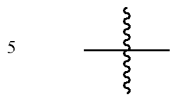

independently represents a connection to a nucleoside.

In some embodiments, a provided oligonucleotide has the structure of formula O—I, wherein each variable is independently as defined and described in the present disclosure. In some embodiments, one or more PL has the structure of formula I.

In some embodiments, $R^{5s}$ is R'. In some embodiments, $R^{5s}$ is —Y—R'. In some embodiments, $R^{5s}$ is hydrogen. In some embodiments, $R^{5s}$ is —OH.

In some embodiments, R' is R. In some embodiments, R' is hydrogen. In some embodiments, R' is —C(O)R. In some embodiments, R' is —CO$_2$R. In some embodiments, R' is —SO$_2$R.

In some embodiments, a heteroatom, for example, in a heteroaliphatic, heterocyclic, and/or a heteroaryl group is oxygen, nitrogen, or sulfur. In some embodiments, a heteroatom is oxygen, nitrogen, silicon, or sulfur. In some embodiments, a heteroatom is oxygen, nitrogen, phosphorus, or sulfur. In some embodiments, a heteroatom is oxygen, nitrogen, boron, or sulfur. In some embodiments, a heteroatom is oxygen, nitrogen, selenium, or sulfur. In some embodiments, a heteroatom is oxygen, nitrogen, silicon, boron, phosphorus, or sulfur. In some embodiments, a heteroatom is oxygen, nitrogen, silicon, boron, phosphorus, selenium or sulfur.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —CO$_2$R, or —SO$_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl; and each

independently represents a connection to a nucleoside.

In some embodiments, Ring A is an optionally substituted multivalent, monocyclic, bicyclic or polycyclic, saturated, partially unsaturated, or aryl 3-30 membered ring having, in addition to the intervening atoms, 0-10 heteroatoms. In some embodiments, Ring A is monocyclic. In some embodiments, Ring A is bicyclic. In some embodiments, Ring A is polycyclic. In some embodiments, Ring A is saturated. In some embodiments, Ring A is polysaturated. In some embodiments, Ring A is aryl. In some embodiments, a connection to $R^s$ is considered a valent no matter what $R^s$ is. In some embodiments, a connection to $R^s$ is considered a valent when $R^s$ is not hydrogen.

In some embodiments, each $R^s$ is independently $R^1$, -L-$R^1$, R', or -L-R'. In some embodiments, $R^s$ is $R^1$. In some embodiments, $R^s$ is -L-$R^1$. In some embodiments, $R^s$ is R'. In some embodiments, $R^s$ is -L-R'. In some embodiments, $R^s$ is hydrogen.

In some embodiments, t is 0-5. In some embodiments, t is 1-5. In some embodiments, t is 0. In some embodiments, t is 1. In some embodiments, t is 2. In some embodiments, t is 3. In some embodiments, t is 4. In some embodiments, t is 5.

In some embodiments, SU is L. In some embodiments, SU is a monocyclic, bicyclic or polycyclic cycloheteroaliphatic. In some embodiments, SU is a monocyclic, bicyclic or polycyclic cycloheteroaliphatic having one or more oxygen atoms. In some embodiments, SU is monocyclic. In some embodiments, SU is bicyclic. In some embodiments, SU is polycyclic. In some embodiments, SU is L and is a moiety found in an LNA sugar.

In some embodiments,

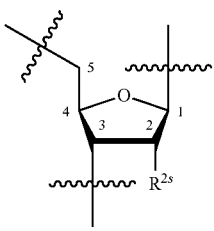

wherein SU is connected to PL through C3. In some embodiments,

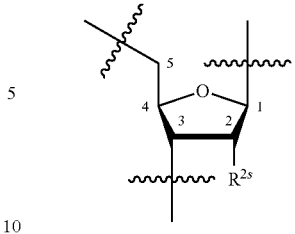

wherein SU is connected to PL through C3 and C5, and BA through C1.

In some embodiments, SU is a sugar moiety as described in the present disclosure. In some embodiments, PL is a internucleotidic linkage as described in the present disclosure.

In some embodiments, PL is

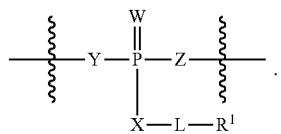

In some embodiments, PL is

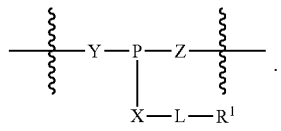

In some embodiments, PL is a natural phosphate linkage. In some embodiments, W, Y, Z is O and X is S. In some embodiments, W, Y, Z is O and —X-L-$R^1$ is —SH. In some embodiments, PL is chiral in that the phosphorus atom in PL is chiral. In some embodiments, PL has the structure of formula I. In some embodiments, PL is a modified internucleotidic linkage as described in the present disclosure. In some embodiments, a stretch of consecutive PL groups are chiral having the structure of formula I. In some embodiments, a stretch of consecutive PL groups are phosphorothioate linkages. In some embodiments, a stretch of consecutive PL groups are natural phosphate linkages. In some embodiments, a stretch comprises 2, 3, 4, 5, 6, 7, 8, 9, 10, 11, 12, 13, 14, 15 or more PL groups. In some embodiments, a stretch comprises 2 or more PL groups. In some embodiments, a stretch comprises 3 or more PL groups. In some embodiments, a stretch comprises 4 or more PL groups. In some embodiments, a stretch comprises 5 or more PL groups. In some embodiments, a stretch comprises 6 or more PL groups. In some embodiments, a stretch comprises 7 or more PL groups. In some embodiments, a stretch comprises 8 or more PL groups. In some embodiments, a stretch comprises 9 or more PL groups. In some embodiments, a stretch comprises 10 or more PL groups. In some embodiments, a stretch comprises 11 or more PL groups. In some embodiments, a stretch comprises 12 or more PL groups. In some embodiments, a stretch comprises 13 or more PL groups. In some embodiments, a stretch comprises 14 or more PL groups. In some embodiments, a stretch comprises 15 or more PL groups. In some embodiments, a provided oligonucleotide comprises one or more stretches of chiral PL groups, and one or more stretches of natural phosphate linkages. In some embodiments, a provided oligonucleotide comprises one or more stretches of chiral PL groups, and two or more stretches of natural phosphate linkages. In some embodiments, a provided oligonucleotide comprises a stretch of chiral PL groups, and two or more stretches of natural phosphate linkages. In some embodiments, a stretch of chiral PL groups comprises a linkage phosphorus stereochemistry pattern as described in the present disclosure, for example, (Sp)t(Rp)n(Sp)m. In some embodiments, n is 1 and each of t and m is independently 2 or more. In some embodiments, each of t and m is independently 2 or more, and at least one of t and m is 5 or more.

In some embodiments, a chirally controlled oligonucleotide comprises one or more modified internucleotidic phosphorus linkages. In some embodiments, a chirally controlled oligonucleotide comprises, e.g., a phosphorothioate or a phosphorothioate triester linkage. In some embodiments, a chirally controlled oligonucleotide comprises a phosphorothioate triester linkage. In some embodiments, a chirally controlled oligonucleotide comprises at least two phosphorothioate triester linkages. In some embodiments, a chirally controlled oligonucleotide comprises at least three phosphorothioate triester linkages. In some embodiments, a chirally controlled oligonucleotide comprises at least four phosphorothioate triester linkages. In some embodiments, a chirally controlled oligonucleotide comprises at least five phosphorothioate triester linkages. Examples of such modified internucleotidic phosphorus linkages are described further herein.

In some embodiments, a chirally controlled oligonucleotide comprises different internucleotidic phosphorus linkages. In some embodiments, a chirally controlled oligonucleotide comprises at least one phosphate diester internucleotidic linkage and at least one modified internucleotidic linkage. In some embodiments, a chirally controlled oligonucleotide comprises at least one phosphate diester internucleotidic linkage and at least one phosphorothioate triester linkage. In some embodiments, a chirally controlled oligonucleotide comprises at least one phosphate diester internucleotidic linkage and at least two phosphorothioate triester linkages. In some embodiments, a chirally controlled oligonucleotide comprises at least one phosphate diester internucleotidic linkage and at least three phosphorothioate triester linkages. In some embodiments, a chirally controlled oligonucleotide comprises at least one phosphate diester internucleotidic linkage and at least four phosphorothioate triester linkages. In some embodiments, a chirally controlled oligonucleotide comprises at least one phosphate diester internucleotidic linkage and at least five phosphorothioate triester linkages. Examples of such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, a chirally controlled oligonucleotide is a blockmer. In some embodiments, a chirally controlled oligonucleotide is a stereoblockmer. In some embodiments, a chirally controlled oligonucleotide is a P-modification blockmer. In some embodiments, a chirally controlled oligonucleotide is a linkage blockmer.

In some embodiments, a chirally controlled oligonucleotide is an altmer. In some embodiments, a chirally controlled oligonucleotide is a stereoaltmer. In some embodiments, a chirally controlled oligonucleotide is a P-modification altmer. In some embodiments, a chirally controlled oligonucleotide is a linkage altmer.

In some embodiments, a chirally controlled oligonucleotide is a unimer. In some embodiments, a chirally controlled oligonucleotide is a stereounimer. In some embodiments, a chirally controlled oligonucleotide is a P-modification unimer. In some embodiments, a chirally controlled oligonucleotide is a linkage unimer.

In some embodiments, a chirally controlled oligonucleotide is a gapmer.

In some embodiments, a chirally controlled oligonucleotide is a skipmer.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —CO$_2$R, or —SO$_2$R, or:
  two R' on the same nitrogen are taken together with their intervening atoms to form an optionally substituted heterocyclic or heteroaryl ring, or
  two R' on the same carbon are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl; and each

independently represents a connection to a nucleoside.

In some embodiments, P* is an asymmetric phosphorus atom and is either Rp or Sp. In some embodiments, P* is Rp. In other embodiments, P* is Sp. In some embodiments, an oligonucleotide comprises one or more internucleotidic linkages of formula I wherein each P* is independently Rp or Sp. In some embodiments, an oligonucleotide comprises one or more internucleotidic linkages of formula I wherein each P* is Rp. In some embodiments, an oligonucleotide comprises one or more internucleotidic linkages of formula I wherein each P* is Sp. In some embodiments, an oligonucleotide comprises at least one internucleotidic linkage of formula I wherein P* is Rp. In some embodiments, an oligonucleotide comprises at least one internucleotidic linkage of formula I wherein P* is Sp. In some embodiments, an oligonucleotide comprises at least one internucleotidic linkage of formula I wherein P* is Rp, and at least one internucleotidic linkage of formula I wherein P* is Sp.

In some embodiments, W is O, S, or Se. In some embodiments, W is O. In some embodiments, W is S. In some embodiments, W is Se. In some embodiments, an oligonucleotide comprises at least one internucleotidic linkage of formula I wherein W is O. In some embodiments, an oligonucleotide comprises at least one internucleotidic linkage of formula I wherein W is S. In some embodiments, an oligonucleotide comprises at least one internucleotidic linkage of formula I wherein W is Se.

In some embodiments, each R is independently hydrogen, or an optionally substituted group selected from $C_{1-30}$ aliphatic, $C_{1-30}$ heteroaliphatic having 1-10 heteroatoms, $C_{6-30}$ aryl, a 5-30 membered heteroaryl ring having 1-10 heteroatoms, and a 3-30 membered heterocyclic ring having 1-10 heteroatoms; or:
two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms.

In some embodiments, each R is independently hydrogen, or an optionally substituted group selected from $C_1$-$C_6$ aliphatic, phenyl, carbocyclyl, aryl, heteroaryl, or heterocyclyl.

In some embodiments, R is hydrogen. In some embodiments, R is an optionally substituted group selected from $C_1$-$C_6$ aliphatic, phenyl, carbocyclyl, aryl, heteroaryl, or heterocyclyl.

In some embodiments, R is an optionally substituted $C_1$-$C_6$ aliphatic. In some embodiments, R is an optionally substituted $C_1$-$C_6$ alkyl. In some embodiments, R is optionally substituted, linear or branched hexyl. In some embodiments, R is optionally substituted, linear or branched pentyl. In some embodiments, R is optionally substituted, linear or branched butyl. In some embodiments, R is optionally substituted, linear or branched propyl. In some embodiments, R is optionally substituted ethyl. In some embodiments, R is optionally substituted methyl.

In some embodiments, R is optionally substituted phenyl. In some embodiments, R is substituted phenyl. In some embodiments, R is phenyl.

In some embodiments, R is optionally substituted carbocyclyl. In some embodiments, R is optionally substituted $C_3$-$C_{10}$ carbocyclyl. In some embodiments, R is optionally substituted monocyclic carbocyclyl. In some embodiments, R is optionally substituted cycloheptyl. In some embodiments, R is optionally substituted cyclohexyl. In some embodiments, R is optionally substituted cyclopentyl. In some embodiments, R is optionally substituted cyclobutyl. In some embodiments, R is an optionally substituted cyclopropyl. In some embodiments, R is optionally substituted bicyclic carbocyclyl.

In some embodiments, R is an optionally substituted aryl. In some embodiments, R is an optionally substituted bicyclic aryl ring.

In some embodiments, R is an optionally substituted heteroaryl. In some embodiments, R is an optionally substituted 5-6 membered monocyclic heteroaryl ring having 1-3 heteroatoms independently selected from nitrogen, sulfur, or oxygen. In some embodiments, R is a substituted 5-6 membered monocyclic heteroaryl ring having 1-3 heteroatoms independently selected from nitrogen, oxygen, or sulfur. In some embodiments, R is an unsubstituted 5-6 membered monocyclic heteroaryl ring having 1-3 heteroatoms independently selected from nitrogen, sulfur, or oxygen.

In some embodiments, R is an optionally substituted 5 membered monocyclic heteroaryl ring having 1-3 heteroatoms independently selected from nitrogen, oxygen or sulfur. In some embodiments, R is an optionally substituted 6 membered monocyclic heteroaryl ring having 1-3 heteroatoms independently selected from nitrogen, oxygen, or sulfur.

In some embodiments, R is an optionally substituted 5-membered monocyclic heteroaryl ring having 1 heteroatom selected from nitrogen, oxygen, or sulfur. In some embodiments, R is selected from pyrrolyl, furanyl, or thienyl.

In some embodiments, R is an optionally substituted 5-membered heteroaryl ring having 2 heteroatoms independently selected from nitrogen, oxygen, or sulfur. In certain embodiments, R is an optionally substituted 5-membered heteroaryl ring having 1 nitrogen atom, and an additional heteroatom selected from sulfur or oxygen. Example R groups include optionally substituted pyrazolyl, imidazolyl, thiazolyl, isothiazolyl, oxazolyl or isoxazolyl.

In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having 2 nitrogen atoms. In certain embodiments, R is an optionally substituted 6-membered heteroaryl ring having 1 nitrogen. Example R groups include optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having 1 heteroatom independently selected from nitrogen, oxygen, or sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, or sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, or sulfur.

In certain embodiments, R is an optionally substituted 6,6-fused heteroaryl ring having 1-4 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having 1 heteroatom independently selected from nitrogen, oxygen, or sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, or sulfur. In some embodiments, R is a quinazoline or a quinoxaline.

In some embodiments, R is an optionally substituted heterocyclyl. In some embodiments, R is an optionally substituted 3-7 membered saturated or partially unsaturated heterocyclic ring having 1-2 heteroatoms independently selected from nitrogen, oxygen, or sulfur. In some embodiments, R is a substituted 3-7 membered saturated or partially unsaturated heterocyclic ring having 1-2 heteroatoms independently selected from nitrogen, oxygen, or sulfur. In some embodiments, R is an unsubstituted 3-7 membered saturated or partially unsaturated heterocyclic ring having 1-2 heteroatoms independently selected from nitrogen, oxygen, or sulfur.

In some embodiments, R is an optionally substituted heterocyclyl. In some embodiments, R is an optionally substituted 6 membered saturated or partially unsaturated heterocyclic ring having 1-2 heteroatoms independently selected from nitrogen, oxygen, or sulfur. In some embodiments, R is an optionally substituted 6 membered partially unsaturated heterocyclic ring having 2 heteroatoms independently selected from nitrogen, oxygen, or sulfur. In some embodiments, R is an optionally substituted 6 membered partially unsaturated heterocyclic ring having 2 oxygen atom.

In certain embodiments, R is a 3-7 membered saturated or partially unsaturated heterocyclic ring having 1-2 heteroatoms independently selected from nitrogen, oxygen, or sulfur. In certain embodiments, R is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, R is an optionally substituted 5 membered saturated or partially unsaturated heterocyclic ring having 1-2 heteroatoms independently selected from nitrogen, oxygen, or sulfur.

In certain embodiments, R is an optionally substituted 5-6 membered partially unsaturated monocyclic ring having 1-2 heteroatoms independently selected from nitrogen, oxygen, or sulfur. In certain embodiments, R is an optionally substituted tetrahydropyridinyl, dihydrothiazolyl, dihydrooxazolyl, or oxazolinyl group.

In some embodiments, R is an optionally substituted 8-10 membered bicyclic saturated or partially unsaturated heterocyclic ring having 1-4 heteroatoms independently selected from nitrogen, oxygen, or sulfur. In some embodiments, R is an optionally substituted indolinyl. In some embodiments, R is an optionally substituted isoindolinyl. In some embodiments, R is an optionally substituted 1, 2, 3, 4-tetrahydroquinoline. In some embodiments, R is an optionally substituted 1, 2, 3, 4-tetrahydroisoquinoline.

In some embodiments, each R' is independently —R, —C(O)R, —CO$_2$R, or —SO$_2$R, or:
  two R' on the same nitrogen are taken together with their intervening atoms to form an optionally substituted heterocyclic or heteroaryl ring, or
  two R' on the same carbon are taken together with their intervening atoms to form an optionally substituted aryl, carbocyclic, heterocyclic, or heteroaryl ring.

In some embodiments, R' is —R, —C(O)R, —CO$_2$R, or —SO$_2$R, wherein R is as defined above and described herein.

In some embodiments, R' is —R, wherein R is as defined and described above and herein. In some embodiments, R' is hydrogen.

In some embodiments, R' is —C(O)R, wherein R is as defined above and described herein. In some embodiments, R' is —CO$_2$R, wherein R is as defined above and described herein. In some embodiments, R' is —SO$_2$R, wherein R is as defined above and described herein.

In some embodiments, two R' on the same nitrogen are taken together with their intervening atoms to form an optionally substituted heterocyclic or heteroaryl ring. In some embodiments, two R' on the same carbon are taken together with their intervening atoms to form an optionally substituted aryl, carbocyclic, heterocyclic, or heteroaryl ring.

In some embodiments, -Cy-is an optionally substituted bivalent ring selected from 3-30 membered carbocyclylene, 6-30 membered arylene, 5-30 membered heteroarylene having 1-10 heteroatoms, and 3-30 membered heterocyclylene having 1-10 heteroatoms. In some embodiments, -Cy-is monocyclic. In some embodiments, -Cy-is bicyclic. In some embodiments, -Cy-is polycyclic. In some embodiments, -Cy-is an optionally substituted bivalent 3-30 membered carbocyclylene. In some embodiments, -Cy-is an optionally substituted bivalent 6-30 membered arylene. In some embodiments, -Cy-is an optionally substituted bivalent 5-30 membered heteroarylene having 1-10 heteroatoms. In some embodiments, In some embodiments, -Cy-is an optionally substituted bivalent 3-30 membered heterocyclylene having 1-10 heteroatoms In some embodiments, -Cy-is an optionally substituted bivalent ring selected from phenylene, carbocyclylene, arylene, heteroarylene, or heterocyclylene.

In some embodiments, -Cy-is optionally substituted phenylene. In some embodiments, -Cy-is optionally substituted carbocyclylene. In some embodiments, -Cy-is optionally substituted arylene. In some embodiments, -Cy-is optionally substituted heteroarylene. In some embodiments, -Cy-is optionally substituted heterocyclylene.

In some embodiments, BA is optionally substituted $C_{1-30}$ cycloaliphatic. In some embodiments, BA is optionally substituted $C_{6-30}$ aryl. In some embodiments, BA is optionally substituted $C_{3-30}$ heterocyclyl having 1-10 heteroatoms. In some embodiments, BA is optionally substituted $C_{5-30}$ heteroaryl having 1-10 heteroatoms. In some embodiments, BA is optionally substituted natural nucleobase moiety. In some embodiments, BA is optionally substituted modified nucleobase moiety. In some embodiments, BA is

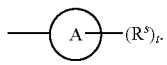

In some embodiments, BA is a nucleobase as described in the present disclosure.

In some embodiments, —SU(BA)- is an optionally substituted natural nucleoside moiety. In some embodiments, —SU(BA)- is a natural nucleoside moiety. In some embodiments, —SU(BA)- is a nucleoside moiety as described in the present disclosure, having nucleobase and sugar moieties independently as described in the present disclosure.

In some embodiments, each of X, Y and Z is independently —O—, —S—, —N(-L-$R^1$)—, or L, wherein each of L and $R^1$ is independently as defined above and described in the present disclosure.

In some embodiments, X is —O—. In some embodiments, X is —S—. In some embodiments, X is —O— or —S—. In some embodiments, an oligonucleotide comprises at least one internucleotidic linkage of formula I wherein X is —O—. In some embodiments, an oligonucleotide comprises at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—, and at least one internucleotidic linkage of formula I wherein L is an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, X is —N(-L-$R^1$)—. In some embodiments, X is —N($R^1$)—. In some embodiments, X is —N(R')—. In some embodiments, X is —N(R)—. In some embodiments, X is —NH—.

In some embodiments, X is L. In some embodiments, X is a covalent bond. In some embodiments, X is or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$-, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, X is an optionally substituted $C_1$-$C_{10}$ alkylene or $C_1$-$C_{10}$ alkenylene. In some embodiments, X is methylene.

In some embodiments, Y is —O—. In some embodiments, Y is —S—.

In some embodiments, Y is —N(-L-$R^1$)—. In some embodiments, Y is —N($R^1$)—. In some embodiments, Y is —N(R')—. In some embodiments, Y is —N(R)—. In some embodiments, Y is —NH—.

In some embodiments, Y is L. In some embodiments, Y is a covalent bond. In some embodiments, Y is or an optionally substituted, linear or branched $C_1$-$C_{10}$ alkylene, wherein one or more methylene units of L are optionally and independently replaced by an optionally substituted $C1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Y is an optionally substituted $C_1$-$C_{10}$ alkylene or $C_1$-$C_{10}$ alkenylene. In some embodiments, Y is methylene.

In some embodiments, Z is —O—. In some embodiments, Z is —S—.

In some embodiments, Z is —N(-L-$R^1$)—. In some embodiments, Z is —N($R^1$)—. In some embodiments, Z is —N(R')—. In some embodiments, Z is —N(R)—. In some embodiments, Z is —NH—.

In some embodiments, Z is L. In some embodiments, Z is a covalent bond. In some embodiments, Z is or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Z is an optionally substituted $C_1$-$C_{10}$ alkylene or $C_1$-$C_{10}$ alkenylene. In some embodiments, Z is methylene.

In some embodiments, $R^{2s}$ is hydrogen. In some embodiments, $R^{2s}$ is —F. In some embodiments, $R^{2s}$ is —OR'. In some embodiments, $R^{2s}$ is —OMe. In some embodiments, $R^{2S}$ is MOE. In some embodiments, $R^{2s}$ is -L- connecting C2 with C1, C2, C3, C4 or C5. In some embodiments, $R^{2s}$ is -L- connecting C2 with C4. In some embodiments, $R^{2s}$ is —O—CH$_2$—. In some embodiments, $R^{2s}$ is —O—CH(CH$_3$)—.

In some embodiments, n is an integer greater than 3 and no more than 500. In some embodiments, n is an integer greater than 3 and no more than 200. In some embodiments, n is 4-200. In some embodiments, n is 5-200. In some embodiments, n is 6-200. In some embodiments, n is 7-200. In some embodiments, n is 8-200. In some embodiments, n is 9-200. In some embodiments, n is 10-200. In some embodiments, n is 11-200. In some embodiments, n is 12-200. In some embodiments, n is 13-200. In some embodiments, n is 14-200. In some embodiments, n is 15-200. In some embodiments, n is 16-200. In some embodiments, n is 17-200. In some embodiments, n is 18-200. In some embodiments, n is 19-200. In some embodiments, n is no more than 200. In some embodiments, n is no more than 150. In some embodiments, n is no more than 100. In some embodiments, n is no more than 90. In some embodiments, n is no more than 80. In some embodiments, n is no more than 70. In some embodiments, n is no more than 60. In some embodiments, n is no more than 50. In some embodiments, n is no more than 40. In some embodiments, n is no more than 30. In some embodiments, n is no more than 25.

In some embodiments, $R^{3s}$ is R', —Y—R', —SU(BA)-Y—R', or —SU(BA)-Y-solid support. In some embodiments, $R^{3s}$ is R'. In some embodiments, $R^{3s}$ is —Y—R'.

In some embodiments, $R^{3s}$ is —SU(BA)-Y—R'. In some embodiments, —Y—R' is —OH.

In some embodiments, $R^{3s}$ is —SU(BA)-Y-solid support. As appreciated by a person having ordinary skill in the art, a number of solid support, for example, those described in the present disclosure, can be used for oligonucleotide synthesis in accordance with the present disclosure.

In some embodiments, L is a covalent bond, or a bivalent or multivalent, optionally substituted, linear or branched group selected from $C_{1-30}$ aliphatic and $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, when L is in SU, L is multivalent, for example, trivalent.

In some embodiments, L is a covalent bond. In some embodiments, L is an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L has the structure of -L$^1$-V—, wherein: L$^1$ is an optionally substituted group selected from

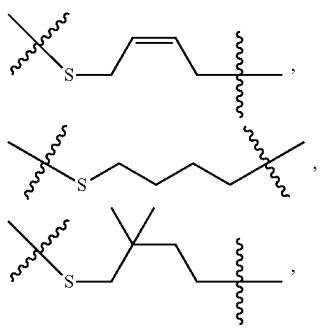

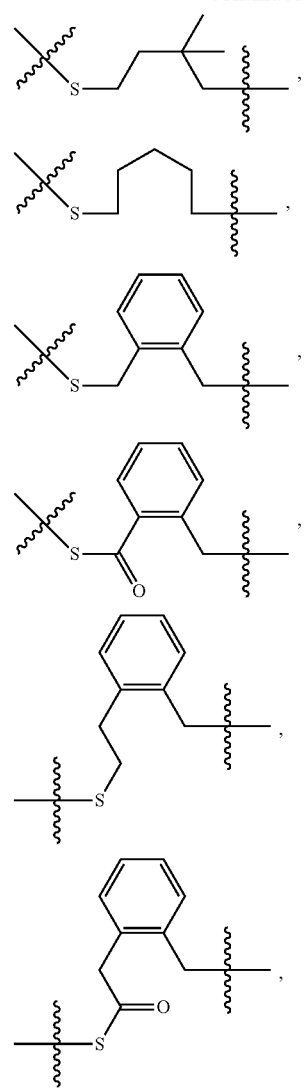

$C_1$-$C_6$ alkylene, $C_1$-$C_6$ alkenylene, carbocyclylene, arylene, $C_1$-$C_6$ heteroalkylene, heterocyclylene, and heteroarylene;

V is selected from —O—, —S—, —NR'—, C(R')$_2$, —S—S—, —B—S—S—C—,

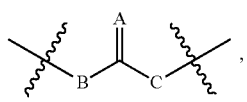

or an optionally substituted group selected from $C_1$-$C_6$ alkylene, arylene, $C_1$-$C_6$ heteroalkylene, heterocyclylene, and heteroarylene;

A is =O, =S, =NR', or =C(R')$_2$;

each of B and C is independently —O—, —S—, —NR'—, —C(R')$_2$—, or an optionally substituted group selected from $C_1$-$C_6$ alkylene, carbocyclylene, arylene, heterocyclylene, or heteroarylene; and each R' is independently as defined above and described herein.

In some embodiments, L¹ is

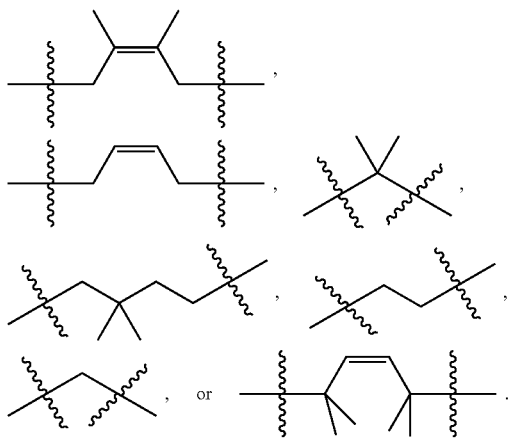

In some embodiments, L¹ is

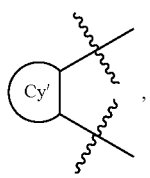

wherein Ring Cy' is an optionally substituted arylene, carbocyclylene, heteroarylene, or heterocyclylene. In some embodiments, L¹ is optionally substituted

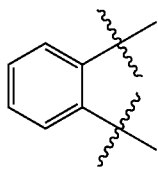

In some embodiments, L¹ is

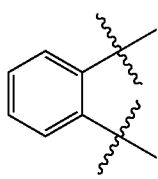

In some embodiments, L¹ is connected to X. In some embodiments, L¹ is an optionally substituted group selected from

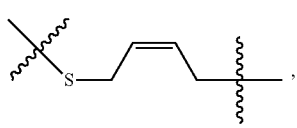

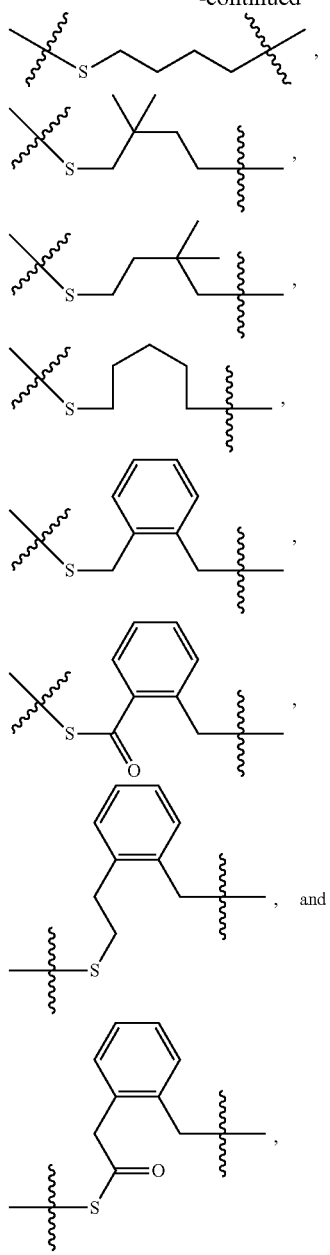

and the sulfur atom is connect to V. In some embodiments, L¹ is an optionally substituted group selected from

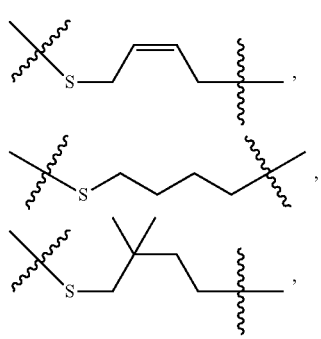

-continued

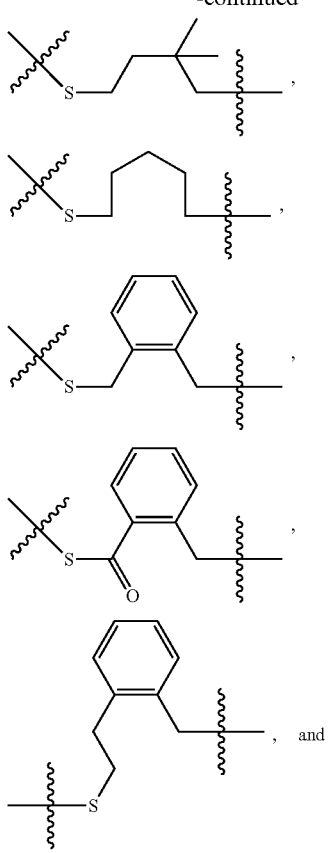

and the carbon atom is connect to X.

In some embodiments, L has the structure of:

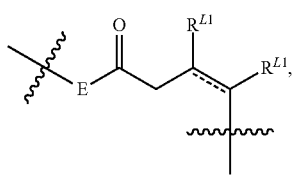

wherein:

E is —O—, —S—, —NR'— or —C(R')$_2$-;

┅┅ is a single or double bond;

the two $R^{L1}$ are taken together with the two carbon atoms to which they are bound to form an optionally substituted aryl, carbocyclic, heteroaryl or heterocyclic ring; and each R' is independently as defined above and described herein.

In some embodiments, L has the structure of:

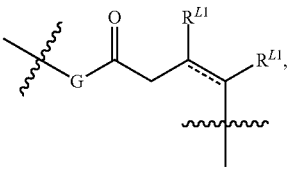

wherein:

G is —O—, —S—, or —NR';

┅┅ is a single or double bond; and the two $R^{L1}$ are taken together with the two carbon atoms to which they are bound to form an optionally substituted aryl, $C_3$-$C_{10}$ carbocyclic, heteroaryl or heterocyclic ring.

In some embodiments, L has the structure of:

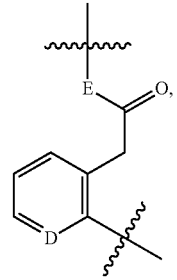

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

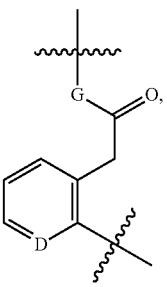

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

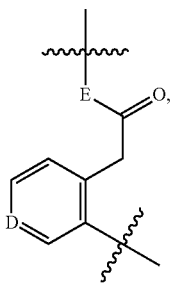

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

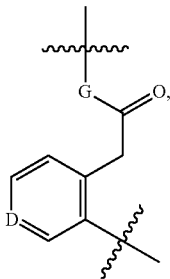

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—.

In some embodiments, L has the structure of:

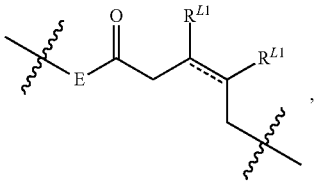

wherein:

E is —O—, —S—, —NR'— or —C(R')$_2$—;

==== is a single or double bond;

the two R$^{L1}$ are taken together with the two carbon atoms to which they are bound to form an optionally substituted aryl, C$_3$-C$_{10}$ carbocyclic, heteroaryl or heterocyclic ring;

and each R' is independently as defined above and described herein.

In some embodiments, L has the structure of:

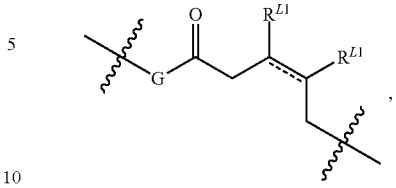

wherein:

G is —O—, —S—, or —NR';

==== is a single or double bond;

the two R$^{L1}$ are taken together with the two carbon atoms to which they are bound to form an optionally substituted aryl, C$_3$-C$_{10}$ carbocyclic, heteroaryl or heterocyclic ring;

and each R' is independently as defined above and described herein.

In some embodiments, L has the structure of:

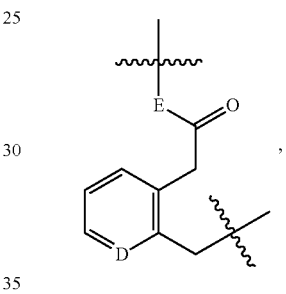

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

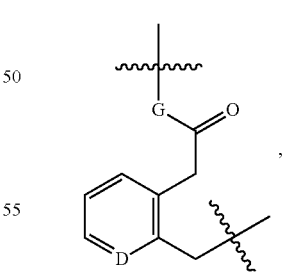

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

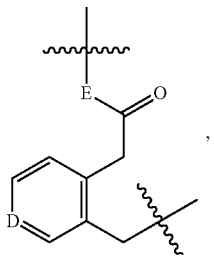

wherein:
E is —O—, —S—, —NR'— or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

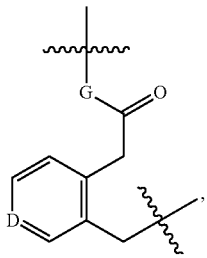

wherein:
G is —O—, —S—, or —NR';
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

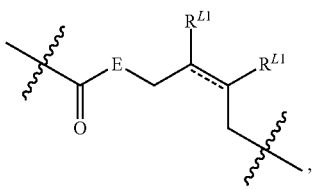

wherein:
E is —O—, —S—, —NR'— or —C(R')$_2$—;
==== is a single or double bond;
the two $R^{L1}$ are taken together with the two carbon atoms to which they are bound to form an optionally substituted aryl, C$_3$-C$_{10}$ carbocyclic, heteroaryl or heterocyclic ring; and each R' is independently as defined above and described herein.

In some embodiments, L has the structure of:

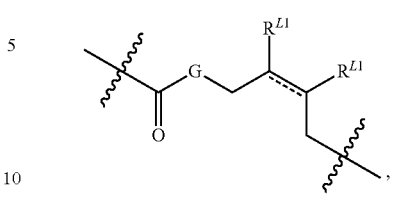

wherein:
G is —O—, —S—, or —NR';
==== is a single or double bond;
the two $R^{L1}$ are taken together with the two carbon atoms to which they are bound to form an optionally substituted aryl, C$_3$-C$_{10}$ carbocyclic, heteroaryl or heterocyclic ring; and each R' is independently as defined above and described herein.

In some embodiments, L has the structure of:

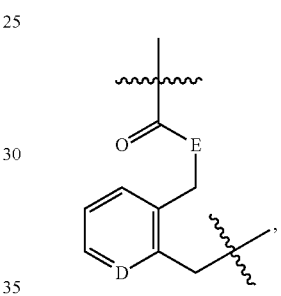

wherein:
E is —O—, —S—, —NR'— or —C(R')$_2$—;
D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and
each R' is independently as defined above and described herein.

In some embodiments, L has the structure of:

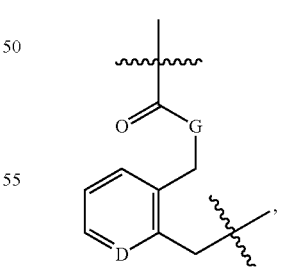

wherein:
G is —O—, —S—, or —NR';
D is =N—, =C(F)—, =C(Cl)—, =C(Br)—, =C(I)—, =C(CN)—, =C(NO$_2$)—, =C(CO$_2$—(C1-C$_6$ aliphatic))- or =C(CF$_3$)—; and
R' is as defined above and described herein.

In some embodiments, L has the structure of:

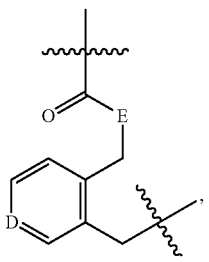

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

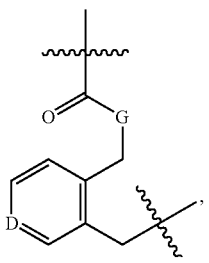

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and R' is as defined above and described herein.

In some embodiments, L has the structure of:

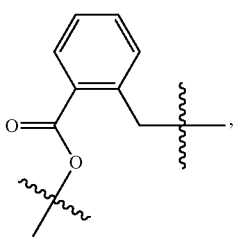

wherein the phenyl ring is optionally substituted. In some embodiments, the phenyl ring is not substituted. In some embodiments, the phenyl ring is substituted.

In some embodiments, L has the structure of:

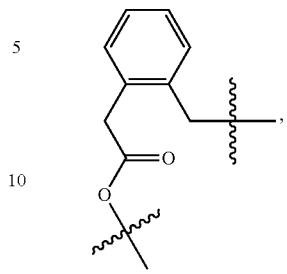

wherein the phenyl ring is optionally substituted. In some embodiments, the phenyl ring is not substituted. In some embodiments, the phenyl ring is substituted.

In some embodiments, L has the structure of:

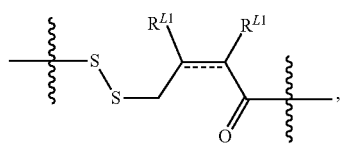

wherein:
==== is a single or double bond; and
the two $R^{L1}$ are taken together with the two carbon atoms to which they are bound to form an optionally substituted aryl, C$_3$-C$_{10}$ carbocyclic, heteroaryl or heterocyclic ring.

In some embodiments, L has the structure of:

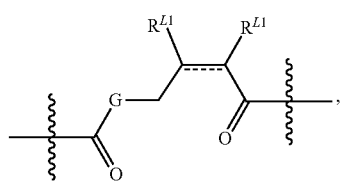

wherein:
G is —O—, —S—, or —NR';
==== is a single or double bond; and
the two $R^{L1}$ are taken together with the two carbon atoms to which they are bound to form an optionally substituted aryl, C$_3$-C$_{10}$ carbocyclic, heteroaryl or heterocyclic ring.

In some embodiments, E is —O—, —S—, —NR'— or —C(R')$_2$—, wherein each R' independently as defined above and described herein. In some embodiments, E is —O—, —S—, or —NR'—. In some embodiments, E is —O—, —S—, or —NH—. In some embodiments, E is —O—. In some embodiments, E is —S—. In some embodiments, E is —NH—.

In some embodiments, G is —O—, —S—, or —NR', wherein each R' independently as defined above and described herein. In some embodiments, G is —O—, —S—, or —NH—. In some embodiments, G is —O—. In some embodiments, G is —S—. In some embodiments, G is —NH—.

In some embodiments, L is -L$^3$-G-, wherein:

L$^3$ is an optionally substituted C$_1$-C$_5$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

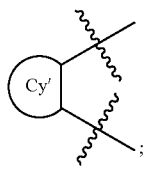

and wherein each of G, R' and Ring Cy' is independently as defined above and described herein.

In some embodiments, L is -L$^3$-S—, wherein L$^3$ is as defined above and described herein. In some embodiments, L is -L$^3$-O—, wherein L$^3$ is as defined above and described herein. In some embodiments, L is -L$^3$-N(R')—, wherein each of L$^3$ and R' is independently as defined above and described herein. In some embodiments, L is -L$^3$-NH—, wherein each of L$^3$ and R' is independently as defined above and described herein.

In some embodiments, L$^3$ is an optionally substituted Cs alkylene or alkenylene, wherein one or more methylene units are optionally and independently replaced by —O—, —S—, —N(R')—, —C(O)—, —C(S)—, —C(NR')—, —S(O)—, —S(O)$_2$—, or

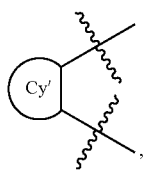 [SMILES: *CC*]

and each of R' and Ring Cy' is independently as defined above and described herein. In some embodiments, L$^3$ is an optionally substituted C$_5$ alkylene. In some embodiments, -L$^3$-G- is

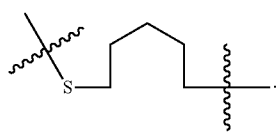

In some embodiments, L$^3$ is an optionally substituted C4 alkylene or alkenylene, wherein one or more methylene units are optionally and independently replaced by —O—, —S—, —N(R')—, —C(O)—, —C(S)—, —C(NR')—, —S(O)—, —S(O)$_2$—, or

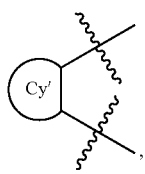

and each of R' and Cy' is independently as defined above and described herein.

In some embodiments, -L$^3$-G- is

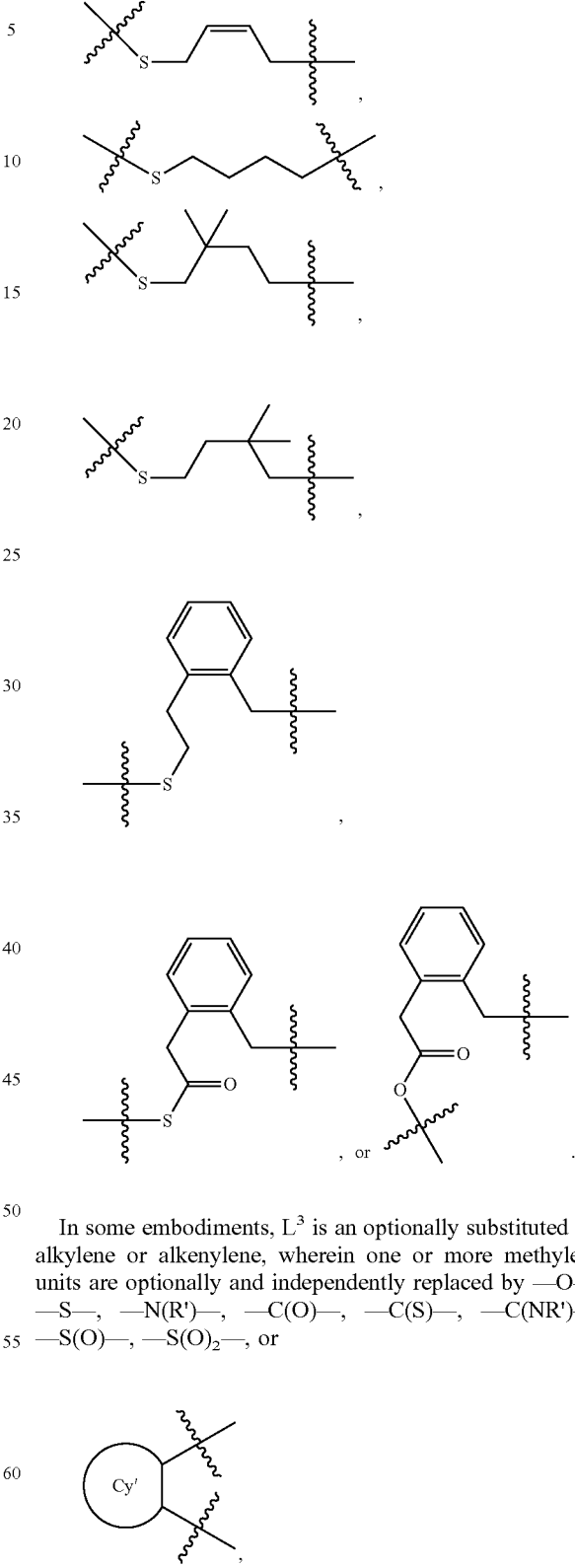

In some embodiments, L$^3$ is an optionally substituted C3 alkylene or alkenylene, wherein one or more methylene units are optionally and independently replaced by —O—, —S—, —N(R')—, —C(O)—, —C(S)—, —C(NR')—, —S(O)—, —S(O)$_2$—, or and each of R' and Cy' is independently as defined above and described herein.

In some embodiments, -L³-G- is

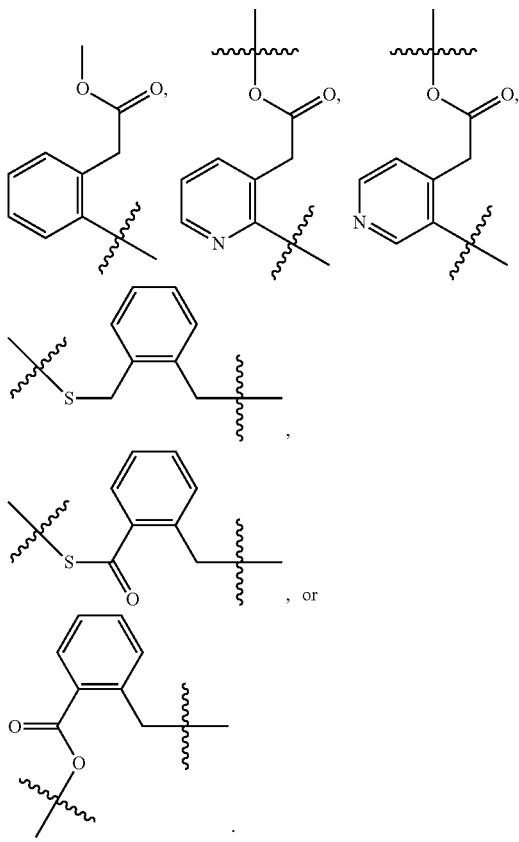

, or

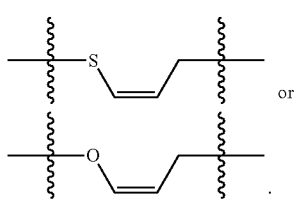

In some embodiments, L is

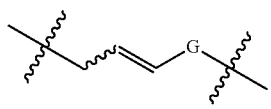

In some embodiments, L is

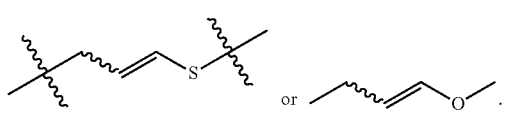

In some embodiments, L is

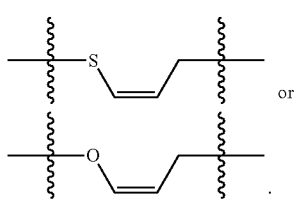

or

In some embodiments, L³ is an optionally substituted C₂ alkylene or alkenylene, wherein one or more methylene units are optionally and independently replaced by —O—, —S—, —N(R')—, —C(O)—, —C(S)—, —C(NR')—, —S(O)—, —S(O)₂—, or

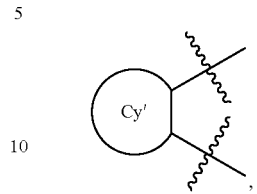

and each of R' and Cy' is independently as defined above and described herein.

In some embodiments, -L³-G- is

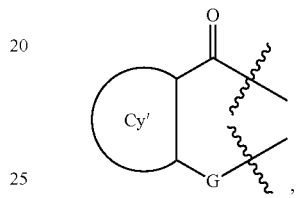

wherein each of G and Cy' is independently as defined above and described herein. In some embodiments, L is

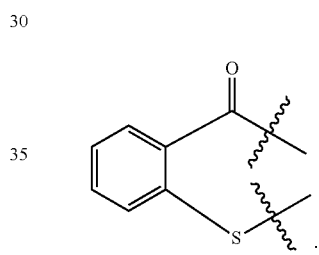

In some embodiments, L is -L⁴-G-, wherein L⁴ is an optionally substituted C₁-C₂ alkylene; and G is as defined above and described herein. In some embodiments, L is -L⁴-G-, wherein L⁴ is an optionally substituted C₁-C₂ alkylene; G is as defined above and described herein; and G is connected to R¹. In some embodiments, L is -L⁴-G-, wherein L⁴ is an optionally substituted methylene; G is as defined above and described herein; and G is connected to R¹. In some embodiments, L is -L⁴-G-, wherein L⁴ is methylene; G is as defined above and described herein; and G is connected to R¹. In some embodiments, L is -L⁴-G-, wherein L⁴ is an optionally substituted —(CH₂)₂—; G is as defined above and described herein; and G is connected to R¹. In some embodiments, L is -L⁴-G-, wherein L⁴ is —(CH₂)₂—; G is as defined above and described herein; and G is connected to R¹.

In some embodiments, L is

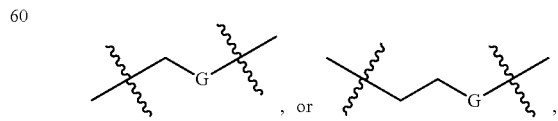

wherein G is as defined above and described herein, and G is connected to R¹. In some embodiments, L is

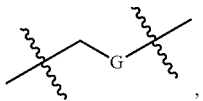

wherein G is as defined above and described herein, and G is connected to R¹. In some embodiments, L is

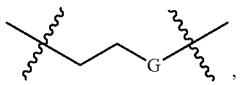

wherein G is as defined above and described herein, and G is connected to R¹. In some embodiments, L is

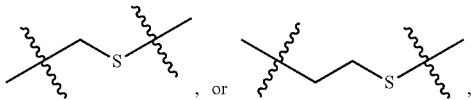

wherein the sulfur atom is connected to R¹. In some embodiments, L is

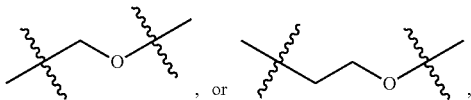

wherein the oxygen atom is connected to R¹.

In some embodiments, L is

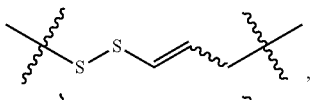

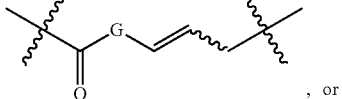

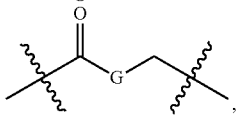

wherein G is as defined above and described herein.

In some embodiments, L is —S—$R^{L3}$— or —S—C(O)—$R^{L3}$—, wherein $R^{L3}$ is an optionally substituted, linear or branched, $C_1$-$C_9$ alkylene, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each of R' and -Cy- is independently as defined above and described herein. In some embodiments, L is —S—$R^{L3}$— or —S—C(O)—$R^{L3}$—, wherein $R^{L3}$ is an optionally substituted $C_1$-$C_6$ alkylene. In some embodiments, L is —S—$R^{L3}$— or —S—C(O)—$R^{L3}$—, wherein $R^{L3}$ is an optionally substituted $C_1$-$C_6$ alkenylene. In some embodiments, L is —S—$R^{L3}$— or —S—C(O)—$R^{L3}$—, wherein $R^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, In some embodiments, $R^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-.

In some embodiments, L is

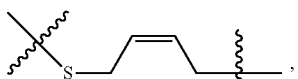

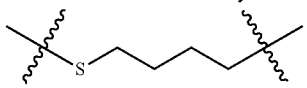

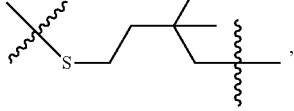

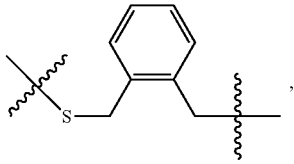

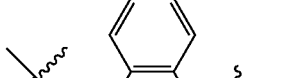

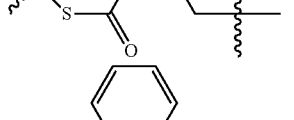

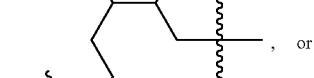, or

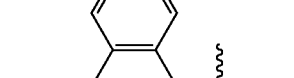

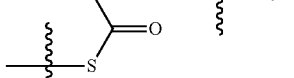.

In some embodiments, L is

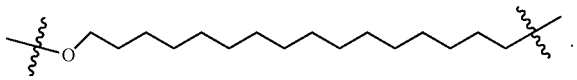 [SMILES: *CCCCCCCCCCCCCCCCO*]

In some embodiments, L is

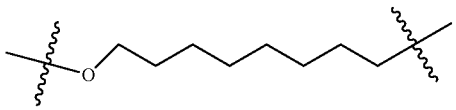

In some embodiments,

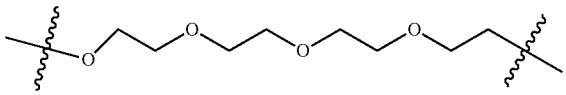

In some embodiments, the sulfur atom in the L embodiments described above and herein is connected to X. In some embodiments, the sulfur atom in the L embodiments described above and herein is connected to $R^1$.

In some embodiments, $R^1$ is halogen, R, or an optionally substituted $C_1$-$C_{50}$ aliphatic wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, $R^1$ is R. In some embodiments, $R^1$ is hydrogen. In some embodiments, $R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is halogen, R, or an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein.

In some embodiments, $R^1$ is hydrogen. In some embodiments, $R^1$ is halogen. In some embodiments, $R^1$ is —F. In some embodiments, $R^1$ is —Cl. In some embodiments, $R^1$ is —Br. In some embodiments, $R^1$ is —I.

In some embodiments, $R^1$ is R wherein R is as defined above and described herein.

In some embodiments, $R^1$ is hydrogen. In some embodiments, $R^1$ is an optionally substituted group selected from $C_1$-$C_{50}$ aliphatic, phenyl, carbocyclyl, aryl, heteroaryl, or heterocyclyl.

In some embodiments, $R^1$ is an optionally substituted $C_1$-$C_{50}$ aliphatic. In some embodiments, $R^1$ is an optionally substituted $C_1$-$C_{10}$ aliphatic. In some embodiments, $R^1$ is an optionally substituted $C_1$-$C_6$ aliphatic. In some embodiments, $R^1$ is an optionally substituted $C_1$-$C_6$ alkyl. In some embodiments, $R^1$ is optionally substituted, linear or branched hexyl. In some embodiments, $R^1$ is optionally substituted, linear or branched pentyl. In some embodiments, $R^1$ is optionally substituted, linear or branched butyl. In some embodiments, $R^1$ is optionally substituted, linear or branched propyl. In some embodiments, $R^1$ is optionally substituted ethyl. In some embodiments, $R^1$ is optionally substituted methyl.

In some embodiments, $R^1$ is optionally substituted phenyl. In some embodiments, $R^1$ is substituted phenyl. In some embodiments, $R^1$ is phenyl.

In some embodiments, $R^1$ is optionally substituted carbocyclyl. In some embodiments, $R^1$ is optionally substituted $C_3$-$C_{10}$ carbocyclyl. In some embodiments, $R^1$ is optionally substituted monocyclic carbocyclyl. In some embodiments, $R^1$ is optionally substituted cycloheptyl. In some embodiments, $R^1$ is optionally substituted cyclohexyl. In some embodiments, $R^1$ is optionally substituted cyclopentyl. In some embodiments, $R^1$ is optionally substituted cyclobutyl. In some embodiments, $R^1$ is an optionally substituted cyclopropyl. In some embodiments, $R^1$ is optionally substituted bicyclic carbocyclyl.

In some embodiments, $R^1$ is an optionally substituted $C_1$-$C_{50}$ polycyclic hydrocarbon. In some embodiments, $R^1$ is an optionally substituted $C_1$-$C_{50}$ polycyclic hydrocarbon wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is optionally substituted

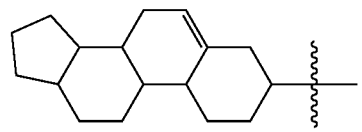

In some embodiments, $R^1$ is

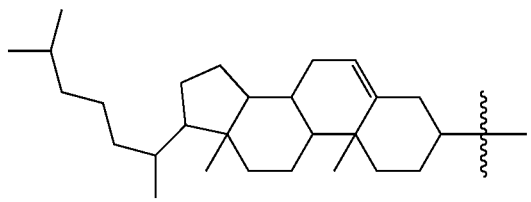

In some embodiments, $R^1$ is optionally substituted

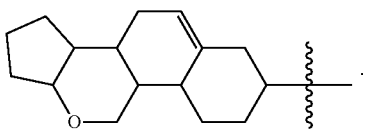 [SMILES: *C1CCC2C(=CCC3C4CCCC4OCC23)C1]

In some embodiments, $R^1$ is an optionally substituted $C_1$-$C_{50}$ aliphatic comprising one or more optionally substituted polycyclic hydrocarbon moieties. In some embodiments, $R^1$ is an optionally substituted $C_1$-$C_{50}$ aliphatic comprising one or more optionally substituted polycyclic hydrocarbon moieties, wherein one or more methylene units are optionally and independently replaced by an optionally substituted $C_1$-$C_6$ alkylene, $C_1$-$C_6$ alkenylene, —C≡C—, —C(R')$_2$-, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{50}$ aliphatic comprising one or more optionally substituted

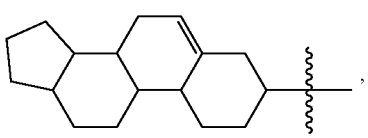,

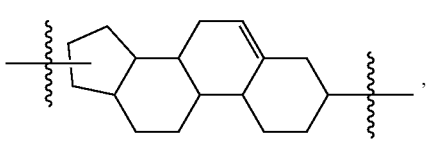,

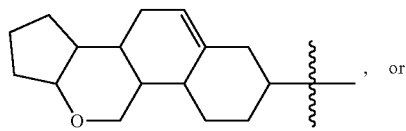, or

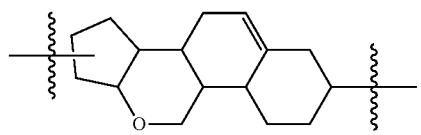

In some embodiments, $R^1$ is

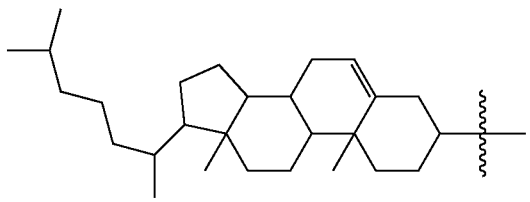

In some embodiments, $R^1$ is

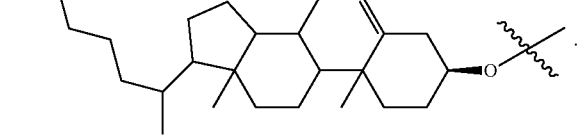.

In some embodiments, $R^1$ is

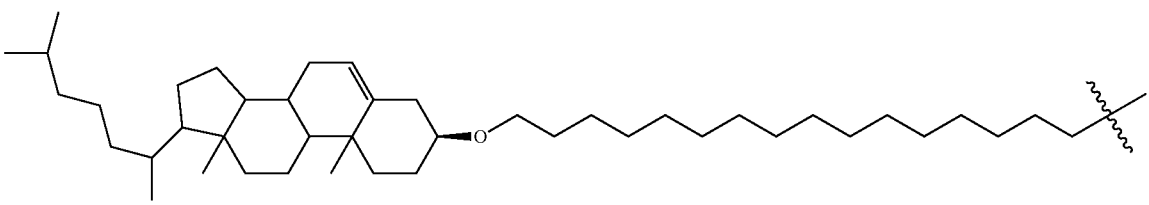 [SMILES: *CCCCCCCCCCCCCCCCO[C@H]1CCC2(C)C(=CCC3C2CCC2(C)C(C(C)CCCC(C)C)CCC32)C1].

In some embodiments, $R^1$ is

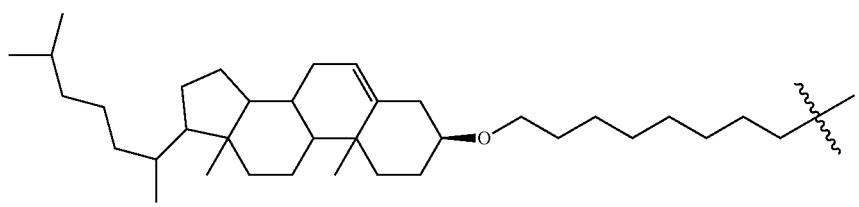.

In some embodiments, R¹ is

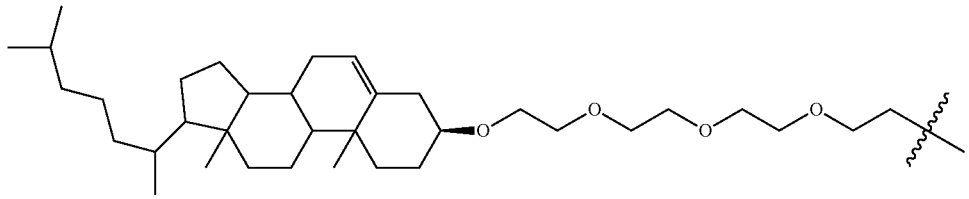

In some embodiments, R¹ is an optionally substituted aryl. In some embodiments, R¹ is an optionally substituted bicyclic aryl ring.

In some embodiments, R¹ is an optionally substituted heteroaryl. In some embodiments, R¹ is an optionally substituted 5-6 membered monocyclic heteroaryl ring having 1-3 heteroatoms independently selected from nitrogen, sulfur, or oxygen. In some embodiments, R¹ is a substituted 5-6 membered monocyclic heteroaryl ring having 1-3 heteroatoms independently selected from nitrogen, oxygen, or sulfur. In some embodiments, R¹ is an unsubstituted 5-6 membered monocyclic heteroaryl ring having 1-3 heteroatoms independently selected from nitrogen, sulfur, or oxygen.

In some embodiments, R¹ is an optionally substituted 5 membered monocyclic heteroaryl ring having 1-3 heteroatoms independently selected from nitrogen, oxygen or sulfur. In some embodiments, R¹ is an optionally substituted 6 membered monocyclic heteroaryl ring having 1-3 heteroatoms independently selected from nitrogen, oxygen, or sulfur.

In some embodiments, R¹ is an optionally substituted 5-membered monocyclic heteroaryl ring having 1 heteroatom selected from nitrogen, oxygen, or sulfur. In some embodiments, R¹ is selected from pyrrolyl, furanyl, or thienyl.

In some embodiments, R¹ is an optionally substituted 5-membered heteroaryl ring having 2 heteroatoms independently selected from nitrogen, oxygen, or sulfur. In certain embodiments, R¹ is an optionally substituted 5-membered heteroaryl ring having 1 nitrogen atom, and an additional heteroatom selected from sulfur or oxygen. Example R¹ groups include optionally substituted pyrazolyl, imidazolyl, thiazolyl, isothiazolyl, oxazolyl or isoxazolyl.

In some embodiments, R¹ is a 6-membered heteroaryl ring having 1-3 nitrogen atoms. In other embodiments, R¹ is an optionally substituted 6-membered heteroaryl ring having 1-2 nitrogen atoms. In some embodiments, R¹ is an optionally substituted 6-membered heteroaryl ring having 2 nitrogen atoms. In certain embodiments, R¹ is an optionally substituted 6-membered heteroaryl ring having 1 nitrogen. Example R¹ groups include optionally substituted pyridinyl, pyrimidinyl, pyrazinyl, pyridazinyl, triazinyl, or tetrazinyl.

In certain embodiments, R¹ is an optionally substituted 8-10 membered bicyclic heteroaryl ring having 1-4 heteroatoms independently selected from nitrogen, oxygen, or sulfur. In some embodiments, R¹ is an optionally substituted 5,6-fused heteroaryl ring having 1-4 heteroatoms independently selected from nitrogen, oxygen, or sulfur. In other embodiments, R¹ is an optionally substituted 5,6-fused heteroaryl ring having 1-2 heteroatoms independently selected from nitrogen, oxygen, or sulfur. In certain embodiments, R¹ is an optionally substituted 5,6-fused heteroaryl ring having 1 heteroatom independently selected from nitrogen, oxygen, or sulfur. In some embodiments, R¹ is an optionally substituted indolyl. In some embodiments, R¹ is an optionally substituted azabicyclo[3.2.1]octanyl. In certain embodiments, R¹ is an optionally substituted 5,6-fused heteroaryl ring having 2 heteroatoms independently selected from nitrogen, oxygen, or sulfur. In some embodiments, R¹ is an optionally substituted azaindolyl. In some embodiments, R¹ is an optionally substituted benzimidazolyl. In some embodiments, R¹ is an optionally substituted benzothiazolyl. In some embodiments, R¹ is an optionally substituted benzoxazolyl. In some embodiments, R¹ is an optionally substituted indazolyl. In certain embodiments, R¹ is an optionally substituted 5,6-fused heteroaryl ring having 3 heteroatoms independently selected from nitrogen, oxygen, or sulfur.

In certain embodiments, R¹ is an optionally substituted 6,6-fused heteroaryl ring having 1-4 heteroatoms independently selected from nitrogen, oxygen, or sulfur. In some embodiments, R¹ is an optionally substituted 6,6-fused heteroaryl ring having 1-2 heteroatoms independently selected from nitrogen, oxygen, or sulfur. In other embodiments, R¹ is an optionally substituted 6,6-fused heteroaryl ring having 1 heteroatom independently selected from nitrogen, oxygen, or sulfur. In some embodiments, R¹ is an optionally substituted quinolinyl. In some embodiments, R¹ is an optionally substituted isoquinolinyl. According to one aspect, R¹ is an optionally substituted 6,6-fused heteroaryl ring having 2 heteroatoms independently selected from nitrogen, oxygen, or sulfur. In some embodiments, R¹ is a quinazoline or a quinoxaline.

In some embodiments, R¹ is an optionally substituted heterocyclyl. In some embodiments, R¹ is an optionally substituted 3-7 membered saturated or partially unsaturated heterocyclic ring having 1-2 heteroatoms independently selected from nitrogen, oxygen, or sulfur. In some embodiments, R¹ is a substituted 3-7 membered saturated or partially unsaturated heterocyclic ring having 1-2 heteroatoms independently selected from nitrogen, oxygen, or sulfur. In some embodiments, R¹ is an unsubstituted 3-7 membered saturated or partially unsaturated heterocyclic ring having 1-2 heteroatoms independently selected from nitrogen, oxygen, or sulfur.

In some embodiments, R¹ is an optionally substituted heterocyclyl. In some embodiments, R¹ is an optionally substituted 6 membered saturated or partially unsaturated heterocyclic ring having 1-2 heteroatoms independently selected from nitrogen, oxygen, or sulfur. In some embodiments, R¹ is an optionally substituted 6 membered partially unsaturated heterocyclic ring having 2 heteroatoms independently selected from nitrogen, oxygen, or sulfur. In some embodiments, R¹ is an optionally substituted 6 membered partially unsaturated heterocyclic ring having 2 oxygen atoms.

In certain embodiments, R¹ is a 3-7 membered saturated or partially unsaturated heterocyclic ring having 1-2 heteroatoms independently selected from nitrogen, oxygen, or sulfur. In certain embodiments, $R^1$ is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, $R^1$ is an optionally substituted 5 membered saturated or partially unsaturated heterocyclic ring having 1-2 heteroatoms independently selected from nitrogen, oxygen, or sulfur.

In certain embodiments, $R^1$ is an optionally substituted 5-6 membered partially unsaturated monocyclic ring having 1-2 heteroatoms independently selected from nitrogen, oxygen, or sulfur. In certain embodiments, $R^1$ is an optionally substituted tetrahydropyridinyl, dihydrothiazolyl, dihydrooxazolyl, or oxazolinyl group.

In some embodiments, $R^1$ is an optionally substituted 8-10 membered bicyclic saturated or partially unsaturated heterocyclic ring having 1-4 heteroatoms independently selected from nitrogen, oxygen, or sulfur. In some embodiments, $R^1$ is an optionally substituted indolinyl. In some embodiments, $R^1$ is an optionally substituted isoindolinyl. In some embodiments, $R^1$ is an optionally substituted 1, 2, 3, 4-tetrahydroquinoline. In some embodiments, $R^1$ is an optionally substituted 1, 2, 3, 4-tetrahydroisoquinoline.

In some embodiments, $R^1$ is an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —C(S)—, —C(NR')—, —C(O)N (R')—, —N(R')C(O)N(R')—, —N(R')C(O)—, —N(R')C(O) O—, —OC(O)N(R')—, —S(O)—, —S(O)$_2$—, —S(O)$_2$N (R')—, —N(R')S(O)$_2$—, —OC(O)—, or —C(O)O—, wherein each R' is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —OC(O)—, or —C(O)O—, wherein each R' is independently as defined above and described herein.

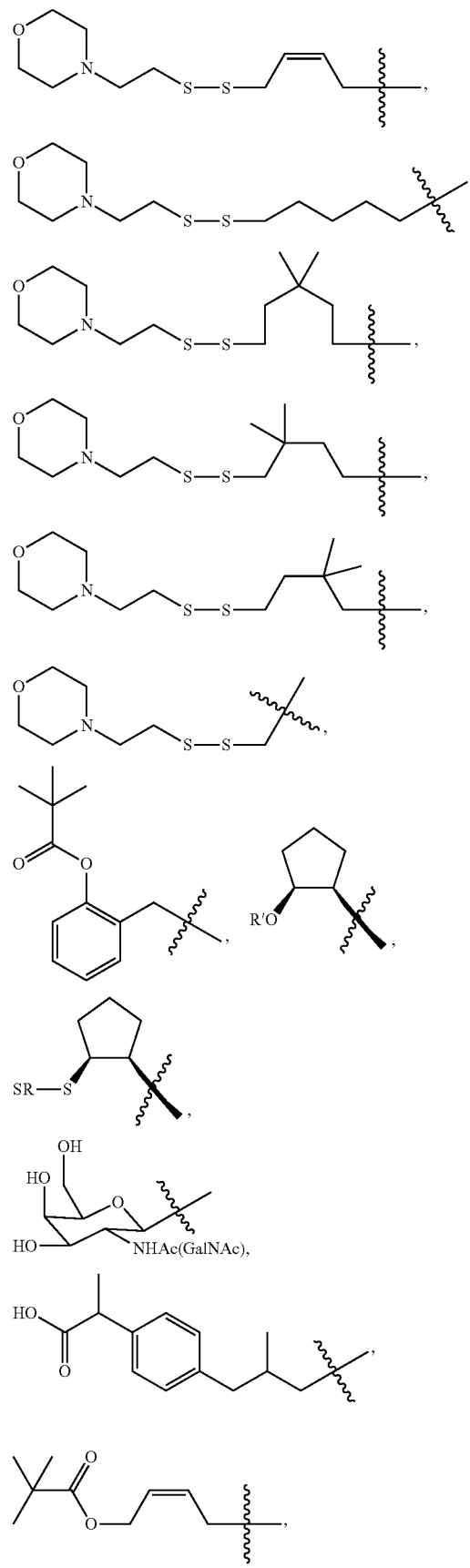

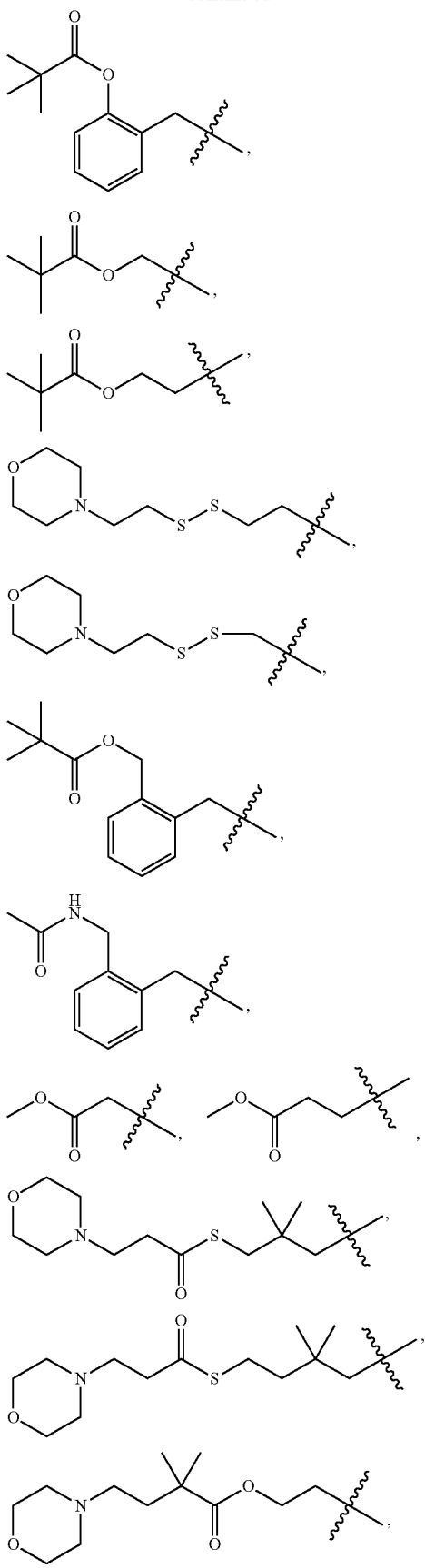
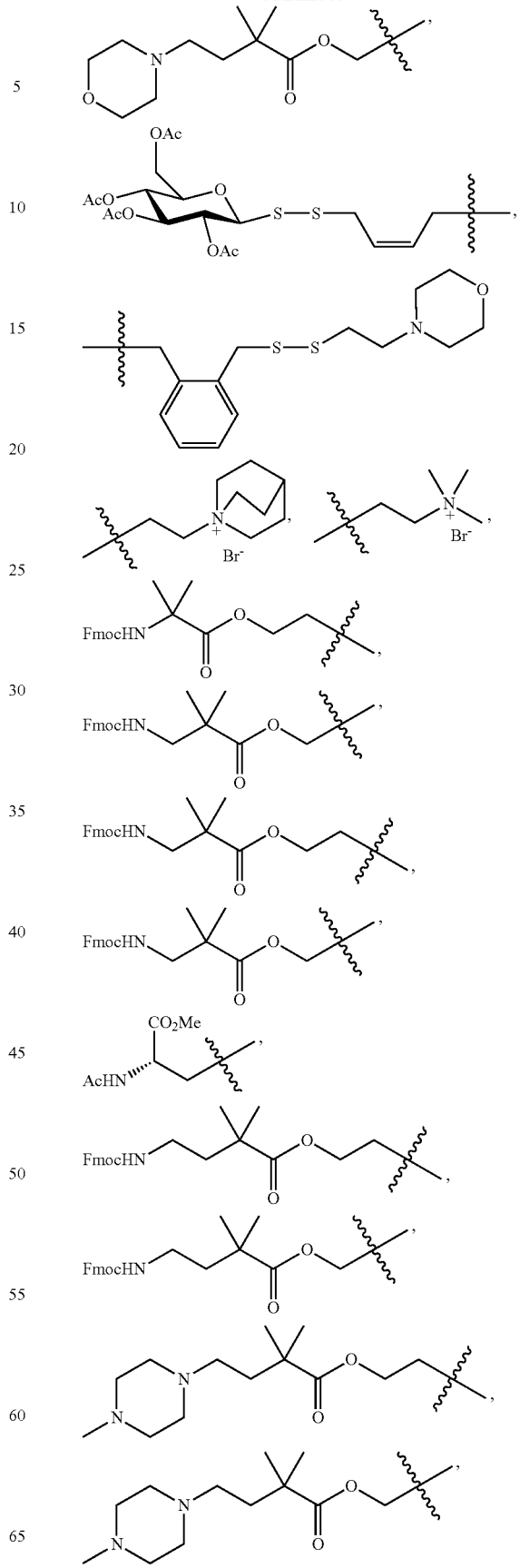

-continued
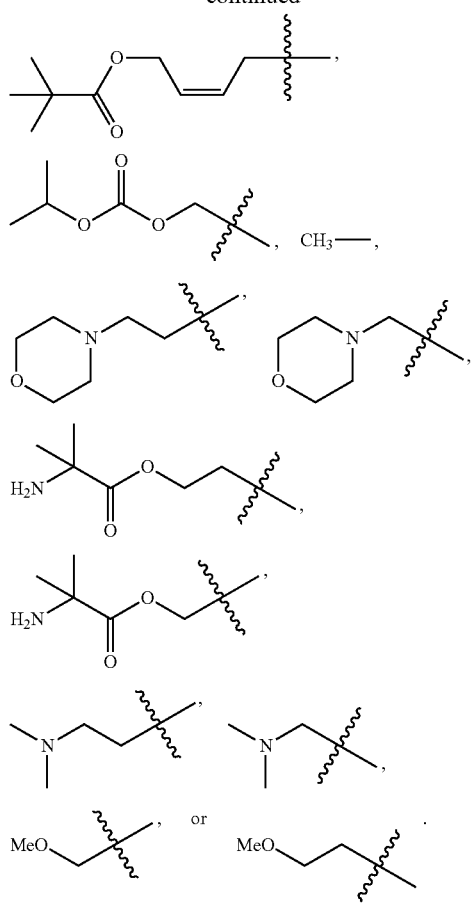
In some embodiments, $R^1$ is $CH_3$—,
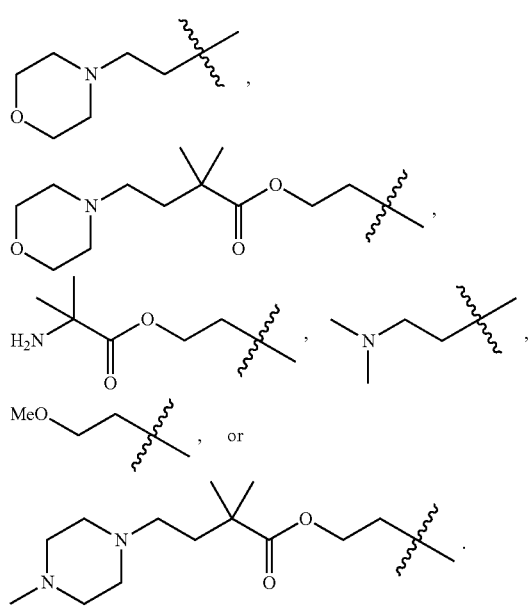
In some embodiments, $R^1$ comprises a terminal optionally substituted —$(CH_2)_2$-moiety which is connected to L. Examples of such $R^1$ groups are depicted below:
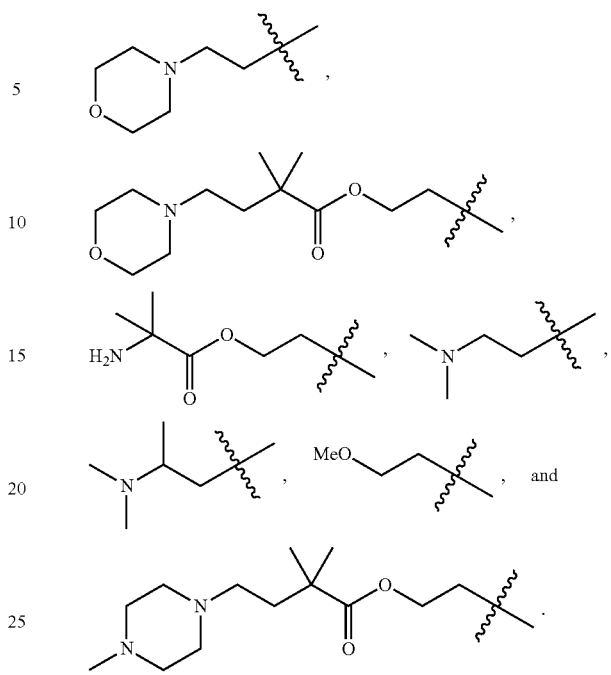
In some embodiments, $R^1$ comprises a terminal optionally substituted —$(CH_2)$-moiety which is connected to L. Example such $R^1$ groups are depicted below:
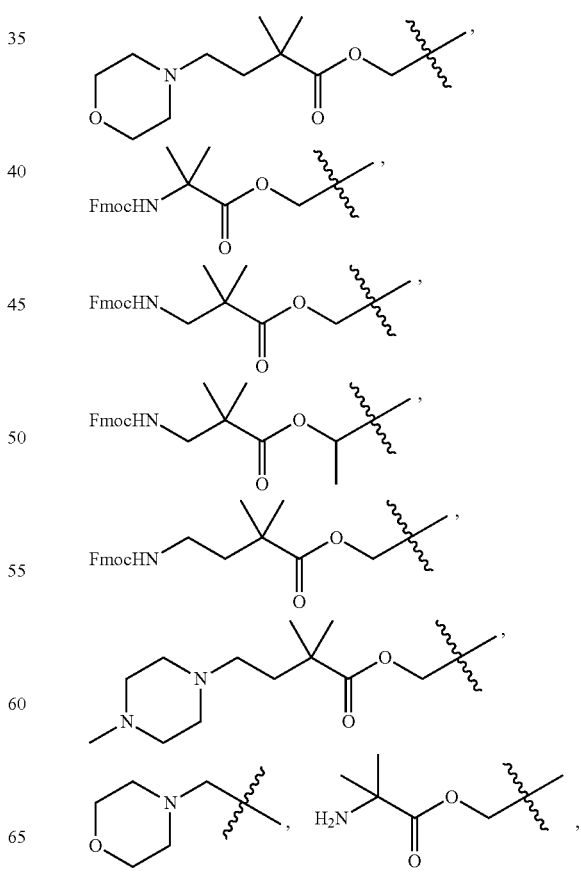

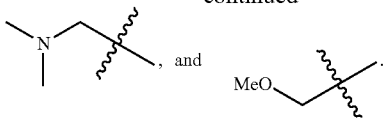

In some embodiments, $R^1$ is —S—$R^{L2}$, wherein $R^{L2}$ is an optionally substituted $C_1$-C9 aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each of R' and -Cy- is independently as defined above and described herein. In some embodiments, $R^1$ is —S—$R^{L2}$, wherein the sulfur atom is connected with the sulfur atom in L group.

In some embodiments, $R^1$ is —C(O)—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each of R' and -Cy- is independently as defined above and described herein. In some embodiments, $R^1$ is —C(O)—$R^{L2}$, wherein the carbonyl group is connected with G in L group. In some embodiments, $R^1$ is —C(O)—$RL^2$, wherein the carbonyl group is connected with the sulfur atom in L group.

In some embodiments, $R^{L2}$ is optionally substituted $C_1$-$C_9$ aliphatic. In some embodiments, $R^{L2}$ is optionally substituted $C_1$-$C_9$ alkyl. In some embodiments, $R^{L2}$ is optionally substituted $C_1$-$C_9$ alkenyl. In some embodiments, $R^{L2}$ is optionally substituted $C_1$-$C_9$ alkynyl. In some embodiments, $R^{L2}$ is an optionally substituted $C_1$-$C_9$ aliphatic wherein one or more methylene units are optionally and independently replaced by -Cy- or —C(O)—. In some embodiments, $R^{L2}$ is an optionally substituted $C_1$-$C_9$ aliphatic wherein one or more methylene units are optionally and independently replaced by -Cy-. In some embodiments, $R^{L2}$ is an optionally substituted $C_1$-$C_9$ aliphatic wherein one or more methylene units are optionally and independently replaced by an optionally substituted heterocycylene. In some embodiments, $R^{L2}$ is an optionally substituted $C_1$-$C_9$ aliphatic wherein one or more methylene units are optionally and independently replaced by an optionally substituted arylene. In some embodiments, $R^{L2}$ is an optionally substituted $C_1$-$C_9$ aliphatic wherein one or more methylene units are optionally and independently replaced by an optionally substituted heteroarylene. In some embodiments, $R^{L2}$ is an optionally substituted $C_1$-$C_9$ aliphatic wherein one or more methylene units are optionally and independently replaced by an optionally substituted $C_3$-$C_{10}$ carbocyclylene. In some embodiments, $R^{L2}$ is an optionally substituted $C_1$-$C_9$ aliphatic wherein two methylene units are optionally and independently replaced by -Cy- or —C(O)—. In some embodiments, $R^{L2}$ is an optionally substituted $C_1$-$C_9$ aliphatic wherein two methylene units are optionally and independently replaced by -Cy- or —C(O)—. Example $R^{L2}$ groups are depicted below:

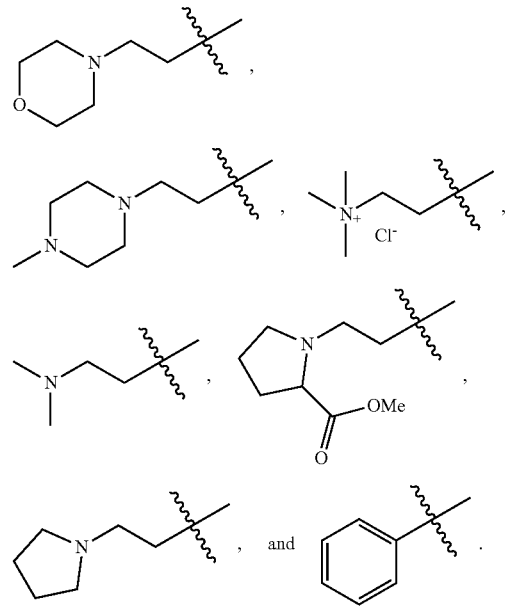

In some embodiments, $R^1$ is hydrogen, or an optionally substituted group selected from

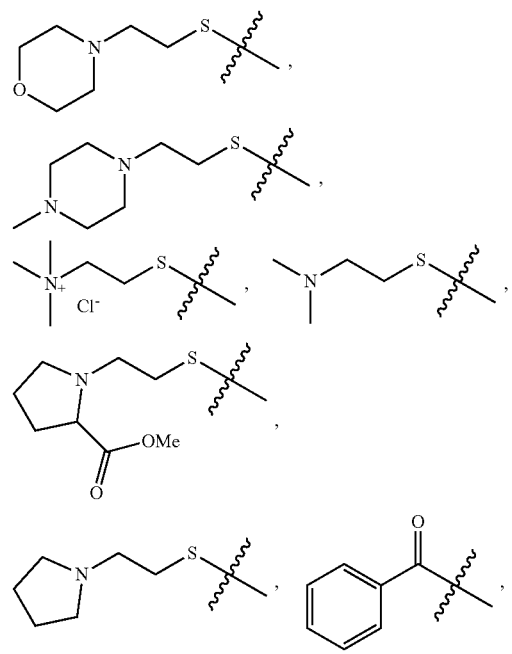

—S—($C_1$-$C_{10}$ aliphatic), $C_1$-$C_{10}$ aliphatic, aryl, $C_1$-$C_6$ heteroalkyl, heteroaryl and heterocyclyl. In some embodiments, $R^1$ is

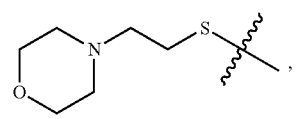

-continued

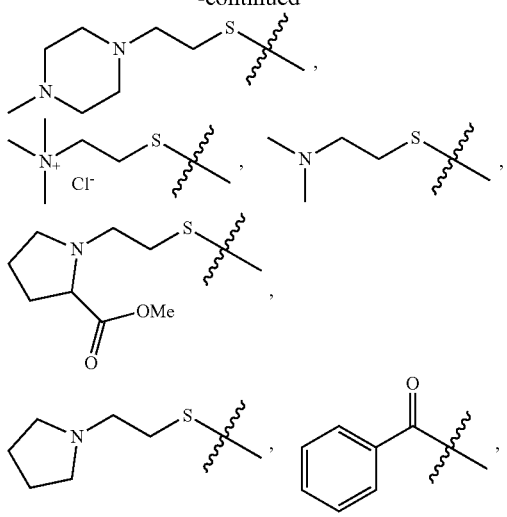

aliphatic). In some embodiments, $R^1$ is

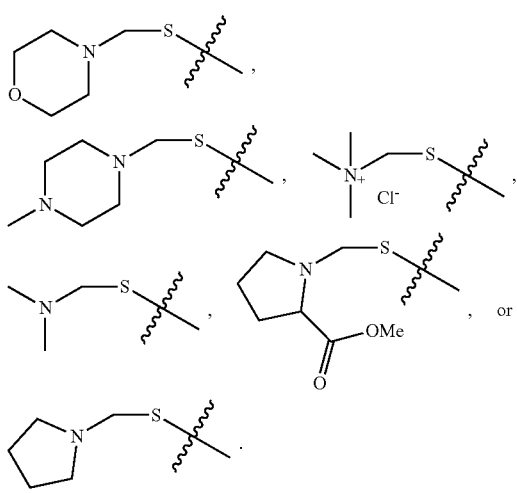

In some embodiments, $R^1$ is an optionally substituted group selected from —S—($C_1$-$C_6$ aliphatic), $C_1$-$C_{10}$ aliphatic, $C_1$-$C_6$ heteroaliphatic, aryl, heterocyclyl and heteroaryl.

In some embodiments, $R^1$ is

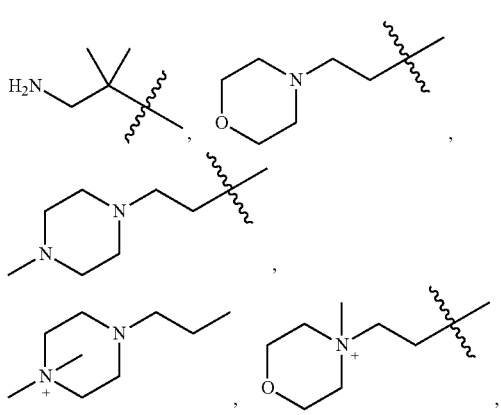

-continued

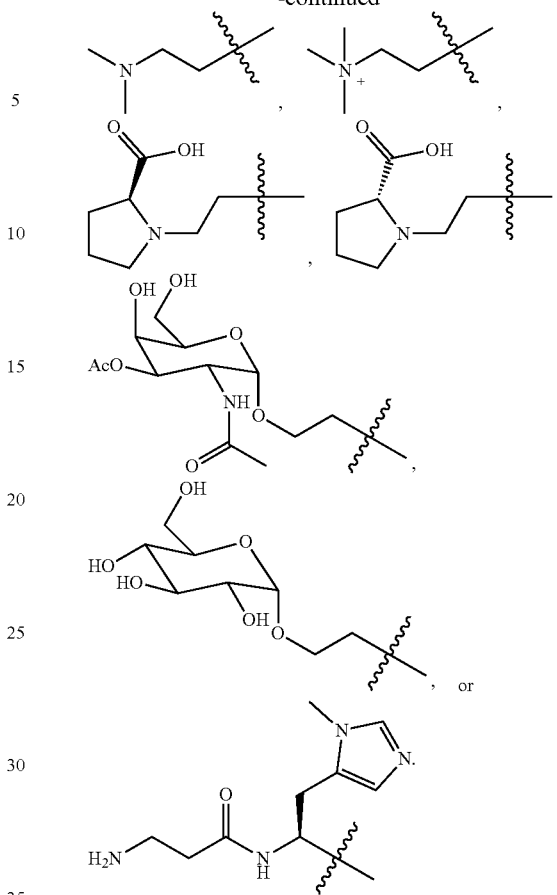

In some embodiments, the sulfur atom in the $R^1$ embodiments described above and herein is connected with the sulfur atom, G, E, or —C(O)— moiety in the L embodiments described above and herein. In some embodiments, the —C(O)— moiety in the $R^1$ embodiments described above and herein is connected with the sulfur atom, G, E, or —C(O)— moiety in the L embodiments described above and herein.

In some embodiments, -L-$R^1$ is any combination of the L embodiments and $R^1$ embodiments described above and herein.

In some embodiments, -L-$R^1$ is -$L^3$-G-$R^1$ wherein each variable is independently as defined above and described herein.

In some embodiments, -L-$R^1$ is -$L^4$-G-$R^1$ wherein each variable is independently as defined above and described herein.

In some embodiments, -L-$R^1$ is -$L^3$-G-S—$R^{L2}$, wherein each variable is independently as defined above and described herein.

In some embodiments, -L-$R^1$ is -$L^3$-G-C(O)—$R^{L2}$, wherein each variable is independently as defined above and described herein.

In some embodiments, -L-$R^1$ is

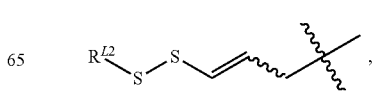

-continued

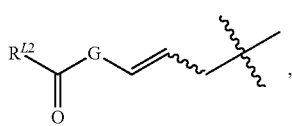

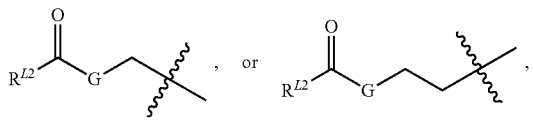

wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each G is independently as defined above and described herein.

In some embodiments, -L-R$^1$ is —R$^{L3}$—S—S—R$^{L2}$, wherein each variable is independently as defined above and described herein. In some embodiments, -L-R$^1$ is —R$^{L3}$—C(O)—S—S—R$^{L2}$, wherein each variable is independently as defined above and described herein.

In some embodiments, -L-R$^1$ has the structure of:

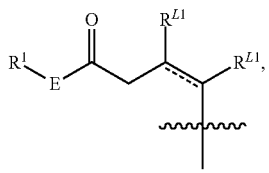

wherein each variable is independently as defined above and described herein.

In some embodiments, -L-R$^1$ has the structure of:

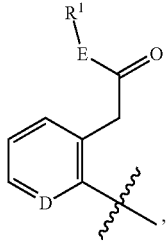

wherein each variable is independently as defined above and described herein.

In some embodiments, -L-R$^1$ has the structure of:

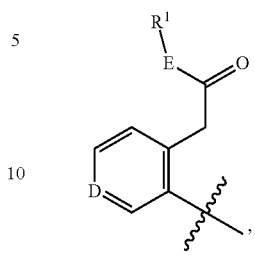

wherein each variable is independently as defined above and described herein.

In some embodiments, -L-R$^1$ has the structure of:

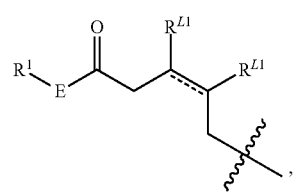

wherein each variable is independently as defined above and described herein.

In some embodiments, -L-R$^1$ has the structure of:

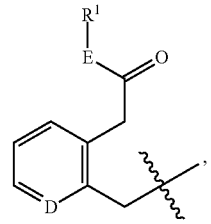

wherein each variable is independently as defined above and described herein.

In some embodiments, -L-R$^1$ has the structure of:

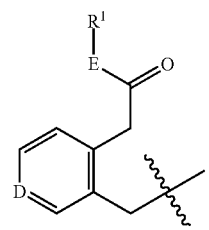

wherein each variable is independently as defined above and described herein.

In some embodiments, -L-R¹ has the structure of:

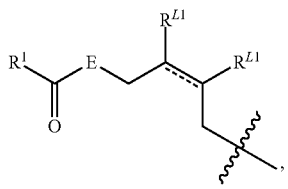

wherein each variable is independently as defined above and described herein.

In some embodiments, -L-R¹ has the structure of:

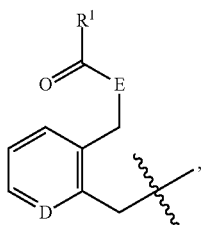

wherein each variable is independently as defined above and described herein.

In some embodiments, -L-R¹ has the structure of:

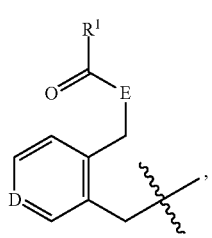

wherein each variable is independently as defined above and described herein.

In some embodiments, -L-R¹ has the structure of:

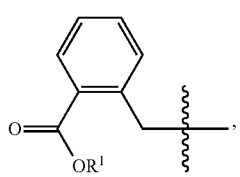

wherein each variable is independently as defined above and described herein.

In some embodiments, -L-R¹ has the structure of:

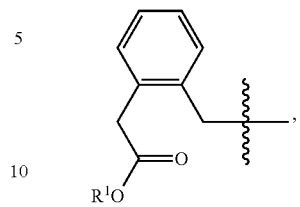

wherein each variable is independently as defined above and described herein.

In some embodiments, -L-R¹ has the structure of:

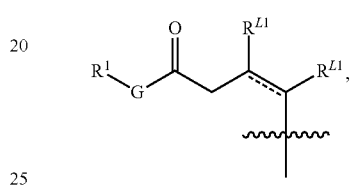

wherein each variable is independently as defined above and described herein.

In some embodiments, -L-R¹ has the structure of:

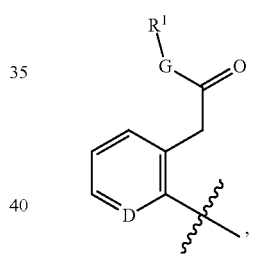

wherein each variable is independently as defined above and described herein.

In some embodiments, -L-R¹ has the structure of:

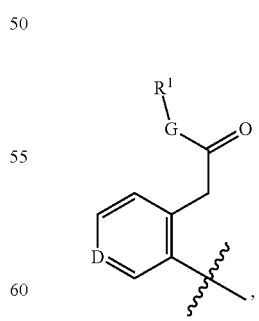

wherein each variable is independently as defined above and described herein.

In some embodiments, -L-R¹ has the structure of:

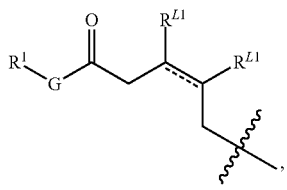

wherein each variable is independently as defined above and described herein.

In some embodiments, -L-R¹ has the structure of:

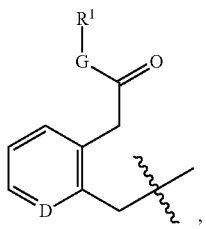

wherein each variable is independently as defined above and described herein.

In some embodiments, -L-R¹ has the structure of:

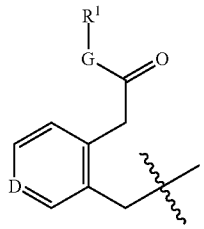

wherein each variable is independently as defined above and described herein.

In some embodiments, -L-R¹ has the structure of:

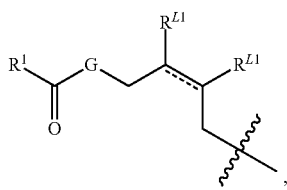

wherein each variable is independently as defined above and described herein.

In some embodiments, -L-R¹ has the structure of:

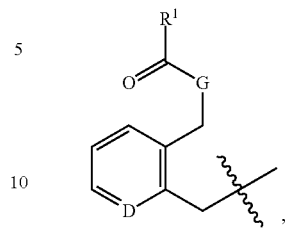

wherein each variable is independently as defined above and described herein.

In some embodiments, -L-R¹ has the structure of:

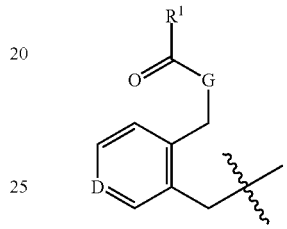

wherein each variable is independently as defined above and described herein.

In some embodiments, -L-R¹ has the structure of:

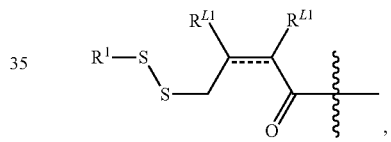

wherein each variable is independently as defined above and described herein.

In some embodiments, L has the structure of:

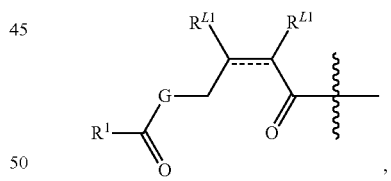

wherein each variable is independently as defined above and described herein.

In some embodiments, —X-L-R¹ has the structure of:

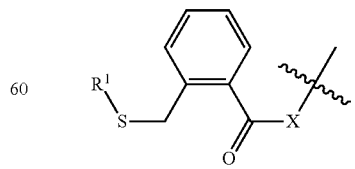

wherein:
the phenyl ring is optionally substituted, and
each of R¹ and X is independently as defined above and described herein.

In some embodiments, -L-R[1] is
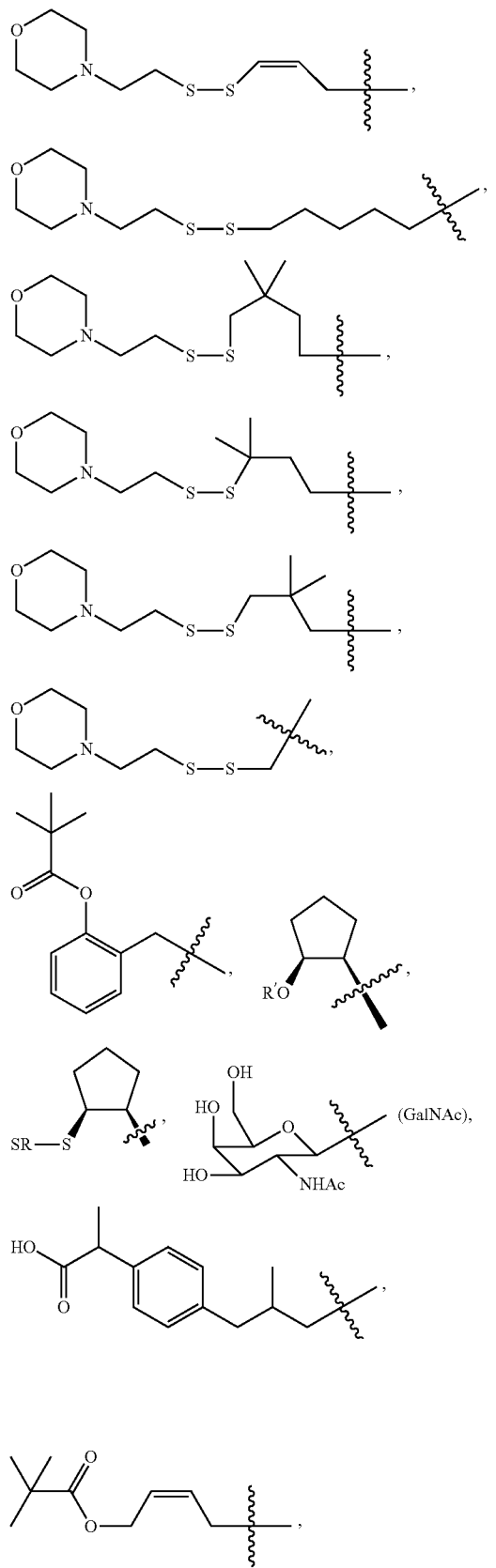
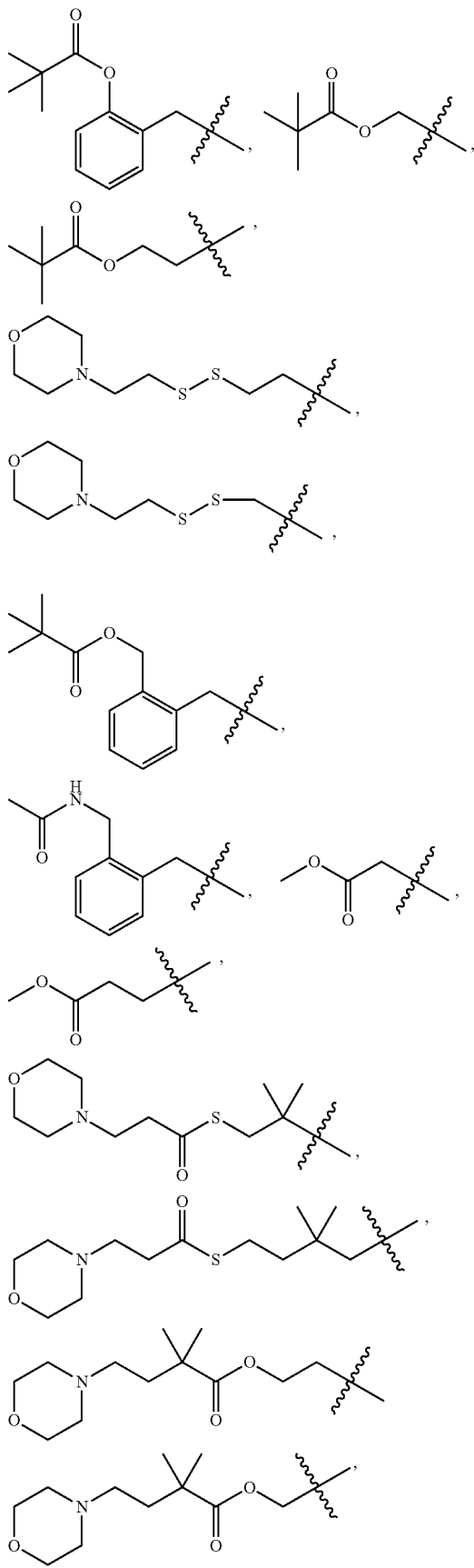

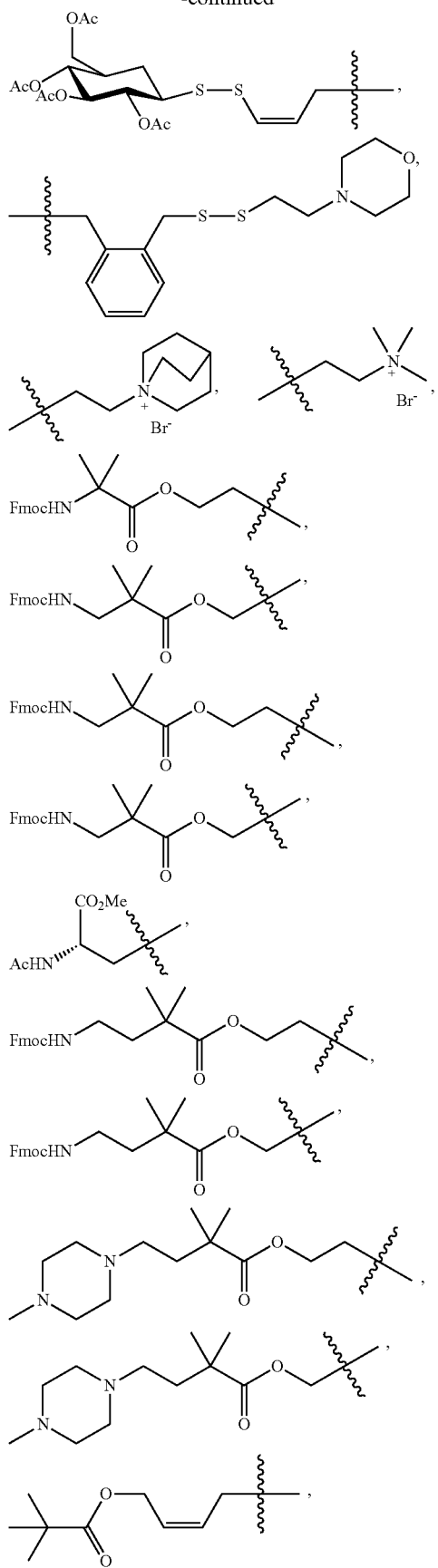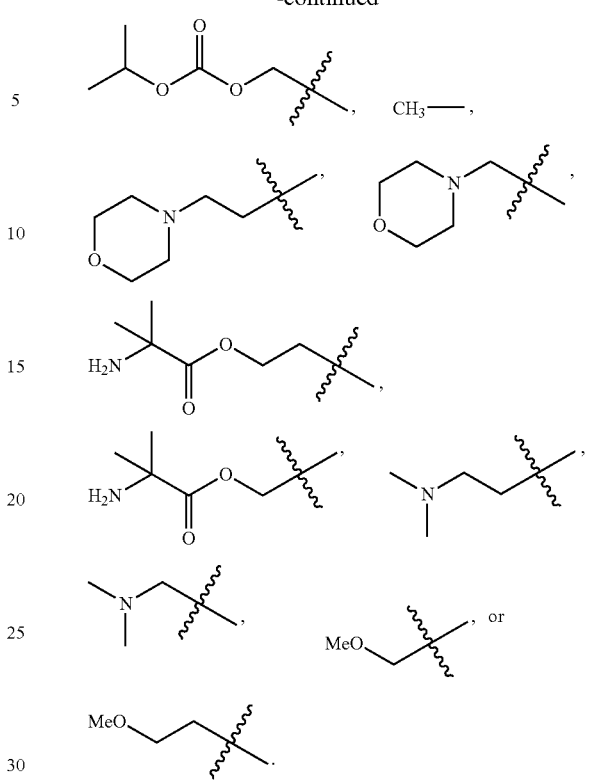
In some embodiments, -L-R[1] is:
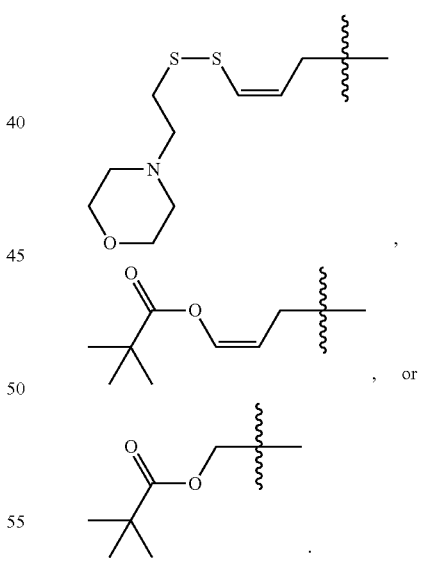
In some embodiments, -L-R[1] is CH₃—,
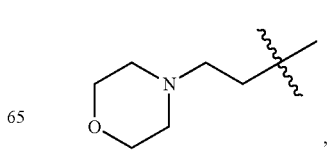

-continued

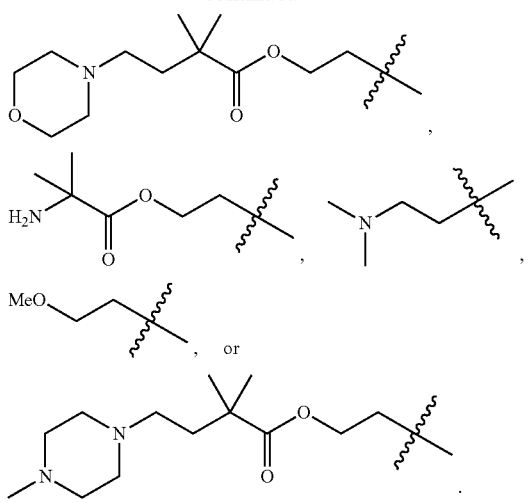

In some embodiments, -L-R$^1$ is

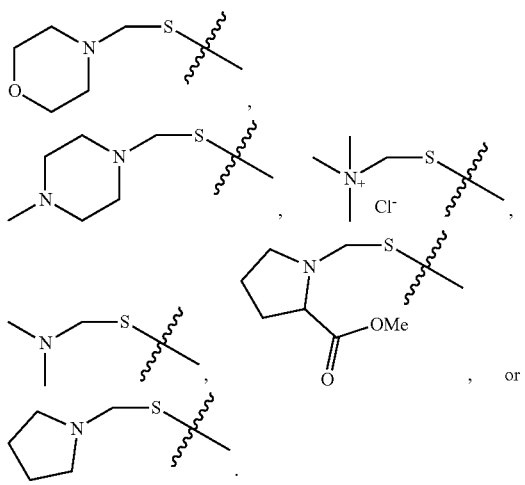

In some embodiments, -L-R$^1$ comprises a terminal optionally substituted —(CH$_2$)$_2$— moiety which is connected to X. In some embodiments, -L-R$^1$ comprises a terminal —(CH$_2$)$_2$— moiety which is connected to X. Examples of such -L-R$^1$ moieties are depicted below:

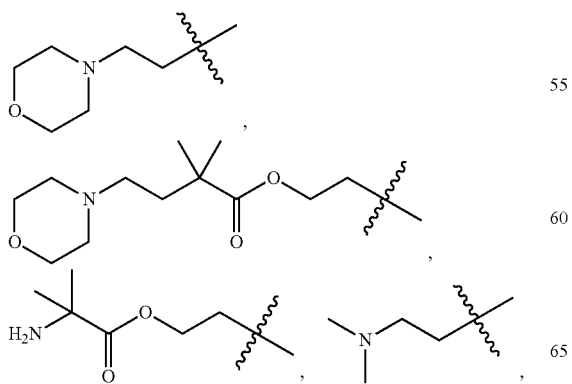

-continued

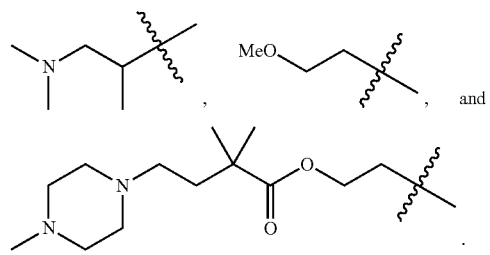

In some embodiments, -L-R$^1$ comprises a terminal optionally substituted —(CH$_2$)— moiety which is connected to X. In some embodiments, -L-R$^1$ comprises a terminal —(CH$_2$)— moiety which is connected to X. Examples of such -L-R$^1$ moieties are depicted below:

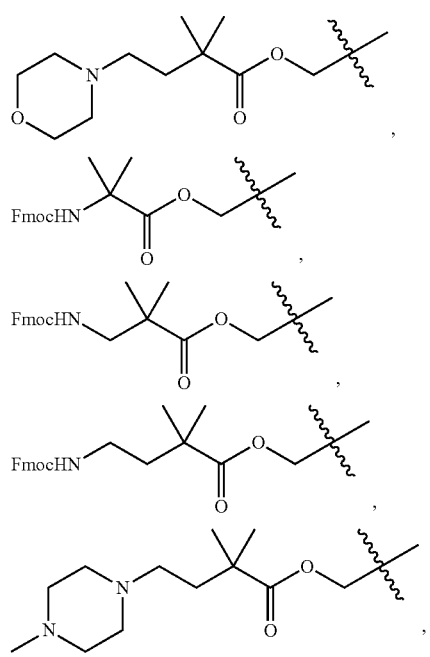

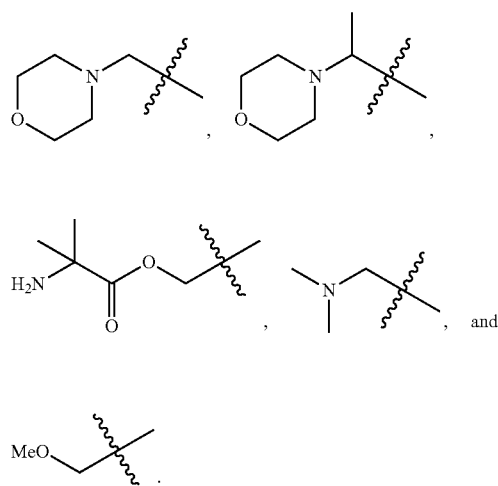

In some embodiments, -L-R¹ is
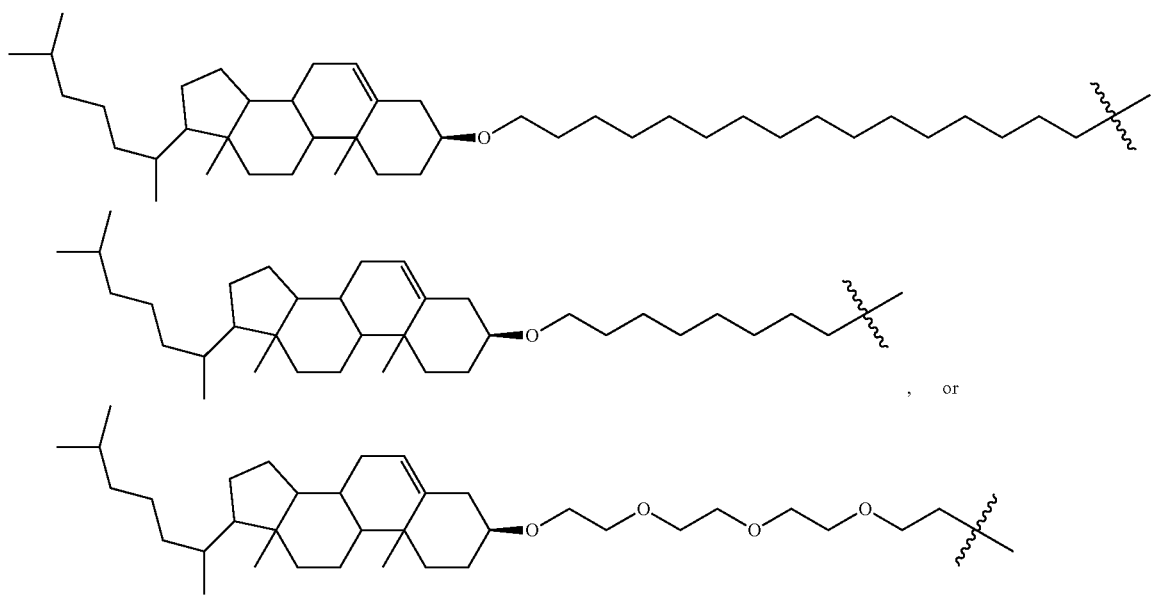
,
In some embodiments, -L-R¹ is CH₃—,
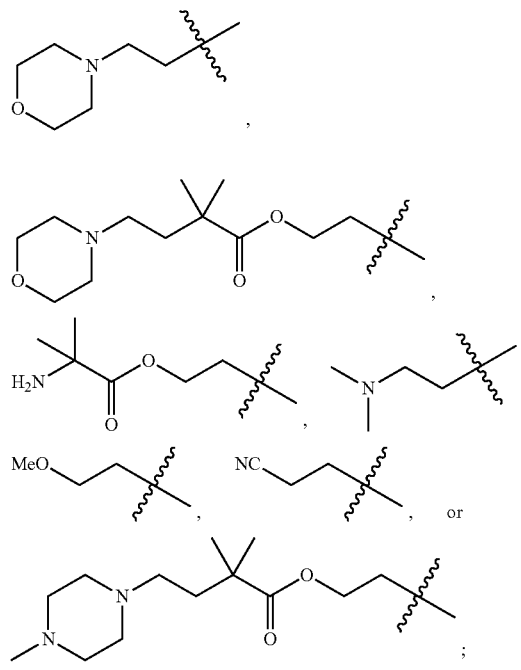
;
and X is —S—.
In some embodiments, -L-R¹ is CH₃—,
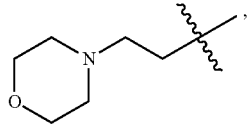
,
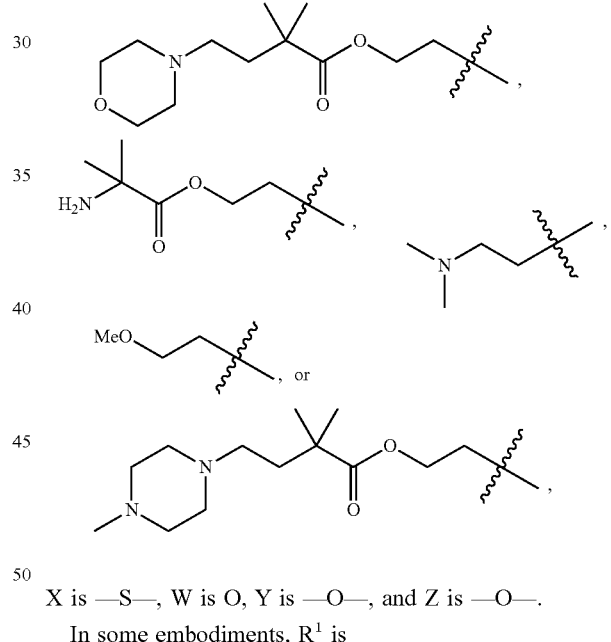
X is —S—, W is O, Y is —O—, and Z is —O—.
In some embodiments, R¹ is
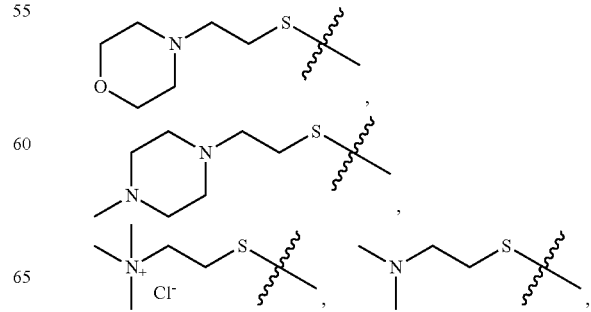

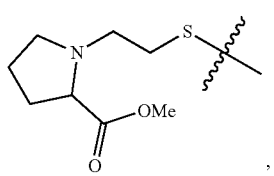
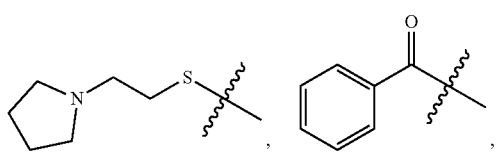
or —S—(C$_1$-C$_{10}$ aliphatic).
In some embodiments, R$^1$ is
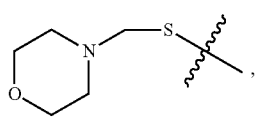
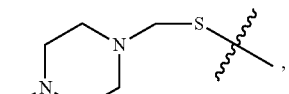
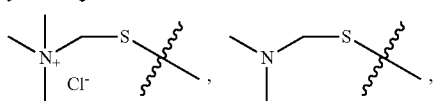
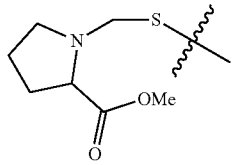, or
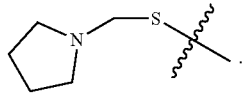.
In some embodiments, X is —O— or —S—, and R$^1$ is
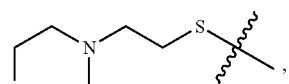
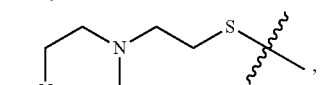
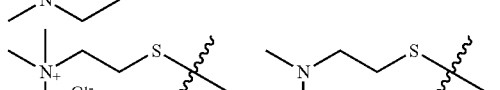
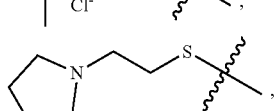
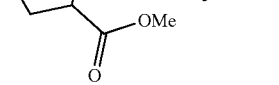
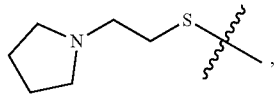
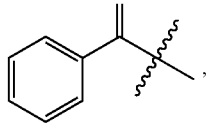
or —S—(C$_1$-C$_{10}$ aliphatic).
In some embodiments, X is —O— or —S—, and R$^1$ is
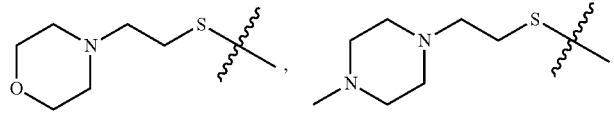
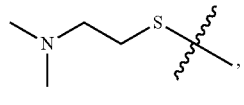
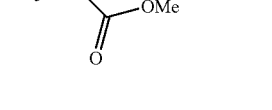
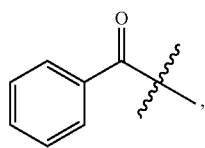
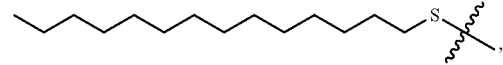
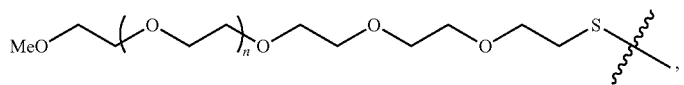

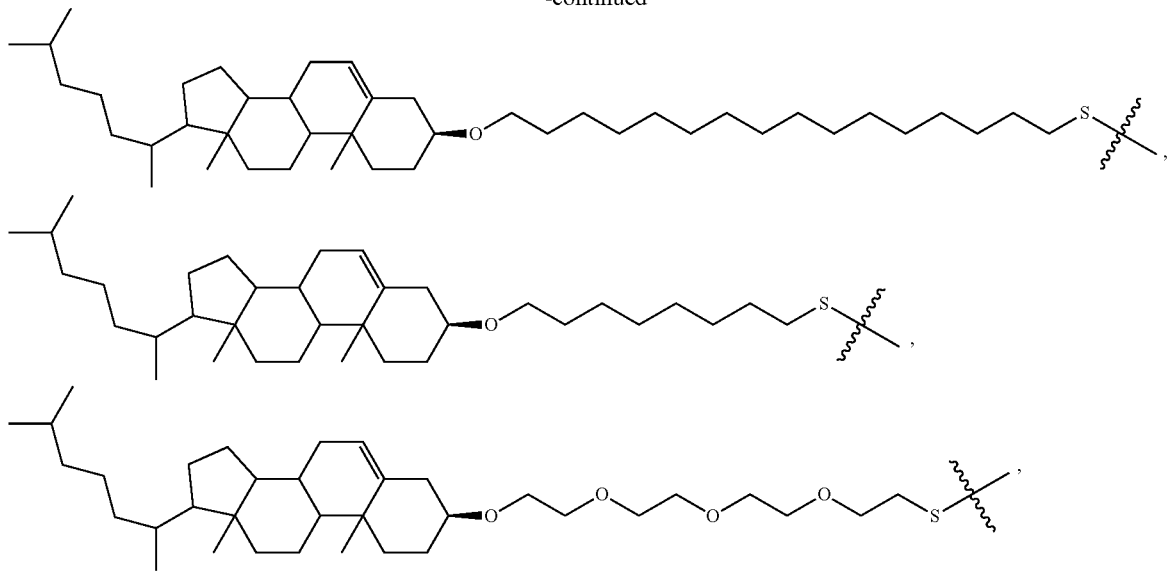
—S—($C_1$-$C_{10}$ aliphatic) or —S—($C_1$-$C_{50}$ aliphatic).
In some embodiments, L is a covalent bond and -L-$R^1$ is $R^1$.
In some embodiments, -L-$R^1$ is not hydrogen.
In some embodiments, —X-L-$R^1$ is $R^1$ is
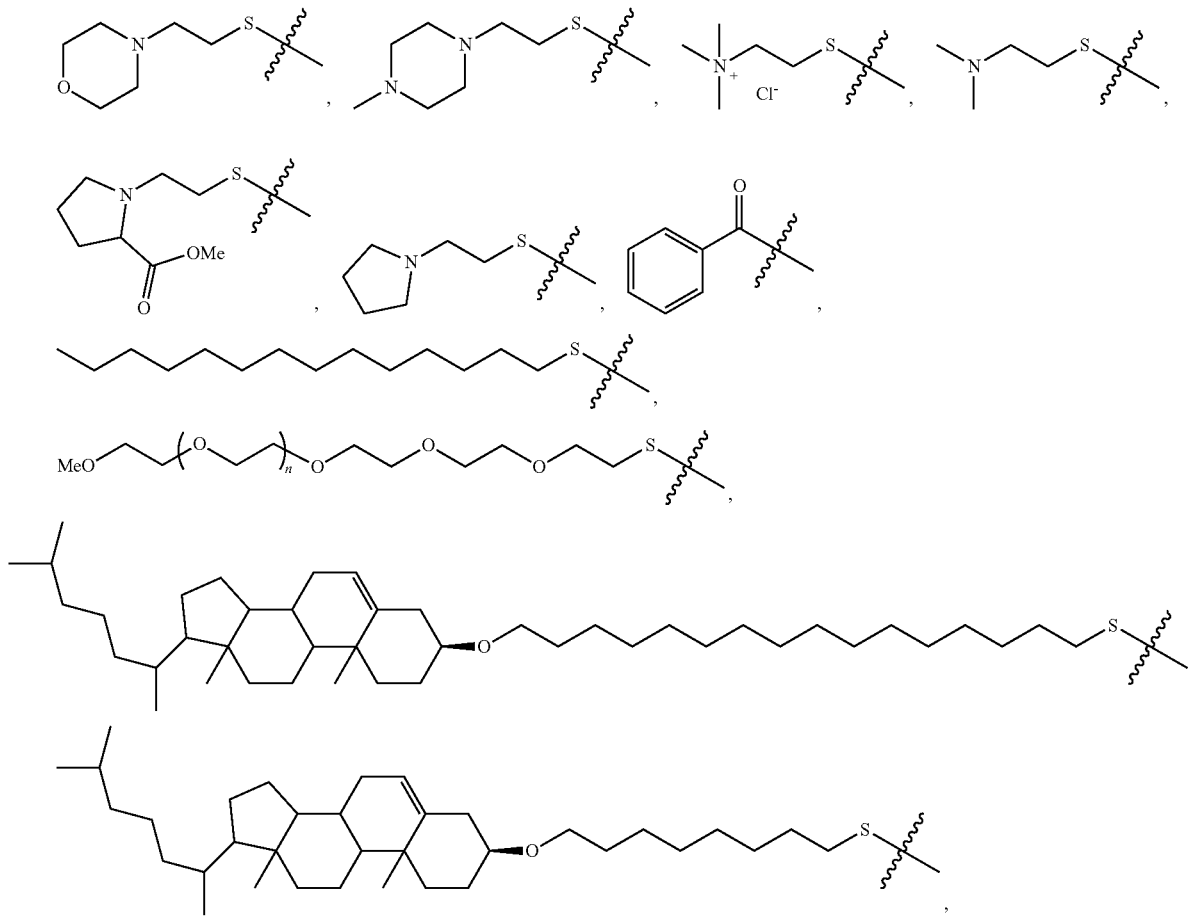

-continued

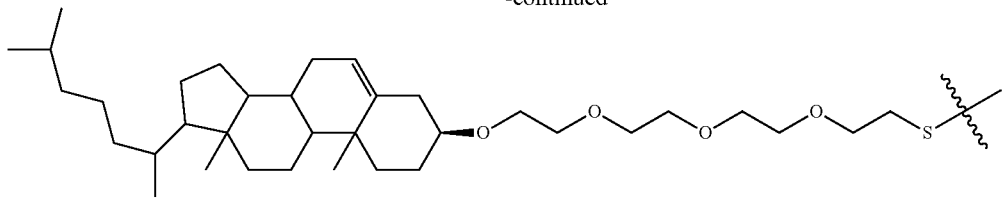

—S—(C$_1$-C$_{10}$ aliphatic) or —S—(C$_1$-C$_{50}$ aliphatic).

In some embodiments, —X-L-R$^1$ has the structure of

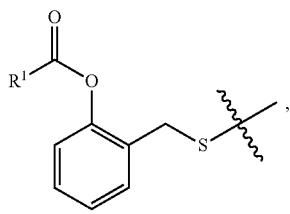

wherein the

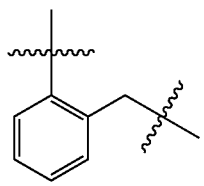 [SMILES: *Cc1ccccc1*]

moiety is optionally substituted. In some embodiments, —X-L-R$^1$ is

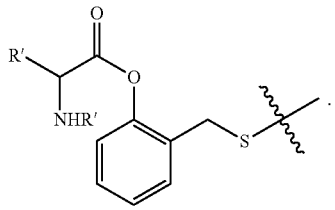

In some embodiments, —X-L-R$^1$ is.

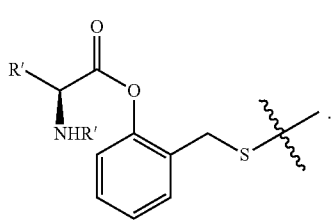

In some embodiments, —X-L-R$^1$ is

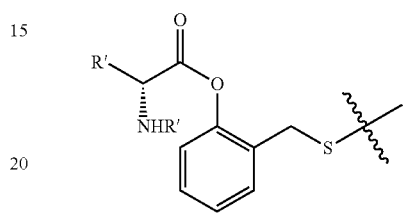

In some embodiments, —X-L-R$^1$ has the structure of

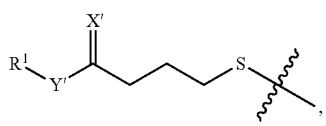

wherein X' is O or S, Y' is —O—, —S— or —NR'—, and the

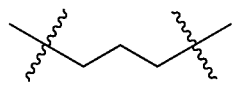 [SMILES: *CCC*]

moiety is optionally substituted. In some embodiments, Y' is —O—, —S— or —NH—. In some embodiments,

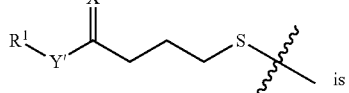

is

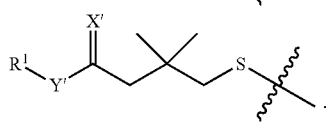

In some embodiments,

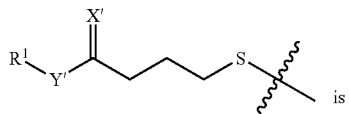

is

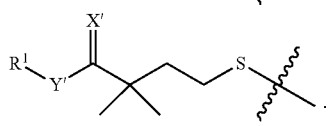

In some embodiments,

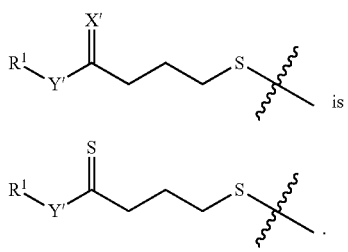

is

In some embodiments, —X-L-R¹ has the structure of

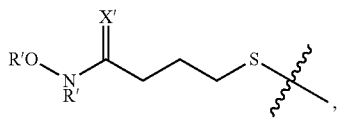

wherein X' is O or S, and the

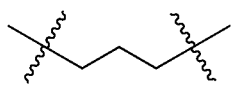

moiety is optionally substituted. In some embodiments,

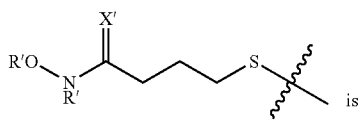

is

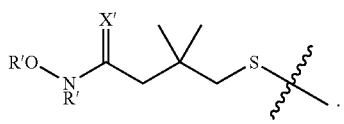

In some embodiments, —X-L-R¹ is

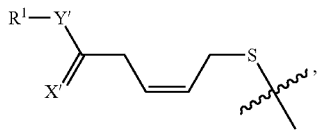

wherein the

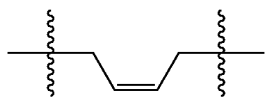

is optionally substituted. In some embodiments, —X-L-R¹ is

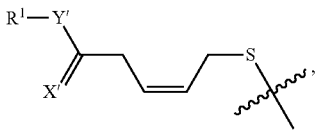

wherein the

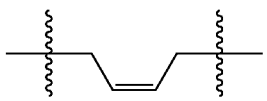

is substituted. In some embodiments, —X-L-R¹ is

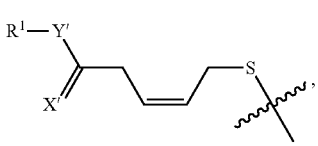

wherein the

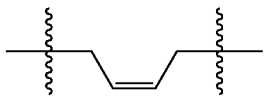 [SMILES: *C/C=C\C*]

is unsubstituted.

In some embodiments, —X-L-R¹ is R¹—C(O)—S-L$^x$-S—, wherein L$^x$ is an optionally substituted group selected from

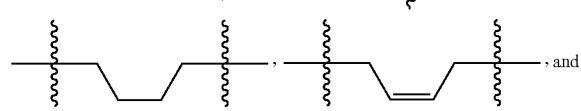

, and

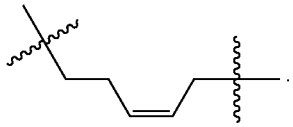

.

In some embodiments, L$^x$ is

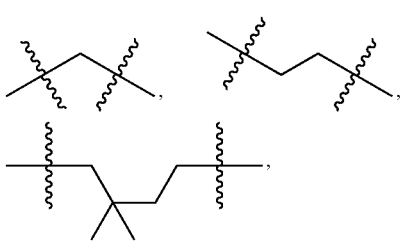

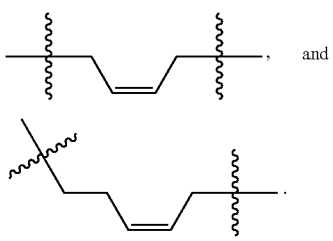, and

In some embodiments, —X-L-R$^1$ is (CH$_3$)$_3$C—S—S-L$^x$-S—. In some embodiments, —X-L-R$^1$ is R$^1$—C(=X')—Y'—C(R)$_2$—S-L$^x$-S—. In some embodiments, —X-L-R$^1$ is R—C(=X')—Y'—CH$_2$—S-L$^x$-S—. In some embodiments, —X-L-R$^1$ is

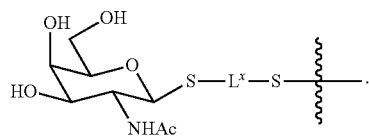

As will be appreciated by a person skilled in the art, many of the —X-L-R$^1$ groups described herein are cleavable and can be converted to —X— after administration to a subject. In some embodiments, —X-L-R$^1$ is cleavable. In some embodiments, —X-L-R$^1$ is —S-L-R$^1$, and is converted to —S— after administration to a subject. In some embodiments, the conversion is promoted by an enzyme of a subject. As appreciated by a person skilled in the art, methods of determining whether the —S-L-R$^1$ group is converted to —S— after administration is widely known and practiced in the art, including those used for studying drug metabolism and pharmacokinetics.

In some embodiments, the internucleotidic linkage having the structure of formula I is

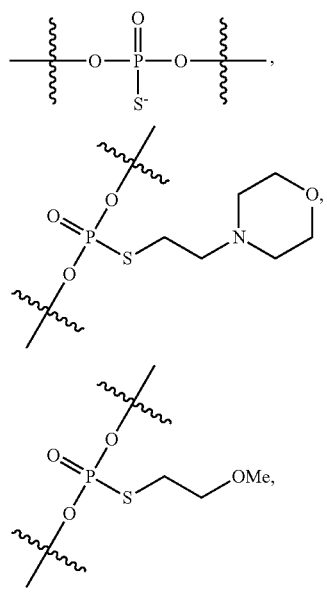

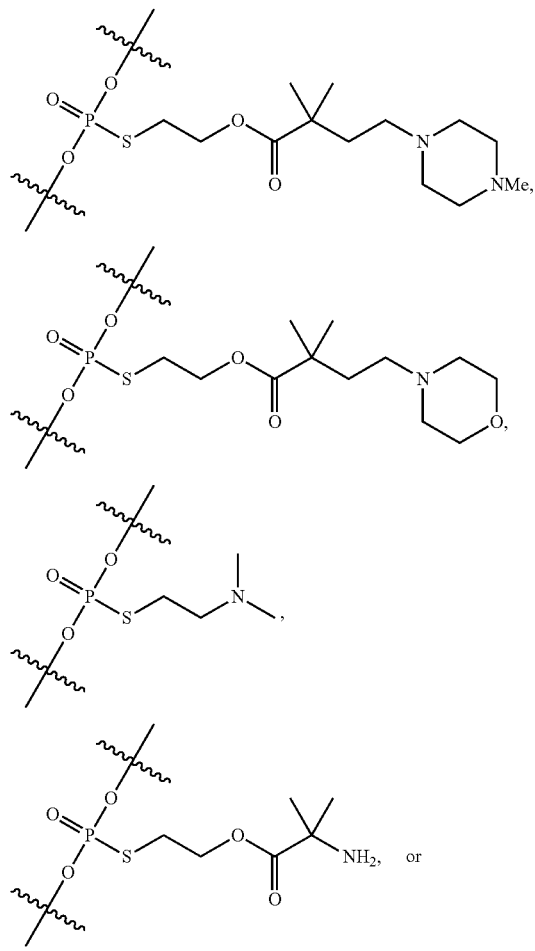

In some embodiments, the internucleotidic linkage of formula I has the structure of formula I-a:

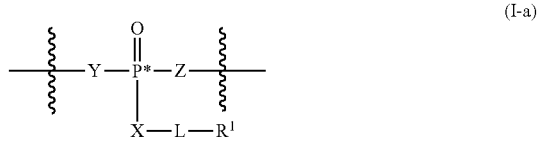

(I-a)

wherein each variable is independently as defined above and described herein.

In some embodiments, the internucleotidic linkage of formula I has the structure of formula I-b:

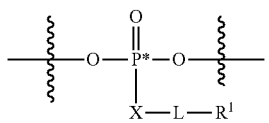

(I-b)

wherein each variable is independently as defined above and described herein.

In some embodiments, the internucleotidic linkage of formula I is an phosphorothioate triester linkage having the structure of formula I-c:

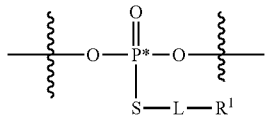

(I-c)

wherein:
P* is an asymmetric phosphorus atom and is either Rp or Sp;
L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
  two R' on the same nitrogen are taken together with their intervening atoms to form an optionally substituted heterocyclic or heteroaryl ring, or
  two R' on the same carbon are taken together with their intervening atoms to form an optionally substituted aryl, carbocyclic, heterocyclic, or heteroaryl ring;
Cy- is an optionally substituted bivalent ring selected from phenylene, carbocyclylene, arylene, heteroarylene, or heterocyclylene;
each R is independently hydrogen, or an optionally substituted group selected from $C_1$-$C_6$ aliphatic, phenyl, carbocyclyl, aryl, heteroaryl, or heterocyclyl;
each independently represents a connection to a nucleoside; and
$R^1$ is not —H when L is a covalent bond.

In some embodiments, the internucleotidic linkage having the structure of formula I is

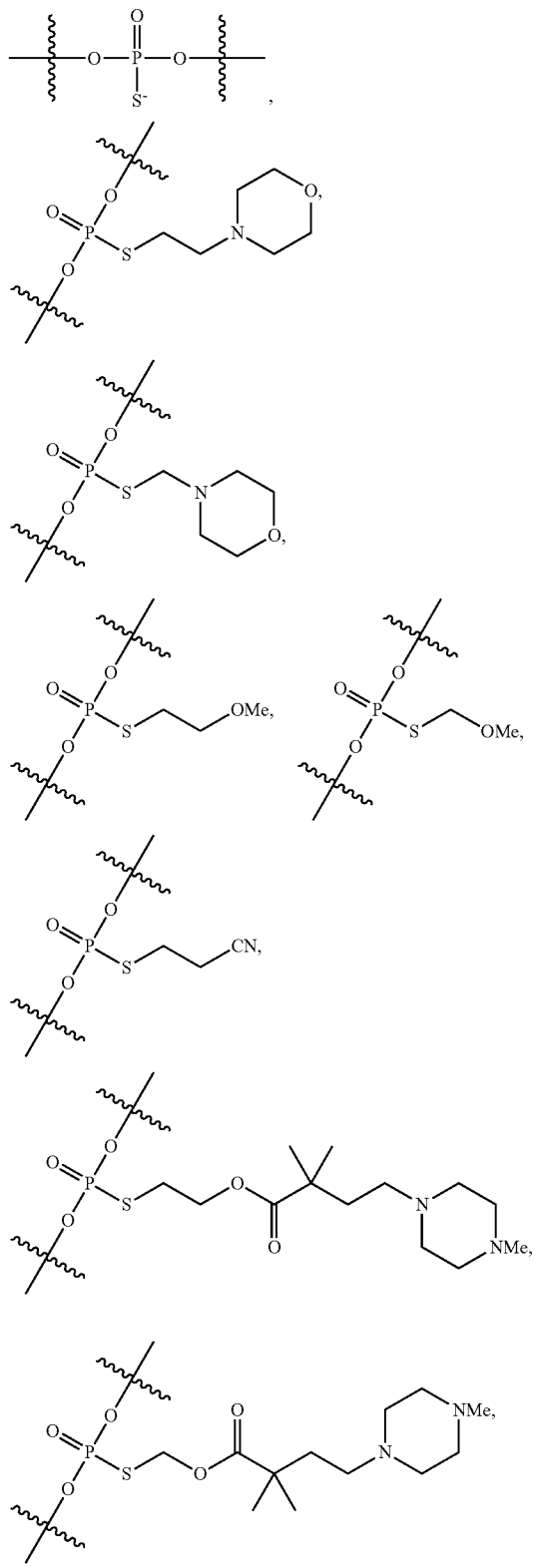

217
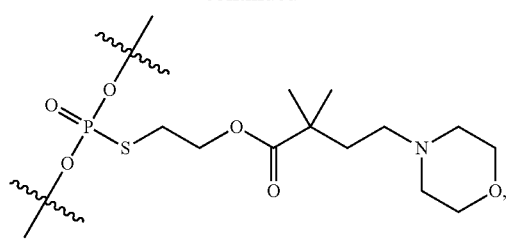
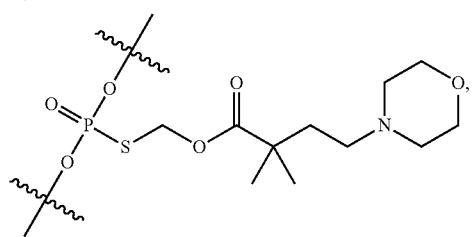
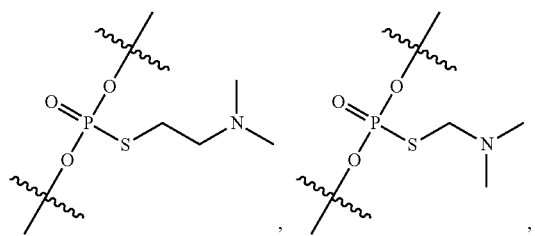
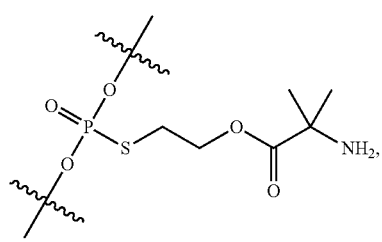
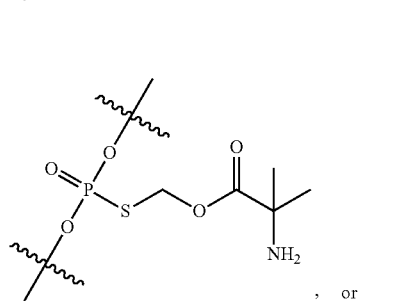
, or
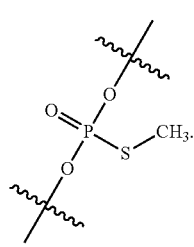 [SMILES: *OP(=O)(O*)SC]
218
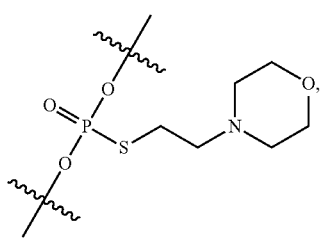
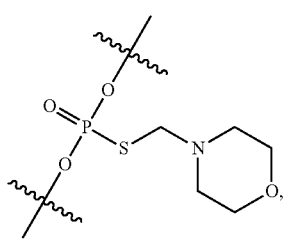
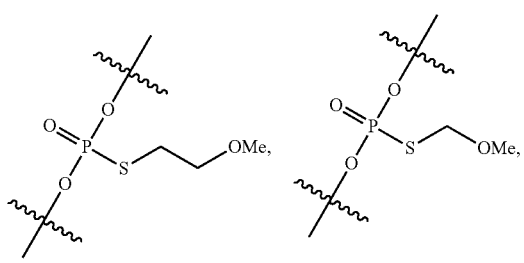
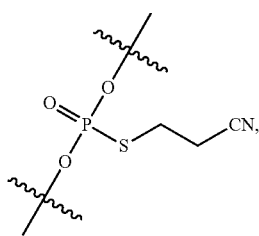
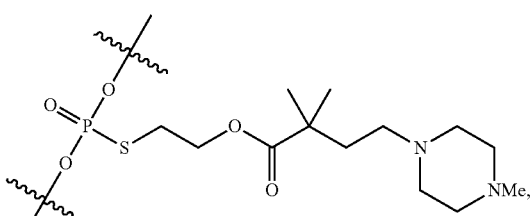
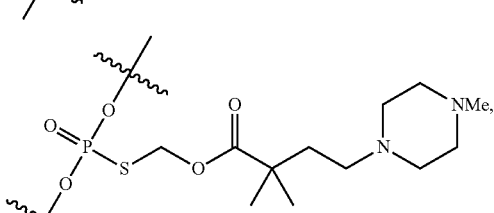
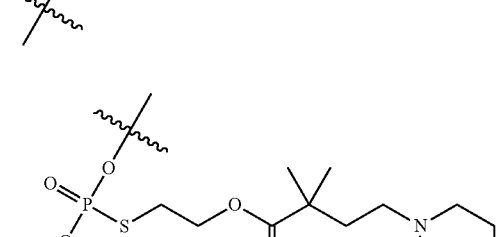
In some embodiments, the internucleotidic linkage having the structure of formula I-c is

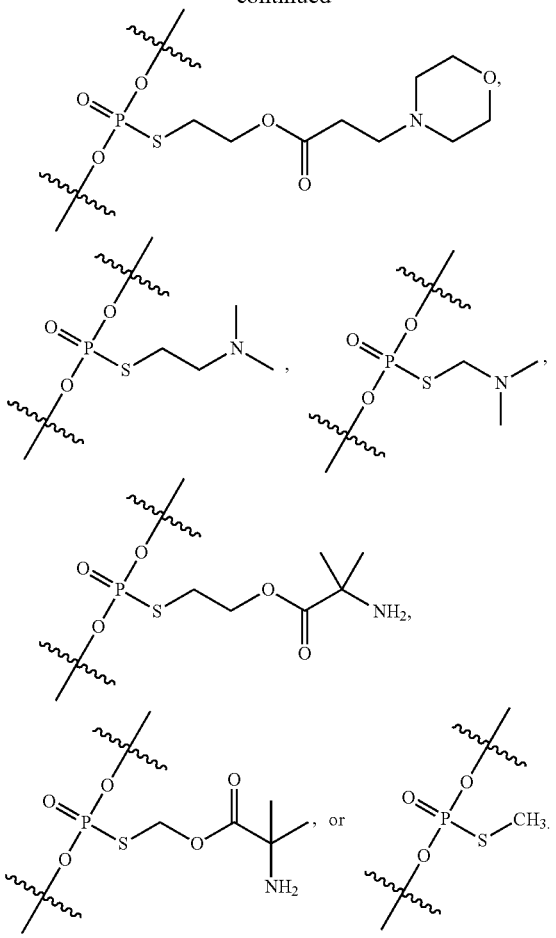

In some embodiments, the present disclosure provides a chirally controlled oligonucleotide comprising one or more phosphate diester linkages, and one or more modified internucleotide linkages having the formula of I-a, I-b, or I-c.

In some embodiments, the present disclosure provides a chirally controlled oligonucleotide comprising at least one phosphate diester internucleotidic linkage and at least one phosphorothioate triester linkage having the structure of formula I-c. In some embodiments, the present disclosure provides a chirally controlled oligonucleotide comprising at least one phosphate diester internucleotidic linkage and at least two phosphorothioate triester linkages having the structure of formula I-c. In some embodiments, the present disclosure provides a chirally controlled oligonucleotide comprising at least one phosphate diester internucleotidic linkage and at least three phosphorothioate triester linkages having the structure of formula I-c. In some embodiments, the present disclosure provides a chirally controlled oligonucleotide comprising at least one phosphate diester internucleotidic linkage and at least four phosphorothioate triester linkages having the structure of formula I-c. In some embodiments, the present disclosure provides a chirally controlled oligonucleotide comprising at least one phosphate diester internucleotidic linkage and at least five phosphorothioate triester linkages having the structure of formula I-c.

In some embodiments, the present disclosure provides a chirally controlled oligonucleotide comprising a sequence found in GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 50% identity with GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 60% identity with GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 70% identity with GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 80% identity with GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 90% identity with GGCACAAGGGCACAGACTTC (SEQ ID NO: 41). In some embodiments, the present disclosure provides a chirally controlled oligonucleotide comprising a sequence found in GGCACAAGGGCACAGACTTC (SEQ ID NO: 41), wherein the said sequence has over 95% identity with GGCACAAGGGCACAGACTTC (SEQ ID NO: 41). In some embodiments, the present disclosure provides a chirally controlled oligonucleotide comprising the sequence of GGCACAAGGGCACAGACTTC (SEQ ID NO: 41). In some embodiments, the present disclosure provides a chirally controlled oligonucleotide having the sequence of GGCACAAGGGCACAGACTTC (SEQ ID NO: 41).

In some embodiments, the present disclosure provides a chirally controlled oligonucleotide comprising a sequence found in GGCACAAGGGCACAGACTTC (SEQ ID NO: 41), wherein at least one internucleotidic linkage has a chiral linkage phosphorus. In some embodiments, the present disclosure provides a chirally controlled oligonucleotide comprising a sequence found in GGCACAAGGGCACAGACTTC (SEQ ID NO: 41), wherein at least one internucleotidic linkage has the structure of formula I. In some embodiments, the present disclosure provides a chirally controlled oligonucleotide comprising a sequence found in GGCACAAGGGCACAGACTTC (SEQ ID NO: 41), wherein each internucleotidic linkage has the structure of formula I. In some embodiments, the present disclosure provides a chirally controlled oligonucleotide comprising a sequence found in GGCACAAGGGCACAGACTTC (SEQ ID NO: 41), wherein at least one internucleotidic linkage has the structure of formula I-c. In some embodiments, the present disclosure provides a chirally controlled oligonucleotide comprising a sequence found in GGCACAAGGGCACAGACTTC (SEQ ID NO: 41), wherein each internucleotidic linkage has the structure of formula I-c. In some embodiments, the present disclosure provides a chirally controlled oligonucleotide comprising a sequence found in GGCACAAGGGCACAGACTTC (SEQ ID NO: 41), wherein at least one internucleotidic

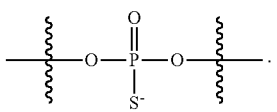 [SMILES: *OP(=O)([S-])O*]

linkage is In some embodiments, the present disclosure provides a chirally controlled oligonucleotide comprising a sequence found in GGCACAAGGGCACAGACTTC

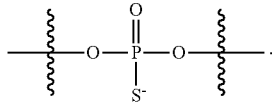

(SEQ ID NO: 41), wherein each internucleotidic linkage is In some embodiments, the present disclosure provides a chirally controlled oligonucleotide comprising a sequence found in GGCACAAGGGCACAGACTTC (SEQ ID NO: 41), wherein at least one

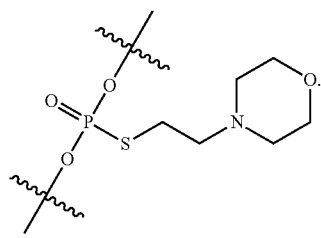 [SMILES: *OP(=O)(O*)SCCN1CCOCC1]

internucleotidic linkage In some embodiments, the present disclosure provides a chirally controlled oligonucleotide comprising a sequence found in GGCACAAGGGCACAGACTTC (SEQ ID NO: 41), wherein each internucleotidic linkage is

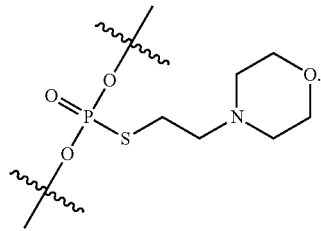 [SMILES: *OP(=O)(O*)SCCN1CCOCC1]

In some embodiments, the present disclosure provides a chirally controlled oligonucleotide comprising the sequence of GGCACAAGGGCACAGACTTC (SEQ ID NO: 41), wherein at least one internucleotidic linkage has a chiral linkage phosphorus. In some embodiments, the present disclosure provides a chirally controlled oligonucleotide comprising the sequence of GGCACAAGGGCACAGACTTC (SEQ ID NO: 41), wherein at least one internucleotidic linkage has the structure of formula I. In some embodiments, the present disclosure provides a chirally controlled oligonucleotide comprising the sequence of GGCACAAGGGCACAGACTTC (SEQ ID NO: 41), wherein each internucleotidic linkage has the structure of formula I. In some embodiments, the present disclosure provides a chirally controlled oligonucleotide comprising the sequence of GGCACAAGGGCACAGACTTC (SEQ ID NO: 41), wherein at least one internucleotidic linkage has the structure of formula I-c. In some embodiments, the present disclosure provides a chirally controlled oligonucleotide comprising the sequence of GGCACAAGGGCACAGACTTC (SEQ ID NO: 41), wherein each internucleotidic linkage has the structure of formula I-c. In some embodiments, the present disclosure provides a chirally controlled oligonucleotide comprising the sequence of GGCACAAGGGCACAGACTTC (SEQ ID NO: 41), wherein at least one internucleotidic

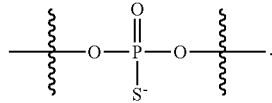 [SMILES: *OP(=O)([S-])O*]

linkage is In some embodiments, the present disclosure provides a chirally controlled oligonucleotide comprising the sequence of GGCACAAGGGCACAGACTTC (SEQ ID NO: 41), wherein each internucleotidic linkage is

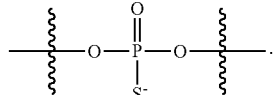

In some embodiments, the present disclosure provides a chirally controlled oligonucleotide comprising the sequence of GGCACAAGGGCACAGACTTC (SEQ ID NO: 41), wherein at least one internucleotidic

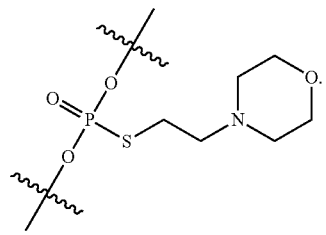 [SMILES: *OP(=O)(O*)SCCN1CCOCC1]

linkage is In some embodiments, the present disclosure provides a chirally controlled oligonucleotide comprising the sequence of GGCACAAGGGCACAGACTTC (SEQ ID NO: 41), wherein each internucleotidic linkage is

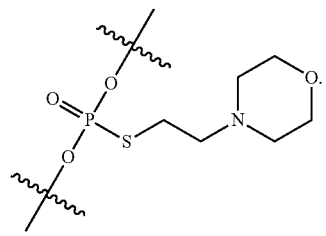 [SMILES: *OP(=O)(O*)SCCN1CCOCC1]

In some embodiments, the present disclosure provides a chirally controlled oligonucleotide having the sequence of GGCACAAGGGCACAGACTTC (SEQ ID NO: 41), wherein at least one internucleotidic linkage has a chiral linkage phosphorus. In some embodiments, the present disclosure provides a chirally controlled oligonucleotide having the sequence of GGCACAAGGGCACAGACTTC (SEQ ID NO: 41), wherein at least one internucleotidic linkage has the structure of formula I. In some embodiments, the present disclosure provides a chirally controlled oligonucleotide having the sequence of GGCACAAGGGCACA-GACTTC (SEQ ID NO: 41), wherein each internucleotidic linkage has the structure of formula I. In some embodiments, the present disclosure provides a chirally controlled oligonucleotide having the sequence of GGCACAAGGGCACAGACTTC (SEQ ID NO: 41), wherein at least one internucleotidic linkage has the structure of formula I-c. In some embodiments, the present disclosure provides a chirally controlled oligonucleotide having the sequence of GGCACAAGGGCACAGACTTC (SEQ ID NO: 41), wherein each internucleotidic linkage has the structure of formula I-c. In some embodiments, the present disclosure provides a chirally controlled oligonucleotide having the sequence of GGCACAAGGGCACAGACTTC

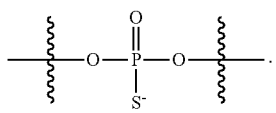 [SMILES: *OP(=O)([S-])O*]

(SEQ ID NO: 41), wherein at least one internucleotidic linkage is In some embodiments, the present disclosure provides a chirally controlled oligonucleotide having the sequence of GGCACAAGGGCACAGACTTC (SEQ ID NO: 41), wherein each internucleotidic

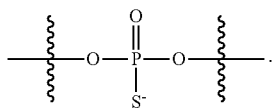

linkage is In some embodiments, the present disclosure provides a chirally controlled oligonucleotide having the sequence of GGCACAAGGGCACAGACTTC (SEQ ID NO: 41), wherein at least one internucleotidic linkage is

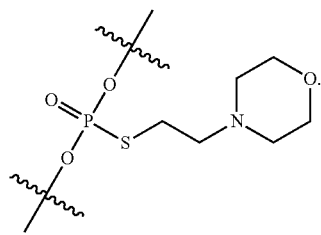 [SMILES: *OP(=O)(O*)SCCN1CCOCC1]

In some embodiments, the present disclosure provides a chirally controlled oligonucleotide having the sequence of GGCACAAGGGCACAGACTTC (SEQ ID NO: 41), wherein each internucleotidic

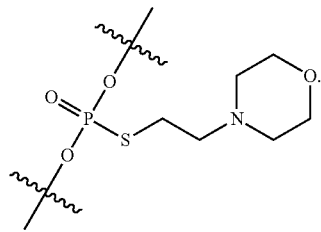 [SMILES: *OP(=O)(O*)SCCN1CCOCC1]

linkage is
In some embodiments, the present disclosure provides a chirally controlled oligonucleotide having the sequence of GGCACAAGGGCACAGACTTC (SEQ ID NO: 41), wherein at least one linkage phosphorus is Rp. It is understood by a person of ordinary skill in the art that in certain embodiments wherein the chirally controlled oligonucleotide comprises an RNA sequence, each T is independently and optionally replaced with U. In some embodiments, the present disclosure provides a chirally controlled oligonucleotide having the sequence of GGCACAAGGGCACAGACTTC (SEQ ID NO: 41), wherein each linkage phosphorus is Rp. In some embodiments, the present disclosure provides a chirally controlled oligonucleotide having the sequence of GGCACAAGGGCACAGACTTC (SEQ ID NO: 41), wherein at least one linkage phosphorus is Sp. In some embodiments, the present disclosure provides a chirally controlled oligonucleotide having the sequence of GGCACAAGGGCACAGACTTC (SEQ ID NO: 41), wherein each linkage phosphorus is Sp. In some embodiments, the present disclosure provides a chirally controlled oligonucleotide having the sequence of GGCACAAGGGCACAGACTTC (SEQ ID NO: 41), wherein the oligonucleotide is a blockmer. In some embodiments, the present disclosure provides a chirally controlled oligonucleotide having the sequence of GGCACAAGGGCACAGACTTC (SEQ ID NO: 41), wherein the oligonucleotide is a stereoblockmer. In some embodiments, the present disclosure provides a chirally controlled oligonucleotide having the sequence of GGCACAAGGGCACAGACTTC (SEQ ID NO: 41), wherein the oligonucleotide is a P-modification blockmer. In some embodiments, the present disclosure provides a chirally controlled oligonucleotide having the sequence of GGCACAAGGGCACAGACTTC (SEQ ID NO: 41), wherein the oligonucleotide is a linkage blockmer. In some embodiments, the present disclosure provides a chirally controlled oligonucleotide having the sequence of GGCACAAGGGCACAGACTTC (SEQ ID NO: 41), wherein the oligonucleotide is an altmer. In some embodiments, the present disclosure provides a chirally controlled oligonucleotide having the sequence of GGCACAAGGGCACAGACTTC (SEQ ID NO: 41), wherein the oligonucleotide is a stereoaltmer. In some embodiments, the present disclosure provides a chirally controlled oligonucleotide having the sequence of GGCACAAGGGCACAGACTTC (SEQ ID NO: 41), wherein the oligonucleotide is a P-modification altmer. In some embodiments, the present disclosure provides a chirally controlled oligonucleotide having the sequence of GGCACAAGGGCACAGACTTC (SEQ ID NO: 41), wherein the oligonucleotide is a linkage altmer. In some embodiments, the present disclosure provides a chirally controlled oligonucleotide having the sequence of GGCACAAGGGCACAGACTTC (SEQ ID NO: 41), wherein the oligonucleotide is a unimer. In some embodiments, the present disclosure provides a chirally controlled oligonucleotide having the sequence of GGCACAAGGGCACAGACTTC (SEQ ID NO: 41), wherein the oligonucleotide is a stereounimer. In some embodiments, the present disclosure provides a chirally controlled oligonucleotide having the sequence of GGCACAAGGGCACAGACTTC (SEQ ID NO: 41), wherein the oligonucleotide is a P-modification unimer. In some embodiments, the present disclosure provides a chirally controlled oligonucleotide having the sequence of GGCACAAGGGCACAGACTTC (SEQ ID NO: 41), wherein the oligonucleotide is a linkage unimer. In some embodiments, the present disclosure provides a chirally controlled oligonucleotide having the sequence of GGCACAAGGGCACAGACTTC (SEQ ID NO: 41), wherein the oligonucleotide is a gapmer. In some embodiments, the present disclosure provides a chirally controlled oligonucleotide having the sequence of GGCA-CAAGGGCACAGACTTC (SEQ ID NO: 41), wherein the oligonucleotide is a skipmer.

In some embodiments, the present disclosure provides a chirally controlled oligonucleotide having the sequence of GGCACAAGGGCACAGACTTC (SEQ ID NO: 41), wherein each cytosine is optionally and independently replaced by 5-methylcytosine. In some embodiments, the present disclosure provides a chirally controlled oligonucleotide having the sequence of GGCACAAGGGCACAGACTTC (SEQ ID NO: 41), wherein at least one cytosine is optionally and independently replaced by 5-methylcytosine. In some embodiments, the present disclosure provides a chirally controlled oligonucleotide having the sequence of GGCACAAGGGCACAGACTTC (SEQ ID NO: 41), wherein each cytosine is optionally and independently replaced by 5-methylcytosine.

In some embodiments, a chirally controlled oligonucleotide is designed such that one or more nucleotides comprise a phosphorus modification prone to "autorelease" under certain conditions. That is, under certain conditions, a particular phosphorus modification is designed such that it self-cleaves from the oligonucleotide to provide, e.g., a phosphate diester such as those found in naturally occurring DNA and RNA. In some embodiments, such a phosphorus modification has a structure of wherein each of L and R' is independently as defined above and described herein. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a phosphate diester as is found in naturally occurring DNA and RNA.

In some embodiments, the present disclosure provides a chirally controlled oligonucleotide comprising any sequence disclosed herein (including, as non-limiting examples, any sequence disclosed in any Table). In some embodiments, the present disclosure provides a chirally controlled oligonucleotide comprising a sequence having over 50% identity with any sequence disclosed herein. In some embodiments, the present disclosure provides a chirally controlled oligonucleotide comprising a sequence having over 60% identity with any sequence disclosed herein. In some embodiments, the present disclosure provides a chirally controlled oligonucleotide comprising a sequence having over 70% identity with any sequence disclosed herein. In some embodiments, the present disclosure provides a chirally controlled oligonucleotide comprising a sequence having over 80% identity with any sequence disclosed herein. In some embodiments, the present disclosure provides a chirally controlled oligonucleotide comprising a sequence having over 90% identity with any sequence disclosed herein. In some embodiments, the present disclosure provides a chirally controlled oligonucleotide comprising a sequence having over 95% identity with any sequence disclosed herein. In some embodiments, the present disclosure provides a chirally controlled oligonucleotide comprising any sequence disclosed herein. In some embodiments, the present disclosure provides a chirally controlled oligonucleotide having any sequence disclosed herein.

In some embodiments, the present disclosure provides a chirally controlled oligonucleotide comprising any sequence disclosed herein, wherein at least one internucleotidic linkage has a chiral linkage phosphorus. In some embodiments, the present disclosure provides a chirally controlled oligonucleotide comprising any sequence disclosed herein, wherein at least one internucleotidic linkage has the structure of formula I. In some embodiments, the present disclosure provides a chirally controlled oligonucleotide comprising any sequence disclosed herein, wherein each internucleotidic linkage has the structure of formula I. In some embodiments, the present disclosure provides a chirally controlled oligonucleotide comprising any sequence disclosed herein, wherein at least one internucleotidic linkage has the structure of formula I-c. In some embodiments, the present disclosure provides a chirally controlled oligonucleotide comprising any sequence disclosed herein, wherein each internucleotidic linkage has the structure of formula I-c. In some embodiments, the present disclosure provides a chirally controlled oligonucleotide comprising any sequence disclosed herein, wherein at least one internucleotidic linkage is

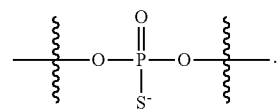

In some embodiments, the present disclosure provides a chirally controlled oligonucleotide comprising any sequence disclosed herein, wherein each internucleotidic linkage is

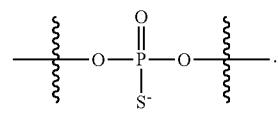 [SMILES: *OP(=O)([S-])O*]

In some embodiments, the present disclosure provides a chirally controlled oligonucleotide comprising any sequence disclosed herein, wherein at least one internucleotidic linkage is

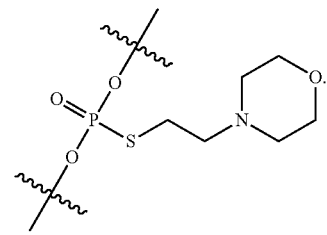 [SMILES: *OP(=O)(O*)SCCN1CCOCC1]

In some embodiments, the present disclosure provides a chirally controlled oligonucleotide comprising any sequence disclosed herein, wherein each internucleotidic linkage is

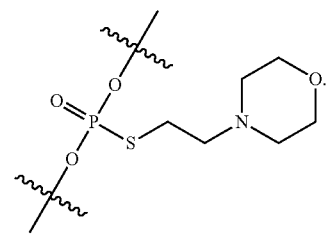 [SMILES: *OP(=O)(O*)SCCN1CCOCC1]

In some embodiments, the present disclosure provides a chirally controlled oligonucleotide comprising any sequence disclosed herein, wherein at least one internucleotidic linkage has a chiral linkage phosphorus. In some embodiments, the present disclosure provides a chirally controlled oligonucleotide comprising any sequence disclosed herein, wherein at least one internucleotidic linkage has the structure of formula I. In some embodiments, the present disclosure provides a chirally controlled oligonucleotide comprising any sequence disclosed herein, wherein each internucleotidic linkage has the structure of formula I. In some embodiments, the present disclosure provides a chirally controlled oligonucleotide comprising any sequence disclosed herein, wherein at least one internucleotidic linkage has the structure of formula I-c. In some embodiments, the present disclosure provides a chirally controlled oligonucleotide comprising any sequence disclosed herein, wherein each internucleotidic linkage has the structure of formula I-c. In some embodiments, the present disclosure provides a chirally controlled oligonucleotide comprising any sequence disclosed herein, wherein at least one internucleotidic linkage is

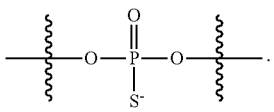 [SMILES: *OP(=O)([S-])O*]

In some embodiments, the present disclosure provides a chirally controlled oligonucleotide comprising any sequence disclosed herein, wherein each internucleotidic linkage is

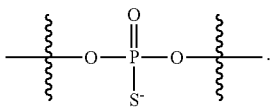 [SMILES: *OP(=O)([S-])O*]

In some embodiments, the present disclosure provides a chirally controlled oligonucleotide comprising any sequence disclosed herein, wherein at least one internucleotidic linkage is

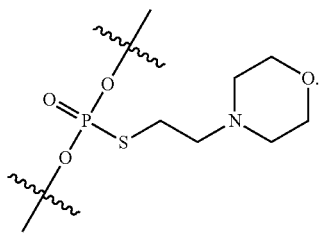 [SMILES: *OP(=O)(O*)SCCN1CCOCC1]

In some embodiments, the present disclosure provides a chirally controlled oligonucleotide comprising any sequence disclosed herein, wherein each internucleotidic linkage is

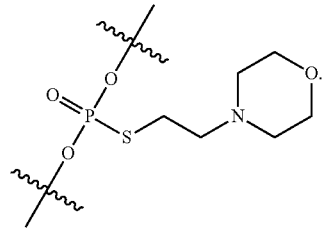 [SMILES: *OP(=O)(O*)SCCN1CCOCC1]

In some embodiments, the present disclosure provides a chirally controlled oligonucleotide having any sequence disclosed herein, wherein at least one internucleotidic linkage has a chiral linkage phosphorus. In some embodiments, the present disclosure provides a chirally controlled oligonucleotide having any sequence disclosed herein, wherein at least one internucleotidic linkage has the structure of formula I. In some embodiments, the present disclosure provides a chirally controlled oligonucleotide having any sequence disclosed herein, wherein each internucleotidic linkage has the structure of formula I. In some embodiments, the present disclosure provides a chirally controlled oligonucleotide having any sequence disclosed herein, wherein at least one internucleotidic linkage has the structure of formula I-c. In some embodiments, the present disclosure provides a chirally controlled oligonucleotide having any sequence disclosed herein, wherein each internucleotidic linkage has the structure of formula I-c. In some embodiments, the present disclosure provides a chirally controlled oligonucleotide having any sequence disclosed herein, wherein at least one internucleotidic linkage is

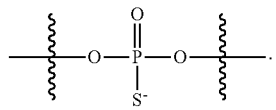 [SMILES: *OP(=O)([S-])O*]

In some embodiments, the present disclosure provides a chirally controlled oligonucleotide having any sequence disclosed herein, wherein each internucleotidic linkage is

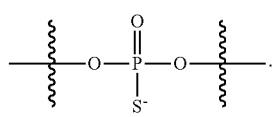 [SMILES: *OP(=O)([S-])O*]

In some embodiments, the present disclosure provides a chirally controlled oligonucleotide having any sequence disclosed herein, wherein at least one internucleotidic linkage is

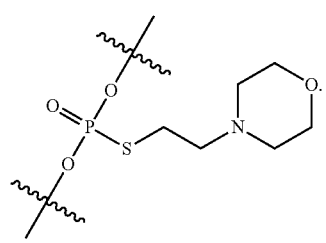 [SMILES: *OP(=O)(O*)SCCN1CCOCC1]

In some embodiments, the present disclosure provides a chirally controlled oligonucleotide having any sequence disclosed herein, wherein each internucleotidic linkage is

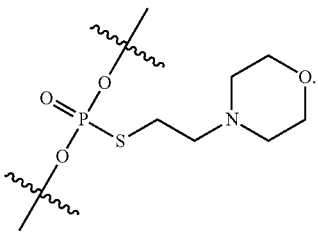 [SMILES: *OP(=O)(O*)SCCN1CCOCC1]

In some embodiments, the present disclosure provides a chirally controlled oligonucleotide having any sequence disclosed herein, wherein at least one linkage phosphorus is Rp. It is understood by a person of ordinary skill in the art that in certain embodiments wherein the chirally controlled oligonucleotide comprises an RNA sequence, each T is independently and optionally replaced with U. In some embodiments, the present disclosure provides a chirally controlled oligonucleotide having any sequence disclosed herein, wherein each linkage phosphorus is Rp. In some embodiments, the present disclosure provides a chirally controlled oligonucleotide having any sequence disclosed herein, wherein at least one linkage phosphorus is Sp. In some embodiments, the present disclosure provides a chirally controlled oligonucleotide having any sequence disclosed herein, wherein each linkage phosphorus is Sp. In some embodiments, the present disclosure provides a chirally controlled oligonucleotide having any sequence disclosed herein, wherein the oligonucleotide is a blockmer. In some embodiments, the present disclosure provides a chirally controlled oligonucleotide having any sequence disclosed herein, wherein the oligonucleotide is a stereoblockmer. In some embodiments, the present disclosure provides a chirally controlled oligonucleotide having any sequence disclosed herein, wherein the oligonucleotide is a P-modification blockmer. In some embodiments, the present disclosure provides a chirally controlled oligonucleotide having any sequence disclosed herein, wherein the oligonucleotide is a linkage blockmer. In some embodiments, the present disclosure provides a chirally controlled oligonucleotide having any sequence disclosed herein, wherein the oligonucleotide is an altmer. In some embodiments, the present disclosure provides a chirally controlled oligonucleotide having any sequence disclosed herein, wherein the oligonucleotide is a stereoaltmer. In some embodiments, the present disclosure provides a chirally controlled oligonucleotide having any sequence disclosed herein, wherein the oligonucleotide is a P-modification altmer. In some embodiments, the present disclosure provides a chirally controlled oligonucleotide having any sequence disclosed herein, wherein the oligonucleotide is a linkage altmer. In some embodiments, the present disclosure provides a chirally controlled oligonucleotide having any sequence disclosed herein, wherein the oligonucleotide is a unimer. In some embodiments, the present disclosure provides a chirally controlled oligonucleotide having any sequence disclosed herein, wherein the oligonucleotide is a stereounimer. In some embodiments, the present disclosure provides a chirally controlled oligonucleotide having any sequence disclosed herein, wherein the oligonucleotide is a P-modification unimer. In some embodiments, the present disclosure provides a chirally controlled oligonucleotide having any sequence disclosed herein, wherein the oligonucleotide is a linkage unimer. In some embodiments, the present disclosure provides a chirally controlled oligonucleotide having any sequence disclosed herein, wherein the oligonucleotide is a gapmer. In some embodiments, the present disclosure provides a chirally controlled oligonucleotide having any sequence disclosed herein, wherein the oligonucleotide is a skipmer.

In some embodiments, the present disclosure provides a chirally controlled oligonucleotide having any sequence disclosed herein, wherein each cytosine is optionally and independently replaced by 5-methylcytosine. In some embodiments, the present disclosure provides a chirally controlled oligonucleotide having any sequence disclosed herein, wherein at least one cytosine is optionally and independently replaced by 5-methylcytosine. In some embodiments, the present disclosure provides a chirally controlled oligonucleotide having any sequence disclosed herein, wherein each cytosine is optionally and independently replaced by 5-methylcytosine.

In various embodiments, any sequence disclosed herein can be combined with one or more of the following as disclosed herein or known in the art: pattern of backbone linkages; pattern of backbone chiral centers; and pattern of backbone P-modifications; pattern of base modification; pattern of sugar modification; pattern of backbone linkages; pattern of backbone chiral centers; and pattern of backbone P-modifications.

In some embodiments, a chirally controlled oligonucleotide is designed such that the resulting pharmaceutical properties are improved through one or more particular modifications at phosphorus. It is well documented in the art that certain oligonucleotides are rapidly degraded by nucleases and exhibit poor cellular uptake through the cytoplasmic cell membrane [Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1): 196-208; Bologna et al., (2002), Antisense & Nucleic Acid Drug Development 12:33-41]. For instance, Vives et al., Nucleic Acids Research (1999), 27(20):4071-76, found that tert-butyl SATE pro-oligonucleotides displayed markedly increased cellular penetration compared to the parent oligonucleotide.

In some embodiments, a modification at a linkage phosphorus is characterized by its ability to be transformed to a phosphate diester, such as those present in naturally occurring DNA and RNA, by one or more esterases, nucleases, and/or cytochrome P450 enzymes, including but not limited to, those listed in Table 1A, below.

TABLE 1A

Example enzymes.

| Family | Gene |
|---|---|
| CYP1 | CYP1A1, CYP1A2, CYP1B1 |
| CYP2 | CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1 |
| CYP3 | CYP3A4, CYP3A5, CYP3A7, CYP3A43 |
| CYP4 | CYP4A11, CYP4A22, CYP4B1, CYP4F2, CYP4F3, CYP4F8, CYP4F11, CYP4F12, CYP4F22, CYP4V2, CYP4X1, CYP4Z1 |
| CYP5 | CYP5A1 |
| CYP7 | CYP7A1, CYP7B1 |

TABLE 1A-continued

Example enzymes.

| Family | Gene |
|---|---|
| CYP8 | CYP8A1 (prostacyclin synthase), CYP8B1 (bile acid biosynthesis) |
| CYP11 | CYP11A1, CYP11B1, CYP11B2 |
| CYP17 | CYP17A1 |
| CYP19 | CYP19A1 |
| CYP20 | CYP20A1 |
| CYP21 | CYP21A2 |
| CYP24 | CYP24A1 |
| CYP26 | CYP26A1, CYP26B1, CYP26C1 |
| CYP27 | CYP27A1 (bile acid biosynthesis), CYP27B1 (vitamin D3 1-alpha hydroxylase, activates vitamin D3), CYP27C1 (unknown function) |
| CYP39 | CYP39A1 |
| CYP46 | CYP46A1 |
| CYP51 | CYP51A1 (lanosterol 14-alpha demethylase) |

In some embodiments, a modification at phosphorus results in a P-modification moiety characterized in that it acts as a pro-drug, e.g., the P-modification moiety facilitates delivery of an oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of an oligonucleotide.

In some embodiments, a PEGylation reagent for use in accordance with the present disclosure is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500. In certain embodiments, a PEGylation reagent is PEG1000. In certain embodiments, a PEGylation reagent is PEG3000. In certain embodiments, a PEGylation reagent is PEG5000.

In some embodiments, a P-modification moiety is characterized in that it acts as a PK enhancer, e.g., lipids, PEGylated lipids, etc.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. The phrase "targeting agent," as used herein, is an entity that is associates with a payload of interest (e.g., with an oligonucleotide or oligonucleotide composition) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent may be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Examples of such targeting agents include, but are not limited to, proteins (e.g. Transferrin), oligopeptides (e.g., cyclic and acylic RGD-containing oligopedptides), antibodies (monoclonal and polyclonal antibodies, e.g. IgG, IgA, IgM, IgD, IgE antibodies), sugars/carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; cholesterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is a targeting agent of formula —X-L-$R^1$ wherein each of X, L, and $R^1$ are as defined in Formula I above.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present disclosure.

Nucleobases

In some embodiments, a nucleobase present in a provided oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are disclosed in Chiu and Rana, *RNA*, 2003, 9, 1034-1048, Limbach et al. *Nucleic Acids Research*, 1994, 22, 2183-2196 and Revankar and Rao, *Comprehensive Natural Products Chemistry*, vol. 7, 313.

Compounds represented by the following general formulae are also contemplated as modified nucleobases:

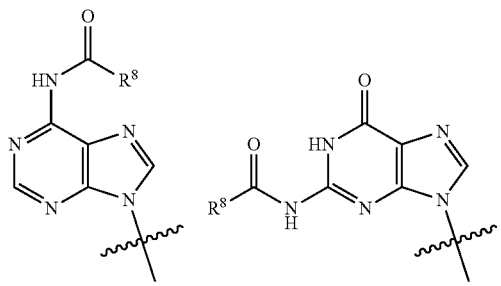

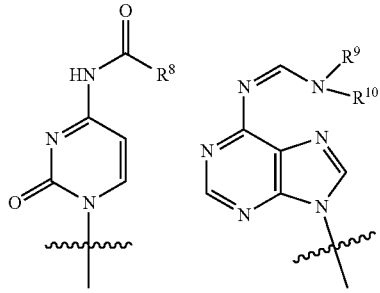

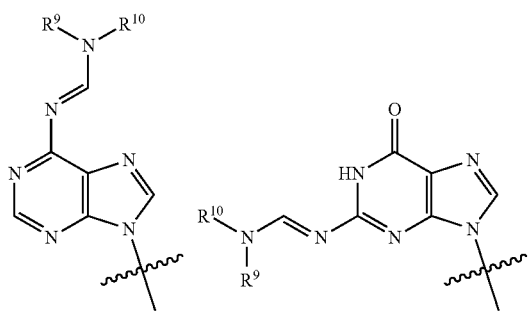

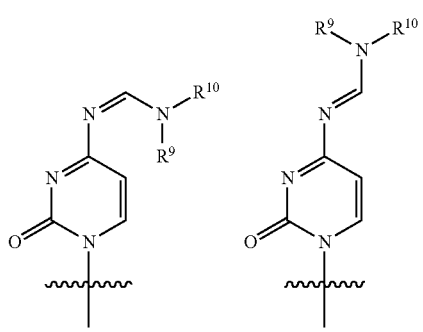

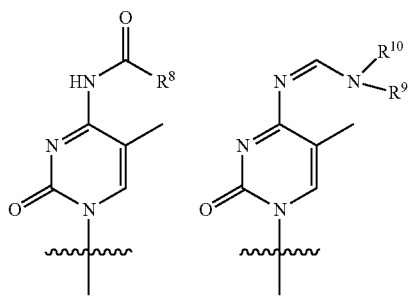

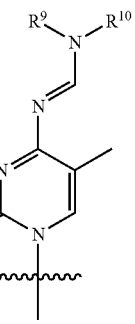

wherein R[8] is an optionally substituted, linear or branched group selected from aliphatic, aryl, aralkyl, aryloxylalkyl, carbocyclyl, heterocyclyl or heteroaryl group having 1 to 15 carbon atoms, including, by way of example only, a methyl, isopropyl, phenyl, benzyl, or phenoxymethyl group; and each of R[9] and R[10] is independently an optionally substituted group selected from linear or branched aliphatic, carbocyclyl, aryl, heterocyclyl and heteroaryl.

Modified nucleobases also include expanded-size nucleobases in which one or more aryl rings, such as phenyl rings, have been added. Nucleic base replacements described in the Glen Research catalog (www.glenresearch.com); Krueger A T et al, *Acc. Chem. Res.,* 2007, 40, 141-150; Kool, E T, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin. Chem. Biol.,* 2006, 10, 622-627, are contemplated as useful for the synthesis of the nucleic acids described herein. Some examples of these expanded-size nucleobases are shown below:

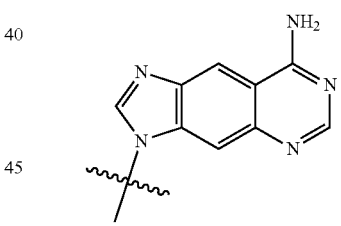

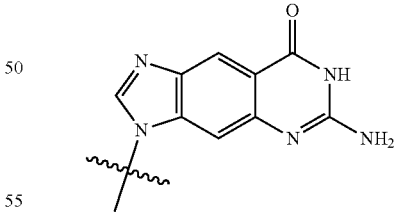

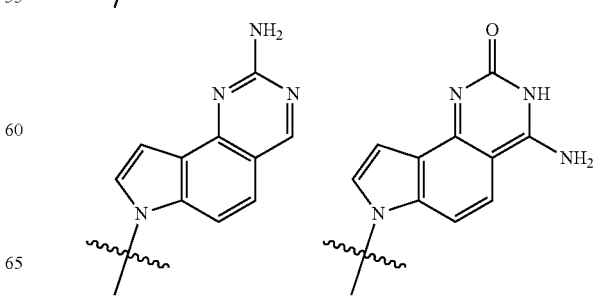

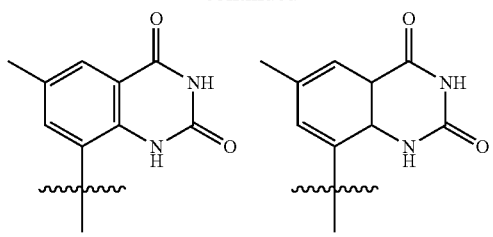

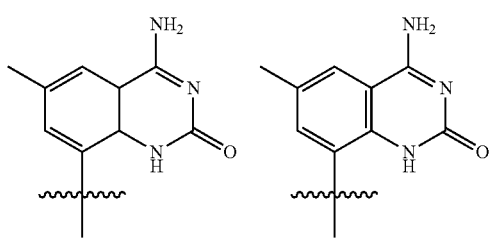

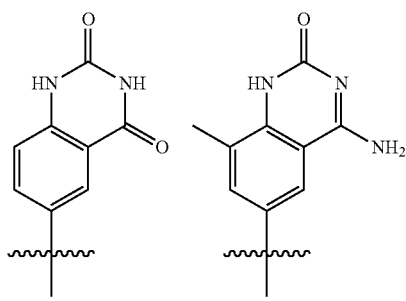

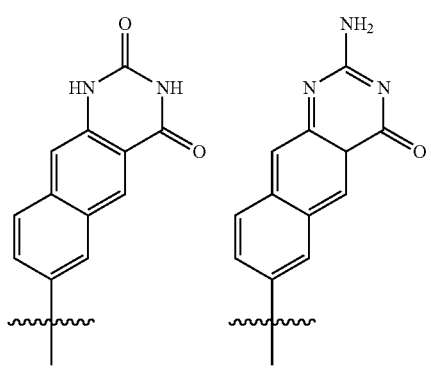

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, *Org. Lett.*, 2002, 4, 4377-4380. Shown below is an example of a porphyrin-derived ring which can be used as a base replacement:

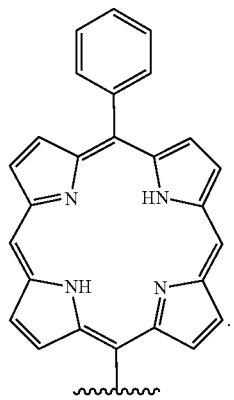 [SMILES: *c1c2nc(cc3ccc([nH]3)c(-c3ccccc3)c3nc(cc4ccc1[nH]4)C=C3)C=C2]

In some embodiments, modified nucleobases are of any one of the following structures, optionally substituted:

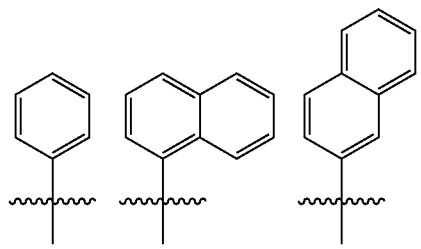

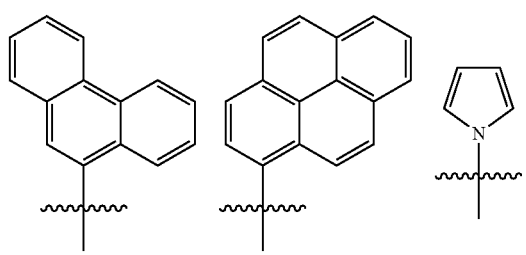

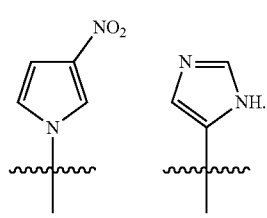

In some embodiments, a modified nucleobase is fluorescent. Examples of such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

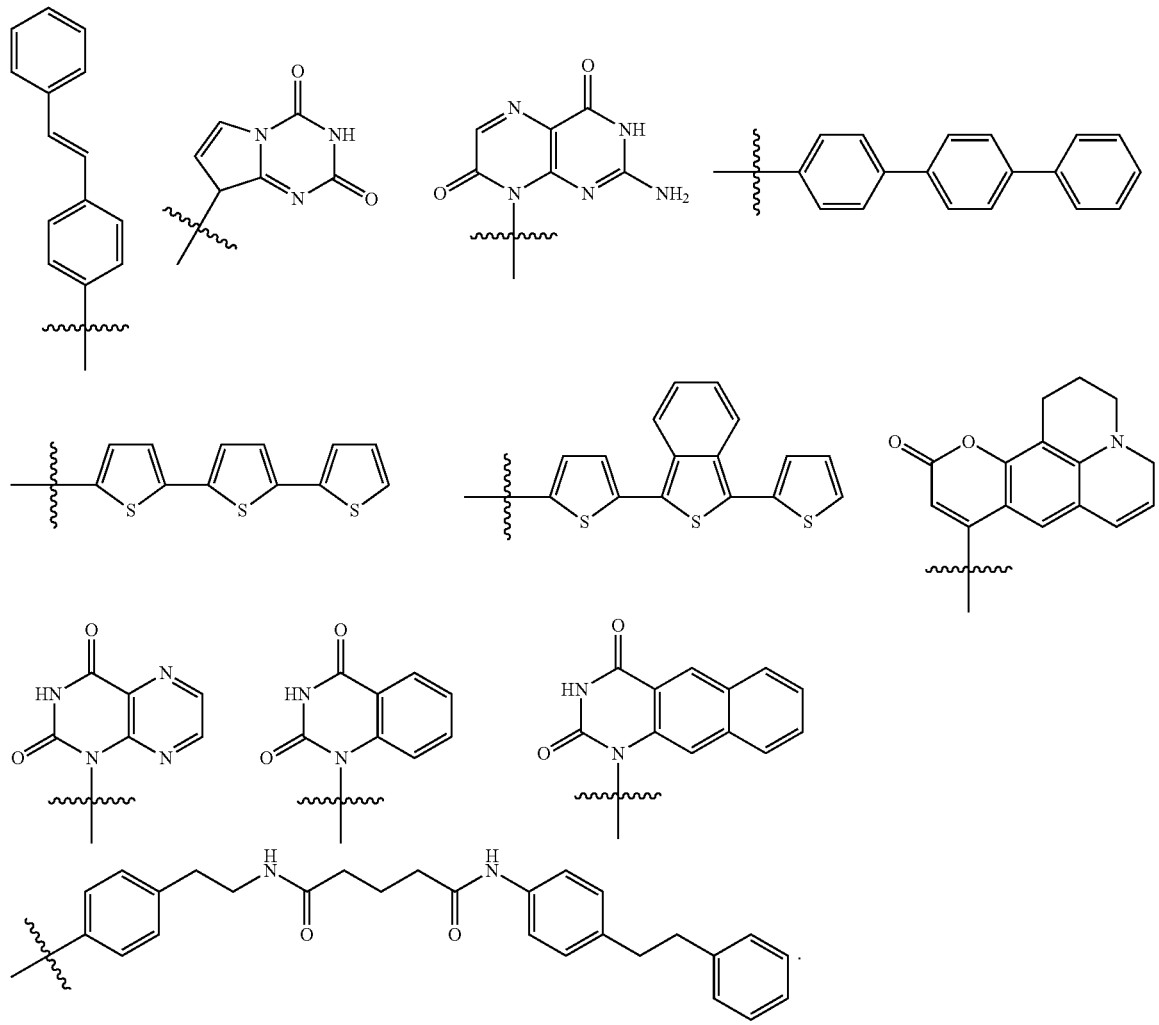

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; -methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

In some embodiments, a base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom ring atoms. In some embodiments, a modified base is optionally substituted A, T, C, G or U, wherein one or more —$NH_2$ are independently and optionally replaced with —$C(-L-R^1)_3$, one or more —NH— are independently and optionally replaced with $C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom ring atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleotide or nucleotide analog is any modified nucleotide or nucleotide analog described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

Sugars

In some embodiments, provided oligonucleotides comprise one or more modified sugar moieties beside the natural sugar moieties.

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present disclosure.

Other modified sugars can also be incorporated within a provided oligonucleotide. In some embodiments, a modified sugar contains one or more substituents at the 2' position including one of the following: —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —$N(C_1$-$C_{10}$ alkyl$)_2$; —O—($C_2$-$C_{10}$ alkenyl), —S—($C_2$-$C_{10}$ alkenyl), —NH—($C_2$-$C_{10}$ alkenyl), or —$N(C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —$N(C_2$-$C_{10}$ alkynyl$)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl$)_2$, —NH—($C_1$-$C_{10}$ alkylene)-O—($C_1$-$C_{10}$ alkyl), or —$N(C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted. Examples of substituents include, and are not limited to, —O($CH_2)_nOCH_3$, and —O($CH_2)_nNH_2$, wherein n is from 1 to about 10, MOE, DMAOE, DMAEOE. Also contemplated herein are modified sugars described in WO 2001/088198; and Martin et al., *Helv. Chim. Acta,* 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —OCH$_2$CH$_2$OMe.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, -L- is —O—CH$_2$—, wherein —CH$_2$— is optionally substituted. In some embodiments, -L- is —O—CH$_2$—. In some embodiments, -L- is —O—CH(Et)-. In some embodiments, -L- is between C2 and C4 of a sugar moiety. In some embodiments, a locked nucleic acid has the structure indicated below. A locked nucleic acid of the structure below is indicated, wherein Ba represents a nucleobase or modified nucleobase as described herein, and wherein R$^{2s}$ is —OCH$_2$C4'-.

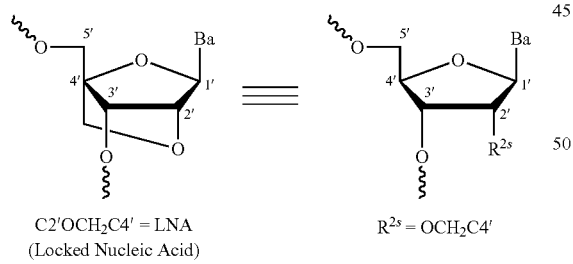

C2'OCH$_2$C4' = LNA
(Locked Nucleic Acid)

R$^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is shown below and is described in Zhang, R et al., *J. Am. Chem. Soc.,* 2008, 130, 5846-5847; Zhang L, et al., *J. Am. Chem. Soc.,* 2005, 127, 4174-4175 and Tsai C H et al., *PNAS,* 2007, 14598-14603 (X=O$^-$):

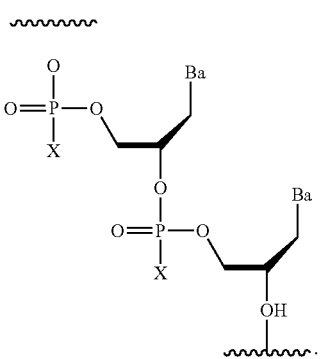

Another example of a GNA derived analogue, flexible nucleic acid (FNA) based on the mixed acetal aminal of formyl glycerol, is described in Joyce G F et al., *PNAS,* 1987, 84, 4398-4402 and Heuberger BD and Switzer C, *J. Am. Chem. Soc.,* 2008, 130, 412-413, and is shown below:

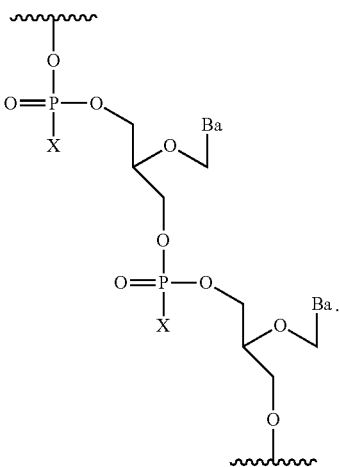

Additional non-limiting examples of modified sugars include hexopyranosyl (6' to 4'), pentopyranosyl (4' to 2'), pentopyranosyl (4' to 3'), or tetrofuranosyl (3' to 2') sugars. In some embodiments, a hexopyranosyl (6' to 4') sugar is of any one in the following formulae:

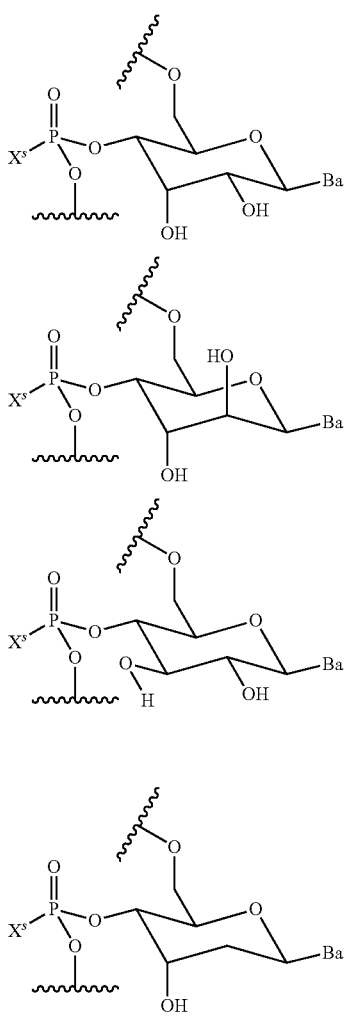

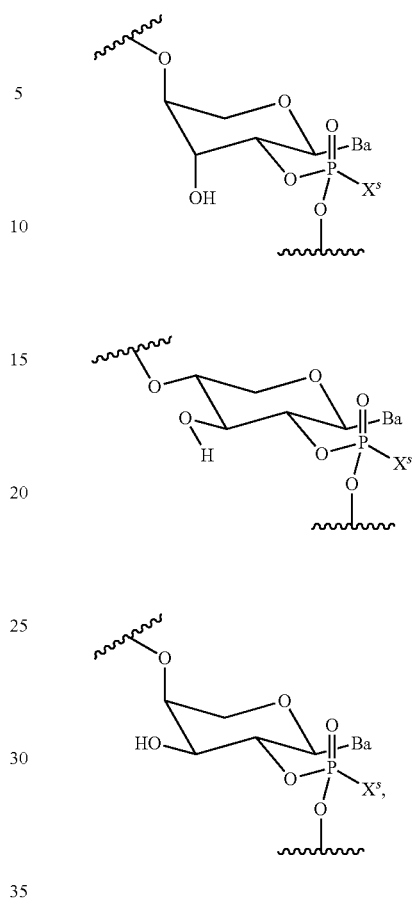

wherein $X^s$ corresponds to the P-modification group "—XLR¹" described herein and Ba is as defined herein.

In some embodiments, a pentopyranosyl (4' to 3') sugar is of any one in the following formulae:

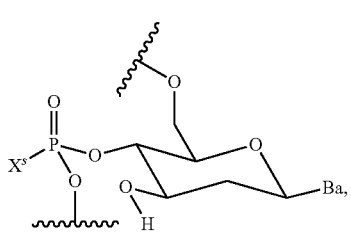

wherein $X^s$ corresponds to the P-modification group "—XLR¹" described herein and Ba is as defined herein.

In some embodiments, a pentopyranosyl (4' to 2') sugar is of any one in the following formulae:

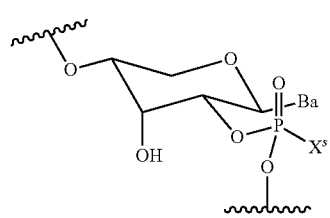

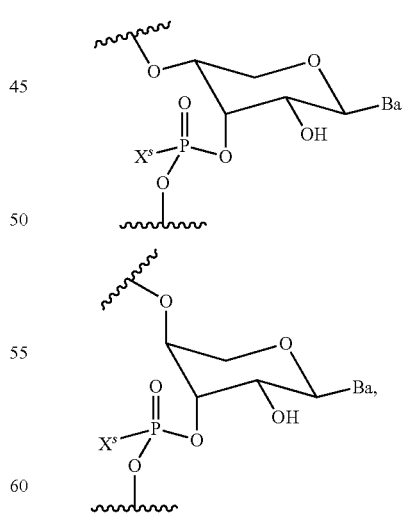

wherein $X^s$ corresponds to the P-modification group "—XLR¹" described herein and Ba is as defined herein.

In some embodiments, a tetrofuranosyl (3' to 2') sugar is of either in the following formulae:

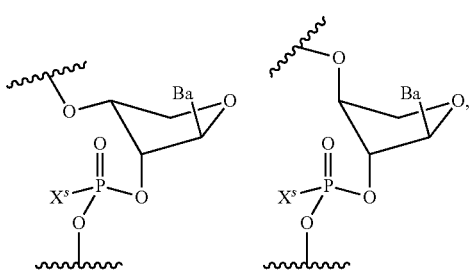

wherein $X^s$ corresponds to the P-modification group "—XLR$^1$" described herein and Ba is as defined herein.

In some embodiments, a modified sugar is of any one in the following formulae:

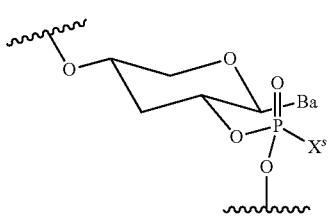

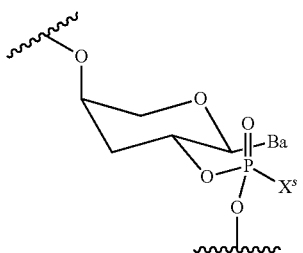

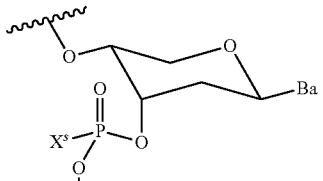

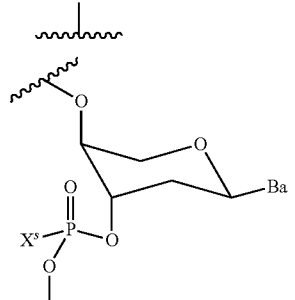

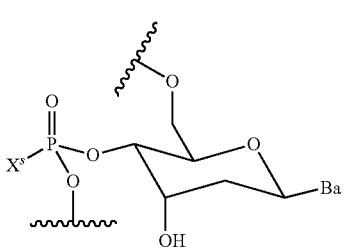

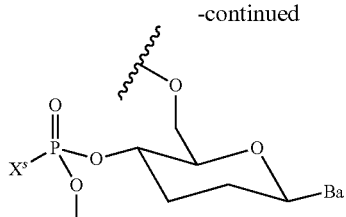

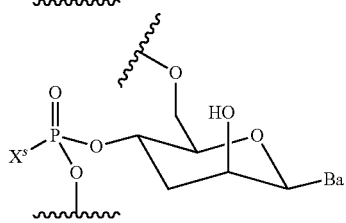

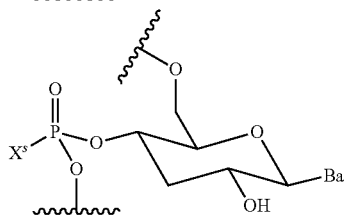

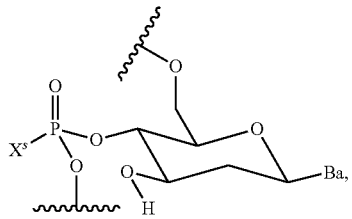

wherein $X^s$ corresponds to the P-modification group "—XLR$^1$" described herein and Ba is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a sugar mimetic is as illustrated below, wherein $X^s$ corresponds to the P-modification group "—XLR$^1$" described herein, Ba is as defined herein, and $X^1$ is selected from —S—, —Se—, —CH$_2$—, —NMe-, -NEt- or —NiPr—.

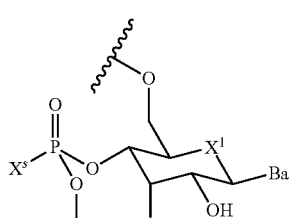

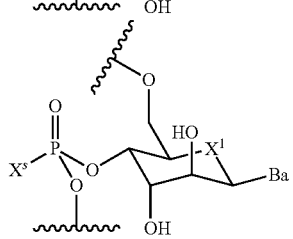

247
-continued
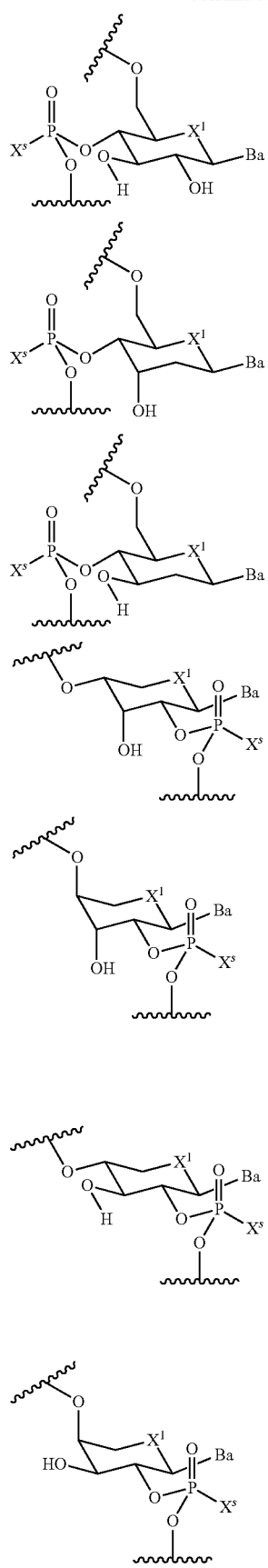
248
-continued
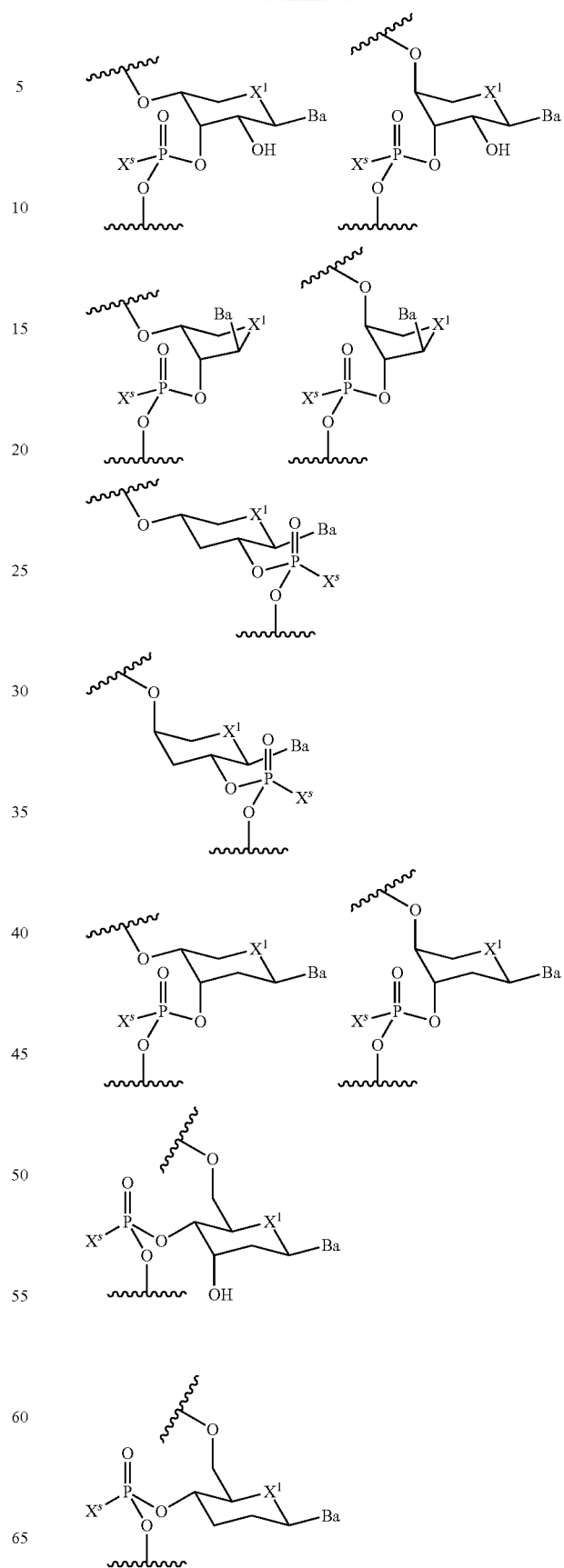

-continued

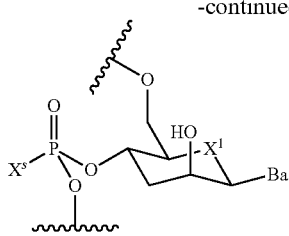

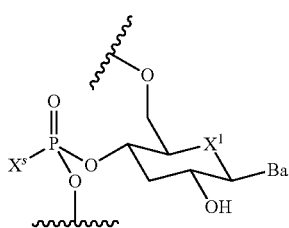

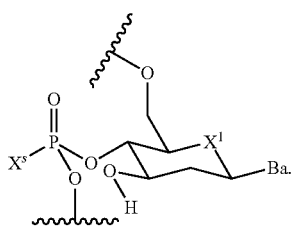

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310). In some embodiments, a modified sugar is any of those described in PCT Publication No. WO2012/030683, incorporated herein by reference, and depicted in the FIGS. 26-30 of the present application. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar is selected from:

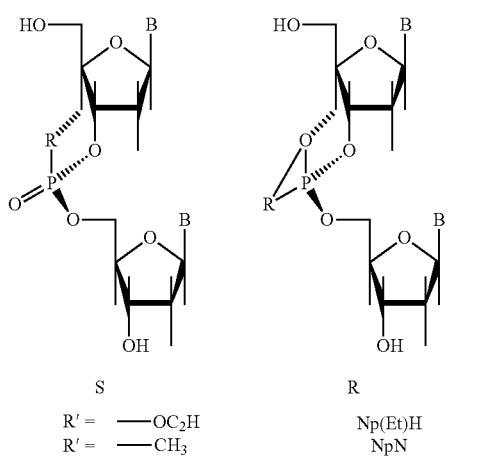
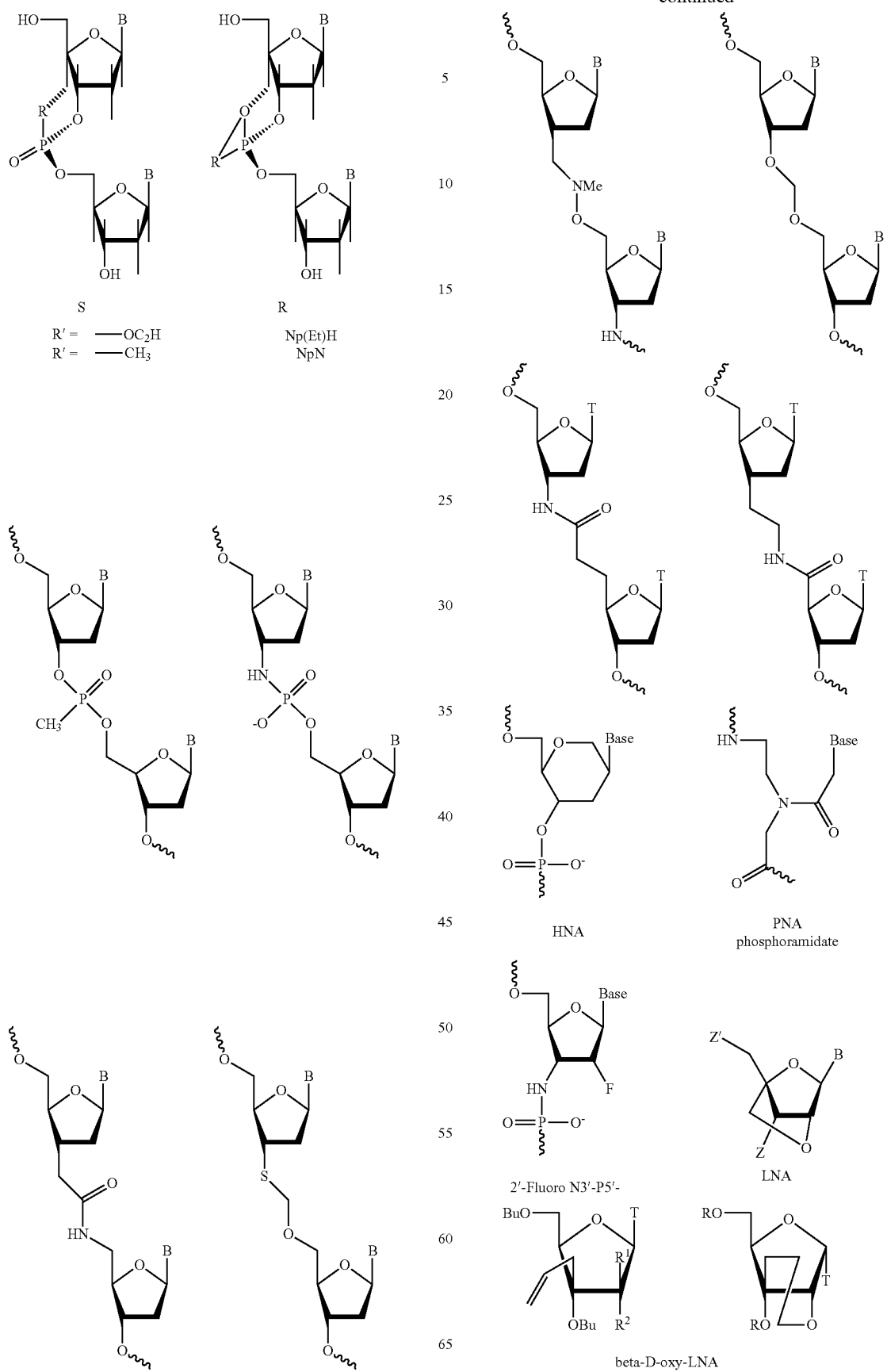

-continued

2-O,3'-C-linked bicyclic

LNA:
2'-Thio-LNA:
2'-Phosphorothioate-LNA:
X = O, Y = O
X = S, Y = O
X = O, Y = S
PS-LNA beta- D-thio-LNA beta-D-amino-LNA xylo-LNA [c]

alpha-L-LNA

ENA beta-D-ENA

-continued amide-linked LNA methylphosphonate-LNA (R, S)-cEt (R,S)-cMOE
(R,S)-cMOE (R, S)-5'-Me-LNA S-Me cLNA Methylene-cLNA 3'-Me-alpha-L-LNA R-6'-Me-alpha-L-LNA S-5'-Me-alpha-L-LNA

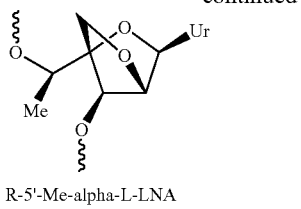

R-5'-Me-alpha-L-LNA

In some embodiments, $R^1$ is R as defined and described. In some embodiments, $R^2$ is R. In some embodiments, $R^e$ is R. In some embodiments, $R^e$ is H, $CH_3$, Bn, $COCF_3$, benzoyl, benzyl, pyren-1-ylcarbonyl, pyren-1-ylmethyl, 2-aminoethyl. In some embodiments, an example modified internucleotidic linkage and/or sugar is selected from those described in Ts'o et al. Ann. N. Y. Acad. Sci. 1988, 507, 220; Gryaznov, S.; Chen, J.-K. J. Am. Chem. Soc. 1994, 116, 3143; Mesmaeker et al. Angew. Chem., Int. Ed. Engl. 1994, 33, 226; Jones et al. J. Org. Chem. 1993, 58, 2983; Vasseur et al. J. Am. Chem. Soc. 1992, 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 20070900071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, the base and sugar modifications of each of which is herein incorporated by reference.

Oligonucleotides

In some embodiments, the present disclosure provides oligonucleotides and oligonucleotide compositions that are chirally controlled. For instance, in some embodiments, a provided composition contains predetermined levels of one or more individual oligonucleotide types, wherein an oligonucleotide type is defined by: 1) base sequence; 2) pattern of backbone linkages; 3) pattern of backbone chiral centers; and 4) pattern of backbone P-modifications. In some embodiments, a particular oligonucleotide type may be defined by 1A) base identity; 1B) pattern of base modification; 1C) pattern of sugar modification; 2) pattern of backbone linkages; 3) pattern of backbone chiral centers; and 4) pattern of backbone P-modifications. In some embodiments, oligonucleotides of the same oligonucleotide type are identical.

As described herein, the present disclosure provides various oligonucleotides. In some embodiments, the present disclosure provides oligonucleotides comprising a sequence that shares greater than about 50%, 60%, 70%, 75%, 80%, 85%, 90%, 95% identity with a sequence found in a provided example oligonucleotide, such as those listed in various tables. In some embodiments, a provided oligonucleotide is WV-937. In some embodiments, a provided oligonucleotide is WV-1090. In some embodiments, a provided oligonucleotide is WV-1091. In some embodiments, a provided oligonucleotide is WV-1087. In some embodiments, a provided oligonucleotide is WV-937. In some embodiments, a provided oligonucleotide is WV-2611. In some embodiments, a provided oligonucleotide is WV-1092. In some embodiments, a provided oligonucleotide is WV-2595. In some embodiments, a provided oligonucleotide is WV-2378. In some embodiments, a provided oligonucleotide is WV-2380. In some embodiments, a provided oligonucleotide is WV-1510. In some embodiments, a provided oligonucleotide is WV-2619. In some embodiments, a provided oligonucleotide is WV-2611. In some embodiments, a provided oligonucleotide is WV-1497. In some embodiments, a provided oligonucleotide is WV-2601. In some embodiments, a provided oligonucleotide is WV-2602. In some embodiments, a provided oligonucleotide is WV-2618. In some embodiments, a provided oligonucleotide is WV-2603. In some embodiments, the present disclosure provides oligonucleotides comprising or consisting of a sequence found in a provided example oligonucleotide. In some embodiments, the present disclosure provides oligonucleotides comprising or consisting of a sequence found in WV-937. In some embodiments, the present disclosure provides oligonucleotides comprising or consisting of a sequence found in WV-1087. In some embodiments, the present disclosure provides oligonucleotides comprising or consisting of a sequence found in WV-1090. In some embodiments, the present disclosure provides oligonucleotides comprising or consisting of a sequence found in WV-1091. In some embodiments, the present disclosure provides oligonucleotides comprising or consisting of a sequence found in WV-2611. In some embodiments, the present disclosure provides oligonucleotides comprising or consisting of a sequence found in WV-937. In some embodiments, the present disclosure provides oligonucleotides comprising or consisting of a sequence found in WV-1091. In some embodiments, the present disclosure provides oligonucleotides comprising or consisting of a sequence found in WV-1092. In some embodiments, the present disclosure provides oligonucleotides comprising or consisting of a sequence found in WV-2595. In some embodiments, the present disclosure provides oligonucleotides comprising or consisting of a sequence found in WV-2603. In some embodiments, the present disclosure provides oligonucleotides comprising or consisting of a sequence found in WV-2378. In some embodiments, the present disclosure provides oligonucleotides comprising or consisting of a sequence found in WV-2380. In some embodiments, the present disclosure provides oligonucleotides comprising or consisting of a sequence found in WV-1510. In some embodiments, the present disclosure provides oligonucleotides comprising or consisting of a sequence found in WV-2619. In some embodiments, the present disclosure provides oligonucleotides comprising or consisting of a sequence found in WV-2611. In some embodiments, the present disclosure provides oligonucleotides comprising or consisting of a sequence found in WV-1497. In some embodiments, the present disclosure provides oligonucleotides comprising or consisting of a sequence found in WV-2602. In some embodiments, the present disclosure provides oligonucleotides comprising or consisting of a sequence found in WV-2618. In some embodiments, the present disclosure provides oligonucleotides comprising or consisting of a sequence found in or WV-2601. In some embodiments, a provided oligonucleotide further comprises one or more natural phosphate linkages and one or more modified internucleotidic linkages. In some embodiments, a provided oligonucleotide comprises two or more natural phosphate linkages. In some embodiments, a provided oligonucleotide comprises two or more consecutive natural phosphate linkages. In some embodiments, a provided oligonucleotide comprises two or more modified internucleotidic linkages. In some embodiments, a provided oligonucleotide comprises two or more consecutive modified internucleotidic linkages. In some embodiments, a provided oligonucleotide comprises 3, 4, 5, 6, 7, 8, 9, 10, 11, 12, 13, 14, 15, 16, 17, 18, 19, 20 or more consecutive modified internucleotidic linkages. In some embodiments, a provided oligonucleotide comprises 5 or more consecutive modified internucleotidic linkages. In some embodiments, a provided oligonucleotide comprises 5 or more consecutive modified internucleotidic linkages. In some embodiments, a provided oligonucleotide comprises 6 or more consecutive modified internucleotidic linkages. In some embodiments, a provided oligonucleotide comprises 7 or more consecutive modified internucleotidic linkages. In some embodiments, a provided oligonucleotide comprises 8 or more consecutive modified internucleotidic linkages. In some embodiments, a provided oligonucleotide comprises 9 or more consecutive modified internucleotidic linkages. In some embodiments, a provided oligonucleotide comprises 10 or more consecutive modified internucleotidic linkages. In some embodiments, at least one of the modified internucleotidic linkages is a chirally controlled internucleotidic linkage in that oligonucleotides having the same sequence and chemical modifications within a composition share the same configuration, either Rp or Sp, at the chiral phosphorus atom of the modified internucleotidic linkage. In some embodiments, at least two modified internucleotidic linkages are chirally controlled. In some embodiments, at least one modified internucleotidic linkage within a consecutive modified internucleotidic linkage region is chirally controlled. In some embodiments, at least two modified internucleotidic linkages within a consecutive modified internucleotidic linkage region are chirally controlled. In some embodiments, each modified internucleotidic linkage within a consecutive modified internucleotidic linkage region is chirally controlled. In some embodiments, each modified internucleotidic linkage is chirally controlled. In some embodiments, a provided oligonucleotide comprises a (Sp)xRp(Sp)y pattern, wherein each of x and y is independently 1-20, and the sum of x and y is 1-50. In some embodiments, each of x and y is independently 2-20. In some embodiments, at least one of x and y is greater than 5, 6, 7, 8, 9, or 10. In some embodiments, the sum of x and y is greater than 5, 6, 7, 8, 9, 10, 11, 12, 13, 14, 15, 16, 17, 18, 19 or 20. In some embodiments, a provided oligonucleotide comprises one or more chemical modifications as presented in a provided example oligonucleotide. In some embodiments, a provided oligonucleotide comprises one or more base modifications as presented in a provided example oligonucleotide. In some embodiments, a provided oligonucleotide comprises one or more sugar modifications as presented in a provided example oligonucleotide. In some embodiments, a sugar modification is a 2'-modification. In some embodiments, a sugar modification is LNA. In some embodiments, a sugar modification is ENA. In some embodiments, a provided oligonucleotide is a chirally controlled oligonucleotide. In some embodiments, the present disclosure provides an oligonucleotide composition comprising a provided oligonucleotide. In some embodiments, a provided oligonucleotide composition is a chirally controlled oligonucleotide composition.

In some embodiments, a provided oligonucleotide is a unimer. In some embodiments, a provided oligonucleotide is a P-modification unimer. In some embodiments, a provided oligonucleotide is a stereounimer. In some embodiments, a provided oligonucleotide is a stereounimer of configuration Rp. In some embodiments, a provided oligonucleotide is a stereounimer of configuration Sp.

In some embodiments, a provided oligonucleotide is an altmer. In some embodiments, a provided oligonucleotide is a P-modification altmer. In some embodiments, a provided oligonucleotide is a stereoaltmer.

In some embodiments, a provided oligonucleotide is a blockmer. In some embodiments, a provided oligonucleotide is a P-modification blockmer. In some embodiments, a provided oligonucleotide is a stereoblockmer.

In some embodiments, a provided oligonucleotide is a gapmer.

In some embodiments, a provided oligonucleotide is a skipmer.

In some embodiments, a provided oligonucleotide is a hemimer. In some embodiments, a hemimer is an oligonucleotide wherein the 5'-end or the 3'-end has a sequence that possesses a structure feature that the rest of the oligonucleotide does not have. In some embodiments, the 5'-end or the 3'-end has or comprises 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is an oligonucleotide in which each sugar moiety of the 5'-end sequence shares a common modification. In some embodiments, a hemimer is an oligonucleotide in which each sugar moiety of the 3'-end sequence shares a common modification. In some embodiments, a common sugar modification of the 5' or 3' end sequence is not shared by any other sugar moieties in the oligonucleotide. In some embodiments, an example hemimer is an oligonucleotide comprising a sequence of substituted or unsubstituted 2'-O-alkyl sugar modified nucleosides, bicyclic sugar modified nucleosides, (3-D-ribonucleosides or β-D- deoxyribonucleosides (for example 2'-MOE modified nucleosides, and LNA™ or ENA™ bicyclic sugar modified nucleosides) at one terminus and a sequence of nucleosides with a different sugar moiety (such as a substituted or unsubstituted 2'-O-alkyl sugar modified nucleosides, bicyclic sugar modified nucleosides or natural ones) at the other terminus. In some embodiments, a provided oligonucleotide is a combination of one or more of unimer, altmer, blockmer, gapmer, hemimer and skipmer. In some embodiments, a provided oligonucleotide is a combination of one or more of unimer, altmer, blockmer, gapmer, and skipmer. For instance, in some embodiments, a provided oligonucleotide is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided oligonucleotide in accordance with methods of the present disclosure. In some embodiments, a hemimer structure provides advantageous benefits, as exemplified by FIG. 29. In some embodiments, provided oligonucleotides are 5'-hemmimers that comprises modified sugar moieties in a 5'-end sequence. In some embodiments, provided oligonucleotides are 5'-hemmimers that comprises modified 2'-sugar moieties in a 5'-end sequence.

In some embodiments, a provided oligonucleotide comprises one or more optionally substituted nucleotides. In some embodiments, a provided oligonucleotide comprises one or more modified nucleotides. In some embodiments, a provided oligonucleotide comprises one or more optionally substituted nucleosides. In some embodiments, a provided oligonucleotide comprises one or more modified nucleosides. In some embodiments, a provided oligonucleotide comprises one or more optionally substituted LNAs.

In some embodiments, a provided oligonucleotide comprises one or more optionally substituted nucleobases. In some embodiments, a provided oligonucleotide comprises one or more optionally substituted natural nucleobases. In some embodiments, a provided oligonucleotide comprises one or more optionally substituted modified nucleobases. In some embodiments, a provided oligonucleotide comprises one or more 5-methylcytidine; 5-hydroxymethylcytidine, 5-formylcytosine, or 5-carboxylcytosine. In some embodiments, a provided oligonucleotide comprises one or more 5-methylcytidine.

In some embodiments, a provided oligonucleotide comprises one or more optionally substituted sugars. In some embodiments, a provided oligonucleotide comprises one or more optionally substituted sugars found in naturally occurring DNA and RNA. In some embodiments, a provided oligonucleotide comprises one or more optionally substituted ribose or deoxyribose. In some embodiments, a provided oligonucleotide comprises one or more optionally substituted ribose or deoxyribose, wherein one or more hydroxyl groups of the ribose or deoxyribose moiety is optionally and independently replaced by halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen. In some embodiments, a provided oligonucleotide comprises one or more optionally substituted deoxyribose, wherein the 2' position of the deoxyribose is optionally and independently substituted with one or more —F. halogen. In some embodiments, a provided oligonucleotide comprises one or more optionally substituted deoxyribose, wherein the 2' position of the deoxyribose is optionally and independently substituted with —OR', wherein each R' is independently as defined above and described herein. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ aliphatic. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ alkyl. In some embodiments, a provided oligonucleotide comprises one or more optionally substituted deoxyribose, wherein the 2' position of the deoxyribose is optionally and independently substituted with —OMe. In some embodiments, a provided oligonucleotide comprises one or more optionally substituted deoxyribose, wherein the 2' position of the deoxyribose is optionally and independently substituted with —O— methoxyethyl.

In some embodiments, a provided oligonucleotide is single-stranded oligonucleotide.

In some embodiments, a provided oligonucleotide is a hybridized oligonucleotide strand. In certain embodiments, a provided oligonucleotide is a partially hybridized oligonucleotide strand. In certain embodiments, a provided oligonucleotide is a completely hybridized oligonucleotide strand. In certain embodiments, a provided oligonucleotide is a double-stranded oligonucleotide. In certain embodiments, a provided oligonucleotide is a triple-stranded oligonucleotide (e.g., a triplex).

In some embodiments, a provided oligonucleotide is chimeric. For example, in some embodiments, a provided oligonucleotide is DNA-RNA chimera, DNA-LNA chimera, etc.

In some embodiments, any one of the structures comprising an oligonucleotide depicted in WO2012/030683 can be modified in accordance with methods of the present disclosure to provide chirally controlled variants thereof. For example, in some embodiments the chirally controlled variants comprise a stereochemical modification at any one or more of the linkage phosphorus and/or a P-modification at any one or more of the linkage phosphorus. For example, in some embodiments, a particular nucleotide unit of an oligonucleotide of WO2012/030683 is preselected to be stereochemically modified at the linkage phosphorus of that nucleotide unit and/or P-modified at the linkage phosphorus of that nucleotide unit. In some embodiments, a chirally controlled oligonucleotide is of any one of the structures depicted in FIGS. 26-30. In some embodiments, a chirally controlled oligonucleotide is a variant (e.g., modified version) of any one of the structures depicted in FIGS. 26-30. The disclosure of WO2012/030683 is herein incorporated by reference in its entirety.

In some embodiments, a provided oligonucleotide is a therapeutic agent.

In some embodiments, a provided oligonucleotide is an antisense oligonucleotide.

In some embodiments, a provided oligonucleotide is an antigene oligonucleotide.

In some embodiments, a provided oligonucleotide is a decoy oligonucleotide.

In some embodiments, a provided oligonucleotide is part of a DNA vaccine.

In some embodiments, a provided oligonucleotide is an immunomodulatory oligonucleotide, e.g., immunostimulatory oligonucleotide and immunoinhibitory oligonucleotide.

In some embodiments, a provided oligonucleotide is an adjuvant.

In some embodiments, a provided oligonucleotide is an aptamer.

In some embodiments, a provided oligonucleotide is a ribozyme.

In some embodiments, a provided oligonucleotide is a deoxyribozyme (DNAzymes or DNA enzymes).

In some embodiments, a provided oligonucleotide is an siRNA.

In some embodiments, a provided oligonucleotide is a microRNA, or miRNA.

In some embodiments, a provided oligonucleotide is a ncRNA (non-coding RNAs), including a long non-coding RNA (lncRNA) and a small non-coding RNA, such as piwi-interacting RNA (piRNA).

In some embodiments, a provided oligonucleotide is complementary to a structural RNA, e.g., tRNA.

In some embodiments, a provided oligonucleotide is a nucleic acid analog, e.g., GNA, LNA, PNA, TNA, GNA, ANA, FANA, CeNA, HNA, UNA, ZNA, or Morpholino.

In some embodiments, a provided oligonucleotide is a P-modified prodrug.

In some embodiments, a provided oligonucleotide is a primer. In some embodiments, a primers is for use in polymerase-based chain reactions (i.e., PCR) to amplify nucleic acids. In some embodiments, a primer is for use in any known variations of PCR, such as reverse transcription PCR (RT-PCR) and real-time PCR.

In some embodiments, a provided oligonucleotide is characterized as having the ability to modulate RNase H activation. For example, in some embodiments, RNase H activation is modulated by the presence of stereocontrolled phosphorothioate nucleic acid analogs, with natural DNA/RNA being more or equally susceptible than the Rp stereoisomer, which in turn is more susceptible than the corresponding Sp stereoisomer.

In some embodiments, a provided oligonucleotide is characterized as having the ability to indirectly or directly increase or decrease activity of a protein or inhibition or promotion of the expression of a protein. In some embodiments, a provided oligonucleotide is characterized in that it is useful in the control of cell proliferation, viral replication, and/or any other cell signaling process.

In some embodiments, a provided oligonucleotide is from about 2 to about 200 nucleotide units in length. In some embodiments, a provided oligonucleotide is from about 2 to about 180 nucleotide units in length. In some embodiments, a provided oligonucleotide is from about 2 to about 160 nucleotide units in length. In some embodiments, a provided oligonucleotide is from about 2 to about 140 nucleotide units in length. In some embodiments, a provided oligonucleotide is from about 2 to about 120 nucleotide units in length. In some embodiments, a provided oligonucleotide is from about 2 to about 100 nucleotide units in length. In some embodiments, a provided oligonucleotide is from about 2 to about 90 nucleotide units in length. In some embodiments, a provided oligonucleotide is from about 2 to about 80 nucleotide units in length. In some embodiments, a provided oligonucleotide is from about 2 to about 70 nucleotide units in length. In some embodiments, a provided oligonucleotide is from about 2 to about 60 nucleotide units in length. In some embodiments, a provided oligonucleotide is from about 2 to about 50 nucleotide units in length. In some embodiments, a provided oligonucleotide is from about 2 to about 40 nucleotide units in length. In some embodiments, a provided oligonucleotide is from about 2 to about 30 nucleotide units in length. In some embodiments, a provided oligonucleotide is from about 2 to about 29 nucleotide units in length. In some embodiments, a provided oligonucleotide is from about 2 to about 28 nucleotide units in length. In some embodiments, a provided oligonucleotide is from about 2 to about 27 nucleotide units in length. In some embodiments, a provided oligonucleotide is from about 2 to about 26 nucleotide units in length. In some embodiments, a provided oligonucleotide is from about 2 to about 25 nucleotide units in length. In some embodiments, a provided oligonucleotide is from about 2 to about 24 nucleotide units in length. In some embodiments, a provided oligonucleotide is from about 2 to about 23 nucleotide units in length. In some embodiments, a provided oligonucleotide is from about 2 to about 22 nucleotide units in length. In some embodiments, a provided oligonucleotide is from about 2 to about 21 nucleotide units in length. In some embodiments, a provided oligonucleotide is from about 2 to about 20 nucleotide units in length.

In some embodiments, a provided oligonucleotide is from about 4 to about 200 nucleotide units in length. In some embodiments, a provided oligonucleotide is from about 4 to about 180 nucleotide units in length. In some embodiments, a provided oligonucleotide is from about 4 to about 160 nucleotide units in length. In some embodiments, a provided oligonucleotide is from about 4 to about 140 nucleotide units in length. In some embodiments, a provided oligonucleotide is from about 4 to about 120 nucleotide units in length. In some embodiments, a provided oligonucleotide is from about 4 to about 100 nucleotide units in length. In some embodiments, a provided oligonucleotide is from about 4 to about 90 nucleotide units in length. In some embodiments, a provided oligonucleotide is from about 4 to about 80 nucleotide units in length. In some embodiments, a provided oligonucleotide is from about 4 to about 70 nucleotide units in length. In some embodiments, a provided oligonucleotide is from about 4 to about 60 nucleotide units in length. In some embodiments, a provided oligonucleotide is from about 4 to about 50 nucleotide units in length. In some embodiments, a provided oligonucleotide is from about 4 to about 40 nucleotide units in length. In some embodiments, a provided oligonucleotide is from about 4 to about 30 nucleotide units in length. In some embodiments, a provided oligonucleotide is from about 4 to about 29 nucleotide units in length. In some embodiments, a provided oligonucleotide is from about 4 to about 28 nucleotide units in length. In some embodiments, a provided oligonucleotide is from about 4 to about 27 nucleotide units in length. In some embodiments, a provided oligonucleotide is from about 4 to about 26 nucleotide units in length. In some embodiments, a provided oligonucleotide is from about 4 to about 25 nucleotide units in length. In some embodiments, a provided oligonucleotide is from about 4 to about 24 nucleotide units in length. In some embodiments, a provided oligonucleotide is from about 4 to about 23 nucleotide units in length. In some embodiments, a provided oligonucleotide is from about 4 to about 22 nucleotide units in length. In some embodiments, a provided oligonucleotide is from about 4 to about 21 nucleotide units in length. In some embodiments, a provided oligonucleotide is from about 4 to about 20 nucleotide units in length.

In some embodiments, a provided oligonucleotide is from about 5 to about 10 nucleotide units in length. In some embodiments, a provided oligonucleotide is from about 10 to about 30 nucleotide units in length. In some embodiments, a provided oligonucleotide is from about 15 to about 25 nucleotide units in length. In some embodiments, a provided oligonucleotide is from about 5, 6, 7, 8, 9, 10, 11, 12, 13, 14, 15, 16, 17, 18, 19, 20, 21, 22, 23, 24, or 25 nucleotide units in length.

In some embodiments, an oligonucleotide is at least 2 nucleotide units in length. In some embodiments, an oligonucleotide is at least 3 nucleotide units in length. In some embodiments, an oligonucleotide is at least 4 nucleotide units in length. In some embodiments, an oligonucleotide is at least 5 nucleotide units in length. In some embodiments, an oligonucleotide is at least 6 nucleotide units in length. In some embodiments, an oligonucleotide is at least 7 nucleotide units in length. In some embodiments, an oligonucleotide is at least 8 nucleotide units in length. In some embodiments, an oligonucleotide is at least 9 nucleotide units in length. In some embodiments, an oligonucleotide is at least 10 nucleotide units in length. In some embodiments, an oligonucleotide is at least 11 nucleotide units in length. In some embodiments, an oligonucleotide is at least 12 nucleotide units in length. In some embodiments, an oligonucleotide is at least 13 nucleotide units in length. In some embodiments, an oligonucleotide is at least 14 nucleotide units in length. In some embodiments, an oligonucleotide is at least 15 nucleotide units in length. In some embodiments, an oligonucleotide is at least 16 nucleotide units in length. In some embodiments, an oligonucleotide is at least 17 nucleotide units in length. In some embodiments, an oligonucleotide is at least 18 nucleotide units in length. In some embodiments, an oligonucleotide is at least 19 nucleotide units in length. In some embodiments, an oligonucleotide is at least 20 nucleotide units in length. In some embodiments, an oligonucleotide is at least 21 nucleotide units in length. In some embodiments, an oligonucleotide is at least 22 nucleotide units in length. In some embodiments, an oligonucleotide is at least 23 nucleotide units in length. In some embodiments, an oligonucleotide is at least 24 nucleotide units in length. In some embodiments, an oligonucleotide is at least 25 nucleotide units in length. In some other embodiments, an oligonucleotide is at least 30 nucleotide units in length. In some other embodiments, an oligonucleotide is a duplex of complementary strands of at least 18 nucleotide units in length. In some other embodiments, an oligonucleotide is a duplex of complementary strands of at least 21 nucleotide units in length.

In some embodiments, the 5'-end and/or the 3'-end of a provided oligonucleotide is modified. In some embodiments, the 5'-end and/or the 3'-end of a provided oligonucleotide is modified with a terminal cap moiety. Examples of such modifications, including terminal cap moieties are extensively described herein and in the art, for example but not limited to those described in US Patent Application Publication US 2009/0023675A1.

In some embodiments, oligonucleotides of an oligonucleotide type characterized by 1) a common base sequence and length, 2) a common pattern of backbone linkages, and 3) a common pattern of backbone chiral centers, have the same chemical structure. For example, they have the same base sequence, the same pattern of nucleoside modifications, the same pattern of backbone linkages (i.e., pattern of internucleotidic linkage types, for example, phosphate, phosphorothioate, etc), the same pattern of backbone chiral centers (i.e. pattern of linkage phosphorus stereochemistry (Rp/Sp)), and the same pattern of backbone phosphorus modifications (e.g., pattern of "—XLR$^1$" groups in formula I).

Example Oligonucleotides and Compositions

In some embodiments, a provided chirally controlled oligonucleotide comprises the sequence of, or part of the sequence of mipomersen. Mipomersen is based on the following base sequence GCCT/UCAGT/UCT/UGCT/UT/UCGCACC (SEQ ID NO: 42). In some embodiments, one or more of any of the nucleotide or linkages may be modified in accordance of the present disclosure. In some embodiments, the present disclosure provides a chirally controlled oligonucleotide having the sequence of G*-C*-C*-U*-C*-dA-dG-dT-dC-dT-dG-dmC-dT-dT-dmC-G*-C*-A*-C*-C* (SEQ ID NO: 43) [d=2'-deoxy, *=2'-O-(2-methoxyethyl)] with 3'→5' phosphorothioate linkages. Example modified mipomersen sequences are described throughout the application, including but not limited to those in Table 2.

In certain embodiments, a provided oligonucleotide is a mipomersen unimer. In certain embodiments, a provided oligonucleotide is a mipomersen unimer of configuration Rp. In certain embodiments, a provided oligonucleotide is a mipomersen unimer of configuration Sp.

Exempary chirally controlled oligonucleotides comprising the sequence of, or part of the sequence of mipomersen is depicted in Table 2, below.

TABLE 2

Example oligonucleotides.

| Oligo | Stereochemistry/Sequence | Description | SEQ ID NO: |
|---|---|---|---|
| 101 | All-(Rp)-d[GsCsCsTsCsAsGsTsCsTsGsCsTsTsCsGsCsAsCsC] | All-R | 44 |
| 102 | All-(Sp)-d[GsCsCsTsCsAsGsTsCsTsGsCsTsTsCsGsCsAsCsC] | All-S | 45 |
| 103 | (Rp, Rp, Rp, Rp, Rp, Sp, Sp, Sp, Sp, Sp Sp, Sp, Sp, Sp, Rp, Rp, Rp, Rp, Rp)-d[GsCsCsTsCsAsGsTsCsTsGsCsTsTsCsGsCsAsCsC] | 5R-9S-5R | 46 |
| 104 | (Sp, Sp, Sp, Sp, Sp, Rp, Rp, Rp, Rp, Rp Rp, Rp, Rp, Rp, Sp, Sp, Sp, Sp, Sp)-d[GsCsCsTsCsAsGsTsCsTsGsCsTsTsCsGsCsAsCsC] | 5S-9R-5S | 47 |
| 105 | (Sp, Rp, Rp, Rp, Rp, Rp, Rp, Rp, Rp, Rp Rp, Rp, Rp, Rp, Rp, Rp, Rp, Rp, Sp)-d[GsCsCsTsCsAsGsTsCsTsGsCsTsTsCsGsCsAsCsC] | 1S-17R-1S | 48 |
| 106 | (Rp, Sp, Sp, Sp, Sp, Sp, Sp, Sp, Sp, Sp Sp, Sp, Sp, Sp, Sp, Sp, Sp, Sp, Rp)-d[GsCsCsTsCsAsGsTsCsTsGsCsTsTsCsGsCsAsCsC] | 1R-17S-1R | 49 |
| 107 | (Rp, Sp, Rp, Sp, Rp, Sp, Rp, Sp, Rp, Sp Rp, Sp, Rp, Sp, Rp, Sp, Rp, Sp, Rp)-d[GsCsCsTsCsAsGsTsCsTsGsCsTsTsCsGsCsAsCsC] | (R/S)$_9$R | 50 |
| 108 | (Sp, Rp, Sp, Rp, Sp, Rp, Sp, Rp, Sp, Rp Sp, Rp, Sp, Rp, Sp, Rp, Sp, Rp, Sp)-d[GsCsCsTsCsAsGsTsCsTsGsCsTsTsCsGsCsAsCsC] | (S/R)$_9$S | 51 |
| 109 | (Sp, Sp, Sp, Rp, Rp, Rp, Rp, Rp, Rp, Rp Rp, Rp, Rp, Rp, Rp, Sp, Sp, Sp)d[GsCsCsTsCsAsGsTsCsTsGsCsTsTsCsGsCsAsCsC] | 3S-13R-3S | 52 |

TABLE 2-continued

Example oligonucleotides.

| Oligo | Stereochemistry/Sequence | Description | SEQ ID NO: |
|---|---|---|---|
| 110 | (Rp, Rp, Rp, Sp, Sp, Sp, Sp, Sp, Sp, Sp Sp, Sp, Sp, Sp, Sp, Rp, Rp, Rp)-d[GsCsCsTsCsAsGsTsCsTsGsCsTsTsCsGsCsAsCsC] | 3R-13S-3R | 53 |
| 111 | (Sp, Sp, Sp, Sp, Sp, Sp, Sp, Sp, Sp Sp, Sp, Sp, Sp, Sp, Sp, Sp, Sp, Rp)-d[GsCsCsTsCsAsGsTsCsTsGsCsTsTsCsGsCsAsCsC] | 18S/R[19] | 54 |
| 112 | (Sp, Sp, Sp, Sp, Sp, Sp, Sp, Sp, Rp, Sp Sp, Sp, Sp, Sp, Sp, Sp, Sp, Sp, Sp)-d[GsCsCsTsCsAsGsTsCsTsGsCsTsTsCsGsCsAsCsC] | 18S/R[9] | 55 |
| 113 | (Sp, Rp, Sp, Sp, Sp, Sp, Sp, Sp, Sp Sp, Sp, Sp, Sp, Sp, Sp, Sp, Sp, Sp)-d[GsCsCsTsCsAsGsTsCsTsGsCsTsTsCsGsCsAsCsC] | 18S/R[2] | 56 |
| 114 | (Rp, Rp, Sp, Rp, Rp, Sp, Rp, Rp, Sp, Rp Rp, Sp, Rp, Rp, Sp, Rp, Rp, Sp, Rp)-d[GsCsCsTsCsAsGsTsCsTsGsCsTsTsCsGsCsAsCsC] | (RRS)$_6$-R | 57 |
| 115 | (Sp, Rp, Rp, Sp, Rp, Rp, Sp, Rp, Rp, Sp, Rp Rp, Sp, Rp, Rp, Sp, Rp, Rp, Sp)-d[GsCsCsTsCsAsGsTsCsTsGsCsTsTsCsGsCsAsCsC] | S-(RRS)$_6$ | 58 |
| 116 | (Rp, Sp, Rp, Rp, Sp, Rp, Rp, Sp, Rp Rp, Sp, Rp, Rp, Sp, Rp, Rp, Sp, Rp Rp)d[GsCsCsTsCsAsGsTsCsTsGsCsTsTsCsGsCsAsCsC] | RS-(RRS)$_5$-RR | 59 |
| 122 | All-(Rp)-d[Gs1Cs1Cs1Ts1Cs1As1Gs1Ts1Cs1Ts1Gs1Cs1Ts1Ts1Cs1Gs1Cs1As1Cs1C] | All-R | 60 |
| 123 | (Sp, Rp, Rp, Rp, Rp, Rp, Rp, Rp, Rp, Rp Rp, Rp, Rp, Rp, Rp, Rp, Rp, Rp, Sp)-d[Gs1Cs1Cs1Ts1Cs1As1Gs1Ts1Cs1Ts1Gs1Cs1Ts1Ts1Cs1Gs1Cs1As1Cs1C] | 1S-17R-1S | 61 |
| 124 | All-(Sp)-d[Gs1Cs1Cs1Ts1Cs1As1Gs1Ts1Cs1Ts1Gs1Cs1Ts1Ts1Cs1Gs1Cs1As1Cs1C] | All-S | 62 |
| 126 | All-(Rp)-d[Cs2As2Gs2T] | All-R | |
| 127 | All-(Rp)-d[Cs3As3Gs3T] | All-R | |
| 128 | All-(Sp)-d[Cs4As4Gs4T] | All-S | |
| 129 | All-(Sp)-d[Cs5As5Gs5T] | All-S | |
| 130 | All-(Sp)-d[Cs6As6Gs6T] | All-S | |
| 131 | All-(Rp)-d[Gs7Cs7Cs7Ts7Cs7As7Gs7Ts7Cs7Ts7Gs7Cs7Ts7Ts7Cs7Gs7Cs7As7Cs7C] | All-R | 63 |
| 132 | All-(Sp)-d[Gs7Cs7Cs7Ts7Cs7As7Gs7Ts7Cs7Ts7Gs7Cs7Ts7Ts7Cs7Gs7Cs7As7Cs7C] | All-S | 64 |
| 133 | (Rp, Rp, Rp, Rp, Rp, Sp, Sp, Sp, Sp, Sp Sp, Sp, Sp, Sp, Rp, Rp, Rp, Rp, Rp)-d[Gs15mCs15mCs1Ts1mCs1As1Gs1Ts15mCs1Ts1Gs15mCs1Ts1Ts15mCs1Gs15mCs1As15mCs1mC] | 5R-9S-5R | 65 |
| 134 | (Sp, Sp, Sp, Sp, Sp, Rp, Rp, Rp, Rp, Rp Rp, Rp, Rp, Rp, Sp, Sp, Sp, Sp, Sp)-d[Gs15mCs15mCs1Ts15mCs1As1Gs1Ts15mCs1Ts1Gs15mCs1Ts1Ts15mCs1Gs15mCs1As15mCs1mC] | 5S-9R-5S | 66 |
| 135 | All-(Rp)-d[5mCs1As1Gs1Ts15mCs1Ts1Gs15mCs1Ts1Ts15mCs1G] | All-R | 67 |
| 136 | All-(Sp)-d[5mCs1As1Gs1Ts15mCs1Ts1Gs15mCs1Ts1Ts15mCs1G] | All-S | 68 |
| 137 | (Sp, Rp, Rp, Rp, Rp, Rp, Rp, Rp, Rp, Rp, Sp)-d[5mCs1As1Gs1Ts15mCs1Ts1Gs15mCs1Ts1Ts15mCs1G] | 1S-9R-1S | 69 |
| 138 | (Sp, Sp, Rp, Rp, Rp, Rp, Rp, Rp, Rp, Sp, Sp)-d[5mCs1As1Gs1Ts15mCs1Ts1Gs15mCs1Ts1Ts15mCs1G] | 2S-7R-2S | 70 |
| 139 | (Rp, Sp, Sp, Sp, Sp, Sp, Sp, Sp, Sp, Sp, Rp)-d[5mCs1As1Gs1Ts15mCs1Ts1Gs15mCs1Ts1Ts15mCs1G] | 1R-9S-1R | 71 |
| 140 | (Rp, Rp, Sp, Sp, Sp, Sp, Sp, Sp, Sp, Rp, Rp)-d[5mCs1As1Gs1Ts15mCs1Ts1Gs15mCs1Ts1Ts15mCs1G] | 2R-7S-2R | 72 |

TABLE 2-continued

Example oligonucleotides.

| Oligo | Stereochemistry/Sequence | Description | SEQ ID NO: |
|---|---|---|---|
| 141 | (Sp, Sp, Sp, Rp, Rp, Rp, Rp, Rp, Sp, Sp, Sp)-d[5mCs1As1Gs1Ts15mCs1Ts1Gs15mCs1Ts1Ts15mCs1G] | 3S-5R-3S | 73 |
| 142 | (Rp, Rp, Rp, Sp, Sp, Sp, Sp, Sp, Rp, Rp, Rp)-d[5mCs1As1Gs1Ts15mCs1Ts1Gs15mCs1Ts1Ts15mCs1G] | 3R-5S-3R | 74 |
| 143 | (Sp, Sp, Rp, Sp, Sp, Rp, Sp, Sp, Rp, Sp, Sp)-d[5mCs1As1Gs1Ts15mCs1Ts1Gs15mCs1Ts1Ts15mCs1G] | (SSR)$_3$-SS | 75 |
| 144 | (Rp, Rp, Sp, Rp, Rp, Sp, Rp, Rp, Sp, Rp, Rp)-d[5mCs1As1Gs1Ts15mCs1Ts1Gs15mCs1Ts1Ts15mCs1G] | (RRS)$_3$-RR | 76 |
| 145 | All-(Rp)-d[5mCs1Ts15mCs1As1Gs1Ts15mCs1Ts1Gs15mCs1Ts1Ts15mCs1Gs15mC] | All-R | 77 |
| 146 | All-(Rp)-d[Gs15mCs1Ts1G] | All-R | |
| 147 | All-(Rp)-d[5mCs1As1Gs1T] | All-R | |
| 148 | All-(Rp)-d[5mCs2As2Gs2Ts25mCs2Ts2Gs25mCs2Ts2Ts25mCs2G] | All-R | 78 |
| 149 | All-(Rp)-d[5mCs4As4Gs4Ts45mCs4Ts4Gs45mCs4Ts4Ts45mCs4G] | All-R | 79 |
| 151 | All-(Sp)-d[Cs1AsGs1T] | All-S | |
| 152 | All-(Sp)-d[Cs1AGs1T] | All-S | |
| 153 | All-(Sp)-d[CAs1GsT] | All-S | |
| 157 | All-(Sp)-d[5mCs1As1Gs1T] | All-S | |
| 158 | (Sp, Sp, Sp, Sp, Sp, Rp, Rp, Rp, Rp Rp, Rp, Rp, Rp, Rp, Sp, Sp, Sp, Sp)-d[GsCsCsTsCsAsGsTsCsTsGsCsTsTsCs1GsCsAcsC] | 5S-9R-4S | 80 |
| 159 | (Sp, Sp, Sp, Sp, Sp, Rp, Rp, Rp, Rp Rp, Rp, Rp, Rp, Sp, Sp, Sp, Sp, Sp)-d[Gs1Cs1Cs1Ts1CsAsGsTsCsTsGsCsTsTsCs1GsCs2As2Cs2C] | 5S-9R-5S | 81 |
| 160 | All-(Rp)-(Gs5mCs5mCsTs5mCs)$_{MOE}$d[AsGsTs5mCsTsGs5mCsTsTs5mCs](Gs5mCsAs5mCs5mC)$_{MOE}$ | All-R | 82 |
| 161 | All-(Sp)-(Gs5mCs5mCsTs5mCs)$_{MOE}$d[AsGsTs5mCsTsGs5mCsTsTs5mCs](Gs5mCsAs5mCs5mC)$_{MOE}$ | All-S | 83 |
| 162 | (Rp, Rp, Rp, Rp, Rp, Sp, Sp, Sp, Sp Sp, Sp, Sp, Sp, Rp, Rp, Rp, Rp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 5R-9S-5R | 84 |
| 163 | (Sp, Sp, Sp, Sp, Sp, Rp, Rp, Rp, Rp Rp, Rp, Rp, Rp, Sp, Sp, Sp, Sp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 5S-9R-5S | 85 |
| 164 | (Sp, Rp, Rp, Rp, Rp, Rp, Rp, Rp, Rp Rp, Rp, Rp, Rp, Rp, Rp, Rp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | 1S-17R-1S | 86 |
| 165 | (Rp, Sp, Sp, Sp, Sp, Sp, Sp, Sp, Sp Sp, Sp, Sp, Sp, Sp, Sp, Sp, Sp, Rp)-(Gs5mCs5mCsTs5mCs)$_{MOE}$d[AsGsTs5mCsTsGs5mCsTsTs5mCs](Gs5mCsAs5mCs5mC)$_{MOE}$ | 1R-17S-1R | 87 |
| 166 | (Rp, Sp, Rp, Sp, Rp, Sp, Rp, Sp, Rp Sp, Rp, Sp, Rp, Sp, Rp, Sp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | (R/S)$_9$R | 88 |
| 167 | (Sp, Rp, Sp, Rp, Sp, Rp, Sp, Rp, Sp, Rp Sp, Rp, Sp, Rp, Sp, Rp, Sp, Rp, Sp)-(Gs5mCs5mCsTs5mCs)$_{MOE}$d[AsGsTs5mCsTsGs5mCsTsTs5mCs](Gs5mCsAs5mCs5mC)$_{MOE}$ | (S/R)$_9$S | 89 |

TABLE 2-continued

Example oligonucleotides.

| Oligo | Stereochemistry/Sequence | Description | SEQ ID NO: |
|---|---|---|---|
| 168 | (Sp, Sp, Sp, Rp, Rp, Rp, Rp, Rp, Rp, Rp Rp, Rp, Rp, Rp, Rp, Sp, Sp, Sp) (Gs5mCs5mCsTs5mCs)$_{MOE}$d[AsGsTs5mCsTsGs5mCsTsTs5mCs] (Gs5mCsAs5mCs5mC)$_{MOE}$ | 3S-13R-3S | 90 |
| 169 | (Rp, Rp, Rp, Sp, Sp, Sp, Sp, Sp, Sp, Sp Sp, Sp, Sp, Sp, Sp, Rp, Rp, Rp) - (Gs5mCs5mCsTs5mCs)$_{MOE}$d[AsGsTs5mCsTsGs5mCsTsTs5mCs] (Gs5mCsAs5mCs5mC)$_{MOE}$ | 3R-13S-3R | 91 |
| 170 | (Sp, Sp, Sp, Sp, Sp, Sp, Sp, Sp, Sp Sp, Sp, Sp, Sp, Sp, Sp, Sp, Sp, Rp) - (Gs5mCs5mCsTs5mCs)$_{MOE}$d[AsGsTs5mCsTsGs5mCsTsTs5mCs] (Gs5mCsAs5mCs5mC)$_{MOE}$ | 18S/R$^{19}$ | 92 |
| 171 | (Sp, Sp, Sp, Sp, Sp, Sp, Sp, Rp, Sp Sp, Sp, Sp, Sp, Sp, Sp, Sp, Sp, Sp) - (Gs5mCs5mCsTs5mCs)$_{MOE}$d[AsGsTs5mCsTsGs5mCsTsTs5mCs] (Gs5mCsAs5mCs5mC)$_{MOE}$ | 18S/R$^{9}$ | 93 |
| 172 | (Sp, Rp, Sp, Sp, Sp, Sp, Sp, Sp Sp, Sp, Sp, Sp, Sp, Sp, Sp, Sp, Sp) - (Gs5mCs5mCsTs5mCs)$_{MOE}$d[AsGsTs5mCsTsGs5mCsTsTs5mCs] (Gs5mCsAs5mCs5mC)$_{MOE}$ | 18S/R$^{2}$ | 94 |
| 173 | (Rp, Rp, Sp, Rp, Rp, Sp, Rp, Rp, Sp Rp, Rp, Sp, Rp, Rp, Sp, Rp, Rp, Rp) - (Gs5mCs5mCsTs5mCs)$_{MOE}$d[AsGsTs5mCsTsGs5mCsTsTs5mCs] (Gs5mCsAs5mCs5mC)$_{MOE}$ | (RRS)$_6$-R | 95 |
| 174 | (Sp, Rp, Rp, Sp, Rp, Rp, Sp, Rp, Rp, Sp Rp, Rp, Sp, Rp, Rp, Sp, Rp, Rp, Sp) - (Gs5mCs5mCsTs5mCs)$_{MOE}$d[AsGsTs5mCsTsGs5mCsTsTs5mCs] (Gs5mCsAs5mCs5mC)$_{MOE}$ | S-(RRS)$_6$ | 96 |
| 175 | (Rp, Sp, Rp, Rp, Sp, Rp, Rp, Sp, Rp Rp, Sp, Rp, Rp, Sp, Rp, Rp, Sp, Rp Rp) (Gs5mCs5mCsTs5mCs)$_{MOE}$d[AsGsTs5mCsTsGs5mCsTsTs5mCs] (Gs5mCsAs5mCs5mC)$_{MOE}$ | RS-(RRS)$_5$-RR | 97 |
| 176 | (Rp, Sp, Rp, Rp, Sp, Rp, Rp, Sp, Rp Rp, Sp, Rp, Rp, Sp, Rp, Rp, Sp, Rp Rp) (Gs15mCs15mCs1Ts15mCs1)$_{MOE}$[As1Gs1Ts15mCs1Ts1Gs15mCs1Ts1Ts15mCs1] (Gs15mCs1As15mCs15mC)$_{MOE}$ | RS-(RRS)$_5$-RR | 98 |
| 177 | (Rp, Sp, Rp, Rp, Sp, Rp, Rp, Sp, Rp Rp, Sp, Rp, Rp, Sp, Rp, Rp, Sp, Rp Rp) (Gs15mCs15mCs1Ts15mCs1)$_{MOE}$d[AGT5mCTG5mCTT5mC] (Gs25mCs2As25mCs25mC)$_{MOE}$ | RS-(RRS)$_5$-RR | 99 |
| 178 | (Sp, Rp, Rp, Sp, Rp, Rp, Sp, Rp, Rp, Sp Rp, Rp, Sp, Rp, Rp, Sp, Rp, Rp, Sp) - (Gs5mCs5mCsTs5mCs)$_{MOE}$d[AsGsTs5mCsTsGs5mCsTsTs5mCs] (Gs5mCsAs5mCs5mC)$_F$ (F: 2-fluorodeoxyribose) | S-(RRS)$_6$ | 100 |
| 179 | (Rp, Sp, Rp, Rp, Sp, Rp, Rp, Sp, Rp Rp, Sp, Rp, Rp, Sp, Rp, Rp, Sp, Rp Rp)d[Gs8Cs8Cs8Ts8Cs8As8Gs8Ts8Cs8Ts8Gs8Cs8Ts8Ts8Cs8Gs8Cs8As8Cs8C] | RS-(RRS)$_5$-RR | 101 |
| 180 | (Rp, Sp, Rp, Rp, Sp, Rp, Rp, Sp, Rp Rp, Sp, Rp, Rp, Sp, Rp, Rp, Sp, Rp Rp)d[Gs9Cs9Cs9Ts9Cs9As9Gs9Ts9Cs9Ts9Gs9Cs9Ts9Ts9Cs9Gs9Cs9As9Cs9C] | RS-(RRS)$_5$-RR | 102 |
| 181 | (Rp, Sp, Rp, Rp, Sp, Rp, Rp, Sp, Rp Rp, Sp, Rp, Rp, Sp, Rp, Rp, Sp, Rp Rp)d[Gs10Cs10Cs10Ts10Cs10As10Gs10Ts10Cs10Ts10Gs10Cs10Ts10Ts10Cs10Gs10Cs10As10Cs10C] | RS-(RRS)$_5$-RR | 103 |
| 182 | (Rp, Sp, Rp, Rp, Sp, Rp, Rp, Sp, Rp Rp, Sp, Rp, Rp, Sp, Rp, Rp, Sp, Rp Rp)d[Gs11Cs11Cs11Ts11Cs11As11Gs11Ts11Cs11Ts11Gs11Cs11Ts11Ts11Cs11Gs11Cs11As11Cs11C] | RS-(RRS)$_5$-RR | 104 |
| 183 | (Rp, Sp, Rp, Rp, Sp, Rp, Rp, Sp, Rp Rp, Sp, Rp, Rp, Sp, Rp, Rp, Sp, Rp Rp)d[Gs12Cs12Cs12Ts12Cs12As12Gs12Ts12Cs12Ts12Gs12Cs12Ts12Ts12Cs12Gs12Cs12As12Cs12C] | RS-(RRS)$_5$-RR | 105 |
| 184 | (Rp, Sp, Rp, Rp, Sp, Rp, Rp, Sp, Rp Rp, Sp, Rp, Rp, Sp, Rp, Rp, Sp, Rp Rp)d[Gs13Cs13Cs13Ts13Cs13As13Gs13Ts13Cs13Ts13Gs13Cs13Ts13Ts13Cs13Gs13Cs13As13Cs13C] | RS-(RRS)$_5$-RR | 106 |

TABLE 2-continued

Example oligonucleotides.

| Oligo | Stereochemistry/Sequence | Description | SEQ ID NO: |
|---|---|---|---|
| 185 | (Rp, Sp, Rp, Rp, Sp, Rp, Rp, Sp, Rp Rp, Sp, Rp, Rp, Sp, Rp, Rp, Sp, Rp Rp)d[Gs14Cs14Cs14Ts14Cs14As14Gs14Ts14Cs14Ts14Gs14Cs14Ts14Ts14Cs14Gs14Cs14As14Cs14C] | RS-(RRS)₅-RR | 107 |
| 186 | (Rp, Sp, Rp, Rp, Sp, Rp, Rp, Sp, Rp Rp, Sp, Rp, Rp, Sp, Rp, Rp, Sp, Rp Rp)d[Gs15Cs15Cs15Ts15Cs15As15Gs15Ts15Cs15Ts15Gs15Cs15Ts15Ts15Cs15Gs15Cs15As15Cs15C] | RS-(RRS)₅-RR | 108 |
| 187 | (Rp, Sp, Rp, Rp, Sp, Rp, Rp, Sp, Rp Rp, Sp, Rp, Rp, Sp, Rp, Rp, Sp, Rp Rp)d[GsCsCs1TsCsAs]GsUs2CsUsGsd[CsTs3TsCsGs]CsAs4CsC | RS-(RRS)₅-RR | 109 |
| 188 | (Sp, Sp, Sp, Sp, Sp, Rp, Rp, Rp, Rp, Rp Rp, Rp, Rp, Rp, Sp, Sp, Sp, Sp)-d[GsCsCsTsCsAsGsTsCsTsGsCsTsTsCsGsCsACsC] | 5S-9R-4S | 110 |
| 189 | (Sp, Sp, Sp, Sp, Sp, Rp, Rp, Rp, Rp, Rp Rp, Rp, Rp, Rp, Sp, Sp, Sp, Sp)-d[Gs1Cs1Cs1Ts1Cs1As1Gs1Ts1Cs1Ts1Gs1Cs1Ts1Ts1Cs1Gs1Cs1ACs1C] | 5S-9R-4S | 111 |
| 190 | (Sp, Sp, Sp, Sp, Sp, Rp, Rp, Rp, Rp, Rp Rp, Rp, Rp, Rp, Sp, Sp, Sp, Sp)-d[Gs8Cs8Cs8Ts8Cs8As8Gs8Ts8Cs8Ts8Gs8Cs8Ts8Ts8Cs8Gs8Cs1ACs8C] | 5S-9R-4S | 112 |
| 191 | (Sp, Sp, Sp, Sp, Sp, Rp, Rp, Rp, Rp, Rp Rp, Rp, Rp, Rp, Sp, Sp, Sp, Sp)-d[Gs9Cs9Cs9Ts9Cs9As9Gs9Ts9Cs9Ts9Gs9Cs9Ts9Ts9Cs9Gs9Cs1ACs9C] | 5S-9R-4S | 113 |
| 192 | (Sp, Sp, Sp, Sp, Sp, Rp, Rp, Rp, Rp, Rp Rp, Rp, Rp, Rp, Sp, Sp, Sp, Sp)-d[Gs10Cs10Cs10Ts10Cs10As10Gs10Ts10Cs10Ts10Gs10Cs10Ts10Ts10Cs10Gs10Cs1ACs10C] | 5S-9R-4S | 114 |
| 193 | (Sp, Sp, Sp, Sp, Sp, Rp, Rp, Rp, Rp, Rp Rp, Rp, Rp, Rp, Sp, Sp, Sp, Sp)-d[Gs11Cs11Cs11Ts11Cs11As11Gs11Ts11Cs11Ts11Gs11Cs11Ts11Ts11Cs11Gs11Cs1ACs11C] | 5S-9R-4S | 115 |
| 194 | (Sp, Sp, Sp, Sp, Sp, Rp, Rp, Rp, Rp, Rp Rp, Rp, Rp, Rp, Sp, Sp, Sp, Sp)-d[Gs12Cs12Cs12Ts12Cs12As12Gs12Ts12Cs12Ts12Gs12Cs12Ts12Ts12Cs12Gs12Cs1ACs12C] | 5S-9R-4S | 116 |
| 195 | (Sp, Sp, Sp, Sp, Sp, Rp, Rp, Rp, Rp, Rp Rp, Rp, Rp, Rp, Sp, Sp, Sp, Sp)-d[Gs13Cs13Cs13Ts13Cs13As13Gs13Ts13Cs13Ts13Gs13Cs13Ts13Ts13Cs13Gs13Cs1ACs13C] | 5S-9R-4S | 117 |
| 196 | (Sp, Sp, Sp, Sp, Sp, Rp, Rp, Rp, Rp, Rp Rp, Rp, Rp, Rp, Sp, Sp, Sp, Sp)-d[Gs14Cs14Cs14Ts14Cs14As14Gs14Ts14Cs14Ts14Gs14Cs14Ts14Ts14Cs14Gs14Cs1ACs14C] | 5S-9R-4S | 118 |
| 197 | (Sp, Sp, Sp, Sp, Sp, Rp, Rp, Rp, Rp, Rp Rp, Rp, Rp, Rp, Sp, Sp, Sp, Sp)-d[Gs15Cs15Cs15Ts15Cs15As15Gs15Ts15Cs15Ts15Gs15Cs15Ts15Ts15Cs15Gs15Cs1ACs15C] | 5S-9R-4S | 119 |
| 198 | (Sp, Sp, Sp, Sp, Sp, Rp, Rp, Rp, Rp, Rp Rp, Rp, Rp, Rp, Sp, Sp, Sp, Sp)-GsCsCsUsCsAsGsUsCsUsGsCsUsUsCsGsCsACsC | 5S-9R-4S | 120 |
| 199 | (Sp, Sp, Sp, Sp, Sp, Rp, Rp, Rp, Rp, Rp Rp, Rp, Rp, Rp, Sp, Sp, Sp, Sp)-Gs1Cs1Cs1Us1Cs1As1Gs1Us1Cs1Us1Gs1Cs1Us1Us1Cs1Gs1CsACs1C | 5S-9R-4S | 121 |
| 200 | (Sp, Sp, Sp, Sp, Sp, Rp, Rp, Rp, Rp, Rp Rp, Rp, Rp, Rp, Sp, Sp, Sp, Sp)-Gs8Cs8Cs8Us8Cs8As8Gs8Us8Cs8Us8Gs8Cs8Us8Us8Cs8Gs8Cs1ACs8C | 5S-9R-4S | 122 |
| 201 | (Sp, Sp, Sp, Sp, Sp, Rp, Rp, Rp, Rp, Rp Rp, Rp, Rp, Rp, Sp, Sp, Sp, Sp)-Gs9Cs9Cs9Us9Cs9As9Gs9Us9Cs9Us9Gs9Cs9Us9Us9Cs9Gs9Cs1ACs9C | 5S-9R-4S | 123 |
| 202 | (Sp, Sp, Sp, Sp, Sp, Rp, Rp, Rp, Rp, Rp Rp, Rp, Rp, Rp, Sp, Sp, Sp, Sp)-Gs10Cs10Cs10Us10Cs10As10Gs10Us10Cs10Us10Gs10Cs10Us10Us10Cs10Gs10Cs1ACs10C | 5S-9R-4S | 124 |
| 203 | (Sp, Sp, Sp, Sp, Sp, Rp, Rp, Rp, Rp, Rp Rp, Rp, Rp, Rp, Sp, Sp, Sp, Sp)-Gs11Cs11Cs11Us11Cs11As11Gs11Us11Cs11Us11Gs11Cs11Us11Us11Cs11Gs11Cs1ACs11C | 5S-9R-4S | 125 |

TABLE 2-continued

Example oligonucleotides.

| Oligo | Stereochemistry/Sequence | Description | SEQ ID NO: |
|---|---|---|---|
| 204 | (Sp, Sp, Sp, Sp, Sp, Rp, Rp, Rp, Rp, Rp Rp, Rp, Rp, Rp, Sp, Sp, Sp, Sp)-Gs12Cs12Cs12Us12Cs12As12Gs12Cs12Us12Gs12Cs12Us12Us 12Cs12Gs12Cs1ACs12C | 5S-9R-4S | 126 |
| 205 | (Sp, Sp, Sp, Sp, Sp, Rp, Rp, Rp, Rp, Rp Rp, Rp, Rp, Rp, Sp, Sp, Sp, Sp)-Gs13Cs13Cs13Us13Cs13As13Gs13Cs13Us13Cs13Us13Gs13Cs13Us13Us 13Cs13Gs13Cs1ACs13C | 5S-9R-4S | 127 |
| 206 | (Sp, Sp, Sp, Sp, Sp, Rp, Rp, Rp, Rp, Rp Rp, Rp, Rp, Rp, Sp, Sp, Sp, Sp)-Gs14Cs14Cs14Us14Cs14As14Gs14Cs14Us14Cs14Us14Gs14Cs14Us14Us 14Cs14Gs14Cs1ACs14C | 5S-9R-4S | 128 |
| 207 | (Sp, Sp, Sp, Sp, Sp, Rp, Rp, Rp, Rp, Rp Rp, Rp, Rp, Rp, Sp, Sp, Sp, Sp)-Gs15Cs15Cs15Us15Cs15As15Gs15Cs15Us15Cs15Us15Gs15Cs15Us15Us 15Cs15Gs15Cs1ACs15C | 5S-9R-4S | 129 |

In some embodiments, the present disclosure provides oligonucleotides and/or oligonucleotide compositions that are useful for treating Huntington's disease, for example, selected from:

TABLE N1

Example sequences targeting rs362307

| | | | SEQ ID NO: |
|---|---|---|---|
| WV-904 | G*G*G*C*A*C*A*A*G*G*G*C*A*C*A*G*A*C*T*T | rs362307 P13 | 130 |
| WV-905 | G*G*C*A*C*A*A*G*G*G*C*A*C*A*G*A*C*T*T*C | rs362307 P12 | 131 |
| WV-906 | G*C*A*C*A*A*G*G*G*C*A*C*A*G*A*C*T*T*C*C | rs362307 P11 | 132 |
| WV-907 | C*A*C*A*A*G*G*G*C*A*C*A*G*A*C*T*T*C*C*A | rs362307 P10 | 133 |
| WV-908 | A*C*A*A*G*G*G*C*A*C*A*G*A*C*T*T*C*C*A*A | rs362307 P9 | 134 |
| WV-909 | C*A*A*G*G*G*C*A*C*A*G*A*C*T*T*C*C*A*A*A | rs362307 P8 | 135 |
| WV-910 | mG*mG*mG*mC*mA*C*A*A*G*G*G*C*A*C*A*G*A*C*T*T | rs362307 P13 | 136 |
| WV-911 | mG*mG*mC*mA*mC*A*A*G*G*G*C*A*C*A*G*A*C*T*T*C | rs362307 P12 | 137 |
| WV-912 | mG*mC*mA*mC*mA*A*G*G*G*C*A*C*A*G*A*C*T*T*C*C | rs362307 P11 | 138 |
| WV-913 | mC*mA*mC*mA*mA*G*G*G*C*A*C*A*G*A*C*T*T*C*C*A | rs362307 P10 | 139 |
| WV-914 | mA*mC*mA*mA*mG*G*G*C*A*C*A*G*A*C*T*T*C*C*A*A | rs362307 P9 | 140 |
| WV-915 | mC*mA*mA*mG*mG*G*C*A*C*A*G*A*C*T*T*C*C*A*A*A | rs362307 P8 | 141 |
| WV-916 | mG*mG*mG*mC*mA*C*A*A*G*G*G*C*A*C*A*mG*mA*mC*mU*mU | rs362307 P13 | 142 |
| WV-917 | mG*mG*mC*mA*mC*A*A*G*G*G*C*A*C*A*G*mA*mC*mU*mU*mC | rs362307 P12 | 143 |
| WV-918 | mG*mC*mA*mC*mA*A*G*G*G*C*A*C*A*G*A*mC*mU*mU*mC*mC | rs362307 P11 | 144 |
| WV-919 | mC*mA*mC*mA*mA*G*G*G*C*A*C*A*G*A*C*mU*mU*mC*mC*mA | rs362307 P10 | 145 |
| WV-920 | mA*mC*mA*mA*mG*G*G*C*A*C*A*G*A*C*T*mU*mC*mC*mA*mA | rs362307 P9 | 146 |
| WV-921 | mC*mA*mA*mG*mG*G*C*A*C*A*G*A*C*T*T*mC*mC*mA*mA*mA | rs362307 P8 | 147 |
| WV-922 | mG*mC*mA*mC*mA*mA*mG*mG*G*C*A*C*A*G*A*mC*mU*mU*mC*mC | rs362307 P11 | 148 |
| WV-923 | mC*mA*mC*mA*mA*mG*mG*G*C*A*C*A*G*A*C*mU*mU*mC*mC*mA | rs362307 P10 | 149 |
| WV-924 | mA*mC*mA*mA*mG*mG*G*C*A*C*A*G*A*C*mU*mU*mC*mC*mA*mA | rs362307 P9 | 150 |

TABLE N1-continued

Example sequences targeting rs362307

| | | | SEQ ID NO: |
|---|---|---|---|
| WV-925 | mC*mA*mA*mG*mG*G*C*A*C*A*G*A*mC*mU*mU*mC*mC*mA*mA*mA | rs362307P8 | 151 |
| WV-926 | mGmCmAmCmAmAmGmG*G*C*A*C*A*G*A*mCmUmUmCmC | rs362307P11 | 152 |
| WV-927 | mCmAmCmAmAmGmG*G*C*A*C*A*G*A*mCmUmUmCmCmA | rs362307P10 | 153 |
| WV-928 | mAmCmAmAmGmG*G*C*A*C*A*G*A*mCmUmUmCmCmAmA | rs362307P9 | 154 |
| WV-929 | mCmAmAmGmG*G*C*A*C*A*G*A*mCmUmUmCmCmAmAmA | rs362307P8 | 155 |
| WV-930 | mGmGmCmC*A*A*G*G*C*A*C*A*mGmAmCmUmU | rs362307P13 | 156 |
| WV-931 | mGmCmAmC*A*A*G*G*C*A*C*A*G*mAmCmUmUmC | rs362307P12 | 157 |
| WV-932 | mGmCmAmCmA*A*G*G*C*A*C*A*G*A*mCmUmUmCmC | rs362307P11 | 158 |
| WV-933 | mCmAmCmAmA*G*G*C*A*C*A*G*A*C*mUmUmCmCmA | rs362307P10 | 159 |
| WV-934 | mAmCmAmAmG*G*C*A*C*A*G*A*C*T*mUmCmCmAmA | rs362307P9 | 160 |
| WV-935 | mCmAmAmGmG*G*C*A*C*A*G*A*C*T*T*mCmCmAmAmA | rs362307P8 | 161 |
| WV-936 | G*SG*SG*SC*SA*SC*SA*SA*SG*SG*SG*SC*SA*SC*RA*SG*SA*SC*ST*ST | rs362307P13 | 162 |
| WV-937 | G*SG*SC*SA*SC*SA*SA*SG*SG*SG*SC*SA*SC*RA*SG*SA*SC*ST*ST*SC | rs362307P12 | 163 |
| WV-938 | G*SC*SA*SC*SA*SA*SG*SG*SG*SC*SA*SC*RA*SG*SA*SC*ST*ST*SC*SC | rs362307P11 | 164 |
| WV-939 | C*SA*SC*SA*SA*SG*SG*SG*SC*SA*SC*RA*SG*SA*SC*ST*ST*SC*SC*SA | rs362307P10 | 165 |
| WV-940 | A*SC*SA*SA*SG*SG*SG*SC*SA*SC*RA*SG*SA*SC*ST*ST*SC*SC*SA*SA | rs362307P9 | 166 |
| WV-941 | C*SA*SA*SG*SG*SG*SC*SA*SC*RA*SG*SA*SC*ST*ST*SC*SC*SA*SA*SA | rs362307P8 | 167 |
| WV-1085 | mG*SmG*SmC*SmA*SmC*SA*SA*SG*SG*SG*SC*SA*SC*RA*SG*SmA*SmC*SmU*SmU*SmC | rs362307P12 | 168 |
| WV-1086 | mG*RmG*RmC*RmA*RmC*SA*SA*SG*SG*SG*SC*SA*SC*RA*SG*SmA*RmC*RmU*RmU*RmC | rs362307P12 | 169 |
| WV-1087 | mGmGmCmAmC*SA*SA*SG*SG*SG*SC*SA*SC*RA*SG*SmAmCmUmUmC | rs362307P12 | 170 |
| WV-1088 | mG*SmG*SmC*SmA*SmC*SmA*SmA*SmG*SG*SG*SC*SA*SC*RA*SG*SA*SC*ST*ST*SC | rs362307P12 | 171 |
| WV-1089 | mG*RmG*RmC*RmA*RmC*RmA*RmA*RmG*SG*SG*SC*SA*SC*RA*SG*SA*SC*ST*ST*SC | rs362307P12 | 172 |
| WV-1090 | mGmGmCmAmCmAmAmG*SG*SG*SC*SA*SC*RA*SG*SA*SC*ST*ST*SC | rs362307P12 | 173 |
| WV-1091 | mG*RmGmCmAmC*SA*SA*SG*SG*SG*SC*SA*SC*RA*SG*SmAmCmUmU*RmC | rs362307P12 | 174 |
| WV-1092 | mG*SmGmCmAmC*SA*SA*SG*SG*SG*SC*SA*SC*RA*SG*SmAmCmUmU*5mC | rs362307P12 | 175 |
| WV-982 | G*SC*SA*SG*SG*SG*SC*SA*SC*SA*SA*SG*SG*SG*SC*SA*SC*RA*SG*SA | rs362307P16 | 176 |
| WV-983 | C*SA*SG*SG*SG*SC*SA*SC*SA*SA*SG*SG*SG*SC*SA*SC*RA*SG*SA*SC | rs362307P15 | 177 |
| WV-984 | A*SG*SG*SG*SC*SA*SC*SA*SA*SG*SG*SG*SC*SA*SC*RA*SG*SA*SC*ST | rs362307P14 | 178 |
| WV-985 | A*SA*SG*SG*SG*SC*SA*SC*RA*SG*SA*SC*ST*ST*SC*SC*SA*SA*SA*SG | rs362307P7 | 179 |
| WV-986 | A*SG*SG*SG*SC*SA*SC*RA*SG*SA*SC*ST*ST*SC*SC*SA*SA*SA*SG*SG | rs362307P6 | 180 |
| WV-987 | G*SG*SG*SC*SA*SC*RA*SG*SA*SC*ST*ST*SC*SC*SA*SA*SA*SG*SG*SC | rs362307P5 | 181 |
| WV-1234 | mG*mG*mC*mA*mC*A*A*G*G*C*A*C*A*G*mA*mC*mU*BrdU*mC | rs362307P12 | 182 |
| WV-1235 | mG*mG*mC*mA*mC*A*A*G*G*C*A*C*A*G*mA*mC*BrdU*BrdU*mC | rs362307P12 | 183 |
| WV-1067 | G*G*G*C*A*C*A*A*G*G*G*C*d2AP*C*A*G*A*C*T*T | rs362307P13 | 184 |
| WV-1068 | G*G*C*A*C*A*A*G*G*G*C*d2AP*C*A*G*A*C*T*T*C | rs362307P12 | 185 |

TABLE N1-continued

Example sequences targeting rs362307

| | | | SEQ ID NO: |
|---|---|---|---|
| WV-1069 | G*C*A*C*A*A*G*G*G*C*d2AP*C*A*G*A*C*T*T*C*C | rs362307 P11 | 186 |
| WV-1070 | G*G*G*C*A*C*A*A*G*G*G*C*dDAP*C*A*G*A*C*T*T | rs362307 P13 | 187 |
| WV-1071 | G*G*C*A*C*A*A*G*G*G*C*dDAP*C*A*G*A*C*T*T*C | rs362307 P12 | 188 |
| WV-1072 | G*C*A*C*A*A*G*G*G*C*dDAP*C*A*G*A*C*T*T*C*C | rs362307 P11 | 189 |
| WV-1510 | G*SmGmCmAmC*SA*SA*SG*SG*SG*SC*SA*SC*RA*SG*SmAmCmUmU*SC | rs362307 P12 | 190 |
| WV-1511 | G*mGmCmAmC*A*A*G*G*C*A*C*A*G*mAmCmUmU*C | rs362307 P12 | 191 |
| WV-1497 | mG*mGmCmAmC*A*A*G*G*C*A*C*A*G*mAmCmUmU*mC | rs362307 P12 | 192 |
| WV-1655 | Geo*Geom5CeoAeom5Ceo*A*A*G*G*C*A*C*A*G*Aeom5CeoTeoTeo*m5Ceo | rs362307 P12 | 193 |

TABLE N2

Example sequences targeting rs362306

| WV-1001 | G*A*G*C*A*G*C*T*G*C*A*A*C*C*T*G*G*C*A*A | rs362306 P10 | 194 |
|---|---|---|---|
| WV-1002 | A*G*C*A*G*C*T*G*C*A*A*C*C*T*G*G*C*A*A*C | rs362306 P9 | 195 |
| WV-1003 | G*C*A*G*C*T*G*C*A*A*C*C*T*G*G*C*A*A*C*A | rs362306 P8 | 196 |
| WV-1004 | C*A*G*C*T*G*C*A*A*C*C*T*G*G*C*A*A*C*A*A | rs362306 P7 | 197 |
| WV-1005 | A*G*C*T*G*C*A*A*C*C*T*G*G*C*A*A*C*A*A*C | rs362306 P6 | 198 |
| WV-1006 | G*C*T*G*C*A*A*C*C*T*G*G*C*A*A*C*A*A*C*C | rs362306 P5 | 199 |
| WV-1007 | mG*mA*mG*mC*mA*G*C*T*G*C*A*A*C*C*T*G*G*C*A*A | rs362306 P10 | 200 |
| WV-1008 | mA*mG*mC*mA*mG*C*T*G*C*A*A*C*C*T*G*G*C*A*A*C | rs362306 P9 | 201 |
| WV-1009 | mG*mC*mA*mG*mC*T*G*C*A*A*C*C*T*G*G*C*A*A*C*A | rs362306 P8 | 202 |
| WV-1010 | mC*mA*mG*mC*mU*G*C*A*A*C*C*T*G*G*C*A*A*C*A*A | rs362306 P7 | 203 |
| WV-1011 | mA*mG*mC*mU*mG*C*A*A*C*C*T*G*G*C*A*A*C*A*A*C | rs362306 P6 | 204 |
| WV-1012 | mG*mC*mU*mG*mC*A*A*C*C*T*G*G*C*A*A*C*A*A*C*C | rs362306 P5 | 205 |
| WV-1013 | mG*mA*mG*mC*mA*G*C*T*G*C*A*A*C*C*T*mG*mG*mC*mA*mA | rs362306 P10 | 206 |
| WV-1014 | mA*mG*mC*mA*mG*C*T*G*C*A*A*C*C*T*G*mG*mC*mA*mA*mC | rs362306 P9 | 207 |
| WV-1015 | mG*mC*mA*mG*mC*T*G*C*A*A*C*C*T*G*G*mC*mA*mA*mC*mA | rs362306 P8 | 208 |
| WV-1016 | mC*mA*mG*mC*mU*G*C*A*A*C*C*T*G*G*C*mA*mA*mC*mA*mA | rs362306 P7 | 209 |
| WV-1017 | mA*mG*mC*mU*mG*C*A*A*C*C*T*G*G*C*A*mA*mC*mA*mA*mC | rs362306 P6 | 210 |
| WV-1018 | mG*mC*mU*mG*mC*A*A*C*C*T*G*G*C*A*A*mC*mA*mA*mC*mC | rs362306 P5 | 211 |
| WV-1019 | mG*mA*mG*mC*mA*mG*mC*T*G*C*A*A*C*C*mU*mG*mG*mC*mA*mA | rs362306 P10 | 212 |
| WV-1020 | mGmAmGmCmAmGmC*T*G*C*A*A*C*C*mUmGmGmCmAmA | rs362306 P10 | 213 |
| WV-1021 | mA*mG*mC*mA*mG*mC*T*G*C*A*A*C*C*T*G*mG*mC*mA*mA*mC | rs362306 P9 | 214 |
| WV-1022 | mAmGmCmAmGmC*T*G*C*A*A*C*C*T*G*mGmCmAmAmC | rs362306 P9 | 215 |
| WV-1023 | mG*mC*mA*mG*mC*T*G*C*A*A*C*C*mU*mG*mG*mC*mA*mA*mC*mA | rs362306 P8 | 216 |
| WV-1024 | mGmCmAmGmC*T*G*C*A*A*C*C*mUmGmGmCmAmAmCmA | rs362306 P8 | 217 |
| WV-1025 | mGmAmGmCmA*G*C*T*G*C*A*A*C*C*T*mGmGmCmAmA | rs362306 P10 | 218 |
| WV-1026 | mAmGmCmAmG*C*T*G*C*A*A*C*C*T*G*mGmCmAmAmC | rs362306 P9 | 219 |

TABLE N2-continued

Example sequences targeting rs362306

| | | | |
|---|---|---|---|
| WV-1027 | mGmCmAmGmC*T*G*C*A*A*C*C*T*G*G*mCmAmAmCmA | rs362306 P8 | 220 |
| WV-1028 | mCmAmGmCmU*G*C*A*A*C*C*T*G*G*C*mAmAmCmAmA | rs362306 P7 | 221 |
| WV-1029 | mAmGmCmUmG*C*A*A*C*C*T*G*G*C*A*mAmCmAmAmC | rs362306 P6 | 222 |
| WV-1030 | mGmCmUmGmC*A*A*C*C*T*G*G*C*A*A*mCmAmAmCmC | rs362306 P5 | 223 |
| WV-952 | G*SA*SG*SC*SA*SG*SC*ST*SG*SC*SA*RA*SC*SC*ST*SG*SG*SC*SA*SA | rs362306 P10 | 224 |
| WV-953 | A*SG*SC*SA*SG*SC*ST*SG*SC*SA*RA*SC*SC*ST*SG*SG*SC*SA*SA*SC | rs362306 P9 | 225 |
| WV-954 | G*SC*SA*SG*SC*ST*SG*SC*SA*RA*SC*SC*ST*SG*SG*SC*SA*SA*SC*SA | rs362306 P8 | 226 |
| WV-955 | C*SA*SG*SC*ST*SG*SC*SA*RA*SC*SC*ST*SG*SG*SC*SA*SA*SC*SA*SA | rs362306 P7 | 227 |
| WV-956 | A*SG*SC*ST*SG*SC*SA*RA*SC*SC*ST*SG*SG*SC*SA*SA*SC*SA*SA*SC | rs362306 P6 | 228 |
| WV-957 | G*SC*ST*SG*SC*SA*RA*SC*SC*ST*SG*SG*SC*SA*SA*SC*SA*SA*SC*SC | rs362306 P5 | 229 |

TABLE N3

Example sequences targeting rs362268

| | | | |
|---|---|---|---|
| WV-1031 | G*G*C*A*A*C*A*G*C*C*A*G*C*C*T*G*C*A | rs362268 P10 | 230 |
| WV-1032 | G*C*C*A*A*C*A*G*C*C*A*G*C*C*T*G*C*A*G | rs362268 P9 | 231 |
| WV-1033 | G*C*C*A*A*C*A*G*C*C*A*G*C*C*T*G*C*A*G*G | rs362268 P8 | 232 |
| WV-1034 | C*C*A*A*C*A*G*C*C*A*G*C*C*T*G*C*A*G*G*A | rs362268 P7 | 233 |
| WV-1035 | C*A*A*C*A*G*C*C*A*G*C*C*T*G*C*A*G*G*A*G | rs362268 P6 | 234 |
| WV-1036 | A*A*C*A*G*C*C*A*G*C*C*T*G*C*A*G*G*A*G*G | rs362268 P5 | 235 |
| WV-1037 | mG*mG*mG*mC*mC*A*A*C*A*G*C*C*A*G*C*C*T*G*C*A | rs362268 P10 | 236 |
| WV-1038 | mG*mG*mC*mC*mA*A*C*A*G*C*C*A*G*C*C*T*G*C*A*G | rs362268 P9 | 237 |
| WV-1039 | mG*mC*mC*mA*mA*C*A*G*C*C*A*G*C*C*T*G*C*A*G*G | rs362268 P8 | 238 |
| WV-1040 | mC*mC*mA*mA*mC*A*G*C*C*A*G*C*C*T*G*C*A*G*G*A | rs362268 P7 | 239 |
| WV-1041 | mC*mA*mA*mC*mA*G*C*C*A*G*C*C*T*G*C*A*G*G*A*G | rs362268 P6 | 240 |
| WV-1042 | mA*mA*mC*mA*mG*C*C*A*G*C*C*T*G*C*A*G*G*A*G*G | rs362268 P5 | 241 |
| WV-1043 | mG*mG*mG*mC*mC*A*A*C*A*G*C*C*A*G*C*mC*mU*mG*mC*mA | rs362268 P10 | 242 |
| WV-1044 | mG*mG*mC*mC*mA*A*C*A*G*C*C*A*G*C*C*mU*mG*mC*mA*mG | rs362268 P9 | 243 |
| WV-1045 | mG*mC*mC*mA*mA*C*A*G*C*C*A*G*C*C*T*mG*mC*mA*mG*mG | rs362268 P8 | 244 |
| WV-1046 | mC*mC*mA*mA*mC*A*G*C*C*A*G*C*C*T*G*mC*mA*mG*mG*mA | rs362268 P7 | 245 |
| WV-1047 | mC*mA*mA*mC*mA*G*C*C*A*G*C*C*T*G*C*mA*mG*mG*mA*mG | rs362268 P6 | 246 |
| WV-1048 | mA*mA*mC*mA*mG*C*C*A*G*C*C*T*G*C*A*mG*mG*mA*mG*mG | rs362268 P5 | 247 |
| WV-1049 | mG*mG*mG*mC*mC*mA*mA*C*A*G*C*C*A*mG*mC*mC*mU*mG*mC*mA | rs362268 P10 | 248 |
| WV-1050 | mGmGmGmCmCmAmA*C*A*G*C*C*A*G*mCmCmUmGmCmA | rs362268 P10 | 249 |
| WV-1051 | mG*mG*mC*mC*mA*mA*C*A*G*C*C*A*G*C*C*mU*mG*mC*mA*mG | rs362268 P9 | 250 |
| WV-1052 | mGmGmCmCmAmA*C*A*G*C*C*A*G*C*C*mUmGmCmAmG | rs362268 P9 | 251 |
| WV-1053 | mG*mC*mC*mA*mA*C*A*G*C*C*A*G*C*mC*mU*mG*mC*mA*mG*mG | rs362268 P8 | 252 |
| WV-1054 | mGmCmCmAmA*C*A*G*C*C*A*G*mCmCmUmGmCmAmGmG | rs362268 P8 | 253 |
| WV-1055 | mGmGmGmCmC*A*A*C*A*G*C*C*A*G*C*mCmUmGmCmA | rs362268 P10 | 254 |

TABLE N3-continued

Example sequences targeting rs362268

| | | | |
|---|---|---|---|
| WV-1056 | mGmGmCmCmA*A*C*A*G*C*C*A*G*C*C*mUmGmCmAmG | rs362268 P9 | 255 |
| WV-1057 | mGmCmCmAmA*C*A*G*C*C*A*G*C*C*T*mGmCmAmGmG | rs362268 P8 | 256 |
| WV-1058 | mCmCmAmAmC*A*G*C*C*A*G*C*C*T*G*mCmAmGmGmA | rs362268 P7 | 257 |
| WV-1059 | mCmAmAmCmA*G*C*C*A*G*C*C*T*G*C*mAmGmGmAmG | rs362268 P6 | 258 |
| WV-1060 | mAmAmCmAmG*C*C*A*G*C*C*T*G*C*A*mGmGmAmGmG | rs362268 P5 | 259 |
| WV-960 | G*SG*SG*SC*SC*SA*SA*SC*SA*SG*SC*RC*SA*SG*SC*SC*ST*SG*SC*SA | rs362268 P10 | 260 |
| WV-961 | G*SG*SC*SC*SA*SA*SC*SA*SG*SC*RC*SA*SG*SC*SC*ST*SG*SC*SA*SG | rs362268 P9 | 261 |
| WV-962 | G*SC*SC*SA*SA*SC*SA*SG*SC*RC*SA*SG*SC*SC*ST*SG*SC*SA*SG*SG | rs362268 P8 | 262 |
| WV-963 | C*SC*SA*SA*SC*SA*SG*SC*RC*SA*SG*SC*SC*ST*SG*SC*SA*SG*SG*SA | rs362268 P7 | 263 |
| WV-964 | C*SA*SA*SC*SA*SG*SC*RC*SA*SG*SC*SC*ST*SG*SC*SA*SG*SG*SA*SG | rs362268 P6 | 264 |
| WV-965 | A*SA*SC*SA*SG*SC*RC*SA*SG*SC*SC*ST*SG*SC*SA*SG*SG*SA*SG*SG | rs362268 P5 | 265 |

TABLE N4

Example sequences targeting rs7685686

| | | | |
|---|---|---|---|
| ONT-450 | A*T*T*A*A*T*A*A*A*T*T*G*T*C*A*T*C*A*C*C | rs7685686 P13 | 266 |
| ONT-451 | A*ST*ST*SA*SA*ST*SA*SA*SA*ST*ST*SG*ST*SC*RA*ST*SC*SA*SC*SC | rs7685686 P13 | 267 |
| ONT-452 | A*ST*ST*SA*SA*ST*SA*SA*SA*ST*ST*SG*ST*SC*SA*RT*SC*SA*SC*SC | rs7685686 P13 | 268 |
| WV-1077 | mA*SmU*SmU*SmA*SmA*SmU*SA*SA*SA*ST*ST*SG*ST*SC*RA*ST*SmC*SmA*SmC*SmC | rs7685686 P13 | 269 |
| WV-1078 | mA*RmU*RmU*RmA*RmA*RmU*SA*SA*SA*ST*ST*SG*ST*SC*RA*ST*SmC*RmA*RmC*RmC | rs7685686 P13 | 270 |
| WV-1079 | mA*SmU*SmU*SmA*SmA*SmU*SmA*SmA*SA*ST*ST*SG*ST*SC*RA*ST*SC*SA*SC*SC | rs7685686 P13 | 271 |
| WV-1080 | mA*RmU*RmU*RmA*RmA*RmU*RmA*RmA*SA*ST*ST*SG*ST*SC*RA*ST*SC*SA*SC*SC | rs7685686 P13 | 272 |
| WV-1081 | mAmUmUmAmAmUmA*SA*ST*ST*SG*ST*SC*RA*ST*SC*SA*SC*SC | rs7685686 P13 | 273 |
| WV-1082 | mAmUmUmAmAmU*SA*SA*SA*ST*ST*SG*ST*SC*RA*ST*SmCmAmC*C | rs7685686 P13 | 274 |
| WV-1083 | mA*SmUmUmAmAmU*SA*SA*SA*ST*ST*SG*ST*SC*RA*ST*SmCmAmC*SmC | rs7685686 P13 | 275 |
| WV-1084 | mA*RmUmUmAmAmU*SA*SA*SA*ST*ST*SG*ST*SC*RA*ST*SmCmAmC*RmC | rs7685686 P13 | 276 |
| WV-1508 | A*SmUmUmAmAmU*SA*SA*ST*ST*SG*ST*SC*RA*ST*SmCmAmC*SC | rs7685686 P13 | 277 |
| WV-1509 | A*mUmUmAmAmU*A*A*A*T*T*G*T*C*A*T*mCmAmC*C | rs7685686 P13 | 278 |
| WV-2023 | T*G*T*C*A*T*C*A*C*C*A*G*A*A*A*mA*mA*mG*mU*mC | rs7685686 P3 | 279 |
| WV-2024 | mU*T*G*T*C*A*T*C*A*C*C*A*G*A*A*mA*mA*mA*mG*mU | rs7685686 P4 | 280 |
| WV-2025 | T*T*G*T*C*A*T*C*A*C*C*A*G*A*A*mA*mA*mA*mG*mU | rs7685686 P4 | 281 |
| WV-2026 | mA*mU*T*G*T*C*A*T*C*A*C*C*A*G*A*mA*mA*mA*mA*mG | rs7685686 P5 | 282 |
| WV-2027 | mA*T*T*G*T*C*A*T*C*A*C*C*A*G*A*mA*mA*mA*mA*mG | rs7685686 P5 | 283 |
| WV-2028 | mA*mA*mU*T*G*T*C*A*T*C*A*C*C*A*G*mA*mA*mA*mA*mA | rs7685686 P6 | 284 |
| WV-2029 | mA*mA*T*T*G*T*C*A*T*C*A*C*C*A*G*mA*mA*mA*mA*mA | rs7685686 P6 | 285 |
| WV-2030 | mA*mA*mA*T*T*G*T*C*A*T*C*A*C*C*A*mG*mA*mA*mA*mA | rs7685686 P7 | 286 |
| WV-2031 | mA*mA*mA*mU*T*G*T*C*A*T*C*A*C*C*A*mG*mA*mA*mA*mA | rs7685686 P7 | 287 |
| WV-2032 | mU*mA*mA*mA*mU*T*G*T*C*A*T*C*A*C*C*A*mG*mA*mA*mA*mA | rs7685686 P8 | 288 |

TABLE N4-continued

Example sequences targeting rs7685686

| | | | |
|---|---|---|---|
| WV-2033 | mU*mA*mA*mA*mU*T*G*T*C*A*T*C*A*C*C*mA*mG*mA*mA*mA | rs7685686 P8 | 289 |
| WV-2034 | mA*mU*mA*mA*mA*T*T*G*T*C*A*T*C*A*C*C*mA*mG*mA*mA | rs7685686 P9 | 290 |
| WV-2035 | mA*mU*mA*mA*mA*T*T*G*T*C*A*T*C*A*C*mC*mA*mG*mA*mA | rs7685686 P9 | 291 |
| WV-2036 | mA*mA*mU*mA*mA*A*T*T*G*T*C*A*T*C*A*C*C*mA*mG*mA | rs7685686 P10 | 292 |
| WV-2037 | mA*mA*mU*mA*mA*A*T*T*G*T*C*A*T*C*A*C*mC*mA*mG*mA | rs7685686 P10 | 293 |
| WV-2038 | mA*mA*mU*mA*mA*A*T*T*G*T*C*A*T*C*A*mC*mC*mA*mG*mA | rs7685686 P10 | 294 |
| WV-2039 | mU*mA*mA*mU*mA*A*A*T*T*G*T*C*A*T*C*A*C*C*mA*mG | rs7685686 P11 | 295 |
| WV-2040 | mU*mA*mA*mU*mA*A*A*T*T*G*T*C*A*T*C*A*C*mC*mA*mG | rs7685686 P11 | 296 |
| WV-2041 | mU*mA*mA*mU*mA*A*A*T*T*G*T*C*A*T*C*A*mC*mC*mA*mG | rs7685686 P11 | 297 |
| WV-2042 | mU*mA*mA*mU*mA*A*A*T*T*G*T*C*A*T*C*mA*mC*mC*mA*mG | rs7685686 P11 | 298 |
| WV-2043 | mU*mU*mA*mA*mU*A*A*A*T*T*G*T*C*A*T*C*A*C*C*mA | rs7685686 P12 | 299 |
| WV-2044 | mU*mU*mA*mA*mU*A*A*A*T*T*G*T*C*A*T*C*A*C*mC*mA | rs7685686 P12 | 300 |
| WV-2045 | mU*mU*mA*mA*mU*A*A*A*T*T*G*T*C*A*T*C*A*mC*mC*mA | rs7685686 P12 | 301 |
| WV-2046 | mU*mU*mA*mA*mU*A*A*A*T*T*G*T*C*A*T*C*mA*mC*mC*mA | rs7685686 P12 | 302 |
| WV-2047 | mA*mU*mU*mA*mA*T*A*A*A*T*T*G*T*C*A*T*C*A*C*C | rs7685686 P13 | 303 |
| WV-2048 | mA*mU*mU*mA*mA*T*A*A*A*T*T*G*T*C*A*T*C*A*C*mC | rs7685686 P13 | 304 |
| WV-2049 | mA*mU*mU*mA*mA*T*A*A*A*T*T*G*T*C*A*T*C*A*mC*mC | rs7685686 P13 | 305 |
| WV-2050 | mA*mU*mU*mA*mA*T*A*A*A*T*T*G*T*C*A*T*C*mA*mC*mC | rs7685686 P13 | 306 |
| WV-2051 | mU*mA*mU*mU*mA*A*T*A*A*A*T*T*G*T*C*A*T*C*A*C | rs7685686 P14 | 307 |
| WV-2052 | mU*mA*mU*mU*mA*A*T*A*A*A*T*T*G*T*C*A*T*C*A*mC | rs7685686 P14 | 308 |
| WV-2053 | mU*mA*mU*mU*mA*A*T*A*A*A*T*T*G*T*C*A*T*C*mA*mC | rs7685686 P14 | 309 |
| WV-2054 | mC*mU*mA*mU*mU*A*A*T*A*A*A*T*T*G*T*C*A*T*C*A | rs7685686 P15 | 310 |
| WV-2055 | mC*mU*mA*mU*mU*A*A*T*A*A*A*T*T*G*T*C*A*T*C*mA | rs7685686 P15 | 311 |
| WV-2056 | mA*mC*mU*mA*mU*T*A*A*T*A*A*A*T*T*G*T*C*A*T*C | rs7685686 P16 | 312 |
| WV-2057 | T*G*T*C*A*T*C*A*C*C*A*G*A*A*mAmAmGmU*mC | rs7685686 P3 | 313 |
| WV-2058 | mU*T*G*T*C*A*T*C*A*C*C*A*G*A*A*mAmAmGmG*mU | rs7685686 P4 | 314 |
| WV-2059 | T*T*G*T*C*A*T*C*A*C*C*A*G*A*A*mAmAmGmG*mU | rs7685686 P4 | 315 |
| WV-2060 | mA*mU*T*G*T*C*A*T*C*A*C*C*A*G*A*mAmAmAmA*mG | rs7685686 P5 | 316 |
| WV-2061 | mA*T*T*G*T*C*A*T*C*A*C*C*A*G*A*mAmAmAmA*mG | rs7685686 P5 | 317 |
| WV-2062 | mA*mAmU*T*G*T*C*A*T*C*A*C*C*A*G*mAmAmAmA*mA | rs7685686 P6 | 318 |
| WV-2063 | mA*mA*T*T*G*T*C*A*T*C*A*C*C*A*G*mAmAmAmA*mA | rs7685686 P6 | 319 |
| WV-2064 | mA*mAmA*T*T*G*T*C*A*T*C*A*C*C*A*mGmAmAmA*mA | rs7685686 P7 | 320 |
| WV-2065 | mA*mAmAmU*T*G*T*C*A*T*C*A*C*C*A*mGmAmAmA*mA | rs7685686 P7 | 321 |
| WV-2066 | mU*mAmAmAmU*T*G*T*C*A*T*C*A*C*C*A*mGmAmA*mA | rs7685686 P8 | 322 |
| WV-2067 | mU*mAmAmAmU*T*G*T*C*A*T*C*A*C*C*mAmGmAmA*mA | rs7685686 P8 | 323 |
| WV-2068 | mA*mUmAmAmA*T*T*G*T*C*A*T*C*A*C*C*mAmGmA*mA | rs7685686 P9 | 324 |
| WV-2069 | mA*mUmAmAmA*T*T*G*T*C*A*T*C*A*C*mCmAmGmA*mA | rs7685686 P9 | 325 |
| WV-2070 | mA*mAmUmAmA*A*T*T*G*T*C*A*T*C*A*C*C*mAmG*mA | rs7685686 P10 | 326 |
| WV-2071 | mA*mAmUmAmA*A*T*T*G*T*C*A*T*C*A*C*mCmAmG*mA | rs7685686 P10 | 327 |

TABLE N4-continued

Example sequences targeting rs7685686

| | | | |
|---|---|---|---|
| WV-2072 | mA*mAmUmAmA*A*T*T*G*T*C*A*T*C*A*mCmCmAmG*mA | rs7685686 | P10 328 |
| WV-2073 | mU*mAmAmUmA*A*A*T*T*G*T*C*A*T*C*A*C*C*mA*mG | rs7685686 | P11 329 |
| WV-2074 | mU*mAmAmUmA*A*A*T*T*G*T*C*A*T*C*A*C*mCmA*mG | rs7685686 | P11 330 |
| WV-2075 | mU*mAmAmUmA*A*A*T*T*G*T*C*A*T*C*A*mCmCmA*mG | rs7685686 | P11 331 |
| WV-2076 | mU*mAmAmUmA*A*A*T*T*G*T*C*A*T*C*mAmCmCmA*mG | rs7685686 | P11 332 |
| WV-2077 | mU*mUmAmAmU*A*A*A*T*T*G*T*C*A*T*C*A*C*C*mA | rs7685686 | P12 333 |
| WV-2078 | mU*mUmAmAmU*A*A*A*T*T*G*T*C*A*T*C*A*C*mC*mA | rs7685686 | P12 334 |
| WV-2079 | mU*mUmAmAmU*A*A*A*T*T*G*T*C*A*T*C*A*mCmC*mA | rs7685686 | P12 335 |
| WV-2080 | mU*mUmAmAmU*A*A*A*T*T*G*T*C*A*T*C*mAmCmC*mA | rs7685686 | P12 336 |
| WV-2081 | mA*mUmUmAmA*T*A*A*A*T*T*G*T*C*A*T*C*A*C*C | rs7685686 | P13 337 |
| WV-2082 | mA*mUmUmAmA*T*A*A*A*T*T*G*T*C*A*T*C*A*C*mC | rs7685686 | P13 338 |
| WV-2083 | mA*mUmUmAmA*T*A*A*A*T*T*G*T*C*A*T*C*A*mC*mC | rs7685686 | P13 339 |
| WV-2084 | mA*mUmUmAmA*T*A*A*A*T*T*G*T*C*A*T*C*mAmC*mC | rs7685686 | P13 340 |
| WV-2085 | mU*mAmUmUmA*A*T*A*A*A*T*T*G*T*C*A*T*C*A*C | rs7685686 | P14 341 |
| WV-2086 | mU*mAmUmUmA*A*T*A*A*A*T*T*G*T*C*A*T*C*A*mC | rs7685686 | P14 342 |
| WV-2087 | mU*mAmUmUmA*A*T*A*A*A*T*T*G*T*C*A*T*C*mA*mC | rs7685686 | P14 343 |
| WV-2088 | mC*mUmAmUmU*A*A*T*A*A*A*T*T*G*T*C*A*T*C*A | rs7685686 | P15 344 |
| WV-2089 | mC*mUmAmUmU*A*A*T*A*A*A*T*T*G*T*C*A*T*C*mA | rs7685686 | P15 345 |
| WV-2090 | mA*mCmUmAmU*T*A*A*T*A*A*A*T*T*G*T*C*A*T*C | rs7685686 | P16 346 |

TABLE N1

Example sequences targeting rs362307-continued (certain features)

| | | | |
|---|---|---|---|
| WV-904 | All DNA, stereorandom PS | rs362307 | P13 |
| WV-905 | All DNA, stereorandom PS | rs362307 | P12 |
| WV-906 | All DNA, stereorandom PS | rs362307 | P11 |
| WV-907 | All DNA, stereorandom PS | rs362307 | P10 |
| WV-908 | All DNA, stereorandom PS | rs362307 | P9 |
| WV-909 | All DNA, stereorandom PS | rs362307 | P8 |
| WV-910 | 5-15 (2'-OMe-DNA), stereorandom PS | rs362307 | P13 |
| WV-911 | 5-15 (2'-OMe-DNA), stereorandom PS | rs362307 | P12 |
| WV-912 | 5-15 (2'-OMe-DNA), stereorandom PS | rs362307 | P11 |
| WV-913 | 5-15 (2'-OMe-DNA), stereorandom PS | rs362307 | P10 |
| WV-914 | 5-15 (2'-OMe-DNA), stereorandom PS | rs362307 | P9 |
| WV-915 | 5-15 (2'-OMe-DNA), stereorandom PS | rs362307 | P8 |
| WV-916 | 5-10-5 (2'-OMe-DNA-2'-OMe), stereorandom PS | rs362307 | P13 |
| WV-917 | 5-10-5 (2'-OMe-DNA-2'-OMe), stereorandom PS | rs362307 | P12 |
| WV-918 | 5-10-5 (2'-OMe-DNA-2'-OMe), stereorandom PS | rs362307 | P11 |
| WV-919 | 5-10-5 (2'-OMe-DNA-2'-OMe), stereorandom PS | rs362307 | P10 |
| WV-920 | 5-10-5 (2'-OMe-DNA-2'-OMe), stereorandom PS | rs362307 | P9 |
| WV-921 | 5-10-5 (2'-OMe-DNA-2'-OMe), stereorandom PS | rs362307 | P8 |
| WV-922 | 8-7-5 (2'-OMe-DNA-2'-OMe), stereorandom PS | rs362307 | P11 |
| WV-923 | 7-7-6 (2'-OMe-DNA-2'-OMe), stereorandom PS | rs362307 | P10 |
| WV-924 | 6-7-5 (2'-OMe-DNA-2'-OMe), stereorandom PS | rs362307 | P9 |
| WV-925 | 5-7-8 (2'-OMe-DNA-2'-OMe), stereorandom PS | rs362307 | P8 |
| WV-926 | 8-7-5 (2'-OMe-DNA-2'-OMe), stereorandom PS, PO in the wings | rs362307 | P11 |
| WV-927 | 7-7-6 (2'-OMe-DNA-2'-OMe), stereorandom PS, PO in the wings | rs362307 | P10 |
| WV-928 | 6-7-5 (2'-OMe-DNA-2'-OMe), stereorandom PS, PO in the wings | rs362307 | P9 |
| WV-929 | 5-7-8 (2'-OMe-DNA-2'-OMe), stereorandom PS, PO in the wings | rs362307 | P8 |
| WV-930 | 5-10-5 (2'-OMe-DNA-2'-OMe), stereorandom PS, PO in the wings | rs362307 | P13 |
| WV-931 | 5-10-5 (2'-OMe-DNA-2'-OMe), stereorandom PS, PO in the wings | rs362307 | P12 |
| WV-932 | 5-10-5 (2'-OMe-DNA-2'-OMe), stereorandom PS, PO in the wings | rs362307 | P11 |
| WV-933 | 5-10-5 (2'-OMe-DNA-2'-OMe), stereorandom PS, PO in the wings | rs362307 | P10 |
| WV-934 | 5-10-5 (2'-OMe-DNA-2'-OMe), stereorandom PS, PO in the wings | rs362307 | P9 |
| WV-935 | 5-10-5 (2'-OMe-DNA-2'-OMe), stereorandom PS, PO in the wings | rs362307 | P8 |

TABLE N1-continued

Example sequences targeting rs362307-continued (certain features)

| | | | |
|---|---|---|---|
| WV-936 | All DNA, stereopure, One Rp | rs362307 | P13 |
| WV-937 | All DNA, stereopure, One Rp | rs362307 | P12 |
| WV-938 | All DNA, stereopure, One Rp | rs362307 | P11 |
| WV-939 | All DNA, stereopure, One Rp | rs362307 | P10 |
| WV-940 | All DNA, stereopure, One Rp | rs362307 | P9 |
| WV-941 | All DNA, stereopure, One Rp | rs362307 | P8 |
| WV-1085 | 5-10-5 (2'-OMe-DNA-2'-OMe) Gapmer, Stereopure, One Rp in DNA | rs362307 | P12 |
| WV-1086 | 5-10-5 (2'-OMe-DNA-2'-OMe) Gapmer, Stereopure, One Rp in DNA and Rp wings | rs362307 | P12 |
| WV-1087 | 5-10-5 (2'-OMe-DNA-2'-OMe) Gapmer, Stereopure, One Rp in DNA, PO wings | rs362307 | P12 |
| WV-1088 | 8-12 (2'-OMe-DNA) hemimer, Stereopure, One Rp in DNA, Sp wing | rs362307 | P12 |
| WV-1089 | 8-12 (2'-OMe-DNA) hemimer, Stereopure, One Rp in DNA and Rp wing | rs362307 | P12 |
| WV-1090 | 8-12 (2'-OMe-DNA) hemimer, Srereopure, One Rp in DNA and PO wing | rs362307 | P12 |
| WV-1091 | 5-10-5 (2'-OMe-DNA-2'-OMe) gapmer, Stereopure, One Rp in DNA, First and last PS as Rp and rest PO wing | rs362307 | P12 |
| WV-1092 | 5-10-5 (2'-OMe-DNA-2'-OMe) gapmer, Stereopure, One Rp in DNA, First and last PS as Sp and rest PO wing | rs362307 | P12 |
| WV-982 | All DNA, stereopure, One Rp | rs362307 | P16 |
| WV-983 | All DNA, stereopure, One Rp | rs362307 | P15 |
| WV-984 | All DNA, stereopure, One Rp | rs362307 | P14 |
| WV-985 | All DNA, stereopure, One Rp | rs362307 | P7 |
| WV-986 | All DNA, stereopure, One Rp | rs362307 | P6 |
| WV-987 | All DNA, stereopure, One Rp | rs362307 | P5 |
| WV-1234 | 5-10-5 (2'-OMe-DNA-2'-OMe) Gapmer, Stereorandom, One Br-dU | rs362307 | P12 |
| WV-1235 | 5-10-5 (2'-OMe-DNA-2'-OMe) Gapmer, Stereorandom, Two Br-dU | rs362307 | P12 |
| WV-1067 | All DNA, stereorandom PS, one 2-amino purine | rs362307 | P13 |
| WV-1068 | All DNA, stereorandom PS, one 2-amino purine | rs362307 | P12 |
| WV-1069 | All DNA, stereorandom PS, one 2-amino purine | rs362307 | P11 |
| WV-1070 | All DNA, stereorandom PS, one 2,6-diamino purine | rs362307 | P13 |
| WV-1071 | All DNA, stereorandom PS, one 2,6-diamino purine | rs362307 | P12 |
| WV-1072 | All DNA, stereorandom PS, one 2,6-diamino purine | rs362307 | P11 |
| WV-1510 | 1-4-10-4-1 (DNA/2'-OMe) gapmer, Stereopure, one Rp in the DNA, first and last nucletotide is DNA and first and last PS are Sp | rs362307 | P12 |
| WV-1511 | 1-4-10-4-1 (DNA/2'-OMe) gapmer, Stereorandom, 1st and last PS, rest of the wing is PO | rs362307 | P12 |
| WV-1497 | 5-10-5 (2'-OMe-DNA-2'-OMe) gapmer, Stereorandom, First and last PS and rest PO wing | rs362307 | P12 |
| WV-1655 | 5-10-5 (2'-MOE-DNA-2'-MOE) Gapmer, Stereorandom, PO wings with One PS on each end | rs362307 | P12 |

TABLE N2

Example sequences targeting rs362306-continued (certain features)

| | | | |
|---|---|---|---|
| WV-1001 | All DNA, stereorandom PS | rs362306 | P10 |
| WV-1002 | All DNA, stereorandom PS | rs362306 | P9 |
| WV-1003 | All DNA, stereorandom PS | rs362306 | P8 |
| WV-1004 | All DNA, stereorandom PS | rs362306 | P7 |
| WV-1005 | All DNA, stereorandom PS | rs362306 | P6 |
| WV-1006 | All DNA, stereorandom PS | rs362306 | P5 |
| WV-1007 | 5-15 (2'-OMe-DNA), stereorandom PS | rs362306 | P10 |
| WV-1008 | 5-15 (2'-OMe-DNA), stereorandom PS | rs362306 | P9 |
| WV-1009 | 5-15 (2'-OMe-DNA), stereorandom PS | rs362306 | P8 |
| WV-1010 | 5-15 (2'-OMe-DNA), stereorandom PS | rs362306 | P7 |
| WV-1011 | 5-15 (2'-OMe-DNA), stereorandom PS | rs362306 | P6 |
| WV-1012 | 5-15 (2'-OMe-DNA), stereorandom PS | rs362306 | P5 |
| WV-1013 | 5-10-5 (2'-OMe-DNA-2'-OMe), stereorandom PS | rs362306 | P10 |
| WV-1014 | 5-10-5 (2'-OMe-DNA-2'-OMe), stereorandom PS | rs362306 | P9 |
| WV-1015 | 5-10-5 (2'-OMe-DNA-2'-OMe), stereorandom PS | rs362306 | P8 |
| WV-1016 | 5-10-5 (2'-OMe-DNA-2'-OMe), stereorandom PS | rs362306 | P7 |
| WV-1017 | 5-10-5 (2'-OMe-DNA-2'-OMe), stereorandom PS | rs362306 | P6 |
| WV-1018 | 5-10-5 (2'-OMe-DNA-2'-OMe), stereorandom PS | rs362306 | P5 |
| WV-1019 | 7-7-6 (2'-OMe-DNA-2'-OMe), stereorandom PS | rs362306 | P10 |
| WV-1020 | 7-7-6 (2'-OMe-DNA-2'-OMe), stereorandom PS, PO in wings | rs362306 | P10 |
| WV-1021 | 6-7-5 (2'-OMe-DNA-2'-OMe), stereorandom PS | rs362306 | P9 |
| WV-1022 | 6-7-5 (2'-OMe-DNA-2'-OMe), stereorandom PS, PO in the wings | rs362306 | P9 |
| WV-1023 | 5-7-8 (2'-OMe-DNA-2'-OMe), stereorandom PS | rs362306 | P8 |
| WV-1024 | 5-7-8 (2'-OMe-DNA-2'-OMe), stereorandom PS, PO in the wings | rs362306 | P8 |
| WV-1025 | 5-10-5 (2'-OMe-DNA-2'-OMe), stereorandom PS, PO in the wings | rs362306 | P10 |
| WV-1026 | 5-10-5 (2'-OMe-DNA-2'-OMe), stereorandom PS, PO in the wings | rs362306 | P9 |
| WV-1027 | 5-10-5 (2'-OMe-DNA-2'-OMe), stereorandom PS, PO in the wings | rs362306 | P8 |
| WV-1028 | 5-10-5 (2'-OMe-DNA-2'-OMe), stereorandom PS, PO in the wings | rs362306 | P7 |
| WV-1029 | 5-10-5 (2'-OMe-DNA-2'-OMe), stereorandom PS, PO in the wings | rs362306 | P6 |
| WV-1030 | 5-10-5 (2'-OMe-DNA-2'-OMe), stereorandom PS, PO in the wings | rs362306 | P5 |
| WV-952 | All DNA, stereopure, One Rp | rs362306 | P10 |
| WV-953 | All DNA, stereopure, One Rp | rs362306 | P9 |

TABLE N2-continued

Example sequences targeting rs362306-continued (certain features)

| | | | |
|---|---|---|---|
| WV-954 | All DNA, stereopure, One Rp | rs362306 | P8 |
| WV-955 | All DNA, stereopure, One Rp | rs362306 | P7 |
| WV-956 | All DNA, stereopure, One Rp | rs362306 | P6 |
| WV-957 | All DNA, stereopure, One Rp | rs362306 | P5 |

TABLE N3

Example sequences targeting rs362268-continued (certain features)

| | | | |
|---|---|---|---|
| WV-1031 | All DNA, stereorandom PS | rs362268 | P10 |
| WV-1032 | All DNA, stereorandom PS | rs362268 | P9 |
| WV-1033 | All DNA, stereorandom PS | rs362268 | P8 |
| WV-1034 | All DNA, stereorandom PS | rs362268 | P7 |
| WV-1035 | All DNA, stereorandom PS | rs362268 | P6 |
| WV-1036 | All DNA, stereorandom PS | rs362268 | P5 |
| WV-1037 | 5-15 (2'-OMe-DNA), stereorandom PS | rs362268 | P10 |
| WV-1038 | 5-15 (2'-OMe-DNA), stereorandom PS | rs362268 | P9 |
| WV-1039 | 5-15 (2'-OMe-DNA), stereorandom PS | rs362268 | P8 |
| WV-1040 | 5-15 (2'-OMe-DNA), stereorandom PS | rs362268 | P7 |
| WV-1041 | 5-15 (2'-OMe-DNA), stereorandom PS | rs362268 | P6 |
| WV-1042 | 5-15 (2'-OMe-DNA), stereorandom PS | rs362268 | P5 |
| WV-1043 | 5-10-5 (2'-OMe-DNA-2'-OMe), stereorandom PS | rs362268 | P10 |
| WV-1044 | 5-10-5 (2'-OMe-DNA-2'-OMe), stereorandom PS | rs362268 | P9 |
| WV-1045 | 5-10-5 (2'-OMe-DNA-2'-OMe), stereorandom PS | rs362268 | P8 |
| WV-1046 | 5-10-5 (2'-OMe-DNA-2'-OMe), stereorandom PS | rs362268 | P7 |
| WV-1047 | 5-10-5 (2'-OMe-DNA-2'-OMe), stereorandom PS | rs362268 | P6 |
| WV-1048 | 5-10-5 (2'-OMe-DNA-2'-OMe), stereorandom PS | rs362268 | P5 |
| WV-1049 | 7-7-6 (2'-OMe-DNA-2'-OMe), stereorandom PS | rs362268 | P10 |
| WV-1050 | 7-7-6 (2'-OMe-DNA-2'-OMe), stereorandom PS, PO in wings | rs362268 | P10 |
| WV-1051 | 6-7-5 (2'-OMe-DNA-2'-OMe), stereorandom PS | rs362268 | P9 |
| WV-1052 | 6-7-5 (2'-OMe-DNA-2'-OMe), stereorandom PS, PO in the wings | rs362268 | P9 |
| WV-1053 | 5-7-8 (2'-OMe-DNA-2'-OMe), stereorandom PS | rs362268 | P8 |
| WV-1054 | 5-7-8 (2'-OMe-DNA-2'-OMe), stereorandom PS, PO in the wings | rs362268 | P8 |
| WV-1055 | 5-10-5 (2'-OMe-DNA-2'-OMe), stereorandom PS, PO in the wings | rs362268 | P10 |
| WV-1056 | 5-10-5 (2'-OMe-DNA-2'-OMe), stereorandom PS, PO in the wings | rs362268 | P9 |
| WV-1057 | 5-10-5 (2'-OMe-DNA-2'-OMe), stereorandom PS, PO in the wings | rs362268 | P8 |
| WV-1058 | 5-10-5 (2'-OMe-DNA-2'-OMe), stereorandom PS, PO in the wings | rs362268 | P7 |
| WV-1059 | 5-10-5 (2'-OMe-DNA-2'-OMe), stereorandom PS, PO in the wings | rs362268 | P6 |
| WV-1060 | 5-10-5 (2'-OMe-DNA-2'-OMe), stereorandom PS, PO in the wings | rs362268 | P5 |
| WV-960 | All DNA, stereopure, One Rp | rs362268 | P10 |
| WV-961 | All DNA, stereopure, One Rp | rs362268 | P9 |
| WV-962 | All DNA, stereopure, One Rp | rs362268 | P8 |
| WV-963 | All DNA, stereopure, One Rp | rs362268 | P7 |
| WV-964 | All DNA, stereopure, One Rp | rs362268 | P6 |
| WV-965 | All DNA, stereopure, One Rp | rs362268 | P5 |

TABLE N4

Example sequences targeting rs7685686-continued (certain features)

| | | | |
|---|---|---|---|
| ONT-450 | All DNA, stereorandom PS | rs7685686 | P13 |
| ONT-451 | All DNA, stereopure, One Rp in DNA between position 14 and 15 | rs7685686 | P13 |
| ONT-452 | All DNA, stereopure, One Rp in DNA between position 15 and 16 | rs7685686 | P13 |
| WV-1077 | 6-10-4 (2'-OMe-DNA-2'-OMe) Gapmer, stereopure with one Rp in DNA between position 14 and 15 | rs7685686 | P13 |
| WV-1078 | 6-10-4 (2'-OMe-DNA-2'-OMe) Gapmer, stereopure with one Rp in DNA between position 14 and 15 and Rp wings | rs7685686 | P13 |
| WV-1079 | 8-12 (2'-OMe-DNA) Hemimer, stereopure with one Rp in DNA between position 14 and 15 and Sp wing | rs7685686 | P13 |
| WV-1080 | 8-12 (2'-OMe-DNA) Hemimer, stereopure with one Rp in DNA between position 14 and 15 and Rp wing | rs7685686 | P13 |
| WV-1081 | 8-12 (2'-OMe-DNA) Hemimer, stereopure with one Rp in DNA between position 14 and 15 and PO wing | rs7685686 | P13 |
| WV-1082 | 6-10-4 (2'-OMe-DNA-2'-OMe), stereopure with one Rp in DNA between position 14 and 15 and PO wings | rs7685686 | P13 |
| WV-1083 | 6-10-4 (2'-OMe-DNA-2'-OMe), stereopure with one Rp in DNA between position 14 and 15, first and last PS Sp and rest PO wing | rs7685686 | P13 |
| WV-1084 | 6-10-4 (2'-OMe-DNA-2'-OMe), stereopure with one Rp in DNA between position 14 and 15, first and last PS Rp and rest PO wing | rs7685686 | P13 |

TABLE N4-continued

Example sequences targeting rs7685686-continued (certain features)

| | | | |
|---|---|---|---|
| WV-1508 | 1-5-10-3-1 (DNA/2'-OMe) Gapmer, Stereopure, one Rp in the core, first and last PS is Sp, rest is PO in the wing | rs7685686 | P13 |
| WV-1509 | 1-5-10-3-1 (DNA/2'-OMe) Gapmer, Stereorandom, first and last PS, rest is PO in the wing | rs7685686 | P13 |

In Table N1-N4, * only represents a stereorandom phosphorothioate linkage; *S represents an Sp phosphorothioate linkage, *R represents an Rp phosphorothioate linkage, all non-labeled linkage is a natural phosphate linkage, m preceding a base represents 2'-OMe, d2AP represents a 2-amino purine, and dDAP represents a 2,6-diamino purine.

In some embodiments, the present disclosure provides oligonucleotides and/or oligonucleotide compositions that are useful for treating Huntington's disease, for example, selected from:

TABLE N1A

Example sequences targeting rs362307

| | | SEQ ID NO: |
|---|---|---|
| WV-936 | G*SG*SG*SC*SA*SC*SA*SA*SG*SG*SG*SC*SA*SC*RA*SG*SA*SC*ST*ST | 347 |
| WV-937 | G*SG*SC*SA*SC*SA*SA*SG*SG*SG*SC*SA*SC*RA*SG*SA*SC*ST*ST*SC | 348 |
| WV-938 | G*SC*SA*SC*SA*SA*SG*SG*SG*SC*SA*SC*RA*SG*SA*SC*ST*ST*SC*SC | 349 |
| WV-939 | C*SA*SC*SA*SA*SG*SG*SG*SC*SA*SC*RA*SG*SA*SC*ST*ST*SC*SC*SA | 350 |
| WV-940 | A*SC*SA*SA*SG*SG*SG*SC*SA*SC*RA*SG*SA*SC*ST*ST*SC*SC*SA*SA | 351 |
| WV-941 | C*SA*SA*SG*SG*SG*SC*SA*SC*RA*SG*SA*SC*ST*ST*SC*SC*SA*SA*SA | 352 |
| WV-1085 | mG*SmG*SmC*SmA*SmC*SA*SA*SG*SG*SG*SC*SA*SC*RA*SG*SmA*SmC*SmU*SmU*SmC | 353 |
| WV-1086 | mG*RmG*RmC*RmA*RmC*SA*SA*SG*SG*SG*SC*SA*SC*RA*SG*SmA*RmC*RmU*RmU*RmC | 354 |
| WV-1087 | mGmGmCmAmC*SA*SA*SG*SG*SG*SC*SA*SC*RA*SG*SmAmCmUmUmC | 355 |
| WV-1088 | mG*SmG*SmC*SmA*SmC*SmA*SmA*SmG*SG*SG*SC*SA*SC*RA*SG*SA*SC*ST*ST*SC | 356 |
| WV-1089 | mG*RmG*RmC*RmA*RmC*RmA*RmA*RmG*SG*SG*SC*SA*SC*RA*SG*SA*SC*ST*ST*SC | 357 |
| WV-1090 | mGmGmCmAmCmAmAmG*SG*SG*SC*SA*SC*RA*SG*SA*SC*ST*ST*SC | 358 |
| WV-1091 | mG*RmGmCmAmC*SA*SA*SG*SG*SG*SC*SA*SC*RA*SG*SmAmCmUmU*RmC | 359 |
| WV-1092 | mG*SmGmCmAmC*SA*SA*SG*SG*SG*SC*SA*SC*RA*SG*SmAmCmUmU*SmC | 360 |
| WV-982 | G*SC*SA*SG*SG*SG*SC*SA*SC*SA*SA*SG*SG*SG*SC*SA*SC*RA*SG*SA | 361 |
| WV-983 | C*SA*SG*SG*SG*SC*SA*SC*SA*SA*SG*SG*SG*SC*SA*SC*RA*SG*SA*SC | 362 |
| WV-984 | A*SG*SG*SG*SC*SA*SC*SA*SA*SG*SG*SG*SC*SA*SC*RA*SG*SA*SC*ST | 363 |

TABLE N1A-continued

Example sequences targeting rs362307

| | | SEQ ID NO: |
|---|---|---|
| WV-985 | A*SA*SG*SG*SG*SC*SA*SC*RA*SG*SA*SC*ST*ST*SC*SC*SA*SA*SA*SG | 364 |
| WV-986 | A*SG*SG*SG*SC*SA*SC*RA*SG*SA*SC*ST*ST*SC*SC*SA*SA*SA*SG*SG | 365 |
| WV-987 | G*SG*SG*SC*SA*SC*RA*SG*SA*SC*ST*ST*SC*SC*SA*SA*SA*SG*SG*SC | 366 |
| WV-1510 | G*SmGmCmAmC*SA*SA*SG*SG*SG*SC*SA*SC*RA*SG*SmAmCmUmU*SC | 367 |

TABLE N2A

Example sequences targeting rs362306

| | |
|---|---|
| WV-952 G*SA*SG*SC*SA*SG*SC*ST*SG*SC*SA*RA*SC*SC*ST*SG*SG*SC*SA*SA | 368 |
| WV-953 A*SG*SC*SA*SG*SC*ST*SG*SC*SA*RA*SC*SC*ST*SG*SG*SC*SA*SA*SC | 369 |
| WV-954 G*SC*SA*SG*SC*ST*SG*SC*SA*RA*SC*SC*ST*SG*SG*SC*SA*SA*SC*SA | 370 |
| WV-955 C*SA*SG*SC*ST*SG*SC*SA*RA*SC*SC*ST*SG*SG*SC*SA*SA*SC*SA*SA | 371 |
| WV-956 A*SG*SC*ST*SG*SC*SA*RA*SC*SC*ST*SG*SG*SC*SA*SA*SC*SA*SA*SC | 372 |
| WV-957 G*SC*ST*SG*SC*SA*RA*SC*SC*ST*SG*SG*SC*SA*SA*SC*SA*SA*SC*SC | 373 |

TABLE N3A

Example sequences targeting rs362268

| | |
|---|---|
| WV-960 G*SG*SG*SC*SC*SA*SA*SC*SA*SG*SC*RC*SA*SG*SC*SC*ST*SG*SC*SA | 374 |
| WV-961 G*SG*SC*SC*SA*SA*SC*SA*SG*SC*RC*SA*SG*SC*SC*ST*SG*SC*SA*SG | 375 |
| WV-962 G*SC*SC*SA*SA*SC*SA*SG*SC*RC*SA*SG*SC*SC*ST*SG*SC*SA*SG*SG | 376 |
| WV-963 C*SC*SA*SA*SC*SA*SG*SC*RC*SA*SG*SC*SC*ST*SG*SC*SA*SG*SG*SA | 377 |
| WV-964 C*SA*SA*SC*SA*SG*SC*RC*SA*SG*SC*SC*ST*SG*SC*SA*SG*SG*SA*SG | 378 |
| WV-965 A*SA*SC*SA*SG*SC*RC*SA*SG*SC*SC*ST*SG*SC*SA*SG*SG*SA*SG*SG | 379 |

TABLE N4A

Example sequences targeting rs7685686

| | |
|---|---|
| ONT-450 A*T*T*A*A*T*A*A*A*T*T*G*T*C*A*T*C*A*C*C | 380 |
| ONT-451 A*ST*ST*SA*SA*ST*SA*SA*SA*ST*ST*SG*ST*SC*RA*ST*SC*SA*SC*SC | 381 |

TABLE N4A-continued

Example sequences targeting rs7685686

| | | |
|---|---|---|
| ONT-452 | A*ST*ST*SA*SA*ST*SA*SA*SA*ST*ST*SG*ST*SC*SA*RT*SC*SA*SC*SC | 382 |
| WV-1077 | mA*SmU*SmU*SmA*SmA*SmU*SA*SA*SA*ST*ST*SG*ST*SC*RA*ST*SmC*SmA*SmC*SmC | 383 |
| WV-1078 | mA*RmU*RmU*RmA*RmA*RmU*SA*SA*SA*ST*ST*SG*ST*SC*RA*ST*SmC*RmA*RmC*RmC | 384 |
| WV-1079 | mA*SmU*SmU*SmA*SmA*SmU*SmA*SmA*SA*ST*ST*SG*ST*SC*RA*ST*SC*SA*SC*SC | 385 |
| WV-1080 | mA*RmU*RmU*RmA*RmA*RmU*RmA*RmA*SA*ST*ST*SG*ST*SC*RA*ST*SC*SA*SC*SC | 386 |
| WV-1081 | mAmUmUmAmUmAmA*SA*ST*ST*SG*ST*SC*RA*ST*SC*SA*SC*SC | 387 |
| WV-1082 | mAmUmUmAmUmAmU*SA*SA*SA*ST*ST*SG*ST*SC*RA*ST*SmCmAmCmC | 388 |
| WV-1083 | mA*SmUmUmAmAmU*SA*SA*SA*ST*ST*SG*ST*SC*RA*ST*SmCmAmC*SmC | 389 |
| WV-1084 | mA*RmUmUmAmAmU*SA*SA*SA*ST*ST*SG*ST*SC*RA*ST*SmCmAmC*RmC | 390 |
| WV-1508 | A*SmUmUmAmAmU*SA*SA*SA*ST*ST*SG*ST*SC*RA*ST*SmCmAmC*SC | 391 |

TABLE N1A

Example sequences targeting rs362307-continued

| | |
|---|---|
| WV-936 | All DNA, stereopure, One Rp |
| WV-937 | All DNA, stereopure, One Rp |
| WV-938 | All DNA, stereopure, One Rp |
| WV-939 | All DNA, stereopure, One Rp |
| WV-940 | All DNA, stereopure, One Rp |
| WV-941 | All DNA, stereopure, One Rp |
| WV-1085 | 5-10-5 (2'-OMe-DNA-2'-OMe) Gapmer, Stereopure, One Rp in DNA |
| WV-1086 | 5-10-5 (2'-OMe-DNA-2'-OMe) Gapmer, Stereopure, One Rp in DNA and Rp wings |
| WV-1087 | 5-10-5 (2'-OMe-DNA-2'-OMe) Gapmer, Stereopure, One Rp in DNA, PO wings |
| WV-1088 | 8-12 (2'-OMe-DNA) hemimer, Stereopure, One Rp in DNA, Sp wing |
| WV-1089 | 8-12 (2'-OMe-DNA) hemimer, Stereopure, One Rp in DNA and Rp wing |
| WV-1090 | 8-12 (2'-OMe-DNA) hemimer, Srereopure, One Rp in DNA and PO wing |
| WV-1091 | 5-10-5 (2'-OMe-DNA-2'-OMe) gapmer, Stereopure, One Rp in DNA, First and last PS as Rp and rest PO wing |
| WV-1092 | 5-10-5 (2'-OMe-DNA-2'-OMe) gapmer, Stereopure, One Rp in DNA, First and last PS as Sp and rest PO wing |
| WV-982 | All DNA, stereopure, One Rp |
| WV-983 | All DNA, stereopure, One Rp |
| WV-984 | All DNA, stereopure, One Rp |
| WV-985 | All DNA, stereopure, One Rp |
| WV-986 | All DNA, stereopure, One Rp |
| WV-987 | All DNA, stereopure, One Rp |
| WV-1510 | 1-4-10-4-1 (DNA/2'-OMe) gapmer, Stereopure, one Rp in the DNA, first and last nucletotide is DNA and first and last PS are Sp |

TABLE N2A

Example sequences targeting rs362306-continued

| | |
|---|---|
| WV-952 | All DNA, stereopure, One Rp |
| WV-953 | All DNA, stereopure, One Rp |
| WV-954 | All DNA, stereopure, One Rp |
| WV-955 | All DNA, stereopure, One Rp |
| WV-956 | All DNA, stereopure, One Rp |
| WV-957 | All DNA, stereopure, One Rp |

TABLE N3A

Example sequences targeting rs362268-continued

| | |
|---|---|
| WV-960 | All DNA, stereopure, One Rp |
| WV-961 | All DNA, stereopure, One Rp |
| WV-962 | All DNA, stereopure, One Rp |
| WV-963 | All DNA, stereopure, One Rp |
| WV-964 | All DNA, stereopure, One Rp |
| WV-965 | All DNA, stereopure, One Rp |

TABLE N4A

Example sequences targeting rs7685686-continued

| | |
|---|---|
| ONT-451 | All DNA, stereopure, One Rp in DNA between position 14 and 15 |
| ONT-452 | All DNA, stereopure, One Rp in DNA between position 15 and 16 |
| WV-1077 | 6-10-4 (2'-OMe-DNA-2'-OMe) Gapmer, stereopure with one Rp in DNA between position 14 and 15 |
| WV-1078 | 6-10-4 (2'-OMe-DNA-2'-OMe) Gapmer, stereopure with one Rp in DNA between position 14 and 15 and Rp wings |
| WV-1079 | 8-12 (2'-OMe-DNA) Hemimer, stereopure with one Rp in DNA between position 14 and 15 and Sp wing |
| WV-1080 | 8-12 (2'-OMe-DNA) Hemimer, stereopure with one Rp in DNA between position 14 and 15 and Rp wing |
| WV-1081 | 8-12 (2'-OMe-DNA) Hemimer, stereopure with one Rp in DNA between position 14 and 15 and PO wing |
| WV-1082 | 6-10-4 (2'-OMe-DNA-2'-OMe), stereopure with one Rp in DNA between position 14 and 15 and PO wings |
| WV-1083 | 6-10-4 (2'-OMe-DNA-2'-OMe), stereopure with one Rp in DNA between position 14 and 15, first and last PS Sp and rest PO wing |
| WV-1084 | 6-10-4 (2'-OMe-DNA-2'-OMe), stereopure with one Rp in DNA between position 14 and 15, first and last PS Rp and rest PO wing |
| WV-1508 | 1-5-10-3-1 (DNA/2'-OMe) Gapmer, Stereopure, one Rp in the core, first and last PS is Sp, rest is PO in the wing |

In Table N1A-N4A, * only represents a stereorandom phosphorothioate linkage; *S represents an Sp phosphorothioate linkage, *R represents an Rp phosphorothioate linkage, all non-labeled linkage is a natural phosphate linkage, m preceding a base represents 2'-OMe, d2AP represents a 2-amino purine, and dDAP represents a 2,6-diamino purine.

In some embodiments, a provided oligonucleotide composition is a chirally controlled oligonucleotide composition of an oligonucleotide type listed in Table N1A, Table N2A, Table N3A, and Table N4A. In some embodiments, a provided composition is of WV-1087. In some embodiments, a provided composition is of WV-1090. In some embodiments, a provided composition is of WV-1091. In some embodiments, a provided composition is of WV-937. In some embodiments, a provided composition is of WV-2378. In some embodiments, a provided composition is of WV-2380. In some embodiments, a provided composition is of WV-1510. In some embodiments, a provided composition is of WV-2619. In some embodiments, a provided composition is of WV-2611. In some embodiments, a provided composition is of WV-1497. In some embodiments, a provided composition is of WV-2602. In some embodiments, a provided composition is of WV-2618. In some embodiments, a provided composition is of WV-2601. In some embodiments, a provided composition is of WV-2603. In some embodiments, a provided composition is of WV-1092. Each oligonucleotide described herein comprising a HTT sequence represents an HTT oligonucleotide which was designed, constructed and tested in various assays, for example, in vitro assays, in accordance with the present disclosure. For example, each HTT oligonucleotide listed in any of Tables N1A, N2A, N3A, N4A and 8, or described elsewhere herein were designed, constructed and tested in vitro in accordance with the present disclosure. Among others, every HTT oligonucleotide described herein was tested in a dual luciferase reporter assay. In some embodiments, HTT oligonucleotides which were found to be particularly efficacious in the dual luciferase assay were tested in further in vitro and in vivo. In some embodiments, a provided composition is selected from: WV-2618; WV-2601; WV-1497; WV-1087; WV-1090; WV-1091; WV-937; WV-2611; WVE120101; WV-2603; WV-2595; WV-1510; WV-2378; and WV-2380; each of which was found to be highly efficacious, for example, as demonstrated in vitro in the dual luciferase reporter assay in accordance with the present disclosure. In some embodiments, a provided composition is selected from: WV-1092; WV-1497; WV-1085; WV-1086; ONT-905; and WV-2623; each of which was found to be highly efficacious, for example, as demonstrated in vitro in the dual luciferase reporter assay in accordance with the present disclosure. Various additional HTT oligonucleotides were also shown to be particularly efficacious. In some embodiments, a provided composition is of WV-937. In some embodiments, a provided composition is of WV-1087. In some embodiments, a provided composition is of WV-1090. In some embodiments, a provided composition is of WV-1091. In some embodiments, a provided composition is of WV-937. In some embodiments, a provided composition is of WV-2601. In some embodiments, a provided composition is of WV-1092. In some embodiments, a provided composition is of WV-1497. In some embodiments, a provided composition is of WV-1085. In some embodiments, a provided composition is of WV-1086. In some embodiments, a provided composition is of ONT-905. In some embodiments, a provided composition is of WV-2623. In some embodiments, a provided composition is of WV-2603. In some embodiments, a provided composition is of WV-1092. In some embodiments, a provided composition is of WV-2378. In some embodiments, a provided composition is of WV-2380. In some embodiments, a provided composition is of WV-1510. In some embodiments, a provided composition is of WV-2619. In some embodiments, a provided composition is of WV-2611. In some embodiments, a provided composition is of WV-1497. In some embodiments, a provided composition is of WV-2602. In some embodiments, a provided composition is of WV-2618. In some embodiments, a provided composition is of or WV-2601. The present disclosure provides compositions comprising or consisting of a plurality of provided oligonucleotides (e.g., chirally controlled oligonucleotide compositions). In some embodiments, all such provided oligonucleotides are of the same type, i.e., all have the same base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR$^1$" groups in formula I). In some embodiments, all oligonucleotides of the same type are identical. In many embodiments, however, provided compositions comprise a plurality of oligonucleotides types, typically in pre-determined relative amounts.

In some embodiments, a provided composition comprises a predetermined level of an oligonucleotide selected from a Table. In some embodiments, a provided composition comprises a predetermined level of an oligonucleotide selected from Tables N1-N4. In some embodiments, a provided composition comprises a predetermined level of WV-1087. In some embodiments, a provided composition comprises a predetermined level of WV-1090. In some embodiments, a provided composition comprises a predetermined level of WV-1091. In some embodiments, a provided composition comprises a predetermined level of WV-937. In some embodiments, a provided composition comprises a predetermined level of WV-2611. In some embodiments, a provided composition comprises a predetermined level of WV-937. In some embodiments, a provided composition comprises a predetermined level of WV-2601. In some embodiments, a provided composition comprises a predetermined level of WV-1092. In some embodiments, a provided composition comprises a predetermined level of WV-2595. In some embodiments, a provided composition comprises a predetermined level of WV-2603. In some embodiments, a provided composition comprises a predetermined level of WV-2378. In some embodiments, a provided composition comprises a predetermined level of WV-2380. In some embodiments, a provided composition comprises a predetermined level of WV-1510. In some embodiments, a provided composition comprises a predetermined level of WV-2619. In some embodiments, a provided composition comprises a predetermined level of WV-2611. In some embodiments, a provided composition comprises a predetermined level of WV-1497. In some embodiments, a provided composition comprises a predetermined level of WV-2602. In some embodiments, a provided composition comprises a predetermined level of WV-2618. In some embodiments, a provided composition comprises a predetermined level of or WV-2601. In some embodiments, a provided composition comprises a predetermined level of mG*SmGmCmAmC*SA*SA*SG*SG*SG*SC*SA*SC*RA*SG*SmAmCmUmU*SmC (SEQ ID NO: 1554), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mG*SmCmAmCmA*SA*SG*SG*SG*SC*SA*SC*RA*SG*SA*SmCmUmUmC*SmC (SEQ ID NO: 1094), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of G*SmGmCmAmC*SA*SA*SG*SG*SG*SC*SA*SC*RA*SG*SmAmCmU-mU*SC(SEQ ID NO: 190), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mG*mUmGmCmA*C*A*C*A*G*T*A*G*A*T*mGmA-mGmG*mG (SEQ ID NO: 12), wherein the oligonucleotide has a free 5'-OH and 3'-OH, m preceding a base represents 2'-OMe modification in the nucleoside containing the base, * represents a non-chirally controlled phosphorothioate linkage, and all non-labeled linkage is a natural phosphate linkage. In some embodiments, a provided composition comprises a predetermined level of mG*mGmGmUmC*C*T*C*C*C*C*A*C*A*G*mAmG-mGmG*mA (SEQ ID NO: 10), wherein the oligonucleotide has a free 5'-OH and 3'-OH, m preceding a base represents 2'-OMe modification in the nucleoside containing the base, * represents a non-chirally controlled phosphorothioate linkage, and all non-labeled linkage is a natural phosphate linkage. In some embodiments, a provided composition comprises a predetermined level of mG*mGmCmAmC*A*A*G*G*G*C*A*C*A*G*mAm-CmUmU*mC (SEQ ID NO: 192), wherein the oligonucleotide has a free 5'-OH and 3'-OH, m preceding a base represents 2'-OMe modification in the nucleoside containing the base, * represents a non-chirally controlled phosphorothioate linkage, and all non-labeled linkage is a natural phosphate linkage. In some embodiments, a provided composition comprises a predetermined level of mG*SmCmAmCmA*SC*SA*SG*ST*SA*SG*RA*ST*SG*SA*SmGmGmGmA*SmG (SEQ ID NO: 1465), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mU*SmGmCmAmC*SA*SC*SA*SG*ST*SA*SG*RA*ST*SG*SmAmGmGmG*SmA (SEQ ID NO: 1466), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mU*mGmCm-AmC*A*C*A*G*T*A*G*A*T*G*mAmGmGmG*mA (SEQ ID NO: 1482), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mG*SmGmGmUmC*SC*ST*SC*SC*SC*SC*SA*SC*RA*SG*SmAmGmGmG*S mA (SEQ ID NO: 11), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage. In some embodiments, a provided composition comprises a predetermined level of mG*SmUmGmCmA*SC * SA*SC*SA*SG*ST*SA*SG*RA*ST*SmGmAmGmG*S mG (SEQ ID NO: 13), wherein the oligonucleotide has a free 5'-OH and 3'-OH, m preceding a base represents 2'-OMe modification in the nucleoside containing the base, *S represents an Sp phosphorothioate linkage, *R represents an Rp phosphorothioate linkage, and all non-labeled linkage is a natural phosphate linkage.

In some embodiments, a provided oligonucleotide of formula O—I is an oligonucleotide selected from Tables N1-N4 and 8. In some embodiments, a provided oligonucleotide of formula O—I is WV-1087. In some embodiments, a provided oligonucleotide of formula O—I is WV-1090. In some embodiments, a provided oligonucleotide of formula O—I is WV-1091. In some embodiments, a provided oligonucleotide of formula O—I is WV-937. In some embodiments, a provided oligonucleotide of formula O—I is WV-2611. In some embodiments, a provided oligonucleotide of formula O—I is WV-937. In some embodiments, a provided oligonucleotide of formula O—I is WV-1092. In some embodiments, a provided oligonucleotide of formula O—I is WV-1497. In some embodiments, a provided oligonucleotide of formula O—I is WV-1510. In some embodiments, a provided oligonucleotide of formula O—I is WV-2378. In some embodiments, a provided oligonucleotide of formula O—I is WV-2380. In some embodiments, a provided oligonucleotide of formula O—I is WV-2595. In some embodiments, a provided oligonucleotide of formula O—I is WV-2601. In some embodiments, a provided oligonucleotide of formula O—I is WV-2602. In some embodiments, a provided oligonucleotide of formula O—I is WV-2603. In some embodiments, a provided oligonucleotide of formula O—I is WV-2611. In some embodiments, a provided oligonucleotide of formula O—I is WV-266618. In some embodiments, a provided oligonucleotide of formula O—I is WV-2619.

In some embodiments, a provided chirally controlled oligonucleotide composition is a chirally pure mipomersen composition. That is to say, in some embodiments, a provided chirally controlled oligonucleotide composition provides mipomersen as a single diastereomer with respect to the configuration of the linkage phosphorus. In some embodiments, a provided chirally controlled oligonucleotide composition is a chirally uniform mipomersen composition. That is to say, in some embodiments, every linkage phosphorus of mipomersen is in the Rp configuration or every linkage phosphorus of mipomersen is in the Sp configuration.

In some embodiments, a provided chirally controlled oligonucleotide composition comprises a combination of one or more provided oligonucleotide types. One of skill in the chemical and medicinal arts will recognize that the selection and amount of each of the one or more types of provided oligonucleotides in a provided composition will depend on the intended use of that composition. That is to say, one of skill in the relevant arts would design a provided chirally controlled oligonucleotide composition such that the amounts and types of provided oligonucleotides contained therein cause the composition as a whole to have certain desirable characteristics (e.g., biologically desirable, therapeutically desirable, etc.).

In some embodiments, a provided chirally controlled oligonucleotide composition comprises a combination of two or more provided oligonucleotide types. In some embodiments, a provided chirally controlled oligonucleotide composition comprises a combination of three or more provided oligonucleotide types. In some embodiments, a provided chirally controlled oligonucleotide composition comprises a combination of four or more provided oligonucleotide types. In some embodiments, a provided chirally controlled oligonucleotide composition comprises a combination of five or more provided oligonucleotide types. In some embodiments, a provided chirally controlled oligonucleotide composition comprises a combination of six or more provided oligonucleotide types. In some embodiments, a provided chirally controlled oligonucleotide composition comprises a combination of seven or more provided oligonucleotide types. In some embodiments, a provided chirally controlled oligonucleotide composition comprises a combination of eight or more provided oligonucleotide types. In some embodiments, a provided chirally controlled oligonucleotide composition comprises a combination of nine or more provided oligonucleotide types. In some embodiments, a provided chirally controlled oligonucleotide composition comprises a combination of ten or more provided oligonucleotide types. In some embodiments, a provided chirally controlled oligonucleotide composition comprises a combination of fifteen or more provided oligonucleotide types.

In some embodiments, a provided chirally controlled oligonucleotide composition is a combination of an amount of chirally uniform mipomersen of the Rp configuration and an amount of chirally uniform mipomersen of the Sp configuration.

In some embodiments, a provided chirally controlled oligonucleotide composition is a combination of an amount of chirally uniform mipomersen of the Rp configuration, an amount of chirally uniform mipomersen of the Sp configuration, and an amount of one or more chirally pure mipomersen of a desired diastereomeric form.

In some embodiments, a provided oligonucleotide type is selected from those described in PCT/US2013/050407, which is incorporated herein by reference. In some embodiments, a provided chirally controlled oligonucleotide composition comprises oligonucleotides of an oligonucleotide type selected from those described in PCT/US2013/050407.

Example Methods for Preparing Oligonucleotides and Compositions

The present disclosure provides methods for making chirally controlled oligonucleotides and chirally controlled compositions comprising one or more specific nucleotide types. In some embodiments, the phrase "oligonucleotide type," as used herein, defines an oligonucleotide that has a particular base sequence, pattern of backbone linkages, pattern of backbone chiral centers, and pattern of backbone phosphorus modifications (e.g., "—XLR$^1$" groups). Oligonucleotides of a common designated "type" are structurally identical to one another with respect to base sequence, pattern of backbone linkages, pattern of backbone chiral centers, and pattern of backbone phosphorus modifications. In some embodiments, oligonucleotides of an oligonucleotide type are identical.

In some embodiments, a provided chirally controlled oligonucleotide in the disclosure has properties different from those of the corresponding stereorandom oligonucleotide mixture. In some embodiments, a chirally controlled oligonucleotide has lipophilicity different from that of the stereorandom oligonucleotide mixture. In some embodiments, a chirally controlled oligonucleotide has different retention time on HPLC. In some embodiments, a chirally controlled oligonucleotide may have a peak retention time significantly different from that of the corresponding stereorandom oligonucleotide mixture. During oligonucleotide purification using HPLC as generally practiced in the art, certain chirally controlled oligonucleotides will be largely if not totally lost. During oligonucleotide purification using HPLC as generally practiced in the art, certain chirally controlled oligonucleotides will be largely if not totally lost. One of the consequences is that certain diastereomers of a stereorandom oligonucleotide mixture (certain chirally controlled oligonucleotides) are not tested in assays. Another consequence is that from batches to batches, due to the inevitable instrumental and human errors, the supposedly "pure" stereorandom oligonucleotide will have inconsistent compositions in that diastereomers in the composition, and their relative and absolute amounts, are different from batches to batches. The chirally controlled oligonucleotide and chirally controlled oligonucleotide composition provided in this disclosure overcome such problems, as a chirally controlled oligonucleotide is synthesized in a chirally controlled fashion as a single diastereomer, and a chirally controlled oligonucleotide composition comprise predetermined levels of one or more individual oligonucleotide types.

One of skill in the chemical and synthetic arts will appreciate that synthetic methods of the present disclosure provide for a degree of control during each step of the synthesis of a provided oligonucleotide such that each nucleotide unit of the oligonucleotide can be designed and/or selected in advance to have a particular stereochemistry at the linkage phosphorus and/or a particular modification at the linkage phosphorus, and/or a particular base, and/or a particular sugar. In some embodiments, a provided oligonucleotide is designed and/or selected in advance to have a particular combination of stereocenters at the linkage phosphorus of the internucleotidic linkage.

In some embodiments, a provided oligonucleotide made using methods of the present disclosure is designed and/or determined to have a particular combination of linkage phosphorus modifications. In some embodiments, a provided oligonucleotide made using methods of the present disclosure is designed and/or determined to have a particular combination of bases. In some embodiments, a provided oligonucleotide made using methods of the present disclosure is designed and/or determined to have a particular combination of sugars. In some embodiments, a provided oligonucleotide made using methods of the present disclosure is designed and/or determined to have a particular combination of one or more of the above structural characteristics.

Methods of the present disclosure exhibit a high degree of chiral control. For instance, methods of the present disclosure facilitate control of the stereochemical configuration of every single linkage phosphorus within a provided oligonucleotide. In some embodiments, methods of the present disclosure provide an oligonucleotide comprising one or more modified internucleotidic linkages independently having the structure of formula I.

In some embodiments, methods of the present disclosure provide an oligonucleotide which is a mipomersen unimer. In some embodiments, methods of the present disclosure provide an oligonucleotide which is a mipomersen unimer of configuration Rp. In some embodiments, methods of the present disclosure provide an oligonucleotide which is a mipomersen unimer of configuration Sp.

In some embodiments, methods of the present disclosure provide a chirally controlled oligonucleotide composition, i.e., an oligonucleotide composition that contains predetermined levels of individual oligonucleotide types. In some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a plurality of oligonucleotide types. Example chirally controlled oligonucleotide compositions made in accordance with the present disclosure are described herein.

In some embodiments, methods of the present disclosure provide chirally pure mipomersen compositions with respect to the configuration of the linkage phosphorus. That is to say, in some embodiments, methods of the present disclosure provide compositions of mipomersen wherein mipomersen exists in the composition in the form of a single diastereomer with respect to the configuration of the linkage phosphorus.

In some embodiments, methods of the present disclosure provide chirally uniform mipomersen compositions with respect to the configuration of the linkage phosphorus. That is to say, in some embodiments, methods of the present disclosure provide compositions of mipomersen in which all nucleotide units therein have the same stereochemistry with respect to the configuration of the linkage phosphorus, e.g., all nucleotide units are of the Rp configuration at the linkage phosphorus or all nucleotide units are of the Sp configuration at the linkage phosphorus.

In some embodiments, a provided chirally controlled oligonucleotide is over 50% pure. In some embodiments, a provided chirally controlled oligonucleotide is over about 55% pure. In some embodiments, a provided chirally controlled oligonucleotide is over about 60% pure. In some embodiments, a provided chirally controlled oligonucleotide is over about 65% pure. In some embodiments, a provided chirally controlled oligonucleotide is over about 70% pure. In some embodiments, a provided chirally controlled oligonucleotide is over about 75% pure. In some embodiments, a provided chirally controlled oligonucleotide is over about 80% pure. In some embodiments, a provided chirally controlled oligonucleotide is over about 85% pure. In some embodiments, a provided chirally controlled oligonucleotide is over about 90% pure. In some embodiments, a provided chirally controlled oligonucleotide is over about 91% pure. In some embodiments, a provided chirally controlled oligonucleotide is over about 92% pure. In some embodiments, a provided chirally controlled oligonucleotide is over about 93% pure. In some embodiments, a provided chirally controlled oligonucleotide is over about 94% pure. In some embodiments, a provided chirally controlled oligonucleotide is over about 95% pure. In some embodiments, a provided chirally controlled oligonucleotide is over about 96% pure. In some embodiments, a provided chirally controlled oligonucleotide is over about 97% pure. In some embodiments, a provided chirally controlled oligonucleotide is over about 98% pure. In some embodiments, a provided chirally controlled oligonucleotide is over about 99% pure. In some embodiments, a provided chirally controlled oligonucleotide is over about 99.5% pure. In some embodiments, a provided chirally controlled oligonucleotide is over about 99.6% pure. In some embodiments, a provided chirally controlled oligonucleotide is over about 99.7% pure. In some embodiments, a provided chirally controlled oligonucleotide is over about 99.8% pure. In some embodiments, a provided chirally controlled oligonucleotide is over about 99.9% pure. In some embodiments, a provided chirally controlled oligonucleotide is over at least about 99% pure.

In some embodiments, a chirally controlled oligonucleotide composition is a composition designed to comprise a single oligonucleotide type. In certain embodiments, such compositions are about 50% diastereomerically pure. In some embodiments, such compositions are about 50% diastereomerically pure. In some embodiments, such compositions are about 50% diastereomerically pure. In some embodiments, such compositions are about 55% diastereomerically pure. In some embodiments, such compositions are about 60% diastereomerically pure. In some embodiments, such compositions are about 65% diastereomerically pure. In some embodiments, such compositions are about 70% diastereomerically pure. In some embodiments, such compositions are about 75% diastereomerically pure. In some embodiments, such compositions are about 80% diastereomerically pure. In some embodiments, such compositions are about 85% diastereomerically pure. In some embodiments, such compositions are about 90% diastereomerically pure. In some embodiments, such compositions are about 91% diastereomerically pure. In some embodiments, such compositions are about 92% diastereomerically pure. In some embodiments, such compositions are about 93% diastereomerically pure. In some embodiments, such compositions are about 94% diastereomerically pure. In some embodiments, such compositions are about 95% diastereomerically pure. In some embodiments, such compositions are about 96% diastereomerically pure. In some embodiments, such compositions are about 97% diastereomerically pure. In some embodiments, such compositions are about 98% diastereomerically pure. In some embodiments, such compositions are about 99% diastereomerically pure. In some embodiments, such compositions are about 99.5% diastereomerically pure. In some embodiments, such compositions are about 99.6% diastereomerically pure. In some embodiments, such compositions are about 99.7% diastereomerically pure. In some embodiments, such compositions are about 99.8% diastereomerically pure. In some embodiments, such compositions are about 99.9% diastereomerically pure. In some embodiments, such compositions are at least about 99% diastereomerically pure.

Among other things, the present disclosure recognizes the challenge of stereoselective (rather than stereorandom or racemic) preparation of oligonucleotides. Among other things, the present disclosure provides methods and reagents for stereoselective preparation of oligonucleotides comprising multiple (e.g., more than 5, 6, 7, 8, 9, or 10) internucleotidic linkages, and particularly for oligonucleotides comprising multiple (e.g., more than 5, 6, 7, 8, 9, or 10) chiral internucleotidic linkages. In some embodiments, in a stereorandom or racemic preparation of oligonucleotides, at least one chiral internucleotidic linkage is formed with less than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 95:5 diastereoselectivity. In some embodiments, for a stereoselective or chirally controlled preparation of oligonucleotides, each chiral internucleotidic linkage is formed with greater than 96:4 diastereoselectivity. In some embodiments, for a stereoselective or chirally controlled preparation of oligonucleotides, each chiral internucleotidic linkage is formed with greater than 97:3 diastereoselectivity. In some embodiments, for a stereoselective or chirally controlled preparation of oligonucleotides, each chiral internucleotidic linkage is formed with greater than 98:2 diastereoselectivity. In some embodiments, for a stereoselective or chirally controlled preparation of oligonucleotides, each chiral internucleotidic linkage is formed with greater than 99:1 diastereoselectivity. In some embodiments, diastereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

In some embodiments, a chirally controlled oligonucleotide composition is a composition designed to comprise multiple oligonucleotide types. In some embodiments, methods of the present disclosure allow for the generation of a library of chirally controlled oligonucleotides such that a pre-selected amount of any one or more chirally controlled oligonucleotide types can be mixed with any one or more other chirally controlled oligonucleotide types to create a chirally controlled oligonucleotide composition. In some embodiments, the pre-selected amount of an oligonucleotide type is a composition having any one of the above-described diastereomeric purities.

In some embodiments, the present disclosure provides methods for making a chirally controlled oligonucleotide comprising steps of:
(1) coupling;
(2) capping;
(3) modifying;
(4) deblocking; and
(5) repeating steps (1)-(4) until a desired length is achieved.

When describing the provided methods, the word "cycle" has its ordinary meaning as understood by a person of ordinary skill in the art. In some embodiments, one round of steps (1)-(4) is referred to as a cycle.

In some embodiments, the present disclosure provides methods for making chirally controlled oligonucleotide compositions, comprising steps of:
(a) providing an amount of a first chirally controlled oligonucleotide; and
(b) optionally providing an amount of one or more additional chirally controlled oligonucleotides.

In some embodiments, a first chirally controlled oligonucleotide is an oligonucleotide type, as described herein. In some embodiments, a one or more additional chirally controlled oligonucleotide is a one or more oligonucleotide type, as described herein.

One of skill in the relevant chemical and synthetic arts will recognize the degree of versatility and control over structural variation and stereochemical configuration of a provided oligonucleotide when synthesized using methods of the present disclosure. For instance, after a first cycle is complete, a subsequent cycle can be performed using a nucleotide unit individually selected for that subsequent cycle which, in some embodiments, comprises a nucleobase and/or a sugar that is different from the first cycle nucleobase and/or sugar. Likewise, the chiral auxiliary used in the coupling step of the subsequent cycle can be different from the chiral auxiliary used in the first cycle, such that the second cycle generates a phosphorus linkage of a different stereochemical configuration. In some embodiments, the stereochemistry of the linkage phosphorus in the newly formed internucleotidic linkage is controlled by using stereochemically pure phosphoramidites. Additionally, the modification reagent used in the modifying step of a subsequent cycle can be different from the modification reagent used in the first or former cycle. The cumulative effect of this iterative assembly approach is such that each component of a provided oligonucleotide can be structurally and configurationally tailored to a high degree. An additional advantage to this approach is that the step of capping minimizes the formation of "n-1" impurities that would otherwise make isolation of a provided oligonucleotide extremely challenging, and especially oligonucleotides of longer lengths.

In some embodiments, an example cycle of the method for making chirally controlled oligonucleotides is illustrated in example schemes described in the present disclosure. In some embodiments, an example cycle of the method for making chirally controlled oligonucleotides is illustrated in Scheme I. In some embodiments,

represents the solid support, and optionally a portion of the growing chirally controlled oligonucleotide attached to the solid support. The chiral auxiliary exemplified has the structure of formula 3-I:

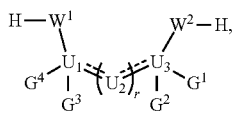

Formula 3-I which is further described below. "Cap" is any chemical moiety introduced to the nitrogen atom by the capping step, and in some embodiments, is an amino protecting group. One of ordinary skill in the art understands that in the first cycle, there may be only one nucleoside attached to the solid support when started, and cycle exit can be performed optionally before deblocking. As understood by a person of skill in the art, $B^{PRO}$ is a protected base used in oligonucleotide synthesis. Each step of the above-depicted cycle of Scheme I is described further below.

ments, reactive groups present on a solid support are protected. In some embodiments, reactive groups present on a solid support are unprotected. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. A first nucleoside is bound to a solid support via a linker moiety, i.e. a diradical with covalent bonds between either of a CPG, a polymer or other solid support and a nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as RE34,

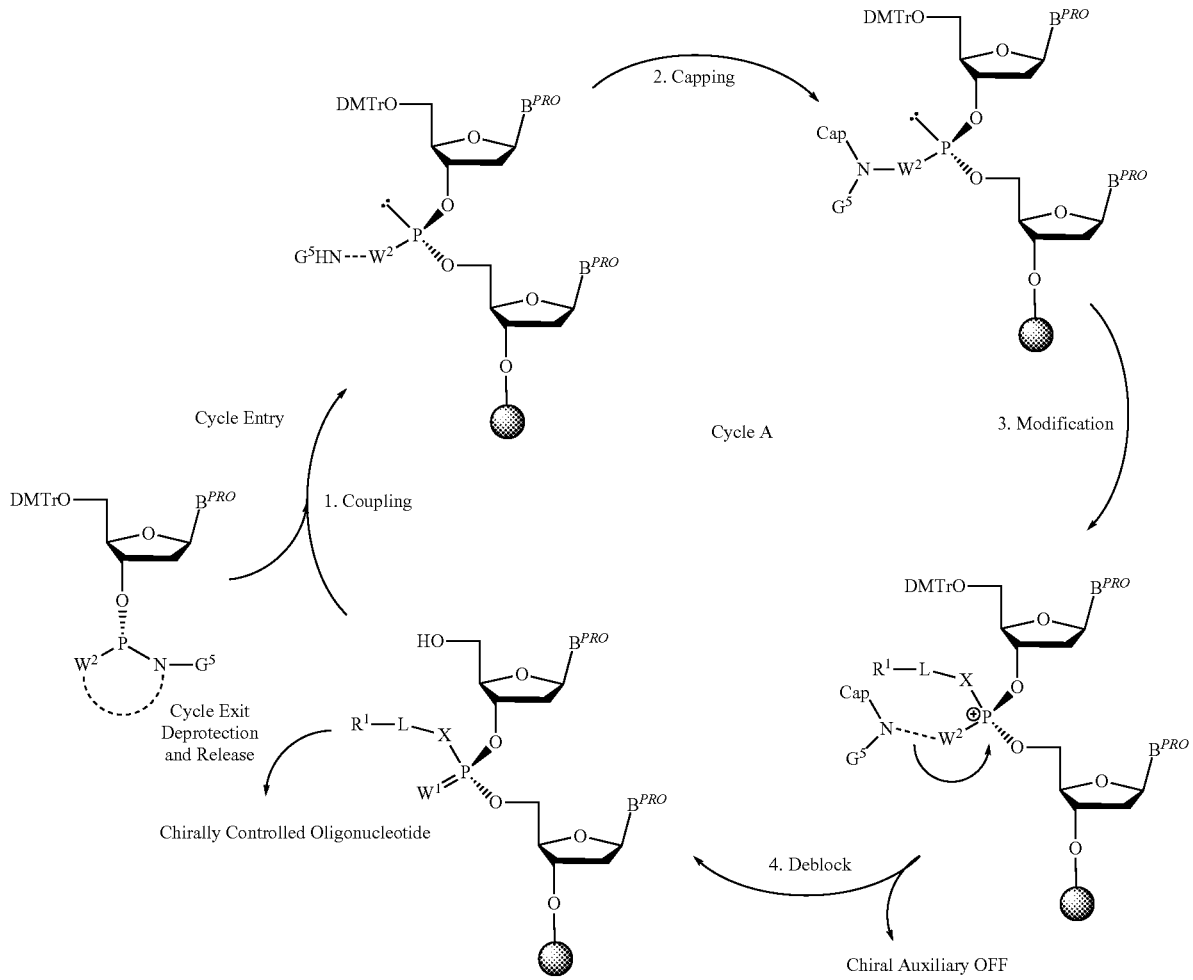

Scheme I. Synthesis of chirally controlled oligonucleotide.

Synthesis on Solid Support

In some embodiments, the synthesis of a provided oligonucleotide is performed on solid phase. In some embodi- 069). In some embodiments, a solid phase is an organic polymer support. In some embodiments, a solid phase is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.*, 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane is also used in some embodiments to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research*, 1991, 19, 1527), TentaGel Support-an aminopolyethyleneglycol derivatized support (see, e.g., Wright, et al., Tetrahedron Lett., 1993, 34, 3373), and Poros-a copolymer of polystyrene/divinylbenzene.

Surface activated polymers have been demonstrated for use in synthesis of natural and modified nucleic acids and proteins on several solid supports mediums. A solid support material can be any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. Other materials can serve as a solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, a solid support is derivatized to provide an acid labile trialkoxytrityl group, such as a trimethoxytrityl group (TMT). Without being bound by theory, it is expected that the presence of a trialkoxytrityl protecting group will permit initial detritylation under conditions commonly used on DNA synthesizers. For a faster release of oligonucleotide material in solution with aqueous ammonia, a diglycoate linker is optionally introduced onto the support.

In some embodiments, a provided oligonucleotide alternatively is synthesized from the 5' to 3' direction. In some embodiments, a nucleic acid is attached to a solid support through its 5' end of the growing nucleic acid, thereby presenting its 3' group for reaction, i.e. using 5'-nucleoside phosphoramidites or in enzymatic reaction (e.g. ligation and polymerization using nucleoside 5'-triphosphates). When considering the 5' to 3' synthesis the iterative steps of the present disclosure remain unchanged (i.e. capping and modification on the chiral phosphorus).

Linking Moiety

A linking moiety or linker is optionally used to connect a solid support to a compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—CH$_2$—CH$_2$—CO—), or an oxalyl linker (—CO—CO—). In some embodiments, the linking moiety and the nucleoside are bonded together through an ester bond. In some embodiments, a linking moiety and a nucleoside are bonded together through an amide bond. In some embodiments, a linking moiety connects a nucleoside to another nucleotide or nucleic acid. Suitable linkers are disclosed in, for example, *Oligonucleotides And Analogues A Practical Approach*, Ekstein, F. Ed., IRL Press, N.Y., 1991, Chapter 1 and Solid-Phase Supports for Oligonucleotide Synthesis, Pon, R. T., *Curr. Prot. Nucleic Acid Chem.*, 2000, 3.1.1-3.1.28.

A linker moiety is used to connect a compound comprising a free nucleophilic moiety to another nucleoside, nucleotide, or nucleic acid. In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attached the oligonucleotide to the solid support (Ravikumar et al., *Org. Process Res. Dev.*, 2008, 12 (3), 399-410). In some embodiments, other universal linkers are used (Pon, R. T., *Curr. Prot. Nucleic Acid Chem.*, 2000, 3.1.1-3.1.28). In some embodiments, various orthogonal linkers (such as disulfide linkers) are used (Pon, R. T., *Curr. Prot. Nucleic Acid Chem.*, 2000, 3.1.1-3.1.28).

Among other things, the present disclosure recognizes that a linker can be chosen or designed to be compatible with a set of reaction conditions employed in oligonucleotide synthesis. In some embodiments, to avoid degradation of oligonucleotides and to avoid desulfurization, auxiliary groups are selectively removed before de-protection. In some embodiments, DPSE group can selectively be removed by F$^-$ ions. In some embodiments, the present disclosure provides linkers that are stable under a DPSE de-protection condition, e.g., 0.1M TBAF in MeCN, 0.5M HF-Et$_3$N in THF or MeCN, etc. In some embodiments, a provided linker is the SP linker. In some embodiments, the present disclosure demonstrates that the SP linker is stable under a DPSE de-protection condition, e.g., 0.1M TBAF in MeCN, 0.5M HF-Et$_3$N in THF or MeCN, etc.; they are also stable, e.g., under anhydrous basic conditions, such as om1M DBU in MeCN.

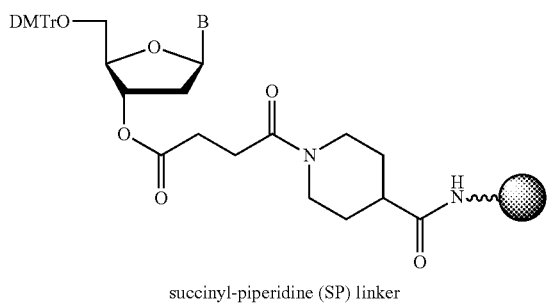

succinyl-piperidine (SP) linker

In some embodiments, an example linker is:

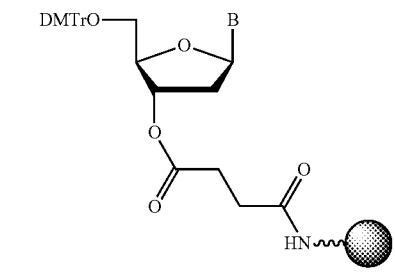

succinyl linker

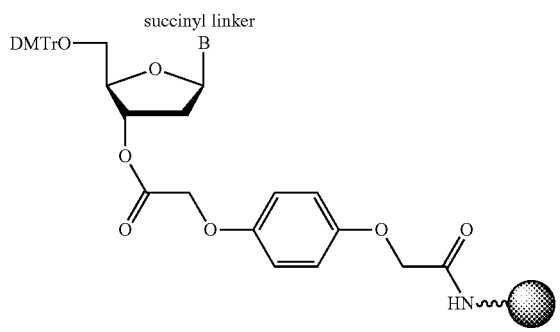

Q-linker

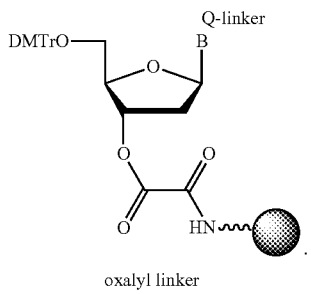

oxalyl linker

In some embodiments, the succinyl linker, Q-linker or oxalyl linker is not stable to one or more DPSE-deprotection conditions using F.

General Conditions—Solvents for Synthesis

Syntheses of provided oligonucleotides are generally performed in aprotic organic solvents. In some embodiments, a solvent is a nitrile solvent such as, e.g., acetonitrile. In some embodiments, a solvent is a basic amine solvent such as, e.g., pyridine. In some embodiments, a solvent is an ethereal solvent such as, e.g., tetrahydrofuran. In some embodiments, a solvent is a halogenated hydrocarbon such as, e.g., dichloromethane. In some embodiments, a mixture of solvents is used. In certain embodiments a solvent is a mixture of any one or more of the above-described classes of solvents.

In some embodiments, when an aprotic organic solvent is not basic, a base is present in the reacting step. In some embodiments where a base is present, the base is an amine base such as, e.g., pyridine, quinoline, or N,N-dimethylaniline. Examples of other amine bases include pyrrolidine, piperidine, N-methyl pyrrolidine, pyridine, quinoline, N,N-dimethylaminopyridine (DMAP), or N,N-dimethylaniline.

In some embodiments, a base is other than an amine base.

In some embodiments, an aprotic organic solvent is anhydrous. In some embodiments, an anhydrous aprotic organic solvent is freshly distilled. In some embodiments, a freshly distilled anhydrous aprotic organic solvent is a basic amine solvent such as, e.g., pyridine. In some embodiments, a freshly distilled anhydrous aprotic organic solvent is an ethereal solvent such as, e.g., tetrahydrofuran. In some embodiments, a freshly distilled anhydrous aprotic organic solvent is a nitrile solvent such as, e.g., acetonitrile.

Chiral Reagent/Chiral Auxiliary

In some embodiments, chiral reagents are used to confer stereoselectivity in the production of chirally controlled oligonucleotides. Many different chiral reagents, also referred to by those of skill in the art and herein as chiral auxiliaries, may be used in accordance with methods of the present disclosure. Examples of such chiral reagents are described herein and in Wada I, II and III, referenced above. In certain embodiments, a chiral reagent is as described by Wada I. In some embodiments, a chiral reagent for use in accordance with the methods of the present disclosure are of Formula 3-I, below:

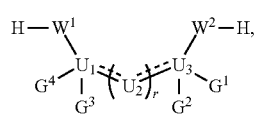

Formula 3-I wherein $W^1$ and $W^2$ are any of —O—, —S—, or -$NG^5$-, $U_1$ and $U_3$ are carbon atoms which are bonded to $U_2$ if present, or to each other if r is 0, via a single, double or triple bond. $U_2$ is —C—, -$CG^8$-, -$CG^8G^8$-, -$NG^8$-, —N—, —O—, or —S— where r is an integer of 0 to 5 and no more than two heteroatoms are adjacent. When any one of $U_2$ is C, a triple bond must be formed between a second instance of $U_2$, which is C, or to one of $U_1$ or $U_3$. Similarly, when any one of $U_2$ is —$CG^8$, a double bond is formed between a second instance of $U_2$ which is -$CG^8$- or —N—, or to one of $U_1$ or $U_3$.

In some embodiments, —$U_1(G_3G_4)$—$(U_2)_r$—$U_3(G_1G_2)$- is -$CG^3G^4$-$CG^1G^2$-. In some embodiments, —$U_1$—$(U_2)_r$—$U_3$— is -$CG^3$=$CG^1$-. In some embodiments, —$U_1$—$(U_2)_r$—$U_3$— is —C≡C—. In some embodiments, —$U_1$—$(U_2)_r$—$U_3$— is -$CG^3$=CG-$CG^1G^2$-. In some embodiments, —$U_1$—$(U_2)_r$—$U_3$— is -$CG^3G^4$-O-$CG^1G^2$-. In some embodiments, —$U_1$—$(U_2)_r$—$U_3$— is -$CG^3G^4$-NG-$CG^1G^2$-. In some embodiments, —$U_1$—$(U_2)_r$—$U_3$— is -$CG^3G^4$-N-$CG^2$-. In some embodiments, —$U_1$—$(U_2)_r$—$U_3$— is -$CG^3G^4$-N=C $G^8$-$CG^1G^2$-.

As defined herein, $G^1$, $G^2$, $G^3$, $G^4$, $G^5$, and $G^8$ are independently hydrogen, or an optionally substituted group selected from alkyl, aralkyl, cycloalkyl, cycloalkylalkyl, heterocyclyl, heteroaryl, and aryl; or two of $G^1$, $G^2$, $G^3$, $G^4$, and $G^5$ are $G^6$ (taken together to form an optionally substituted, saturated, partially unsaturated or unsaturated carbocyclic or heteroatom-containing ring of up to about 20 ring atoms which is monocyclic or polycyclic, and is fused or unfused). In some embodiments, a ring so formed is substituted by oxo, thioxo, alkyl, alkenyl, alkynyl, heteroaryl, or aryl moieties. In some embodiments, when a ring formed by taking two $G^6$ together is substituted, it is substituted by a moiety which is bulky enough to confer stereoselectivity during the reaction.

In some embodiments, a ring formed by taking two of $G^6$ together is optionally substituted cyclopentyl, pyrrolyl, cyclopropyl, cyclohexenyl, cyclopentenyl, tetrahydropyranyl, or piperazinyl. In some embodiments, a ring formed by taking two of $G^6$ together is optionally substituted cyclopentyl, pyrrolyl, cyclopropyl, cyclohexenyl, cyclopentenyl, tetrahydropyranyl, pyrrolidinyl, or piperazinyl.

In some embodiments, G' is optionally substituted phenyl. In some embodiments, G' is phenyl. In some embodiments, $G^2$ is methyl or hydrogen. In some embodiments, G' is optionally substituted phenyl and $G^2$ is methyl. In some embodiments, G' is phenyl and $G^2$ is methyl.

In some embodiments, r is 0.

In some embodiments, $W^1$ is —$NG^5$—. In some embodiments, one of $G^3$ and $G^4$ is taken together with $G^5$ to form an optionally substituted pyrrolidinyl ring. In some embodiments, one of $G^3$ and $G^4$ is taken together with $G^5$ to form a pyrrolidinyl ring.

In some embodiments, $W^2$ is —O—.

In some embodiments, a chiral reagent is a compound of Formula 3-AA:

Formula 3-AA

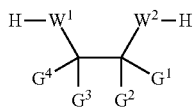

wherein each variable is independently as defined above and described herein.

In some embodiments of Formula 3AA, $W^1$ and $W^2$ are independently -$NG^5$-, —O—, or —S—; G', $G^2$, $G^3$, $G^4$, and $G^5$ are independently hydrogen, or an optionally substituted group selected from alkyl, aralkyl, cycloalkyl, cycloalkylalkyl, heterocyclyl, heteroaryl, or aryl; or two of G', $G^2$, $G^3$, $G^4$, and $G^5$ are $G^6$ (taken together to form an optionally substituted saturated, partially unsaturated or unsaturated carbocyclic or heteroatom-containing ring of up to about 20 ring atoms which is monocyclic or polycyclic, fused or unfused), and no more than four of G', $G^2$, $G^3$, $G^4$, and $G^5$ are $G^6$. Similarly to the compounds of Formula 3-I, any of G', $G^2$, $G^3$, $G^4$, or $G^5$ are optionally substituted by oxo, thioxo, alkyl, alkenyl, alkynyl, heteroaryl, or aryl moieties. In some embodiments, such substitution induces stereoselectivity in chirally controlled oligonucleotide production.

In some embodiments, a provided chiral reagent has the structure of

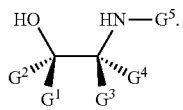

In some embodiments, a provided chiral reagent has the structure of

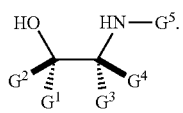

In some embodiments, a provided chiral reagent has the structure of

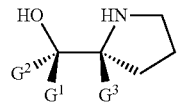

In some embodiments, a provided chiral reagent has the structure of

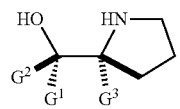

In some embodiments, a provided chiral reagent has the structure of

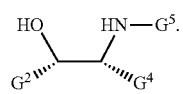

In some embodiments, a provided chiral reagent has the structure of

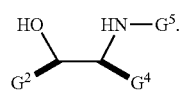

In some embodiments, a provided chiral reagent has the structure of

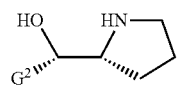

In some embodiments, a provided chiral reagent has the structure of

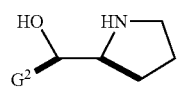

In some embodiments, $W^1$ is —$NG^5$, $W^2$ is O, each of $G^1$ and $G^3$ is independently hydrogen or an optionally substituted group selected from $C_{1-10}$ aliphatic, heterocyclyl, heteroaryl and aryl, $G^2$ is —$C(R)_2Si(R)_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused. In some embodiments, each R is independently hydrogen, or an optionally substituted group selected from $C_1$-$C_6$ aliphatic, carbocyclyl, aryl, heteroaryl, and heterocyclyl. In some embodiments, $G^2$ is —$C(R)_2Si(R)_3$, wherein —$C(R)_2$— is optionally substituted —$CH_2$—, and each R of —$Si(R)_3$ is independently an optionally substituted group selected from $C_{1-10}$ aliphatic, heterocyclyl, heteroaryl and aryl. In some embodiments, at least one R of —Si(R)₃ is independently optionally substituted $C_{1-10}$ alkyl. In some embodiments, at least one R of —Si(R)₃ is independently optionally substituted phenyl. In some embodiments, one R of —Si(R)₃ is independently optionally substituted phenyl, and each of the other two R is independently optionally substituted $C_{1-10}$ alkyl. In some embodiments, one R of —Si(R)₃ is independently optionally substituted $C_{1-10}$ alkyl, and each of the other two R is independently optionally substituted phenyl. In some embodiments, $G^2$ is optionally substituted —CH₂Si(Ph)(Me)₂. In some embodiments, $G^2$ is optionally substituted —CH₂Si(Me)(Ph)₂. In some embodiments, $G^2$ is —CH₂Si(Me)(Ph)₂. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen.

In some embodiments, a chiral reagent has one of the following formulae:

Formulae-3-AB

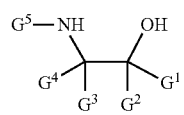

3-BB

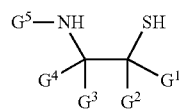

3-CC

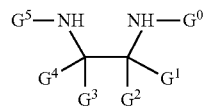

3-DD

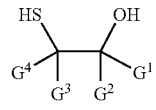

3-EE

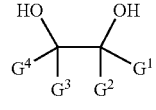

3-FF

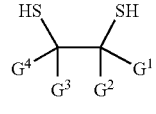

In some embodiments, a chiral reagent is an aminoalcohol. In some embodiments, a chiral reagent is an aminothiol. In some embodiments, a chiral reagent is an aminophenol. In some embodiments, a chiral reagent is (S)- and (R)-2-methylamino-1-phenylethanol, (1R, 2S)-ephedrine, or (1R, 2S)-2-methylamino-1,2-diphenylethanol.

In some embodiments of the disclosure, a chiral reagent is a compound of one of the following formulae:

Formula O

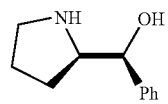

Formula P

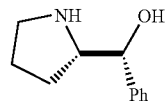

Formula Q

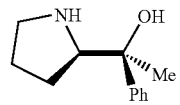

Formula R

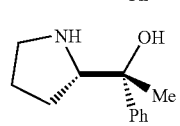

DPSE

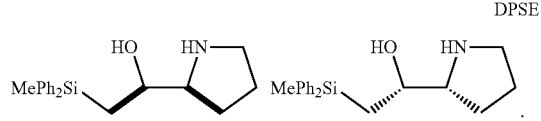

As demonstrated herein, when used for preparing a chiral internucleotidic linkage, to obtain stereoselectivity generally stereochemically pure chiral reagents are utilized. Among other things, the present disclosure provides stereochemically pure chiral reagents, including those having structures described.

The choice of chiral reagent, for example, the isomer represented by Formula Q or its stereoisomer, Formula R, permits specific control of chirality at a linkage phosphorus. Thus, either an Rp or Sp configuration can be selected in each synthetic cycle, permitting control of the overall three dimensional structure of a chirally controlled oligonucleotide. In some embodiments, a chirally controlled oligonucleotide has all Rp stereocenters. In some embodiments of the disclosure, a chirally controlled oligonucleotide has all Sp stereocenters. In some embodiments of the disclosure, each linkage phosphorus in the chirally controlled oligonucleotide is independently Rp or Sp. In some embodiments of the disclosure, each linkage phosphorus in the chirally controlled oligonucleotide is independently Rp or Sp, and at least one is Rp and at least one is Sp. In some embodiments, the selection of Rp and Sp centers is made to confer a specific three dimensional superstructure to a chirally controlled oligonucleotide. Examples of such selections are described in further detail herein.

In some embodiments, a chiral reagent for use in accordance with the present disclosure is selected for its ablility to be removed at a particular step in the above-depicted cycle. For example, in some embodiments it is desirable to remove a chiral reagent during the step of modifying the linkage phosphorus. In some embodiments, it is desirable to remove a chiral reagent before the step of modifying the linkage phosphorus. In some embodiments, it is desirable to remove a chiral reagent after the step of modifying the linkage phosphorus. In some embodiments, it is desirable to remove a chiral reagent after a first coupling step has occurred but before a second coupling step has occurred, such that a chiral reagent is not present on the growing oligonucleotide during the second coupling (and likewise for additional subsequent coupling steps). In some embodiments, a chiral reagent is removed during the "deblock"

reaction that occurs after modification of the linkage phosphorus but before a subsequent cycle begins. Example methods and reagents for removal are described herein.

In some embodiments, removal of chiral auxiliary is achieved when performing the modification and/or deblocking step, as illustrated in Scheme I. It can be beneficial to combine chiral auxiliary removal together with other transformations, such as modification and deblocking. A person of ordinary skill in the art would appreciate that the saved steps/transformation could improve the overall efficiency of synthesis, for instance, with respect to yield and product purity, especially for longer oligonucleotides. One example wherein the chiral auxiliary is removed during modification and/or deblocking is illustrated in Scheme I.

In some embodiments, a chiral reagent for use in accordance with methods of the present disclosure is characterized in that it is removable under certain conditions. For instance, in some embodiments, a chiral reagent is selected for its ability to be removed under acidic conditions. In certain embodiments, a chiral reagent is selected for its ability to be removed under mildly acidic conditions. In certain embodiments, a chiral reagent is selected for its ability to be removed by way of an E1 elimination reaction (e.g., removal occurs due to the formation of a cation intermediate on the chiral reagent under acidic conditons, causing the chiral reagent to cleave from the oligonucleotide). In some embodiments, a chiral reagent is characterized in that it has a structure recognized as being able to accommodate or facilitate an E1 elimination reaction. One of skill in the relevant arts will appreciate which structures would be envisaged as being prone toward undergoing such elimination reactions.

In some embodiments, a chiral reagent is selected for its ability to be removed with a nucleophile. In some embodiments, a chiral reagent is selected for its ability to be removed with an amine nucleophile. In some embodiments, a chiral reagent is selected for its ability to be removed with a nucleophile other than an amine.

In some embodiments, a chiral reagent is selected for its ability to be removed with a base. In some embodiments, a chiral reagent is selected for its ability to be removed with an amine. In some embodiments, a chiral reagent is selected for its ability to be removed with a base other than an amine.

Additional chiral auxiliaries and their use can be found in e.g., Wada I (JP4348077; WO2005/014609; WO2005/092909), Wada II (WO2010/064146), Wada III (WO2012/039448), Chiral Control (WO2010/064146), etc.

Activation

An achiral H-phosphonate moiety is treated with the first activating reagent to form the first intermediate. In one embodiment, the first activating reagent is added to the reaction mixture during the condensation step. Use of the first activating reagent is dependent on reaction conditions such as solvents that are used for the reaction. Examples of the first activating reagent are phosgene, trichloromethyl chloroformate, bis(trichloromethyl)carbonate (BTC), oxalyl chloride, $Ph_3PCl_2$, $(PhO)_3PCl_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

The example of achiral H-phosphonate moiety is a compound shown in the above Scheme. DBU represents 1,8-diazabicyclo[5.4.0]undec-7-ene. $H^+DBU$ may be, for example, ammonium ion, alkylammonium ion, heteroaromatic iminium ion, or heterocyclic iminium ion, any of which is primary, secondary, tertiary or quaternary, or a monovalent metal ion.

Reacting with Chiral Reagent

After the first activation step, the activated achiral H-phosphonate moiety reacts with a chiral reagent, which is represented by formula (Z-I) or (Z-I'), to form a chiral intermediate of formula (Z-Va), (Z-Vb), (Z-Va'), or (Z-Vb').

Stereospecific Condensation Step

A chiral intermediate of Formula Z-Va ((Z-Vb), (Z-Va'), or (Z-Vb')) is treated with the second activating reagent and a nucleoside to form a condensed intermediate. The nucleoside may be on solid support. Examples of the second activating reagent are 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate. A chiral intermediate of Formula Z-Va ((Z-Vb), (Z-Va'), or (Z-Vb')) may be isolated as a monomer. Usually, the chiral intermediate of Z-Va ((Z-Vb), (Z-Va'), or (Z-Vb')) is not isolated and undergoes a reaction in the same pot with a nucleoside or modified nucleoside to provide a chiral phosphite compound, a condensed intermediate. In other embodiments, when the method is performed via solid phase synthesis, the solid support comprising the compound is filtered away from side products, impurities, and/or reagents.

Capping Step

If the final nucleic acid is larger than a dimer, the unreacted —OH moiety is capped with a blocking group and the chiral auxiliary in the compound may also be capped with a blocking group to form a capped condensed intermediate. If the final nucleic acid is a dimer, then the capping step is not necessary.

Modifying Step

The compound is modified by reaction with an electrophile. The capped condensed intermediate may be executed modifying step. In some embodiments, the modifying step is performed using a sulfur electrophile, a selenium electrophile or a boronating agent. Examples of modifying steps are step of oxidation and sulfurization.

In some embodiments of the method, the sulfur electrophile is a compound having one of the following formulas:

or $Z^{z1}$—S—S—$Z^{z2}$, or $Z^{z1}$—S—$V^z$—$Z^{z2}$;   $S_8$ (Formula Z-B), wherein $Z^{z1}$ and $Z^{z2}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z1}$ and $Z^{z2}$ are taken together to form a 3 to 8 membered alicyclic or heterocyclic ring, which may be substituted or unsubstituted; $V^z$ is $SO_2$, O, or $NR^f$; and $R^f$ is hydrogen, alkyl, alkenyl, alkynyl, or aryl.

In some embodiments of the method, the sulfur electrophile is a compound of following Formulae Z-A, Z-B, Z-C, Z-D, Z-E, or Z-F:

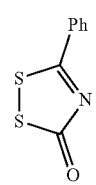

Formula Z-A

-continued

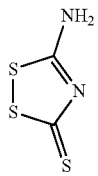

$S_8$

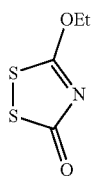

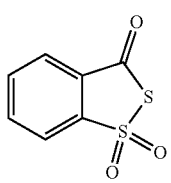

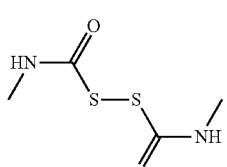

In some embodiments, a sulfurization reagent is 3-phenyl-1,2,4-dithiazolin-5-one.

In some embodiments, the selenium electrophile is a compound having one of the following formulae:

$Z^{z3}$—Se—Se—$Z^{z4}$, or $Z^{z3}$—Se—$V^z$—$Z^{z4}$;    Se (Formula Z-G), wherein $Z^{z3}$ and $Z^{z4}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z3}$ and $Z^{z4}$ are taken together to form a 3 to 8 membered alicyclic or heterocyclic ring, which may be substituted or unsubstituted; $V^z$ is $SO_2$, S, O, or $NR^f$; and $R^f$ is hydrogen, alkyl, alkenyl, alkynyl, or aryl.

In some embodiments, the selenium electrophile is a compound of Formula Z-G, Z-H, Z-I, Z-J, Z-K, or Z-L.

Formula Z-G

Se

Formula Z-H

KSeCN

Formula Z-I

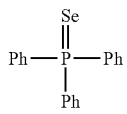

Formula Z-J

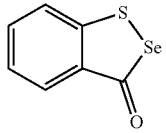

Formula Z-B

Formula Z-C

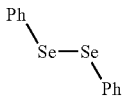

Formula Z-K

Formula Z-L

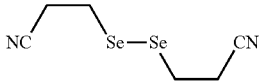

Formula Z-D

In some embodiments, the boronating agent is borane-N,N-diisopropylethylamine ($BH_3$ DIPEA), borane-pyridine ($BH_3$ Py), borane-2-chloropyridine ($BH_3$ CPy), borane-aniline ($BH_3$ An), borane-tetrahydrofiirane ($BH_3$ THF), or borane-dimethylsulfide ($BH_3$ $Me_2S$).

Formula Z-E

In some embodiments, after the modifying step, a chiral auxiliary group falls off from the growing oligonucleotide chain. In some embodiments, after the modifying step, a chiral auxiliary group remains connected to the internucleotidic phosphorus atom.

In some embodiments of the method, the modifying step is an oxidation step. In some embodiments of the method, the modifying step is an oxidation step using similar conditions as described above in this application. In some embodiments, an oxidation step is as disclosed in, e.g., JP 2010-265304 A and WO2010/064146.

Formula Z-F

Chain Elongation Cycle and De Protection Step

The capped condensed intermediate is deblocked to remove the blocking group at the 5'-end of the growing nucleic acid chain to provide a compound. The compound is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups for, e.g., nucleobase, modified nucleobase, sugar and modified sugar protecting groups, to provide a nucleic acid. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. In embodiments where a solid support is used, the phosphorus-atom modified nucleic acid is then cleaved from the solid support. In certain embodiments, the nucleic acids is left attached on the solid support for purification purposes and then cleaved from the solid support following purification.

In yet other embodiments, the nucleoside comprising a 5'-OH moiety is an intermediate obtained from another known nucleic acid synthetic method. In yet other embodiments, the nucleoside comprising a 5'-OH moiety is an intermediate obtained from another known nucleic acid synthetic method as described in this application. In yet other embodiments, the nucleoside comprising a 5'-OH moiety is an intermediate obtained from another known nucleic acid synthetic method comprising one or more cycles illustrated in Scheme I. In yet other embodiments, the nucleoside comprising a 5'-OH moiety is an intermediate obtained from another known nucleic acid synthetic method comprising one or more cycles illustrated in Scheme I-b, I-c or I-d.

In some embodiments, the present disclosure provides oligonucleotide synthesis methods that use stable and commercially available materials as starting materials. In some embodiments, the present disclosure provides oligonucleotide synthesis methods to produce stereocontrolled phosphorus atom-modified oligonucleotide derivatives using an achiral starting material.

In some embodiments, the method of the present disclosure does not cause degradations under the de-protection steps. Further the method does not require special capping agents to produce phosphorus atom-modified oligonucleotide derivatives.

Condensing Reagent

Condensing reagents ($C_R$) useful in accordance with methods of the present disclosure are of any one of the following general formulae:

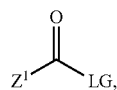 $C_R1$

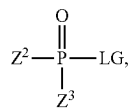 $C_R2$

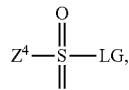 $C_R3$

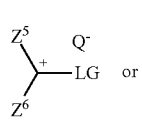 $C_R4$

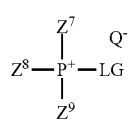 $C_R5$ wherein $Z^1$, $Z^2$, $Z^3$, $Z^4$, $Z^5$, $Z^6$, $Z^7$, $Z^8$, and $Z^9$ are independently optionally substituted group selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; and LG is a leaving group.

In some embodiments, a counter ion of a condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In some embodiments, a leaving group of a condensing reagent $C_R$ is F, Cl, Br, I, 3-nitro-1,2,4-triazole, imidazole, alkyltriazole, tetrazole, pentafluorobenzene, or 1-hydroxybenzotriazole.

Examples of condensing reagents used in accordance with methods of the present disclosure include, but are not limited to, pentafluorobenzoyl chloride, carbonyldiimidazole (CDI), 1-mesitylenesulfonyl-3-nitrotriazole (MSNT), 1-ethyl-3-(3'-dimethylaminopropyl)carbodiimide hydrochloride (EDCI-HCl), benzotriazole-1-yloxytris(dimethylamino)phosphonium hexafluorophosphate (PyBOP), N,N'-bis(2-oxo-3-oxazolidinyl)phosphinic chloride (BopCl), 2-(1H-7-azabenzotriazol-1-yl)-1,1,3,3-tetramethyluronium hexafluorophosphate (HATU), and O-benzotriazole-N,N,N',N'-tetramethyluronium hexafluorophosphate (HBTU), DIP-CDI; N,N'-bis(2-oxo-3-oxazolidinyl)phosphinic bromide (BopBr), 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bromotripyrrolidinophosphonium hexafluorophosphate (PyBrOP); O-(benzotriazol-1-yl)-N,N,N',N'-tetramethyluronium tetrafluoroborate (TBTU); and tetramethylfluoroformamidinium hexafluorophosphate (TFFH). In certain embodiments, a counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$.

In some embodiments, a condensing reagent is 1-(2,4,6-triisopropylbenzenesulfonyl)-5-(pyridin-2-yl) tetrazolide, pivaloyl chloride, bromotrispyrrolidinophosphonium hexafluorophosphate, N,N'-bis(2-oxo-3-oxazolidinyl) phosphinic chloride (BopCl), or 2-chloro-5,5-dimethyl-2-oxo-1,3,2-dioxaphosphinane. In some embodiment, a condensing reagent is N,N'-bis(2-oxo-3-oxazolidinyl)phosphinic chloride (BopCl). In some embodiments, a condensing reagent is selected from those described in WO/2006/066260).

In some embodiments, a condensing reagent is 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP):

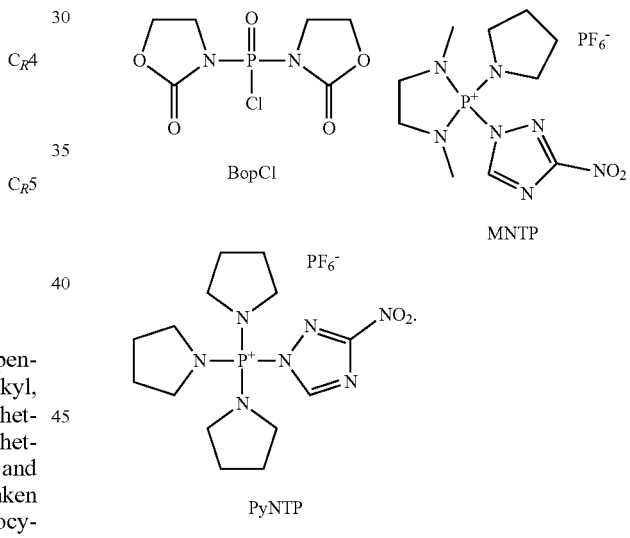

BopCl

MNTP

PyNTP

Selection of Base and Sugar of Nucleoside Coupling Partner

As described herein, nucleoside coupling partners for use in accordance with methods of the present disclosure can be the same as one another or can be different from one another. In some embodiments, nucleoside coupling partners for use in the synthesis of a provided oligonucleotide are of the same structure and/or stereochemical configuration as one another. In some embodiments, each nucleoside coupling partner for use in the synthesis of a provided oligonucleotide is not of the same structure and/or stereochemical configuration as certain other nucleoside coupling partners of the oligonucleotide. Example nucleobases and sugars for use in accordance with methods of the present disclosure are described herein. One of skill in the relevant chemical and synthetic arts will recognize that any combination of nucleobases and sugars described herein are contemplated for use in accordance with methods of the present disclosure.

Coupling Step

Example coupling procedures and chiral reagents and condensing reagents for use in accordance with the present disclosure are outlined in, inter alia, Wada I (JP4348077; WO2005/014609; WO2005/092909), Wada II (WO2010/064146), Wada III (WO2012/039448), and Chiral Control (WO2010/064146). Chiral nucleoside coupling partners for use in accordance with the present disclosure are also referred to herein as "Wada amidites." In some embodiments, a coupling partner has the structure of

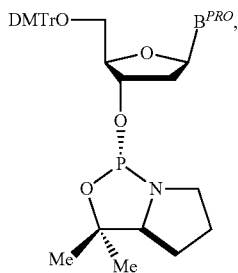

wherein $B^{PRO}$ is a protected nucleobase. In some embodiments, a coupling partner has the structure of

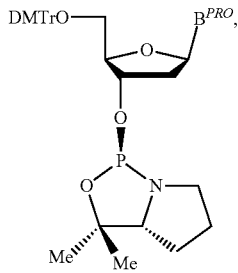

wherein $B^{PRO}$ is a protected nucleobase. In some embodiments, a coupling partner has the structure of

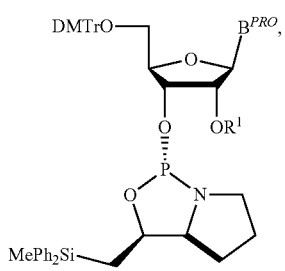

wherein $B^{PRO}$ is a protected nucleobase, and $R^1$ is as defined and described herein. In some embodiments, a coupling partner has the structure of

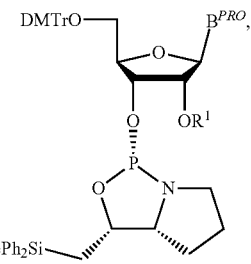

wherein $B^{PRO}$ is a protected nucleobase, and $R^1$ is as defined and described herein. In some embodiments, $R^1$ is optionally substituted $C_{1-6}$ alkyl. In some embodiments, $R^1$ is Me.

Example chiral phosphoramidites as coupling partner are depicted below:

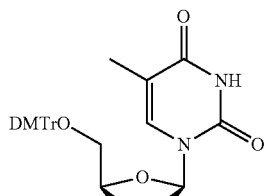

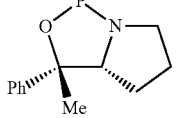

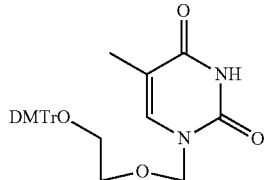

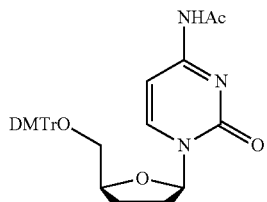

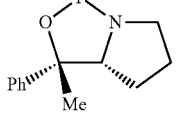

325
-continued
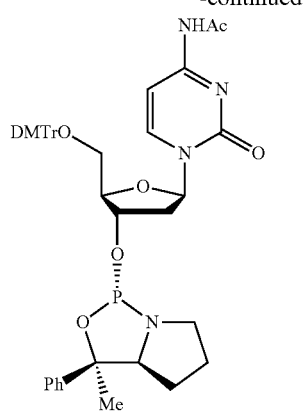
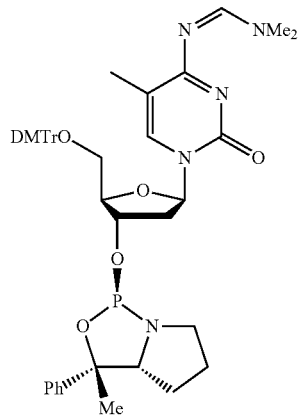
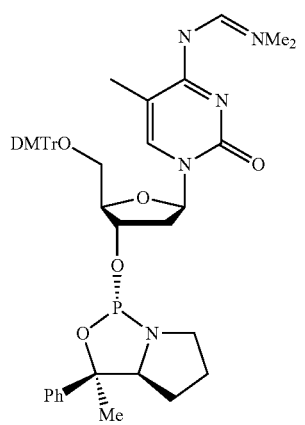
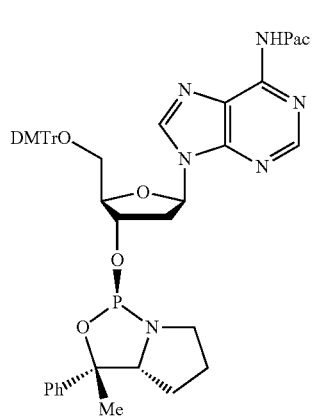
326
-continued
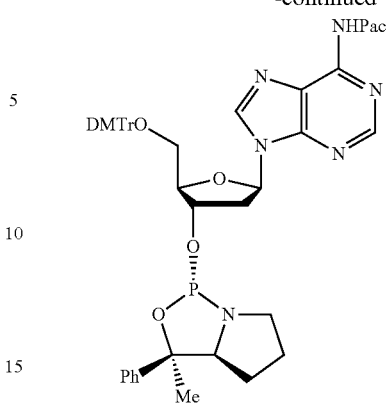
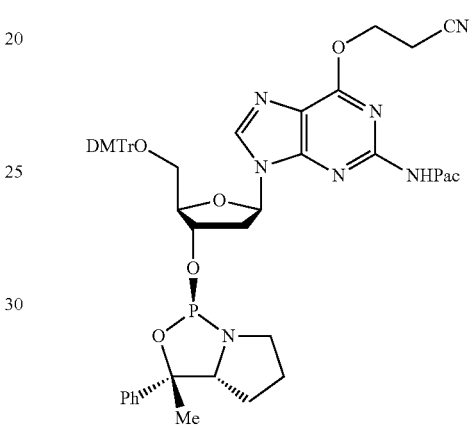
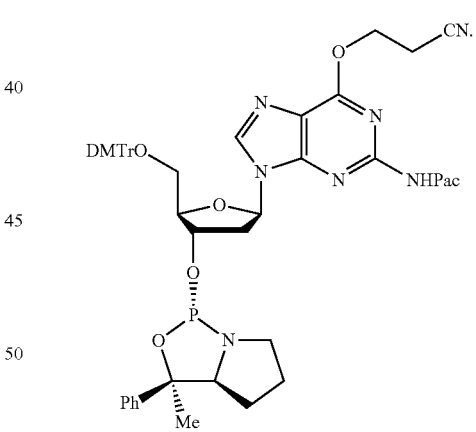
Additional examples are described in Chiral Control (WO2010/064146).
One of the methods used for synthesizing the coupling partner is depicted in Scheme II, below.
Scheme II. Example synthesis of coupling partner.
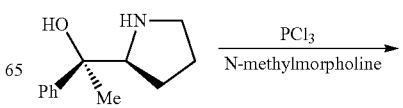

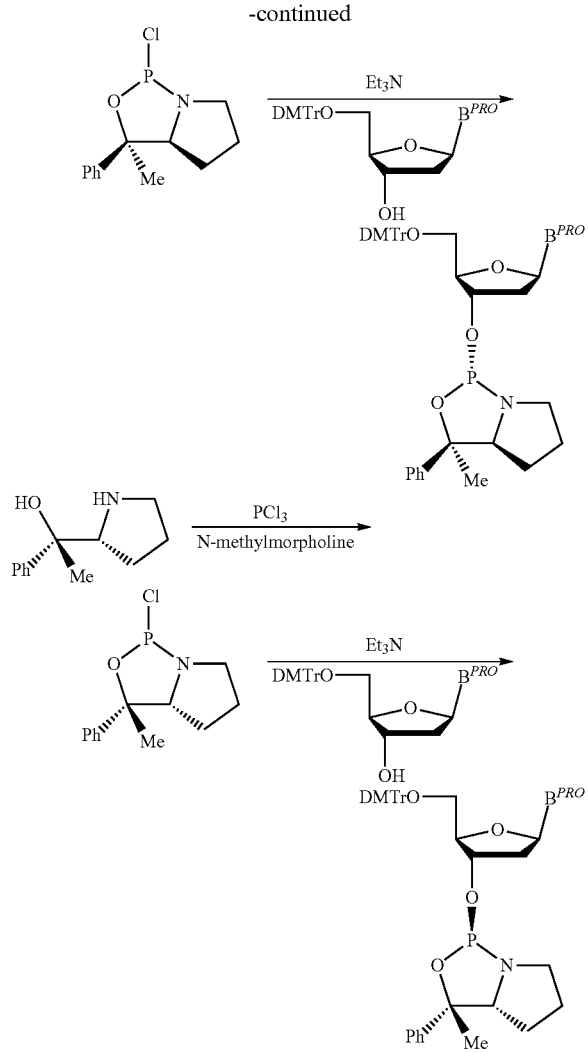

In some embodiments, the step of coupling comprises reacting a free hydroxyl group of a nucleotide unit of an oligonucleotide with a nucleoside coupling partner under suitable conditions to effect the coupling. In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

Once the appropriate hydroxyl group of the growing oligonucleotide has been deblocked, the support is washed and dried in preparation for delivery of a solution comprising a chiral reagent and a solution comprising an activator. In some embodiments, a chiral reagent and an activator are delivered simultaneously. In some embodiments, co-delivery comprises delivering an amount of a chiral reagent in solution (e.g., a phosphoramidite solution) and an amount of activator in a solution (e.g., a CMPT solution) in a polar aprotic solvent such as a nitrile solvent (e.g., acetonitrile).

In some embodiments, the step of coupling provides a crude product composition in which the chiral phosphite product is present in a diastereomeric excess of >95%. In some embodiments, the chiral phosphite product is present in a diastereomeric excess of >96%. In some embodiments, the chiral phosphite product is present in a diastereomeric excess of >97%. In some embodiments, the chiral phosphite product is present in a diastereomeric excess of >98%. In some embodiments, the chiral phosphite product is present in a diastereomeric excess of >99%.

Capping Step:

Provided methods for making chirally controlled oligonucleotides comprise a step of capping. In some embodiments, a step of capping is a single step. In some embodiments, a step of capping is two steps. In some embodiments, a step of capping is more than two steps.

In some embodiments, a step of capping comprises steps of capping the free amine of the chiral auxiliary and capping any residual unreacted 5' hydroxyl groups. In some embodiments, the free amine of the chiral auxiliary and the unreacted 5' hydroxyl groups are capped with the same capping group. In some embodiments, the free amine of the chiral auxiliary and the unreacted 5' hydroxyl groups are capped with different capping groups. In certain embodiments, capping with different capping groups allows for selective removal of one capping group over the other during synthesis of the oligonucleotide. In some embodiments, the capping of both groups occurs simultaneously. In some embodiments, the capping of both groups occurs iteratively.

In certain embodiments, capping occurs iteratively and comprises a first step of capping the free amine followed by a second step of capping the free 5' hydroxyl group, wherein both the free amine and the 5' hydroxyl group are capped with the same capping group. For instance, in some embodiments, the free amine of the chiral auxiliary is capped using an anhydride (e.g., phenoxyacetic anhydride, i.e., $Pac_2O$) prior to capping of the 5' hydroxyl group with the same anhydride. In certain embodiments, the capping of the 5' hydroxyl group with the same anhydride occurs under different conditions (e.g., in the presence of one or more additional reagents). In some embodiments, capping of the 5' hydroxyl group occurs in the presence of an amine base in an etherial solvent (e.g., NMI (N-methylimidazole) in THF). The phrase "capping group" is used interchangeably herein with the phrases "protecting group" and "blocking group".

In some embodiments, an amine capping group is characterized in that it effectively caps the amine such that it prevents rearrangement and/or decomposition of the intermediate phosphite species. In some embodiments, a capping group is selected for its ability to protect the amine of the chiral auxiliary in order to prevent intramolecular cleavage of the internucleotide linkage phosphorus.

In some embodiments, a 5' hydroxyl group capping group is characterized in that it effectively caps the hydroxyl group such that it prevents the occurrence of "shortmers," e.g., "n-m" (m and n are integers and m<n; n is the number of bases in the targeted oligonucleotide) impurities that occur from the reaction of an oligonucleotide chain that fails to react in a first cycle but then reacts in one or more subsequent cycles. The presence of such shortmers, especially "n-1", has a deleterious effect upon the purity of the crude oligonucleotide and makes final purification of the oligonucleotide tedious and generally low-yielding.

In some embodiments, a particular cap is selected based on its tendency to facilitate a particular type of reaction under particular conditions. For instance, in some embodiments, a capping group is selected for its ability to facilitate an E1 elimination reaction, which reaction cleaves the cap and/or auxiliary from the growing oligonucleotide. In some embodiments, a capping group is selected for its ability to facilitate an E2 elimination reaction, which reaction cleaves the cap and/or auxiliary from the growing oligonucleotide.

In some embodiments, a capping group is selected for its ability to facilitate a β-elimination reaction, which reaction cleaves the cap and/or auxiliary from the growing oligonucleotide.

Modifying Step:

As used herein, the phrase "modifying step", "modification step" and "P-modification step" are used interchangeably and refer generally to any one or more steps used to install a modified internucleotidic linkage. In some embodiments, the modified internucleotidic linkage having the structure of formula I. A P-modification step of the present disclosure occurs during assembly of a provided oligonucleotide rather than after assembly of a provided oligonucleotide is complete. Thus, each nucleotide unit of a provided oligonucleotide can be individually modified at the linkage phosphorus during the cycle within which the nucleotide unit is installed.

In some embodiments, a suitable P-modification reagent is a sulfur electrophile, selenium electrophile, oxygen electrophile, boronating reagent, or an azide reagent.

For instance, in some embodiments, a selemium reagent is elemental selenium, a selenium salt, or a substituted diselenide. In some embodiments, an oxygen electrophile is elemental oxygen, peroxide, or a substituted peroxide. In some embodiments, a boronating reagent is a borane-amine (e.g., N,N-diisopropylethylamine (BH$_3$.DIPEA), borane-pyridine (BH$_3$.Py), borane-2-chloropyridine (BH$_3$.CPy), borane-aniline (BH$_3$.An)), a borane-ether reagent (e.g., borane-tetrahydrofuran (BH$_3$.THF)), a borane-dialkylsulfide reagent (e.g., BH$_3$.Me$_2$S), aniline-cyanoborane, or a triphenylphosphine-carboalkoxyborane. In some embodiments, an azide reagent is comprises an azide group capable of undergoing subsequent reduction to provide an amine group.

In some embodiments, a P-modification reagent is a sulfurization reagent as described herein. In some embodiments, a step of modifying comprises sulfurization of phosphorus to provide a phosphorothioate linkage or phosphorothioate triester linkage. In some embodiments, a step of modifying provides an oligonucleotide having an internucleotidic linkage of formula I.

In some embodiments, the present disclosure provides sulfurizing reagents, and methods of making, and use of the same.

In some embodiments, such sulfurizing reagents are thiosulfonate reagents. In some embodiments, a thiosulfonate reagent has a structure of formula S-I:

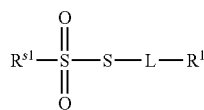

S-I wherein:

R$^{s1}$ is R; and each of R, L and R$^1$ is independently as defined and described above and herein.

In some embodiments, the sulfurizing reagent is a bis(thiosulfonate) reagent. In some embodiments, the bis(thiosulfonate) reagent has the structure of formula S-II:

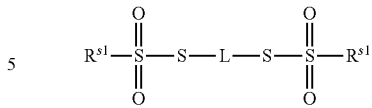

S-II wherein each of R$^{s1}$ and L is independently as defined and described above and herein.

As defined generally above, R$^{s1}$ is R, wherein R is as defined and described above and herein. In some embodiments, R$^{s1}$ is optionally substituted aliphatic, aryl, heterocyclyl or heteroaryl. In some embodiments, R$^{s1}$ is optionally substituted alkyl. In some embodiments, R$^{s1}$ is optionally substituted alkyl. In some embodiments, R$^{s1}$ is methyl. In some embodiments, R$^{s1}$ is cyanomethyl. In some embodiments, R$^{s1}$ is nitromethyl. In some embodiments, R$^{s1}$ is optionally substituted aryl. In some embodiments, R$^{s1}$ is optionally substituted phenyl. In some embodiments, R$^{s1}$ is phenyl. In some embodiments, R$^{s1}$ is p-nitrophenyl. In some embodiments, R$^{s1}$ is p-methylphenyl. In some embodiments, R$^{s1}$ is p-chlorophenyl. In some embodiments, R$^{s1}$ is o-chlorophenyl. In some embodiments, R$^{s1}$ is 2,4,6-trichlorophenyl. In some embodiments, R$^{s1}$ is pentafluorophenyl. In some embodiments, R$^{s1}$ is optionally substituted heterocyclyl. In some embodiments, R$^{s1}$ is optionally substituted heteroaryl.

In some embodiments, R$^{s1}$—S(O)$_2$S— is

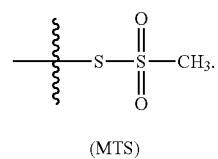 [SMILES: *SS(C)(=O)=O]

(MTS)

In some embodiments, R$^{s1}$—S(O)$_2$S— is

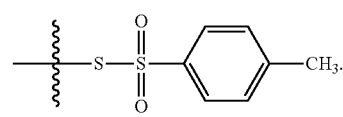

(TTS)

In some embodiments, R$^{s1}$—S(O)$_2$S— is

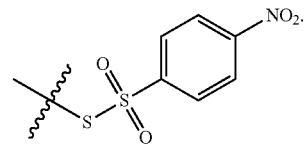

(NO$_2$PheTS)

In some embodiments, $R^{s1}$—$S(O)_2S$— is

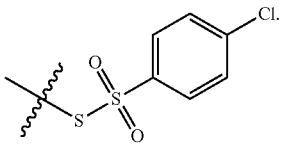

(p-ClPheTS)

In some embodiments, $R^{s1}$—$S(O)_2S$— is

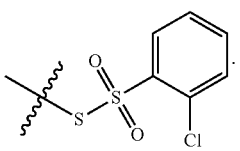

(o-ClPheTS)

In some embodiments, $R^{s1}$—$S(O)_2S$— is

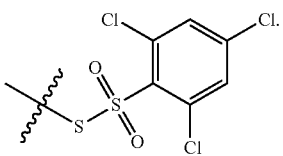

(2,4,6-TriClPheTS)

In some embodiments, $R^{s1}$—$S(O)_2S$— is

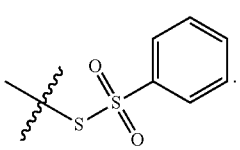

(PheTS)

In some embodiments, $R^{s1}$—$S(O)_2S$— is

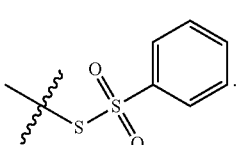

(PFPHeTS)

In some embodiments, $R^{s1}$—$S(O)_2S$— is

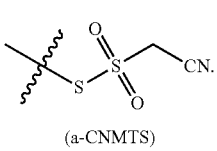

(a-CNMTS)

In some embodiments, $R^{s1}$—$S(O)_2S$— is

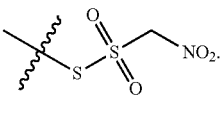

(a-NO$_2$MTS)

In some embodiments, $R^{s1}$—$S(O)_2S$— is

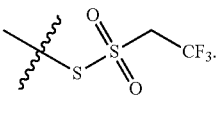

(a-CF$_3$MTS)

In some embodiments, $R^{s1}$—$S(O)_2S$— is

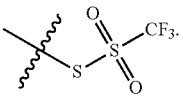

(a-CF$_3$TS)

In some embodiments, $R^{s1}$—$S(O)_2S$— is

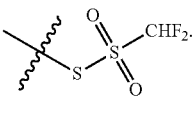

(a-CHF$_2$TS)

In some embodiments, $R^{s1}$—$S(O)_2S$— is

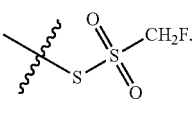

(a-CH$_2$FTS)

In some embodiments, the sulfurizing reagent has the structure of S-I or S-II, wherein L is —S—$R^{L3}$- or —S—C(O)—$R^{L3}$—. In some embodiments, L is —S—$R^{L3}$— or —S—C(O)—$R^{L3}$—, wherein $R^{L3}$ is an optionally substituted $C_1$-$C_6$ alkylene. In some embodiments, L is —S—$R^{L3}$— or —S—C(O)—$R^{L3}$—, wherein $R^{L3}$ is an optionally substituted $C_1$-$C_6$ alkenylene. In some embodiments, L is —S—$R^{L3}$— or —S—C(O)—$R^{L3}$—, wherein $R^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, $R^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-. In some embodiments, the sulfurizing reagent has the structure of S-I or S-II, wherein L is —S—$R^{L3}$- or —S—C(O)—$R^{L3}$—, and the sulfur atom is connected to $R^1$.

In some embodiments, the sulfurizing reagent has the structure of S-I or S-II, wherein L is alkylene, alkenylene, arylene or heteroarylene.

In some embodiments, the sulfurizing reagent has the structure of S-I or S-II, wherein L is
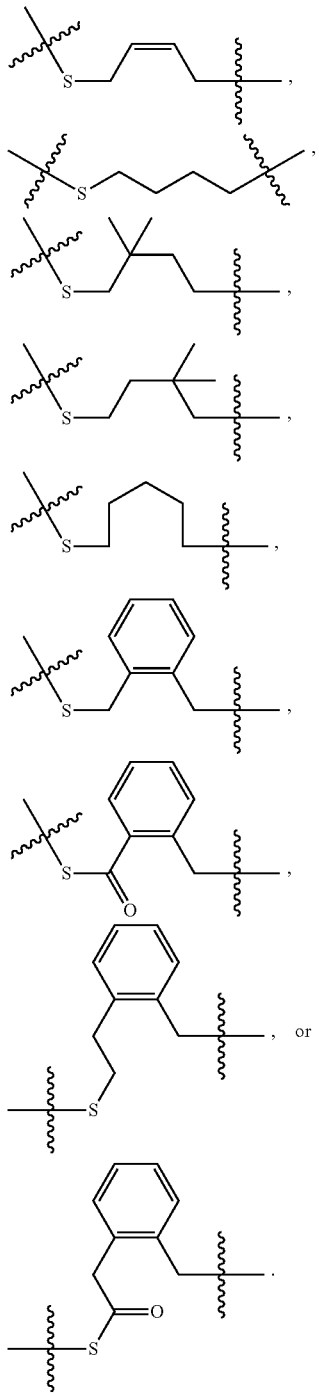
In some embodiments, L is
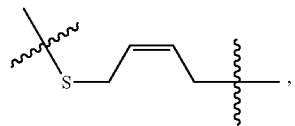
-continued
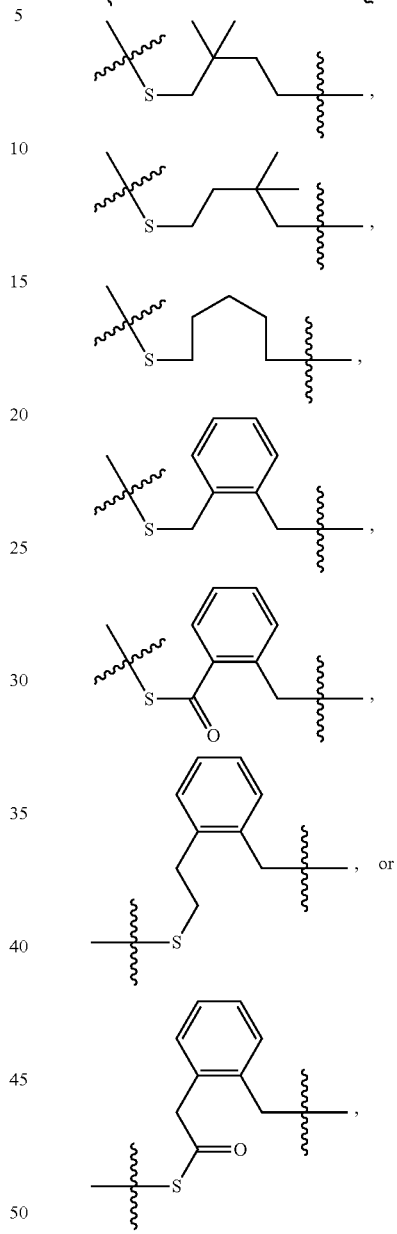
wherein the sulfur atom is connected to $R^1$.
In some embodiments, the sulfurizing reagent has the structure of S-I or S-II, wherein $R^1$ is
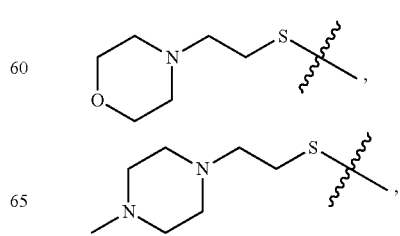

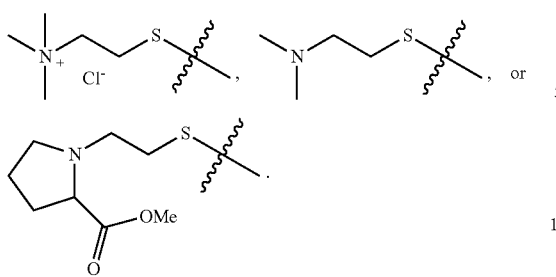

In some embodiments, $R^1$ is

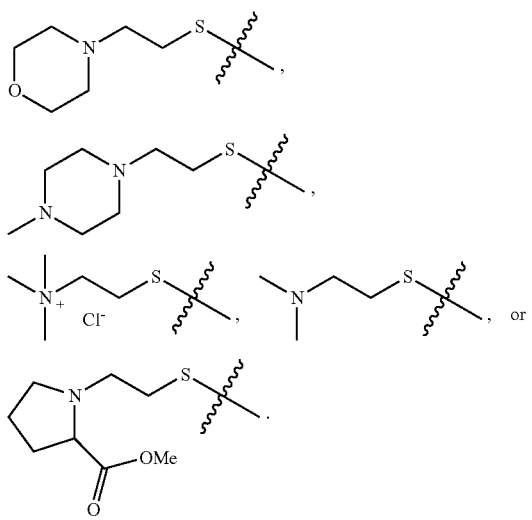

wherein the sulfur atom is connected to L.

In some embodiments, the sulfurizing reagent has the structure of S-I or S-II, wherein L is

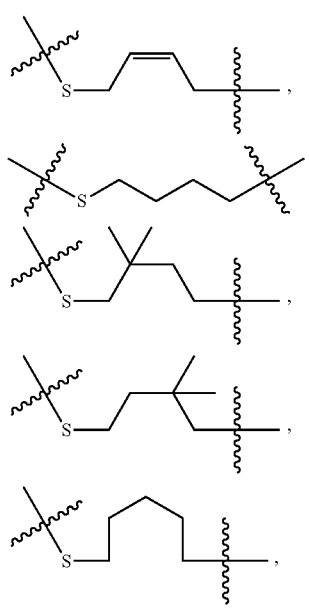

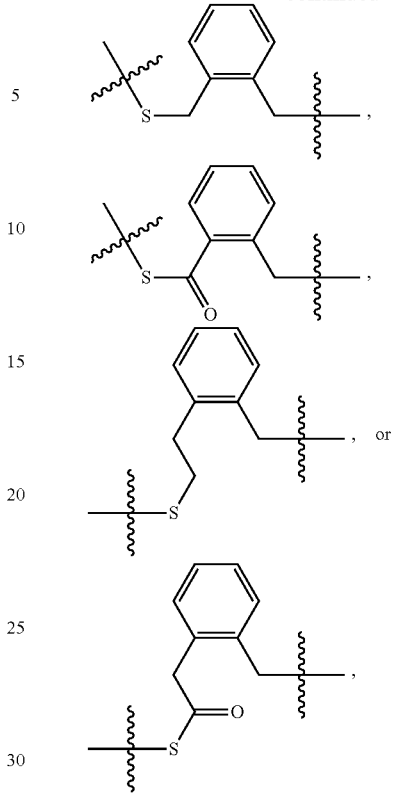

wherein the sulfur atom is connected to $R^1$; and $R^1$ is

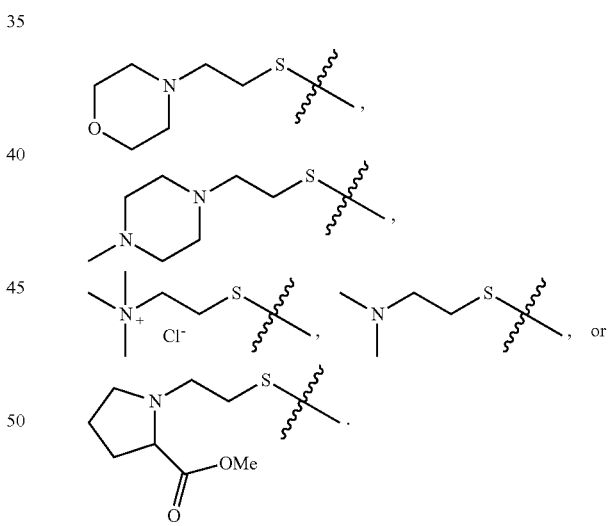

wherein the sulfur atom is connected to L.

In some embodiments, the sulfurizing reagent has the structure of S-I or S-II, wherein $R^1$ is —S—$R^{L2}$, wherein $R^{L2}$ is as defined and described above and herein. In some embodiments, $R^{L2}$ is an optionally substituted group selected from —S—($C_1$-$C_6$ alkylene)-heterocyclyl, —S—($C_1$-$C_6$ alkenylene)-heterocyclyl, —S—($C_1$-$C_6$ alkylene)-N$(R')_2$, —S—($C_1$-$C_6$ alkylene)-N$(R')_3$, wherein each R' is as defined above and described herein.

In some embodiments, -L-$R^1$ is —$R^{L3}$—S—S—$R^{L2}$, wherein each variable is independently as defined above and described herein. In some embodiments, -L-$R^1$ is —$R^{L3}$—

C(O)—S—S—$R^{L2}$, wherein each variable is independently as defined above and described herein.

Example bis(thiosulfonate) reagents of formula S—II are depicted below:

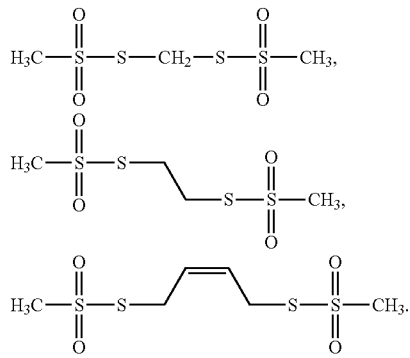

In some embodiments, the sulfurization reagent is a compound having one of the following formulae:

$$S_8, R^{s2}\text{—S—S—}R^{s3}, \text{ or } R^{s2}\text{—S—}X^s\text{—}R^{s3},$$

wherein:
each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or
$R^{s2}$ and $R^{s3}$ are taken together with the atoms to which they are bound to form an optionally substituted heterocyclic or heteroaryl ring;
$X^s$ is —S(O)$_2$—, —O—, or —N(R')—; and
R' is as defined and described above and herein.

In some embodiments, the sulfurization reagent is $S_8$,

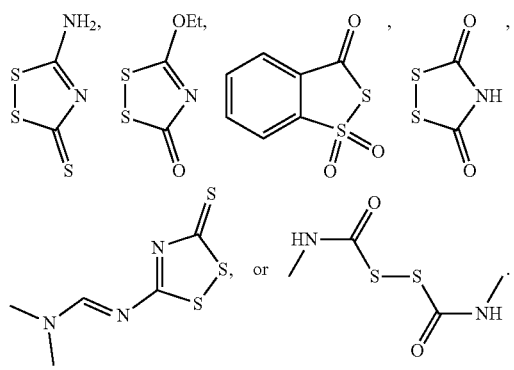

In some embodiments, the sulfurization reagent is $S_8$,

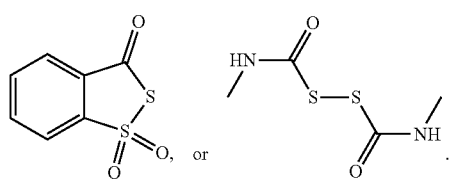

In some embodiments, the sulfurization reagent is

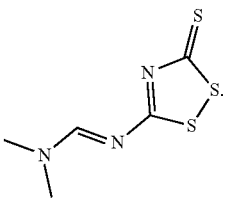

Example sulfuring reagents are depicted in Table 5 below.

TABLE 5

Example sulfurization reagents.

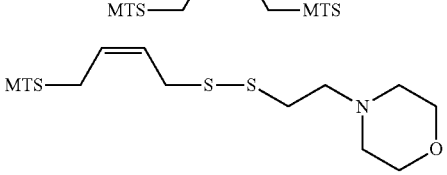

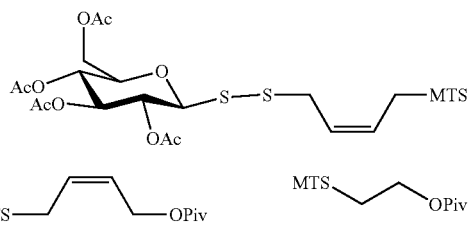

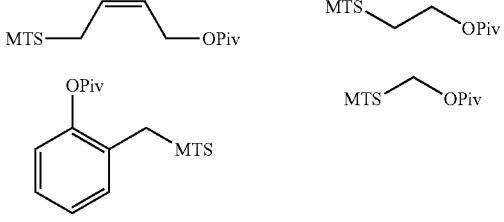

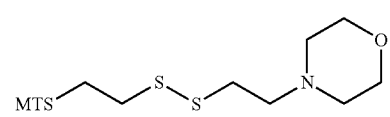

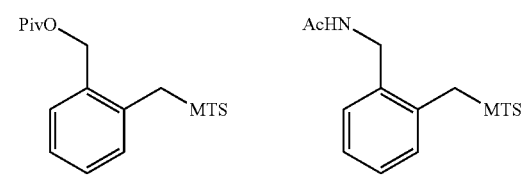

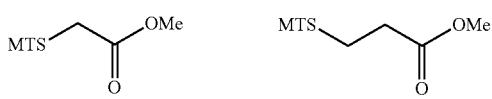

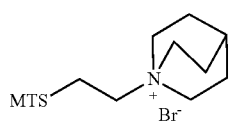

TABLE 5-continued

Example sulfurization reagents.

TABLE 5-continued

Example sulfurization reagents.

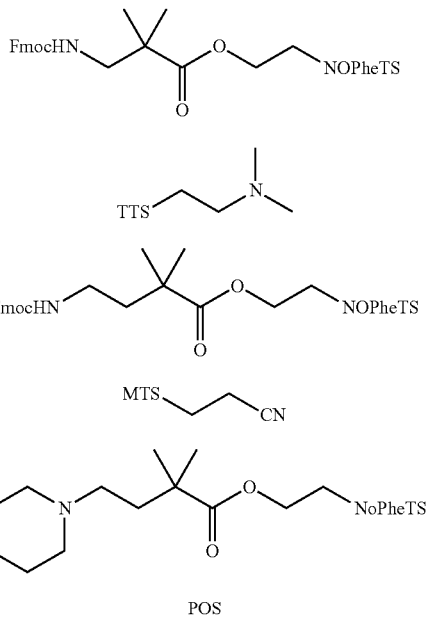

In some embodiments, a provided sulfurization reagent is used to modify an H-phosphonate. For instance, in some embodiments, an H-phosphonate oligonucleotide is synthesized using, e.g., a method of Wada I or Wada II, and is modified using a sulfurization reagent of formula S-I or S-II:

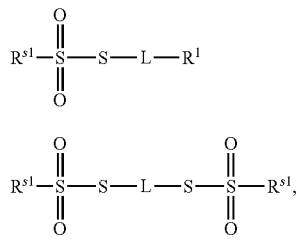

wherein each of $R^{S1}$, L, and $R^1$ are as described and defined above and herein.

In some embodiments, the present disclosure provides a process for synthesizing a phosphorothioate triester, comprising steps of:

i) reacting an H-phosphonate of structure:

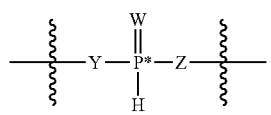

wherein each of W, Y, and Z are as described and defined above and herein, with a silylating reagent to provide a silyloxyphosphonate; and ii) reacting the silyloxyphosphonate with a sulfurization reagent of structure S-I or S-II:

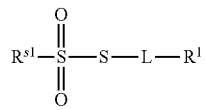

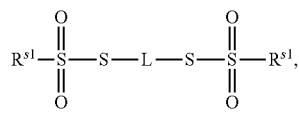

to provide a phosphorothiotriester.

In some embodiments, a selenium electrophile is used instead of a sulfurizing reagent to introduce modification to the internucleotidic linkage. In some embodiments, a selenium electrophile is a compound having one of the following formulae:

Se, $R^{s2}$—Se—Se—$R^{s3}$, or $R^{s2}$—Se—$X^s$—$R^{s3}$, wherein:

each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or $R^{s2}$ and $R^{s3}$ are taken together with the atoms to which they are bound to form an optionally substituted heterocyclic or heteroaryl ring;

$X^s$ is —S(O)$_2$—, —O—, or —N(R')—; and

R' is as defined and described above and herein.

In other embodiments, the selenium electrophile is a compound of Se, KSeCN,

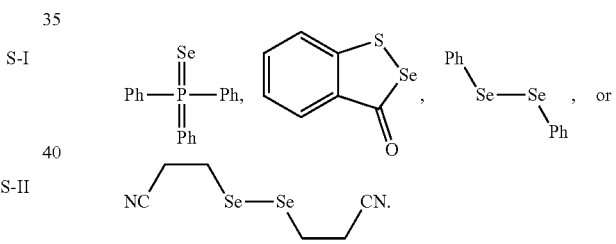

In some embodiments, the selenium electrophile is Se or

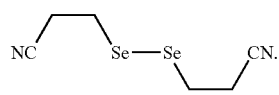

In some embodiments, a sulfurization reagent for use in accordance with the present disclosure is characterized in that the moiety transferred to phosphorus during sulfurization is a substituted sulfur (e.g., —SR) as opposed to a single sulfur atom (e.g., —S⁻ or =S).

In some embodiments, a sulfurization reagent for use in accordance with the present disclosure is characterized in that the activity of the reagent is tunable by modifying the reagent with a certain electron withdrawing or donating group.

In some embodiments, a sulfurization reagent for use in accordance with the present disclosure is characterized in that it is crystalline. In some embodiments, a sulfurization reagent for use in accordance with the present disclosure is characterized in that it has a high degree of crystallinity. In certain embodiments, a sulfurization reagent for use in accordance with the present disclosure is characterized by ease of purification of the reagent via, e.g., recrystallization. In certain embodiments, a sulfurization reagent for use in accordance with the present disclosure is characterized in that it is substantially free from sulfur-containing impurities. In some embodiments, sulfurization reagents which are substantially free from sulfur-containing impurities show increased efficiency.

In some embodiments, the provided chirally controlled oligonucleotide comprises one or more phosphate diester linkages. To synthesize such chirally controlled oligonucleotides, one or more modifying steps are optionally replaced with an oxidation step to install the corresponding phosphate diester linkages. In some embodiments, the oxidation step is performed in a fashion similar to ordinary oligonucleotide synthesis. In some embodiments, an oxidation step comprises the use of 12. In some embodiments, an oxidation step comprises the use of 12 and pyridine. In some embodiments, an oxidation step comprises the use of 0.02 M 12 in a THF/pyridine/water (70:20:10-v/v/v) co-solvent system. An example cycle is depicted in Scheme I-c.

In some embodiments, a phosphorothioate is directly formed through sulfurization by a sulfurization reagents, e.g., 3-phenyl-1,2,4-dithiazolin-5-one. In some embodiments, after a direct installation of a phosphorothioate, a chiral auxiliary group remains attached to the internucleotidic phosphorus atom. In some embodiments, an additional de-protecting step is required to remove the chiral auxiliary (e.g., for DPSE-type chiral auxiliary, using TBAF, HF-Et₃N, etc.).

In some embodiments, a phosphorothioate precursor is used to synthesize chirally controlled oligonucleotides comprising phosphorothioate linkages. In some embodiments, such a phosphorothioate precursor is

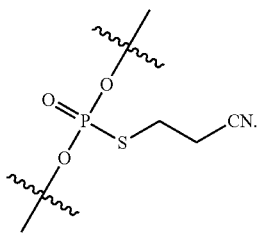 [SMILES: *OP(=O)(O*)SCCC#N]

In some embodiments,

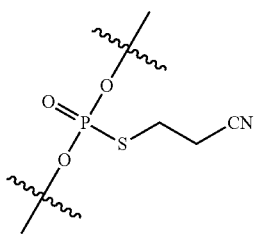 [SMILES: *OP(=O)(O*)SCCC#N]

is converted into phosphorothioate diester linkages during standard deprotection/release procedure after cycle exit. Examples are further depicted below.

In some embodiments, the provided chirally controlled oligonucleotide comprises one or more phosphate diester linkages and one or more phosphorothioate diester linkages.

In some embodiments, the provided chirally controlled oligonucleotide comprises one or more phosphate diester linkages and one or more phosphorothioate diester linkages, wherein at least one phosphate diester linkage is installed after all the phosphorothioate diester linkages when synthesized from 3' to 5'. To synthesize such chirally controlled oligonucleotides, in some embodiments, one or more modifying steps are optionally replaced with an oxidation step to install the corresponding phosphate diester linkages, and a phosphorothioate precursor is installed for each of the phosphorothioate diester linkages. In some embodiments, a phosphorothioate precursor is converted to a phosphorothioate diester linkage after the desired oligonucleotide length is achieved. In some embodiments, the deprotection/release step during or after cycle exit converts the phosphorothioate precursors into phosphorothioate diester linkages. In some embodiments, a phosphorothioate precursor is characterized in that it has the ability to be removed by a beta-elimination pathway. In some embodiments, a phosphorothioate precursor is

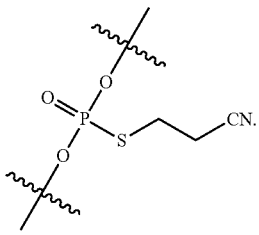 [SMILES: *OP(=O)(O*)SCCC#N]

As understood by one of ordinary skill in the art, one of the benefits of using a phosphorothioate precursor, for instance,

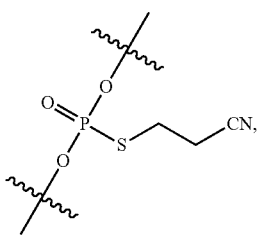 [SMILES: *OP(=O)(O*)SCCC#N]

during synthesis is that

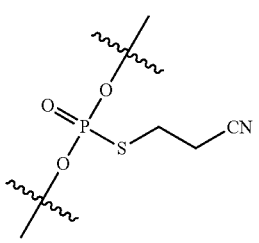

is more stable than phosphorothioate in certain conditions.

In some embodiments, a phosphorothioate precursor is a phosphorus protecting group as described herein, e.g., 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1- butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 44N-methyl-N-(2,2,2-trifluoroacetyl)amino]butyl. Examples are further depicted below.

Methods for synthesizing a desired sulfurization reagent are described herein and in the examples section.

As noted above, in some embodiments, sulfurization occurs under conditions which cleave the chiral reagent from the growing oligonucleotide. In some embodiments, sulfurization occurs under conditions which do not cleave the chiral reagent from the growing oligonucleotide.

In some embodiments, a sulfurization reagent is dissolved in a suitable solvent and delivered to the column. In certain embodiments, the solvent is a polar aprotic solvent such as a nitrile solvent. In some embodiments, the solvent is acetonitrile. In some embodiments, a solution of sulfurization reagent is prepared by mixing a sulfurization reagent (e.g., a thiosulfonate derivative as described herein) with BSTFA (N,O-bis-trimethylsilyl-trifluoroacetamide) in a nitrile solvent (e.g., acetonitrile). In some embodiments, BSTFA is not included. For example, the present inventors have found that relatively more reactive sulfurization reagents of general formula $R^{s2}$—S—S(O)$_2$—$R^{s3}$ can often successfully participate in sulfurization reactions in the absence of BSTFA. To give but one example, the inventors have demonstrated that where $R^{s2}$ is p-nitrophenyl and $R^{s3}$ is methyl then no BSTFA is required. In light of this disclosure, those skilled in the art will readily be able to determine other situations and/or sulfurization reagents that do not require BSTFA.

In some embodiments, the sulfurization step is performed at room temperature. In some embodiments, the sulfurization step is performed at lower temperatures such as about 0° C., about 5° C., about 10° C., or about 15° C. In some embodiments, the sulfurization step is performed at elevated temperatures of greater than about 20° C.

In some embodiments, a sulfurization reaction is run for about 1 minute to about 120 minutes. In some embodiments, a sulfurization reaction is run for about 1 minute to about 90 minutes. In some embodiments, a sulfurization reaction is run for about 1 minute to about 60 minutes. In some embodiments, a sulfurization reaction is run for about 1 minute to about 30 minutes. In some embodiments, a sulfurization reaction is run for about 1 minute to about 25 minutes. In some embodiments, a sulfurization reaction is run for about 1 minute to about 20 minutes. In some embodiments, a sulfurization reaction is run for about 1 minute to about 15 minutes. In some embodiments, a sulfurization reaction is run for about 1 minute to about 10 minutes. In some embodiments, a sulfurization reaction is run for about 5 minute to about 60 minutes.

In some embodiments, a sulfurization reaction is run for about 5 minutes. In some embodiments, a sulfurization reaction is run for about 10 minutes. In some embodiments, a sulfurization reaction is run for about 15 minutes. In some embodiments, a sulfurization reaction is run for about 20 minutes. In some embodiments, a sulfurization reaction is run for about 25 minutes. In some embodiments, a sulfurization reaction is run for about 30 minutes. In some embodiments, a sulfurization reaction is run for about 35 minutes. In some embodiments, a sulfurization reaction is run for about 40 minutes. In some embodiments, a sulfurization reaction is run for about 45 minutes. In some embodiments, a sulfurization reaction is run for about 50 minutes. In some embodiments, a sulfurization reaction is run for about 55 minutes. In some embodiments, a sulfurization reaction is run for about 60 minutes.

It was unexpectedly found that certain of the sulfurization modification products made in accordance with methods of the present disclosure are unexpectedly stable. In some embodiments, it the unexpectedly stable products are phosphorothioate triesters. In some embodiments, the unexpectedly stable products are chirally controlled oligonucleotides comprising one or more internucleotidic linkages having the structure of formula I-c.

One of skill in the relevant arts will recognize that sulfurization methods described herein and sulfurization reagents described herein are also useful in the context of modifying H-phosphonate oligonucleotides such as those described in Wada II (WO2010/064146).

In some embodiments, the sulfurization reaction has a stepwise sulfurization efficiency that is at least about 80%, 85%, 90%, 95%, 96%, 97%, or 98%. In some embodiments, the sulfurization reaction provides a crude dinucleotide product composition that is at least 98% pure. In some embodiments, the sulfurization reaction provides a crude tetranucleotide product composition that is at least 90% pure. In some embodiments, the sulfurization reaction provides a crude dodecanucleotide product composition that is at least 70% pure. In some embodiments, the sulfurization reaction provides a crude icosanucleotide product composition that is at least 50% pure.

Once the step of modifying the linkage phosphorus is complete, the oligonucleotide undergoes another deblock step in preparation for re-entering the cycle. In some embodiments, a chiral auxiliary remains intact after sulfurization and is deblocked during the subsequent deblock step, which necessarily occurs prior to re-entering the cycle. The process of deblocking, coupling, capping, and modifying, are repeated until the growing oligonucleotide reaches a desired length, at which point the oligonucleotide can either be immediately cleaved from the solid support or left attached to the support for purification purposes and later cleaved. In some embodiments, one or more protecting groups are present on one or more of the nucleotide bases, and cleaveage of the oligonucleotide from the support and deprotection of the bases occurs in a single step. In some embodiments, one or more protecting groups are present on one or more of the nucleotide bases, and cleaveage of the oligonucleotide from the support and deprotection of the bases occurs in more than one step. In some embodiments, deprotection and cleavage from the support occurs under basic conditions using, e.g., one or more amine bases. In certain embodiments, the one or more amine bases comprise propyl amine. In certain embodiments, the one or more amine bases comprise pyridine.

In some embodiments, cleavage from the support and/or deprotection occurs at elevated temperatures of about 30° C. to about 90° C. In some embodiments, cleavage from the support and/or deprotection occurs at elevated temperatures of about 40° C. to about 80° C. In some embodiments, cleavage from the support and/or deprotection occurs at elevated temperatures of about 50° C. to about 70° C. In some embodiments, cleavage from the support and/or deprotection occurs at elevated temperatures of about 60° C. In some embodiments, cleavage from the support and/or deprotection occurs at ambient temperatures.

Example purification procedures are described herein and/or are known generally in the relevant arts.

Noteworthy is that the removal of the chiral auxiliary from the growing oligonucleotide during each cycle is beneficial for at least the reasons that (1) the auxiliary will not have to be removed in a separate step at the end of the oligonucleotide synthesis when potentially sensitive functional groups are installed on phosphorus; and (2) unstable phosphorus-auxiliary intermediates prone to undergoing side reactions and/or interfering with subsequent chemistry are avoided. Thus, removal of the chiral auxiliary during each cycle makes the overall synthesis more efficient.

While the step of deblocking in the context of the cycle is described above, additional general methods are included below.

Deblocking Step

In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring and or other sugar ring. In some embodiments, an acid is selected from $R^{a1}COOH$, $R^{a1}SO_3H$, $R^{a3}SO_3H$,

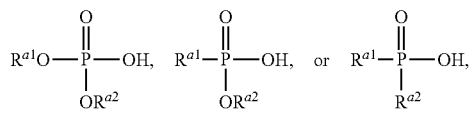

wherein each of $R^{a1}$ and $R^{a2}$ is independently hydrogen or an optionally substituted alkyl or aryl, and $R^{a3}$ is an optionally substituted alkyl or aryl.

In some embodiments, acidification is accomplished by a Lewis acid in an organic solvent. Examples of such useful Lewis acids are $Zn(X^a)_2$ wherein $X^a$ is Cl, Br, I, or $CF_3SO_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10% dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is deblocked by acidification, which comprises adding 1% trifluoroacetic acid in an organic solvent. In some embodiments, a blocking group is deblocked by acidification, which comprises adding 3% dichloroacetic acid in an organic solvent. In some embodiments, a blocking group is deblocked by acidification, which comprises adding 3% trichloroacetic acid in an organic solvent. In some embodiments, a blocking group is deblocked by acidification, which comprises adding 3% trichloroacetic acid in dichloromethane.

In certain embodiments, methods of the present disclosure are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, the chiral auxiliary is removed before the deblocking step. In some embodiments, the chiral auxiliary is removed during the deblocking step.

In some embodiments, cycle exit is performed before the deblocking step. In some embodiments, cycle exit is preformed after the deblocking step.

General Conditions for Blocking Group/Protecting Group Removal

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-m ethoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., *Tetrahedron*, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a C1-10 amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, the oligonucleotide is deprotected during cleavage.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C. or 100° C. In some embodiments, cleavage of oligonucleotide from solid support, or deprotection of oligonucleotide, is performed at about 30° C., 40° C., 50° C., 60° C., 70° C., 80° C. 90° C. or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Example conditions are 20% propylamine in pyridine at room temperature for about 18 hrs, and 20% propylamine in pyridine at 60° C. for about 18 hrs, In some embodiments, prior to cleavage from solid support, a step is performed to remove a chiral auxiliary group, if one is still attached to an internucleotidic phosphorus atom. In some embodiments, for example, one or more DPSE type chiral auxiliary groups remain attached to internucleotidic phosphorus atoms during the oligonucleotide synthesis cycle. Suitable conditions for removing remaining chiral auxiliary groups are widely known in the art, e.g., those described in Wada I, Wada II, Wada III, Chiral Control, etc. In some embodiments, a condition for removing DPSE type chiral auxiliary is TBAF or HF-Et$_3$N, e.g., 0.1M TBAF in MeCN, 0.5M HF-Et$_3$N in THF or MeCN, etc. In some embodiments, the present disclosure recognizes that a linker may be cleaved during the process of removing a chiral auxiliary group. In some embodiments, the present disclosure provides linkers, such as the SP linker, that provides better stability during chiral auxiliary group removal. Among other things, certain linkers provided by the present disclosure provided improved yield and/or purity.

In some embodiments, an activator is a "Wada" activator, i.e., the activator is from any one of Wada I, II, or III documents cited above.

Example activating groups are depicted below:

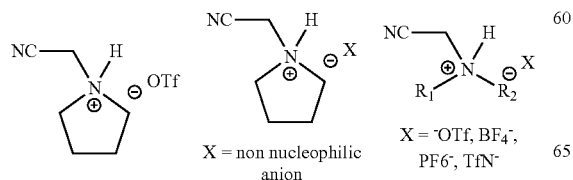

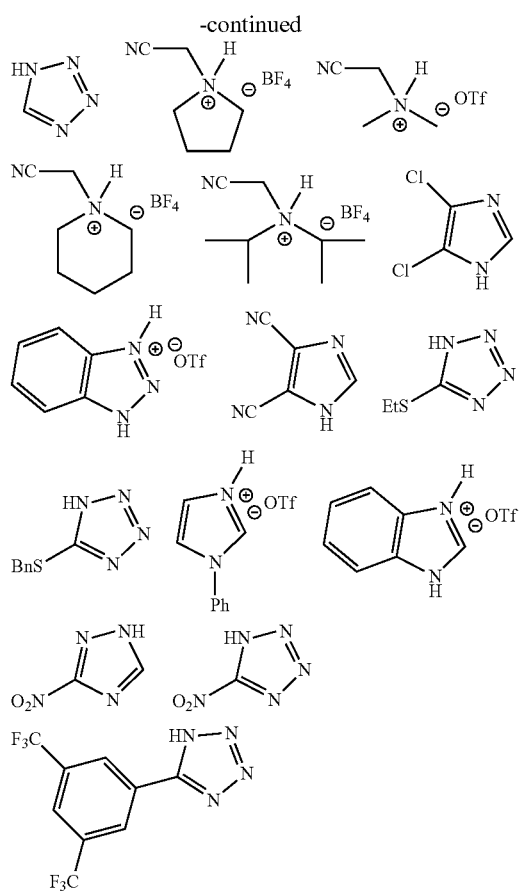

In some embodiments, an activating reagent is selected from

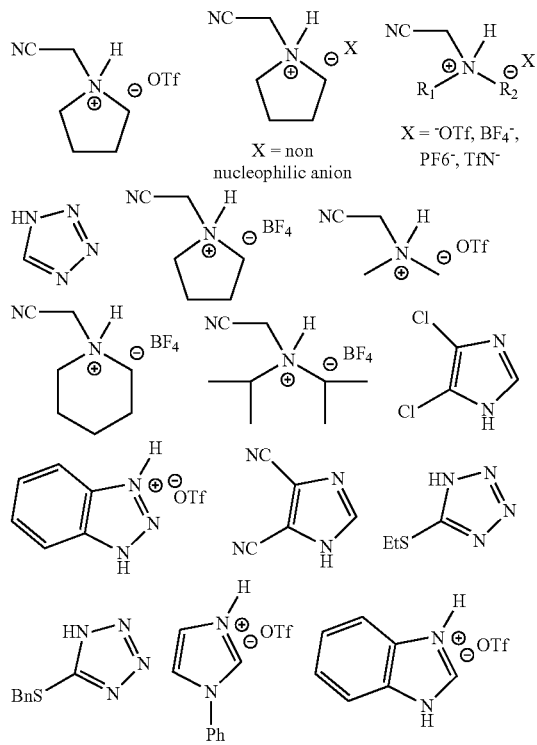

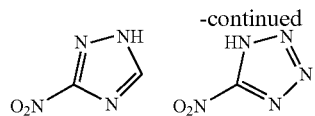
In some embodiments, an example cycle is depicted in Scheme I-b.
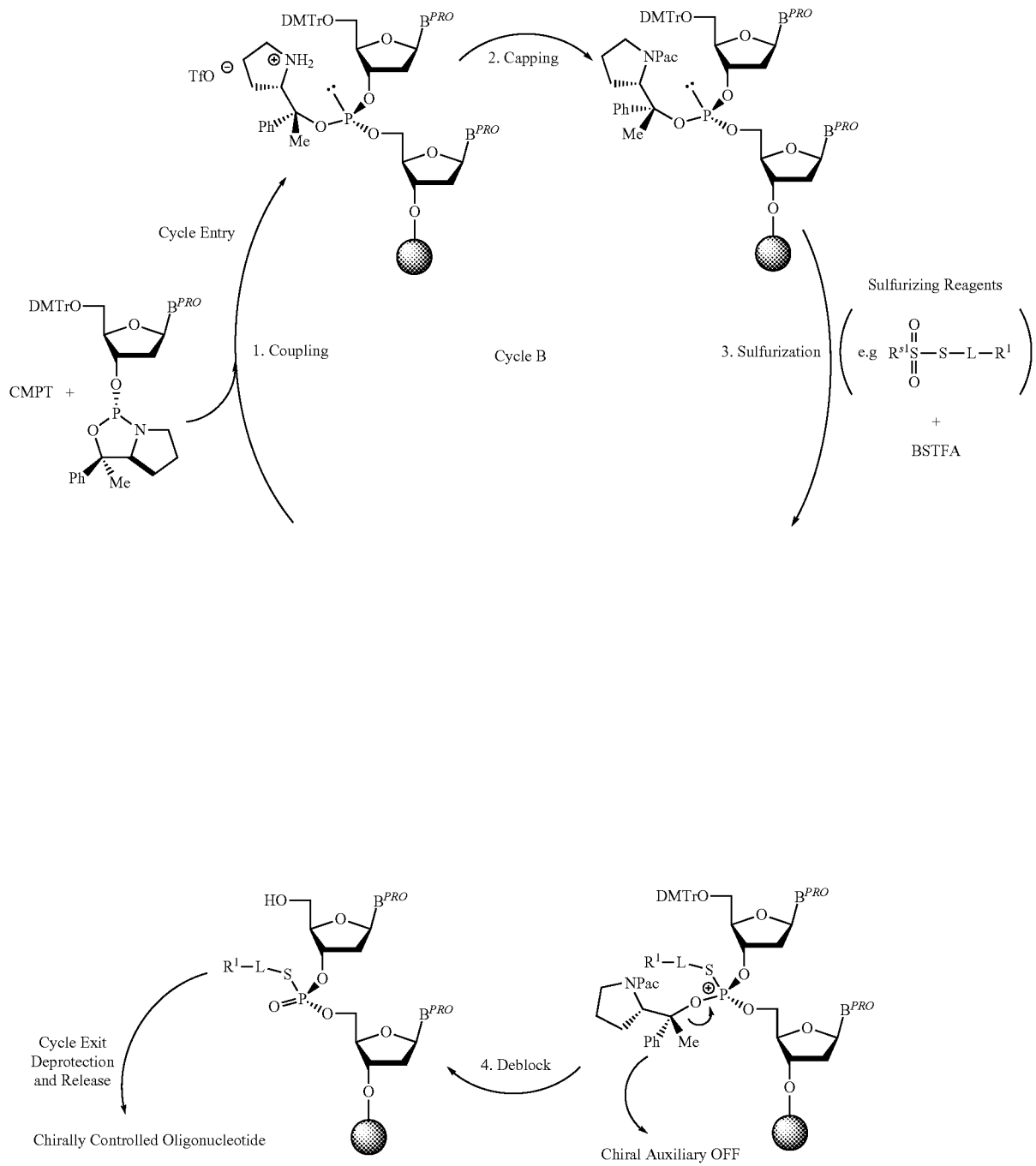
In some embodiments, an example cycle is illustrated in Scheme I-c.

Scheme I-c. Installation of both phosphate diester and modified internucleotides linkages in a chirally controlled oligonucleotide.

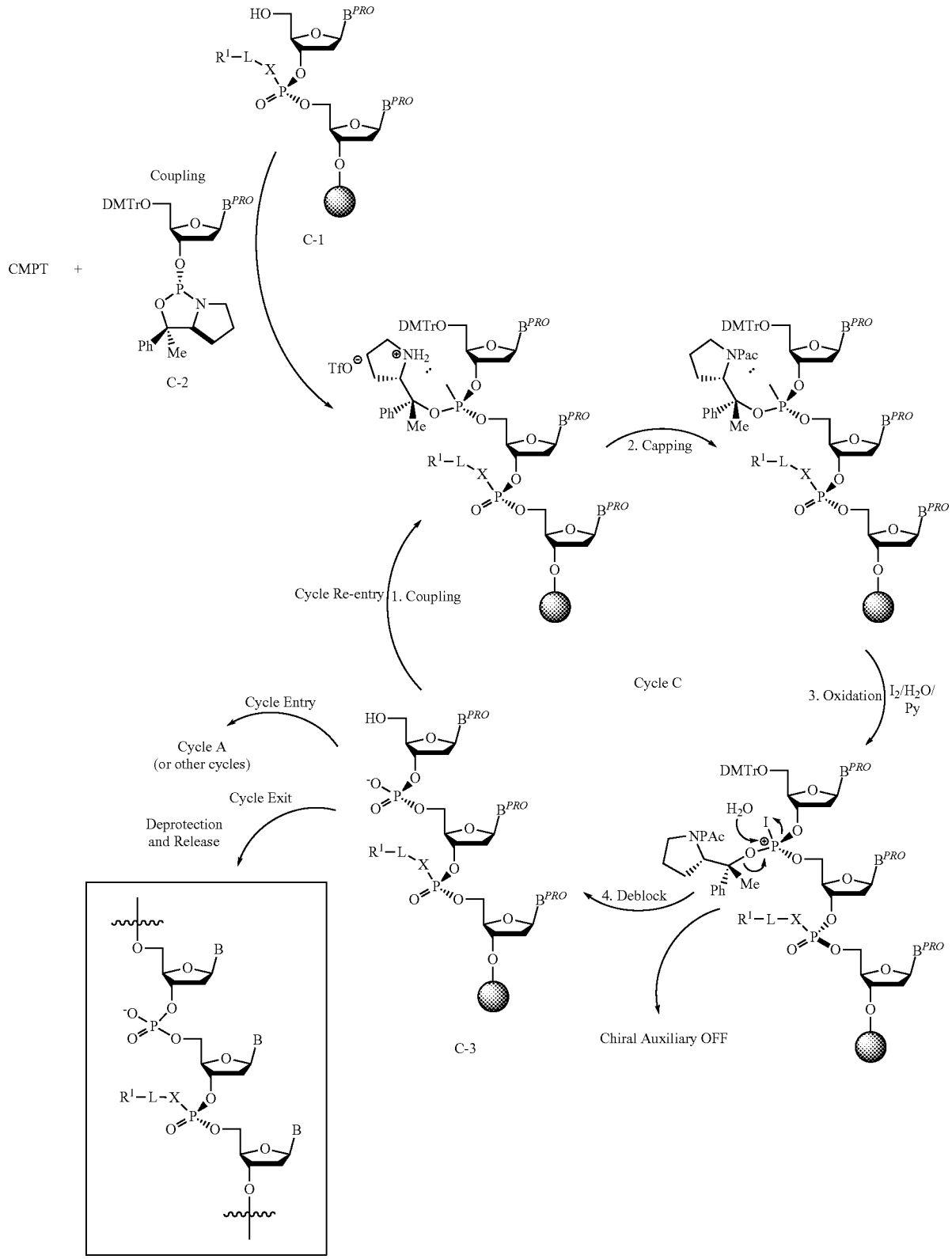

In Scheme I-c, oligonucleotide (or nucleotide, or oligonucleotide with modified internucleotidic linkage) on solid support (C-1) is coupled with phosphoramidite C-2. After coupling and capping, an oxidation step is performed. After deblocking, a phosphate diester linkage is formed. The cycle product C-3 can either re-enter cycle C to install more phosphate diester linkage, or enter other cycles to install other types of internucleotidic linkages, or go to cycle exit.

In some embodiments, non-chirally pure phosphoramidite can be used instead of C-2 in Scheme I-c. In some embodiments, β-cyanoethylphosphoramidites protected with DMTr is used. In some embodiments, the phosphoramidite being used has the structure of

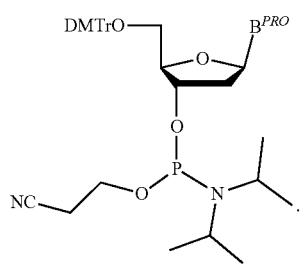

In some embodiments, the use of a phosphorothioate diester precursor increases the stability of oligonucleotide during synthesis. In some embodiments, the use of a phosphorothioate diester precursor improves the efficiency of chirally controlled oligonucleotide synthesis. In some embodiments, the use of a phosphorothioate diester precursor improves the yield of chirally controlled oligonucleotide synthesis. In some embodiments, the use of a phosphorothioate diester precursor improves the product purity of chirally controlled oligonucleotide synthesis.

In some embodiments, the phosphorothioate diester precursor in the above-mentioned methods is In some embodiments,

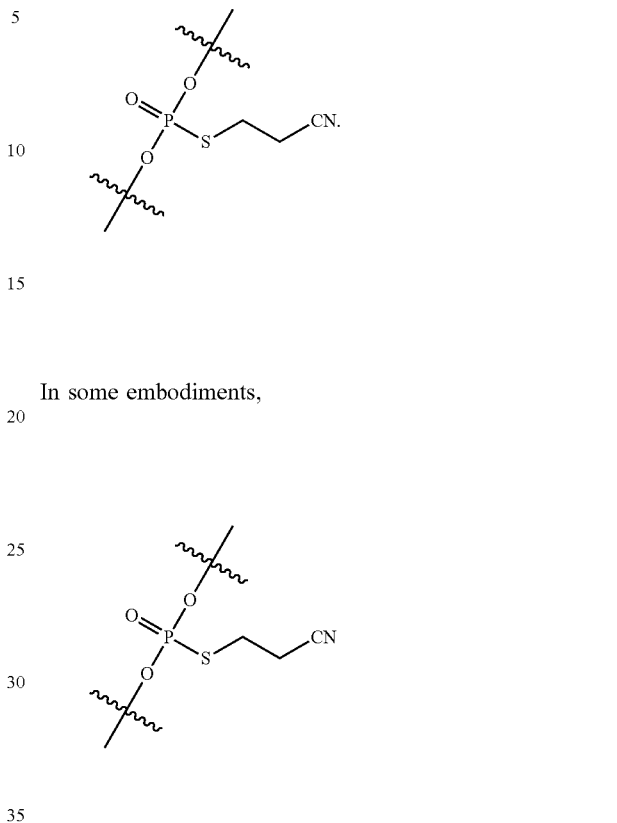

is converted to a phosphorothioate diester linkage during deprotection/release. In some embodiments, an example cycle is depicted in Scheme I-d. More examples are depicted below.

Scheme I-d. Phosphorothioate diester precursor in chirally controlled oligonucleotide synthesis.

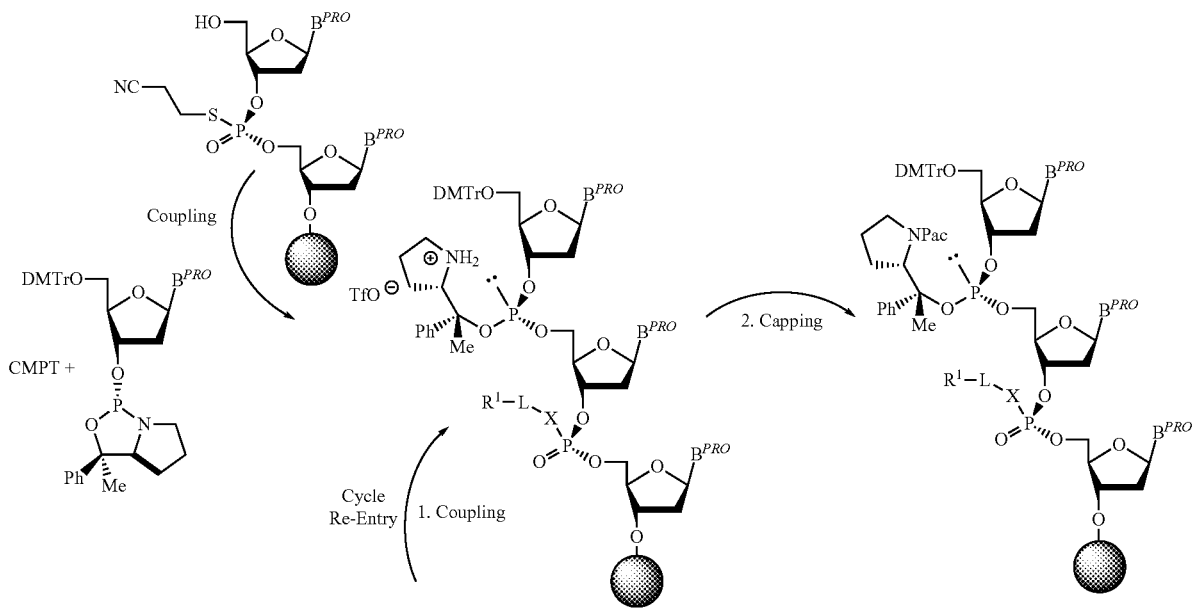

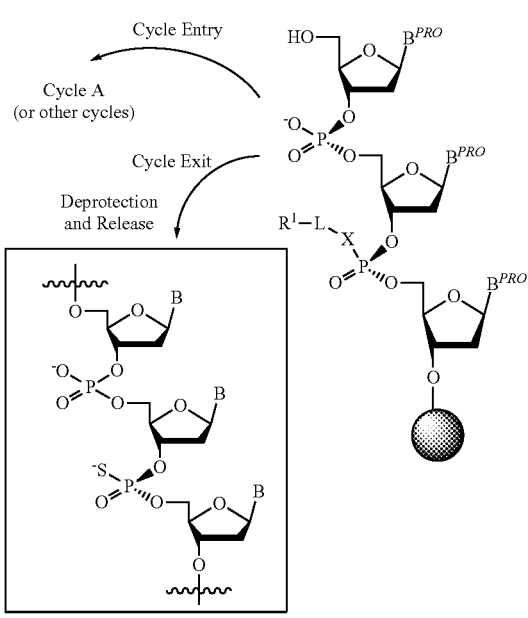
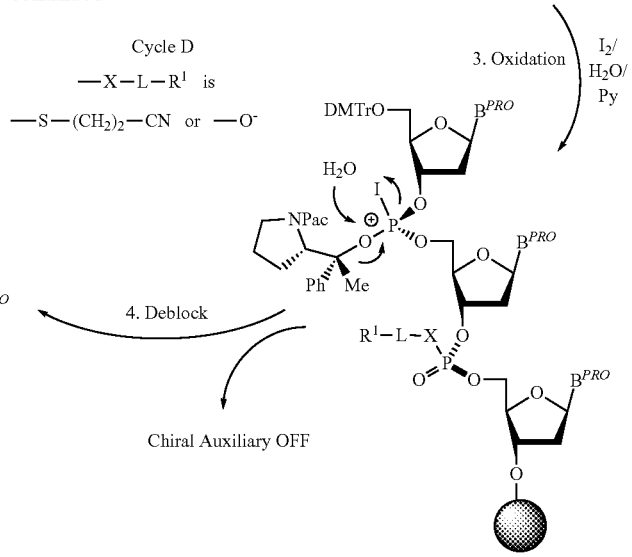

As illustrated in Scheme I-d, both phosphorothioate and phosphate diester linkages can be incorporated into the same chirally controlled oligonucleotide. As understood by a person of ordinary skill in the art, the provided methods do not require that the phosphorothioate diester and the phosphate diester to be consecutive—other internucleotidic linkages can form between them using a cycle as described above. In Scheme I-d, phosphorothioate diester precursors,

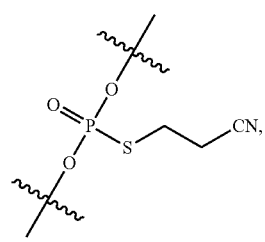 [SMILES: *OP(=O)(O*)SCCC#N]

are installed in place of the phosphorothioate diester linkages. In some embodiments, such replacement provided increased synthesis efficiency during certain steps, for instance, the oxidation step. In some embodiments, the use of phosphorothioate diester precursors generally improve the stability of chirally controlled oligonucleotides during synthesis and/or storage. After cycle exit, during deprotection/release, the phosphorothioate diester precursor is converted to phosphorothioate diester linkage. In some embodiments, it is benefical to use phosphorothioate diester precursor even when no phosphate diester linkage is present in the chirally controlled oligonucleotide, or no oxidation step is required during synthesis.

As in Scheme I-c, in some embodiments, non-chirally pure phosphoramidite can be used for cycles comprising oxidation steps. In some embodiments, β-cyanoethylphosphoramidites protected with DMTr is used. In some embodiments, the phosphoramidite being used has the structure of

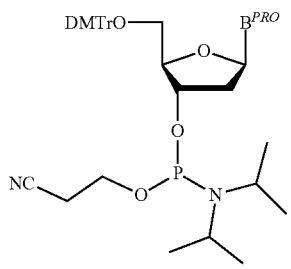

In some embodiments, methods of the present disclosure provide chirally controlled oligonucleotide compositions that are enriched in a particular oligonucleotide type.

In some embodiments, at least about 10% of a provided crude composition is of a particular oligonucleotide type. In some embodiments, at least about 20% of a provided crude composition is of a particular oligonucleotide type. In some embodiments, at least about 30% of a provided crude composition is of a particular oligonucleotide type. In some embodiments, at least about 40% of a provided crude composition is of a particular oligonucleotide type. In some embodiments, at least about 50% of a provided crude composition is of a particular oligonucleotide type. In some embodiments, at least about 60% of a provided crude composition is of a particular oligonucleotide type. In some embodiments, at least about 70% of a provided crude composition is of a particular oligonucleotide type. In some embodiments, at least about 80% of a provided crude composition is of a particular oligonucleotide type. In some embodiments, at least about 90% of a provided crude composition is of a particular oligonucleotide type. In some embodiments, at least about 95% of a provided crude composition is of a particular oligonucleotide type.

In some embodiments, at least about 1% of a provided composition is of a particular oligonucleotide type. In some embodiments, at least about 2% of a provided composition is of a particular oligonucleotide type. In some embodiments, at least about 3% of a provided composition is of a particular oligonucleotide type. In some embodiments, at least about 4% of a provided composition is of a particular oligonucleotide type. In some embodiments, at least about 5% of a provided composition is of a particular oligonucleotide type. In some embodiments, at least about 10% of a provided composition is of a particular oligonucleotide type. In some embodiments, at least about 20% of a provided composition is of a particular oligonucleotide type. In some embodiments, at least about 30% of a provided composition is of a particular oligonucleotide type. In some embodiments, at least about 40% of a provided composition is of a particular oligonucleotide type. In some embodiments, at least about 50% of a provided composition is of a particular oligonucleotide type. In some embodiments, at least about 60% of a provided composition is of a particular oligonucleotide type. In some embodiments, at least about 70% of a provided composition is of a particular oligonucleotide type. In some embodiments, at least about 80% of a provided composition is of a particular oligonucleotide type. In some embodiments, at least about 90% of a provided composition is of a particular oligonucleotide type. In some embodiments, at least about 95% of a provided composition is of a particular oligonucleotide type.

In some embodiments, an example cycle is depicted in Scheme I-e, below.

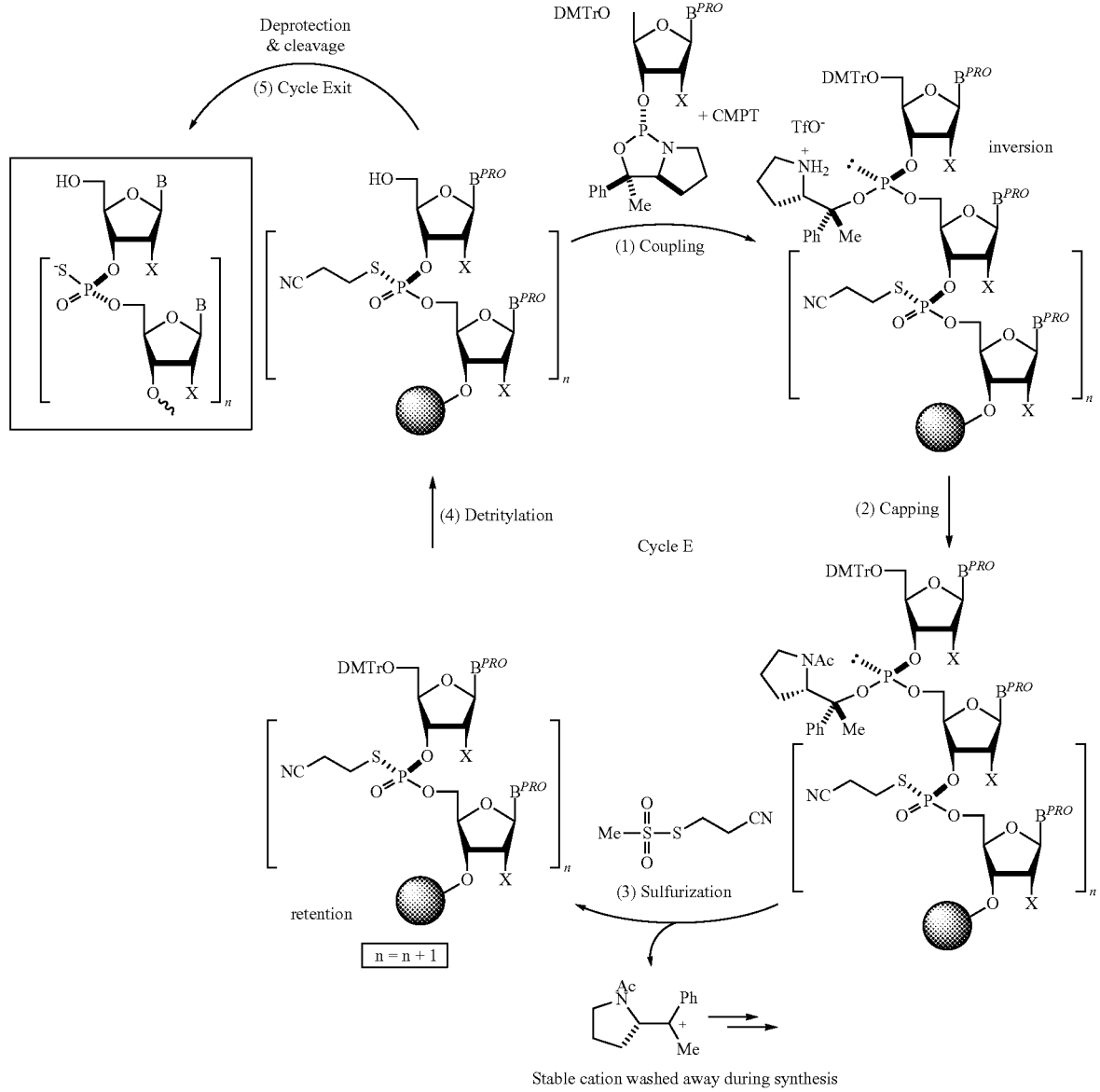

Scheme I-e. Example cycle using PhMe chiral auxiliary.

In some embodiments, X is H or a 2'-modification. In some embodiments, X is H or —OR$^1$ wherein R$^1$ is not hydrogen. In some embodiments, X is H or —OR$^1$ wherein R$^1$ is optionally substituted $C_{1-6}$ alkyl. In some embodiments, X is H. In some embodiments, X is —OMe. In some embodiments, X is —OCH$_2$CH$_2$OCH$_3$. In some embodiments, X is —F.

In some embodiments, an example cycle is depicted in Scheme I-f.

methods comprising providing a provided chiral reagent having the structure of

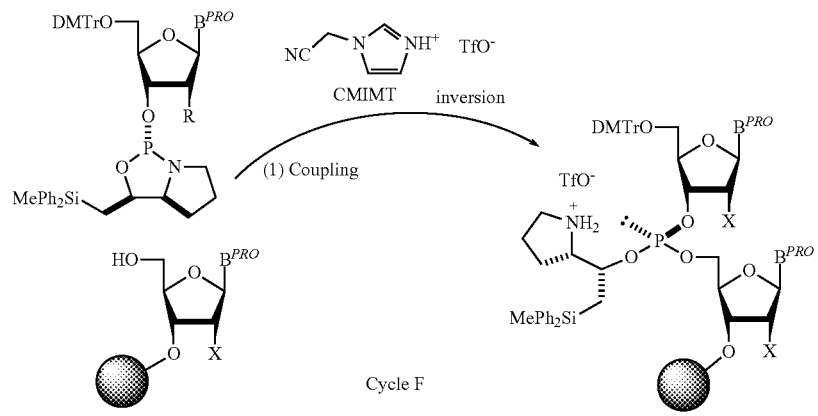

Scheme I-e. Example cycle using DPME chiral auxiliary.

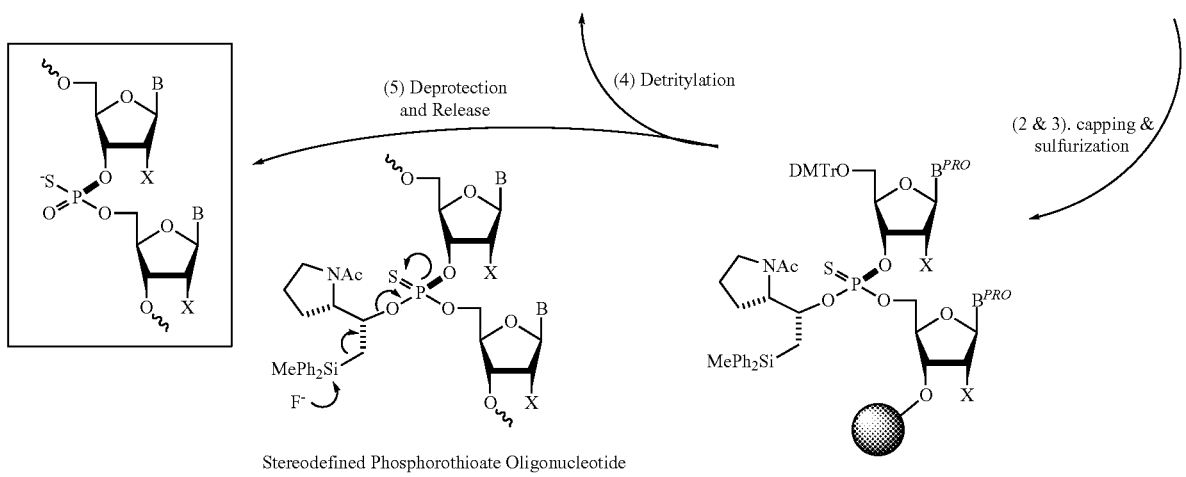

Stereodefined Phosphorothioate Oligonucleotide

In some embodiments, X is H or a 2'-modification. In some embodiments, X is H or —OR', wherein $R^1$ is not hydrogen. In some embodiments, X is H or —OR', wherein $R^1$ is optionally substituted $C_{1-6}$ alkyl. In some embodiments, X is H. In some embodiments, X is —OMe. In some embodiments, X is —OCH$_2$CH$_2$OCH$_3$. In some embodiments, X is —F.

It is understood by a person having ordinary skill in the art that different types of cycles may be combined to provide complete control of the chemical modifications and stereochemistry of oligonucleotides. In some embodiments, for example, an oligonucleotide synthesis process may contain one or more Cycles A-F. In some embodiments, a provided method comprises at least one cycle using a DPSE-type chiral auxiliary.

In some embodiments, the present disclosure provides methods for preparing provided oligonucleotide and oligonucleotide compositions. In some embodiments, a provide

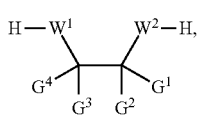

wherein $W^1$ is —NG$^5$, $W^2$ is O, each of $G^1$ and $G^3$ is independently hydrogen or an optionally substituted group selected from $C_{1-10}$ aliphatic, heterocyclyl, heteroaryl and aryl, $G^2$ is —C(R)$_2$Si(R)$_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused, wherein each R is independently hydrogen, or an optionally substituted group selected from $C_1$-$C_6$ aliphatic, carbocyclyl, aryl, heteroaryl, and heterocyclyl. In some embodiments, a provided chiral reagent has the structure of

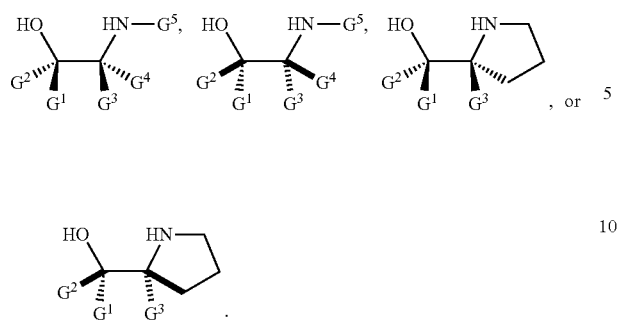

In some embodiments, a provided methods comprises providing a phosphoramidite comprising a moiety from a chiral reagent having the structure of

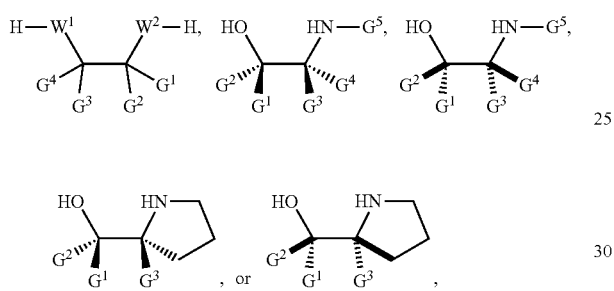

wherein —W¹H and —W²H, or the hydroxyl and amino groups, form bonds with the phosphorus atom of the phosphoramidite. In some embodiments, —W¹H and —W²H, or the hydroxyl and amino groups, form bonds with the phosphorus atom of the phosphoramidite, e.g., in

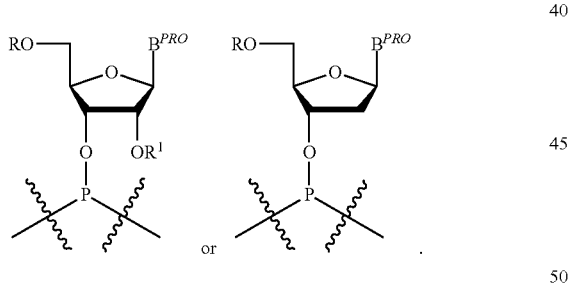

In some embodiments, a phosphoramidite has the structure of

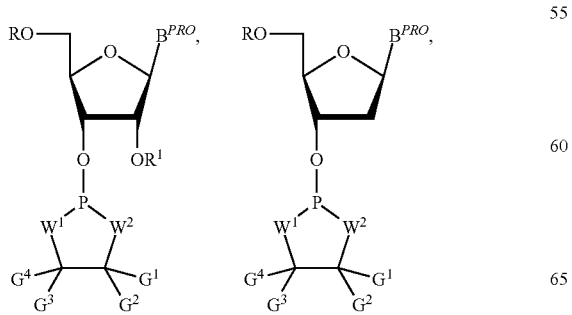

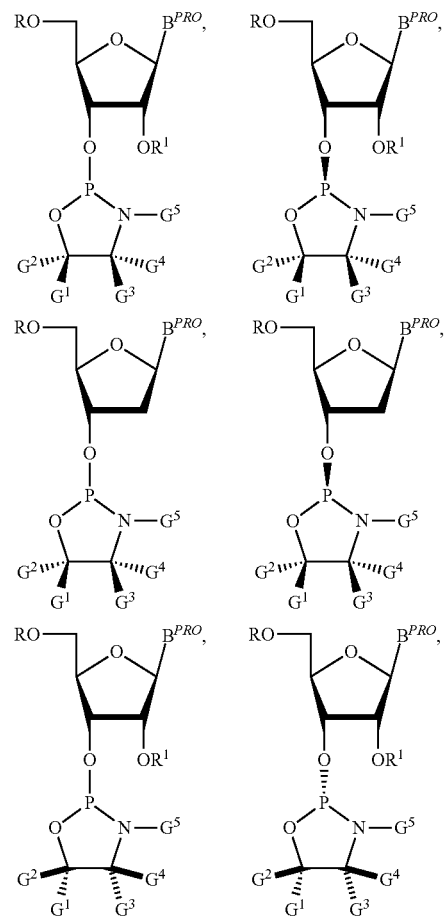

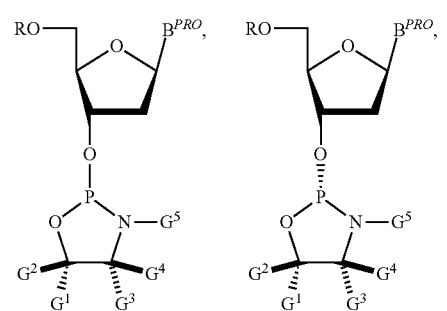

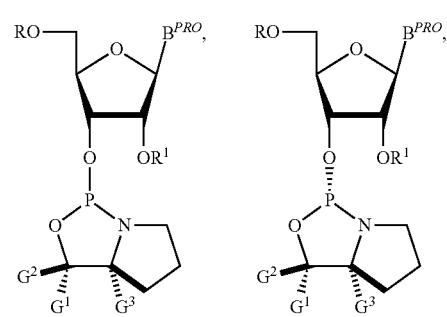

367
-continued
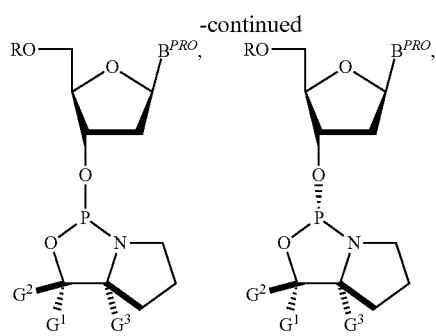
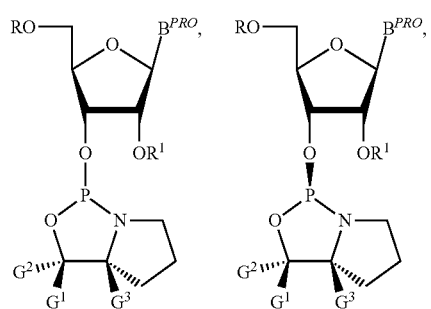
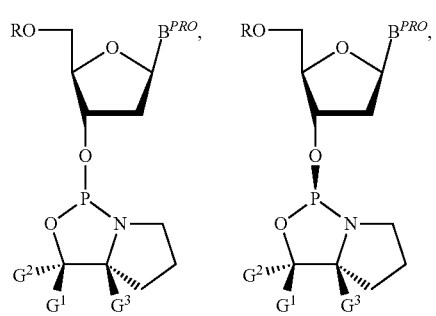
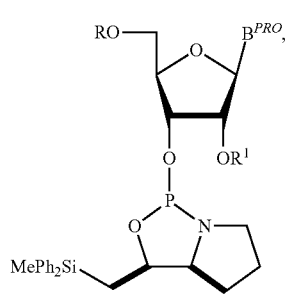
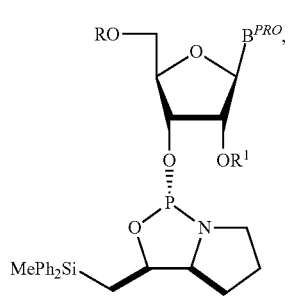
368
-continued
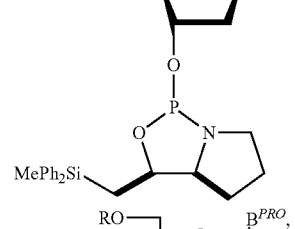
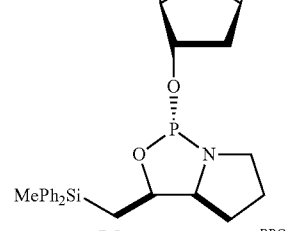
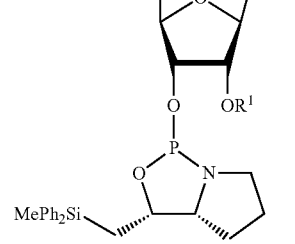
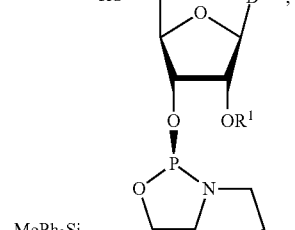
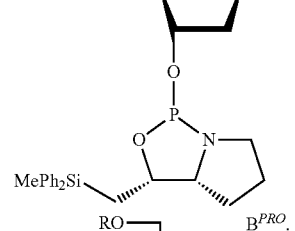
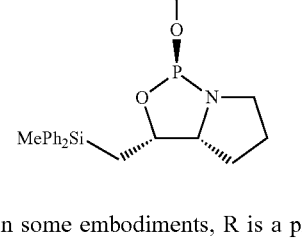
In some embodiments, R is a protection group. In some embodiments, R is DMTr. In some embodiments, $G^2$ is —C(R)₂Si(R)₃, wherein —C(R)₂— is optionally substituted —CH₂—, and each R of —Si(R)₃ is independently an optionally substituted group selected from $C_{1-10}$ aliphatic, heterocyclyl, heteroaryl and aryl. In some embodiments, at least one R of —Si(R)₃ is independently optionally substituted $C_{1-10}$ alkyl. In some embodiments, at least one R of —Si(R)₃ is independently optionally substituted phenyl. In some embodiments, one R of —Si(R)₃ is independently optionally substituted phenyl, and each of the other two R is independently optionally substituted $C_{1-10}$ alkyl. In some embodiments, one R of —Si(R)₃ is independently optionally substituted $C_{1-10}$ alkyl, and each of the other two R is independently optionally substituted phenyl. In some embodiments, $G^2$ is optionally substituted $CH_2Si(Ph)(Me)_2$. In some embodiments, $G^2$ is optionally substituted —$CH_2Si(Me)(Ph)_2$. In some embodiments, $G^2$ is —$CH_2Si(Me)(Ph)_2$. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen. In some embodiments, both $G^1$ and $G^3$ are hydrogen, $G^2$ is —C(R)₂Si(R)₃, wherein —C(R)₂— is optionally substituted —CH₂—, and each R of —Si(R)₃ is independently an optionally substituted group selected from $C_{1-10}$ aliphatic, heterocyclyl, heteroaryl and aryl, and $G^4$ and $G^5$ are taken together to form an optionally substituted saturated 5-membered ring containing one nitrogen atom. In some embodiments, a provided method further comprises providing a fluoro-containing reagent. In some embodiments, a provided fluoro-containing reagent removes a chiral reagent, or a product formed from a chiral reagent, from oligonucleotides after synthesis. Various known fluoro-containing reagents, including those F⁻ sources for removing —SiR₃ groups, can be utilized in accordance with the present disclosure, for example, TBAF, HF₃-Et₃N etc. In some embodiments, a fluoro-containing reagent provides better results, for example, shorter treatment time, lower temperature, less desulfurization, etc, compared to traditional methods, such as concentrated ammonia. In some embodiments, for certain fluoro-containing reagent, the present disclosure provides linkers for improved results, for example, less cleavage of oligonucleotides from support during removal of chiral reagent (or product formed therefrom during oligonucleotide synthesis). In some embodiments, a provided linker is an SP linker. In some embodiments, the present disclosure demonstrated that a HF-base complex can be utilized, such as HF—NR₃, to control cleavage during removal of chiral reagent (or product formed therefrom during oligonucleotide synthesis). In some embodiments, HF—NR₃ is HF-NEt₃. In some embodiments, HF—NR₃ enables use of traditional linkers, e.g., succinyl linker.

Biological Applications and Example of Use

Among other things, the present disclosure recognizes that properties and activities of an oligonucleotide can be adjusted by optimizing its pattern of backbone chiral centers through the use of provided chirally controlled oligonucleotide compositions. In some embodiments, the present disclosure provides chirally controlled oligonucleotide compositions, wherein the oligonucleotides have a common pattern of backbone chiral centers which enhances their stability and/or biological activity. In some embodiments, a pattern of backbone chiral centers provides unexpectedly increased stability. In some embodiments, a pattern of backbone chiral centers, surprisingly, provides greatly increased activity. In some embodiments, a pattern of backbone chiral centers provides both increased stability and activity. In some embodiments, when an oligonucleotide is utilized to cleave a nucleic acid polymer, a pattern of backbone chiral centers of the oligonucleotide, surprisingly by itself, changes the cleavage pattern of a target nucleic acid polymer. In some embodiments, a pattern of backbone chiral centers effectively prevents cleavage at secondary sites. In some embodiments, a pattern of backbone chiral centers creates new cleavage sites. In some embodiments, a pattern of backbone chiral centers minimizes the number of cleavage sites. In some embodiments, a pattern of backbone chiral centers minimizes the number of cleavage sites so that a target nucleic acid polymer is cleaved at only one site within the sequence of the target nucleic acid polymer that is complementary to the oligonucleotide. In some embodiments, a pattern of backbone chiral centers enhances cleavage efficiency at a cleavage site. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity among target sequences differing by point mutations or single nucleotide polymorphisms (SNPs). In some embodiments, a pattern of backbone chiral centers increase selectivity, e.g., cleavage selectivity among target sequences differing by only one point mutation or single nucleotide polymorphism (SNP).

Among other things, it is surprisingly found that certain provided oligonucleotide compositions achieve unprecedented control of cleavage of target sequences, e.g., cleavage of target RNA by RNase H. In some embodiments, the present disclosure demonstrates that precise control of chemical and stereochemical attributes of oligonucleotides achieves improved activity of oligonucleotide preparations as compared with otherwise comparable preparations for which stereochemical attributes are not controlled. Among other things, the present disclosure specifically demonstrates improved rate, degree, and or specificity of cleavage of nucleic acid targets to which provided oligonucleotides hybridize.

In some embodiments, the present disclosure provides various uses of oligonucleotide compositions. Among other things, the present disclosure demonstrates that by controlling structural elements of oligonucleotides, such as base sequence, chemical modifications, stereochemistry, etc., properties of oligonucleotides can be greatly improved. For example, in some embodiments, the present disclosure provides methods for highly selective suppression of transcripts of a target nucleic acid sequence. In some embodiments, the present disclosure provides methods for treating a subject by suppressing transcripts from a diseasing-causing copy (e.g., a disease-causing allele). In some embodiments, the present disclosure provides methods for designing and preparing oligonucleotide compositions with surprisingly enhanced activity and/or selectivity when suppressing a transcript of a target sequence. In some embodiments, the present disclosure provides methods for designing and/or preparing oligonucleotide compositions which provide allele-specific suppression of a transcript from a target nucleic acid sequence.

In some embodiments, the present disclosure provides a method for controlled cleavage of a nucleic acid polymer, the method comprising steps of:

contacting a nucleic acid polymer whose nucleotide sequence comprises a target sequence with a chirally controlled oligonucleotide composition comprising oligonucleotides of a particular oligonucleotide type characterized by:
1) a common base sequence and length, wherein the common base sequence is or comprises a sequence that is complementary to a target sequence found in the nucleic acid polymer;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type.

In some embodiments, the present disclosure provides a method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
1) the particular base sequence and length;
2) a particular pattern of backbone linkages; and
3) a particular pattern of backbone chiral centers.

In some embodiments, the present disclosure provides a method for controlled cleavage of a nucleic acid polymer, comprising providing a chirally controlled oligonucleotide composition comprising oligonucleotides defined by having:
1) a common base sequence and length, wherein the common base sequence is or comprises a sequence that is complementary to a sequence found in the nucleic acid polymer;
2) a common pattern of backbone linkages;
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers; and wherein the nucleic acid polymer is cleaved in a cleavage pattern that is different than the cleavage pattern when chirally uncontrolled oligonucleotide composition is provided.

As used herein, a cleavage pattern of a nucleic acid polymer is defined by the number of cleavage sites, the locations of the cleavage sites, and the percentage of cleavage at each sites. In some embodiments, a cleavage pattern has multiple cleavage sites, and the percentage of cleavage at each site is different. In some embodiments, a cleavage pattern has multiple cleavage sites, and the percentage of cleavage at each site is the same. In some embodiments, a cleavage pattern has only one cleavage site. In some embodiments, cleavage patterns differ from each other in that they have different numbers of cleavage sites. In some embodiments, cleavage patterns differ from each other in that at least one cleavage location is different. In some embodiments, cleavage patterns differ from each other in that the percentage of cleavage at at least one common cleavage site is different. In some embodiments, cleavage patterns differ from each other in that they have different numbers of cleavage sites, and/or at least one cleavage location is different, and/or the percentage of cleavage at at least one common cleavage site is different.

In some embodiments, the present disclosure provides a method for controlled cleavage of a nucleic acid polymer, the method comprising steps of:
contacting a nucleic acid polymer whose nucleotide sequence comprises a target sequence with a chirally controlled oligonucleotide composition comprising oligonucleotides of a particular oligonucleotide type characterized by:
1) a common base sequence and length, wherein the common base sequence is or comprises a sequence that is complementary to a target sequence found in the nucleic acid polymer;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type, the contacting being performed under conditions so that cleavage of the nucleic acid polymer occurs.

In some embodiments, the present disclosure provides a method for changing a first cleavage pattern of a nucleic acid polymer resulted from using a first oligonucleotide composition, comprising providing a second chirally controlled oligonucleotide composition comprising oligonucleotides defined by having:
1) a common base sequence and length, wherein the common base sequence is or comprises a sequence that is complementary to a sequence found in the nucleic acid polymer;
2) a common pattern of backbone linkages;
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers; and wherein the nucleic acid polymer is cleaved in a cleavage pattern that is different than the first cleavage pattern.

In some embodiments, the present disclosure provides a method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
1) the particular base sequence and length;
2) a particular pattern of backbone linkages; and
3) a particular pattern of backbone chiral centers,
the contacting being performed under conditions so that cleavage of the nucleic acid polymer occurs.

In some embodiments, a provided chirally controlled oligonucleotide composition reduces the number of cleavage sites within the target sequence. In some embodiments, a provided chirally controlled oligonucleotide composition provides single-site cleavage within the target sequence. In some embodiments, a chirally controlled oligonucleotide composition provides enhanced cleavage rate at a cleavage site within the target sequence. In some embodiments, a chirally controlled oligonucleotide composition provides enhanced efficiency at a cleavage site within the target sequence. In some embodiments, a chirally controlled oligonucleotide composition provides increased turn-over in cleaving a target nucleic acid polymer. In some embodiments, a chirally controlled oligonucleotide composition increase percentage of cleavage at a site within or in the vicinity of a characteristic sequence element. In some embodiments, a chirally controlled oligonucleotide composition increase percentage of cleavage at a site in the vicinity of a mutation. In some embodiments, a chirally controlled oligonucleotide composition increase percentage of cleavage at a site in the vicinity of a SNP. Example embodiments of a site within or in the vicinity of a characteristic sequence element, in the vicinity of a mutation, in the vicinity of a SNP, are described in the present disclosure. For example, in some embodiments, a cleavage site in the vicinity is a cleavage site 0, 1, 2, 3, 4, or 5 internucleotidic linkages away from a mutation; in some other embodiments, a cleavage site in the vicinity is a cleavage site 0, 1, 2, 3, 4, or 5 internucleotidic linkages away from a SNP.

In some embodiments, cleavage occurs with a cleavage pattern differs from a reference cleavage pattern. In some embodiments, a reference cleavage pattern is one observed when a nucleic acid polymer is contacted under comparable conditions with a reference oligonucleotide composition. In some embodiments, a reference oligonucleotide composition is a chirally uncontrolled (e.g., stereorandom) oligonucleotide composition of oligonucleotides that share the common base sequence and length of a chirally controlled oligonucleotide composition. In some embodiments, a reference oligonucleotide composition is a substantially racemic preparation of oligonucleotides that share the common sequence and length.

In some embodiments, a nucleic acid polymer is RNA. In some embodiments, a nucleic acid polymer is an oligonucleotide. In some embodiments, a nucleic acid polymer is an RNA oligonucleotide. In some embodiments, a nucleic acid polymer is a transcript. In some embodiments, oligonucleotides of a provided chirally controlled oligonucleotide composition form duplexes with a nucleic acid polymer to be cleaved.

In some embodiments, a nucleic acid polymer is cleaved by an enzyme. In some embodiments, an enzyme cleaves a duplex formed by a nucleic acid polymer. In some embodiments, an enzyme is RNase H. In some embodiments, an enzyme is Dicer. In some embodiments, an enzyme is an Argonaute protein. In some embodiments, an enzyme is Ago2. In some embodiments, an enzyme is within a protein complex. An example protein complex is RNA-induced silencing complex (RISC).

In some embodiments, a provided chirally controlled oligonucleotide composition comprising oligonucleotides with a common pattern of backbone chiral centers provides unexpectedly high selectivity so that nucleic acid polymers that have only small sequence variations within a target region can be selectively targeted. In some embodiments, a nucleic acid polymer is a transcript from an allele. In some embodiments, transcripts from different alleles can be selectively targeted by provided chirally controlled oligonucleotide compositions.

Figure 21:
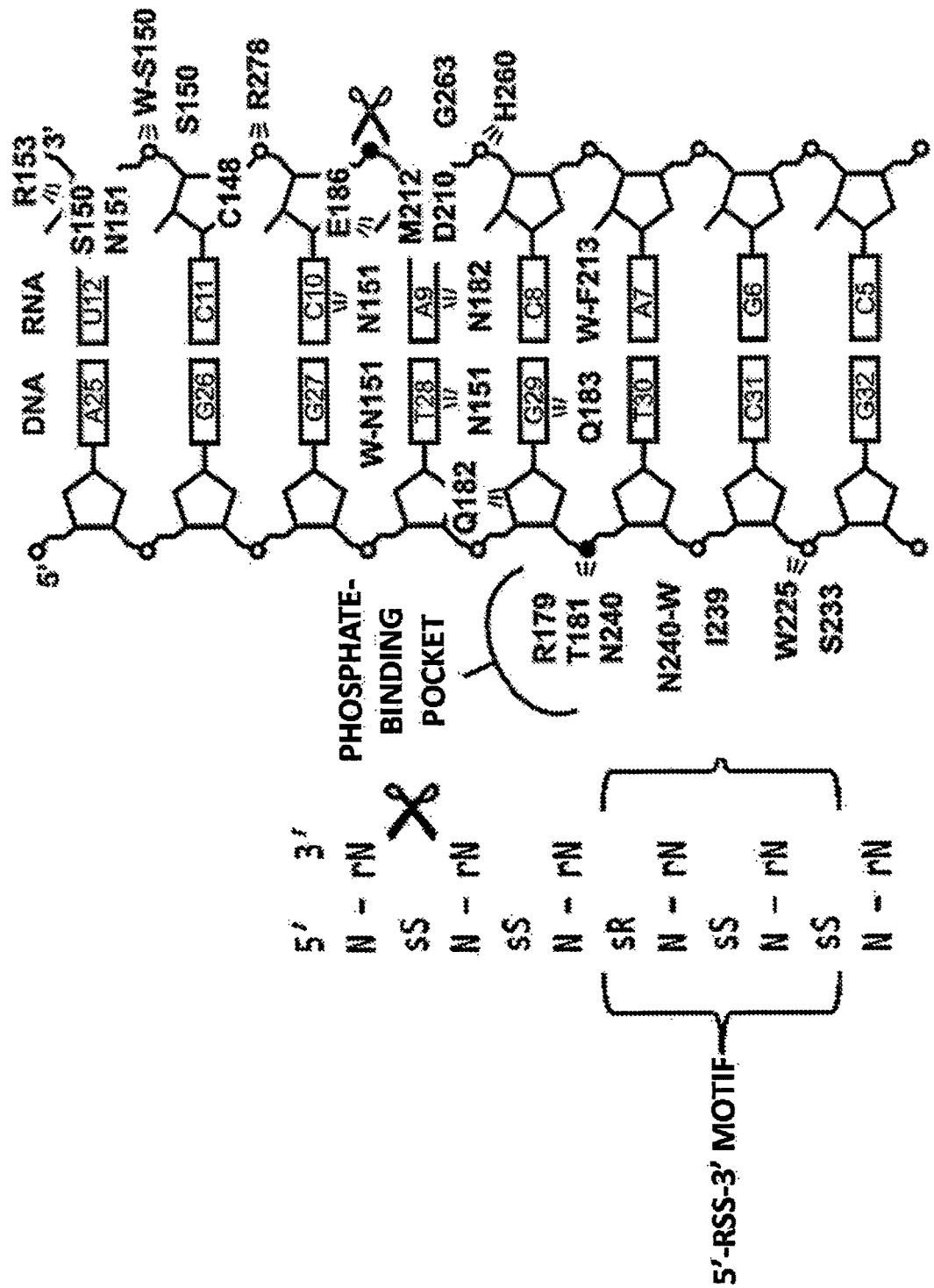
FIG. 21. An example proposed cleavage. Provided chirally controlled oligonucleotide compositions are capable of cleaving targets as depicted.

In some embodiments, provided chirally controlled oligonucleotide compositions and methods thereof enables precise control of cleavage sites within a target sequence. In some embodiments, a cleavage site is around a sequence of RpSpSp backbone chiral centers. In some embodiments, a cleavage site is upstream of and near a sequence of RpSpSp backbone chiral centers. In some embodiments, a cleavage site is within 5 base pairs upstream of a sequence of RpSpSp backbone chiral centers. In some embodiments, a cleavage site is within 4 base pairs upstream of a sequence of RpSpSp backbone chiral centers. In some embodiments, a cleavage site is within 3 base pairs upstream of a sequence of RpSpSp backbone chiral centers. In some embodiments, a cleavage site is within 2 base pairs upstream of a sequence of RpSpSp backbone chiral centers. In some embodiments, a cleavage site is within 1 base pair upstream of a sequence of RpSpSp backbone chiral centers. In some embodiments, a cleavage site is downstream of and near a sequence of RpSpSp backbone chiral centers. In some embodiments, a cleavage site is within 5 base pairs downstream of a sequence of RpSpSp backbone chiral centers. In some embodiments, a cleavage site is within 4 base pairs downstream of a sequence of RpSpSp backbone chiral centers. In some embodiments, a cleavage site is within 3 base pairs downstream of a sequence of RpSpSp backbone chiral centers. In some embodiments, a cleavage site is within 2 base pairs downstream of a sequence of RpSpSp backbone chiral centers. In some embodiments, a cleavage site is within 1 base pair downstream of a sequence of RpSpSp backbone chiral centers. Among other things, the present disclosure therefore provides control of cleavage sites with in a target sequence. In some embodiments, an example cleavage is depicted in FIG. 21. In some embodiments, cleavage depicted in FIG. 21 is designated as cleavage at a site two base pairs downstream a sequence of RpSpSp backbone chiral centers. As extensively described in the present disclosure, a sequence of RpSpSp backbone chiral centers can be found in a single or repeating units of $(Np)_m(Rp)_n(Sp)_t$, $(Np)_t(Rp)_n(Sp)_m$, $(Sp)_m(Rp)_n(Sp)_t$, $(Sp)_t(Rp)_n(Sp)_m$, $(Rp)_n(Sp)_m$, $(Rp)_m(Sp)_n$, $(Sp)_m Rp$ and/or $Rp(Sp)_m$, each of which is independently as defined above and described herein. In some embodiments, a provided chirally controlled oligonucleotide composition creates a new cleavage site 2 base pairs downstream of RpSpSp backbone chiral centers in a target molecule (e.g., see FIG. 21), wherein said new cleavage site does not exist if a reference (e.g., chirally uncontrolled) oligonucleotide composition is used (cannot be detected). In some embodiments, a provided chirally controlled oligonucleotide composition enhances cleavage at a cleavage site 2 base pairs downstream of RpSpSp backbone chiral centers in a target molecule (e.g., see FIG. 21), wherein cleavage at such a site occurs at a higher percentage than when a reference (e.g., chirally uncontrolled) oligonucleotide composition is used. In some embodiments, cleavage at such a site by a provided chirally controlled oligonucleotide composition is at least 2, 3, 4, 5, 6, 7, 8, 9, 10, 20, 30, 40, 50, 60, 70, 80, 90, 100, 200, 500 or 1000 fold of that by a reference oligonucleotide composition (for example, when measured by percentage of cleavage at a site). In some embodiments, a provided chirally controlled oligonucleotide composition provides accelerated cleavage at a cleavage site 2 base pairs downstream of RpSpSp backbone chiral centers in a target molecule (e.g., see FIG. 21), compared to when a reference (e.g., chirally uncontrolled) oligonucleotide composition is used. In some embodiments, cleavage by a provided chirally controlled oligonucleotide composition is at least 2, 3, 4, 5, 6, 7, 8, 9, 10, 20, 30, 40, 50, 60, 70, 80, 90, 100, 200, 500 or 1000 fold faster than that by a reference oligonucleotide composition. In some embodiments, a cleavage site of a provided chirally controlled oligonucleotide composition 2 base pairs downstream of RpSpSp backbone chiral centers in a target molecule (e.g., see FIG. 21) is a cleavage site when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule (e.g., see FIG. 21) is within one base pair of a cleavage site when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule (e.g., see FIG. 21) is within 2 base pairs of a cleavage site when a reference (e.g., chirally uncontrolled) oligonucleotide composition is used. In some embodiments, it is within 3 base pairs. In some embodiments, it is within 4 base pairs. In some embodiments, it is within 5 base pairs. In some embodiments, a cleavage site of a provided chirally controlled oligonucleotide composition 2 base pairs downstream of RpSpSp backbone chiral centers in a target molecule is one of the major cleavage sites when a reference (e.g., chirally uncontrolled) oligonucleotide composition is used. In some embodiments, such a site is the cleavage site with the highest cleavage percentage when a reference (e.g., chirally uncontrolled) oligonucleotide composition is used. In some embodiments, a cleavage site of a provided chirally controlled oligonucleotide composition 2 base pairs downstream of RpSpSp backbone chiral centers in a target molecule is one of the cleavage sites with higher cleavage rate when a reference (e.g., chirally uncontrolled) oligonucleotide composition is used. In some embodiments, such a site is the cleavage site with the highest cleavage rate when a reference (e.g., chirally uncontrolled) oligonucleotide composition is used.

Figure 18:
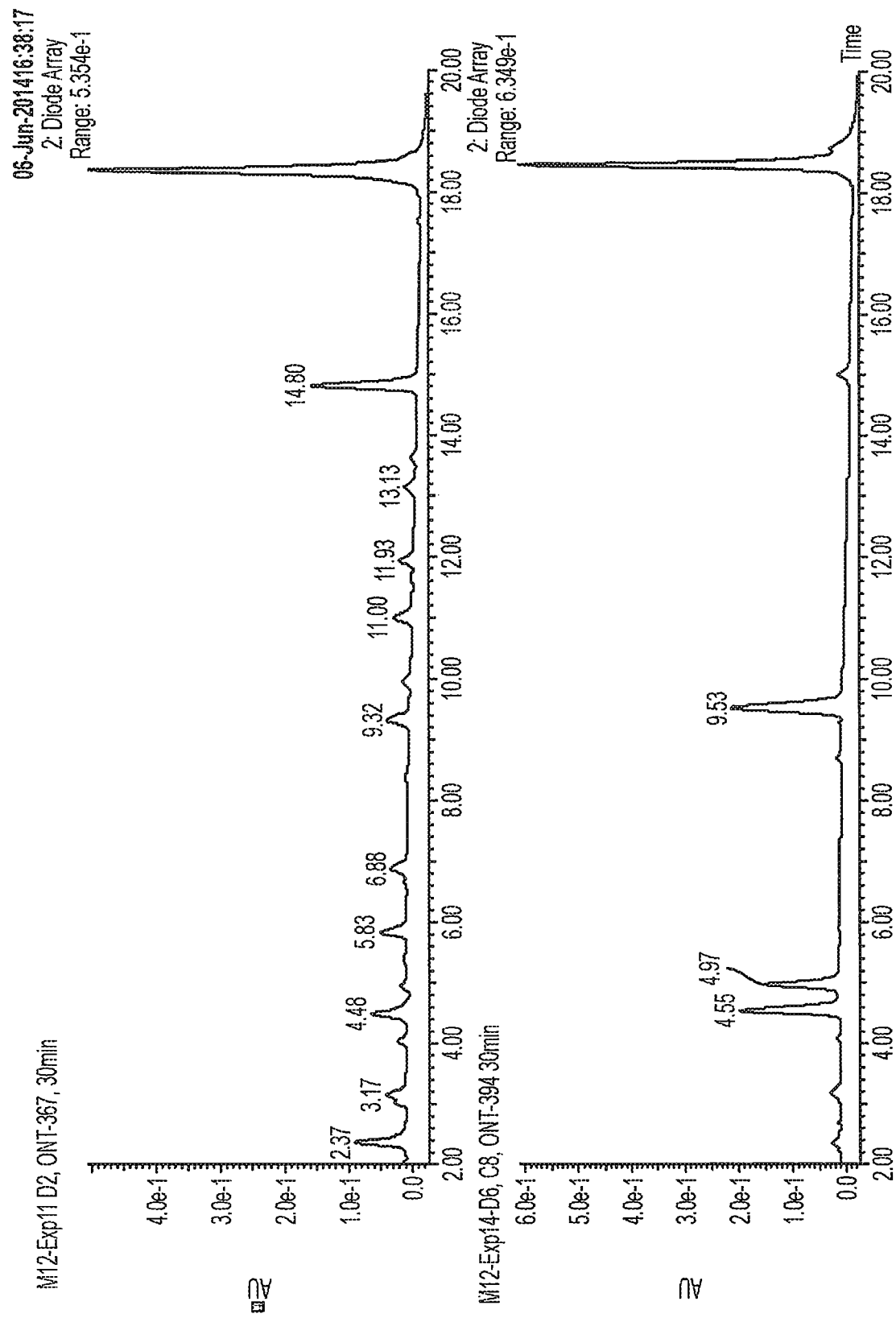
FIG. 18. Example UV chromatograms of RNA cleavage products obtained when RNA (ONT-388) was duplexed with stereorandom DNA, ONT-367 (top) and stereopure DNA with repeat triplet motif-3'-SSR-5', ONT-394 (bottom).). 2.35 min: 7mer; 3.16 min: 8mer and p-6mer; 4.48 min: P-7mer; 5.83 min: P-8mer; 6.88 min: 12mer; 9.32 min: 13mer; 10.13 min: P-11mer; 11.0 min: P-12mer and 14mer; 11.93 min: P-13mer; 13.13 min: P-14mer. ONT-394 (on the bottom) peak assignment: 4.55 min: p-7mer; 4.97 min: 10mer; 9.53 min: 13mer.
Figure 19:
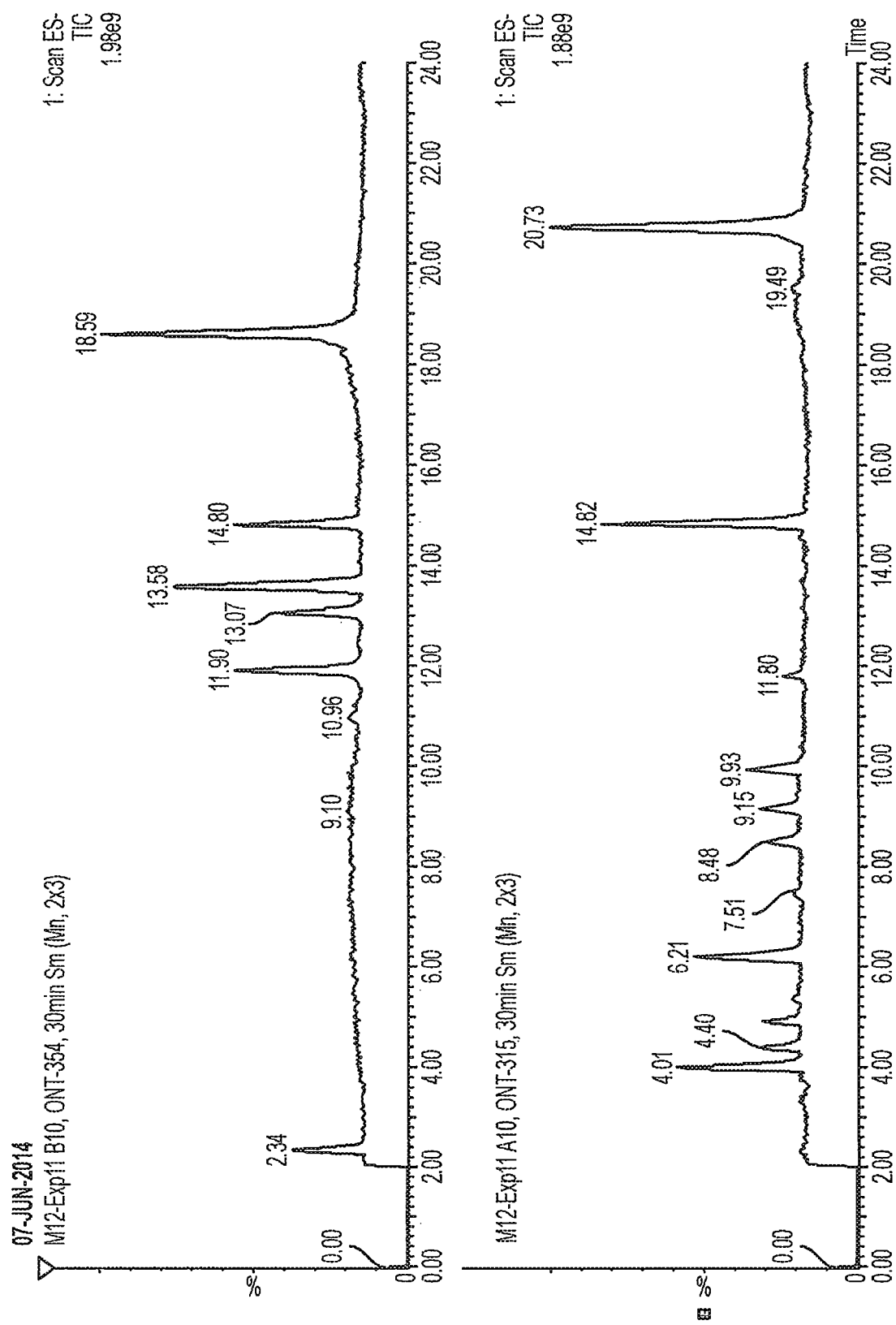
FIG. 19. Electrospray Ionization Spectrum of RNA cleavage products. RNA fragments obtained from the duplex ONT-387, RNA/ONT-354, (7-6-7, DNA-2'-OMe-DNA) on the top and ONT-387, RNA/ONT-315, (5-10-5,2'-MOE Gapmer) at the bottom when these duplexes were incubated with RNase H for 30 min in the presence of 1×RNase H buffer.
Figure 30:
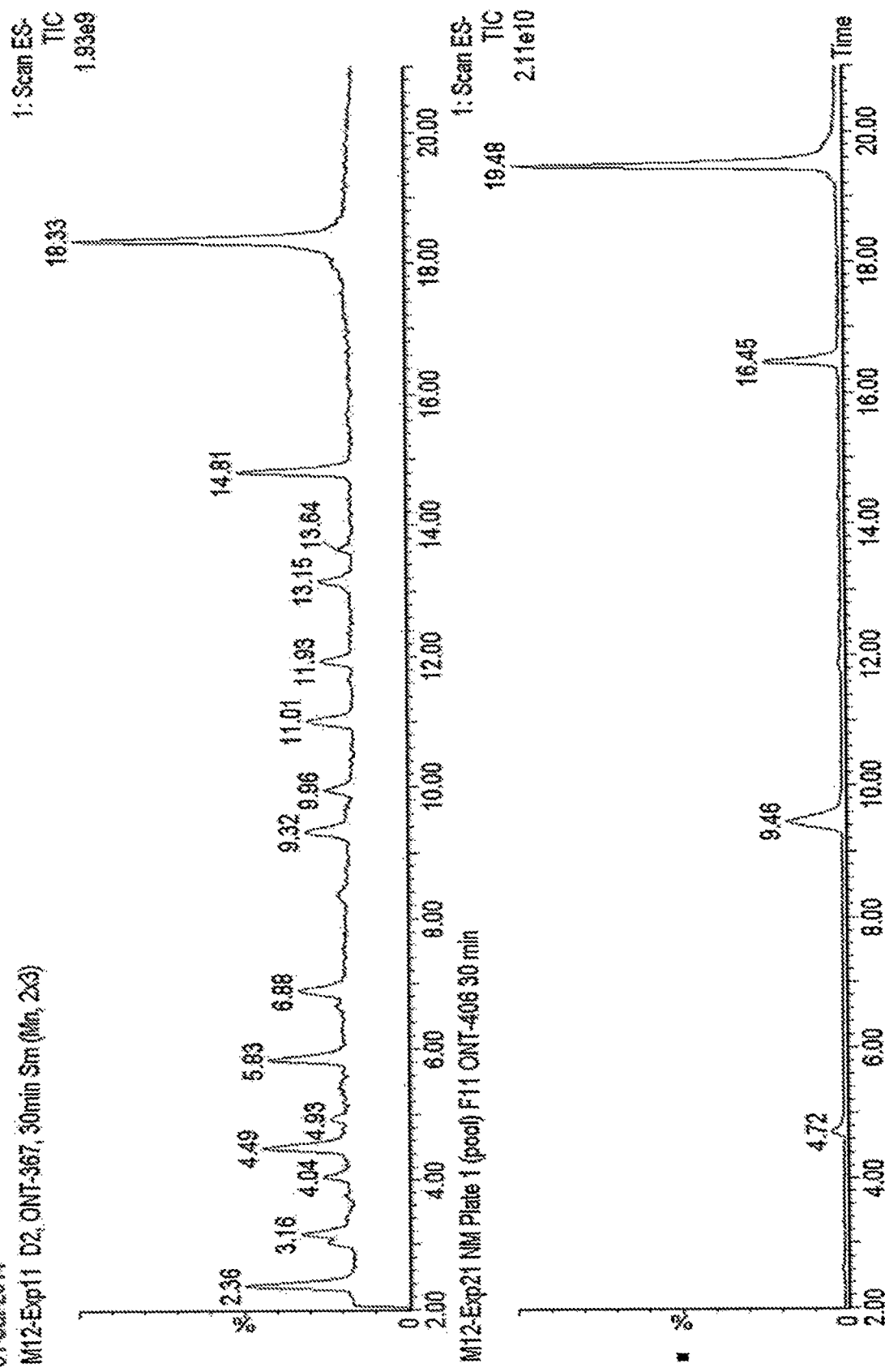
FIG. 30. Example mass spectrometry data of cleavage assay. Top: data for ONT-367: 2.35 min: 7 mer; 3.16 min: 8 mer and P-6 mer; 4.58 min: P-7 mer; 5.91 min: P-8 mer; 7.19 min: 12 mer; 9.55 min: 13 mer; 10.13 min: P-11 mer; 11.14 min: P-12 mer and 14 mer; 12.11 min: P-13 mer; 13.29 min: P-14 mer; 14.80 min: full length RNA (ONT-388) and 18.33 min: stereorandom DNA (ONT-367). Bottom: data for ONT-406: 4.72 min: p-rArUrGrGrCrUrA, 5'-phosphorylated 7 mer RNA; 9.46 min: 5'-rGrUrGrArGrCrArGrCrUrGrCrA (SEQ ID NO: 9), 5'-OH 3'-OH 13 mer RNA; 16.45 min: full length RNA (ONT-388); 19.48 and 19.49 min: stereopure DNA (ONT-406).

In some embodiments, a provided chirally controlled oligonucleotide composition enhances cleavage at one or more sites, e.g., relative to a reference (e.g., chirally uncontrolled/stereorandom) oligonucleotide composition. In some embodiments, a provided chirally controlled oligonucleotide composition selectively enhances cleavage at a single site relative to a reference (e.g., chirally uncontrolled/stereorandom) composition. In some embodiments, a chirally controlled oligonucleotide composition enhances cleavage at a site by providing a higher cleavage rate. In some embodiments, a chirally controlled oligonucleotide composition enhances cleavage at a site by providing a higher percentage of cleavage at said site. Percentage of cleavage at a site can be determined by various methods widely known and practiced in the art. In some embodiments, percentage of cleavage at a site is determined by analysis of cleavage products, for example, as by HPLC-MS as illustrated in FIG. 18, FIG. 19 and FIG. 30; see also example cleavage maps such as FIG. 9, FIG. 10, FIG. 11, FIG. 14, FIG. 22, FIG. 25 and FIG. 26. In some embodiments, enhancement is relative to a reference oligonucleotide composition. In some embodiments, enhancement is relative to another cleavage site. In some embodiments, a provided chirally controlled oligonucleotide composition enhances cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition enhances cleavage at a site that is a preferred cleavage site of an enzyme. In some embodiments, a provided chirally controlled oligonucleotide composition enhances cleavage at a site that is not a preferred cleavage site of a reference oligonucleotide composition. In some embodiments, a provided chirally controlled oligonucleotide composition enhances cleavage at a site that is not a cleavage site of a reference oligonucleotide composition, effectively creating a new cleavage site which does not exist when a reference oligonucleotide composition is used. In some embodiments, a provided chirally controlled oligonucleotide composition enhances cleavage at a site within 5 base pairs from a targeted mutation or SNP, thereby increasing selective cleavage of the undesired target oligonucleotide. In some embodiments, a provided chirally controlled oligonucleotide composition enhances cleavage at a site within 4 base pairs from a targeted mutation or SNP, thereby increasing selective cleavage of the undesired target oligonucleotide. In some embodiments, a provided chirally controlled oligonucleotide composition enhances cleavage at a site within 3 base pairs from a targeted mutation or SNP, thereby increasing selective cleavage of the undesired target oligonucleotide. In some embodiments, a provided chirally controlled oligonucleotide composition enhances cleavage at a site within 2 base pairs from a targeted mutation or SNP, thereby increasing selective cleavage of the undesired target oligonucleotide. In some embodiments, a provided chirally controlled oligonucleotide composition enhances cleavage at a site immediately upstream or downstream targeted mutation or SNP, thereby increasing selective cleavage of the undesired target oligonucleotide (e.g., FIG. 22, Panel D, muRNA).

In some embodiments, a provided chirally controlled oligonucleotide composition suppresses cleavage at one or more sites, e.g., relative to a reference (e.g., chirally uncontrolled/stereorandom) oligonucleotide composition. In some embodiments, a provided chirally controlled oligonucleotide composition selectively suppresses cleavage at a single site relative to a reference (e.g., chirally uncontrolled/stereorandom) composition. In some embodiments, a chirally controlled oligonucleotide composition suppresses cleavage at a site by providing a lower cleavage rate. In some embodiments, a chirally controlled oligonucleotide composition suppresses cleavage at a site by providing a lower percentage of cleavage at said site. In some embodiments, suppression is relative to a reference oligonucleotide composition. In some embodiments, suppression is relative to another cleavage site. In some embodiments, a provided chirally controlled oligonucleotide composition suppresses cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition suppresses cleavage at a site that is a preferred cleavage site of an enzyme. In some embodiments, a provided chirally controlled oligonucleotide composition suppresses cleavage at a site that is not a preferred cleavage site of a reference oligonucleotide composition. In some embodiments, a provided chirally controlled oligonucleotide composition suppresses all cleavage sites of a reference oligonucleotide composition. In some embodiments, a provided chirally controlled oligonucleotide composition generally enhances cleavage of target oligonucleotides. In some embodiments, a provided chirally controlled oligonucleotide composition generally suppresses cleavage of non-target oligonucleotides. In some embodiments, a provided chirally controlled oligonucleotide composition enhances cleavage of target oligonucleotides and suppresses cleavage of non-target oligonucleotides. Using FIG. 22, Panel D, as an example, a target oligonucleotide for cleavage is muRNA, while a non-target oligonucleotide is wtRNA. In a subject comprising a diseased tissue comprising a mutation or SNP, a target oligonucleotide for cleavage can be transcripts with a mutation or SNP, while a non-target oligonucleotide can be normal transcripts without a mutation or SNP, such as those expressed in healthy tissues.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide with all phosphate linkages.

In some embodiments, besides patterns of backbone chiral centers described herein, provided oligonucleotides optionally comprises modified bases, modified sugars, modified backbone linkages and any combinations thereof. In some embodiments, a provided oligonucleotide is a unimer, altmer, blockmer, gapmer, hemimer and skipmer. In some embodiments, a provided oligonucleotide comprises one or more unimer, altmer, blockmer, gapmer, hemimer or skipmer moieties, or any combinations thereof. In some embodiments, besides patterns of backbone chiral centers herein, a provided oligonucleotide is a hemimer. In some embodiments, besides patterns of backbone chiral centers herein, a provided oligonucleotide is a 5'-hemimer with modified sugar moieties. In some embodiments, a provided oligonucleotide is 5'-hemimer with 2'-modified sugar moieties. Suitable modifications are widely known in the art, e.g., those described in the present application. In some embodiments, a modification is 2'—F. In some embodiments, a modification is 2'-MOE. In some embodiments, a modification is s-cEt.

In some embodiments, the present disclosure provides a method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
  1) a common base sequence and length; and
  2) a common pattern of backbone linkages;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

In some embodiments, the present disclosure provides a method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
  1) a common base sequence and length; and
  2) a common pattern of backbone linkages;
  3) a common pattern of backbone chiral centers;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

In some embodiments, a common base sequence is or comprises a sequence that is 100% complementary to the characteristic sequence elements. In some embodiments, suppression can be assessed through various suitable assays as known by a person having ordinary skill in the art. In some embodiments, an assay is a RNase H assay as described in the present disclosure, which can assess suppression by evaluating cleavage of a sequence found in a transcript of a target nucleic acid sequence comprising the characteristic sequence element and cleavage of a sequence found in a transcript of a similar sequence. In some embodiments, transcripts of the target nucleic acid sequence are suppressed at a greater level than a level of suppression observed for any one of the similar nucleic acid sequence. In some embodiments, example target and similar sequences are described in the present disclosure.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
  contacting a sample comprising transcripts of the target nucleic acid sequence with an oligonucleotide composition comprising oligonucleotides having:
  1) a common base sequence and length; and
  2) a common pattern of backbone linkages;
  wherein the common base sequence is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
   which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
   which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence, the contacting being performed under conditions determined to permit the composition to suppress transcripts of the particular allele.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with an oligonucleotide composition comprising oligonucleotides having:
      1) a common base sequence and length;
      2) a common pattern of backbone linkages;
   wherein the common base sequence is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
      a) greater than when the composition is absent;
      b) greater than a level of suppression observed for another allele of the same nucleic acid sequence; or
      c) both greater than when the composition is absent, and greater than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
   which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
      a) greater than when the composition is absent;
      b) greater than a level of suppression observed for another allele of the same nucleic acid sequence; or
      c) both greater than when the composition is absent, and greater than a level of suppression observed for another allele of the same nucleic acid sequence.

In some embodiments, the present disclosure provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with a chirally controlled oligonucleotide composition comprising oligonucleotides of a particular oligonucleotide type characterized by:
      1) a common base sequence and length;
      2) a common pattern of backbone linkages;
      3) a common pattern of backbone chiral centers;
   which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
  a) greater than when the composition is absent;
  b) greater than a level of suppression observed for another allele of the same nucleic acid sequence; or
  c) both greater than when the composition is absent, and greater than a level of suppression observed for another allele of the same nucleic acid sequence,
the contacting being performed under conditions determined to permit the composition to suppress transcripts of the particular allele.

In some embodiments, a transcript is suppressed by cleavage of said transcript. In some embodiments, a specific nucleotide characteristic sequence element is in an intron. In some embodiments, a specific nucleotide characteristic sequence element is in an exon. In some embodiments, a specific nucleotide characteristic sequence element is partially in an exon and partially in an intron. In some embodiments, a specific nucleotide characteristic sequence element comprises a mutation that differentiates an allele from other alleles. In some embodiments, a mutation is a deletion. In some embodiments, a mutation is an insertion. In some embodiments, a mutation is a point mutation. In some embodiments, a specific nucleotide characteristic sequence element comprises at least one single nucleotide polymorphism (SNP) that differentiates an allele from other alleles.

In some embodiments, a target nucleic acid sequence is a target gene.

In some embodiments, the present disclosure provides a method for allele-specific suppression of a gene whose sequence comprises at least one single nucleotide polymorphism (SNP), comprising providing a chirally controlled oligonucleotide composition comprising oligonucleotides defined by having:
  1) a common base sequence and length, wherein the common base sequence is or comprises a sequence that is completely complementary to a sequence found in a transcript from the first allele but not to the corresponding sequence found in a transcript from the second allele, wherein the sequence found in the transcripts comprises a SNP site;
  2) a common pattern of backbone linkages;
  3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers;
wherein the transcript from the first allele is suppressed at least five folds more than that from the second allele.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with an oligonucleotide composition comprising oligonucleotides having:
    1) a common base sequence and length;
    2) a common pattern of backbone linkages;
    wherein the common base sequence is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
    1) a common base sequence and length;
    2) a common pattern of backbone linkages;
    3) a common pattern of backbone chiral centers;
  which composition is chirally controlled in that it is enriched, relative to a substantially racemic preparation of oligonucleotides having the same base sequence and length, for oligonucleotides of the particular oligonucleotide type;
  wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:
  contacting a sample comprising transcripts of the target gene with a chirally controlled oligonucleotide composition comprising oligonucleotides of a particular oligonucleotide type characterized by:
    1) a common base sequence and length;
    2) a common pattern of backbone linkages;
    3) a common pattern of backbone chiral centers;
  which composition is chirally controlled in that it is enriched, relative to a substantially racemic preparation of oligonucleotides having the same base sequence and length, for oligonucleotides of the particular oligonucleotide type;
  wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene, the contacting being performed under conditions determined to permit the composition to suppress transcripts of the particular allele.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of both the target allele and another allele of the same gene, transcripts of the particular allele are suppressed at a level at least 2 fold greater than a level of suppression observed for another allele of the same gene, the contacting being performed under conditions determined to permit the composition to suppress expression of the particular allele.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with an oligonucleotide composition comprising oligonucleotides having:
1) a common base sequence and length; and
2) a common pattern of backbone linkages;
wherein the common base sequence is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
a) at least 2 fold in that transcripts from the particular allele are detected in amounts that are 2 fold lower when the composition is present relative to when it is absent;

b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene, the contacting being performed under conditions determined to permit the composition to suppress transcripts of the particular allele.

In some embodiments, the present disclosure provides a method for allele-specific suppression of a transcript from a target gene for which a plurality of alleles exist within a population, each of which contains a specific nucleotide characteristic sequence element that defines the allele relative to other alleles of the same target gene, the method comprising steps of:

contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;

which composition is chirally controlled in that it is enriched, relative to a substantially racemic preparation of oligonucleotides having the same base sequence and length, for oligonucleotides of the particular oligonucleotide type; wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:

a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene, the contacting being performed under conditions determined to permit the composition to suppress expression of the particular allele.

As described herein, in some embodiments, in a provided method contacting is performed under conditions determined to permit a composition to suppress transcripts of a particular allele. In some embodiments, contacting is performed under conditions determined to permit a composition to suppress expression of a particular allele.

In some embodiments, suppression of transcripts of a particular allele is at a level that is greater than when the composition is absent. In some embodiments, suppression of transcripts of a particular allele is at a level that is at least 1.1 fold relative to when the composition is absent, in that transcripts from the particular allele are detected in amounts that are at least 1.1 fold lower when the composition is present relative to when it is absent. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than a level of suppression observed for another allele of the same nucleic acid sequence. In some embodiments, suppression of transcripts of a particular allele is at a level that is at least 1.1 fold greater than a level of suppression observed for another allele of the same nucleic acid sequence. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than when the composition is absent, and at a level that is greater than a level of suppression observed for another allele of the same nucleic acid sequence. In some embodiments, suppression of transcripts of a particular allele is at a level that is at least 1.1 fold relative to when the composition is absent, and at least 1.1 fold greater than a level of suppression observed for another allele of the same nucleic acid sequence. In some embodiments, each fold is independently as described above.

In some embodiments, a system is a composition comprising a transcript. In some embodiments, a system is a composition comprising transcripts from different alleles. In some embodiments, a system can be in vivo or in vitro, and in either way can comprise one or more cells, tissues, organs or organisms. In some embodiments, a system comprises one or more cells. In some embodiments, a system comprises one or more tissues. In some embodiments, a system comprises one or more organs. In some embodiments, a system comprises one or more organisms. In some embodiments, a system is a subject.

In some embodiments, suppression of a transcript, or suppression of expression of an allele from which a transcript is transcribed, can be measured in in vitro assay. In some embodiments, a sequence from a transcript and comprising a specific nucleotide characteristic sequence element is used in assays instead of the full-length transcript. In some embodiments, an assay is a biochemical assay. In some embodiments, an assay is a biochemical assay wherein a nucleic acid polymer, for example, a transcript or a sequence from a transcript and comprising a specific nucleotide characteristic sequence element, is tested for cleavage by an enzyme in the presence of a chirally controlled oligonucleotide composition.

In some embodiments, a provided chirally controlled oligonucleotide composition is administered to a subject. In some embodiments, a subject is an animal. In some embodiments, a subject is a plant. In some embodiments, a subject is a human.

In some embodiments, for allele-specific suppression of transcripts from a particular allele, transcripts are cleaved at a site near a sequence difference, for example a mutation, within a specific nucleotide characteristic sequence element, which sequence difference differentiates transcripts from a particular allele from transcripts from the other alleles. In some embodiments, transcripts are selectively cleaved at a site near such a sequence difference. In some embodiments, transcripts are cleaved at a higher percentage at a site near such a sequence difference that when a chirally uncontrolled oligonucleotide composition is used. In some embodiments, transcripts are cleaved at the site of a sequence difference. In some embodiments, transcripts are cleaved only at the site of a sequence difference within a specific nucleotide characteristic sequence element. In some embodiments, transcripts are cleaved at a site within 5 base pairs downstream or upstream a sequence difference. In some embodiments, transcripts are cleaved at a site within 4 base pairs downstream or upstream a sequence difference. In some embodiments, transcripts are cleaved at a site within 3 base pairs downstream or upstream a sequence difference. In some embodiments, transcripts are cleaved at a site within 2 base pairs downstream or upstream a sequence difference. In some embodiments, transcripts are cleaved at a site within 1 base pair downstream or upstream a sequence difference. In some embodiments, transcripts are cleaved at a site within 5 base pairs downstream a sequence difference. In some embodiments, transcripts are cleaved at a site within 4 base pairs downstream a sequence difference. In some embodiments, transcripts are cleaved at a site within 3 base pairs downstream a sequence difference. In some embodiments, transcripts are cleaved at a site within 2 base pairs downstream a sequence difference. In some embodiments, transcripts are cleaved at a site within 1 base pair downstream a sequence difference. In some embodiments, transcripts are cleaved at a site within 5 base pairs upstream a sequence difference. In some embodiments, transcripts are cleaved at a site within 4 base pairs upstream a sequence difference. In some embodiments, transcripts are cleaved at a site within 3 base pairs upstream a sequence difference. In some embodiments, transcripts are cleaved at a site within 2 base pairs upstream a sequence difference. In some embodiments, transcripts are cleaved at a site within 1 base pair upstream a sequence difference. Such precise control of cleavage patterns, and the resulting highly selective suppression of transcripts from a particular allele, would not be possible without chirally controlled oligonucleotide compositions and methods thereof provided by Applicant in this disclosure.

In some embodiments, the present disclosure provides methods for treating a subject, or preventing a disease in a subject, by specifically suppress transcripts from a particular allele, for example, an allele that causes or may cause a disease. In some embodiments, the present disclosure provides methods for treating a subject suffering from a disease, comprising administering to the subject a pharmaceutical composition comprising a chirally controlled oligonucleotide composition, wherein transcripts from an allele that causes or contributes to the disease is selectively suppressed. In some embodiments, the present disclosure provides methods for treating a subject suffering from a disease, comprising administering to the subject a pharmaceutical composition comprising a chirally controlled oligonucleotide composition, wherein transcripts from an allele that causes the disease is selectively suppressed. In some embodiments, the present disclosure provides methods for treating a subject suffering from a disease, comprising administering to the subject a pharmaceutical composition comprising a chirally controlled oligonucleotide composition, wherein transcripts from an allele that contributes to the disease is selectively suppressed. In some embodiments, the present disclosure provides methods for treating a subject suffering from a disease, comprising administering to the subject a pharmaceutical composition comprising a chirally controlled oligonucleotide composition, wherein transcripts from an allele that is related to the disease is selectively suppressed. In some embodiments, the present disclosure provides methods for preventing a disease in a subject, by specifically suppress transcripts from a particular allele that may cause a disease. In some embodiments, the present disclosure provides methods for preventing a disease in a subject, by specifically suppress transcripts from a particular allele that increases risk of a disease in the subject. In some embodiments, a provided method comprises administering to the subject a pharmaceutical composition comprising a chirally controlled oligonucleotide composition. In some embodiments, a pharmaceutical composition further comprises a pharmaceutical carrier.

In some embodiments, a nucleotide characteristic sequence comprises a mutation that defines the target sequence relative to other similar sequences. In some embodiments, a nucleotide characteristic sequence comprises a point mutation that defines the target sequence relative to other similar sequences. In some embodiments, a nucleotide characteristic sequence comprises a SNP that defines the target sequence relative to other similar sequences.

In some embodiments, the present disclosure provides a method for preparing an oligonucleotide composition for selective suppression of a transcript of a target nucleic acid sequence, comprising providing an oligonucleotide composition comprising a predetermined level of oligonucleotides of a particular oligonucleotide type characterized by:
1) a common base sequence;
2) a common pattern of backbone linkages; and
3) a common pattern of backbone chiral centers, which pattern comprises $(Sp)_m(Rp)_n$, $(Rp)_n(Sp)_m$, $(Np)_t(Rp)_n(Sp)_m$, or $(Sp)_t(Rp)_n(Sp)_m$, wherein each of m, n, t, Np is independently as defined and described herein;
wherein the target nucleic acid sequence comprises a characteristic sequence element that defines the target nucleic acid sequence relative to a similar nucleic acid sequence;
wherein the common base sequence is a sequence whose DNA cleavage pattern and/or stereorandom cleavage pattern has a cleavage site within or in the vicinity of the characteristic sequence element.

In some embodiments, the present disclosure provides a method for preparing an oligonucleotide composition for selective suppression of a transcript of a target nucleic acid sequence, comprising providing an oligonucleotide composition comprising a predetermined level of oligonucleotides of a particular oligonucleotide type characterized by:
1) a common base sequence;
2) a common pattern of backbone linkages; and
3) a common pattern of backbone chiral centers, which pattern comprises $(Sp)_m(Rp)_n$, $(Rp)_n(Sp)_m$, $(Np)_t(Rp)_n(Sp)_m$, or $(Sp)_t(Rp)_n(Sp)_m$, wherein each of m, n, t, Np is independently as defined and described herein;
wherein the target nucleic acid sequence comprises a characteristic sequence element that defines the target nucleic acid sequence relative to a similar nucleic acid sequence;
wherein the common base sequence is a sequence whose DNA cleavage pattern and/or stereorandom cleavage pattern has a major cleavage site within or in the vicinity of characteristic sequence element.

In some embodiments, a common pattern of backbone chiral centers comprises $(Sp)_m(Rp)_n$, $(Rp)_n(Sp)_m$, $(Np)_t(Rp)_n(Sp)_m$, or $(Sp)_t(Rp)_n(Sp)_m$ as described above. In some embodiments, a common pattern of backbone chiral centers comprises $(Sp)_m(Rp)_n$ as described above. In some embodiments, a common pattern of backbone chiral centers comprises $(Rp)_n(Sp)_m$ as described above. In some embodiments, a common pattern of backbone chiral centers comprises $(Np)_t(Rp)_n(Sp)_m$ as described above. In some embodiments, a common pattern of backbone chiral centers comprises $(Sp)_t(Rp)_n(Sp)_m$ as described above. In some embodiments, n is 1. In some embodiments, m>2. In some embodiments, n is 1 and m>2. In some embodiments, t>2. In some embodiments, n is 1, m>2, and t>2.

In some embodiments, oligonucleotides of the particular oligonucleotide type have a wing-core structure. In some embodiments, oligonucleotides of the particular oligonucleotide type have a core-wing structure. In some embodiments, oligonucleotides of the particular oligonucleotide type have a wing-core-wing structure. In some embodiments, each sugar moieties in the wing regions has a sugar modification. In some embodiments, each sugar moiety in the wing regions has a 2'-modification. In some embodiments, each sugar moieties in the wing regions has a 2'-modification, wherein the 2'-modification is 2'-OR', wherein R' is optionally substituted $C_{1-6}$ alkyl. In some embodiments, each sugar moiety in the wing regions has 2'-OMe. In some embodiments, each wing independently comprises a chiral internucleotidic linkage and a natural phosphate linkage. In some embodiments, a chiral internucleotidic linkage is phosphorothioate. In some embodiments, for a wing-core-wing structure, like in WV-1092, the 5'-wing has an Sp internucleotidic linkage at each of its 5'- and 3'-end, and phosphate linkages in between, and 3'-wing has an Sp internucleotidic linkage at its 3'-end, and the rest of its internucleotidic linkages are phosphate. Additional embodiments for the wing and/or core, e.g., sugar modification, stereochemistry, etc., are described in the present disclosure.

Common base sequences which are sequences whose DNA cleavage patterns and/or stereorandom cleavage patterns have cleavage sites within or in the vicinity of the target nucleic acid sequence are extensively described in the present disclose. In some embodiments, a cleavage site within or in the vicinity of the target nucleic acid sequence is a cleavage site in the vicinity of a mutation which defines the target sequence from its similar sequences. In some embodiments, a cleavage site within or in the vicinity of the target nucleic acid sequence is a cleavage site in the vicinity of a SNP which defines the target sequence from its similar sequences. In some embodiments, as described above, in the vicinity of a mutation or a SNP is 0, 1, 2, 3, 4, 5 internucleotidic linkages away from the mutation or SNP. Additional embodiments are described above in the present disclosure.

In some embodiments, a common base sequence is a sequence whose DNA cleavage pattern and/or stereorandom cleavage pattern has a major cleavage site within or in the vicinity of the target nucleic acid sequence. In some embodiments, a major cleavage site is defined by absolute cleavage at that site (% of cleavage at that site over total target sequence). Additional example embodiments of a major cleavage site are described in the present disclosure. In some embodiments, as exemplified by FIG. 33, a common base sequence (P12) may be identified by comparing cleavage maps of different sequences complementary to the characteristic sequence element.

In some embodiments, the present disclosure provides a method for preparing an oligonucleotide composition comprising oligonucleotides of a particular sequence, which composition provides selective suppression of a transcript of a target sequence, comprising providing a chirally controlled oligonucleotide composition comprising oligonucleotides of a particular oligonucleotide type characterized by:
1) a common base sequence which is the same as the particular sequence;
2) a common pattern of backbone linkages; and
3) a common pattern of backbone chiral centers, which pattern comprises $(Sp)_m(Rp)_n$, $(Rp)_n(Sp)_m$, $(Np)_t(Rp)_n(Sp)_m$, or $(Sp)_t(Rp)_n(Sp)_m$, wherein:
each n and t is independently 1, 2, 3, 4, 5, 6, 7 or 8;
m is 2, 3, 4, 5, 6, 7 or 8, and
each Np is independent Rp or Sp.

Diseases that involves disease-causing alleles are widely known in the art, including but not limited to those described in Hohjoh, *Pharmaceuticals* 2013, 6, 522-535; US patent application publication US 2013/0197061; Østergaard et al., *Nucleic Acids Research* 2013, 41(21), 9634-9650; and Jiang et al., *Science* 2013, 342, 111-114. In some embodiments, a disease is Huntington's disease. In some embodiments, a disease is human hypertrophic cardiomyopathy (HCM). In some embodiments, a disease is dilated cardiomyopathy. In some embodiments, a disease-causing allele is an allele of myosin heavy chains (MHC). In some embodiments, an example disease is selected from:

| Disease | Target gene | Target variation |
|---|---|---|
| Familial Alzheimer's disease | Amyloid precursor protein (APP) | K670N-M671L (Swedish mutant) |
| | Amyloid precursor protein (APP) | K670N-M671L (Swedish mutant) |
| | Amyloid precursor protein (APP) | V717F (London mutant) |
| | Amyloid precursor protein (APP) | V717I (London mutant) |
| | Preseniline 1 (PSEN1) | L392V |
| Amyotrophic lateral sclerosis (ALS) | Superoxide dismutase (SOD1) | G93A |
| | Superoxide dismutase (SOD1) | G85R |
| Slow channel congenital myasthenic syndrome (SCCMS) | Acetylcholine receptor (AChR) | aS226F, aT254I, aS269I |
| Frontotemporal dementia with parkinsonism linked to chromosome 17 (FTDP-17) | Microtubule-associated protein TAU (MAPT) | V337M |
| Ehlers-Danlos syndrome (vEDS) | Procollagen type III (COL3A1) | G252V |
| Sickle cell anemia | Hemoglobin-beta locus (HBB) | E6V |
| Familial amyloidotic polyneuropathy (FAP) | Transthyretin (TTR) | V30M |
| Fibrodysplasia ossificans progressiva (FOP) | Activin A receptor type I (ACVR1) | R206H, G356D |
| | Activin A receptor type I (ACVR1) | R206H |
| Tumors | KRAS | G12V, G12D, G13D |
| Tumors | Phosphoinositide-3-kinase, catalytic, alpha polypeptide (PIK3CA) | G1633A, A3140G |
| Spinocerebellar ataxia type 1 (SCA1) | Ataxin-1 (ATXN1) | SNPs linked to expanded CAG repeat |
| Spinocerebellar ataxia type 7 (SCA7) | Ataxin-7 (ATXN7) | SNPs linked to expanded CAG repeat |
| Spinocerebellar Ataxia Type 3 (SCA3)/Machado-Joseph Disease | Ataxin-3 (ATXN3) | SNPs linked to expanded CAG repeat |
| Parkinson's disease | Leucine-rich repeat kinase 2 (LRRK2) | R1441G, R1441C |
| | Leucine-rich repeat kinase 2 (LRRK2) | G20195S |
| | Alpha-synuclein (SNCA) | A30P, A53T, E46K |
| Huntington's disease | Huntingtin (HTT) | SNPs linked to expanded CAG repeat |
| Huntington's disease-like 2 | JPH3 | SNPs linked to expanded CTG repeat |
| Friedreich's ataxia | FXN | SNPs linked to expanded GAA repeat |
| Fragile X mental retardation syndrome/fragile X tremor ataxia syndrome | FMR1 | SNPs linked to expanded CGG repeat |
| Myotonic Dystophy (DM1) | DMPK | SNPs linked to expanded CTG repeat |
| Myotonic Dystophy (DM2) | ZNF9 | SNPs linked to expanded CTG repeat |
| Spinal-Bulbar Muscular Atrophy | AR | SNPs linked to expanded CAG repeat |
| Hypertrophic cardiomyopathy | MHY7 | R403Q |

In some embodiments, example targets of, and diseases that can be treated by, provided chirally controlled oligonucleotide compositions and methods, comprises:

In some embodiments, oligonucleotide compositions and technologies described herein are particularly useful in the treatment of Huntington's disease. For example, in some embodiments, the present disclosure defines stereochemically controlled oligonucleotide compositions that direct cleavage (e.g., RNAse H-mediated cleavage) of nucleic acids associated with Huntington's disease. In some embodiments, such compositions direct preferential cleavage of a Huntington's disease-associated allele of a particular target sequence, relative to one or more (e.g., all non-Huntington's disease-associated) other alleles of the sequence.

In some embodiments, a provided method for treating or preventing Huntington's disease in a subject, comprising administering to the subject a chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type. In some embodiments, oligonucleotides of a particular oligonucleotide type are identical. In some embodiments, a provided composition is a chirally controlled oligonucleotide composition.

SNPs related to Huntington's disease are widely known in the art. In some embodiments, a common base sequence is complementary to a nucleic acid sequence comprising a SNP related to Huntington's disease. In some embodiments, a provided composition selectively suppresses transcripts from the disease-causing allele. In some embodiments, a provided composition selectively cleaves transcripts from the disease-causing allele. Example SNPs that can be targeted by a provided composition (target Huntingtin sites) are described herein.

In some embodiments, a target Huntingtin site is selected from rs9993542_C, rs362310_C, rs362303_C, rs10488840_G, rs363125_C, rs363072_A, rs7694687_C, rs363064_C, rs363099_C, rs363088_A, rs34315806_C, rs2298967_T, rs362272_G, rs362275_C, rs362306_G, rs3775061_A, rs1006798_A, rs16843804_C, rs3121419_C, rs362271_G, rs362273_A, rs7659144_C, rs3129322_T, rs3121417_G, rs3095074_G, rs362296_C, rs108850_C, rs2024115_A, rs916171_C, rs7685686_A, rs6844859_T, rs4690073_A, rs2285086_A, rs362331_T, rs363092_C, rs3856973_G, rs4690072_T, rs7691627_G, rs2298969_A, rs2857936_C, rs6446723_T, rs762855_A, rs1263309_T, rs2798296_G, rs363096_T, rs10015979_G, rs11731237_T, rs363080_C, rs2798235 G and rs362307 T. In some embodiments, a target Huntingtin site is selected from rs34315806_C, rs362273_A, rs362331_T, rs363099_C, rs7685686_A, rs362306_G, rs363064_C, rs363075_G, rs2276881_G, rs362271_G, rs362303_C, rs362322_A, rs363088_A, rs6844859_T, rs3025838_C, rs363081_G, rs3025849_A, rs3121419_C, rs2298967_T, rs2298969_A, rs16843804_C, rs4690072_T, rs362310_C, rs3856973_G, rs2530595_C, rs2530595_T, and rs2285086 A. In some embodiments, a target Huntingtin site is selected from rs34315806_C, rs362273_A, rs362331_T, rs363099_C, rs7685686_A, rs362306_G, rs363064_C, rs363075_G, rs2276881_G, rs362271_G, rs362303_C, rs362322_A, rs363088_A, rs6844859_T, rs3025838_C, rs363081_G, rs3025849_A, rs3121419_C, rs2298967_T, rs2298969_A, rs16843804_C, rs4690072_T, rs362310_C, rs3856973_G, and rs2285086 A. In some embodiments, a target Huntingtin site is selected from rs362331_T, rs7685686_A, rs6844859_T, rs2298969_A, rs4690072_T, rs2024115_A, rs3856973_G, rs2285086_A, rs363092_C, rs7691627_G, rs10015979_G, rs916171_C, rs6446723_T, rs11731237_T, rs362272_G, rs4690073_G, and rs363096_T. In some embodiments, a target Huntingtin site is selected from rs362267, rs6844859, rs1065746, rs7685686, rs362331, rs362336, rs2024115, rs362275, rs362273, rs362272, rs3025805, rs3025806, rs35892913, rs363125, rs17781557, rs4690072, rs4690074, rs1557210, rs363088, rs362268, rs362308, rs362307, rs362306, rs362305, rs362304, rs362303, rs362302, rs363075, rs2530595, and rs2298969. In some embodiments, a target Huntingtin site is selected from rs362267, rs6844859, rs1065746, rs7685686, rs362331, rs362336, rs2024115, rs362275, rs362273, rs362272, rs3025805, rs3025806, rs35892913, rs363125, rs17781557, rs4690072, rs4690074, rs1557210, rs363088, rs362268, rs362308, rs362307, rs362306, rs362305, rs362304, rs362303, rs362302, rs363075 and rs2298969. In some embodiments, a target Huntingtin site is selected from:

| Frequency of Heterozygosity for 24 SNP Sites in the Huntingtin mRNA | | | |
|---|---|---|---|
| Location in mRNA (Position, nt) | Reference Number | Percent Heterozygosity | |
| | | Controls | HD Patients |
| ORF, exon 20 (2822) | rs363075 | G/A, 10.3% (G/G, 89.7%) | G/A, 12.8% (G/G, 86.2%; A/A, 0.9%) |
| ORF, exon 25 (3335) | rs35892913 | G/A, 10.3% (G/G, 89.7%) | G/A, 13.0% (G/G, 86.1%; A/A, 0.9%) |
| ORF, exon 25 (3389) | rs1065746 | G/C, 0% (G/G, 100%) | G/C, 0.9% (G/G, 99.1%) |
| ORF, exon 25 (3418) | rs17781557 | T/G, 12.9% (T/T, 87.1%) | T/G, 1.9% (T/T, 98.1%) |
| ORF, exon 29 (3946) | rs4690074 | C/T, 37.9% (C/C, 50.9%; T/T, 11.2) | C/T, 35.8% (C/C, 59.6%; T/T, 4.6%) |
| ORF, exon 39 (5304) | rs363125 | C/A, 17.5% (C/C, 79.0%; A/A, 3.5%) | C/A, 11.0% (C/C, 87.2%; A/A, 1.8%) |
| ORF, exon 44 (6150) | exon 44 | G/A, 0% (G/G, 100%) | G/A, 2.8% (G/G, 97.2%) |
| ORF, exon 48 (6736) | rs362336 | G/A, 38.7% (G/G, 49.6%; A/A, 11.7%) | G/A, 37.4% (G/G, 57.9%; A/A, 4.7%) |
| ORF, exon 50 (7070) | rs362331 | T/C, 45.7% (T/T, 31.0%; C/C, 23.3%) | T/C, 39.4% (T/T, 49.5%; C/C, 11.0%) |
| ORF, exon 57 (7942) | rs362273 | A/G, 40.3% (A/A, 48.2%; G/G, 11.4%) | A/G, 35.2% (A/A, 60.2%; G/G, 4.6%) |
| ORF, exon 61 (8501) | rs362272 | G/A, 37.1% (G/G, 51.7%; A/A, 11.2%) | G/A, 36.1% (G/G, 59.3%; A/A, 4.6%) |
| ORF, exon 65 (9053) | rs3025806 | A/T, 0% (C/C, 100%) | A/T, 0% (C/C, 100%) |
| ORF, exon 65 (9175) | exon 65 | G/A, 2.3% (G/G, 97.7%) | G/A, 0% (G/G, 100%) |
| ORF, exon 67 (9523) | rs362308 | T/C, 0% (T/T, 100%) | T/C, 0% (T/T, 100%) |
| 3'UTR, exon 67 (9633) | rs362307 | C/T, 13.0% (C/C, 87.0%) | C/T, 48.6% (C/C, 49.5%; T/T, 1.9%) |
| 3'UTR, exon 67 (9888) | rs362306 | G/A, 36.0% (G/G, 52.6%; A/A, 11.4%) | G/A, 35.8% (G/G, 59.6%; A/A, 4.6%) |
| 3'UTR, exon 67 (9936) | rs362268 | C/G, 36.8% (C/C, 50.0%; G/G 13.2%) | C/G, 35.8% (C/C, 59.6%; G/G, 4.6%) |
| 3'UTR, exon 67 (9948) | rs362305 | C/G, 20.2% (C/C, 78.1%; G/G 1.8%) | C/G, 11.9% (C/C, 85.3%; G/G, 2.8%) |
| 3'UTR, exon 67 (10060) | rs362304 | C/A, 22.8% (C/C, 73.7%; A/A, 3.5%) | C/A, 11.9% (C/C, 85.3%; A/A, 2.8%) |
| 3'UTR, exon 67 (10095) | rs362303 | C/T, 18.4% (C/C, 79.8%; T/T, 1.8%) | C/A, 11.9% (C/C, 85.3%; T/T, 2.8%) |
| 3'UTR, exon 67 (10704) | rs1557210 | C/T, 0% (C/C, 100%) | C/T, 0% (C/C, 100%) |
| 3'UTR, exon 67 (10708) | rs362302 | C/T, 4.3% (C/C, 95.7%) | C/T, 0% (C/C, 100%) |
| 3'UTR, exon 67 (10796) | rs3025805 | G/T, 0% (G/G, 100%) | G/T, 0% (G/G, 100%) |
| 3'UTR, exon 67 (11006) | rs362267 | C/T, 36.2% (C/C, 52.6%; T/T, 11.2%) | C/T, 35.5% (C/C, 59.8%; T/T, 4.7%) |

In some embodiments, a chirally controlled oligonucleotide composition targets two or more sites. In some embodiments, targeted two or more sites are selected from sited listed herein. In some embodiments, a targeted SNP is rs362307, rs7685686, rs362268, rs2530595, rs362331, or rs362306. In some embodiments, a targeted SNP is rs362307, rs7685686, rs362268 or rs362306. In some embodiments, a targeted SNP is rs362307. In some embodiments, a targeted SNP is rs7685686. In some embodiments, a targeted SNP is not rs7685686. In some embodiments, a targeted SNP is rs362268. In some embodiments, a targeted SNP is rs362306.

In some embodiments, a chirally controlled oligonucleotide composition is able to differentiate between two alleles of a particular SNP.

A chirally controlled oligonucleotide compositions of both WVE120101 and WV-1092 were able to differentiate between wt and mutant versions of SNP rs362307, which differ by one nt; both WVE120101 and WV-1092 chirally controlled oligonucleotide compositions significantly knocked down the mutant allele but not the wt, while the stereorandom oligonucleotide composition, WV-1497, was not able to significantly differentiate between the wt and mutant alleles (see FIG. 39D).

A chirally controlled oligonucleotide composition of WV-2595 was also able to differentiate between the C and T alleles at SNP rs2530595, which also differ at only the one nt. A chirally controlled WV-2595 oligonucleotide composition significantly knocked down the T allele but not the C allele, unlike the stereorandom oligonucleotide composition of WV-2611, which was not able to significantly differentiate the alleles (see FIG. 39F).

A chirally controlled oligonucleotide composition of WV-2603 was able to differentiate between the C and T alleles of SNP rs362331, which also differ at only the one nt. A chirally controlled WV-2603 oligonucleotide composition significantly knocked down the T allele but not the C allele, unlike the stereorandom oligonucleotide composition of WV-2619, which was not able to significantly differentiate between the alleles (see FIGS. 39A, 39B, 39C and 39E).

In some embodiments, a provided composition for treating Huntington's disease is selected from Tables N1, N2, N3 or N4. In some embodiments, a provided composition for treating Huntington's disease is selected from Table N1. In some embodiments, a provided composition for treating Huntington's disease is selected from Table N2. In some embodiments, a provided composition for treating Huntington's disease is selected from Table N3. In some embodiments, a provided composition for treating Huntington's disease is selected from Table N4. In some embodiments, a provided composition for treating Huntington's disease is selected from Tables N1A, N2A, N3A or N4A. In some embodiments, a provided composition for treating Huntington's disease is selected from Table N1A. In some embodiments, a provided composition for treating Huntington's disease is selected from Table N2A. In some embodiments, a provided composition for treating Huntington's disease is selected from Table N3A. In some embodiments, a provided composition for treating Huntington's disease is selected from Table N4A. In some embodiments, a provided composition is WV-1087. In some embodiments, a provided composition is WV-1090. In some embodiments, a provided composition is WV-1091. In some embodiments, a provided composition is WV-937. In some embodiments, a provided composition is WV-2378. In some embodiments, a provided composition is WV-1510. In some embodiments, a provided composition is WV-2619. In some embodiments, a provided composition is WV-2611. In some embodiments, a provided composition is WV-2618. In some embodiments, a provided composition is WV-937. In some embodiments, a provided composition is WV-2611. In some embodiments, a provided composition is WV-2601. In some embodiments, a provided composition is WV-2603. In some embodiments, a provided composition is WV-1090. In some embodiments, a provided composition is WV-937. In some embodiments, a provided composition is WV-1091. In some embodiments, a provided composition is WV-1092. In some embodiments, a provided composition is WV-2618. In some embodiments, a provided composition is WV-937. In some embodiments, a provided composition is selected from: an oligonucleotide having a sequence of WV-937; WVE120101; WV-1087; WV-1090; WV-1091; WV-937; WV-2603; WV-2595; WV-1510; WV-2378; and WV-2380; each of these was constructed and found to be very effective, for example, as demonstrated in vitro in the dual luciferase reporter assay. In some embodiments, a provided composition is a chirally controlled oligonucleotide composition of WV-1087, WV-1090, WV-1091, WV-937, WVE120101, WV-2603, WV-2595, WV-1510, WV-2378, or WV-2380. In some embodiments, a provided composition is a chirally controlled oligonucleotide composition of WV-937. In some embodiments, a provided composition is a chirally controlled oligonucleotide composition of WV-1087. In some embodiments, a provided composition is a chirally controlled oligonucleotide composition of WV-1090. In some embodiments, a provided composition is a chirally controlled oligonucleotide composition of WV-1091. In some embodiments, a provided composition is a chirally controlled oligonucleotide composition of WV-1092. In some embodiments, a provided composition is a chirally controlled oligonucleotide composition of WV-1510. In some embodiments, a provided composition is a chirally controlled oligonucleotide composition of WV-2378. In some embodiments, a provided composition is a chirally controlled oligonucleotide composition of WV-2380. In some embodiments, a provided composition is a chirally controlled oligonucleotide composition of WV-2595. In some embodiments, a provided composition is a chirally controlled oligonucleotide composition of WV-2603. In some embodiments, a provided composition is a chirally controlled oligonucleotide composition of WV-2378. In some embodiments, a provided composition is a chirally controlled oligonucleotide composition of WV-2380. In some embodiments, a provided composition is a chirally controlled oligonucleotide composition of WV-1510. In some embodiments, a provided composition is a chirally controlled oligonucleotide composition of WV-2619. In some embodiments, a provided composition is a chirally controlled oligonucleotide composition of WV-2611. In some embodiments, a provided composition is a chirally controlled oligonucleotide composition of WV-1497. In some embodiments, a provided composition is a chirally controlled oligonucleotide composition of WV-2602. In some embodiments, a provided composition is a chirally controlled oligonucleotide composition of WV-2618. In some embodiments, a provided composition is a chirally controlled oligonucleotide composition of or WV-2601. In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein.

In some embodiments, a provided composition is not a composition of ONT-451, ONT-452 or ONT-450. In some embodiments, a provided composition is not a composition of ONT-451. In some embodiments, a provided composition is not a composition of ONT-452. In some embodiments, a provided composition is not a composition of ONT-450. In some embodiments, a composition does not contain a pre-determined level of ONT-451 or ONT-452. In some embodiments, a composition does not contain a pre-determined level of ONT-451. In some embodiments, a composition does not contain a pre-determined level of ONT-452. In some embodiments, an oligonucleotide type is not ONT-451 or ONT-452. In some embodiments, an oligonucleotide type is not ONT-451. In some embodiments, an oligonucleotide type is not ONT-452. In some embodiments, a composition is not a chirally controlled oligonucleotide composition of ONT-451 or ONT-452. In some embodiments, a composition is not a chirally controlled oligonucleotide composition of ONT-451. In some embodiments, a composition is not a chirally controlled oligonucleotide composition of ONT-452.

In some embodiments, a provided method ameliorates a symptom of Huntington's disease. In some embodiments, a provided method slows onset of Huntington's disease. In some embodiments, a provided method slows progression of Huntington's disease. In some embodiments, a provided method stops progression of Huntington's disease. In some embodiments, a provided method cures Huntington's disease according to a clinical standard.

In some embodiments, the present disclosure provides methods for identifying patients for a given oligonucleotide composition. In some embodiments, the present disclosure provides methods for patient stratification. In some embodiments, a provided method comprises identifying a mutation and/or SNP associated with a disease-causing allele. For example, in some embodiments, a provided method comprises identifying in a subject a SNP associated with expanded CAG repeats that are associated with or causing Huntington's disease. In some embodiments, a provided method comprises identifying in a subject a SNP associated with more than 35 CAG repeats in Huntingtin. In some embodiments, a provided method comprises identifying in a subject a SNP associated with more than 36 CAG repeats in Huntingtin. In some embodiments, a provided method comprises identifying in a subject a SNP associated with more than 37 CAG repeats in Huntingtin. In some embodiments, a provided method comprises identifying in a subject a SNP associated with more than 38 CAG repeats in Huntingtin. In some embodiments, a provided method comprises identifying in a subject a SNP associated with more than 39 CAG repeats in Huntingtin. In some embodiments, a provided method comprises identifying in a subject a SNP associated with more than 40 CAG repeats in Huntingtin.

In some embodiments, a subject has a SNP in the subject's Huntingtin gene. In some embodiments, a subject has a SNP, wherein one allele is mutant Huntingtin associated with expanded CAG repeats. In some embodiments, a subject has a SNP as described herein. In some embodiments, a subject has a SNP selected from rs362307, rs7685686, rs362268, rs2530595, rs362331, or rs362306. In some embodiments, a subject has a SNP selected from rs362307, rs7685686, rs362268, or rs362306. In some embodiments, a subject has a SNP selected from rs362307. In some embodiments, a subject has a SNP selected from rs7685686. In some embodiments, a subject has a SNP selected from rs362268. In some embodiments, a subject has a SNP selected from rs362306.

In some embodiments, oligonucleotides of a provided composition have a sequence complementary to a sequence comprising a SNP from the disease-causing allele (mutant), and the composition selectively suppresses expression from the diseasing-causing allele. In some embodiments, a SNP is rs362307, rs7685686, rs362268, rs2530595, rs362331, or rs362306. In some embodiments, a SNP is rs362307, rs7685686, rs362268, or rs362306. In some embodiments, a SNP is rs362307. In some embodiments, a SNP is rs7685686. In some embodiments, a SNP is rs362268. In some embodiments, a SNP is rs362306. In some embodiments, a SNP is rs2530595. In some embodiments, a SNP is rs362331.

As understood by a person having ordinary skill in the art, various methods may be used to monitor a treatment process. In some embodiments, mutant HTT (mHTT) may be assessed from cerebrospinal fluid (Wild et al., Quantification of mutant Huntingtin protein in cerebrospinal fluid from Huntington's disease patients, *J Clin Invest*. 2015; 125 (5): 1979-86), and may be used to monitor a treatment. In some embodiments, this approach may be used to determined and/or optimize a regimen, monitor pharmacodynamic endpoints, and/or determine dosage and frequency for administration, etc.

It is understood by a person having ordinary skill in the art that provided methods apply to any similar targets containing a mismatch. In some embodiments, a mismatch is between a maternal and paternal gene. Additional example targets for suppression and/or knockdown, including allele-specific suppression and/or knockdown, can be any genetic abnormalties, e.g., mutations, related to any diseases. In some embodiments, a target, or a set of targets, is selected from genetic determinants of diseases, e.g., as disclosed in Xiong, et al., The human splicing code reveals new insights into the genetic determinants of disease. Science Vol. 347 no. 6218 DOI: 10.1126/science.1254806. In some embodiments, a mismatch is between a mutant and a wild type.

In some embodiments, provided chirally controlled oligonucleotide compositions and methods are used to selectively suppress oligonucleotides with a mutation in a disease. In some embodiments, a disease is cancer. In some embodiments, provided chirally controlled oligonucleotide compositions and methods are used to selectively suppress transcripts with mutations in cancer. In some embodiments, provided chirally controlled oligonucleotide compositions and methods are used to suppress transcripts of KRAS. Example target KRAS sites comprises G12V=GGU→GUU Position 227 G→U, G12D=GGU→GAU Position 227 G→A and G13D=GGC→GAC Position 230 G→A.

In some embodiments, provided chirally controlled oligonucleotide compositions and methods provide allele-specific suppression of a transcript in an organism. In some embodiments, an organism comprises a target gene for which two or more alleles exist. For example, a subject has a wild type gene in its normal tissues, while the same gene is mutated in diseased tissues such as in a tumor. In some embodiments, the present disclosure provides chirally controlled oligonucleotide compositions and methods that selectively suppress one allele, for example, one with a mutation or SNP. In some embodiments, the present disclosure provides treatment with higher efficacy and/or low toxicity, and/or other benefits as described in the application.

In some embodiments, provided chirally controlled oligonucleotide compositions comprises oligonucleotides of one oligonucleotide type. In some embodiments, provided chirally controlled oligonucleotide compositions comprises oligonucleotides of only one oligonucleotide type. In some embodiments, provided chirally controlled oligonucleotide compositions has oligonucleotides of only one oligonucleotide type. In some embodiments, provided chirally controlled oligonucleotide compositions comprises oligonucleotides of two or more oligonucleotide types. In some embodiments, using such compositions, provided methods can target more than one target. In some embodiments, a chirally controlled oligonucleotide composition comprising two or more oligonucleotide types targets two or more targets. In some embodiments, a chirally controlled oligonucleotide composition comprising two or more oligonucleotide types targets two or more mismatches. In some embodiments, a single oligonucleotide type targets two or more targets, e.g., mutations. In some embodiments, a target region of oligonucleotides of one oligonucleotide type comprises two or more "target sites" such as two mutations or SNPs.

In some embodiments, oligonucleotides in a provided chirally controlled oligonucleotide composition optionally comprise modified bases or sugars. In some embodiments, a provided chirally controlled oligonucleotide composition does not have any modified bases or sugars. In some embodiments, a provided chirally controlled oligonucleotide composition does not have any modified bases. In some embodiments, oligonucleotides in a provided chirally controlled oligonucleotide composition comprise modified bases and sugars. In some embodiments, oligonucleotides in a provided chirally controlled oligonucleotide composition comprise a modified base. In some embodiments, oligonucleotides in a provided chirally controlled oligonucleotide composition comprise a modified sugar. Modified bases and sugars for oligonucleotides are widely known in the art, including but not limited in those described in the present disclosure. In some embodiments, a modified base is 5-mC. In some embodiments, a modified sugar is a 2'-modified sugar. Suitable 2'-modification of oligonucleotide sugars are widely known by a person having ordinary skill in the art. In some embodiments, 2'-modifications include but are not limited to 2'—OR', wherein $R^1$ is not hydrogen. In some embodiments, a 2'-modification is 2'-OR', wherein $R^1$ is optionally substituted $C_{1-6}$ aliphatic. In some embodiments, a 2'-modification is 2'-MOE. In some embodiments, a modification is 2'-halogen. In some embodiments, a modification is 2'-F. In some embodiments, modified bases or sugars may further enhance activity, stability and/or selectivity of a chirally controlled oligonucleotide composition, whose common pattern of backbone chiral centers provides unexpected activity, stability and/or selectivity.

In some embodiments, a provided chirally controlled oligonucleotide composition does not have any modified sugars. In some embodiments, a provided chirally controlled oligonucleotide composition does not have any 2'-modified sugars. In some embodiments, the present disclosure surprisingly found that by using chirally controlled oligonucleotide compositions, modified sugars are not needed for stability, activity, and/or control of cleavage patterns. Furthermore, in some embodiments, the present disclosure surprisingly found that chirally controlled oligonucleotide compositions of oligonucleotides without modified sugars deliver better properties in terms of stability, activity, turnover and/or control of cleavage patterns. For example, in some embodiments, it is surprisingly found that chirally controlled oligonucleotide compositions of oligonucleotides having no modified sugars dissociates much faster from cleavage products and provide significantly increased turnover than compositions of oligonucleotides with modified sugars.

In some embodiments, oligonucleotides of provided chirally controlled oligonucleotide compositions useful for provided methods have structures as extensively described in the present disclosure. In some embodiments, an oligonucleotide has a wing-core-wing structure as described. In some embodiments, the common pattern of backbone chiral centers of a provided chirally controlled oligonucleotide composition comprises $(Sp)_mRp$ as described. In some embodiments, the common pattern of backbone chiral centers of a provided chirally controlled oligonucleotide composition comprises $(Sp)_2Rp$. In some embodiments, the common pattern of backbone chiral centers of a provided chirally controlled oligonucleotide composition comprises $(Sp)_m(Rp)_n$ as described. In some embodiments, the common pattern of backbone chiral centers of a provided chirally controlled oligonucleotide composition comprises $(Rp)_n(Sp)_m$ as described. In some embodiments, the common pattern of backbone chiral centers of a provided chirally controlled oligonucleotide composition comprises $Rp(Sp)_m$ as described. In some embodiments, the common pattern of backbone chiral centers of a provided chirally controlled oligonucleotide composition comprises $Rp(Sp)_2$. In some embodiments, the common pattern of backbone chiral centers of a provided chirally controlled oligonucleotide composition comprises $(Sp)_m(Rp)_n(Sp)_t$ as described. In some embodiments, the common pattern of backbone chiral centers of a provided chirally controlled oligonucleotide composition comprises $(Sp)_mRp(Sp)_t$ as described. In some embodiments, the common pattern of backbone chiral centers of a provided chirally controlled oligonucleotide composition comprises $(Sp)_t(Rp)_n(Sp)_m$ as described. In some embodiments, the common pattern of backbone chiral centers of a provided chirally controlled oligonucleotide composition comprises $(Sp)_tRp(Sp)_m$ as described. In some embodiments, the common pattern of backbone chiral centers of a provided chirally controlled oligonucleotide composition comprises SpRpSpSp. In some embodiments, the common pattern of backbone chiral centers of a provided chirally controlled oligonucleotide composition comprises $(Sp)_2Rp(Sp)_2$. In some embodiments, the common pattern of backbone chiral centers of a provided chirally controlled oligonucleotide composition comprises $(Sp)_3Rp(Sp)_3$. In some embodiments, the common pattern of backbone chiral centers of a provided chirally controlled oligonucleotide composition comprises $(Sp)_4Rp(Sp)_4$. In some embodiments, the common pattern of backbone chiral centers of a provided chirally controlled oligonucleotide composition comprises $(Sp)_tRp(Sp)_5$. In some embodiments, the common pattern of backbone chiral centers of a provided chirally controlled oligonucleotide composition comprises $SpRp(Sp)_5$. In some embodiments, the common pattern of backbone chiral centers of a provided chirally controlled oligonucleotide composition comprises $(Sp)_2Rp(Sp)_5$. In some embodiments, the common pattern of backbone chiral centers of a provided chirally controlled oligonucleotide composition comprises $(Sp)_3Rp(Sp)_5$. In some embodiments, the common pattern of backbone chiral centers of a provided chirally controlled oligonucleotide composition comprises $(Sp)_4Rp(Sp)_5$. In some embodiments, the common pattern of backbone chiral centers of a provided chirally controlled oligonucleotide composition comprises $(Sp)_5 Rp(Sp)_5$. In some embodiments, a common pattern of backbone chiral centers has only one Rp, and each of the other internucleotidic linkages is Sp. In some embodiments, a common base length is greater than 10, 11, 12, 13, 14, 15, 16, 17, 18, 19, 20, 21, 22, 23, 24, 25, 26, 27, 28, 29, 30, 32, 35, 40, 45 or 50 as described in the present disclosure. In some embodiments, a common base length is greater than 10. In some embodiments, a common base length is greater than 11. In some embodiments, a common base length is greater than 12. In some embodiments, a common base length is greater than 13. In some embodiments, a common base length is greater than 14. In some embodiments, a common base length is greater than 15. In some embodiments, a common base length is greater than 16. In some embodiments, a common base length is greater than 17. In some embodiments, a common base length is greater than 18. In some embodiments, a common base length is greater than 19. In some embodiments, a common base length is greater than 20. In some embodiments, a common base length is greater than 21. In some embodiments, a common base length is greater than 22. In some embodiments, a common base length is greater than 23. In some embodiments, a common base length is greater than 24. In some embodiments, a common base length is greater than 25. In some embodiments, a common base length is greater than 26. In some embodiments, a common base length is greater than 27. In some embodiments, a common base length is greater than 28. In some embodiments, a common base length is greater than 29. In some embodiments, a common base length is greater than 30. In some embodiments, a common base length is greater than 31. In some embodiments, a common base length is greater than 32. In some embodiments, a common base length is greater than 33. In some embodiments, a common base length is greater than 34. In some embodiments, a common base length is greater than 35.

In some embodiments, a provided chirally controlled oligonucleotide composition provides higher turn-over. In some embodiments, cleavage products from a nucleic acid polymer dissociate from oligonucleotides of a provided chirally controlled oligonucleotide composition at a faster rate than from oligonucleotides of a reference oligonucleotide composition, for example, a chirally uncontrolled oligonucleotide composition. In some embodiments, a provided chirally controlled oligonucleotide composition can be administered in lower unit dosage, and/or total dosage, and/or fewer doses than chirally uncontrolled oligonucleotide composition.

In some embodiments, a chirally controlled oligonucleotide composition provides fewer cleavage sites in the sequence of a nucleic acid polymer that is complementary to its common base sequence or a sequence within its common base sequence when compared to a reference oligonucleotide composition. In some embodiments, a chirally controlled oligonucleotide composition provides fewer cleavage sites in the sequence of a nucleic acid polymer that is complementary to its common base sequence. In some embodiments, a nucleic acid polymer is selectively cleaved at a single site within the sequence that is complementary to the common base sequence, or a sequence within the common base sequence, of a chirally controlled oligonucleotide composition. In some embodiments, a chirally controlled oligonucleotide composition provides higher cleavage percentage at a cleavage site within the sequence that is complementary to the common base sequence, or a sequence within the common base sequence, of the chirally controlled oligonucleotide composition. In some embodiments, a chirally controlled oligonucleotide composition provides higher cleavage percentage at a cleavage site within the sequence that is complementary to the common base sequence of the chirally controlled oligonucleotide composition. In some embodiments, a site having a higher cleavage percentage is a cleavage site when a reference oligonucleotide composition is used. In some embodiments, a site having a higher cleavage percentage is a cleavage site that is not present when a reference oligonucleotide composition is used.

It is surprisingly found that with reduced number of cleavage sites in the complementary sequence, cleavage rate can be unexpectedly increased and/or higher cleavage percentage can be achieved. As demonstrated in the examples of this disclosure, provided chirally controlled oligonucleotide compositions that produce fewer cleavage sites, especially those that provide single-site cleavage, within the complementary sequences of target nucleic acid polymers provide much higher cleavage rates and much lower levels of remaining un-cleaved nucleic acid polymers. Such results are in sharp contrast to general teachings in the art in which more cleavage sites have been pursued in order to increase the cleavage rate.

In some embodiments, a chirally controlled oligonucleotide composition increases cleavage rate by 1.5 fold compared to a reference oligonucleotide composition. In some embodiments, cleavage rate is increased by at least 2 fold. In some embodiments, cleavage rate is increased by at least 3 fold. In some embodiments, cleavage rate is increased by at least 4 fold. In some embodiments, cleavage rate is increased by at least 5 fold. In some embodiments, cleavage rate is increased by at least 6 fold. In some embodiments, cleavage rate is increased by at least 7 fold. In some embodiments, cleavage rate is increased by at least 8 fold. In some embodiments, cleavage rate is increased by at least 9 fold. In some embodiments, cleavage rate is increased by at least 10 fold. In some embodiments, cleavage rate is increased by at least 11 fold. In some embodiments, cleavage rate is increased by at least 12 fold. In some embodiments, cleavage rate is increased by at least 13 fold. In some embodiments, cleavage rate is increased by at least 14 fold. In some embodiments, cleavage rate is increased by at least 15 fold. In some embodiments, cleavage rate is increased by at least 20 fold. In some embodiments, cleavage rate is increased by at least 30 fold. In some embodiments, cleavage rate is increased by at least 40 fold. In some embodiments, cleavage rate is increased by at least 50 fold. In some embodiments, cleavage rate is increased by at least 60 fold. In some embodiments, cleavage rate is increased by at least 70 fold. In some embodiments, cleavage rate is increased by at least 80 fold. In some embodiments, cleavage rate is increased by at least 90 fold. In some embodiments, cleavage rate is increased by at least 100 fold. In some embodiments, cleavage rate is increased by at least 200 fold. In some embodiments, cleavage rate is increased by at least 300 fold. In some embodiments, cleavage rate is increased by at least 400 fold. In some embodiments, cleavage rate is increased by at least 500 fold. In some embodiments, cleavage rate is increased by at least more than 500 fold.

In some embodiments, a chirally controlled oligonucleotide composition provides a lower level of remaining, un-cleaved target nucleic acid polymer compared to a reference oligonucleotide composition. In some embodiments, it is 1.5 fold lower. In some embodiments, it is at least 2 fold lower. In some embodiments, it is at least 3 fold lower. In some embodiments, it is at least 4 fold lower. In some embodiments, it is at least 5 fold lower. In some embodiments, it is at least 6 fold lower. In some embodiments, it is at least 7 fold lower. In some embodiments, it is at least 8 fold lower. In some embodiments, it is at least 9 fold lower. In some embodiments, it is at least 10 fold lower. In some embodiments, it is at least 11 fold lower. In some embodiments, it is at least 12 fold lower. In some embodiments, it is at least 13 fold lower. In some embodiments, it is at least 14 fold lower. In some embodiments, it is at least 15 fold lower. In some embodiments, it is at least 20 fold lower. In some embodiments, it is at least 30 fold lower. In some embodiments, it is at least 40 fold lower. In some embodiments, it is at least 50 fold lower. In some embodiments, it is at least 60 fold lower. In some embodiments, it is at least 70 fold lower. In some embodiments, it is at least 80 fold lower. In some embodiments, it is at least 90 fold lower. In some embodiments, it is at least 100 fold lower. In some embodiments, it is at least 200 fold lower. In some embodiments, it is at least 300 fold lower. In some embodiments, it is at least 400 fold lower. In some embodiments, it is at least 500 fold lower. In some embodiments, it is at least 1000 fold lower.

As discussed in detail herein, the present disclosure provides, among other things, a chirally controlled oligonucleotide composition, meaning that the composition contains a plurality of oligonucleotides of at least one type. Each oligonucleotide molecule of a particular "type" is comprised of preselected (e.g., predetermined) structural elements with respect to: (1) base sequence; (2) pattern of backbone linkages; (3) pattern of backbone chiral centers; and (4) pattern of backbone P-modification moieties. In some embodiments, provided oligonucloetide compositions contain oligonucleotides that are prepared in a single synthesis process. In some embodiments, provided compositions contain oligonucloetides having more than one chiral configuration within a single oligonucleotide molecule (e.g., where different residues along the oligonucleotide have different stereochemistry); in some such embodiments, such oligonucleotides may be obtained in a single synthesis process, without the need for secondary conjugation steps to generate individual oligonucleotide molecules with more than one chiral configuration.

Oligonucleotide compositions as provided herein can be used as agents for modulating a number of cellular processes and machineries, including but not limited to, transcription, translation, immune responses, epigenetics, etc. In addition, oligonucleotide compositions as provided herein can be used as reagents for research and/or diagnostic purposes. One of ordinary skill in the art will readily recognize that the present disclosure disclosure herein is not limited to particular use but is applicable to any situations where the use of synthetic oligonucleitides is desirable. Among other things, provided compositions are useful in a variety of therapeutic, diagnostic, agricultural, and/or research applications.

In some embodiments, provided oligonucloetide compositions comprise oligonucleotides and/or residues thereof that include one or more structural modifications as described in detail herein. In some embodiments, provided oligonucleotide compositions comprise oligonucleoties that contain one or more nucleic acid analogs. In some embodiments, provided oligonucleotide compositions comprise oligonucleotides that contain one or more artificial nucleic acids or residues (e.g., a nucleotide analog), including but not limited to: a peptide nucleic acid (PNA), locked nucleic acid (LNA), morpholino, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA), threose nucleic acids (TNA), and/or Xeno nucleic acids (XNA), and any combination thereof.

In any of the embodiments, the disclosure is useful for oligonucleotide-based modulation of gene expression, immune response, etc. Accordingly, stereo-defined, oligonucleotide compositions of the disclosure, which contain oligonucleotides of predetermined type (i.e., which are chirally controlled, and optionally chirally pure), can be used in lieu of conventional stereo-random or chirally impure counterparts. In some embodiments, provided compositions show enhanced intended effects and/or reduced unwanted side effects. Certain embodiments of biological and clinical/therapeutic applications of the disclosure are discussed explicitly below.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week for more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks for more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month for more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, a chirally controlled oligonucleotide composition is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, a chirally controlled oligonucleotide composition is administered according to a dosing regimen that is reduced as compared with that of a chirally uncontrolled (e.g., sterorandom) oligonucleotide composition of the same sequence in that it achieves a lower level of total exposure over a given unit of time, involves one or more lower unit doses, and/or includes a smaller number of doses over a given unit of time. In some embodiments, a chirally controlled oligonucleotide composition is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, a chirally controlled oligonucleotide composition has a longer dosing regimen compared to the corresponding chirally uncontrolled oligonucleotide composition. In some embodiments, a chirally controlled oligonucleotide composition has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

A single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

Biologically Active Oligonucleotides

A provided oligonucleotide composition as used herein may comprise single stranded and/or multiply stranded oligonucleotides. In some embodiments, single-stranded oligonucleotides contain self-complementary portions that may hybridize under relevant conditions so that, as used, even single-stranded oligonucleotides may have at least partially double-stranded character. In some embodiments, an oligonucleotide included in a provided composition is single-stranded, double-stranded, or triple-stranded. In some embodiments, an oligonucleotide included in a provided composition comprises a single-stranded portion and a multiple-stranded portion within the oligonucleotide. In some embodiments, as noted above, individual single-stranded oligonucleotides can have double-stranded regions and single-stranded regions.

In some embodiments, provided compositions include one or more oligonucleotides fully or partially complementary to strand of: structural genes, genes control and/or termination regions, and/or self-replicating systems such as viral or plasmid DNA. In some embodiments, provided compositions include one or more oligonucleotides that are or act as siRNAs or other RNA interference reagents (RNAi agents or iRNA agents), shRNA, antisense oligonucleotides, self-cleaving RNAs, ribozymes, fragment thereof and/or variants thereof (such as Peptidyl transferase 23S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, U1 adaptors, triplex-forming oligonucleotides, RNA activators, long non-coding RNAs, short non-coding RNAs (e.g., piRNAs), immunomodulatory oligonucleotides (such as immunostimulatory oligonucleotides, immunoinhibitory oligonucleotides), GNA, LNA, ENA, PNA, TNA, HNA, TNA, XNA, HeNA, CeNA, morpholinos, G-quadruplex (RNA and DNA), antiviral oligonucleotides, and decoy oligonucleotides.

In some embodiments, provided compositions include one or more hybrid (e.g., chimeric) oligonucleotides. In the context of the present disclosure, the term "hybrid" broadly refers to mixed structural components of oligonucloetides. Hybrid oligonucleotides may refer to, for example, (1) an oligonucleotide molecule having mixed classes of nucleotides, e.g., part DNA and part RNA within the single molecule (e.g., DNA-RNA); (2) complementary pairs of nucleic acids of different classes, such that DNA:RNA base pairing occurs either intramolecularly or intermolecularly; or both; (3) an oligonucleotide with two or more kinds of the backbone or internucleotide linkages.

In some embodiments, provided compositions include one or more oligonucleotide that comprises more than one classes of nucleic acid residues within a single molecule. For example, in any of the embodiments described herein, an oligonucleotide may comprise a DNA portion and an RNA portion. In some embodiments, an oligonucleotide may comprise a unmodified portion and modified portion.

Provided oligonucleotide compositions can include oligonucleotides containing any of a variety of modifications, for example as described herein. In some embodiments, particular modifications are selected, for example, in light of intended use. In some embodiments, it is desirable to modify one or both strands of a double-stranded oligonucleotide (or a double-stranded portion of a single-stranded oligonucleotie). In some embodiments, the two strands (or portions) include different modifications. In some embodiments, the two strands include the same modificatinons. One of skill in the art will appreciate that the degree and type of modifications enabled by methods of the present disclosure allow for numerous permutations of modifications to be made. Examples of such modifications are described herein and are not meant to be limiting.

The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The terms "antisense strand" and "guide strand" are used interchangeably herein.

The phrase "sense strand" refers to an oligonucleotide that has the same nucleoside sequence, in whole or in part, as a target sequence such as a messenger RNA or a sequence of DNA. The terms "sense strand" and "passenger strand" are used interchangeably herein.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, a target sequence is associated with a disease or disorder. In some embodiments, a target sequence is or comprises a portion of the Huntingtin gene. In some embodiments, a target sequence is or comprises a portion of the Huntingtin gene comprising a SNP.

By "specifically hybridizable" and "complementary" is meant that a nucleic acid can form hydrogen bond(s) with another nucleic acid sequence by either traditional Watson-Crick or other non-traditional types. In reference to the nucleic molecules of the present disclosure, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol. LIT pp.* 123-133; Frier et al., 1986, *Proc. Nat. Acad. Sci. USA* 83:9373-9377; Turner et al., 1987, *I. Ain. Chem. Soc.* 109:3783-3785)

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9,10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the poly- nucleotide strands, such as overhangs, that are selected so as to be noncomplementary. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. In some embodiments, non-target sequences differ from corresponding target sequences by at least 5 nucleotides.

When used as therapeutics, a provided oligonucleotide is administered as a pharmaceutical composition. In some embodiments, the pharmaceutical composition comprises a therapeutically effective amount of a provided oligonucleotide comprising, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In another embodiment, the pharmaceutical composition is formulated for intravenous injection, oral administration, buccal administration, inhalation, nasal administration, topical administration, ophthalmic administration, intrathecal administration, or otic administration. In another embodiment, the pharmaceutical composition is formulated for intravenous injection, oral administration, buccal administration, inhalation, nasal administration, topical administration, ophthalmic administration or otic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop, an ear drop, or a preparation comprising artificial cerebrospinal fluid. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop. In some embodiments, a pharmaceutical composition comprises cerebrospinal fluid. In some embodiments, a pharmaceutical composition comprises artificial cerebrospinal fluid. In some embodiments, a pharmaceutical composition comprises an oligonucleotide, wherein the sequence of the oligonucleotide comprises a sequence which targets a portion of the Huntingtin gene. In some embodiments, the sequence targets a portion of the Huntingtin gene comprising a SNP. In some embodiments, the base sequence, pattern of backbone linkages, pattern of backbone chiral centers, and/or pattern of sugar modifications of the oligonucleotide is or comprises the base sequence, pattern of backbone linkages, pattern of backbone chiral centers, and/or pattern of sugar modifications of any oligonucleotide disclosed herein, and the oligonucleotide is comprised in a pharmaceutical composition comprising any component of a pharmaceutical composition disclosed herein. In some embodiments, the oligonucleotide targets the Huntingtin gene (as a non-limiting example, a SNP in the Huntingtin gene), and the base sequence, pattern of backbone linkages, pattern of backbone chiral centers, and/or pattern of sugar modifications of the oligonucleotide is or comprises the base sequence, pattern of backbone linkages, pattern of backbone chiral centers, and/or pattern of sugar modifications of any oligonucleotide disclosed herein, and the oligonucleotide is comprised in a pharmaceutical composition comprising artificial cerebrospinal fluid, and the pharmaceutical composition is administered via intrathecal administration.

Pharmaceutical Compositions

When used as therapeutics, a provided oligonucleotide or oligonucleotide composition described herein is administered as a pharmaceutical composition. In some embodiments, the pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, the present disclosure provides pharmaceutically acceptable salts of provided oligonucleotides. In some embodiments, a provided pharmaceutically acceptable salt is a sodium salt. In some embodiments, a provided pharmaceutically acceptable salt is an all-sodium salt, wherein each acidic internucleotidic linkages exist as a sodium salt (for example, for WV-1092, 19 Na$^+$ per oligonucleotide as there are 19 phosphoate and phosphorothioate linkages in WV-1092). In some embodiments, a provided oligonucleotide is:

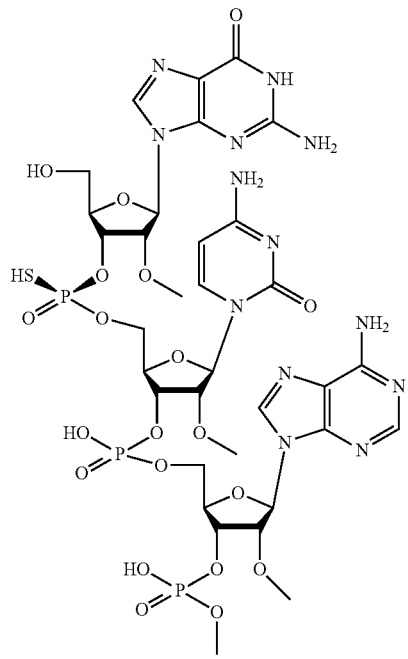

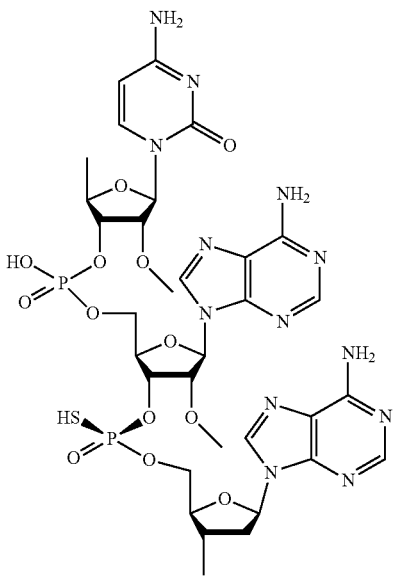

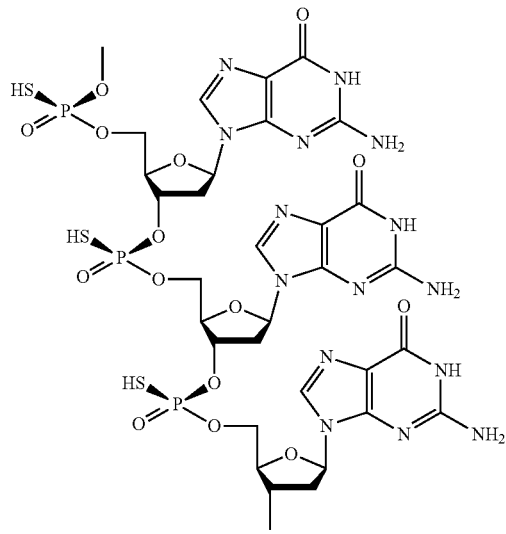

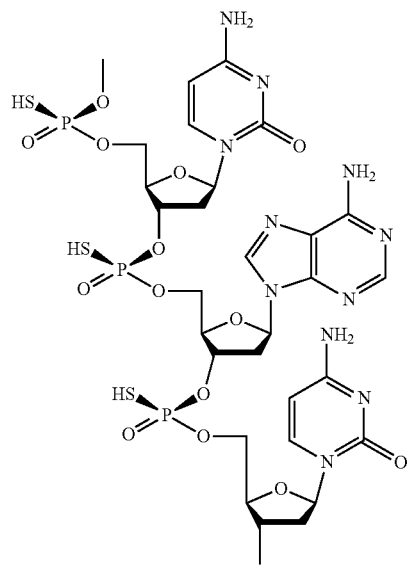

411
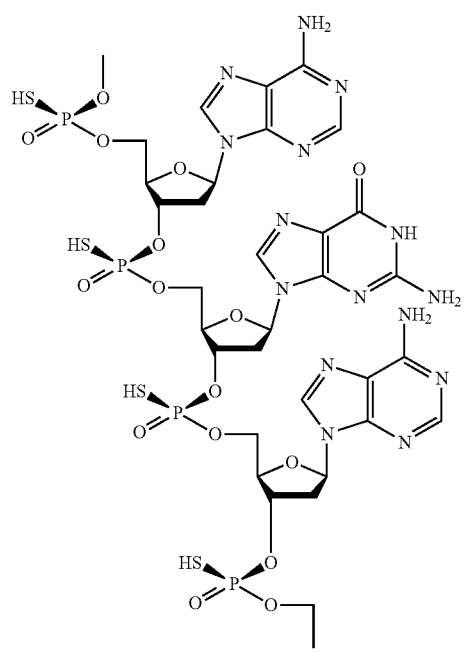
412
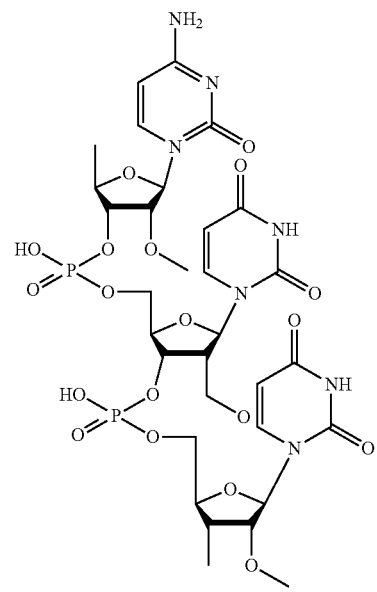
(O-I-1)
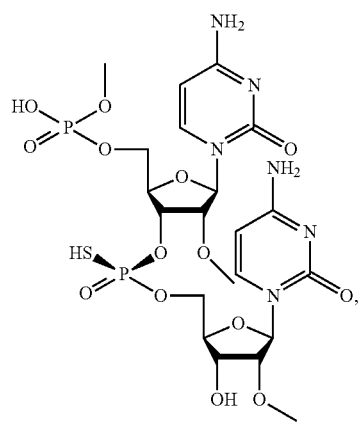
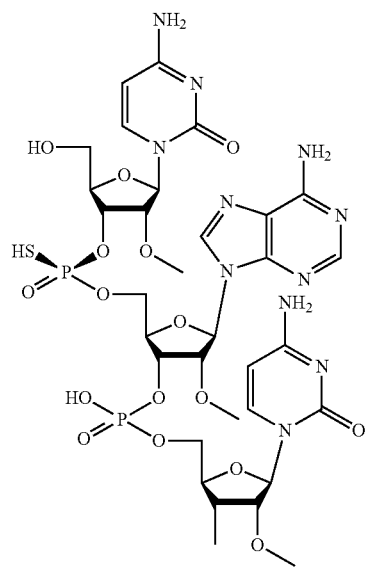
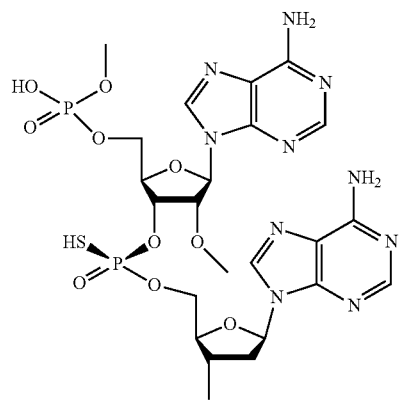

413
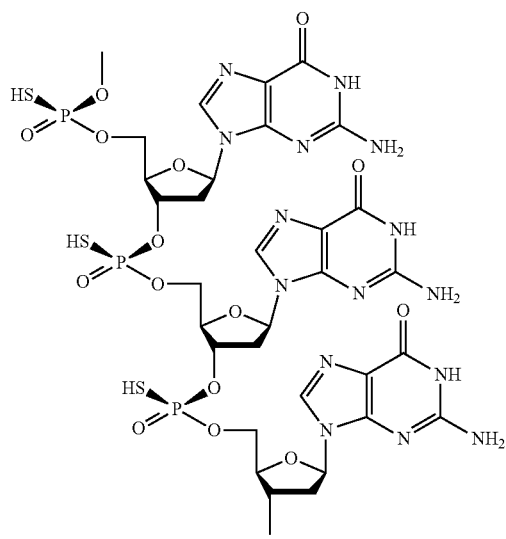
414
-continued
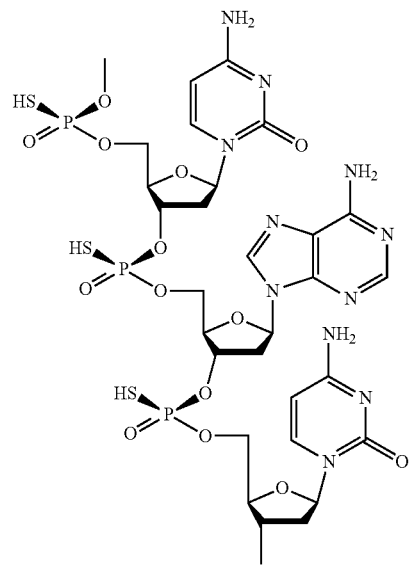
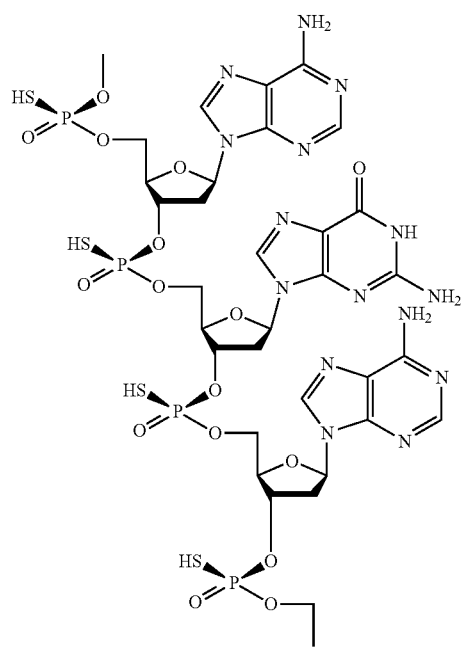
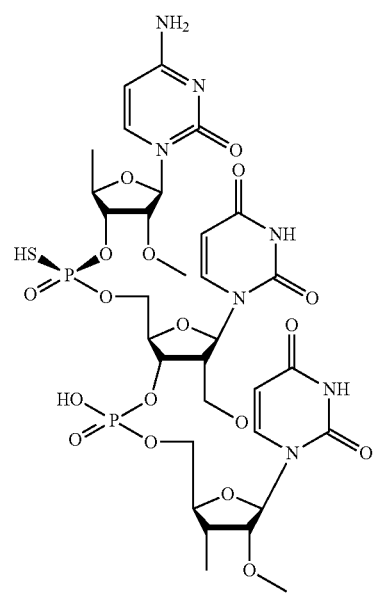

415
-continued
(O-I-2)
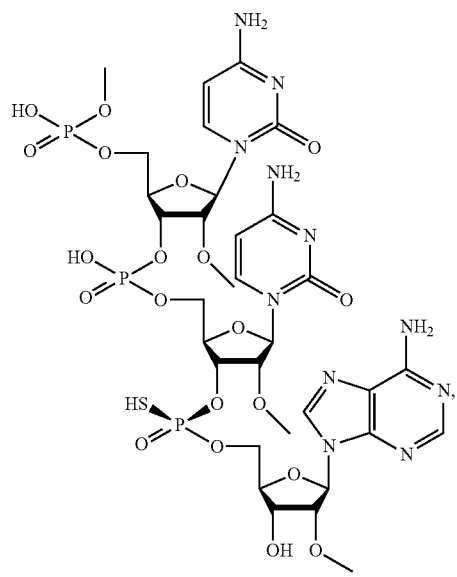
416
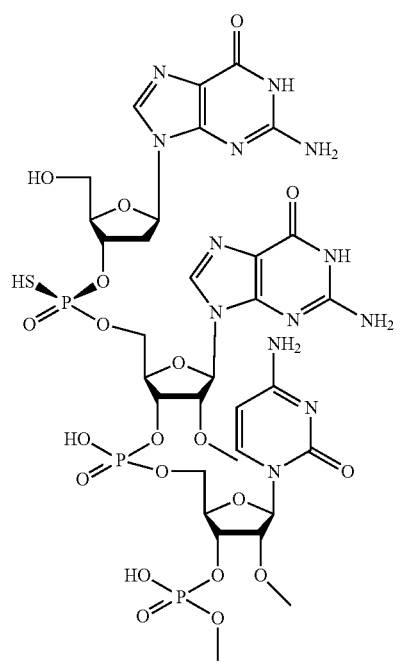

-continued
417
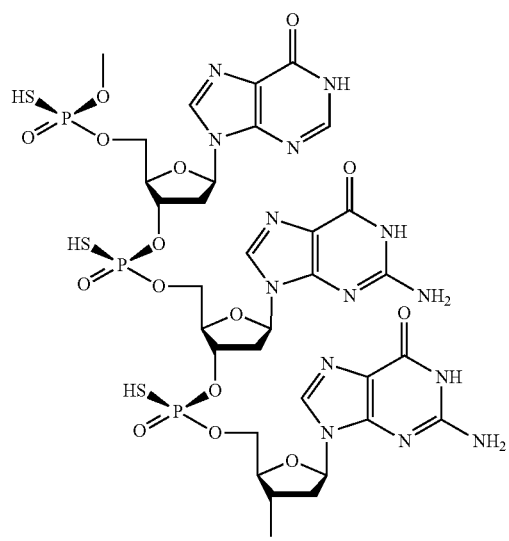
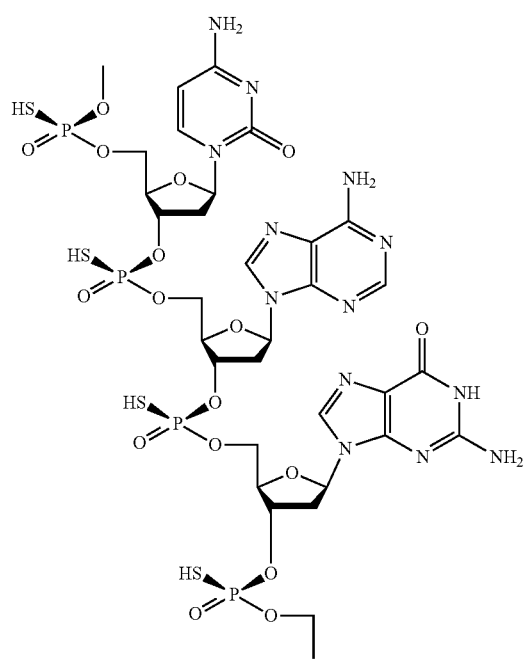
418
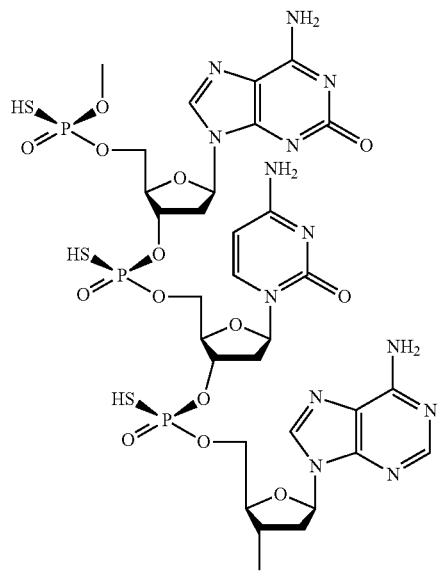
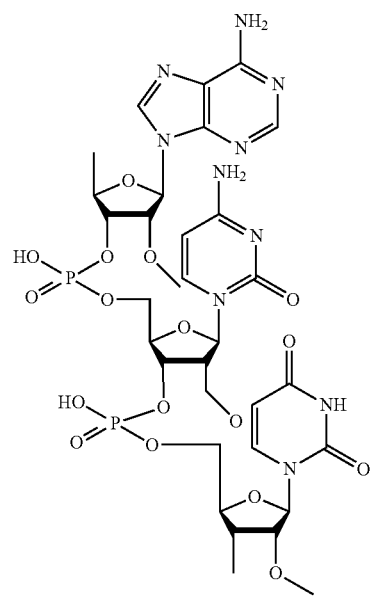
(O-I-3)
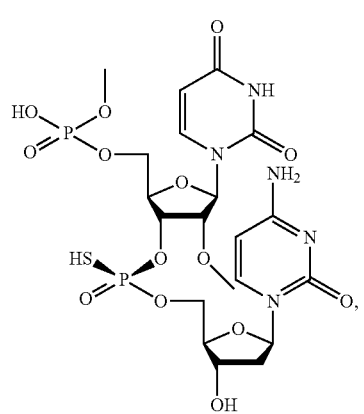

419
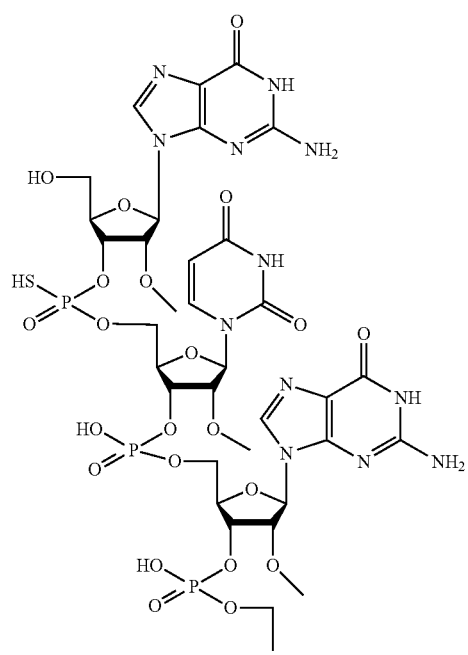
420
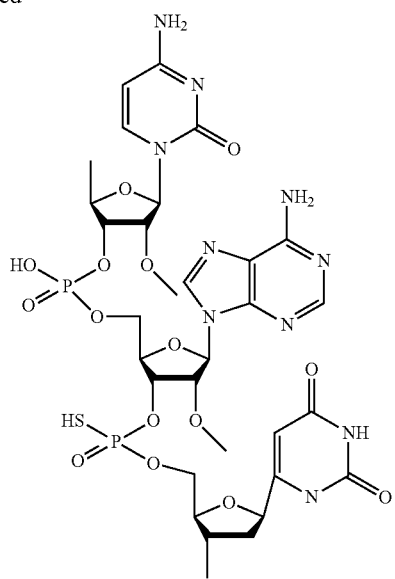
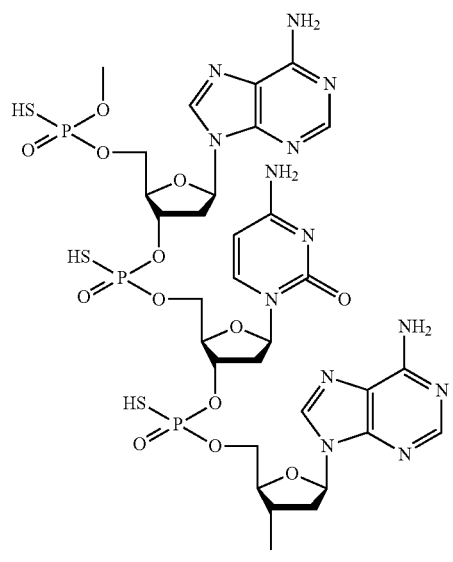
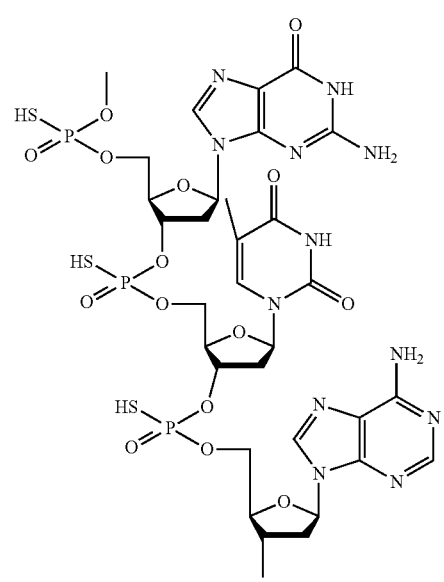

421
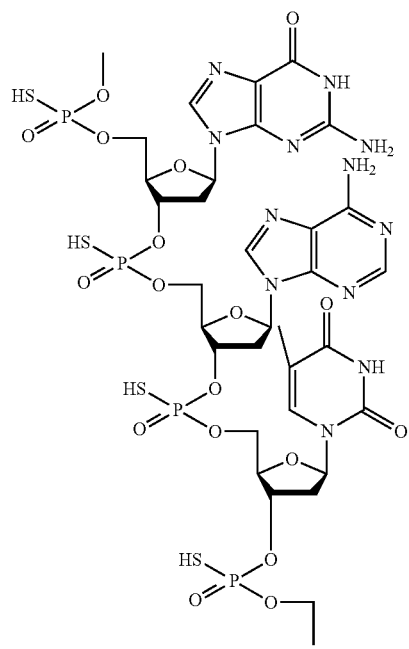
422
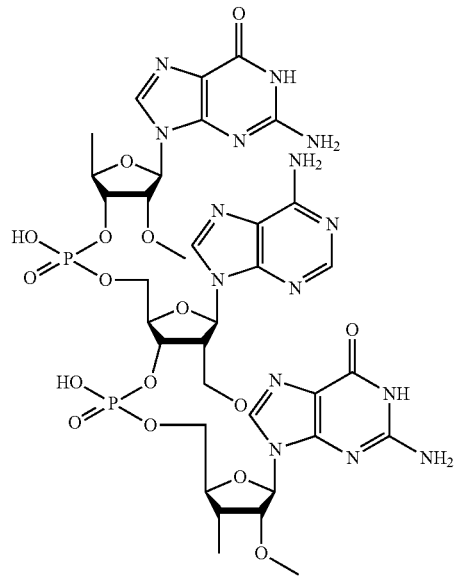
(O-I-4)
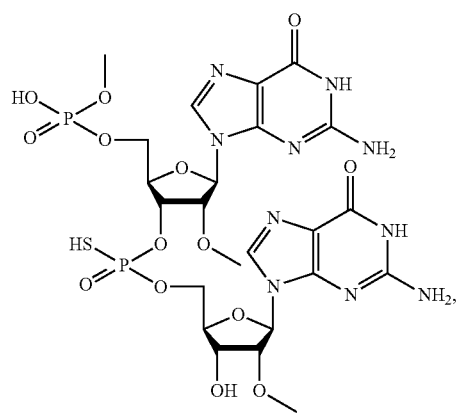
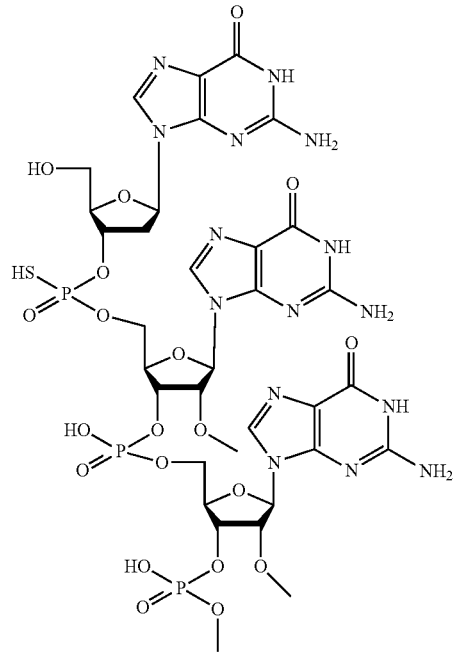
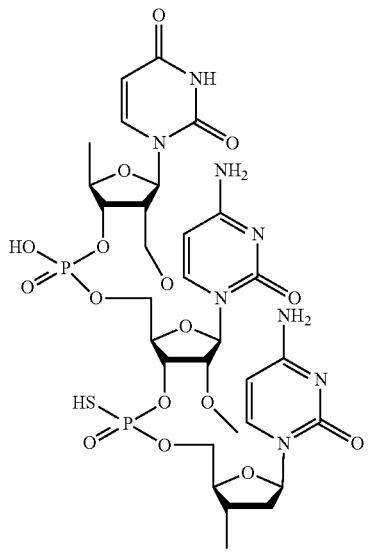

423
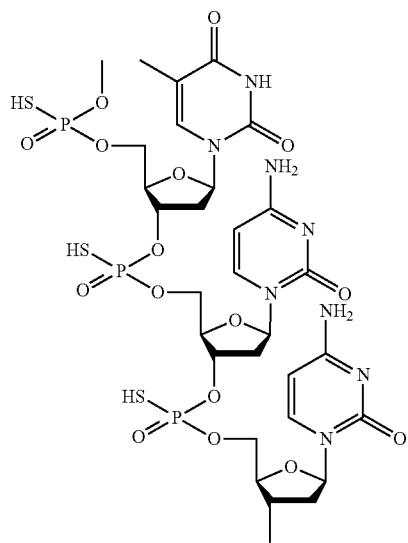
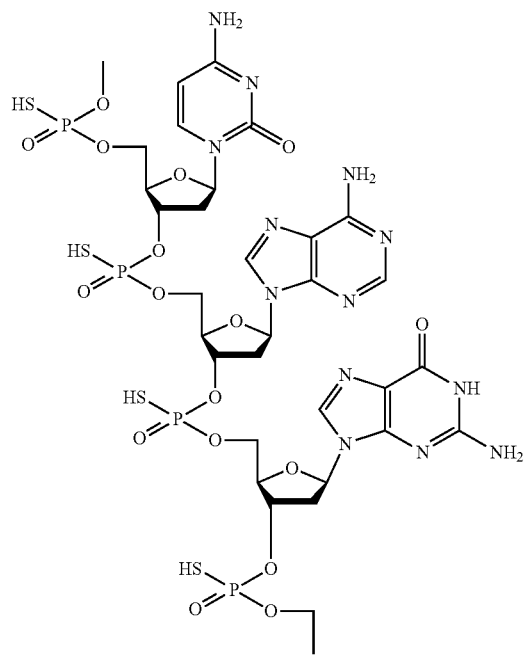
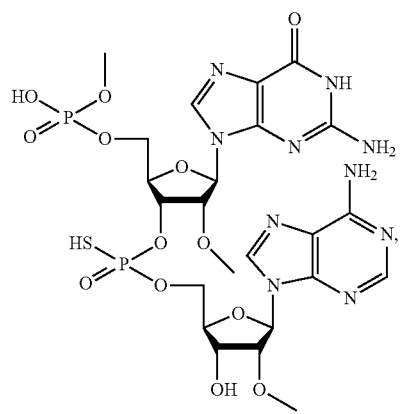
424
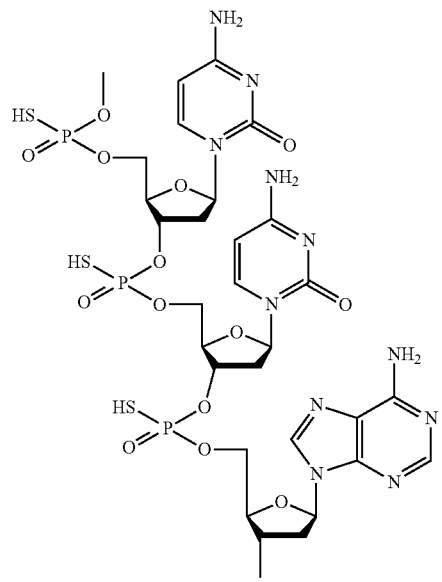
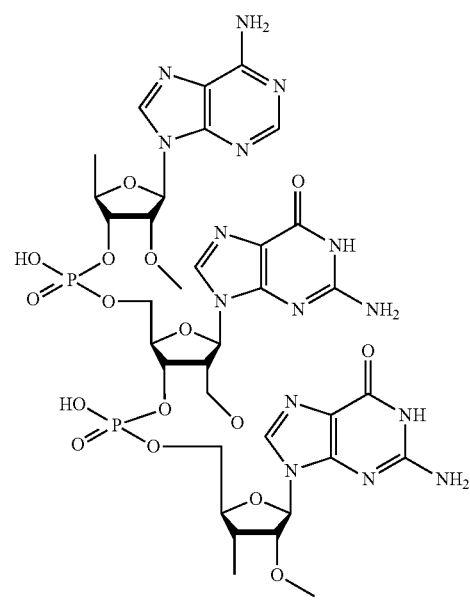
(O-I-5)

-continued
425
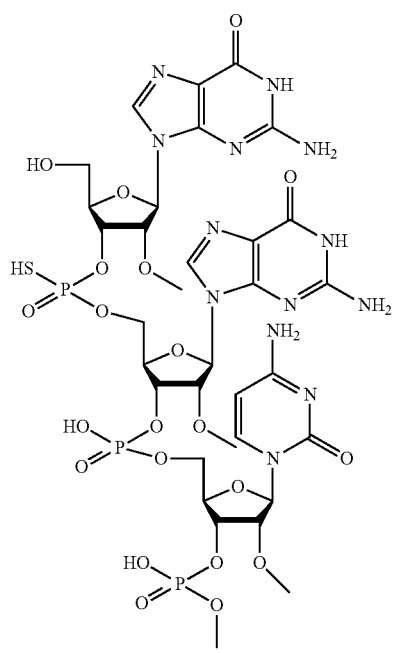
426
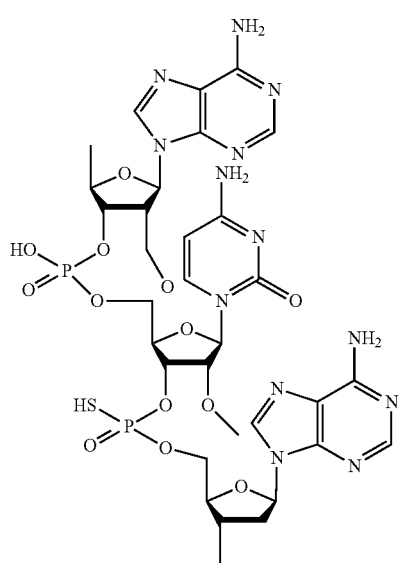
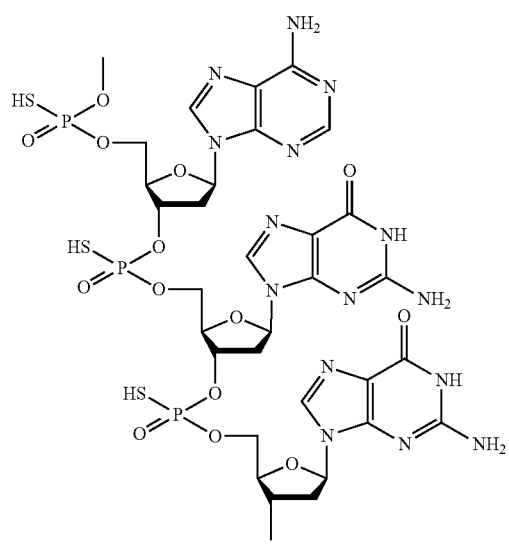
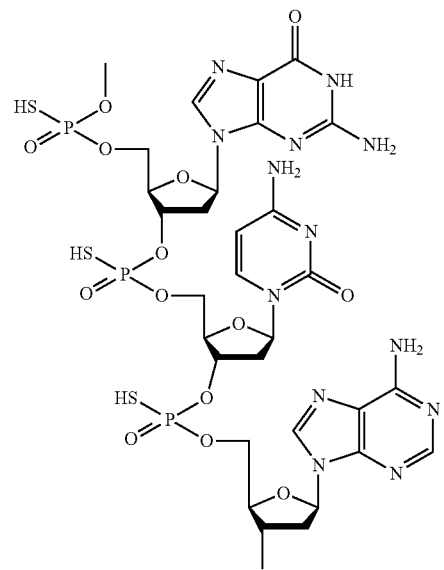

427
428
-continued
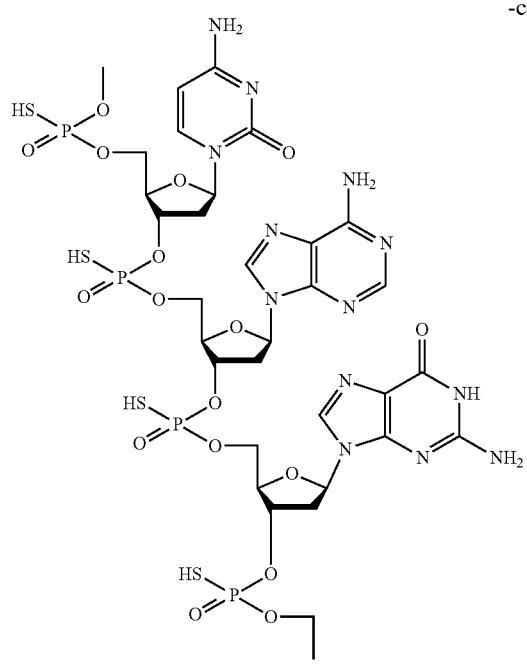
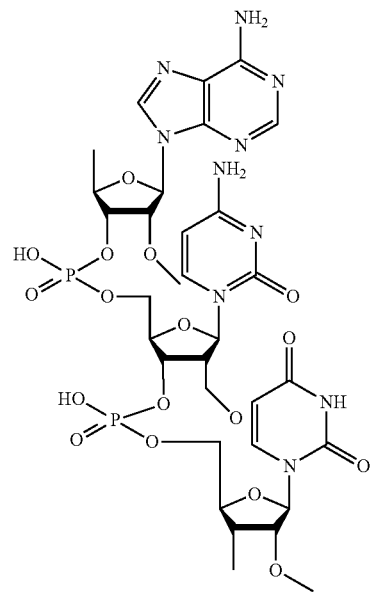
(O-I-6)
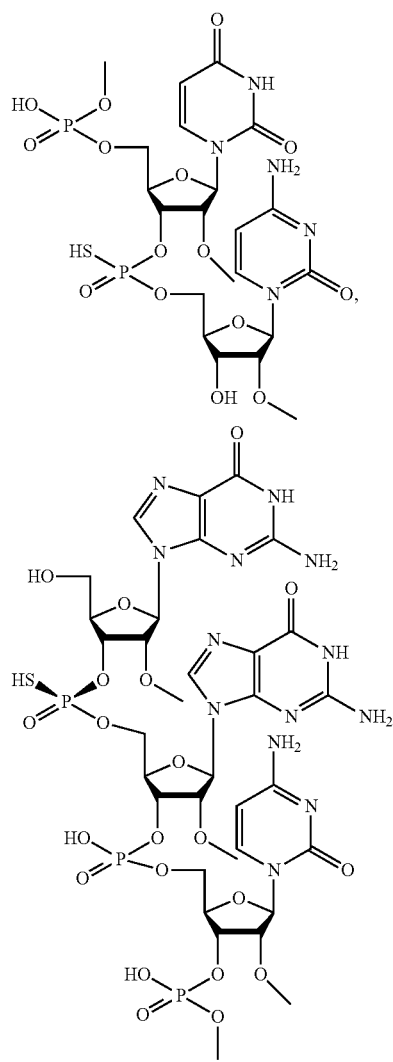
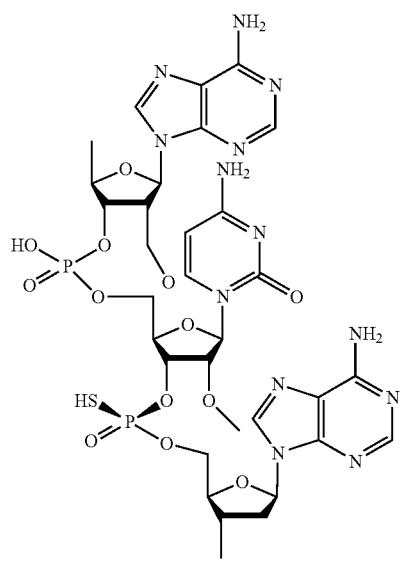

429
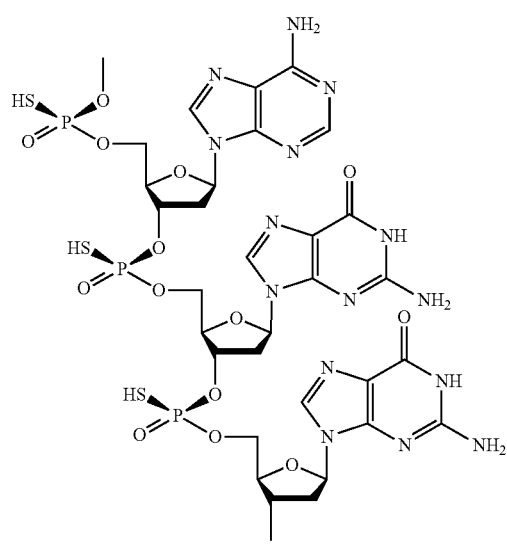
430
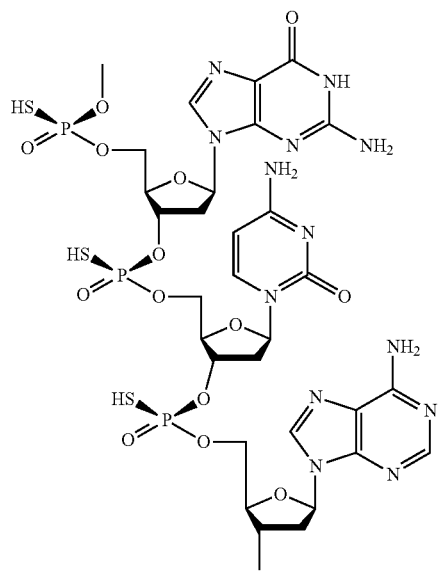
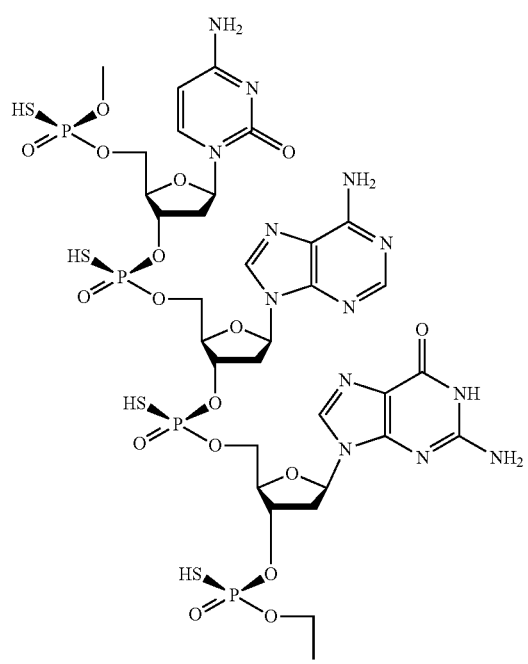
($C_{202}H_{259}N_{82}O_{111}P_{19}S_{13}$)
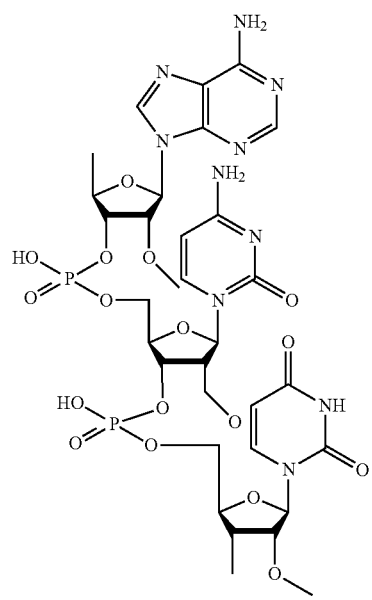
(O-I-7)
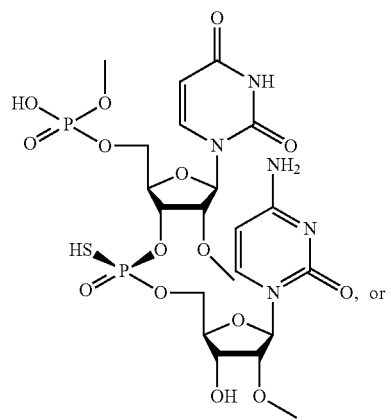
, or -continued
431
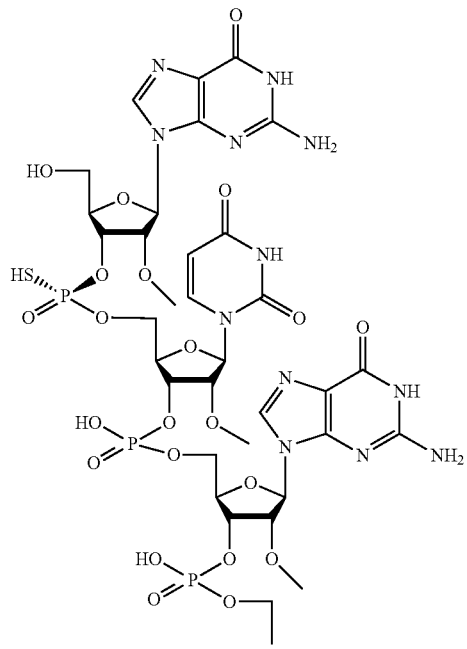
432
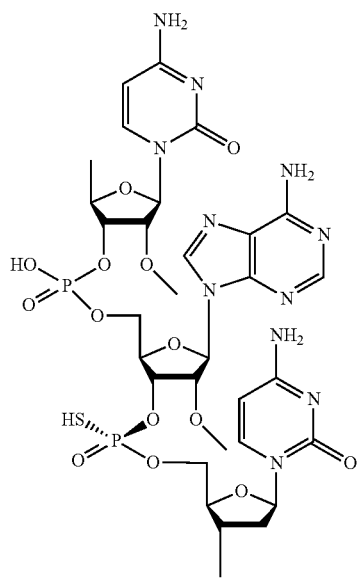
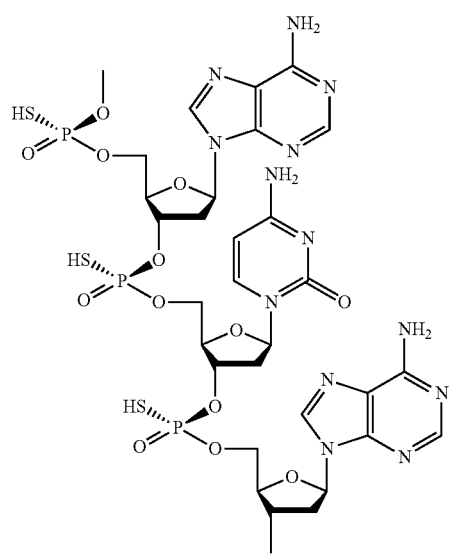
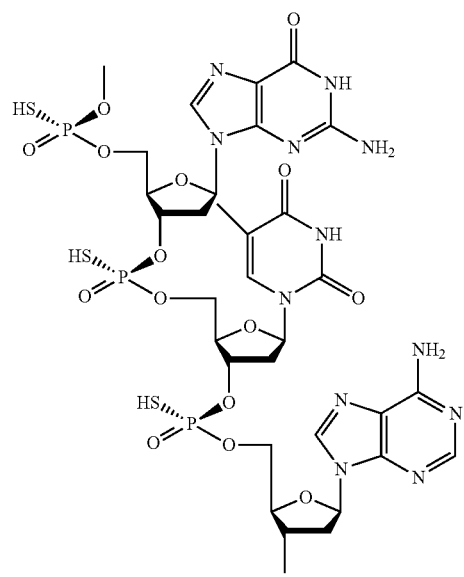

433

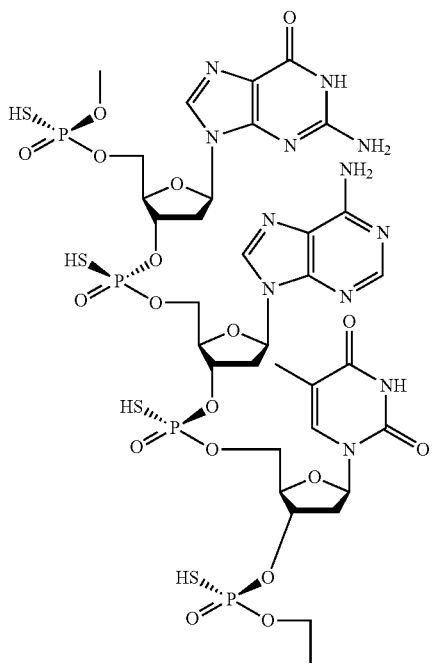

(O-I-8)

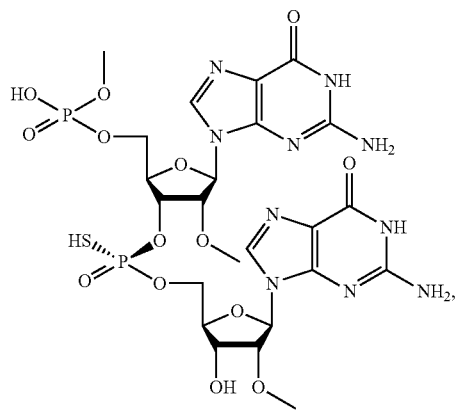

or a pharmaceutically acceptable salt thereof. In some embodiments, a provided oligonucleotide is a sodium salt of O—I-1, O—I-2, O—I-3, O—I-4, O—I-5, O—I-6, O—I-7, or O—I-8. In some embodiments, a provided oligonucleotide is a all-sodium salt of O—I-1, O—I-2, O—I-3, O—I-4, O—I-5, O—I-6, O—I-7, or O—I-8. In some embodiments, a provided oligonucleotide of formula O—I is O—I-1 or a pharmaceutically acceptable salt thereof. In some embodiments, a provided oligonucleotide of formula O—I is O—I-2 or a pharmaceutically acceptable salt thereof. In some embodiments, a provided oligonucleotide of formula O—I is O—I-3 or a pharmaceutically acceptable salt thereof. In some embodiments, a provided oligonucleotide of formula O—I is O—I-4 or a pharmaceutically acceptable salt thereof. In some embodiments, a provided oligonucleotide of formula O—I is O—I-5 or a pharmaceutically acceptable salt thereof. In some embodiments, a provided oligonucleotide of formula O—I is O—I-6 or a pharmaceutically acceptable salt thereof. In some embodiments, a provided oligonucleotide of formula O—I is O—I-7 or a pharmaceutically acceptable salt thereof. In some embodiments, a provided oligonucleotide of formula O—I is

434

O—I-8 or a pharmaceutically acceptable salt thereof. In some embodiments, a provided oligonucleotide of formula O—I is an all-sodium salt (19 $Na^+$) of O—I-1. In some embodiments, a provided oligonucleotide of formula O—I is an all-sodium salt (19 $Na^r$) of O—I-2. In some embodiments, a provided oligonucleotide of formula O—I is an all-sodium salt (19 $Na^r$) of O—I-3. In some embodiments, a provided oligonucleotide of formula O—I is an all-sodium salt (19 $Na^r$) of O—I-4. In some embodiments, a provided oligonucleotide of formula O—I is an all-sodium salt (19 $Na^+$) of O—I-5. In some embodiments, a provided oligonucleotide of formula O—I is an all-sodium salt (19 $Na^r$) of O—I-6. In some embodiments, a provided oligonucleotide of formula O—I is an all-sodium salt (19 $Na^r$) of O—I-7. In some embodiments, a provided oligonucleotide of formula O—I is an all-sodium salt (19 $Na^r$) of O—I-8.

In some embodiments, the pharmaceutical composition is formulated for intravenous injection, oral administration, buccal administration, inhalation, nasal administration, topical administration, ophthalmic administration, intrathecal administration, or otic administration. In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop, an ear drop, or a preparation comprising artificial cerebrospinal fluid. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop. In some embodiments, a provided composition comprises cerebrospinal fluid. In some embodiments, a provided composition comprises artificial cerebrospinal fluid.

In some embodiments, the present disclosure provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, polymer micelles, quantum dots and lipoplexes.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

In some embodiments of a method or composition of the present disclosure, a composition comprising an oligonucleotide is administered via intrathecal administration. In some embodiments of a method or composition of the present disclosure, a composition comprising an oligonucleotide comprises artificial cerebrospinal fluid and is administered via intrathecal administration. In some embodiments of a method or composition of the present disclosure, a composition comprising an oligonucleotide comprises one or more components of artificial cerebrospinal fluid (for example, NaCl, NaHCO$_3$, KCl, NaH$_2$PO$_4$, MgCl$_2$ and glucose) and is administered via intrathecal administration. In some embodiments of a method or composition of the present disclosure, a composition comprising an oligonucleotide comprises one or more components of artificial cerebrospinal fluid (for example, NaCl, NaHCO$_3$, KCl, NaH$_2$PO$_4$, MgCl$_2$ and glucose) and is administered via intrathecal administration, wherein the sequence of the oligonucleotide comprises a sequence which targets a portion of the Huntingtin gene. In some embodiments of a method or composition of the present disclosure, a composition comprising an oligonucleotide comprises two or more components of artificial cerebrospinal fluid (for example, NaCl, NaHCO$_3$, KCl, NaH$_2$PO$_4$, MgCl$_2$ and glucose) and is administered via intrathecal administration, wherein the sequence of the oligonucleotide comprises a sequence which targets a portion of the Huntingtin gene. In some embodiments of a method or composition of the present disclosure, a composition comprising an oligonucleotide comprises three or more components of artificial cerebrospinal fluid (for example, NaCl, NaHCO$_3$, KCl, NaH$_2$PO$_4$, MgCl$_2$ and glucose) and is administered via intrathecal administration, wherein the sequence of the oligonucleotide comprises a sequence which targets a portion of the Huntingtin gene. In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein. In some embodiments, the sequence targets a portion of the Huntingtin gene comprising a SNP.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with oligonucleotides of this disclosure. For example, chemotherapeutic agents or other anti-proliferative agents may be combined with the oligonucleotides of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

The function and advantage of these and other embodiments of the present disclosure will be more fully understood from the examples described below. The following examples are intended to illustrate the benefits of the present disclosure, but do not exemplify the full scope of the disclosure.

Lipids

In some embodiments, provided oligonucleotide compositions further comprise one or more lipids. In some embodiments, the lipids are conjugated to provided oligonucleotides in the compositions. In some embodiments, two or more same or different lipids can be conjugated to one oligonucleotide, through either the same or differently chemistry and/or locations. In some embodiments, a composition can comprise an oligonucleotide disclosed herein (as non-limiting examples, a chirally controlled oligonucleotide composition, or a chirally controlled oligonucleotide composition wherein the sequence of the oligonucleotide comprises, consists of or is the sequence of any oligonucleotide disclosed herein, or a chirally controlled oligonucleotide composition wherein the sequence of the oligonucleotide comprises, consists of or is the sequence of any oligonucleotide disclosed in Table 8 or any other Table herein, etc.) and a lipid. In some embodiments, a provided oligonucleotide comprises base sequence, pattern of backbone linkages, pattern or backbone chiral centers, and/or pattern of chemical modifications (e.g., base modifications, sugar modifications, etc.) of any oligonucleotide disclosed herein, and is conjugated to a lipid. In some embodiments, a provided composition comprises an oligonucleotide disclosed herein and a lipid, wherein the lipid is conjugated to the oligonucleotide.

In some embodiments, the present disclosure provides a composition comprising an oligonucleotide amd a lipid. Many lipids can be utilized in provided technologies in accordance with the present disclosure.

In some embodiments, a lipid comprises an $R^{LD}$ group, wherein $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, a lipid comprises an $R^{LD}$ group, wherein $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, a lipid comprises an $R^{LD}$ group, wherein $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:
each R' is independently —R, —C(O)R, —CO$_2$R, or —SO$_2$R, or:
    two R' are taken together with their intervening atoms to form an optionally substituted aryl, carbocyclic, heterocyclic, or heteroaryl ring;
-Cy- is an optionally substituted bivalent ring selected from carbocyclylene, arylene, heteroarylene, and heterocyclylene; and
each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

The aliphatic group of $R^{LD}$ can be a variety of suitable length. In some embodiments, it is $C_{10}$-$C_{80}$. In some embodiments, it is $C_{10}$-$C_{75}$. In some embodiments, it is $C_{10}$-$C_{70}$. In some embodiments, it is $C_{10}$-$C_{65}$. In some embodiments, it is $C_{10}$-$C_{60}$. In some embodiments, it is $C_{10}$-$C_{50}$. In some embodiments, it is $C_{10}$-$C_{40}$. In some embodiments, it is $C_{10}$-$C_{35}$. In some embodiments, it is $C_{10}$-$C_{30}$. In some embodiments, it is $C_{10}$-$C_{25}$. In some embodiments, it is $C_{10}$-$C_{24}$. In some embodiments, it is $C_{10}$-$C_{23}$. In some embodiments, it is $C_{10}$-$C_{22}$. In some embodiments, it is $C_{10}$-$C_{21}$. In some embodiments, it is $C_{12}$-$C_{22}$. In some embodiments, it is $C_{13}$-$C_{22}$. In some embodiments, it is $C_{14}$-$C_{22}$. In some embodiments, it is C1s-$C_{22}$. In some embodiments, it is $C_{16}$-$C_{22}$. In some embodiments, it is $C_{17}$-$C_{22}$. In some embodiments, it is $C_{18}$-$C_{22}$. In some embodiments, it is $C_{10}$-$C_{20}$. In some embodiments, the lower end of the range is $C_{10}$, $C_{11}$, $C_{12}$, $C_{13}$, $C_{14}$, $C_{15}$, $C_{16}$, $C_{17}$, or $C_{18}$. In some embodiments, the higher end of the range is Cis, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{55}$, or $C_{60}$. In some embodiments, it is $C_{10}$. In some embodiments, it is $C_{11}$. In some embodiments, it is $C_{12}$. In some embodiments, it is $C_{13}$. In some embodiments, it is $C_{14}$. In some embodiments, it is $C_{15}$. In some embodiments, it is $C_{16}$. In some embodiments, it is $C_{17}$. In some embodiments, it is $C_{18}$. In some embodiments, it is $C_{19}$. In some embodiments, it is $C_{20}$. In some embodiments, it is $C_{21}$. In some embodiments, it is $C_{22}$. In some embodiments, it is $C_{23}$. In some embodiments, it is $C_{24}$. In some embodiments, it is $C_{25}$. In some embodiments, it is $C_{30}$. In some embodiments, it is $C_{35}$. In some embodiments, it is $C_{40}$. In some embodiments, it is $C_{45}$. In some embodiments, it is $C_{50}$. In some embodiments, it is $C_{55}$. In some embodiments, it is $C_{60}$.

In some embodiments, a lipid comprises no more than one $R^{LD}$ group. In some embodiments, a lipid comprises two or more $R^{LD}$ groups.

In some embodiments, a lipid is conjugated to a biologically active agent, optionally through a linker, as a moiety comprising an $R^{LD}$ group. In some embodiments, a lipid is conjugated to a biologically active agent, optionally through a linker, as a moiety comprising no more than one $R^{LD}$ group. In some embodiments, a lipid is conjugated to a biologically active agent, optionally through a linker, as an $R^{LD}$ group. In some embodiments, a lipid is conjugated to a biologically active agent, optionally through a linker, as a moiety comprising two or more $R^{LD}$ groups.

In some embodiments, $R^{LD}$ is an optionally substituted, $C_{10}$-$C_{40}$ saturated or partially unsaturated, aliphatic chain. In some embodiments, a lipid comprises an optionally substituted $C_{10}$-$C_{40}$ saturated or partially unsaturated, aliphatic chain.

In some embodiments, $R^{LD}$ is an optionally substituted, $C_{10}$-$C_{40}$ linear, saturated or partially unsaturated, aliphatic chain. In some embodiments, a lipid comprises an optionally substituted $C_{10}$-$C_{40}$ linear, saturated or partially unsaturated, aliphatic chain.

In some embodiments, $R^{LD}$ is a $C_{10}$-$C_{40}$ linear, saturated or partially unsaturated, aliphatic chain, optionally substituted with one or more $C_{1-4}$ aliphatic groups. In some embodiments, a lipid comprises a $C_{10}$-$C_{40}$ linear, saturated or partially unsaturated, aliphatic chain, optionally substituted with one or more $C_{1-4}$ aliphatic groups. In some embodiments, $R^{LD}$ is a $C_{10}$-$C_{40}$ linear, saturated or partially unsaturated, aliphatic chain, optionally substituted with one or more $C_{1-2}$ aliphatic groups. In some embodiments, a lipid comprises a $C_{10}$-$C_{40}$ linear, saturated or partially unsaturated, aliphatic chain, optionally substituted with one or more $C_{1-2}$ aliphatic groups. In some embodiments, $R^{LD}$ is a $C_{10}$-$C_{40}$ linear, saturated or partially unsaturated, aliphatic chain, optionally substituted with one or more methyl groups. In some embodiments, a lipid comprises a $C_{10}$-$C_{40}$ linear, saturated or partially unsaturated, aliphatic chain, optionally substituted with one or more methyl groups.

In some embodiments, $R^{LD}$ is an unsubstituted $C_{10}$-$C_{40}$ linear, saturated or partially unsaturated, aliphatic chain. In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain.

In some embodiments, $R^{LD}$ is an optionally substituted, $C_{10}$-$C_{60}$ saturated or partially unsaturated, aliphatic chain. In some embodiments, a lipid comprises an optionally substituted $C_{10}$-$C_{60}$ saturated or partially unsaturated, aliphatic chain.

In some embodiments, $R^{LD}$ is an optionally substituted $C_{10}$-$C_{60}$ linear, saturated or partially unsaturated, aliphatic chain. In some embodiments, a lipid comprises an optionally substituted $C_{10}$-$C_{60}$ linear, saturated or partially unsaturated, aliphatic chain.

In some embodiments, $R^{LD}$ is a $C_{10}$-$C_{60}$ linear, saturated or partially unsaturated, aliphatic chain, optionally substituted with one or more $C_{1-4}$ aliphatic groups. In some embodiments, a lipid comprises a $C_{10}$-$C_{60}$ linear, saturated or partially unsaturated, aliphatic chain, optionally substituted with one or more $C_{1-4}$ aliphatic groups. In some embodiments, $R^{LD}$ is a $C_{10}$-$C_{60}$ linear, saturated or partially unsaturated, aliphatic chain, optionally substituted with one or more $C_{1-2}$ aliphatic groups. In some embodiments, a lipid comprises a $C_{10}$-$C_{60}$ linear, saturated or partially unsaturated, aliphatic chain, optionally substituted with one or more $C_{1-2}$ aliphatic groups. In some embodiments, $R^{LD}$ is a $C_{10}$-$C_{60}$ linear, saturated or partially unsaturated, aliphatic chain, optionally substituted with one or more methyl groups. In some embodiments, a lipid comprises a $C_{10}$-$C_{60}$ linear, saturated or partially unsaturated, aliphatic chain, optionally substituted with one or more methyl groups.

In some embodiments, $R^{LD}$ is an unsubstituted $C_{10}$-$C_{60}$ linear, saturated or partially unsaturated, aliphatic chain. In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, $R^{LD}$ is an optionally substituted, $C_{10}$-$C_{80}$ saturated or partially unsaturated, aliphatic chain. In some embodiments, a lipid comprises an optionally substituted $C_{10}$-$C_{80}$ saturated or partially unsaturated, aliphatic chain.

In some embodiments, $R^{LD}$ is an optionally substituted $C_{10}$-$C_{80}$ linear, saturated or partially unsaturated, aliphatic chain. In some embodiments, a lipid comprises an optionally substituted $C_{10}$-$C_{80}$ linear, saturated or partially unsaturated, aliphatic chain.

In some embodiments, $R^{LD}$ is a $C_{10}$-$C_{60}$ linear, saturated or partially unsaturated, aliphatic chain, optionally substituted with one or more $C_{1-4}$ aliphatic groups. In some embodiments, a lipid comprises a $C_{10}$-$C_{80}$ linear, saturated or partially unsaturated, aliphatic chain, optionally substituted with one or more $C_{1-4}$ aliphatic groups. In some embodiments, $R^{LD}$ is a $C_{10}$-$C_{80}$ linear, saturated or partially unsaturated, aliphatic chain, optionally substituted with one or more $C_{1-2}$ aliphatic groups. In some embodiments, a lipid comprises a $C_{10}$-$C_{80}$ linear, saturated or partially unsaturated, aliphatic chain, optionally substituted with one or more $C_{1-2}$ aliphatic groups. In some embodiments, $R^{LD}$ is a $C_{10}$-$C_{80}$ linear, saturated or partially unsaturated, aliphatic chain, optionally substituted with one or more methyl groups. In some embodiments, a lipid comprises a $C_{10}$-$C_{80}$ linear, saturated or partially unsaturated, aliphatic chain, optionally substituted with one or more methyl groups.

In some embodiments, $R^{LD}$ is an unsubstituted $C_{10}$-$C_{80}$ linear, saturated or partially unsaturated, aliphatic chain. In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, $R^{LD}$ is or comprises a $C_{10}$ saturated linear aliphatic chain. In some embodiments, $R^{LD}$ is or comprises a $C_{10}$ partially unsaturated linear aliphatic chain. In some embodiments, $R^{LD}$ is or comprises a $C_{11}$ saturated linear aliphatic chain. In some embodiments, $R^{LD}$ is or comprises a $C_{11}$ partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a $C_{13}$ saturated linear aliphatic chain. In some embodiments, $R^{LD}$ is or comprises a $C_{13}$ partially unsaturated linear aliphatic chain. In some embodiments, $R^{LD}$ is or comprises a $C_{14}$ saturated linear aliphatic chain. In some embodiments, $R^{LD}$ is or comprises a $C_{14}$ partially unsaturated linear aliphatic chain. In some embodiments, $R^{LD}$ is or comprises a $C_{15}$ saturated linear aliphatic chain. In some embodiments, $R^{LD}$ is or comprises a $C_{15}$ partially unsaturated linear aliphatic chain. In some embodiments, $R^{LD}$ is or comprises a $C_{16}$ saturated linear aliphatic chain. In some embodiments, $R^{LD}$ is or comprises a $C_{16}$ partially unsaturated linear aliphatic chain. In some embodiments, $R^{LD}$ is or comprises a $C_{17}$ saturated linear aliphatic chain. In some embodiments, $R^{LD}$ is or comprises a $C_{17}$ partially unsaturated linear aliphatic chain. In some embodiments, $R^{LD}$ is or comprises a Cis saturated linear aliphatic chain. In some embodiments, $R^{LD}$ is or comprises a Cis partially unsaturated linear aliphatic chain. In some embodiments, $R^{LD}$ is or comprises a $C_{19}$ saturated linear aliphatic chain. In some embodiments, $R^{LD}$ is or comprises a $C_{19}$ partially unsaturated linear aliphatic chain. In some embodiments, $R^{LD}$ is or comprises a $C_{20}$ saturated linear aliphatic chain. In some embodiments, $R^{LD}$ is or comprises a $C_{20}$ partially unsaturated linear aliphatic chain. In some embodiments, $R^{LD}$ is or comprises a $C_{21}$ saturated linear aliphatic chain. In some embodiments, $R^{LD}$ is or comprises a $C_{21}$ partially unsaturated linear aliphatic chain. In some embodiments, $R^{LD}$ is or comprises a $C_{22}$ saturated linear aliphatic chain. In some embodiments, $R^{LD}$ is or comprises a $C_{22}$ partially unsaturated linear aliphatic chain. In some embodiments, $R^{LD}$ is or comprises a $C_{23}$ saturated linear aliphatic chain. In some embodiments, $R^{LD}$ is or comprises a $C_{23}$ partially unsaturated linear aliphatic chain. In some embodiments, $R^{LD}$ is or comprises a $C_{24}$ saturated linear aliphatic chain. In some embodiments, $R^{LD}$ is or comprises a $C_{24}$ partially unsaturated linear aliphatic chain. In some embodiments, $R^{LD}$ is or comprises a $C_{25}$ saturated linear aliphatic chain. In some embodiments, $R^{LD}$ is or comprises a $C_{25}$ partially unsaturated linear aliphatic chain. In some embodiments, $R^{LD}$ is or comprises a $C_{26}$ saturated linear aliphatic chain. In some embodiments, $R^{LD}$ is or comprises a $C_{26}$ partially unsaturated linear aliphatic chain. In some embodiments, $R^{LD}$ is or comprises a $C_{27}$ saturated linear aliphatic chain. In some embodiments, $R^{LD}$ is or comprises a $C_{27}$ partially unsaturated linear aliphatic chain. In some embodiments, $R^{LD}$ is or comprises a $C_{28}$ saturated linear aliphatic chain. In some embodiments, $R^{LD}$ is or comprises a $C_{28}$ partially unsaturated linear aliphatic chain. In some embodiments, $R^{LD}$ is or comprises a $C_{29}$ saturated linear aliphatic chain. In some embodiments, $R^{LD}$ is or comprises a $C_{29}$ partially unsaturated linear aliphatic chain. In some embodiments, $R^{LD}$ is or comprises a $C_{30}$ saturated linear aliphatic chain. In some embodiments, $R^{LD}$ is or comprises a $C_{30}$ partially unsaturated linear aliphatic chain.

In some embodiments, a lipid has the structure of $R^{LD}$—OH. In some embodiments, a lipid has the structure of $R^{LD}$—C(O)OH. In some embodiments, $R^{LD}$ is

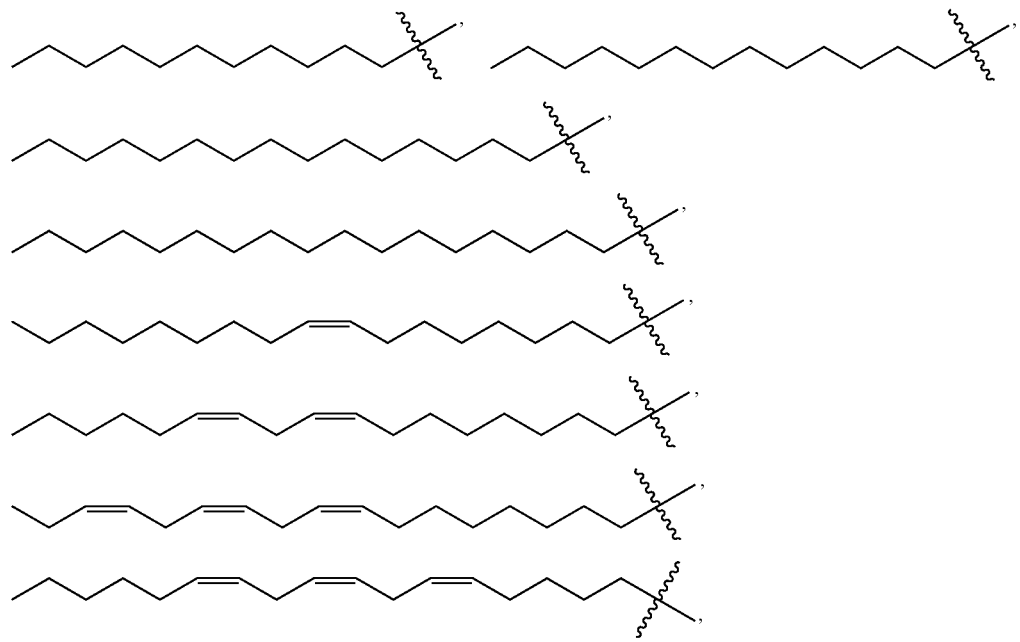

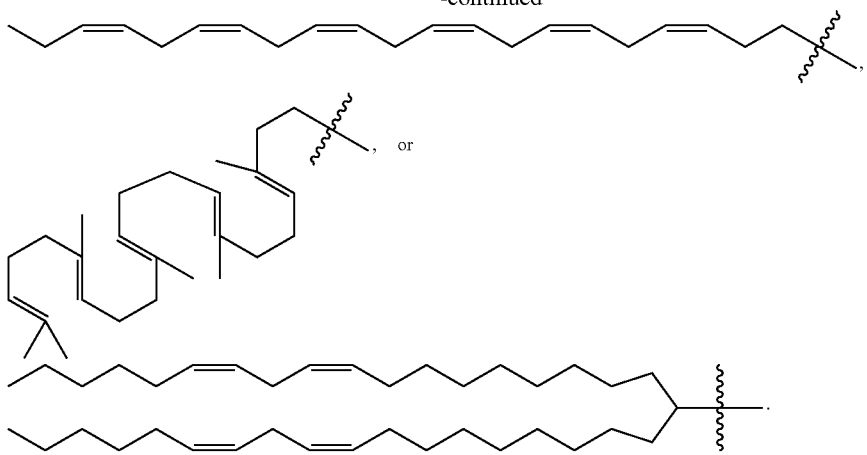

In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, arachidonic acid, and dilinoleyl. In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, and dilinoleyl. In some embodiments, a lipid has a structure of:

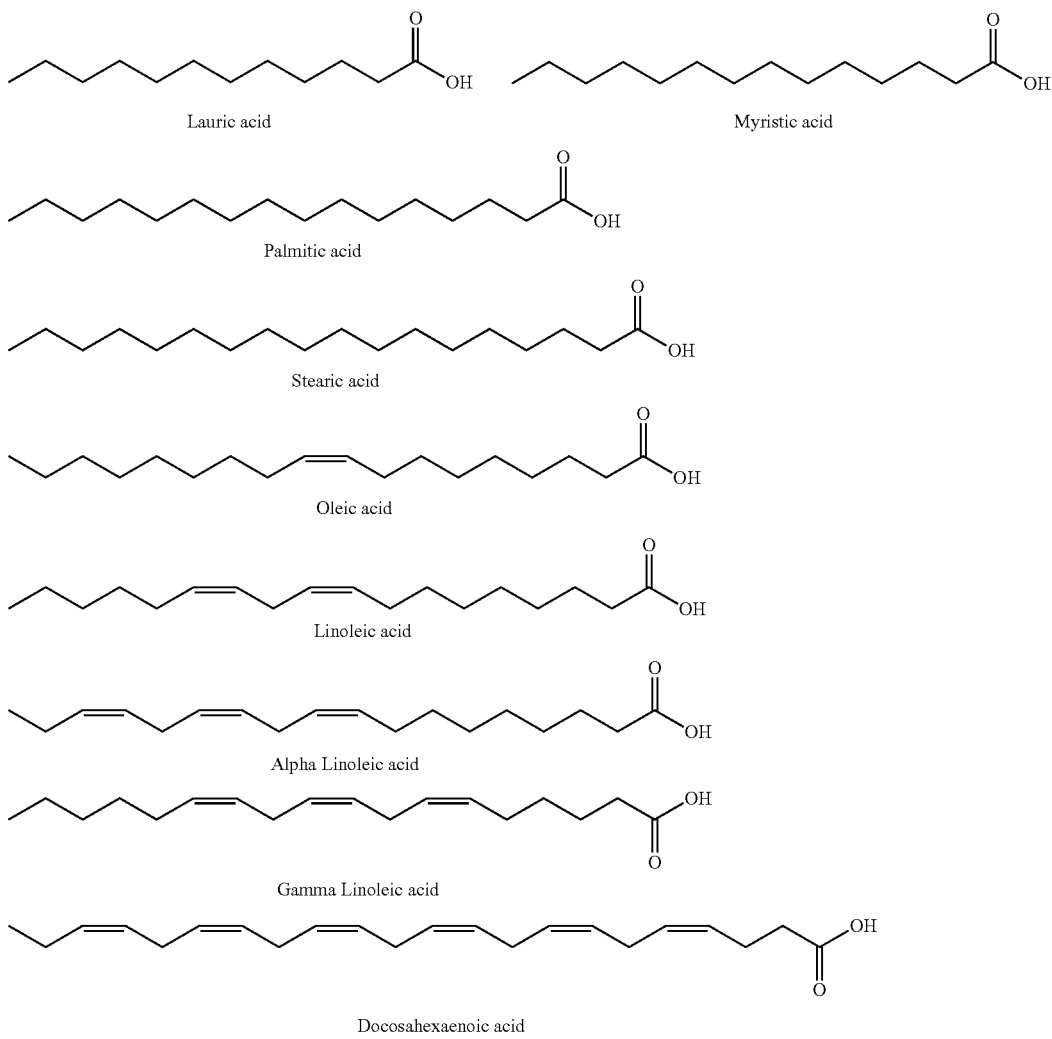

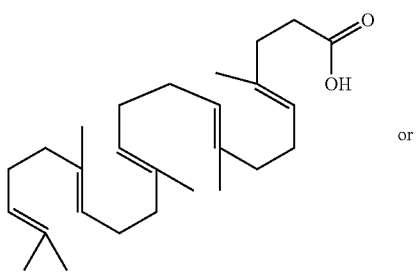

Turbinaric acid

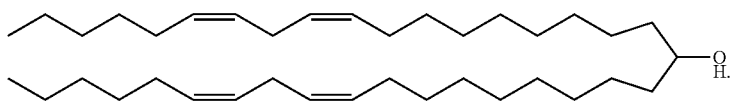

Dilinoleyl alcohol

In some embodiments, a lipid is, comprises or consists of any of: an at least partially hydrophobic or amphiphilic molecule, a phospholipid, a triglyceride, a diglyceride, a monoglyceride, a fat-soluble vitamin, a sterol, a fat and a wax. In some embodiments, a lipid is any of: a fatty acid, glycerolipid, glycerophospholipid, sphingolipid, sterol lipid, prenol lipid, saccharolipid, polyketide, and other molecule.

Lipids can be incorporated into provided technologies through many types of methods in accordance with the present disclosure. In some embodiments, lipids are physically mixed with provided oligonucleotides to form provided compositions. In some embodiments, lipids are chemically conjugated with oligonucleotides.

In some embodiments, provided compositions comprise two or more lipids. In some embodiments, provided oligonucleotides comprise two or more conjugated lipids. In some embodiments, the two or more conjugated lipids are the same. In some embodiments, the two or more conjugated lipids are different. In some embodiments, provided oligonucleotides comprise no more than one lipid. In some embodiments, oligonucleotides of a provided composition comprise different types of conjugated lipids. In some embodiments, oligonucleotides of a provided composition comprise the same type of lipids.

Lipids can be conjugated to oligonucleotides optionally through linkers. Various types of linkers in the art can be utilized in accordance with the present disclosure. In some embodiments, a linker comprise a phosphate group, which can, for example, be used for conjugating lipids through chemistry similar to those employed in oligonucleotide synthesis. In some embodiments, a linker comprises an amide, ester, or ether group. In some embodiments, a linker has the structure of -L-. In some embodiments, after conjugation to oligonucleotides, a lipid forms a moiety having the structure of -L-$R^{LD}$, wherein each of L and $R^{LD}$ is independently as defined and described herein.

In some embodiments, -L- comprises a bivalent aliphatic chain. In some embodiments, -L- comprises a phosphate group. In some embodiments, -L- comprises a phosphorothioate group. In some embodiments, -L- has the structure of —C(O)NH—$(CH_2)_6$—OP($=$O)($S^-$)—.

Lipids, optionally through linkers, can be conjugated to oligonucleotides at various suitable locations. In some embodiments, lipids are conjugated through the 5'-OH group. In some embodiments, lipids are conjugated through the 3'-OH group. In some embodiments, lipids are conjugated through one or more sugar moieties. In some embodiments, lipids are conjugated through one or more bases. In some embodiments, lipids are incorporated through one or more internucleotidic linkages. In some embodiments, an oligonucleotide may contain multiple conjugated lipids which are independently conjugated through its 5'-OH, 3'-OH, sugar moieties, base moieties and/or internucleotidic linkages.

In some embodiments, a lipid is conjugated to an oligonucleotide optionally through a linker moiety. A person having ordinary skill in the art appreciates that various technologies can be utilized to conjugate lipids to an oligonucleotide in accordance with the present disclosure. For example, for lipids comprising carboxyl groups, such lipids can be conjugated through the carboxyl groups. In some embodiments, a lipid is conjugated through a linker having the structure of -L-, wherein L is as defined and described in formula I. In some embodiments, L comprises a phosphate diester or modified phosphate diester moiety. In some embodiments, a compound formed by lipid conjugation has the structure of ($R^{LD}$-L-)$_x$-(oligonucleotide), wherein x is 1 or an integer greater than 1, and each of $R^{LD}$ and L is independently as defined and described herein. In some embodiments, x is 1. In some embodiments, x is greater than 1. In some embodiments, an oligonucleotide is an oligonucleotide. For example, in some embodiments, a conjugate has the following structures:

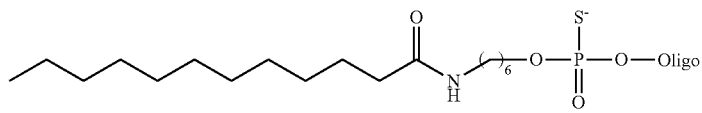

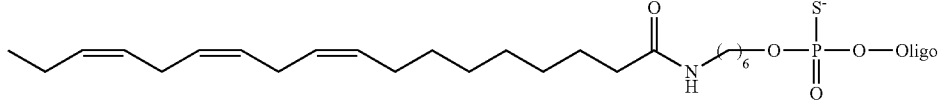

In some embodiments, a linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; and a linker comprising at least one peptide-based cleavage group.

In some embodiments, a lipid is not conjugated to an oligonucleotide.

In some embodiments, the present disclosure pertains to compositions and methods related to a composition comprising an oligonucleotide and a lipid comprising a $C_{10}$-$C_{40}$ linear, saturated or partially unsaturated, aliphatic chain, wherein the lipid is conjugated to the biologically active agent. In some embodiments, the present disclosure pertains to compositions and methods related to a composition comprising an oligonucleotide and a lipid comprising a $C_{10}$-$C_{40}$ linear, saturated or partially unsaturated, aliphatic chain, optionally substituted with one or more $C_{1-4}$ aliphatic group, wherein the lipid is conjugated to the biologically active agent.

In some embodiments, the present disclosure pertains to compositions and methods related to a composition comprising an oligonucleotide and a lipid comprising a $C_{10}$-$C_{40}$ linear, saturated or partially unsaturated, aliphatic chain, wherein the lipid is not conjugated to the biologically active agent. In some embodiments, the present disclosure pertains to compositions and methods related to a composition comprising an oligonucleotide and a lipid comprising a $C_{10}$-$C_{40}$ linear, saturated or partially unsaturated, aliphatic chain, optionally substituted with one or more $C_{1-4}$ aliphatic group, wherein the lipid is not conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is not conjugated to the biologically active agent. In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is not conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is conjugated to the biologically active agent. In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is directly conjugated to the biologically active agent (without a linker interposed between the lipid and the biologically active agent). In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is directly conjugated to the biologically active agent (without a linker interposed between the lipid and the biologically active agent).

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is indirectly conjugated to the biologically active agent (with a linker interposed between the lipid and the biologically active agent). In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is indirectly conjugated to the biologically active agent (with a linker interposed between the lipid and the biologically active agent).

A linker is a moiety that connects two parts of a composition; as a non-limiting example, a linker physically connects an oligonucleotide to a lipid.

Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

In some embodiments, a linker comprises an uncharged linker or a charged linker.

In some embodiments, a linker comprises an alkyl.

In some embodiments, a linker comprises a phosphate. In various embodiments, a phosphate can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon can be done. When the bridging oxygen is the 5'-oxygen of a nucleoside, replacement with nitrogen can be done. In various embodiments, the linker comprising a phosphate comprises any one or more of: a phosphorodithioate, phosphoramidate, boranophosphonate, or a compound of formula (I):

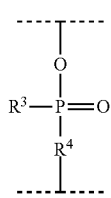

where $R^3$ is selected from OH, SH, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_6$-io aryl are unsubstituted or optionally independently substituted with 1 to 3 groups independently selected from halo, hydroxyl and $NH_2$; and $R^4$ is selected from O, S, NH, or $CH_2$.

In some embodiments, a linker comprises a direct bond or an atom such as oxygen or sulfur, a unit such as $NR^1$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherероaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, a linker is a branched linker. In some embodiments, a branchpoint of the branched linker may be at least trivalent, but may be a tetravalent, pentavalent or hexavalent atom, or a group presenting such multiple valencies. In some embodiments, a branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

In one embodiment, a linker comprises at least one cleavable linking group.

As a non-limiting example, a cleavable linking group can be sufficiently stable outside the cell, but which upon entry into a target cell is cleaved to release the two parts the linker is holding together. As a non-limiting example, a cleavable linking group is cleaved at least 10 times or more, at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

As a non-limiting example, a cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a desired pH, thereby releasing the cationic lipid from the ligand inside the cell, or into the desired compartment of the cell.

As a non-limiting example, a linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

As a non-limiting example, a linker can contain a peptide bond, which can be used when targeting cell types rich in peptidases, such as liver cells and synoviocytes.

As a non-limiting example, suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. As a non-limiting example, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, a linker comprises a redox cleavable linking group. As a non-limiting example, one class of cleavable linking groups are redox cleavable linking groups that are cleaved upon reduction or oxidation. A non-limiting example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. As a non-limiting example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. As a non-limiting example, candidate compounds are cleaved by at most 10% in the blood. As a non-limiting example, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In some embodiments, a linker comprises a phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —S—P(O)(Rk)-O—, —S—P(S)(Rk)-O—, —S—P(O)(Rk)-S—, —O—P(S)(Rk)-S—. Additional non-limiting examples are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. An additional non-limiting examples is —O—P(O)(OH)—O—.

In some embodiments, a linker comprises an acid cleavable linking groups are linking groups that are cleaved under acidic conditions. As a non-limiting example, acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). In an additional non-limiting example, when the carbon attached to the oxygen of the ester (the alkoxy group) is an aryl group, substituted alkyl group, or tertiary alkyl group such as dimethyl pentyl or t-butyl.

In some embodiments, a linker comprises an ester-based linking groups. As a non-limiting example, ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In some embodiments, a linker comprises a peptide-based cleaving group. Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. As a non-limiting example, peptide-based cleavable groups do not include the amide group (—C(O)NH—). The amide group can be formed between any alkylene, alkenylene or alkynylene. A peptide bond is a special type of amide bond formed between amino acids to yield peptides and proteins. As a non-limiting example, a peptide based cleavage group can be limited to the peptide bond (i.e., the amide bond) formed between amino acids yielding peptides and proteins and does not include the entire amide functional group. As a non-limiting example, a peptide-based cleavable linking groups can have the general formula —NHCHR$^A$C(O)NHCHR$^B$C(O)—, where R$^A$ and R$^B$ are the R groups of the two adjacent amino acids. These candidates can be evaluated using methods analogous to those described above.

Any linker reported in the art can be used, including, as non-limiting examples, those described in: U.S. Pat. App. No. 20150265708.

A non-limiting example of a method of conjugating a lipid and an oligonucleotide is presented in Example 1.

A non-limiting example of a linker is a C6 amino linker.

Target Components

In some embodiments, a provided composition further comprises a targeting component (targeting compound or moiety). A target component can be either conjugated or not conjugated to a lipid or a biologically active agent. In some embodiments, a target component is conjugated to a biologically active agent. In some embodiments, a biologically active agent is conjugated to both a lipid and a targeting component. As described in here, in some embodiments, a biologically active agent is a provided oligonucleotide. Thus, in some embodiments, a provided oligonucleotide composition further comprises, besides a lipid and oligonucleotides, a target elements. Various targeting components can be used in accordance with the present disclosure, e.g., lipids, antibodies, peptides, carbohydrates, etc.

Target components can be incorporated into provided technologies through many types of methods in accordance with the present disclosure. In some embodiments, target components are physically mixed with provided oligonucleotides to form provided compositions. In some embodiments, target components are chemically conjugated with oligonucleotides.

In some embodiments, provided compositions comprise two or more target components. In some embodiments, provided oligonucleotides comprise two or more conjugated target components. In some embodiments, the two or more conjugated target components are the same. In some embodiments, the two or more conjugated target components are different. In some embodiments, provided oligonucleotides comprise no more than one target component. In some embodiments, oligonucleotides of a provided composition comprise different types of conjugated target components. In some embodiments, oligonucleotides of a provided composition comprise the same type of target components.

Target components can be conjugated to oligonucleotides optionally through linkers. Various types of linkers in the art can be utilized in accordance of the present disclosure. In some embodiments, a linker comprise a phosphate group, which can, for example, be used for conjugating target components through chemistry similar to those employed in oligonucleotide synthesis. In some embodiments, a linker comprises an amide, ester, or ether group. In some embodiments, a linker has the structure of -L-. Target components can be conjugated through either the same or different linkers compared to lipids.

Target components, optionally through linkers, can be conjugated to oligonucleotides at various suitable locations. In some embodiments, target components are conjugated through the 5'-OH group. In some embodiments, target components are conjugated through the 3'-OH group. In some embodiments, target components are conjugated through one or more sugar moieties. In some embodiments, target components are conjugated through one or more bases. In some embodiments, target components are incorporated through one or more internucleotidic linkages. In some embodiments, an oligonucleotide may contain multiple conjugated target components which are independently conjugated through its 5'-OH, 3'-OH, sugar moieties, base moieties and/or internucleotidic linkages. Target components and lipids can be conjugated either at the same, neighboring and/or separated locations. In some embodiments, a target component is conjugated at one end of an oligonucleotide, and a lipid is conjugated at the other end.

In some embodiments, the oligonucleotide or oligonucleotides in a chirally controlled oligonucleotide composition is or are antisense oligonucleotide or oligonucleotides. In some embodiments, the sequence of the oligonucleotide(s) comprises or consists of the sequence of any oligonucleotide disclosed herein. In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein. In some embodiments, the sequence of the oligonucleotide(s) comprises or consists of the sequence of any oligonucleotide disclosed in Table 8.

In some embodiments, an antisense oligonucleotide is an oligonucleotide which participates in RNaseH-mediated cleavage; for example, an antisense oligonucleotide hybridizes in a sequence-specific manner to a portion of a target mRNA, thus targeting the mRNA for cleavage by RNaseH. In some embodiments, an antisense oligonucleotide is able to differentiate between different alleles of the same gene or target. In some embodiments, an antisense oligonucleotide is able to differentiate between a wild-type and a mutant allele of a target. In some embodiments, an antisense oligonucleotide significantly participates in RNaseH-mediated cleavage of a mutant allele but participates in RNaseH-mediated cleavage of a wild-type allele to a much less degree (e.g., does not significantly participate in RNaseH-mediated cleavage of the wild-type allele of the target). In some embodiments, an antisense oligonucleotide is capable of participating in RNAseH-mediated cleavage of a nucleic acid comprising a mutation. In some embodiments, an antisense oligonucleotide targets a mutant allele. In some embodiments, an antisense oligonucleotide targets a mutant allele of the Huntingtin gene.

In some embodiments, an antisense oligonucleotide is able to differentiate between a wild-type and a mutant allele of a target in the Huntingtin gene.

In some embodiments, the present disclosure pertains to:

A method for inhibiting expression of a mutant Huntingtin gene in a mammal comprising preparing a composition comprising a lipid and an oligonucleotide (as a non-limiting example, an antisense oligonucleotide that targets a mutant allele of the Huntingtin gene) and administering the composition to the mammal.

A method of treating a disease that is caused by the over-expression of a mutant Huntingtin gene in a subject, said method comprising the administration of a composition comprising a lipid and an oligonucleotide (as a non-limiting example, an antisense oligonucleotide that targets a mutant allele of the Huntingtin gene).

A method of treating Huntington's Disease, said method comprising the administration of a composition comprising a lipid and an oligonucleotide (as a non-limiting example, an antisense oligonucleotide that targets a mutant allele of the Huntingtin gene).

A method for treating a sign and/or symptom of Huntington's Disease in a subject by providing a composition comprising a lipid and an oligonucleotide (as a non-limiting example, an antisense oligonucleotide that targets a mutant allele of the Huntingtin gene) and administering a therapeutically effective amount of the composition to the subject.

A method of administering an oligonucleotide to a subject in need thereof, comprising steps of providing a composition comprising an oligonucleotide and a lipid, and administering the composition to the subject, wherein the biologically active compound is an oligonucleotide (as a non-limiting example, an antisense oligonucleotide that targets a mutant allele of the Huntingtin gene), and wherein the lipid is any lipid disclosed herein.

A method of treating a disease in a subject, the method comprising steps of providing a composition comprising an oligonucleotide and a lipid, and administering a therapeutically effective amount of the composition to the subject, wherein the biologically active compound is an oligonucleotide (as a non-limiting example, an antisense oligonucleotide that targets a mutant allele of the Huntingtin gene), and wherein the lipid is any lipid disclosed herein, and wherein the disease is any disease disclosed herein.

A method for inhibiting expression of a mutant Huntingtin gene in a mammal, the method comprising steps of preparing a composition comprising a lipid and an oligonucleotide (as a non-limiting example, an antisense oligonucleotide that targets a mutant allele of the Huntingtin gene) and administering the composition to the mammal.

A method of administering a biologically active agent to a subject in need thereof, comprising steps of providing a composition comprising a biologically active agent and a lipid, and administering the composition to the subject, wherein the biologically active compound is an oligonucleotide (as a non-limiting example, an antisense oligonucleotide that targets a mutant allele of the Huntingtin gene), and wherein the lipid is any lipid disclosed herein.

A method of treating Huntington's Disease in a subject, the method comprising steps of providing a composition comprising a biologically active agent and a lipid, and administering a therapeutically effective amount of the composition to the subject, wherein the biologically active compound is an oligonucleotide (as a non-limiting example, an antisense oligonucleotide that targets a mutant allele of the Huntingtin gene), and wherein the lipid is any lipid disclosed herein.

A method for mediating RNAseH-mediated cleavage of a nucleic acid comprising a mutant Huntingtin gene in a mammal, the method comprising steps of preparing a composition comprising a lipid and an antisense oligonucleotide and administering the composition to the mammal.

A method of treating a disease that is caused by a mutation in a Huntingtin gene, said method comprising the administration of a composition comprising a lipid and an antisense oligonucleotide, wherein the oligonucleotide is capable of participating in RNaseH-mediated cleavage of a nucleic acid comprising the mutation.

A method for treating a sign and/or symptom of Huntington's Disease in a subject by providing a composition comprising a lipid and an oligonucleotide (as a non-limiting example, an antisense oligonucleotide that targets a mutant allele of the Huntingtin gene) and administering a therapeutically effective amount of the composition to the subject.

A method of administering an oligonucleotide to a subject in need thereof, comprising steps of providing a composition comprising an oligonucleotide and a lipid, and administering the composition to the subject, wherein the oligonucleotide is capable of participating in RNaseH-mediated cleavage of a nucleic acid comprising a mutation, and wherein the lipid is any lipid disclosed herein.

A method of treating Huntington's Disease in a subject, wherein the disease or disorder is related to a mutation in a gene, the method comprising steps of providing a composition comprising an oligonucleotide and a lipid, and administering a therapeutically effective amount of the composition to the subject, wherein the oligonucleotide is capable of participating in RNaseH-mediated cleavage of a nucleic acid comprising the mutation, and wherein the lipid is any lipid disclosed herein.

A method for mediating RNAseH-mediated cleavage of a nucleic acid comprising a mutant Huntingtin gene in a mammal, the method comprising steps of preparing a composition comprising a lipid and an antisense oligonucleotide and administering the composition to the mammal.

A method of treating a disease related to a mutation in the Huntingtin gene, said method comprising the administration of a composition comprising a lipid and an antisense oligonucleotide, wherein the antisense oligonucleotide is capable of participating in RNaseH-mediated cleavage of a nucleic acid comprising the mutation.

A method of treating a disease that is caused by a mutation in the Huntingtin gene, said method comprising the administration of a composition comprising a lipid and an oligonucleotide, wherein the oligonucleotide is capable of participating in RNaseH-mediated cleavage of a nucleic acid comprising the mutation.

A method for treating a sign and/or symptom of Huntington's Disease in a subject by providing a composition comprising a lipid and an oligonucleotide (as a non-limiting example, an antisense oligonucleotide that targets a mutant allele of the Huntingtin gene) and administering a therapeutically effective amount of the composition to the subject.

A method of administering an oligonucleotide to a subject in need thereof, comprising steps of providing a composition comprising an oligonucleotide and a lipid, and administering the composition to the subject, wherein the oligonucleotide is capable of participating in RNaseH-mediated cleavage of a nucleic acid comprising the mutation, and wherein the lipid is any lipid disclosed herein.

A method of treating Huntington's Disease in a subject, wherein the Huntington's Disease is related to a mutation in the Huntingtin gene, the method comprising steps of providing a composition comprising an oligonucleotide and a lipid, and administering a therapeutically effective amount of the composition to the subject, wherein the oligonucleotide is capable of participating in RNaseH-mediated cleavage of a nucleic acid comprising the mutation, and wherein the lipid is any lipid disclosed herein.

A method for mediating RNAseH-mediated cleavage of a nucleic acid comprising a mutant Huntingtin gene in a mammal, the method comprising steps of preparing a composition comprising a lipid and an antisense oligonucleotide and administering the composition to the mammal, wherein the lipid is any lipid disclosed herein, and wherein the sequence of the antisense oligonucleotide comprises or consists of the sequence of any antisense oligonucleotide disclosed herein (e.g., in Table 8). In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein (e.g., in Table 8).

A method of treating a disease related to a mutation in the Huntingtin gene, said method comprising the administration of a composition comprising a lipid and an antisense oligonucleotide, wherein the antisense oligonucleotide is capable of participating in RNaseH-mediated cleavage of a nucleic acid comprising the mutation, wherein the lipid is any lipid disclosed herein, and wherein the sequence of the antisense oligonucleotide comprises or consists of the sequence of any antisense oligonucleotide disclosed herein (e.g., in Table 8).

A method of treating a disease that is caused by a mutation in the Huntingtin gene, said method comprising the administration of a composition comprising a lipid and an oligonucleotide, wherein the oligonucleotide is capable of participating in RNaseH-mediated cleavage of a nucleic acid comprising the mutation, wherein the lipid is any lipid disclosed herein, and wherein the oligonucleotide comprises or consists of the sequence of any antisense oligonucleotide disclosed herein (e.g., in Table 8).

A method for treating a sign and/or symptom of Huntington's Disease in a subject by providing a composition comprising a lipid and an oligonucleotide (as a non-limiting example, an antisense oligonucleotide that targets a mutant allele of the Huntingtin gene) and administering a therapeutically effective amount of the composition to the subject, wherein the lipid is any lipid disclosed herein, and wherein the sequence of the oligonucleotide comprises or consists of the sequence of any antisense oligonucleotide disclosed herein (e.g., in Table 8).

A method of administering an oligonucleotide to a subject in need thereof, comprising steps of providing a composition comprising an oligonucleotide and a lipid, and administering the composition to the subject, wherein the oligonucleotide is capable of participating in RNaseH-mediated cleavage of a nucleic acid comprising the mutation, and wherein the lipid is any lipid disclosed herein, wherein the lipid is any lipid disclosed herein, and wherein the sequence of the oligonucleotide comprises or consists of the sequence of any antisense oligonucleotide disclosed herein (e.g., in Table 8).

A method of treating Huntington's Disease in a subject, wherein the Huntington's Disease is related to a mutation in the Huntingtin gene, the method comprising steps of providing a composition comprising an oligonucleotide and a lipid, and administering a therapeutically effective amount of the composition to the subject, wherein the oligonucleotide is capable of participating in RNaseH-mediated cleavage of a nucleic acid comprising the mutation, and wherein the lipid is any lipid disclosed herein, and wherein the oligonucleotide comprises or consists of the sequence of any antisense oligonucleotide disclosed herein (e.g., in Table 8).

In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein.

In some embodiments, an oligonucleotide composition comprises a plurality of oligonucleotides, which share:

1) a common base sequence;
2) a common pattern of backbone linkages; and
3) a common pattern of backbone phosphorus modifications;
wherein one or more oligonucleotides of the plurality are individually conjugated to a lipid.

In some embodiments, a chirally controlled oligonucleotide composition comprises a plurality of oligonucleotides, which share:
1) a common base sequence;
2) a common pattern of backbone linkages; and
3) a common pattern of backbone phosphorus modifications;
wherein:
the composition is chirally controlled in that the plurality of oligonucleotides share the same stereochemistry at one or more chiral internucleotidic linkages;
one or more oligonucleotides of the plurality are individually conjugated to a lipid; and
one or more oligonucleotides of the plurality are optionally and individually conjugated to a targeting compound or moiety.

In some embodiments, an antisense oligonucleotide is in a chirally controlled oligonucleotide composition. In some embodiments, an oligonucleotide is in a chirally controlled oligonucleotide composition.

Various oligonucleotides are listed in Table 8. Many of these are capable of participating in RNaseH-mediated cleavage of the human Huntingtin gene, as shown in data presented in U.S. Pat. Application No. 62/195,779, filed Jul. 22, 2015, and U.S. Pat. Application No. 62/331,960, filed May 4, 2016, which are incorporated by reference in its entirety; and in data shown here.

Various oligonucleotides particularly capable of participating in RNaseH-mediated cleavage of human Huntingtin gene target or a mutant variant thereof include: WV-1087, WV-937, WV-1090, WV-1091, WV-937, WV-2601, WV-2611, WV-1092, WVE120101, WV-2603, WV-2595, WV-2378, WV-2380, WV-1510, WV-2619, WV-2611, WV-1497, WV-2602, WV-2618, and WV-2601, or any other nucleic acid disclosed herein (including, but not limited to, those listed in Table 8). In some embodiments, the present disclosure provides:
An oligonucleotide:

(SEQ ID NO: 1554)
mG*SmGmCmAmC*SA*SA*SG*SG*SG*SC*SA*SC*RA*SG*SmAmCm

UmU*SmC, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide:

(SEQ ID NO: 1094)
mG*SmCmAmCmA*SA*SG*SG*SG*SC*SA*SC*RA*SG*SA*SmCmUm

UmC*SmC, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.

An oligonucleotide:

(SEQ ID NO: 1465)
mG*SmCmAmCmA*SC*SA*SG*ST*SA*SG*RA*ST*SG*SA*SmGmG mGmA*SmG, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide:

(SEQ ID NO: 190)
G*SmGmCmAmC*SA*SA*SG*SG*SG*SC*SA*SC*RA*SG*

SmAmCmUmU*SC, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide:

(SEQ ID NO: 192)
mG*mGmCmAmC*A*A*G*G*G*C*A*C*A*G*mAmCmUmU*mC, pharmaceutically acceptable salt thereof, wherein:
* is a phosphorothioate linkage,
each non-labeled linkage is a natural phosphate linkage, and
m preceding a base represents 2'-OMe.
An oligonucleotide:

(SEQ ID NO: 11)
mG*SmGmGmUmC*SC*ST*SC*SC*SC*SC*SA*SC*RA*SG*SmAmGmG mG*SmA, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide:

(SEQ ID NO: 10)
mG*mGmGmUmC*C*T*C*C*C*C*A*C*A*G*mAmGmGmG*mA, pharmaceutically acceptable salt thereof, wherein:
* is a phosphorothioate linkage,
each non-labeled linkage is a natural phosphate linkage, and
m preceding a base represents 2'-OMe.
An oligonucleotide:

(SEQ ID NO: 13)
mG*SmUmGmCmA*SC*SA*SC*SA*SG*ST*SA*SG*RA*ST*SmGmAm

GmG*SmG, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.

An oligonucleotide:

(SEQ ID NO: 12)
mG*mUmGmCmA*C*A*C*A*G*T*A*G*A*T*mGmAmGmG*mG, pharmaceutically acceptable salt thereof, wherein:
* is a phosphorothioate linkage,
each non-labeled linkage is a natural phosphate linkage, and
m preceding a base represents 2'-OMe.

An oligonucleotide:

(SEQ ID NO: 1448)
mC*SmAmCmAmA*SG*SG*SG*SC*SA*SC*RA*SG*SA*SC*SmUmUm
CmC*SmA, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.

An oligonucleotide:

(SEQ ID NO: 1466)
mU*SmGmCmAmC*SA*SC*SA*SG*ST*SA*SG*RA*ST*SG*SmAmGm
GmG*SmA, or a pharmaceutically acceptable salt thereof, wherein:
*S is an Sp phosphorothioate linkage,
*R is an Rp phosphorothioate linkage,
each non-labeled linkage is a natural phosphate linkage, and
m preceding a base represents 2'-OMe.

An oligonucleotide:

(SEQ ID NO: 1482)
mU*mGmCmAmC*A*C*A*G*T*A*G*A*T*G*mAmGmG*mA, pharmaceutically acceptable salt thereof, wherein:
* is a phosphorothioate linkage,
each non-labeled linkage is a natural phosphate linkage, and
m preceding a base represents 2'-OMe.

An oligonucleotide, wherein:
the base sequence comprises (SEQ ID NO: 821)
GGCACAAGGGCACAGACUUC, the length of the oligonucleotide is no more than 50 bases, and
the oligonucleotide comprises one or more chiral modified internucleotidic linkages.

An oligonucleotide, wherein:
the base sequence comprises (SEQ ID NO: 1114)
UGCACACAGTAGATGAGGGA, the length of the oligonucleotide is no more than 50 bases, and
the oligonucleotide comprises one or more chiral modified internucleotidic linkages.

An oligonucleotide, wherein:
the base sequence comprises (SEQ ID NO: 823)
CACAAGGGCACAGACUUCCA, the length of the oligonucleotide is no more than 50 bases, and
the oligonucleotide comprises one or more chiral modified internucleotidic linkages.

An oligonucleotide, wherein:
the base sequence comprises (SEQ ID NO: 1115)
GUGCACACAGTAGATGAGGG, the length of the oligonucleotide is no more than 50 bases, and
the oligonucleotide comprises one or more chiral modified internucleotidic linkages.

An oligonucleotide, wherein:
the base sequence comprises (SEQ ID NO: 1107)
GGGUCCTCCCCACAGAGGGA, the length of the oligonucleotide is no more than 50 bases, and
the oligonucleotide comprises one or more chiral modified internucleotidic linkages.

An oligonucleotide, wherein:
the base sequence comprises (SEQ ID NO: 821)
GGCACAAGGGCACAGACUUC, the length of the oligonucleotide is no more than 50 bases, and
the oligonucleotide comprises one or more chiral modified internucleotidic linkages.

An oligonucleotide, wherein:
the base sequence comprises (SEQ ID NO: 1113)
GCACACAGTAGATGAGGGAG, the length of the oligonucleotide is no more than 50 bases, and
the oligonucleotide comprises one or more chiral modified internucleotidic linkages.

An oligonucleotide, wherein:
the base sequence comprises (SEQ ID NO: 822)
GCACAAGGGCACAGACUUCC, the length of the oligonucleotide is no more than 50 bases, and
the oligonucleotide comprises one or more chiral modified internucleotidic linkages.

An oligonucleotide, wherein:
the base sequence is (SEQ ID NO: 821)
GGCACAAGGGCACAGACUUC, and
the oligonucleotide comprises one or more chiral modified internucleotidic linkages.

An oligonucleotide, wherein:
the base sequence is (SEQ ID NO: 1114)
UGCACACAGTAGATGAGGGA, and
the oligonucleotide comprises one or more chiral modified internucleotidic linkages.

An oligonucleotide, wherein:
the base sequence is (SEQ ID NO: 823)
CACAAGGGCACAGACUUCCA, and
the oligonucleotide comprises one or more chiral modified internucleotidic linkages.

An oligonucleotide, wherein:
the base sequence is (SEQ ID NO: 1115)
GUGCACACAGTAGATGAGGG, and
the oligonucleotide comprises one or more chiral modified internucleotidic linkages.

An oligonucleotide, wherein:
the base sequence is (SEQ ID NO: 1107)
GGGUCCTCCCCACAGAGGGA, and
the oligonucleotide comprises one or more chiral modified internucleotidic linkages.

An oligonucleotide, wherein:
the base sequence is (SEQ ID NO: 821)
GGCACAAGGGCACAGACUUC, and
the oligonucleotide comprises one or more chiral modified internucleotidic linkages.

An oligonucleotide, wherein:
the base sequence is (SEQ ID NO: 1113)
GCACACAGTAGATGAGGGAG, and
the oligonucleotide comprises one or more chiral modified internucleotidic linkages.

An oligonucleotide, wherein:
the base sequence is (SEQ ID NO: 822)
GCACAAGGGCACAGACUUCC, and
the oligonucleotide comprises one or more chiral modified internucleotidic linkages.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 1554)
mG*SmGmCmAmC*SA*SA*SG*SG*SG*SC*SA*SC*RA*SG*SmAmCmU mU*SmC, wherein:
*S is an Sp phosphorothioate linkage,
*R is an Rp phosphorothioate linkage,
each non-labeled linkage is a natural phosphate linkage, and
m preceding a base represents 2'-OMe,
wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 1094)
mG*SmCmAmCmA*SA*SG*SG*SG*SC*SA*SC*RA*SG*SA*SmCmUmU mC*SmC, wherein:
*S is an Sp phosphorothioate linkage,
*R is an Rp phosphorothioate linkage,
each non-labeled linkage is a natural phosphate linkage, and
m preceding a base represents 2'-OMe, wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 1465)
mG*SmCmAmCmA*SC*SA*SG*ST*SA*SG*RA*ST*SG*SA*SmGmGmG mA*SmG, wherein:
*S is an Sp phosphorothioate linkage,
*R is an Rp phosphorothioate linkage,
each non-labeled linkage is a natural phosphate linkage, and m preceding a base represents 2'-OMe,
wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 190)
G*SmGmCmAmC*SA*SA*SG*SG*SG*SC*SA*SC*RA*SG*SmAmCmUm

U*SC, wherein:
*S is an Sp phosphorothioate linkage,
*R is an Rp phosphorothioate linkage,
each non-labeled linkage is a natural phosphate linkage, and m preceding a base represents 2'-OMe,
wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 11)
mG*SmGmGmUmC*SC*ST*SC*SC*SC*SC*SA*SC*RA*SG*SmAmGmG mG*SmA, wherein:
*S is an Sp phosphorothioate linkage,
*R is an Rp phosphorothioate linkage,
each non-labeled linkage is a natural phosphate linkage, and m preceding a base represents 2'-OMe,
wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 13)
mG*SmUmGmCmA*SC*SA*SC*SA*SG*ST*SA*SG*RA*ST*SmGmAmG mG*SmG, wherein:
*S is an Sp phosphorothioate linkage,
*R is an Rp phosphorothioate linkage, each non-labeled linkage is a natural phosphate linkage, and m preceding a base represents 2'-OMe, wherein the substantially racemic preparation of oligonucleotides is prepared by nonstereoselective preparation, wherein at least one chiral internucleotidic linkage is formed with less than 80:20 diastereomeric selectivity.

A chirally controlled oligonucleotide composition comprising oligonucleotides defined by having:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the common base sequence and length, the common pattern of backbone linkages, and the common pattern of backbone chiral centers are those of:

(SEQ ID NO: 1466)
mU*SmGmCmAmC*SA*SC*SA*SG*ST*SA*SG*RA*ST*SG*SmAmGmG mG*SmA, wherein:
*S is an Sp phosphorothioate linkage,
*R is an Rp phosphorothioate linkage, each non-labeled linkage is a natural phosphate linkage, and m preceding a base represents 2'-OMe, wherein the substantially racemic preparation of oligonucleotides is prepared by nonstereoselective preparation, wherein at least one chiral internucleotidic linkage is formed with less than 80:20 diastereomeric selectivity.

An oligonucleotide composition comprising oligonucleotides defined by having:
1) a common base sequence and length; and
2) a common pattern of backbone linkages;
wherein the common base sequence and length and the common pattern of backbone linkages are those of:

(SEQ ID NO: 1482)
mU*mGmCmAmC*A*C*A*G*T*A*G*A*T*G*mAmGmGmG*mA, wherein:
* is a phosphorothioate linkage,
each non-labeled linkage is a natural phosphate linkage, and m preceding a base represents 2'-OMe.

An oligonucleotide composition comprising oligonucleotides defined by having: 1) a common base sequence and length; and
2) a common pattern of backbone linkages;
wherein the common base sequence and length and common pattern of backbone linkages are those of:

(SEQ ID NO: 192)
mG*mGmCmAmC*A*A*G*G*G*C*A*C*A*G*mAmCmUmU*mC, wherein:
* is a phosphorothioate linkage,
each non-labeled linkage is a natural phosphate linkage, and m preceding a base represents 2'-OMe.

An oligonucleotide composition comprising oligonucleotides defined by having: 1) a common base sequence and length; and
2) a common pattern of backbone linkages;
wherein the common base sequence and length and common pattern of backbone linkages are those of:

(SEQ ID NO: 10)
mG*mGmGmUmC*C*T*C*C*C*A*C*A*G*mAmGmGmG*mA, wherein:
* is a phosphorothioate linkage,
each non-labeled linkage is a natural phosphate linkage, and m preceding a base represents 2'-OMe.

An oligonucleotide composition comprising oligonucleotides defined by having:
1) a common base sequence and length; and
2) a common pattern of backbone linkages;
wherein the common base sequence and length and common pattern of backbone linkages are those of:

(SEQ ID NO: 12)
mG*mUmGmCmA*C*A*C*A*G*T*A*G*A*T*mGmAmGmG*mG, wherein:
* is a phosphorothioate linkage,
each non-labeled linkage is a natural phosphate linkage, and m preceding a base represents 2'-OMe.

An oligonucleotide composition comprising oligonucleotides defined by having:
1) a common base sequence and length; and
2) a common pattern of backbone linkages;
the common pattern of backbone linkages, and the common pattern of backbone chiral centers are those of:

(SEQ ID NO: 1448)
mC*SmAmCmAmA*SG*SG*SG*SC*SA*SC*RA*SG*SA*SC*SmUmUm CmC*SmA, wherein:
*S is an Sp phosphorothioate linkage,
*R is an Rp phosphorothioate linkage,
each non-labeled linkage is a natural phosphate linkage, and m preceding a base represents 2'-OMe.

A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 1554)
mG*SmGmCmAmC*SA*SA*SG*SG*SG*SC*SA*SC*RA*SG*SmAmCmU mU*SmC, wherein:
*S is an Sp phosphorothioate linkage,
*R is an Rp phosphorothioate linkage,
each non-labeled linkage is a natural phosphate linkage, and m preceding a base represents 2'-OMe.

A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 1094)
mG*SmCmAmCmA*SA*SG*SG*SG*SC*SA*SC*RA*SG*SA*SmCmUmU mC*SmC, wherein:
*S is an Sp phosphorothioate linkage,
*R is an Rp phosphorothioate linkage,
each non-labeled linkage is a natural phosphate linkage, and m preceding a base represents 2'-OMe.

A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 1465)
mG*SmCmAmCmA*SC*SA*SG*ST*SA*SG*RA*ST*SG*SA*SmGmGmG mA*SmG, wherein:
*S is an Sp phosphorothioate linkage,
*R is an Rp phosphorothioate linkage,
each non-labeled linkage is a natural phosphate linkage, and
m preceding a base represents 2'-OMe.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 190)
G*SmGmCmAmC*SA*SA*SG*SG*SG*SC*SA*SC*RA*SG*SmAmCmUm

U*SC, wherein:
*S is an Sp phosphorothioate linkage,
*R is an Rp phosphorothioate linkage,
each non-labeled linkage is a natural phosphate linkage, and
m preceding a base represents 2'-OMe.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 11)
mG*SmGmGmUmC*SC*ST*SC*SC*SC*SC*SA*SC*RA*SG*SmAmGmG mG*SmA, wherein:
*S is an Sp phosphorothioate linkage,
*R is an Rp phosphorothioate linkage,
each non-labeled linkage is a natural phosphate linkage, and
m preceding a base represents 2'-OMe.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 13)
mG*SmUmGmCmA*SC*SA*SC*SA*SG*ST*SA*SG*RA*ST*SmGmAmG mG*SmG, wherein:
*S is an Sp phosphorothioate linkage,
*R is an Rp phosphorothioate linkage,
each non-labeled linkage is a natural phosphate linkage, and
m preceding a base represents 2'-OMe.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers of:

(SEQ ID NO: 1466)
mU*SmGmCmAmC*SA*SC*SA*SG*ST*SA*SG*RA*ST*SG*SmAmGmG mG*SmA, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide composition comprising oligonucleotides defined by having:
1) a common base sequence and length; and
2) a common pattern of backbone linkages;
wherein the common base sequence and length and the common pattern of backbone linkages of:

(SEQ ID NO: 1482)
mU*mGmCmAmC*A*C*A*G*T*A*G*A*T*G*mAmGmGmG*mA, wherein:
*S is an Sp phosphorothioate linkage,
*R is an Rp phosphorothioate linkage,
each non-labeled linkage is a natural phosphate linkage, and
m preceding a base represents 2'-OMe.
An oligonucleotide composition comprising oligonucleotides defined by having:
1) a common base sequence and length and
2) a common pattern of backbone linkages,
wherein the common base sequence and length and the common pattern of backbone linkages are those of:

(SEQ ID NO: 192)
mG*mGmCmAmC*A*A*G*G*C*A*C*A*G*mAmCmUmU*mC, wherein:
* is a phosphorothioate linkage,
each non-labeled linkage is a natural phosphate linkage, and
m preceding a base represents 2'-OMe.
An oligonucleotide composition comprising oligonucleotides defined by having:
1) a common base sequence and length and
2) a common pattern of backbone linkages, which composition is a substantially pure preparation of a single oligonucleotide in that at least about 10% of the oligonucleotides in the composition have the common base sequence and length and the common pattern of backbone linkages:

(SEQ ID NO: 10)
mG*mGmGmUmC*C*T*C*C*C*A*C*A*G*mAmGmGmG*mA, wherein:
* is a phosphorothioate linkage,
each non-labeled linkage is a natural phosphate linkage, and
m preceding a base represents 2'-OMe.
An oligonucleotide composition comprising oligonucleotides defined by having:
1) a common base sequence and length and
2) a common pattern of backbone linkages,
wherein the common base sequence and length and the common pattern of backbone linkages are those of:

(SEQ ID NO: 12)
mG*mUmGmCmA*C*A*C*A*G*T*A*G*A*T*mGmAmGmG*mG, wherein:
* is a phosphorothioate linkage,
each non-labeled linkage is a natural phosphate linkage, and
m preceding a base represents 2'-OMe.
An oligonucleotide composition comprising oligonucleotides defined by having:
1) a common base sequence and length and
2) a common pattern of backbone linkages,
which composition is a substantially pure preparation of a single oligonucleotide in that at least about 10% of the oligonucleotides in the composition have the common base sequence and length and the common pattern of backbone linkages:

(SEQ ID NO: 1448)
mC*SmAmCmAmA*SG*SG*SG*SC*SA*SC*RA*SG*SA*SC*SmUmUmC
mC*SmA, wherein:
*S is an Sp phosphorothioate linkage,
*R is an Rp phosphorothioate linkage,
each non-labeled linkage is a natural phosphate linkage, and
m preceding a base represents 2'-OMe.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises (SEQ ID NO: 1114)
UGCACACAGTAGATGAGGGA, and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises (SEQ ID NO: 823)
CACAAGGGCACAGACUUCCA, and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises (SEQ ID NO: 1115)
GUGCACACAGTAGATGAGGG, and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises (SEQ ID NO: 1107)
GGGUCCTCCCCACAGAGGGA, and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises (SEQ ID NO: 821)
GGCACAAGGGCACAGACUUC, and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises

GGCACAAGGGCACAGACUUC, (SEQ ID NO: 821)

and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises

GCACACAGTAGATGAGGGAG, (SEQ ID NO: 1113)

and wherein the length is no more than about 50 bases.
A chirally controlled oligonucleotide composition comprising oligonucleotides defined by having:
1) a common base sequence and length;
2) a common pattern of backbone linkages; and
3) a common pattern of backbone chiral centers,
which composition is a substantially pure preparation of a single oligonucleotide in that at least about 10% of the oligonucleotides in the composition have the common base sequence and length, the common pattern of backbone linkages, and the common pattern of backbone chiral centers, wherein the common base sequence comprises

GCACAAGGGCACAGACUUCC, (SEQ ID NO: 822)

and wherein the length is no more than about 50 bases.
A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises

UGCACACAGTAGATGAGGGA, (SEQ ID NO: 1114)

the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation, wherein at least one chiral internucleotidic linkage is formed with less than 80:20 diastereomeric selectivity.
A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises

CACAAGGGCACAGACUUCCA, (SEQ ID NO: 823)

the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation, wherein at least one chiral internucleotidic linkage is formed with less than 80:20 diastereomeric selectivity.
A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises

GUGCACACAGTAGATGAGGG, (SEQ ID NO: 1115)

the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation, wherein at least one chiral internucleotidic linkage is formed with less than 80:20 diastereomeric selectivity.
A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:

the common base sequence comprises (SEQ ID NO: 1107)
GGGUCCUCCCCACAGAGGGA, the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation,
wherein at least one chiral internucleotidic linkage is formed with less than 80:20 diastereomeric selectivity.

A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises (SEQ ID NO: 821)
GGCACAAGGGCACAGACUUC, the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation,
wherein at least one chiral internucleotidic linkage is formed with less than 80:20 diastereomeric selectivity.

A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises (SEQ ID NO: 821)
GGCACAAGGGCACAGACUUC, the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation,
wherein at least one chiral internucleotidic linkage is formed with less than 80:20 diastereomeric selectivity.

A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises (SEQ ID NO: 1113)
GCACACAGTAGATGAGGGAG, the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation,
wherein at least one chiral internucleotidic linkage is formed with less than 80:20 diastereomeric selectivity.

A chirally controlled oligonucleotide composition comprising oligonucleotides of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein:
the common base sequence comprises (SEQ ID NO: 822)
GCACAAGGGCACAGACUUCC, the length is no more than about 50 nucleotides,
the backbone linkages comprise at least one phosphorothioate,
the pattern of backbone chiral centers comprises at least one Rp chiral center and at least one Sp chiral center,
wherein the substantially racemic preparation of oligonucleotides is prepared by nonstereoselective preparation,
wherein at least one chiral internucleotidic linkage is formed with less than 80:20 diastereomeric selectivity.

Any oligonucleotide or chirally controlled oligonucleotide composition can be used in combination with any method or composition (e.g., any pharmaceutical composition, modification, and/or method of use and/or manufacture) disclosed herein.

In some embodiments, the present disclosure provides the following embodiments:
1. A chirally controlled oligonucleotide composition comprising oligonucleotides defined by having:
   1) a common base sequence and length;
   2) a common pattern of backbone linkages; and
   3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

2. A chirally controlled oligonucleotide composition comprising oligonucleotides of a particular oligonucleotide type characterized by:
 1) a common base sequence and length;
 2) a common pattern of backbone linkages; and
 3) a common pattern of backbone chiral centers;
which composition is chirally controlled in that it is enriched, relative to a substantially racemic preparation of oligonucleotides having the same base sequence and length, for oligonucleotides of the particular oligonucleotide type.

3. A chirally controlled oligonucleotide composition comprising oligonucleotides of a particular oligonucleotide type characterized by:
 1) a common base sequence and length;
 2) a common pattern of backbone linkages; and
 3) a common pattern of backbone chiral centers;
which composition is chirally controlled in that it is enriched, relative to a substantially racemic preparation of oligonucleotides having the same base sequence and length, for oligonucleotides of the particular oligonucleotide type, wherein the oligonucleotides target a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation.

4. A chirally controlled oligonucleotide composition comprising oligonucleotides defined by having:
 1) a common base sequence and length;
 2) a common pattern of backbone linkages; and
 3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

5. The composition of any one of the preceding embodiments, wherein the oligonucleotides comprise one or more wing regions and a common core region, wherein:
 each wing region independently has a length of two or more bases, and independently and optionally comprises one or more chiral internucleotidic linkages; and
 the core region independently has a length of two or more bases and independently comprises one or more chiral internucleotidic linkages.

6. An oligonucleotide composition comprising a predetermined level of oligonucleotides which comprise one or more wing regions and a common core region, wherein:
 each wing region independently has a length of two or more bases, and independently and optionally comprises one or more chiral internucleotidic linkages;
 the core region independently has a length of two or more bases, and independently comprises one or more chiral internucleotidic linkages, and the common core region has:
 1) a common base sequence and length;
 2) a common pattern of backbone linkages; and
 3) a common pattern of backbone chiral centers.

7. An oligonucleotide composition comprising a predetermined level of oligonucleotides which comprise one or more wing regions and a common core region, wherein:
 each wing region independently has a length of two or more bases, and independently and optionally comprises one or more chiral internucleotidic linkages;
 the core region independently has a length of two or more bases, and independently comprises one or more chiral internucleotidic linkages, and the core region has:
 1) a common base sequence;
 2) a common pattern of backbone linkages;
 3) a common pattern of backbone chiral centers; and
 4) a common pattern of backbone phosphorus modifications.

8. The composition of any one of the preceding embodiments, wherein oligonucleotides of the oligonucleotide type comprises at least one wing region and a core region, wherein:
 each wing region independently has a length of two or more bases, and independently and optionally comprises one or more chiral internucleotidic linkages;
 the core region independently has a length of two or more bases, and independently comprises one or more chiral internucleotidic linkages; and
 wherein at least one nucleotide in a wing region differs from at least one nucleotide of the core region, wherein the difference is in one or more of:
 1) backbone linkage;
 2) pattern of backbone chiral centers;
 3) sugar modification.

9. The composition of any one of the preceding embodiments, wherein the oligonucleotides are defined by having a common pattern of backbone phosphorus modifications.

10. The composition of any one of the preceding embodiments, wherein the composition contains a predetermined level of oligonucleotides of an individual oligonucleotide type, wherein an oligonucleotide type is defined by:
 1) base sequence;
 2) pattern of backbone linkages;
 3) pattern of backbone chiral centers; and
 4) pattern of backbone phosphorus modifications.

11. The composition of any one of the preceding embodiments, wherein oligonucleotides having a common base sequence is of the same oligonucleotide type characterized by base sequence, pattern of backbone linkages, pattern of backbone chiral centers, and pattern of backbone phosphorus modifications.

12. The composition of any one of the preceding embodiments, wherein the composition contains predetermined levels of oligonucleotides of two or more individual oligonucleotide types, wherein an oligonucleotide type is defined by:
 1) base sequence;
 2) pattern of backbone linkages;
 3) pattern of backbone chiral centers; and
 4) pattern of backbone phosphorus modifications.

13. An oligonucleotide composition that is chirally controlled in that the composition contains a predetermined level of oligonucleotides of an individual oligonucleotide type, wherein an oligonucleotide type is defined by:
 1) base sequence;
 2) pattern of backbone linkages;
 3) pattern of backbone chiral centers; and
 4) pattern of backbone phosphorus modifications.

14. The composition of any one of the preceding embodiments, wherein the composition comprises two or more individual oligonucleotide types.

15. The composition of any one of the preceding embodiments, wherein an oligonucleotide type is defined by base identity, pattern of base modification, pattern of sugar modification, pattern of backbone linkages, pattern of backbone chiral centers, and pattern of backbone phosphorus modifications.

16. A composition comprising an oligonucleotide having the structure of formula O—I:

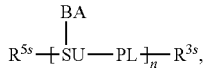

or a salt thereof, wherein:

$R^{5s}$ is R' or —Y—R';

each R' is independently —R, —C(O)R, —CO$_2$R, or —SO$_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms;

each R is independently hydrogen, or an optionally substituted group selected from $C_{1-30}$ aliphatic, $C_{1-30}$ heteroaliphatic having 1-10 heteroatoms, $C_{6-30}$ aryl, a 5-30 membered heteroaryl ring having 1-10 heteroatoms, and a 3-30 membered heterocyclic ring having 1-10 heteroatoms; or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms;

Y is O, S, N(-L-R$^1$)—, or L;

L is a covalent bond, or a bivalent, optionally substituted, linear or branched group selected from $C_{1-30}$ aliphatic and $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

R$^1$ is halogen, R, or an optionally substituted $C_1$-$C_{50}$ aliphatic wherein one or more methylene units are optionally and independently replaced by an optionally substituted group selected from $C_{1-6}$ alkylene, $C_{1-6}$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

-Cy- is an optionally substituted bivalent ring selected from 3-30 membered carbocyclylene, 6-30 membered arylene, 5-30 membered heteroarylene having 1-10 heteroatoms, and 3-30 membered heterocyclylene having 1-10 heteroatoms;

BA is an optionally substituted group selected from $C_{1-30}$ cycloaliphatic, $C_{6-30}$ aryl, $C_{3-30}$ heterocyclyl having 1-10 heteroatoms, $C_{5-30}$ heteroaryl having 1-10 heteroatoms, a natural nucleobase moiety, and a modified nucleobase moiety, or

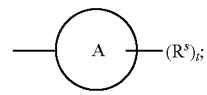

Ring A is an optionally substituted multivalent, monocyclic, bicyclic or polycyclic, saturated, partially unsaturated, or aryl 3-30 membered ring having, in addition to the intervening atoms, 0-10 heteroatoms;

each RS is independently R', -L-R', R', or -L-R';

t is 0-5;

SU is L, or

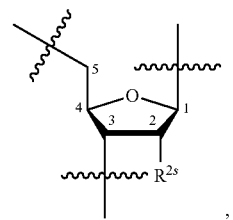

wherein SU is connected to PL through C3;

PL is

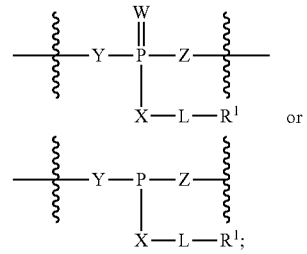

W is O, S or Se;

each of X and Z is independently —O—, —S—, —N(L R$^1$)—, or L;

R$^{2s}$ is —F, —CN, —N$_3$, —NO, —NO$_2$, —R'—OR', —SR', —N(R')$_2$, —O-L-OR', —O-L-SR', or —O-L-N(R')$_2$, or R$^{2s}$ is L connecting C2 with C1, C2, C3, C4 or C5;

n is an integer greater than 3; and

R$^{3s}$ is R', —Y—R', —SU(BA)-Y—R', or —SU(BA)-Y-solid support.

17. The composition of embodiment 16, wherein the oligonucleotide comprises at least at least 5, 6, 7, 8, 9, 10, 11, 12, 13, 14, 15, 16, 17, 18, 19 or 20 PL that are chiral in that the phosphorus atom is asymmetric.

18. The composition of embodiment 17, wherein each chiral PL independently has a diastereopurity of 80%, 85%, 90%, 91%, 92%, 93%, 94%, 95%, 96%, 97%, 98%, 99% or more within the composition.

19. The composition of embodiment 17, wherein each chiral PL independently has a diastereopurity of 90%, 91%, 92%, 93%, 94%, 95%, 96%, 97%, 98%, 99% or more within the composition.

20. The composition of any one of embodiments 1-15, wherein the oligonucleotides are of the structure of formula O—I.

21. The composition of any one of the preceding embodiments, wherein oligonucleotides having a common sequence have identical structure.

22. The composition of any one of the preceding embodiments, wherein oligonucleotides of the same oligonucleotide type have identical structure.
23. The composition of any one of the preceding embodiments, wherein the oligonucleotides have one wing.
24. The composition of any one of the preceding embodiments, wherein the oligonucleotides are hemimers having the structure of wing-core.
25. The composition of any one of the preceding embodiments, wherein the oligonucleotides are hemimers having the structure of core-wing.
26. The composition of any one of embodiments 1-22, wherein the oligonucleotides have two wings.
27. The composition of any one of embodiments 1-22, wherein the oligonucleotides are gapmers having the structure of wing-core-wing.
28. The composition of any one of the preceding embodiments, wherein a wing comprises a chiral internucleotidic linkage.
29. The composition of any one of the preceding embodiments, wherein each wing independently comprises a chiral internucleotidic linkage.
30. The composition of any one of embodiments 1-24 and 26-29, wherein a wing to the 5'-end of the core comprises a chiral internucleotidic linkage at the 5'-end of the wing.
31. The composition of any one of embodiments 1-23 and 25-29, wherein a wing to the 3'-end of the core comprises a chiral internucleotidic linkage at the 3'-end of the wing.
32. The composition of any one the preceding embodiments, wherein a wing has only one chiral internucleotidic linkage, and each of the other internucleotidic linkages of the wing is a natural phosphate linkage

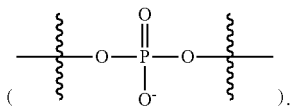 [SMILES: *OP(=O)([O-])O*]

33. The composition of any one of the preceding embodiments, wherein the chiral internucleotidic linkage has the structure of formula I.
34. The composition of any one of the preceding embodiments, wherein a chiral internucleotidic linkage has the structure of formula I, and wherein X is S, and Y and Z are O.
35. The composition of any one of the preceding embodiments, wherein a chiral internucleotidic linkage is a phosphorothioate linkage.
36. The composition of any one of the preceding embodiments, wherein a chiral internucleotidic linkage is Sp.
37. The composition of any one of the preceding embodiments, wherein each chiral internucleotidic linkage is Sp.
38. The composition of any one of embodiments 1-36, wherein a chiral internucleotidic linkage is Rp.
39. The composition of any one of embodiments 1-35, wherein each chiral internucleotidic linkage is Rp.
40. The composition of any one of embodiments 1-38, wherein a wing comprises an Sp phosphorothioate linkage.
41. The composition of any one of embodiments 1-38, wherein each wing independently comprises an Sp phosphorothioate linkage.
42. The composition of any one of embodiments 1-24, 26-38, and 40-41, wherein a wing is to the 5'-end of the core, and the wing has an Sp phosphorothioate linkage.

43. The composition of any one of embodiments 1-24, 26-38, and 40-42, wherein a wing is to the 5'-end of the core, and the wing has an Sp phosphorothioate linkage at the 5'-end of the wing.
44. The composition of any one of embodiments 1-24, 26-38, and 40-43, wherein a wing is to the 5'-end of the core, the wing has an Sp phosphorothioate linkage at the 5'-end of the wing, and each of the other internucleotidic linkages of the wing is a natural phosphate linkage

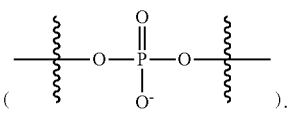

45. The composition of any one of embodiments 1-23, 25-38 and 40-41, wherein a wing is to the 3'-end of the core, and the wing has an Sp phosphorothioate linkage at the 3'-end of the wing.
46. The composition of any one of embodiments 1-23, 25-38, 40-41 and 45, wherein a wing is to the 3'-end of the core, and the wing has an Sp phosphorothioate linkage at the 3'-end of the wing.
47. The composition of any one of embodiments 1-23, 25-38, 40-41 and 45-46, wherein one wing is to the 3'-end of the common core, the wing has an Sp phosphorothioate linkage at the 3'-end of the wing, and each of the other internucleotidic linkages of the wing is a natural phosphate linkage

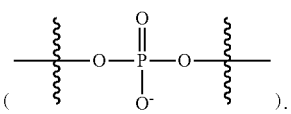

48. The composition of any one of embodiments 1-36 and 38-47, wherein a wing comprises an Rp phosphorothioate linkage.
49. The composition of any one of embodiments 1-36 and 38-47, wherein each wing independently comprises an Rp phosphorothioate linkage.
50. The composition of any one of embodiments 1-24, 26-36 and 38-49, wherein a wing is to the 5'-end of the core, and the wing has an Rp phosphorothioate linkage.
51. The composition of any one of embodiments 1-24, 26-36 and 38-50, wherein a wing is to the 5'-end of the core, and the wing has an Rp phosphorothioate linkage at the 5'-end of the wing.
52. The composition of any one of embodiments 1-24, 26-36 and 38-51, wherein a wing is to the 5'-end of the core, the wing has an Rp phosphorothioate linkage at the 5'-end of the wing, and each of the other internucleotidic linkages of the wing is a natural phosphate linkage

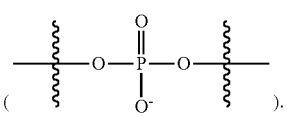 [SMILES: *OP(=O)([O-])O*]

53. The composition of any one of embodiments 1-23, 25-36 and 38-49, wherein a wing is to the 3'-end of the core, and the wing has an Rp phosphorothioate.

54. The composition of any one of embodiments 1-23, 25-36 and 38-49, wherein a wing is to the 3'-end of the core, and the wing has an Rp phosphorothioate linkage at the 3'-end of the wing.
55. The composition of any one of embodiments 1-23, 25-36 and 38-49, wherein one wing is to the 3'-end of the common core, the wing has an Rp phosphorothioate linkage at the 3'-end of the wing, and each of the other internucleotidic linkages of the wing is a natural phosphate linkage

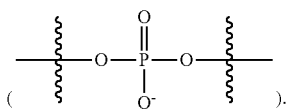 [SMILES: *OP(=O)([O-])O*]

56. The composition of any one of embodiments 1-35, wherein a wing is to the 5'-end of a core, and its 5'-end internucleotidic linkage is a chiral internucleotidic linkage.
57. The composition of any one of embodiments 1-35, wherein a wing is to the 5'-end of a core, and its 5'-end internucleotidic linkage is an Sp chiral internucleotidic linkage.
58. The composition of any one of embodiments 1-35, wherein a wing is to the 5'-end of a core, and its 5'-end internucleotidic linkage is an Rp chiral internucleotidic linkage.
59. The composition of any one of embodiments 1-35 and 56-58, wherein a wing is to the 3'-end of a core, and its 3'-end internucleotidic linkage is a chiral internucleotidic linkage.
60. The composition of any one of embodiments 1-35 and 56-58, wherein a wing is to the 3'-end of a core, and its 3'-end internucleotidic linkage is an Sp chiral internucleotidic linkage.
61. The composition of any one of embodiments 1-35 and 56-58, wherein a wing is to the 3'-end of a core, and its 3'-end internucleotidic linkage is an Rp chiral internucleotidic linkage.
62. The composition of any one of the preceding embodiments, wherein each wing independently comprises a natural phosphate linkage

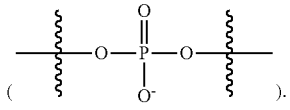 [SMILES: *OP(=O)([O-])O*]

63. The composition of any one of the preceding embodiments, wherein each wing independently comprises two or more natural phosphate linkages

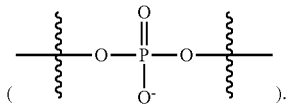 [SMILES: *OP(=O)([O-])O*]

64. The composition of any one of the preceding embodiments, wherein each wing independently comprises two or more natural phosphate linkages, and all natural phosphate linkages are consecutive.
65. The composition of any one of the preceding embodiments, wherein a wing has a length of three or more bases.
66. The composition of any one of the preceding embodiments, wherein one wing has a length of four or more bases.
67. The composition of any one of the preceding embodiments, wherein one wing has a length of five or more bases.
68. The composition of any one of the preceding embodiments, wherein one wing has a length of six or more bases.
69. The composition of any one of the preceding embodiments, wherein one wing has a length of seven or more bases.
70. The composition of any one of the preceding embodiments, wherein one wing has a length of eight or more bases.
71. The composition of any one of the preceding embodiments, wherein one wing has a length of nine or more bases.
72. The composition of any one of the preceding embodiments, wherein one wing has a length of ten or more bases.
73. The composition of any one of the preceding embodiments, wherein each wing independently has a length of three or more bases.
74. The composition of any one of the preceding embodiments, wherein each wing independently has a length of four or more bases.
75. The composition of any one of the preceding embodiments, wherein each wing independently has a length of five or more bases.
76. The composition of any one of the preceding embodiments, wherein each wing independently has a length of six or more bases.
77. The composition of any one of the preceding embodiments, wherein each wing independently has a length of seven or more bases.
78. The composition of any one of the preceding embodiments, wherein each wing independently has a length of eight or more bases.
79. The composition of any one of the preceding embodiments, wherein each wing independently has a length of nine or more bases.
80. The composition of any one of the preceding embodiments, wherein each wing independently has a length of ten or more bases.
81. The composition of any one of embodiments 1-64, wherein a wing has a length of two bases.
82. The composition of any one of embodiments 1-64, wherein a wing has a length of three bases.
83. The composition of any one of embodiments 1-64, wherein a wing has a length of four bases.
84. The composition of any one of embodiments 1-64, wherein a wing has a length of five bases.
85. The composition of any one of embodiments 1-64, wherein a wing has a length of six bases.
86. The composition of any one of embodiments 1-64, wherein a wing has a length of seven bases.
87. The composition of any one of embodiments 1-64, wherein a wing has a length of eight bases.
88. The composition of any one of embodiments 1-64, wherein a wing has a length of nine bases.
89. The composition of any one of embodiments 1-64, wherein a wing has a length of ten bases.
90. The composition of any one of embodiments 1-64, wherein a wing has a length of 11 bases.
91. The composition of any one of embodiments 1-64, wherein a wing has a length of 12 bases.
92. The composition of any one of embodiments 1-64, wherein a wing has a length of 13 bases.
93. The composition of any one of embodiments 1-64, wherein a wing has a length of 14 bases.
94. The composition of any one of embodiments 1-64, wherein a wing has a length of 15 bases.

95. The composition of any one of embodiments 1-18 and 22-83, wherein each wing has the same length.
96. The composition of any one of the preceding embodiments, wherein a wing is defined by sugar modifications relative to a core.
97. The composition of any one of the preceding embodiments, wherein each wing independently comprises a modified sugar moiety.
98. The composition of any one of the preceding embodiments, wherein each wing sugar moiety is independently a modified sugar moiety.
99. The composition of any one of the preceding embodiments, wherein a modified sugar moiety comprises a high-affinity sugar modification.
100. The composition of any one of the preceding embodiments, wherein a modified sugar moiety has a 2'-modification.
101. The composition of any one of the preceding embodiments, wherein a modified sugar moiety comprises a bicyclic sugar modification.
102. The composition of any one of the preceding embodiments, wherein a modified sugar moiety comprises a bicyclic sugar modification having a -L- or —O-L-bridge connecting two ring carbon atoms.
103. The composition of any one of the preceding embodiments, wherein a modified sugar moiety comprises a bicyclic sugar modification having a 4'-CH(CH$_3$)—O-2' bridge.
104. The composition of any one of embodiments 1-100, wherein a modified sugar moiety comprises a 2'-modification, wherein a 2'-modification is 2'-OR'.
105. The composition of any one of embodiments 1-100, wherein a modified sugar moiety comprises a 2'-modification, wherein a 2'-modification is 2'-OR', wherein $R^1$ is optionally substituted $_{C_{1-6}}$ alkyl.
106. The composition of any one of embodiments 1-100, wherein a modified sugar moiety comprises a 2'-modification, wherein a 2'-modification is 2'-MOE.
107. The composition of any one of embodiments 1-100, wherein a modified sugar moiety comprises a 2'-modification, wherein a 2'-modification is 2'-OMe.
108. The composition of any one of embodiments 1-103, wherein a modified sugar moiety comprises a 2'-modification, wherein the 2'-modification is S-cEt.
109. The composition of any one of embodiments 1-100, wherein a modified sugar moiety comprises a 2'-modification, wherein the 2'-modification is FANA.
110. The composition of any one of embodiments 1-100, wherein a modified sugar moiety comprises a 2'-modification, wherein the 2'-modification is FRNA.
111. The composition of any one of embodiments 1-99, wherein a modified sugar moiety has a 5'-modification.
112. The composition of any one of embodiments 1-99, wherein a modified sugar moiety is R-5'-Me-DNA.
113. The composition of any one of embodiments 1-99, wherein a modified sugar moiety is S-5'-Me-DNA.
114. The composition of any one of embodiments 1-99, wherein a modified sugar moiety is FHNA.
115. The composition of any one of the preceding embodiments, wherein each wing sugar moiety is modified.
116. The composition of any one of the preceding embodiments, wherein all modified wing sugar moieties within a wing have the same modification.
117. The composition of any one of the preceding embodiments, wherein all modified wing sugar moieties have the same modification.
118. The composition of any one of embodiments 1-108, wherein at least one modified wing sugar moiety is different than another modified wing sugar moiety.
119. The composition of any one of the preceding embodiments, wherein a wing comprises a modified base.
120. The composition of any one of the preceding embodiments, wherein a wing comprises a 2S-dT.
121. The composition of any one of the preceding embodiments, wherein the core region has a length of five or more bases.
122. The composition of any one of the preceding embodiments, wherein the core region has a length of six or more bases.
123. The composition of any one of the preceding embodiments, wherein the core region has a length of seven or more bases.
124. The composition of any one of the preceding embodiments, wherein the core region has a length of eight or more bases.
125. The composition of any one of the preceding embodiments, wherein the core region has a length of nine or more bases.
126. The composition of any one of the preceding embodiments, wherein the core region has a length of ten or more bases.
127. The composition of any one of the preceding embodiments, wherein the core region has a length of 11 or more bases.
128. The composition of any one of the preceding embodiments, wherein the core region has a length of 12 or more bases.
129. The composition of any one of the preceding embodiments, wherein the core region has a length of 13 or more bases.
130. The composition of any one of the preceding embodiments, wherein the core region has a length of 14 or more bases.
131. The composition of any one of the preceding embodiments, wherein the core region has a length of 15 or more bases.
132. The composition of any one of 1-120, wherein the core region has a length of five bases.
133. The composition of any one of 1-120, wherein the core region has a length of six bases.
134. The composition of any one of 1-120, wherein the core region has a length of seven bases.
135. The composition of any one of 1-120, wherein the core region has a length of eight bases.
136. The composition of any one of 1-120, wherein the core region has a length of nine bases.
137. The composition of any one of 1-120, wherein the core region has a length of ten bases.
138. The composition of any one of 1-120, wherein the core region has a length of 11 bases.
139. The composition of any one of 1-120, wherein the core region has a length of 12 bases.
140. The composition of any one of 1-120, wherein the core region has a length of 13 bases.
141. The composition of any one of 1-120, wherein the core region has a length of 14 bases.
142. The composition of any one of 1-120, wherein the core region has a length of 15 bases.
143. The composition of any one of the preceding embodiments, wherein the core region does not have any 2'-modification.
144. The composition of any one of the preceding embodiments, wherein each core sugar moiety is not modified.

145. The composition of any one of the preceding embodiments, wherein each sugar moiety of the core region is the natural DNA sugar moiety.
146. The composition of any one of the preceding embodiments, wherein the core region comprises a chiral internucleotidic linkage.
147. The composition of any one of the preceding embodiments, wherein each internucleotidic linkage of the core region is a chiral internucleotidic linkage.
148. The composition of any one of the preceding embodiments, wherein each internucleotidic linkage of the core region is a chiral internucleotidic linkage having the structure of formula I.
149. The composition of any one of the preceding embodiments, wherein each internucleotidic linkage of the core region is a chiral internucleotidic linkage having the structure of formula I, and wherein X is S, and Y and Z are O.
150. The composition of any one of the preceding embodiments, wherein each internucleotidic linkage of the core region is a chiral internucleotidic linkage having the structure of formula I, and wherein one -L-$R^1$ is not —H.
151. The composition of any one of embodiments 1-149, wherein each internucleotidic linkage of the core region is a phosphorothioate linkage.
152. The composition of any one of the preceding embodiments, wherein the core region has a pattern of backbone chiral center comprises $(Sp)_m(Rp)_n$, wherein m is 1-50, and n is 1-10.
153. The composition of any one of the preceding embodiments, wherein the core region has a pattern of backbone chiral center comprises $(Sp)_m(Rp)_n$, wherein m is 1-50, n is 1-10, and m>n.
154. The composition of any one of the preceding embodiments, wherein the core region has a pattern of backbone chiral center comprises $(Sp)_m(Rp)_n$, wherein m is 2, 3, 4, 5, 6, 7 or 8, and n is 1.
155. The composition of any one of embodiments 1-151, wherein the core region has a pattern of backbone chiral centers comprising $(Rp)_n(Sp)_m$, wherein m is 1-50 and n is 1-10.
156. The composition of any one of embodiments 1-151 and 155, wherein the core region has a pattern of backbone chiral centers comprising $Rp(Sp)_m$, wherein m is 2, 3, 4, 5, 6, 7 or 8.
157. The composition of any one of embodiments 1-151 and 155-156, wherein the core region has a pattern of backbone chiral centers comprising $Rp(Sp)_2$.
158. The composition of any one of embodiments 1-151, wherein the core region has a pattern of backbone chiral centers comprising $(Np)_t(Rp)_n(Sp)_m$, wherein t is 1-10, n is 1-10, m is 1-50, and each Np is independent Rp or Sp.
159. The composition of any one of embodiments 1-151 and 158, wherein the core region has a pattern of backbone chiral centers comprising $(Sp)_t(Rp)_n(Sp)_m$, wherein t is 1-10, n is 1-10, m is 1-50.
160. The composition of any one of embodiments 1-151 and 158-159, wherein n is 1.
161. The composition of any one of embodiments 1-151 and 158-160, wherein t is 2, 3, 4, 5, 6, 7 or 8.
162. The composition of any one of embodiments 1-151 and 158-161, wherein m is 2, 3, 4, 5, 6, 7 or 8.
163. The composition of any one of embodiments 1-151 and 158-162, wherein at least one of t and m is greater than 5.
164. The composition of any one of the preceding embodiments, wherein the core region has a pattern of backbone chiral centers comprising SpSpRpSpSp.
165. The composition of any one of the preceding embodiments, wherein 50% or more of the chiral internucleotidic linkages in the core region have Sp configuration.
166. The composition of any one of the preceding embodiments, wherein 60% or more of the chiral internucleotidic linkages in the core region have Sp configuration.
167. The composition of any one of the preceding embodiments, wherein 70% or more of the chiral internucleotidic linkages in the core region have Sp configuration.
168. The composition of any one of the preceding embodiments, wherein 80% or more of the chiral internucleotidic linkages in the core region have Sp configuration.
169. The composition of any one of the preceding embodiments, wherein 90% or more of the chiral internucleotidic linkages in the core region have Sp configuration.
170. The composition of any one of the preceding embodiments, wherein each internucleotidic linkage in the core region is chiral, the core region has only one Rp, and each of the other internucleotidic linkages in the core region is Sp.
171. The composition of any one of the preceding embodiments, wherein each base moiety in the core is not modified.
172. The composition of any one of embodiments 1-170, wherein the core region comprises a modified base.
173. The composition of any one of embodiments 1-170, wherein the core region comprises a modified base, wherein a modified base is substituted A, T, C or G.
174. The composition of any one of embodiments 1-171, wherein each base moiety in the core region is independently selected from A, T, C and G.
175. The composition of any one of embodiments 1-170, wherein the core region is a DNA sequence whose phosphate linkages are independently replaced with phosphorothioate linkages.
176. The composition of any one of the preceding embodiments, wherein the oligonucleotides are single stranded.
177. The composition of any one of the preceding embodiments, wherein the oligonucleotides are antisense oligonucleotide, antagomir, microRNA, pre-microRNs, antimir, supermir, ribozyme, UI adaptor, RNA activator, RNAi agent, decoy oligonucleotide, triplex forming oligonucleotide, aptamer or adjuvant.
178. The composition of any one of the preceding embodiments, wherein the oligonucleotides are antisense oligonucleotides.
179. The composition of any one of embodiments 1-178, wherein the oligonucleotides have a length of greater than 10 bases.
180. The composition of any one of embodiments 1-178, wherein the oligonucleotides have a length of greater than 11 bases.
181. The composition of any one of embodiments 1-178, wherein the oligonucleotides have a length of greater than 12 bases.
182. The composition of any one of embodiments 1-178, wherein the oligonucleotides have a length of greater than 13 bases.
183. The composition of any one of embodiments 1-178, wherein the oligonucleotides have a length of greater than 14 bases.
184. The composition of any one of embodiments 1-178, wherein the oligonucleotides have a length of greater than 15 bases.
185. The composition of any one of embodiments 1-178, wherein the oligonucleotides have a length of greater than 16 bases.

186. The composition of any one of embodiments 1-178, wherein the oligonucleotides have a length of greater than 17 bases.
187. The composition of any one of embodiments 1-178, wherein the oligonucleotides have a length of greater than 18 bases.
188. The composition of any one of embodiments 1-178, wherein the oligonucleotides have a length of greater than 19 bases.
189. The composition of any one of embodiments 1-178, wherein the oligonucleotides have a length of greater than 20 bases.
190. The composition of any one of embodiments 1-178, wherein the oligonucleotides have a length of greater than 21 bases.
191. The composition of any one of embodiments 1-178, wherein the oligonucleotides have a length of greater than 22 bases.
192. The composition of any one of embodiments 1-178, wherein the oligonucleotides have a length of greater than 23 bases.
193. The composition of any one of embodiments 1-178, wherein the oligonucleotides have a length of greater than 24 bases.
194. The composition of any one of embodiments 1-178, wherein the oligonucleotides have a length of greater than 25 bases.
195. The composition of any one of the preceding embodiments, wherein the oligonucleotides have a length of less than about 200 bases.
196. The composition of any one of the preceding embodiments, wherein the oligonucleotides have a length of less than about 150 bases.
197. The composition of any one of the preceding embodiments, wherein the oligonucleotides have a length of less than about 100 bases.
198. The composition of any one of the preceding embodiments, wherein the oligonucleotides have a length of less than about 50 bases.
199. The composition of any one of the preceding embodiments, wherein the oligonucleotides have a length of less than about 40 bases.
200. The composition of any one of the preceding embodiments, wherein the oligonucleotides have a length of less than about 30 bases.
201. The composition of any one of embodiments 1-178, wherein the oligonucleotides have a length of 10 bases.
202. The composition of any one of embodiments 1-178, wherein the oligonucleotides have a length of 11 bases.
203. The composition of any one of embodiments 1-178, wherein the oligonucleotides have a length of 12 bases.
204. The composition of any one of embodiments 1-178, wherein the oligonucleotides have a length of 13 bases.
205. The composition of any one of embodiments 1-178, wherein the oligonucleotides have a length of 14 bases.
206. The composition of any one of embodiments 1-178, wherein the oligonucleotides have a length of 15 bases.
207. The composition of any one of embodiments 1-178, wherein the oligonucleotides have a length of 16 bases.
208. The composition of any one of embodiments 1-178, wherein the oligonucleotides have a length of 17 bases.
209. The composition of any one of embodiments 1-178, wherein the oligonucleotides have a length of 18 bases.
210. The composition of any one of embodiments 1-178, wherein the oligonucleotides have a length of 19 bases.
211. The composition of any one of embodiments 1-178, wherein the oligonucleotides have a length of 20 bases.
212. The composition of any one of embodiments 1-178, wherein the oligonucleotides have a length of 21 bases.
213. The composition of any one of embodiments 1-178, wherein the oligonucleotides have a length of 22 bases.
214. The composition of any one of embodiments 1-178, wherein the oligonucleotides have a length of 23 bases.
215. The composition of any one of embodiments 1-178, wherein the oligonucleotides have a length of 24 bases.
216. The composition of any one of embodiments 1-178, wherein the oligonucleotides have a length of 25 bases.
217. The composition of any one of the preceding embodiments, wherein the oligonucleotide type is not (Sp, Sp, Rp, Sp, Sp, Rp, Sp, Sp, Rp, Sp, Sp)-d [5mCs1As1Gs1Ts15mCs1Ts1Gs15mCs1Ts1Ts15mCs1G] (SEQ ID NO: 1505) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTsGs5mCsTsTs5mCs-Gs5mCsAs5mCs5mC (5R-(SSR)3-5R) (SEQ ID NO: 1506), wherein in the underlined nucleotide are 2'-MOE modified.
218. The composition of any one of the preceding embodiments, wherein the oligonucleotide is not an oligonucleotide selected from: (Sp, Sp, Rp, Sp, Sp, Rp, Sp, Sp, Rp, Sp, Sp)-d [5mCs1As1Gs1Ts15mCs1Ts1Gs15mCs1Ts1Ts15mCs1G] (SEQ ID NO: 1505) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTsGs5mCsTsTs5mCs-Gs5mCsAs5mCs5mC (5R-(SSR)3-5R) (SEQ ID NO: 1506), wherein in the underlined nucleotide are 2'-MOE modified.
219. The composition of any one of the preceding embodiments, wherein the oligonucleotide is not an oligonucleotide selected from:

```
ONT-106  (Rp)-uucuAGAccuGuuuuGcuudTsdT        PCSK9 sense      (SEQ ID NO: 1507)

ONT-107  (Sp)-uucuAGAccuGuuuuGcuudTsdT        PCSK9 sense      (SEQ ID NO: 1508)

ONT-108  (Rp)-AAGcAAAAcAGGUCuAGAAdTsdT        PCSK9 antisense  (SEQ ID NO: 1509)

ONT-109  (Sp)-AAGcAAAAcAGGUCuAGAAdTsdT        PCSK9 antisense  (SEQ ID NO: 1510)

ONT-110  (Rp, Rp)-asAGcAAAAcAGGUCuAGAAdTsdT   PCSK9 antisense  (SEQ ID NO: 1511)

ONT-111  (Sp, Rp)-asGcAAAAcAGGUCuAGAAdTsdT    PCSK9 antisense  (SEQ ID NO: 1512)

ONT-112  (Sp, Sp)-asGcAAAAcAGGUCuAGAAdTsdT    PCSK9 antisense  (SEQ ID NO: 1513)

ONT-113  (Rp, Sp)-asGcAAAAcAGGUCuAGAAdTsdT    PCSK9 antisense  (SEQ ID NO: 1514)
``` wherein lower case letters represent 2'OMe RNA residues;
capital letters represent 2'OH RNA residues; and bolded and
"s" indicates a phosphorothioate moiety; and

```
PCSK9 (1)  (All (Sp))-ususcsusAsGsAscscsusGsususususGscsusus-     (SEQ ID NO: 1515)
           dTsdT PCSK9 (2)  (All (Rp))-ususcsusAsGsAscscsusGsususususGscsusus-     (SEQ ID NO: 1516)
           dTsdT PCSK9 (3)  (All (Sp))-usucuAsGsAsccuGsuuuuGscuusdTsdT              (SEQ ID NO: 1517)

PCSK9 (4)  (All (Rp))-usucuAsGsAsccuGsuuuuGscuusdTsdT              (SEQ ID NO: 1518)

PCSK9 (5)  (Rp, Sp, Rp, Sp, Rp, Sp, Rp, Sp, Rp, Sp, Rp, Sp,       (SEQ ID NO: 1519)

Rp, Sp, Rp, Sp, Rp, Sp, Rp, Sp)-ususcsusAsGs
           AscscsusGsususususGscsususdTsdT
PCSK9 (6)  (Sp, Rp, Sp, Rp, Sp, Rp, Sp, Rp, Sp, Rp, Sp, Rp,       (SEQ ID NO: 1520)

Sp, Rp, Sp, Rp, Sp, Rp, Sp, Rp)-
           ususcsusAsGsAscscsusGsususususGscsususdTsdT
``` wherein lower case letters represent 2'-OMe RNA residues;
capital letters represent RNA residues; d=2'-deoxy residues;
and "s" indicates a phosphorothioate moiety; and

```
PCSK9 (7)  All (Rp))-AsAsGscsAsAsAsAscsAsGsGsUsCsusAsGsAsAsdTsdT   (SEQ ID NO: 1521)

PCSK9 (8)  (All (Sp))-AsAsGscsAsAsAsAscsAsGsGsUsCsusAsGsAsAsdTsdT  (SEQ ID NO: 1522)

PCSK9 (9)  (All (Rp))-AsAGcAAAAcsAsGsGsUsCsusAsGsAsAsdTsdT         (SEQ ID NO: 1523)

PCSK9 (10) (All (Sp))-AsAGcAAAAcsAsGsGsUsCsusAsGsAsAsdTsdT         (SEQ ID NO: 1524)

PCSK9 (11) (All (Rp))-AAsGscsAsAsAsAscAGGUCuAGAAdTsdT              (SEQ ID NO: 1525)

PCSK9 (12) (All (Sp))-AAsGscsAsAsAsAscAGGUCuAGAAdTsdT              (SEQ ID NO: 1526)

PCSK9 (13) (All (Rp))-AsAsGscAsAsAsAscAsGsGsUsCsuAsGsAsAsdTsdT     (SEQ ID NO: 1527)

PCSK9 (14) (All (Sp))-AsAsGscAsAsAsAscAsGsGsUsCsuAsGsAsAsdTsdT     (SEQ ID NO: 1528)

PCSK9 (15) (All (Rp))-AsAGcAAAsAscAsGsGsUsCsusAsGsAsAsdTsdT        (SEQ ID NO: 1529)

PCSK9 (16) (All (Sp))-AsAGcAAAsAscAsGsGsUsCsusAsGsAsAsdTsdT        (SEQ ID NO: 1530)

PCSK9 (17) (Rp, Sp, Rp, Sp, Rp, Sp, Rp, Sp, Rp, Sp, Rp, Sp,       (SEQ ID NO: 1531)

Rp, Sp)-AsAGcAAAsAscAsGsGsUsCsusAsGsAsAsdTsdT
PCSK9 (18) (Sp, Rp, Sp, Rp, Sp, Rp, Sp, Rp, Sp, Rp, Sp, Rp,       (SEQ ID NO: 1532)

Sp, Rp)-AsAGcAAAsAscAsGsGsUsCsusAsGsAsAsdTsdT
``` wherein lower case letters represent 2'-OMe RNA residues;
capital letters represent RNA residues; d=2'-deoxy residues;
"s" indicates a phosphorothioate moiety; and

```
PCSK9 (19)  (All (Rp))-UfsusCfsusAfsgsAfscsCfsusGfsusUfsus        (SEQ ID NO: 1533)

UfsgsCfsusUfsdTsdT
PCSK9 (20)  (All (Sp))-UfsusCfsusAfsgsAfscsCfsusGfsusUfsus        (SEQ ID NO: 1534)

UfsgsCfsusUfsdTsdT
PCSK9 (21)  (All (Rp))-                                          (SEQ ID NO: 1535)

UfsuCfsuAfsgAfscCfsuGfsuUfsuUfsgCfsuUfsdTsdT
PCSK9 (22)  (All (Sp))-
                                                                 (SEQ ID NO: 1536)
            UfsuCfsuAfsgAfscCfsuGfsuUfsuUfsgCfsuUfsdTsdT
PCSK9 (23)  (Rp, Sp, Rp, Sp, Rp, Sp, Rp, Sp, Rp, Sp, Rp, Sp,     (SEQ ID NO: 1537)

Rp, Sp, Rp, Sp, Rp, Sp, Rp, Sp)-UfsusCfsusAfsgs
            AfscsCfsusGfsusUfsusUfsgsCfsusUfsdTsdT
```

-continued

PCSK9 (24)  (Sp, Rp, Sp, Rp, Sp, Rp, Sp, Rp, Sp, Rp, Sp, Rp,  (SEQ ID NO: 1538)

Sp, Rp, Sp, Rp, Sp, Rp, Sp, Rp)-UfsusCfsusAfsgs
            AfscsCfsusGfsusUfsgsUfsusUfsgsCfsusUfsdTsdT PCSK9 (25)  (All (Rp))-asAfsgsCfsasAfsasAfscsAfsgsGfsusCfsus  (SEQ ID NO: 1539)

AfsgsAfsasdTsdT
PCSK9 (26)  (All (Sp))-asAfsgsCfsasAfsasAfscsAfsgsGfsusCfsus  (SEQ ID NO: 1540)

AfsgsAfsasdTsdT
PCSK9 (27)  (All (Rp))-                                        (SEQ ID NO: 1541)

asAfgCfaAfaAfcsAfsgsGfsusCfsusAfsgsAfsasdTsdT
PCSK9 (28)  (All (Sp))-                                        (SEQ ID NO: 1542)

asAfgCfaAfaAfcsAfsgsGfsusCfsusAfsgsAfsasdTsdT
PCSK9 (29)  (All (Rp))-                                        (SEQ ID NO: 1543)

asAfsgCfsaAfsaAfscAfsgGfsuCfsuAfsgAfsadTsdT
PCSK9 (30)  (All (Sp))-asAfsgCfsaAfsaAfscAfsgGfsuCfsuAfsg     (SEQ ID NO: 1544)

AfsadTsdT
PCSK9 (31)  (Rp, Sp, Rp, Sp, Rp, Sp, Rp, Sp, Rp, Sp, Rp,      (SEQ ID NO: 1545)

Sp, Rp, Sp)-asAfgCfaAfasAfscAfsgsGfsusCfsus
            AfsgsAfsasdTsdT
PCSK9 (32)  (Sp, Rp, Sp, Rp, Sp, Rp, Sp, Rp, Sp, Rp, Sp,      (SEQ ID NO: 1546)

Rp, Sp, Rp)-asAfgCfaAfasAfscAfsgsGfsusCfsus
            AfsgsAfsasdTsdT wherein lower case letters represent 2'-OMe RNA residues; capital letters represent 2'-F RNA residues; d=2'-deoxy residues; and "s" indicates a phosphorothioate moiety; and 220. The composition of any one of the preceding embodiments, wherein the oligonucleotide is not an oligonucleotide selected from:
d[A$_R$C$_S$A$_R$C$_S$A$_R$C$_S$A$_R$C$_S$A$_R$C] (SEQ ID NO: 1555), d[C$_S$C$_S$C$_S$C$_R$C$_R$C$_S$C$_S$C$_S$C$_S$C] (SEQ ID NO: 1556), d[C$_S$C$_S$C$_S$C$_S$C$_S$C$_S$C$_R$C$_R$C$_S$C] (SEQ ID NO: 1557) and d[C$_S$C$_S$C$_S$C$_S$C$_S$C$_R$C$_R$C$_S$C$_S$C] (SEQ ID NO: 1558), wherein R is Rp phosphorothioate linkage, and S is Sp phosphorothioate linkage. 221. The composition of any one of the preceding embodiments, wherein the oligonucleotide is not an oligonucleotide selected from: GGA$_R$T$_S$G$_R$T$_S$T$_R$$^m$C$_S$TCGA (SEQ ID NO: 1547), GGA$_R$T$_R$G$_S$T$_S$T$_R$$^m$C$_R$TCGA (SEQ ID NO: 1548), GGA$_S$T$_S$G$_R$T$_R$T$_S$$^m$C$_S$TCGA (SEQ ID NO: 1549), wherein R is Rp phosphorothioate linkage, S is Sp phosphorothioate linkage, all other linkages are PO, and each $^m$C is a 5-methylcytosine modified nucleoside.
222. The composition of any one of the preceding embodiments, wherein the oligonucleotide is not an oligonucleotide selected from: T$_k$T$_k$$^m$C$_k$AGT$^m$CATGA$^m$CT$_k$T$^m$C$_k$$^m$C$_k$ (SEQ ID NO: 1550), wherein each nucleoside followed by a subscript 'k' indicates a (S)-cEt modification, R is Rp phosphorothioate linkage, S is Sp phosphorothioate linkage, each $^m$C is a 5-methylcytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RSRSSSRRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSS.

223. The composition of any one of the preceding embodiments, wherein the common pattern of backbone chiral centers comprises SSR, RSS, SSRSS, SSRSSR, RSSSRSR-RRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSR-RRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RSRSSSRRRR, RSRRRRSRSR, SSRSSSRRRS, RSSRSRSRSR, RSRSSSRSS, RRRSSRRSRS, SRRSS-RRSRS, RRRRSRSRRR, or SSSSRRRRSR.
224. The composition of any one of the preceding embodiments, wherein the common pattern of backbone chiral centers comprises SSRSS, SSRSSR, RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSR-RRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRRR, RSRRRRSRSR, SSRSSSRRRS, RSSRSRSRSR, RSRSSSRSS, RRRSSRRSRS, SRRSS-RRSRS, RRRRSRSRRR, or SSSSRRRRSR.
225. The composition of any one of the preceding embodiments, wherein the common pattern of backbone chiral centers comprises RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RSRSSSRRRR, RSRRRRSRSR, SSRSSSRRRS, RSSRSRSRSR, RSRSSSRSS, RRRSSRRSRS, SRRSS-RRSRS, RRRRSRSRRR, or SSSSRRRRSR.

226. The composition of any one of the preceding embodiments, wherein the oligonucleotide is not an oligonucleotide selected from:

(SEQ ID NO: 1551)
$T_k T_k{}^m C_k \underline{AGT{}^m CATGA{}^m CTT}_k{}^m C_k{}^m C_k$, wherein each nucleoside followed by a subscript 'k' indicates a (S)-cEt modification, R is Rp phosphorothioate linkage, S is Sp phosphorothioate linkage, each $^m C$ is a 5-methylcytosine modified nucleoside and all internucleoside linkages in the underlined core are phosphorothioates (PS) with stereochemistry patterns selected from: RSSSRSRRRS, RSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSSRSRSR, RSRSRSSRSS, RRRSSRRSRS, SRRSSRRSRS, RRRRSRSRRR, SSSSRRRRSR, RRRRRRRRRR and SSSSSSSSSS.

227. The composition of embodiment 215 or 216, wherein each phosphorothioate moiety of each nucleotide comprising (S)-cEt modification is stereorandom.

228. The composition of any one of the preceding embodiments, wherein the base sequence is or comprises a sequence that is complementary to a target sequence, wherein when contacted with a nucleic acid polymer comprising the target sequence, the composition provides an altered cleavage pattern than a reference cleavage pattern from a reference oligonucleotide composition.

229. The composition of any one of the preceding embodiments, wherein the nucleic acid polymer is RNA, and a reference oligonucleotide composition is a substantially racemic preparation of oligonucleotides that share the common sequence and length.

230. The composition of any one of the preceding embodiments, wherein the nucleic acid polymer is RNA, and a reference oligonucleotide composition is a chirally uncontrolled oligonucleotide composition of oligonucleotides that share the common sequence and length.

231. The composition of any one of the preceding embodiments, wherein the altered cleavage pattern has fewer cleavage sites than the reference cleavage pattern.

232. The composition of any one of the preceding embodiments, wherein the altered cleavage pattern has only one cleavage site within the target sequence, and the reference cleavage pattern has two or more cleavage sites within the target sequence.

233. The composition of any one of the preceding embodiments, wherein the base sequence for the oligonucleotides is or comprises a sequence that is complementary to a characteristic sequence element that defines a particular allele of a target gene relative to other alleles of the same target gene that exist in a population, the composition being characterized in that, when it is contacted with a system expressing transcripts of both the target allele and another allele of the same gene, transcripts of the particular allele are suppressed at a level at least 2 fold greater than a level of suppression observed for another allele of the same gene.

234. The composition of any one of the preceding embodiments, wherein the base sequence for the oligonucleotides is or comprises a sequence that is complementary to a characteristic sequence element that defines a particular allele of a target gene relative to other alleles of the same target gene that exist in a population, the composition being characterized in that, when it is contacted with a system expressing transcripts of the target gene, it shows suppression of expression of transcripts of the particular allele at a level that is:
  a) at least 2 fold in that transcripts from the particular allele are detected in amounts that are 2 fold lower when the composition is present relative to when it is absent;
  b) at least 2 fold greater than a level of suppression observed for another allele of the same gene; or
  c) both at least 2 fold in that transcripts from the particular allele are detected in amounts that are 2 fold lower when the composition is present relative to when it is absent, and at least 2 fold greater than a level of suppression observed for another allele of the same gene.

235. The composition of any one of the preceding embodiments, wherein the base sequence comprises a sequence that is complementary to a characteristic sequence element of a target, wherein a characteristic sequence element defines that target sequence relative to a similar sequence.

236. The composition of any one of the preceding embodiments, wherein the base sequence of a core region comprises a sequence that is complementary to a characteristic sequence element of a target, wherein a characteristic sequence element defines that target sequence relative to a similar sequence.

237. The composition of any one of the preceding embodiments, wherein a target sequence is a sequence comprising a mutation, and a similar sequence is the wild-type sequence.

238. The composition of any one of the preceding embodiments, wherein a characteristic sequence element defines a particular allele of a target sequence relative to other alleles of the same target sequence.

239. The composition of any one of the preceding embodiments, wherein a characteristic sequence element defines a particular allele of a target gene relative to other alleles of the same target gene.

240. The composition of any one of the preceding embodiments, wherein the sequence is 100% complementary to a characteristic sequence element.

241. The composition of any one of the preceding embodiments, wherein position 11, 12, or 13 of the oligonucleotides as counted from the 5'-terminus of the oligonucleotides aligns with a characteristic sequence element.

242. The composition of any one of embodiments 1-237, wherein position 11 of the oligonucleotides as counted from the 5'-terminus of the oligonucleotides aligns with a characteristic sequence element.

243. The composition of any one of embodiments 1-237, wherein position 12 of the oligonucleotides as counted from the 5'-terminus of the oligonucleotides aligns with a characteristic sequence element.

244. The composition of any one of embodiments 1-237, wherein position 13 of the oligonucleotides as counted from the 5'-terminus of the oligonucleotides aligns with a characteristic sequence element.

245. The composition of any one of embodiments 1-237, wherein position 8, 9 or 10 of the oligonucleotides as counted from the 3'-terminus of the oligonucleotides aligns with a characteristic sequence element.

246. The composition of any one of embodiments 1-237, wherein position 8 of the oligonucleotides as counted from the 3'-terminus of the oligonucleotides aligns with a characteristic sequence element.
247. The composition of any one of embodiments 1-237, wherein position 9 of the oligonucleotides as counted from the 3'-terminus of the oligonucleotides aligns with a characteristic sequence element.
248. The composition of any one of embodiments 1-237, wherein position 10 of the oligonucleotides as counted from the 3'-terminus of the oligonucleotides aligns with a characteristic sequence element.
249. The composition of any one of embodiments 1-237, wherein position 6, 7 or 8 of the core region as counted from the 5'-terminus of the core region aligns with a characteristic sequence element.
250. The composition of any one of embodiments 1-237, wherein position 6 of the core region as counted from the 5'-terminus of the core region aligns with a characteristic sequence element.
251. The composition of any one of embodiments 1-237, wherein position 7 of the core region as counted from the 5'-terminus of the core region aligns with a characteristic sequence element.
252. The composition of any one of embodiments 1-237, wherein position 8 of the core region as counted from the 5'-terminus of the core region aligns with a characteristic sequence element.
253. The composition of any one of embodiments 1-237, wherein position 3, 4 or 5 of the core region as counted from the 3'-terminus of the core region aligns with a characteristic sequence element.
254. The composition of any one of embodiments 1-237, wherein position 3 of the core region as counted from the 3'-terminus of the core region aligns with a characteristic sequence element.
255. The composition of any one of embodiments 1-237, wherein position 4 of the core region as counted from the 3'-terminus of the core region aligns with a characteristic sequence element.
256. The composition of any one of embodiments 1-237, wherein position 5 of the core region as counted from the 3'-terminus of the core region aligns with a characteristic sequence element.
257. The composition of any one of the preceding embodiments, wherein a common base sequence or a base sequence of an oligonucleotide type is a sequence whose DNA cleavage pattern has a cleavage site within or in the vicinity of a characteristic sequence element of a target nucleic acid sequence.
258. The composition of any one of the preceding embodiments, wherein the DNA cleavage pattern is the cleavage pattern of an oligonucleotide composition of DNA oligonucleotides having the sequence, wherein each oligonucleotide in the composition has the same structure.
259. The composition of any one of the preceding embodiments, wherein a common base sequence or a base sequence of an oligonucleotide type is a sequence whose stereorandom cleavage pattern has a cleavage site within or in the vicinity of a characteristic sequence element of a target nucleic acid sequence.
260. The composition of any one of the preceding embodiments, wherein the stereorandom cleavage pattern is the cleavage pattern of a stereorandom composition of oligonucleotides having the sequence, wherein each internucleotidic linkage is phosphorothioate.
261. The composition of any one of the preceding embodiments, wherein the cleavage site with or in the vicinity of a characteristic sequence element of a target nucleic acid sequence is in a core region.
262. The composition of any one of the preceding embodiments, wherein the cleavage site is in the vicinity of a characteristic sequence element of a target nucleic acid sequence.
263. The composition of any one of the preceding embodiments, wherein a cleavage site in the vicinity is a cleavage site 0, 1, 2, 3, 4, or 5 internucleotidic linkages away from the characteristic sequence element.
264. The composition of any one of the preceding embodiments, wherein a cleavage site in the vicinity is a cleavage site 0 internucleotidic linkage away from the characteristic sequence element.
265. The composition of any one of the preceding embodiments, wherein a cleavage site in the vicinity is a cleavage site 1 internucleotidic linkage away from the characteristic sequence element.
266. The composition of any one of the preceding embodiments, wherein a cleavage site in the vicinity is a cleavage site 2 internucleotidic linkages away from the characteristic sequence element.
267. The composition of any one of the preceding embodiments, wherein a cleavage site in the vicinity is a cleavage site 3 internucleotidic linkages away from the characteristic sequence element.
268. The composition of any one of the preceding embodiments, wherein a cleavage site in the vicinity is a cleavage site 4 internucleotidic linkages away from the characteristic sequence element.
269. The composition of any one of the preceding embodiments, wherein a cleavage site in the vicinity is a cleavage site 5 internucleotidic linkages away from the characteristic sequence element.
270. The composition of any one of the preceding embodiments, wherein a cleavage site in the vicinity is a cleavage site is 5' to the cleavage site.
271. The composition of any one of the preceding embodiments, wherein a cleavage site in the vicinity is a cleavage site is 3' to the cleavage site.
272. The composition of any one of the preceding embodiments, wherein a cleavage site within or in the vicinity of a characteristic sequence element is a major cleavage site.
273. The composition of any one of the preceding embodiments, wherein a cleavage site within or in the vicinity of a characteristic sequence element is a relative major cleavage site.
274. The composition of any one of the preceding embodiments, wherein a cleavage site within or in the vicinity of a characteristic sequence element is a relative major cleavage site, wherein greater than 40% of total cleavage occurs at the site.
275. The composition of any one of the preceding embodiments, wherein a cleavage site within or in the vicinity of a characteristic sequence element is a relative major cleavage site, wherein greater than 50% of total cleavage occurs at the site.
276. The composition of any one of the preceding embodiments, wherein a cleavage site within or in the vicinity of a characteristic sequence element is a relative major cleavage site, wherein greater than 60% of total cleavage occurs at the site.
277. The composition of any one of the preceding embodiments, wherein a cleavage site within or in the vicinity of a characteristic sequence element is a relative major cleavage site, wherein greater than 70% of total cleavage occurs at the site.
278. The composition of any one of the preceding embodiments, wherein a cleavage site within or in the vicinity of a characteristic sequence element is a relative major cleavage site, wherein greater than 80% of total cleavage occurs at the site.
279. The composition of any one of the preceding embodiments, wherein a cleavage site within or in the vicinity of a characteristic sequence element is a relative major cleavage site, wherein greater than 90% of total cleavage occurs at the site.
280. The composition of any one of the preceding embodiments, wherein a cleavage site within or in the vicinity of a characteristic sequence element is a relative major cleavage site, wherein greater than 95% of total cleavage occurs at the site.
281. The composition of any one of the preceding embodiments, wherein a cleavage site within or in the vicinity of a characteristic sequence element is a relative major cleavage site, wherein greater than 100% of total cleavage occurs at the site.
282. The composition of any one of the preceding embodiments, wherein a cleavage site within or in the vicinity of a characteristic sequence element is an absolute major cleavage site, wherein greater than 5% of total target is cleaved at the site.
283. The composition of any one of the preceding embodiments, wherein a cleavage site within or in the vicinity of a characteristic sequence element is an absolute major cleavage site, wherein greater than 10% of total target is cleaved at the site.
284. The composition of any one of the preceding embodiments, wherein a cleavage site within or in the vicinity of a characteristic sequence element is an absolute major cleavage site, wherein greater than 15% of total target is cleaved at the site.
285. The composition of any one of the preceding embodiments, wherein a cleavage site within or in the vicinity of a characteristic sequence element is an absolute major cleavage site, wherein greater than 20% of total target is cleaved at the site.
286. The composition of any one of the preceding embodiments, wherein a cleavage site within or in the vicinity of a characteristic sequence element is an absolute major cleavage site, wherein greater than 25% of total target is cleaved at the site.
287. The composition of any one of the preceding embodiments, wherein a cleavage site within or in the vicinity of a characteristic sequence element is an absolute major cleavage site, wherein greater than 30% of total target is cleaved at the site.
288. The composition of any one of the preceding embodiments, wherein a cleavage site within or in the vicinity of a characteristic sequence element is an absolute major cleavage site, wherein greater than 35% of total target is cleaved at the site.
289. The composition of any one of the preceding embodiments, wherein a cleavage site within or in the vicinity of a characteristic sequence element is an absolute major cleavage site, wherein greater than 40% of total target is cleaved at the site.
290. The composition of any one of the preceding embodiments, wherein a cleavage site within or in the vicinity of a characteristic sequence element is an absolute major cleavage site, wherein greater than 45% of total target is cleaved at the site.
291. The composition of any one of the preceding embodiments, wherein a cleavage site within or in the vicinity of a characteristic sequence element is an absolute major cleavage site, wherein greater than 50% of total target is cleaved at the site.
292. The composition of any one of the preceding embodiments, wherein a cleavage site within or in the vicinity of a characteristic sequence element is an absolute major cleavage site, wherein greater than 60% of total target is cleaved at the site.
293. The composition of any one of the preceding embodiments, wherein a cleavage site within or in the vicinity of a characteristic sequence element is an absolute major cleavage site, wherein greater than 70% of total target is cleaved at the site.
294. The composition of any one of the preceding embodiments, wherein a cleavage site within or in the vicinity of a characteristic sequence element is an absolute major cleavage site, wherein greater than 80% of total target is cleaved at the site.
295. The composition of any one of the preceding embodiments, wherein a cleavage site within or in the vicinity of a characteristic sequence element is an absolute major cleavage site, wherein greater than 90% of total target is cleaved at the site.
296. The composition of any one the preceding embodiments, wherein a relative or absolute major cleavage site is determined by RNase H assay.
297. The composition of any one of the preceding embodiments, wherein the characteristic sequence element comprises a single nucleotide polymorphism (SNP) or a mutation.
298. The composition of any one of the preceding embodiments, wherein the characteristic sequence element comprises a single nucleotide polymorphism.
299. The composition of any one of the preceding embodiments, wherein the characteristic sequence element is a single nucleotide polymorphism.
300. The composition of any one of the preceding embodiments, wherein the oligonucleotides comprise a sequence that matches the SNP on the same allele as the expanded CAG repeats of the Huntingtin gene.
301. The composition of any one of the preceding embodiments, wherein the single nucleotide polymorphism is a single nucleotide polymorphism associated with Huntington's disease.
302. The composition of any one of the preceding embodiments, wherein the single nucleotide polymorphism is a single nucleotide polymorphism found in the Huntingtin gene.
303. The composition of embodiment 302, wherein the oligonucleotides comprise a sequence that matches the SNP on the same allele as the expanded CAG repeats of the Huntingtin gene.
304. The composition of any one of the preceding embodiments, wherein the single nucleotide polymorphism is selected from rs362307, rs7685686, rs362268, rs2530595, rs362331, or rs362306.
305. The composition of any one of the preceding embodiments, wherein the single nucleotide polymorphism is selected from rs362307, rs7685686, rs362268, or rs362306.
306. The composition of any one of the preceding embodiments, wherein the single nucleotide polymorphism is rs362307.

307. The composition of any one of the preceding embodiments, wherein the single nucleotide polymorphism is rs7685686.
308. The composition of any one of the preceding embodiments, wherein the single nucleotide polymorphism is rs362268.
309. The composition of any one of the preceding embodiments, wherein the single nucleotide polymorphism is rs362306.
310. The composition of any one of the preceding embodiments, wherein the single nucleotide polymorphism is rs2530595.
311. The composition of any one of the preceding embodiments, wherein the single nucleotide polymorphism is rs362331.
312. The composition of any one of embodiments 1-297, wherein the single nucleotide polymorphism is in an exon.
313. The composition of any one of embodiments 1-297, wherein the single nucleotide polymorphism is in an intron.
314. The composition of any one of embodiments 1-297, wherein the composition is selected from Tables N1, N2, N3, N4 and 8.
315. The composition of any one of embodiments 1-297, wherein the composition is selected from Tables N1, N2, N3 and N4.
316. The composition of any one of embodiments 1-297, wherein the composition is selected from Tables N1A, N2A, N3A, N4A and 8; and WV-937, WV-1087, WV-1090, WV-1091, WV-1092, WV-2603, WV-2595, WV-2378, WV-2380, WV-1510, WV-2619, WV-2611, WV-1497, WV-2602, WV-2618, and WV-2601.
317. The composition of any one of embodiments 1-297, wherein the composition is selected from Tables N1A, N2A, N3A and N4A.
318. The composition of any one of embodiments 1-297, wherein the composition is WV-1092.
319. The composition of any one of embodiments 1-297, wherein the composition is WV-2603.
320. The composition of any one of embodiments 1-297, wherein the composition is WV-2595.
321. The composition of any one of embodiments 1-297, wherein the composition is WV-2378.
322. The composition of any one of embodiments 1-297, wherein the composition is WV-2380.
323. The composition of any one of embodiments 1-297, wherein the composition is WV-1510.
324. The composition of any one of embodiments 1-297, wherein the composition is WV-2619.
325. The composition of any one of embodiments 1-297, wherein the composition is WV-2611.
326. The composition of any one of embodiments 1-297, wherein the composition is WV-1497.
327. The composition of any one of embodiments 1-297, wherein the composition is WV-2602.
328. The composition of any one of embodiments 1-297, wherein the composition is WV-2618.
329. The composition of any one of embodiments 1-297, wherein the composition is WV-2601.
330. The composition of any one of embodiments 1-297, wherein the composition is not ONT-450, ONT-451, or ONT-452.
331. The composition of any one of the preceding embodiments, wherein the characteristic sequence element comprises a mutation.
332. The composition of any one of the preceding embodiments, wherein the characteristic sequence element is a mutation.
333. The composition of any one of the preceding embodiments, wherein the oligonucleotides are at least 95% complementary to a mutant allele.
334. The composition of any one of the preceding embodiments, wherein the oligonucleotides are 100% complementary to a mutant allele.
335. The composition of any one of the preceding embodiments, wherein the oligonucleotides are at least 95% complementary to a target sequence comprising a SNP, wherein the SNP is associated with a disease.
336. The composition of any one of the preceding embodiments, wherein the oligonucleotides are 100% complementary to a target sequence comprising a SNP, wherein the SNP is associated with a disease.
337. The composition of embodiment 336, wherein the target sequence is 10, 11, 12, 13, 14, 15, 16, 17, 18, 19, 20 or more bases in length.
338. The composition of any one of the preceding embodiments, wherein the oligonucleotides selectively reduce RNA level of a mutant allele.
339. The composition of any one of embodiments 16-338, wherein $R^{5s}$ is —OR'.
340. The composition of any one of embodiments 16-338, wherein $R^{5s}$ is —OH.
341. The composition of any one of embodiments 16-340, wherein Y is —O—.
342. The composition of any one of embodiments 16-341, wherein BA is an optionally substituted nucleobase selected from A, T, C, U and G.
343. The composition of any one of embodiments 16-341, wherein BA is an optionally substituted nucleobase selected from A, T, C, U, G and 5mC.
344. The composition of any one of embodiments 16-341, wherein BA is a nucleobase selected from A, T, C, G and 5mC.
345. The composition of any one of embodiments 16-344, wherein SU is

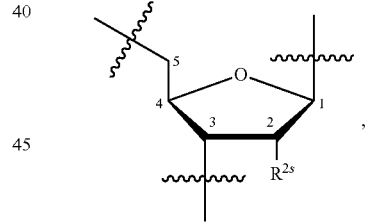

wherein SU is connected to PL through C3, and BA through C1.
346. The composition of any one of embodiments 16-345, wherein at least one $R^{2s}$ is hydrogen.
347. The composition of any one of embodiments 16-346, wherein at least one $R^{2s}$ is —F.
348. The composition of any one of embodiments 16-347, wherein at least one $R^{2s}$ is —OR'.
349. The composition of any one of embodiments 16-348, wherein at least one $R^{2s}$ is —OMe.
350. The composition of any one of embodiments 16-349, wherein at least one $R^{2s}$ is L connecting C2 with C1, C2, C3, C4 or C5.
351. The composition of any one of embodiments 16-350, wherein at least one $R^{2s}$ is L connecting C2 with C4.
352. The composition of any one of embodiments 16-351, wherein at least one $R^{2s}$ is —O—CH$_2$— connecting C2 with C4.

353. The composition of any one of embodiments 16-351, wherein at least one $R^{2s}$ is —O—CH(CH$_3$)— connecting C2 with C4.

354. The composition of any one of embodiments 16-353, wherein at least 1, 2, 3, 4, 5, 6, 7, 8, 9, 10, 11, 12, 13, 14, 15, 16, 17, 18, 19, 20 PL are

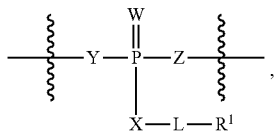

wherein the phosphorus in PL is chiral.

355. The composition of any one of embodiments 16-353, wherein at least 5 PL are wherein the phosphorus in PL is chiral.

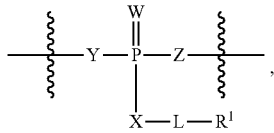

356. The composition of any one of embodiments 16-353, wherein at least 6 PL are

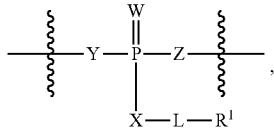

wherein the phosphorus in PL is chiral.

357. The composition of any one of embodiments 16-353, wherein at least 7 PL are

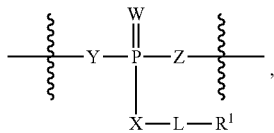

wherein the phosphorus in PL is chiral.

358. The composition of any one of embodiments 16-353, wherein at least 8 PL are

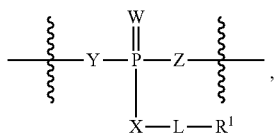

wherein the phosphorus in PL is chiral.

359. The composition of any one of embodiments 16-353, wherein at least 9 PL are

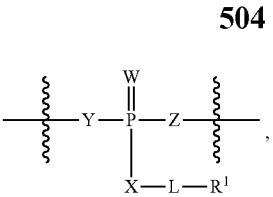

wherein the phosphorus in PL is chiral.

360. The composition of any one of embodiments 16-353, wherein at least 10 PL are

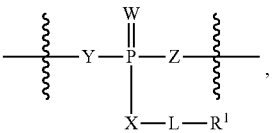

wherein the phosphorus in PL is chiral.

361. The composition of any one of embodiments 354-360, where the chiral PL are consecutive.

362. The composition of any one of embodiments 16-361, wherein at least one PL is

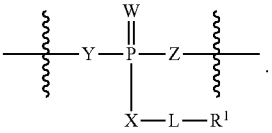

363. The composition of any one of embodiments 16-362, wherein W is O.
364. The composition of any one of embodiments 16-363, wherein Z is —O—.
365. The composition of any one of embodiments 16-364, wherein X is —S—.
366. The composition of any one of embodiments 16-365, wherein n is 4-200.
367. The composition of any one of embodiments 16-365, wherein n is 9-200.
368. The composition of any one of embodiments 16-365, wherein n is 14-200.
369. The composition of any one of embodiments 16-368, wherein $R^a$s is —SU(BA)-L-R'.
370. The composition of any one of embodiments 16-368, wherein $R^a$s is —SU(BA)-OH.
371. The composition of any one of embodiments 16-368, wherein $R^a$s is —SU(BA)-L-solid support.
372. The composition of any one of embodiments 16-371, wherein each chiral PL independently has a diastereopurity of 80%, 85%, 90%, 91%, 92%, 93%, 94%, 95%, 96%, 97%, 98%, 99% or more.
373. The composition of any one of embodiments 16-371, wherein each chiral PL independently has a diastereopurity of 90%, 91%, 92%, 93%, 94%, 95%, 96%, 97%, 98%, 99% or more as measured by formation of a dimer comprising the chiral PL.
374. The composition of any one of embodiments 16-373, wherein at least 1, 2, 3, 4, 5, 6, 7, 8, 9, 10, 11, 12, 13, 14, 15, 16, 17, 18, 19 or 20 PL are natural phosphate linkages.
375. The composition of any one of embodiments 16-373, wherein at least 2, 3, 4, 5, 6, 7, 8, 9, 10, 11, 12, 13, 14, 15, 16, 17, 18, 19 or 20 PL are natural phosphate linkages.

376. The composition of any one of embodiments 16-373, wherein at least 5, 6, 7, 8, 9, 10, 11, 12, 13, 14, 15, 16, 17, 18, 19 or 20 PL are natural phosphate linkages.
377. The composition of any one of embodiments 16-376, wherein the oligonucleotides comprise one or more stretches of consecutive natural phosphate linkages, wherein each stretch independently comprises 2, 3, 4, 5, 6, 7, 8, 9, 10, 11, 12, 13, 14, 15, 16, 17, 18, 19 or 20 natural phosphate linkages.
378. The composition of any one of embodiments 16-376, wherein the oligonucleotides comprise two or more stretches of consecutive natural phosphate linkages, wherein each stretch independently comprises 2, 3, 4, 5, 6, 7, 8, 9, 10, 11, 12, 13, 14, 15, 16, 17, 18, 19 or 20 natural phosphate linkages.
379. The composition of any one of embodiments 16-376, wherein the oligonucleotides comprise two or more stretches of consecutive natural phosphate linkages, wherein each stretch independently comprises 3, 4, 5, 6, 7, 8, 9, 10, 11, 12, 13, 14, 15, 16, 17, 18, 19 or 20 natural phosphate linkages.
380. The pharmaceutical composition, comprising a composition of any one of the preceding embodiments, and a pharmaceutical carrier.
381. The composition of any one of the preceding embodiments, further comprising cerebrospinal fluid.
382. The composition of any one of the preceding embodiments, further comprising artificial cerebrospinal fluid.
383. The composition of any one of the preceding embodiments, comprising a salt of the oligonucleotides.
384. The composition of any one of the preceding embodiments, comprising a pharmaceutically acceptable salt of the oligonucleotides.
385. The composition of any one of the preceding embodiments, comprising the sodium salt of the oligonucleotides.
386. The composition of any one of the preceding embodiments, wherein the oligonucleotides exist as all-sodium salt.
387. The composition of any one of embodiments 1-382, wherein the oligonucleotides are O—I-1 or a pharmaceutically acceptable salt thereof.
388. The composition of any one of embodiments 1-382, wherein the oligonucleotides are O—I-2 or a pharmaceutically acceptable salt thereof.
389. The composition of any one of embodiments 1-382, wherein the oligonucleotides are O—I-3 or a pharmaceutically acceptable salt thereof.
390. The composition of any one of embodiments 1-382, wherein the oligonucleotides are O—I-4 or a pharmaceutically acceptable salt thereof.
391. The composition of any one of embodiments 1-382, wherein the oligonucleotides are O—I-5 or a pharmaceutically acceptable salt thereof.
392. The composition of any one of embodiments 1-382, wherein the oligonucleotides are O—I-6 or a pharmaceutically acceptable salt thereof.
393. The composition of any one of embodiments 1-382, wherein the oligonucleotides are O—I-7 or a pharmaceutically acceptable salt thereof.
394. The composition of any one of embodiments 1-382, wherein the oligonucleotides are O—I-8 or a pharmaceutically acceptable salt thereof.
395. The composition of any one of embodiments 387-394, wherein the oligonucleotides are a sodium salt.
396. The composition of any one of embodiments 387-394, wherein the oligonucleotides are an all-sodium salt containing n Na$^+$ per oligonucleotide.
397. A method for controlled cleavage of a nucleic acid polymer, the method comprising steps of:

contacting a nucleic acid polymer whose nucleotide sequence comprises a target sequence with a chirally controlled oligonucleotide composition comprising oligonucleotides of a particular oligonucleotide type characterized by:
1) a common base sequence and length, wherein the common base sequence is or comprises a sequence that is complementary to a target sequence found in the nucleic acid polymer;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type.
398. A method for cleavage of a nucleic acid having a base sequence comprising a target sequence, the method comprising steps of:
(a) contacting a nucleic acid having a base sequence comprising a target sequence with a chirally controlled oligonucleotide composition comprising oligonucleotides of a particular oligonucleotide type characterized by:
1) a common base sequence and length, wherein the common base sequence is or comprises a sequence that is complementary to the target sequence in the nucleic acid;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type, wherein the oligonucleotide targets a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation.
399. A method for cleavage of a nucleic acid having a base sequence comprising a target sequence, the method comprising steps of:
(a) contacting a nucleic acid having a base sequence comprising a target sequence with a chirally controlled oligonucleotide composition comprising oligonucleotides of a particular oligonucleotide type characterized by:
1) a common base sequence and length, wherein the common base sequence is or comprises a sequence that is complementary to the target sequence in the nucleic acid;
2) a common pattern of backbone linkages; and
3) a common pattern of backbone chiral centers;
which composition is chirally controlled in that it is enriched, relative to a substantially racemic preparation of oligonucleotides having the particular base sequence and length, for oligonucleotides of the particular oligonucleotide type, wherein the oligonucleotide targets a mutant Huntingtin gene, and the length is from about 10 to about 50 nucleotides, wherein the backbone linkages comprise at least one phosphorothioate, and wherein the pattern of backbone chiral centers comprises at least one chiral center in a Rp conformation and at least one chiral center in a Sp conformation; and (b) cleavage of the nucleic acid mediated by a RNAse H or RNA interference mechanism.

400. The method of embodiment 399, wherein the contacting being performed under conditions so that cleavage of the nucleic acid polymer occurs.

401. The method of any one of embodiments 399-400, wherein the cleavage occurs with a cleavage pattern that differs from a reference cleavage pattern observed when the nucleic acid polymer is contacted under comparable conditions with a reference oligonucleotide composition.

402. A method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising:
  contacting the nucleic acid polymer with a chirally controlled oligonucleotide composition of oligonucleotides having the particular base sequence and length, which composition is chirally controlled in that it is enriched, relative to a substantially racemic preparation of oligonucleotides having the particular base sequence and length, for oligonucleotides of a single oligonucleotide type characterized by:
    1) the particular base sequence and length;
    2) a particular pattern of backbone linkages; and
    3) a particular pattern of backbone chiral centers.

403. The method of embodiment 402, wherein the contacting being performed under conditions so that cleavage of the nucleic acid polymer occurs.

404. The method of any one of embodiments 401-403, wherein the reference oligonucleotide composition is a substantially racemic preparation of oligonucleotides that share the common sequence and length.

405. The method of any one of embodiments 401-403, wherein the reference oligonucleotide composition is a chirally uncontrolled oligonucleotide composition of oligonucleotides that share the common sequence and length.

406. The method of any one of embodiments 401-405, wherein the cleavage pattern provided by the chirally controlled oligonucleotide composition differs from a reference cleavage pattern in that it has fewer cleavage sites within the target sequence found in the nucleic acid polymer than the reference cleavage pattern.

407. The method of embodiment 406, wherein the cleavage pattern provided by the chirally controlled oligonucleotide composition has a single cleavage site within the target sequence found in the nucleic acid polymer than the reference cleavage pattern.

408. The method of embodiment 407, wherein the single cleavage site is a cleavage site in the reference cleavage pattern.

409. The method of embodiment 406, wherein the single cleavage site is a cleavage site not in the reference cleavage pattern.

410. The method of any one of embodiments 401-405, wherein the cleavage pattern provided by the chirally controlled oligonucleotide composition differs from a reference cleavage pattern in that it increases cleavage percentage at a cleavage site.

411. The method of embodiment 410, wherein the cleavage site with increased cleavage percentage is a cleavage site in the reference cleavage pattern.

412. The method of embodiment 410, wherein the cleavage site with increased cleavage percentage is a cleavage site not in the reference cleavage pattern.

413. The method of any one of embodiments 399-412, wherein the chirally controlled oligonucleotide composition provides a higher cleavage rate of the target nucleic acid polymer than a reference oligonucleotide composition.

414. The method of any one of embodiments 399-413, where the cleavage rate is at least 5 fold higher.

415. The method of any one of embodiments 399-414, wherein the chirally controlled oligonucleotide composition provides a lower level of remaining un-cleaved target nucleic acid polymer than a reference oligonucleotide composition.

416. The method of any one of embodiments 399-415, wherein the remaining un-cleaved target nucleic acid polymer is at least 5 fold lower.

417. The methods of any one of embodiments 399-416, wherein the cleavage products from the nucleic acid polymer dissociate from oligonucleotides of the particular oligonucleotide type in the chirally controlled oligonucleotide composition at a faster rate than from oligonucleotides of the reference oligonucleotide composition.

418. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
    1) a common base sequence and length; and
    2) a common pattern of backbone linkages;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

419. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
  contacting a sample comprising transcripts of the target nucleic acid sequence with an oligonucleotide composition comprising oligonucleotides having:
    1) a common base sequence and length; and
    2) a common pattern of backbone linkages;
    3) a common pattern of backbone chiral centers;
  wherein the common base sequence is or comprises a sequence that is complementary to the characteristic sequence element that defines the target nucleic acid sequence, the composition being characterized in that, when it is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

420. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
contacting a sample comprising transcripts of the target nucleic acid sequence with an oligonucleotide composition comprising oligonucleotides having:
1) a common base sequence and length; and
2) a common pattern of backbone linkages;
wherein the common base sequence is or comprises a sequence that is complementary to the characteristic sequence element that defines a particular target sequence relative to its similar sequences, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

421. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
contacting a sample comprising transcripts of the target nucleic acid sequence with an oligonucleotide composition comprising oligonucleotides having:
1) a common base sequence and length; and
2) a common pattern of backbone linkages;
3) a common pattern of backbone chiral centers;
wherein the common base sequence is or comprises a sequence that is complementary to the characteristic sequence element that defines a particular target sequence relative to its similar sequences, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

422. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
contacting a sample comprising transcripts of the target nucleic acid sequence with an oligonucleotide composition comprising oligonucleotides having:
1) a common base sequence and length;
2) a common pattern of backbone linkages;
wherein the common base sequence is or comprises a sequence that is complementary to the characteristic sequence element that defines a particular target sequence relative to its similar sequences, the composition being characterized in that, when it is contacted with a system comprising transcripts of the same target nucleic acid sequence, it shows suppression of transcripts of the particular target sequence at a level that is:
a) greater than when the composition is absent;
b) greater than a level of suppression observed for a similar; or
c) both greater than when the composition is absent, and greater than a level of suppression observed for a similar sequence.

423. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of:
contacting a sample comprising transcripts of the target nucleic acid sequence with an oligonucleotide composition comprising oligonucleotides having:
1) a common base sequence and length;
2) a common pattern of backbone linkages;
3) a common pattern of backbone chiral centers;
wherein the common base sequence is or comprises a sequence that is complementary to the characteristic sequence element that defines a particular target sequence relative to its similar sequences, the composition being characterized in that, when it is contacted with a system comprising transcripts of the same target nucleic acid sequence, it shows suppression of transcripts of the particular target sequence at a level that is:
a) greater than when the composition is absent;
b) greater than a level of suppression observed for a similar; or
c) both greater than when the composition is absent, and greater than a level of suppression observed for a similar sequence.

424. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of: contacting a sample comprising transcripts of the target gene with an oligonucleotide composition comprising oligonucleotides having:
1) a common base sequence and length; and
2) a common pattern of backbone linkages;
wherein the common base sequence is or comprises a sequence that is complementary to the characteristic sequence element that defines a particular target nucleic acid sequence, the composition being characterized in that, when it is contacted with a system expressing transcripts of the target nucleic acid sequence, it shows suppression of expression of transcripts of the particular target nucleic acid sequence at a level that is:
a) at least 2 fold in that transcripts from the particular target nucleic acid sequence are detected in amounts that are 2 fold lower when the composition is present relative to when it is absent;
b) at least 2 fold greater than a level of suppression observed for a similar sequence; or
c) both at least 2 fold in that transcripts from the particular target nucleic acid sequence are detected in amounts that are 2 fold lower when the composition is present relative to when it is absent, and at least 2 fold greater than a level of suppression observed for a similar sequence.

425. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising steps of: contacting a sample comprising transcripts of the target gene with an oligonucleotide composition comprising oligonucleotides having:
1) a common base sequence and length; and
2) a common pattern of backbone linkages;
3) a common pattern of backbone chiral centers;
wherein the common base sequence is or comprises a sequence that is complementary to the characteristic sequence element that defines a particular target nucleic acid sequence, the composition being characterized in that, when it is contacted with a system expressing transcripts of the target nucleic acid sequence, it shows suppression of expression of transcripts of the particular target nucleic acid sequence at a level that is:
a) at least 2 fold in that transcripts from the particular target nucleic acid sequence are detected in amounts that are 2 fold lower when the composition is present relative to when it is absent;
b) at least 2 fold greater than a level of suppression observed for a similar sequence; or
c) both at least 2 fold in that transcripts from the particular target nucleic acid sequence are detected in amounts that are 2 fold lower when the composition is present relative to when it is absent, and at least 2 fold greater than a level of suppression observed for a similar sequence.

426. The method of any one of the preceding embodiments, wherein a target sequence is a sequence comprising a mutation, and a similar sequence is the wild-type sequence.

427. The method of any one of the preceding embodiments, wherein a characteristic sequence element defines a particular allele of a target sequence relative to other alleles of the same target sequence.

428. The method of any one of the preceding embodiments, wherein a characteristic sequence element defines a particular allele of a target gene relative to other alleles of the same target gene.

429. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
contacting a sample comprising transcripts of the target nucleic acid sequence with an oligonucleotide composition comprising oligonucleotides having:
1) a common base sequence and length; and
2) a common pattern of backbone linkages;
wherein the common base sequence is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

430. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
contacting a sample comprising transcripts of the target nucleic acid sequence with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same nucleic acid sequence, transcripts of the particular allele are suppressed at a greater level than a level of suppression observed for another allele of the same nucleic acid sequence.

431. A method for allele-specific suppression of a transcript from a target gene for which a plurality of alleles exist within a population, each of which contains a specific nucleotide characteristic sequence element that defines the allele relative to other alleles of the same target gene, the method comprising steps of:
contacting a sample comprising transcripts of the target gene with an oligonucleotide composition comprising oligonucleotides having:
1) a common base sequence and length;
2) a common pattern of backbone linkages;
wherein the common base sequence is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

432. A method for allele-specific suppression of a transcript from a target gene for which a plurality of alleles exist within a population, each of which contains a specific nucleotide characteristic sequence element that defines the allele relative to other alleles of the same target gene, the method comprising steps of:
contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of both the target allele and another allele of the same gene, transcripts of the particular allele are suppressed at a level at least 2 fold greater than a level of suppression observed for another allele of the same gene.

433. The method of embodiment 429 or 431, the contacting being performed under conditions determined to permit the composition to suppress transcripts of the particular allele.

434. A method for allele-specific suppression of a transcript from a target gene for which a plurality of alleles exist within a population, each of which contains a specific nucleotide characteristic sequence element that defines the allele relative to other alleles of the same target gene, the method comprising steps of:
contacting a sample comprising transcripts of the target gene with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of both the target allele and another allele of the same gene, transcripts of the particular allele are suppressed at a level at least 2 fold greater than a level of suppression observed for another allele of the same gene.

435. The method of embodiment 434, wherein the contacting being performed under conditions determined to permit the composition to suppress expression of the particular allele.

436. The method of any one of embodiments 429-435, wherein transcripts of the particular allele are suppressed at a level at least 5, 10, 20, 50, 100, 200 or 500 fold greater than a level of suppression observed for another allele of the same gene.

437. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
contacting a sample comprising transcripts of the target nucleic acid sequence with an oligonucleotide composition comprising oligonucleotides having:
1) a common base sequence and length;
2) a common pattern of backbone linkages;
wherein the common base sequence is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
a) greater than when the composition is absent;
b) greater than a level of suppression observed for another allele of the same nucleic acid sequence; or
c) both greater than when the composition is absent, and greater than a level of suppression observed for another allele of the same nucleic acid sequence.

438. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
contacting a sample comprising transcripts of the target nucleic acid sequence with a chirally controlled oligonucleotide composition comprising oligonucleotides of a particular oligonucleotide type characterized by:
1) a common base sequence and length;
2) a common pattern of backbone linkages;
3) a common pattern of backbone chiral centers;
which composition is chirally controlled in that it is enriched, relative to a substantially racemic preparation of oligonucleotides having the same base sequence and length, for oligonucleotides of the particular oligonucleotide type;
wherein the common base sequence for the oligonucleotides of the particular oligonucleotide type is or comprises a sequence that is complementary to the characteristic sequence element that defines a particular allele, the composition being characterized in that, when it is contacted with a system comprising transcripts of the same target nucleic acid sequence, it shows suppression of transcripts of the particular allele at a level that is:
a) greater than when the composition is absent;
b) greater than a level of suppression observed for another allele of the same nucleic acid sequence; or
c) both greater than when the composition is absent, and greater than a level of suppression observed for another allele of the same nucleic acid sequence.

439. A method for controlled cleavage of a nucleic acid polymer, the method comprising contacting a nucleic acid polymer whose nucleotide sequence comprises a target sequence with an oligonucleotide or an oligonucleotide composition of any one of embodiments 638-684.

440. A method for suppression of a transcript from a target nucleic acid sequence for which one or more similar nucleic acid sequences exist within a population, each of the target and similar sequences contains a specific nucleotide characteristic sequence element that defines the target sequence relative to the similar sequences, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines the target nucleic acid sequence.

441. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines a particular allele.

442. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines a particular allele, the oligonucleotide or oligonucleotide composition being characterized in that, when it is contacted with a system comprising transcripts of both the target allele and another allele of the same gene, transcripts of the particular allele are suppressed at a level at least 2 fold greater than a level of suppression observed for another allele of the same gene.

443. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines a particular allele, the oligonucleotide or oligonucleotide composition being characterized in that, when it is contacted with a system expressing transcripts of both the target allele and another allele of the same gene, transcripts of the particular allele are suppressed at a level at least 2 fold greater than a level of suppression observed for another allele of the same gene.

444. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines a particular allele, the oligonucleotide or oligonucleotide composition being characterized in that, when it is contacted with a system comprising transcripts of the same target nucleic acid sequence, it shows suppression of transcripts of the particular allele at a level that is:
   a) greater than when the composition is absent;
   b) greater than a level of suppression observed for another allele of the same nucleic acid sequence; or
   c) both greater than when the composition is absent, and greater than a level of suppression observed for another allele of the same nucleic acid sequence.

445. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising contacting a sample comprising transcripts of the target nucleic acid sequence with an oligonucleotide or an oligonucleotide composition of any one of embodiments 638-684, wherein the base sequence of the oligonucleotide is or comprises a sequence that is complementary to the characteristic sequence element that defines a particular allele, the oligonucleotide or oligonucleotide composition being characterized in that, when it is contacted with a system expressing transcripts of the same target nucleic acid sequence, it shows suppression of transcripts of the particular allele at a level that is:
   a) greater than when the composition is absent;
   b) greater than a level of suppression observed for another allele of the same nucleic acid sequence; or
   c) both greater than when the composition is absent, and greater than a level of suppression observed for another allele of the same nucleic acid sequence.

446. A method for allele-specific suppression of a transcript from a target gene for which a plurality of alleles exist within a population, each of which contains a specific nucleotide characteristic sequence element that defines the allele relative to other alleles of the same target gene, the method comprising steps of:
   contacting a sample comprising transcripts of the target gene with an oligonucleotide composition comprising oligonucleotides having:
   1) a common base sequence and length; and
   2) a common pattern of backbone linkages;
   wherein the common base sequence is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:
   a) at least 2 fold in that transcripts from the particular allele are detected in amounts that are 2 fold lower when the composition is present relative to when it is absent;
   b) at least 2 fold greater than a level of suppression observed for another allele of the same gene; or
   c) both at least 2 fold in that transcripts from the particular allele are detected in amounts that are 2 fold lower when the composition is present relative to when it is absent, and at least 2 fold greater than a level of suppression observed for another allele of the same gene.

447. A method for allele-specific suppression of a transcript from a target gene for which a plurality of alleles exist within a population, each of which contains a specific nucleotide characteristic sequence element that defines the allele relative to other alleles of the same target gene, the method comprising steps of:
   contacting a sample comprising transcripts of the target gene with a chirally controlled oligonucleotide composition comprising oligonucleotides of a particular oligonucleotide type characterized by:
   1) a common base sequence and length;
   2) a common pattern of backbone linkages;
   3) a common pattern of backbone chiral centers;
   which composition is chirally controlled in that it is enriched, relative to a substantially racemic preparation of oligonucleotides having the same base sequence and length, for oligonucleotides of the particular oligonucleotide type;
   wherein the common base sequence for the oligonucleotides of the particular oligonucleotide type is or comprises a sequence that is complementary to the characteristic sequence element that defines a particular allele, the composition being characterized in that, when it is contacted with a system expressing transcripts of the target gene, it shows suppression of expression of transcripts of the particular allele at a level that is:

a) at least 2 fold in that transcripts from the particular allele are detected in amounts that are 2 fold lower when the composition is present relative to when it is absent;
b) at least 2 fold greater than a level of suppression observed for another allele of the same gene; or
c) both at least 2 fold in that transcripts from the particular allele are detected in amounts that are 2 fold lower when the composition is present relative to when it is absent, and at least 2 fold greater than a level of suppression observed for another allele of the same gene.

448. The method of any one of the preceding embodiments, wherein transcripts from the particular allele are detected in amounts that are 2 fold or more when the composition is absent relative to when it is present.

449. The method of any one of the preceding embodiments, wherein the level of transcripts of another allele of the same gene is at least 2 fold greater than the level of transcripts of the particular allele.

450. The method of any one of the preceding embodiments, wherein transcripts from the particular allele are detected in amounts that are 2 fold or more when the composition is absent relative to when it is present, and the level of transcripts of another allele of the same gene is at least 2 fold greater than the level of transcripts of the particular allele.

451. The method of any one of the preceding embodiments, the contacting being performed under conditions determined to permit the composition to suppress transcripts of the particular allele.

452. The method of any one of the preceding embodiments, wherein the contacting being performed under conditions determined to permit the composition to suppress expression of the particular allele.

453. The method of any one of the preceding embodiments, wherein transcripts of the particular allele are suppressed at a level that is at least 5, 10, 20, 50, 100, 200 or 500 fold in that transcripts from the particular allele are detected in amounts that are 2 fold lower when the composition is present relative to when it is absent.

454. The method of any one of the preceding embodiments, wherein transcripts of the particular allele are suppressed at a level that is at least 5, 10, 20, 50, 100, 200 or 500 fold greater than a level of suppression observed for another allele of the same gene.

455. The method of any one of the preceding embodiments, wherein the system is an in vitro or in vivo system.

456. The method of any one of the preceding embodiments, wherein the method is performed in vitro or in vivo.

457. The method of any one of the preceding embodiments, wherein the system comprises one or more cells, tissues or organs.

458. The method of any one of the preceding embodiments, wherein the system comprises one or more organisms.

459. The method of any one of the preceding embodiments, wherein the system comprises one or more subjects.

460. The method of any one of the preceding embodiments, wherein transcripts of the particular allele are cleaved.

461. The method of any one of the preceding embodiments, wherein the specific nucleotide characteristic sequence element is present within an intron of the target nucleic acid sequence or gene.

462. The method of any one of the preceding embodiments, wherein the specific nucleotide characteristic sequence element is present within an exon of the target nucleic acid sequence or gene.

463. The method of any one of the preceding embodiments, wherein the specific nucleotide characteristic sequence element spans an exon and an intron of the target nucleic acid sequence or gene.

464. The method of any one of the preceding embodiments, wherein the specific nucleotide characteristic sequence element comprises a mutation.

465. The method of any one of the preceding embodiments, wherein the specific nucleotide characteristic sequence element is a mutation.

466. The method of any one of the preceding embodiments, wherein the specific nucleotide characteristic sequence element comprises a SNP.

467. The method of any one of the preceding embodiments, wherein the specific nucleotide characteristic sequence element is a SNP.

468. The method of any one of the preceding embodiments, wherein the oligonucleotide composition is administered to a subject.

469. The method of any one of the preceding embodiments, wherein the target nucleic acid polymer or transcripts are oligonucleotides.

470. The method of any one of the preceding embodiments, wherein the target nucleic acid polymer or transcripts are RNA.

471. The method of any one of the preceding embodiments, wherein the target nucleic acid polymer or transcripts are newly transcribed RNA.

472. The method of any one of the preceding embodiments, wherein oligonucleotides of the particular oligonucleotide type in the chirally controlled oligonucleotide composition form duplexes with the nucleic acid polymer or transcripts.

473. The method of any one of the preceding embodiments, wherein the nucleic acid polymer or transcripts are cleaved by an enzyme.

474. The method of any one of the preceding embodiments, wherein the enzyme is RNase H.

475. The method of any one of the preceding embodiments, wherein the SNP is a SNP related to Huntington's disease.

476. The method of any one of the preceding embodiments, wherein the SNP is a SNP found in the Huntingtin gene.

477. The method of any one of the preceding embodiments, wherein the SNP is selected from rs362307, rs7685686, rs362268, or rs362306.

478. The method of embodiments 397-477, wherein the SNP is rs362307.

479. The method of embodiments 397-477, wherein the single nucleotide polymorphism is rs7685686.

480. The method of embodiments 397-477, wherein the single nucleotide polymorphism is rs362268.

481. The method of embodiments 397-477, wherein the single nucleotide polymorphism is rs362306.

482. The method of embodiments 397-481, wherein position 11 of the oligonucleotides as counted from the 5'-terminus of the oligonucleotides aligns with a single nucleotide polymorphism.

483. The method of embodiments 397-481, wherein position 12 of the oligonucleotides as counted from the 5'-terminus of the oligonucleotides aligns with a single nucleotide polymorphism.

484. The method of embodiments 397-481, wherein position 13 of the oligonucleotides as counted from the 5'-terminus of the oligonucleotides aligns with a single nucleotide polymorphism.

485. The method of embodiments 397-481, wherein position 8 of the oligonucleotides as counted from the 3'-terminus of the oligonucleotides aligns with a single nucleotide polymorphism.
486. The method of embodiments 397-481, wherein position 9 of the oligonucleotides as counted from the 3'-terminus of the oligonucleotides aligns with a single nucleotide polymorphism.
487. The method of embodiments 397-481, wherein position 10 of the oligonucleotides as counted from the 3'-terminus of the oligonucleotides aligns with a single nucleotide polymorphism.
488. The method of any one of the preceding embodiments, wherein the oligonucleotides comprise one or more wing regions and a common core region, wherein:
    each wing region independently has a length of two or more bases, and independently and optionally comprises one or more chiral internucleotidic linkages; and
    the core region independently has a length of two or more bases and independently comprises one or more chiral internucleotidic linkages.
489. The method of any one of embodiments 397-488, wherein position 6 of the core region as counted from the 5'-terminus of the core region aligns with a single nucleotide polymorphism.
490. The method of any one of embodiments 397-488, wherein position 7 of the core region as counted from the 5'-terminus of the core region aligns with a single nucleotide polymorphism.
491. The method of any one of embodiments 397-488, wherein position 8 of the core region as counted from the 5'-terminus of the core region aligns with a single nucleotide polymorphism.
492. The method of any one of embodiments 397-488, wherein position 3 of the core region as counted from the 3'-terminus of the core region aligns with a single nucleotide polymorphism.
493. The method of any one of embodiments 397-488, wherein position 4 of the core region as counted from the 3'-terminus of the core region aligns with a single nucleotide polymorphism.
494. The method of any one of embodiments 397-488, wherein position 5 of the core region as counted from the 3'-terminus of the core region aligns with a single nucleotide polymorphism.
495. The method of any one of the preceding embodiments, wherein:
    each wing region independently has a length of two or more bases, and independently comprises one or more chiral internucleotidic linkages and one or more natural phosphate linkage; and
    the core region independently has a length of two or more bases, wherein each internucleotidic linkage in the core region is chiral, only one of internucleotidic linkage in the core region is Rp, and each of the other internucleotidic linkages in the core region is Sp.
496. The method of any one of the preceding embodiments, wherein the oligonucleotides are hemimers having the structure of wing-core.
497. The method of any one of embodiments 397-495, wherein the oligonucleotides are hemimers having the structure of core-wing.
498. The method of any one of embodiments 397-495, wherein the oligonucleotides are gapmers having the structure of wing-core-wing.
499. The method of any one of the preceding embodiments, wherein level of transcripts from a disease-causing allele is selectively suppressed.
500. The method of any one of the preceding embodiments, wherein level of a protein translated from transcripts from a disease-causing allele are suppressed.
501. A method for treating or preventing Huntington's Disease in a subject, comprising administering to the subject an oligonucleotide composition comprising oligonucleotides having:
    1) a common base sequence and length; and
    2) a common pattern of backbone linkages.
502. A method for treating or preventing Huntington's Disease in a subject, comprising administering to the subject a chirally controlled oligonucleotide composition comprising oligonucleotides of a particular oligonucleotide type characterized by:
    1) a common base sequence and length;
    2) a common pattern of backbone linkages; and
    3) a common pattern of backbone chiral centers;
which composition is chirally controlled in that it is enriched, relative to a substantially racemic preparation of oligonucleotides having the same base sequence and length, for oligonucleotides of the particular oligonucleotide type.
503. The method of embodiment 501 or 502, wherein the oligonucleotides comprise one or more wing regions and a common core region, wherein:
    each wing region independently has a length of two or more bases, and independently and optionally comprises one or more chiral internucleotidic linkages; and
    the core region independently has a length of two or more bases and independently comprises one or more chiral internucleotidic linkages.
504. The method of any one of embodiments 501-503, wherein:
    each wing region independently has a length of two or more bases, and independently comprises one or more chiral internucleotidic linkages and one or more natural phosphate linkage; and
    the core region independently has a length of two or more bases, wherein each internucleotidic linkage in the core region is chiral, only one of internucleotidic linkage in the core region is Rp, and each of the other internucleotidic linkages in the core region is Sp.
505. The method of any one of embodiments 501-504, wherein the oligonucleotides are hemimers having the structure of wing-core.
506. The method of any one of embodiments 501-504, wherein the oligonucleotides are hemimers having the structure of core-wing.
507. The method of any one of embodiments 501-504, wherein the oligonucleotides are gapmers having the structure of wing-core-wing.
508. The method of any one of embodiments 501-507, wherein position 11 of the oligonucleotides as counted from the 5'-terminus of the oligonucleotides aligns with a single nucleotide polymorphism.
509. The method of any one of embodiments 501-507, wherein position 12 of the oligonucleotides as counted from the 5'-terminus of the oligonucleotides aligns with a single nucleotide polymorphism.
510. The method of any one of embodiments 501-507, wherein position 13 of the oligonucleotides as counted from the 5'-terminus of the oligonucleotides aligns with a single nucleotide polymorphism.

511. The method of any one of embodiments 501-507, wherein position 8 of the oligonucleotides as counted from the 3'-terminus of the oligonucleotides aligns with a single nucleotide polymorphism.
512. The method of any one of embodiments 501-507, wherein position 9 of the oligonucleotides as counted from the 3'-terminus of the oligonucleotides aligns with a single nucleotide polymorphism.
513. The method of any one of embodiments 501-507, wherein position 10 of the oligonucleotides as counted from the 3'-terminus of the oligonucleotides aligns with a single nucleotide polymorphism.
514. The method of any one of embodiments 501-507, wherein position 6 of the core region as counted from the 5'-terminus of the core region aligns with a single nucleotide polymorphism.
515. The method of any one of embodiments 501-507, wherein position 7 of the core region as counted from the 5'-terminus of the core region aligns with a single nucleotide polymorphism.
516. The method of any one of embodiments 501-507, wherein position 8 of the core region as counted from the 5'-terminus of the core region aligns with a single nucleotide polymorphism.
517. The method of any one of embodiments 501-507, wherein position 3 of the core region as counted from the 3'-terminus of the core region aligns with a single nucleotide polymorphism.
518. The method of any one of embodiments 501-507, wherein position 4 of the core region as counted from the 3'-terminus of the core region aligns with a single nucleotide polymorphism.
519. The method of any one of embodiments 501-507, wherein position 5 of the core region as counted from the 3'-terminus of the core region aligns with a single nucleotide polymorphism.
520. The method of any one of embodiments 501-519, wherein the method ameliorating a symptom of Huntington's Disease.
521. The method of any one of embodiments 501-519, wherein the method slowing onset of Huntington's Disease.
522. The method of any one of embodiments 501-519, wherein the method slowing progression of Huntington's Disease.
523. The method of any one of embodiments 501-522, wherein the subject has a SNP related to Huntington's Disease.
524. The method of any one of embodiments 501-523, wherein the subject has a SNP in the subject's Huntingtin gene.
525. The method of any one of embodiments 501-524, wherein the subject has a SNP, wherein one allele is mutant Huntingtin associated with expanded CAG repeats, and the oligonucleotides administered comprise a sequence having 5, 6, 7, 8, 9, 10, 11, 12, 13, 14, 15, 16, 17, 18, 19 or 20 bases in length and 100% matching the sequence comprising the SNP on the same allele as the expanded CAG repeats.
526. The method of any one of embodiments 501-524, wherein the subject has a SNP, wherein one allele is mutant Huntingtin associated with expanded CAG repeats, and the oligonucleotides administered comprise a sequence having 10, 11, 12, 13, 14, 15, 16, 17, 18, 19 or 20 bases in length and 100% matching the sequence comprising the SNP on the same allele as the expanded CAG repeats.
527. The method of any one of embodiments 501-524, wherein the subject has a SNP, wherein one allele is mutant Huntingtin associated with expanded CAG repeats, and the oligonucleotides administered comprise a sequence having 15, 16, 17, 18, 19 or 20 bases in length and 100% matching the sequence comprising the SNP on the same allele as the expanded CAG repeats.
528. The method of any one of embodiments 501-527, wherein the subject has a SNP, wherein one allele is mutant Huntingtin associated with expanded CAG repeats.
529. The method of any one of embodiments 501-528, wherein the subject has a SNP selected from rs362307, rs7685686, rs362268, rs2530595, rs362331, or rs362306.
530. The method of any one of embodiments 501-529, wherein the subject has a SNP selected from rs362307, rs7685686, rs362268, or rs362306.
531. The method of any one of embodiments 501-530, wherein the subject has the SNP rs362307.
532. The method of any one of embodiments 501-530, wherein the subject has the SNP rs7685686.
533. The method of any one of embodiments 501-530, wherein the subject has the SNP rs362268.
534. The method of any one of embodiments 501-530, wherein the subject has the SNP rs362306.
535. The method of any one of embodiments 501-530, wherein the subject has the SNP rs2530595.
536. The method of any one of embodiments 501-530, wherein the subject has the SNP rs362331.
537. The composition of any of embodiments 1-396, wherein a substantially racemic preparation of oligonucleotides is prepared by non-stereoselective preparation.
538. The composition of any one of embodiments 1-396 and 537, wherein a substantially racemic preparation of oligonucleotides is prepared by non-stereoselective preparation, wherein a chiral auxiliary is not used for formation of a chiral internucleotidic linkage.
539. The composition of any one of embodiments 1-396 and 537-538, wherein a substantially racemic preparation of oligonucleotides is prepared by non-stereoselective preparation, wherein at least one chiral internucleotidic linkage is formed with less than 80:20 diastereomeric selectivity.
540. The composition of any one of embodiments 1-396 and 537-539, wherein a substantially racemic preparation of oligonucleotides is prepared by non-stereoselective preparation, wherein at least one chiral internucleotidic linkage is formed with less than 90:10 diastereomeric selectivity.
541. The composition of any one of embodiments 1-396 and 537-540, wherein a substantially racemic preparation of oligonucleotides is prepared by non-stereoselective preparation, wherein at least one chiral internucleotidic linkage is formed with less than 95:5 diastereomeric selectivity.
542. The composition of any one of embodiments 1-396 and 537-541, wherein a substantially racemic preparation of oligonucleotides is prepared by non-stereoselective preparation, wherein at least one chiral internucleotidic linkage is formed with less than 97:3 diastereomeric selectivity.
543. The composition of any one of embodiments 1-396, wherein each chiral internucleotidic linkage is formed with greater than 90:10 diastereomeric selectivity.
544. The composition of any one of embodiments 1-396, wherein each chiral internucleotidic linkage is formed with greater than 95:5 diastereomeric selectivity.
545. The composition of any one of embodiments 1-396, wherein each chiral internucleotidic linkage is formed with greater than 96:4 diastereomeric selectivity.
546. The composition of any one of embodiments 1-396, wherein each chiral internucleotidic linkage is formed with greater than 97:3 diastereomeric selectivity.

547. The composition of any one of embodiments 1-396, wherein each chiral internucleotidic linkage is formed with greater than 98:2 diastereomeric selectivity.

548. The composition of any one of embodiments 1-309, wherein each chiral internucleotidic linkage is formed with greater than 98:2 diastereomeric selectivity.

549. The composition of any one of embodiments 539-548, wherein the diastereomeric selectivity for forming a chiral internucleotidic linkage is measured by forming a dimeric oligonucleotide comprising the chiral internucleotidic linkage and the nucleosides to both sides of the chiral internucleotidic linkage under the same or comparable reaction conditions.

550. A method for preparing an oligonucleotide composition for selective suppression of a transcript of a target nucleic acid sequence, comprising providing an oligonucleotide composition comprising a predetermined level of oligonucleotides of a particular oligonucleotide type characterized by:
  1) a common base sequence;
  2) a common pattern of backbone linkages; and
  3) a common pattern of backbone chiral centers, which pattern comprises $(Sp)_m(Rp)_n$, $(Rp)_n(Sp)_m$, $(Np)_t(Rp)_n(Sp)_m$, or $(Sp)_t(Rp)_n(Sp)_m$, wherein:
    m is 1-50;
    n is 1-10;
    t is 1-50;
    each Np is independently Rp or Sp;
  wherein the target nucleic acid sequence comprises a characteristic sequence element that defines the target nucleic acid sequence from a similar nucleic acid sequence;
  wherein the common base sequence is a sequence whose DNA cleavage pattern and/or stereorandom cleavage pattern has a cleavage site within or in the vicinity of the target nucleic acid sequence.

551. The method of embodiment 658, wherein the pattern comprises $(Sp)_m(Rp)_n$.

552. The method of embodiment 658, wherein the pattern comprises $(Rp)_n(Sp)_m$.

553. The method of embodiment 658, wherein the pattern comprises $(Np)_t(Rp)_n(Sp)_m$.

554. The method of embodiment 658, wherein the pattern comprises $(Sp)_t(Rp)_n(Sp)_m$.

555. The method of embodiment 658, wherein the pattern is a pattern in any one of embodiments 152-164.

556. The method of any one of embodiments 550-554, wherein a cleavage site is in any one of embodiments 257-296.

557. The method of any one of the preceding embodiments, wherein the oligonucleotide composition is a composition of any one of embodiments 1-396 and 537-549.

558. The composition or method of any one of the preceding embodiments, wherein the sequence of the oligonucleotide in a chirally controlled oligonucleotide composition comprises, consists of, or is the sequence of any oligonucleotide described herein, or selected from Tables N1A, N2A, N3A, N4A or 8; or WV-937, WV-1090, WV-1091, WV-1087, WV-1092, WV-2603, WV-2595, WV-2378, WV-2380, WV-1510, WV-2619, WV-2611, WV-1497, WV-2602, WV-2618, and WV-2601.

559. A composition comprising a lipid and an oligonucleotide.

560. The composition of any one of the preceding embodiments, wherein the composition comprises one or more lipids conjugated with one or more oligonucleotides in the composition.

561. A composition comprising an oligonucleotide and a lipid selected from the list of: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl.

562. A composition comprising an oligonucleotide and a lipid selected from the list of: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl.

563. A composition comprising an oligonucleotide and a lipid selected from:

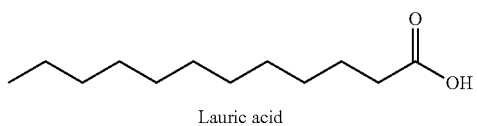
Lauric acid

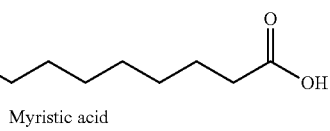
Myristic acid

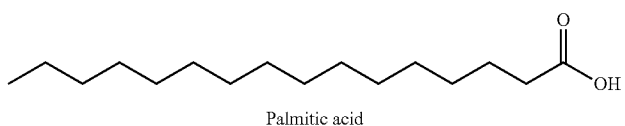
Palmitic acid

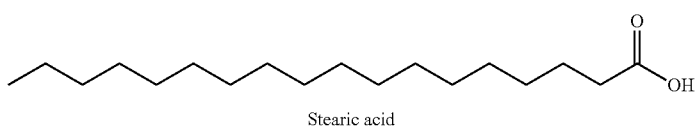
Stearic acid

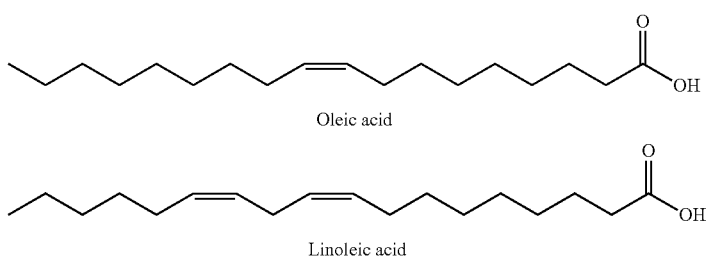
Oleic acid

Linoleic acid

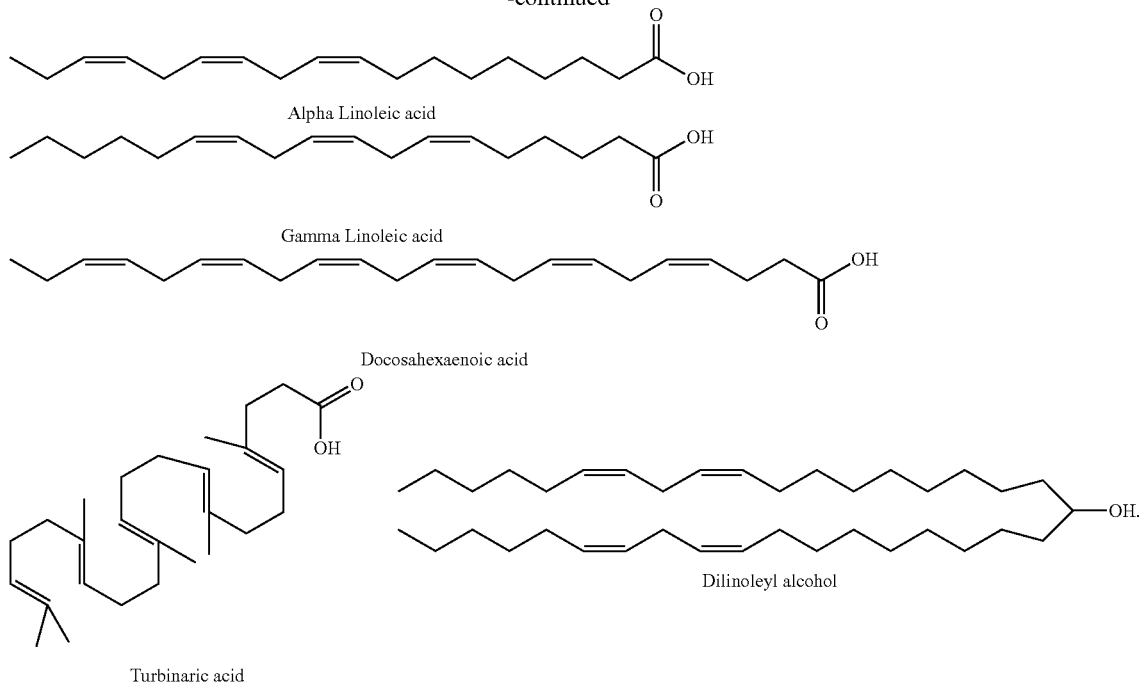

564. A composition comprising an oligonucleotide and a lipid, wherein the lipid comprises a $C_{10}$-$C_{40}$ linear, saturated or partially unsaturated, aliphatic chain, optionally substituted with one or more $C_{1-4}$ aliphatic group.

565. An oligonucleotide composition comprising a plurality of oligonucleotides, which share:
1) a common base sequence;
2) a common pattern of backbone linkages; and
3) a common pattern of backbone phosphorus modifications;
wherein one or more oligonucleotides of the plurality are individually conjugated to a lipid.

566. A chirally controlled oligonucleotide composition comprising a plurality of oligonucleotides, which share:
1) a common base sequence;
2) a common pattern of backbone linkages; and
3) a common pattern of backbone phosphorus modifications;
wherein:
the composition is chirally controlled in that the plurality of oligonucleotides share the same stereochemistry at one or more chiral internucleotidic linkages;
one or more oligonucleotides of the plurality are individually conjugated to a lipid; and one or more oligonucleotides of the plurality are optionally and individually conjugated to a targeting compound or moiety.

567. A method of delivering an oligonucleotide to a cell or tissue in a human subject, comprising:
(a) providing a composition of any one of the preceding embodiments; and
(b) Administering the composition to the human subject such that the oligonucleotide is delivered to a cell or tissue in the subject.

568. A method for delivering an oligonucleotide to a cell or tissue comprising preparing a composition according to any one of the preceding embodiments and treating [contacting] the cell or tissue with the composition.

569. A method of modulating the level of a transcript or gene product of a gene in a cell, the method comprising the step of contacting the cell with a composition according to any one of the preceding embodiments, wherein the oligonucleotide is capable of modulating the level of the transcript or gene product.

570. A method for inhibiting expression of a gene in a cell or tissue comprising preparing a composition according to any one of the preceding embodiments and treating the cell or tissue with the composition.

571. A method for inhibiting expression of a gene in a cell or tissue in a mammal comprising preparing a composition according to any one of the preceding embodiments and administering the composition to the mammal.

572. A method of treating a disease that is caused by the over-expression of one or several proteins in a cell or tissue in a subject, said method comprising the administration of a composition according to any one of the preceding embodiments to the subject.

573. A method of treating a disease that is caused by a reduced, suppressed or missing expression of one or several proteins in a subject, said method comprising the administration of a composition according to any one of the preceding embodiments to the subject.

574. A method for generating an immune response in a subject, said method comprising the administration of a composition according to any one of the preceding embodiments to the subject, wherein the biologically active compound is an immunomodulating nucleic acid.

575. A method for treating a sign and/or symptom of Huntington's Disease by providing a composition of any one of the preceding embodiments and administering the composition to the subject.

576. A method of modulating the amount of RNaseH-mediated cleavage in a cell, the method comprising the step of contacting the cell with a composition according to any one of the preceding embodiments, wherein the oligonucleotide is capable of modulating the amount of RNaseH-mediated cleavage.

577. A method of administering an oligonucleotide to a subject in need thereof, comprising steps of providing a composition comprising the agent a lipid, and administering the composition to the subject, wherein the agent is any agent disclosed herein, and wherein the lipid is any lipid disclosed herein.

578. A method of treating a disease in a subject, the method comprising steps of providing a composition comprising the agent a lipid, and administering a therapeutically effective amount of the composition to the subject, wherein the agent is any agent disclosed herein, and wherein the lipid is any lipid disclosed herein, and wherein the disease is any disease disclosed herein.

579. The composition or method of any one of the preceding embodiments, wherein a lipid comprises an optionally substituted $C_{10}$-$C_{40}$ saturated or partially unsaturated aliphatic chain.

580. The composition or method of any one of the preceding embodiments, wherein a lipid comprises an optionally substituted $C_{10}$-$C_{40}$ linear, saturated or partially unsaturated, aliphatic chain.

581. The composition or method of any one of the preceding embodiments, wherein a lipid comprises a $C_{10}$-$C_{40}$ linear, saturated or partially unsaturated, aliphatic chain, optionally substituted with one or more $_{C1-4}$ aliphatic group.

582. The composition or method of any one of the preceding embodiments, wherein a lipid comprises an unsubstituted $C_{10}$-$C_{40}$ linear, saturated or partially unsaturated, aliphatic chain.

583. The composition or method of any one of the preceding embodiments, wherein a lipid comprises no more than one optionally substituted $C_{10}$-$C_{40}$ linear, saturated or partially unsaturated, aliphatic chain.

584. The composition or method of any one of the preceding embodiments, wherein a lipid comprises two or more optionally substituted $C_{10}$-$C_{40}$ linear, saturated or partially unsaturated, aliphatic chain.

585. The composition or method of any one of the preceding embodiments, wherein a lipid comprises no tricyclic or polycyclic moiety.

586. The composition or method of any one of the preceding embodiments, wherein a lipid has the structure of $R^1$—COOH, wherein $R^1$ is an optionally substituted $C_{10}$-$C_{40}$ saturated or partially unsaturated aliphatic chain.

587. The composition or method of any one of the preceding embodiments, wherein the lipid is conjugated through its carboxyl group.

588. The composition or method according to any one of the preceding embodiments, wherein the lipid is selected from:

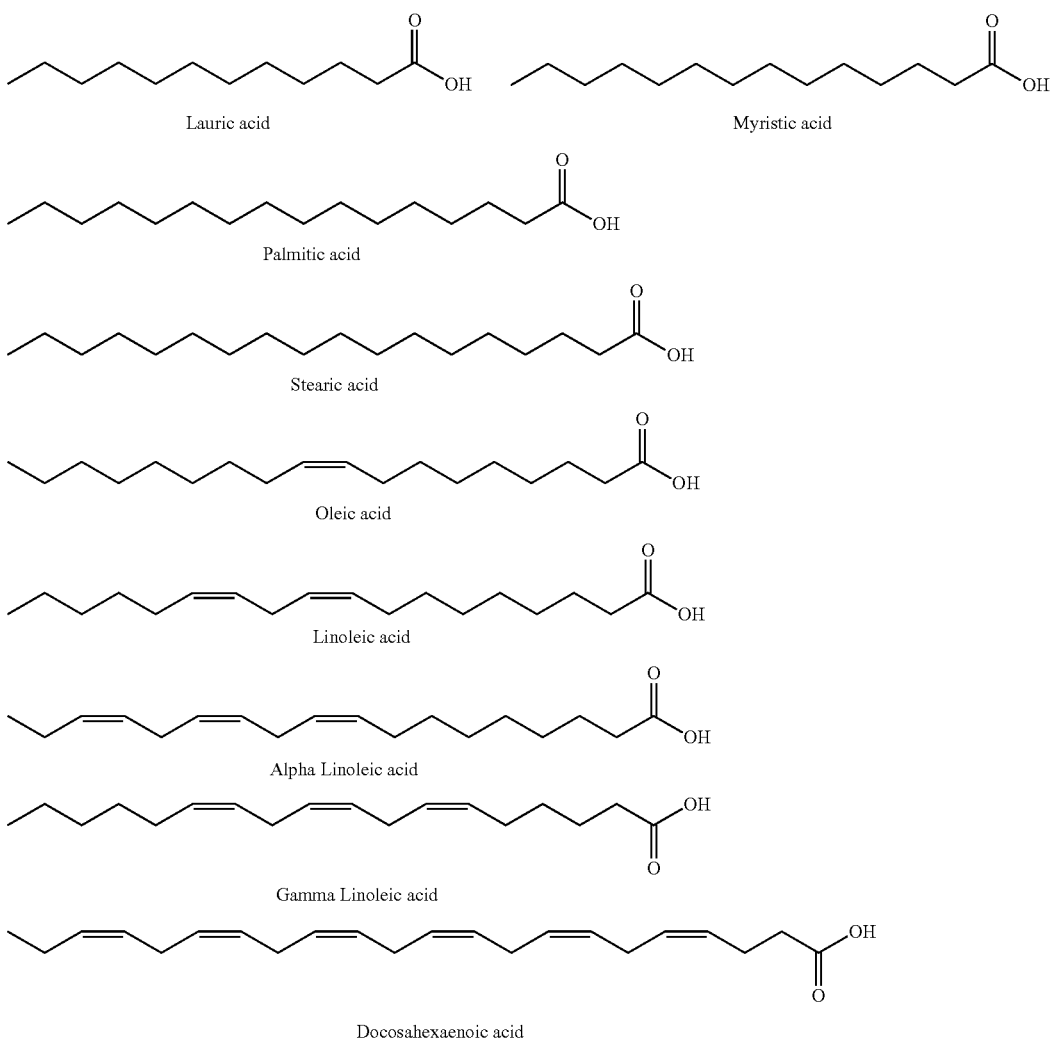

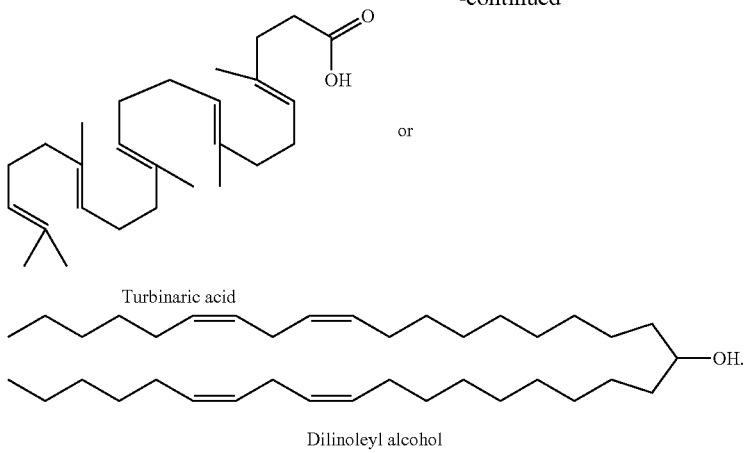

Turbinaric acid

Dilinoleyl alcohol

589. The composition or method of any one of the preceding embodiments, wherein the lipid is conjugated to the oligonucleotide.

590. The composition or method of any one of the preceding embodiments, wherein the lipid is directly conjugated to the oligonucleotide.

591. The composition or method of any one of the preceding embodiments, wherein the lipid is conjugated to the oligonucleotide via a linker.

592. The composition or method of any one of the preceding embodiments, wherein the linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; and a linker comprising at least one peptide-based cleavage group.

593. The composition or method of any one of the preceding embodiments, wherein each oligonucleotide of the plurality is individually conjugated to the same lipid at the same location.

594. The composition or method of any one of the preceding embodiments, wherein a lipid is conjugated to an oligonucleotide through a linker.

595. The composition or method of any one of the preceding embodiments, wherein one or more oligonucleotides of the plurality are independently conjugated to a targeting compound or moiety.

596. The composition or method of any one of the preceding embodiments, wherein one or more oligonucleotides of the plurality are independently conjugated to a lipid and a targeting compound or moiety.

597. The composition or method of any one of the preceding embodiments, wherein one or more oligonucleotides of the plurality are independently conjugated to a lipid at one end and a targeting compound or moiety at the other.

598. The composition or method of any one of the preceding embodiments, wherein oligonucleotides of the plurality share the same chemical modification patterns.

599. The composition or method of any one of the preceding embodiments, wherein oligonucleotides of the plurality share the same chemical modification patterns comprising one or more base modifications.

600. The composition or method of any one of the preceding embodiments, wherein oligonucleotides of the plurality share the same chemical modification patterns comprising one or more sugar modifications.

601. The composition or method of any one of the preceding embodiments, wherein the common base sequence is capable of hybridizing with a transcript in a cell, which transcript contains a mutation that is linked to a muscle disease, or whose level, activity and/or distribution is linked to a muscle disease.

602. The composition or method of any one of the preceding embodiments, wherein the oligonucleotide is a nucleic acid.

603. The composition or method of any one of the preceding embodiments, wherein the oligonucleotide is an oligonucleotide.

604. The composition or method of any one of the preceding embodiments, wherein the oligonucleotide is an oligonucleotide which mediates exon skipping.

605. The composition or method of any one of the preceding embodiments, wherein the oligonucleotide is a stereodefined oligonucleotide which mediates exon skipping.

606. The composition or method of any one of the preceding embodiments, wherein the disease or disorder is a muscle-related disease or disorder.

607. The composition or method of any one of the preceding embodiments, wherein the lipid comprises an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

608. The composition or method of any one of the preceding embodiments, wherein the lipid comprises an optionally substituted $C_{10}$-$C_{80}$ saturated or partially unsaturated, aliphatic chain.

609. The composition or method of any one of the preceding embodiments, wherein the lipid comprises an optionally substituted $C_{10}$-$C_{80}$ linear, saturated or partially unsaturated, aliphatic chain.

610. The composition or method of any one of the preceding embodiments, wherein the lipid comprises an optionally substituted $C_{10}$-$C_{60}$ saturated or partially unsaturated, aliphatic chain.

611. The composition or method of any one of the preceding embodiments, wherein the lipid comprises an optionally substituted $C_{10}$-$C_{60}$ linear, saturated or partially unsaturated, aliphatic chain.

612. The composition or method of any one of the preceding embodiments, wherein the lipid comprises an optionally substituted $C10$-$C_{40}$ saturated or partially unsaturated, aliphatic chain.

613. The composition or method of any one of the preceding embodiments, wherein the lipid comprises an optionally substituted $C10$-$C_{40}$ linear, saturated or partially unsaturated, aliphatic chain.

614. The composition or method of any one of the preceding embodiments, wherein the lipid comprises an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

615. The composition or method of any one of the preceding embodiments, wherein the lipid comprises an optionally substituted $C_{10}$-$C_{80}$ saturated or partially unsaturated, aliphatic chain.

616. The composition or method of any one of the preceding embodiments, wherein the lipid comprises an optionally substituted $C_{10}$-$C_{60}$ linear, saturated or partially unsaturated, aliphatic chain.

617. The composition or method of any one of the preceding embodiments, wherein the lipid comprises an optionally substituted $C_{10}$-$C_{40}$ linear, saturated or partially unsaturated, aliphatic chain.

618. The composition or method of any one of the preceding embodiments, wherein the lipid comprises an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

619. The composition or method of any one of the preceding embodiments, wherein the lipid comprises an optionally substituted $C_{10}$-$C_{40}$ saturated or partially unsaturated, aliphatic chain.

620. The composition or method of any one of the preceding embodiments, wherein the lipid comprises an optionally substituted $C_{10}$-$C_{40}$ linear, saturated or partially unsaturated, aliphatic chain.

621. The composition or method of any one of the preceding embodiments, wherein the composition further comprises one or more additional components selected from: a polynucleotide, carbonic anhydrase inhibitor, a dye, an intercalating agent, an acridine, a cross-linker, psoralene, mitomycin C, a porphyrin, TPPC4, texaphyrin, Sapphyrin, a polycyclic aromatic hydrocarbon phenazine, dihydrophenazine, an artificial endonuclease, a chelating agent, EDTA, an alkylating agent, a phosphate, an amino, a mercapto, a PEG, PEG-40K, MPEG, [MPEG]$_2$, a polyamino, an alkyl, a substituted alkyl, a radiolabeled marker, an enzyme, a hapten biotin, a transport/absorption facilitator, aspirin, vitamin E, folic acid, a synthetic ribonuclease, a protein, a glycoprotein, a peptide, a molecule having a specific affinity for a co-ligand, an antibody, a hormone, a hormone receptor, a non-peptidic species, a lipid, a lectin, a carbohydrate, a vitamin, a cofactor, or a drug.

622. The composition or method of any one of the preceding embodiments, wherein the lipid comprises a $C_{10}$-$C_{80}$ linear, saturated or partially unsaturated, aliphatic chain.

623. The composition or method of any one of the preceding embodiments, wherein the composition further comprises a linker linking the oligonucleotide and the lipid, wherein the linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

624. The composition or method of any one of the preceding embodiments, wherein the oligonucleotide comprises or consists of or is an oligonucleotide or oligonucleotide composition or chirally controlled oligonucleotide composition.

625. The composition or method of any one of the preceding embodiments, wherein the oligonucleotide comprises or consists of or is an oligonucleotide or oligonucleotide composition or chirally controlled oligonucleotide composition, wherein the sequence of the oligonucleotide comprises or consists of the sequence of any oligonucleotide described herein.

626. The composition or method of any one of the preceding embodiments, wherein the oligonucleotide comprises or consists of or is an oligonucleotide or oligonucleotide composition or chirally controlled oligonucleotide composition, wherein the sequence of the oligonucleotide comprises or consists of the sequence of any oligonucleotide listed in Table 4.

627. The composition or method of any one of the preceding embodiments, wherein the oligonucleotide comprises or consists of or is an oligonucleotide or oligonucleotide composition or chirally controlled oligonucleotide composition, wherein the sequence of the oligonucleotide comprises or consists of the sequence of a splice-switching oligonucleotide.

628. The composition or method of any one of the preceding embodiments, wherein the oligonucleotide comprises or consists of or is an oligonucleotide or oligonucleotide composition or chirally controlled oligonucleotide composition, wherein the sequence of the oligonucleotide comprises or consists of the sequence of an oligonucleotide capable of skipping or mediating skipping of an exon in the dystrophin gene.

629. The composition or method of any of the preceding embodiments, wherein the oligonucleotide is a chirally controlled oligonucleotide composition.

630. The composition or method of any of the preceding embodiments, wherein the disease or disorder is Huntington's Disease.
631. The composition or method of any of the preceding embodiments, wherein the oligonucleotide is capable of participating in RNaseH-mediated cleavage of a mutant Huntingtin gene mRNA.
632. The composition or method of any of the preceding embodiments, wherein the oligonucleotide comprises, consists of or is the sequence of any oligonucleotide disclosed herein.
633. The composition or method of any of the preceding embodiments, wherein the oligonucleotide is capable of differentiating between a wild-type and a mutant Huntingtin allele.
634. The composition or method of any of the preceding embodiments, wherein the oligonucleotide is capable of participating in RNaseH-mediated cleavage of a mutant Huntingtin gene mRNA.
635. The composition or method of any of the preceding embodiments, wherein the oligonucleotide comprises, consists of or is the sequence of any oligonucleotide disclosed in Table 4.
636. The composition or method of any one of the preceding embodiments, wherein the oligonucleotide comprises or consists of or is an oligonucleotide or oligonucleotide composition or chirally controlled oligonucleotide composition, wherein the sequence of the oligonucleotide comprises or consists of the sequence of any of: WV-937, WV-1087, WV-1090, WV-1091, WV-1092, WV-2603, WV-2595, WV-2378, WV-2380, WV-1510, WV-2619, WV-2611, WV-1497, WV-2602, WV-2618, and WV-2601.
637. The composition or method of any one of the preceding embodiments, wherein the sequence of an oligonucleotide includes any one or more of: base sequence (including length); pattern of chemical modifications to sugar and base moieties; pattern of backbone linkages; pattern of natural phosphate linkages, phosphorothioate linkages, phosphorothioate triester linkages, and combinations thereof; pattern of backbone chiral centers; pattern of stereochemistry (Rp/Sp) of chiral internucleotidic linkages; pattern of backbone phosphorus modifications; pattern of modifications on the internucleotidic phosphorus atom, such as —S⁻, and -L-R¹ of formula I.
638. An oligonucleotide comprising a sequence that shares greater than about 50%, 60%, 70%, 75%, 80%, 85%, 90%, 95% identity with a sequence found in a provided example oligonucleotide.
639. The oligonucleotide of embodiment 638, wherein the sequence of the oligonucleotide is the sequence of a provided example oligonucleotide.
640. The oligonucleotide of embodiment 638 or 639, wherein the provided example oligonucleotide is an oligonucleotide selected from Table N1A, N2A, N3A, N4A or 8.
641. The oligonucleotide of embodiment 638, wherein the provided example oligonucleotide is WV-1092.
642. The oligonucleotide of embodiment 638, wherein the provided example oligonucleotide is WV-2595.
643. The oligonucleotide of embodiment 638, wherein the provided example oligonucleotide is WV-2603.
644. The oligonucleotide of embodiment 638, wherein the provided example oligonucleotide is WV-2378.
645. The oligonucleotide of embodiment 638, wherein the provided example oligonucleotide is WV-2380.
646. The oligonucleotide of embodiment 638, wherein the provided example oligonucleotide is WV-1510.
647. The oligonucleotide of embodiment 638, wherein the provided example oligonucleotide is WV-2619.
648. The oligonucleotide of embodiment 638, wherein the provided example oligonucleotide is WV-2611.
649. The oligonucleotide of embodiment 638, wherein the provided example oligonucleotide is WV-1497.
650. The oligonucleotide of embodiment 638, wherein the provided example oligonucleotide is WV-2602.
651. The oligonucleotide of embodiment 638, wherein the provided example oligonucleotide is WV-2618.
652. The oligonucleotide of embodiment 638, wherein the provided example oligonucleotide is WV-2601.
653. The oligonucleotide of any one of the preceding embodiments, wherein the oligonucleotide comprises the sequence found in the provided example oligonucleotide.
654. The oligonucleotide of any one of the preceding embodiments, wherein the oligonucleotide consists of the sequence found in the provided example oligonucleotide.
655. An oligonucleotide of any one of the preceding embodiments, wherein the oligonucleotide comprises one or more natural phosphate linkages and one or more modified internucleotidic linkages.
656. The oligonucleotide of embodiment 655, wherein the oligonucleotide is an oligonucleotide of any one of embodiments 638-654.
657. The oligonucleotide of any one of the preceding embodiments, wherein the oligonucleotide comprises 2, 3, 4, 5, 6, 7, 8, 9, 10, or more natural phosphate linkages.
658. The oligonucleotide of any one of the preceding embodiments, wherein the oligonucleotide comprises one or more modified internucleotidic linkages.
659. The oligonucleotide of any one of the preceding embodiments, wherein the oligonucleotide comprises two or more modified internucleotidic linkages.
660. The oligonucleotide of any one of the preceding embodiments, wherein the oligonucleotide comprises 3, 4, 5, 6, 7, 8, 9, 10, 11, 12, 13, 14, 15, 16, 17, 18, 19, 20 or more modified internucleotidic linkages.
661. The oligonucleotide of any one of the preceding embodiments, wherein the oligonucleotide comprises 5, 6, 7, 8, 9, 10, 11, 12, 13, 14, 15, 16, 17, 18, 19, 20 or more modified internucleotidic linkages.
662. The oligonucleotide of any one of the preceding embodiments, wherein the oligonucleotide comprises 10 or more modified internucleotidic linkages.
663. The oligonucleotide of any one of the preceding embodiments, wherein at least one of the modified internucleotidic linkages is a chirally controlled internucleotidic linkage in that oligonucleotides having the same sequence and chemical modifications within a composition share the same configuration, either Rp or Sp, at the chiral phosphorus atom of the modified internucleotidic linkage.
664. The oligonucleotide of any one of the preceding embodiments, wherein at least two modified internucleotidic linkages are chirally controlled.
665. The oligonucleotide of any one of the preceding embodiments, wherein at least 3, 4, 5, 6, 7, 8, 9, 10, 11, 12, 13, 14, 15, 16, 17, 18, 19, 20 modified internucleotidic linkages are chirally controlled.
666. The oligonucleotide of any one of the preceding embodiments, wherein at least one modified internucleotidic linkage within a consecutive modified internucleotidic linkage region is chirally controlled.
667. The oligonucleotide of any one of the preceding embodiments, wherein at least two modified internucleotidic linkages within a consecutive modified internucleotidic linkage region are chirally controlled.

668. The oligonucleotide of any one of the preceding embodiments, wherein at least 3, 4, 5, 6, 7, 8, 9, 10, 11, 12, 13, 14, 15, 16, 17, 18, 19, 20 modified internucleotidic linkages within a consecutive modified internucleotidic linkage region are chirally controlled.
669. The oligonucleotide of any one of the preceding embodiments, wherein each modified internucleotidic linkage within a consecutive modified internucleotidic linkage region is chirally controlled.
670. The oligonucleotide of any one of the preceding embodiments, wherein each modified internucleotidic linkage is chirally controlled.
671. The oligonucleotide of any one of the preceding embodiments, wherein a provided oligonucleotide comprises a (Sp)xRp(Sp)y pattern, wherein each of x and y is independently 1-20, and the sum of x and y is 1-50.
672. The oligonucleotide of any one of the preceding embodiments, wherein each of x and y is independently 2-20.
673. The oligonucleotide of any one of the preceding embodiments, wherein at least one of x and y is greater than 5, 6, 7, 8, 9, or 10.
674. The oligonucleotide of any one of the preceding embodiments, wherein the sum of x and y is greater than 5, 6, 7, 8, 9, 10, 11, 12, 13, 14, 15, 16, 17, 18, 19 or 20.
675. The oligonucleotide of any one of the preceding embodiments, wherein a provided oligonucleotide comprises one or more chemical modifications.
676. The oligonucleotide of any one of the preceding embodiments, wherein a provided oligonucleotide comprises one or more base modifications.
677. The oligonucleotide of any one of the preceding embodiments, wherein a provided oligonucleotide comprises one or more sugar modifications.
678. The oligonucleotide of any one of the preceding embodiments, wherein a sugar modification is a 2'-modification.
679. The oligonucleotide of any one of the preceding embodiments, wherein a sugar modification is LNA.
680. The oligonucleotide of any one of the preceding embodiments, wherein a provided oligonucleotide is a chirally controlled oligonucleotide.
681. The oligonucleotide of any one of the preceding embodiments, wherein the oligonucleotide is conjugated to a targeting component.
682. A oligonucleotide composition, comprising an oligonucleotide of any one of the preceding embodiments.
683. The composition of embodiment 682, wherein the composition is a chirally controlled oligonucleotide composition comprising a predetermined level of the oligonucleotide.
684. The composition of any one of the preceding embodiments, or the composition in the method of any one of the preceding embodiments, further comprising a selectivity agent selected from: the group of compounds which binds specifically to one or more neurotransmitter transporters selected from the group consisting of a dopamine transporter (DAT), a serotonin transporter (SERT), and a norepinephrine transporter (NET); the group consisting of a dopamine reuptake inhibitor (DRI), a selective serotonin reuptake inhibitor (SSRI), a noradrenaline reuptake inhibitor (NRI), a norepinephrine-dopamine reuptake inhibitor (NDRI), and a serotonin-norepinephrine-dopamine reuptake inhibitor (SNDRI); the group consisting of a triple reuptake inhibitor, a noradrenaline dopamine double reuptake inhibitor, a serotonin single reuptake inhibitor, a noradrenaline single reuptake inhibitor, and a dopamine single reuptake inhibitor; and the group consisting of a dopamine reuptake inhibitor (DRI), a Norepinephrine-Dopamine Reuptake Inhibitor (NDRI) and a serotonin-Norepinephrine-Dopamine Reuptake Inhibitor (SNDRI).
685. A method for treating or preventing Huntington's Disease in a subject, comprising administering to the subject an oligonucleotide or a composition of any one of the preceding embodiments.
686. A method of any one of the preceding embodiments, wherein the oligonucleotide or composition is administered via intrathecal administration.
687. A method for preparing an oligonucleotide, comprising providing a chiral reagent having the structure of Formula 3-AA.
688. A method for preparing an oligonucleotide, comprising providing a chiral reagent having the structure of

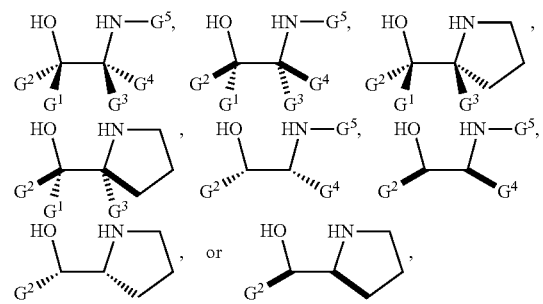

689. The method of any one of the preceding embodiments, wherein the chiral reagent is chirally pure.
690. A method for preparing an oligonucleotide, comprising providing a compound comprising a moiety from a chiral reagent having the structure of any one of the preceding embodiments, wherein —W¹H and —W²H, or the hydroxyl and amino groups, form bonds with the phosphorus atom of the phosphoramidite.
691. The method of embodiment 690, wherein the compound has the structure of

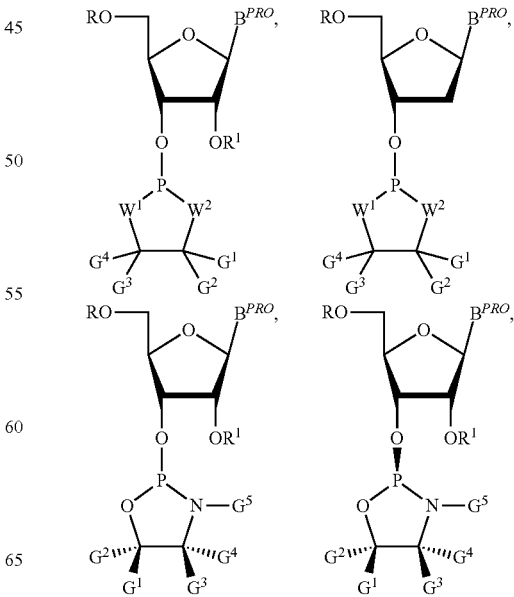

537
-continued
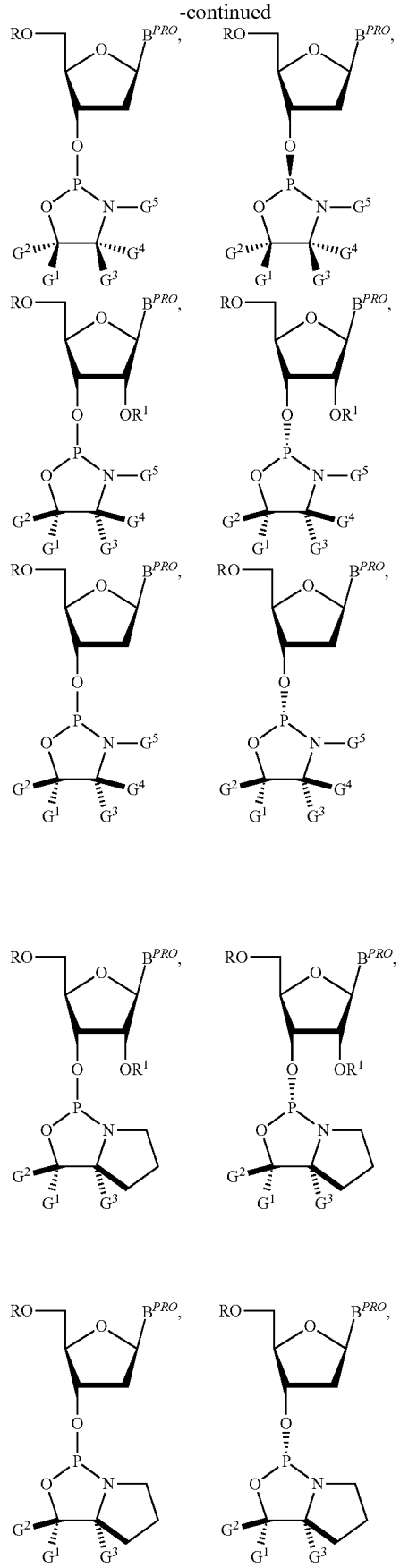
538
-continued
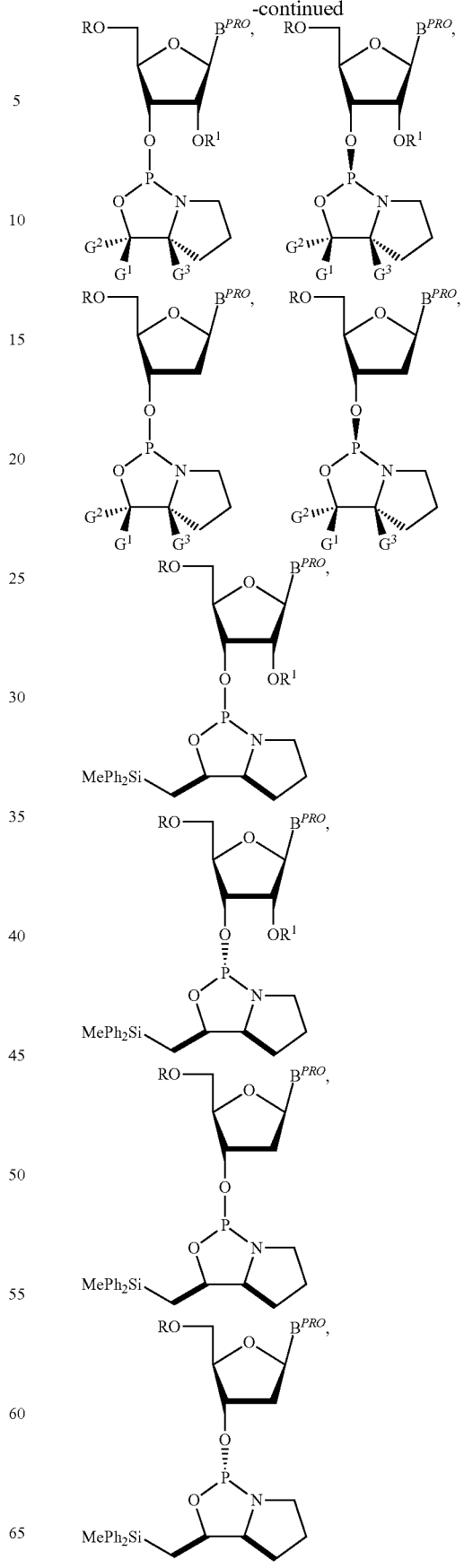

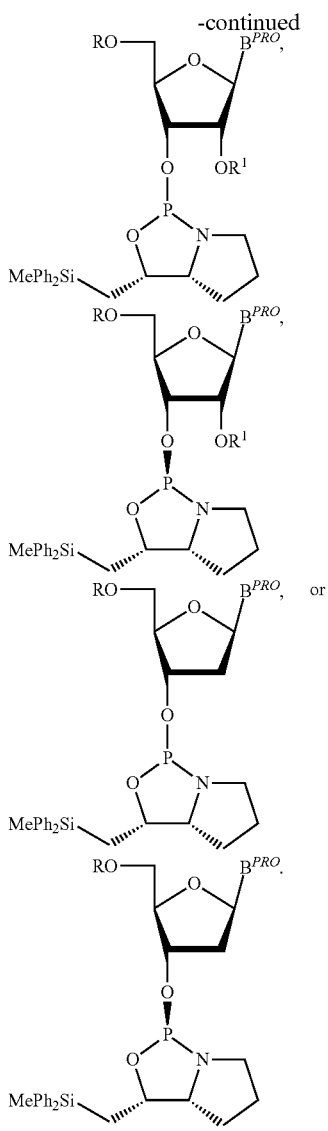

or

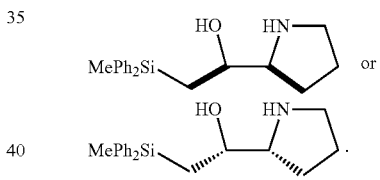

692. The method of embodiment 691, wherein R connected to the 5'-O is a hydroxyl protecting group.
693. The method of embodiment 692, wherein the hydroxyl protecting group is DMTr.
694. The method of embodiment 693, wherein $B^{PRO}$ is a protected nucleobase.
695. The method of embodiment 694, wherein the nucleobase is an optionally substituted nucleobase selected from A, T, C and G.
696. The method of any one of the preceding embodiments, wherein $W^1$ is —$NG^5$, $W^2$ is O.
697. The method of any one of the preceding embodiments, wherein each of $G^1$ and $G^3$ is independently hydrogen or an optionally substituted group selected from $C_{1-10}$ aliphatic, heterocyclyl, heteroaryl and aryl, $G^2$ is —$C(R)_2Si(R)_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused.
698. The method of any one of the preceding embodiments, wherein each R is independently hydrogen, or an optionally substituted group selected from $C_1$-$C_6$ aliphatic, carbocyclyl, aryl, heteroaryl, and heterocyclyl.
699. The method of any one of the preceding embodiments, wherein $G^1$ is hydrogen.
700. The method of any one of the preceding embodiments, wherein $G^2$ is —$C(R)_2Si(R)_3$, wherein —$C(R)_2$— is optionally substituted —$CH_2$—, and each R of —$Si(R)_3$ is independently an optionally substituted group selected from $C_{1-10}$ aliphatic, heterocyclyl, heteroaryl and aryl.
701. The method of any one of the preceding embodiments, wherein at least one R of —$Si(R)_3$ is independently optionally substituted $C_{1-10}$ alkyl.
702. The method of any one of the preceding embodiments, wherein at least one R of —$Si(R)_3$ is independently optionally substituted phenyl.
703. The method of any one of the preceding embodiments, wherein one R of —$Si(R)_3$ is independently optionally substituted $C_{1-10}$ alkyl, and each of the other two R is independently optionally substituted phenyl.
704. The method of any one of the preceding embodiments, wherein $G^2$ is optionally substituted —$CH_2Si(Me)(Ph)_2$.
705. The method of any one of the preceding embodiments, wherein $G^2$ is —$CH_2Si(Me)(Ph)_2$.
706. The method of any one of the preceding embodiments, wherein $G^3$ is hydrogen.
707. The method of any one of the preceding embodiments, wherein $G^4$ and $G^5$ are taken together to form an optionally substituted saturated 5-6 membered ring containing one nitrogen atom.
708. The method of any one of the preceding embodiments, wherein $G^4$ and $G^5$ are taken together to form an optionally substituted saturated 5-membered ring containing one nitrogen atom.

709. The method of any one of the preceding embodiments, comprising providing a fluoro-containing reagent.
710. The method of any one of the preceding embodiments, wherein the fluoro-containing reagent is TBAF.
711. The method of any one of the preceding embodiments, comprising using a linker that is stable to a TBAF condition for removing the chiral reagent.
712. The method of any one of the preceding embodiments, wherein the linker is an SP linker.
713. The method of any one of embodiments 687-709, wherein the fluoro-containing reagent is HF—$NR_3$.
714. The method of embodiment 713, wherein the fluoro-containing reagent is HF-$NEt_3$.
715. The method of embodiment 713 or 714, comprising using a linker that is stable to a HF—$NR_3$ condition for removing the chiral reagent.
716. The method of any one of embodiments 713-715, wherein the linker is a succinyl linker.

EXAMPLES

The foregoing has been a description of certain non-limiting embodiments of the disclosure. Accordingly, it is to be understood that the embodiments of the disclosure herein described are merely illustrative of the application of the principles of the disclosure. Reference herein to details of the illustrated embodiments is not intended to limit the scope of the claims.

Example 1. In Vitro Metabolic Stabilities of Human Chiromersens in Preincubated Rat Whole Liver Homogenates The present Example describes comparisons of in vitro whole rat liver homogenate stability of Mipomersen (stereochemical mixture) with chirally controlled oligonucleotide compositions of Mipomersen ("chiromersens"). The method, among other things, is useful in screening compounds to predict in vivo half lives.

As is known in the art, Mipomersen (previously ISIS 301012, sold under the trade name Kynamro) is a 20mer oligonucleotide whose base sequence is antisense to a portion of the apolipoprotein B gene. Mipomersen inhibits apolipoprotein B gene expression, presumably by targeting mRNA. Mipomersen has the following structure:

G*-C*-C*-U*-C*-dA-dG-dT-dC-dT-dG-dmC-dT-dT-dmC-G*-C*-A*-C*-C*

[d = 2'-deoxy, *= 2'-O-(2-methoxyethyl)]

with 3'→5' phosphorothioate linkages. Thus, Mipomersen has 2'-O-methoxyethyl-modified ribose residues at both ends, and deoxyribose residues in the middle.

Tested chirally pure Mipomersen analogs described in this Example included phosphorothioate linkages. In some embodiments, tested analogs include one or more 2'-O-(2-methoxyethyl)-modified residues; in some embodiments, tested analogs include only 2'-deoxy residues. Particular tested analogs had the structures set forth below in Tables 3 and 4.

Protocol: We used the protocol reported by Geary et al. (Oligonucleotides, Volume 20, Number 6, 2010) with some modifications.

Test system: Six male Sprague-Dawley rats (*Rattus norvegicus*) were supplied by Charles River Laboratories, Inc., (Hollister, Calif.), and were received at SNBL USA.

Tissue Collection: Animals were acclimated to the study room for two days prior to tissue collection. At the time of tissue collection, animals were anesthetized with an intraperitoneal (IP) injection of sodium pentobarbital solution. Liver perfusion was performed using 500 mL of chilled saline/animal, administered via the hepatic portal vein. After perfusion, the livers were dissected and maintained on ice. Livers were minced into small pieces then weighed.

Liver Homogenate Preparation: The minced pieces of liver tissues were transferred to tared 50 mL centrifuge tubes and weighed. Chilled homogenization buffer (100 mM Tris pH 8.0, 1 mM magnesium acetate, with antibiotic-antimycotic agents) was added to each tube, such that the tube(s) contained 5 mL of buffer per gram of tissue. Using a QIAGEN TissueRuptor tissue homogenizer, the liver/buffer mixture was homogenized while maintaining the tube on ice. The protein concentration of the liver homogenate pool was determined using a Pierce BCA protein assay. Liver homogenates were divided into 5 mL aliquots, transferred to appropriately sized labeled cryovials and stored at −60° C.

Incubation Conditions: 5 ml aliquots of frozen liver homogenate (protein concentration=22.48 mg/ml) were thawed and incubated at 37° C. for 24 hrs. Six eppendorf tubes (2 ml) were taken for each oligomer in table 1and 450 ul of homogenate was added in each tube. 50 ul ASO (200 uM) was added to each tube. Immediately after mixing, 125 ul of (5×) stop buffer (2.5% IGEPAL, 0.5M NaCl, 5 mM EDTA, 50 mM Tris, pH=8.0) and 12.5 ul of 20 mg/ml Proteinase K (Ambion, # AM2546) was added to one tube for 0 hour time point. The remaining reaction mixtures were incubated at 37° C. with shaking at 400 rpm on VWR Incubating Microplate shaker. After incubation for a designated period (1, 2, 3, 4, and 5 days), each mixture was treated with 125 ul of (5×) stop buffer (2.5% IGEPAL, 0.5M NaCl, 5 mM EDTA, 50 mM Tris, pH=8.0) and 12.5 ul of 20 mg/ml Proteinase K (Ambion, # AM2546).

Work up and Bioanalysis: ISIS 355868 (5'-GCGTTT GCTCTTCTTCTTGCGTTTTTT-3' (SEQ ID NO: 392)), a 27-mer oligonucleotide (underlined bases are MOE modified) was used as the internal standard for quantitation of chiromersens. 50 ul of internal standard (200 uM) was added to each tube followed by addition of 250 ul of 30% ammonium hydroxide, 800 ul of Phenol: Chloroform: isoamyl alcohol (25:24:1). After mixing and centrifugation at 600 rpg, the aqueous layer was evaporated on speed vac to 100 ul and loaded on Sep Pak column (C18, 1 g, WAT 036905). All the aqueous washings (2×20 ml) of Sep pak column were tested with quick Ion Exchange method to ensure that no product was found there. 50% ACN (3.5 ml) was used to elute the oligonucleotide and metabolites and the column was further washed with 70% CAN (3.5) ensure that there was nothing left on the column. Five fractions were collected for each sequence. Water wash1, 2, 3, ACN1 and 2 using Visiprep system (Sigma, part number: 57031-U).

Ion Exchange Method

|   | Time | Flow (ml/min) | % A | % B | Curve |
|---|------|---------------|-----|-----|-------|
|   | Time | 1.0 | 95 | 5 |   |
| 1 | 2 | 1.0 | 95 | 5 | 1 |
| 2 | 3 | 1.0 | 75 | 25 | 6 |
| 3 | 10 | 1.0 | 35 | 65 | 6 |
| 4 | 10.1 | 1.0 | 95 | 5 | 6 |
| 5 | 12.5 | 1.0 | 95 | 5 | 1 |

Buffer A=10 mM Tris HCl, 50% ACN, pH=8.0
Buffer B=A+800 mM NaClO4
Column=DNA pac 100
Column Temperature 60° C.
Wash method was used after each run (Described in M9-Exp21) using the same buffers as above and 50:50 (methanol:water) in buffer line C.

|   | Time | Flow (ml/min) | % A | % B | % C | Curve |
|---|------|---------------|-----|-----|-----|-------|
|   | Time | 1.0 | 0 | 0 | 100 |   |
| 1 | 5.5 | 1.0 | 0 | 0 | 100 | 1 |
| 2 | 5.6 | 1.0 | 100 | 0 | 0 | 6 |
| 3 | 7.5 | 1.0 | 100 | 0 | 0 | 6 |

-continued

| Time | Flow (ml/min) | % A | % B | % C | Curve |
|---|---|---|---|---|---|
| 4  7.6 | 1.0 | 95 | 5 | 0 | 6 |
| 5  12.5 | 1.0 | 95 | 5 | 0 | 1 |

Acetonitrile eluate was concentrated to dryness and dissolved in 100 ul water to be analyzed using RPHPIPC.
Eluant A=10 mM Tributylammonium acetate, pH=7.0
Eluant B=ACN (HPLC grade, B& J)
Column: XTerra MS C18, 3.5 um, 4.6×50 mm, Part number: 186000432
Guard column from Phenomenex, part number: KJ0-4282
Column Temperature=60° C.
 HPLC Gradient:

| Time | Flow (ml/min) | % A | % B | Curve |
|---|---|---|---|---|
| 1 |  | 1.0 | 65 | 35 |  |
| 2 | 5.0 | 1.0 | 65 | 35 | 1 |
| 3 | 30.0 | 1.0 | 40 | 60 | 6 |
| 4 | 35.0 | 1.0 | 5 | 90 | 6 |
| 5 | 36.0 | 1.0 | 65 | 35 | 6 |
| 6 | 40.0 | 1.0 | 65 | 35 | 1 |

For Analytical RP HPLC, 10 ul of this stock solution was added to 40 ul water and 40 ul was injected.
Table 3.

TABLE 3

| S. NO. | Sequence | Description |
|---|---|---|
| ONT-41 | Gs5mCs5mCs Ts5mCsAs GsTs5mCs TsGs5mCs TsTs5mCs Gs5mCsAs 5mCs5mC (SEQ ID NO: 393) | Mipomersen |
| ONT-87 | Gs5mCs5mCsTs5mCsAsGsTs5mCsTsGs5mCsTsTs5mCsGs5mCsAs5mCs5mC (SEQ ID NO: 394) | MOE-wing-core-wing design— (human) RNAse H substrate 1 5R-(SSR)₃-5R |
| ONT-154 | Gs5mCs5mCsTs5mCsAsGsTs5mCsTsGs5mCsTsTs5mCsGs5mCsAs5mCs5mC (SEQ ID NO: 395) | All deoxy, (5S-(SSR)₃-5S) |
| ONT-70 | Gs5mCsGsTsTsTsGs5mCsTs5mCsTsTs5mCsTsTs5mCsTsTsGs5mCGsTsTsTsTsT (SEQ ID NO: 396) | ISIS 355868 internal standard for quantitation of Mipomersen |

Discussion:

2' modifications in antisense and siRNAs are predicted to stabilize these molecules and increase their the persistence in plasma and tissues compared with wild-type DNAs and siRNAs.

2'-MOE Wing-Core-Wing Design in Mipomersen.

The first generation antisense oligonucleotides employed in the first antisense clinical trials had 2'-deoxy ribonucleotide residues and phosphorothioate internucleoside linkages. Subsequently, second generation antisense oligonucleotides were developed, which were typically of what is referred to herein as "5-10-5 2'-MOE wing-core-wing design", in that five (5) residues at each end were 2'-O-methoxyethyl (2'-MOE)-modified residues and ten (10) residues in the middle were 2'-deoxy ribonucleotides; the internucleotide linkages of such oligonucleotides were phosphorothioates. Such "5-10-5 2'-MOE wing-core-wing" oligonucleotides exhibited marked improvement in potency over first generation (PCT/US2005/033837). Similar wing-core-wing motifs like 2-16-2, 3-14-3, 4-12-4, or 5-10-5 were designed to improve the stability of oligonucleotides to nucleases, while at the same time maintaining enough DNA structure for RNase activity.

Chirally pure oligonucleotides. The present disclosure provides chirally pure oligonucleotides and demonstrates, among other things, that selection of stereochemistry in and of itself can improve oligonucleotide stability (i.e., independent of residue modification such as 2'MOE modification). Indeed, the present disclosure demonstrates that chirally pure phosphorothioate oligonucleotides can provide same or better stability than corresponding 2'-modified stereorandom phosphorothioate compounds.

In some embodiments, tested chirally pure oligonucleotides are of the general structure X—Y—X with respect to stereochemistry in that they contain wing "X" regions (typically about 1-10 residues long) where all residues have the same stereochemistry flanking a core "Y" region in which stereochemistry varies. In many embodiments, about 20-50% of the nucleotide analogs in tested such oligonucleotides are not substrates for RNase H. The ability to control the stereochemistry of phosphorothioates in DNA enables us to protect the oligomers from degradation by nucleases while maintaining the RNase active sites. One of these designs is ONT-154 where wings of the oligonucleotide have been stabilized by Sp phosphorothioate chemistry with retention of few Rp phosphorothioates which are better substrates for RNase H (Molecular Cell, 2007). The crystal structure of human RNase H complexed with DNA/RNA duplex shows that the Phosphate-binding pocket of the enzyme makes contacts with four contiguous phosphates of DNA. The first three contacts seem stronger than fourth one and they prefer Pro-R/Pro-R/Pro-S oxygen atoms of each of these three phosphates. Combining the stability advantage coming from Sp stereochemistry with RNase H active sites, several sequences can be designed to compete with/or improve upon 2'-modifications. From rat whole liver homogenate stability experiment comparing Mipomersen (ONT-41) with our rational (chiral control) design with and without 2'-modifications (ONT-87 and ONT-154) (Table 1 and FIG. 1), it is evident that through removal of the 2'-modifications and careful chiral control with Rp and Sp phosphorothioates, we can improve the stability of these oligonucleotides which later affect the efficacy in vivo.

TABLE 4

Hu chiromersens studied for rat whole live homogenate stability

| Sequence | Description | Target | Tm (° C.) | SEQ ID NO: |
|---|---|---|---|---|
| ONT-41 | Gs5mCs5mCs Ts5mCsAs GsTs5mCs TsGs5mCs TsTs5mCs Gs5mCsAs 5mCs5mC | Hu ApoB | 80.7 | 397 |
| ONT-75 | Gs5mCs5mCsTs5mCsAsGsTs5mCsTsGs5mCsTs Ts5mCsGs5mCsAs5mCs5mC | Hu ApoB | 85.0 | 398 |
| ONT-77 | Gs5mCs5mCsTs5mCsAsGsTs5mCsTsGs5mCsTs Ts5mCsGs5mCsAs5mCs5mC | Hu ApoB | 79.9 | 399 |
| ONT-80 | Gs5mCs5mCsTs5mCsAsGsTs5mCsTsGs5mCsTsT s5mCsGs5mCsAs5mCs5mC | Hu ApoB | 75.8 | 400 |
| ONT-81 | Gs5mCs5mCsTs5mCsAsGsTs5mCsTsGs5mCsTsT s5mCsGs5mCsAs5mCs5mC | Hu ApoB | 80.7 | 401 |
| ONT-87 | Gs5mCs5mCsTs5mCsAsGsTs5mCsTsGs5mCsTsT s5mCsGs5mCsAs5mCs5mC | Hu ApoB | 82.4 | 402 |
| ONT-88 | Gs5mCs5mCsTs5mCsAsGsTs5mCsTsGs5mCsTsT s5mCsGs5mCsAs5mCs5mC | Hu ApoB | 78.9 | 403 |
| ONT-89 | Gs5mCs5mCsTs5mCsAsGsTs5mCsTsGs5mCsTsT s5mCsGs5mCsAs5mCs5mC | Hu ApoB | 80.9 | 404 |
| ONT-70 | Gs5mCsGsTsTsTsGs5mCsTs5mCsTsTs5mCsTsTs 5mCsTsTsGs5mCGsTsTsTsTsT | ISIS 355868 internal standard | | 405 |

TABLE 5

Mouse chiromersens studied for rat whole live homogenate stability

| Sequence | Description | Target | SEQ ID NO: |
|---|---|---|---|
| ONT-83 | GsTs5mCs5mCs5mCsTsGsAsAsGsAsTsGsTs5mCsAsAsTsGs5mC | Mouse ApoB | 406 |
| ONT-82 | GsTs5mCs5mCs5mCsTsGsAsAsGsAsTsGsTs5mCsAsAsTsGs5mC | Mouse ApoB | 407 |
| ONT-84 | GsTs5mCs5mCs5mCsTsGsAsAsGsAsTsGsTs5mCsAsAsTsGs5mC | Mouse ApoB | 408 |
| ONT-85 | GsTs5mCs5mCs5mCsTsGsAsAsGsAsTsGsTs5mCsAsAsTsGs5mC | Mouse ApoB | 409 |
| ONT-86 | GsTs5mCs5mCs5mCsTsGsAsAsGsAsTsGsTs5mCsAsAsTsGs5mC | Mouse ApoB | 410 |

Example 2. Example Chirally Controlled siRNA Molecules

TABLE 1

Summary of Phosphodiester Polar interactions with h-Ago-2 and h-Ago-1

| Science 2012 hAgo-2 | | | | Cell 2012 hAgo-2 | | | | Cell Rep 2013, h-Ago-1[†] | | | |
|---|---|---|---|---|---|---|---|---|---|---|---|
| Phosphate* | Residue | Length/Å | Config | Phosphate | Residue | Length/Å | Config | Phosphate | Residue | Length/Å | Config |
| 2 | Asn551 | 2.7 | Pro(S) | 2 | Asn551 | 2.7 | Pro(S) | 2 | Asn549 | 2.7 | Pro(S) |
| | Gln548 | 2.9 | Pro(S) | | Gln548 | 3.1 | Pro(S) | | Gln546 | 2.9 | Pro(S) |
| | | | | | Gln548 | 2.9 | Pro(R) | | | 2.8 | Pro(R) |
| 3 | Lys566 | 3.1 | Pro(R) | 3 | Lys566 | 2.9 | Pro(R) | 3 | Lys564 | 2.9 | Pro(R) |
| | Arg792 | 3.4 | Pro(R) | | Arg792 | 3.3 | Pro(R) | | Arg790 | 3.4 | Pro(R) |
| | | | | | | | | | | 3.3 | Pro(R) |

TABLE 1-continued

Summary of Phosphodiester Polar interactions with h-Ago-2 and h-Ago-1

| | Science 2012 hAgo-2 | | | | Cell 2012 hAgo-2 | | | | Cell Rep 2013, h-Ago-1† | | |
|---|---|---|---|---|---|---|---|---|---|---|---|
| Phosphate* | Residue | Length/Å | Config | Phosphate | Residue | Length/Å | Config | Phosphate | Residue | Length/Å | Config |
| 4 | Tyr790 | 2.6 | Pro(R) | 4 | Tyr790 | 2.8 | Pro(R) | 4 | Tyr788 | 2.7 | Pro(R) |
|  | Arg792 | 3.0 | Pro(R) |  | Arg792 | 2.8 | Pro(R) |  | Arg790 | 3.3 | Pro(R) |
|  |  | 2.8 | Pro(R) |  |  |  |  |  |  |  |  |
|  |  | 3.4 | Pro(S) |  |  |  |  |  |  |  |  |
| 5 | Ser798 | 2.7 | Pro(R) | 5 | Ser798 | 2.6 | Pro(R) | 5 | Ser796 | 2.5 | Pro(R) |
|  |  | 2.9 | Pro(R) |  |  | 2.9 | Pro(R) |  |  | 2.8 | Pro(R) |
|  | Tyr804 | 2.8 | Pro(S) |  | Tyr804 | 2.5 | Pro(S) |  | Tyr802 | 2.6 | Pro(S) |
| 6 | Lys709 | 3.0 | Pro(S) | 6 | Lys709 | 3.2 | Pro(S) | 6 | Lys707 | 2.8 | Pro(S) |
|  | Arg761 | 2.9 | Pro(R) |  | Arg761 | 2.8 | Pro(R) |  | Arg759 | 2.7 | Pro(R) |
|  | His753 | 2.8 | Pro(R) |  | His753 | 3.0 | Pro(R) |  | His751 | 3.0 | Pro(R) |
| 7 | Arg714 | 2.9 | Pro(R) | 7 | Arg714 | 2.8 | Pro(R) | 7 | Arg712 | 3.1 | Pro(S) |
|  |  | 3.0 | Pro(R) |  |  | 3.1 | Pro(R) |  |  | 3.3 | Pro(S) |
|  | Arg761 | 3.0 | Pro(S) |  | Arg761 | 2.8 | Pro(S) |  | Arg373 | 3.4 | Pro(R) |
|  |  |  |  |  |  |  |  |  | Thr757 | 2.9 | Pro(R) |
|  |  |  |  | 8 | Arg761 | 2.4 | Pro(S) | 8 | Arg759 | 2.2 | Pro(S) |
|  |  |  |  |  | Ala221 | 3.5 | Pro(R) |  | His710 | 3.4 | Pro(R) |
|  |  |  |  |  |  |  |  |  | Ser218 | 2.7 | Pro(R) |
|  |  |  |  | 9 | Arg351 | 2.2 | Pro(R) | 9 | Arg349 | 3.5 | Pro(R) |
|  |  |  |  |  |  |  |  |  | Arg708 | 2.9 | Pro(S) |
|  |  |  |  | 10 | Arg710 | 2.5 | Pro(R) | 10 | Arg708 | 3.5 | Pro(R) |
|  |  |  |  |  |  |  |  |  |  | 2.9 | Pro(R) |
|  |  |  |  | 18 | No contacts |  |  | 21 | Tyr309 | 2.6 | Pro(S) |
|  |  |  |  | 19 | Tyr311 | 3.1 | Pro(R) |  | Tyr314 | 2.6 | Pro(S) |
|  |  |  |  |  | Arg315 | 2.8 | Pro(R) |  | His269 | 3.0 | Pro(R) |
|  |  |  |  | 20 | His271 | 3.1 | Pro(R) |  |  |  |  |
|  |  |  |  |  | His319 | 3.4 | Pro(S) |  |  |  |  |
|  |  |  |  |  | Tyr311 | 2.2 | Pro(S) |  |  |  |  |

*Phosphate No. from 5'-end
†Complexed with h-let-7 22mer

The present disclosure, despite teachings in the art to the contrary, recognizes that stereochemistry of internucleotidic linkages can be utilized to increase stability and activity of oligonucleotides through chirally controlled oligonucleotide compositions. Such chirally controlled oligonucleotide compositions can provide much better results than chirally uncontrolled oligonucleotide compositions as demonstrated in this disclosure.

There are two reported crystal structures of RNA complexed with human Argonaute-2 protein (hAgo2): The Crystal Structure of Human Argonaute-2, Science, 2012 (PDB-4ei3); and The Structure of Human Argonaute-2 in Complex with miR-20a Cell, 2012 PDB-4f3t). In addition, there is one reported crystal structure of Let-7 RNA complexed with human Argonaute-1 protein (hAgo-1): The Making of a Slicer: Activation of Human Argonaute-1, Cell Rep. 2013 (PDB-4krf).

Based upon the information contained in these publications, it was anticipated that some judgments could be made about advantageous preferences for stereochemistry at the internucleotidic phosphate linkage if the phosphodiester bonds were to be replaced by phosphorothioate diester bonds. These advantages could relate to significantly improved potency, stability and other pharmacological properties. With this in mind, the computer program Pymol was used to locate all polar interactions between the protein and the internucleotidic phosphodiester linkage of the crystallized RNA for all three structures. Polar interactions at a distance of more than 3.5 Å were ignored.

The results of this analysis are summarized in Table 1. A particular phosphorus atom from the phosphodiester backbone on the RNA was assigned a Pro(R) or a Pro(S) configuration based upon the assumption that in the phosphorothioate diester analog the quite similar bond would be made between the polar group on an amino acid residue and the respectful phosphate oxygen atom. The sulfur substitution, instead of non-bridging oxygen would therefore confer a unique stereochemistry (either (Sp) or (Rp) absolute configuration) on the phosphorus atom within that motif Of note is the extraordinarily good agreement between the two structures of hAgo-2 in complex with RNA. Also, there is an excellent agreement between the structures of hAgo-1 and hAgo-2 in complex with RNA, indicating that the conformation that the RNA molecule adopts is highly conserved between these two proteins. Any conclusions or rules which are formed based upon the results of this analysis are likely, therefore, to be valid for both protein molecules.

As can be seen, there is usually more than one polar interaction at any one phospodiester group, with the exception of those between the phosphodiesters at phosphate positions 9 and 10 and hAgo-2 (Cell 2012) which adopt exclusively Pro(Rp) preference through bonding with Arg351 and Arg710 respectively.

However, shorter distances (corresponding to stronger interactions) as well as the number of bonds per oxygen can suggest a predominant interaction for the Pro(Rp) or the Pro(Sp) oxygens: hence resulting in several interactions which are predominantly of one stereochemical type or the other. Within this group are the interactions between the phosphodiesters at phosphate positions 2 (Sp), 3 (Rp), 4 (Rp), 6 (Rp), 8 (Sp), 19 (Rp), 20 (Sp) and 21 (Sp).

Of the remaining interactions, there does not appear to be a preference for one particular stereochemistry to be adopted over the other, so the preferred stereochemistry could be either (Sp) or (Rp).

Within this category are the interactions formed between the phosphodiesters at phosphate positions 5 (Rp or Sp) and 7 (Rp or Sp).

For interactions at the other phosphate backbone, there is no crystal structure information, so stereochemistry at these positions can similarly be either (Rp) or (Sp) until empirical data shows otherwise.

To this end, Table 6 contains several non-limiting example siRNA general constructs which can be conceived to take advantage of this preference for stereochemistry at individual phosphorothioate diester motifs.

TABLE 6

Example general siRNA constructs

| PS* | Chirally Controlled Antisense Strand Construct | | | | | |
|---|---|---|---|---|---|---|
| 2 | (Sp) | (Rp) | (Sp) | (Rp) | (Sp) | (Rp) |
| 3 | (Rp) | (Sp) | (Rp) | (Sp) | (Rp) | (Sp) |
| 4 | (Rp) | (Sp) | PO | PO | (Rp) | (Sp) |
| 5 | (Rp) or (Sp) | (Sp) or (Rp) | PO | PO | PO | PO |
| 6 | (Rp) | (Sp) | PO | PO | (Rp) | (Sp) |
| 7 | (Rp) or (Sp) | (Sp) or (Rp) | PO | PO | PO | PO |
| 8 | (Sp) | (Rp) | PO | PO | (Sp) | (Rp) |
| 9 | (Rp) | (Sp) | PO | PO | (Rp) | (Sp) |
| 10 | (Rp) | (Sp) | PO | PO | (Rp) | (Sp) |
| 11 | (Rp) or (Sp) | (Sp) or (Rp) | PO | PO | PO | PO |
| 12 | (Rp) or (Sp) | (Sp) or (Rp) | PO | PO | PO | PO |
| 13 | (Rp) or (Sp) | (Sp) or (Rp) | PO | PO | PO | PO |
| 14 | (Rp) or (Sp) | (Sp) or (Rp) | PO | PO | PO | PO |
| 15 | (Rp) or (Sp) | (Sp) or (Rp) | PO | PO | PO | PO |
| 16 | (Rp) or (Sp) | (Sp) or (Rp) | PO | PO | PO | PO |
| 17 | (Rp) or (Sp) | (Sp) or (Rp) | PO | PO | PO | PO |
| 18 | (Rp) or (Sp) | (Sp) or (Rp) | PO | PO | PO | PO |
| 19 | (Rp) | (Sp) | PO | PO | (Rp) | (Sp) |
| 20 | (Sp) | (Rp) | (Sp) | (Rp) | (Sp) | (Rp) |
| 21 | (Sp) | (Rp) | (Sp) | (Rp) | (Sp) | (Rp) |

*The number indicates the phosphate position from the 5' end of the antisense strand of the siRNA, (e.g. #2 is located between nucleotides 1 and 2 and #21 is located between nucleotides 20 and 21). (Sp) and (Rp) designates stereochemistry of phosphorus atom on phosphorothioate (PS) diester internucleotidic linkage at the indicated position. PO designates a phosphodiester internucleotidic linkage at the indicated position.

Example siRNAs include but are not limited to siRNAs having a Sp configuration for a chiral phosphorothioate at the 3'end and at the 5'end of the antisense strand of the siRNA duplex, which confers unprecedentedly increased stability in human serum or biological fluids. That same Sp configuration for the chiral phosphorothioate at the 3'end and at the 5'end of the antisense strand of the siRNA duplex confers unprecedentedly increased biological potency caused by increased affinity to the Ago2 protein leading to increased activity within the RISC RNAi silencing complex.

In one embodiment, a single chiral phosphorothioate motif is introduced independently at each position along the antisense or sense strand of the siRNA molecule. For a 21mer, this provides 80 unique sequences, with either an (Sp) or an (Rp) chirally controlled phosphorothioate group. When duplexed independently, 1600 unique combinations of siRNAs are prepared.

siRNA Transfection of Chiral siRNA Molecules

Hep3B, or HeLa cells are reverse transfected at a density of $2.0 \times 10^4$ cells/well in 96-well plates. Transfection of siRNA is carried out with lipofectamine RNAiMax (Life Technologies, cat. No. 13778-150) using the manufacturer's protocol, except with a decreased amount of Lipofectamine RNAiMax of 0.2 ul per well. Twelve, 1:3 siRNA duplex dilutions are created starting at 1 uM. 10 ul of 10× siRNA duplex is then lipoplexed with a prepared mixture of 9.8 ul of serum-free medium and 0.2 ul of Lipofectamine RNAiMax per well. After a 10-15 minute incubation, $2.0 \times 10^4$ cells in 80 ul of EMEM cell growing media (ATCC, 30-2003) is added to bring the final volume to 100 ul per well. Two separate transfection events are performed for each dose.

24 hours after transfection Hep3B or HeLa cells are lysed and mRNA against which the siRNA is targeted is purified using MagMAX™-96 Total RNA Isolation Kit (Life Technologies, AM1830); 15 ul of cDNA is synthesized with High Capacity cDNA Reverse Transcription Kit with RNase Inhibitor (Life Technologies, 4374967). Gene expression is evaluated by Real-Time PCR on a Lightcycler 480(Roche) using a Probes Master Mix (Roche, 04 707 494 001) according to manufacturer's protocol.

IC50s and Data Analysis

Delta delta Ct method is used to calculate values. Samples are normalized to hGAPDH and calibrated to mock transfected and untreated samples. A stereo-random molecule is used as a control. The data is represented as a mean of 2 biological replicates using Graphpad Prism. A four-parameter linear regression curve is fitted to the data and the bottom and top are constrained to a 0 and 100 constants respectively in order to calculate a relative IC50.

The present Example demonstrates successful inhibition of target gene expression using siRNA agents comprised of chirally controlled oligonucleotides as described herein. Specifically, this Example describes hybridization of individual oligonucleotide strands prepared through chirally controlled synthesis as described herein, so that double-stranded chirally controlled siRNA oligonucleotide compositions are provided. This Example further demonstrates successful transfection of cells with such agents and, moreover, successful inhibition of target gene expression.

In Vitro Metabolic Stabilities of Human PCSK9 siRNA Duplexes Having Stereocontrolled Phosphorothioate Diester Linkages in Human Serum.

10 μM siRNA duplexes were incubated in 90% human serum (50 μL, Sigma, H4522) at 37° C. for 24 hours. A 0 min time point (50 μL) was prepared as well as a PBS control incubation time point (50 μL), where the 10 μM siRNA duplex was incubated in 90% 1×PBS (50 μL at 37° C. for 24 hours. After completion of the incubation, to each time point, were added 10 μL of Stop-Solution (0.5 M NaCl, 50 mM TRIS, 5 mM EDTA, 2.5% IGEPAL), followed by 3.2 μL of Proteinase K (20 mg/mL, Ambion). The samples were incubated at 60° C. for 20 min, and then centrifuged at 2000 rpm for 15 min. The final reaction mixtures were directly analyzed in denaturing IEX HPLC (injection volume 50 μL). The ratio of integrated area at 24 h and 0 min was used to determine the % of degradation for each siRNA.

Figure 1:
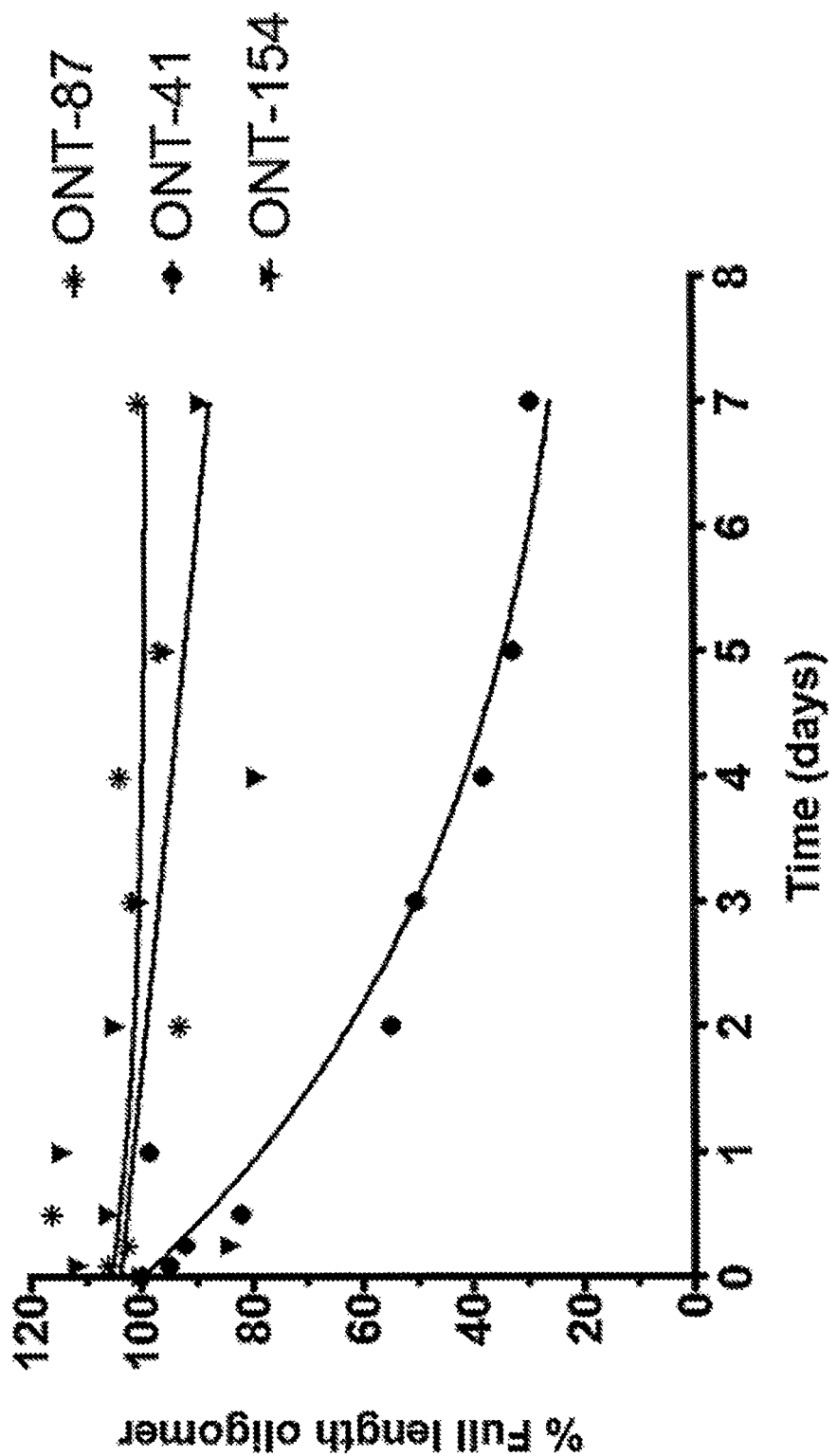
FIG. 1. Reverse phase HPLCs after incubation with rat liver homogenate. Total amounts of oligonucleotides remaining when incubated with rat whole liver homogenate at 37° C. at different days were measured. The in-vitro metabolic stability of ONT-154 was found to be similar to ONT-87, which has 2'-MOE wings, while both have much better stability than 2'-MOE gapmer which is stereorandom (ONT-41, Mipomersen). The amount of full length oligomer remaining was measured by reverse phase HPLC where peak area of the peak of interest was normalized with internal standard.
Figure 2:
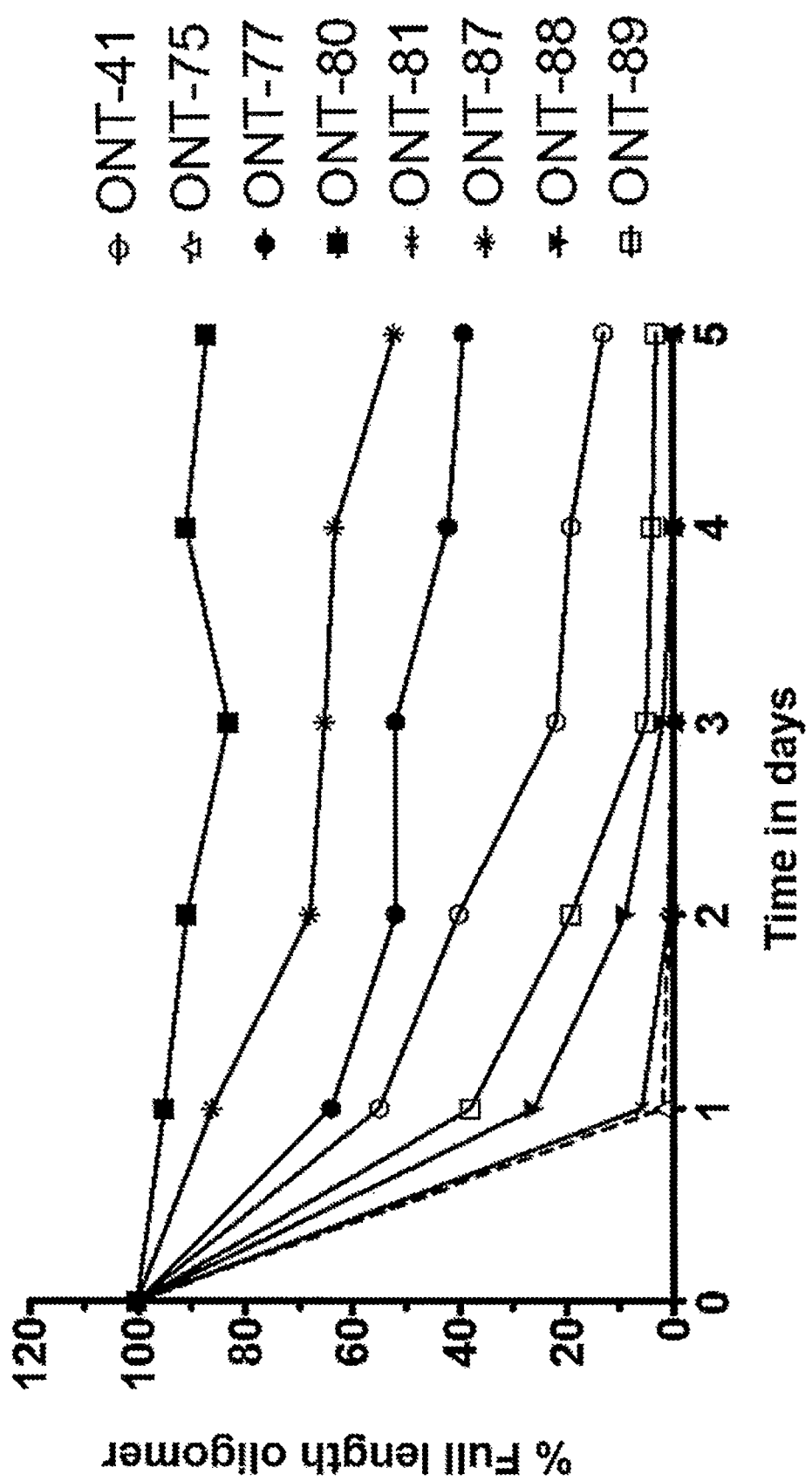
FIG. 2. Degradation of various chirally pure analogues of Mipomersen (ONT-41) in rat whole liver homogenate. Total amounts of oligonucleotide remaining when incubated with rat whole liver homogenate at 37° C. at different days were measured. The in-vitro metabolic stability of chirally pure diastereomers of human ApoB sequence ONT-41 (Mipomersen) was found to increase with increased Sp internucleotidic linkages. The amount of full length oligomer remaining was measured by reverse phase HPLC where peak area of the peak of interest was normalized with internal standard. Compositions used include: ONT-41, ONT-75, ONT-77, ONT-80, ONT-81, ONT-87, ONT-88 and ONT-89.
Figure 3:
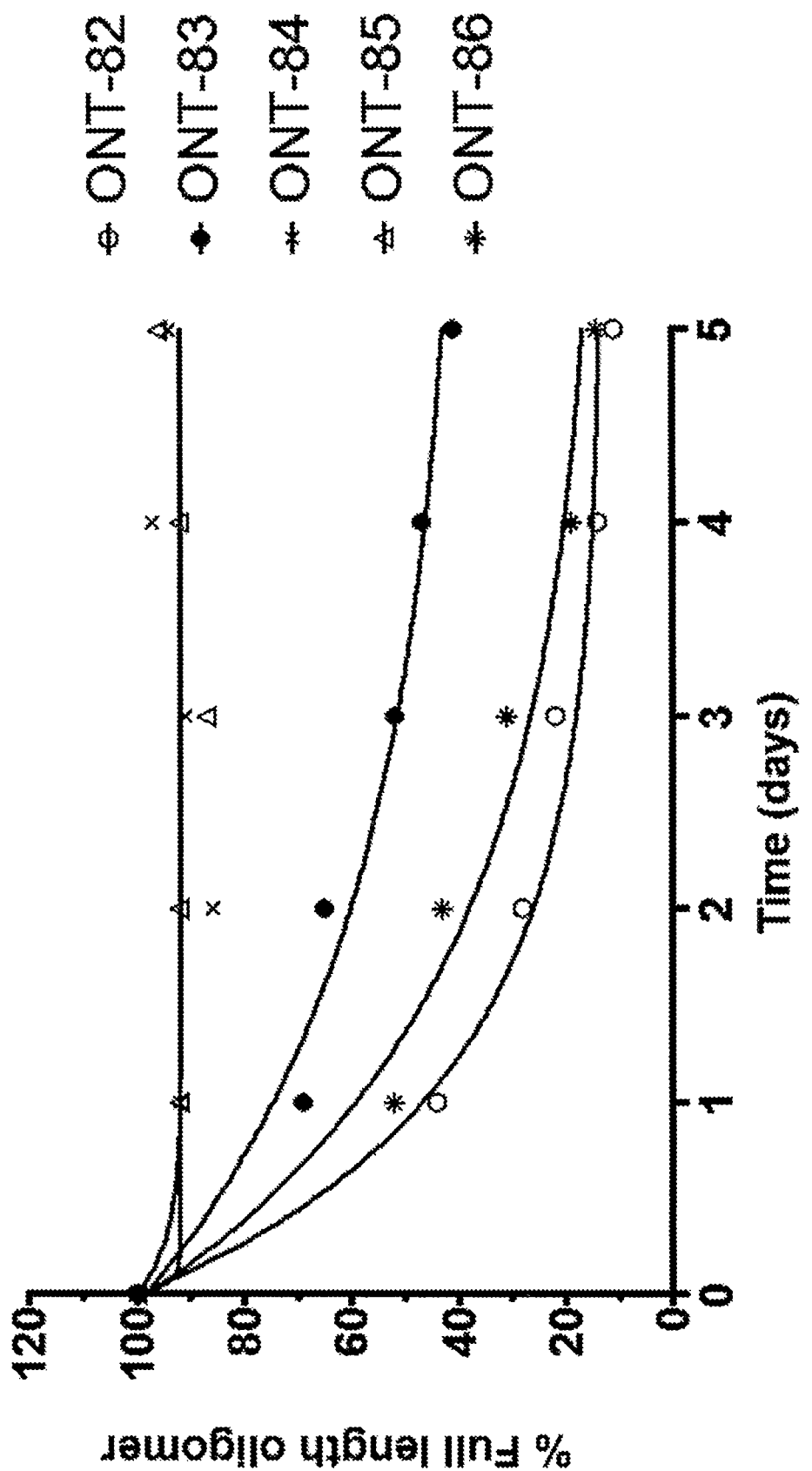
FIG. 3. Degradation of various chirally pure analogues of mouse ApoB sequence (ISIS 147764, ONT-83) in rat whole liver homogenate. Total amounts of oligonucleotide remaining when incubated with rat whole liver homogenate at 37° C. at different days were measured. The in-vitro metabolic stability of chirally pure diastereomers of murine ApoB sequence (ONT-83, 2'-MOE gapmer, stereorandom phosphorothioate) was found to increase with increased Sp internucleotidic linkages. The amount of full length oligomer remaining was measured by reverse phase HPLC where peak area of the peak of interest was normalized with internal standard. Compositions used include: ONT-82 to ONT-86.
Figure 4:
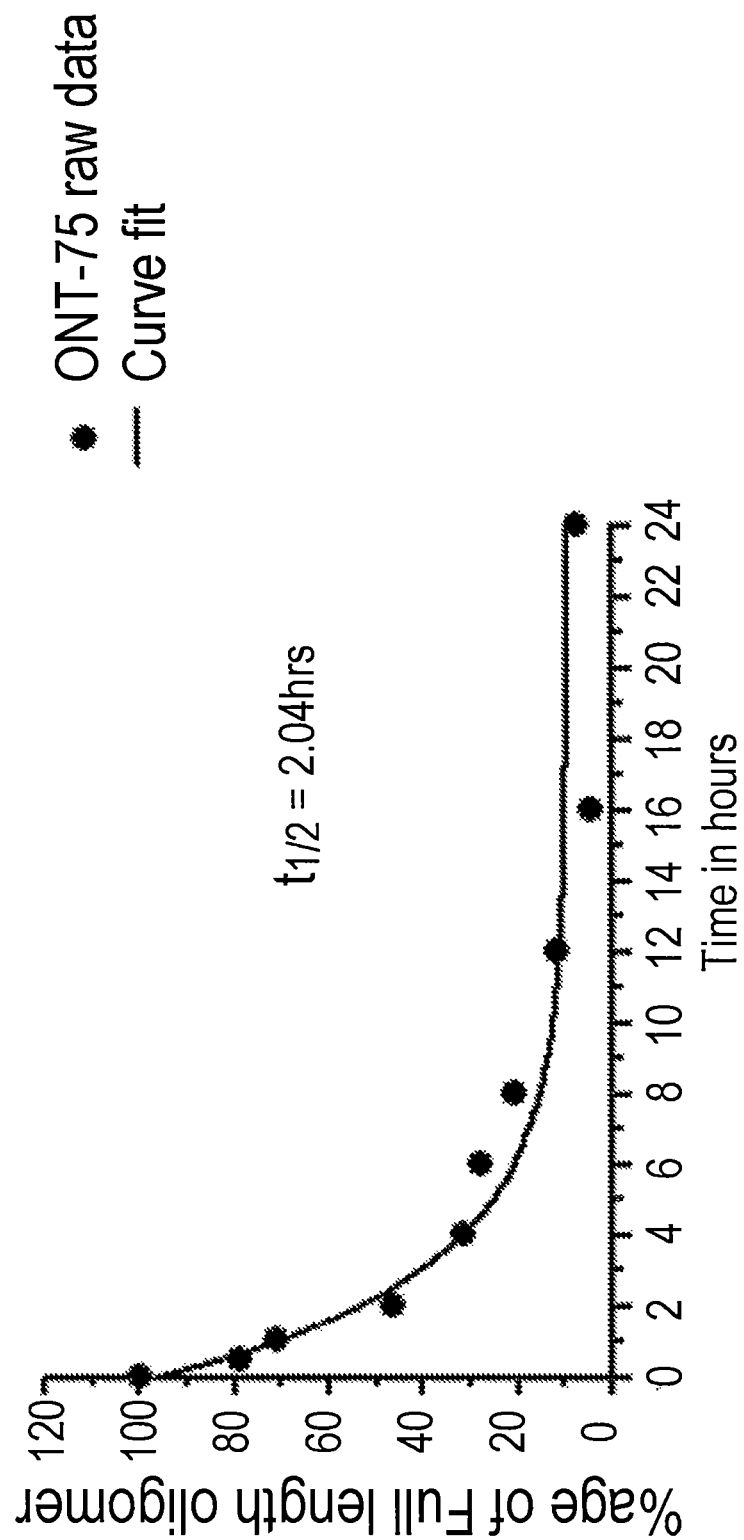
FIG. 4. Degradation of Mipomersen analogue ONT-75 in rat whole liver homogenate over a period of 24 hrs. This figure illustrates stability of ONT-75 in rate whole liver homogenate.
Figure 5:
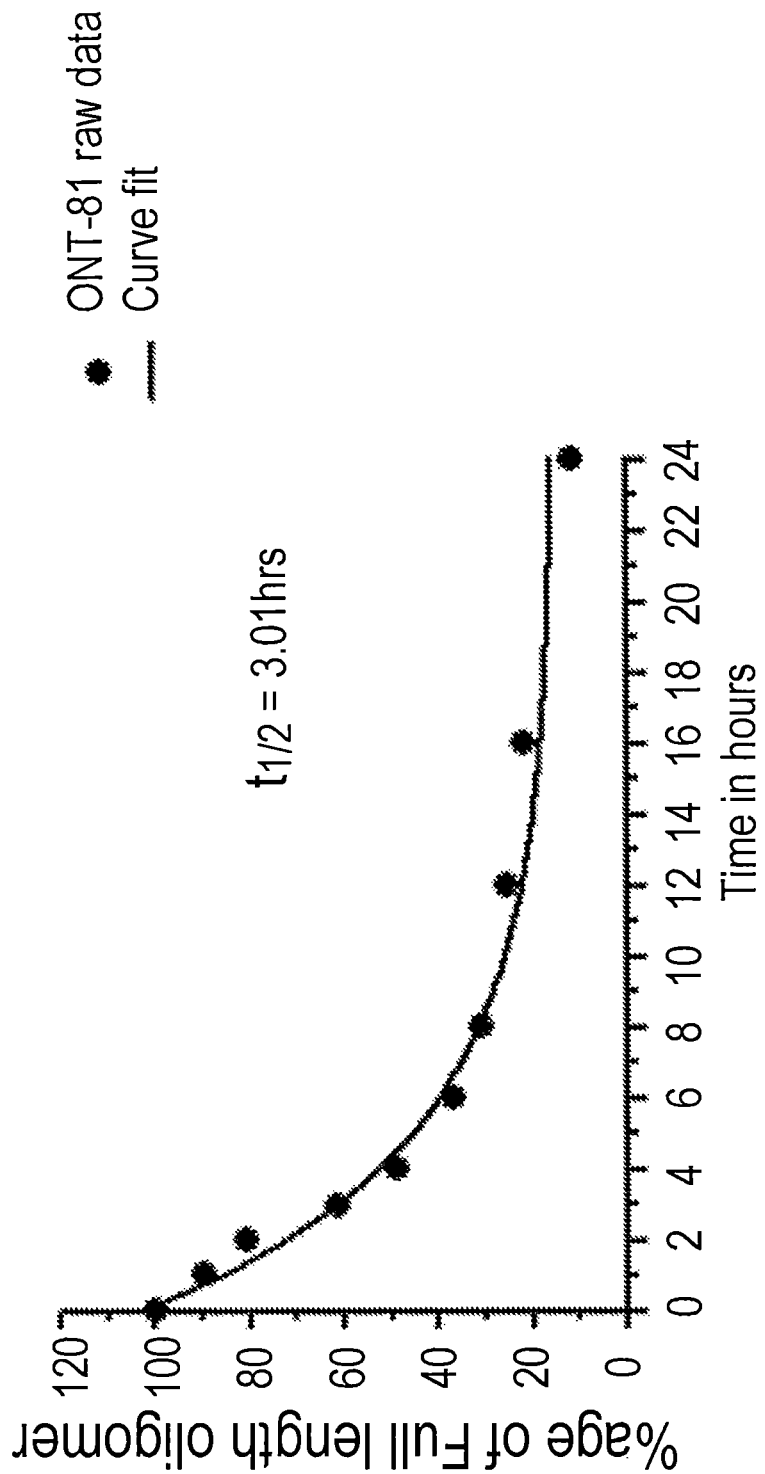
FIG. 5. Degradation of Mipomersen analogue ONT-81 in rat whole liver homogenate over a period of 24 hrs. This figure illustrates stability of ONT-81 in rate whole liver homogenate.

It was observed that the stereochemistry configuration of the single phosphorothioate at position 21 (3'end) of both the antisense strand and the sense strand of the siRNA had a crucial impact on the stability of the duplex upon incubation in Human Serum (FIG. 1). As illustrated in the FIG. 1 and as determined following the integration ratio of the degradation pattern, an (Rp, Rp) siRNA duplex exhibited a significant 55.0% degradation after 24 h. The stereorandom mixture of phosphorothioates in the stereorandom siRNA showed 25.2% degradation after 24 h. The (Sp/Sp) siRNA showed only minor 7.3% degradation after 24 h. This illustrates the drastic impact that phosphorothioate stereochemistry confers to therapeutic siRNAs. Additional example data were presented in FIG. 2, FIG. 3, FIG. 4 and FIG. 5.

It is observed that each of the stereopure constructs show different potency ($IC_{50}$ values) dependent on the position of the phosphorothioate motif along the backbone. It is also observed that different $IC_{50}$ values are obtained dependent upon whether the phosphorothioate motif at any single position is (Sp) or (Rp). The impact of stereochemistry upon stability is likewise clear and differentiating, using either Human Serum described above, or Human Hepatic Cytosol extract or Snake Venom Phosphodiesterase, or isolated endonuclease or isolated exonuclease.

Certain design rules may be formulated based upon data obtained in the above example. These design information can be applied for the introduction of multiple chiral phosphorothioate linkages within the antisense and/or sense strand of the siRNA as exemplified below. The present disclosure recognizes that an increased amount of chiral phosphorothioate within the antisense and/or sense strand of the siRNA, introduced at the right positions and having the right stereochemistry configuration leads to greatly improved siRNA constructs in terms of potency and metabolic stability in vitro—translating into greatly pharmacologically enhanced therapeutic siRNAs.

Example Chirally Controlled siRNA Oligonucleotides Targeting PCSK9

Proprotein convertase subtilisin/kexin type 9 (PCSK9), is an enzyme involved in cholesterol metabolism. PCSK9 binds to the receptor for low density lipoprotein (LDL), triggering its destruction. Although LDL associated with the receptor is also eliminated when the receptor is destroyed, the net effect of PCSK9 binding in fact increases LDL levels, as the receptor would otherwise cycle back to the cell surface and remove more cholesterol.

Several companies are developing therapeutic agents that target PCSK9. Of particular relevance to the present disclosure, each of Isis Pharmaceuticals, Santaris Pharma, and Alnylam Pharmaceuticals is developing a nucleic acid agent that inhibits PCSK9. The Isis Pharmaceuticals product, an antisense oligonucleotide, has been shown to increase expression of the LDLR and decrease circulating total cholesterol levels in mice (Graham et al "Antisense inhibition of proprotein convertase subtilisin/kexin type 9 reduces serum LDL in hyperlipidemic mice". *J. Lipid Res.* 48 (4): 763-7, April 2007). Initial clinical trials with the Alnylam Pharmaceuticals product, ALN-PCS, reveal that RNA interference offers an effective mechanism for inhibiting PCSK9 (Frank-Kamenetsky et al "Therapeutic RNAi targeting PCSK9 acutely lowers plasma cholesterol in rodents and LDL cholesterol in nonhuman primates". *Proc. Natl. Acad. Sci. U.S.A.* 105 (33): 11915-20, August 2008).

In some embodiments, despite known results to the contrary, the present disclosure recognizes that phosphorothioate motifs of one stereochemical conformation or another can be rationally designed to take advantage of increased potency, stability and other pharmacological qualities through chirally controlled oligonucleotide compositions. To reinforce this concept, table 3 contains example stereochemically pure constructs based on an siRNA sequence which targets PCSK9 messenger RNA.

In this example embodiment, a single chiral phosphorothioate motif is introduced independently at each position along the antisense or sense strand of the siRNA molecule. For a 21mer, this provides 80 unique sequences, with either an (Sp) or an (Rp) chirally controlled phosphorothioate group. When duplexed independently, 1600 unique combinations of siRNAs are prepared.

In other example embodiments, a single chiral phosphorothioate motif is introduced independently at each position along the antisense or sense strand of the siRNA molecule, while a 3'-(Sp) phosphorothioate linkage is conserved. For a 21mer, this provides another additional 80 unique sequences, with either an (Sp) or an (Rp) chirally controlled phosphorothioate group. When duplexed independently, 1600 unique combinations of siRNAs are prepared.

In other example embodiments, multiple chiral phosphorothioate motifs are introduced independently at several positions along the antisense or sense strand of the siRNA molecule, following the codes described in Table 7, while a 3'-(Sp) phosphorothioate linkage is conserved.

TABLE 7

Example of PCSK-9 Sense and Antisense RNAs

| | PCSK9 siRNA Sense Strands | SEQ ID NO: |
|---|---|---|
| PCSK9 (1) | (Rp)-uucuAGAccuGuuuuGcuudTsdT | 411 |
| PCSK9 (2) | (Sp)-uucuAGAccuGuuuuGcuudTsdT | 412 |
| PCSK9 (3) | (Rp)-uucuAGAccuGuuuuGcuusdTdT | 413 |
| PCSK9 (4) | (Sp)-uucuAGAccuGuuuuGcuusdTdT | 414 |
| PCSK9 (5) | (Rp)-uucuAGAccuGuuuuGcusudTdT | 415 |
| PCSK9 (6) | (Sp)-uucuAGAccuGuuuuGcusudTdT | 416 |
| PCSK9 (7) | (Rp)-uucuAGAccuGuuuuGcsuudTdT | 417 |
| PCSK9 (8) | (Sp)-uucuAGAccuGuuuuGcsuudTdT | 418 |
| PCSK9 (9) | (Rp)-uucuAGAccuGuuuuGscuudTdT | 419 |
| PCSK9 (10) | (Sp)-uucuAGAccuGuuuuGscuudTdT | 420 |
| PCSK9 (11) | (Rp)-uucuAGAccuGuuuusGcuudTdT | 421 |
| PCSK9 (12) | (Sp)-uucuAGAccuGuuuusGcuudTdT | 422 |
| PCSK9 (13) | (Rp)-uucuAGAccuGuuusuGcuudTdT | 423 |
| PCSK9 (14) | (Sp)-uucuAGAccuGuuusuGcuudTdT | 424 |
| PCSK9 (15) | (Rp)-uucuAGAccuGuusuuGcuudTdT | 425 |
| PCSK9 (16) | (Sp)-uucuAGAccuGuusuuGcuudTdT | 426 |
| PCSK9 (17) | (Rp)-uucuAGAccuGusuuuGcuudTdT | 427 |
| PCSK9 (18) | (Sp)-uucuAGAccuGusuuuGcuudTdT | 428 |
| PCSK9 (19) | (Rp)-uucuAGAccuGsuuuuGcuudTdT | 429 |
| PCSK9 (20) | (Sp)-uucuAGAccuGsuuuuGcuudTdT | 430 |
| PCSK9 (21) | (Rp)-uucuAGAccusGuuuuGcuudTdT | 431 |
| PCSK9 (22) | (Sp)-uucuAGAccusGuuuuGcuudTdT | 432 |
| PCSK9 (23) | (Rp)-uucuAGAccsuGuuuuGcuudTdT | 433 |
| PCSK9 (24) | (Sp)-uucuAGAccsuGuuuuGcuudTdT | 434 |
| PCSK9 (25) | (Rp)-uucuAGAcscuGuuuuGcuudTdT | 435 |
| PCSK9 (26) | (Sp)-uucuAGAcscuGuuuuGcuudTdT | 436 |
| PCSK9 (27) | (Rp)-uucuAGAsccuGuuuuGcuudTdT | 437 |
| PCSK9 (28) | (Sp)-uucuAGAsccuGuuuuGcuudTdT | 438 |
| PCSK9 (29) | (Rp)-uucuAGsAccuGuuuuGcuudTdT | 439 |
| PCSK9 (30) | (Sp)-uucuAGsAccuGuuuuGcuudTdT | 440 |
| PCSK9 (31) | (Rp)-uucuAsGAccuGuuuuGcuudTdT | 441 |

TABLE 7-continued

Example of PCSK-9 Sense and Antisense RNAs

| PCSK9 siRNA Sense Strands | | SEQ ID NO: |
|---|---|---|
| PCSK9 (32) | (Sp)-uucuAsGAccuGuuuuGcuudTdT | 442 |
| PCSK9 (33) | (Rp)-uucusAGAccuGuuuuGcuudTdT | 443 |
| PCSK9 (34) | (Sp)-uucusAGAccuGuuuuGcuudTdT | 444 |
| PCSK9 (35) | (Rp)-uucsuAGAccuGuuuuGcuudTdT | 445 |
| PCSK9 (36) | (Sp)-uucsuAGAccuGuuuuGcuudTdT | 446 |
| PCSK9 (37) | (Rp)-uuscuAGAccuGuuuuGcuudTdT | 447 |
| PCSK9 (38) | (Sp)-uuscuAGAccuGuuuuGcuudTdT | 448 |
| PCSK9 (38) | (Rp)-usucuAGAccuGuuuuGcuudTdT | 449 |
| PCSK9 (40) | (Sp)-usucuAGAccuGuuuuGcuudTdT | 450 |

NOTE:
lower case letters represent 2'-OMe RNA residues; capital letters represent RNA residues;
d = 2'-deoxy residues; and
"s" indicates a phosphorothioate moiety.

Synthesis examples for Human PCSK9 siRNA Antisense Strands having several chiral phosphorothioate internucleotide linkages and full chiral phosphorothioate internucleotide linkages.

| Human PCSK9 siRNA Antisense Strands | | SEQ ID NO: |
|---|---|---|
| PCSK9 (41) | (Rp)-AAGcAAAAcAGGUCuAGAAdTsdT | 451 |
| PCSK9 (42) | (Sp)-AAGcAAAAcAGGUCuAGAAdTsdT | 452 |
| PCSK9 (43) | (Rp)-AAGcAAAAcAGGUCuAGAAsdTdT | 453 |
| PCSK9 (44) | (Sp)-AAGcAAAAcAGGUCuAGAAsdTdT | 454 |
| PCSK9 (45) | (Rp)-AAGcAAAAcAGGUCuAGAsAdTdT | 455 |
| PCSK9 (46) | (Sp)-AAGcAAAAcAGGUCuAGAsAdTdT | 456 |
| PCSK9 (47) | (Rp)-AAGcAAAAcAGGUCuAGsAAdTdT | 457 |
| PCSK9 (48) | (Sp)-AAGcAAAAcAGGUCuAGsAAdTdT | 458 |
| PCSK9 (49) | (Rp)-AAGcAAAAcAGGUCuAsGAAdTdT | 459 |
| PCSK9 (50) | (Sp)-AAGcAAAAcAGGUCuAsGAAdTdT | 460 |
| PCSK9 (51) | (Rp)-AAGcAAAAcAGGUCusAGAAdTdT | 461 |
| PCSK9 (52) | (Sp)-AAGcAAAAcAGGUCusAGAAdTdT | 462 |
| PCSK9 (53) | (Rp)-AAGcAAAAcAGGUCsuAGAAdTdT | 463 |
| PCSK9 (54) | (Sp)-AAGcAAAAcAGGUCsuAGAAdTdT | 464 |
| PCSK9 (55) | (Rp)-AAGcAAAAcAGGUsCuAGAAdTdT | 465 |
| PCSK9 (56) | (Sp)-AAGcAAAAcAGGUsCuAGAAdTdT | 466 |
| PCSK9 (57) | (Rp)-AAGcAAAAcAGGsUCuAGAAdTdT | 467 |
| PCSK9 (58) | (Sp)-AAGcAAAAcAGGsUCuAGAAdTdT | 468 |
| PCSK9 (59) | (Rp)-AAGcAAAAcAGsGUCuAGAAdTdT | 469 |
| PCSK9 (60) | (Sp)-AAGcAAAAcAGsGUCuAGAAdTdT | 470 |
| PCSK9 (61) | (Rp)-AAGcAAAAcAsGGUCuAGAAdTdT | 471 |
| PCSK9 (62) | (Sp)-AAGcAAAAcAsGGUCuAGAAdTdT | 472 |
| PCSK9 (63) | (Rp)-AAGcAAAAcsAGGUCuAGAAdTdT | 473 |
| PCSK9 (64) | (Sp)-AAGcAAAAcsAGGUCuAGAAdTdT | 474 |
| PCSK9 (65) | (Rp)-AAGcAAAAscAGGUCuAGAAdTdT | 475 |
| PCSK9 (66) | (Sp)-AAGcAAAAscAGGUCuAGAAdTdT | 476 |
| PCSK9 (67) | (Rp)-AAGcAAAsAcAGGUCuAGAAdTdT | 477 |
| PCSK9 (68) | (Sp)-AAGcAAAsAcAGGUCuAGAAdTdT | 478 |

-continued

| | Human PCSK9 siRNA Antisense Strands | SEQ ID NO: |
|---|---|---|
| PCSK9 (69) | (Rp)-AAGcAAsAAcAGGUCuAGAAdTdT | 479 |
| PCSK9 (70) | (Sp)-AAGcAAsAAcAGGUCuAGAAdTdT | 480 |
| PCSK9 (71) | (Rp)-AAGcAsAAAcAGGUCuAGAAdTdT | 481 |
| PCSK9 (72) | (Sp)-AAGcAsAAAcAGGUCuAGAAdTdT | 482 |
| PCSK9 (73) | (Rp)-AAGcsAAAAcAGGUCuAGAAdTdT | 483 |
| PCSK9 (74) | (Sp)-AAGcsAAAAcAGGUCuAGAAdTdT | 484 |
| PCSK9 (75) | (Rp)-AAGscAAAAcAGGUCuAGAAdTdT | 485 |
| PCSK9 (76) | (Sp)-AAGscAAAAcAGGUCuAGAAdTdT | 486 |
| PCSK9 (77) | (Rp)-AAsGcAAAAcAGGUCuAGAAdTdT | 487 |
| PCSK9 (78) | (Sp)-AAsGcAAAAcAGGUCuAGAAdTdT | 488 |
| PCSK9 (77) | (Rp)-AsAGcAAAAcAGGUCuAGAAdTdT | 489 |
| PCSK9 (78) | (Sp)-AsAGcAAAAcAGGUCuAGAAdTdT | 490 |
| PCSK9 (79) | (Rp, Sp)-AAGcAAAAcAGGUCuAGAAsdTsdT | 491 |
| PCSK9 (80) | (Sp, Sp)-AAGcAAAAcAGGUCuAGAAsdTsdT | 492 |
| PCSK9 (81) | (Rp, Sp)-AAGcAAAAcAGGUCuAGAsAdTsdT | 493 |
| PCSK9 (82) | (Sp, Sp)-AAGcAAAAcAGGUCuAGAsAdTsdT | 494 |
| PCSK9 (83) | (Rp, Sp)-AAGcAAAAcAGGUCuAGsAAdTsdT | 495 |
| PCSK9 (84) | (Sp, Sp)-AAGcAAAAcAGGUCuAGsAAdTsdT | 496 |
| PCSK9 (85) | (Rp, Sp)-AAGcAAAAcAGGUCuAsGAAdTsdT | 497 |
| PCSK9 (86) | (Sp, Sp)-AAGcAAAAcAGGUCuAsGAAdTsdT | 498 |
| PCSK9 (87) | (Rp, Sp)-AAGcAAAAcAGGUCusAGAAdTsdT | 499 |
| PCSK9 (88) | (Sp, Sp)-AAGcAAAAcAGGUCusAGAAdTsdT | 500 |
| PCSK9 (89) | (Rp, Sp)-AAGcAAAAcAGGUCsuAGAAdTsdT | 501 |
| PCSK9 (90) | (Sp, Sp)-AAGcAAAAcAGGUCsuAGAAdTsdT | 502 |
| PCSK9 (91) | (Rp, Sp)-AAGcAAAAcAGGUsCuAGAAdTsdT | 503 |
| PCSK9 (92) | (Sp, Sp)-AAGcAAAAcAGGUsCuAGAAdTsdT | 504 |
| PCSK9 (93) | (Rp, Sp)-AAGcAAAAcAGGsUCuAGAAdTsdT | 505 |
| PCSK9 (94) | (Sp, Sp)-AAGcAAAAcAGGsUCuAGAAdTsdT | 506 |
| PCSK9 (95) | (Rp, Sp)-AAGcAAAAcAGsGUCuAGAAdTsdT | 507 |
| PCSK9 (96) | (Sp, Sp)-AAGcAAAAcAGsGUCuAGAAdTsdT | 508 |
| PCSK9 (97) | (Rp, Sp)-AAGcAAAAcAsGGUCuAGAAdTsdT | 509 |
| PCSK9 (98) | (Sp, Sp)-AAGcAAAAcAsGGUCuAGAAdTsdT | 510 |
| PCSK9 (99) | (Rp, Sp)-AAGcAAAAcsAGGUCuAGAAdTsdT | 511 |
| PCSK9 (100) | (Sp, Sp)-AAGcAAAAcsAGGUCuAGAAdTsdT | 512 |
| PCSK9 (101) | (Rp, Sp)-AAGcAAAAscAGGUCuAGAAdTsdT | 513 |
| PCSK9 (102) | (Sp, Sp)-AAGcAAAAscAGGUCuAGAAdTsdT | 514 |
| PCSK9 (103) | (Rp, Sp)-AAGcAAAsAcAGGUCuAGAAdTsdT | 515 |
| PCSK9 (104) | (Sp, Sp)-AAGcAAAsAcAGGUCuAGAAdTsdT | 516 |

-continued

| Human PCSK9 siRNA Antisense Strands | SEQ ID NO: |
|---|---|
| PCSK9 (105) (Rp, Sp)-AAGcAAsAAcAGGUCuAGAAdTsdT | 517 |
| PCSK9 (106) (Sp, Sp)-AAGcAAsAAcAGGUCuAGAAdTsdT | 518 |
| PCSK9 (107) (Rp, Sp)-AAGcAsAAAcAGGUCuAGAAdTsdT | 519 |
| PCSK9 (108) (Sp, Sp)-AAGcAsAAAcAGGUCuAGAAdTsdT | 520 |
| PCSK9 (109) (Rp, Sp)-AAGcsAAAAcAGGUCuAGAAdTsdT | 521 |
| PCSK9 (110) (Sp, Sp)-AAGcsAAAAcAGGUCuAGAAdTsdT | 522 |
| PCSK9 (111) (Rp, Sp)-AAGscAAAAcAGGUCuAGAAdTsdT | 523 |
| PCSK9 (112) (Sp, Sp)-AAGscAAAAcAGGUCuAGAAdTsdT | 524 |
| PCSK9 (113) (Rp, Sp)-AAsGcAAAAcAGGUCuAGAAdTsdT | 525 |
| PCSK9 (114) (Sp, Sp)-AAsGcAAAAcAGGUCuAGAAdTsdT | 526 |
| PCSK9 (115) (Rp, Sp)-AsAGcAAAAcAGGUCuAGAAdTsdT | 527 |
| PCSK9 (116) (Sp, Sp)-AsAGcAAAAcAGGUCuAGAAdTsdT | 528 |
| PCSK9 (117) (Rp, Sp, Sp, Sp, Rp, Sp, Sp, Sp, Rp, Rp)-AsAsGscAsAAsAscsAGGUCuAGAsAsdTsdT | 529 |
| PCSK9 (118) (Sp, Rp, Rp, Rp, Sp, Rp, Rp, Rp, Sp, Sp)-AsAsGscAsAAsAscsAGGUCuAGAsAsdTsdT | 530 |

NOTE:
lower case letters represent 2'-OMe RNA residues; capital letters represent RNA residues;
d = 2'-deoxy residues; and
"s" indicates a phosphorothioate moiety.

Example 3. Stereopure FOXO-1 Antisense Analogs

Rational Design—Chirally Controlled Antisense Oligonucleotide Compositions

The unprecedented nuclease stability determined in vivo and in a whole rat liver homogenate model of the Sp-chiral phosphorothioate internucleotide linkage is applied in the novel design of new types of RNaseH substrate gapmers, whereby the external flanks are composed of unmodified DNA and the internal gap core is modified with 2' chemical modifications (2'OMe, 2'MOE, 2'LNA, 2'F, etc). Eventually this design is extended to fully unmodified DNA therapeutic oligonucleotides wherein careful chiral control of the phosphorothioate backbone confers the desired pharmacological properties of the RNaseH therapeutic oligonucleotide.

The application of the triplet-phosphate repeating motif designed after studying the crystal structure of human RNaseH has been employed as well. The crystal structure of RNaseH has been previously published (Structure of Human RNase H1 Complexed with an RNA/DNA Hybrid: Insight into HIV Reverse Transcription, Nowotny et al., Molecular Cell, Volume 28, Issue 2, 264-276, 2007, pdb file: 2qkb). Among other things, the present disclosure recognizes the importance of internucleotidic linkage stereochemistry of oligonucleotides, for example, in settings herein. Upon performing in silico analysis upon this structure using the program Pymol, Applicant found that the phosphate-binding pocket of Human RNase H1 makes polar contacts with three contiguous phosphates of the complexed DNA, and interacts preferentially with the Pro-R/Pro-R/Pro-S (or with the Pro-S/Pro-S/Pro-R) respective oxygen atoms of each of these three phosphates. Based on this observation we designed two chiral architectures with repeating (RRS) and (SSR) triplet phosphorothioates motifs as designed RNase H substrates. Applicant also designed other internucleotidic linkage stereochemical patterns. As demonstrated by example results provide herein, provided chirally controlled oligonucleotide compositions of oligonucleotide types that comprises certain backbone internucleotidic linkage patterns (patterns backbone chiral centers) provides significantly increased activity and/or kinetics. Among others, a sequence of 5'-RSS-3' backbone chiral centers is particularly useful and delivers unexpected results as described in the present disclosure.

The combination of increased Sp chiral backbone (for enzymatic stability and other pharmacologically advantageous properties) and (RRS) or (SSR) repeating triplet chiral backbone motifs (for enhancing the property as RNase H substrate) are also utilized in the novel designs; "S" represents Sp-phosphorothioate linkage and "R" represents Rp-phosphorothioate linkage.

Another alternative design is based on the increased amount of Sp chiral phosphorothioate backbone in extended repeating motifs such as: $(SSSR)_n$, $SR(SSSR)_n$, $SSR(SSSR)_n$, $SSR(SSSR)_n$; $(SSSSR)_n$, $SR(SSSSR)_n$, $SSR(SSSSR)_n$, $SSR(SSSSR)_n$, $SSSR(SSSSR)_n$; $(SSSSSR)_n$; $SR(SSSSSR)_n$, $SSR(SSSSSR)_n$, $SSR(SSSSSR)_n$, $SSSR(SSSSSR)_n$, $SSSSR(SSSSSR)_n$; etc., where n=0-50, depending on the number of respective internucleotide linkages; "S" represents Sp-phosphorothioate linkage and "R" represents Rp-phosphorothioate linkage. In some embodiments, n is 0. In some embodiments, R is 1-50. In some embodiments, R is 1. In some embodiments, a common pattern of backbone chiral centers of a provided chirally controlled oligonucleotide composition comprises a motif described herein. In some embodiments, a motif is in the core region. In some embodiments, n is 0. In some embodiments, R is 1-50. In some embodiments, R is 1. In some embodiments, n is 2. In some embodiments, n is 3. In some embodiments, n is 4. In some embodiments, n is 5.

Another alternative design is based on the "invert" architecture design of the stereo backbone ("stereo invert-mers"). These result from positioning the stereochemistry of the chiral phosphorothioate in a inverting manner, exposing some Sp-rich motifs at the 5' and 3' end extremities of the oligonucleotide as well as the middle portion of the oligonucleotide and having the repeating stereochemistry motifs positioned in a invert image manner on both sides, such as:

SS(SSR)$_n$(SSS)(RSS)$_n$SS;
SS(SSR)$_n$(SRS)(RSS)$_n$SS;
SS(SSR)$_n$(SSR)(RSS)$_n$SS;
SS(SSR)$_n$(RSS)(RSS)$_n$SS;
SS(RSS)$_n$(SSS)(SSR)$_n$SS;
SS(RSS)$_n$(SRS)(SSR)$_n$SS;
SS(RSS)$_n$(SSR)(SSR)$_n$SS;
SS(RSS)$_n$(RSS)(SSR)$_n$SS; etc., where n=0-50, depending on the number of respective internucleotide linkages. "S" represents Sp-phosphorothioate linkage and "R" represents Rp-phosphorothioate linkage. In some embodiments, a common pattern of backbone chiral centers of a provided chirally controlled oligonucleotide composition comprises a motif described herein. In some embodiments, a motif is in the core region. In some embodiments, n is 0. In some embodiments, n is 1. In some embodiments, n is 1-50. In some embodiments, n is 2. In some embodiments, n is 3. In some embodiments, n is 4. In some embodiments, n is 5.

Initial Screen

Synthesis: Summary for Oligonucleotide Synthesis on a DNA/RNA Synthesizer MerMade-12 (2'-Deoxy and 2'-OMe Cycle)

| step | reaction | reagent | delivery volume (mL) | wait time (sec) |
|---|---|---|---|---|
| 1 | detritylation | 3% TCA in DCM | 4 × 1 | N.A. |
| 2 | coupling | 0.15M phosphoramidite in ACN + 0.45M ETT in ACN | 2 × 0.5 mL | 60 + 60 (DNA), 300 + 300 (2'-OMe RNA) |
| 3 | capping | 5% Pac$_2$O in THF/2,6-lutidine + 16% NMI in THF | 1 | 60 |
| 4 | oxidation | 0.02 Iodine in water/pyridine | 1 | 240 |

Stereorandom PS Oligonucleotides Having DNA-2'-OMe-DNA (7-6-7) Design:

```
ONT-141
                                    (SEQ ID NO: 531)
d(CsCsCsTsCsTsGs)gsaststsgsasd(GsCsAsTsCsCsA)

ONT-142
                                    (SEQ ID NO: 532)
d(AsAsGsCsTsTs)gsgststsgsgsd(GsCsAsAsCsAsC)

ONT-143
                                    (SEQ ID NO: 533)
d(AsGsTsCsAsCsTs)tsgsgsgsasgsd(CsTsTsCsTsCsC)

ONT-144
                                    (SEQ ID NO: 534)
d(CsAsCsTsGsGs)gsasgscststsd(CsTsCsCsTsGsG)

ONT-145
                                    (SEQ ID NO: 535)
d(AsTsAsGsCsCsAs)tststsgscsasgsd(CsTsGsCsTsCsA)

ONT-146
                                    (SEQ ID NO: 536)
d(TsGsGsAsTsTsGs)asgscsastscsd(CsAsCsCsAsAsG)

ONT-147
                                    (SEQ ID NO: 537)
d(CsCsAsTsAsGsCs)csaststsgscsd(AsGsCsTsGsCsT)

ONT-148
                                    (SEQ ID NO: 538)
d(GsTsCsAsCsTsTs)gsgsgsasgscsd(TsTsCsTsCsT)

ONT-149
                                    (SEQ ID NO: 539)
d(CsCsAsGsGsGsCs)ascstscsastsd(CsTsGsCsAsTsG)

ONT-150
                                    (SEQ ID NO: 540)
d(GsCsCsAsTsCsCs)asasgstscsasd(CsTsTsGsGsGsA)

ONT-151
                                    (SEQ ID NO: 541)
d(GsAsAsGsCsTsTs)tsgsgststsgsd(GsGsCsAsAsCsA)

ONT-152
                                    (SEQ ID NO: 542)
d(CsTsGsGsAsTsTs)gsasgscsastsd(CsCsAsCsCsAsA)

ONT-183
                                    (SEQ ID NO: 543)
d(CsAsAsGsTsCsAs)cststsgsgsgsd(AsGsCsTsTsCsT)

ONT-184
                                    (SEQ ID NO: 544)
d(AsTsGsCsCsAsTs)cscsasasgstsd(CsAsCsTsTsGsG)

ONT-185
                                    (SEQ ID NO: 545)
d(AsTsAsAsGsAsTs)gscscstsgsgsd(CsTsGsCsCsAsT)

ONT-186
                                    (SEQ ID NO: 546)
d(TsTsGsGsGsAsGs)cststscstscsd(CsTsGsGsTsGsG)

ONT-187
                                    (SEQ ID NO: 547)
d(TsGsGsGsAsGsCs)tstscstscscsd(TsGsGsTsGsGsA)

ONT-188
                                    (SEQ ID NO: 548)
d(TsTsAsTsGsAsGs)astsgscscstsd(GsGsCsTsGsCsC)

ONT-189
                                    (SEQ ID NO: 549)
d(GsTsTsAsTsGsAs)gsastsgscscsd(TsGsGsCsTsGsC)

ONT-190
                                    (SEQ ID NO: 550)
d(CsCsAsAsGsTsCs)ascststsgsgsd(GsAsGsCsTsTsC)

ONT-191
                                    (SEQ ID NO: 551)
d(AsGsCsTsTsTsGs)gststsgsgsgsd(CsAsAsCsAsCsA)

ONT-192
                                    (SEQ ID NO: 552)
d(TsAsTsGsAsGsAs)tsgscscstsgsd(GsCsTsGsCsCsA)

ONT-193
                                    (SEQ ID NO: 553)
d(TsGsTsTsAsTsGs)asgsastsgscsd(CsTsGsGsCsTsG)
```

ONT-194
(SEQ ID NO: 554)
d(AsTsCsAsAsAsGs)tscsascststsd(GsGsGsAsGsCsT)

ONT-195
(SEQ ID NO: 555)
d(GsGsGsAsAsGsCs)tststsgsgstsd(TsGsGsCsAsA)

ONT-196
(SEQ ID NO: 556)
d(CsTsCsCsAsTsCs)csastsgsasgsd(GsTsCsAsTsTsC)

ONT-197
(SEQ ID NO: 557)
d(AsAsGsTsCsAsCs)tstsgsgsgsasd(GsCsTsTsCsTsC)

ONT-198
(SEQ ID NO: 558)
d(CsCsAsTsCsCsAs)asgstscsascsd(TsTsGsGsGsAsG)

ONT-199
(SEQ ID NO: 559)
d(TsCsCsAsAsGsTs)csascststsgsd(GsGsAsGsCsTsT)

ONT-200
(SEQ ID NO: 560)
d(CsCsTsCsTsGsGs)aststsgsasgsd(CsAsTsCsCsAsC)

ONT-201
(SEQ ID NO: 561)
d(AsCsTsTsGsGsGs)asgscststscsd(TsCsCsTsGsGsT)

ONT-202
(SEQ ID NO: 562)
d(CsTsTsGsGsGsAs)gscststscstsd(CsCsTsGsGsTsG)

ONT-203
(SEQ ID NO: 563)
d(CsAsTsGsCsCsAs)tscscsasasgsd(TsCsAsCsTsTsG)

ONT-204
(SEQ ID NO: 564)
d(TsGsCsCsAsTsCs)csasasgstscsd(AsCsTsTsGsGsG)

ONT-205
(SEQ ID NO: 565)
d(TsCsCsAsTsCsCs)astsgsasgsgsd(TsCsAsTsTsCsC)

ONT-206
(SEQ ID NO: 566)
d(AsGsGsGsCsAsCs)tscsastscstsd(GsCsAsTsGsGsG)

ONT-207
(SEQ ID NO: 567)
d(CsCsAsGsTsTsCs)cststscsastsd(TsCsTsGsCsAsC)

ONT-208
(SEQ ID NO: 568)
d(CsAsTsAsGsCsCs)aststsgscsasd(GsCsTsGsCsTsC)

ONT-209
(SEQ ID NO: 569)
d(TsCsTsGsGsAsTs)tsgsasgscsasd(TsCsCsAsCsCsA)

ONT-210
(SEQ ID NO: 570)
d(GsGsAsTsTsGsAs)gscsastscscsd(AsCsCsAsAsGsA)

Biology In Vitro Data in HepG2 Cells for the Initial DNA-2'-OMe-DNA (7-6-7) Design: (d Upper Case)=DNA; Lower Case=2'-OMe; s=Phosphorothioate.

FOXO1

| Levels at 20 nM | (%) | SD |
| --- | --- | --- |
| ONT-141 | 89 | 6 |
| ONT-142 | 45 | 1 |
| ONT-143 | 98 | 2 |
| ONT-144 | 89 | 1 |
| ONT-145 | 46 | 5 |
| ONT-146 | 99 | 1 |
| ONT-147 | 66 | 6 |
| ONT-148 | 101 | 2 |
| ONT-149 | 95 | 6 |
| ONT-150 | 58 | 4 |
| ONT-151 | 41 | 5 |
| ONT-152 | 84 | 5 |
| ONT-183 | 95 | 2 |
| ONT-184 | 58 | 4 |
| ONT-185 | 42 | 2 |
| ONT-186 | 96 | 4 |
| ONT-187 | 92 | 3 |
| ONT-188 | 47 | 5 |
| ONT-189 | 63 | 5 |
| ONT-190 | 83 | 2 |
| ONT-191 | 58 | 4 |
| ONT-192 | 46 | 2 |
| ONT-193 | 58 | 2 |
| ONT-194 | 76 | 1 |
| ONT-195 | 66 | 0 |
| ONT-196 | 77 | 2 |
| ONT-197 | 90 | 6 |
| ONT-198 | 42 | 4 |
| ONT-199 | 68 | 1 |
| ONT-200 | 89 | 6 |
| ONT-201 | 91 | 2 |
| ONT-202 | 94 | 2 |
| ONT-203 | 86 | 1 |
| ONT-204 | 58 | 2 |
| ONT-205 | 75 | 3 |
| ONT-206 | 94 | 5 |
| ONT-207 | 96 | 0 |
| ONT-208 | 54 | 0 |
| ONT-209 | 87 | 4 |
| ONT-210 | 92 | 4 |

FOXO1

| Levels at 200 nM | (%) | SD |
| --- | --- | --- |
| ONT-141 | 37 | 4 |
| ONT-142 | 45 | 4 |
| ONT-143 | 46 | 2 |
| ONT-144 | 42 | 5 |
| ONT-145 | 53 | 4 |
| ONT-146 | 31 | 2 |
| ONT-147 | 28 | 8 |
| ONT-148 | 45 | 4 |
| ONT-149 | 29 | 5 |
| ONT-150 | 32 | 6 |
| ONT-151 | 38 | 4 |
| ONT-152 | 30 | 5 |
| ONT-183 | 60 | 5 |
| ONT-184 | 34 | 2 |
| ONT-185 | 50 | 2 |
| ONT-186 | 86 | 3 |
| ONT-187 | 76 | 6 |
| ONT-188 | 50 | 5 |
| ONT-189 | 38 | 2 |
| ONT-190 | 51 | 1 |
| ONT-191 | 43 | 5 |
| ONT-192 | 54 | 7 |
| ONT-193 | 41 | 6 |
| ONT-194 | 50 | 1 |
| ONT-195 | 43 | 6 |
| ONT-196 | 33 | 7 |
| ONT-197 | 57 | 4 |
| ONT-198 | 40 | 5 |
| ONT-199 | 50 | 5 |
| ONT-200 | 28 | 9 |
| ONT-201 | 46 | 6 |
| ONT-202 | 57 | 9 |
| ONT-203 | 27 | 7 |
| ONT-204 | 36 | 6 |

-continued

| Levels at 200 nM | (%) | SD |
|---|---|---|
| ONT-205 | 29 | 5 |
| ONT-206 | 81 | 0 |
| ONT-207 | 37 | 4 |
| ONT-208 | 43 | 3 |
| ONT-209 | 35 | 4 |
| ONT-210 | 40 | 4 |

Stereorandom PS Oligonucleotides Having 2'-OMe-DNA-2'OMe (3-14-3) Design: (d Upper Case)=DNA; Lower Case=2'-OMe; s=Phosphorothioate.

```
ONT-129
                             (SEQ ID NO: 571)
cscscsd(TsCsTsGsGsAsTsTsGsAsGsCsAsTs)cscsa ONT-130
                             (SEQ ID NO: 572)
asasgsd(CsTsTsGsTsTsGsGsGsCsAsAs)csasc ONT-131
                             (SEQ ID NO: 573)
asgstsd(CsAsCsTsTsGsGsGsAsGsCsTsTsCs)tscsc ONT-132
                             (SEQ ID NO: 574)
csascsd(TsTsGsGsGsAsGsCsTsTsCsTsCsCs)tsgsg ONT-133
                             (SEQ ID NO: 575)
astsasd(GsCsCsAsTsTsGsCsAsGsCsTsGsCs)tscsa ONT-134
                             (SEQ ID NO: 576)
tsgsgsd(AsTsTsGsAsGsCsAsTsCsCsAsCsCs)asasg ONT-135
                             (SEQ ID NO: 577)
cscsasd(TsAsGsCsCsAsTsTsGsCsAsGsCsTs)gscst ONT-136
                             (SEQ ID NO: 578)
gstscsd(AsCsTsTsGsGsGsAsGsCsTsTsCsTs)cscst ONT-137
                             (SEQ ID NO: 579)
cscsasd(GsGsGsCsAsCsTsCsAsTsCsTsGsCs)astsg ONT-138
                             (SEQ ID NO: 580)
gscscsd(AsTsCsAsAsGsTsCsAsCsTsTsGs)gsgsa ONT-139
                             (SEQ ID NO: 581)
gsasasd(GsCsTsTsTsGsGsTsTsGsGsGsCsAs)ascsa ONT-140
                             (SEQ ID NO: 582)
cstsgsd(GsAsTsGsAsGsCsAsTsCsCsAsCs)csasa ONT-155
                             (SEQ ID NO: 583)
csasasd(GsTsCsAsCsTsTsGsGsGsAsGsCsTs)tscst ONT-156
                             (SEQ ID NO: 584)
astsgsd(CsCsAsTsCsCsAsAsGsTsCsAsCsTs)tsgsg ONT-157
                             (SEQ ID NO: 585)
astsgsd(AsGsAsTsGsCsCsTsGsGsCsTsGsCs)csast ONT-158
                             (SEQ ID NO: 586)
tstsgsd(GsGsAsGsCsTsTsCsTsCsCsTsGsGs)tsgsg ONT-159
                             (SEQ ID NO: 587)
tsgsgsd(GsAsGsCsTsTsCsTsCsCsTsGsGsTs)gsgsa ONT-160
                             (SEQ ID NO: 588)
tstsasd(TsGsAsGsAsTsGsCsCsTsGsGsCsTs)gscsc ONT-161
                             (SEQ ID NO: 589)
gststsd(AsTsAsGsAsTsGsCsCsTsGsGsCs)tsgsc ONT-162
                             (SEQ ID NO: 590)
cscsasd(AsGsTsCsAsCsTsTsGsGsGsAsGsCs)tstsc ONT-163
                             (SEQ ID NO: 591)
asgscsd(TsTsTsGsGsTsGsGsGsCsAsAsCs)ascsa ONT-164
                             (SEQ ID NO: 592)
tsastsd(GsAsGsAsTsGsCsCsTsGsGsCsTsGs)cscsa ONT-165
                             (SEQ ID NO: 593)
tsgstsd(TsAsTsGsAsGsAsTsGsCsCsTsGsGs)cstsg ONT-166
                             (SEQ ID NO: 594)
astscsd(CsAsAsGsTsCsAsCsTsTsGsGsGsAs)gscst ONT-167
                             (SEQ ID NO: 595)
gsgsgsd(AsAsGsCsTsTsTsGsGsTsTsGsGsGs)csasa ONT-168
                             (SEQ ID NO: 596)
cstscsd(CsAsTsCsCsAsTsGsAsGsGsTsCsAs)tstsc ONT-169
                             (SEQ ID NO: 597)
asasgsd(TsCsAsCsTsTsGsGsGsAsGsCsTsTs)cstsc ONT-170
                             (SEQ ID NO: 598)
cscsasd(TsCsCsAsAsGsTsCsAsCsTsTsGsGs)gsasg ONT-171
                             (SEQ ID NO: 599)
tscscsd(AsAsGsTsCsAsCsTsTsGsGsGsAsGs)cstst ONT-172
                             (SEQ ID NO: 600)
cscstsd(CsTsGsGsAsTsGsAsGsCsAsTsCs)csasc ONT-173
                             (SEQ ID NO: 601)
ascstsd(TsGsGsAsGsCsTsTsCsTsCsCsTs)gsgst ONT-174
                             (SEQ ID NO: 602)
cststsd(GsGsGsAsGsCsTsTsCsTsCsCsTsGs)gstsg ONT-175
                             (SEQ ID NO: 603)
csastsd(GsCsCsAsTsCsCsAsAsGsTsCsAsCs)tstsg ONT-176
                             (SEQ ID NO: 604)
tsgscsd(CsAsTsCsCsAsAsGsTsCsAsCsTsTs)gsgsg ONT-177
                             (SEQ ID NO: 605)
tscscsd(AsTsCsCsAsTsGsAsGsGsTsCsAsTs)tscsc ONT-178
                             (SEQ ID NO: 606)
asgsgsd(GsCsAsCsTsCsAsTsCsTsGsCsAsTs)gsgsg
```

-continued

```
ONT-179
                                 (SEQ ID NO: 607)
cscsasd(GsTsTsCsCsTsTsCsAsTsCsTsGs)csasc ONT-180
                                 (SEQ ID NO: 608)
csastsd(AsGsCsCsAsTsTsGsCsAsGsCsTsGs)cstsc ONT-181
                                 (SEQ ID NO: 609)
tscstsd(GsGsAsTsTsGsAsGsCsAsTsCsCsAs)cscsa ONT-182
                                 (SEQ ID NO: 610)
gsgsasd(TsTsGsAsGsCsAsTsCsCsAsCsCsAs)asgsa
```

Biology In Vitro Data in HepG2 Cells for the 2'-OMe-DNA-2'-OMe (3-14-3) Design:

FOXO1

| Levels at 20 nM | (%) | SD |
|---|---|---|
| ONT-129 | 82 | 5 |
| ONT-130 | 49 | 4 |
| ONT-131 | 92 | 3 |
| ONT-132 | 91 | 2 |
| ONT-133 | 58 | 3 |
| ONT-134 | 73 | 2 |
| ONT-135 | 65 | 5 |
| ONT-136 | 92 | 2 |
| ONT-137 | 94 | 2 |
| ONT-138 | 78 | 1 |
| ONT-139 | 61 | 1 |
| ONT-140 | 82 | 4 |
| ONT-155 | 95 | 2 |
| ONT-156 | 74 | 1 |
| ONT-157 | 56 | 2 |
| ONT-158 | 93 | 1 |
| ONT-159 | 94 | 1 |
| ONT-160 | 71 | 1 |
| ONT-161 | 67 | 1 |
| ONT-162 | 89 | 1 |
| ONT-163 | 55 | 7 |
| ONT-164 | 68 | 4 |
| ONT-165 | 70 | 1 |
| ONT-166 | 89 | 4 |
| ONT-167 | 81 | 0 |
| ONT-168 | 81 | 0 |
| ONT-169 | 94 | 0 |
| ONT-170 | 88 | 1 |
| ONT-171 | 92 | 4 |
| ONT-172 | 86 | 2 |
| ONT-173 | 90 | 1 |
| ONT-174 | 93 | 2 |
| ONT-175 | 84 | 1 |
| ONT-176 | 80 | 2 |
| ONT-177 | 83 | 2 |
| ONT-178 | 95 | 2 |
| ONT-179 | 93 | 8 |
| ONT-180 | 68 | 7 |
| ONT-181 | 85 | 5 |
| ONT-182 | 80 | 5 |

FOXO1

| Levels at 200 nM | (%) | SD |
|---|---|---|
| ONT-129 | 27 | 1 |
| ONT-130 | 46 | 4 |
| ONT-131 | 53 | 9 |
| ONT-132 | 53 | 2 |
| ONT-133 | 48 | 6 |
| ONT-134 | 35 | 9 |
| ONT-135 | 45 | 15 |
| ONT-136 | 40 | 7 |
| ONT-137 | 50 | 4 |
| ONT-138 | 80 | 3 |
| ONT-139 | 40 | 3 |
| ONT-140 | 33 | 13 |
| ONT-155 | 52 | 2 |
| ONT-156 | 35 | 4 |
| ONT-157 | 39 | 2 |
| ONT-158 | 87 | 6 |
| ONT-159 | 89 | 5 |
| ONT-160 | 33 | 10 |
| ONT-161 | 40 | 11 |
| ONT-162 | 60 | 7 |
| ONT-163 | 42 | 8 |
| ONT-164 | 34 | 10 |
| ONT-165 | 38 | 1 |
| ONT-166 | 62 | 9 |
| ONT-167 | 64 | 1 |
| ONT-168 | 38 | 2 |
| ONT-169 | 67 | 3 |
| ONT-170 | 74 | 8 |
| ONT-171 | 65 | 5 |
| ONT-172 | 33 | 18 |
| ONT-173 | 72 | 15 |
| ONT-174 | 65 | 15 |
| ONT-175 | 38 | 21 |
| ONT-176 | 48 | 8 |
| ONT-177 | 28 | 5 |
| ONT-178 | 97 | 11 |
| ONT-179 | 47 | 6 |
| ONT-180 | 56 | 12 |
| ONT-181 | 45 | 26 |
| ONT-182 | 33 | 17 |

Hit Selection:

```
ONT-151
                                 (SEQ ID NO: 611)
d(GsAsAsGsCsTsTs)tsgsgststsgsd(GsGsCsAsAsCsA)

ONT-198
                                 (SEQ ID NO: 612)
d(CsCsAsTsCsCsAs)asgstscsascsd(TsTsGsGsAsG)

ONT-185
                                 (SEQ ID NO: 613)
d(AsTsGsAsGsAsTs)gscscstsgsgsd(CsTsGsCsCsAsT)

ONT-142
                                 (SEQ ID NO: 614)
d(AsAsGsCsTsTsTs)gsgststsgsgsd(GsCsAsAsCsAsC)

ONT-145
                                 (SEQ ID NO: 615)
d(AsTsAsGsCsCsAs)tstsgscsasgsd(CsTsGsCsTsCsA)

ONT-192
                                 (SEQ ID NO: 616)
d(TsAsTsGsAsGsAs)tsgscscstsgsd(GsCsTsGsCsCsA)

ONT-188
                                 (SEQ ID NO: 617)
d(TsTsAsTsGsAsGs)astsgscscstsd(GsGsCsTsGsCsC)
```

Secondary Screen. Chemistry and Stereochemistry Screen Summary for Oligonucleotide Synthesis on a DNA/RNA Synthesizer MerMade-12 (Stereodefined Phosphorothioate 2'-Deoxy and 2'-OMe Cycle)

| step | reaction | reagent | delivery vol (mL) | wait time (sec) |
|---|---|---|---|---|
| 1 | detritylation | 3% TCA in DCM | 4 × 1 | N. A. |
| 2 | coupling | 0.15M chiral phosphoramidite in ACN + 2M CMPT in ACN | 2 × 0.5 | 2 × 450 (2'-OMe RNA) 2 × 300 (DNA) |
| 3 | capping 1 | 5% Pac$_2$O in THF/2,6-lutidine | 1 | 60 |
| 4 | capping 2 | 5% Pac$_2$O in THF/2,6-lutidine + 16% NMI in THF | 1 | 60 |
| 5 | sulfurization | 0.3M S-(2-cyanoethyl) methylthiosulfonate in ACN/BSTFA | 1 | 600 |

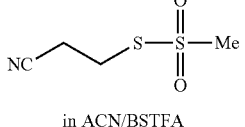

Examples Applied on the FOXO1 Hit Sequences:
Examples Include but are not Limited to:

(SEQ ID NO: 618)
(Sp, Sp, Sp, Sp, Sp, Sp, Sp, Rp, Sp, Sp, Rp, Sp, Sp, Rp, Sp, Sp, Sp, Sp, Sp) d[CsCsAsTsCsCsAsAsGsTsCsAsCsTsTsGsGsGsAsG]

(SEQ ID NO: 619)
(Sp, Sp, Sp, Sp, Sp, Rp, Sp, Sp, Rp, Sp, Sp, Rp, Sp, Sp, Rp, Sp, Sp, Sp, Sp) d[CsCsAsTsCsCsAsAsGsTsCsAsCsTsTsGsGsGsAsG]

(SEQ ID NO: 620)
(Sp, Sp, Sp, Rp, Sp, Sp, Rp, Sp, Sp, Rp, Sp, Sp, Rp, Sp, Sp, Rp, Sp, Sp, Sp) d[GsAsAsGsCsTsTsTsGsGsTsTsGsGsGsCsAsAsCsA]

(SEQ ID NO: 621)
(Sp, Sp, Rp, Sp, Sp, Rp, Sp, Sp, Rp, Sp, Sp, Rp, Sp, Sp, Rp, Sp, Sp, Rp, Sp) d[CsCsAsTsCsCsAsAsGsTsCsAsCsTsTsGsGsGsAsG]

(SEQ ID NO: 622)
(Sp, Sp, Sp, Sp, Rp, Rp, Sp, Rp, Rp, Sp, Rp, Rp, Sp, Sp, Sp, Sp, Sp, Sp, Sp) d[CsCsAsTsCsCsAsAsGsTsCsAsCsTsTsGsGsGsAsG]

(SEQ ID NO: 623)
(Sp, Sp, Sp, Sp, Rp, Rp, Sp, Rp, Rp, Sp, Rp, Rp, Sp, Rp, Rp, Sp, Sp, Sp, Sp) d[GsAsAsGsCsTsTsTsGsGsTsTsGsGsGsCsAsAsCsA]

(SEQ ID NO: 624)
(Sp, Sp, Sp, Sp, Sp, Sp, Sp, Rp, Sp, Rp, Sp, Sp, Rp, Sp, Sp, Sp, Sp, Sp, Sp) d[AsTsGsAsGsAsTsGsCsCsTsGsGsCsTsGsCsCsAsT]

(SEQ ID NO: 625)
(Sp, Sp, Sp, Sp, Rp, Sp, Sp, Rp, Sp, Sp, Rp, Sp, Sp, Rp, Sp, Sp, Sp, Sp, Sp) d[AsTsGsAsGsAsTsGsCsCsTsGsGsCsTsGsCsCsAsT]

(SEQ ID NO: 626)
(Sp, Sp, Sp, Rp, Sp, Sp, Rp, Sp, Sp, Rp, Sp, Sp, Rp, Sp, Sp, Rp, Sp, Sp, Sp) d[AsTsGsAsGsAsTsGsCsCsTsGsGsCsTsGsCsCsAsT]

(SEQ ID NO: 627)
(Sp, Sp, Rp, Sp, Sp, Rp, Sp, Sp, Rp, Sp, Sp, Rp, Sp, Sp, Rp, Sp, Sp, Rp, Sp) d[AsTsGsAsGsAsTsGsCsCsTsGsGsCsTsGsCsCsAsT]

(SEQ ID NO: 628)
(Sp, Sp, Sp, Sp, Sp, Rp, Rp, Sp, Rp, Rp, Sp, Rp, Rp, Sp, Sp, Sp, Sp, Sp, Sp) d[GsAsAsGsCsTsTsTsGsGsTsTsGsGsGsCsAsAsCsA]

(SEQ ID NO: 629)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](<u>AsGsTsCsAsCs</u>)$_{OMe}$d[TsTsGsGsGsAsG]

(SEQ ID NO: 630)
(Sp, Sp, Rp, Sp, Sp, Rp, Sp, Sp, Rp, Sp, Rp, Sp, Sp, Rp, Sp, Sp, Rp, Sp, Sp)d[AsTsGsAsGsAsTs](<u>GsCsCsTsGsGs</u>)$_{OMe}$d[CsTsGsCsCsAsT]

(SEQ ID NO: 631)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](<u>AsGsTsCsAsCs</u>)$_{LNA}$d[TsTsGsGsGsAsG]

(SEQ ID NO: 632)
(Sp, Sp, Rp, Sp, Sp, Rp, Sp, Sp, Rp, Sp, Rp, Sp, Sp, Rp, Sp, Sp, Rp, Sp, Sp)d[AsTsGsAsGsAsTs](<u>GsCsCsTsGsGs</u>)$_{LNA}$d[CsTsGsCsCsAsT]

(SEQ ID NO: 633)
(Sp, Sp, Rp, Sp, Sp, Rp, Sp, Sp, Rp, Sp, Rp, Sp, Sp, Rp, Sp, Sp, Rp, Sp, Sp)d[CsCsAsTsCsCsAs](<u>AsGsTsCsAsCs</u>)$_{MOE}$d[TsTsGsGsGsAsG]

(SEQ ID NO: 634)
(Sp, Sp, Rp, Sp, Sp, Rp, Sp, Sp, Rp, Sp, Rp, Sp, Sp, Rp, Sp, Sp, Rp, Sp, Sp)d[AsTsGsAsGsAsTs](<u>GsCsCsTsGsGs</u>)$_{MOE}$d[CsTsGsCsCsAsT]

(SEQ ID NO: 635)
(Sp, Sp, Sp, Sp, Sp, Rp, Sp, Sp, Rp, Sp, Sp, Rp, Sp, Sp, Rp, Sp, Rp, Sp, Sp)(<u>CsCsAs</u>)$_{OMe}$d[TsCsCsAsAsGsTsCsAsCsTsTsGsGs](<u>GsAsG</u>)$_{OMe}$ (SEQ ID NO: 636)
(Sp, Sp, Sp, Sp, Sp, Rp, Sp, Sp, Rp, Sp, Sp, Rp, Sp, Sp, Rp, Sp, Rp, Sp, Sp)(<u>AsTsGs</u>)$_{MOE}$d[AsGsAsTsGsCsCsTsGsGsGsCsTsGsCs](<u>CsAsT</u>)$_{MOE}$ (SEQ ID NO: 637)
(Sp, Sp, Sp, Sp, Sp, Rp, Sp, Sp, Rp, Sp, Sp, Rp, Sp, Sp, Rp, Sp, Sp, Sp, Sp)(<u>CsCsAs</u>)$_{LNA}$d[TsCsCsAsAsGsTsCsAsCsTsTsGsGs](<u>GsAsG</u>)$_{LNA}$ (SEQ ID NO: 638)
(Sp, Sp, Sp, Sp, Sp, Rp, Sp, Sp, Rp, Sp, Sp, Rp, Sp, Sp, Rp, Sp, Sp, Sp, Sp)(<u>AsTsGs</u>)$_{OMe}$d[AsGsAsTsGsCsCsTsGsGsGsCsTsGsCs](<u>CsAsT</u>)$_{OMe}$ (SEQ ID NO: 639)
(Sp, Sp, Sp, Rp, Sp, Sp, Sp, Rp, Sp, Sp, Sp, Rp, Sp, Sp, Sp, Rp, Sp, Sp, Sp)d[CsCsAsTsCsCsAsAsGsTsCsAsCsTsTsGsGsGsAsG]

(SEQ ID NO: 640)
(Sp, Sp, Sp, Rp, Sp, Sp, Sp, Rp, Sp, Sp, Sp, Rp, Sp, Sp, Sp, Rp, Sp, Sp)d[AsTsGsAsGsAsTsGsCsCsTsGsGsGsCsTsGsCsCsAsT]

(SEQ ID NO: 641)
(Sp, Sp, Rp, Sp, Sp, Sp, Rp, Sp, Sp, Sp, Rp, Sp, Sp, Sp, Rp, Sp, Sp, Sp, Sp)d[GsAsAsGsCsTsTsTsGsGsTsTsGsGsGsCsAsAsCsA]

(SEQ ID NO: 642)
(Sp, Rp, Sp, Sp, Sp, Rp, Sp, Sp, Sp, Rp, Sp, Sp, Sp, Rp, Sp, Sp, Sp, Rp, Sp)d[AsTsGsAsGsAsTsGsCsCsTsGsGsGsCsTsGsCsCsAsT]

(SEQ ID NO: 643)
(Sp, Sp, Sp, Sp, Rp, Sp, Sp, Sp, Rp, Sp, Sp, Sp, Rp, Sp, Sp, Sp, Sp)d[CsCsAsTsCsCsAsAsGsTsCsAsCsTsTsGsGsGsAsG]

(SEQ ID NO: 644)
(Sp, Sp, Sp, Rp, Sp, Sp, Sp, Sp, Rp, Sp, Sp, Sp, Sp, Rp, Sp, Sp, Sp, Sp)d[AsTsGsAsGsAsTsGsCsCsTsGsGsGsCsTsGsCsCsAsT]

-continued (SEQ ID NO: 645)
(Sp, Sp, Rp, Sp, Sp, Sp, Sp, Rp, Sp, Sp, Sp, Sp, Rp, Sp, Sp, Sp, Sp, Rp, Sp)
d[GsAsAsGsCsTsTsTsGsGsTsTsGsGsGsGsCsAsAsCsA]

(SEQ ID NO: 646)
(Sp, Rp, Sp, Sp, Sp, Sp, Rp, Sp, Sp, Sp, Sp, Rp, Sp, Sp, Sp, Sp, Rp, Sp, Sp)d[AsTsGsAsGsAsTsGsCsCsTsGsGsCsTsGsCsCsAsT]

(SEQ ID NO: 647)
(Sp, Sp, Sp, Sp, Sp, Rp, Sp, Sp, Sp, Sp, Rp, Sp, Sp, Sp, Sp, Sp, Rp, Sp)d[CsCsAsTsCsCsAsAsGsTsCsAsCsTsTsGsGsGsAsG]

(SEQ ID NO: 648)
(Sp, Sp, Rp, Sp, Sp, Sp, Sp, Sp, Rp, Sp, Sp, Sp, Sp, Sp, Rp, Sp, Sp, Sp, Sp)d[CsCsAsTsCsCsAsAsGsTsCsAsCsTsTsGsGsGsAsG]

(SEQ ID NO: 649)
(Sp, Rp, Sp, Sp, Sp, Sp, Rp, Sp, Sp, Sp, Sp, Sp, Rp, Sp, Sp, Sp, Sp, Sp)d[AsTsGsAsGsAsTsGsCsCsTsGsGsCsTsGsCsCsAsT]

(SEQ ID NO: 650)
(Sp, Sp, Sp, Sp, Rp, Sp, Sp, Rp, Sp, Sp, Sp, Rp, Sp, Sp, Rp, Sp, Sp, Sp, Sp)d[CsCsAsTsCsCsAsAsGsTsCsAsCsTsTsGsGsGsAsG]

(SEQ ID NO: 651)
(Sp, Sp, Sp, Sp, Rp, Sp, Sp, Rp, Sp, Rp, Sp, Rp, Sp, Sp, Rp, Sp, Sp, Sp, Sp)d[CsCsAsTsCsCsAsAsGsTsCsAsCsTsTsGsGsGsAsG]

(SEQ ID NO: 652)
(Sp, Sp, Sp, Sp, Rp, Sp, Sp, Rp, Sp, Rp, Sp, Rp, Sp, Sp, Rp, Sp, Sp, Sp, Sp)d[CsCsAsTsCsCsAsAsGsTsCsAsCsTsTsGsGsGsAsG]

(SEQ ID NO: 653)
(Sp, Sp, Rp, Sp, Sp, Rp, Sp, Sp, Sp, Rp, Sp, Sp, Sp, Rp, Sp, Sp, Rp, Sp)d[CsCsAsTsCsCsAsAsGsTsCsAsCsTsTsGsGsGsAsG]

(SEQ ID NO: 654)
(Sp, Sp, Rp, Sp, Sp, Rp, Sp, Sp, Sp, Sp, Sp, Sp, Rp, Sp, Sp, Rp, Sp, Sp)d[CsCsAsTsCsCsAsAsGsTsCsAsCsTsTsGsGsGsAsG]

(SEQ ID NO: 655)
(Sp, Sp, Sp, Sp, Rp, Sp, Sp, Rp, Sp, Sp, Sp, Rp, Sp, Sp, Rp, Sp, Sp, Sp, Sp)d[CsCsAsTsCsCsAsAsGsTsCsAsCsTsTsGsGsGsAsG]

(SEQ ID NO: 656)
(Sp, Sp, Sp, Sp, Rp, Sp, Sp, Rp, Sp, Rp, Sp, Rp, Sp, Sp, Rp, Sp, Sp, Sp, Sp) (CsCs)$_{OMe}$d[AsTsCsCsAsAs](GsTsCs)$_{OMe}$d[AsCsTsTsGsGsGs](AsG)$_{OMe}$ (SEQ ID NO: 657)
(Sp, Sp, Sp, Sp, Rp, Sp, Sp, Rp, Sp, Rp, Sp, Rp, Sp, Sp, Rp, Sp, Sp, Sp, Sp) (CsCs)$_{LNA}$d[AsTsCsCsAsAsGsTsCsAsCsTsTsGsGsGs](AsG)$_{LNA}$ (SEQ ID NO: 658)
(Sp, Sp, Rp, Sp, Sp, Rp, Sp, Sp, Sp, Rp, Sp, Sp, Sp, Rp, Sp, Sp, Rp, Sp, Sp) (CsCs)$_{MOE}$d[AsTsCsCsAsAsGsTsCsAsCsTsTsGsGsGs](AsG)$_{MOE}$ (SEQ ID NO: 659)
(Sp, Sp, Rp, Sp, Sp, Rp, Sp, Sp, Sp, Rp, Sp, Sp, Sp, Rp, Sp, Sp, Rp, Sp, Sp) (CsCs)$_{OMe}$d[AsTsCsCsAsAsGsTsCsAsCsTsTsGsGsGs](AsG)$_{OMe}$

Example 4. Suppression of Nucleic Acid Polymer

Among other things, the present disclosure provides chirally controlled oligonucleotide compositions and methods thereof that deliver unexpected results when, e.g., used for suppressing nucleic acid polymers through, in some cases, cleavage of such nucleic acid polymers. Examples include but are not limited to those presented herein.

RNase H Assay

Cleavage rate of nucleic acid polymers by nucleases, for example, RNA by RNase H, is important with respect to the use of oligonucleotides in therapeutic technologies such as antisense technology. Using our assay, we investigated the cleavage rates and analyzed the metabolites for chirally controlled oligonucleotide compositions of particular oligonucleotide types (P-diastereomers) when oligonucleotides of the particular oligonucleotide types are bound to complementary RNA. Results below also illustrate the importance of cleavage patterns recognized by the present disclosure.

RNase H used herein is a ubiquitously expressed endonuclease that hydrolyses the RNA strand of a RNA/DNA hybrid. It plays an important role in the mode of action of antisense oligonucleotides. In some embodiments, RNase H cleavage rate is significantly reduced when the RNA substrate is structured (Lima, W. F., Venkatraman, M., Crooke, S. T. The Influence of Antisense Oligonucleotide-induced RNA Structure on *Escherichia coli* RNase H1 Activity *The Journal Of Biological Chemistry* 272, No. 29, 18191-18199, (1997)). Furthermore, the 2'-MOE gapmer designs (5-10-5) offer higher affinities for RNA targets leading to minimal turnover of the antisense strand. Presence of 2'-MOE modifications in the wings also reduce the number of RNase H cleavage sites.

To study the RNA cleavage rate, the present disclosure provides a simple assay to quantify the length of RNA remaining after incubation with RNase H. The provided method, among other things, provides the relative rates of RNase H cleavage for stereorandom 2'-modified gapmers, stereorandom DNA oligonucleotide compositions and chirally pure P-diastereomers (chirally controlled oligonucleotide compositions of a corresponding oligonucleotide type) for various oligomers for different targets. Changing the stereochemistry at 2'-modified regions and the DNA core provides information with respect to how stereochemistry in these regions affects the interaction of RNase H to its substrates. RNase H reaction mixtures at different time points were analyzed by LCMS to determine the cleavage pattern. The present disclosure, among other things, provides nucleic acid polymer, for example RNA, cleavage rates and cleavage patterns (maps) that are critical to design stereochemical nucleic acid architectures for optimal activity, e.g., antisense activity.

Equipment:
Alliance HPLC, 2489-TUV, 2695E—Equipped with autosampler
Cary100 (Agilent Technologies)
Methods:
DNA/RNA Duplex Preparation:
Oligonucleotide concentrations were determined by measuring the absorbance in water at 260 nm. DNA/RNA duplexes were prepared by mixing equimolar solutions oligonucleotides with each strand concentration of 10 uM. The mixtures were heated at 90° C. for 2 minutes in water bath and were cooled down slowly over several hours.

Human RNase H Protein Expression and Purification:
Human RNase HC clone was obtained from Prof. Wei Yang's laboratory at NIH Bethesda. The protocol for obtaining this human RNase HC (residues 136-286) has been described (Nowotny, M. et al. Structure of Human RNase H1 Complexed with an RNA/DNA Hybrid: Insight into HIV Reverse Transcription. *Molecular Cell* 28, 264-276, (2007). The protein expression was carried out by following reported protocol with the exception that the resulting protein had an N-terminal His6 tag (SEQ ID NO: 1552). BL21(DE3) *E. coli* cells in LB medium were used for protein expression. Cells were grown at 37° C. till OD600 reached around 0.7. The cultures were then cooled and 0.4 mM IPTG was added to induce protein expression overnight at 16° C. *E. coli* extract was prepared by sonication in buffer A (40 mM $NaH_2PO_4$ (pH 7.0), 1 M NaCl, 5% glycerol, 2.8 mM β-mercaptoethanol and 10 mM imidazole) with the addition of protease inhibitors (Sigma-Aldrich). The extract was purified by Ni affinity column using buffer A plus 60 mM imidazole. The protein was eluted with a linear gradient of 60 to 300 mM imidazole. The protein peak was collected and was further purified on a Mono S column (GE Healthcare) with a 100 mM-500 mM gradient of NaCl in buffer B. Fractions containing RNase HC were concentrated to 0.3 mg/ml in the storage buffer (20 mM HEPES (pH 7.0), 100 mM NaCl, 5% glycerol, 0.5 mM EDTA, 2 mM DTT) and stored at −20° C. 0.3 mg/ml enzyme concentration corresponds to 17.4 uM based on its reported extinction coefficient (32095 $cm^{-1}M^{-1}$) and MW (18963.3 Da units).

RNase H Assay:
In a 96-well plate, to 25 μL DNA/RNA duplex (10 μM) was added 5 μL of 10× RNase H buffer followed by 15 μL water. The mixture was incubated at 37° C. for a few minutes and then 5 μL of 0.1 μM stock solution of enzyme was added to give total volume of 50 μL with final substrate/enzyme concentration 5 μM/0.01 μM (500:1) and was further incubated at 37° C. Various ratios of the DNA/RNA duplex: RNase H protein were studied using these conditions to find an optimal ratio to study the kinetics. The reactions were quenched at different time points using 10 μL of 500 mM EDTA disodium solution in water. For zero min time point, EDTA was added to the reaction mixture before the addition of enzyme. Controls were run to ensure that EDTA was able to successfully inhibit the enzyme activity completely. After all the reactions were quenched 10 μL of each reaction mixture was injected on to analytical HPLC column (XBridge C18, 3.5 um, 4.6×150 mm, Waters Part #186003034). Kcat/Km can be measured by a number of methods, such as FRET (Fluorescence Resonance Energy Transfer) dependent RNase H assay using dual labeled RNA and monitored by SpectraMax.

Solid Phase Extraction Protocol for Sample Preparation for LCMS:
96 well plate (Waters part #186002321) was used to clean the RNase H reaction mixture before running LCMS. 500 μL of acetonitrile followed by water was used to equilibrate the plate under mild vacuum with the help of manifold (Millipore part # MSV MHTS00). Precaution was taken not to let the plate dry. About 50-100 μL of RNase H reaction mixture was loaded in each well followed by water washings (2 mL) under mild vacuum. 2×500 μL of 70% ACN/Water was used to recover the sample. The recovered samples were transferred to 2 mL centrifuge tubes and were concentrated to dryness in speed vac. Each dry sample was reconstituted in 100 μL water and 10 μL was injected on Acquity UPLC@OST C18 1.7 um, 2.1×50 mm (part #186003949) for LCMS analysis.

For mass spectrometry analysis, the reaction mixtures after quenching were cleaned using $C_{18}$ 96 well plate (Waters). The oligomers were eluted in 70% Acetonitrile/Water.

The Acetonitrile was evaporated using speedvac and the resulting residue was reconstituted in water for injection.
Eluent A=50 mM Triethyl ammonium acetate
Eluent B=Acetonitrile
Column Temperature=60° C.
UV was recorded at 254 nm and 280 nm
RP-HPLC Gradient Method

| | Time (min) | Flow (ml/min) | % A | % B | Curve |
|---|---|---|---|---|---|
| 1 | 0.0 | 1.00 | 95.0 | 5.0 | |
| 2 | 2.00 | 1.00 | 95.0 | 5.0 | 1 |
| 3 | 22.00 | 1.00 | 80.0 | 20.0 | 6 |
| 4 | 25.00 | 1.00 | 5.0 | 95.0 | 6 |
| 5 | 25.5 | 1.00 | 95.0 | 5.0 | 1 |
| 6 | 30 | 1.00 | 95.0 | 5.0 | 1 |

Figure 6:
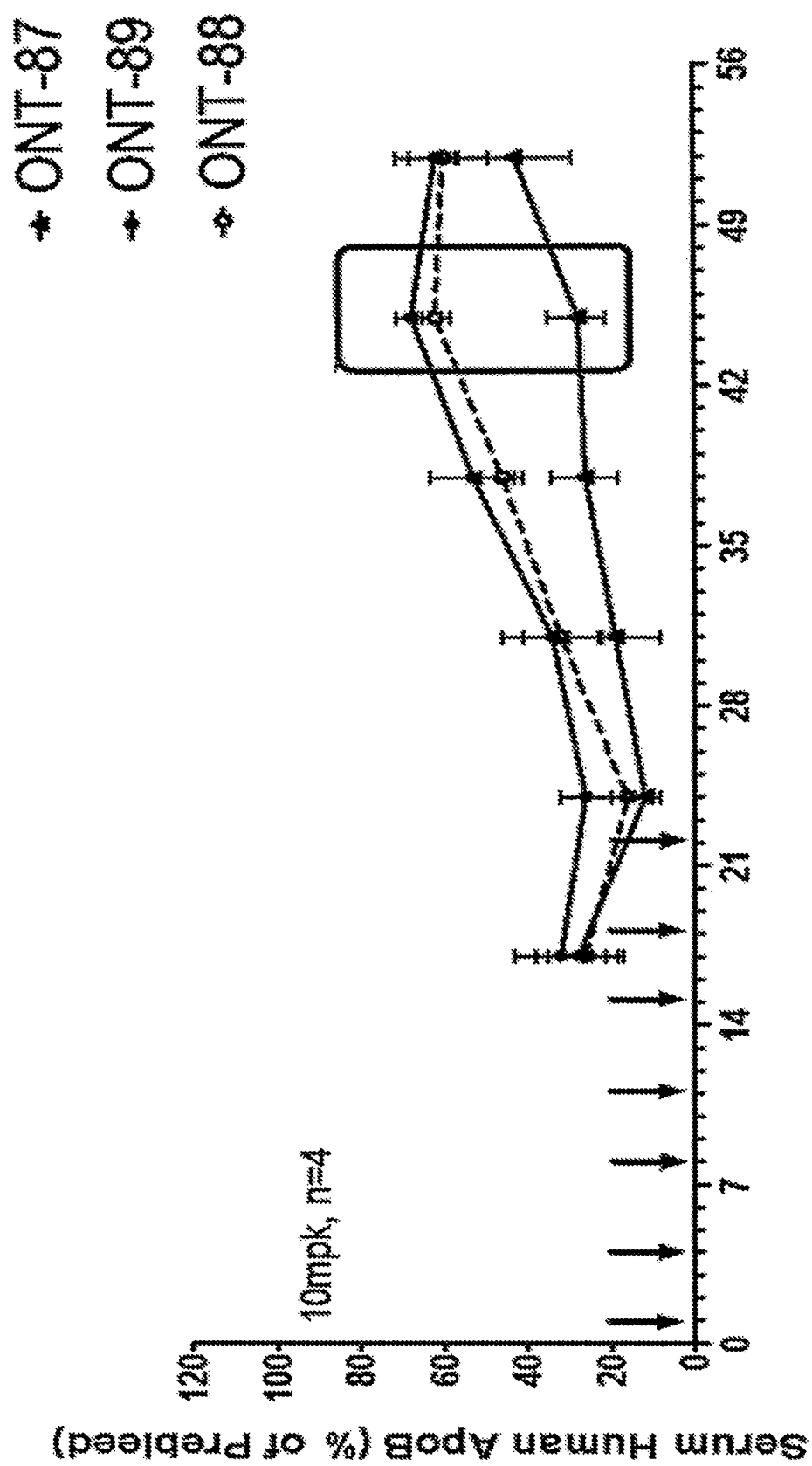
FIG. 6. Durations of knockdown for ONT-87, ONT-88, and ONT-89. Stereoisomers can exhibit substantially different durations of knockdown. ONT-87 results in substantially more durable suppression than other stereoisomers. Increased duration of action of ONT-87 in multiple in vivo studies was observed. ONT-88 showed similar efficacy and recovery profile as ONT-41 (Mipomersen) in certain in-vivo studies. Hu ApoB transgenic mice, n=4, were dosed with 10 mpk IP bolus, 2×/week for three weeks. The mice were randomized to study groups, and dosed intraperitoneally (IP) at 10 mg/kg on Days 1, 4, 8, 11, 15, 18, and 22, based on individual mouse body weight measured prior to dosing on each dosing day. Blood was collected on days 0, 17, 24, 31, 38, 45 and 52 by submandibular (cheek) bleed and at sacrifice on Day 52 by cardiac puncture and then processed to serum. ApoB was measured by ELISA. Highlighted: 72% vs. 35% knock-down maintained at 3 weeks postdose.
Figure 8:
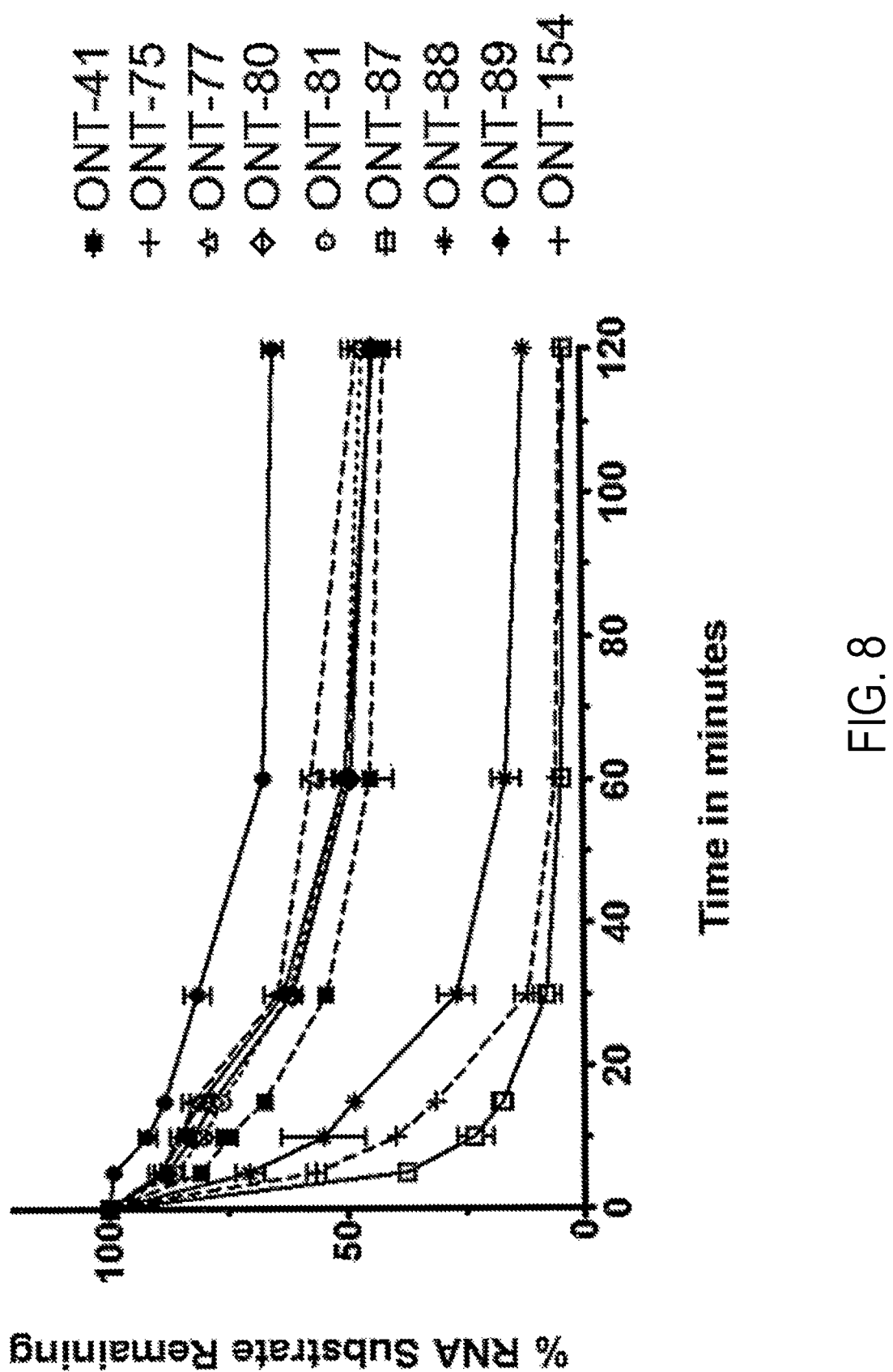
FIG. 8. Effect of stereochemistry on RNase H activity. Oligonucleotides were hybridized with RNA and then incubated with RNase H at 37° C. in the presence of 1×RNase H buffer. From top to bottom at 120 min: ONT-89, ONT-77, ONT-81, ONT-80, ONT-75, ONT-41, ONT-88, ONT-154, ONT-87, with ONT-77/154 very close to each other.
Figure 9:
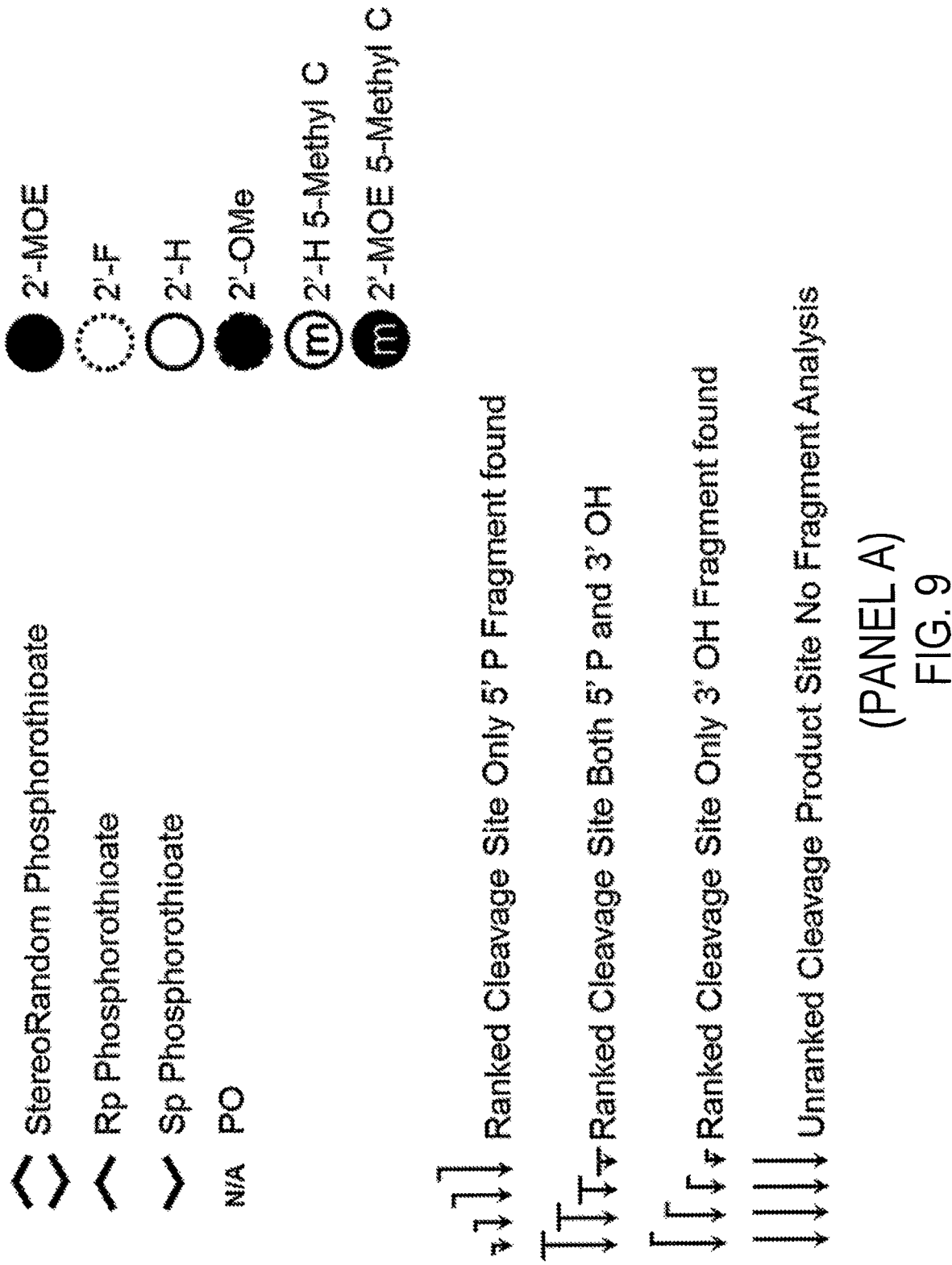
FIG. 9. Analysis of human RNase H1 cleavage of a 20-mer RNA when hybridized with different preparations of stereoisomers of phosphorothioate oligonucleotides targeting the same region of human ApoB mRNA. Specific sites of cleavage are strongly influenced by the distinct stereochemistries. Arrows represent position of cleavage (cleavage sites). Products were analyzed by UPLC/MS. The length of the arrow signifies the amount of products present in the reaction mixture which was determined from the ratio of UV peak area to theoretical extinction coefficient of that fragment (the larger the arrow, the more the detected cleavage products). (A): Legend for cleavage maps. (B) and (C): cleavage maps of oligonucleotides. In the figures: (┬) indicates that both RNase H1 cleavage fragments (5'-phosphate species as well as 5'-OH 3'-OH species) were identified in reaction mixtures. (┌) indicates that only 5'-phosphate species was detected and (┐) indicates that 5'-OH 3'-OH component was detected in mass spectrometry analysis. Compositions used include: ONT-41, ONT-75, ONT-77, ONT-80, ONT-81, ONT-87, ONT-88, ONT-89 and ONT-154. (SEQ ID NOS 397-401 and 758-761, respectively). Figure also discloses SEQ ID NO: 1559.
Figure 9:
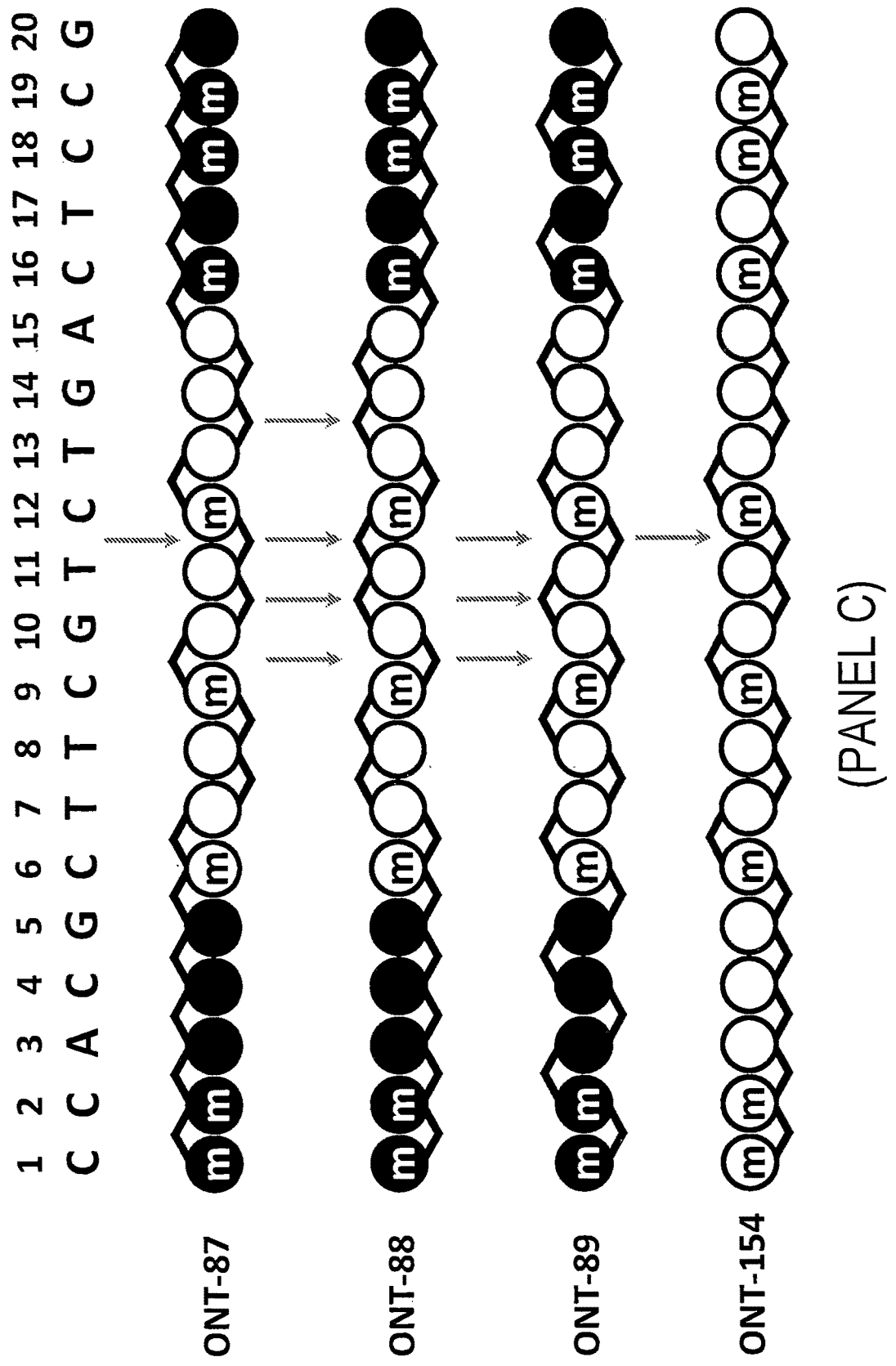
Figure 10:
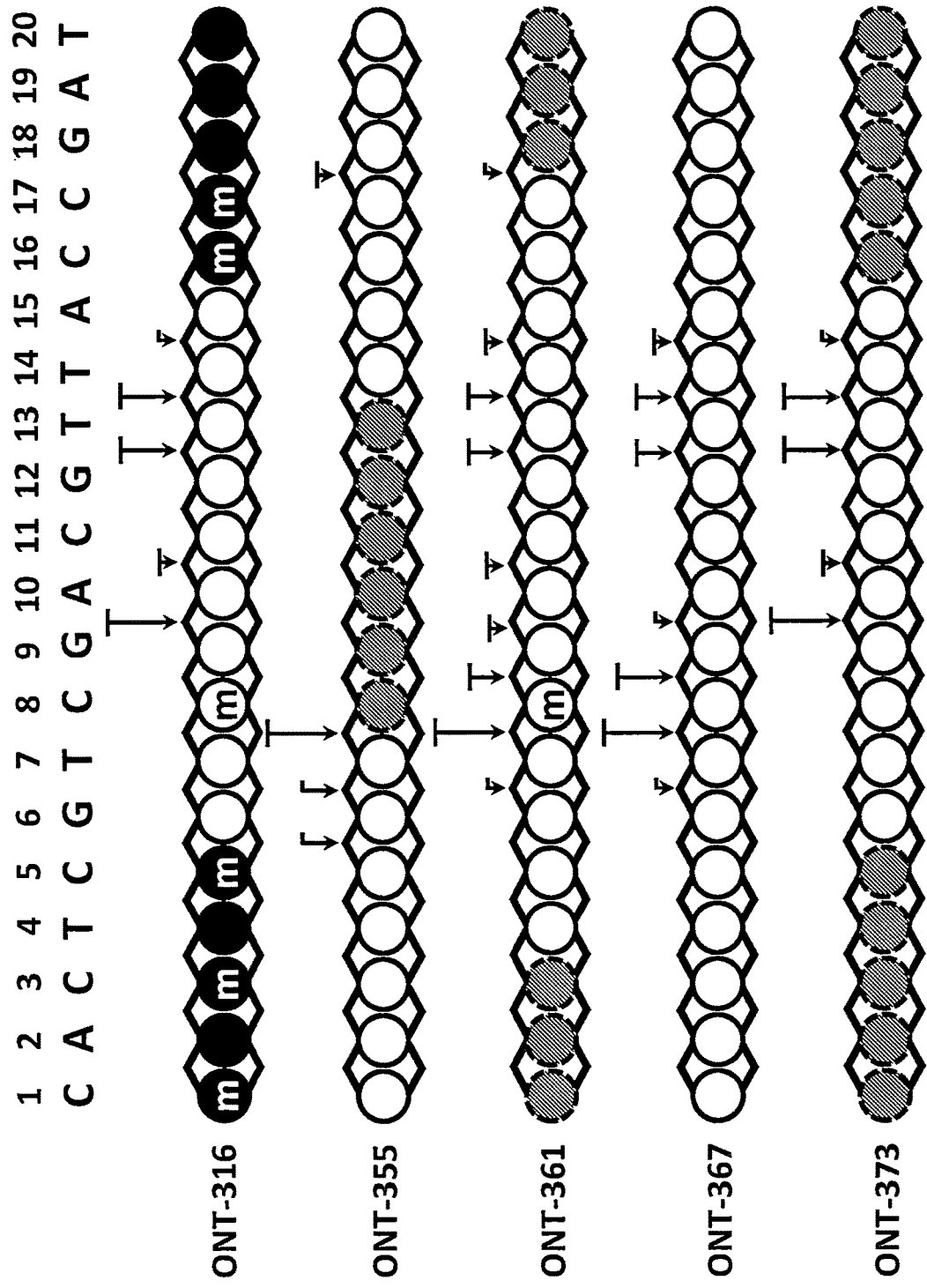
FIG. 10. Cleavage maps of different oligonucleotide compositions ((A)-(C)). These three sequences target different regions in FOXO1 mRNA. Each sequence was studied with five different chemistries. Cleavage maps are derived from reaction mixtures obtained after 30 minutes of incubation of respective duplexes with RNase H1C in the presence of 1×PBS buffer at 37° C. Arrows indicate sites of cleavage. The length of the arrow signifies the amount of products present in the reaction mixture which was determined from the ratio of UV peak area to theoretical extinction coefficient of that fragment (the larger the arrow, the more the detectable cleavage products). Only in the cases where 5'-OH 3'-OH was not detected in the reaction mixture, 5'-phosphate species peak was used for quantification. Cleavage rates were determined by measuring amount of full length RNA remaining in the reaction mixtures by reverse phase HPLC. Reactions were quenched at fixed time points by 30 mM Na$_2$EDTA. Compositions used include: ONT-316, ONT-355, ONT-361, ONT-367, ONT-373, ONT-302, ONT-352, ONT-358, ONT-364, ONT-370, ONT-315, ONT-354, ONT-360, ONT-366, and ONT-372 (SEQ ID NOS 670-674, 676-680 and 682-686, respectively). Figure also discloses SEQ ID NO: 1560 in panel A and SEQ ID NO: 1561 in panels B and C.
Figure 10:
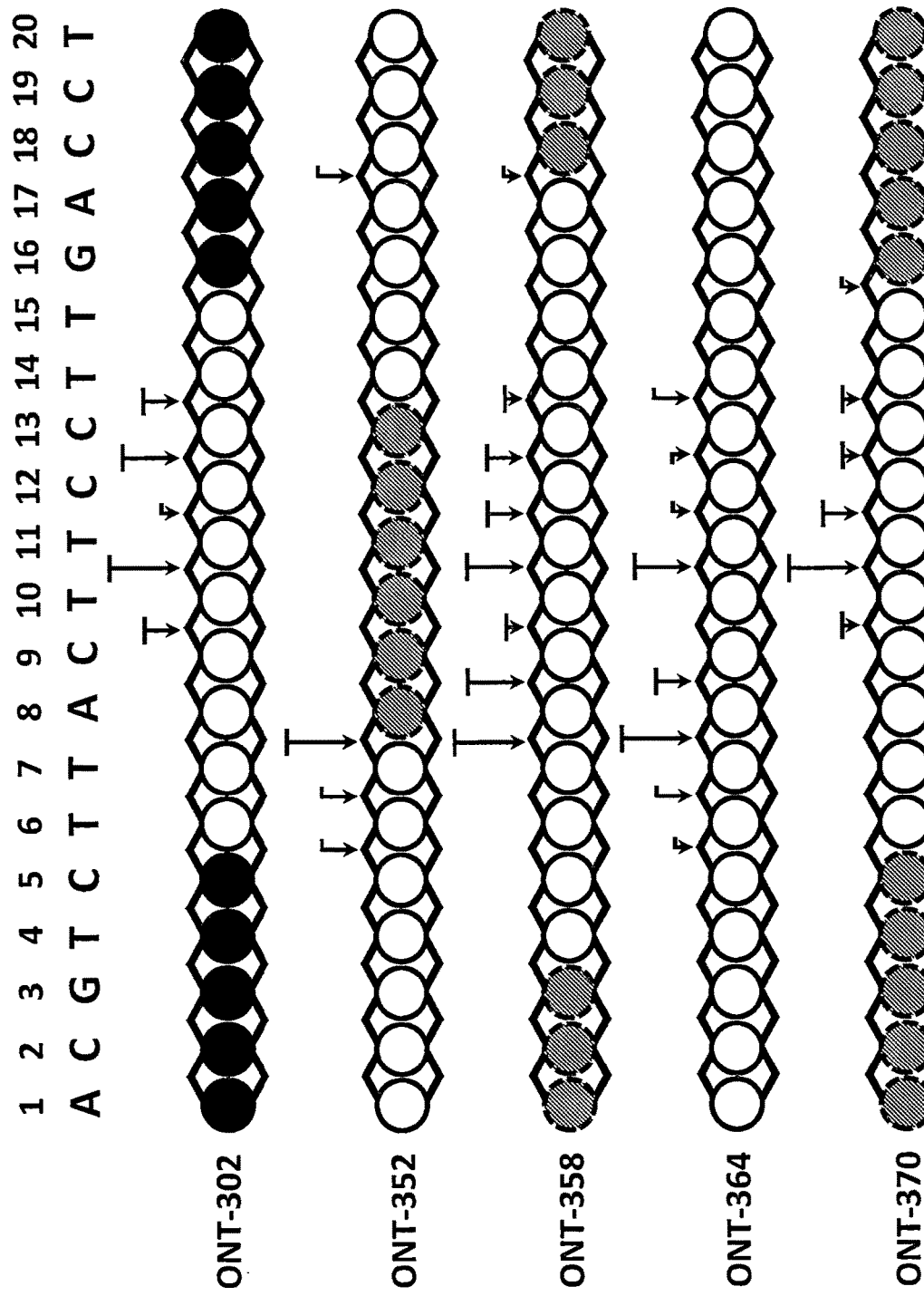
Figure 24:
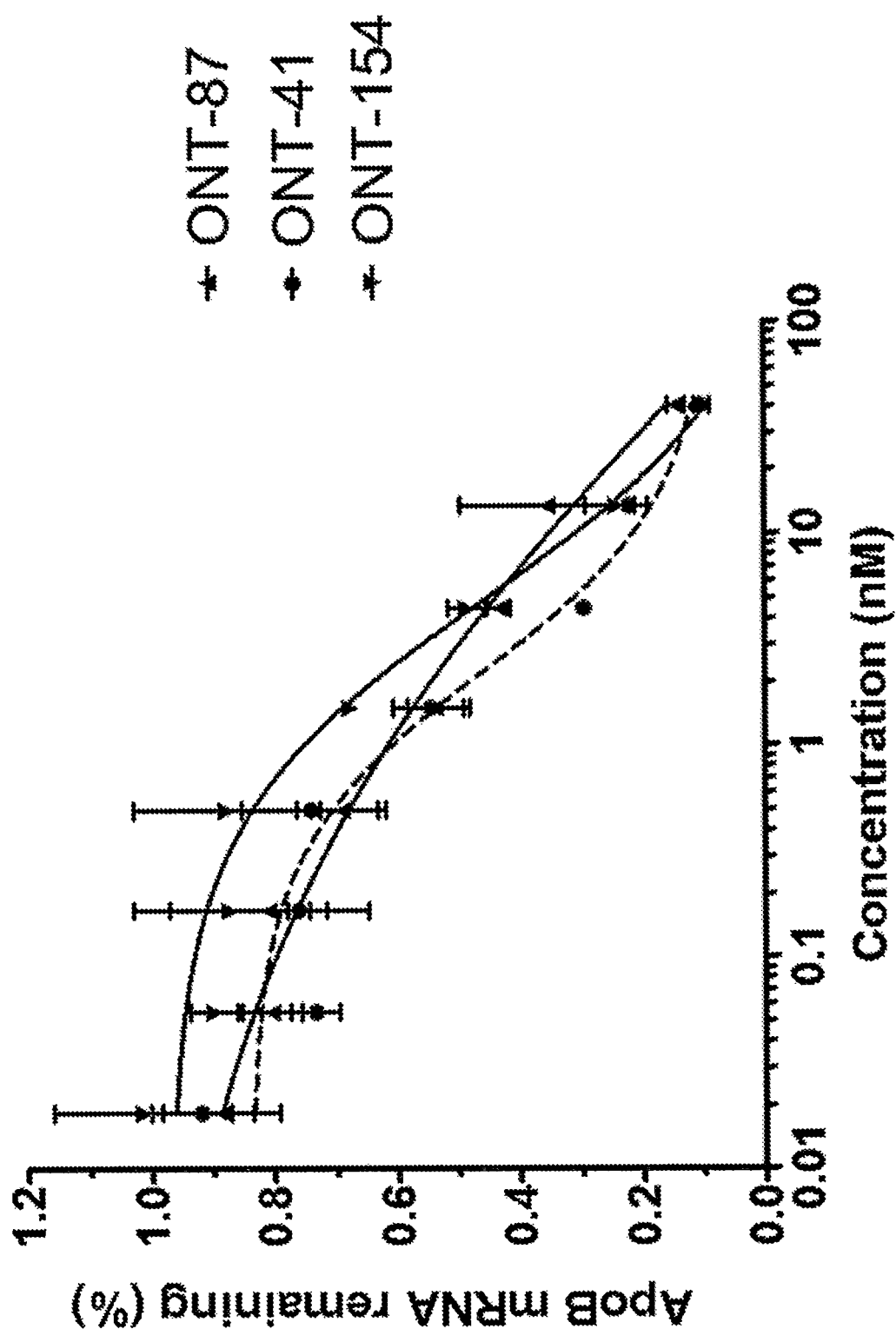
FIG. 24. In vitro dose response silencing of ApoB mRNA after treatment with ApoB oligonucleotides. Stereochemically pure diastereomers with and without 2'-MOE wings show similar efficacy as ONT-41 (Mipomersen). Compositions used include: ONT-87, ONT-41, and ONT-154.
Figure 25:
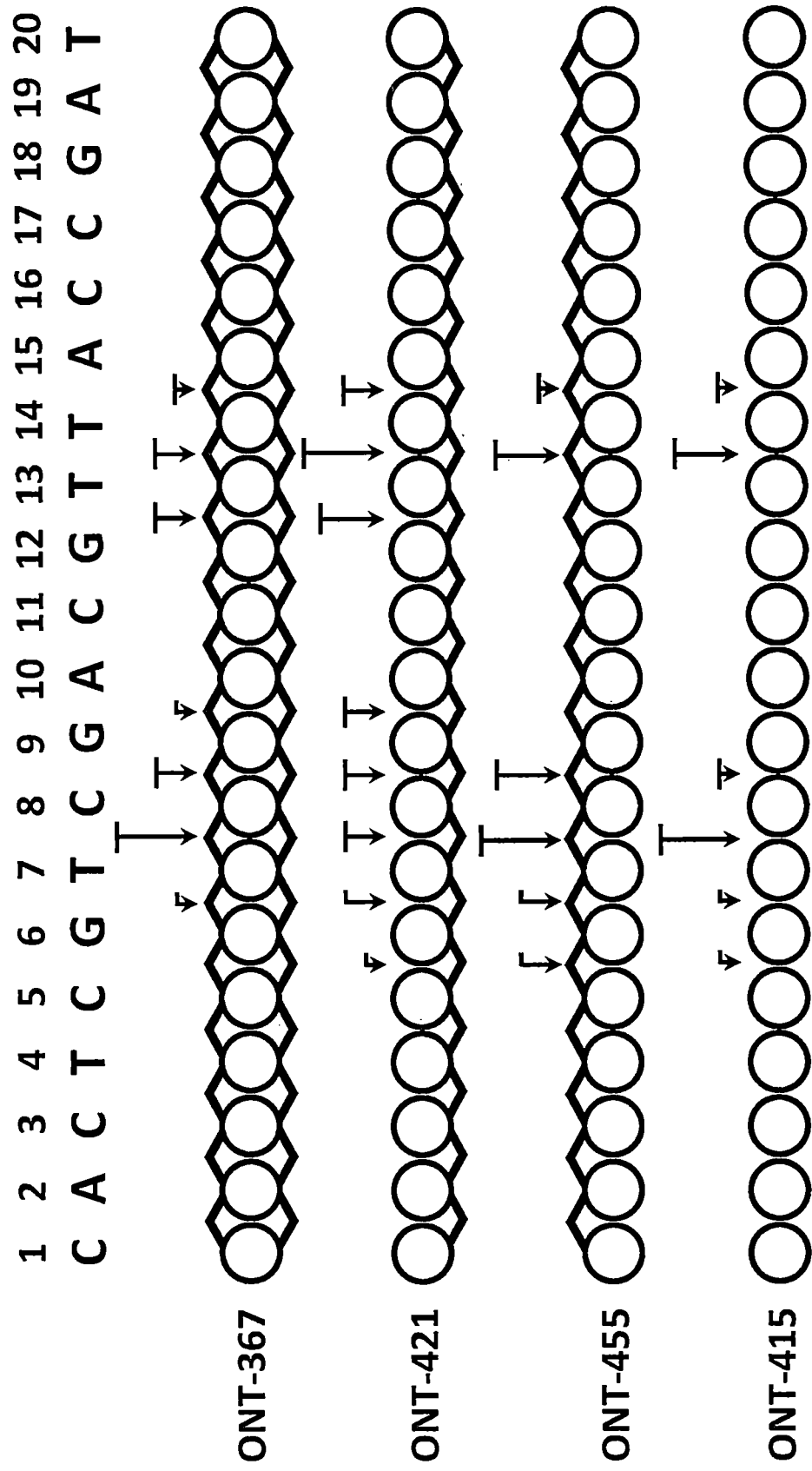
FIG. 25. Comparison of RNase H cleavage maps (A) and RNA cleavage rates (B) for stereorandom composition (ONT-367 (SEQ ID NO: 769)) and chirally controlled oligonucleotide compositions (ONT-421 (SEQ ID NO: 772), all Sp and ONT-455 (SEQ ID NO: 767), all Rp) and DNA (ONT-415 (SEQ ID NO: 770)). These sequences target the same region in FOXO1 mRNA. Cleavage maps were derived from the reaction mixtures obtained after 5 minutes of incubation of respective duplexes with RNase H1C in the presence of 1×PBS buffer at 37° C. Arrows indicate sites of cleavage. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate species peak was used for quantification. Cleavage rates were determined by measuring amount of full length RNA remaining in the reaction mixtures by reverse phase HPLC. Reactions are quenched at fixed time points by 30 mM Na$_2$EDTA. Figure also discloses SEQ ID NO: 1560.
Figure 25:
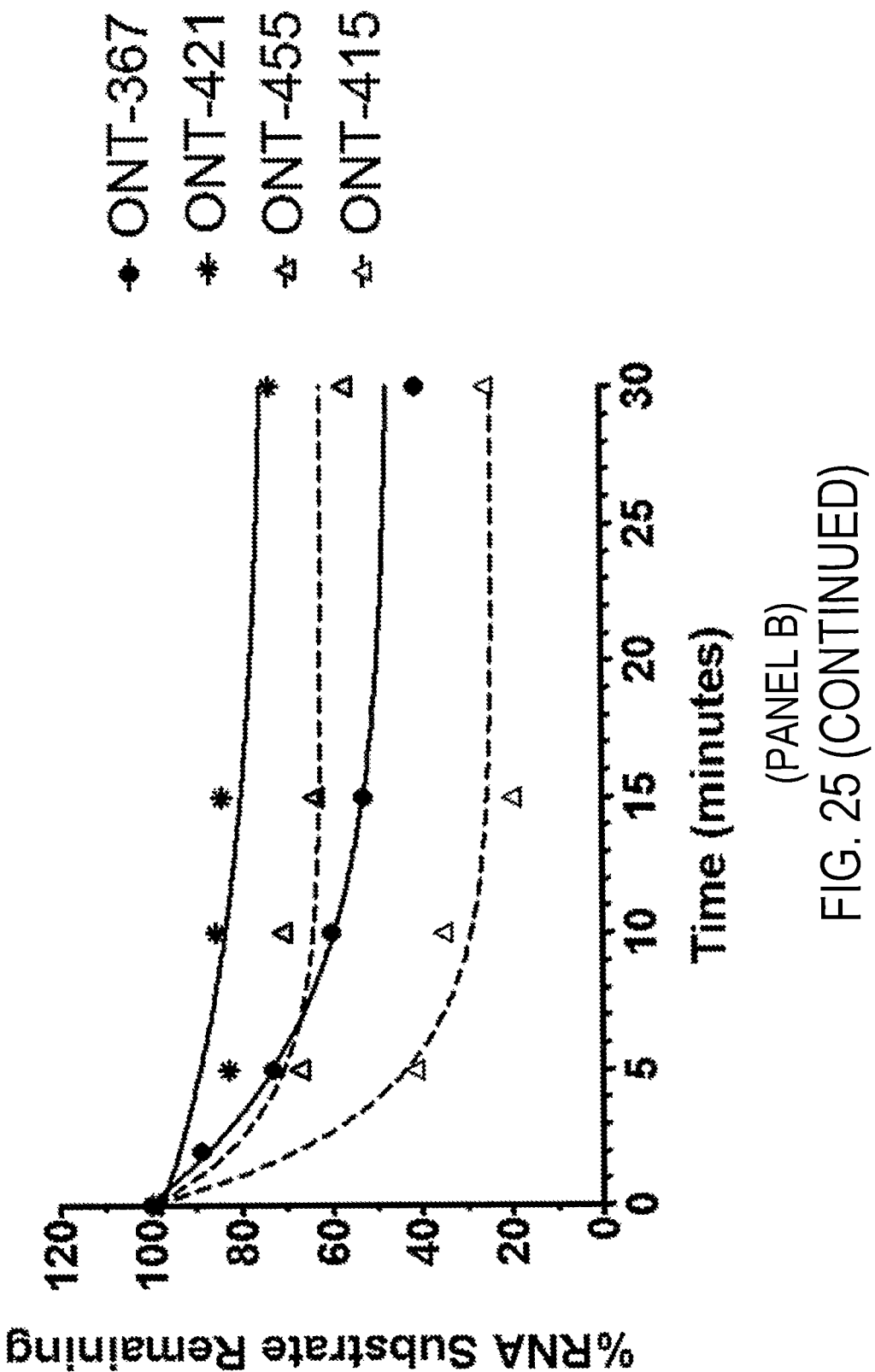

On HPLC chromatograms, peak areas corresponding to full length RNA oligomer (ONT-28) were integrated, normalized using the DNA peak and were plotted against time (FIG. 8). ONT-87 demonstrated superior cleavage for complementary RNA when in duplex form, in comparison to the other product candidates and Mipomersen. Since all the diastereomers in this panel have 2'-MOE modified wings that do not activate RNase H enzyme, without the intention to be limited by theory, Applicant notes that activity is likely dictated by the stereochemistry in the DNA core. Heteroduplexes with ONT-77 to ONT-81 including Mipomersen in the antisense strand show very similar RNA cleavage rates. ONT-89 with alternating Sp/Rp stereochemistry showed the least activity in the tested time frame under the tested conditions. Among the tested oligonucleotides with MOE modifications, ONT-87 and ONT-88 units in the antisense strand exhibited increased in activity in comparison to the rest of the heteroduplexes. Particularly, ONT-87 provided surprisingly high cleavage rate and unexpected low level of remaining target RNA. Additional example data were illustrated in FIG. 6 and FIG. 24.

In Vitro Oligonucleotide Transfection Assay:

Transfection assays are widely known and practiced by persons having ordinary skill in the art. An example protocol is described herein. Hep3B cells are reverse transfected with Lipofectamine 2000 (Life Technologies, Cat. No. 11668-019) at 18×10³ cells/well density in 96-well plates using the manufacturer's protocol. For dose response curves eight ⅓ serial dilutions are used starting from 60-100 nM. 25 µL of 6× oligonucleotide concentration is mixed with a prepared mixture of 0.4 µL Lipofectamine 2000 with 25 µL of serum-free Opti-MEM medium (Gibco, Cat. No. 31985-062) per well. After a 20 min minute incubation, 100 µL of 180×10³ cells/ml suspended in 10% FBS in DMEM cell culture media (Gibco, Cat. No. 11965-092) is added to bring the final volume to 150 µL per well. 24-48 hours post transfection Hep3B cells are lysed by adding 75 µL of Lysis Mixture with 0.5 mg/ml Proteinase K using QuantiGene Sample Processing Kit for Cultured Cells (Affymetrix, Cat. No. QS0103). The Target mRNA and GAPDH mRNA expression levels in cell lysates are measured using Affymetrix QuantiGene 2.0 Assay Kit (Cat. No. QS0011) according to the manufacturer's protocol. The Target mRNA expression is normalized to GAPDH mRNA expression from the same sample; and relative Target/GAPDH levels are compared to transfections using Lipofectamine 2000 only (no oligonucleotide) control. Dose response curves are generated by GraphPad Prism 6 using nonlinear regression log (inhibitor) vs. response curve fit with variable slope (4 parameters). For example results, see FIG. 24, FIG. 27 and FIG. 29.

Example 5. Provided Compositions and Methods Provide Control of Cleavage Patterns The present disclosure surprisingly found that internucleotidic linkage stereochemistry pattern has unexpected impact on cleavage patterns of nucleic acid polymers. By changing common patterns of backbone chiral centers of chirally controlled oligonucleotide compositions, numbers of cleavage sites, cleavage percentage at a cleavage site, and/or locations of cleavage sits can be surprisingly altered, both independently and in combination. As described in the example herein, provided compositions and methods can provide control over cleavage patterns of nucleic acid polymers.

Using similar assay conditions, various chirally controlled oligonucleotide compositions of different oligonucleotide types were tested. Example cleavage patterns of the target RNA sequence is presented in FIG. 9. Certain pattern of backbone chiral centers, such as that in ONT-87 and ONT-154, surprisingly produces only one cleavage site in the target sequence. Moreover, it is surprisingly found that oligonucleotides providing single cleavage site, such as ONT-87 and ONT-154, provide unexpectedly high cleavage rate and low level of remaining target nucleic acid polymer. See also FIG. 8, FIG. 10 and FIG. 11.

Example 6. Example Cleavage of FOXO1 mRNA

Figure 11:
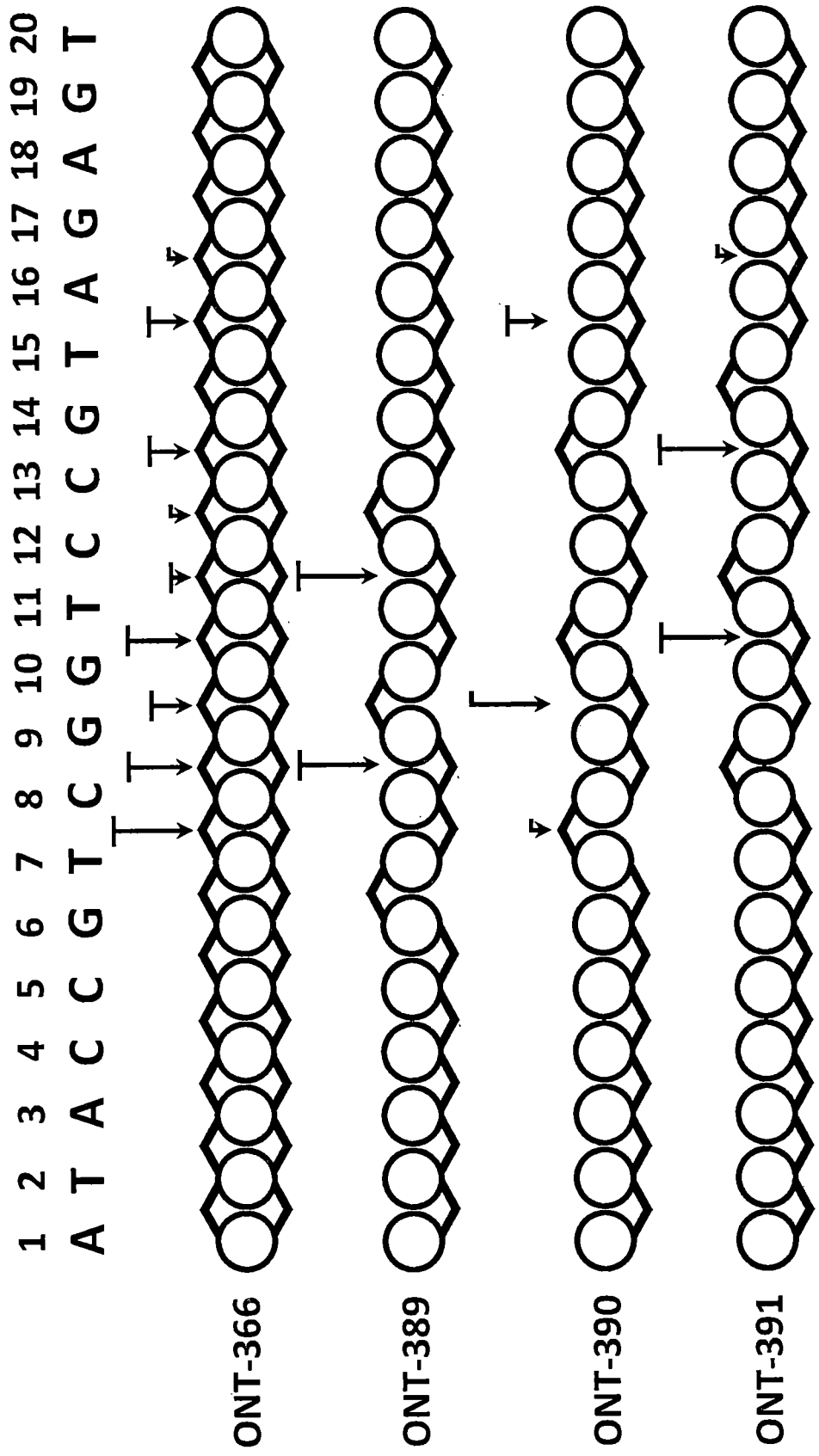
FIG. 11. Cleavage maps of oligonucleotide compositions having different common base sequences and lengths ((A)-(B)). The maps show a comparison of stereorandom DNA compositions (top panel) with three distinct and stereochemically pure oligonucleotide compositions. Data compare results of chirally controlled oligonucleotide compositions with two stereorandom phosphorothioate oligonucleotide compositions (ONT-366 and ONT-367) targeting different regions in FOXO1 mRNA. Each panel shows a comparison of stereorandom DNA (top panel) with three distinct and stereochemically pure oligonucleotide preparations. Cleavage maps were derived from reaction mixtures obtained after 30 minutes of incubation of respective duplexes with RNase H1C in the presence of 1×PBS buffer at 37° C. Arrows indicate sites of cleavage. The length of the arrow signifies the amount of metabolite present in the reaction mixture which was determined from the ratio of UV peak area to theoretical extinction coefficient of that fragment (the larger the arrow, the more the detectable cleavage products). Only in the cases where 5'-OH 3'-OH was not detected in the reaction mixture, 5'-phosphate species peak was used for quantification. Compositions used include: ONT-366, ONT-389, ONT-390, ONT-391, ONT-367, ONT-392, ONT-393, and ONT-394 (SEQ ID NOS 660-663 and 665-668, respectively). Figure also discloses SEQ ID NO: 1562 in panel A and SEQ ID NO: 1560 in panel B.
Figure 12:
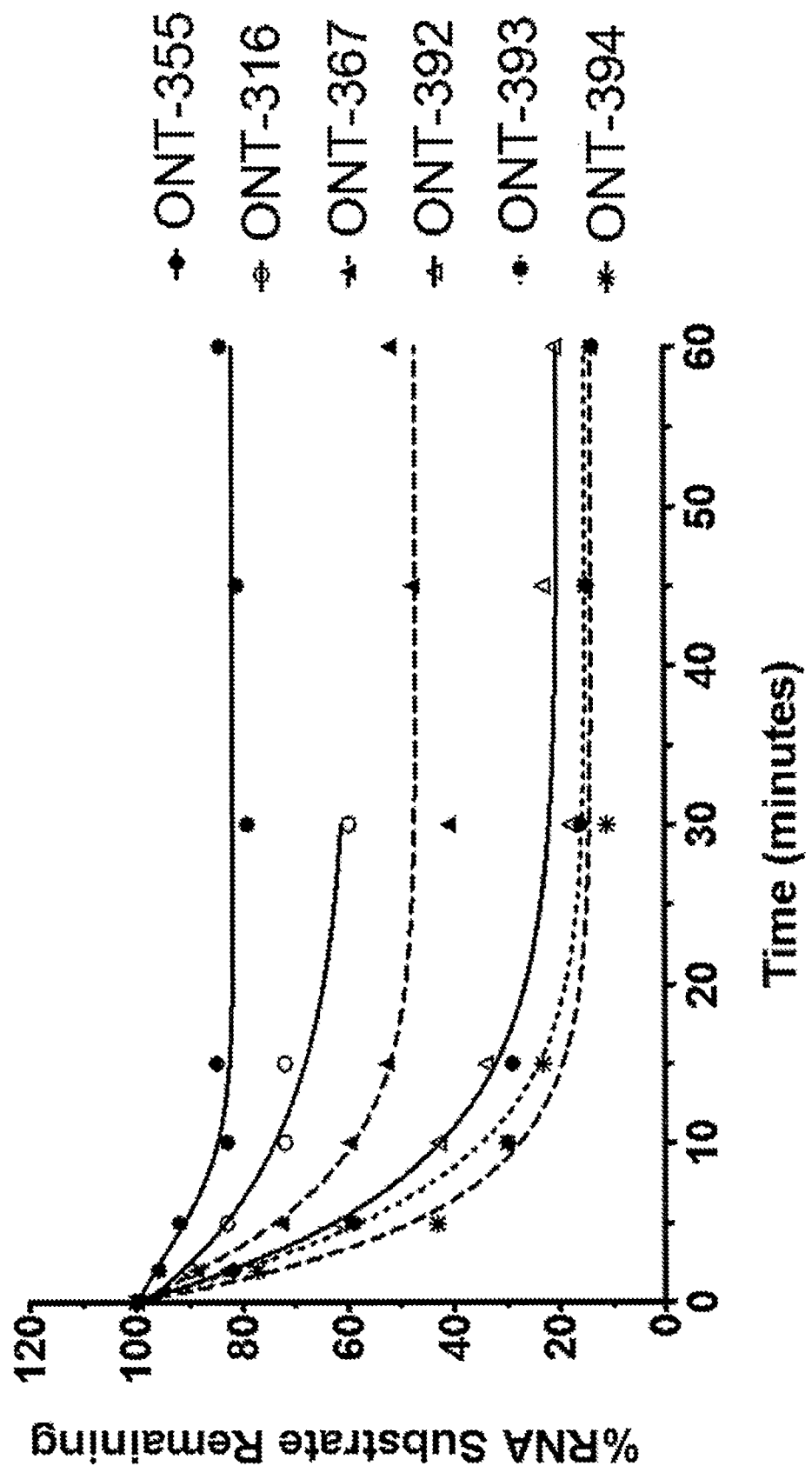
FIG. 12. Effect of stereochemistry on RNase H activity. In two independent experiments, antisense oligonucleotides targeting an identical region of FOXO1 mRNA were hybridized with RNA and then incubated with RNase H at 37° C. in the presence of 1×RNase H buffer. Disappearance of full length RNA was measured from its peak area at 254 nm using RP-HPLC. (A): from top to bottom at 60 min: ONT-355, ONT-316, ONT-367, ONT-392, ONT-393 and ONT-394 (ONT-393 and ONT-394 about the same at 60 min; ONT-393 had higher % RNA substrate remaining at 5 min). (B): from top to bottom at 60 min: ONT-315, ONT-354, ONT-366, ONT-391, ONT-389 and ONT-390. Cleavage rates were determined by measuring amount of full length RNA remaining in the reaction mixtures by reverse phase HPLC. Reactions were quenched at fixed time points by 30 mM Na$_2$EDTA.
Figure 12:
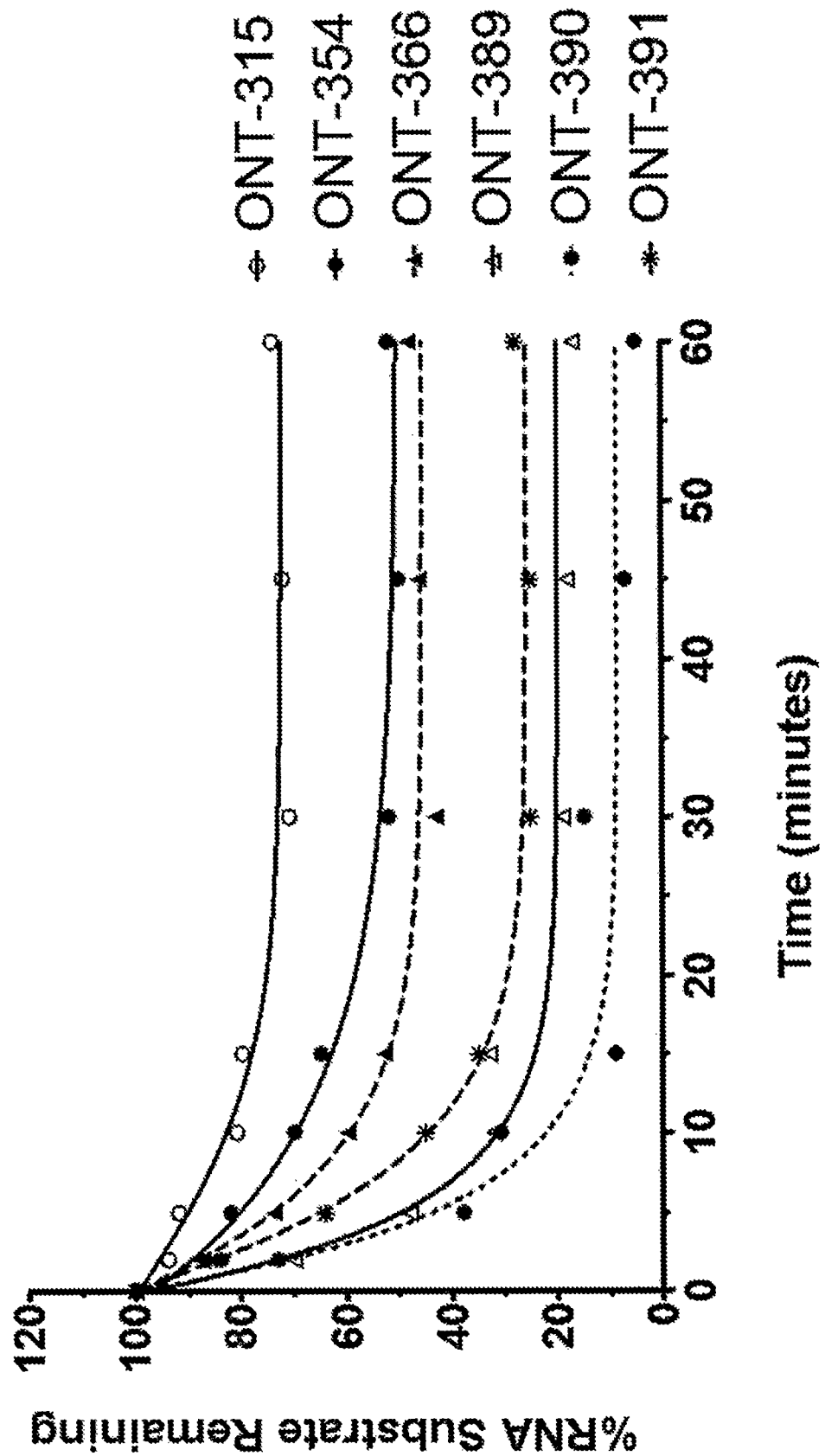

Oligonucleotide compositions targeting different regions of FOXO1 mRNA were tested in cleavage assays as described above. In each case, chirally controlled oligonucleotide compositions were shown to be capable of providing altered cleavage patterns relative to reference cleavage patterns from chirally uncontrolled oligonucleotide compositions sharing the same common base sequence and length. For example results, see FIG. 10 and FIG. 11. As shown in FIG. 12, example chirally controlled oligonucleotide compositions provide both significantly faster cleavage rates and unexpectedly low levels of remaining substrates when compared to reference chirally uncontrolled oligonucleotide compositions. In some embodiments, as shown in FIG. 11, the cleavage sites are associated with RpSpSp backbone chiral center sequence. In some embodiments, cleavage sites are two base pairs upstream of RpSpSp.

Example oligonucleotide compositions are listed below.

| Oligo | Sequence | Description | Tm (° C.) | SEQ ID NO: |
|---|---|---|---|---|
| ONT-366 | dTsdGsdAsdGsdAsdTsdGsdCsdCsdTsdGsdGsdCsdTsd GsdCsdCsdAsdTsdA | All DNA | 66.5 | 660 |
| ONT-389 | dTsdGsdAsdGsdAsdTsdGsdCsdCsdTsdGsdGsdCsdTsd GsdCsdCsdAsdTsdA | $S_7$RSSRSSR $S_5$ | 64.3 | 661 |

-continued

| Oligo | Sequence | Description | Tm (° C.) | SEQ ID NO: |
|---|---|---|---|---|
| ONT-390 | dTsdGsdAsdGsdAsdTsdGsdCsdCsdTsdGsdGsdCsdTsd GsdCsdCsdAsdTsdA | $S_6$RSSRSSR $S_6$ | 64.6 | 662 |
| ONT-391 | dTsdGsdAsdGsdAsdTsdGsdCsdCsdTsdGsdGsdCsdTsd GsdCsdCsdAsdTsdA | $S_5$RSSRSSR $S_7$ | 64.3 | 663 |
| ONT-387 | rUrArUrGrGrCrArGrCrCrArGrGrCrArUrCrUrCrA | complementary RNA | | 664 |
| ONT-367 | dTsdAsdGsdCsdCsdAsdTsdTsdGsdCsdAsdGsdCsdTsd GsdCsdTsdCsdAsdC | All DNA | 62.9 | 665 |
| ONT-392 | dTsdAsdGsdCsdCsdAsdTsdTsdGsdCsdAsdGsdCsdTsd GsdCsdTsdCsdAsdC | $S_7$RSSRSSR $S_5$ | 59.5 | 666 |
| ONT-393 | dTsdAsdGsdCsdCsdAsdTsdTsdGsdCsdAsdGsdCsdTsd GsdCsdTsdCsdAsdC | $S_6$RSSRSSR $S_6$ | 60 | 667 |
| ONT-394 | dTsdAsdGsdCsdCsdAsdTsdTsdGsdCsdAsdGsdCsdTsd GsdCsdTsdCsdAsdC | $S_5$RSSRSSR $S_7$ | 59.5 | 668 |
| ONT-388 | rGrUrGrArGrCrArGrCrUrGrCrArArUrGrGrCrUrA | complementary RNA | | 669 |

Figure 13:
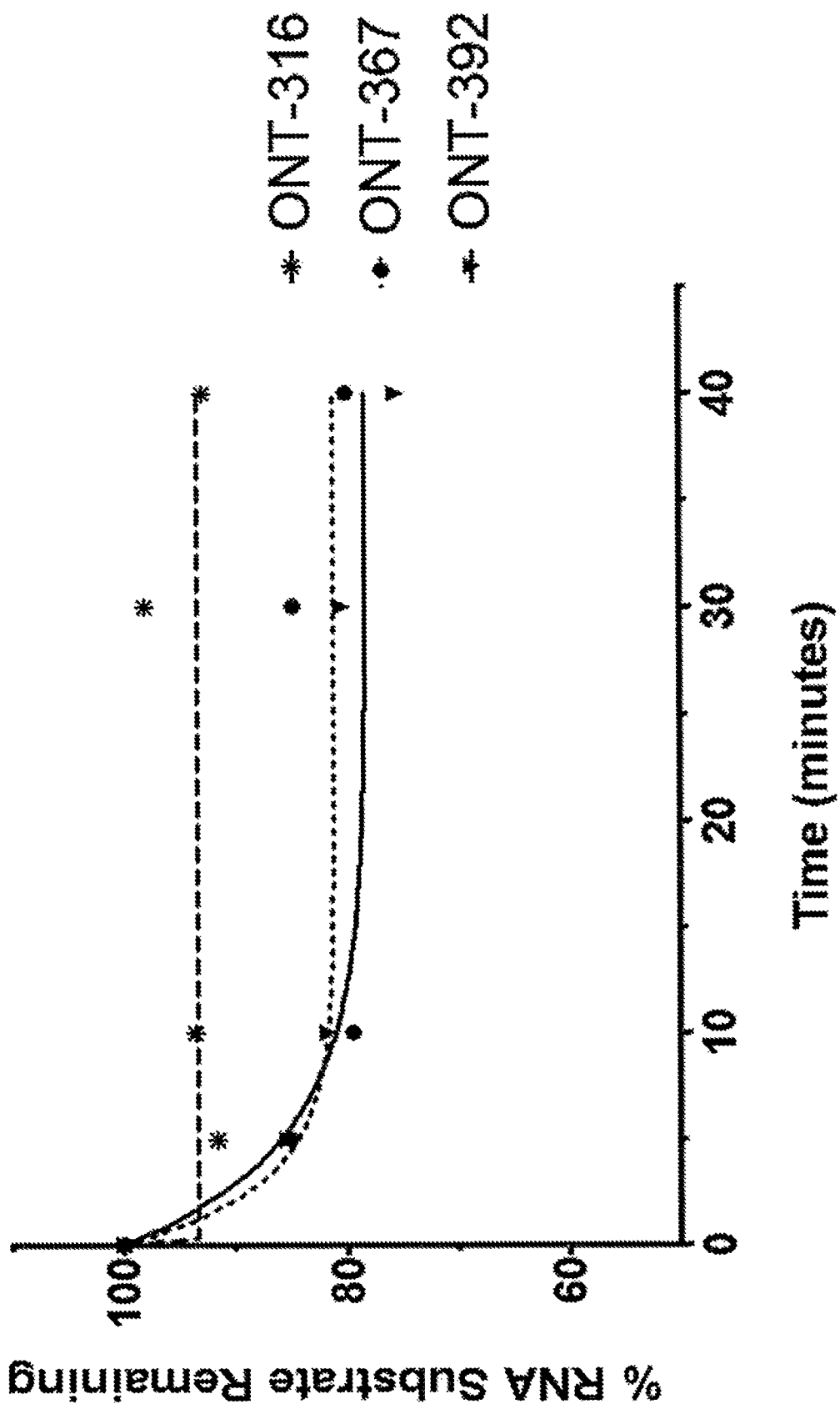
FIG. 13. Turnover of antisense oligonucleotides. The duplexes were made with each DNA strand concentration equal to 6 μM and RNA being 100 μM. These duplexes were incubated with 0.02 μM RNase H enzyme and disappearance of full length RNA was measured from its peak area at 254 nm using RP-HPLC. Cleavage rates were determined by measuring amount of full length RNA remaining in the reaction mixtures by reverse phase HPLC. Reactions were quenched at fixed time points by 30 mM Na$_2$EDTA. From top to bottom at 40 min: ONT-316, ONT-367 and ONT-392.

Example 7. Example Chirally Controlled Oligonucleotide Compositions Provide Higher Turn-Over In cases where the Tm of cleaved nucleic acid polymer fragments, for example RNA fragments, to oligonucleotides is greater than a physiological temperature, product dissociation may be inhibited and oligonucleotides may not be able to dissociate and find other target strands to form duplexes and cause the target strands to be cleaved. The Tm of ONT-316 (5-10-5 2'-MOE Gapmer) to complementary RNA is 76° C. After a cut or a few cuts in the RNA sequence complementary to the oligonucleotides, the 2'-MOE fragments may remain bound to RNA and thus cannot cause the other target molecules to be cleaved. Thermal melting temperatures of DNA strands generally are much lower when duplexed to RNA, for example, ONT-367 (63° C.) and ONT-392 60° C.). Additionally, thermal stability in DNA sequences is often relatively uniformly distributed compared to 2'-MOE modified oligonucleotides. In some embodiments, oligonucleotides in provided chirally controlled oligonucleotide compositions do not contain 2'-modifications such as 2'-MOE. In some embodiments, oligonucleotides in provided chirally controlled oligonucleotide compositions, which do not contain 2'-modifications such as 2'-MOE, more easily dissociate from nucleic acid polymer cleavage fragments, and have higher turn-over than oligonucleotides having 2'-modifications such as 2'-MOE. In some embodiments, the present disclosure provides an all DNA designs, in which oligonucleotides do not have 2'-modifications. In some embodiments, chirally controlled oligonucleotide compositions wherein oligonucleotides having no 2'-modification provides higher turn-over of a nuclease such as RNase H. In some embodiments, after cleavage RNase H dissociates more easily from duplex formed by RNA and oligonucleotides of provided chirally controlled oligonucleotide compositions. Using similar protocols as described above, turn-over of two example chirally controlled oligonucleotide compositions of oligonucleotide type ONT-367 and ONT-392 indeed showed higher turn-over rate than reference chirally uncontrolled oligonucleotide compositions (see FIG. 13).

Example 8. Example Cleavage of FOXO1 mRNA

Figure 14:
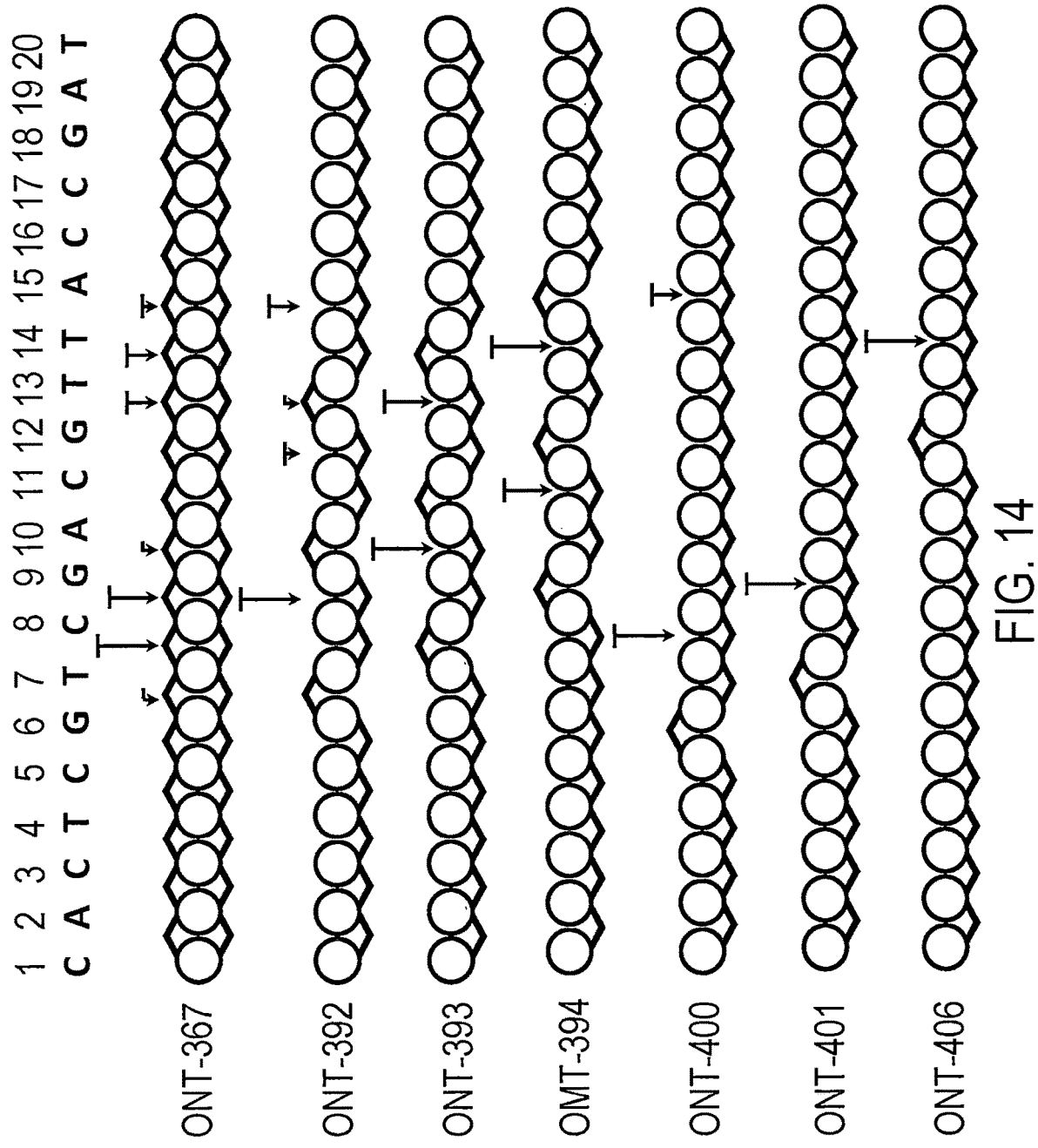
FIG. 14. Cleavage map comparing a stereorandom phosphorothioate oligonucleotide with six distinct and stereochemically pure oligonucleotide preparations targeting the same FOXO1 mRNA region. Compositions used include: ONT-367, ONT-392, ONT-393, ONT-394, ONT-400, ONT-401, and ONT-406 (SEQ ID NOS 665-668, 729-730 and 735, respectively). Figure also discloses SEQ ID NO: 1560.

As exemplified in FIG. 14, chirally controlled oligonucleotide compositions and methods thereof in the present disclosure can provide controlled cleavage of nucleic acid polymers. In some embodiments, chirally controlled oligonucleotide compositions of the present disclosure produces altered cleavage pattern in terms of number of cleavage sites, location of cleavage sites, and/or relative cleavage percentage of cleavage sites. In some embodiments, as exemplified by ONT-401 and ONT-406, chirally controlled oligonucleotide compositions provide single site cleavage.

In some embodiments, only one component from RNA cleavage was detected. Without the intention to be limited by theory, Applicant notes that such observation could be due to the processive nature of RNase H enzyme which could make multiple cuts on the same duplex resulting in much shorter 5'-OH 3'-OH fragments.

Figure 15:
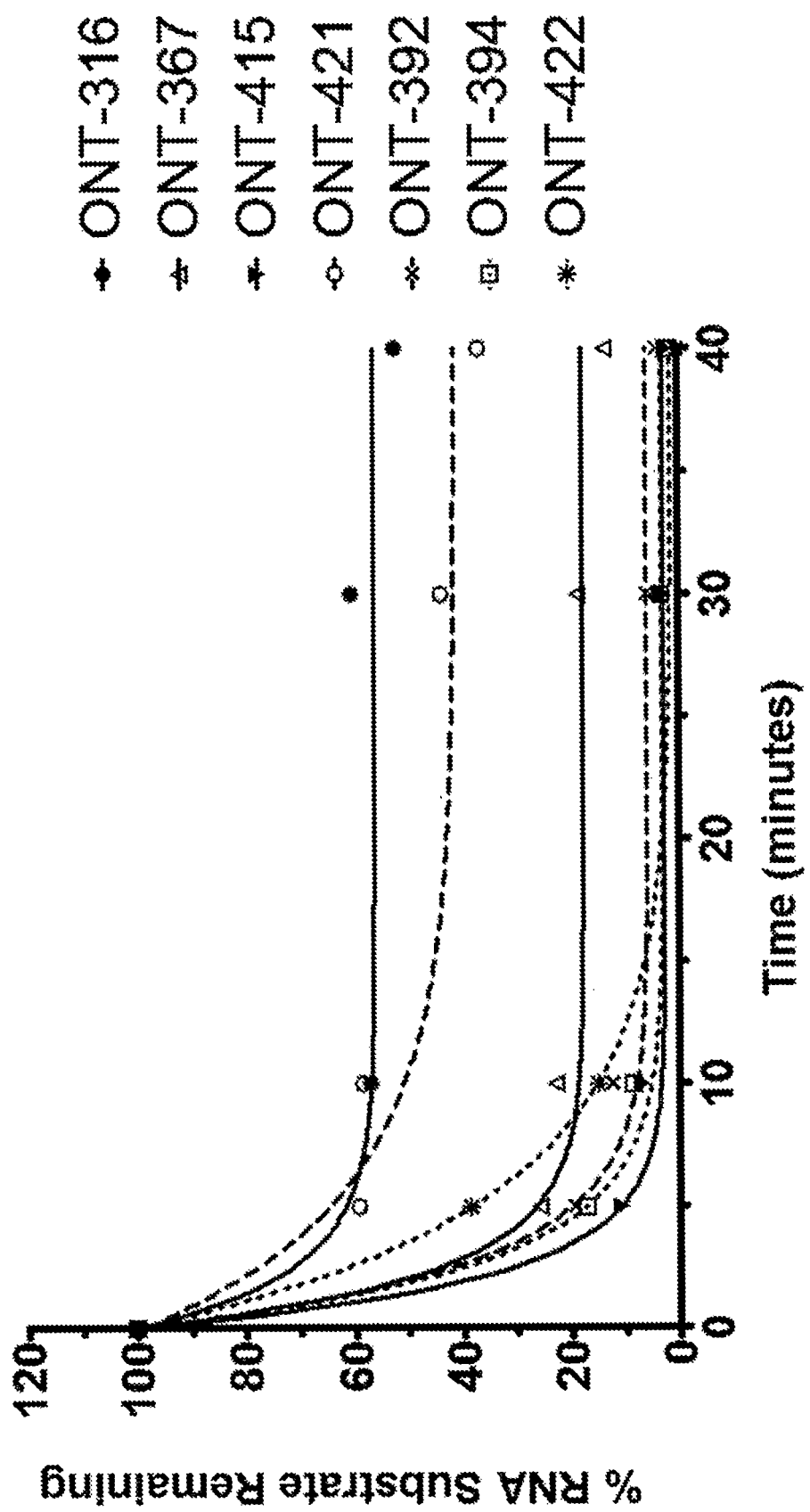
FIG. 15. Effect of stereochemistry on RNase H activity. Antisense oligonucleotides were hybridized with RNA and then incubated with RNase H at 37° C. in the presence of 1×RNase H buffer. Dependence of stereochemistry upon RNase H activity was observed. Also evident in comparing ONT-367 (stereorandom DNA) and ONT-316 (5-10-5 2'-MOE Gapmer) is the strong dependence of compositional chemistry upon RNase H activity. From top to bottom at 40 min: ONT-316, ONT-421, ONT-367, ONT-392, ONT-394, ONT-415, and ONT-422 (ONT-394/415/422 have similar levels at 40 min; at 5 min, ONT-422>ONT-394>ONT-415 in % RNA remaining in DNA/RNA duplex).
Figure 16:
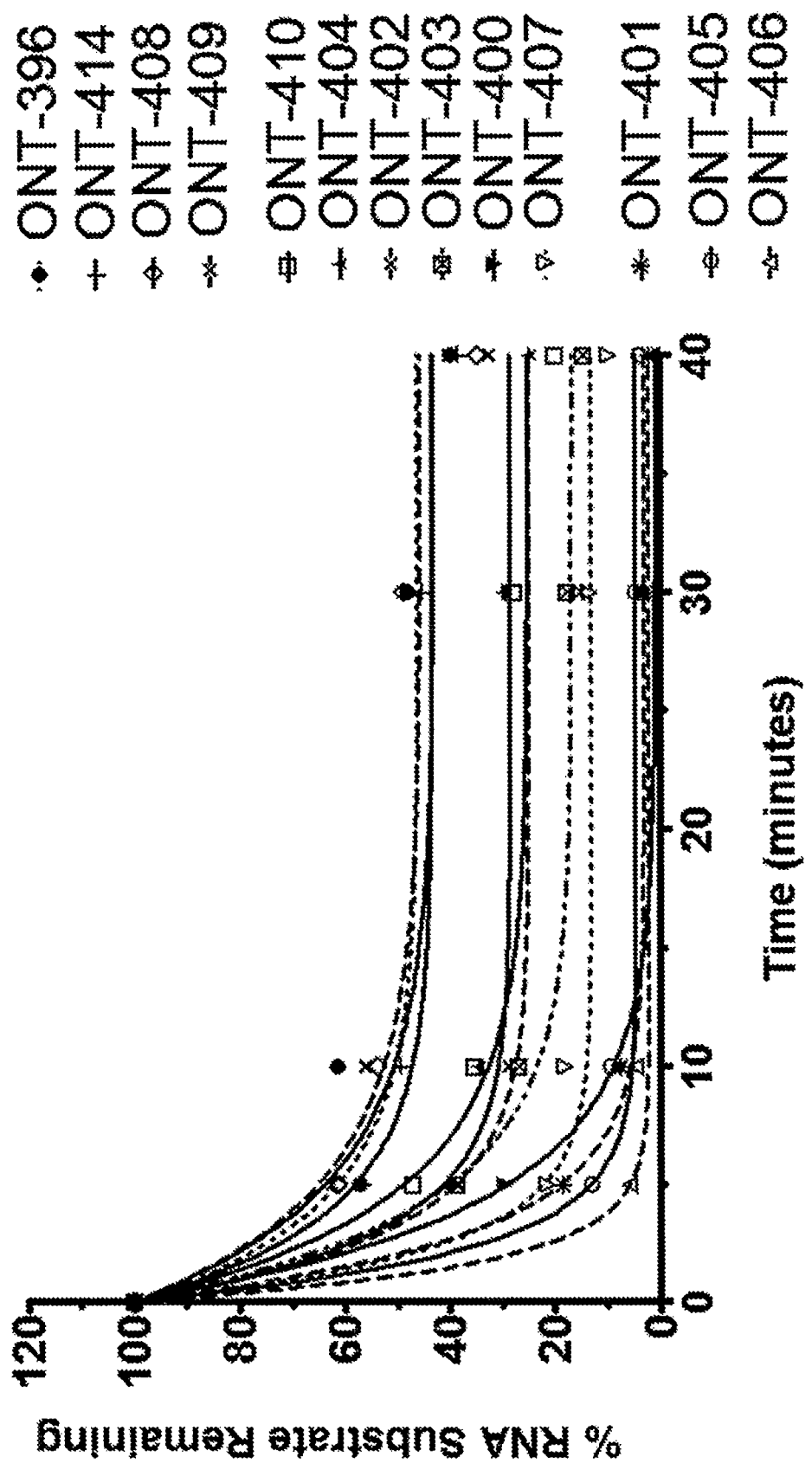
FIG. 16. Effect of stereochemistry on RNase H activity. Antisense oligonucleotides targeting an identical region of FOXO1 mRNA were hybridized with RNA and then incubated with RNase H at 37° C. in the presence of 1×RNase H buffer. Dependence of stereochemistry upon RNase H activity was observed. Form top to bottom at 40 min: ONT-396, ONT-409, ONT-414, ONT-408 (ONT-396/409/414/408 have similar levels at 40 min), ONT-404, ONT-410, ONT-402 (ONT-404/410/408 have similar levels at 40 min), ONT-403, ONT-407, ONT-405, ONT-401, ONT-406 and ONT-400 (ONT-401/405/406/400 have similar levels at 40 min).
Figure 17:
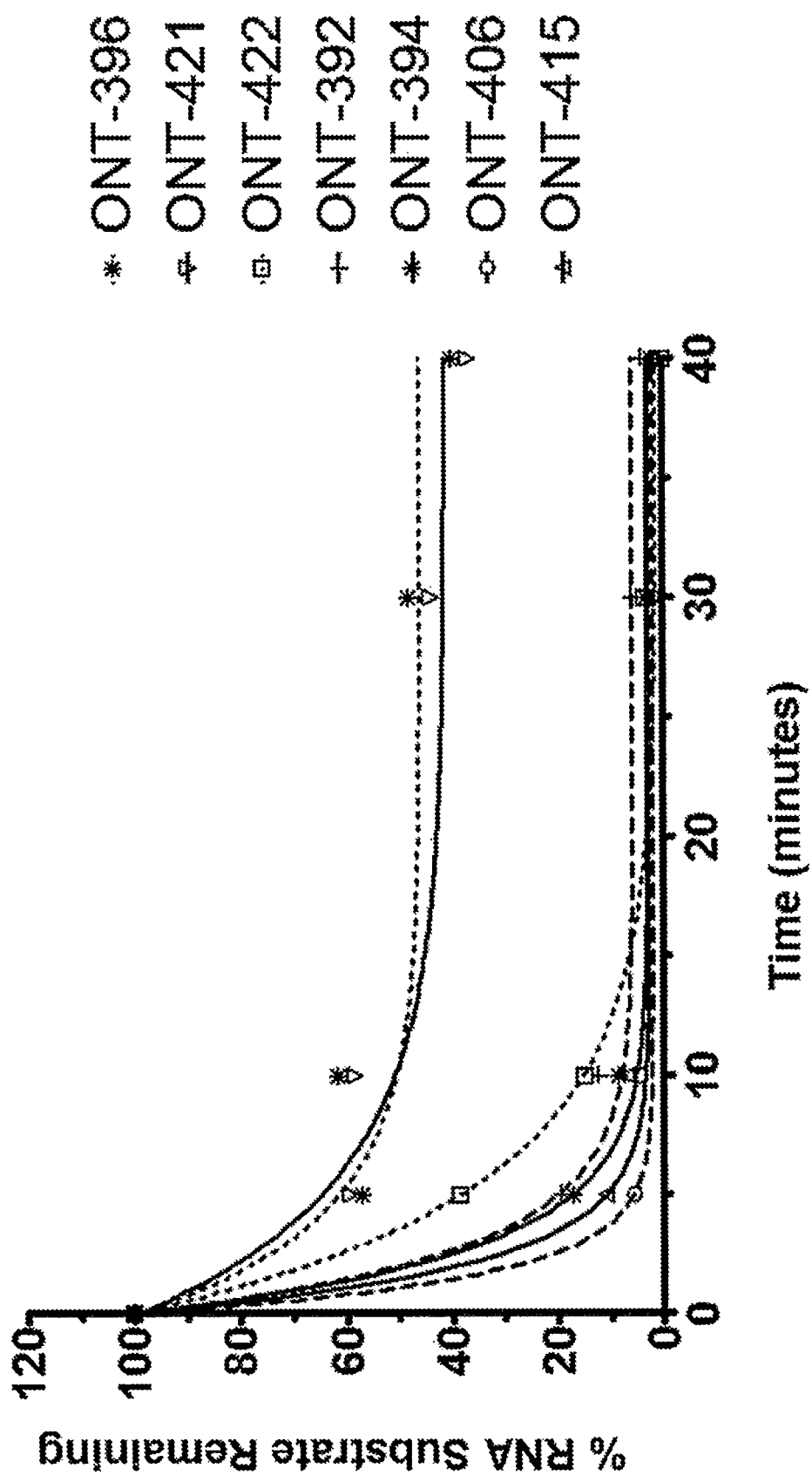
FIG. 17. Effect of stereochemistry on RNase H activity. Antisense oligonucleotides targeting an identical region of FOXO1 mRNA were hybridized with RNA and then incubated with RNase H at 37° C. in the presence of 1×RNase H buffer. Dependence of stereochemistry upon RNase H activity was observed. ONT-406 was observed to elicit cleavage of duplexed RNA at a rate in slight excess of that of the phosphodiester oligonucleotide ONT-415. From top to bottom at 40 min: ONT-396, ONT-421, ONT-392, ONT-394, ONT-415 ONT-406, and ONT-422 (ONT-394/415/406 have similar levels at 40 min; at 5 min, ONT-394>ONT-415>ONT-406 in % RNA remaining in DNA/RNA duplex).
Figure 20:
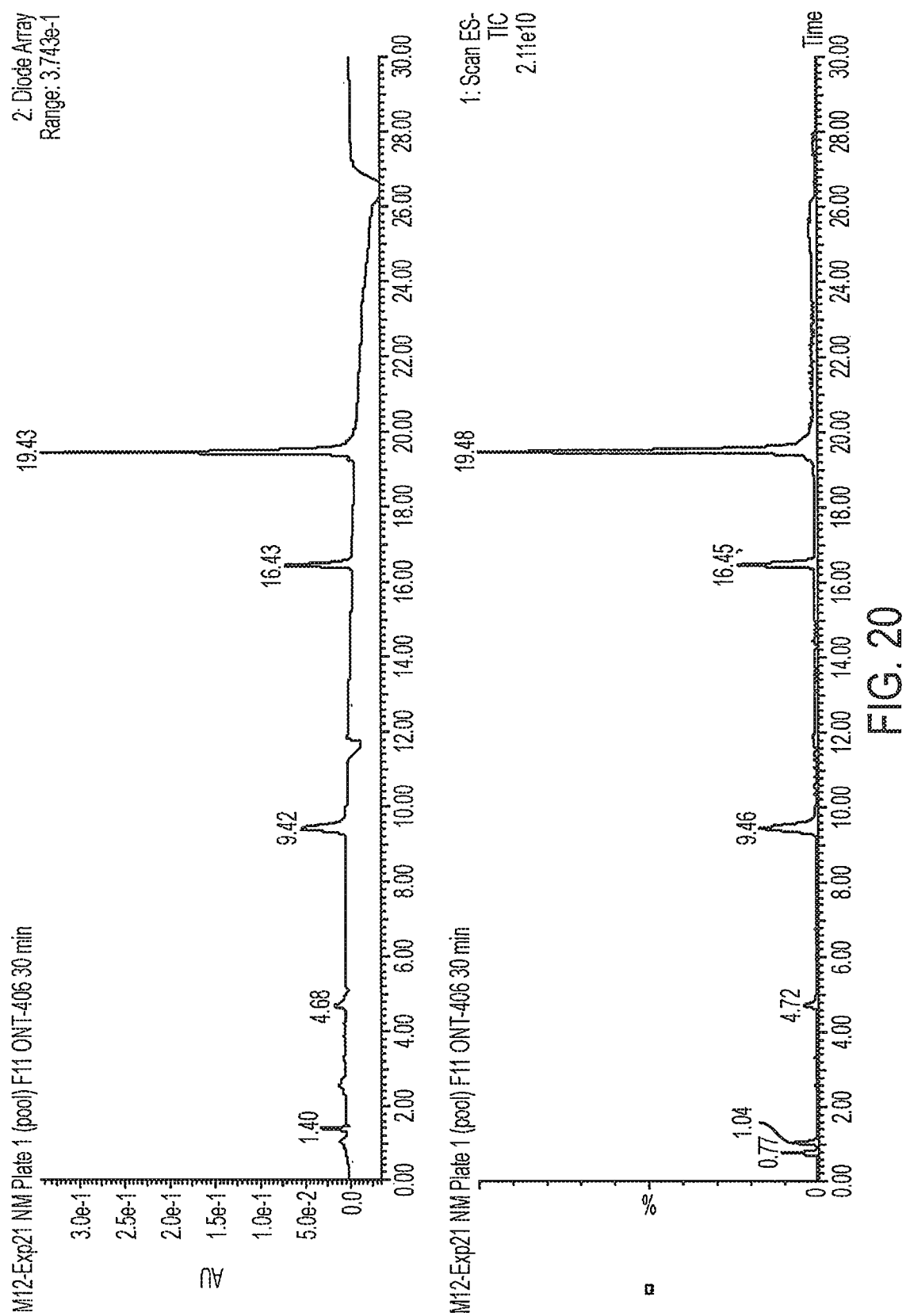
FIG. 20. UV Chromatogram and TIC of ONT-406 and ONT-388 duplex after 30 minutes of incubation with RNase H.

Additional chirally controlled oligonucleotide compositions were further tested. As described above, provided chirally controlled oligonucleotide compositions provides unexpected results, for example, in terms of cleavage rate and % RNA remaining in DNA/RNA duplex. See FIGS. 15-17. Example analytical data were presented in FIGS. 18-20. Without the intention to be limited by theory, Applicant notes that in some embodiments, cleavage may happen as depicted in FIG. 21. In FIG. 17, it is noted ONT-406 was observed to elicit cleavage of duplexed RNA at a rate in slight excess of that of the natural DNA oligonucleotide ONT-415 having the same base sequence and length. Applicant notes that chirally controlled oligonucleotide compositions of ONT-406, and other chirally controlled oligonucleotide compositions provided in this disclosure, have other preferred properties that an ONT-415 composition does not have, for example, better stability profiles in vitro and/or in vivo. Additional example data were presented in FIG. 25. Also, as will be appreciated by those skilled in the art, example data illustrated in FIG. 26 and FIG. 27 confirm that provided example chirally controlled oligonucleotide compositions, especially when so designed to control the cleavage patterns through patterns of backbone chiral centers, produced much better results than reference oligonucleotide compositions, e.g., a stereorandom oligonucleotide composition. As exemplified in FIG. 26, controlled patterns of backbone chiral centers, among other things, can selectively increase and/or decrease cleavage at existing cleavage site when a DNA oligonucleotide is used, or creates entirely new cleavage sites that do not exist when a DNA oligonucleotide is used (see FIG. 25, ONT-415). In some embodiments, cleavage sites from a DNA oligonucleotide indicate endogenous cleavage preference of RNase H. As confirmed by FIG. 27, provided chirally controlled oligonucleotide compositions are capable of modulating target cleavage rate. In some embodiments, approximately 75% of the variance in cellular activity is accounted for by differences in cleavage rate which can be controlled through patterns of backbone chiral centers. As provided in this Application, further structural features such as base modifications and their patterns, sugar modification and their patterns, internucleotidic linkage modifications and their patterns, and/or any combinations thereof, can be combined with patterns of backbone chiral centers to provide desired oligonucleotide properties.

Example 9. Example Allele-Specific Suppression of mHTT

In some embodiments, the present disclosure provides chirally controlled oligonucleotide compositions and methods thereof for allele-specific suppression of transcripts from one particular allele with selectivity over the others. In some embodiments, the present disclosure provides allele-specific suppression of mHTT.

Figure 22:
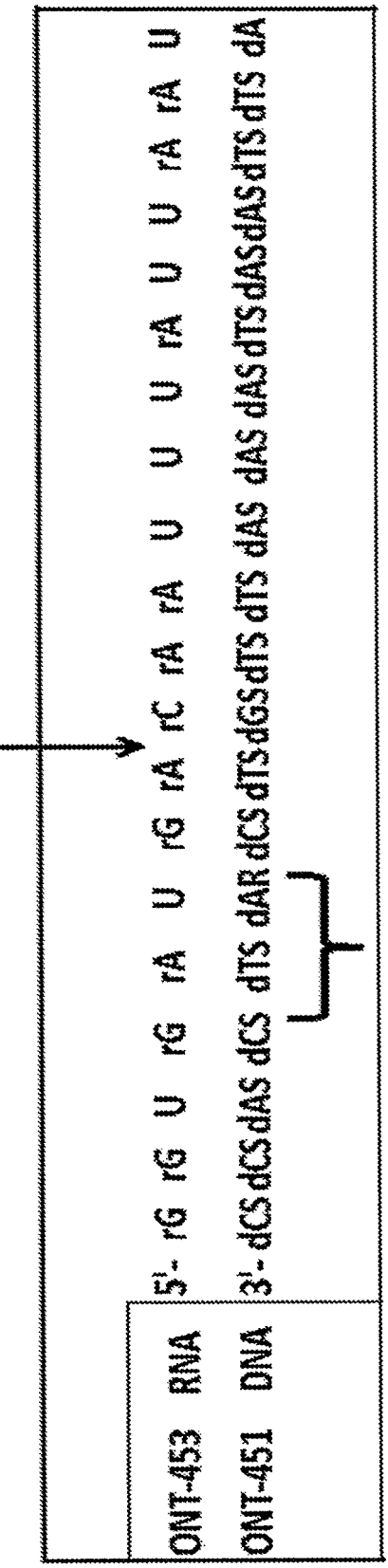
FIG. 22. Example allele specific cleavage targeting mutant Huntingtin mRNA. (A) and (B): example oligonucleotides. (C)-(E): cleavage maps. (F)—(H): RNA cleavage. Stereorandom and chirally controlled oligonucleotide compositions were prepared to target single nucleotide polymorphisms for allele selective suppression of mutant Huntingtin. ONT-450 (stereorandom) targeting ONT-453 (muHTT) and ONT-454 (wtHTT) showed marginal differentiation in RNA cleavage and their cleavage maps. Chirally controlled ONT-451 with selective placement of 3'-SSR-5' motif in RNase H recognition site targeting ONT-453 (muHTT) and ONT-454 (wtHTT) showed large differentiation in RNA cleavage rate. From the cleavage map, it is notable that 3'-SSR—S' motif is placed to direct the cleavage between positions 8 and 9 which is after the mismatch if read from 5'-end of RNA. ONT-452 with selective placement of 3'-SSR—S' motif in RNase H recognition site targeting ONT-453 (muHTT) and ONT-454 (wtHTT) showed moderate differentiation in RNA cleavage rate. 3'-SSR-5' motif was placed to direct the cleavage at positions 7 and 8 which is before the mismatch if read from 5'-end of RNA. Example data illustrate significance of position in placement of 3'-SSR-5' motif to achieve enhanced discrimination for allele specific cleavage. All cleavage maps are derived from the reaction mixtures obtained after 5 minutes of incubation of respective duplexes with RNase H1C in the presence of 1×PBS buffer at 37° C. Arrows indicate sites of cleavage. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate species peak was used for quantification. Compositions used include: ONT-450 to ONT-454 (SEQ ID NOS 380, 267, 268, 799 and 718, respectively). Figure also discloses SEQ ID NOS 1563-1565 in panels C-E, respectively, in order of appearance.
Figure 22:
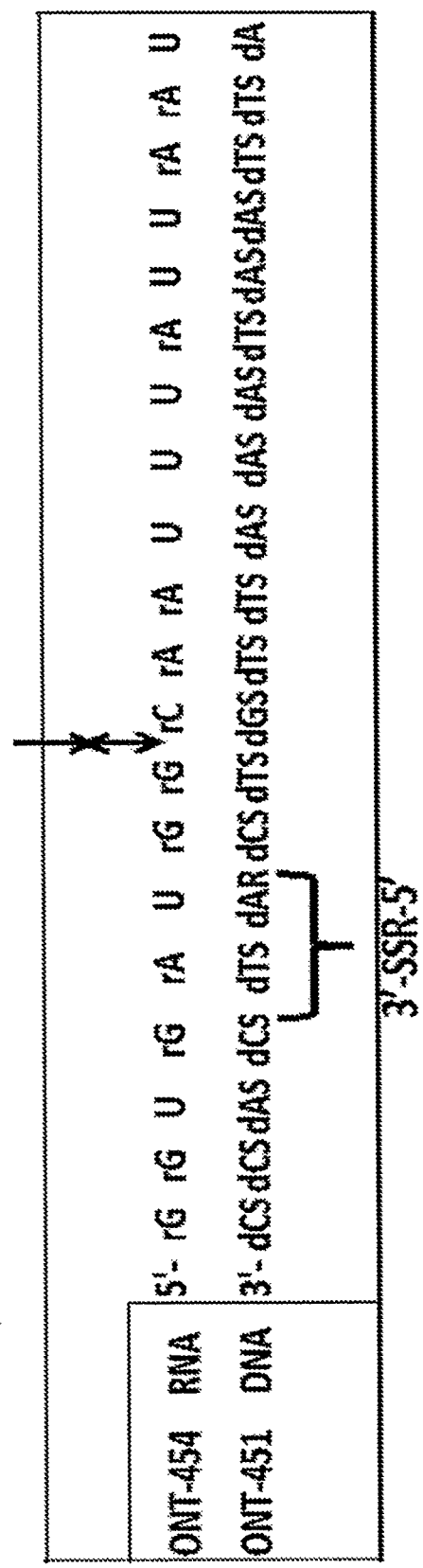
Figure 22:
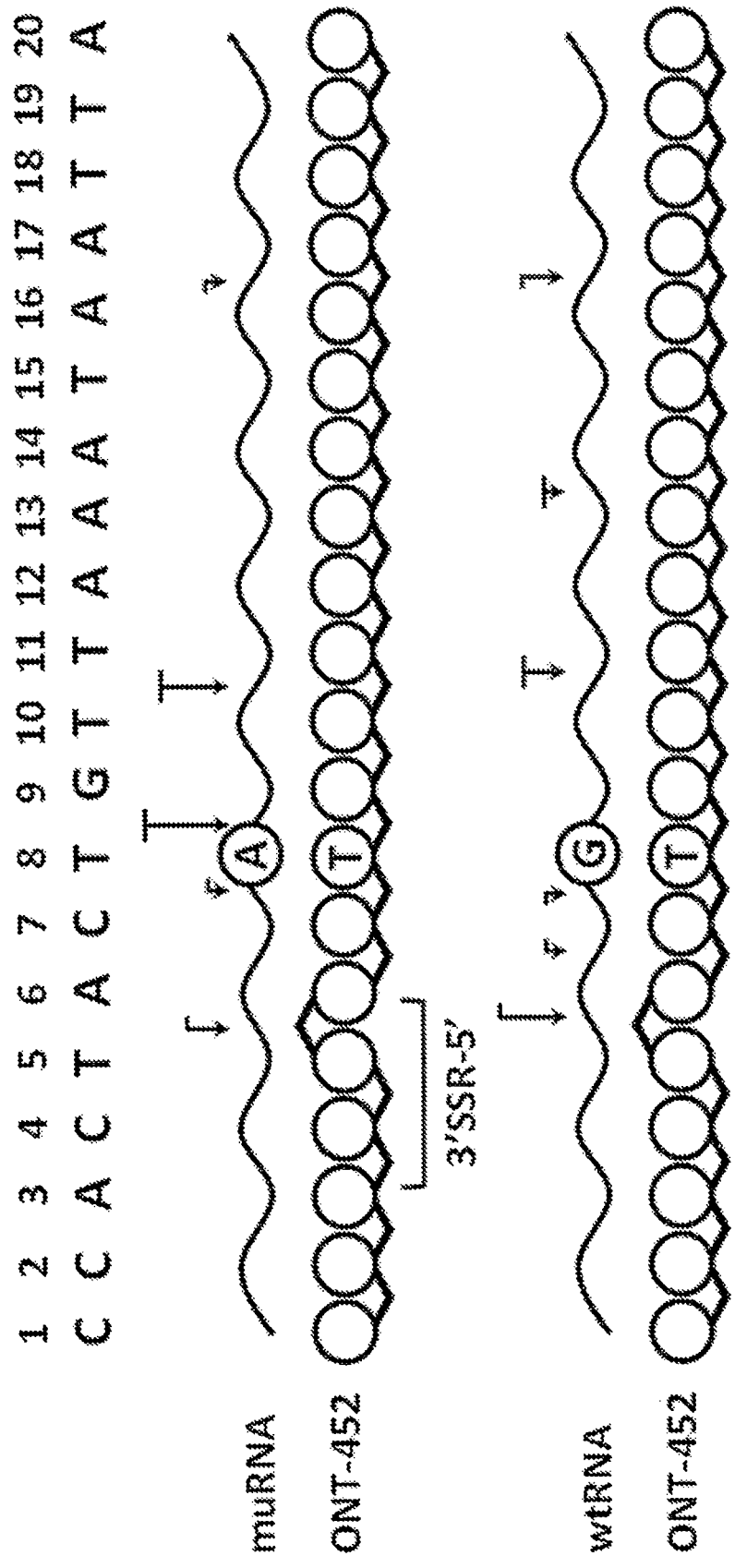
Figure 22:
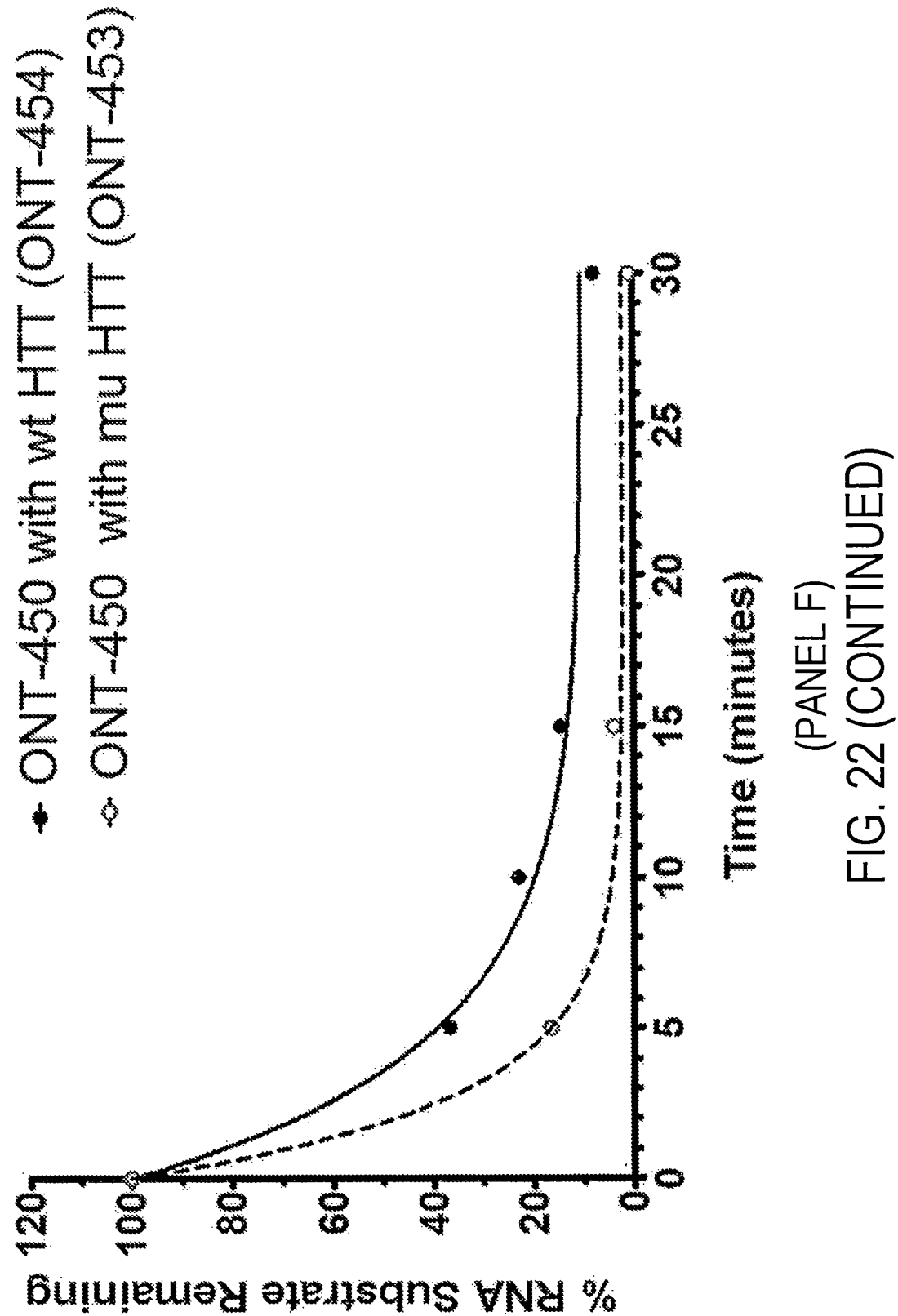
Figure 22:
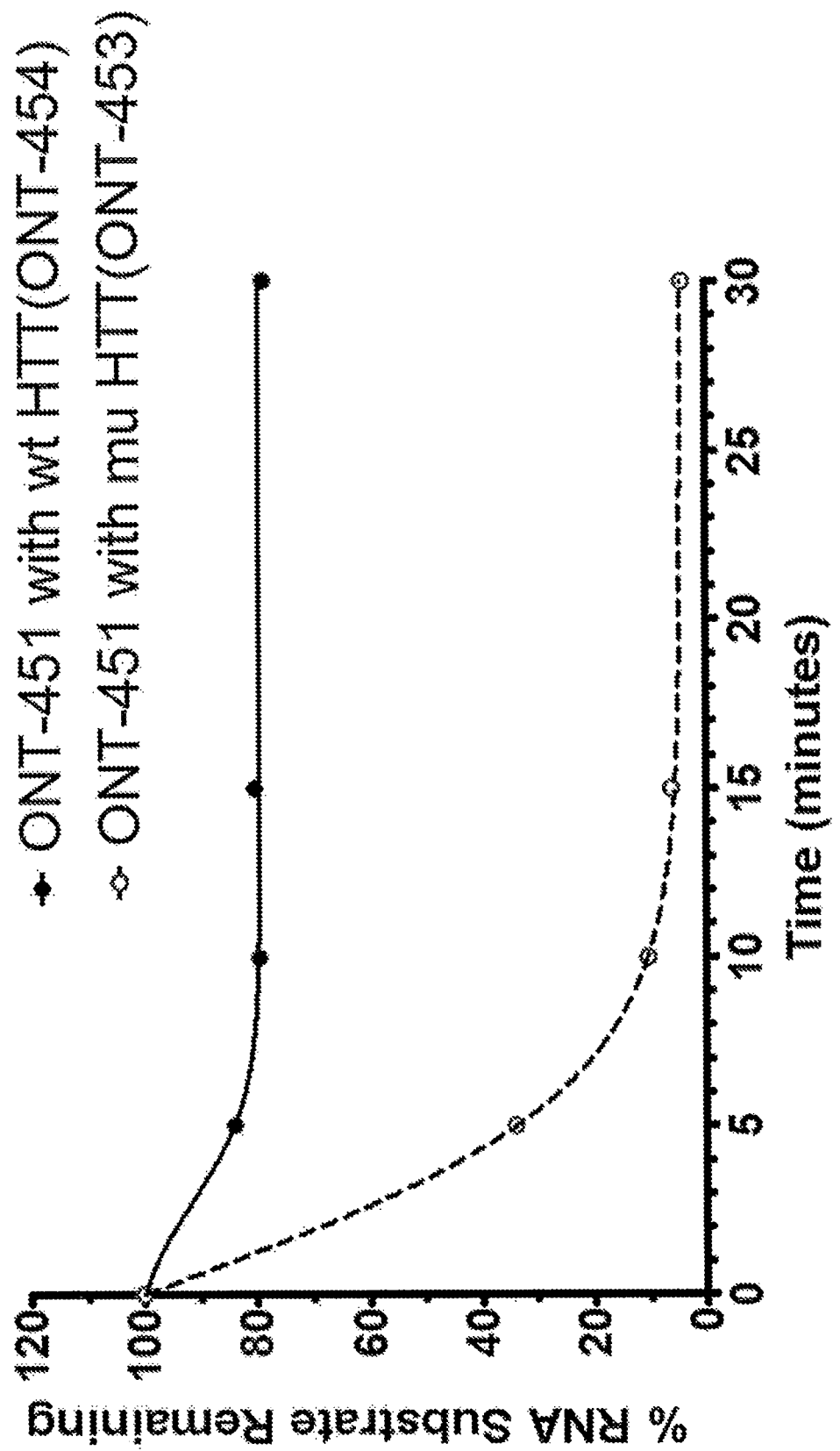
Figure 22:
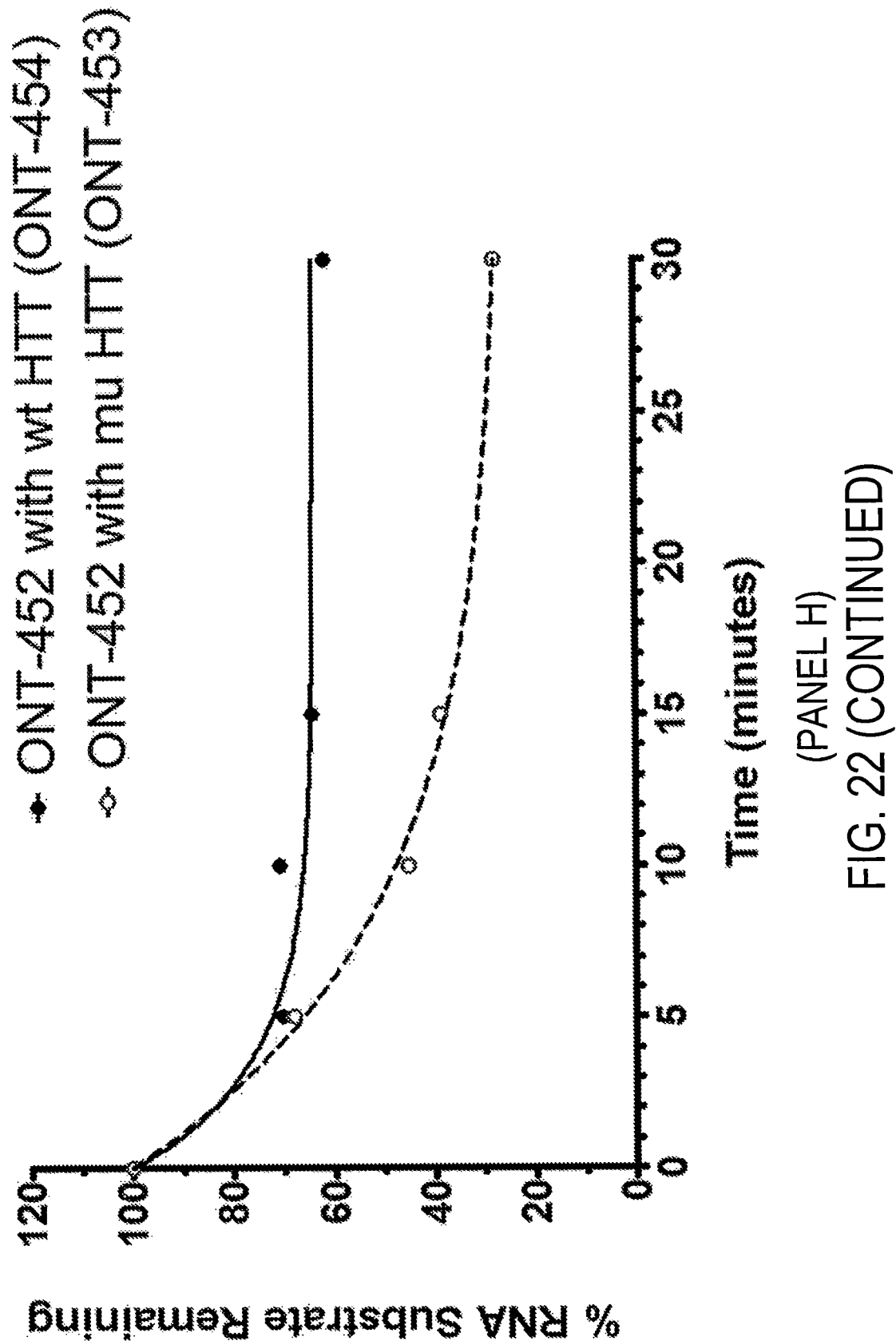

FIG. 22 illustrates example chirally controlled oligonucleotide compositions that specifically suppress transcripts from one allele but not the others. Oligonucleotides 451 and 452 were tested with transcripts from both exemplified alleles using biochemical assays described above. Allele-specific suppression is also tested in cells and animal models using similar procedures as described in Hohjoh, *Pharmaceuticals* 2013, 6, 522-535; US patent application publication US 2013/0197061; and Østergaard et al., *Nucleic Acids Research,* 2013, 41(21), 9634-9650. In all cases, transcripts from the target allele are selectively suppressed over those from the other alleles. As will be appreciated by those skilled in the art, example data illustrated in FIG. 22 confirm that provided example chirally controlled oligonucleotide compositions, especially when so designed to control the cleavage patterns through stereochemistry, produced much better results than reference oligonucleotide compositions, in this case, a stereorandom oligonucleotide composition. As confirmed by FIG. 22, patterns of backbone chiral centers can dramatically change cleavage patterns (FIG. 22 C-E), and stereochemistry patterns can be employed to position cleavage site at the mismatch site (FIG. 22 C-E), and/or can dramatically improve selectivity between the mutant and wild type (FIG. 22 G-H). In some embodiments, chirally controlled oligonucleotide compositions are incubated with wtRNA and muRNA of a target and both the duplexes are incubated with RNase H.

Huntingtin Allele Tm

| | |
|---|---|
| Mutant Huntingtin Allele ONT-453/ONT-451 | 38.8° C. |
| Wild Type Huntingtin Allele ONT-454/ONT-451 | 37.3° C. |
| Mutant Huntingtin Allele ONT-453/ONT-452 | 38.8° C. |
| Wild Type Huntingtin Allele ONT-454/ONT-452 | 36.5° C. |
| Mutant Huntingtin Allele ONT-453/ONT-450 | 40.3° C. |
| Wild Type Huntingtin Allele ONT-454/ONT-450 | 38.8° C. |

Example 10. Example Allele-Specific Suppression of FOXO1

In some embodiments, the present disclosure provides allele-specific suppression of FOXO1.

Figure 23:
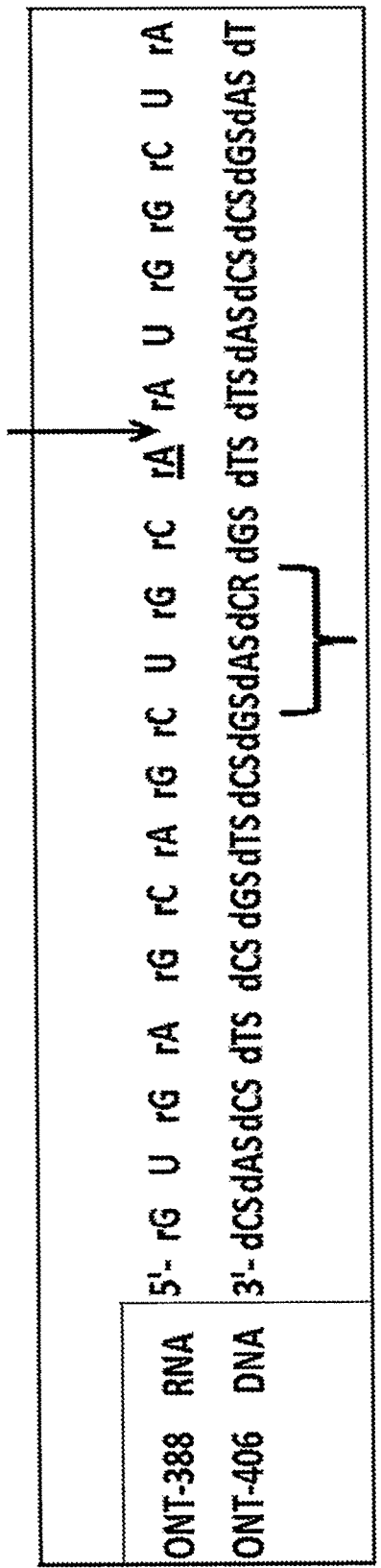
FIG. 23. (A)-(C): example allele specific cleavage targeting FOXO1 mRNA (SEQ ID NOS 669, 731, 715, 731, 699, 729, 715, 729, 699, 735, 716 and 735, respectively, in order of appearance).
Figure 23:
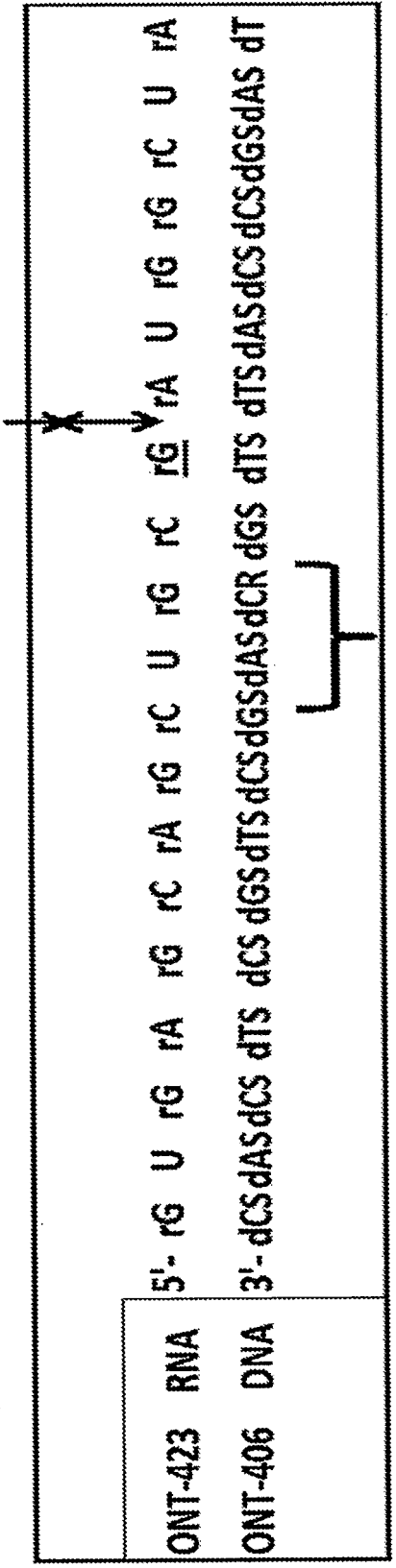

FIG. 23 illustrates example chirally controlled oligonucleotide compositions that specifically suppress transcripts from one allele but not the others. Oligonucleotides ONT-400, ONT-402 and ONT-406 were tested with transcripts from both exemplified alleles using biochemical assays described above. Allele-specific suppression is also tested in cells and animal models using similar procedures as described in Hohjoh, *Pharmaceuticals* 2013, 6, 522-535; US patent application publication US 2013/0197061; Østergaard et al., *Nucleic Acids Research* 2013, 41(21), 9634-9650; and Jiang et al., *Science* 2013, 342, 111-114. Transcripts from the target allele are selectively suppressed over those from the other alleles. In some cases, two RNAs with mismatch ONT-442 (A/G, position 7th) and ONT-443 (A/G, position 13$^{th}$) from ONT-388 are synthesized and are duplexed with ONT-396 to ONT-414. RNase H assay are performed to obtain cleavage rates and cleavage maps.

Example 11. Certain Example Oligonucleotides and Oligonucleotide Compositions Stereorandom oligonucleotides with different 2' substitution chemistries targeting three distinct regions of FOXO1 mRNA with the thermal melting temperatures when duplexed with complementary RNA. The concentration of each strand was 1 uM in 1×PBS buffer.

| Oligo | Sequence | Description | Tm (° C.) | SEQ ID NO: |
|---|---|---|---|---|
| ONT-316 | TeosAeosGeos5mCeos5mCeosdAsdTsdTsdGs5md CsdAsdGs5mdCsdTsdGs5mCeosTeos5mCeosAeos 5mCeo | 5-10-5 (2'-MOE Gapmer) | 76.7 | 670 |
| ONT-355 | dTsdAsdGsdCsdCsdAsdTstsgscsasgscsdTsdGsdCs dTsdCsdAsdC | 7-6-7 (DNA-2'-OMe-DNA) Gapmer | 71.2 | 671 |
| ONT-361 | tsasgsdCsdCsdAsdTsdTsdGsdCsdAsdGsdCsdTsdG sdCsdTscsascs | 3-14-3 (2'-OMe-DNA-2'-OMe) Gapmer | 65.8 | 672 |

| Oligo | Sequence | Description | Tm (° C.) | SEQ ID NO: |
|---|---|---|---|---|
| ONT-367 | dTsdAsdGsdCsdCsdAsdTsdTsdGsdCsdAsdGsdCsd TsdGsdCsdTsdCsdAsdC | All DNA | 62.9 | 673 |
| ONT-373 | tsasgscscsdAsdTsdTsdGsdCsdAsdGsdCsdTsdGscst scsasc | 5-10-5 (2'-OMe Gapmer) | 71.8 | 674 |
| ONT-388 | rGrUrGrArGrCrArGrCrUrGrCrArArGrGrCrUrA | Complementary RNA | | 675 |
| ONT-302 | Teos5mCeos5mCeosAeosGeosdTsdTs5mdCs5mdC sdTsdTs5mdCsdAsdTsdTs5mCeosTeosGeos5mCe osAeo | 5-10-5 (2'-MOE Gapmer) | 72.5 | 676 |
| ONT-352 | dTsdCsdCsdAsdGsdTsdTscscststscsasdTsdTsdCsd TsdGsdCsdA | 7-6-7 (DNA-2'-OMe-DNA) Gapmer | 65.4 | 677 |
| ONT-358 | tscscsdAsdGsdTsdTsdCsdCsdTsdTsdCsdAsdTsdTs dCsdTsgscsas | 3-14-3 (2'-OMe-DNA-2'-OMe) Gapmer | 62.6 | 678 |
| ONT-364 | dTsdCsdCsdAsdGsdTsdTsdCsdCsdTsdTsdCsdAsd TsdTsdCsdTsdGsdCsdA | All DNA | 58.4 | 679 |
| ONT-370 | tscscsasgsdTsdTsdCsdCsdTsdTsdCsdAsdTsdTscsts gscsa | 5-10-5 (2'-OMe Gapmer) | 68 | 680 |
| ONT-386 | rUrGrCrArGrArArUrGrArArGrGrArArCrUrGrGrA | Complementary RNA | | 681 |
| ONT-315 | TeosGeosAeosGeosAeosdTsdGs5mdCs5mdCsdTs dGsdGs5mdCsdTsdGs5mCeos5mCeosAeosTeosAeo | 5-10-5 (2'-MOE Gapmer) | 77.5 | 682 |
| ONT-354 | dTsdGsdAsdGsdAsdTsdGscscstsgsgscsdTsdGsdCs dCsdAsdTsdA | 7-6-7 (DNA-2'-OMe-DNA) Gapmer | 75.5 | 683 |
| ONT-360 | tsgsasdGsdAsdTsdGsdCsdCsdTsdGsdGsdCsdTsdG sdCsdCsastsas | 3-14-3 (2'-OMe-DNA-2'-OMe) Gapmer | 69 | 684 |
| ONT-366 | dTsdGsdAsdGsdAsdTsdGsdCsdCsdTsdGsdGsdCs dTsdGsdCsdCsdAsdTsdA | All DNA | 66.5 | 685 |
| ONT-372 | tsgsasgsasdTsdGsdCsdCsdTsdGsdGsdCsdTsdGscs csastsa | 5-10-5 (2'-OMe Gapmer) | 74.4 | 686 |
| ONT-387 | rUrArUrGrGrCrArGrCrCrArGrGrCrArUrCrUrCrA | Complementary RNA | | 687 |

Additional example stereorandom oligonucleotide compositions are listed below.

| Oligo | Sequence (5' to 3') | SEQ ID NO: |
|---|---|---|
| ONT-41 | (Gs5mCs5mCsTs5mCs)$_{MOE}$d[AsGsTs5mCsTsGs5mCsTsTs5mCs](Gs 5mCsAs5mCs5mC)$_{MOE}$ | 688 |
| ONT-70 | (Gs5mCs)$_{MOE}$d[GsTsTsTsGs5mCsTsTs5mCsTsTs](5mCsTsT sGs5mCGs)$_{MOE}$d[TsTsTsTs](TsT)$_{MOE}$ | 689 |
| ONT-83 | (GsTs5mCs5mCs5mCs)$_{MOE}$d(TsGsAsAsGsAsTsGsTs5mCs](AsAsTs Gs5mC)$_{MOE}$ | 690 |
| ONT-302 | (Ts5mCs5mCsAsGs)$_{MOE}$d[TsTs5mCs5mCsTsTs5mCsAsTsTs](5mCs TsGs5mCsA)$_{MOE}$ | 691 |
| ONT-315 | (TsGsAsGsAs)$_{MOE}$d[TsGs5mCs5mCsTsGsGs5mCsTsGs](5mCs5mCs AsTsA)$_{MOE}$ | 692 |

| Oligo | Sequence (5' to 3') | SEQ ID NO: |
|---|---|---|
| ONT-316 | (TsAsGs5mCs5mCs)_MOEd[AsTsTsGs5mCsAsGs5mCsTsGs5m](CsTs5mCsAs5mC)_MOE | 693 |
| ONT-352 | [TsCsCsAsGsTsTs](cscststscsas)_OMed[TsTsCsTsGsCsA] | 694 |
| ONT-354 | [TsGsAsGsAsTsGs](CsCsTsGsGsCs)_OMed[TsGsCsCsAsTsA] | 695 |
| ONT-355 | [TsAsGsCsCsAsTs](TsGsCsAsGsCs)_OMed[TsGsCsTsCsAsC] | 696 |
| ONT-358 | (TsCsCs)_OMed[AsGsTsTsCsCsTsTsCsAsTsTsCsTs](GsCsA)_OMe | 697 |
| ONT-360 | (TsGsAs)_OMed[GsAsTsGsCsCsTsGsGsGsCsTsGsCsCs](AsTsA)_OMe | 698 |
| ONT-361 | (TsAsGs)_OMed[CsCsAsTsTsGsCsAsGsCsTsGsCsTs](CsAsC)_OMe | 699 |
| ONT-364 | [TsCsCsAsGsTsTsCsCsTsTsCsAsTsTsCsTsGsCsA] | 700 |
| ONT-366 | [TsGsAsGsAsTsGsCsCsTsGsGsCsTsGsCsCsAsTsA] | 701 |
| ONT-367 | [TsAsGsCsCsAsTsTsGsCsAsGsCsTsGsCsTsCsAsC] | 702 |
| ONT-370 | (TsCsCsAsGs)_OMed[TsTsCsCsTsTsCsAsTsTs](CsTsGsCsA)_OMe | 703 |
| ONT-372 | (TsGsAsGsAs)_OMed[TsGsCsCsTsGsGsGsCsTsGs](CsCsAsTsA)_OMe | 704 |
| ONT-373 | (TsAsGsCsCs)_OMed[AsTsTsGsCsAsGsCsTsGs](CsTsCsAsC)_OMe | 705 |
| ONT-440 | (UsAsGsCsCs)_Fd[AsTsTsGsCsAsGsGsCsTsGsCsAsC] | 706 |
| ONT-441 | (UsAsGsCsCs)_Fd[AsTsTsGsCsAsGsGsCsTsGsC] | 707 |
| ONT-460 | (TsAsGsCsCs)_OMed[AsTsTsGsCsAsGsGsCsTsGsCsTsCsAsC] | 708 |
| ONT-450 | [AsTsTsAsAsTsAsAsAsTsGsGsTsCsAsTsCsAsCsC] | 709 |

Example RNA and DNA oligonucleotides are listed below.

| Oligo | Sequence (5' to 3') | SEQ ID NO: |
|---|---|---|
| ONT-28 | rGrGrUrGrCrGrArArGrCrArGrArArCrUrGrArGrC | 710 |
| ONT-386 | rUrGrCrArGrArArUrGrArArGrGrArArCrUrGrGrA | 711 |
| ONT-387 | rUrArUrGrGrCrArGrCrCrArGrGrCrArUrCrUrCrA | 712 |
| ONT-388 | rGrUrGrArGrCrArGrCrUrGrCrArArUrGrGrCrUrA | 713 |
| ONT-415 | d[TAGCCATTGCAGCTGCTCAC] | 714 |
| ONT-442 | rGrUrGrArGrCrGrGrCrUrGrCrArArUrGrGrCrUrA | 715 |
| ONT-443 | rGrUrGrArGrCrArGrCrUrGrCrGrArUrGrGrCrUrA | 716 |
| ONT-453 | rGrUrGrArUrGrArCrArArUrUrUrArUrArArArU | 717 |
| ONT-454 | rGrUrGrArUrGrGrCrArArUrUrUrArUrUrArArArU | 718 |

Example chirally pure oligonucleotides are presented below. In some embodiments, the present disclosure provides corresponding chirally controlled oligonucleotide compositions of each of the following example oligonucleotides.

| Oligo | Stereochemistry/Sequence (5' to 3') | Description | SEQ ID NO: |
|---|---|---|---|
| ONT-389 | (Sp, Sp, Sp, Sp, Sp, Sp, Sp, Rp, Sp, Sp, Rp, Sp, Sp, Rp, Sp, Sp, Sp, Sp, Sp)-d[TsGsAsGsAsTsGsCsCsTsGsGsCsTsGsCsCsAsTsA] | 7S-(RSS)_3-3S | 719 |
| ONT-390 | (Sp, Sp, Sp, Sp, Sp, Sp, Rp, Sp, Sp, Rp, Sp, Sp, Rp, Sp, Sp, Sp, Sp, Sp)-d[TsGsAsGsAsTsGsCsCsTsGsGsCsTsGsCsCsAsTsA] | 6S-(RSS)_3-4S | 720 |

-continued

| Oligo | Stereochemistry/Sequence (5' to 3') | Description | SEQ ID NO: |
|---|---|---|---|
| ONT-391 | (Sp, Sp, Sp, Sp, Sp, Rp, Sp, Sp, Rp, Sp, Sp, Rp, Sp, Sp, Sp, Sp, Sp, Sp)-d[TsGsAsGsAsTsGsCsCsTsGsGsCsTsGsCsAsTsA] | 5S-(RSS)₃-5S | 721 |
| ONT-392 | (Sp, Sp, Sp, Sp, Sp, Sp, Sp, Rp, Sp, Sp, Rp, Sp, Sp, Rp, Sp, Sp, Sp, Sp, Sp)-d[TsAsGsCsCsAsTsTsGsCsAsGsCsTsGsCsTsCsAsC] | 7S-(RSS)₃-3S | 722 |
| ONT-393 | (Sp, Sp, Sp, Sp, Sp, Sp, Rp, Sp, Sp, Rp, Sp, Sp, Rp, Sp, Sp, Sp, Sp, Sp, Sp)-d[TsAsGsCsCsAsTsTsGsCsAsGsCsTsGsCsTsCsAsC] | 6S-(RSS)₃-4S | 723 |
| ONT-394 | (Sp, Sp, Sp, Sp, Sp, Rp, Sp, Sp, Rp, Sp, Sp, Rp, Sp, Sp, Sp, Sp, Sp, Sp)-d[TsAsGsCsCsAsTsTsGsCsAsGsCsTsGsCsTsCsAsC] | 5S-(RSS)₃-5S | 724 |
| ONT-396 | (Sp, Sp, Sp, Sp, Sp, Sp, Sp, Sp, Sp, Sp, Sp, Sp, Sp, Sp, Sp, Sp, Sp, Rp)-d[TsAsGsCsCsAsTsTsGsCsAsGsCsTsGsCsTsCsAsC] | 18S-1R | 725 |
| ONT-397 | (Sp, Sp, Sp, Sp, Sp, Sp, Sp, Sp, Sp, Sp, Sp, Sp, Sp, Sp, Sp, Sp, Rp, Sp)-d[TsAsGsCsCsAsTsTsGsCsAsGsCsTsGsCsTsCsAsC] | 17S-RS | 726 |
| ONT-398 | (Sp, Sp, Sp, Sp, Sp, Sp, Sp, Sp, Sp, Sp, Sp, Sp, Sp, Sp, Sp, Rp, Sp, Sp)-d[TsAsGsCsCsAsTsTsGsCsAsGsCsTsGsCsTsCsAsC] | 16S-(RSS) | 727 |
| ONT-399 | (Sp, Sp, Sp, Sp, Sp, Sp, Sp, Sp, Sp, Sp, Sp, Sp, Sp, Sp, Rp, Sp, Sp, Sp)-d[TsAsGsCsCsAsTsTsGsCsAsGsCsTsGsCsTsCsAsC] | 15S-(RSS)-1S | 728 |
| ONT-400 | (Sp, Sp, Sp, Sp, Sp, Sp, Sp, Sp, Sp, Sp, Sp, Sp, Sp, Rp, Sp, Sp, Sp, Sp)-d[TsAsGsCsCsAsTsTsGsCsAsGsCsTsGsCsTsCsAsC] | 14S-(RSS)-2S | 729 |
| ONT-401 | (Sp, Sp, Sp, Sp, Sp, Sp, Sp, Sp, Sp, Sp, Sp, Sp, Rp, Sp, Sp, Sp, Sp, Sp)-d[TsAsGsCsCsAsTsTsGsCsAsGsCsTsGsCsTsCsAsC] | 13S-(RSS)-3S | 730 |
| ONT-402 | (Sp, Sp, Sp, Sp, Sp, Sp, Sp, Sp, Sp, Sp, Sp, Sp, Rp, Sp, Sp, Sp, Sp, Sp, Sp)-d[TsAsGsCsCsAsTsTsGsCsAsGsCsTsGsCsTsCsAsC] | 12S-(RSS)-4S | 731 |
| ONT-403 | (Sp, Sp, Sp, Sp, Sp, Sp, Sp, Sp, Sp, Sp, Sp, Rp, Sp, Sp, Sp, Sp, Sp, Sp)-d[TsAsGsCsCsAsTsTsGsCsAsGsCsTsGsCsTsCsAsC] | 11S-(RSS)-5S | 732 |
| ONT-404 | (Sp, Sp, Sp, Sp, Sp, Sp, Sp, Sp, Sp, Sp, Rp, Sp, Sp, Sp, Sp, Sp, Sp, Sp)-d[TsAsGsCsCsAsTsTsGsCsAsGsCsTsGsCsTsCsAsC] | 10S-(RSS)-6S | 733 |
| ONT-405 | (Sp, Sp, Sp, Sp, Sp, Sp, Sp, Sp, Sp, Rp, Sp, Sp, Sp, Sp, Sp, Sp, Sp, Sp)-d[TsAsGsCsCsAsTsTsGsCsAsGsCsTsGsCsTsCsAsC] | 9S-(RSS)-7S | 734 |
| ONT-406 | (Sp, Sp, Sp, Sp, Sp, Sp, Sp, Sp, Rp, Sp, Sp, Sp, Sp, Sp, Sp, Sp, Sp, Sp)-d[TsAsGsCsCsAsTsTsGsCsAsGsCsTsGsCsTsCsAsC] | 8S-(RSS)-8S | 735 |
| ONT-407 | (Sp, Sp, Sp, Sp, Sp, Sp, Sp, Rp, Sp, Sp, Sp, Sp, Sp, Sp, Sp, Sp, Sp, Sp)-d[TsAsGsCsCsAsTsTsGsCsAsGsCsTsGsCsTsCsAsC] | 7S-(RSS)-9S | 736 |
| ONT-408 | (Sp, Sp, Sp, Sp, Sp, Sp, Rp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 6S-(RSS)-10S | 737 |
| ONT-409 | (Sp, Sp, Sp, Sp, Sp, Rp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 5S-(RSS)-11S | 738 |
| ONT-410 | (Sp, Sp, Sp, Sp, Rp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 4S-(RSS)-12S | 739 |

-continued

| Oligo | Stereochemistry/Sequence (5' to 3') | Description | SEQ ID NO: |
|---|---|---|---|
| ONT-411 | (Sp, Sp, Sp, Rp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 3S-(RSS)-13S | 740 |
| ONT-412 | (Sp, Sp, Rp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | 2S-(RSS)-14S | 741 |
| ONT-413 | (Sp, Rp, Sp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | S-(RSS)-15S | 742 |
| ONT-414 | (Rp, Sp, Sp, Sp, Sp, Sp, Sp, Sp, Sp, Sp, Sp, Sp, Sp, Sp, Sp, Sp, Sp, Sp)-d[TsAsGsCsCsAsTsTsGsCsAsGsCsTsGsCsTsCsAsC] | (RSS)-16S | 743 |
| ONT-421 | All-(Sp)-d[TsAsGsCsCsAsTsTsGsCsAsGsCsTsGsCsTsCsAsC] | All S | 744 |
| ONT-422 | (Sp, Sp, Sp, Sp, Sp, Sp, Sp, Sp, Rp, Sp, Sp, Sp, Sp, Sp, Rp, Sp, Sp, Sp, Sp)-C6-amino-d[TsAsGsCsCsAsTsTsGsCsAsGsCsTsGsCsTsCsAsC] | 8S-(RSS)-3S-(RSS)-2S | 745 |
| ONT-455 | All-(Rp)-d[TsAsGsCsCsAsTsTsGsCsAsGsCsTsGsCsTsCsAsC] | All R | 746 |
| ONT-451 | (Sp, Sp, Sp, Sp, Sp, Sp, Sp, Sp, Sp, Sp, Sp, Sp, Rp, Sp, Sp, Sp, Sp, Sp)-d[AsTsTsAsAsTsAsAsAsAsTsTsGsTsCsAsTsCsAsCsC] | 13S-(RSS)-3S | 747 |
| ONT-452 | (Sp, Sp, Sp, Sp, Sp, Sp, Sp, Sp, Sp, Sp, Sp, Sp, Sp, Sp, Rp, Sp, Sp, Sp, Sp)-d[AsTsTsAsAsTsAsAsAsAsTsTsGsTsCsAsTsCsAsCsC] | 14S-(RSS)-2S | 748 |
| ONT-75 | All-(Rp)-(Gs5mCs5mCsTs5mCs)<sub>MOE</sub>d[AsGsTs5mCsTsGs5mCsTss5mCs](Gs5mCsAs5mCs5mC)<sub>MOE</sub> | All R | 749 |
| ONT-76 | (Sp, Rp, Rp, Sp, Rp, Sp, Sp, Sp, Sp, Sp, Sp, Sp, Sp, Sp, Sp, Sp, Rp, Sp, Rp)-(Gs5mCs5mCsTs5mCs)<sub>MOE</sub>d[AsGsTs5mCsTsGs5mCsTss5mCs](Gs5mCsAs5mCs5mC)<sub>MOE</sub> | SRRSR-11S-RSR | 750 |
| ONT-77 | (Rp, Rp, Rp, Rp, Rp, Sp, Sp, Sp, Sp, Sp, Sp, Sp, Sp, Sp, Sp, Rp, Rp, Rp, Rp)-(Gs5mCs5mCsTs5mCs)<sub>MOE</sub>d[AsGsTs5mCsTsGs5mCsTss5mCs](Gs5mCsAs5mCs5mC)<sub>MOE</sub> | 5R-10S-4R | 751 |
| ONT-80 | All-(Sp)-(Gs5mCs5mCsTs5mCs)<sub>MOE</sub>d[AsGsTs5mCsTsGs5mCsTss5mCs](Gs5mCsAs5mCs5mC)<sub>MOE</sub> | All S | 752 |
| ONT-81 | (Sp, Sp, Sp, Sp, Sp, Rp, Rp, Rp, Rp, Rp, Rp, Rp, Rp, Rp, Rp, Sp, Sp, Sp, Sp)-(Gs5mCs5mCsTs5mCs)<sub>MOE</sub>d[AsGsTs5mCsTsGs5mCsTss5mCs](Gs5mCsAs5mCs5mC)<sub>MOE</sub> | 5S-10R-4S | 753 |
| ONT-82 | All-(Rp)-(GsTs5mCs5mCs5mCs)<sub>MOE</sub>d[TsGsAsAsGsAsTsGsTs5mCs](AsAsTsGs5mC)<sub>MOE</sub> | All R | 754 |
| ONT-84 | All-(Sp)-(GsTs5mCs5mCs5mCs)<sub>MOE</sub>d[TsGsAsAsGsAsTsGsTs5mCs](AsAsTsGs5mC)<sub>MOE</sub> | All S | 755 |
| ONT-85 | (Rp, Rp, Rp, Rp, Rp, Sp, Sp, Sp, Sp, Sp, Sp, Sp, Sp, Sp, Sp, Rp, Rp, Rp, Rp)-(GsTs5mCs5mCs5mCs)<sub>MOE</sub>d[TsGsAsAsGsAsTsGsTs5mCs](AsAsTsGs5mC)<sub>MOE</sub> | 5R-10S-4R | 756 |
| ONT-86 | (Sp, Sp, Sp, Sp, Sp, Rp, Rp, Rp, Rp, Rp, Rp, Rp, Rp, Rp, Rp, Sp, Sp, Sp, Sp)-(GsTs5mCs5mCs5mCs)<sub>MOE</sub>d[TsGsAsAsGsAsTsGsTs5mCs](AsAsTsGs5mC)<sub>MOE</sub> | 5S-10R-4S | 757 |

-continued

| Oligo | Stereochemistry/Sequence (5' to 3') | Description | SEQ ID NO: |
|---|---|---|---|
| ONT-87 | (Rp, Rp, Rp, Rp, Rp, Sp, Sp, Rp, Sp, Sp, Rp, Sp, Sp, Rp, Rp, Rp, Rp, Rp, Rp)-(Gs5mCs5mCsTs5mCs)$_{MOE}$d[AsGsTs5mCsTsGs5mCs Ts5mCs](Gs5mCsAs5mCs5mC)$_{MOE}$ | 5R-2S-(RSS)$_2$-6R | 758 |
| ONT-88 | (Sp, Sp, Sp, Sp, Sp, Rp, Rp, Sp, Rp, Rp, Sp, Rp, Rp, Sp, Sp, Sp, Sp, Sp, Sp)-(Gs5mCs5mCsTs5mCs)$_{MOE}$d[AsGsTs5mCsTsGs5mCsTs Ts5mCs](Gs5mCsAs5mCs5mC)$_{MOE}$ | 5S-(RRS)$_3$-5S | 759 |
| ONT-89 | (Sp, Rp, Sp, Rp, Sp, Rp, Sp, Rp, Sp, Rp, Sp, Rp, Sp, Rp, Sp, Rp, Sp, Rp, Sp)-(Gs5mCs5mCsTs5mCs)$_{MOE}$d[AsGsTs5mCsTsGs5mCs TsTs5mCs](Gs5mCsAs5mCs5mC)$_{MOE}$ | (SR)$_9$S | 760 |
| ONT-154 | (Sp, Sp, Sp, Sp, Sp, Sp, Sp, Rp, Sp, Sp, Rp, Sp, Sp, Rp, Sp, Sp, Sp, Sp, Sp)-d[Gs5mCs5mCsTs5mCsAsGsTs5mCsTsGs5mCsTsTs 5mCsGs5mCsAs5mCs5mC] | 7S-(RSS)$_3$-3S | 761 |
| ONT-75 | All-(Rp)-(Gs5mCs5mCsTs5mCs)$_{MOE}$d[AsGsTs5mCsTsGs5mCs TsTs5mCs] (Gs5mCsAs5mCs5mC)$_{MOE}$ | All-R | 762 |
| ONT-80 | All-(Sp)-(Gs5mCs5mCsTs5mCs)$_{MOE}$d[AsGsTs5mCsTsGs5mCs TsTs5mCs] (Gs5mCsAs5mCs5mC)$_{MOE}$ | All-S | 763 |

Additional example oligonucleotides targeting FOXO1 with Tm are presented below. In some embodiments, the present disclosure provides corresponding chirally controlled oligonucleotide compositions of each of the following example oligonucleotides.

| Oligo | Sequence (5' to 3') | Tm (° C.) | SEQ ID NO: |
|---|---|---|---|
| ONT-439 | [UsAsGs]$_F$d[CsCsAsTsTsGsCsAsGsCsTsGsCsTs][CsAs C]$_F$ | 68.3 | 764 |
| ONT-440 | [UsAsGsCsCs]$_F$d[AsTsTsGsCsAsGsCsTsGsCsTsCsAsC] | 70.0 | 765 |
| ONT-441 | [UsAsGsCsCs]$_F$d[AsTsTsGsCsAsGsCsTsGsC] | 65.5 | 766 |
| ONT-455 | All-(Rp)-d[TsAsGsCsCsAsTsTsGsCsAsGsCsTsGsCsTsCsAsC] | 66.8 | 767 |
| ONT-316 | [TsAsGsCs5mCs]$_{MOE}$d[AsTsTsGs5mCsAsGs5mCsTs Gs][5mCsTs5mCsAs5mC]$_{MOE}$ | 76.9 | 768 |
| ONT-367 | d[TsAsGsCsCsAsTsTsGsCsAsGsCsTsGsCsTsCsAsC] | 62.8 | 769 |
| ONT-415 | d[TAGCCATTGCAGCTGCTCAC] | 72.6 | 770 |
| ONT-416 | [TsAsGsCsCsAsTsTsGsCsAsGsCs]$_{OMe}$d[TsGsCsTsCsAs C] | 78.4 | 771 |
| ONT-421 | All-(Sp)-d[TsAsGsCsCsAsTsTsGsCsAsGsCsTsGsCsTsCsAsC] | 59.2 | 772 |
| ONT-394 | (Sp, Sp, Sp, Sp, Sp, Rp, Sp, Rp, Sp, Sp, Rp, Sp, Sp, Sp, Sp, Sp, Sp, Sp, Sp)-d[TsAsGsCsCsAsTsTsGsCsAsGsCsTsGsCsTsCsAsC] | 60.0 | 773 |
| ONT-406 | (Sp, Sp, Sp, Sp, Sp, Sp, Sp, Sp, Rp, Sp, Sp, Sp, Sp, Sp, Sp, Sp, Sp, Sp, Sp)-d[TsAsGsCsCsAsTsTsGsCsAsGsCsTsGsCsTsCsAsC] | 58.5 | 774 |

Example 12. Example Additional Controlled Cleavage by Provided Chirally Controlled Oligonucleotide Compositions As will be appreciated by those skilled in the art, example data illustrated in FIG. 26 confirm that provided chirally controlled oligonucleotide compositions and methods thereof provided unexpected results compared to reference compositions, such as stereorandom oligonucleotide compositions. Among other things, chirally controlled oligonucleotide compositions can produce controlled cleavage patterns, including but not limited to controlling of positions of cleavage sites, numbers of cleavage sites, and relative cleavage percentage of cleavage sites. See also example data presented in FIG. 27.

Example 13. Stability of Chirally Controlled Oligonucleotide Compositions

Figure 7:
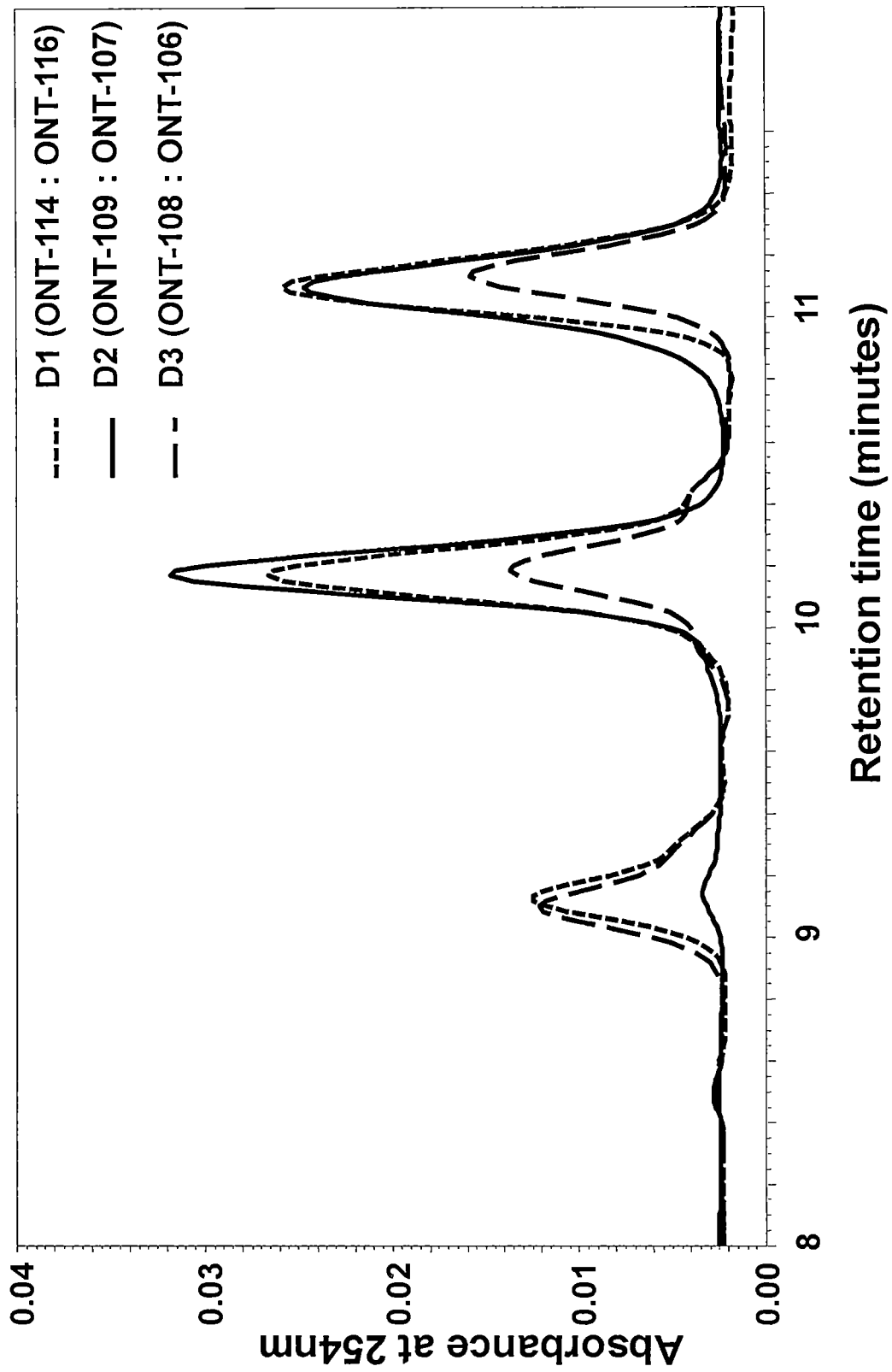
FIG. 7. HPLC profiles exhibiting the difference in metabolic stability determined in Human Serum for siRNA duplexes having several Rp, Sp or stereorandom phosphorothioate linkages. Compositions used include: ONT-114, ONT-116, ONT-109, ONT-107, ONT-108 and ONT-106.
Figure 26:
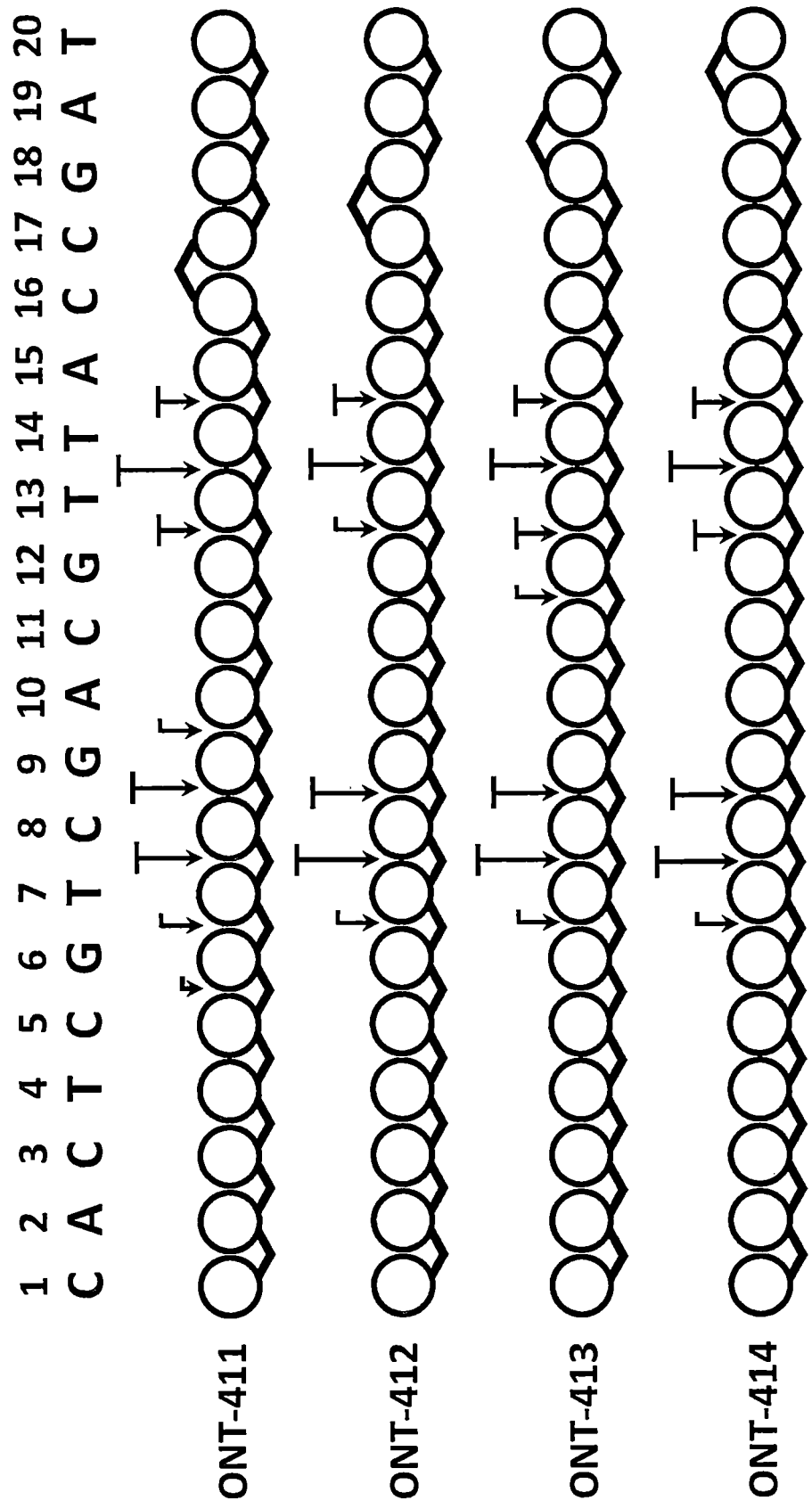
FIG. 26. Comparison of cleavage maps of sequences containing one Rp with change of position starting from 3'-end of DNA. Compositions used include: ONT-396 to ONT-414 (SEQ ID NOS 725-743, respectively). These sequences target the same region in FOXO1 mRNA. Cleavage maps are derived from the reaction mixtures obtained after 5 minutes of incubation of respective duplexes with RNase H1C in the presence of 1×RNase H buffer at 37° C. Arrows indicate sites of cleavage. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate species peak was used for quantification. Figure also discloses SEQ ID NO: 1560 in panels A-D.
Figure 27:
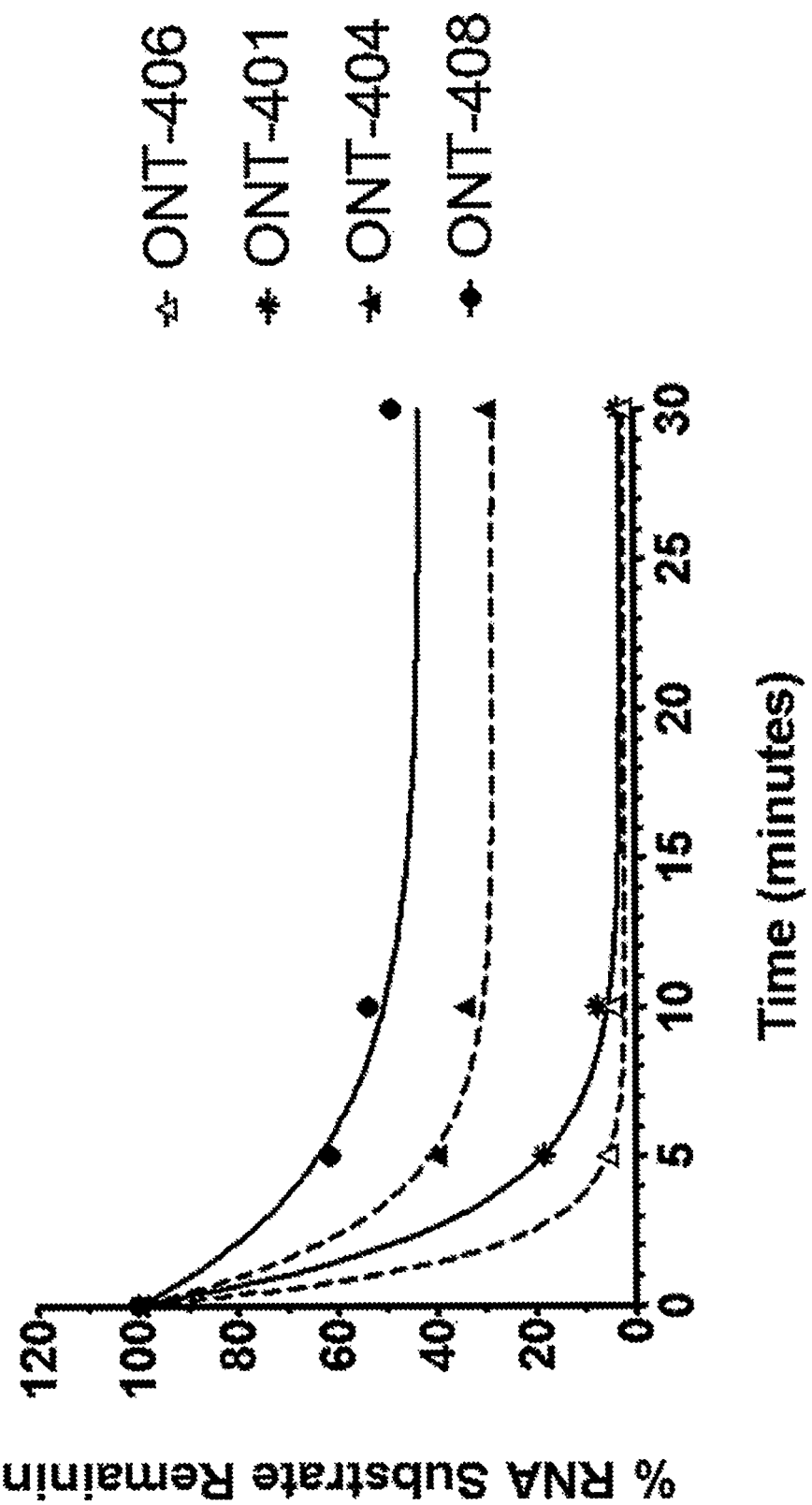
FIG. 27. (A) Comparison of RNase H cleavage rates for stereopure oligonucleotides (ONT-406), (ONT-401), (ONT-404) and (ONT-408). All four sequences are stereopure phosphorothioates with one Rp linkage. These sequences target the same region in FOXO1 mRNA. All duplexes were incubation with RNase H1C in the presence of 1×RNase H buffer at 37° C. Reactions were quenched at fixed time points by 30 mM Na$_2$EDTA. Cleavage rates were determined by measuring amount of full length RNA remaining in the reaction mixtures by reverse phase HPLC. ONT-406 and ONT-401 were found to have superior cleavage rates. (B) Correlation between % RNA cleaved in RNase H assay (10 μM oligonucleotide) and % mRNA knockdown in in vitro assay (20 nM oligonucleotide). All sequences target the same region of mRNA in the FOXO1 target. The quantity of RNA remaining is determined by UV peak area for RNA when normalized to DNA in the same reaction mixture. All of the above maps are derived from the reaction mixture obtained after 5 minutes of incubation of respective duplexes with RNase H1C in the presence of 1×PBS buffer at 37° C. All sequences from ONT-396 to ONT-414 have one Rp phosphorothioate and they vary in the position of Rp. ONT-421 (All Sp) phosphorothioate was inactive in-vitro assay. It relates poor cleavage rate of RNA in RNase H assay when ONT-421 is duplexed with complementary RNA.
Figure 28:
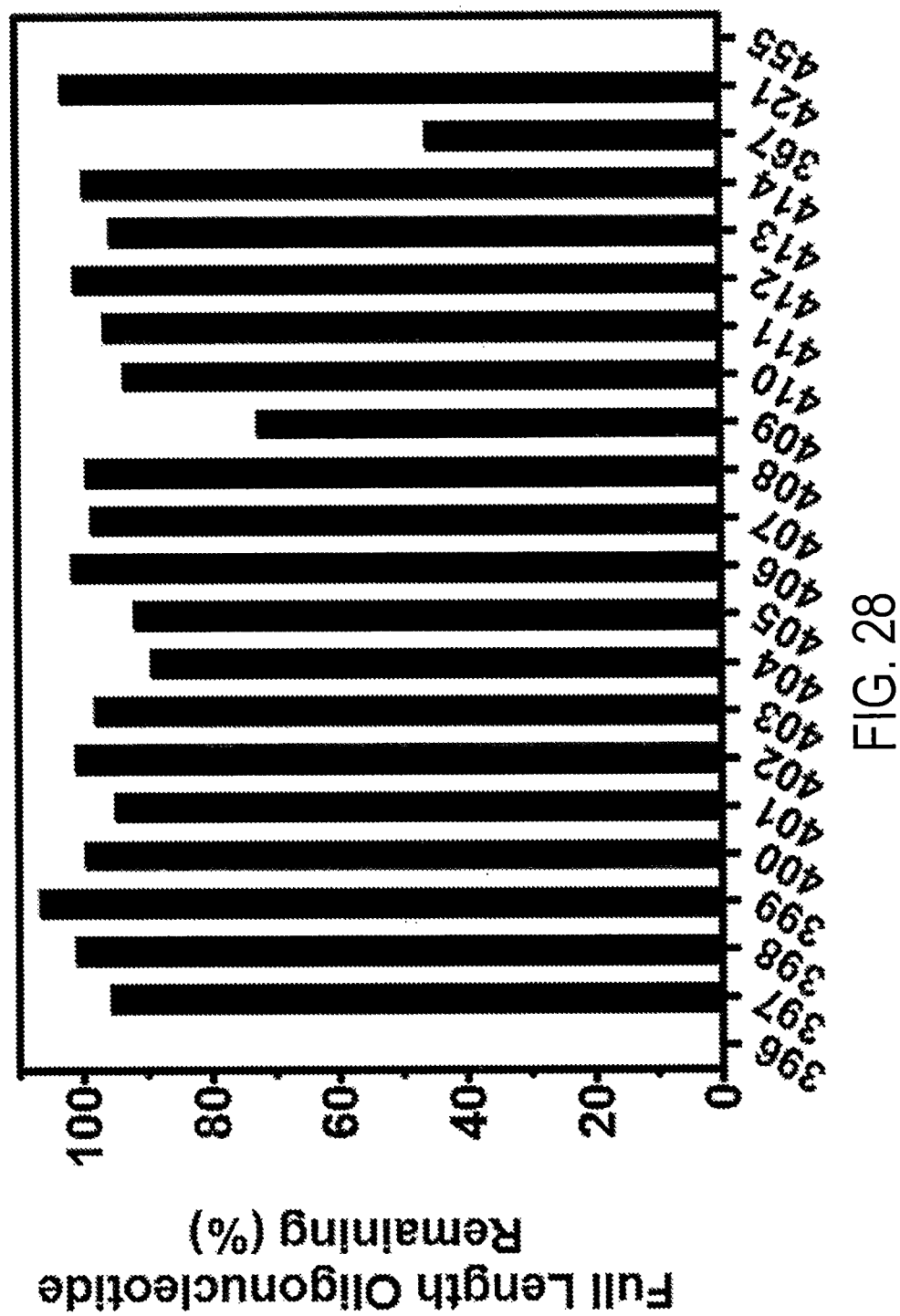
FIG. 28. Serum stability assay of single Rp walk PS DNA (ONT-396-ONT-414), stereorandom PS DNA(ONT-367), all-Sp PS DNA (ONT-421) and all-Rp PS DNA (ONT-455) in rat serum for 2 days. Note ONT-396 and ONT-455 decomposed at tested time point. Compositions used include: ONT-396 to ONT-414, ONT-367, ONT-421, and ONT-455.
Figure 29:
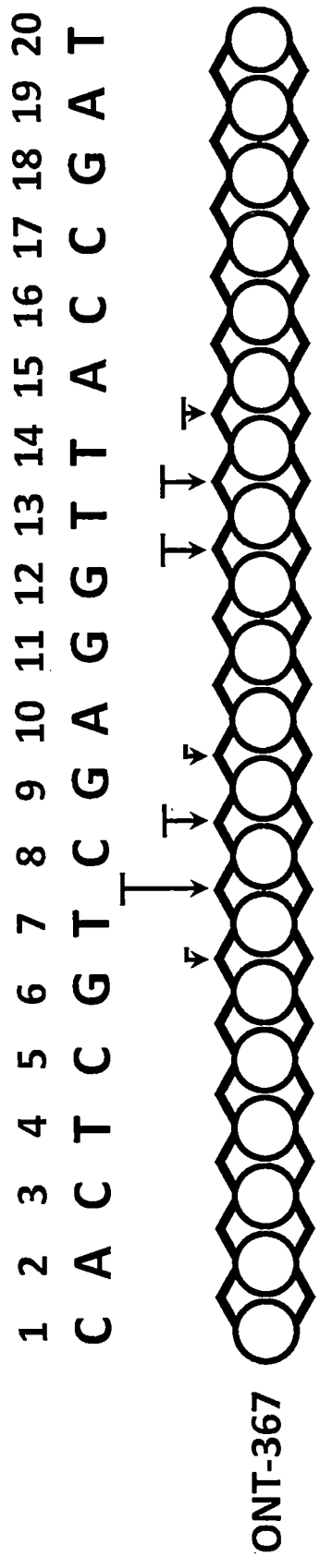
FIG. 29. Example oligonucleotides including hemimers. (A): cleavage maps. (B): RNA cleavage assay. (C): FOXO1 mRNA knockdown. ONT-440 (SEQ ID NO: 765), ONT-441 (SEQ ID NO: 766), and ONT-367 (SEQ ID NO: 769) are used. In some embodiments, introduction of 2'-modifications on 5'-end of the sequences increases stability for binding to target RNA while maintaining RNase H activity. ONT-367 (stereorandom phosphorothioate DNA) and ONT-440 (5-15, 2'-F-DNA) have similar cleavage maps and similar rate of RNA cleavage in RNase H assay (10 μM oligonucleotide). In some embodiments, ONT-440 (5-11, 2'-F-DNA) sequence can have better cell penetration properties. In some embodiments, asymmetric 2'-modifications provide Tm advantage while maintaining RNase H activity. Introduction of RSS motifs can further enhance RNase H efficiency in the hemimers. Cleavage maps are derived from the reaction mixtures obtained after 5 minutes of incubation of respective duplexes with RNase H1C in the presence of 1×RNase H buffer at 37° C. Arrows indicate sites of cleavage. (⊤) indicates that both fragments, 5'-phosphate species as well as 5'-OH 3'-OH species were identified in reaction mixtures. (Γ) indicates that only 5'-phosphate species was detected and (⌐) indicates that 5'-OH 3'-OH component was detected in mass spectrometry analysis. The length of the arrow signifies the amount of metabolite present in the reaction mixture which was determined from the ratio of UV peak area to theoretical extinction coefficient of that fragment. Only in the cases where 5'-OH 3'-OH was not detected in the reaction mixture, 5'-phosphate species peak was used for quantification. Figure also discloses SEQ ID NO: 1560 in panel A.
Figure 29:
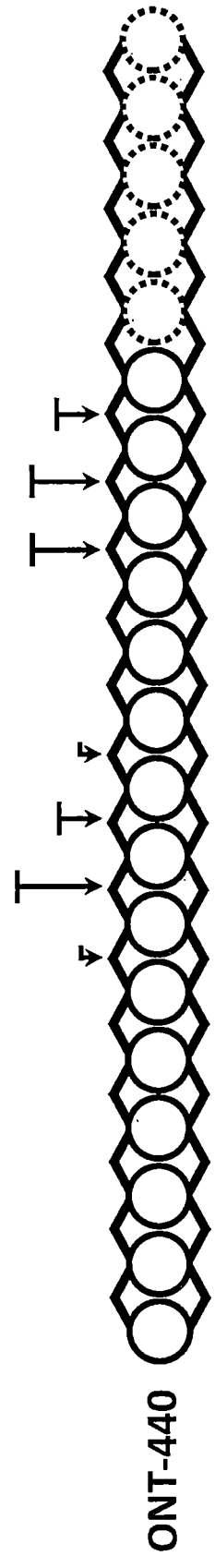
Figure 29:
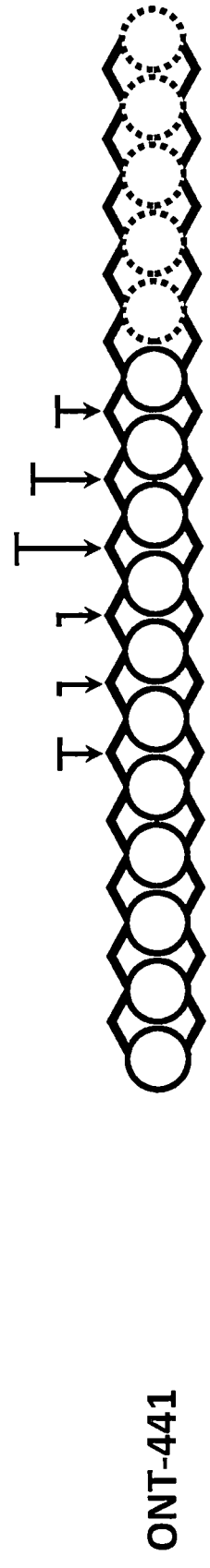
Figure 29:
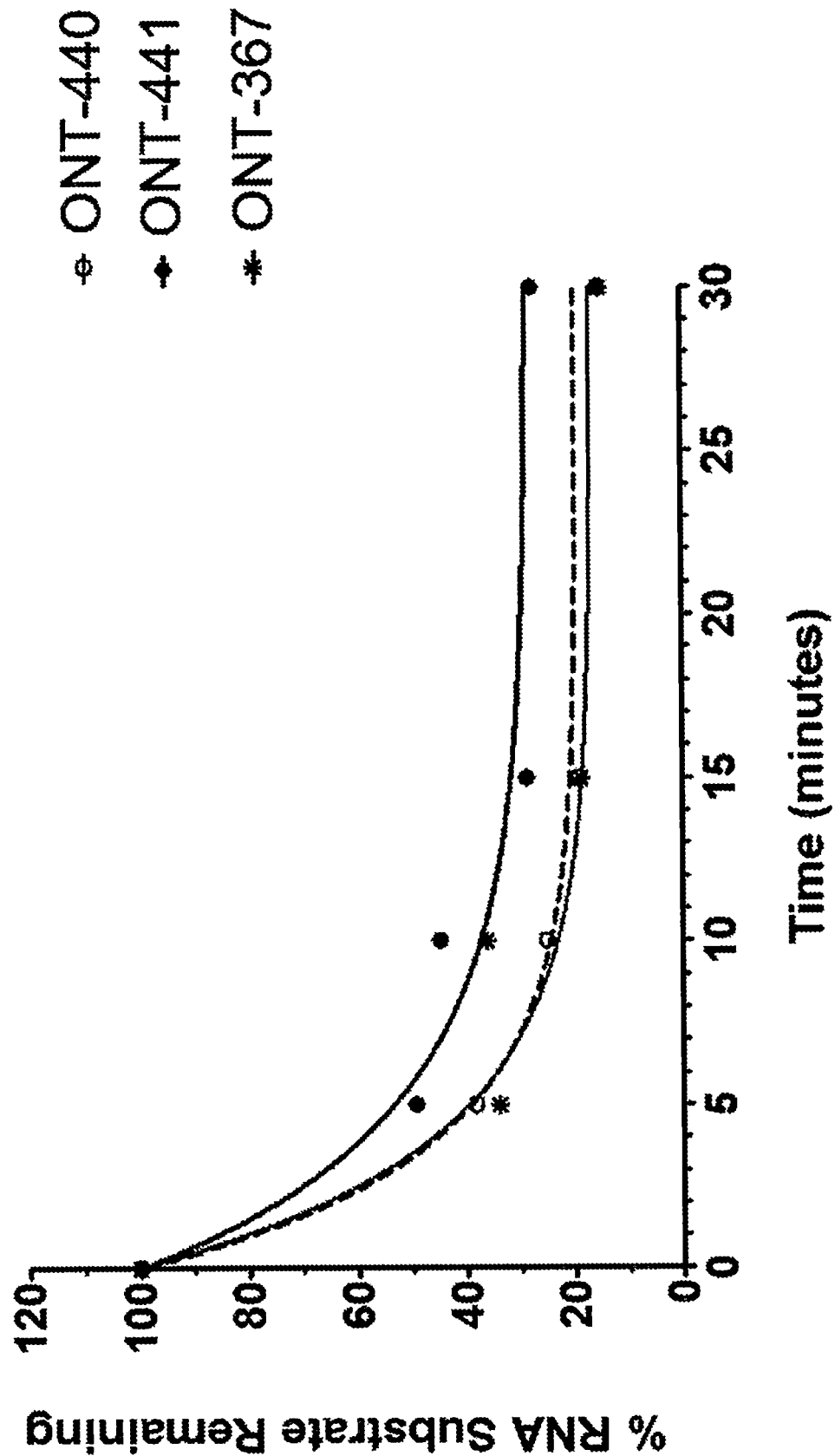

As will be appreciated by those skilled in the art, example data illustrated in FIG. 26 confirm that stability of provided chirally controlled oligonucleotide compositions can be adjusted by varying patterns of backbone chiral centers. For example data, see FIG. 7 and FIG. 28. An example protocol for performing serum stability experiment is described below.

Protocol:

P-stereochemically pure PS DNA (ONT-396-ONT-414 (single Rp walk from 3' end to 5' end)), stereorandom PS DNA (ONT-367), all-Sp PS DNA (ONT-421) and all-Rp PS DNA (ONT-455) were incubated in Rat serum (Sigma, R9759) (0 h and 48 h) and analyzed by IEX-HPLC.

Incubation Method:

5 µL of 250 µM of each DNA solutions and 45 µL of Rat serum were mixed and incubated at 37° C. for each time points (0 h and 48 h). At each time points, reaction was stopped by adding 25 µL of 150 mM EDTA solution, 30 µL of Lysis buffer (erpicentre, MTC096H) and 3 µL of Proteinase K solution (20 mg/mL). The mixture was incubated at 60° C. for 20 min then 20 µL of the mixture was injected to IEX-HPLC and analyzed.

Incubation Control Sample:

Mixture of 5 µL of 250 µM of each DNA solutions and 103 µL of 1×PBS buffer were prepared and 20 µL of the mixture was analyzed by IEX-HPLC as controls in order to check the absolute quantification.

Example Analytical Method:
IEx-HPLC
A: 10 mM TrisHCl, 50% ACN (pH 8.0)
B: 10 mM TrisHCl, 800 mM NaCl, 50% ACN (pH 8.0)
C: Water-ACN (1:1, v/v)
Temp: 60° C.
Column: DIONEX DNAPac PA-100, 250×4 mm Gradient:

|   | Time | Flow | % A | % B | % C | % D | Curve |
|---|------|------|-----|-----|-----|-----|-------|
| 1 | 0.00 | 1.00 | 95.0 | 5.0 | 0.0 | 0.0 | 6 |
| 2 | 1.00 | 1.00 | 95.0 | 5.0 | 0.0 | 0.0 | 1 |
| 3 | 2.00 | 1.00 | 75.0 | 25.0 | 0.0 | 0.0 | 6 |
| 4 | 10.00 | 1.00 | 5.0 | 95.0 | 0.0 | 0.0 | 6 |
| 5 | 10.10 | 1.00 | 95.0 | 5.0 | 0.0 | 0.0 | 6 |
| 6 | 12.50 | 1.00 | 95.0 | 5.0 | 0.0 | 0.0 | 1 |

Washing:

|   | Time | Flow | % A | % B | % C | % D | Curve |
|---|------|------|-----|-----|-----|-----|-------|
| 1 | 0.01 | 1.00 | 0.0 | 0.0 | 100.0 | 0.0 | 6 |
| 2 | 5.50 | 1.00 | 0.0 | 0.0 | 100.0 | 0.0 | 1 |
| 3 | 5.60 | 1.00 | 0.0 | 100.0 | 0.0 | 0.0 | 6 |
| 4 | 7.50 | 1.00 | 0.0 | 100.0 | 0.0 | 0.0 | 1 |
| 5 | 7.60 | 1.00 | 95.0 | 5.0 | 0.0 | 0.0 | 6 |
| 6 | 12.50 | 1.00 | 95.0 | 5.0 | 0.0 | 0.0 | 1 |

Column Temperature: 60° C.

Washing was performed every after the sample run.

Percentage of remained PS DNA was calculated by the analysis of the ratio from the 0 h to 48 h using the area of integration of HPLC chromatogram.

Example 14. Example Analytical Results (FIG. 19)

Peak assignments for FIG. 19 (Top panel, M12-Exp11 B10, ONT-354, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 2.34 | 1100.6 | 733.7 | | | |
| 11.91 | | 1390.6 | 1042.6 | | |
| 13.07 | | 1500.08 | 1125.5 | | 750.73 |
| | | 1805.29 | 1354.19 | | |
| 13.58 | | 1603.39 | 1202.2 | 961.35 | 801.15 |
| 14.80 | | | 1589.9 | 1271.4 | 1059.5 |
| 18.59 | | | 1653.3 | 1323.3 | 1101.6 |

| Retention time (minutes) | Observed MW | Assignment based on mass match | | |
|---|---|---|---|---|
| | | 5'-p-RNA fragment | 3'-OH and 5'-OH, RNA | DNA |
| 2.34 | 2203.2 | | 7mer | |
| 11.91 | 4176 | 13mer | | |
| 13.07 | 4505.7 | 14mer | | |
| | 5418.87 | | 17mer | |
| 13.58 | 4812.8 | 15mer | | |
| 14.80 | 6362.5 | | 20mer, ONT-387 | |
| 18.59 | 6615.4 | | | ONT-354 |

Peak assignments for FIG. 19 (Bottom panel, M12-Exp11 A10, ONT-315, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 4.01 | 1425.33 | 950.15 | | | |
| 4.4 | 1100.83 | 733.69 | | | |
| 4.94 | 1578.34 | 1051.54 | | | |
| 6.21 | 1741.91 | 1161.89 | 870.37 | | |
| | 1445.42 | 963.31 | 722.97 | | |
| 8.48 | 1610 | 1073.3 | | | |
| 9.15 | | 1391.2 | 1043.1 | | |
| 9.93 | 1763.4 | 1174.7 | | | |
| 11.8 | | 1602.3 | 1201.7 | | |
| 14.82 | | | | | |
| 20.73 | | | 1809.94 | 1447.82 | 1205.9 |

| Retention time (minutes) | Observed MW | 5'-p-RNA fragment | Assignment based on mass match 3'-OH and 5'-OH, RNA | DNA |
|---|---|---|---|---|
| 4.01 | 2853.45 | | 9mer | |
| 4.4 | 2203.66 | 7mer | | |
| 4.94 | 3158.47 | | 10mer | |
| 6.21 | 3487.52 | | 11mer | |
| | 2892.84 | 9mer | | |
| 8.48 | 3220.94 | 10mer | | |
| 9.15 | 4177 | | 13mer | |
| 9.93 | 3528.88 | 11mer | | |
| 11.8 | 4810 | | 15mer | |
| 14.82 | | | 20mer, ONT-387 | |
| 20.73 | 7244.3 | | | ONT-315 |

Example 15. Example Analytical Results (FIG. 30)

Peak assignments for FIG. 30 (Top panel, M12-Exp11 D2, ONT-367, 30 min)

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 2.36 | 1120.28 | 746.25 | | | |
| 3.15 | 1292.41 | 861.32 | | | |
| 4.04 | 975.92 | | | | |
| 4.49 | 1140.6 | 759.78 | | | |
| 5.83 | 1305.21 | 869.65 | 652.31 | | |
| 6.88 | 1923.23 | 1281.69 | 961.28 | | |
| 9.32 | | 1390.76 | 1043.29 | 833.72 | |
| 9.96 | 1783.85 | 1187.98 | 891.6 | 712.94 | |
| 11.01 | 1936.14 | 1289.93 | | | |
| | | 1501.52 | 1125.4 | 899.89 | |
| 11.93 | | 1405.25 | 1053.78 | 842.84 | |
| 13.15 | | 1514.72 | 1135.72 | | |
| 14.81 | | | 1609.95 | 1287.53 | 1072.58 |
| 18.33 | | | 1587.9 | 1270.2 | 1058.3 |

| Retention time (minutes) | Observed MW | 5'-p-RNA fragment | Assignment based on mass match 3'-OH and 5'-OH, RNA | DNA |
|---|---|---|---|---|
| 2.36 | 2242.56 | | 7mer | |
| 3.15 | 2586.82 | | 8mer | |
| 4.04 | 1953.84 | 6mer | | |
| 4.49 | 2283.2 | 7mer | | |
| 5.83 | 2612.42 | 8mer | | |
| 6.88 | 3849.14 | | 12mer | |
| 9.32 | 4175.28 | | 13mer | |
| 9.96 | 3569.7 | 11mer | | |
| 11.01 | 3874.28 | 12mer | | |
| | 4507.56 | | 14mer | |
| 11.93 | 4218.75 | 13mer | | |
| 13.15 | 4547.16 | 14mer | | |
| 14.81 | 6441.8 | | 20mer, ONT-388 | |
| 18.33 | 6355.6 | | | ONT-367 |

Peak assignments for FIG. 30 (Bottom panel, M12-Exp21 NM Plate1 (pool) F11 ONT-406 30 min

| Retention time (minutes) | $(M-2)^{2-}$ | $(M-3)^{3-}$ | $(M-4)^{4-}$ | $(M-5)^{5-}$ | $(M-6)^{6-}$ |
|---|---|---|---|---|---|
| 4.72 | 1140.6 | 759.78 | | | |
| 9.46 | | 1390.76 | 1043.29 | 833.72 | |
| 16.45 | | | 1609.95 | 1287.53 | 1072.58 |
| 19.48 | | | 1588.1 | 1270.4 | 1058.4 |

| Retention time (minutes) | Observed MW | 5'-p-RNA fragment | Assignment based on mass match 3'-OH and 5'-OH, RNA | DNA |
|---|---|---|---|---|
| 4.72 | 2203.2 | 2283.2 | 7mer | |
| 9.46 | 4176 | 4175.28 | | 13mer |
| 16.45 | 6362.5 | 6441.8 | | 20mer, ONT-388 |
| 19.48 | 6615.4 | 6355.9 | | |

Example 16. Example Preparation of Linkers

In some embodiments, the SP linker was prepared following the scheme below:

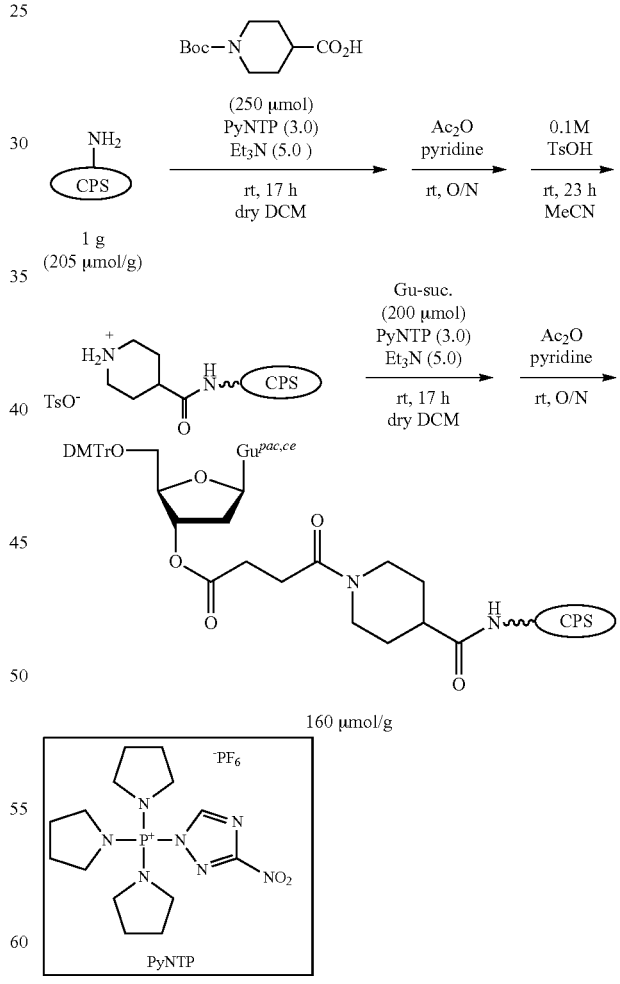

Example 17. Example Designs of Base Sequence

As described in the present disclosure, the present disclosure recognizes the importance of base sequence, e.g., for provided chirally controlled oligonucleotide composition. In some embodiments, the present disclosure, as exemplified herein, provides methods for designing base sequence for oligonucleotides, such as antisense oligonucleotides.

In some embodiments, among other things, bioinformatics is used to design a sequence for a target, e.g., a disease-associated mutant allele of Huntington's disease. The present example describes example steps that may be used for design antisense oligonucleotides for, e.g. rs362268, rs362306, rs2530595, rs362331, rs362307, etc. In some embodiments, a provided methods comprising a step of examining sequence features for off-target, binding affinity with target, contiguous Gs, and palindromic moieties. In some embodiments, a provided methods comprising a step of examining off-target effects in the presence of mismatches. In some embodiments, a sequence found in a target comprising a characteristic sequence element, e.g., a mutation, a SNP, etc., and having a length of about 10-1000, e.g., about 10, about 20, about 30, about 40, about 50, about 60, about 70, about 80, about 90, about 100, about 110, about 120, about 130, about 140, about 150, about 200, about 250, about 300, about 400, about 500, about 600, about 700, about 800, about 900, about 1000, about 2000, about 3000, about 4000, about 5000, etc., nucleotides are used in assays, e.g., RNase H assay, reporter assay, etc. In some embodiments, as in the present example, 40-bp flanking sequences for a SNP, e.g., rs362268, rs362306, rs2530595, rs362331, rs362307, etc., were used. A number of such sequences, for example 6 to 12, could be readily assessed by provided methods. Example tested sequences are listed in FIG. 42.

As described in the present disclosure and understood by a person having ordinary skill in the art, in some embodiments, assays, for example, RNase cleavage assay described herein, are useful in the assessment of one or more features (e.g., rate, extent, and/or selectivity of cleavage). In some embodiments, an RNase cleavage assay provides a cleavage pattern of an oligonucleotide composition. In some embodiments, a composition of DNA oligonucleotides having the same sequence is used, an RNase H assay may provide a DNA cleavage pattern of the sequence. In some embodiments, for generating a DNA cleavage pattern, all DNA oligonucleotides in the composition are identical. In some embodiments, when a stereorandom composition of all-phosphorothioate oligonucleotides having the same sequence is used, an RNase H assay may provide a stereorandom cleavage pattern of the sequence. In some embodiments, for generating stereorandom cleavage pattern, all oligonucleotides in the stereorandom composition are identical. In some embodiments, when a chirally controlled oligonucleotide composition is used, an RNase H assay may provide a stereorandom cleavage pattern of the chirally controlled oligonucleotide composition. In some embodiments, for generating cleavage pattern of a chirally controlled oligonucleotide composition, all oligonucleotides in the chirally controlled oligonucleotide composition are identical. In some embodiments, an RNase H assay provides cleavage rate information. In some embodiments, an RNase H assay provides relative cleavage extent, e.g., (cleavage at a site)/(all cleavage). In some embodiments, an RNase H assay provides absolute cleavage extent, (cleaved target at a site)/(all target both cleaved and non-cleaved). In some embodiments, an RNase H assay provides selectivity. In some embodiments, an RNase H assay provides suppression level information.

In some embodiments, as exemplified herein, an RNase H assay provides cleavage rates. For example results, see FIG. 31. P represents position of mismatch in oligonucleotides from the 5'-end.

Analysis of human RNase H1 cleavage of a 25-mer RNA when hybridized with different phosphorothioate oligonucleotides targeting rs362307 SNP was performed. WV-944 and WV-945 are 25mer RNAs which include WT and mutant variant of rs362307, respectively. WV-936 to WV-941 are stereopure DNAs while WV-904 to WV-909 are all stereorandom DNAs. All duplexes were incubated with RNase H1C in the presence of 1× RNase H buffer at 37° C. Reactions were quenched at fixed time points by 30 mM Na$_2$EDTA. One tenth of this reaction mixture was injected on Reverse Phase HPLC and peak areas were measured for full length RNA remaining in the reaction mixtures at different time points. Cleavage rates were determined by plotting these peak areas with respective time points. In some embodiments, differentiation between rates of cleavage of WT RNA vs. mu RNA was observed.

In some embodiments, as shown in FIG. 31, when position 11, 12 or 13 of a sequence as counted from its 5'-terminus aligns with a SNP, or position 8, 9 or 10 of a sequence as counted from its 3'-terminus aligns with a SNP, better cleavage selectivity was observed.

Example 18. Example Wing, Core, Wing-Core, Core-Wing and Wing-Core-Wing Designs

Among other things, the present disclosure provides various embodiments of wing, core, wing-core, core-wing, and wing-core-wing structures. In some embodiments, it was surprisingly found that oligonucleotides with wings comprising phosphate linkages and cores comprising phosphorothioate linkages provided unexpectedly increased cleavage efficiency and selectivity. For example, see FIG. 32 C, F, G, H, etc.

Analysis of human RNase H1 cleavage of a 25-mer RNA when hybridized with different chirally controlled oligonucleotide compositions targeting rs362307 SNP. WV-944 and WV-945 are 25mer RNAs which include WT and mutant variant of rs362307, respectively. WV-1085 to WV-1092 are all stereopure 2'-OMe/DNAs with mixed PO/PS backbone. All duplexes were incubated with RNase H1C in the presence of 1×RNase H buffer at 37° C. Reactions were quenched at fixed time points by 30 mM Na$_2$EDTA. One tenth of this reaction mixture was injected on Reverse Phase HPLC and peak areas were measured for full length RNA remaining in the reaction mixtures at different time points. Cleavage rates were determined by plotting these peak areas with respective time points.

In some embodiments, 2'-OMe phosphate wings change cleavage rate and/or selectivity. In some embodiments, 2'-OMe phosphate wings change cleavage rate and selectivity. In some embodiments, 2'-OMe phosphate wings change cleavage rate or selectivity. In some embodiments, 2'-OMe phosphate wing change cleavage rate. In some embodiments, 2'-OMe phosphate wing change cleavage rates of both the mutant and the wild-type allele. In some embodiments, 2'-OMe phosphate wing change cleavage selectivity. In some embodiments, 2'-OMe phosphate wing change cleavage pattern.

In some embodiments, incorporation of a phosphate internucleotidic linkage surprisingly improves cleavage rate and/or selectivity. In some embodiments, incorporation of a phosphate internucleotidic linkage surprisingly improves cleavage rate and selectivity. In some embodiments, incorporation of a phosphate internucleotidic linkage surprisingly improves cleavage rate or selectivity. In some embodiments, incorporation of a phosphate internucleotidic linkage surprisingly improves cleavage rate. In some embodiments, a phosphate internucleotidic linkage improves cleavage rates of both the mutant and the wild-type allele, but at a greater level for the mutant than for the wild-type allele. In some embodiments, incorporation of a phosphate internucleotidic linkage surprisingly improves cleavage selectivity.

In some embodiments, as demonstrated by data exemplified herein, stereopure oligonucleotide compositions provided surprisingly high cleavage rate and/or selectivity compared to corresponding stereorandom compositions; for examples, see stereopure WV-1497/stereorandom WV-1092, 905/937, 931/1087, etc.

Example 19. Example Cleavage Maps

As described herein, in some embodiments, an assay, such as RNase H assay, provides cleavage maps for stereorandom or chirally controlled oligonucleotide compositions. Example cleavage maps are illustrated in FIG. 33, which exemplifies stereorandom cleavage patterns of multiple base sequences. Additional cleavage maps are presented in FIG. 35, which exemplifies, among other things, stereorandom cleavage patterns of base sequence having no nucleoside modifications (WV-905), as well as base sequence having nucleoside modifications.

Example cleavage patterns of chirally controlled stereopure oligonucleotide compositions are presented in FIG. 34. As described in the present disclosure, major cleavage sites may be identified through assays such RNase H assay from cleavage patterns. For example, for WV-937, the relative major cleavage site, as assessed by (cleavage at the site/total cleavage) and reflected by the lengths of the arrows, are between GCGC and CCUU for the wild-type (2 internucleotidic linkages away from the SNP), and between CUGU and GCCC for the mutant (at the SNP site, 0 internucleotidic linkage away from the SNP). In some embodiments, a relative major cleavage site is not necessarily an absolute major cleavage site, which requires certain percentage of the total target, in this case, RNA, is cleaved at the site. For example, in some embodiments, the site between GCGC and CCUU for WV-937/wild type is not a major cleavage site if over 20% of total target needs to be cleaved at a site for a site to qualify as a major cleavage site (see FIG. 32, M); the site between CUGU and GCCC for WV-937/mutant remains a major cleavage site if the threshold for a major site is 20% of total target being cleaved at that site.

In some embodiments, different oligonucleotide compositions have different cleave rates. In some embodiments, cleavage maps are generated at different time points. For example, for an oligonucleotide composition having a faster cleavage rate, its cleavage map can be generated at an earlier time point (e.g., 5 minutes, 10 minutes, 15 minutes, etc.) than an oligonucleotide composition having a slower cleavage rate (e.g., 30 minutes, 45 minutes, 60 minutes, etc.).

In some embodiments, when cleavage products at only one site can be identified by an analytical methods, e.g., HPLC, HPLC-MS, etc., the corresponding cleavage pattern is considered to have a single cleavage site. In some embodiments, when greater than about 90%, greater than about 91%, greater than about 92%, greater than about 93%, greater than about 94%, greater than about 95%, greater than about 96%, greater than about 97%, greater than about 98%, greater than about 99%, or greater than about 99.5% of total cleavage occurs at a site, the corresponding cleavage pattern may be considered to have a single cleavage site. In some embodiments, as understood by a person having ordinary skill in the art, selectivity in e.g., cells, tissues, organs, subjects, etc., may be higher than that observed in an RNase H assay. In some embodiments, a site having greater than about 90%, greater than about 91%, greater than about 92%, greater than about 93%, greater than about 94%, greater than about 95%, greater than about 96%, greater than about 97%, greater than about 98%, greater than about 99%, or greater than about 99.5% of total cleavage in an RNase H assay may have higher selectivity in cells, tissues, organs, or subjects. In some embodiments, a site having greater than about 90% of total cleavage in an RNase H assay may be the only cleavage site (e.g., greater than about 99%, greater than about 99.5%, 100%, etc.) in cells, tissues, organs, or subjects.

In some embodiments, selectivity may be assessed by comparing absolute values of remaining transcripts (or representative sequences thereof, such as RNA sequences used in examples described herein) of a target sequence and a similar sequence, e.g., RNA, or representative synthetic sequences, of a mutant allele as a target, and a wild-type allele as a similar sequence. In some embodiments, selectivity may be assessed by comparing absolute amounts of remaining transcripts (or representative sequences thereof, such as RNA sequences used in examples described herein) of a target sequence and a similar sequence, when the starting amounts are the same. In some embodiments, selectivity may be assessed by percentages of cleavage of transcripts (or representative sequences thereof, such as RNA sequences used in examples described herein) of a target sequence and a similar sequence. In some embodiments, selectivity may be assessed by comparing ratios of cleaved and non-cleaved transcripts (or representative sequences thereof, such as RNA sequences used in examples described herein).

In some embodiments, selectivity can be assessed by one or more assays exemplified herein. In some embodiments, selectivity can be measured by an RNase H cleavage assay. For example, selective cleavage of a target (e.g., RNA from a mutant allele) can be measured by a biochemical RNase H cleavage assay, wherein cleavage of a mutant target sequence is compared to that of a wild-type RNA sequence, and the selectivity can be represented by either the rate of cleavage, ratio of cleaved mutant RNA and wild-type RNA at a time point, or ratio of remaining mutant RNA and wild-type RNA at a time point, or combinations thereof. In some embodiments, a time point is 5, 10, 15, 20, 25, 30, 35, 40, 45, 50, 55, 60 or more minutes. In some embodiments, a time point is 10 minutes. In some embodiments, a time point is 15 minutes. In some embodiments, a time point is 20 minutes. In some embodiments, a time point is 25 minutes. In some embodiments, a time point is 30 minutes. In some embodiments, a time point is 35 minutes. In some embodiments, a time point is 40 minutes. In some embodiments, a time point is 45 minutes. In some embodiments, a time point is 50 minutes. In some embodiments, a time point is 55 minutes. In some embodiments, a time point is 60 minutes. In some embodiments, a time point is 60 or minutes. A person having ordinary skill in the art understands how to choose a time point, for example, for cleavage shown in FIG. 32, one or more time points of 5, 10, 15, 20, 20, 45 and 60 minutes can be chosen to assess selectivity. In some embodiments, selectivity can be measured by ratios of IC50 for target (e.g., mutant) and non-target (e.g., wild-type) sequences, e.g., from cell-based assays or animal models.

Example HPLC-MS traces are presented in FIG. 36. In some embodiments, example RNase H assay conditions were described below.

DNA/RNA Duplex Preparation: Oligonucleotide concentrations were determined by measuring the absorbance in water at 260 nm. DNA/RNA duplexes were prepared by mixing equimolar solutions oligonucleotides with each strand concentration of 20 µM. The mixtures were heated at 90° C. for 2 minutes in water bath and were cooled down slowly over several hours.

Human RNase H Protein Expression and Purification: Human RNase HC clone was obtained from Prof. Wei Yang's laboratory at NIH Bethesda. The protocol for obtaining this human RNase HC (residues 136-286) has been described (Nowotny, M. et al. Structure of Human RNase H1 Complexed with an RNA/DNA Hybrid: Insight into HIV Reverse Transcription. *Molecular Cell* 28, 264-276, (2007)). The protein expression was carried out by following reported protocol with the exception that the resulting protein had an N-terminal His6 tag (SEQ ID NO: 1552). BL21(DE3) *E. coli* cells in LB medium were used for protein expression. Cells were grown at 37° C. till $OD_{600nm}$ reached around 0.7. The cultures were then cooled and 0.4 mM IPTG was added to induce protein expression overnight at 16° C. *E. coli* extract was prepared by sonication in buffer A (40 mM $NaH_2PO_4$ (pH 7.0), 1 M NaCl, 5% glycerol, 2.8 mM β-mercaptoethanol and 10 mM imidazole) with the addition of protease inhibitors (Sigma-Aldrich). The extract was purified by Ni affinity column using buffer A plus 60 mM imidazole. The protein was eluted with a linear gradient of 60 to 300 mM imidazole. The protein peak was collected and was further purified on a Mono S column (GE Healthcare) with a 100 mM-500 mM gradient of NaCl in buffer B. Fractions containing RNase HC were concentrated to 0.3 mg/mL in the storage buffer (20 mM HEPES (pH 7.0), 100 mM NaCl, 5% glycerol, 0.5 mM EDTA, 2 mM DTT) and stored at −20° C. 0.3 mg/mL enzyme concentration corresponds to 17.4 µM based on its reported extinction coefficient (32095 $cm^{-1}M^{-1}$) and MW (18963.3 Da units).

In a 96-well plate, to 50 µL DNA/RNA duplex (20 µM) was added 10 µL of 10×RNase H buffer followed by 30 µL water. The mixture was incubated at 37° C. for a few minutes and then 10 µL of 0.2 µM stock solution of enzyme was added to give a total volume of 100 µL with final substrate/enzyme concentration 10 µM/0.02 µM (500:1) and was further incubated at 37° C. Various ratios of the DNA/RNA duplex to RNase H protein were previously studied using these conditions to find this optimal ratio (500:1) to study the kinetics. The reactions were quenched at different time points using 7 µL of 500 mM EDTA disodium solution in water. For zero min time point, EDTA was added to the reaction mixture before the addition of enzyme. Controls were run to ensure that EDTA was able to inhibit the enzyme activity completely. After all the reactions were quenched 10 µL or 20 µL of each reaction mixture was injected on to LCMS-TOF using analytical column (Agilent Poroshell 120 EC-C18 2.7 micron, 2.1×150 mm, Part #699775-902). Ratio of peak area of remaining full length RNA to DNA in each reaction mixture was normalized against this ratio at zero point reaction to obtain the % of full length RNA remaining.

In some embodiments, an example HPLC condition is:
Eluant A=8 mM TEA, 200 mM HFIP in Water
Eluant B=50:50 (Eluant A: Methanol)
Column Temperature=50° C.
Auto sampler temperature=4° C.
UV was recorded at 254 nm and 280 nm
LC Gradient Method

| | Time (min) | Flow (mL/min) | % A | % B |
|---|---|---|---|---|
| 1 | 0.0 | 0.2 | 90 | 10 |
| 2 | 15.0 | 0.2 | 65 | 35 |
| 3 | 22.0 | 0.2 | 40 | 60 |
| 4 | 25.0 | 0.2 | 5.0 | 95.0 |
| 5 | 25.5 | 0.2 | 90 | 10 |
| 6 | 30 | 0.2 | 90 | 10 |

Example 20. Example Assays for Assessing Oligonucleotides

In some embodiments, the present disclosure provides reporter assays for assessing properties of provided oligonucleotides and compositions. In some embodiments, a provided reporter assay is a dual-luciferase assay, e.g., as described below.

Determination of mRNA inhibition by oligonucleotides using Dual Glo Luciferase System: The psiCheck2 vector system from Promega is a commercially available vector which encodes both *Photinus pyralis* and *Renilla reniformis* luciferase genes on a single plasmid with a multiple cloning site in the 3' UTR of *Renilla* luciferase for insertion of oligonucleotides encoding the miRNA target sites (or other cloned regulatory sequences, such as target 3'UTRs). A 250 base pairs fragment containing the targeting region of interest and its reverse complement and having appropriate overhanging bases corresponding to the restriction enzyme(s) used to digest the psiCheck vector was cloned into the psiCHECK-2 vector (Promega, C8021) between NotI and XhoI restriction enzyme sites. The vector containing the insert was sequenced to confirm correct orientation of insert, expanded and purified. Multiple vectors were generated using above design for SNPs of interest. In a typical co-transfection experiment, after the cells were at the correct density (30 to 40% confluency), oligonucleotides and vector were reverse-transfected using Lipofectamine 2000 (Life Technologies). Effects of oligonucleotides on target mRNA can be seen as early as 24 h post-transfection and were still present after 48 h. 24 hour or 48 hours after transfection of psiCheck vectors, cells were assayed for luciferase activity. Briefly, cells are washed with PBS, lysed in passive lysis buffer, luciferin reagents were added, and samples were read on a Spectramax M5 instrument (Molecular Devices). Measurements were taken at vector concentrations of 20 ng per well of a 96-well plate. The experiments were performed at various oligonucleotide concentrations (30, 10 and 3.3 nM) and two time points (24 and 48 hours). The relative levels of *Renilla* luciferase vs. Firefly were measured for untreated cells and cells which were treated with oligonucleotides targeting *Renilla* (WV-975) to measure the maximum *Renilla* knockdown. Control oligonucleotides (e.g., WV-437, WV-993, etc.) were chosen to normalize the R/F levels. In some embodiments, dual luciferase reporter assay was used to assess oligonucleotides in Cos7 cell line. In some embodiments, the cell line was cotransfected for 24 hrs with oligonucleotides and either of the psiCHECK2 plasmids, including rs362307 (T) or rs362307 (C) SNP. In some embodiments, rs362307 (T) and rs362307 (C) are referred as mu and wt.

Various chirally controlled and stereorandom oligonucleotide compositions were tested at 30 nM using the dual-luciferase assay. For oligonucleotides with mismatch at the same position (e.g., positions 8, 9, 10, 11, 12 and 13 relative to the 5'-end), chirally controlled compositions maintained high levels of wide-type measurements.

In some embodiments, when tested at 30 nM, WV-1092 selectively suppressed expression of the mutant sequence at 24 and/or 48 hours as shown by the dual luciferase reporter assay. In some embodiments, the observed selectivity for WV-1092 at 30 nM 24 hours and/or 48 hours was several fold more than other oligonucleotide compositions, e.g., WV-917, WV-1497, certain P12 stereopure oligonucleotides, etc. In some embodiments, at 30 nM, 48 hours, WV-1092 maintained over 90% wild-type, and decreased the mutant to about 30%, while WV-917 decreased the wild-type to about 60%, and mutant to about 30%. Oligonucleotides are tested at multiple conditions (e.g., concentrations, time points, etc.), and show improved properties, e.g., activity, selectivity, etc.

As understood by a person having ordinary skill in the art, oligonucleotide properties, e.g., activity, selectivity, etc., may be assessed by many other assays, such as cell-based assays, animal models, etc. In some embodiments, allele-specific suppression may be tested in cells and animal models using similar procedures as described in Hohjoh, *Pharmaceuticals* 2013, 6, 522-535; US patent application publication US 2013/0197061; Østergaard et al., *Nucleic Acids Research* 2013, 41(21), 9634-9650; Jiang et al., *Science* 2013, 342, 111-114; and U.S. Pat. No. 9,006,198. In some embodiments, selectivity can be assessed by $IC_{50}$ values for the wild-type and the mutant allele. Provided compositions, including those targeting SNPs associated with Huntington's disease, suppress disease-associated alleles selectively over wild type alleles.

Example 21. Example Methods for Preparing Oligonucleotides and Compositions

Abbreviations
AMA: conc. $NH_3$-40% $MeNH2$ in $H_2O$ (1:1, v/v)
CMIMT: N-cyanomethylimidazolium triflate
DBU: 1,8-diazabicyclo[5.4.0]undec-7-ene
DCA: dichloroacetic acid
DCM: dichloromethane, $CH_2Cl_2$
DMTr: 4,4'-dimethoxytrityl
DVB: divinylbenzene
HCP: highly cross-linked polystyrene (contains 50% DVB, non-swelling polystyrene)
MeIm: N-methylimidazole
MQ: water obtained from "Milli-Q Reference"
PhIMT: N-phenylimidazolium triflate
POS: 3-phenyl-1,2,4-dithiazolin-5-one
PS200: primer support 200, commercially available from GE Healthcare
PS5G: primer support 5G, commercially available from GE Healthcare
TBAF: tetrabutylammonium fluoride
TBHP: tert-butylhydroperoxide
TEAA: triethylammonium acetate Solid support: Various types of solid support (varied nucleosides loading) were tested. In some embodiments, HCP>PS5G≈PS200≥CPG. In some embodiments, a solid support is HCP. In some embodiments, a solid support is PS5G. In some embodiments, a solid support is PS200. In some embodiments, a solid support is CPG. For nucleosides loading, various range (30~300 μmol/g) were tested. In some embodiments, 70~80 μmol/g loading performed better than others. In some embodiments, nucleoside loading is 70~80 μmol/g. CPG was purchased from various suppliers (Glen-Reseach, LinkTechnologies, ChemGenes, PrimeSynthesis, and 3-Prime).

Various linkers were tested and can be used. In some embodiments, during preparation of chirally controlled oligonucleotide compositions by using DPSE-type chemistry, SP-linker was used.

Various activators were prepared and/or purchased, and evaluated. In some embodiments, for DPSE-type chemistry, CMIMT was used.

Example Analytical conditions:
1) RP-UPLC-MS
System: Waters, Aquity UPLC I-Class, Xevo G2-Tof
Column: Waters, BEH C18, 1.7 μm, 2.1×150 mm
Temp. & Flow rate: 55° C., 0.3 mL/min
Buffer: A: 0.1M TEAA; B: MeCN
Gradient: % B: 1-30%/30 min
2) AEX-HPLC
System: Waters, Alliance e2695
Column: Thermo, DNAPac PA-200, 4×250 mm
Temp. & Flow rate: 50° C., 1 mL/min
Buffer: A: 20 mM NaOH; B: A+1M $NaClO_4$
Gradient: % B: 10-50%/30 min Example procedure for the synthesis of chiral oligonucleotides (1 μmol scale):

Automated solid-phase synthesis of chiral oligonucleotides was performed according to example cycles shown herein. After the synthesis cycles, the resin was treated with 0.1M TBAF in MeCN (1 mL) for 2 h (30 min usually enough) at room temperature, washed with MeCN, dried, and add AMA (1 mL) for 30 min at 45° C. The mixture was cooled to room temperature and the resin was removed by membrane filtration. The filtrate was concentrated under reduced pressure to about 1 mL. The residue was diluted with 1 mL of $H_2O$ and analyzed by AEX-HPLC and RP-UPLC-MS (example conditions: refer to the analytical conditions).

| step | operation | reagents and solvent | volume | waiting time |
|---|---|---|---|---|
| 1 | detritylation | 3% DCA in toluene | 10 mL | 65 s |
| 2 | coupling | 0.15M monomer in $^iPrCN$ + 0.5M CMIMT in MeCN | 0.5 mL | 5 min |
| 3 | capping | 20% $Ac_2O$, 30% 2,6-lutidine in MeCN + 20% MeIm in MeCN | 1.2 mL | 60 s |
| 4 | oxidation or sulfurization | 1.1M TBHP in DCM-decane or 0.1M POS in MeCN | 1.0 mL | 300 s |

As described, in some embodiments, TBAF treatment can provide better results, for example, less desulfurization. In some embodiments, SP linker provided better yields and/or purity through, without the intention to be limited by theory, better stability during chiral auxiliary removal as described. In some embodiments, fluoro-containing reagents such as HF—$NR_3$ (e.g., HF-TEA (triethylamine)), provided better yields and/or purity when succinyl linker was used by, without the intention to be limited by theory, less cleavage during chiral auxiliary removal. In some embodiments, after synthesis, the resin was treated with 1M TEA-HF in DMF-$H_2O$ (3:1, v/v; 1 mL) for 2 h at 50° C. PS5G support was washed with MeCN, $H_2O$, and add AMA (conc. $NH_3$-40% MeNH2 (1:1, v/v)) (1 mL) for 45 min at 50° C. The mixture was cooled to room temperature and the resin was removed by membrane filtration (washed with $H_2O$ for 2 mL). The filtrate was concentrated under reduced pressure until it becomes about 1 mL. The residue was diluted with 1 mL of $H_2O$ and analyzed by AEX-HPLC and RP-UPLC-MS (conditions: refer to the analytical conditions section).

Example procedure for the purification of chiral oligonucleotides (1 µmol scale): in some embodiments, crude oligonucleotides were purified by AEX-MPLC according to the following example conditions:

System: AKTA Purifier-10
Column: TOHSOH, DNA STAT, 4.6×100 mm
Temp. & Flow rate: 60° C., 0.5 mL/min
Buffer: A: 20 mM Tris-HCl (pH 9.0)+20% MeCN, B: A+1.5M NaCl
Gradient: % B: 20-70%/25CV (2%/CV)

All fractions were analyzed by analytical AEX-HPLC, and fractions containing chiral oligonucleotide more than 80% purity were corrected and desalted by Sep-Pak Plus tC18 (WAT036800) using example conditions below:

1. Conditioning Sep-Pak Plus with 15 mL of MeCN.
2. Rinse cartridge with 15 mL of 50% MeCN/MQ.
3. Equilibrate cartridge with 30 mL of MQ.
4. Load sample, and wash with 40 mL of MQ.
5. Elute chiral oligonucleotides with 10 mL of 50% MeCN/MQ.

Eluted sample were evaporated under reduced pressure to remove MeCN, and lyophilized. The product were dissolved in MQ (1 mL), filtered by 0.2 µm mesh syringe filter, and analyzed. After yield calculation by UV absorbance, the preparation was lyophilized again.

In some embodiments, crude, deprotected oligonucleotides were processed by anion exchange purification. The deprotected material was loaded onto an anion exchange column (for example, SourceA15, GE). The column was equilibrated with 20 mM sodium hydroxide. The product was eluted with a gradient of 2.5 M sodium chloride in 20 mM sodium hydroxide. Fractions were collected and analyzed for % purity and pooled. The pooled product was desalted by tangential flow filtration on a regenerated cellulose 2 Kd membrane and diafiltered against water to remove the excess slat. For example, in an example procedure, regenerated cellulose membranes with MW cutoff of 2 k were used for desalting of the pooled oligonucleotides. Before desalting, one part of the pool oligonucleotides was diluted with one part of water and this solution was concentrated approximately 10×. The solution was then diafiltered with purified water for approximately 15 volumes. UV and conductivity of the permeate lines were periodically monitored. Desalting completed with a conductivity of ≤50 µS/cm for the retentate. In some embodiments, oligonucleotides were provided as salt, for example, sodium salt. In some embodiments, oligonucleotides were provided as all-sodium salt in that each acidic phosphate and/or phosphorothioate linkage independently existed as a sodium salt.

Example methods, conditions and reagents were described in, e.g., JP 2002-33436, WO2005/092909, WO2010/064146, WO2012/039448, WO2011/108682, WO2014/010250, WO2014/010780, WO2014/012081, etc., and may be useful for preparing provided oligonucleotides and/or compositions.

Additional example oligonucleotides are listed below. In some embodiments, one or more of the oligonucleotides below are used as controls. In some embodiments, one or more of the oligonucleotides below are RNA sequences as cleavage targets in one or more assays.

TABLE 5N

Example Control Oligonucleotides.

| | |
|---|---|
| WV-975 | G*T*A*G*G*A*G*T*A*G*T*G*A*A*A*G*G*C*C*A (SEQ ID NO: 783) |
| WV-1061 | mG*mU*mA*mG*mG*A*G*T*A*G*T*G*A*A*A*mG*mG*mC*mC*mA (SEQ ID NO: 784) |
| WV-1062 | mGmUmAmGmG*A*G*T*A*G*T*G*A*A*A*mGmGmCmCmA (SEQ ID NO: 785) |
| WV-1063 | mG*mU*mA*mG*mG*A*G*T*A*G*T*G*A*A*A*G*G*C*C*A (SEQ ID NO: 786) |
| WV-1064 | mC*mU*mC*mU*mU*A*C*T*G*T*G*C*T*G*T*mG*mG*mA*mC*mA (SEQ ID NO: 787) |
| WV-1065 | mCmUmCmUmU*A*C*T*G*T*G*C*T*G*T*mGmGmAmCmA (SEQ ID NO: 788) |
| WV-1066 | mC*mU*mC*mU*mU*A*C*T*G*T*G*C*T*G*T*G*G*A*C*A (SEQ ID NO: 789) |
| WV-993 | mC*mC*mU*mU*mC*C*C*T*G*A*A*G*G*T*T*mC*mC*mU*mC*mC (SEQ ID NO: 790) |
| WV-975 | All DNA, Stereorandom PS, positive control for Renilla luciferase in psiCHECK2 plasmid |
| WV-1061 | 5-10-5 (2'-OMe-DNA-2'-OMe), stereorandom PS, +ve Luciferase control for psiCHECK2 |
| WV-1062 | 5-10-5 (2'-OMe-DNA-2'-OMe), stereorandom PS, PO in the wings: +ve Luciferase control for psiCHECK2 |
| WV-1063 | 5-15 (2'-OMe-DNA), stereorandom PS, +ve Luciferase control for psiCHECK2 |
| WV-1064 | 5-10-5 (2'-OMe-DNA-2'-OMe), stereorandom PS, Negative Luciferase control for psiCHECK2 |
| WV-1065 | 5-10-5 (2'-OMe-DNA-2'-OMe), stereorandom PS, PO in the wings: Negative Luciferase control for psiCHECK2 |

TABLE 5N-continued

Example Control Oligonucleotides.

WV-1066  5-15 (2'-OMe-DNA), stereorandom PS, Negative Luciferase control for psiCHECK2

WV-993   5-10-5 (2'-OMe-DNA-2'-OMe), stereorandom PS, Negative Luciferase control for psiCHECK2

TABLE 6N

Example RNA Sequences.

| | | |
|---|---|---|
| WV-944 | rUrUrUrGrGrArArGrUrCrUrGrCrGrCrCrCrUrUrGrUrGrCrCrC (SEQ ID NO: 791) | |
| WV-945 | rUrUrUrGrGrArArGrUrCrUrGrUrGrCrCrCrUrUrGrUrGrCrCrC (SEQ ID NO: 792) | |
| WV-1073 | rGrArGrCrCrUrUrUrGrGrArArGrUrCrUrGrCrGrCrCrCrUrUrGrUrGrCrCrCrUrGrCrCrU (SEQ ID NO: 793) | |
| WV-1074 | rGrArGrCrCrUrUrUrGrGrArArGrUrCrUrGrUrGrCrCrCrUrUrGrUrGrCrCrCrUrGrCrCrU (SEQ ID NO: 794) | |
| WV-950 | rGrGrUrUrGrUrUrGrCrCrArGrGrUrUrArCrArGrCrUrGrCrUrC (SEQ ID NO: 795) | |
| WV-951 | rGrGrUrUrGrUrUrGrCrCrArGrGrUrUrArGrArGrCrUrGrCrUrC (SEQ ID NO: 796) | |
| WV-958 | rCrCrUrCrCrUrGrCrArGrGrCrUrGrGrGrUrUrGrGrCrCrC (SEQ ID NO: 797) | |
| WV-959 | rCrCrUrCrCrUrGrCrArGrGrCrUrGrGrGrCrUrGrUrUrGrGrCrCrC (SEQ ID NO: 798) | |
| ONT-453 | rGrGrUrGrArUrGrArCrArArUrUrUrArUrUrArArU (SEQ ID NO: 799) | |
| ONT-454 | rGrGrUrGrArUrGrGrCrArArUrUrArUrUrArArU (SEQ ID NO: 800) | |
| WV-944 | rs362307 | WT |
| WV-945 | rs362307 | mu |
| WV-1073 | rs362307 | WT |
| WV-1074 | rs362307 | mu |
| WV-950 | rs362306 | WT |
| WV-951 | rs362306 | mu |
| WV-958 | rs362268 | WT |
| WV-959 | rs362268 | mu |
| ONT-453 | rs7685686 | WT |
| ONT-454 | rs7685686 | mu |

Example 22. Example Oligonucleotides

Additional example oligonucleotides are listed below in Table 8.

TABLE 8

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| ONT-450 | ATTAATA AATTGTC ATCACC | 801 | A * T * T * A * A * T * A * A * T * G * T * C * A * T * C * A * C * C | 1153 | XXXXXXXXX XXXXXXXXX X | Stereorandom Htt sequence | Htt SNP rs7685686 |
| ONT-451 | ATTAATA AATTGTC ATCACC | 802 | A * ST * ST * SA * SA * ST * SA * SA * SA * ST * ST * SG * ST * SC * RA * ST * SC * SA * SC * SC | 1154 | SSSSSSSSSSS SSRSSSSS | Stereopure Htt sequence I | Htt SNP rs7685686 |
| ONT-452 | ATTAATA AATTGTC ATCACC | 803 | A * ST * ST * SA * SA * ST * SA * SA * SA * ST * ST * SG * ST * SC * SA * RT * SC * SA * SC * SC | 1155 | SSSSSSSSSSS SSSRSSSS | Stereopure Htt sequence II | Htt SNP rs7685686 |
| ONT-453 | GGUGAUG ACAAUUU AUUAAU | 804 | rGrGrUrGrArUrGrArCrArArUrUrArUrUrArArU | 1156 | 000000000 000000000 0 | RNA against Htt sequence Mutant | Htt SNP rs7685686 |
| ONT-454 | GGUGAUG GCAAUUU AUUAAU | 805 | rGrGrUrGrArUrGrGrCrArArUrUrArUrUrArArU | 1157 | 000000000 000000000 0 | RNA against Htt sequence Wild Type | Htt SNP rs7685686 |
| WV-902 | UUUGGAA GUCUGCG CCCUUGU GCCC | 806 | rUrUrUrGrGrArArGrUrCrUrGrCrGrCrCrCrUrUrGrUrGrCrCrC | 1158 | 000000000 000000000 000000 | wtRNA | muHTT SNP 362307 |
| WV-903 | UUUGGAA GUCUGUG CCCUUGU GCCC | 807 | rUrUrUrGrGrArArGrUrCrUrGrUrGrCrCrCrUrUrGrUrGrCrCrC | 1159 | 000000000 000000000 000000 | mRNA | muHTT SNP 362307 |
| WV-904 | GGGCACA AGGGCAC AGACTT | 808 | G * G * G * C * A * C * A * A * G * G * G * C * A * C * A * G * A * C * T * T | 1160 | XXXXXXXXX XXXXXXXXX X | ASO1 All DNA; stereorandom PS | muHTT SNP 362307 |
| WV-905 | GGCACAA GGGCACA GACTTC | 809 | G * G * C * A * C * A * A * G * G * G * C * A * C * A * G * A * C * T * T * C | 1161 | XXXXXXXXX XXXXXXXXX X | ASO2 All DNA; stereorandom PS | muHTT SNP 362307 |
| WV-906 | GCACAAG GGCACAG ACTTCC | 810 | G * C * A * C * A * A * G * G * G * C * A * C * A * G * A * C * T * T * C * C | 1162 | XXXXXXXXX XXXXXXXXX X | ASO3 All DNA; stereorandom PS | muHTT SNP 362307 |
| WV-907 | CACAAGG GCACAGA CTTCCA | 811 | C * A * C * A * A * G * G * G * C * A * C * A * G * A * C * T * T * C * C * A | 1163 | XXXXXXXXX XXXXXXXXX X | ASO4 All DNA; stereorandom PS | muHTT SNP 362307 |
| WV-908 | ACAAGGG CACAGAC TTCCAA | 812 | A * C * A * A * G * G * G * C * A * C * A * G * A * C * T * T * C * C * A * A | 1164 | XXXXXXXXX XXXXXXXXX X | ASO5 All DNA; stereorandom PS | muHTT SNP 362307 |
| WV-909 | CAAGGGC ACAGACT TCCAAA | 813 | C * A * A * G * G * G * C * A * C * A * G * A * C * T * T * C * C * A * A * A | 1165 | XXXXXXXXX XXXXXXXXX X | ASO6 All DNA; stereorandom PS | muHTT SNP 362307 |
| WV-910 | GGGCACA AGGGCAC AGACTT | 814 | mG * mG * mG * mC * mA * C * A * A * G * G * G * C * A * C * A * G * A * C * T * T | 1166 | XXXXXXXXX XXXXXXXXX X | ASO7 5-15 (2'-OMe-DNA); stereorandom PS | muHTT SNP 362307 |
| WV-911 | GGCACAA GGGCACA GACTTC | 815 | mG * mG * mC * mA * mC * A * A * G * G * G * C * A * C * A * G * A * C * T * T * C | 1167 | XXXXXXXXX XXXXXXXXX X | ASO8 5-15 (2'-OMe-DNA); stereorandom PS | muHTT SNP 362307 |
| WV-912 | GCACAAG GGCACAG ACTTCC | 816 | mG * mC * mA * mC * mA * A * G * G * G * C * A * C * A * G * A * C * T * T * C * C | 1168 | XXXXXXXXX XXXXXXXXX X | ASO9 5-15 (2'-OMe-DNA); stereorandom PS | muHTT SNP 362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-913 | CACAAGGGCACAGACTTCCA | 817 | mC * mA * mC * mA * mA * G * G * C * A * C * A * G * A * C * T * T * C * C * A | 1169 | XXXXXXXXXXXXXXXXXXX | ASO10 5-15 (2'-OMe-DNA); stereorandom PS | muHTT SNP 362307 |
| WV-914 | ACAAGGGCACAGACTTCCAA | 818 | mA * mC * mA * mA * mG * G * G * C * A * C * A * G * A * C * T * T * C * C * A * A | 1170 | XXXXXXXXXXXXXXXXXXX | ASO11 5-15 (2'-OMe-DNA); stereorandom PS | muHTT SNP 362307 |
| WV-915 | CAAGGGCACAGACTTCCAAA | 819 | mC * mA * mA * mG * mG * G * C * A * C * A * G * A * C * T * T * C * C * A * A * A | 1171 | XXXXXXXXXXXXXXXXXXX | ASO12 5-15 (2'-OMe-DNA); stereorandom PS | muHTT SNP 362307 |
| WV-916 | GGGCACAAGGGCACAGACUU | 820 | mG * mG * mG * mC * mA * C * A * A * G * G * G * C * A * C * A * mG * mA * mC * mU * mU | 1172 | XXXXXXXXXXXXXXXXXXX | ASO13 5-10-5 (2'-OMe-DNA-2'-OMe); stereorandom PS | muHTT SNP 362307 |
| WV-917 | GGCACAAGGGCACAGACUUC | 821 | mG * mG * mC * mA * mC * A * A * G * G * G * C * A * C * A * G * mA * mC * mU * mU * mC | 1173 | XXXXXXXXXXXXXXXXXXX | ASO14 5-10-5 (2'-OMe-DNA-2'-OMe); stereorandom PS | muHTT SNP 362307 |
| WV-918 | GCACAAGGGCACAGACUUCC | 822 | mG * mC * mA * mC * mA * A * G * G * G * C * A * C * A * G * A * mC * mU * mU * mC * mC | 1174 | XXXXXXXXXXXXXXXXXXX | ASO15 5-10-5 (2'-OMe-DNA-2'-OMe); stereorandom PS | muHTT SNP 362307 |
| WV-919 | CACAAGGGCACAGACUUCCA | 823 | mC * mA * mC * mA * mA * G * G * C * A * C * A * G * A * C * mU * mU * mC * mC * mA | 1175 | XXXXXXXXXXXXXXXXXXX | ASO16 5-10-5 (2'-OMe-DNA-2'-OMe); stereorandom PS | muHTT SNP 362307 |
| WV-920 | ACAAGGGCACAGACUUCCAA | 824 | mA * mC * mA * mA * mG * G * G * C * A * C * A * G * A * C * T * mU * mC * mC * mA * mA | 1176 | XXXXXXXXXXXXXXXXXXX | ASO17 5-10-5 (2'-OMe-DNA-2'-OMe); stereorandom PS | muHTT SNP 362307 |
| WV-921 | CAAGGGCACAGACUUCCAAA | 825 | mC * mA * mA * mG * mG * G * C * A * C * A * G * A * C * T * mC * mC * mA * mA * mA | 1177 | XXXXXXXXXXXXXXXXXXX | ASO18 5-10-5 (2'-OMe-DNA-2'-OMe); stereorandom PS | muHTT SNP 362307 |
| WV-922 | GCACAAGGGCACAGACUUCC | 826 | mG * mC * mA * mC * mA * mA * mG * mG * G * C * A * C * A * G * A * mC * mU * mU * mC * mC | 1178 | XXXXXXXXXXXXXXXXXXX | ASO19 8-7-5 (2'-OMe-DNA-2'-OMe); stereorandom PS | muHTT SNP 362307 |
| WV-923 | CACAAGGGCACAGACUUCCA | 827 | mC * mA * mC * mA * mA * mG * mG * G * C * A * C * A * G * A * mC * mU * mU * mC * mC * mA | 1179 | XXXXXXXXXXXXXXXXXXX | ASO20 7-7-6 (2'-OMe-DNA-2'-OMe); stereorandom PS | muHTT SNP 362307 |
| WV-924 | ACAAGGGCACAGACUUCCAA | 828 | mA * mC * mA * mA * mG * mG * G * C * A * C * A * G * A * mC * mU * mU * mC * mC * mA * mA | 1180 | XXXXXXXXXXXXXXXXXXX | ASO21 6-7-5 (2'-OMe-DNA-2'-OMe); stereorandom PS; PO in the wings | muHTT SNP 362307 |
| WV-925 | CAAGGGCACAGACUUCCAAA | 829 | mC * mA * mA * mG * mG * G * C * A * C * A * G * A * mC * mU * mU * mC * mC * mA * mA * mA | 1181 | XXXXXXXXXXXXXXXXXXX | ASO22 5-7-8 (2'-OMe-DNA-2'-OMe); stereorandom PS; PO in the wings | muHTT SNP 362307 |
| WV-926 | GCACAAGGGCACAGACUUCC | 830 | mGmCmAmCmAmAmGmG * G * C * A * C * A * G * A * mCmUmUmCmC | 1182 | OOOOOOOOXXXXXXXOOOO | ASO23 8-7-5 (2'-OMe-DNA-2'-OMe); stereorandom PS; PO in the wings | muHTT SNP 362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-927 | CACAAGG GCACAGA CUUCCA | 831 | mCmAmCmAmAmGmG * G * C * A * C * A * G * A * mCmUmUmCmCmA | 1183 | OOOOOOXXX XXXXXOOOO O | ASO24 7-7-6 (2'-OMe-DNA-2'-OMe); stereorandom PS; PO in the wings | muHTT SNP 362307 |
| WV-928 | ACAAGGG CACAGAC UUCCAA | 832 | mAmCmAmAmGmG * G * C * A * C * A * G * A * mCmUmUmCmCmAmA | 1184 | OOOOOXXXX XXXXOOOOO O | ASO25 6-7-5 (2'-OMe-DNA-2'-OMe); stereorandom PS; PO in the wings | muHTT SNP 362307 |
| WV-929 | CAAGGGC ACAGACU UCCAAA | 833 | mCmAmAmGmG * G * C * A * C * A * G * A * mCmUmUmCmCmAmAmA | 1185 | OOOOXXXXX XXXOOOOOO O | ASO26 5-7-8 (2'-OMe-DNA-2'-OMe); stereorandom PS; PO in the wings | muHTT SNP 362307 |
| WV-930 | GGGCACA AGGGCAC AGACUU | 834 | mGmGmGmCmA * C * A * A * G * G * G * C * A * C * A * mGmAmCmUmU | 1186 | OOOOOXXXXX XXXXXXOOO O | ASO27 5-10-5 (2'-OMe-DNA-2'-OMe); stereorandom PS; PO in the wings | muHTT SNP 362307 |
| WV-931 | GGCACAA GGGCACA GACUUC | 835 | mGmGmCmAmC * A * A * G * G * G * C * A * C * A * G * mAmCmUmUmC | 1187 | OOOOOXXXXX XXXXXXOOO O | ASO28 5-10-5 (2'-OMe-DNA-2'-OMe); stereorandom PS; PO in the wings | muHTT SNP 362307 |
| WV-932 | GCACAAG GGCACAG ACUUCC | 836 | mGmCmAmCmA * A * G * G * G * C * A * C * A * G * A * mCmUmUmCmC | 1188 | OOOOOXXXXX XXXXXXOOO O | ASO29 5-10-5 (2'-OMe-DNA-2'-OMe); stereorandom PS; PO in the wings | muHTT SNP 362307 |
| WV-933 | CACAAGG GCACAGA CUUCCA | 837 | mCmAmCmAmA * G * G * G * C * A * C * A * G * A * C * mUmUmCmCmA | 1189 | OOOOOXXXXX XXXXXXOOO O | ASO30 5-10-5 (2'-OMe-DNA-2'-OMe); stereorandom PS; PO in the wings | muHTT SNP 362307 |
| WV-934 | ACAAGGG CACAGAC TUCCAA | 838 | mAmCmAmAmG * G * G * C * A * C * A * G * A * C * T * mUmCmCmAmA | 1190 | OOOOOXXXXX XXXXXXOOO O | ASO31 5-10-5 (2'-OMe-DNA-2'-OMe); stereorandom PS; PO in the wings | muHTT SNP 362307 |
| WV-935 | CAAGGGC ACAGACT TCCAAA | 839 | mCmAmAmGmG * G * C * A * C * A * G * A * C * T * T * mCmCmAmAmA | 1191 | OOOOOXXXXX XXXXXXOOO O | ASO32 5-10-5 (2'-OMe-DNA-2'-OMe); stereorandom PS; PO in the wings | muHTT SNP 362307 |
| WV-936 | GGGCACA AGGGCAC AGACTT | 840 | G * SG * SG * SC * SA * SC * SA * SA * SG * SG * SG * SC * SA * SC * RA * SG * SA * SC * ST * ST | 1192 | SSSSSSSSSS SSRSSSSS | ASO33 Stereopure DNA; One Rp; position 14 | muHTT SNP 362307 |
| WV-937 | GGCACAA GGGCACA GACTTC | 841 | G * SG * SC * SA * SC * SA * SA * SG * SG * SG * SC * SA * SC * RA * SG * SA * SC * ST * ST * SC | 1193 | SSSSSSSSSS SRSSSSSS | ASO34 Stereopure DNA; One Rp; position 13 | muHTT SNP 362307 |
| WV-938 | GCACAAG GGCACAG ACTTCC | 842 | G * SC * SA * SC * SA * SA * SG * SG * SG * SC * SA * SC * RA * SG * SA * SC * ST * ST * SC * SC | 1194 | SSSSSSSSSS RSSSSSSS | ASO35 Stereopure DNA; One Rp; position 12 | muHTT SNP 362307 |
| WV-939 | CACAAGG GCACAGA CTTCCA | 843 | C * SA * SC * SA * SA * SG * SG * SG * SC * SA * SC * RA * SG * SA * SC * ST * ST * SC * SC * SA | 1195 | SSSSSSSSSSR SSSSSSSS | ASO36 Stereopure DNA; One Rp; position 11 | muHTT SNP 362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-940 | ACAAGGGCACAGACTTCCAA | 844 | A * SC * SA * SA * SG * SG * SG * SC * SA * SC * RA * SG * SA * SC * ST * ST * SC * SC * SA * SA | 1196 | SSSSSSSSSRSSSSSSSSS | ASO37 Stereopure DNA; One Rp; position 10 | muHTT SNP 362307 |
| WV-941 | CAAGGGCACAGACTTCCAAA | 845 | C * SA * SA * SG * SG * SG * SC * SA * SC * RA * SG * SA * SC * ST * ST * SC * SC * SA * SA * SA | 1197 | SSSSSSSSRSSSSSSSSS | ASO38 Stereopure DNA; One Rp; position 9 | muHTT SNP 362307 |
| WV-944 | UUUGGAAGUCUGCGCCCUUGUGCCC | 846 | rUrUrUrGrGrArArGrUrCrUrGrCrGrCrCrCrUrUrGrUrGrCrCrC | 1198 | 000000000000000000000000 | HTT-rs362307 human | Huntington |
| WV-945 | UUUGGAAGUCUGUGCCCUUGUGCCC | 847 | rUrUrUrGrGrArArGrUrCrUrGrUrGrCrCrCrUrUrGrUrGrCrCrC | 1199 | 000000000000000000000000 | HTT-rs362307 human | Huntington |
| WV-948 | GAGCAGCTGCAACCTGGCAA | 848 | G * A * G * C * A * G * C * T * G * C * A * A * C * C * T * G * G * C * A * A | 1200 | XXXXXXXXXXXXXXXXXXX | HTT-rs362306 | HTT-rs362306 |
| WV-949 | GGGCCAACAGCCAGCCTGCA | 849 | G * G * G * C * C * A * A * C * A * G * C * C * A * G * C * C * T * G * C * A | 1201 | XXXXXXXXXXXXXXXXXXX | HTT-rs362268 | HTT-rs362268 |
| WV-950 | GGUUGUUGCCAGGUUACAGCUGCUCGGUUGUU | 850 | rGrGrUrUrGrUrUrGrCrCrArGrGrUrUrArCrArGrCrUrGrCrUrC | 1202 | 000000000000000000000000 | | HTT-rs362306 |
| WV-951 | GCCAGGUUGCAGCUGCUC | 851 | rGrGrUrUrGrUrUrGrCrCrArGrGrUrUrGrCrArGrCrUrGrCrUrC | 1203 | 000000000000000000000000 | | HTT-rs362306 |
| WV-952 | GAGCAGCTGCAACCTGGCAA | 852 | G * SA * SG * SC * SA * SG * SC * ST * SG * SC * SA * RA * SC * SC * ST * SG * SG * SC * SA * SA | 1204 | SSSSSSSSSSRSSSSSSSS | Stereopure PS DNA; One Rp at position 11 | HTT-rs362306 |
| WV-953 | AGCAGCTGCAACCTGGCAAC | 853 | A * SG * SC * SA * SG * SC * ST * SG * SC * SA * RA * SC * SC * ST * SG * SG * SC * SA * SA * SC | 1205 | SSSSSSSSSRSSSSSSSSS | Stereopure PS DNA; One Rp at position 10 | HTT-rs362306 |
| WV-954 | GCAGCTGCAACCTGGCAACA | 854 | G * SC * SA * SG * SC * ST * SG * SC * SA * RA * SC * SC * ST * SG * SG * SC * SA * SA * SC * SA | 1206 | SSSSSSSSRSSSSSSSSS | Stereopure PS DNA; One Rp at position 9 | HTT-rs362306 |
| WV-955 | CAGCTGCAACCTGGCAACAA | 855 | C * SA * SG * SC * ST * SG * SC * SA * RA * SC * SC * ST * SG * SG * SC * SA * SA * SC * SA * SA | 1207 | SSSSSSSRSSSSSSSSS | Stereopure PS DNA; One Rp at position 8 | HTT-rs362306 |
| WV-956 | AGCTGCAACCTGGCAACAAC | 856 | A * SG * SC * ST * SG * SC * SA * RA * SC * SC * ST * SG * SG * SC * SA * SA * SC * SA * SA * SC | 1208 | SSSSSSRSSSSSSSSS | Stereopure PS DNA; One Rp at position 7 | HTT-rs362306 |
| WV-957 | GCTGCAACCTGGCAACAACC | 857 | G * SC * ST * SG * SC * SA * RA * SC * SC * ST * SG * SG * SC * SA * SA * SC * SA * SA * SC * SC | 1209 | SSSSSRSSSSSSSSS | Stereopure PS DNA; One Rp at position 6 | HTT-rs362306 |
| WV-958 | CCUCCUGCAGGCUGGGUGUUGCCC | 858 | rCrCrUrCrCrUrGrCrArGrGrCrUrGrGrGrUrGrUrUrGrCrCrC | 1210 | 000000000000000000000000 | | HTT-rs362268 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-959 | CCUCCUG CAGGCUG GCUGUUG GCCC | 859 | rCrCrUrCrCrUrGrCrArGrGrCrU rGrCrUrGrUrUrGrGrCrCrC | 1211 | 000000000 000000000 000000 | | HTT-rs362268 |
| WV-960 | GGGCCAA CAGCCAG CCTGCA | 860 | G * SG * SG * SC * SC * SA * SA * SC * SA * SG * SC * RC * SA * SG * SC * SC * ST * SG * SC * SA | 1212 | SSSSSSSSSR SSSSSSSS | Stereopure PS DNA; One Rp at position 11 | HTT-rs362268 |
| WV-961 | GGCCAAC AGCCAGC CTGCAG | 861 | G * SG * SC * SC * SA * SA * SC * SA * SG * SC * RC * SA * SG * SC * SC * ST * SG * SC * SA * SG | 1213 | SSSSSSSSSRS SSSSSSSS | Stereopure PS DNA; One Rp at position 10 | HTT-rs362268 |
| WV-962 | GCCAACA GCCAGCC TGCAGG | 862 | G * SC * SC * SA * SA * SC * SA * SG * SC * RC * SA * SG * SC * SC * ST * SG * SC * SA * SG * SG | 1214 | SSSSSSSSRSS SSSSSSSS | Stereopure PS DNA; One Rp at position 9 | HTT-rs362268 |
| WV-963 | CCAACAG CCAGCCT GCAGGA | 863 | C * SC * SA * SA * SC * SA * SG * SC * RC * SA * SG * SC * SC * ST * SG * SC * SA * SG * SA | 1215 | SSSSSSSRSSS SSSSSSSS | Stereopure PS DNA; One Rp at position 8 | HTT-rs362268 |
| WV-964 | CAACAGC CAGCCTG CAGGAG | 864 | C * SA * SA * SC * SA * SG * SC * RC * SA * SG * SC * SC * ST * SG * SC * SA * SG * SG * SA * SG | 1216 | SSSSSSRSSSS SSSSSSSS | Stereopure PS DNA; One Rp at position 7 | HTT-rs362268 |
| WV-965 | AACAGCC AGCCTGC AGGAGG | 865 | A * SA * SC * SA * SG * SC * RC * SA * SG * SC * SC * ST * SG * SC * SA * SG * SG * SA * SG * SG | 1217 | SSSSSRSSSSS SSSSSSSS | Stereopure PS DNA; One Rp at position 6 | HTT-rs362268 |
| WV-973 | GGCCUUU CACUACU CCUACTT | 866 | rGrGrCrCrUrUrUrCrArCrUrArC rUrCrCrUrArCTT | 1218 | 000000000 000000000 00 | siRNA (+control for Renilla luciferase in psiCHECK2 plasmid) antisense strand | Htt |
| WV-974 | GUAGGAG UAGUGAA AGGCCTT | 867 | rGrUrArGrGrArGrUrArGrUrGr ArArArGrGrCrCTT | 1219 | 000000000 000000000 00 | siRNA (+control for Renilla luciferase in psiCHECK2 plasmid) sense strand | Htt SNP rs362268 |
| WV-975 | GTAGGAG TAGTGAA AGGCCA | 868 | G * T * A * G * G * A * G * T * A * G * T * G * A * A * A * G * G * C * C * A | 1220 | XXXXXXXXX XXXXXXXXX X | ASO (+control for Renilla luciferase in psiCHECK2 plasmid) | Htt SNP rs362268 |
| WV-982 | GCAGGGC ACAAGGG CACAGA | 869 | G * SC * SA * SG * SG * SG * SC * SA * SC * SA * SA * SG * SG * SG * SC * SA * SC * RA * SG * SA | 1221 | SSSSSSSSSSS SSSSSRSS | Htt seq 307 expanding 3 nt towards 3' example 3 | Htt rs362307 |
| WV-983 | CAGGGCA CAAGGGC ACAGAC | 870 | C * SA * SG * SG * SG * SC * SA * SC * SA * SA * SG * SG * SG * SC * SA * SC * RA * SG * SA * SC | 1222 | SSSSSSSSSSS SSSSSRSSS | Htt seq 307 expanding 3 nt towards 3' example 2 | Htt rs362307 |
| WV-984 | AGGGCAC AAGGGCA CAGACT | 871 | A * SG * SG * SG * SC * SA * SC * SA * SA * SG * SG * SG * SC * SA * SC * RA * SG * SA * SC * ST | 1223 | SSSSSSSSSSS SSSRSSSS | Htt seq 307 expanding 3 nt towards 3' example 1 | Htt rs362307 |
| WV-985 | AAGGGCA CAGACTT CCAAAG | 872 | A * SA * SG * SG * SG * SC * SA * SC * SA * RA * SG * SA * SC * ST * ST * SC * SC * SA * SA * SA * SG | 1224 | SSSSSSSRSSS SSSSSSSS | Htt seq 307 expanding 3 nt towards 5' example 1 | Htt rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-986 | AGGGCAC AGACTTC CAAAGG | 873 | A * SG * SG * SG * SC * SA * SC * RA * SG * SA * SC * ST * ST * SC * SC * SA * SA * SA * SG * SG | 1225 | SSSSSRSSSS SSSSSSSS | Htt seq 307 expanding 3 nt towards 5' example 2 | Htt rs362307 |
| WV-987 | GGGCACA GACTTCC AAAGGC | 874 | G * SG * SG * SC * SA * SC * RA * SG * SA * SC * ST * ST * SC * SC * SA * SA * SA * SG * SC | 1226 | SSSSSRSSSS SSSSSSSS | Htt seq 307 expanding 3 nt towards 5' example 3 | Htt rs362307 |
| WV-1001 | GAGCAGC TGCAACC TGGCAA | 875 | G * A * G * C * A * G * C * T * G * C * A * A * C * C * T * G * G * C * A * A | 1227 | XXXXXXXXX XXXXXXXXX X | All DNA; stereorandom PS | HTT-rs362306 |
| WV-1002 | AGCAGCT GCAACCT GGCAAC | 876 | A * G * C * A * G * C * T * G * C * A * A * C * C * T * G * G * C * A * A * C | 1228 | XXXXXXXXX XXXXXXXXX X | All DNA; stereorandom PS | HTT-rs362306 |
| WV-1003 | GCAGCTG CAACCTG GCAACA | 877 | G * C * A * G * C * T * G * C * A * A * C * C * T * G * G * C * A * A * C * A | 1229 | XXXXXXXXX XXXXXXXXX X | All DNA; stereorandom PS | HTT-rs362306 |
| WV-1004 | CAGCTGC AACCTGG CAACAA | 878 | C * A * G * C * T * G * C * A * A * C * C * T * G * G * C * A * A * C * A * A | 1230 | XXXXXXXXX XXXXXXXXX X | All DNA; stereorandom PS | HTT-rs362306 |
| WV-1005 | AGCTGCA ACCTGGC AACAAC | 879 | A * G * C * T * G * C * A * A * C * C * T * G * G * C * A * A * C * A * A * C | 1231 | XXXXXXXXX XXXXXXXXX X | All DNA; stereorandom PS | HTT-rs362306 |
| WV-1006 | GCTGCAA CCTGGCA ACAACC | 880 | G * C * T * G * C * A * A * C * C * T * G * G * C * A * A * C * A * A * C * C | 1232 | XXXXXXXXX XXXXXXXXX X | All DNA; stereorandom PS | HTT-rs362306 |
| WV-1007 | GAGCAGC TGCAACC TGGCAA | 881 | mG * mA * mG * mC * mA * G * C * T * G * C * A * A * C * C * T * G * G * C * A * A | 1233 | XXXXXXXXX XXXXXXXXX X | 5-15 (2'-OMe-DNA); stereorandom PS | HTT-rs362306 |
| WV-1008 | AGCAGCT GCAACCT GGCAAC | 882 | mA * mG * mC * mA * mG * C * T * G * C * A * A * C * C * T * G * G * C * A * A * C | 1234 | XXXXXXXXX XXXXXXXXX X | 5-15 (2'-OMe-DNA); stereorandom PS | HTT-rs362306 |
| WV-1009 | GCAGCTG CAACCTG GCAACA | 883 | mG * mC * mA * mG * mC * T * G * C * A * A * C * C * T * G * G * C * A * A * C * A | 1235 | XXXXXXXXX XXXXXXXXX X | 5-15 (2'-OMe-DNA); stereorandom PS | HTT-rs362306 |
| WV-1010 | CAGCUGC AACCTGG CAACAA | 884 | mC * mA * mG * mC * mU * G * C * A * A * C * C * T * G * G * C * A * A * C * A * A | 1236 | XXXXXXXXX XXXXXXXXX X | 5-15 (2'-OMe-DNA); stereorandom PS | HTT-rs362306 |
| WV-1011 | AGCUGCA ACCTGGC AACAAC | 885 | mA * mG * mC * mU * mG * C * A * A * C * C * T * G * G * C * A * A * C * A * A * C | 1237 | XXXXXXXXX XXXXXXXXX X | 5-15 (2'-OMe-DNA); stereorandom PS | HTT-rs362306 |
| WV-1012 | GCUGCAA CCTGGCA ACAACC | 886 | mG * mC * mU * mG * mC * A * A * C * C * T * G * G * C * A * A * C * A * A * C * C | 1238 | XXXXXXXXX XXXXXXXXX X | 5-15 (2'-OMe-DNA); stereorandom PS | HTT-rs362306 |
| WV-1013 | GAGCAGC TGCAACC TGGCAA | 887 | mG * mA * mG * mC * mA * G * C * T * G * C * A * A * C * C * T * mG * mG * mC * mA * mA | 1239 | XXXXXXXXX XXXXXXXXX X | 5-10-5 (2'-OMe-DNA-2'-OMe); stereorandom PS | HTT-rs362306 |
| WV-1014 | AGCAGCT GCAACCT GGCAAC | 888 | mA * mG * mC * mA * mG * C * T * G * C * A * A * C * C * T * G * mG * mC * mA * mA * mC | 1240 | XXXXXXXXX XXXXXXXXX X | 5-10-5 (2'-OMe-DNA-2'-OMe); stereorandom PS | HTT-rs362306 |
| WV-1015 | GCAGCTG CAACCTG GCAACA | 889 | mG * mC * mA * mG * mC * T * G * C * A * A * C * C * T * G * mG * mC * mA * mA * mC * mA | 1241 | XXXXXXXXX XXXXXXXXX X | 5-10-5 (2'-OMe-DNA-2'-OMe); stereorandom PS | HTT-rs362306 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1016 | CAGCUGC AACCTGG CAACAA | 890 | mC * mA * mG * mC * mU * G * C * A * A * C * C * T * G * G * C * mA * mA * mC * mA * mA | 1242 | XXXXXXXXX XXXXXXXXX X | 5-10-5 (2'-OMe-DNA-2'-OMe); stereorandom PS | HTT-rs362306 |
| WV-1017 | AGCUGCA ACCTGGC AACAAC | 891 | mA * mG * mC * mU * mG * C * A * A * C * C * T * G * G * C * mA * mA * mC * mA * mA * mC | 1243 | XXXXXXXXX XXXXXXXXX X | 5-10-5 (2'-OMe-DNA-2'-OMe); stereorandom PS | HTT-rs362306 |
| WV-1018 | GCUGCAA CCTGGCA ACAACC | 892 | mG * mC * mU * mG * mC * A * A * C * C * T * G * G * C * A * A * mC * mA * mA * mC * mC | 1244 | XXXXXXXXX XXXXXXXXX X | 5-10-5 (2'-OMe-DNA-2'-OMe); stereorandom PS | HTT-rs362306 |
| WV-1019 | GAGCAGC TGCAACC UGGCAA | 893 | mG * mA * mG * mC * mA * mG * mC * T * G * C * A * A * C * C * mU * mG * mG * mC * mA * mA | 1245 | XXXXXXXXX XXXXXXXXX X | 7-7-6 (2'-OMe-DNA-2'-OMe); stereorandom PS | HTT-rs362306 |
| WV-1020 | GAGCAGC TGCAACC UGGCAA | 894 | mGmAmGmCmAmGmC * T * G * C * A * A * C * C * mUmGmGmCmAmA | 1246 | OOOOOOXXX XXXXXOOOO O | 7-7-6 (2'-OMe-DNA-2'-OMe); stereorandom PS; PO in wings | HTT-rs362306 |
| WV-1021 | AGCAGCT GCAACCT GGCAAC | 895 | mA * mG * mC * mA * mG * mC * T * G * C * A * A * C * C * T * G * mG * mC * mA * mA * mC | 1247 | XXXXXXXXX XXXXXXXXX X | 6-7-5 (2'-OMe-DNA-2'-OMe); stereorandom PS | HTT-rs362306 |
| WV-1022 | AGCAGCT GCAACCT GGCAAC | 896 | mAmGmCmAmGmC * T * G * C * A * A * C * C * T * G * mGmCmAmAmC | 1248 | OOOOOXXXX XXXXXXOOO O | 6-7-5 (2'-OMe-DNA-2'-OMe); stereorandom PS; PO in the wings | HTT-rs362306 |
| WV-1023 | GCAGCTG CAACCUG GCAACA | 897 | mG * mC * mA * mG * mC * T * G * C * A * A * C * C * mU * mG * mG * mC * mA * mA * mC * mA | 1249 | XXXXXXXXX XXXXXXXXX X | 5-7-8 (2'-OMe-DNA-2'-OMe); stereorandom PS | HTT-rs362306 |
| WV-1024 | GCAGCTG CAACCUG GCAACA | 898 | mGmCmAmGmC * T * G * C * A * A * C * C * mUmGmGmCmAmAmCmA | 1250 | OOOOOXXXX XXXOOOOOO O | 5-7-8 (2'-OMe-DNA-2'-OMe); stereorandom PS; PO in the wings | HTT-rs362306 |
| WV-1025 | GAGCAGC TGCAACC TGGCAA | 899 | mGmAmGmCmA * G * C * T * G * C * A * A * C * C * T * mGmGmCmAmA | 1251 | OOOOOXXXX XXXXXXOOO O | 5-10-5 (2'-OMe-DNA-2'-OMe); stereorandom PS; PO in the wings | HTT-rs362306 |
| WV-1026 | AGCAGCT GCAACCT GGCAAC | 900 | mAmGmCmAmG * C * T * G * C * A * A * C * C * T * G * mGmCmAmAmC | 1252 | OOOOOXXXX XXXXXXOOO O | 5-10-5 (2'-OMe-DNA-2'-OMe); stereorandom PS; PO in the wings | HTT-rs362306 |
| WV-1027 | GCAGCTG CAACCTG GCAACA | 901 | mGmCmAmGmCT * G * C * A * A * C * C * T * G * G * mCmAmAmCmA | 1253 | OOOOOXXXX XXXXXXOOO O | 5-10-5 (2'-OMe-DNA-2'-OMe); stereorandom PS; PO in the wings | HTT-rs362306 |
| WV-1028 | CAGCUGC AACCTGG CAACAA | 902 | mCmAmGmCmU * G * C * A * A * C * C * T * G * G * C * mAmAmCmAmA | 1254 | OOOOOXXXX XXXXXXOOO O | 5-10-5 (2'-OMe-DNA-2'-OMe); stereorandom PS; PO in the wings | HTT-rs362306 |
| WV-1029 | AGCUGCA ACCTGGC AACAAC | 903 | mAmGmCmUmG * C * A * A * C * C * T * G * G * C * A * mAmCmAmAmC | 1255 | OOOOOXXXX XXXXXXOOO O | 5-10-5 (2'-OMe-DNA-2'-OMe); stereorandom PS; PO in the wings | HTT-rs362306 |
| WV-1030 | GCUGCAA CCTGGCA ACAACC | 904 | mGmCmUmGmC * A * A * C * C * T * G * G * C * A * A * mCmAmAmCmC | 1256 | OOOOOXXXX XXXXXXOOO O | 5-10-5 (2'-OMe-DNA-2'-OMe); stereorandom PS; PO in the wings | HTT-rs362306 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1031 | GGGCCAA CAGCCAG CCTGCA | 905 | G * G * G * C * C * A * A * C * A * G * C * C * A * G * C * C * T * G * C * A | 1257 | XXXXXXXXX XXXXXXXXX X | All DNA; stereorandom PS | HTT-rs362268 |
| WV-1032 | GGCCAAC AGCCAGC CTGCAG | 906 | G * G * C * C * A * A * C * A * G * C * C * A * G * C * C * T * G * C * A * G | 1258 | XXXXXXXXX XXXXXXXXX X | All DNA; stereorandom PS | HTT-rs362268 |
| WV-1033 | GCCAACA GCCAGCC TGCAGG | 907 | G * C * C * A * A * C * A * G * C * C * A * G * C * C * T * G * C * A * G * G | 1259 | XXXXXXXXX XXXXXXXXX X | All DNA; stereorandom PS | HTT-rs362268 |
| WV-1034 | CCAACAG CCAGCCT GCAGGA | 908 | C * C * A * A * C * A * G * C * C * A * G * C * C * T * G * C * A * G * G * A | 1260 | XXXXXXXXX XXXXXXXXX X | All DNA; stereorandom PS | HTT-rs362268 |
| WV-1035 | CAACAGC CAGCCTG CAGGAG | 909 | C * A * A * C * A * G * C * C * A * G * C * C * T * G * C * A * G * G * A * G | 1261 | XXXXXXXXX XXXXXXXXX X | All DNA; stereorandom PS | HTT-rs362268 |
| WV-1036 | AACAGCC AGCCTGC AGGAGG | 910 | A * A * C * A * G * C * C * A * G * C * C * T * G * C * A * G * G * A * G * G | 1262 | XXXXXXXXX XXXXXXXXX X | All DNA; stereorandom PS | HTT-rs362268 |
| WV-1037 | GGGCCAA CAGCCAG CCTGCA | 911 | mG * mG * mG * mC * mC * A * A * C * A * G * C * C * A * G * C * C * T * G * C * A | 1263 | XXXXXXXXX XXXXXXXXX X | 5-15 (2'-OMe-DNA); stereorandom PS | HTT-rs362268 |
| WV-1038 | GGCCAAC AGCCAGC CTGCAG | 912 | mG * mG * mC * mC * mA * A * C * A * G * C * C * A * G * C * C * T * G * C * A * G | 1264 | XXXXXXXXX XXXXXXXXX X | 5-15 (2'-OMe-DNA); stereorandom PS | HTT-rs362268 |
| WV-1039 | GCCAACA GCCAGCC TGCAGG | 913 | mG * mC * mC * mA * mA * C * A * G * C * C * A * G * C * C * T * G * C * A * G * G | 1265 | XXXXXXXXX XXXXXXXXX X | 5-15 (2'-OMe-DNA); stereorandom PS | HTT-rs362268 |
| WV-1040 | CCAACAG CCAGCCT GCAGGA | 914 | mC * mC * mA * mA * mC * A * G * C * C * A * G * C * C * T * G * C * A * G * G * A | 1266 | XXXXXXXXX XXXXXXXXX X | 5-15 (2'-OMe-DNA); stereorandom PS | HTT-rs362268 |
| WV-1041 | CAACAGC CAGCCTG CAGGAG | 915 | mC * mA * mA * mC * mA * G * C * C * A * G * C * C * T * G * C * A * G * G * A * G | 1267 | XXXXXXXXX XXXXXXXXX X | 5-15 (2'-OMe-DNA); stereorandom PS | HTT-rs362268 |
| WV-1042 | AACAGCC AGCCTGC AGGAGG | 916 | mA * mA * mC * mA * mG * C * C * A * G * C * C * T * G * C * A * G * G * A * G * G | 1268 | XXXXXXXXX XXXXXXXXX X | 5-15 (2'-OMe-DNA); stereorandom PS | HTT-rs362268 |
| WV-1043 | GGGCCAA CAGCCAG CCUGCA | 917 | mG * mG * mG * mC * mC * A * A * C * A * G * C * C * A * G * C * C * mC * mU * mG * mC * mA | 1269 | XXXXXXXXX XXXXXXXXX X | 5-10-5 (2'-OMe-DNA-2'-OMe); stereorandom PS | HTT-rs362268 |
| WV-1044 | GGCCAAC AGCCAGC CUGCAG | 918 | mG * mG * mC * mC * mA * A * C * A * G * C * C * A * G * C * mC * mU * mG * mC * mA * mG | 1270 | XXXXXXXXX XXXXXXXXX X | 5-10-5 (2'-OMe-DNA-2'-OMe); stereorandom PS | HTT-rs362268 |
| WV-1045 | GCCAACA GCCAGCC TGCAGG | 919 | mG * mC * mC * mA * mA * C * A * G * C * C * A * G * C * C * mT * mG * mC * mA * mG * mG | 1271 | XXXXXXXXX XXXXXXXXX X | 5-10-5 (2'-OMe-DNA-2'-OMe); stereorandom PS | HTT-rs362268 |
| WV-1046 | CCAACAG CCAGCCT GCAGGA | 920 | mC * mC * mA * mA * mC * A * G * C * C * A * G * C * C * T * G * mC * mA * mG * mG * mA | 1272 | XXXXXXXXX XXXXXXXXX X | 5-10-5 (2'-OMe-DNA-2'-OMe); stereorandom PS | HTT-rs362268 |
| WV-1047 | CAACAGC CAGCCTG CAGGAG | 921 | mC * mA * mA * mC * mA * G * C * C * A * G * C * C * T * G * C * mA * mG * mG * mA * mG | 1273 | XXXXXXXXX XXXXXXXXX X | 5-10-5 (2'-OMe-DNA-2'-OMe); stereorandom PS | HTT-rs362268 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
| --- | --- | --- | --- | --- | --- | --- | --- |
| WV-1048 | AACAGCCAGCCTGCAGGAGG | 922 | mA * mA * mC * mA * mG * C * C * A * G * C * C * T * G * C * A * mG * mG * mA * mG * mG | 1274 | XXXXXXXXXXXXXXXXXXXX | 5-10-5 (2'-OMe-DNA-2'-OMe); stereorandom PS | HTT-rs362268 |
| WV-1049 | GGGCCAACAGCCAGCCUGCA | 923 | mG * mG * mG * mC * mC * mA * mA * C * A * G * C * C * A * G * mC * mC * mU * mG * mC * mA | 1275 | XXXXXXXXXXXXXXXXXXXX | 7-7-6 (2'-OMe-DNA-2'-OMe); stereorandom PS | HTT-rs362268 |
| WV-1050 | GGGCCAACAGCCAGCCUGCA | 924 | mGmGmGmCmCmAmA * C * A * G * C * C * A * G * mCmCmUmGmCmA | 1276 | OOOOOOOXXXXXXXOOOOOO | 7-7-6 (2'-OMe-DNA-2'-OMe); stereorandom PS; PO in wings | HTT-rs362268 |
| WV-1051 | GGCCAACAGCCAGCCUGCAG | 925 | mG * mG * mC * mC * mA * mA * C * A * G * C * C * A * G * C * C * mU * mG * mC * mA * mG | 1277 | XXXXXXXXXXXXXXXXXXXX | 6-7-5 (2'-OMe-DNA-2'-OMe); stereorandom PS | HTT-rs362268 |
| WV-1052 | GGCCAACAGCCAGCCUGCAG | 926 | mGmGmCmCmAmA * C * A * G * C * C * A * G * C * C * mUmGmCmAmG | 1278 | OOOOOOXXXXXXXOOOOOOO | 6-7-5 (2'-OMe-DNA-2'-OMe); stereorandom PS; PO in the wings | HTT-rs362268 |
| WV-1053 | GCCAACAGCCAGCCUGCAGG | 927 | mG * mC * mC * mA * mA * C * A * G * C * C * A * G * mC * mC * mU * mG * mC * mA * mG | 1279 | XXXXXXXXXXXXXXXXXXXX | 5-7-8 (2'-OMe-DNA-2'-OMe); stereorandom PS | HTT-rs362268 |
| WV-1054 | GCCAACAGCCAGCCUGCAGG | 928 | mGmCmCmAmA * C * A * G * C * C * A * G * mCmCmUmGmCmAmGmG | 1280 | OOOOOXXXXXXXOOOOOOOO | 5-7-8 (2'-OMe-DNA-2'-OMe); stereorandom PS; PO in the wings | HTT-rs362268 |
| WV-1055 | GGGCCAACAGCCAGCCUGCA | 929 | mGmGmGmCmC * A * A * C * A * G * C * C * A * G * mC * mC * mU * mG * mC * mA | 1281 | OOOOOXXXXXXXXXXOOOOO | 5-10-5 (2'-OMe-DNA-2'-OMe); stereorandom PS; PO in the wings | HTT-rs362268 |
| WV-1056 | GGCCAACAGCCAGCCUGCAG | 930 | mGmGmCmCmA * A * C * A * G * C * C * A * G * C * C * mUmGmCmAmG | 1282 | OOOOOXXXXXXXXXXOOOOO | 5-10-5 (2'-OMe-DNA-2'-OMe); stereorandom PS; PO in the wings | HTT-rs362268 |
| WV-1057 | GCCAACAGCCAGCCUGCAGG | 931 | mGmCmCmAmA * C * A * G * C * C * A * G * C * C * T * mGmCmAmGmG | 1283 | OOOOOXXXXXXXXXXOOOOO | 5-10-5 (2'-OMe-DNA-2'-OMe); stereorandom PS; PO in the wings | HTT-rs362268 |
| WV-1058 | CCAACAGCCAGCCTGCAGGA | 932 | mCmCmAmAmC * A * G * C * C * A * G * C * C * T * G * mCmAmGmGmA | 1284 | OOOOOXXXXXXXXXXOOOOO | 5-10-5 (2'-OMe-DNA-2'-OMe); stereorandom PS; PO in the wings | HTT-rs362268 |
| WV-1059 | CAACAGCCAGCCTGCAGGAG | 933 | mCmAmAmCmA * G * C * C * A * G * C * C * T * G * C * mAmGmGmAmG | 1285 | OOOOOXXXXXXXXXXOOOOO | 5-10-5 (2'-OMe-DNA-2'-OMe); stereorandom PS; PO in the wings | HTT-rs362268 |
| WV-1060 | AACAGCCAGCCTGCAGGAGG | 934 | mAmAmCmAmG * C * C * A * G * C * C * T * G * C * A * mGmGmAmGmG | 1286 | OOOOOXXXXXXXXXXOOOOO | 5-10-5 (2'-OMe-DNA-2'-OMe); stereorandom PS; PO in the wings; HTT-rs362268 | HTT-rs362268 |
| WV-1061 | GUAGGAGTAGTGAAAGGCCA | 935 | mG * mU * mA * mG * mG * A * G * T * A * G * T * G * A * A * A * mG * mG * mC * mC * mA | 1287 | XXXXXXXXXXXXXXXXXXXX | 5-10-5 (2'-OMe-DNA-2'-OMe); stereorandom PS; +ve Luciferase control for psiCHECK2; WV-975 analogue | HTT-rs362268 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1062 | GUAGGAG TAGTGAA AGGCCA | 936 | mGmUmAmGmG * A * G * T * A * G * T * G * A * A * A * mGmGmCmCmA | 1288 | OOOOXXXXX XXXXXXOOO O | 5-10-5 (2'-OMe-DNA-2'-OMe); stereorandom PS; PO in the wings: +ve Luciferase control for psiCHECK2; WV-975 analogue | HTT-control |
| WV-1063 | GUAGGAG TAGTGAA AGGCCA | 937 | mG * mU * mA * mG * mG * A * G * T * A * G * T * G * A * A * A * G * G * C * C * A | 1289 | XXXXXXXXX XXXXXXXXX X | 5-15 (2'-OMe-DNA); stereorandom PS: +ve Luciferase control for psiCHECK2; WV-975 analogue | HTT-control |
| WV-1064 | CUCUUAC TGTGCTG TGGACA | 938 | mC * mU * mC * mU * mU * A * C * T * G * T * G * C * T * G * T * mG * mG * mA * mC * mA | 1290 | XXXXXXXXX XXXXXXXXX X | 5-10-5 (2'-OMe-DNA-2'-OMe); stereorandom PS: Negative Luciferase control for psiCHECK2; ONT-67 analogue | HTT-control |
| WV-1065 | CUCUUAC TGTGCTG TGGACA | 939 | mCmUmCmUmU * A * C * T * G * T * G * C * T * G * T * mGmGmAmCmA | 1291 | OOOOXXXXX XXXXXXOOO O | 5-10-5 (2'-OMe-DNA-2'-OMe); stereorandom PS; PO in the wings: Negative Luciferase control for psiCHECK2; ONT-67 analogue | HTT-control |
| WV-1066 | CUCUUAC TGTGCTG TGGACA | 940 | mC * mU * mC * mU * mU * A * C * T * G * T * G * C * T * G * T * G * G * A * C * A | 1292 | XXXXXXXXX XXXXXXXXX X | 5-15 (2'-OMe-DNA); stereorandom PPS: Negative Luciferase control for psiCHECK2; ONT-67 analogue | HTT-control |
| WV-1067 | GGGCACA AGGGCAC AGACTT | 941 | G * G * G * C * A * C * A * A * G * G * G * C * d2AP * C * A * G * A * C * T * T | 1293 | XXXXXXXXX XXXXXXXXX X | All DNA stereorandom; P13 (2-aminopurine): rs362307; WV-904 analogue | HTT-control |
| WV-1068 | GGCACAA GGGCACA GACTTC | 942 | G * G * C * A * C * A * A * G * G * G * C * d2AP * C * A * G * A * C * T * T * C | 1294 | XXXXXXXXX XXXXXXXXX X | All DNA stereorandom; P12 (2-aminopurine): rs362307; WV-905 analogue | rs362307 |
| WV-1069 | GCACAAG GGCACAG ACTTCC | 943 | G * C * A * C * A * A * G * G * C * d2AP * C * A * G * A * C * T * T * C * C | 1295 | XXXXXXXXX XXXXXXXXX X | All DNA stereorandom; P11 (2-aminopurine): rs362307; WV-906 analogue | rs362307 |
| WV-1070 | GGGCACA AGGGCAC AGACTT | 944 | G * G * G * C * A * C * A * A * G * G * G * C * dDAP * C * A * G * A * C * T * T | 1296 | XXXXXXXXX XXXXXXXXX X | All DNA stereorandom; P13 (2;6-diammopurine): rs362307; WV-904 analogue | rs362307 |
| WV-1071 | GGCACAA GGGCACA GACTTC | 945 | G * G * C * A * C * A * A * G * G * G * C * dDAP * C * A * G * A * C * T * T * C | 1297 | XXXXXXXXX XXXXXXXXX X | All DNA stereorandom; P12 (2;6-diaminopurine): rs362307; WV-905 analogue | rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1072 | GCACAAGGGCACAGACTTCC | 946 | G * C * A * C * A * A * G * G * G * C * dDAP * C * A * G * A * C * T * T * C * C | 1298 | XXXXXXXXXXXXXXXXXXX | All DNA stereorandom; P12 (2;6-diaminopurine): rs362307; WV-906 analogue | rs362307 |
| WV-1073 | GAGCCUUUGGAAGUCUGCGCCCUUGUGCCCUGCCU | 947 | rGrArGrCrCrUrUrUrGrGrArArGrUrCrUrGrCrGrCrCrCrUrUrGrUrGrCrCrCrUrGrCrCrU | 1299 | OOOOOOOOOOOOOOOOOOOOOOOOOOOOOOOOO | wtRNA | rs362307 |
| WV-1074 | GAGCCUUUGGAAGUCUGUGCCCUUGUGCCCUGCCU | 948 | rGrArGrCrCrUrUrUrGrGrArArGrUrCrUrGrUrGrCrCrCrUrUrGrUrGrCrCrCrUrGrCrCrU | 1300 | OOOOOOOOOOOOOOOOOOOOOOOOOOOOOOOOO | muRNA | rs362307 |
| WV-1075 | CACACGGGCACAGACUUCCAA | 949 | rCrArCrArCrGrGrGrCrArCrArGrCrUrUrCrCrArA | 1301 | OOOOOOOOOOOOOOOOOOOO | Antisense strand: Positive control; Curr. Bio. Vol 19 No 9; 776 | rs362307 |
| WV-1076 | GGAAGUCUGUGCCCGUGUGCC | 950 | rGrGrArArGrUrCrUrGrUrGrCrCrCrGrUrGrUrGrCrC | 1302 | OOOOOOOOOOOOOOOOOOOO | Sense strand: Positive control; Curr. Bio. Vol 19 No 9; 777: Note: incorrectly added as rGrGrArArGrUrCrUrGrUrGrCrCrCrGrUrGrUrUrCrC (SEQ ID NO: 1553) in earlier versions of databse | rs362307 |
| WV-1077 | AUUAAUAAATTGTCATCACC | 951 | mA * SmU * SmU * SmA * SmA * SmU * SA * SA * SA * ST * ST * SG * ST * SC * RA * ST * SmC * SmA * SmC * SmC | 1303 | SSSSSSSSSSSSRSSSSS | 6-10-4 (2'-OMe-DNA-2'-OMe) Gapmer: Analogue of WV-451 | HTT rs7685686 |
| WV-1078 | AUUAAUAAATTGTCATCACC | 952 | mA * RmU * RmU * RmA * RmA * RmU * SA * SA * SA * ST * ST * SG * ST * SC * RA * ST * SmC * RmA * RmC * RmC | 1304 | RRRRRSSSSSSSRSSRRR | 6-10-4 (2'-OMe-DNA-2'-OMe) Gapmer: Analogue of WV-451 | HTT rs7685686 |
| WV-1079 | AUUAAUAAATTGTCATCACC | 953 | mA * SmU * SmU * SmA * SmA * SmU * SmA * SmA * SA * ST * ST * SG * ST * SC * RA * ST * SC * SA * SC * SC | 1305 | SSSSSSSSSSSSRSSSSS | 8-12 (2'-OMe-DNA) hemimer: Analogue of WV-451 | HTT rs7685686 |
| WV-1080 | AUUAAUAAATTGTCATCACC | 954 | mA * RmU * RmU * RmA * RmA * RmU * RmA * RmA * SA * ST * ST * SG * ST * SC * RA * ST * SC * SA * SC * SC | 1306 | RRRRRRRSSSSSSRSSSSS | 8-12 (2'-OMe-DNA) hemimer: Analogue of WV-451 | HTT rs7685686 |
| WV-1081 | AUUAAUAAATTGTCATCACC | 955 | mAmUmUmAmAmUmAmA * SA * ST * ST * SG * ST * SC * RA * ST * SC * SA * SC * SC | 1307 | OOOOOOOOSSSSSSRSSSSS | 8-12 (2'-OMe-DNA) hemimer; PO wing: Analogue of WV-451 | HTT rs7685686 |
| WV-1082 | AUUAAUAAATTGTCATCACC | 956 | mAmUmUmAmAmU * SA * SA * SA * ST * ST * SG * ST * SC * RA * ST * SmCmAmCmC | 1308 | OOOOOSSSSSSSRSSOOO | 6-10-4 (2'-OMe-DNA-2'-OMe); PO wings: Analogue of WV-451 | HTT rs7685686 |
| WV-1083 | AUUAAUAAATTGTCATCACC | 957 | mA * SmUmUmAmAmU * SA * SA * SA * ST * ST * SG * ST * SC * RA * ST * SmCmAmC * SmC | 1309 | SOOOOSSSSSSSRSSOOS | 6-10-4 (2'-OMe-DNA-2'-OMe) Gapmer: Analogue of WV-451 | HTT rs7685686 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1084 | AUUAAUA AATTGTC ATCACC | 958 | mA * RmUmUmAmAmU * SA * SA * SA * ST * ST * SG * ST * SC * RA * ST * SmCmAmC * RmC | 1310 | ROOOOSSSSS SSSRSSOOR | 6-10-4 (2'-OMe-DNA-2'-OMe) Gapmer: Analogue of WV-451 | HTT rs7685686 |
| WV-1085 | GGCACAA GGGCACA GACUUC | 959 | mG * SmG * SmC * SmA * SmC * SA * SA * SG * SG * SG * SC * SA * SC * RA * SG * SmA * SmC * SmU * SmU * SmC | 1311 | SSSSSSSSSS SRSSSSSSS | 5-10-5 (2'-OMe-DNA-2'-OMe) Gapmer: Analogue of WV-905 and WV-937 | HTT rs362307 |
| WV-1086 | GGCACAA GGGCACA GACUUC | 960 | mG * RmG * RmC * RmA * RmC * SA * SA * SG * SG * SG * SC * SA * SC * RA * SG * SmA * RmC * RmU * RmU * RmC | 1312 | RRRRSSSSSS SRSSRRRR | 5-10-5 (2'-OMe-DNA-2'-OMe) Gapmer: Analogue of WV-905 and WV-937 | HTT rs362307 |
| WV-1087 | GGCACAA GGGCACA GACUUC | 961 | mGmGmCmAmC * SA * SA * SG * SG * SG * SC * SA * SC * RA * SG * SmAmCmUmUmC | 1313 | OOOOSSSSSS SSRSSOOOO | 5-10-5 (2'-OMe-DNA-2'-OMe); PO wings: Analogue of WV-905 and WV-937 | HTT rs362307 |
| WV-1088 | GGCACAA GGGCACA GACTTC | 962 | mG * SmG * SmC * SmA * SmC * SmA * SmA * SmG * SG * SG * SC * SA * SC * RA * SG * SA * SC * ST * ST * SC | 1314 | SSSSSSSSSS SRSSSSSS | 8-12 (2'-OMe-DNA) hemimer: Analogue of WV-905 and WV-937 | HTT rs362307 |
| WV-1089 | GGCACAA GGGCACA GACTTC | 963 | mG * RmG * RmC * RmA * RmC * RmA * RmA * RmG * SG * SG * SC * SA * SC * RA * SG * SA * SC * ST * ST * SC | 1315 | RRRRRRRSSS SRSSSSSS | 8-12 (2'-OMe-DNA) hemimer: Analogue of WV-905 and WV-937 | HTT rs362307 |
| WV-1090 | GGCACAA GGGCACA GACTTC | 964 | mGmGmCmAmCmAmAmG * SG * SG * SC * SA * SC * RA * SG * SA * SC * ST * ST * SC | 1316 | OOOOOOOSS SSSRSSSSSS | 8-12 (2'-OMe-DNA) hemimer; PO wing: Analogue of WV-905 and WV-937 | HTT rs362307 |
| WV-1091 | GGCACAA GGGCACA GACUUC | 965 | mG * RmGmCmAmC * SA * SA * SG * SG * SG * SC * SA * SC * RA * SG * SmAmCmUmU * RmC | 1317 | ROOOSSSSSS SSRSSOOOR | 8-12 (2'-OMe-DNA) gapmer PO wing: Analogue of WV-905 and WV-937: incorrectly added as gsSgcacsSdAsSdAs SdGsSdGsSdGsSd CsSdAsSdCsRdAs SdGsSacuusSc in earlier version of database | HTT rs362307 |
| WV-1092 | GGCACAA GGGCACA GACUUC | 966 | mG * SmGmCmAmC * SA * SA * SG * SG * SG * SC * SA * SC * RA * SG * SmAmCmUmU * SmC | 1318 | SOOOSSSSSS SSRSSOOOS | 8-12 (2'-OMe-DNA) gapmer PO wing: Analogue of WV-905 and WV-937 | HTT rs362307 |
| WV-1183 | GCAGGGC ACAAGGG CACAGA | 967 | G * C * A * G * G * G * C * A * C * A * A * G * G * G * C * A * C * A * G * A | 1319 | XXXXXXXXXX XXXXXXXXX X | Phosphorothioate DNA; Stereorandom | Huntington rs362307 |
| WV-1184 | GCAGGGC ACAAGGG CACAGA | 968 | mG * mC * mA * mG * mG * G * C * A * C * A * A * G * G * G * C * A * C * A * G * A | 1320 | XXXXXXXXXX XXXXXXXXX X | 5-15 (2'-OMe-DNA) Hemimer | Huntington rs362307 |
| WV-1185 | GCAGGGC ACAAGGG CACAGA | 969 | mGmCmAmGmG * G * C * A * C * A * A * G * G * G * C * A * C * A * G * A | 1321 | OOOOXXXXX XXXXXXXXX X | 5-15 (2'-OMe-DNA) Hemimer; PO wing | Huntington rs362307 |
| WV-1186 | GCAGGGC ACAAGGG CACAGA | 970 | mG * mC * mA * mG * mG * mG * mC * A * C * A * A * G * G * C * A * C * A * G * A | 1322 | XXXXXXXXXX XXXXXXXXX X | 7-13 (2'-OMe-DNA) Hemimer | Huntington rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1187 | GCAGGGC ACAAGGG CACAGA | 971 | mGmCmAmGmGmC * A * C * A * A * G * G * C * A * C * A * G * A | 1323 | OOOOOOXXX XXXXXXXXX X | 7-13 (2'-OMe-DNA) Hemimer; PO wing | Huntington rs362307 |
| WV-1188 | CAGGGCA CAAGGGC ACAGAC | 972 | C * A * G * G * G * C * A * C * A * A * G * G * G * C * A * C * A * G * A * C | 1324 | XXXXXXXXX XXXXXXXXX X | Phosphorothioate DNA; Stereorandom | Huntington rs362307 |
| WV-1189 | CAGGGCA CAAGGGC ACAGAC | 973 | mC * mA * mG * mG * mG * C * A * C * A * A * G * G * G * C * A * C * A * G * A * C | 1325 | XXXXXXXXX XXXXXXXXX X | 5-15 (2'-OMe-DNA) Hemimer | Huntington rs362307 |
| WV-1190 | CAGGGCA CAAGGGC ACAGAC | 974 | mCmAmGmGmG * C * A * C * A * G * G * G * C * A * C * A * G * A * C | 1326 | OOOOOXXXX XXXXXXXXX X | 5-15 (2'-OMe-DNA) Hemimer; PO wing | Huntington rs362307 |
| WV-1191 | CAGGGCA CAAGGGC ACAGAC | 975 | mC * mA * mG * mG * mG * mC * mA * C * A * A * G * G * G * C * A * mC * mA * mG * mA * mC | 1327 | XXXXXXXXX XXXXXXXXX X | 7-13 (2'-OMe-DNA) Hemimer | Huntington rs362307 |
| WV-1192 | CAGGGCA CAAGGGC ACAGAC | 976 | mCmAmGmGmGmCmA * C * A * A * G * G * G * C * A * mCmAmGmAmC | 1328 | OOOOOOXXX XXXXXOOO O | 7-13 (2'-OMe-DNA) Hemimer; PO wing | Huntington rs362307 |
| WV-1193 | AGGGCAC AAGGGCA CAGACT | 977 | A * G * G * G * C * A * C * A * A * G * G * G * C * A * C * A * G * A * C * T | 1329 | XXXXXXXXX XXXXXXXXX X | Phosphorothioate DNA; Stereorandom | Huntington rs362307 |
| WV-1194 | AGGGCAC AAGGGCA CAGACT | 978 | mA * mG * mG * mG * mC * A * C * A * A * G * G * G * C * A * C * A * G * A * C * T | 1330 | XXXXXXXXX XXXXXXXXX X | 5-15 (2'-OMe-DNA) Hemimer | Huntington rs362307 |
| WV-1195 | AGGGCAC AAGGGCA CAGACT | 979 | mAmGmGmGmC * A * C * A * A * G * G * G * C * A * C * A * G * A * C * T | 1331 | OOOOOXXXX XXXXXXXXX X | 5-15 (2'-OMe-DNA) Hemimer; PO wing | Huntington rs362307 |
| WV-1196 | AAGGGCA AGGGCAC CAGACU | 980 | mA * mG * mG * mG * mC * mA * mC * A * A * G * G * C * A * C * A * G * A * C * mU | 1332 | XXXXXXXXX XXXXXXXXX X | 7-12-1 (2'-OMe-DNA-2'-DNA) Gapmer | Huntington rs362307 |
| WV-1197 | AGGGCAC AAGGGCA CAGACU | 981 | mAmGmGmGmCmAmC * A * A * G * G * G * C * A * C * A * G * A * C * mU | 1333 | OOOOOOXXX XXXXXXXXX X | 7-12-1 (2'-OMe-DNA-2'-DNA) Gapmer; PO wings | Huntington rs362307 |
| WV-1198 | AAGGGCA CAGACTT CCAAAG | 982 | A * A * G * G * G * C * A * C * A * G * A * C * T * T * C * C * A * A * A * G | 1334 | XXXXXXXXX XXXXXXXXX X | Phosphorothioate DNA; Stereorandom | Huntington rs362307 |
| WV-1199 | AAGGGCA CAGACTT CCAAAG | 983 | mA * mA * mG * mG * mG * C * A * C * A * G * A * C * T * T * C * C * A * A * A * G | 1335 | XXXXXXXXX XXXXXXXXX X | 5-15 (2'-OMe-DNA) Hemimer | Huntingto rs362307 |
| WV-1200 | AAGGGCA CAGACTT CCAAAG | 984 | mAmAmGmGmG * C * A * C * A * G * A * C * T * T * C * C * A * A * A * G | 1336 | OOOOOXXXX XXXXXXXXX X | 5-15 (2'-OMe-DNA) Hemimer; PO wing | Huntington rs362307 |
| WV-1201 | AAGGGCA CAGACTT CCAAAG | 985 | mA * mA * mG * mG * mG * C * A * C * A * G * A * C * T * T * C * mC * mA * mA * mA * mG | 1337 | XXXXXXXXX XXXXXXXXX X | 5-10-5 (2'-OMe-DNA-2'-DNA) Gapmer | Huntington rs362307 |
| WV-1202 | AAGGGCA CAGACTT CCAAAG | 986 | mAmAmGmGmG * C * A * C * A * G * A * C * T * T * C * mCmAmAmAmG | 1338 | OOOOOXXXX XXXXXOOO O | 5-10-5 (2'-OMe-DNA-2'-DNA) Gapmer; PO wings | Huntington rs362307 |
| WV-1203 | AAGGGCA CAGACTT CCAAAG | 987 | mA * mA * mG * mG * G * C * A * C * A * G * A * C * T * T * mC * mC * mA * mA * mA * mG | 1339 | XXXXXXXXX XXXXXXXXX X | 4-10-6 (2'-OMe-DNA-2'-DNA) Gapmer | Huntington rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1204 | AAGGGCACAGACTTCCAAAG | 988 | mAmAmGmGG * C * A * C * A * G * A * C * T * T * mCmCmAmAmAmG | 1340 | OOOOXXXXXXXXXXOOOOO | 4-10-6 (2'-OMe-DNA-2'-DNA) Gapmer; PO wings | Huntington rs362307 |
| WV-1205 | AGGGCACAGACTTCCAAAGG | 989 | A * G * G * G * C * A * C * A * G * A * C * T * T * C * C * A * A * A * G * G | 1341 | XXXXXXXXXXXXXXXXXXXX | Phosphorothioate DNA; Stereorandom | Huntington rs362307 |
| WV-1206 | AGGGCACAGACTTCCAAAGG | 990 | mA * mG * mG * mG * mC * A * C * A * G * A * C * T * T * C * C * A * A * G * G | 1342 | XXXXXXXXXXXXXXXXXXXX | 5-15 (2'-OMe-DNA) Hemimer | Huntington rs362307 |
| WV-1207 | AGGGCACAGACTTCCAAAGG | 991 | mAmGmGmGmC * A * C * A * G * A * C * T * T * C * C * A * A * G * G | 1343 | OOOOXXXXXXXXXXXXXXXX | 5-15 (2'-OMe-DNA) Hemimer; PO wing | Huntington rs362307 |
| WV-1208 | AGGGCACAGACTTCCAAAGG | 992 | mA * mG * mG * mG * mC * A * C * A * G * A * C * T * T * C * C * mA * mA * mA * mG * mG | 1344 | XXXXXXXXXXXXXXXXXXXX | 5-10-5 (2'-OMe-DNA-2'-DNA) Gapmer | Huntington rs362307 |
| WV-1209 | AGGGCACAGACTTCCAAAGG | 993 | mAmGmGmGmC * A * C * A * G * A * C * T * T * C * C * mAmAmAmGmG | 1345 | OOOOXXXXXXXXXXXOOOOO | 5-10-5 (2'-OMe-DNA-2'-DNA) Gapmer; PO wings | Huntington rs362307 |
| WV-1210 | AGGGCACAGACTTCCAAAGG | 994 | mA * mG * mG * mG * C * A * C * A * G * A * C * T * T * C * mC * mA * mA * mA * mG * mG | 1346 | XXXXXXXXXXXXXXXXXXXX | 4-10-6 (2'-OMe-DNA-2'-DNA) Gapmer | Huntington rs362307 |
| WV-1211 | AGGGCACAGACTTCCAAAGG | 995 | mAmGmGmG * C * A * C * A * G * A * C * T * T * C * mCmAmAmAmGmG | 1347 | OOOXXXXXXXXXXXOOOOOO | 4-10-6 (2'-OMe-DNA-2'-DNA) Gapmer; PO wings | Huntington rs362307 |
| WV-1212 | GGGCACAGACTTCCAAAGGC | 996 | G * G * G * C * A * C * A * G * A * C * T * T * C * C * A * A * A * G * G * C | 1348 | XXXXXXXXXXXXXXXXXXXX | Phosphorothioate DNA; Stereorandom | Huntington rs362307 |
| WV-1213 | GGGCACAGACTTCCAAAGGC | 997 | mG * mG * mG * mC * mA * C * A * G * A * C * T * T * C * C * A * A * A * G * G * C | 1349 | XXXXXXXXXXXXXXXXXXXX | 4-16 (2'-OMe-DNA) Hemimer | Huntington rs362307 |
| WV-1214 | GGGCACAGACTTCCAAAGGC | 998 | mGmGmGmCmA * C * A * G * A * C * T * T * C * C * A * A * A * G * G * C | 1350 | OOOOXXXXXXXXXXXXXXXX | 4-16 (2'-OMe-DNA) Hemimer; PO wing | Huntington rs362307 |
| WV-1215 | GGGCACAGACTTCCAAAGGC | 999 | mG * mG * mG * mC * mA * C * A * G * A * C * T * T * C * C * A * mA * mA * mG * mG * mC | 1351 | XXXXXXXXXXXXXXXXXXXX | 4-10-6 (2'-OMe-DNA-2'-DNA) Gapmer | Huntington rs362307 |
| WV-1216 | GGGCACAGACTTCCAAAGGC | 1000 | mGmGmGmCmA * C * A * G * A * C * T * T * C * C * A * mAmAmGmC | 1352 | OOOOXXXXXXXXXXXOOOOO | 4-10-6 (2'-OMe-DNA-2'-DNA) Gapmer; PO wings | Huntingto rs362307 |
| WV-1234 | GGCACAAGGGCACAGACUTC | 1001 | mG * mG * mC * mA * mC * A * A * G * G * G * C * A * C * A * G * mA * mC * mU * BrdU * mC | 1353 | XXXXXXXXXXXXXXXXXXXX | 5-10-5 (2'-OMe-DNA-2'-OMe) Gapmer; One Br-dU | HTT-rs362307 |
| WV-1235 | GGCACAAGGGCACAGACTTC | 1002 | mG * mG * mC * mA * mC * A * A * G * G * G * C * A * C * A * G * mA * mC * BrdU * BrdU * mC | 1354 | XXXXXXXXXXXXXXXXXXXX | 5-10-5 (2'-OMe-DNA-2'-OMe) Gapmer; two Br-dU | HTT-rs362307 |
| WV-1497 | GGCACAAGGGCACAGACUUC | 1003 | mG * mGmCmAmC * A * A * G * G * G * C * A * C * A * G * mAmCmUmU * mC | 1355 | XOOOXXXXXXXXXXXOOOOO | stereo random version of WV-1092 | HTT rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-1508 | AUUAAUA AATTGTC ATCACC | 1004 | A * SmUmUmAmAmU * SA * SA * SA * ST * ST * SG * ST * SC * RA * ST * SmCmAmC * SC | 1356 | SSSRSSOOS SOOOOSSSSS | 1-5-10-3-1 (DNA/2'-OMe) Gapmer: : Analogue of WV-1083 | HTT rs7685686 |
| WV-1509 | AUUAAUA AATTGTC ATCACC | 1005 | A * mUmUmAmAmU * A * A * A * T * T * G * T * C * A * T * mCmAmC * C | 1357 | XOOOOXXXX XXXXXXXOO X | 1-5-10-3-1 (DNA/2'-OMe) Gapmer; 1st and last PS: : Analogue of WV-1083 | HTT rs7685686 |
| WV-1510 | GGCACAA GGGCACA GACUUC | 1006 | G * SmGmCmAmC * SA * SA * SG * SG * SG * SC * SA * SC * RA * SG * SmAmCmUmU * SC | 1358 | SOOOSSSSSS SSRSSOOOS | 1-4-10-4-1 (DNA/2'-OMe) gapmer: : Analogue of WV-1092 | HTT rs362307 |
| WV-1511 | GGCACAA GGGCACA GACUUC | 1007 | G * mGmCmAmC * A * A * G * G * G * C * A * C * A * G * mAmCmUmU * C | 1359 | XOOOXXXXX XXXXXXOOO X | 1-4-10-4-1 (DNA/2'-OMe) gapmer; 1st and last PS: : Analogue of WV-1092 | HTT rs362307 |
| WV-1654 | GGCACAA GGGCACA GACTTC | 1008 | Geo * Geo * m5Ceo * Aeo * m5Ceo * A * A * G * G * C * A * C * A * G * Aeo * m5Ceo * Teo * Teo * m5Ceo | 1360 | XXXXXXXXX XXXXXXXXX X | 5-10-5; 2'-OMOE gapmer; All PS | HTT rs362307 |
| WV-1655 | GGCACAA GGGCACA GACTTC | 1009 | Geo * Geom5CeoAeom5Ceo * A * A * G * G * C * A * C * A * G * Aeom5CeoTeoTeo * m5Ceo | 1361 | XOOOXXXXX XXXXXXOOO X | 5-10-5; 2'-OMOE gapmer; 1st and last PS n the wing; rest of the wing is PO | HTT rs362307 |
| WV-1656 | CTCAGTA ACATTGA CACCAC | 1010 | m5Ceo * Teo * m5Ceo * Aeo * Geo * T * A * A * C * A * T * T * G * A * C * Aeo * m5Ceo * m5Ceo * Aeo * m5Ceo | 1362 | XXXXXXXXX XXXXXXXXX X | 5-10-5; 2'-OMOE gapmer; All PS | Huntington |
| WV-1657 | CUCAGTA ACATTGA CACCAC | 1011 | mC * mU * mC * mA * mG * T * A * A * C * A * T * T * G * A * C * mA * mC * mC * mA * mC | 1363 | XXXXXXXXX XXXXXXXXX X | 5-10-5; 2'-OMe gapmer; All PS | Huntington |
| WV-1788 | GGCACAA GGGCACA GACUTC | 1012 | mG * mGmCmAmC * A * A * G * G * G * C * A * C * A * G * mAmCmU * BrdU * mC | 1364 | XOOOXXXXX XXXXXXOOX X | 5/10/5 2'Ome Gapmer BrdU PO wings | HTT |
| WV-1789 | CTCAGTA ACATTGA CACCAC | 1013 | mC * BrdU * mC * mA * mG * T * A * A * C * A * T * T * G * A * C * mA * mC * mC * mA * mC | 1365 | XXXXXXXXX XXXXXXXXX X | 5/10/5 2'Ome Gapmer BrdU | HTT |
| WV-1790 | CTCAGTA ACATTGA CACCAC | 1014 | mC * BrdU * mCmAmG * T * A * A * C * A * T * T * G * A * C * mAmCmCmA * mC | 1366 | XXOOXXXXX XXXXXXOOO X | 5/10/5 2'Ome Gapmer BrdU PO wings | HTT |
| WV-1799 | GAAGUCU GUGCCCU UGUGCC | 1015 | rGrArArGrUrCrUrGrUrGrCrCrC rUrUrGrUrGrCrC | 1367 | OOOOOOOOO OOOOOOOOO O | RNA complementary to WV1092 | HTT |
| WV-2022 | GGCACAA GGGCACA GACUTC | 1016 | mG * SmGmCmAmC * SA * SA * SG * SG * SG * SC * SA * SC * RA * SG * SmAmCmU * SBrdU * SmC | 1368 | SOOOSSSSSS SSRSSOOSS | BrdU version of WV-1092 | HTT rs362307 |
| WV-2023 | TGTCATC ACCAGAA AAAGUC | 1017 | T * G * T * C * A * T * C * A * C * C * A * G * A * A * A * mA * mA * mG * mU * mC | 1369 | XXXXXXXXX XXXXXXXXX X | 15-5 hemimer full PS | rs7685686 (A/G) |
| WV-2024 | UTGTCAT CACCAGA AAAAGU | 1018 | mU * T * G * T * C * A * T * C * A * C * C * A * G * A * A * mA * mA * mA * mG * mU | 1370 | XXXXXXXXX XXXXXXXXX X | 1-14-5 gapmer full PS | rs7685686 (A/G) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2025 | TTGTCAT CACCAGA AAAAGU | 1019 | T * T * G * T * C * A * T * C * A * C * A * G * A * mA * mA * mA * mG * mU | 1371 | XXXXXXXXX XXXXXXXXX X | 15-5 hemimer full PS | rs7685686 (A/G) |
| WV-2026 | AUTGTCA TCACCAG AAAAAG | 1020 | mA * mU * T * G * T * C * A * T * C * A * C * C * A * G * A * mA * mA * mA * mA * mG | 1372 | XXXXXXXXX XXXXXXXXX X | 2-13-5 gapmer full PS | rs7685686 (A/G) |
| WV-2027 | ATTGTCA TCACCAG AAAAAG | 1021 | mA * T * T * G * T * C * A * T * C * A * C * C * A * G * A * mA * mA * mA * mA * mG | 1373 | XXXXXXXXX XXXXXXXXX X | 1-14-5 gapmer full PS | rs7685686 (A/G) |
| WV-2028 | AAUTGTC ATCACCA GAAAAA | 1022 | mA * mA * mU * T * G * T * C * A * T * C * A * C * C * A * G * mA * mA * mA * mA * mA | 1374 | XXXXXXXXX XXXXXXXXX X | 3-12-5 gapmer full PS | rs7685686 (A/G) |
| WV-2029 | AATTGTC ATCACCA GAAAAA | 1023 | mA * mA * T * T * G * T * C * A * T * C * A * C * C * A * G * mA * mA * mA * mA * mA | 1375 | XXXXXXXXX XXXXXXXXX X | 2-13-5 gapmer full PS | rs7685686 (A/G) |
| WV-2030 | AAATTGT CATCACC AGAAAA | 1024 | mA * mA * mA * T * T * G * T * C * A * T * C * A * C * C * A * mG * mA * mA * mA * mA | 1376 | XXXXXXXXX XXXXXXXXX X | 3-12-5 gapmer full PS | rs7685686 (A/G) |
| WV-2031 | AAAUTGT CATCACC AGAAAA | 1025 | mA * mA * mA * mU * T * G * T * C * A * T * C * A * C * C * A * mG * mA * mA * mA * mA | 1377 | XXXXXXXXX XXXXXXXXX X | 4-11-5 gapmer full PS | rs7685686 (A/G) |
| WV-2032 | UAAAUTG TCATCAC CAGAAA | 1026 | mU * mA * mA * mA * mU * T * G * T * C * A * T * C * A * C * C * A * mG * mA * mA * mA | 1378 | XXXXXXXXX XXXXXXXXX X | 5-11-4 gapmer full PS | rs7685686 (A/G) |
| WV-2033 | UAAAUTG TCATCAC CAGAAA | 1027 | mU * mA * mA * mA * mU * T * G * T * C * A * T * C * A * C * C * mA * mG * mA * mA * mA | 1379 | XXXXXXXXX XXXXXXXXX X | 5-10-5 gapmer full PS | rs7685686 (A/G) |
| WV-2034 | AUAAATT GTCATCA CCAGAA | 1028 | mA * mU * mA * mA * mA * T * T * G * T * C * A * T * C * A * C * C * mC * mA * mG * mA | 1380 | XXXXXXXXX XXXXXXXXX X | 5-11-4 gapmer full PS | rs7685686 (A/G) |
| WV-2035 | AUAAATT GTCATCA CCAGAA | 1029 | mA * mU * mA * mA * mA * T * T * G * T * C * A * T * C * A * C * mC * mA * mG * mA * mA | 1381 | XXXXXXXXX XXXXXXXXX X | 5-10-5 gapmer full PS | rs7685686 (A/G) |
| WV-2036 | AAUAAAT TGTCATC ACCAGA | 1030 | mA * mA * mU * mA * mA * A * T * T * G * T * C * A * T * C * A * C * C * mA * mG * mA | 1382 | XXXXXXXXX XXXXXXXXX X | 5-12-3 gapmer full PS | rs7685686 (A/G) |
| WV-2037 | AAUAAAT TGTCATC ACCAGA | 1031 | mA * mA * mU * mA * mA * A * T * T * G * T * C * A * T * C * A * C * mC * mA * mG * mA | 1383 | XXXXXXXXX XXXXXXXXX X | 5-11-4 gapmer full PS | rs7685686 (A/G) |
| WV-2038 | AAUAAAT TGTCATC ACCAGA | 1032 | mA * mA * mU * mA * mA * A * T * T * G * T * C * A * T * C * A * mC * mC * mA * mG * mA | 1384 | XXXXXXXXX XXXXXXXXX X | 5-10-5 gapmer full PS | rs7685686 (A/G) |
| WV-2039 | UAAUAAA TTGTCAT CACCAG | 1033 | mU * mA * mA * mU * mA * A * A * T * T * G * T * C * A * T * C * A * C * C * mA * mG | 1385 | XXXXXXXXX XXXXXXXXX X | 5-13-2 gapmer full PS | rs7685686 (A/G) |
| WV-2040 | UAAUAAA TTGTCAT CACCAG | 1034 | mU * mA * mA * mU * mA * A * A * T * T * G * T * C * A * T * C * A * C * mC * mA * mG | 1386 | XXXXXXXXX XXXXXXXXX X | 5-12-3 gapmer full PS | rs7685686 (A/G) |
| WV-2041 | UAAUAAA TTGTCAT CACCAG | 1035 | mU * mA * mA * mU * mA * A * A * T * T * G * T * C * A * T * C * A * mC * mC * mA * mG | 1387 | XXXXXXXXX XXXXXXXXX X | 5-11-4 gapmer full PS | rs7685686 (A/G) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2042 | UAAUAAA TTGTCAT CACCAG | 1036 | mU * mA * mA * mU * mA * A * A * T * T * G * T * C * A * T * C * mA * mC * mC * mA * mG | 1388 | XXXXXXXXX XXXXXXXXX X | 5-10-5 gapmer full PS | rs7685686 (A/G) |
| WV-2043 | UUAUAA ATTGTCA TCACCA | 1037 | mU * mU * mA * mA * mU * A * A * A * T * T * G * T * C * A * T * C * A * C * C * mA | 1389 | XXXXXXXXX XXXXXXXXX X | 5-14-1 gapmer full PS | rs7685686 (A/G) |
| WV-2044 | UUAAUAA ATTGTCA TCACCA | 1038 | mU * mU * mA * mA * mU * A * A * A * T * T * G * T * C * A * T * C * A * C * mC * mA | 1390 | XXXXXXXXX XXXXXXXXX X | 5-13-2 gapmer full PS | rs7685686 (A/G) |
| WV-2045 | UUAAUAA ATTGTCA TCACCA | 1039 | mU * mU * mA * mA * mU * A * A * A * T * T * G * T * C * A * T * C * A * mC * mC * mA | 1391 | XXXXXXXXX XXXXXXXXX X | 5-12-3 gapmer full PS | rs7685686 (A/G) |
| WV-2046 | UUAAUAA ATTGTCA TCACCA | 1040 | mU * mU * mA * mA * mU * A * A * A * T * T * G * T * C * A * T * C * mA * mC * mC * mA | 1392 | XXXXXXXXX XXXXXXXXX X | 5-11-4 gapmer full PS | rs7685686 (A/G) |
| WV-2047 | AUUAATA AATTGTC ATCACC | 1041 | mA * mU * mU * mA * mA * T * A * A * A * T * T * G * T * C * A * T * C * A * C * C | 1393 | XXXXXXXXX XXXXXXXXX X | 5-15 hemimer full PS | rs7685686 (A/G) |
| WV-2048 | AUUAATA AATTGTC ATCACC | 1042 | mA * mU * mU * mA * mA * T * A * A * A * T * T * G * T * C * A * T * C * A * C * mC | 1394 | XXXXXXXXX XXXXXXXXX X | 5-14-1 gapmer full PS | rs7685686 (A/G) |
| WV-2049 | AUUAATA AATTGTC ATCACC | 1043 | mA * mU * mU * mA * mA * T * A * A * A * T * T * G * T * C * A * T * C * A * mC * mC | 1395 | XXXXXXXXX XXXXXXXXX X | 5-13-2 gapmer full PS | rs7685686 (A/G) |
| WV-2050 | AUUAATA AATTGTC ATCACC | 1044 | mA * mU * mU * mA * mA * T * A * A * A * T * T * G * T * C * A * T * C * mA * mC * mC | 1396 | XXXXXXXXX XXXXXXXXX X | 5-12-3 gapmer full PS | rs7685686 (A/G) |
| WV-2051 | UAUUAAT AAATTGT CATCAC | 1045 | mU * mA * mU * mU * mA * A * T * A * A * A * T * T * G * T * C * A * T * C * A * C | 1397 | XXXXXXXXX XXXXXXXXX X | 5-15 hemimer full PS | rs7685686 (A/G) |
| WV-2052 | UAUUAAT AAATTGT CATCAC | 1046 | mU * mA * mU * mU * mA * A * T * A * A * A * T * T * G * T * C * A * T * C * A * mC | 1398 | XXXXXXXXX XXXXXXXXX X | 5-14-1 gapmer full PS | rs7685686 (A/G) |
| WV-2053 | UAUUAAT AAATTGT CATCAC | 1047 | mU * mA * mU * mU * mA * A * T * A * A * A * T * T * G * T * C * A * T * C * mA * mC | 1399 | XXXXXXXXX XXXXXXXXX X | 5-13-2 gapmer full PS | rs7685686 (A/G) |
| WV-2054 | CUAUUAA TAAATTG TCATCA | 1048 | mC * mU * mA * mU * mU * A * A * T * A * A * A * T * T * G * T * C * A * T * C * A | 1400 | XXXXXXXXX XXXXXXXXX X | 5-15 hemimer full PS | rs7685686 (A/G) |
| WV-2055 | CUAUUAA TAAATTG TCATCA | 1049 | mC * mU * mA * mU * mU * A * A * T * A * A * A * T * T * G * T * C * A * T * C * mA | 1401 | XXXXXXXXX XXXXXXXXX X | 5-14-1 gapmer full PS | rs7685686 (A/G) |
| WV-2056 | ACUAUUA ATAAATT GTCATC | 1050 | mA * mC * mU * mA * mU * T * A * A * T * A * A * A * T * T * G * T * C * A * T * C | 1402 | XXXXXXXXX XXXXXXXXX X | 5-15 hemimer full PS | rs7685686 (A/G) |
| WV-2057 | TGTCATC ACCAGAA AAAGUC | 1051 | T * G * T * C * A * T * C * A * C * C * A * G * A * A * A * mAmAmGmU * mC | 1403 | XXXXXXXXX XXXXXOOO X | 15-5 hemimer 1 PS on each end and between dN-mN and dN-dN | rs7685686 (A/G) |
| WV-2058 | UTGTCAT CACCAGA AAAGU | 1052 | mU * T * G * T * C * A * T * C * A * C * C * A * G * A * A * mAmAmAmG * mU | 1404 | XXXXXXXXX XXXXXOOO X | 1-14-5 gapmer 1 PS on each end and between dN-mN and dN-dN | rs7685686 (A/G) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2059 | TTGTCAT CACCAGA AAAAGU | 1053 | T * T * G * T * C * A * T * C * A * C * A * G * A * A * mAmAmAmG * mU | 1405 | XXXXXXXXX XXXXXXOOO X | 15-5 hemimer 1 PS on each end and between dN-mN and dN-dN | rs7685686 (A/G) |
| WV-2060 | AUTGTCA TCACCAG AAAAAG | 1054 | mA * mU * T * G * T * C * A * T * C * A * C * C * A * G * A * mAmAmAmA * mG | 1406 | XXXXXXXXX XXXXXXOOO X | 2-13-5 gapmer 1 PS on each end and between dN-mN and dN-dN | rs7685686 (A/G) |
| WV-2061 | ATTGTCA TCACCAG AAAAAG | 1055 | mA * T * T * G * T * C * A * T * C * A * C * C * A * G * A * mAmAmAmA * mG | 1407 | XXXXXXXXX XXXXXXOOO X | 1-14-5 gapmer 1 PS on each end and between dN-mN and dN-dN | rs7685686 (A/G) |
| WV-2062 | AAUTGTC ATCACCA GAAAAA | 1056 | mA * mAmU * T * G * T * C * A * T * C * A * C * C * A * G * A * mAmAmAmA * mA | 1408 | XOXXXXXXX XXXXXXOOO X | 3-12-5 gapmer 1 PS on each end and between dN-mN and dN-dN | rs7685686 (A/G) |
| WV-2063 | AATTGTC ATCACCA GAAAAA | 1057 | mA * mA * T * T * G * T * C * A * T * C * A * C * C * A * G * A * mAmAmAmA * mA | 1409 | XXXXXXXXX XXXXXXOOO X | 2-13-5 gapmer 1 PS on each end and between dN-mN and dN-dN | rs7685686 (A/G) |
| WV-2064 | AAATTGT CATCACC AGAAAA | 1058 | mA * mAmA * T * T * G * T * C * A * T * C * A * C * C * A * mGmAmAmA * mA | 1410 | XOXXXXXXX XXXXXXOOO X | 3-12-5 gapmer 1 PS on each end and between dN-mN and dN-dN | rs7685686 (A/G) |
| WV-2065 | AAAUTGT CATCACC AGAAAA | 1059 | mA * mAmAmU * T * G * T * C * A * T * C * A * C * C * A * mGmAmAmA * mA | 1411 | XOOXXXXXX XXXXXXOOO X | 4-11-5 gapmer 1 PS on each end and between dN-mN and dN-dN | rs7685686 (A/G) |
| WV-2066 | UAAAUTG TCATCAC CAGAAA | 1060 | mU * mAmAmAmU * T * G * T * C * A * T * C * A * C * C * A * mGmAmA * mA | 1412 | XOOOXXXXX XXXXXXXOO X | 5-11-4 gapmer 1 PS on each end and between dN-mN and dN-dN | rs7685686 (A/G) |
| WV-2067 | UAAAUTG TCATCAC CAGAAA | 1061 | mU * mAmAmAmU * T * G * T * C * A * T * C * A * C * C * mAmGmAmA * mA | 1413 | XOOOXXXXX XXXXXXOOO X | 5-10-5 gapmer 1 PS on each end and between dN-mN and dN-dN | rs7685686 (A/G) |
| WV-2068 | AUAAATT GTCATCA CCAGAA | 1062 | mA * mUmAmAmA * T * T * G * T * C * A * T * C * A * C * C * mAmGmA * mA | 1414 | XOOOXXXXX XXXXXXXOO X | 5-11-4 gapmer 1 PS on each end and between dN-mN and dN-dN | rs7685686 (A/G) |
| WV-2069 | AUAAATT GTCATCA CCAGAA | 1063 | mA * mUmAmAmA * T * T * G * T * C * A * T * C * A * C * mCmAmGmA * mA | 1415 | XOOOXXXXX XXXXXXOOO X | 5-10-5 gapmer 1 PS on each end and between dN-mN and dN-dN | rs7685686 (A/G) |
| WV-2070 | AAUAAAT TGTCATC ACCAGA | 1064 | mA * mAmUmAmA * A * T * T * G * T * C * A * T * C * A * C * C * mAmG * mA | 1416 | XOOOXXXXX XXXXXXXXO X | 5-12-3 gapmer 1 PS on each end and between dN-mN and dN-dN | rs7685686 (A/G) |
| WV-2071 | AAUAAAT TGTCATC ACCAGA | 1065 | mA * mAmUmAmA * A * T * T * G * T * C * A * T * C * A * C * mCmAmG * mA | 1417 | XOOOXXXXX XXXXXXXOO X | 5-11-4 gapmer 1 PS on each end and between dN-mN and dN-dN | rs7685686 (A/G) |
| WV-2072 | AAUAAAT TGTCATC ACCAGA | 1066 | mA * mAmUmAmA * A * T * T * G * T * C * A * T * C * A * mCmCmAmG * mA | 1418 | XOOOXXXXX XXXXXXOOO X | 5-10-5 gapmer 1 PS on each end and between dN-mN and dN-dN | rs7685686 (A/G) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2073 | UAAUAAA TTGTCAT CACCAG | 1067 | mU * mAmAmUmA * A * A * T * T * G * T * C * A * T * C * A * C * mA * mG | 1419 | XOOOXXXXX XXXXXXXXX X | 5-13-2 gapmer 1 PS on each end and between dN-mN and dN-dN | rs7685686 (A/G) |
| WV-2074 | UAAUAAA TTGTCAT CACCAG | 1068 | mU * mAmAmUmA * A * A * T * T * G * T * C * A * T * C * A * C * mCmA * mG | 1420 | XOOOXXXXX XXXXXXXXO X | 5-12-3 gapmer 1 PS on each end and between dN-mN and dN-dN | rs7685686 (A/G) |
| WV-2075 | UAAUAAA TTGTCAT CACCAG | 1069 | mU * mAmAmUmA * A * A * T * T * G * T * C * A * T * C * A * mCmCmA * mG | 1421 | XOOOXXXXX XXXXXXXOO X | 5-11-4 gapmer 1 PS on each end and between dN-mN and dN-dN | rs7685686 (A/G) |
| WV-2076 | UAAUAAA TTGTCAT CACCAG | 1070 | mU * mAmAmUmA * A * A * T * T * G * T * C * A * T * C * mAmCmCmA * mG | 1422 | XOOOXXXXX XXXXXXOOO X | 5-10-5 gapmer 1 PS on each end and between dN-mN and dN-dN | rs7685686 (A/G) |
| WV-2077 | UUAAUAA ATTGTCA TCACCA | 1071 | mU * mUmAmAmU * A * A * T * T * G * T * C * A * T * C * A * C * C * mA | 1423 | XOOOXXXXX XXXXXXXXX X | 5-14-1 gapmer 1 PS on each end and between dN-mN and dN-dN | rs7685686 (A/G) |
| WV-2078 | UUAAUAA ATTGTCA TCACCA | 1072 | mU * mUmAmAmU * A * A * T * T * G * T * C * A * T * C * A * C * mC * mA | 1424 | XOOOXXXXX XXXXXXXXX X | 5-13-2 gapmer 1 PS on each end and between dN-mN and dN-dN | rs7685686 (A/G) |
| WV-2079 | UUAAUAA ATTGTCA TCACCA | 1073 | mU * mUmAmAmU * A * A * T * T * G * T * C * A * T * C * A * mCmC * mA | 1425 | XOOOXXXXX XXXXXXXXO X | 5-12-3 gapmer 1 PS on each end and between dN-mN and dN-dN | rs7685686 (A/G) |
| WV-2080 | UUAAUAA ATTGTCA TCACCA | 1074 | mU * mUmAmAmU * A * A * T * T * G * T * C * A * T * C * mAmCmC * mA | 1426 | XOOOXXXXX XXXXXXXOO X | 5-11-4 gapmer 1 PS on each end and between dN-mN and dN-dN | rs7685686 (A/G) |
| WV-2081 | AUUAAUA AATTGTC ATCACC | 1075 | mA * mUmUmAmA * T * A * A * A * T * T * G * T * C * A * T * C * A * C * C | 1427 | XOOOXXXXX XXXXXXXXX X | 5-15 hemimer 1 PS on each end and between dN-mN and dN-dN | rs7685686 (A/G) |
| WV-2082 | AUUAAUA AATTGTC ATCACC | 1076 | mA * mUmUmAmA * T * A * A * A * T * T * G * T * C * A * T * C * A * C * mC | 1428 | XOOOXXXXX XXXXXXXXX X | 5-14-1 gapmer 1 PS on each end and between dN-mN and dN-dN | rs7685686 (A/G) |
| WV-2083 | AUUAAUA AATTGTC ATCACC | 1077 | mA * mUmUmAmA * T * A * A * A * T * T * G * T * C * A * T * C * A * mC * mC | 1429 | XOOOXXXXX XXXXXXXXX X | 5-13-2 gapmer 1 PS on each end and between dN-mN and dN-dN | rs7685686 (A/G) |
| WV-2084 | AUUAAUA AATTGTC ATCACC | 1078 | mA * mUmUmAmA * T * A * A * A * T * T * G * T * C * A * T * C * mAmC * mC | 1430 | XOOOXXXXX XXXXXXXXO X | 5-12-3 gapmer 1 PS on each end and between dN-mN and dN-dN | rs7685686 (A/G) |
| WV-2085 | UAUUAAU AAATTGT CATCAC | 1079 | mU * mAmUmUmA * A * A * T * A * A * A * T * T * G * T * C * A * T * C * A * C | 1431 | XOOOXXXXX XXXXXXXXX X | 5-15 hemimer 1 PS on each end and between dN-mN and dN-dN | rs7685686 (A/G) |
| WV-2086 | UAUUAAU AAATTGT CATCAC | 1080 | mU * mAmUmUmA * A * A * T * A * A * A * T * T * G * T * C * A * T * C * A * mC | 1432 | XOOOXXXXX XXXXXXXXX X | 5-14-1 gapmer 1 PS on each end and between dN-mN and dN-dN | rs7685686 (A/G) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
| --- | --- | --- | --- | --- | --- | --- | --- |
| WV-2087 | UAUUAAT AAATTGT CATCAC | 1081 | mU * mAmUmUmA * A * T * A * A * T * T * G * T * C * A * T * C * mA * mC | 1433 | XOOOXXXXX XXXXXXXXX X | 5-13-2 gapmer 1 PS on each end and between dN-mN and dN-dN | rs7685686 (A/G) |
| WV-2088 | CUAUUAA TAAATTG TCATCA | 1082 | mC * mUmAmUmU * A * A * T * A * A * A * T * T * G * T * C * A * T * C * A | 1434 | XOOOXXXXX XXXXXXXXX X | 5-15 hemimer 1 PS on each end and between dN-mN and dN-dN | rs7685686 (A/G) |
| WV-2089 | CUAUUAA TAAATTG TCATCA | 1083 | mC * mUmAmUmU * A * A * T * A * A * A * T * T * G * T * C * A * T * C * mA | 1435 | XOOOXXXXX XXXXXXXXX X | 5-14-1 gapmer 1 PS on each end and between dN-mN and dN-dN | rs7685686 (A/G) |
| WV-2090 | ACUAUUA ATAAATT GTCATC | | mA * mCmUmAmU * T * A * A * T * A * A * A * T * T * G * T * C * A * T * C | 1084 | 1436 | XOOOXXXXX XXXXXXXXX X | 5-15 hemimer 1 PS on each end and between dN-mN and dN-dN | rs7685686 (A/G) |
| WV-2163 | GACUUUU UCUGGUG AUGGCAA UUUAUUA AUAG | 1085 | rGrArCrUrUrUrUrUrCrUrGrGr UrGrArUrGrGrCrArArUrUrUrA rUrUrArUrArG | 1437 | OOOOOOOOO OOOOOOOOO OOOOOOOOO OOOO | HTT rs7685686 | HTT rs7685686 |
| WV-2164 | GACUUUU UCUGGUG AUGACAA UUUAUUA AUAG | 1086 | rGrArCrUrUrUrUrUrCrUrGrGr UrGrArUrGrArCrArArUrUrUrA rUrUrArUrArG | 1438 | OOOOOOOOO OOOOOOOOO OOOOOOOOO OOOO | HTT rs7685686 | HTT rs7685686 |
| WV-2269 | UAAAUTG TCATCAC CAGAAA | 1087 | mU * SmAmAmAmU * ST * SG * ST * SC * SA * RT * SC * SA * SC * SC * SmAmGmAmA * SmA | 1439 | SOOOSSSSSR SSSSSOOOS | 5-10-5 2' OMe-DNA-2'-OMe Gapmer 1-3-11-3-1 (PS/PO) | HTT rs7685686 |
| WV-2270 | AUAAAUT GTCATCA CCAGAA | 1088 | mA * SmUmAmAmA * ST * ST * SG * ST * SC * SA * RT * SC * SA * SC * SmCmAmGmA * SmA | 1440 | SOOOSSSSSS RSSSSOOOS | 5-10-5 2' OMe-DNA-2'-OMe Gapmer 1-3-11-3-1 (PS/PO) | HTT rs7685686 |
| WV-2271 | AAUAAAT TGTCATC ACCAGA | 1089 | mA * SmAmUmAmA * SA * ST * ST * SG * ST * SC * SA * RT * SC * SA * SmCmCmAmG * SmA | 1441 | SOOOSSSSSS SRSSSOOOS | 5-10-5 2' OMe-DNA-2'-OMe Gapmer 1-3-11-3-1 (PS/PO) | HTT rs7685686 |
| WV-2272 | UAAUAAA TTGTCAT CACCAG | 1090 | mU * SmAmAmUmA * SA * SA * ST * ST * SG * ST * SC * SA * RT * SC * SmAmCmCmA * SmG | 1442 | SOOOSSSSSS SSRSSOOOS | 5-10-5 2' OMe-DNA-2'-OMe Gapmer 1-3-11-3-1 (PS/PO) | HTT rs7685686 |
| WV-2374 | AAUAAAT TGTCATC ACCAGA | 1091 | mA * SmAmUmAmA * SA * ST * ST * SG * ST * SC * SA * RT * SC * SA * SC * SmCmAmG * SmA | 1443 | SOOOSSSSSS SRSSSOOOS | P10 stereopure analogue of WV-2071 5-11-4 2'-OMe-DNA-2'-OMe Gapmer 1-3-12-2-1 (PS/PO) | HTT rs7685686 |
| WV-2375 | UAAUAAA TTGTCAT CACCAG | 1092 | mU * SmAmAmUmA * SA * SA * ST * ST * SG * ST * SC * SA * RT * SC * SA * SmCmCmA * SmG | 1444 | SOOOSSSSSS SSRSSOOOS | P11 stereopure analogue of WV-20755-11-4 2'-OMe-DNA-2'-OMe Gapmer 1-3-12-2-1 (PS/PO) | HTT rs7685686 |
| WV-2377 | GCACAAG GGCACAC ACUUCC | 1093 | mG * mCmAmCmA * A * G * G * G * C * A * C * A * C * A * mCmUmUmC * mC | 1445 | XOOOXXXXX XXXXXOOO X | P11 stereorandom analogue of WV-932 5-10-5 2'-OMe-DNA-2'-OMe Gapmer and 1-3-11-3-1 (PS/PO) | HTT rs362307 |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2378 | GCACAAG GGCACAG ACUUCC | 1094 | mG * SmCmAmCmA * SA * SG * SG * SG * SC * SA * SC * RA * SG * SA * SmCmUmUmC * SmC | 1446 | SOOOSSSSSS SRSSSOOOS | P11 stereorandom analogue of WV-932 5-10-5 2'-OMe-DNA-2'-OMe Gapmer and 1-3-11-3-1 (PS/PO) | HTT rs362307 |
| WV-2379 | CACAAGG GCACAGA CUUCCA | 1095 | mC * mAmCmAmA * G * G * G * C * A * C * A * G * A * C * mUmUmCmC * mA | 1447 | XOOOXXXXX XXXXXXOOO X | P10 sereorandom analogue of WV-933 5-10-5 2'-OMe-DNA-2'-OMe Gapmer and 1-3-11-3-1 (PS/PO) | HTT rs362307 |
| WV-2380 | CACAAGG GCACAGA CUUCCA | 1096 | mC * SmAmCmAmA * SG * SG * SG * SC * SA * SC * RA * SG * SA * SC * SmUmUmCmC * SmA | 1448 | SOOOSSSSSS RSSSSOOOS | P10 stereopure analogue of WV-933 5-10-5 2'-OMe-DNA-2'-OMe Gapmer and 1-3-11-3-1 (PS/PO) | HTT rs362307 |
| WV-2416 | UAAAUTG TCATCAC CAGAAA | 1097 | mU * SmAmAmAmU * ST * SG * ST * ST * SC * RA * ST * SC * SA * SC * SC * SmAmGmAmA * SmA | 1449 | SOOOSSSSRS SSSSSOOOS | P8 5-10-5 2' OMe-DNA-2'-OMe Gapmer 1-3-11-3-1 (PS/PO) | HTT rs7685686 |
| WV-2417 | AUAAATT GTCATCA CCAGAA | 1098 | mA * SmUmAmAmA * ST * ST * SG * ST * SC * RA * ST * SC * SA * SC * SmCmAmGmA * SmA | 1450 | SOOOSSSSSR SSSSSOOOS | P9 5-10-5 2' OMe-DNA-2'-OMe Gapmer 1-3-11-3-1 (PS/PO) | HTT rs7685686 |
| WV-2418 | AAUAAAT TGTCATC ACCAGA | 1099 | mA * SmAmUmAmA * SA * ST * ST * SG * ST * SC * RA * ST * SC * SA * SmCmCmAmG * SmA | 1451 | SOOOSSSSSS RSSSSOOOS | P10 5-10-5 2' OMe-DNA-2'-OMe Gapmer 1-3-11-3-1 (PS/PO) | HTT rs7685686 |
| WV-2419 | UAAUAAA TTGTCAT CACCAG | 1100 | mU * SmAmAmAmUmA * SA * SA * ST * ST * SG * ST * SC * RA * ST * SC * SmAmCmCmA * SmG | 1452 | SOOOSSSSSS SRSSSOOOS | P11 5-10-5 2' OMe-DNA-2'-OMe Gapmer 1-3-11-3-1 (PS/PO) | HTT rs7685686 |
| WV-2589 | UCCCCAC AGAGGGA GGAAGC | 1101 | mU * SmCmCmCmC * SA * SC * RA * SG * SA * SG * SG * SG * SA * SG * SmGmAmAmG * SmC | 1453 | SOOOSSRSSS SSSSSOOOS | P6 5-10-5 (2'-OMe-DNA-2'-OMe) 1-3-11-3-1 (PS/PO) Gapmer | HTT rs2530595 (C/T) |
| WV-2590 | CUCCCCA CAGAGGG AGGAAG | 1102 | mC * SmUmCmCmC * SC * SA * SC * RA * SG * SA * SG * SG * SG * SA * SmGmGmAmA * SmG | 1454 | SOOOSSSRSS SSSSSOOOS | P7 5-10-5 (2'-OMe-DNA-2'-OMe) 1-3-11-3-1 (PS/PO) Gapmer | HTT rs2530595 (C/T) |
| WV-2591 | CCUCCCC ACAGAGG GAGGAA | 1103 | mC * SmCmUmCmC * SC * SC * SA * SC * RA * SG * SA * SG * SG * SG * SmAmGmGmA * SmA | 1455 | SOOOSSSSRS SSSSSOOOS | P8 5-10-5 (2'-OMe-DNA-2'-OMe) 1-3-11-3-1 (PS/PO) Gapmer | HTT rs2530595 (C/T) |
| WV-2592 | UCCUCCC CACAGAG GGAGGA | 1104 | mU * SmCmCmCmUmC * SC * SC * SA * SC * RA * SG * SA * SG * SG * SmGmAmGmG * SmA | 1456 | SOOOSSSSSR SSSSSOOOS | P9 5-10-5 (2'-OMe-DNA-2'-OMe) 1-3-11-3-1 (PS/PO) Gapmer | HTT rs2530595 (C/T) |
| WV-2593 | GUCCUCC CCACAGA GGGAGG | 1105 | mG * SmUmCmCmU * SC * SC * SC * SC * SA * SC * RA * SG * SA * SG * SmGmGmAmG * SmG | 1457 | SOOOSSSSSS RSSSSOOOS | P10 5-10-5 (2'-OMe-DNA-2'-OMe) 1-3-11-3-1 (PS/PO) Gapmer | HTT rs2530595 (C/T) |
| WV-2594 | GGUCCUC CCCACAG AGGGAG | 1106 | mG * SmGmUmCmU * ST * SC * SC * SC * SC * SC * SA * SC * RA * SG * SmGmGmAmG * SmG | 1458 | SOOOSSSSSS SRSSSOOOS | P11 5-10-5 (2'-OMe-DNA-2'-OMe) 1-3-11-3-1 (PS/PO) Gapmer | HTT rs2530595 (C/T) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2595 | GGGUCCTCCCCACAGAGGGA | 1107 | mG * SmGmGmUmC * SC * ST * SC * SC * SC * SC * SA * SC * RA * SG * SmAmGmGmG * SmA | 1459 | SOOOSSSSSSSRSSOOOS | P12 5-10-5 (2'-OMe-DNA-2'-OMe) 1-3-11-3-1 (PS/PO) Gapmer | HTT rs2530595 (C/T) |
| WV-2596 | CGGGUCCTCCCCACAGAGGG | 1108 | mC * SmGmGmGmU * SC * SC * ST * SC * SC * SC * SC * SA * SC * RA * SmGmAmGmG * SmG | 1460 | SOOOSSSSSSSRSOOOS | P13 5-10-5 (2'-OMe-DNA-2'-OMe) 1-3-11-3-1 (PS/PO) Gapmer | HTT rs2530595 (C/T) |
| WV-2597 | ACAGUAGATGAGGGAGCAGG | 1109 | mA * SmCmAmGmU * SA * SG * RA * ST * SG * SA * SG * SG * SG * SA * SmGmCmAmG * SmG | 1461 | SOOOSSRSSSSSSSOOOS | P6 5-10-5 (2'-OMe-DNA-2'-OMe) 1-3-11-3-1 (PS/PO) Gapmer | HTT (rs362331) (C/T) |
| WV-2598 | CACAGUAGATGAGGGAGCAG | 1110 | mC * SmAmCmAmG * ST * SA * SG * RA * ST * SG * SA * SG * SG * SG * SmAmGmCmA * SmG | 1462 | SOOOSSSRSSSSSSOOOS | P7 5-10-5 (2'-OMe-DNA-2'-OMe) 1-3-11-3-1 (PS/PO) Gapmer | HTT (rs362331) (C/T) |
| WV-2599 | ACACAGUAGATGAGGGAGCA | 1111 | mA * SmCmAmCmA * SG * ST * SA * SG * RA * ST * SG * SA * SG * SG * SmGmAmGmC * SmA | 1463 | SOOOSSSSRSSSSSOOOS | P8 5-10-5 (2'-OMe-DNA-2'-OMe) 1-3-11-3-1 (PS/PO) Gapmer | HTT (rs362331) (C/T) |
| WV-2600 | CACACAGTAGATGAGGGAGC | 1112 | mC * SmAmCmAmC * SA * SG * ST * SA * SG * RA * ST * SG * SA * SG * SmGmGmAmG * SmC | 1464 | SOOOSSSSSRSSSSOOOS | P9 5-10-5 (2'-OMe-DNA-2'-OMe) 1-3-11-3-1 (PS/PO) Gapmer | HTT (rs362331) (C/T) |
| WV-2601 | GCACACAGTAGATGAGGGAG | 1113 | mG * SmCmAmCmA * SC * SA * SG * ST * SA * SG * RA * ST * SG * SA * SmGmGmAmG * SmG | 1465 | SOOOSSSSSSRSSSOOOS | P10 5-10-5 (2'-OMe-DNA-2'-OMe) 1-3-11-3-1 (PS/PO) Gapmer | HTT (rs362331) (C/T) |
| WV-2602 | UGCACACAGTAGATGAGGGA | 1114 | mU * SmGmCmAmC * SA * SC * SA * SG * ST * SA * SG * RA * ST * SG * SmAmGmGmG * SmA | 1466 | SOOOSSSSSSSRSSOOOS | P11 5-10-5 (2'-OMe-DNA-2'-OMe) 1-3-11-3-1 (PS/PO) Gapmer | HTT (rs362331) (C/T) |
| WV-2603 | GUGCACACAGTAGATGAGGG | 1115 | mG * SmUmGmCmA * SC * SA * SC * SA * SG * ST * SA * SG * RA * ST * SmGmAmGmG * SmG | 1467 | SOOOSSSSSSSSRSOOOS | P12 5-10-5 (2'-OMe-DNA-2'-OMe) 1-3-11-3-1 (PS/PO) Gapmer | HTT (rs362331) (C/T) |
| WV-2604 | AGUGCACACAGTAGATGAGG | 1116 | mA * SmGmUmGmC * SA * SC * SA * SC * SA * SG * ST * SA * SG * RA * SmUmGmAmG * SmG | 1468 | SOOOSSSSSSSSSRSOOOS | P13 5-10-5 (2'-OMe-DNA-2'-OMe) 1-3-11-3-1 (PS/PO) Gapmer | HTT (rs362331) (C/T) |
| WV-2605 | UCCCCACAGAGGGAGGAAGC | 1117 | mU * mCmCmCmC * A * C * A * G * A * G * G * A * G * mGmAmAmG * mC | 1469 | XOOOXXXXXXXXXXOOOX | P6 5-10-5 (2'-OMe-DNA-2'-OMe) 1-3-11-3-1 (P/PO) Gapmer | HTT r2530595 (C/T) |
| WV-2606 | CUCCCCACAGAGGGAGGAAG | 1118 | mC * mUmCmCmC * C * A * C * A * G * A * G * G * A * mGmGmAmA * mG | 1470 | XOOOXXXXXXXXXXOOOX | P7 5-10-5 (2'-OMe-DNA-2'-OMe) 1-3-11-3-1 (P/PO) Gapmer | HTT r2530595 (C/T) |
| WV-2607 | CCUCCCCACAGAGGGAGGAA | 1119 | mC * mCmUmCmC * C * C * A * C * A * G * A * G * G * mAmGmGmA * mA | 1471 | XOOOXXXXXXXXXXOOOX | P8 5-10-5 (2'-OMe-DNA-2'-OMe) 1-3-11-3-1 (P/PO) Gapmer | HTT r2530595 (C/T) |
| WV-2608 | UCCUCCCCACAGAGGGAGGA | 1120 | mU * mCmCmUmC * C * C * C * A * C * A * G * A * G * mGmAmGmG * mA | 1472 | XOOOXXXXXXXXXXOOOX | P9 5-10-5 (2'-OMe-DNA-2'-OMe) 1-3-11-3-1 (P/PO) Gapmer | HTT r2530595 (C/T) |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2609 | GUCCUCC CCACAGA GGGAGG | 1121 | mG * mUmCmCmU * C * C * C * C * A * C * A * G * A * G * mGmGmAmG * mG | 1473 | XOOOXXXXX XXXXXXOOO X | P10 5-10-5 (2'-OMe-DNA-2'-OMe) 1-3-11-3-1 (P/PO) Gapmer | HTT r2530595 (C/T) |
| WV-2610 | GGUCCUC CCCACAG AGGGAG | 1122 | mG * mGmUmCmC * T * C * C * C * C * A * C * A * G * A * mGmGmGmA * mG | 1474 | XOOOXXXXX XXXXXXOOO X | P11 5-10-5 (2'-OMe-DNA-2'-OMe) 1-3-11-3-1 (P/PO) Gapmer | HTT r2530595 (C/T) |
| WV-2611 | GGGUCCU CCCCACA GAGGGA | 1123 | mG * mGmGmUmC * C * T * C * C * C * C * A * C * A * G * mAmGmGmG * mA | 1475 | XOOOXXXXX XXXXXXOOO X | P12 5-10-5 (2'-OMe-DNA-2'-OMe) 1-3-11-3-1 (P/PO) Gapmer | HTT r2530595 (C/T) |
| WV-2612 | CGGGUCC UCCCCAC AGAGGG | 1124 | mC * mGmGmGmU * C * C * T * C * C * C * C * C * A * C * A * mGmAmGmG * mG | 1476 | XOOOXXXXX XXXXXXOOO X | P13 5-10-5 (2'-OMe-DNA-2'-OMe) 1-3-11-3-1 (P/PO) Gapmer | HTT r2530595 (C/T) |
| WV-2613 | ACAGUAG ATGAGGG AGCAGG | 1125 | mA * mCmAmGmU * A * G * A * T * G * A * G * G * G * A * mGmCmAmG * mG | 1477 | XOOOXXXXX XXXXXXOOO X | P6 5-10-5 (2'-OMe-DNA-2'-OMe) 1-3-11-3-1 (P/PO) Gapmer | HTT (r362331) (C/T) |
| WV-2614 | CACAGUA GATGAGG GAGCAG | 1126 | mC * mAmCmAmG * T * A * G * A * T * G * A * G * G * G * mGmAmGmC * mG | 1478 | XOOOXXXXX XXXXXXOOO X | P7 5-10-5 (2'-OMe-DNA-2'-OMe) 1-3-11-3-1 (P/PO) Gapmer | HTT (r362331) (C/T) |
| WV-2615 | ACACAGU AGATGAG GGAGCA | 1127 | mA * mCmAmCmA * G * T * A * G * A * T * G * A * G * G * mGmAmGmC * mA | 1479 | XOOOXXXXX XXXXXXOOO X | P8 5-10-5 (2'-OMe-DNA-2'-OMe) 1-3-11-3-1 (P/PO) Gapmer | HTT (r362331) (C/T) |
| WV-2616 | CACACAG TAGATGA GGGAGC | 1128 | mC * mAmCmAmC * A * G * T * A * G * A * T * G * A * G * mGmGmAmG * mC | 1480 | XOOOXXXXX XXXXXXOOO X | P9 5-10-5 (2'-OMe-DNA-2'-OMe) 1-3-11-3-1 (P/PO) Gapmer | HTT (r362331) (C/T) |
| WV-2617 | GCACACA GTAGATG AGGGAG | 1129 | mG * mCmAmCmA * C * A * G * T * A * G * A * T * G * A * mGmGmGmA * mG | 1481 | XOOOXXXXX XXXXXXOOO X | P10 5-10-5 (2'-OMe-DNA-2'-OMe) 1-3-11-3-1 (P/PO) Gapmer | HTT (r362331) (C/T) |
| WV-2618 | UGCACAC AGTAGAT GAGGGA | 1130 | mU * mGmCmAmC * A * C * A * G * T * A * G * A * T * G * mAmGmGmG * mA | 1482 | XOOOXXXXX XXXXXXOOO X | P11 5-10-5 (2'-OMe-DNA-2'-OMe) 1-3-11-3-1 (P/PO) Gapmer | HTT (r362331) (C/T) |
| WV-2619 | GUGCACA CAGTAGA TGAGGG | 1131 | mG * mUmGmCmA * C * A * C * A * G * T * A * G * A * T * mGmAmGmG * mG | 1483 | XOOOXXXXX XXXXXXOOO X | P12 5-10-5 (2'-OMe-DNA-2'-OMe) 1-3-11-3-1 (P/PO) Gapmer | HTT (r362331) (C/T) |
| WV-2620 | AGUGCAC ACAGTAG ATGAGG | 1132 | mA * mGmUmGmC * A * C * A * C * A * G * T * A * G * A * mUmGmAmG * mG | 1484 | XOOOXXXXX XXXXXXOOO X | P13 5-10-5 (2'-OMe-DNA-2'-OMe) 1-3-11-3-1 (P/PO) Gapmer | HTT (r362331) (C/T) |
| WV-2623 | GGCACAA GGGCACA GACTTC | 1133 | GGCACAAGGGCACAGACTTC | 1485 | OOOOOOOOO OOOOOOOOO O | DNA version of WV-1092 | HTT rs362307 (C/T) |
| WV-2659 | GGCACAA GGGCACA GACUUC | 1134 | mG * SmGmCmAmC * SA * SA * SG * SG * SG * SC * SA * SC * SA * SG * SmAmCmUmU * SmC | 1486 | SOOOSSSSS SSSSSOOOS | WV-1092 analogue with All Sp stereochemistry | rs362307 Human HTT |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2671 | GGGUCCTCCCCACAGAGGGA | 1135 | mG * SmG * SmGmUmC * SC * ST * SC * SC * SC * SC * SA * SC * RA * SG * SmAmGmG * SmG * SmA | 1487 | SSOOSSSSSSSRSSOOSS | P12 5-10-5 (2'-OMe-DNA-2'-OMe) 2-2-11-2-2 (PS/PO) Gapmer with Sp wings | HTT rs2530595 (C/T) |
| WV-2672 | GGGUCCTCCCCACAGAGGGA | 1136 | mG * RmG * RmGmUmC * SC * ST * SC * SC * SC * SC * SA * SC * RA * SG * SmAmGmG * RmG * RmA | 1488 | RROOSSSSSSSRSSOORR | P12 5-10-5 (2'-OMe-DNA-2'-OMe) 4-11-4 (PS/PO) Gapmer with Rp wings | HTT rs2530595 (C/T) |
| WV-2673 | GGGUCCTCCCCACAGAGGGA | 1137 | mG * SmG * SmG * SmU * SmC * SC * ST * SC * SC * SC * SC * SA * SC * RA * SG * SmA * SmG * SmG * SmG * SmA | 1489 | SSSSSSSSSSSRSSSSSS | P12 5-10-5 (2'-OMe-DNA-2'-OMe) 2-2-11-2-2 (PS/PO) Gapmer with Sp wings | HTT rs2530595 (C/T) |
| WV-2674 | GGGUCCTCCCCACAGAGGGA | 1138 | mG * RmG * RmG * RmU * RmC * SC * ST * SC * SC * SC * SC * SA * SC * RA * SG * SmA * RmG * RmG * RmG * RmA | 1490 | RRRRSSSSSSSRSSRRRR | P12 5-10-5 (2'-OMe-DNA-2'-OMe) 2-2-11-2-2 (PS/PO) Gapmer with Rp wings | HTT rs2530595 (C/T) |
| WV-2675 | GGGUUCTCCCCACAGAGGGA | 1139 | mG * SmGmGmUmU * SC * ST * SC * SC * SC * SC * SA * SC * RA * SG * SmAmGmGmG * SmA | 1491 | SOOOSSSSSSSRSOOOS | P12 analogue of WV-2595 with G:U mismatch at position 5 | HTT rs2530595 (C/T) |
| WV-2676 | GGCACAAGGGCACAGACUUC | 1140 | mG * RmGmCmAmC * SA * SA * SG * SG * SG * SC * SA * SC * SA * SG * SmAmCmUmU * SmC | 1492 | ROOOSSSSSSSSSOOOS | WV-1092 analogue for CMC | rs362307 Human HTT |
| WV-2682 | GGCACAAGGGCACAGACUUC | 1141 | mG * SmGmCmAmC * RA * SA * SG * SG * SG * SC * SA * SC * SA * SG * SmAmCmUmU * SmC | 1493 | SOOORSSSSSSSSSOOOS | WV-1092 analogue for CMC | rs362307 Human HTT |
| WV-2683 | GGCACAAGGGCACAGACUUC | 1142 | mG * SmGmCmAmC * SA * RA * SG * SG * SG * SC * SA * SC * SA * SG * SmAmCmUmU * SmC | 1494 | SOOOSRSSSSSSSSSOOOS | WV-1092 analogue for CMC | rs362307 Human HTT |
| WV-2684 | GGCACAAGGGCACAGACUUC | 1143 | mG * SmGmCmAmC * SA * SA * RG * SG * SG * SC * SA * SC * SA * SG * SmAmCmUmU * SmC | 1495 | SOOOSSRSSSSSSSSOOOS | WV-1092 analogue for CMC | rs362307 Human HTT |
| WV-2685 | GGCACAAGGGCACAGACUUC | 1144 | mG * SmGmCmAmC * SA * SA * SG * RG * SG * SC * SA * SC * SA * SG * SmAmCmUmU * SmC | 1496 | SOOOSSSRSSSSSSSOOOS | WV-1092 analogue for CMC | rs362307 Human HTT |
| WV-2686 | GGCACAAGGGCACAGACUUC | 1145 | mG * SmGmCmAmC * SA * SA * SG * SG * RG * SC * SA * SC * SA * SG * SmAmCmUmU * SmC | 1497 | SOOOSSSSRSSSSSSSOOOS | WV-1092 analogue for CMC | rs362307 Human HTT |
| WV-2687 | GGCACAAGGGCACAGACUUC | 1146 | mG * SmGmCmAmC * SA * SA * SG * SG * SG * RC * SA * SC * SA * SG * SmAmCmUmU * SmC | 1498 | SOOOSSSSSR SSSSSSOOOS | WV-1092 analogue for CMC | rs362307 Human HTT |
| WV-2688 | GGCACAAGGGCACAGACUUC | 1147 | mG * SmGmCmAmC * SA * SA * SG * SG * SG * SC * RA * SC * SA * SG * SmAmCmUmU * SmC | 1499 | SOOOSSSSSSRSSSSOOOS | WV-1092 analogue for CMC | rs362307 Human HTT |
| WV-2689 | GGCACAAGGGCACAGACUUC | 1148 | mG * SmGmCmAmC * SA * SA * SG * SG * SG * SC * SA * RC * SA * SG * SmAmCmUmU * SmC | 1500 | SOOOSSSSSSSRSSSSOOOS | WV-1092 analogue for CMC | rs362307 Human HTT |

TABLE 8-continued

HTT Oligonucleotides.

| SEQ ID | Naked Sequence | SEQ ID NO: | Modified Sequence | SEQ ID NO: | Stereochemistry | Comment 1 | Comment 2 |
|---|---|---|---|---|---|---|---|
| WV-2690 | GGCACAA GGGCACA GACUUC | 1149 | mG * SmGmCmAmC * SA * SA * SG * SG * SG * SC * SA * SC * SA * RG * SmAmCmUmU * SmC | 1501 | SOOOSSSSSS SSSRSOOOS | WV-1092 analogue for CMC | rs362307 Human HTT |
| WV-2691 | GGCACAA GGGCACA GACUUC | 1150 | mG * SmGmCmAmC * SA * SA * SG * SG * SG * SC * SA * SC * SA * SG * RmAmCmUmU * SmC | 1502 | SOOOSSSSSS SSSSROOOS | WV-1092 analogue for CMC | rs362307 Human HTT |
| WV-2692 | GGCACAA GGGCACA GACUUC | 1151 | mG * SmGmCmAmC * SA * SA * SG * SG * SG * SC * SA * SC * SA * SG * SmAmCmUmU * RmC | 1503 | SOOOSSSSSS SSSSSOOOR | WV-1092 analogue for CMC | rs362307 Human HTT |
| WV-2728 | GGCAC | | mG * SmGmCmAmC | | SOOO | WV-1092 fragment for CMC | rs362307 Human HTT |
| WV-2729 | GGCAC | | mG * RmGmCmAmC | | ROOO | WV-1092 fragment for CMC | rs362307 Human HTT |
| WV-2730 | ACUUC | | mAmCmUmU * SmC | | OOOS | WV-1092 fragment for CMC | rs362307 Human HTT |
| WV-2731 | ACUUC | | mAmCmUmU * RmC | | OOOR | WV-1092 fragment for CMC | rs362307 Human HTT |
| WV-2732 | GGCACAA GGGCACA GACUUC | 1152 | mG * SmGmCmAmC * SA * SA * SG * SG * SG * SC * RA * SC * RA * SG * SmAmCmUmU * SmC | 1504 | SOOOSSSSS RSRSSOOOS | WV-1092 for CM | rs362307 Human HTT |

Abbreviations:
2\': 2'
3\': 3'
5\': 5'
307: SNP rs362307
C6: C6 amino linker
F, f: 2'-F
Htt, HTT: Huntingtin gene or Huntington's Disease
Laurie, Myristic, Palmitic, Stearic, Oleic, Linoleic, alpha-Linolenic, gamma-Linolenic, DHA, Turbinaric, Dilinoleic: Laurie acid, Myristic acid, Palmitic acid, Stearic acid, Oleic acid, Linoleic acid, alpha-Linolenic acid, gamma-Linolenic acid, docosahexaenoic acid, Turbinaric acid, Dilinoreic acid, respectively.
muHtt or muHTT: mutant Huntingtin gene or gene product
OMe: 2'-OMe
O, PO: phoshodiester (phosphate)
*, PS: Phosphorothioate
R, Rp: Phosphorothioate in Rp conformation
S, Sp: Phosphorothioate in Sp conformation
WV: WV-
WV-: WV
X: Phosphorothioate, stereorandom

EQUIVALENTS

Having described some illustrative embodiments of the disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the disclosure. The present disclosure is not to be limited in scope by examples provided, since the examples are intended as a single illustration of one aspect of the disclosure and other functionally equivalent embodiments are within the scope of the disclosure. Various modifications of the disclosure in addition to those shown and described herein will become apparent to those skilled in the art from the foregoing description and fall within the scope of the appended claims. The advantages and objects of the disclosure are not necessarily encompassed by each embodiment of the disclosure.

The invention claimed is:

1. An oligonucleotide having the structure of:

mG * SmUmGmCmA * SC * SA * SC * SA * SG * ST * SA * SG * RA * ST * SmGmAmGmG * SmG (SEQ ID NO: 1467), or a pharmaceutically acceptable salt thereof, wherein:

*S represents a Sp phosphorothioate;
*R represents a Rp phosphorothioate; and
m represents a 2'-OMe modification to a nucleoside.

2. The oligonucleotide of claim 1, wherein the oligonucleotide is in a salt form.

3. The oligonucleotide of claim 1, wherein the salt is a sodium salt.

4. An oligonucleotide, wherein the oligonucleotide is a sodium salt of:

mG * SmUmGmCmA * SC * SA * SC * SA * SG * ST * SA * SG * RA * ST * SmGmAmGmG * SmG (SEQ ID NO: 1467), wherein:

*S represents a Sp phosphorothioate;
*R represents a Rp phosphorothioate;
m represents a 2'-OMe modification to a nucleoside; and
the number of sodium ions in the sodium salt equals the total number of phosphorothioate and phosphate linkages in the oligonucleotide.

5. A chirally controlled composition of an oligonucleotide having the structure of:

mG * SmUmGmCmA * SC * SA * SC * SA * SG * ST * SA * SG * RA * ST * SmGmAmGmG * SmG (SEQ ID NO: 1467), or a pharmaceutically acceptable salt thereof, wherein:

*S represents a Sp phosphorothioate;
*R represents a Rp phosphorothioate; and
m represents a 2'-OMe modification to a nucleoside, wherein the composition is enriched, relative to a substantially racemic preparation of the oligonucleotide for the oligonucleotide.

6. The composition of claim 5, wherein the oligonucleotide is in a salt form.

7. The composition of claim 5, wherein the oligonucleotide is a sodium salt.

8. The composition of claim 7, wherein the number of sodium ions in the sodium salt equals the total number of phosphorothioate and phosphate linkages in the oligonucleotide.

9. A pharmaceutical composition, comprising a therapeutically effective amount of an oligonucleotide and at least one pharmaceutically acceptable inactive ingredient selected from pharmaceutically acceptable diluents, pharmaceutically acceptable excipients, and pharmaceutically acceptable carriers, wherein the oligonucleotide has the structure of:

mG * SmUmGmCmA * SC * SA * SC * SA * SG * ST * SA * SG * RA * ST * SmGmAmGmG * SmG (SEQ ID NO: 1467), or a pharmaceutically acceptable salt thereof, wherein:

*S represents a Sp phosphorothioate;
*R represents a Rp phosphorothioate; and
m represents a 2'-OMe modification to a nucleoside.

10. The composition of claim 9, wherein the oligonucleotide is in a salt form.

11. The composition of claim 9, wherein the oligonucleotide is a sodium salt.

12. The composition of claim 9, wherein the number of sodium ions in the sodium salt equals the total number of phosphorothioate and phosphate linkages in the oligonucleotide.

* * * * *

UNITED STATES PATENT AND TRADEMARK OFFICE
CERTIFICATE OF CORRECTION

PATENT NO. : 10,724,035 B2
APPLICATION NO. : 16/098836
DATED : July 28, 2020
INVENTOR(S) : Vargeese et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 36 days.

Signed and Sealed this
Thirty-first Day of January, 2023

Katherine Kelly Vidal
*Director of the United States Patent and Trademark Office*

SEQUENCE LISTING

```
<160> NUMBER OF SEQ ID NOS: 1565

<210> SEQ ID NO 1
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(105)
<223> OTHER INFORMATION: This sequence may encompass 10-35 "cag"
      repeating units, wherein some positions may be absent

<400> SEQUENCE: 1
cagcagcagc agcagcagca gcagcagcag cagcagcagc agcagcagca gcagcagcag     60
cagcagcagc agcagcagca gcagcagcag cagcagcagc agcag                    105

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcctcagtct gcttcgcacc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcctcagtct gcttcgcacc                                                 20

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aatcgatcga tcg                                                        13

<210> SEQ ID NO 5
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
gcctcagtct gcttcgcacc                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcctcagtct gcttcgcacc                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcctcagtct gcttcgcacc                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcctcagtct gcttcgcacc                                                 20

<210> SEQ ID NO 9
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gugagcagcu gca                                                        13

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
gggucctccc cacagaggga                                                 20

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ggguccuccc cacagaggga                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
gugcacacag tagatgaggg                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
gugcacacag tagatgaggg                                           20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ggcacaaggg cacagacuuc                                           20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ggcacaaggg cacagacuuc                                           20

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
gggacgtctt                                                        10

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcacaaggg cacagacttc                                             20

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuuggaaguc ugugcccuug ugccc                                       25

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcctcagtct gcttcgcacc                                             20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagcagctgc aacctggcaa                                             20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggcacaagg gcacagactt                                             20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22
gcacaagggc acagacttcc                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cacaagggca cagacttcca                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acaagggcac agacttccaa                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
caagggcaca gacttccaaa                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agcagctgca acctggcaac                                                    20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcagctgcaa cctggcaaca                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
```
cagctgcaac ctggcaacaa 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agctgcaacc tggcaacaac 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gctgcaacct ggcaacaacc 20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gggccaacag ccagcctgca 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggccaacagc cagcctgcag 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gccaacagcc agcctgcagg 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaacagcca gcctgcagga                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caacagccag cctgcaggag                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aacagccagc ctgcaggagg                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
attaataaat tgtcatcacc                                              20

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ttcagtcatg acttcc                                                  16

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttcagtcatg acttcc                                                  16

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcctcagtct gcttcgcacc                                              20

```
<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ggcacaaggg cacagacttc                                                   20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: t or u
<220> FEATURE:
<221> NAME/KEY: modified_base
<222> LOCATION: (8)..(8)
<223> OTHER INFORMATION: t or u
<220> FEATURE:
<221> NAME/KEY: modified_base
<222> LOCATION: (10)..(10)
<223> OTHER INFORMATION: t or u
<220> FEATURE:
<221> NAME/KEY: modified_base
<222> LOCATION: (13)..(14)
<223> OTHER INFORMATION: t or u

<400> SEQUENCE: 42
gccncagncn gcnncgcacc                                                   20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
gccucagtct gcttcgcacc                                                   20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcctcagtct gcttcgcacc                                                   20

<210> SEQ ID NO 45
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 45
gcctcagtct gcttcgcacc                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gcctcagtct gcttcgcacc                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcctcagtct gcttcgcacc                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcctcagtct gcttcgcacc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcctcagtct gcttcgcacc                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gcctcagtct gcttcgcacc                                              20

<210> SEQ ID NO 51
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 51
gcctcagtct gcttcgcacc                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gcctcagtct gcttcgcacc                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcctcagtct gcttcgcacc                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcctcagtct gcttcgcacc                                                    20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcctcagtct gcttcgcacc                                                    20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gcctcagtct gcttcgcacc                                                    20

<210> SEQ ID NO 57
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 57
gcctcagtct gcttcgcacc                                                    20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gcctcagtct gcttcgcacc                                                    20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcctcagtct gcttcgcacc                                                    20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gcctcagtct gcttcgcacc                                                    20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcctcagtct gcttcgcacc                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcctcagtct gcttcgcacc                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 63
gcctcagtct gcttcgcacc                                            20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcctcagtct gcttcgcacc                                            20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcctcagtct gcttcgcacc                                            20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gcctcagtct gcttcgcacc                                            20

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagtctgctt cg                                                    12

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cagtctgctt cg                                                    12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 69
cagtctgctt cg                                                    12

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cagtctgctt cg                                                    12

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cagtctgctt cg                                                    12

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cagtctgctt cg                                                    12

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cagtctgctt cg                                                    12

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cagtctgctt cg                                                    12

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 75
cagtctgctt cg                                                         12

<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cagtctgctt cg                                                         12

<210> SEQ ID NO 77
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ctcagtctgc ttcgc                                                      15

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cagtctgctt cg                                                         12

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cagtctgctt cg                                                         12

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gcctcagtct gcttcgcacc                                                 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
```
gcctcagtct gcttcgcacc 20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gcctcagtct gcttcgcacc 20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcctcagtct gcttcgcacc 20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gcctcagtct gcttcgcacc 20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcctcagtct gcttcgcacc 20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gcctcagtct gcttcgcacc 20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcctcagtct gcttcgcacc                          20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gcctcagtct gcttcgcacc                          20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcctcagtct gcttcgcacc                          20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcctcagtct gcttcgcacc                          20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcctcagtct gcttcgcacc                          20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gcctcagtct gcttcgcacc                          20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gcctcagtct gcttcgcacc                          20

```
<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gcctcagtct gcttcgcacc                                                    20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcctcagtct gcttcgcacc                                                    20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gcctcagtct gcttcgcacc                                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcctcagtct gcttcgcacc                                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gcctcagtct gcttcgcacc                                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcctcagtct gcttcgcacc                                                    20
```

```
<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gcctcagtct gcttcgcacc                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gcctcagtct gcttcgcacc                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcctcagtct gcttcgcacc                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcctcagtct gcttcgcacc                                                    20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gcctcagtct gcttcgcacc                                                    20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gcctcagtct gcttcgcacc                                                    20
```

```
<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcctcagtct gcttcgcacc                                                     20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcctcagtct gcttcgcacc                                                     20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gcctcagtct gcttcgcacc                                                     20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
gcctcagucu gcttcgcacc                                                     20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcctcagtct gcttcgcacc                                                     20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcctcagtct gcttcgcacc                                                     20
```

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gcctcagtct gcttcgcacc                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcctcagtct gcttcgcacc                                                20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gcctcagtct gcttcgcacc                                                20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcctcagtct gcttcgcacc                                                20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcctcagtct gcttcgcacc                                                20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcctcagtct gcttcgcacc                                                20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gcctcagtct gcttcgcacc                                             20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcctcagtct gcttcgcacc                                             20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gccucagucu gcuucgcacc                                             20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gccucagucu gcuucgcacc                                             20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gccucagucu gcuucgcacc                                             20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gccucagucu gcuucgcacc                                             20

```
<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gccucagucu gcuucgcacc                                                   20

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gccucagucu gcuucgcacc                                                   20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gccucagucu gcuucgcacc                                                   20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gccucagucu gcuucgcacc                                                   20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gccucagucu gcuucgcacc                                                   20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gccucagucu gcuucgcacc                                                   20

<210> SEQ ID NO 130
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gggcacaagg gcacagactt                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggcacaaggg cacagacttc                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcacaagggc acagacttcc                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cacaagggca cagacttcca                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
acaagggcac agacttccaa                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
caagggcaca gacttccaaa                                              20

<210> SEQ ID NO 136
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gggcacaagg gcacagactt                                                 20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggcacaaggg cacagacttc                                                 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gcacaagggc acagacttcc                                                 20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cacaagggca cagacttcca                                                 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
acaagggcac agacttccaa                                                 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
caagggcaca gacttccaaa                                                 20

<210> SEQ ID NO 142
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 142
gggcacaagg gcacagacuu                                                    20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ggcacaaggg cacagacuuc                                                    20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gcacaagggc acagacuucc                                                    20

<210> SEQ ID NO 145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cacaagggca cagacuucca                                                    20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
acaagggcac agactuccaa                                                    20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
caagggcaca gacttccaaa                                                    20

<210> SEQ ID NO 148
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gcacaagggc acagacuucc                                                 20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
cacaagggca cagacuucca                                                 20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
acaagggcac agacuuccaa                                                 20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
caagggcaca gacuuccaaa                                                 20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gcacaagggc acagacuucc                                                 20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
cacaagggca cagacuucca                                                 20

<210> SEQ ID NO 154
<211> LENGTH: 20
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
acaagggcac agacuuccaa                                                   20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
caagggcaca gacuuccaaa                                                   20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gggcacaagg gcacagacuu                                                   20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ggcacaaggg cacagacuuc                                                   20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gcacaagggc acagacuucc                                                   20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
cacaagggca cagacuucca                                                   20

<210> SEQ ID NO 160
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
acaagggcac agactuccaa                                               20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
caagggcaca gacttccaaa                                               20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gggcacaagg gcacagactt                                               20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggcacaaggg cacagacttc                                               20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gcacaagggc acagacttcc                                               20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cacaagggca cagacttcca                                               20

<210> SEQ ID NO 166

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
acaagggcac agacttccaa                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
caagggcaca gacttccaaa                                              20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ggcacaaggg cacagacuuc                                              20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ggcacaaggg cacagacuuc                                              20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ggcacaaggg cacagacuuc                                              20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggcacaaggg cacagacttc                                              20

<210> SEQ ID NO 172
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggcacaaggg cacagacttc                                              20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggcacaaggg cacagacttc                                              20

<210> SEQ ID NO 174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ggcacaaggg cacagacuuc                                              20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
ggcacaaggg cacagacuuc                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcagggcaca agggcacaga                                              20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cagggcacaa gggcacagac                                              20

<210> SEQ ID NO 178
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 178
agggcacaag ggcacagact                                                   20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aagggcacag acttccaaag                                                   20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
agggcacaga cttccaaagg                                                   20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gggcacagac ttccaaaggc                                                   20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggcacaaggg cacagacuuc                                                   20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
ggcacaaggg cacagacuuc                                                   20

<210> SEQ ID NO 184
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 184
gggcacaagg gcacagactt                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggcacaaggg cacagacttc                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gcacaagggc acagacttcc                                              20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gggcacaagg gcacagactt                                              20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ggcacaaggg cacagacttc                                              20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gcacaagggc acagacttcc                                              20

<210> SEQ ID NO 190
<211> LENGTH: 20
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 190
ggcacaaggg cacagacuuc                                               20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 191
ggcacaaggg cacagacuuc                                               20

<210> SEQ ID NO 192
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 192
ggcacaaggg cacagacuuc                                               20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
ggcacaaggg cacagacttc                                               20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
gagcagctgc aacctggcaa                                               20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
agcagctgca acctggcaac                                               20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
gcagctgcaa cctggcaaca                                              20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cagctgcaac ctggcaacaa                                              20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
agctgcaacc tggcaacaac                                              20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gctgcaacct ggcaacaacc                                              20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gagcagctgc aacctggcaa                                              20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
agcagctgca acctggcaac                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gcagctgcaa cctggcaaca                                              20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
cagcugcaac ctggcaacaa                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
agcugcaacc tggcaacaac                                              20

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
gcugcaacct ggcaacaacc                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gagcagctgc aacctggcaa                                              20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
agcagctgca acctggcaac                                              20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 208
gcagctgcaa cctggcaaca                                           20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 209
cagcugcaac ctggcaacaa                                           20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 210
agcugcaacc tggcaacaac                                           20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 211
gcugcaacct ggcaacaacc                                           20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 212
gagcagctgc aaccuggcaa                                           20

<210> SEQ ID NO 213

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
gagcagctgc aaccuggcaa                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
agcagctgca acctggcaac                                              20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
agcagctgca acctggcaac                                              20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
gcagctgcaa ccuggcaaca                                              20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
gcagctgcaa ccuggcaaca                                              20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 218
gagcagctgc aacctggcaa                                          20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
agcagctgca acctggcaac                                          20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gcagctgcaa cctggcaaca                                          20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
cagcugcaac ctggcaacaa                                          20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
agcugcaacc tggcaacaac                                          20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
gcugcaacct ggcaacaacc                                          20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gagcagctgc aacctggcaa                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
agcagctgca acctggcaac                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gcagctgcaa cctggcaaca                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
cagctgcaac ctggcaacaa                                              20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
agctgcaacc tggcaacaac                                              20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gctgcaacct ggcaacaacc                                              20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gggccaacag ccagcctgca                                              20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggccaacagc cagcctgcag                                              20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gccaacagcc agcctgcagg                                              20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ccaacagcca gcctgcagga                                              20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
caacagccag cctgcaggag                                              20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
aacagccagc ctgcaggagg                                              20

```
<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gggccaacag ccagcctgca                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ggccaacagc cagcctgcag                                              20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gccaacagcc agcctgcagg                                              20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ccaacagcca gcctgcagga                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
caacagccag cctgcaggag                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
aacagccagc ctgcaggagg                                              20

<210> SEQ ID NO 242
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gggccaacag ccagccugca                                              20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ggccaacagc cagccugcag                                              20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gccaacagcc agcctgcagg                                              20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ccaacagcca gcctgcagga                                              20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
caacagccag cctgcaggag                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aacagccagc ctgcaggagg                                              20

<210> SEQ ID NO 248
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gggccaacag ccagccugca                                                    20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
gggccaacag ccagccugca                                                    20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
ggccaacagc cagccugcag                                                    20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ggccaacagc cagccugcag                                                    20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gccaacagcc agccugcagg                                                    20

<210> SEQ ID NO 253
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
gccaacagcc agccugcagg                                                    20

<210> SEQ ID NO 254
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 254
gggccaacag ccagccugca                                                    20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
ggccaacagc cagccugcag                                                    20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
gccaacagcc agcctgcagg                                                    20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
ccaacagcca gcctgcagga                                                    20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
caacagccag cctgcaggag                                                    20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aacagccagc ctgcaggagg                                                    20

<210> SEQ ID NO 260
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 260
gggccaacag ccagcctgca                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ggccaacagc cagcctgcag                                               20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gccaacagcc agcctgcagg                                               20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccaacagcca gcctgcagga                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
caacagccag cctgcaggag                                               20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
aacagccagc ctgcaggagg                                               20

<210> SEQ ID NO 266
<211> LENGTH: 20
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 266
attaataaat tgtcatcacc                                                 20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 267
attaataaat tgtcatcacc                                                 20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 268
attaataaat tgtcatcacc                                                 20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 269
auuaauaaat tgtcatcacc                                                 20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 270
auuaauaaat tgtcatcacc                                                 20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 271
auuaauaaat tgtcatcacc                                         20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
auuaauaaat tgtcatcacc                                         20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
auuaauaaat tgtcatcacc                                         20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
auuaauaaat tgtcatcacc                                         20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
auuaauaaat tgtcatcacc                                         20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
auuaauaaat tgtcatcacc					20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
auuaauaaat tgtcatcacc					20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
auuaauaaat tgtcatcacc					20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
tgtcatcacc agaaaaaguc					20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
utgtcatcac cagaaaaagu					20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
ttgtcatcac cagaaaaagu					20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
autgtcatca ccagaaaaag					20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
attgtcatca ccagaaaaag					20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
aautgtcatc accagaaaaa					20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
aattgtcatc accagaaaaa					20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
aaattgtcat caccagaaaa					20

<210> SEQ ID NO 287
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
aaautgtcat caccagaaaa                                                   20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
uaaautgtca tcaccagaaa                                                   20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
uaaautgtca tcaccagaaa                                                   20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
auaaattgtc atcaccagaa                                                   20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
auaaattgtc atcaccagaa                                                   20

<210> SEQ ID NO 292
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
aauaaattgt catcaccaga                                              20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
aauaaattgt catcaccaga                                              20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
aauaaattgt catcaccaga                                              20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
uaauaaattg tcatcaccag                                              20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
uaauaaattg tcatcaccag                                              20

<210> SEQ ID NO 297
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
uaauaaattg tcatcaccag                                                 20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
uaauaaattg tcatcaccag                                                 20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
uuaauaaatt gtcatcacca                                                 20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
uuaauaaatt gtcatcacca                                                 20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
uuaauaaatt gtcatcacca                                                 20
```

```
<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
uuaauaaatt gtcatcacca                                                    20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
auuaataaat tgtcatcacc                                                    20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
auuaataaat tgtcatcacc                                                    20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
auuaataaat tgtcatcacc                                                    20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
auuaataaat tgtcatcacc                                                    20
```

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
uauuaauaaa ttgtcatcac                                              20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
uauuaauaaa ttgtcatcac                                              20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
uauuaauaaa ttgtcatcac                                              20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
cuauuaauaa attgtcatca                                              20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
cuauuaauaa attgtcatca                                              20

```
<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
acuautaata aattgtcatc                                                 20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
tgtcatcacc agaaaaaguc                                                 20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
utgtcatcac cagaaaaagu                                                 20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
ttgtcatcac cagaaaaagu                                                 20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
```

```
autgtcatca ccagaaaaag                                              20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
attgtcatca ccagaaaaag                                              20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
aautgtcatc accagaaaaa                                              20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
aattgtcatc accagaaaaa                                              20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
aaattgtcat caccagaaaa                                              20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
aaautgtcat caccagaaaa                                              20

<210> SEQ ID NO 322
<211> LENGTH: 20
<212> TYPE: DNA
<213> ORGANISM: Artificial Sequence
<220> FEATURE:
```

<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 322
uaaautgtca tcaccagaaa                                              20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 323
uaaautgtca tcaccagaaa                                              20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 324
auaaattgtc atcaccagaa                                              20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 325
auaaattgtc atcaccagaa                                              20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Description of Combined DNA/RNA Molecule:
       Synthetic oligonucleotide

<400> SEQUENCE: 326
aauaaattgt catcaccaga                                              20

<210> SEQ ID NO 327
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
aauaaattgt catcaccaga                                               20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
aauaaattgt catcaccaga                                               20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
uaauaaattg tcatcaccag                                               20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
uaauaaattg tcatcaccag                                               20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
uaauaaattg tcatcaccag                                               20

<210> SEQ ID NO 332
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
uaauaaattg tcatcaccag                                                 20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
uuaauaaatt gtcatcacca                                                 20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
uuaauaaatt gtcatcacca                                                 20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
uuaauaaatt gtcatcacca                                                 20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
uuaauaaatt gtcatcacca                                                 20

<210> SEQ ID NO 337
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
auuaauaaat tgtcatcacc                                                  20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
auuaauaaat tgtcatcacc                                                  20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
auuaauaaat tgtcatcacc                                                  20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
auuaauaaat tgtcatcacc                                                  20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
uauuaauaaa ttgtcatcac                                                  20

<210> SEQ ID NO 342
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
uauuaataaa ttgtcatcac                                                    20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
uauuaataaa ttgtcatcac                                                    20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
cuauuaataa attgtcatca                                                    20

<210> SEQ ID NO 345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
cuauuaataa attgtcatca                                                    20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
acuautaata aattgtcatc                                                    20
```

```
<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gggcacaagg gcacagactt                                               20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
ggcacaaggg cacagacttc                                               20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
gcacaagggc acagacttcc                                               20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
cacaagggca cagacttcca                                               20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
acaagggcac agacttccaa                                               20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
caagggcaca gacttccaaa                                               20

<210> SEQ ID NO 353
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
ggcacaaggg cacagacuuc                                                   20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
ggcacaaggg cacagacuuc                                                   20

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
ggcacaaggg cacagacuuc                                                   20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ggcacaaggg cacagacttc                                                   20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
ggcacaaggg cacagacttc                                                   20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ggcacaaggg cacagacttc                                                   20

<210> SEQ ID NO 359
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
ggcacaaggg cacagacuuc                                              20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
ggcacaaggg cacagacuuc                                              20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gcagggcaca agggcacaga                                              20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
cagggcacaa gggcacagac                                              20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
agggcacaag ggcacagact                                              20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
aagggcacag acttccaaag                                              20

<210> SEQ ID NO 365
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 365
agggcacaga cttccaaagg                                               20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
gggcacagac ttccaaaggc                                               20

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ggcacaaggg cacagacuuc                                               20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gagcagctgc aacctggcaa                                               20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
agcagctgca acctggcaac                                               20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gcagctgcaa cctggcaaca                                               20

<210> SEQ ID NO 371
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 371
cagctgcaac ctggcaacaa                                              20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
agctgcaacc tggcaacaac                                              20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gctgcaacct ggcaacaacc                                              20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gggccaacag ccagcctgca                                              20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
ggccaacagc cagcctgcag                                              20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gccaacagcc agcctgcagg                                              20

<210> SEQ ID NO 377
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 377
ccaacagcca gcctgcagga                                                    20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
caacagccag cctgcaggag                                                    20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
aacagccagc ctgcaggagg                                                    20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
attaataaat tgtcatcacc                                                    20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
attaataaat tgtcatcacc                                                    20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
attaataaat tgtcatcacc                                                    20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic

```
                          oligonucleotide
<220> FEATURE:
<223> OTHER INFORMATION: Description of Combined DNA/RNA Molecule:
      Synthetic oligonucleotide

<400> SEQUENCE: 383
auuaauaaat tgtcatcacc                                              20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
auuaauaaat tgtcatcacc                                              20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
auuaauaaat tgtcatcacc                                              20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
auuaauaaat tgtcatcacc                                              20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
auuaauaaat tgtcatcacc                                              20

<210> SEQ ID NO 388
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
auuaauaaat tgtcatcacc                                               20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
auuaauaaat tgtcatcacc                                               20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
auuaauaaat tgtcatcacc                                               20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 391
auuaauaaat tgtcatcacc                                               20

<210> SEQ ID NO 392
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
gcgtttgctc ttcttcttgc gtttttt                                       27

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 393
gcctcagtct gcttcgcacc                                              20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gcctcagtct gcttcgcacc                                              20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcctcagtct gcttcgcacc                                              20

<210> SEQ ID NO 396
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gcgtttgctc ttcttcttgc gtttttt                                      27

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gcctcagtct gcttcgcacc                                              20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gcctcagtct gcttcgcacc                                              20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 399
gcctcagtct gcttcgcacc          20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gcctcagtct gcttcgcacc          20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gcctcagtct gcttcgcacc          20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gcctcagtct gcttcgcacc          20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gcctcagtct gcttcgcacc          20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
gcctcagtct gcttcgcacc          20

<210> SEQ ID NO 405
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
gcgtttgctc ttcttcttgc gtttttt                                              27

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
gtccctgaag atgtcaatgc                                                      20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
gtccctgaag atgtcaatgc                                                      20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
gtccctgaag atgtcaatgc                                                      20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
gtccctgaag atgtcaatgc                                                      20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
gtccctgaag atgtcaatgc                                                      20

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 411
uucuagaccu guuuugcuut t                                              21

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 412
uucuagaccu guuuugcuut t                                              21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
uucuagaccu guuuugcuut t                                              21

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
uucuagaccu guuuugcuut t                                              21

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
uucuagaccu guuuugcuut t                                              21

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
            Synthetic oligonucleotide

<400> SEQUENCE: 416
uucuagaccu guuuugcuut t                                              21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
uucuagaccu guuuugcuut t                                              21

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 418
uucuagaccu guuuugcuut t                                              21

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
uucuagaccu guuuugcuut t                                              21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
uucuagaccu guuuugcuut t                                              21

<210> SEQ ID NO 421
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 421
uucuagaccu guuuugcuut t                                              21

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
uucuagaccu guuuugcuut t                                              21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
uucuagaccu guuuugcuut t                                              21

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
uucuagaccu guuuugcuut t                                              21

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
uucuagaccu guuuugcuut t                                              21

<210> SEQ ID NO 426
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 426
uucuagaccu guuuugcuut t                                              21

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 427
uucuagaccu guuuugcuut t                                              21

<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
uucuagaccu guuuugcuut t                                              21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
uucuagaccu guuuugcuut t                                              21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
uucuagaccu guuuugcuut t                                              21

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 431
uucuagaccu guuuugcuut t                                              21

<210> SEQ ID NO 432
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
uucuagaccu guuuugcuut t                                              21

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 433
uucuagaccu guuuugcuut t                                              21

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
uucuagaccu guuuugcuut t                                              21

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 435
uucuagaccu guuuugcuut t                                              21

<210> SEQ ID NO 436
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 436
uucuagaccu guuuugcuut t					21

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 437
uucuagaccu guuuugcuut t					21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 438
uucuagaccu guuuugcuut t					21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 439
uucuagaccu guuuugcuut t					21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 440
uucuagaccu guuuugcuut t					21

<210> SEQ ID NO 441
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
uucuagaccu guuuugcuut t                                             21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
uucuagaccu guuuugcuut t                                             21

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
uucuagaccu guuuugcuut t                                             21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
uucuagaccu guuuugcuut t                                             21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
uucuagaccu guuuugcuut t                                             21

<210> SEQ ID NO 446
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
uucuagaccu guuuugcuut t                                          21

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
uucuagaccu guuuugcuut t                                          21

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
uucuagaccu guuuugcuut t                                          21

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
uucuagaccu guuuugcuut t                                          21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
uucuagaccu guuuugcuut t                                          21

<210> SEQ ID NO 451
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
aagcaaaaca ggucuagaat t                                              21

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
aagcaaaaca ggucuagaat t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
aagcaaaaca ggucuagaat t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
aagcaaaaca ggucuagaat t                                              21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
aagcaaaaca ggucuagaat t                                              21

<210> SEQ ID NO 456
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
aagcaaaaca ggucuagaat t                                          21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
aagcaaaaca ggucuagaat t                                          21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
aagcaaaaca ggucuagaat t                                          21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
aagcaaaaca ggucuagaat t                                          21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
aagcaaaaca ggucuagaat t                                          21
```

```
<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
aagcaaaaca ggucuagaat t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
aagcaaaaca ggucuagaat t                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
aagcaaaaca ggucuagaat t                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
aagcaaaaca ggucuagaat t                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
aagcaaaaca ggucuagaat t                                              21
```

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 466
aagcaaaaca ggucuagaat t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 467
aagcaaaaca ggucuagaat t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 468
aagcaaaaca ggucuagaat t                                              21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 469
aagcaaaaca ggucuagaat t                                              21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 470
aagcaaaaca ggucuagaat t                                              21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 471
aagcaaaaca ggucuagaat t                                         21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 472
aagcaaaaca ggucuagaat t                                         21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 473
aagcaaaaca ggucuagaat t                                         21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 474
aagcaaaaca ggucuagaat t                                         21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 475
aagcaaaaca ggucuagaat t                                            21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
aagcaaaaca ggucuagaat t                                            21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
aagcaaaaca ggucuagaat t                                            21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
aagcaaaaca ggucuagaat t                                            21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
aagcaaaaca ggucuagaat t                                            21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
aagcaaaaca ggucuagaat t                                                 21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
aagcaaaaca ggucuagaat t                                                 21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
aagcaaaaca ggucuagaat t                                                 21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
aagcaaaaca ggucuagaat t                                                 21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
aagcaaaaca ggucuagaat t                                                 21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
aagcaaaaca ggucuagaat t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
aagcaaaaca ggucuagaat t                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
aagcaaaaca ggucuagaat t                                              21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
aagcaaaaca ggucuagaat t                                              21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
aagcaaaaca ggucuagaat t                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 490
aagcaaaaca ggucuagaat t                                                    21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
aagcaaaaca ggucuagaat t                                                    21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
aagcaaaaca ggucuagaat t                                                    21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
aagcaaaaca ggucuagaat t                                                    21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
aagcaaaaca ggucuagaat t                                                    21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 495
aagcaaaaca ggucuagaat t					21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
aagcaaaaca ggucuagaat t					21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
aagcaaaaca ggucuagaat t					21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
aagcaaaaca ggucuagaat t					21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
aagcaaaaca ggucuagaat t					21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 500
aagcaaaaca ggucuagaat t                                            21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
aagcaaaaca ggucuagaat t                                            21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
aagcaaaaca ggucuagaat t                                            21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
aagcaaaaca ggucuagaat t                                            21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
aagcaaaaca ggucuagaat t                                            21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 505
aagcaaaaca ggucuagaat t                                            21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
aagcaaaaca ggucuagaat t                                            21

<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
aagcaaaaca ggucuagaat t                                            21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
aagcaaaaca ggucuagaat t                                            21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
aagcaaaaca ggucuagaat t                                            21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 510
aagcaaaaca ggucuagaat t                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
aagcaaaaca ggucuagaat t                                              21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
aagcaaaaca ggucuagaat t                                              21

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 513
aagcaaaaca ggucuagaat t                                              21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
aagcaaaaca ggucuagaat t                                              21

<210> SEQ ID NO 515
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
aagcaaaaca ggucuagaat t                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
aagcaaaaca ggucuagaat t                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
aagcaaaaca ggucuagaat t                                              21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
aagcaaaaca ggucuagaat t                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
aagcaaaaca ggucuagaat t                                              21

<210> SEQ ID NO 520
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
aagcaaaaca ggucuagaat t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
aagcaaaaca ggucuagaat t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
aagcaaaaca ggucuagaat t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
aagcaaaaca ggucuagaat t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
aagcaaaaca ggucuagaat t                                              21

<210> SEQ ID NO 525
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
aagcaaaaca ggucuagaat t                                         21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
aagcaaaaca ggucuagaat t                                         21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
aagcaaaaca ggucuagaat t                                         21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
aagcaaaaca ggucuagaat t                                         21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
aagcaaaaca ggucuagaat t                                         21

<210> SEQ ID NO 530
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
aagcaaaaca ggucuagaat t                                              21

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ccctctggat tgagcatcca                                                20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
aagctttggt tgggcaacac                                                20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
agtcacttgg gagcttctcc                                                20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
cacttgggag cttctcctgg                                                20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
atagccattg cagctgctca                                                20
```

```
<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
tggattgagc atccaccaag                                              20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ccatagccat tgcagctgct                                              20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
gtcacttggg agcttctcct                                              20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ccagggcact catctgcatg                                              20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
gccatccaag tcacttggga                                              20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
gaagctttgg ttgggcaaca                                              20

<210> SEQ ID NO 542
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
ctggattgag catccaccaa                                                    20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
caagtcactt gggagcttct                                                    20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
atgccatcca agtcacttgg                                                    20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
atgagatgcc tggctgccat                                                    20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
ttgggagctt ctcctggtgg                                                    20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
tgggagcttc tcctggtgga                                                    20

<210> SEQ ID NO 548
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
ttatgagatg cctggctgcc                                                  20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
gttatgagat gcctggctgc                                                  20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
ccaagtcact tgggagcttc                                                  20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
agctttggtt gggcaacaca                                                  20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
tatgagatgc ctggctgcca                                                  20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
tgttatgaga tgcctggctg                                                  20

<210> SEQ ID NO 554
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 554
atccaagtca cttgggagct                                                   20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
gggaagcttt ggttgggcaa                                                   20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
ctccatccat gaggtcattc                                                   20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
aagtcacttg ggagcttctc                                                   20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
ccatccaagt cacttgggag                                                   20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
tccaagtcac ttgggagctt                                                   20

<210> SEQ ID NO 560
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 560
cctctggatt gagcatccac                                                  20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
acttgggagc ttctcctggt                                                  20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
cttgggagct tctcctggtg                                                  20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
catgccatcc aagtcacttg                                                  20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
tgccatccaa gtcacttggg                                                  20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
tccatccatg aggtcattcc                                                  20

<210> SEQ ID NO 566
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 566
agggcactca tctgcatggg                                                    20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
ccagttcctt cattctgcac                                                    20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
catagccatt gcagctgctc                                                    20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
tctggattga gcatccacca                                                    20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
ggattgagca tccaccaaga                                                    20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
ccctctggat tgagcatcca                                                    20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 572
aagctttggt tgggcaacac                                              20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
agtcacttgg gagcttctcc                                              20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
cacttgggag cttctcctgg                                              20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
atagccattg cagctgctca                                              20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
tggattgagc atccaccaag                                              20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ccatagccat tgcagctgct                                              20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 578
gtcacttggg agcttctcct                                              20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
ccagggcact catctgcatg                                              20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
gccatccaag tcacttggga                                              20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
gaagctttgg ttgggcaaca                                              20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
ctggattgag catccaccaa                                              20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
caagtcactt gggagcttct                                              20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 584
atgccatcca agtcacttgg                                                20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
atgagatgcc tggctgccat                                                20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
ttgggagctt ctcctggtgg                                                20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
tgggagcttc tcctggtgga                                                20

<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
ttatgagatg cctggctgcc                                                20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
gttatgagat gcctggctgc                                                20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
```
ccaagtcact tgggagcttc                                                 20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
agctttggtt gggcaacaca                                                 20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
tatgagatgc ctggctgcca                                                 20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tgttatgaga tgcctggctg                                                 20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
atccaagtca cttgggagct                                                 20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
gggaagcttt ggttgggcaa                                                 20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596

```
ctccatccat gaggtcattc                                              20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
aagtcacttg ggagcttctc                                              20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ccatccaagt cacttgggag                                              20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
tccaagtcac ttgggagctt                                              20

<210> SEQ ID NO 600
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
cctctggatt gagcatccac                                              20

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
acttgggagc ttctcctggt                                              20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
cttgggagct tctcctggtg                                              20
```

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
catgccatcc aagtcacttg                                              20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
tgccatccaa gtcacttggg                                              20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
tccatccatg aggtcattcc                                              20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
agggcactca tctgcatggg                                              20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
ccagttcctt cattctgcac                                              20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
catagccatt gcagctgctc                                              20

```
<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
tctggattga gcatccacca                                                   20

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
ggattgagca tccaccaaga                                                   20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
gaagctttgg ttgggcaaca                                                   20

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
ccatccaagt cacttgggag                                                   20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
atgagatgcc tggctgccat                                                   20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
aagctttggt tgggcaacac                                                   20
```

```
<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
atagccattg cagctgctca                                                   20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
tatgagatgc ctggctgcca                                                   20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ttatgagatg cctggctgcc                                                   20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
ccatccaagt cacttgggag                                                   20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
ccatccaagt cacttgggag                                                   20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
gaagctttgg ttgggcaaca                                                   20

<210> SEQ ID NO 621
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
ccatccaagt cacttgggag                                                   20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
ccatccaagt cacttgggag                                                   20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
gaagctttgg ttgggcaaca                                                   20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
atgagatgcc tggctgccat                                                   20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
atgagatgcc tggctgccat                                                   20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
atgagatgcc tggctgccat                                                   20

<210> SEQ ID NO 627
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
atgagatgcc tggctgccat                                                    20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gaagctttgg ttgggcaaca                                                    20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
ccatccaagt cacttgggag                                                    20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
atgagatgcc tggctgccat                                                    20

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ccatccaagt cacttgggag                                                    20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
atgagatgcc tggctgccat                                                    20

<210> SEQ ID NO 633
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 633
ccatccaagt cacttgggag                                                20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
atgagatgcc tggctgccat                                                20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ccatccaagt cacttgggag                                                20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
atgagatgcc tggctgccat                                                20

<210> SEQ ID NO 637
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
ccatccaagt cacttgggag                                                20

<210> SEQ ID NO 638
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
atgagatgcc tggctgccat                                                20

<210> SEQ ID NO 639
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 639
ccatccaagt cacttgggag                                              20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
atgagatgcc tggctgccat                                              20

<210> SEQ ID NO 641
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
gaagctttgg ttgggcaaca                                              20

<210> SEQ ID NO 642
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
atgagatgcc tggctgccat                                              20

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
ccatccaagt cacttgggag                                              20

<210> SEQ ID NO 644
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
atgagatgcc tggctgccat                                              20

<210> SEQ ID NO 645
<211> LENGTH: 20
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 645
gaagctttgg ttgggcaaca                                                   20

<210> SEQ ID NO 646
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 646
atgagatgcc tggctgccat                                                   20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 647
ccatccaagt cacttgggag                                                   20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 648
ccatccaagt cacttgggag                                                   20

<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 649
atgagatgcc tggctgccat                                                   20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 650
ccatccaagt cacttgggag                                                   20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 651
ccatccaagt cacttgggag                                          20

<210> SEQ ID NO 652
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ccatccaagt cacttgggag                                          20

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ccatccaagt cacttgggag                                          20

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ccatccaagt cacttgggag                                          20

<210> SEQ ID NO 655
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
ccatccaagt cacttgggag                                          20

<210> SEQ ID NO 656
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
ccatccaagt cacttgggag                                          20

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
ccatccaagt cacttgggag                                        20

<210> SEQ ID NO 658
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ccatccaagt cacttgggag                                        20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
ccatccaagt cacttgggag                                        20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
tgagatgcct ggctgccata                                        20

<210> SEQ ID NO 661
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
tgagatgcct ggctgccata                                        20

<210> SEQ ID NO 662
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
tgagatgcct ggctgccata                                        20

<210> SEQ ID NO 663
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 663
tgagatgcct ggctgccata                                              20

<210> SEQ ID NO 664
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
uauggcagcc aggcaucuca                                              20

<210> SEQ ID NO 665
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
tagccattgc agctgctcac                                              20

<210> SEQ ID NO 666
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
tagccattgc agctgctcac                                              20

<210> SEQ ID NO 667
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
tagccattgc agctgctcac                                              20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
tagccattgc agctgctcac                                              20

<210> SEQ ID NO 669
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
```
gugagcagcu gcaauggcua                                        20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
tagccattgc agctgctcac                                        20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
tagccattgc agctgctcac                                        20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
tagccattgc agctgctcac                                        20

<210> SEQ ID NO 673
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
tagccattgc agctgctcac                                        20

<210> SEQ ID NO 674
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
tagccattgc agctgctcac                                        20

<210> SEQ ID NO 675
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
gugagcagcu gcaauggcua                                              20

<210> SEQ ID NO 676
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
tccagttcct tcattctgca                                              20

<210> SEQ ID NO 677
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
tccagttcct tcattctgca                                              20

<210> SEQ ID NO 678
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
tccagttcct tcattctgca                                              20

<210> SEQ ID NO 679
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
tccagttcct tcattctgca                                              20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
tccagttcct tcattctgca                                              20

<210> SEQ ID NO 681
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
ugcagaauga aggaacugga                                              20

```
<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
tgagatgcct ggctgccata                                              20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
tgagatgcct ggctgccata                                              20

<210> SEQ ID NO 684
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
tgagatgcct ggctgccata                                              20

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
tgagatgcct ggctgccata                                              20

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
tgagatgcct ggctgccata                                              20

<210> SEQ ID NO 687
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
uauggcagcc aggcaucuca                                              20
```

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
gcctcagtct gcttcgcacc                                               20

<210> SEQ ID NO 689
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gcgtttgctc ttcttcttgc gtttttt                                       27

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
gtccctgaag atgtcaatgc                                               20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
tccagttcct tcattctgca                                               20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
tgagatgcct ggctgccata                                               20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
tagccattgc agctgctcac                                               20

```
<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
tccagttcct tcattctgca                                                   20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
tgagatgcct ggctgccata                                                   20

<210> SEQ ID NO 696
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
tagccattgc agctgctcac                                                   20

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
tccagttcct tcattctgca                                                   20

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
tgagatgcct ggctgccata                                                   20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
tagccattgc agctgctcac                                                   20

<210> SEQ ID NO 700
```

-continued

```
<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
tccagttcct tcattctgca                                                   20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
tgagatgcct ggctgccata                                                   20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
tagccattgc agctgctcac                                                   20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
tccagttcct tcattctgca                                                   20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
tgagatgcct ggctgccata                                                   20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
tagccattgc agctgctcac                                                   20

<210> SEQ ID NO 706
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 706
uagccattgc agctgctcac                                                    20

<210> SEQ ID NO 707
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 707
uagccattgc agctgc                                                        16

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
tagccattgc agctgctcac                                                    20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
attaataaat tgtcatcacc                                                    20

<210> SEQ ID NO 710
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
ggugcgaagc agacugaggc                                                    20

<210> SEQ ID NO 711
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
```

```
ugcagaauga aggaacugga                                          20

<210> SEQ ID NO 712
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
uauggcagcc aggcaucuca                                          20

<210> SEQ ID NO 713
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
gugagcagcu gcaauggcua                                          20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
tagccattgc agctgctcac                                          20

<210> SEQ ID NO 715
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
gugagcggcu gcaauggcua                                          20

<210> SEQ ID NO 716
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
gugagcagcu gcgauggcua                                          20

<210> SEQ ID NO 717
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
ggugaugaca auuuauuaau                                          20
```

<210> SEQ ID NO 718
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
ggugauggca auuuauuaau                                               20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
tgagatgcct ggctgccata                                               20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
tgagatgcct ggctgccata                                               20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
tgagatgcct ggctgccata                                               20

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
tagccattgc agctgctcac                                               20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
tagccattgc agctgctcac                                               20

<210> SEQ ID NO 724
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
tagccattgc agctgctcac                                          20

<210> SEQ ID NO 725
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
tagccattgc agctgctcac                                          20

<210> SEQ ID NO 726
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
tagccattgc agctgctcac                                          20

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
tagccattgc agctgctcac                                          20

<210> SEQ ID NO 728
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
tagccattgc agctgctcac                                          20

<210> SEQ ID NO 729
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
tagccattgc agctgctcac                                          20

```
<210> SEQ ID NO 730
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
tagccattgc agctgctcac                                                20

<210> SEQ ID NO 731
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
tagccattgc agctgctcac                                                20

<210> SEQ ID NO 732
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
tagccattgc agctgctcac                                                20

<210> SEQ ID NO 733
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
tagccattgc agctgctcac                                                20

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
tagccattgc agctgctcac                                                20

<210> SEQ ID NO 735
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
tagccattgc agctgctcac                                                20

<210> SEQ ID NO 736
```

-continued

```
<210> SEQ ID NO 736
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
tagccattgc agctgctcac                                            20

<210> SEQ ID NO 737
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
tagccattgc agctgctcac                                            20

<210> SEQ ID NO 738
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
tagccattgc agctgctcac                                            20

<210> SEQ ID NO 739
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
tagccattgc agctgctcac                                            20

<210> SEQ ID NO 740
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
tagccattgc agctgctcac                                            20

<210> SEQ ID NO 741
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
tagccattgc agctgctcac                                            20

<210> SEQ ID NO 742
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
tagccattgc agctgctcac                                                   20

<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
tagccattgc agctgctcac                                                   20

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
tagccattgc agctgctcac                                                   20

<210> SEQ ID NO 745
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
tagccattgc agctgctcac                                                   20

<210> SEQ ID NO 746
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
tagccattgc agctgctcac                                                   20

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
attaataaat tgtcatcacc                                                   20

<210> SEQ ID NO 748
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 748
attaataaat tgtcatcacc                                             20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
gcctcagtct gcttcgcacc                                             20

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
gcctcagtct gcttcgcacc                                             20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
gcctcagtct gcttcgcacc                                             20

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
gcctcagtct gcttcgcacc                                             20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
gcctcagtct gcttcgcacc                                             20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
gtccctgaag atgtcaatgc                                                  20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
gtccctgaag atgtcaatgc                                                  20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
gtccctgaag atgtcaatgc                                                  20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
gtccctgaag atgtcaatgc                                                  20

<210> SEQ ID NO 758
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
gcctcagtct gcttcgcacc                                                  20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
gcctcagtct gcttcgcacc                                                  20

<210> SEQ ID NO 760
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 760
gcctcagtct gcttcgcacc                                                    20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
gcctcagtct gcttcgcacc                                                    20

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
gcctcagtct gcttcgcacc                                                    20

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
gcctcagtct gcttcgcacc                                                    20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 764
uagccattgc agctgctcac                                                    20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 765
uagccattgc agctgctcac                                                    20
```

```
<210> SEQ ID NO 766
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 766
uagccattgc agctgc                                                    16

<210> SEQ ID NO 767
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
tagccattgc agctgctcac                                                20

<210> SEQ ID NO 768
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
tagccattgc agctgctcac                                                20

<210> SEQ ID NO 769
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
tagccattgc agctgctcac                                                20

<210> SEQ ID NO 770
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
tagccattgc agctgctcac                                                20

<210> SEQ ID NO 771
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
tagccattgc agctgctcac                                                20
```

<210> SEQ ID NO 772
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
tagccattgc agctgctcac                                                20

<210> SEQ ID NO 773
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
tagccattgc agctgctcac                                                20

<210> SEQ ID NO 774
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
tagccattgc agctgctcac                                                20

<210> SEQ ID NO 775
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775
uuuggaaguc ugcgcccuug ugccc                                          25

<210> SEQ ID NO 776
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
uuuggaaguc ugugcccuug ugccc                                          25

<210> SEQ ID NO 777
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
gggcacaagg gcacagactt                                                20

<210> SEQ ID NO 778
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
ggcacaaggg cacagacttc                                            20

<210> SEQ ID NO 779
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
gcacaagggc acagacttcc                                            20

<210> SEQ ID NO 780
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
cacaagggca cagacttcca                                            20

<210> SEQ ID NO 781
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
acaagggcac agacttccaa                                            20

<210> SEQ ID NO 782
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
caagggcaca gacttccaaa                                            20

<210> SEQ ID NO 783
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
gtaggagtag tgaaaggcca                                            20

```
<210> SEQ ID NO 784
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
guaggagtag tgaaaggcca                                                   20

<210> SEQ ID NO 785
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785
guaggagtag tgaaaggcca                                                   20

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 786
guaggagtag tgaaaggcca                                                   20

<210> SEQ ID NO 787
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 787
cucuuactgt gctgtggaca                                                   20

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 788
cucuuactgt gctgtggaca                                                   20
```

```
<210> SEQ ID NO 789
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 789
cucuuactgt gctgtggaca                                              20

<210> SEQ ID NO 790
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 790
ccuuccctga aggttccucc                                              20

<210> SEQ ID NO 791
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
uuuggaaguc ugcgcccuug ugccc                                        25

<210> SEQ ID NO 792
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
uuuggaaguc ugugcccuug ugccc                                        25

<210> SEQ ID NO 793
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
gagccuuugg aagucugcgc ccuugugccc ugccu                             35

<210> SEQ ID NO 794
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 794
gagccuuugg aagucugugc ccuugugccc ugccu                      35

<210> SEQ ID NO 795
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
gguuguugcc agguuacagc ugcuc                                 25

<210> SEQ ID NO 796
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
gguuguugcc agguugcagc ugcuc                                 25

<210> SEQ ID NO 797
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
ccuccugcag gcuggguguu ggccc                                 25

<210> SEQ ID NO 798
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
ccuccugcag gcuggcuguu ggccc                                 25

<210> SEQ ID NO 799
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
ggugaugaca auuuauuaau                                       20

<210> SEQ ID NO 800
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 800
ggugauggca auuuauuaau                                                      20

<210> SEQ ID NO 801
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
attaataaat tgtcatcacc                                                      20

<210> SEQ ID NO 802
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
attaataaat tgtcatcacc                                                      20

<210> SEQ ID NO 803
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
attaataaat tgtcatcacc                                                      20

<210> SEQ ID NO 804
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
ggugaugaca auuuauuaau                                                      20

<210> SEQ ID NO 805
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
ggugauggca auuuauuaau                                                      20

<210> SEQ ID NO 806
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
```
uuuggaaguc ugcgcccuug ugccc                                          25

<210> SEQ ID NO 807
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
uuuggaaguc ugugcccuug ugccc                                          25

<210> SEQ ID NO 808
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
gggcacaagg gcacagactt                                                20

<210> SEQ ID NO 809
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
ggcacaaggg cacagacttc                                                20

<210> SEQ ID NO 810
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
gcacaagggc acagacttcc                                                20

<210> SEQ ID NO 811
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
cacaagggca cagacttcca                                                20

<210> SEQ ID NO 812
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
acaagggcac agacttccaa						20

<210> SEQ ID NO 813
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
caagggcaca gacttccaaa						20

<210> SEQ ID NO 814
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
gggcacaagg gcacagactt						20

<210> SEQ ID NO 815
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
ggcacaaggg cacagacttc						20

<210> SEQ ID NO 816
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
gcacaagggc acagacttcc						20

<210> SEQ ID NO 817
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
cacaagggca cagacttcca						20

<210> SEQ ID NO 818
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
acaagggcac agacttccaa						20

<210> SEQ ID NO 819
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
caagggcaca gacttccaaa                                              20

<210> SEQ ID NO 820
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
gggcacaagg gcacagacuu                                              20

<210> SEQ ID NO 821
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
ggcacaaggg cacagacuuc                                              20

<210> SEQ ID NO 822
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
gcacaagggc acagacuucc                                              20

<210> SEQ ID NO 823
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
cacaagggca cagacuucca                                              20

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 824
acaagggcac agactuccaa                                               20

<210> SEQ ID NO 825
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
caagggcaca gacttccaaa                                               20

<210> SEQ ID NO 826
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
gcacaagggc acagacuucc                                               20

<210> SEQ ID NO 827
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
cacaagggca cagacuucca                                               20

<210> SEQ ID NO 828
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
acaagggcac agacuuccaa                                               20

<210> SEQ ID NO 829
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
caagggcaca gacuuccaaa                                               20

<210> SEQ ID NO 830
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
gcacaagggc acagacuucc                                           20

<210> SEQ ID NO 831
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
cacaagggca cagacuucca                                           20

<210> SEQ ID NO 832
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
acaagggcac agacuuccaa                                           20

<210> SEQ ID NO 833
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
caagggcaca gacuuccaaa                                           20

<210> SEQ ID NO 834
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
gggcacaagg gcacagacuu                                           20

<210> SEQ ID NO 835
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
ggcacaaggg cacagacuuc                                           20

<210> SEQ ID NO 836
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
gcacaagggc acagacuucc                                           20

<210> SEQ ID NO 837
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 837
cacaagggca cagacuucca                                               20

<210> SEQ ID NO 838
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 838
acaagggcac agactuccaa                                               20

<210> SEQ ID NO 839
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 839
caagggcaca gacttccaaa                                               20

<210> SEQ ID NO 840
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 840
gggcacaagg gcacagactt                                               20

<210> SEQ ID NO 841
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 841
ggcacaaggg cacagacttc                                               20

<210> SEQ ID NO 842
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 842
gcacaagggc acagacttcc 20

<210> SEQ ID NO 843
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
cacaagggca cagacttcca 20

<210> SEQ ID NO 844
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
acaagggcac agacttccaa 20

<210> SEQ ID NO 845
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
caagggcaca gacttccaaa 20

<210> SEQ ID NO 846
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
uuuggaaguc ugcgcccuug ugccc 25

<210> SEQ ID NO 847
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
uuuggaaguc ugugcccuug ugccc 25

<210> SEQ ID NO 848
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
gagcagctgc aacctggcaa                                          20

<210> SEQ ID NO 849
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
gggccaacag ccagcctgca                                          20

<210> SEQ ID NO 850
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
gguuguugcc agguuacagc ugcuc                                    25

<210> SEQ ID NO 851
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
gguuguugcc agguugcagc ugcuc                                    25

<210> SEQ ID NO 852
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
gagcagctgc aacctggcaa                                          20

<210> SEQ ID NO 853
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
agcagctgca acctggcaac                                          20

<210> SEQ ID NO 854
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
gcagctgcaa cctggcaaca                                          20

<210> SEQ ID NO 855
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
cagctgcaac ctggcaacaa                                              20

<210> SEQ ID NO 856
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
agctgcaacc tggcaacaac                                              20

<210> SEQ ID NO 857
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
gctgcaacct ggcaacaacc                                              20

<210> SEQ ID NO 858
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
ccuccugcag gcugggguguu ggccc                                       25

<210> SEQ ID NO 859
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
ccuccugcag gcuggcuguu ggccc                                        25

<210> SEQ ID NO 860
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
gggccaacag ccagcctgca                                              20

<210> SEQ ID NO 861
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 861
ggccaacagc cagcctgcag                                        20

<210> SEQ ID NO 862
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 862
gccaacagcc agcctgcagg                                        20

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 863
ccaacagcca gcctgcagga                                        20

<210> SEQ ID NO 864
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 864
caacagccag cctgcaggag                                        20

<210> SEQ ID NO 865
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 865
aacagccagc ctgcaggagg                                        20

<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 866

```
ggccuuucac uacuccuact t                                            21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
guaggaguag ugaaaggcct t                                            21

<210> SEQ ID NO 868
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
gtaggagtag tgaaaggcca                                              20

<210> SEQ ID NO 869
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
gcagggcaca agggcacaga                                              20

<210> SEQ ID NO 870
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
cagggcacaa gggcacagac                                              20

<210> SEQ ID NO 871
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
agggcacaag ggcacagact                                              20

<210> SEQ ID NO 872
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 872
aagggcacag acttccaaag					20

<210> SEQ ID NO 873
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
agggcacaga cttccaaagg					20

<210> SEQ ID NO 874
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 874
gggcacagac ttccaaaggc					20

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
gagcagctgc aacctggcaa					20

<210> SEQ ID NO 876
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
agcagctgca acctggcaac					20

<210> SEQ ID NO 877
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
gcagctgcaa cctggcaaca					20

<210> SEQ ID NO 878
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
cagctgcaac ctggcaacaa                                               20

<210> SEQ ID NO 879
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
agctgcaacc tggcaacaac                                               20

<210> SEQ ID NO 880
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
gctgcaacct ggcaacaacc                                               20

<210> SEQ ID NO 881
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
gagcagctgc aacctggcaa                                               20

<210> SEQ ID NO 882
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
agcagctgca acctggcaac                                               20

<210> SEQ ID NO 883
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
gcagctgcaa cctggcaaca                                               20

<210> SEQ ID NO 884
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
cagcugcaac ctggcaacaa                                          20

<210> SEQ ID NO 885
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
agcugcaacc tggcaacaac                                          20

<210> SEQ ID NO 886
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
gcugcaacct ggcaacaacc                                          20

<210> SEQ ID NO 887
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
gagcagctgc aacctggcaa                                          20

<210> SEQ ID NO 888
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
agcagctgca acctggcaac                                          20

<210> SEQ ID NO 889
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
gcagctgcaa cctggcaaca                                          20

<210> SEQ ID NO 890
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 890
cagcugcaac ctggcaacaa                                            20

<210> SEQ ID NO 891
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 891
agcugcaacc tggcaacaac                                            20

<210> SEQ ID NO 892
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 892
gcugcaacct ggcaacaacc                                            20

<210> SEQ ID NO 893
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 893
gagcagctgc aaccuggcaa                                            20

<210> SEQ ID NO 894
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 894
gagcagctgc aaccuggcaa                                            20

<210> SEQ ID NO 895
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
agcagctgca acctggcaac                                                  20

<210> SEQ ID NO 896
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
agcagctgca acctggcaac                                                  20

<210> SEQ ID NO 897
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
gcagctgcaa ccuggcaaca                                                  20

<210> SEQ ID NO 898
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
gcagctgcaa ccuggcaaca                                                  20

<210> SEQ ID NO 899
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
gagcagctgc aacctggcaa                                                  20

<210> SEQ ID NO 900
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
```

```
agcagctgca acctggcaac                                               20

<210> SEQ ID NO 901
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
gcagctgcaa cctggcaaca                                               20

<210> SEQ ID NO 902
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
cagcugcaac ctggcaacaa                                               20

<210> SEQ ID NO 903
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
agcugcaacc tggcaacaac                                               20

<210> SEQ ID NO 904
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 904
gcugcaacct ggcaacaacc                                               20

<210> SEQ ID NO 905
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
gggccaacag ccagcctgca                                               20

<210> SEQ ID NO 906
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
ggccaacagc cagcctgcag                                              20

<210> SEQ ID NO 907
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
gccaacagcc agcctgcagg                                              20

<210> SEQ ID NO 908
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
ccaacagcca gcctgcagga                                              20

<210> SEQ ID NO 909
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
caacagccag cctgcaggag                                              20

<210> SEQ ID NO 910
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
aacagccagc ctgcaggagg                                              20

<210> SEQ ID NO 911
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
gggccaacag ccagcctgca                                              20

<210> SEQ ID NO 912
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
ggccaacagc cagcctgcag                                               20

<210> SEQ ID NO 913
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
gccaacagcc agcctgcagg                                               20

<210> SEQ ID NO 914
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914
ccaacagcca gcctgcagga                                               20

<210> SEQ ID NO 915
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
caacagccag cctgcaggag                                               20

<210> SEQ ID NO 916
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
aacagccagc ctgcaggagg                                               20

<210> SEQ ID NO 917
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 917
gggccaacag ccagccugca                                               20

<210> SEQ ID NO 918
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 918
ggccaacagc cagccugcag                                                 20

<210> SEQ ID NO 919
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
gccaacagcc agcctgcagg                                                 20

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
ccaacagcca gcctgcagga                                                 20

<210> SEQ ID NO 921
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
caacagccag cctgcaggag                                                 20

<210> SEQ ID NO 922
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
aacagccagc ctgcaggagg                                                 20

<210> SEQ ID NO 923
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
gggccaacag ccagccugca                                                 20

<210> SEQ ID NO 924
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 924
gggccaacag ccagccugca                                                   20

<210> SEQ ID NO 925
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
ggccaacagc cagccugcag                                                   20

<210> SEQ ID NO 926
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
ggccaacagc cagccugcag                                                   20

<210> SEQ ID NO 927
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
gccaacagcc agccugcagg                                                   20

<210> SEQ ID NO 928
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
gccaacagcc agccugcagg                                                   20

<210> SEQ ID NO 929
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
gggccaacag ccagccugca                                                   20

<210> SEQ ID NO 930
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 930
ggccaacagc cagccugcag                                              20

<210> SEQ ID NO 931
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
gccaacagcc agcctgcagg                                              20

<210> SEQ ID NO 932
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
ccaacagcca gcctgcagga                                              20

<210> SEQ ID NO 933
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
caacagccag cctgcaggag                                              20

<210> SEQ ID NO 934
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
aacagccagc ctgcaggagg                                              20

<210> SEQ ID NO 935
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 935
guaggagtag tgaaaggcca                                              20

<210> SEQ ID NO 936
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 936
guaggagtag tgaaaggcca                                                 20

<210> SEQ ID NO 937
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937
guaggagtag tgaaaggcca                                                 20

<210> SEQ ID NO 938
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 938
cucuuactgt gctgtggaca                                                 20

<210> SEQ ID NO 939
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 939
cucuuactgt gctgtggaca                                                 20

<210> SEQ ID NO 940
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 940
cucuuactgt gctgtggaca                                                 20

<210> SEQ ID NO 941
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
gggcacaagg gcacagactt                                                  20

<210> SEQ ID NO 942
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
ggcacaaggg cacagacttc                                                  20

<210> SEQ ID NO 943
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
gcacaagggc acagacttcc                                                  20

<210> SEQ ID NO 944
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
gggcacaagg gcacagactt                                                  20

<210> SEQ ID NO 945
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
ggcacaaggg cacagacttc                                                  20

<210> SEQ ID NO 946
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
gcacaagggc acagacttcc                                                  20

<210> SEQ ID NO 947
<211> LENGTH: 35
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 947
gagccuuugg aagucugcgc ccuugugccc ugccu                                    35

<210> SEQ ID NO 948
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
gagccuuugg aagucugugc ccuugugccc ugccu                                    35

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
cacacgggca cagacuucca a                                                   21

<210> SEQ ID NO 950
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
ggaagucugu gcccgugugc c                                                   21

<210> SEQ ID NO 951
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 951
auuaauaaat tgtcatcacc                                                     20

<210> SEQ ID NO 952
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 952
auuaauaaat tgtcatcacc                                                     20
```

<210> SEQ ID NO 953
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 953
auuaauaaat tgtcatcacc                                                20

<210> SEQ ID NO 954
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 954
auuaauaaat tgtcatcacc                                                20

<210> SEQ ID NO 955
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 955
auuaauaaat tgtcatcacc                                                20

<210> SEQ ID NO 956
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 956
auuaauaaat tgtcatcacc                                                20

<210> SEQ ID NO 957
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 957
auuaauaaat tgtcatcacc                                              20

<210> SEQ ID NO 958
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 958
auuaauaaat tgtcatcacc                                              20

<210> SEQ ID NO 959
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
ggcacaaggg cacagacuuc                                              20

<210> SEQ ID NO 960
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
ggcacaaggg cacagacuuc                                              20

<210> SEQ ID NO 961
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
ggcacaaggg cacagacuuc                                              20

<210> SEQ ID NO 962
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
ggcacaaggg cacagacttc                                              20

<210> SEQ ID NO 963
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 963
ggcacaaggg cacagacttc                                              20

<210> SEQ ID NO 964
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
ggcacaaggg cacagacttc                                              20

<210> SEQ ID NO 965
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 965
ggcacaaggg cacagacuuc                                              20

<210> SEQ ID NO 966
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
ggcacaaggg cacagacuuc                                              20

<210> SEQ ID NO 967
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
gcagggcaca agggcacaga                                              20

<210> SEQ ID NO 968
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
gcagggcaca agggcacaga                                              20

<210> SEQ ID NO 969
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
```

```
gcagggcaca agggcacaga                                              20

<210> SEQ ID NO 970
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
gcagggcaca agggcacaga                                              20

<210> SEQ ID NO 971
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
gcagggcaca agggcacaga                                              20

<210> SEQ ID NO 972
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
cagggcacaa gggcacagac                                              20

<210> SEQ ID NO 973
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
cagggcacaa gggcacagac                                              20

<210> SEQ ID NO 974
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
cagggcacaa gggcacagac                                              20

<210> SEQ ID NO 975
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
```
cagggcacaa gggcacagac 20

<210> SEQ ID NO 976
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
cagggcacaa gggcacagac 20

<210> SEQ ID NO 977
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
agggcacaag ggcacagact 20

<210> SEQ ID NO 978
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
agggcacaag ggcacagact 20

<210> SEQ ID NO 979
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
agggcacaag ggcacagact 20

<210> SEQ ID NO 980
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
agggcacaag ggcacagacu 20

<210> SEQ ID NO 981
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
agggcacaag ggcacagacu 20

```
<210> SEQ ID NO 982
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
aagggcacag acttccaaag                                              20

<210> SEQ ID NO 983
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
aagggcacag acttccaaag                                              20

<210> SEQ ID NO 984
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
aagggcacag acttccaaag                                              20

<210> SEQ ID NO 985
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
aagggcacag acttccaaag                                              20

<210> SEQ ID NO 986
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
aagggcacag acttccaaag                                              20

<210> SEQ ID NO 987
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
aagggcacag acttccaaag                                              20
```

<210> SEQ ID NO 988
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
aagggcacag acttccaaag                                            20

<210> SEQ ID NO 989
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
agggcacaga cttccaaagg                                            20

<210> SEQ ID NO 990
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
agggcacaga cttccaaagg                                            20

<210> SEQ ID NO 991
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
agggcacaga cttccaaagg                                            20

<210> SEQ ID NO 992
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
agggcacaga cttccaaagg                                            20

<210> SEQ ID NO 993
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
agggcacaga cttccaaagg                                            20

<210> SEQ ID NO 994
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
agggcacaga cttccaaagg                                                  20

<210> SEQ ID NO 995
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 995
agggcacaga cttccaaagg                                                  20

<210> SEQ ID NO 996
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
gggcacagac ttccaaaggc                                                  20

<210> SEQ ID NO 997
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
gggcacagac ttccaaaggc                                                  20

<210> SEQ ID NO 998
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
gggcacagac ttccaaaggc                                                  20

<210> SEQ ID NO 999
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
gggcacagac ttccaaaggc                                                  20

<210> SEQ ID NO 1000

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
gggcacagac ttccaaaggc                                                    20

<210> SEQ ID NO 1001
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1001
ggcacaaggg cacagacutc                                                    20

<210> SEQ ID NO 1002
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
ggcacaaggg cacagacttc                                                    20

<210> SEQ ID NO 1003
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
ggcacaaggg cacagacuuc                                                    20

<210> SEQ ID NO 1004
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
auuaauaaat tgtcatcacc                                                    20

<210> SEQ ID NO 1005
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 1005
auuaauaaat tgtcatcacc                                               20

<210> SEQ ID NO 1006
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
ggcacaaggg cacagacuuc                                               20

<210> SEQ ID NO 1007
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
ggcacaaggg cacagacuuc                                               20

<210> SEQ ID NO 1008
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1008
ggcacaaggg cacagacttc                                               20

<210> SEQ ID NO 1009
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1009
ggcacaaggg cacagacttc                                               20

<210> SEQ ID NO 1010
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
ctcagtaaca ttgacaccac                                               20

<210> SEQ ID NO 1011
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 1011
cucagtaaca ttgacaccac                                                     20

<210> SEQ ID NO 1012
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1012
ggcacaaggg cacagacutc                                                     20

<210> SEQ ID NO 1013
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1013
ctcagtaaca ttgacaccac                                                     20

<210> SEQ ID NO 1014
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1014
ctcagtaaca ttgacaccac                                                     20

<210> SEQ ID NO 1015
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
gaagucugug cccuugugcc                                                     20

<210> SEQ ID NO 1016
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1016
ggcacaaggg cacagacutc                                                     20
```

<210> SEQ ID NO 1017
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1017
tgtcatcacc agaaaaaguc                                               20

<210> SEQ ID NO 1018
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1018
utgtcatcac cagaaaaagu                                               20

<210> SEQ ID NO 1019
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1019
ttgtcatcac cagaaaaagu                                               20

<210> SEQ ID NO 1020
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1020
autgtcatca ccagaaaaag                                               20

<210> SEQ ID NO 1021
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1021
attgtcatca ccagaaaaag                                               20

<210> SEQ ID NO 1022

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1022
aautgtcatc accagaaaaa                                              20

<210> SEQ ID NO 1023
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1023
aattgtcatc accagaaaaa                                              20

<210> SEQ ID NO 1024
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1024
aaattgtcat caccagaaaa                                              20

<210> SEQ ID NO 1025
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1025
aaautgtcat caccagaaaa                                              20

<210> SEQ ID NO 1026
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1026
uaaautgtca tcaccagaaa                                              20

<210> SEQ ID NO 1027
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 1027
uaaautgtca tcaccagaaa                                                   20

<210> SEQ ID NO 1028
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1028
auaaattgtc atcaccagaa                                                   20

<210> SEQ ID NO 1029
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1029
auaaattgtc atcaccagaa                                                   20

<210> SEQ ID NO 1030
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1030
aauaaattgt catcaccaga                                                   20

<210> SEQ ID NO 1031
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1031
aauaaattgt catcaccaga                                                   20

<210> SEQ ID NO 1032
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1032
aauaaattgt catcaccaga                                              20

<210> SEQ ID NO 1033
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1033 uauaaattg tcatcaccag                                               20

<210> SEQ ID NO 1034
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1034
uaauaaattg tcatcaccag                                              20

<210> SEQ ID NO 1035
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1035
uaauaaattg tcatcaccag                                              20

<210> SEQ ID NO 1036
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1036
uaauaaattg tcatcaccag                                              20

<210> SEQ ID NO 1037
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1037
uuaauaaatt gtcatcacca                                            20

<210> SEQ ID NO 1038
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1038
uuaauaaatt gtcatcacca                                            20

<210> SEQ ID NO 1039
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1039
uuaauaaatt gtcatcacca                                            20

<210> SEQ ID NO 1040
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1040
uuaauaaatt gtcatcacca                                            20

<210> SEQ ID NO 1041
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1041
auuaataaat tgtcatcacc                                            20

<210> SEQ ID NO 1042
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
auuaataaat tgtcatcacc                                                20

<210> SEQ ID NO 1043
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
auuaataaat tgtcatcacc                                                20

<210> SEQ ID NO 1044
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
auuaataaat tgtcatcacc                                                20

<210> SEQ ID NO 1045
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1045
uauuaataaa ttgtcatcac                                                20

<210> SEQ ID NO 1046
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1046
uauuaataaa ttgtcatcac                                                20

<210> SEQ ID NO 1047
<211> LENGTH: 20

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1047
uauuaataaa ttgtcatcac                                                   20

<210> SEQ ID NO 1048
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1048
cuauuaataa attgtcatca                                                   20

<210> SEQ ID NO 1049
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1049
cuauuaataa attgtcatca                                                   20

<210> SEQ ID NO 1050
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1050
acuautaata aattgtcatc                                                   20

<210> SEQ ID NO 1051
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1051
tgtcatcacc agaaaaaguc                                                   20

<210> SEQ ID NO 1052
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1052
utgtcatcac cagaaaaagu                                              20

<210> SEQ ID NO 1053
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1053
ttgtcatcac cagaaaaagu                                              20

<210> SEQ ID NO 1054
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1054
autgtcatca ccagaaaaag                                              20

<210> SEQ ID NO 1055
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1055
attgtcatca ccagaaaaag                                              20

<210> SEQ ID NO 1056
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1056
aautgtcatc accagaaaaa                                              20

<210> SEQ ID NO 1057
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1057
aattgtcatc accagaaaaa                                                      20

<210> SEQ ID NO 1058
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1058
aaattgtcat caccagaaaa                                                      20

<210> SEQ ID NO 1059
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1059
aaautgtcat caccagaaaa                                                      20

<210> SEQ ID NO 1060
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1060
uaaautgtca tcaccagaaa                                                      20

<210> SEQ ID NO 1061
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1061
uaaautgtca tcaccagaaa                                                      20

<210> SEQ ID NO 1062
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 1062
auaaattgtc atcaccagaa                                                     20

<210> SEQ ID NO 1063
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1063
auaaattgtc atcaccagaa                                                     20

<210> SEQ ID NO 1064
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1064
aauaaattgt catcaccaga                                                     20

<210> SEQ ID NO 1065
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1065
aauaaattgt catcaccaga                                                     20

<210> SEQ ID NO 1066
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1066
aauaaattgt catcaccaga                                                     20

<210> SEQ ID NO 1067
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1067
uaauaaattg tcatcaccag                                                    20

<210> SEQ ID NO 1068
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1068
uaauaaattg tcatcaccag                                                    20

<210> SEQ ID NO 1069
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1069
uaauaaattg tcatcaccag                                                    20

<210> SEQ ID NO 1070
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1070
uaauaaattg tcatcaccag                                                    20

<210> SEQ ID NO 1071
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1071
uuaauaaatt gtcatcacca                                                    20

<210> SEQ ID NO 1072
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide
<220> FEATURE:
<223> OTHER INFORMATION: Description of Combined DNA/RNA Molecule:
      Synthetic oligonucleotide

<400> SEQUENCE: 1072
uuaauaaatt gtcatcacca                                            20

<210> SEQ ID NO 1073
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1073
uuaauaaatt gtcatcacca                                            20

<210> SEQ ID NO 1074
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1074
uuaauaaatt gtcatcacca                                            20

<210> SEQ ID NO 1075
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1075
auuaataaat tgtcatcacc                                            20

<210> SEQ ID NO 1076
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1076
auuaataaat tgtcatcacc                                            20

<210> SEQ ID NO 1077
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1077
auuaauaaat tgtcatcacc                                              20

<210> SEQ ID NO 1078
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1078
auuaauaaat tgtcatcacc                                              20

<210> SEQ ID NO 1079
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1079
uauuaauaaa ttgtcatcac                                              20

<210> SEQ ID NO 1080
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1080
uauuaauaaa ttgtcatcac                                              20

<210> SEQ ID NO 1081
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1081
uauuaauaaa ttgtcatcac                                              20

<210> SEQ ID NO 1082
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1082
cuauuaauaa attgtcatca                                                   20

<210> SEQ ID NO 1083
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1083
cuauuaauaa attgtcatca                                                   20

<210> SEQ ID NO 1084
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1084
acuauuaaua aattgtcatc                                                   20

<210> SEQ ID NO 1085
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
gacuuuuucu ggugauggca auuuauuaau ag                                     32

<210> SEQ ID NO 1086
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
gacuuuuucu ggugaugaca auuuauuaau ag                                     32

<210> SEQ ID NO 1087
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

Synthetic oligonucleotide

<400> SEQUENCE: 1087
uaaautgtca tcaccagaaa                                                      20

<210> SEQ ID NO 1088
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1088
auaaattgtc atcaccagaa                                                      20

<210> SEQ ID NO 1089
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1089
aauaaattgt catcaccaga                                                      20

<210> SEQ ID NO 1090
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1090
uaauaaattg tcatcaccag                                                      20

<210> SEQ ID NO 1091
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1091
aauaaattgt catcaccaga                                                      20

<210> SEQ ID NO 1092
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

<223> OTHER INFORMATION: Description of Combined DNA/RNA Molecule:
      Synthetic oligonucleotide

<400> SEQUENCE: 1092
uaauaaattg tcatcaccag                                                20

<210> SEQ ID NO 1093
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1093
gcacaagggc acagacuucc                                                20

<210> SEQ ID NO 1094
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
gcacaagggc acagacuucc                                                20

<210> SEQ ID NO 1095
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095
cacaagggca cagacuucca                                                20

<210> SEQ ID NO 1096
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
cacaagggca cagacuucca                                                20

<210> SEQ ID NO 1097
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1097
uaaautgtca tcaccagaaa                                                20

<210> SEQ ID NO 1098
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1098
auaaattgtc atcaccagaa                                                   20

<210> SEQ ID NO 1099
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1099
aauaaattgt catcaccaga                                                   20

<210> SEQ ID NO 1100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1100
uaauaaattg tcatcaccag                                                   20

<210> SEQ ID NO 1101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
uccccacaga gggaggaagc                                                   20

<210> SEQ ID NO 1102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
cuccccacag agggaggaag                                                   20

<210> SEQ ID NO 1103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1103 ccucccaca gagggaggaa                                                 20

<210> SEQ ID NO 1104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104 uccucccac agagggagga                                                 20

<210> SEQ ID NO 1105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1105
guccucccca cagagggagg                                                20

<210> SEQ ID NO 1106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1106
ggucctcccc acagagggag                                                20

<210> SEQ ID NO 1107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1107
gggucctccc cacagaggga                                                20

<210> SEQ ID NO 1108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1108
cgggucctcc ccacagaggg                                                20
```

```
<210> SEQ ID NO 1109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1109
acaguagatg agggagcagg                                               20

<210> SEQ ID NO 1110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110
cacagtagat gagggagcag                                               20

<210> SEQ ID NO 1111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1111
acacagtaga tgagggagca                                               20

<210> SEQ ID NO 1112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112
cacacagtag atgagggagc                                               20

<210> SEQ ID NO 1113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
gcacacagta gatgagggag                                               20

<210> SEQ ID NO 1114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 1114
ugcacacagt agatgaggga                                                   20

<210> SEQ ID NO 1115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1115
gugcacacag tagatgaggg                                                   20

<210> SEQ ID NO 1116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1116
agugcacaca gtagaugagg                                                   20

<210> SEQ ID NO 1117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1117
uccccacaga gggaggaagc                                                   20

<210> SEQ ID NO 1118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
cuccccacag agggaggaag                                                   20

<210> SEQ ID NO 1119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
ccuccccaca gagggaggaa                                                   20

<210> SEQ ID NO 1120
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1120 uccucccac agagggagga                                                      20

<210> SEQ ID NO 1121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
guccucccca cagagggagg                                                     20

<210> SEQ ID NO 1122
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1122
ggucctcccc acagagggag                                                     20

<210> SEQ ID NO 1123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1123
gggucctccc cacagaggga                                                     20

<210> SEQ ID NO 1124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1124
cgggucctcc ccacagaggg                                                     20

<210> SEQ ID NO 1125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 1125
acaguagatg agggagcagg                                                    20

<210> SEQ ID NO 1126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1126
cacagtagat gagggagcag                                                    20

<210> SEQ ID NO 1127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1127
acacagtaga tgagggagca                                                    20

<210> SEQ ID NO 1128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
cacacagtag atgagggagc                                                    20

<210> SEQ ID NO 1129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
gcacacagta gatgagggag                                                    20

<210> SEQ ID NO 1130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1130
ugcacacagt agatgaggga                                                    20

<210> SEQ ID NO 1131
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1131
gugcacacag tagatgaggg                                              20

<210> SEQ ID NO 1132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1132
agugcacaca gtagaugagg                                              20

<210> SEQ ID NO 1133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1133
ggcacaaggg cacagacttc                                              20

<210> SEQ ID NO 1134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
ggcacaaggg cacagacuuc                                              20

<210> SEQ ID NO 1135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1135
ggguccuccc cacagaggga                                              20

<210> SEQ ID NO 1136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 1136
ggguccucuc cacagaggga                                              20

<210> SEQ ID NO 1137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1137
ggguccucuc cacagaggga                                              20

<210> SEQ ID NO 1138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1138
ggguccucuc cacagaggga                                              20

<210> SEQ ID NO 1139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1139
ggguuctccc cacagaggga                                              20

<210> SEQ ID NO 1140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
ggcacaaggg cacagacuuc                                              20

<210> SEQ ID NO 1141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1141
ggcacaaggg cacagacuuc                                              20

<210> SEQ ID NO 1142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
ggcacaaggg cacagacuuc                                              20

<210> SEQ ID NO 1143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
ggcacaaggg cacagacuuc                                              20

<210> SEQ ID NO 1144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1144
ggcacaaggg cacagacuuc                                              20

<210> SEQ ID NO 1145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
ggcacaaggg cacagacuuc                                              20

<210> SEQ ID NO 1146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
ggcacaaggg cacagacuuc                                              20

<210> SEQ ID NO 1147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
ggcacaaggg cacagacuuc                                              20

<210> SEQ ID NO 1148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
ggcacaaggg cacagacuuc                                                 20

<210> SEQ ID NO 1149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
ggcacaaggg cacagacuuc                                                 20

<210> SEQ ID NO 1150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1150
ggcacaaggg cacagacuuc                                                 20

<210> SEQ ID NO 1151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1151
ggcacaaggg cacagacuuc                                                 20

<210> SEQ ID NO 1152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1152
ggcacaaggg cacagacuuc                                                 20

<210> SEQ ID NO 1153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1153
attaataaat tgtcatcacc                                                 20

```
<210> SEQ ID NO 1154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1154
attaataaat tgtcatcacc                                                      20

<210> SEQ ID NO 1155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1155
attaataaat tgtcatcacc                                                      20

<210> SEQ ID NO 1156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1156
ggugaugaca auuauuaau                                                       20

<210> SEQ ID NO 1157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1157
ggugauggca auuauuaau                                                       20

<210> SEQ ID NO 1158
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1158
uuuggaaguc ugcgcccuug ugccc                                                25

<210> SEQ ID NO 1159
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1159
uuuggaaguc ugugcccuug ugccc                                                25
```

```
<210> SEQ ID NO 1160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1160
gggcacaagg gcacagactt                                                  20

<210> SEQ ID NO 1161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1161
ggcacaaggg cacagacttc                                                  20

<210> SEQ ID NO 1162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1162
gcacaagggc acagacttcc                                                  20

<210> SEQ ID NO 1163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1163
cacaagggca cagacttcca                                                  20

<210> SEQ ID NO 1164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1164
acaagggcac agacttccaa                                                  20

<210> SEQ ID NO 1165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1165
caagggcaca gacttccaaa                                                  20

<210> SEQ ID NO 1166
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1166
gggcacaagg gcacagactt                                              20

<210> SEQ ID NO 1167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1167
ggcacaaggg cacagacttc                                              20

<210> SEQ ID NO 1168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1168
gcacaagggc acagacttcc                                              20

<210> SEQ ID NO 1169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1169
cacaagggca cagacttcca                                              20

<210> SEQ ID NO 1170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1170
acaagggcac agacttccaa                                              20

<210> SEQ ID NO 1171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1171
caagggcaca gacttccaaa                                              20

<210> SEQ ID NO 1172
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
gggcacaagg gcacagacuu                                                    20

<210> SEQ ID NO 1173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
ggcacaaggg cacagacuuc                                                    20

<210> SEQ ID NO 1174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
gcacaagggc acagacuucc                                                    20

<210> SEQ ID NO 1175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
cacaagggca cagacuucca                                                    20

<210> SEQ ID NO 1176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1176
acaagggcac agactuccaa                                                    20

<210> SEQ ID NO 1177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1177
caagggcaca gacttccaaa                                                    20
```

```
<210> SEQ ID NO 1178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178
gcacaagggc acagacuucc                                              20

<210> SEQ ID NO 1179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
cacaagggca cagacuucca                                              20

<210> SEQ ID NO 1180
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
acaagggcac agacuuccaa                                              20

<210> SEQ ID NO 1181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
caagggcaca gacuuccaaa                                              20

<210> SEQ ID NO 1182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
gcacaagggc acagacuucc                                              20

<210> SEQ ID NO 1183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1183
cacaagggca cagacuucca                                              20

<210> SEQ ID NO 1184
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
acaagggcac agacuuccaa                                                   20

<210> SEQ ID NO 1185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
caagggcaca gacuuccaaa                                                   20

<210> SEQ ID NO 1186
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
gggcacaagg gcacagacuu                                                   20

<210> SEQ ID NO 1187
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1187
ggcacaaggg cacagacuuc                                                   20

<210> SEQ ID NO 1188
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188
gcacaagggc acagacuucc                                                   20

<210> SEQ ID NO 1189
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1189
cacaagggca cagacuucca                                                   20

<210> SEQ ID NO 1190
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1190
acaagggcac agactuccaa                                                   20

<210> SEQ ID NO 1191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1191
caagggcaca gacttccaaa                                                   20

<210> SEQ ID NO 1192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192
gggcacaagg gcacagactt                                                   20

<210> SEQ ID NO 1193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193
ggcacaaggg cacagacttc                                                   20

<210> SEQ ID NO 1194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1194
gcacaagggc acagacttcc                                                   20

<210> SEQ ID NO 1195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195 cacagggca cagacttcca                                                    20
```

```
<210> SEQ ID NO 1196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
acaagggcac agacttccaa                                                   20

<210> SEQ ID NO 1197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
caagggcaca gacttccaaa                                                   20

<210> SEQ ID NO 1198
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
uuuggaaguc ugcgcccuug ugccc                                             25

<210> SEQ ID NO 1199
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
uuuggaaguc ugugcccuug ugccc                                             25

<210> SEQ ID NO 1200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1200
gagcagctgc aacctggcaa                                                   20

<210> SEQ ID NO 1201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1201
gggccaacag ccagcctgca                                                   20

<210> SEQ ID NO 1202
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
gguuguugcc agguuacagc ugcuc                                             25

<210> SEQ ID NO 1203
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
gguuguugcc agguugcagc ugcuc                                             25

<210> SEQ ID NO 1204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1204
gagcagctgc aacctggcaa                                                   20

<210> SEQ ID NO 1205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1205
agcagctgca acctggcaac                                                   20

<210> SEQ ID NO 1206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1206
gcagctgcaa cctggcaaca                                                   20

<210> SEQ ID NO 1207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1207
cagctgcaac ctggcaacaa                                                   20

<210> SEQ ID NO 1208
<211> LENGTH: 20
```

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1208
agctgcaacc tggcaacaac                                              20

<210> SEQ ID NO 1209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1209
gctgcaacct ggcaacaacc                                              20

<210> SEQ ID NO 1210
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
ccuccugcag gcuggguguu ggccc                                        25

<210> SEQ ID NO 1211
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1211
ccuccugcag gcuggcuguu ggccc                                        25

<210> SEQ ID NO 1212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1212
gggccaacag ccagcctgca                                              20

<210> SEQ ID NO 1213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1213
ggccaacagc cagcctgcag                                              20

<210> SEQ ID NO 1214
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1214
gccaacagcc agcctgcagg                                                     20

<210> SEQ ID NO 1215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1215
ccaacagcca gcctgcagga                                                     20

<210> SEQ ID NO 1216
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1216
caacagccag cctgcaggag                                                     20

<210> SEQ ID NO 1217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1217
aacagccagc ctgcaggagg                                                     20

<210> SEQ ID NO 1218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1218
ggccuuucac uacuccuact t                                                   21

<210> SEQ ID NO 1219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1219
guaggaguag ugaaaggcct t                                                   21
```

<210> SEQ ID NO 1220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1220
gtaggagtag tgaaaggcca                                                  20

<210> SEQ ID NO 1221
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1221
gcagggcaca agggcacaga                                                  20

<210> SEQ ID NO 1222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1222
cagggcacaa gggcacagac                                                  20

<210> SEQ ID NO 1223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1223
agggcacaag ggcacagact                                                  20

<210> SEQ ID NO 1224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1224
aagggcacag acttccaaag                                                  20

<210> SEQ ID NO 1225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1225
agggcacaga cttccaaagg                                                  20

```
<210> SEQ ID NO 1226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1226
gggcacagac ttccaaaggc                                               20

<210> SEQ ID NO 1227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1227
gagcagctgc aacctggcaa                                               20

<210> SEQ ID NO 1228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228
agcagctgca acctggcaac                                               20

<210> SEQ ID NO 1229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
gcagctgcaa cctggcaaca                                               20

<210> SEQ ID NO 1230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1230
cagctgcaac ctggcaacaa                                               20

<210> SEQ ID NO 1231
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
agctgcaacc tggcaacaac                                               20
```

<210> SEQ ID NO 1232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1232
gctgcaacct ggcaacaacc                                              20

<210> SEQ ID NO 1233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
gagcagctgc aacctggcaa                                              20

<210> SEQ ID NO 1234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1234
agcagctgca acctggcaac                                              20

<210> SEQ ID NO 1235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1235
gcagctgcaa cctggcaaca                                              20

<210> SEQ ID NO 1236
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1236
cagcugcaac ctggcaacaa                                              20

<210> SEQ ID NO 1237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 1237
agcugcaacc tggcaacaac                                                 20

<210> SEQ ID NO 1238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1238
gcugcaacct ggcaacaacc                                                 20

<210> SEQ ID NO 1239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1239
gagcagctgc aacctggcaa                                                 20

<210> SEQ ID NO 1240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1240
agcagctgca acctggcaac                                                 20

<210> SEQ ID NO 1241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1241
gcagctgcaa cctggcaaca                                                 20

<210> SEQ ID NO 1242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1242
cagcugcaac ctggcaacaa                                                 20

<210> SEQ ID NO 1243
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1243
agcugcaacc tggcaacaac                                                 20

<210> SEQ ID NO 1244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1244
gcugcaaccu ggcaacaacc                                                 20

<210> SEQ ID NO 1245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1245
gagcagctgc aaccuggcaa                                                 20

<210> SEQ ID NO 1246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1246
gagcagctgc aaccuggcaa                                                 20

<210> SEQ ID NO 1247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1247
agcagctgca acctggcaac                                                 20

<210> SEQ ID NO 1248
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1248
agcagctgca acctggcaac                                                   20

<210> SEQ ID NO 1249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1249
gcagctgcaa ccuggcaaca                                                   20

<210> SEQ ID NO 1250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1250
gcagctgcaa ccuggcaaca                                                   20

<210> SEQ ID NO 1251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1251
gagcagctgc aacctggcaa                                                   20

<210> SEQ ID NO 1252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1252
agcagctgca acctggcaac                                                   20

<210> SEQ ID NO 1253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1253
gcagctgcaa cctggcaaca                                                   20
```

```
<210> SEQ ID NO 1254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1254
cagcugcaac ctggcaacaa                                                   20

<210> SEQ ID NO 1255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1255
agcugcaacc tggcaacaac                                                   20

<210> SEQ ID NO 1256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1256
gcugcaacct ggcaacaacc                                                   20

<210> SEQ ID NO 1257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1257
gggccaacag ccagcctgca                                                   20

<210> SEQ ID NO 1258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1258
ggccaacagc cagcctgcag                                                   20

<210> SEQ ID NO 1259
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1259
gccaacagcc agcctgcagg                                                    20

<210> SEQ ID NO 1260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1260
ccaacagcca gcctgcagga                                                    20

<210> SEQ ID NO 1261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1261
caacagccag cctgcaggag                                                    20

<210> SEQ ID NO 1262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1262
aacagccagc ctgcaggagg                                                    20

<210> SEQ ID NO 1263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1263
gggccaacag ccagcctgca                                                    20

<210> SEQ ID NO 1264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1264
ggccaacagc cagcctgcag                                                    20

<210> SEQ ID NO 1265
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1265
gccaacagcc agcctgcagg                                                    20

<210> SEQ ID NO 1266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1266
ccaacagcca gcctgcagga                                                    20

<210> SEQ ID NO 1267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1267
caacagccag cctgcaggag                                                    20

<210> SEQ ID NO 1268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1268
aacagccagc ctgcaggagg                                                    20

<210> SEQ ID NO 1269
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
gggccaacag ccagccugca                                                    20

<210> SEQ ID NO 1270
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
ggccaacagc cagccugcag                                                    20

<210> SEQ ID NO 1271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1271
gccaacagcc agcctgcagg                                              20

<210> SEQ ID NO 1272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1272
ccaacagcca gcctgcagga                                              20

<210> SEQ ID NO 1273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1273
caacagccag cctgcaggag                                              20

<210> SEQ ID NO 1274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1274
aacagccagc ctgcaggagg                                              20

<210> SEQ ID NO 1275
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
gggccaacag ccagccugca                                              20

<210> SEQ ID NO 1276
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
gggccaacag ccagccugca                                              20

<210> SEQ ID NO 1277
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
ggccaacagc cagccugcag                                               20

<210> SEQ ID NO 1278
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
ggccaacagc cagccugcag                                               20

<210> SEQ ID NO 1279
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
gccaacagcc agccugcagg                                               20

<210> SEQ ID NO 1280
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
gccaacagcc agccugcagg                                               20

<210> SEQ ID NO 1281
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
gggccaacag ccagccugca                                               20

<210> SEQ ID NO 1282
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
ggccaacagc cagccugcag                                               20

<210> SEQ ID NO 1283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1283
gccaacagcc agcctgcagg                                              20

<210> SEQ ID NO 1284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1284
ccaacagcca gcctgcagga                                              20

<210> SEQ ID NO 1285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1285
caacagccag cctgcaggag                                              20

<210> SEQ ID NO 1286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1286
aacagccagc ctgcaggagg                                              20

<210> SEQ ID NO 1287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1287
guaggagtag tgaaaggcca                                              20

<210> SEQ ID NO 1288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1288
guaggagtag tgaaaggcca                                              20

<210> SEQ ID NO 1289
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1289
guaggaguag tgaaaggcca                                                   20

<210> SEQ ID NO 1290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1290
cucuuactgt gctgtggaca                                                   20

<210> SEQ ID NO 1291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1291
cucuuactgt gctgtggaca                                                   20

<210> SEQ ID NO 1292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1292
cucuuactgt gctgtggaca                                                   20

<210> SEQ ID NO 1293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1293
gggcacaagg gcacagactt                                                   20

<210> SEQ ID NO 1294
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 1294
ggcacaaggg cacagacttc                                          20

<210> SEQ ID NO 1295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1295
gcacaagggc acagacttcc                                          20

<210> SEQ ID NO 1296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1296
gggcacaagg gcacagactt                                          20

<210> SEQ ID NO 1297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1297
ggcacaaggg cacagacttc                                          20

<210> SEQ ID NO 1298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1298
gcacaagggc acagacttcc                                          20

<210> SEQ ID NO 1299
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1299
gagccuuugg aagucugcgc ccuugugccc ugccu                         35

<210> SEQ ID NO 1300
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1300
gagccuuugg aagucugugc ccuugugccc ugccu                35

<210> SEQ ID NO 1301
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1301
cacacgggca cagacuucca a                               21

<210> SEQ ID NO 1302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1302
ggaagucugu gcccgugugc c                               21

<210> SEQ ID NO 1303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1303
auuaauaaat tgtcatcacc                                 20

<210> SEQ ID NO 1304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1304
auuaauaaat tgtcatcacc                                 20

<210> SEQ ID NO 1305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1305
auuaauaaat tgtcatcacc                                 20

```
<210> SEQ ID NO 1306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1306
auuaauaaat tgtcatcacc                                                  20

<210> SEQ ID NO 1307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1307
auuaauaaat tgtcatcacc                                                  20

<210> SEQ ID NO 1308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1308
auuaauaaat tgtcatcacc                                                  20

<210> SEQ ID NO 1309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1309
auuaauaaat tgtcatcacc                                                  20

<210> SEQ ID NO 1310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1310
auuaauaaat tgtcatcacc                                                  20
```

<210> SEQ ID NO 1311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1311
ggcacaaggg cacagacuuc                                              20

<210> SEQ ID NO 1312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1312
ggcacaaggg cacagacuuc                                              20

<210> SEQ ID NO 1313
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1313
ggcacaaggg cacagacuuc                                              20

<210> SEQ ID NO 1314
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1314
ggcacaaggg cacagacttc                                              20

<210> SEQ ID NO 1315
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1315
ggcacaaggg cacagacttc                                              20

<210> SEQ ID NO 1316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1316
ggcacaaggg cacagacttc                                              20

```
<210> SEQ ID NO 1317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1317
ggcacaaggg cacagacuuc                                                    20

<210> SEQ ID NO 1318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1318
ggcacaaggg cacagacuuc                                                    20

<210> SEQ ID NO 1319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1319
gcagggcaca agggcacaga                                                    20

<210> SEQ ID NO 1320
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1320
gcagggcaca agggcacaga                                                    20

<210> SEQ ID NO 1321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1321
gcagggcaca agggcacaga                                                    20

<210> SEQ ID NO 1322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1322
gcagggcaca agggcacaga                                                    20
```

<210> SEQ ID NO 1323
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1323
gcagggcaca agggcacaga                20

<210> SEQ ID NO 1324
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1324
cagggcacaa gggcacagac                20

<210> SEQ ID NO 1325
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1325
cagggcacaa gggcacagac                20

<210> SEQ ID NO 1326
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1326
cagggcacaa gggcacagac                20

<210> SEQ ID NO 1327
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1327
cagggcacaa gggcacagac                20

<210> SEQ ID NO 1328
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1328
cagggcacaa gggcacagac                20

<210> SEQ ID NO 1329

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1329
agggcacaag ggcacagact                                                   20

<210> SEQ ID NO 1330
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1330
agggcacaag ggcacagact                                                   20

<210> SEQ ID NO 1331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1331
agggcacaag ggcacagact                                                   20

<210> SEQ ID NO 1332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1332
agggcacaag ggcacagacu                                                   20

<210> SEQ ID NO 1333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1333
agggcacaag ggcacagacu                                                   20

<210> SEQ ID NO 1334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1334
aagggcacag acttccaaag                                                   20

<210> SEQ ID NO 1335
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1335
aagggcacag acttccaaag                                                    20

<210> SEQ ID NO 1336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1336
aagggcacag acttccaaag                                                    20

<210> SEQ ID NO 1337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1337
aagggcacag acttccaaag                                                    20

<210> SEQ ID NO 1338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1338
aagggcacag acttccaaag                                                    20

<210> SEQ ID NO 1339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1339
aagggcacag acttccaaag                                                    20

<210> SEQ ID NO 1340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1340
aagggcacag acttccaaag                                                    20

<210> SEQ ID NO 1341
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 1341
agggcacaga cttccaaagg                                                   20

<210> SEQ ID NO 1342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1342
agggcacaga cttccaaagg                                                   20

<210> SEQ ID NO 1343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1343
agggcacaga cttccaaagg                                                   20

<210> SEQ ID NO 1344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1344
agggcacaga cttccaaagg                                                   20

<210> SEQ ID NO 1345
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1345
agggcacaga cttccaaagg                                                   20

<210> SEQ ID NO 1346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1346
agggcacaga cttccaaagg                                                   20

<210> SEQ ID NO 1347
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1347
agggcacaga cttccaaagg                                                  20

<210> SEQ ID NO 1348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1348
gggcacagac ttccaaaggc                                                  20

<210> SEQ ID NO 1349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1349
gggcacagac ttccaaaggc                                                  20

<210> SEQ ID NO 1350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1350
gggcacagac ttccaaaggc                                                  20

<210> SEQ ID NO 1351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1351
gggcacagac ttccaaaggc                                                  20

<210> SEQ ID NO 1352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1352
gggcacagac ttccaaaggc                                                  20

<210> SEQ ID NO 1353
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1353
ggcacaaggg cacagacuuc                                                20

<210> SEQ ID NO 1354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1354
ggcacaaggg cacagacuuc                                                20

<210> SEQ ID NO 1355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1355
ggcacaaggg cacagacuuc                                                20

<210> SEQ ID NO 1356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1356
auuaauaaat tgtcatcacc                                                20

<210> SEQ ID NO 1357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1357
auuaauaaat tgtcatcacc                                                20

<210> SEQ ID NO 1358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1358
ggcacaaggg cacagacuuc                                                20
```

```
<210> SEQ ID NO 1359
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
ggcacaaggg cacagacuuc                                                   20

<210> SEQ ID NO 1360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1360
ggcacaaggg cacagacttc                                                   20

<210> SEQ ID NO 1361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1361
ggcacaaggg cacagacttc                                                   20

<210> SEQ ID NO 1362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1362
ctcagtaaca ttgacaccac                                                   20

<210> SEQ ID NO 1363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1363
cucagtaaca ttgacaccac                                                   20

<210> SEQ ID NO 1364
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1364
ggcacaaggg cacagacuuc                                                   20
```

<210> SEQ ID NO 1365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1365
cucagtaaca ttgacaccac                                              20

<210> SEQ ID NO 1366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1366
cucagtaaca ttgacaccac                                              20

<210> SEQ ID NO 1367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1367
gaagucugug cccuugugcc                                              20

<210> SEQ ID NO 1368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1368
ggcacaaggg cacagacuuc                                              20

<210> SEQ ID NO 1369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1369
tgtcatcacc agaaaaaguc                                              20

<210> SEQ ID NO 1370
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1370
utgtcatcac cagaaaaagu                                                    20

<210> SEQ ID NO 1371
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1371
ttgtcatcac cagaaaaagu                                                    20

<210> SEQ ID NO 1372
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1372
autgtcatca ccagaaaaag                                                    20

<210> SEQ ID NO 1373
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1373
attgtcatca ccagaaaaag                                                    20

<210> SEQ ID NO 1374
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1374
aautgtcatc accagaaaaa                                                    20

<210> SEQ ID NO 1375
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1375
aattgtcatc accagaaaaa                                                    20

<210> SEQ ID NO 1376
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1376
aaattgtcat caccagaaaa                                                    20

<210> SEQ ID NO 1377
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1377
aaautgtcat caccagaaaa                                                    20

<210> SEQ ID NO 1378
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1378
uaaautgtca tcaccagaaa                                                    20

<210> SEQ ID NO 1379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1379
uaaautgtca tcaccagaaa                                                    20

<210> SEQ ID NO 1380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 1380
auaaattgtc atcaccagaa                                         20

<210> SEQ ID NO 1381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1381
auaaattgtc atcaccagaa                                         20

<210> SEQ ID NO 1382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1382
aauaaattgt catcaccaga                                         20

<210> SEQ ID NO 1383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1383
aauaaattgt catcaccaga                                         20

<210> SEQ ID NO 1384
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1384
aauaaattgt catcaccaga                                         20

<210> SEQ ID NO 1385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 1385
uaauaaattg tcatcaccag                                                 20

<210> SEQ ID NO 1386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1386
uaauaaattg tcatcaccag                                                 20

<210> SEQ ID NO 1387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1387
uaauaaattg tcatcaccag                                                 20

<210> SEQ ID NO 1388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1388
uaauaaattg tcatcaccag                                                 20

<210> SEQ ID NO 1389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1389
uuaauaaatt gtcatcacca                                                 20

<210> SEQ ID NO 1390
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1390 uuaauaaaatt gtcatcacca                                               20

<210> SEQ ID NO 1391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1391 uuaauaaaatt gtcatcacca                                               20

<210> SEQ ID NO 1392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1392 uuaauaaaatt gtcatcacca                                               20

<210> SEQ ID NO 1393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1393
auuaataaat tgtcatcacc                                                20

<210> SEQ ID NO 1394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1394
auuaataaat tgtcatcacc                                                20

<210> SEQ ID NO 1395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 1395 auuaautaaat tgtcatcacc                                                    20

<210> SEQ ID NO 1396
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1396
auuaataaat tgtcatcacc                                                     20

<210> SEQ ID NO 1397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1397
uauuaataaa ttgtcatcac                                                     20

<210> SEQ ID NO 1398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1398
uauuaataaa ttgtcatcac                                                     20

<210> SEQ ID NO 1399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1399
uauuaataaa ttgtcatcac                                                     20

<210> SEQ ID NO 1400
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 1400
cuauuaataa attgtcatca                                                    20

<210> SEQ ID NO 1401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1401
cuauuaataa attgtcatca                                                    20

<210> SEQ ID NO 1402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1402
acuautaata aattgtcatc                                                    20

<210> SEQ ID NO 1403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1403
tgtcatcacc agaaaaaguc                                                    20

<210> SEQ ID NO 1404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1404
utgtcatcac cagaaaaagu                                                    20

<210> SEQ ID NO 1405
<211> LENGTH: 20
<212> TYPE: DNA
<213> ORGANISM: Artificial Sequence
<220> FEATURE:
```

<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1405
ttgtcatcac cagaaaaagu                                               20

<210> SEQ ID NO 1406
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1406
autgtcatca ccagaaaaag                                               20

<210> SEQ ID NO 1407
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1407
attgtcatca ccagaaaaag                                               20

<210> SEQ ID NO 1408
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1408
aautgtcatc accagaaaaa                                               20

<210> SEQ ID NO 1409
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1409
aattgtcatc accagaaaaa                                               20

<210> SEQ ID NO 1410
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1410
aaattgtcat caccagaaaa                                                 20

<210> SEQ ID NO 1411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1411
aaautgtcat caccagaaaa                                                 20

<210> SEQ ID NO 1412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1412
uaaautgtca tcaccagaaa                                                 20

<210> SEQ ID NO 1413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1413
uaaautgtca tcaccagaaa                                                 20

<210> SEQ ID NO 1414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1414
auaaattgtc atcaccagaa                                                 20

<210> SEQ ID NO 1415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1415
auaaattgtc atcaccagaa                                              20

<210> SEQ ID NO 1416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1416
aauaaattgt catcaccaga                                              20

<210> SEQ ID NO 1417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1417
aauaaattgt catcaccaga                                              20

<210> SEQ ID NO 1418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1418
aauaaattgt catcaccaga                                              20

<210> SEQ ID NO 1419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1419
uaauaaattg tcatcaccag                                              20

<210> SEQ ID NO 1420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 1420
uaauaaattg tcatcaccag                                                     20

<210> SEQ ID NO 1421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1421
uaauaaattg tcatcaccag                                                     20

<210> SEQ ID NO 1422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1422
uaauaaattg tcatcaccag                                                     20

<210> SEQ ID NO 1423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1423
uuaauaaatt gtcatcacca                                                     20

<210> SEQ ID NO 1424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1424
uuaauaaatt gtcatcacca                                                     20

<210> SEQ ID NO 1425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 1425
uuaauaaatt gtcatcacca                                               20

<210> SEQ ID NO 1426
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1426
uuaauaaatt gtcatcacca                                               20

<210> SEQ ID NO 1427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1427
auuaataaat tgtcatcacc                                               20

<210> SEQ ID NO 1428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1428
auuaataaat tgtcatcacc                                               20

<210> SEQ ID NO 1429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1429
auuaataaat tgtcatcacc                                               20

<210> SEQ ID NO 1430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 1430
auuaauaaat tgtcatcacc                                                      20

<210> SEQ ID NO 1431
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1431
uauuaauaaa ttgtcatcac                                                      20

<210> SEQ ID NO 1432
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1432
uauuaauaaa ttgtcatcac                                                      20

<210> SEQ ID NO 1433
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1433
uauuaauaaa ttgtcatcac                                                      20

<210> SEQ ID NO 1434
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1434
cuauuaauaa attgtcatca                                                      20

<210> SEQ ID NO 1435
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 1435
cuauuaauaa attgtcatca                                                    20

<210> SEQ ID NO 1436
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1436
acuauuaaua aattgtcatc                                                    20

<210> SEQ ID NO 1437
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1437
gacuuuuucu ggugauggca auuuauuaau ag                                      32

<210> SEQ ID NO 1438
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
gacuuuuucu ggugaugaca auuuauuaau ag                                      32

<210> SEQ ID NO 1439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1439 uaaaautgtca tcaccagaaa                                                   20

<210> SEQ ID NO 1440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1440
```
auaaauugtc atcaccagaa                      20

<210> SEQ ID NO 1441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1441
aauaaattgt catcaccaga                      20

<210> SEQ ID NO 1442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1442
uaauaaattg tcatcaccag                      20

<210> SEQ ID NO 1443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1443
aauaaattgt catcaccaga                      20

<210> SEQ ID NO 1444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1444
uaauaaattg tcatcaccag                      20

<210> SEQ ID NO 1445
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1445
gcacaagggc acagacuucc                      20

<210> SEQ ID NO 1446
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1446
gcacaagggc acagacuucc                                                  20

<210> SEQ ID NO 1447
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1447
cacaagggca cagacuucca                                                  20

<210> SEQ ID NO 1448
<211> LENGTH: 20
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 1448
cacaagggca cagacuucca                                                  20

<210> SEQ ID NO 1449
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1449
uaaautgtca tcaccagaaa                                                  20

<210> SEQ ID NO 1450
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 1450
auaaattgtc atcaccagaa                                                  20

<210> SEQ ID NO 1451
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide

<400> SEQUENCE: 1451
aauaaattgt catcaccaga                                                    20

<210> SEQ ID NO 1452
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1452
uaauaaattg tcatcaccag                                                    20

<210> SEQ ID NO 1453
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1453
uccccacaga gggaggaagc                                                    20

<210> SEQ ID NO 1454
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1454
cuccccacag agggaggaag                                                    20

<210> SEQ ID NO 1455
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1455
ccuccccaca gagggaggaa                                                    20

<210> SEQ ID NO 1456
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1456
uccuccccac agagggagga                                                    20

<210> SEQ ID NO 1457
<211> LENGTH: 20
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1457
guccucccca cagagggagg                                               20

<210> SEQ ID NO 1458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1458
ggucctcccc acagagggag                                               20

<210> SEQ ID NO 1459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1459
gggucctccc cacagaggga                                               20

<210> SEQ ID NO 1460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1460
cgggucctcc ccacagaggg                                               20

<210> SEQ ID NO 1461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1461
acaguagatg agggagcagg                                               20

<210> SEQ ID NO 1462
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1462
cacagtagat gagggagcag                                                   20

<210> SEQ ID NO 1463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1463
acacagtaga tgagggagca                                                   20

<210> SEQ ID NO 1464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1464
cacacagtag atgagggagc                                                   20

<210> SEQ ID NO 1465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1465
gcacacagta gatgagggag                                                   20

<210> SEQ ID NO 1466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1466
ugcacacagt agatgaggga                                                   20

<210> SEQ ID NO 1467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1467
gugcacacag tagatgaggg                                                   20
```

<210> SEQ ID NO 1468
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1468
agugcacaca gtagaugagg                                              20

<210> SEQ ID NO 1469
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1469
uccccacaga gggaggaagc                                              20

<210> SEQ ID NO 1470
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1470
cuccccacag agggaggaag                                              20

<210> SEQ ID NO 1471
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1471
ccuccccaca gagggaggaa                                              20

<210> SEQ ID NO 1472
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1472
uccuccccac agagggagga                                              20

<210> SEQ ID NO 1473
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1473 guccuccccacagagggagg                                    20

<210> SEQ ID NO 1474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1474
ggucctcccc acagagggag                                   20

<210> SEQ ID NO 1475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1475
gggucctccc cacagaggga                                   20

<210> SEQ ID NO 1476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1476
cgggucctcc ccacagaggg                                   20

<210> SEQ ID NO 1477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1477
acaguagaug agggagcagg                                   20

<210> SEQ ID NO 1478
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1478
cacagtagat gagggagcag                                   20

<210> SEQ ID NO 1479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1479
acacagtaga tgagggagca                                                    20

<210> SEQ ID NO 1480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1480
cacacagtag atgagggagc                                                    20

<210> SEQ ID NO 1481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1481
gcacacagta gatgagggag                                                    20

<210> SEQ ID NO 1482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1482
ugcacacagt agatgaggga                                                    20

<210> SEQ ID NO 1483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1483
gugcacacag tagatgaggg                                                    20

<210> SEQ ID NO 1484
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 1484
agugcacaca gtagaugagg                                               20

<210> SEQ ID NO 1485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1485
ggcacaaggg cacagacttc                                               20

<210> SEQ ID NO 1486
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1486
ggcacaaggg cacagacuuc                                               20

<210> SEQ ID NO 1487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1487
gggucctccc cacagaggga                                               20

<210> SEQ ID NO 1488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1488
gggucctccc cacagaggga                                               20

<210> SEQ ID NO 1489
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1489
```
gggucctccc cacagaggga                                                  20

<210> SEQ ID NO 1490
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1490
gggucctccc cacagaggga                                                  20

<210> SEQ ID NO 1491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1491
ggguuctccc cacagaggga                                                  20

<210> SEQ ID NO 1492
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
ggcacaaggg cacagacuuc                                                  20

<210> SEQ ID NO 1493
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1493
ggcacaaggg cacagacuuc                                                  20

<210> SEQ ID NO 1494
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1494
ggcacaaggg cacagacuuc                                                  20

<210> SEQ ID NO 1495
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1495
ggcacaaggg cacagacuuc                                               20

<210> SEQ ID NO 1496
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1496
ggcacaaggg cacagacuuc                                               20

<210> SEQ ID NO 1497
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1497
ggcacaaggg cacagacuuc                                               20

<210> SEQ ID NO 1498
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1498
ggcacaaggg cacagacuuc                                               20

<210> SEQ ID NO 1499
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1499
ggcacaaggg cacagacuuc                                               20

<210> SEQ ID NO 1500
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1500
ggcacaaggg cacagacuuc                                               20

<210> SEQ ID NO 1501
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1501
ggcacaaggg cacagacuuc                                              20

<210> SEQ ID NO 1502
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1502
ggcacaaggg cacagacuuc                                              20

<210> SEQ ID NO 1503
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1503
ggcacaaggg cacagacuuc                                              20

<210> SEQ ID NO 1504
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1504
ggcacaaggg cacagacuuc                                              20

<210> SEQ ID NO 1505
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1505
cagtctgctt cg                                                      12

<210> SEQ ID NO 1506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1506
gcctcagtct gcttcgcacc                                              20

<210> SEQ ID NO 1507
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 1507
uucuagaccu guuuugcuut t                                            21

<210> SEQ ID NO 1508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1508
uucuagaccu guuuugcuut t                                            21

<210> SEQ ID NO 1509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1509
aagcaaaaca ggucuagaat t                                            21

<210> SEQ ID NO 1510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1510
aagcaaaaca ggucuagaat t                                            21

<210> SEQ ID NO 1511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1511
aagcaaaaca ggucuagaat t                                            21

<210> SEQ ID NO 1512
<211> LENGTH: 20
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1512
agcaaaacag gucuagaatt                                                     20

<210> SEQ ID NO 1513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1513
agcaaaacag gucuagaatt                                                     20

<210> SEQ ID NO 1514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1514
agcaaaacag gucuagaatt                                                     20

<210> SEQ ID NO 1515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1515
uucuagaccu guuuugcuut t                                                   21

<210> SEQ ID NO 1516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1516
uucuagaccu guuuugcuut t                                                   21

<210> SEQ ID NO 1517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1517
uucuagaccu guuuugcuut t                                              21

<210> SEQ ID NO 1518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1518
uucuagaccu guuuugcuut t                                              21

<210> SEQ ID NO 1519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1519
uucuagaccu guuuugcuut t                                              21

<210> SEQ ID NO 1520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1520
uucuagaccu guuuugcuut t                                              21

<210> SEQ ID NO 1521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1521
aagcaaaaca ggucuagaat t                                              21

<210> SEQ ID NO 1522
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1522
aagcaaaaca ggucuagaat t                                              21

<210> SEQ ID NO 1523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1523
aagcaaaaca ggucuagaat t                                              21

<210> SEQ ID NO 1524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1524
aagcaaaaca ggucuagaat t                                              21

<210> SEQ ID NO 1525
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1525
aagcaaaaca ggucuagaat t                                              21

<210> SEQ ID NO 1526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1526
aagcaaaaca ggucuagaat t                                              21

<210> SEQ ID NO 1527
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1527
aagcaaaaca ggucuagaat t                                                 21

<210> SEQ ID NO 1528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1528
aagcaaaaca ggucuagaat t                                                 21

<210> SEQ ID NO 1529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1529
aagcaaaaca ggucuagaat t                                                 21

<210> SEQ ID NO 1530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1530
aagcaaaaca ggucuagaat t                                                 21

<210> SEQ ID NO 1531
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1531
aagcaaaaca ggucuagaat t                                                 21

<210> SEQ ID NO 1532
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1532
aagcaaaaca ggucuagaat t                                              21

<210> SEQ ID NO 1533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1533
uucuagaccu guuuugcuut t                                              21

<210> SEQ ID NO 1534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1534
uucuagaccu guuuugcuut t                                              21

<210> SEQ ID NO 1535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1535
uucuagaccu guuuugcuut t                                              21

<210> SEQ ID NO 1536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1536
uucuagaccu guuuugcuut t                                              21
```

```
<210> SEQ ID NO 1537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1537
uucuagaccu guuuugcuut t                                              21

<210> SEQ ID NO 1538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1538
uucuagaccu guuuugcuut t                                              21

<210> SEQ ID NO 1539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1539
aagcaaaaca ggucuagaat t                                              21

<210> SEQ ID NO 1540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1540
aagcaaaaca ggucuagaat t                                              21

<210> SEQ ID NO 1541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1541
aagcaaaaca ggucuagaat t                                              21
```

<210> SEQ ID NO 1542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1542
aagcaaaaca ggucuagaat t                                              21

<210> SEQ ID NO 1543
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1543
aagcaaaaca ggucuagaat t                                              21

<210> SEQ ID NO 1544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1544
aagcaaaaca ggucuagaat t                                              21

<210> SEQ ID NO 1545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1545
aagcaaaaca ggucuagaat t                                              21

<210> SEQ ID NO 1546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1546
aagcaaaaca ggucuagaat t                                              21

<210> SEQ ID NO 1547
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1547
ggatgttctc ga                                                             12

<210> SEQ ID NO 1548
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1548
ggatgttctc ga                                                             12

<210> SEQ ID NO 1549
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1549
ggatgttctc ga                                                             12

<210> SEQ ID NO 1550
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1550
ttcagtcatg acttcc                                                         16

<210> SEQ ID NO 1551
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1551
ttcagtcatg acttcc                                                         16

<210> SEQ ID NO 1552
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1552

His His His His His His
1               5

<210> SEQ ID NO 1553
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1553
ggaagucugu gcccguguuc c                                            21

<210> SEQ ID NO 1554
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1554
ggcacaaggg cacagacuuc                                              20

<210> SEQ ID NO 1555
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1555
acacacacac                                                         10

<210> SEQ ID NO 1556
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1556
cccccccccc                                                         10

<210> SEQ ID NO 1557
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1557
cccccccccc                                                         10

<210> SEQ ID NO 1558
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1558
cccccccccc                                                         10

<210> SEQ ID NO 1559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1559
gcctcagtct gcttcgcacc                                                  20

<210> SEQ ID NO 1560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1560
tagccattgc agctgctcac                                                  20

<210> SEQ ID NO 1561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1561
tccagttcct tcattctgca                                                  20

<210> SEQ ID NO 1562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1562
tgagatgcct ggctgccata                                                  20

<210> SEQ ID NO 1563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1563
attaataaat tgtcatcacc                                                  20

<210> SEQ ID NO 1564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1564
attaataaat tgacatcacc                                                  20

```
<210> SEQ ID NO 1565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1565
attaataaat tggcatcacc                                                    20
```